United States Patent
Kim et al.

(10) Patent No.: US 11,877,464 B2
(45) Date of Patent: Jan. 16, 2024

(54) ORGANIC LIGHT EMITTING ELEMENT

(71) Applicant: LG CHEM, LTD., Seoul (KR)

(72) Inventors: Dongheon Kim, Daejeon (KR); Nansra Heo, Daejeon (KR); Wanpyo Hong, Daejeon (KR); Yeon Hwan Kim, Daejeon (KR); Heungwoo Choi, Daejeon (KR); Jun Yun, Daejeon (KR); Hyungjin Lee, Daejeon (KR); Jae Seung Ha, Daejeon (KR)

(73) Assignee: LG Chem, Ltd., Seoul (KR)

( * ) Notice: Subject to any disclaimer, the term of this patent is extended or adjusted under 35 U.S.C. 154(b) by 806 days.

(21) Appl. No.: 16/497,275

(22) PCT Filed: May 11, 2018

(86) PCT No.: PCT/KR2018/005423
§ 371 (c)(1),
(2) Date: Sep. 24, 2019

(87) PCT Pub. No.: WO2018/221871
PCT Pub. Date: Dec. 6, 2018

(65) Prior Publication Data
US 2020/0144552 A1   May 7, 2020

(30) Foreign Application Priority Data
May 31, 2017   (KR) .................. 10-2017-0067686

(51) Int. Cl.
*H01L 51/52* (2006.01)
*C07C 255/47* (2006.01)
(Continued)

(52) U.S. Cl.
CPC ............ *H10K 50/19* (2023.02); *C07C 211/54* (2013.01); *C07C 211/61* (2013.01);
(Continued)

(58) Field of Classification Search
None
See application file for complete search history.

(56) References Cited

U.S. PATENT DOCUMENTS

| | | | |
|---|---|---|---|
| 2003/0189401 A1* | 10/2003 | Kido ................ | C07C 211/58 313/506 |
| 2004/0251816 A1 | 12/2004 | Leo et al. | |

(Continued)

FOREIGN PATENT DOCUMENTS

| | | |
|---|---|---|
| CN | 101548408 | 9/2009 |
| CN | 102239140 | 11/2011 |

(Continued)

OTHER PUBLICATIONS

Machine English translation of Adachi et al. (JP 2006-019357 A). Feb. 26, 2022.*

(Continued)

*Primary Examiner* — Jay Yang
(74) *Attorney, Agent, or Firm* — Bryan Cave Leighton Paisner LLP

(57) ABSTRACT

Provided is an organic light emitting device that includes an anode, a cathode provided to face the anode, and one or more light emitting units provided between the anode and the cathode, wherein the organic light emitting device includes a charge generation layer provided between the anode and the one light emitting unit, or between the two light emitting units adjacent to each other among the light emitting units, the charge generation layer comprises a p-type charge injection layer, a p-type charge generation layer, or a layer which simultaneously injects and generates p-type charges, and the p-type charge injection layer, the p-type charge generation layer, or the layer which simultaneously injects and generates p-type charges has electric conductivity of $1\times10^{-6}$ S/cm or more.

14 Claims, 2 Drawing Sheets

(51) Int. Cl.
  *H01L 51/00* (2006.01)
  *C07C 211/54* (2006.01)
  *C07C 211/61* (2006.01)
  *H10K 50/19* (2023.01)
  *H10K 85/60* (2023.01)

(52) U.S. Cl.
  CPC ......... *C07C 255/47* (2013.01); *H10K 85/615* (2023.02); *H10K 85/631* (2023.02); *H10K 85/633* (2023.02); *C07C 2603/10* (2017.05); *C07C 2603/18* (2017.05); *H10K 85/626* (2023.02)

(56) References Cited

U.S. PATENT DOCUMENTS

| | | |
|---|---|---|
| 2009/0036643 A1† | 2/2009 | Marks |
| 2010/0019659 A1 | 1/2010 | Morishita |
| 2011/0284827 A1 | 11/2011 | Morishita et al. |
| 2014/0225082 A1 | 8/2014 | Park et al. |
| 2014/0246663 A1† | 9/2014 | Kambe |
| 2015/0243891 A1* | 8/2015 | Kato ............ C09B 57/00 257/40 |
| 2016/0155950 A1 | 6/2016 | Kim et al. |
| 2018/0301511 A1 | 10/2018 | Liao |

FOREIGN PATENT DOCUMENTS

| | | |
|---|---|---|
| CN | 106058066 | 10/2016 |
| JP | 2006-019357 | 1/2006 |
| KR | 10-2014-0101226 | 8/2014 |
| KR | 10-2015-0076029 | 7/2015 |
| KR | 10-2016-0064361 | 6/2016 |
| WO | 2009/017798 | 2/2009 |
| WO | 2013-051234 | 4/2013 |
| WO | WO-2014/034795 A1 * | 3/2014 |

OTHER PUBLICATIONS

Endo et al., "Synthesis and Electronic Structure of Dicyanofulvene-Fused Electron Accepting Molecule Based on a 1,5-Dihydro-s-Indacene Framework," Organic Letters 16: 5608-5611 (Oct. 13, 2014).

Irie et al., "syn-Dicyclopenta[b,g]naphthalene-1,8-dione and Its Tetracyanoquinodimethane Derivative: New Electron Acceptors Bearing a π-Extended Indacene Unit," Chem. Lett. 44: 1747-1749 (Oct. 22, 2015).

\* cited by examiner
† cited by third party

[Figure 1]
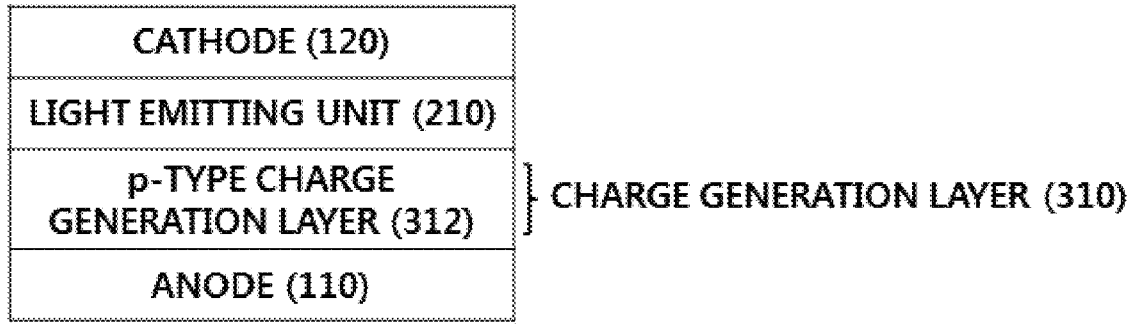
[Figure 2]
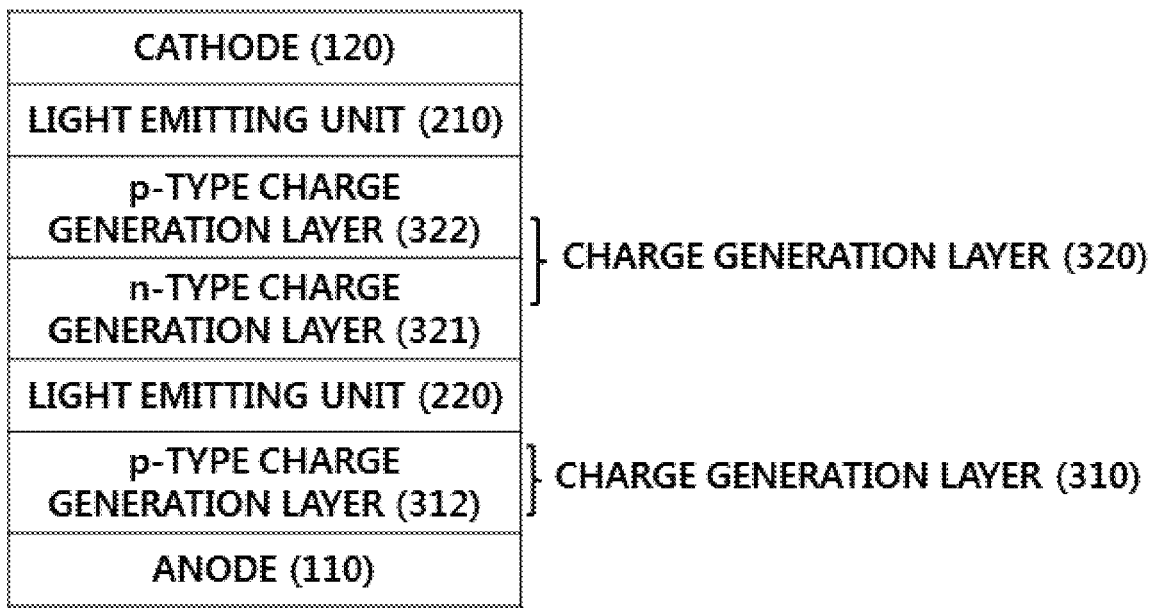

[Figure 3]
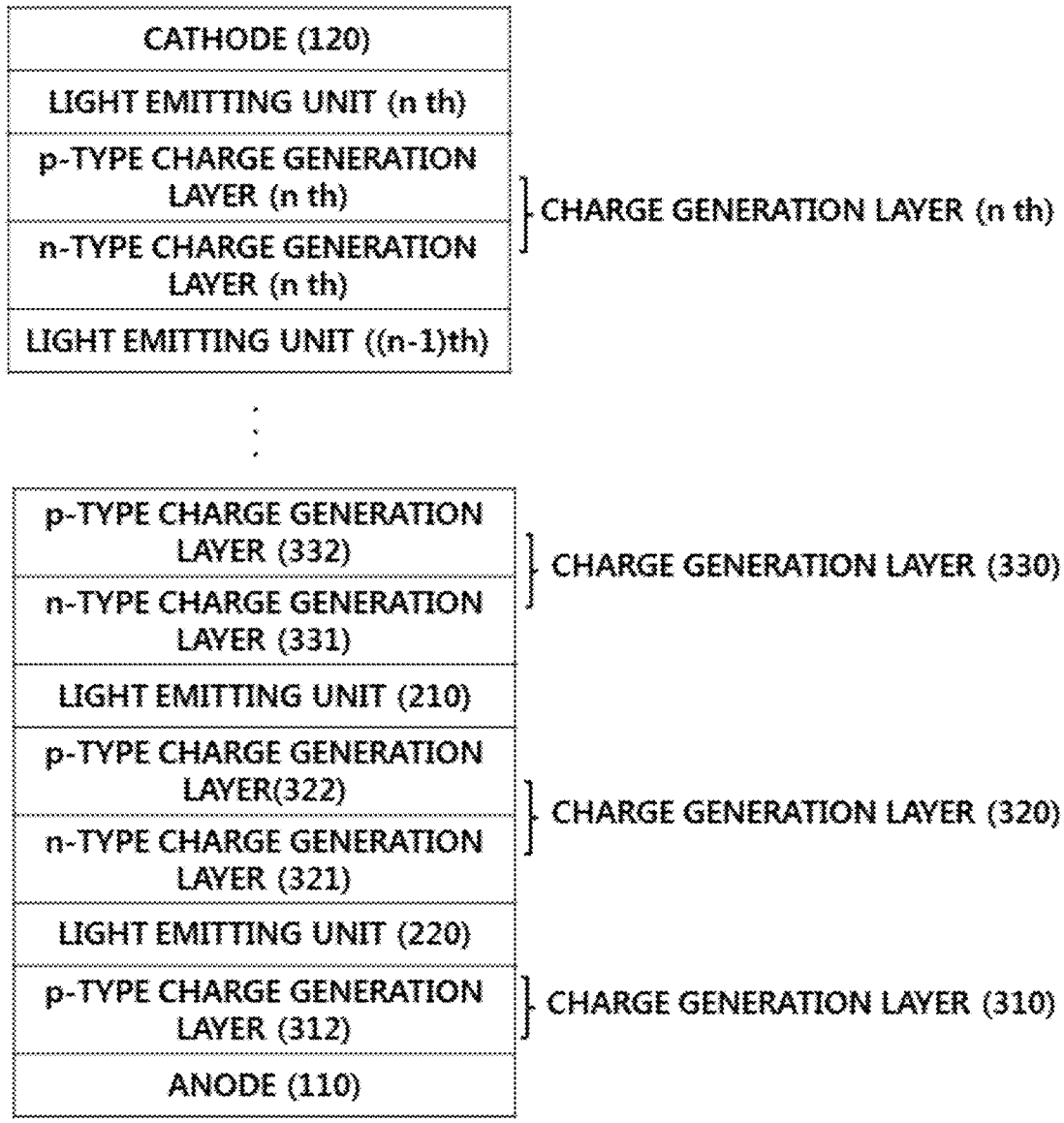
[Figure 4]
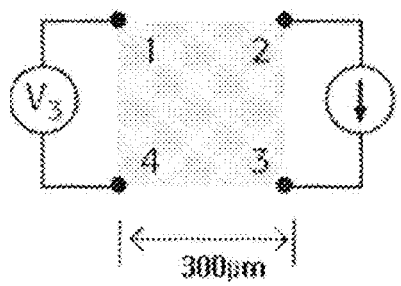

ORGANIC LIGHT EMITTING ELEMENT

CROSS-REFERENCE TO RELATED APPLICATIONS

This application is a National Stage Application of International Application No. PCT/KR2018/005423 filed on May 11, 2018, which claims priority to and the benefit of Korean Patent Application No. 10-2017-0067686 filed in the Korean Intellectual Property Office on May 31, 2017, the entire contents of which are incorporated herein by reference. The present specification relates to an organic light emitting device.

TECHNICAL FIELD

The present specification relates to an organic light emitting device.

BACKGROUND

An organic light emitting device (OLED) is typically composed of two electrodes (an anode and a cathode) and one or more organic material layers positioned between these electrodes. In the organic light emitting device having the aforementioned structure, when a voltage is applied between the two electrodes, holes from the anode and electrons from the cathode each flow into the organic material layer. The holes and the electron are bonded to form excitons. The excitons emit photons that correspond to the energy difference while falling back to the ground state. By the aforementioned principle, the organic light emitting device generates visible light. An information display device or an illumination device can be manufactured by using the organic light emitting device.

Technologies to increase the efficiency of the organic light emitting device and lower the driving voltage thereof have been continuously developed in order to widen the scope of application of the organic light emitting device and commercialize the organic light emitting device.

DETAILED DESCRIPTION OF THE INVENTION

Technical Problem

The present specification provides an organic light emitting device.

Technical Solution

An exemplary embodiment of the present specification provides an organic light emitting device including: an anode; a cathode provided to face the anode; and one or more light emitting units provided between the anode and the cathode, in which the organic light emitting device includes a charge generation layer provided between the anode and the one light emitting unit, or between the two light emitting units adjacent to each other among the light emitting units, the charge generation layer includes a p-type charge injection layer, a p-type charge generation layer, or a layer which simultaneously injects and generates p-type charges, and the p-type charge injection layer, the p-type charge generation layer, or the layer which simultaneously injects and generates p-type charges has electric conductivity of $1 \times 10^{-6}$ S/cm or more.

Advantageous Effects

In an organic light emitting device according to an exemplary embodiment of the present specification, a p-type charge injection layer, a p-type charge generation layer, or a layer which simultaneously injects and generates p-type charges has electric conductivity of $1 \times 10^{-6}$ S/cm or more, and has a high charge density and easily transfers charges, thereby enabling the improvement in efficiency, the achievement of low driving voltage, and/or the improvement in lifetime characteristics in the organic light emitting device.

BRIEF DESCRIPTION OF DRAWINGS

FIGS. 1 to 3 illustrate a structure of an organic light emitting device according to an exemplary embodiment of the present specification.

FIG. 4 is a view illustrating a method for measuring electric conductivity according to an exemplary embodiment of the present specification.

BEST MODE

Hereinafter, the present specification will be described in more detail.

An exemplary embodiment of the present specification provides an organic light emitting device including: an anode; a cathode provided to face the anode; and one or more light emitting units provided between the anode and the cathode, in which the organic light emitting device includes a charge generation layer provided between the anode and the one light emitting unit, or between the two light emitting units adjacent to each other among the light emitting units, the charge generation layer includes a p-type charge injection layer, a p-type charge generation layer, or a layer which simultaneously injects and generates p-type charges, and the p-type charge injection layer, the p-type charge generation layer, or the layer which simultaneously injects and generates p-type charges has electric conductivity of $1 \times 10^{-6}$ S/cm or more.

In the present specification, the electric conductivity was calculated by using a 4-point probe and van der Pauw equation. The 4-point probe for measuring the electric conductivity of the present specification is the same as that in FIG. 4, and the van der Pauw equation is the same as that in the following Equation 1.

$$\rho = \frac{\pi d}{\ln 2} R \quad \text{[Equation 1]}$$

In Equation 1, d represents a thickness (cm) of a p-type charge injection layer, a p-type charge generation layer, or a layer which simultaneously injects and generates p-type charges, R represents resistance (Ω), ρ represents specific resistance (Ω·cm), and the electric conductivity is the reciprocal of the specific resistance (S/cm=1/Ω·cm).

In the present specification, the charge generation layer can further include an n-type charge generation layer.

FIGS. 1 to 3 illustrate a structure of an organic light emitting device according to an exemplary embodiment of the present specification, and in FIG. 1, one light emitting unit 210 is positioned between an anode 110 and a cathode 120 and a charge generation layer 310 is positioned between the anode 110 and the light emitting unit 210, and in this case, the charge generation layer 310 includes a p-type charge generation layer 312 and the p-type charge generation layer 312 is positioned adjacent to the anode 110 and the light emitting unit 210.

According to FIG. 2, two light emitting units 210 and 220 are positioned between the anode 110 and the cathode 120, the charge generation layer 310 is positioned between the anode 110 and the light emitting unit 220 adjacent to the anode 110, and in this case, the charge generation layer 310 includes the p-type charge generation layer 312, the p-type charge generation layer 312 is positioned adjacent to the anode 110 and the light emitting unit 220, and a charge generation layer 320 is positioned between the two light emitting units 210 and 220. In this case, the charge generation layer 320 includes an n-type charge generation layer 321 and a p-type charge generation layer 322, the n-type charge generation layer 321 is positioned adjacent to the light emitting unit 220 adjacent to the anode 110, and the p-type charge generation layer 312 is positioned adjacent to the light emitting unit 210 adjacent to the cathode 120.

FIGS. 1 and 2 illustrate a case where only one or two light emitting unit or units is or are provided between the anode 110 and the cathode 120, but in another exemplary embodiment of the present specification, three or more light emitting units can be disposed between the anode 110 and the cathode 120. A case where three or more light emitting units are provided is illustrated in FIG. 3.

FIG. 3 illustrates a lamination structure of an organic light emitting device including n light emitting units. After the charge generation layer 310, the light emitting unit 220, the charge generation layer 320, the light emitting unit 210, and a charge generation layer 330 are laminated on the anode 110, a light emitting unit and a charge generation layer can be additionally and repeatedly laminated in this order. Subsequently, after the (n−1)th light emitting unit and the nth charge generation layer are laminated, nth light emitting unit and the cathode 120 are laminated.

In FIGS. 1 to 3, the p-type charge generation layers 312, 322, and 332 are described, but the p-type charge generation layers 312, 322, and 332 can be a p-type charge injection layer, a p-type charge generation layer, or a layer which simultaneously injects and generates p-type charges. In the present specification, the n-type means n-type semiconductor characteristics. In other words, the n-type has a characteristic in that electrons are injected or transported through the lowest unoccupied molecular orbital (LUMO) energy level, and the n-type characteristic can be defined as a characteristic of a material having mobility of electrons larger than that of holes. In contrast, the p-type means p-type semiconductor characteristics. In other words, the p-type has a characteristic in that holes are injected or transported through the highest occupied molecular orbital (HOMO) energy level, and the p-type characteristic can be defined as a characteristic of a material having mobility of holes larger than that of electrons. In the present specification, an organic material layer having n-type characteristics can be mentioned as an n-type organic material layer. Further, an organic material layer having p-type characteristics can be mentioned as a p-type organic material layer. In addition, the n-type doping means that doping is conducted so as to have n-type characteristics.

In the present specification, adjacency means an arrangement relationship of the closest layers among the layers mentioned as adjacent ones. For example, adjacent two light emitting units mean an arrangement relationship of two light emitting units disposed closest among a plurality of light emitting units. The adjacency may also mean a case where two layers are brought into physical contact with each other in some cases, and another layer not mentioned may also be disposed between the two layers. For example, a light emitting unit adjacent to a cathode means a light emitting unit disposed closest to the cathode among the light emitting units. Further, the cathode and the light emitting unit can also be brought into physical contact with each other, but another layer other than the light emitting unit can be disposed between the cathode and the light emitting unit. However, a charge generation layer is provided between two adjacent light emitting units.

In the present specification, the light emitting units 210 and 220 are not particularly limited as long as the light emitting units have a function capable of emitting light. For example, the light emitting units 210 and 220 can include one or more light emitting layers. The light emitting units 210 and 220 can include one or more organic material layers in addition to the light emitting layer, if necessary.

According to an exemplary embodiment of the present specification, the light emitting units 210 and 220 can additionally include one or more organic material layers in addition to the light emitting layer. The additional organic material layer can be a hole transport layer, a hole injection layer, a layer which transports and injects holes, a buffer layer, an electron blocking layer, an electron transport layer, an electron injection layer, a layer which transports and injects electrons, a hole blocking layer, or the like. Here, the hole transport layer, the hole injection layer, the layer which transports and injects holes, or the electron blocking layer can be disposed closer to the anode 110 than the light emitting layer. The electron transport layer, the electron injection layer, the layer which transports and injects electrons, or the hole blocking layer can be disposed closer to the cathode 120 than the light emitting layer. Whether to use the hole blocking layer can be determined according to properties of the light emitting layer. For example, when the properties of the light emitting layer are close to the n-type, the hole blocking layer may not be used, but when the properties of the light emitting layer is the p-type, the use of the hole blocking layer can be considered. Further, whether to use the hole blocking layer can be determined in consideration of the relationship between the HOMO energy level of the light emitting layer and the HOMO energy level of the electron transport layer. When the HOMO energy level of the light emitting layer has a value larger than the HOMO energy level of the electron transport layer, it can be contemplated to introduce the hole blocking layer. However, in this case, when the HOMO level of the electron transport layer is larger than the HOMO level of the light emitting layer, the electron transport layer itself can also serve as a hole blocking layer. As one example, the electron transport layer can play both a role of the electron transport layer and a role of the hole blocking layer by using two or more materials for the electron transport layer.

In the present specification, the charge generation layer 310 can allow one or more light emitting units included in the organic light emitting device to emit light by generating charges at the light emitting unit 210 or between the light emitting units 210 and 220.

The charge generation layer 310 according to an exemplary embodiment of the present specification includes a p-type charge injection layer, a p-type charge generation layer, or a layer which simultaneously injects and generates p-type charges.

According to another exemplary embodiment of the present specification, the charge generation layer 310 can further include an n-type charge generation layer.

According to an exemplary embodiment of the present specification, the p-type charge injection layer, the p-type charge generation layer, or the layer which simultaneously injects and generates p-type charges includes: a compound of the following Chemical Formula 1; and one or more of compounds of the following Chemical Formulae 2 to 4.

[Chemical Formula 1]

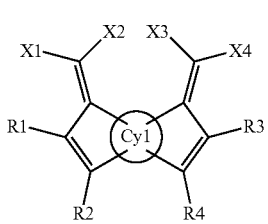

In Chemical Formula 1,

Cy1 is a substituted or unsubstituted aromatic ring,

X1 to X4 are the same as or different from each other, and are each independently hydrogen; a nitrile group; a nitro group; a halogen group; a carboxyl group; a carbonyl group; a substituted or unsubstituted haloalkyl group; a substituted or unsubstituted alkyl group; a substituted or unsubstituted alkoxy group; a substituted or unsubstituted aryloxy group; a substituted or unsubstituted heteroaryloxy group; a substituted or unsubstituted aryl group; or a substituted or unsubstituted heteroaryl group, or adjacent groups can be bonded to each other to form a substituted or unsubstituted ring, and R1 to R4 are the same as or different from each other, and are each independently hydrogen; a nitrile group; a halogen group; a substituted or unsubstituted haloalkyl group; a substituted or unsubstituted haloalkoxy group; a substituted or unsubstituted halothioalkoxy group; a substituted or unsubstituted ether group; a substituted or unsubstituted alkyl group; a substituted or unsubstituted alkoxy group; a substituted or unsubstituted thioalkoxy group; a substituted or unsubstituted silyl group; a substituted or unsubstituted aryl group; or a substituted or unsubstituted heteroaryl group,

[Chemical Formula 2]

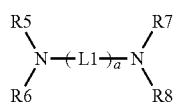

in Chemical Formula 2,

L1 is a substituted or unsubstituted arylene group; or a substituted or unsubstituted heteroarylene group, R5 to R8 are the same as or different from each other, and are each independently a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; or a substituted or unsubstituted heteroaryl group, or adjacent groups can be bonded to each other to form a substituted or unsubstituted ring, a is an integer from 1 to 10, and when a is 2 or more, two or more L1's are the same as or different from each other,

[Chemical Formula 3]

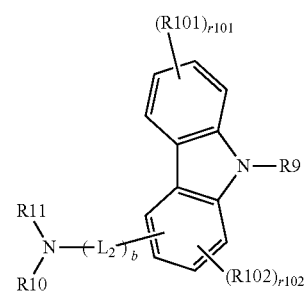

in Chemical Formula 3,

L2 is a substituted or unsubstituted arylene group,

R9 to R11, R101, and R102 are the same as or different from each other, and are each independently a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted arylphosphine group; a substituted or unsubstituted phosphine oxide group; a substituted or unsubstituted aryl group; or a substituted or unsubstituted heteroaryl group, b is an integer from 1 to 10, when b is 2 or more, two or more L2's are the same as or different from each other, r101 is an integer from 1 to 4, r102 is an integer from 1 to 3, and when r101 and r102 are each 2 or more, two or more structures in the parenthesis are the same as or different from each other,

[Chemical Formula 4]

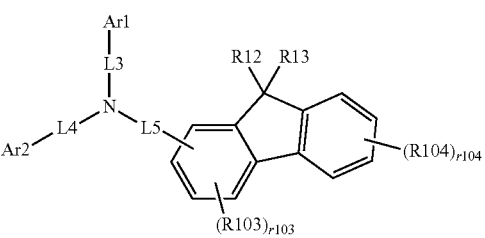

in Chemical Formula 4,

L3 to L5 are the same as or different from each other, and are each independently a direct bond; a substituted or unsubstituted arylene group; or a substituted or unsubstituted heteroarylene group, Ar1 is a substituted or unsubstituted aryl group; or a substituted or unsubstituted heteroaryl group, Ar2 is a substituted or unsubstituted aryl group, R12, R13, R103, and R104 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups are bonded to each other to form a substituted or unsubstituted ring, r103 is an integer from 1 to 3, r104 is an integer from 1 to 4, and when r103 and r104 are each 2 or more, two or more structures in the parenthesis are the same as or different from each other.

The compound of Chemical Formula 1 according to an exemplary embodiment of the present specification has a deep LUMO energy level, and the compounds of Chemical Formulae 2 to 4 can function as an electron acceptor capable of accepting charges from the HOMO energy level, thereby producing charges. Accordingly, in the organic light emitting device including the compounds as the p-type charge injection layer, the p-type charge generation layer, or the layer which simultaneously injects and generates p-type charges, the degree to which charges are generated can vary depending on the LUMO energy level of the compound of Chemical Formula 1 and the HOMO energy levels of the compounds of Chemical Formulae 2 to 4, it is possible to prevent the driving voltage of the organic light emitting device for injecting holes from being increased by adjusting the Fermi level through generation of charges, and there are effects of improving the charge balance in the organic light emitting device and improving the efficiency and lifetime of the organic light emitting device.

Further, the more charges are generated, the higher the density of charges is, so that it is possible to know characteristics of the charge generation layer through the electric conductivity. Accordingly, in the organic light emitting device according to an exemplary embodiment of the present specification, the p-type charge injection layer, the p-type charge generation layer, or the layer which simultaneously injects and generates p-type charges has the electric conductivity of $1 \times 10^{-6}$ S/cm or more, and has a high charge density and easily transfers charges, thereby enabling the improvement in efficiency, the achievement of low driving voltage, and/or the improvement in lifetime characteristics in the organic light emitting device.

When the above electric conductivity range is satisfied, charges are effectively transferred from the charge generation layer to the adjacent light emitting layer.

According to an exemplary embodiment of the present specification, the compounds of Chemical Formulae 2 to 4 include an amine group, which is an electron donor group having an unshared electron pair, and thus transfer charges to the compound of Chemical Formula 1, and generate charges, thereby effectively functioning as the p-type charge injection layer, the p-type charge generation layer, or the layer which simultaneously injects and generates p-type charges.

When only the compound of Chemical Formula 1 is used for the p-type charge injection layer, the p-type charge generation layer, or the layer which simultaneously injects and generates p-type charges, sufficient charges are not generated, so that the compound of Chemical Formula 1 does not function as the p-type charge injection layer, the p-type charge generation layer, or the layer which simultaneously injects and generates p-type charges.

According to an exemplary embodiment of the present specification, the p-type charge injection layer, the p-type charge generation layer, or the layer which simultaneously injects and generates p-type charges is formed by co-depositing the compound of Chemical Formula 1 and one or more of the compounds of Chemical Formulae 2 to 4.

According to an exemplary embodiment of the present specification, in the co-deposition, the compound of Chemical Formula 1; and one or more of the compounds of Chemical Formulae 2 to 4 are included at a weight ratio of 20:80 to 80:20, specifically, a weight ratio of 30:70 to 70:30. When the compound of Chemical Formula 1; and the compounds of Chemical Formulae 2 to 4 are included at a weight ratio of 20:80 to 80:20, p-type charges sufficient to function as an organic light emitting device including the p-type charge injection layer, the p-type charge generation layer, or the layer which simultaneously injects and generates p-type charges, which has the electric conductivity of $1 \times 10^{-6}$ S/cm or more, can be generated, thereby achieving device characteristics of low voltage, high efficiency, and a long lifetime.

When one part "includes" one constituent element in the present specification, unless otherwise specifically described, this does not mean that another constituent element is excluded, but means that another constituent element can be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted haloalkyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification,

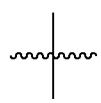

means a moiety bonded to another substituent or a bonding portion.

In the present specification, a halogen group can be fluorine, chlorine, bromine or iodine.

In the present specification, the number of carbon atoms of an imide group is not particularly limited, but is preferably 1 to 30. Specifically, the imide group can be a compound having the following structures, but is not limited thereto.

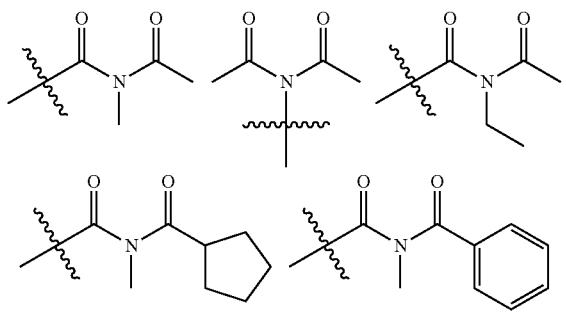

In the present specification, for an amide group, the nitrogen of the amide group can be substituted with hydrogen, a straight-chained, branched, or cyclic alkyl group having 1 to 30 carbon atoms, or an aryl group having 6 to 30 carbon atoms. Specifically, the amide group can be a compound having the following structural formulae, but is not limited thereto.

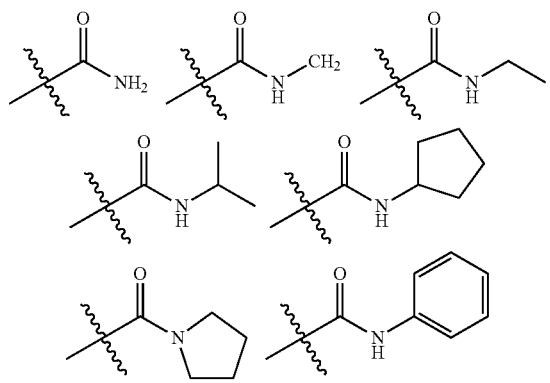

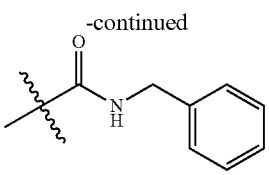

In the present specification, the number of carbon atoms of a carbonyl group is not particularly limited, but is preferably 1 to 30. Specifically, the carbonyl group can be a compound having the following structures, but is not limited thereto.

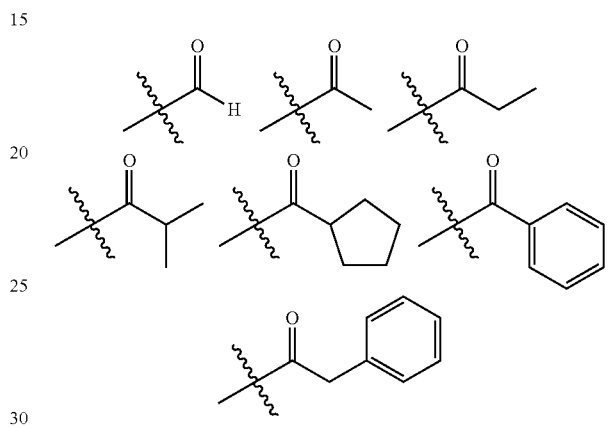

In the present specification, for an ester group, the oxygen of the ester group can be substituted with a straight-chained, branched, or cyclic alkyl group having 1 to 25 carbon atoms, or an aryl group having 6 to 30 carbon atoms. Specifically, the ester group can be a compound having the following structural formulae, but is not limited thereto.

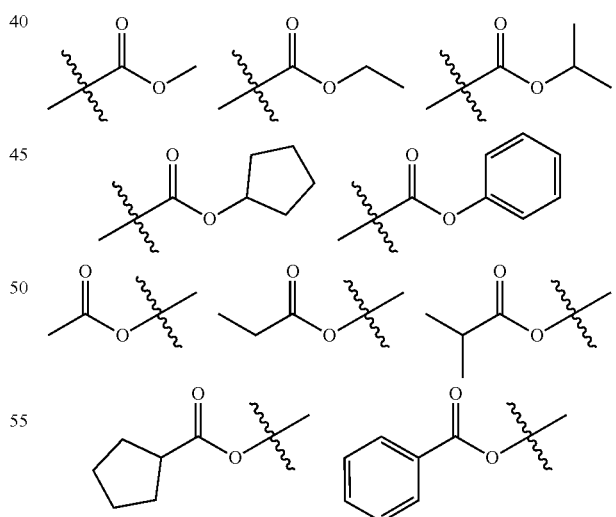

In the present specification, the alkyl group can be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group can be straight-chained, branched, or cyclic. The number of carbon atoms of the alkoxy group is not particularly limited, but is preferably 1 to 30. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group can be selected from the group consisting of —NH$_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenyl-phenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, an N-alkylarylamine group means an amine group in which an alkyl group and an aryl group are substituted with N of the amine group. In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, the N-alkylheteroarylamine group, and the haloalkyl group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group can be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group can be —BR$_{100}$R$_{101}$, and R$_{100}$ and R$_{101}$ are the same as or different from each other, and can be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group can be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

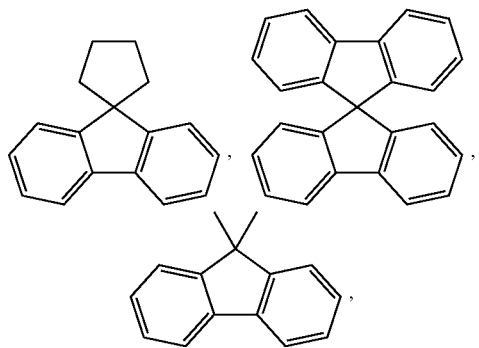

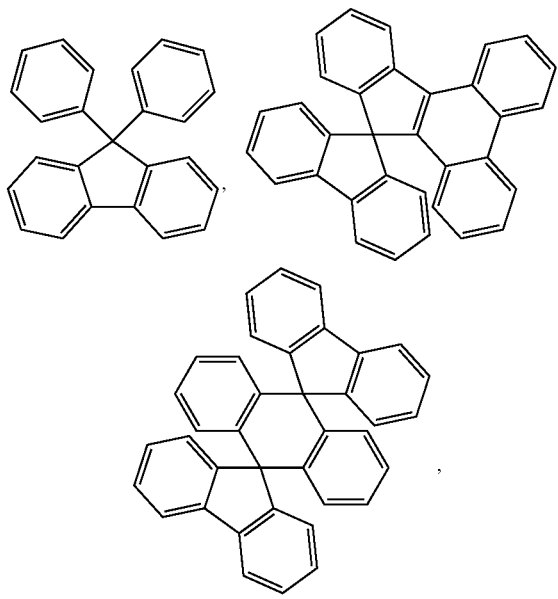

and the like. However, the substituent is not limited thereto.

In the present specification, the "adjacent" group can mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group or a substituted or unsubstituted diarylamine group. The aryl group in the arylamine group can be a monocyclic aryl group or a polycyclic aryl group. The arylamine group including two or more aryl groups can include a monocyclic aryl group, a polycyclic aryl group, or both a monocyclic aryl group and a polycyclic aryl group. For example, the aryl group in the arylamine group can be selected from the above-described examples of the aryl group.

In the present specification, a heteroaryl group includes one or more atoms other than carbon, that is, one or more heteroatoms, and specifically, the heteroatom can include one or more atoms selected from the group consisting of O, N, Se, S, and the like. The number of carbon atoms thereof is not particularly limited, but is preferably 2 to 30, and the heteroaryl group can be monocyclic or polycyclic. Examples of a heterocyclic group include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolyl group, a quinazolyl group, a quinoxalyl group, a phthalazinyl group, a pyridopyrimidyl group, a pyridopyrazinyl group, a pyrazinopyrazinyl group, an isoquinolyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzofuranyl group, and the like, but are not limited thereto.

In the present specification, examples of a heteroarylamine group include a substituted or unsubstituted monoheteroarylamine group or a substituted or unsubstituted diheteroarylamine group. The heteroarylamine group including two or more heteroaryl groups can include a monocyclic heteroaryl group, a polycyclic heteroaryl group, or both a monocyclic heteroaryl group and a polycyclic heteroaryl group. For example, the heteroaryl group in the heteroarylamine group can be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, an arylene group means a group having two bonding positions in an aryl group, that is, a divalent group. The above-described description on the aryl group can be applied to the arylene group, except for a divalent arylene group.

In the present specification, a heteroarylene group means a group having two bonding positions in a heteroaryl group, that is, a divalent group. The above-described description on the heteroaryl group can be applied to the heteroarylene group, except for a divalent heteroarylene group.

In the present specification, in a substituted or unsubstituted ring formed by bonding adjacent groups, the "ring" means a substituted or unsubstituted hydrocarbon ring; or a substituted or unsubstituted hetero ring.

In the present specification, a hydrocarbon ring can be an aromatic ring, an aliphatic ring, or a fused ring of the aromatic ring and the aliphatic ring, and can be selected from the examples of the cycloalkyl group or the aryl group, except for the hydrocarbon ring which is not monovalent.

In the present specification, an aromatic ring can be monocyclic or polycyclic, and can be selected from the examples of the aryl group, except for the aromatic ring which is not monovalent.

In the present specification, a hetero ring includes one or more atoms other than carbon, that is, one or more heteroatoms, and specifically, the heteroatom can include one or more atoms selected from the group consisting of O, N, Se, S, and the like. The hetero ring can be monocyclic or polycyclic, can be an aromatic ring, an aliphatic ring, or a fused ring of the aromatic ring and the aliphatic ring, and can be selected from the examples of the heteroaryl group or the heterocyclic group, except for the hetero ring which is not monovalent.

According to an exemplary embodiment of the present specification, in Chemical Formula 1, Cy1 is a substituted or unsubstituted monocyclic or polycyclic aromatic ring.

According to an exemplary embodiment of the present specification, in Chemical Formula 1, Cy1 is a substituted or unsubstituted monocyclic aromatic ring.

According to an exemplary embodiment of the present specification, in Chemical Formula 1, Cy1 is a substituted or unsubstituted monocyclic benzene ring.

According to an exemplary embodiment of the present specification, Chemical Formula 1 is one of the following Chemical Formula 1-1 or 1-2.

[Chemical Formula 1-1]

[Chemical Formula 1-2]

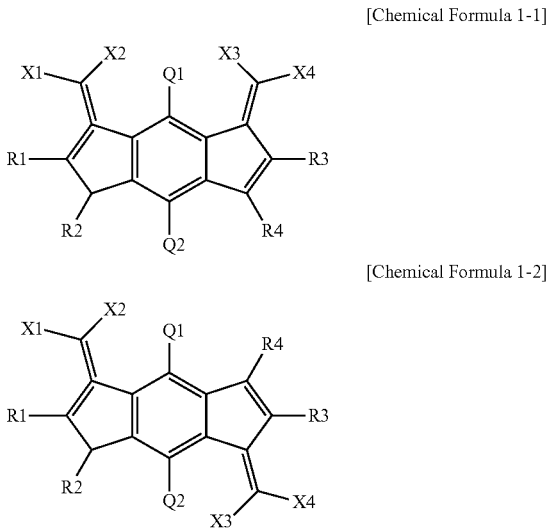

In Chemical Formulae 1-1 and 1-2, definitions of X1 to X4 and R1 to R4 are the same as those defined in Chemical Formula 1, and Q1 and Q2 are the same as or different from each other, and are each independently hydrogen; deuterium; a halogen group; a nitrile group; a nitro group; a hydroxyl group; a carbonyl group; an ester group; an imide group; an amide group; a substituted or unsubstituted haloalkyl group; a substituted or unsubstituted haloalkoxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to an exemplary embodiment of the present specification, in Chemical Formula 1, X1 to X4 are the same as or different from each other, and are each independently hydrogen; a nitrile group; a substituted or unsubstituted aryl group; or a substituted or unsubstituted heteroaryl group.

According to an exemplary embodiment of the present specification, in Chemical Formula 1, X1 to X4 are the same as or different from each other, and are each independently hydrogen; a nitrile group; an aryl group unsubstituted or substituted with one or more selected from the group consisting of a halogen group and a nitrile group; or a heteroaryl group unsubstituted or substituted with one or more selected from the group consisting of a halogen group and a nitrile group.

According to an exemplary embodiment of the present specification, in Chemical Formula 1, X1 to X4 are the same as or different from each other, and are each independently hydrogen; a nitrile group; a phenyl group unsubstituted or substituted with one or more selected from the group consisting of a halogen group and a nitrile group; or a pyridyl group unsubstituted or substituted with one or more selected from the group consisting of a halogen group and a nitrile group.

According to an exemplary embodiment of the present specification, in Chemical Formula 1, X1 to X4 are the same as or different from each other, and are each independently hydrogen; a nitrile group; a phenyl group unsubstituted or substituted with one or more selected from the group consisting of F and a nitrile group; or a pyridyl group unsubstituted or substituted with one or more selected from the group consisting of F and a nitrile group.

According to an exemplary embodiment of the present specification, in Chemical Formula 1, R1 to R4 are the same as or different from each other, and are each independently hydrogen; a halogen group; a nitrile group; a substituted or unsubstituted haloalkyl group; a substituted or unsubstituted haloalkoxy group; a substituted or unsubstituted halothioalkoxy group; a substituted or unsubstituted silyl group; a substituted or unsubstituted aryl group; or a substituted or unsubstituted heteroaryl group.

According to an exemplary embodiment of the present specification, in Chemical Formula 1, R1 to R4 are the same as or different from each other, and are each independently hydrogen; a halogen group; a nitrile group; a haloalkyl group; a haloalkoxy group; a halothioalkoxy group; a silyl group unsubstituted or substituted with an alkyl group; an aryl group unsubstituted or substituted with one or more selected from the group consisting of a halogen group, a nitrile group, a haloalkyl group, a haloalkoxy group, a halothioalkoxy group, and a silyl group substituted with an alkyl group; or a heteroaryl group.

According to an exemplary embodiment of the present specification, in Chemical Formula 1, R1 to R4 are the same as or different from each other, and are each independently hydrogen; a halogen group; a nitrile group; a haloalkyl group; a haloalkoxy group; a halothioalkoxy group; a silyl group unsubstituted or substituted with an alkyl group; a phenyl group unsubstituted or substituted with one or more selected from the group consisting of a halogen group, a nitrile group, a haloalkyl group, a haloalkoxy group, a halothioalkoxy group, and a silyl group substituted with an alkyl group; a pyridyl group; or a pyrimidyl group.

According to an exemplary embodiment of the present specification, in Chemical Formula 1, R1 to R4 are the same as or different from each other, and are each independently hydrogen; F; a nitrile group; —CF$_3$; —OCF$_3$; SCF$_3$; —Si(CH$_3$)$_3$; a phenyl group unsubstituted or substituted from one or more selected from the group consisting of F, a nitrile group, —CF$_3$, —OCF$_3$, SCF$_3$, and —Si(CH$_3$)$_3$; a pyridyl group; or a pyrimidyl group.

According to an exemplary embodiment of the present specification, Q1 and Q2 are the same as or different from each other, and are each independently hydrogen; a halogen group; a nitrile group; a substituted or unsubstituted haloalkyl group; a substituted or unsubstituted haloalkoxy group; a substituted or unsubstituted aryl group; or a substituted or unsubstituted heteroaryl group.

According to an exemplary embodiment of the present specification, Q1 and Q2 are the same as or different from each other, and are each independently hydrogen; a halogen group; a nitrile group; a haloalkyl group; a haloalkoxy group; an aryl group unsubstituted or substituted with one or more selected from the group consisting of a nitrile group, a haloalkyl group, and a haloalkoxy group; or a heteroaryl group.

According to an exemplary embodiment of the present specification, Q1 and Q2 are the same as or different from each other, and are each independently hydrogen; a halogen group; a nitrile group; a haloalkyl group; a haloalkoxy group; a phenyl group unsubstituted or substituted with one or more selected from the group consisting of a nitrile group, a haloalkyl group, and a haloalkoxy group; or a pyridyl group.

According to an exemplary embodiment of the present specification, Q1 and Q2 are the same as or different from each other, and are each independently hydrogen; F; a nitrile group; —$CF_3$; —$OCF_3$; a phenyl group unsubstituted or substituted with one or more selected from the group consisting of a nitrile group, —$CF_3$, and —$OCF_3$; or a pyridyl group.

According to an exemplary embodiment of the present specification, in Chemical Formula 2, L1 is an arylene group unsubstituted or substituted with an alkyl group, an amine group, an aryl group, or a heteroaryl group; or a heteroarylene group unsubstituted or substituted with an aryl group.

According to an exemplary embodiment of the present specification, in Chemical Formula 2, L1 is a phenylene group unsubstituted or substituted with an alkyl group, an amine group, an aryl group, or a heteroaryl group; a biphenylylene group unsubstituted or substituted with an alkyl group; a naphthylene group; a terphenylene group unsubstituted or substituted with an amine group or a heteroaryl group; a fluorenylene group unsubstituted or substituted with an alkyl group; a quaterphenylene group; an anthracenylene group; or a carbazolylene group unsubstituted or substituted with an aryl group.

According to an exemplary embodiment of the present specification, in Chemical Formula 2, L1 is a phenylene group unsubstituted or substituted with a methyl group, a diphenylamine group, a phenyl group, or a carbazole group; a biphenylylene group unsubstituted or substituted with a methyl group; a naphthylene group; a terphenylene group unsubstituted or substituted with a diphenylamine group or a carbazole group; a fluorenylene group unsubstituted or substituted with a methyl group; a quaterphenylene group; an anthracenylene group; or a carbazolylene group unsubstituted or substituted with a phenyl group.

According to an exemplary embodiment of the present specification, in Chemical Formula 2, a is an integer from 1 to 4.

According to an exemplary embodiment of the present specification, in Chemical Formula 2, R5 and R6 are bonded to each other to form a substituted or unsubstituted ring.

According to an exemplary embodiment of the present specification, in Chemical Formula 2, R5 and R6 are bonded to each other to form a substituted or unsubstituted hetero ring.

According to an exemplary embodiment of the present specification, in Chemical Formula 2, R5 and R6 are bonded to each other to form a substituted or unsubstituted carbazole ring.

According to an exemplary embodiment of the present specification, in Chemical Formula 2, R5 and R6 are bonded to each other to form a carbazole ring.

According to an exemplary embodiment of the present specification, in Chemical Formula 2, R7 and R8 are bonded to each other to form a substituted or unsubstituted ring.

According to an exemplary embodiment of the present specification, in Chemical Formula 2, R7 and R8 are bonded to each other to form a substituted or unsubstituted hetero ring.

According to an exemplary embodiment of the present specification, in Chemical Formula 2, R7 and R8 are bonded to each other to form a substituted or unsubstituted carbazole ring.

According to an exemplary embodiment of the present specification, in Chemical Formula 2, R7 and R8 are bonded to each other to form a carbazole ring.

According to an exemplary embodiment of the present specification, in Chemical Formula 2, R5 to R8 are the same as or different from each other, and are each independently a substituted or unsubstituted aryl group.

According to an exemplary embodiment of the present specification, in Chemical Formula 2, R5 to R8 are the same as or different from each other, and are each independently an aryl group unsubstituted or substituted with one or more selected from the group consisting of an alkyl group, an amine group, an aryl group, and a heteroaryl group unsubstituted or substituted with an aryl group.

According to an exemplary embodiment of the present specification, in Chemical Formula 2, R5 to R8 are the same as or different from each other, and are each independently a phenyl group unsubstituted or substituted with one or more selected from the group consisting of an alkyl group, an aryl group, and a heteroaryl group unsubstituted or substituted with an aryl group; a biphenyl group unsubstituted or substituted with one or more selected from the group consisting of an amine group, an aryl group, and a heteroaryl group; a naphtyl group; a terphenyl group unsubstituted or substituted with an amine group; a fluorenyl group unsubstituted or substituted with one or more selected from the group consisting of an alkyl group and a heteroaryl group; or a phenanthrenyl group.

According to an exemplary embodiment of the present specification, in Chemical Formula 2, R5 to R8 are the same as or different from each other, and are each independently a phenyl group unsubstituted or substituted with one or more selected from the group consisting of a methyl group, an ethyl group, a naphthyl group, a biphenyl group, and a thiophene group substituted with a phenyl group; a biphenyl group unsubstituted or substituted with one or more selected from the group consisting of a diphenylamine group, an N-phenylbiphenylamine group, an N-phenylnaphthylamine group, a phenyl group, and a carbazolyl group; a naphthyl group; a terphenyl group unsubstituted or substituted with a diphenylamine group, an N-phenylbiphenylamine group, and an N-phenylnaphthylamine group; a fluorenyl group unsubstituted or substituted with one or more selected from the group consisting of a methyl group and a carbazolyl group; or a phenanthrenyl group.

According to an exemplary embodiment of the present specification, in Chemical Formula 3, L2 is an arylene group.

According to an exemplary embodiment of the present specification, in Chemical Formula 3, L2 is a phenylene group; or a biphenylene group.

According to an exemplary embodiment of the present specification, in Chemical Formula 3, b is 1 or 2.

According to an exemplary embodiment of the present specification, in Chemical Formula 3, R9 is a substituted or unsubstituted aryl group.

According to an exemplary embodiment of the present specification, in Chemical Formula 3, R9 is an aryl group unsubstituted or substituted with an aryl group.

According to an exemplary embodiment of the present specification, in Chemical Formula 3, R9 is a phenyl group unsubstituted or substituted with an aryl group; a biphenyl group; or a naphthyl group.

According to an exemplary embodiment of the present specification, in Chemical Formula 3, R9 is a phenyl group unsubstituted or substituted with a phenyl group; a biphenyl group; or a naphthyl group.

According to an exemplary embodiment of the present specification, in Chemical Formula 3, R10 and R11 are the same as or different from each other, and are each independently a substituted or unsubstituted aryl group.

According to an exemplary embodiment of the present specification, in Chemical Formula 3, R10 and R11 are the same as or different from each other, and are each independently an aryl group unsubstituted or substituted with an alkyl group or an aryl group.

According to an exemplary embodiment of the present specification, in Chemical Formula 3, R10 and R11 are the same as or different from each other, and are each independently a phenyl group unsubstituted or substituted with an aryl group; a biphenyl group unsubstituted or substituted with an aryl group; a naphthyl group unsubstituted or substituted with an aryl group; a terphenyl group; a fluorenyl group unsubstituted or substituted with an alkyl group or an aryl group; or a spirobifluorenyl group.

According to an exemplary embodiment of the present specification, in Chemical Formula 3, R10 and R11 are the same as or different from each other, and are each independently a phenyl group unsubstituted or substituted with a phenyl group or a naphthyl group; a biphenyl group unsubstituted or substituted with a phenyl group; a naphthyl group unsubstituted or substituted with a phenyl group; a terphenyl group; a fluorenyl group unsubstituted or substituted with a methyl group or a phenyl group; or a spirobifluorenyl group.

According to an exemplary embodiment of the present specification, in Chemical Formula 3, R101 and R102 are hydrogen.

According to an exemplary embodiment of the present specification, in Chemical Formula 4, L3 is a direct bond; or a substituted or unsubstituted arylene group.

According to an exemplary embodiment of the present specification, in Chemical Formula 4, L3 is a direct bond; or an arylene group unsubstituted or substituted with an alkyl group or an aryl group.

According to an exemplary embodiment of the present specification, in Chemical Formula 4, L3 is a direct bond; a phenylene group unsubstituted or substituted with an aryl group; a biphenylylene group; or a fluorenylene group unsubstituted or substituted with an alkyl group.

According to an exemplary embodiment of the present specification, in Chemical Formula 4, L3 is a direct bond; a phenylene group unsubstituted or substituted with a phenyl group; a biphenylylene group; or a fluorenylene group unsubstituted or substituted with a methyl group.

According to an exemplary embodiment of the present specification, in Chemical Formula 4, L4 and L5 are the same as or different from each other, and are each independently a direct bond; or a substituted or unsubstituted arylene group.

According to an exemplary embodiment of the present specification, in Chemical Formula 4, L4 and L5 are the same as or different from each other, and are each independently a direct bond; or an arylene group.

According to an exemplary embodiment of the present specification, in Chemical Formula 4, L4 and L5 are the same as or different from each other, and are each independently a direct bond; a phenylene group; or a biphenylylene group.

According to an exemplary embodiment of the present specification, in Chemical Formula 4, Ar1 is an aryl group unsubstituted or substituted with one or more selected from the group consisting of an alkyl group and an aryl group; or a heteroaryl group.

According to an exemplary embodiment of the present specification, in Chemical Formula 4, Ar1 is a phenyl group; a biphenyl group; a naphthyl group; a terphenyl group; a quaterphenyl group; a phenanthrenyl group; a triphenylenyl group; a fluorenyl group unsubstituted or substituted with one or more selected from the group consisting of an alkyl group and an aryl group; a dibenzofuran group; or a dibenzothiophene group.

According to an exemplary embodiment of the present specification, in Chemical Formula 4, Ar1 is a phenyl group; a biphenyl group; a naphthyl group; a terphenyl group; a quaterphenyl group; a phenanthrenyl group; a triphenylenyl group; a fluorenyl group unsubstituted or substituted with one or more selected from the group consisting of a methyl group and a phenyl group; a dibenzofuran group; or a dibenzothiophene group.

According to an exemplary embodiment of the present specification, in Chemical Formula 4, Ar2 is an aryl group unsubstituted or substituted with an alkyl group, an aryl group, or an aryl group substituted with an alkyl group.

According to an exemplary embodiment of the present specification, in Chemical Formula 4, Ar2 is a fluorenyl group unsubstituted or substituted with an alkyl group, an aryl group, or an aryl group substituted with an alkyl group; a triphenylenyl group; or a phenanthrenyl group.

According to an exemplary embodiment of the present specification, in Chemical Formula 4, Ar2 is a fluorenyl group unsubstituted or substituted with a methyl group, a t-butyl group, a phenyl group, a biphenyl group, a naphthyl group, a phenyl group substituted with a methyl group, or a phenyl group substituted with a t-butyl group; a triphenylenyl group; or a phenanthrenyl group.

According to an exemplary embodiment of the present specification, in Chemical Formula 4, R12, R13, R103, and R104 are the same as or different from each other, and each independently hydrogen; a substituted or unsubstituted alkyl group; or a substituted or unsubstituted aryl group.

According to an exemplary embodiment of the present specification, in Chemical Formula 4, R12, R13, R103, and R104 are the same as or different from each other, and each independently hydrogen; an alkyl group; or an aryl group unsubstituted or substituted with an alkyl group.

According to an exemplary embodiment of the present specification, in Chemical Formula 4, R12, R13, R103, and R104 are the same as or different from each other, and each independently hydrogen; a methyl group; a t-butyl group; a phenyl group unsubstituted or substituted with a methyl group or a t-butyl group; a biphenyl group; or a naphthyl group.
According to an exemplary embodiment of the present specification, Chemical Formula 1 is selected from the following compounds.
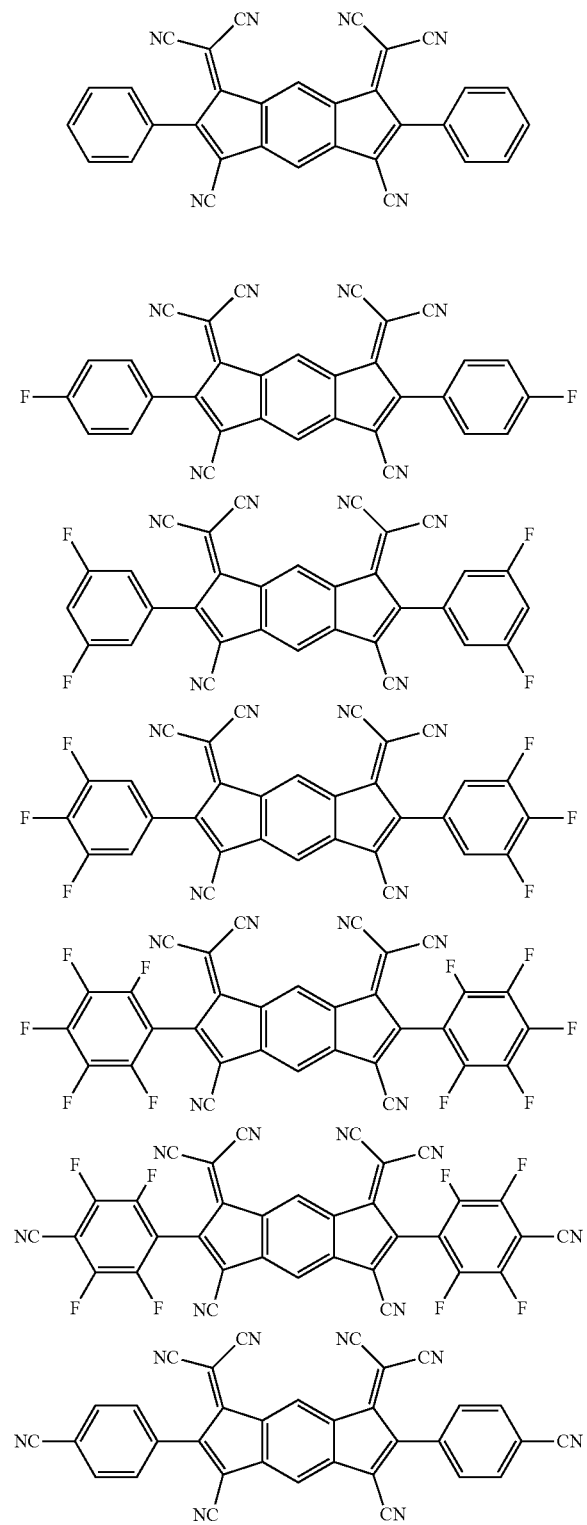
-continued
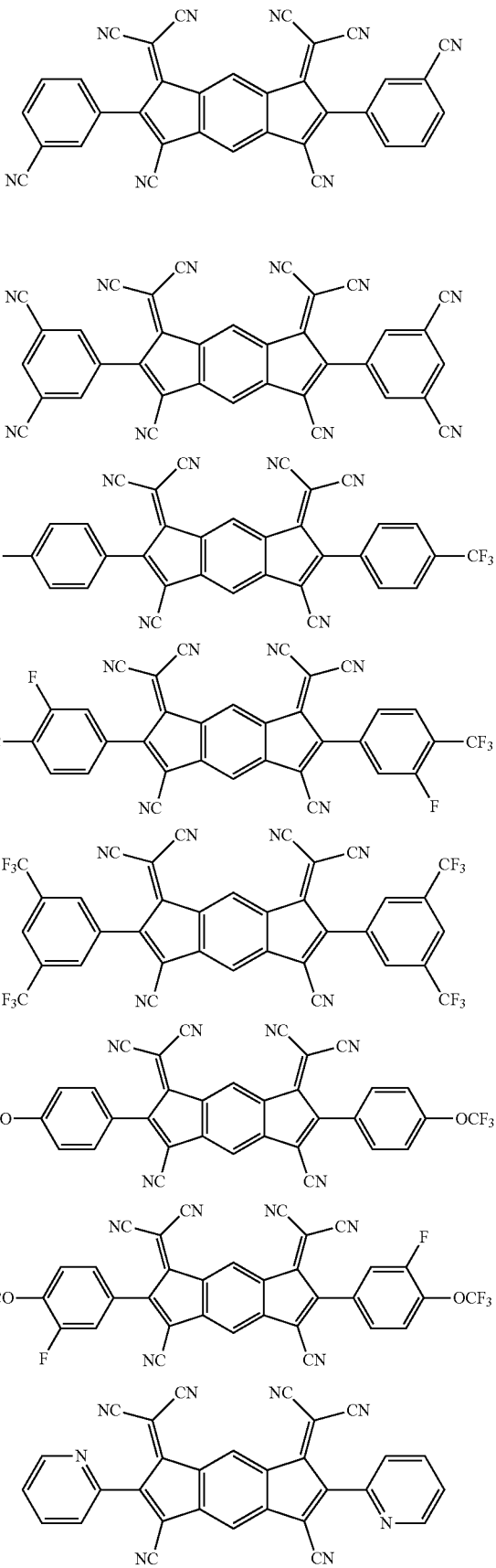

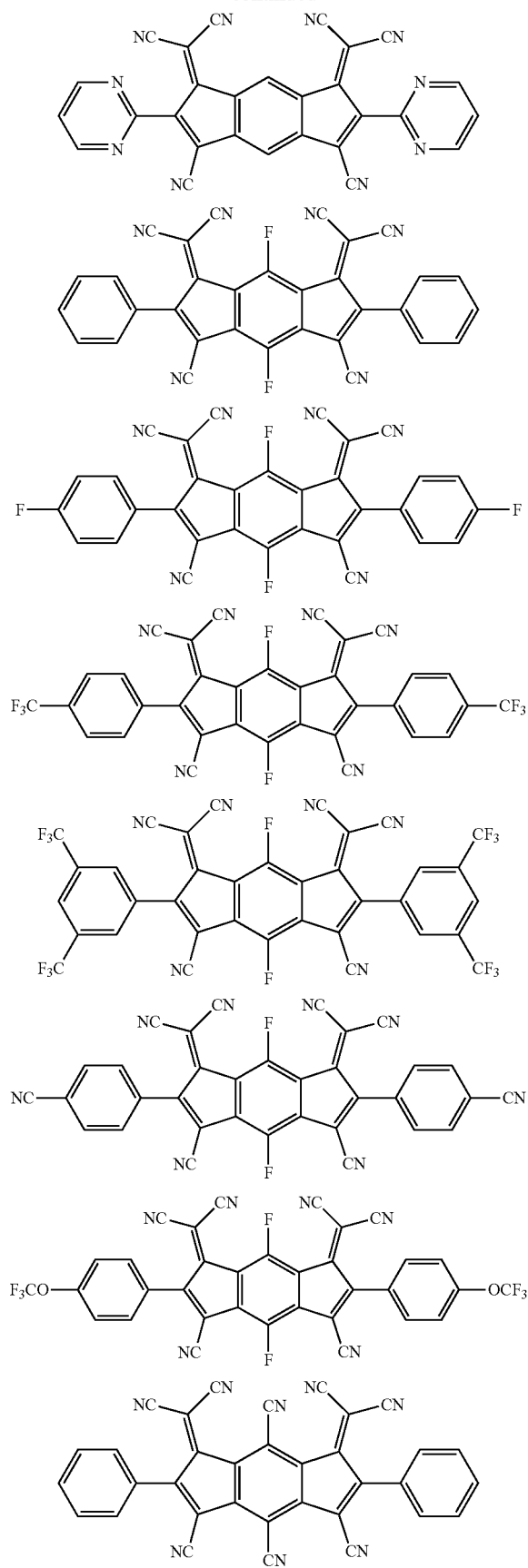
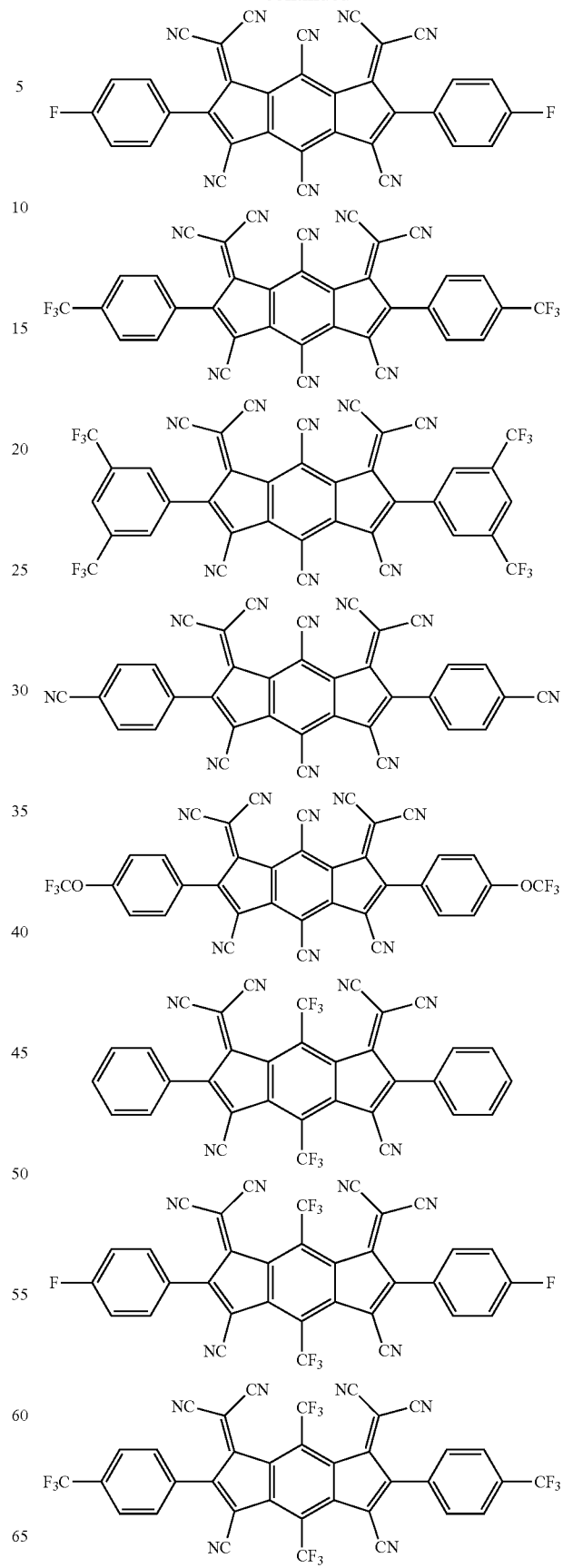

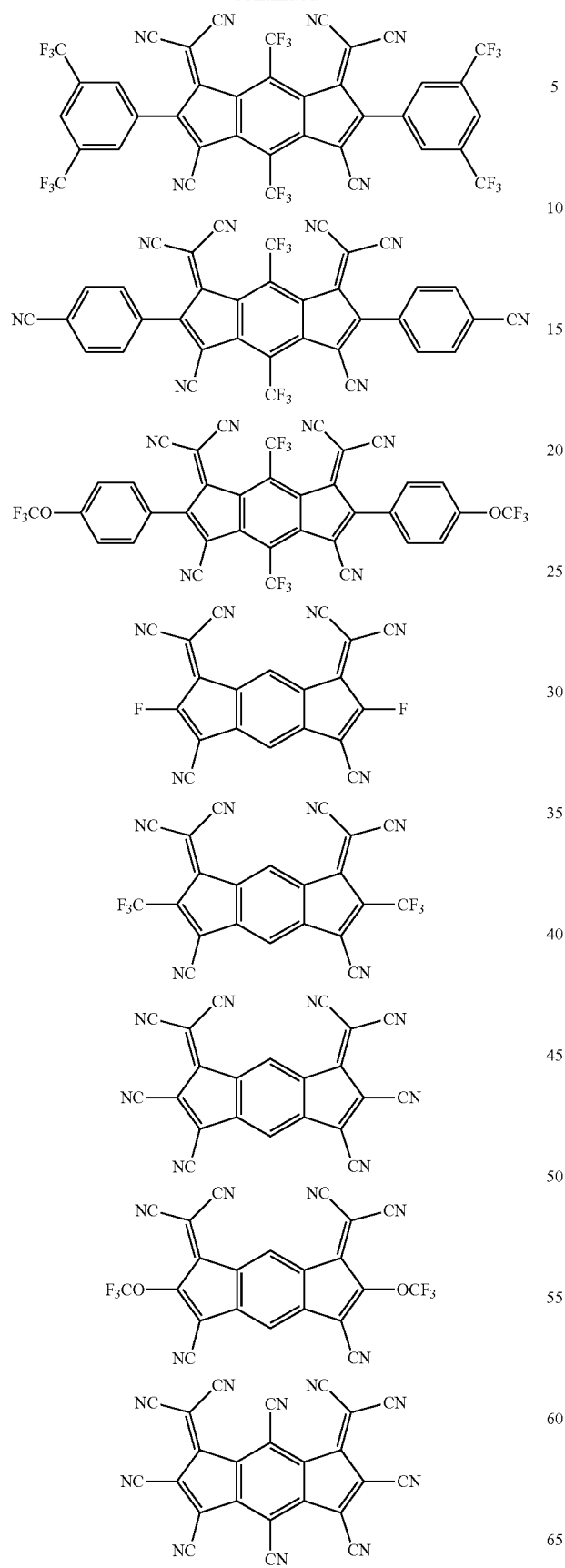
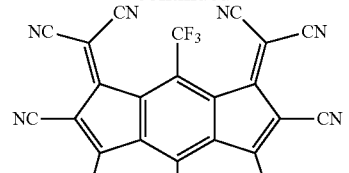
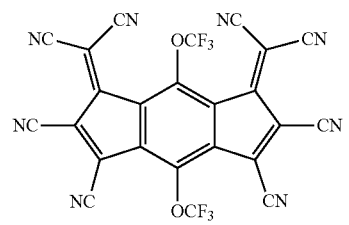
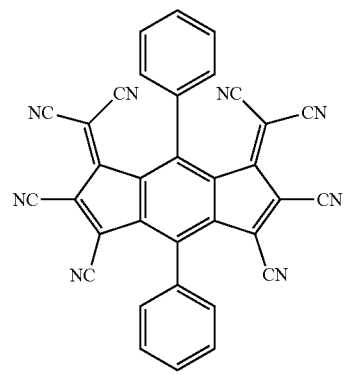
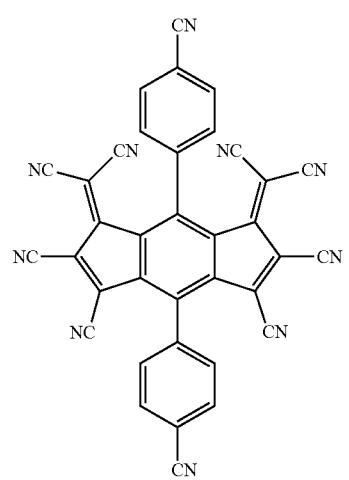

27
-continued
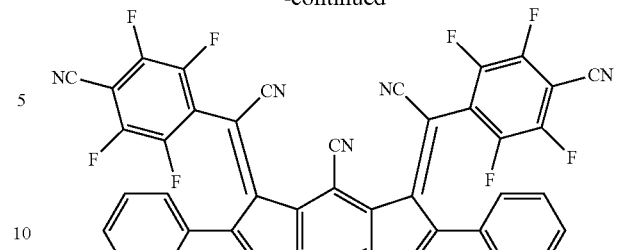
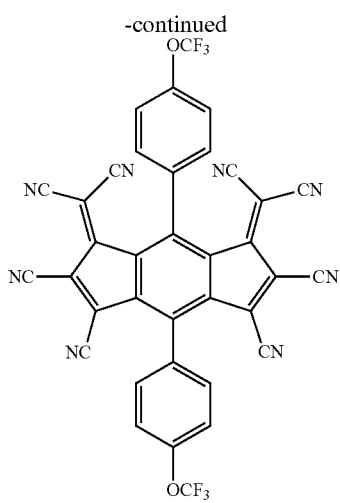
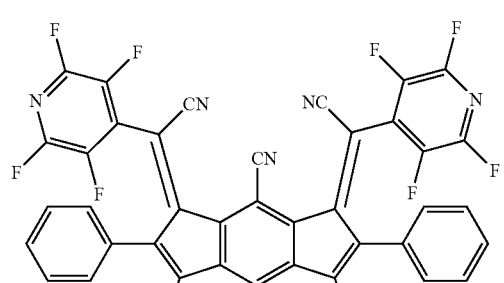
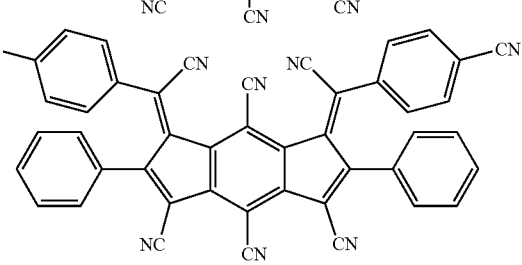
28
-continued
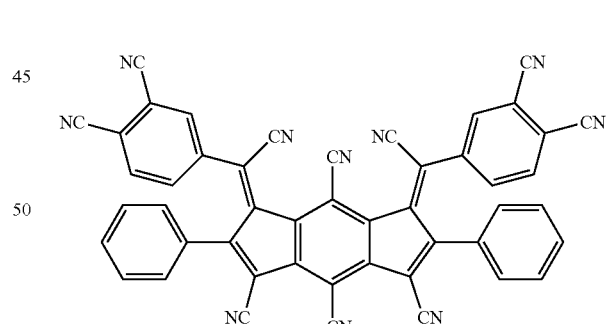
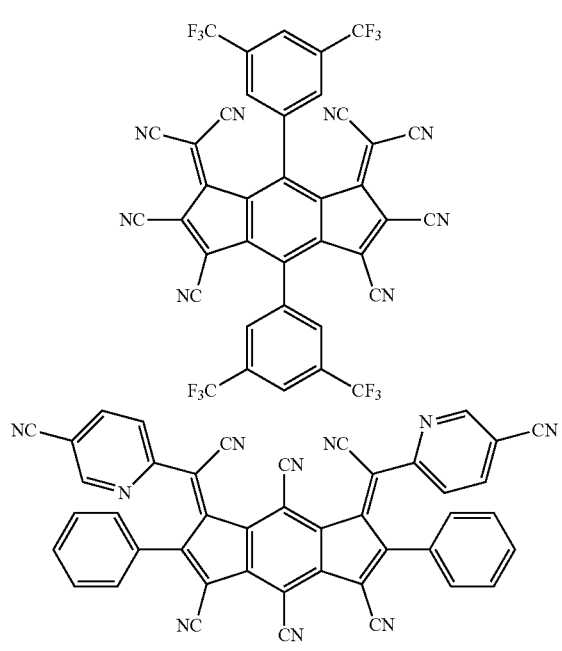
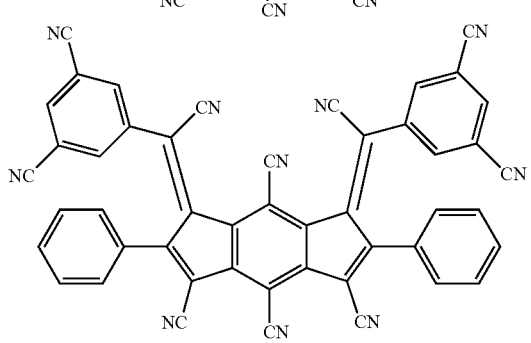

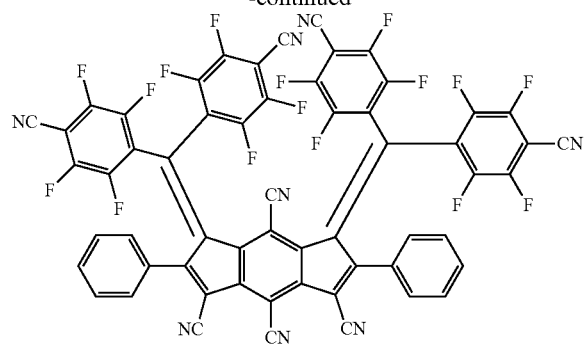
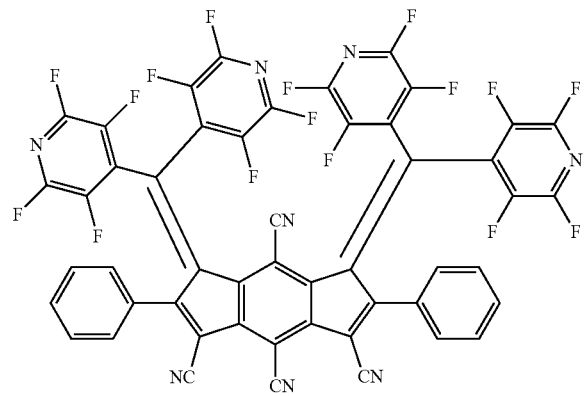
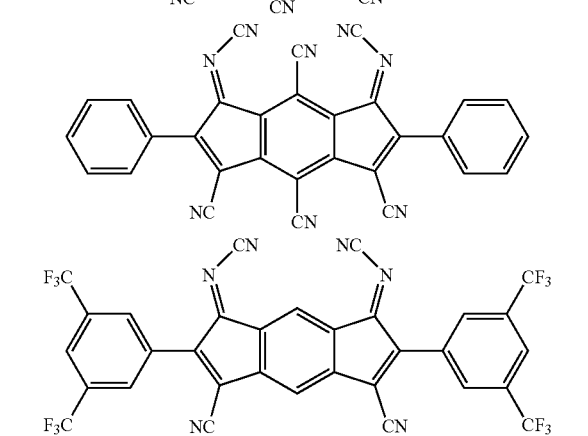
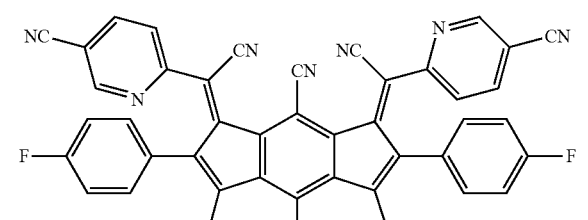
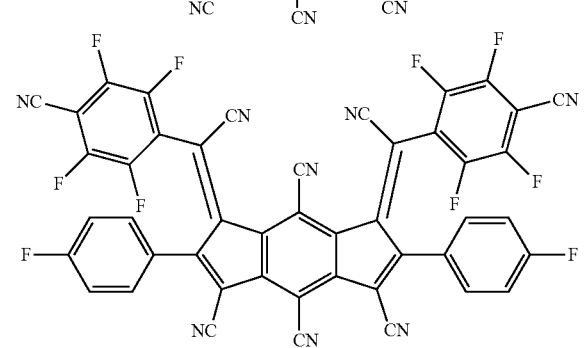
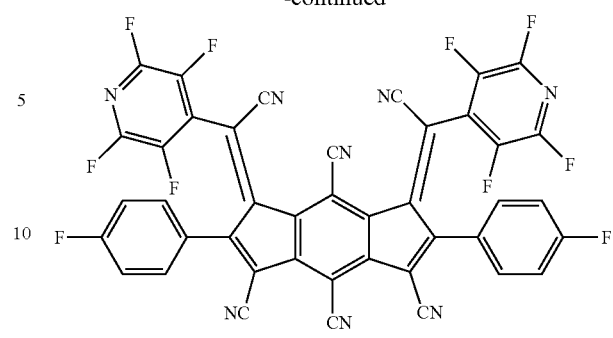
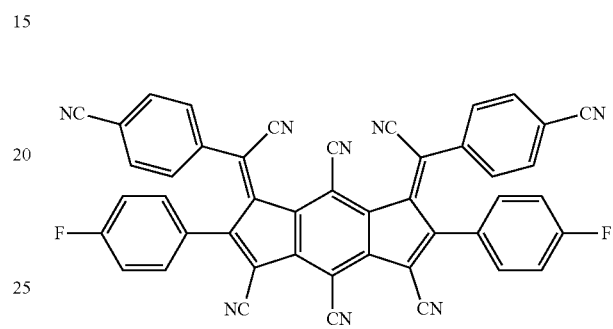
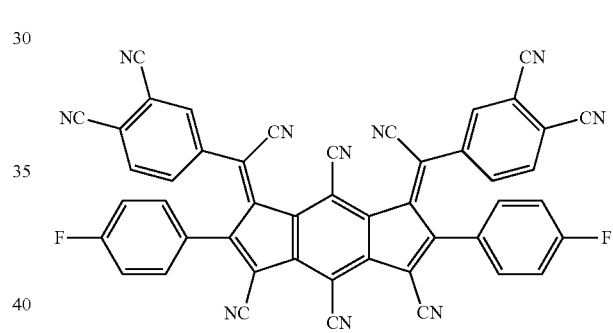
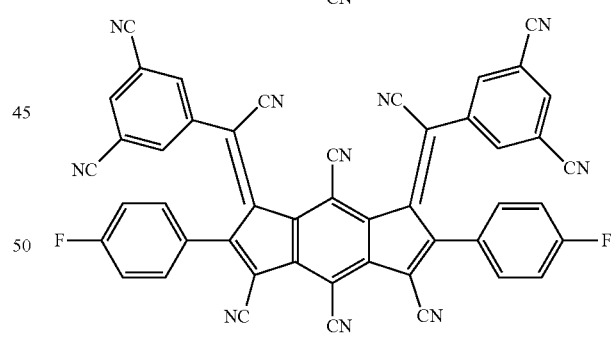
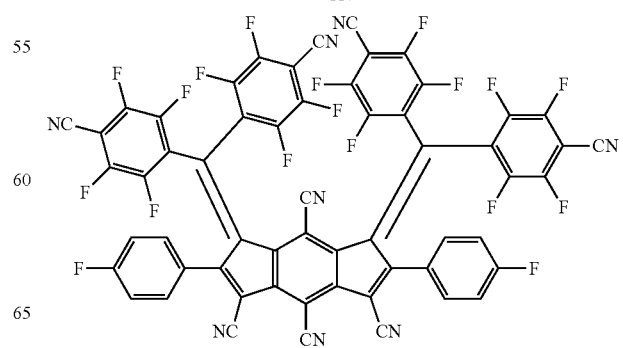

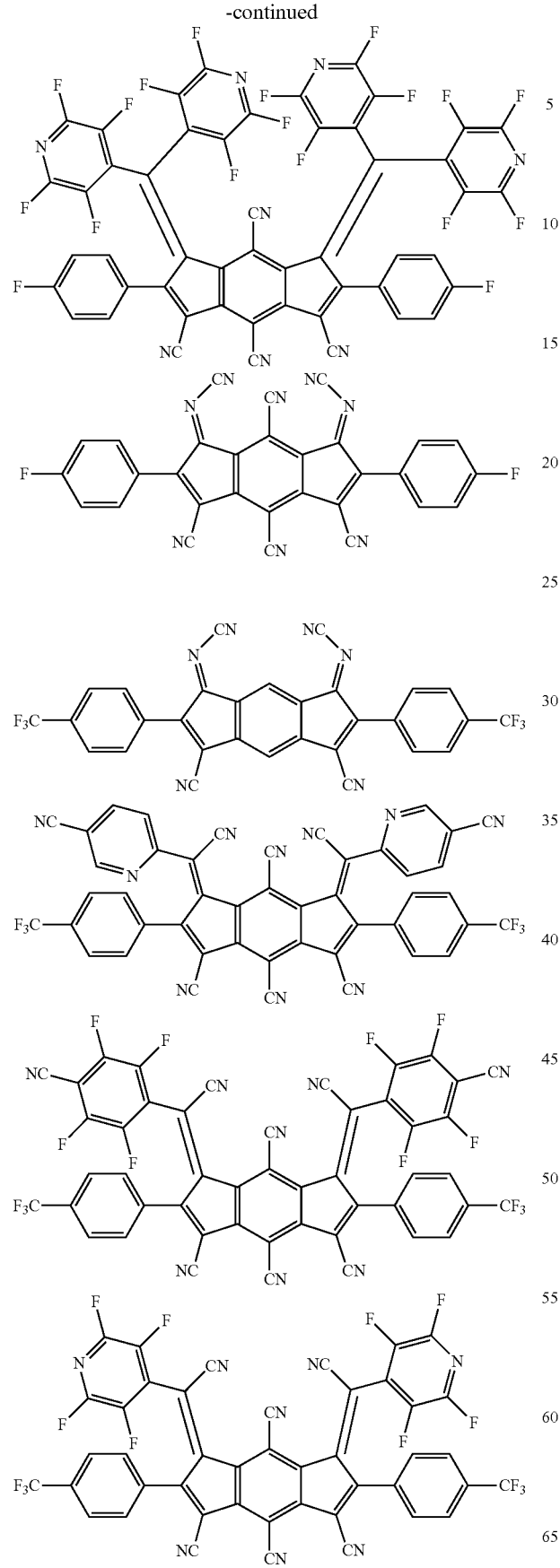
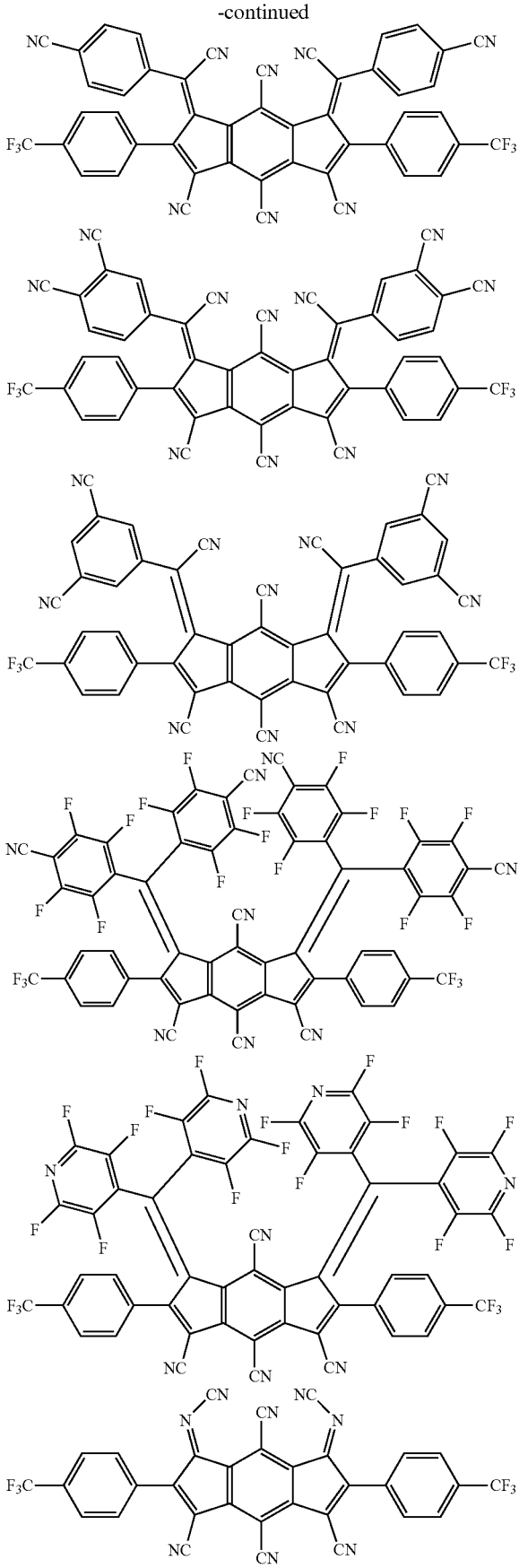

33
-continued
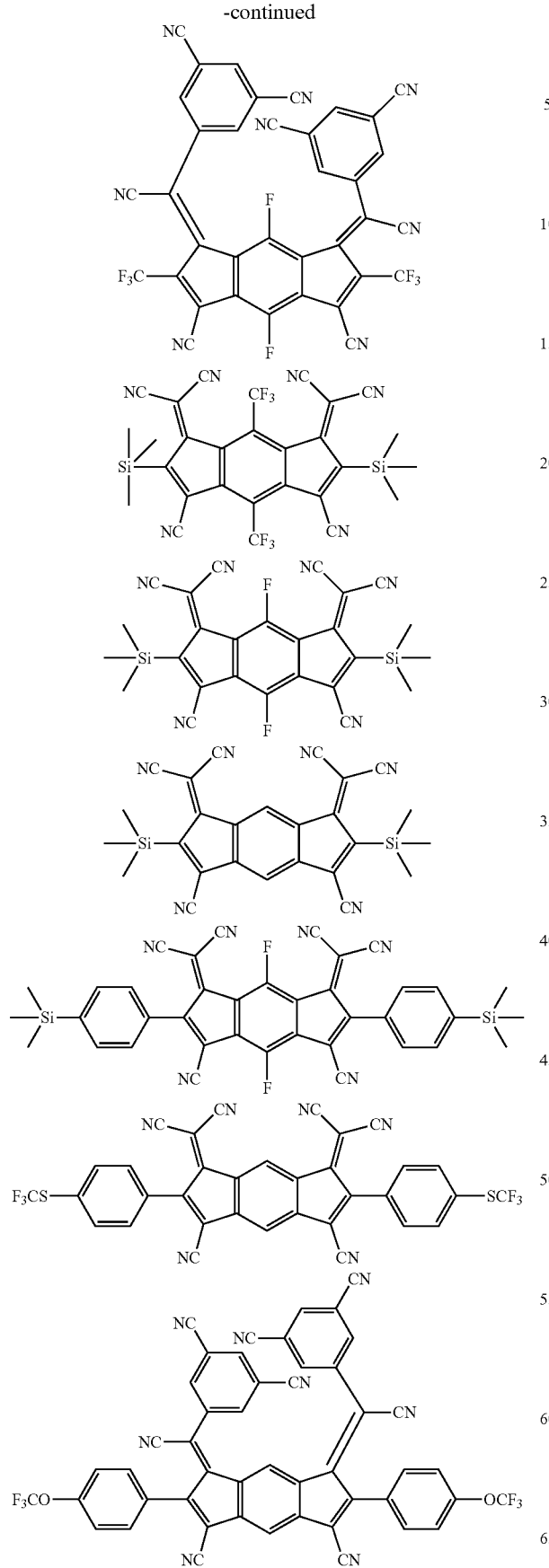
34
-continued
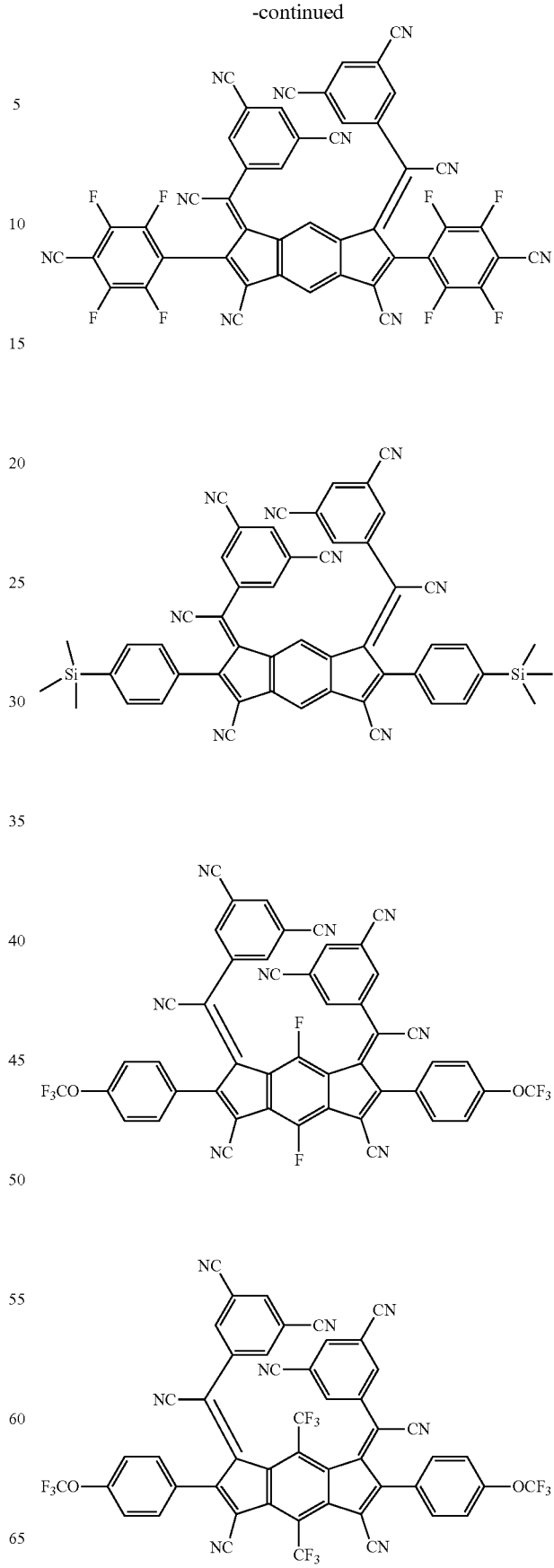

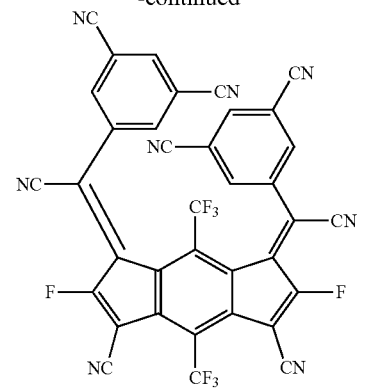
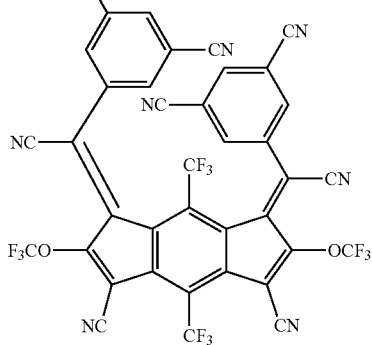
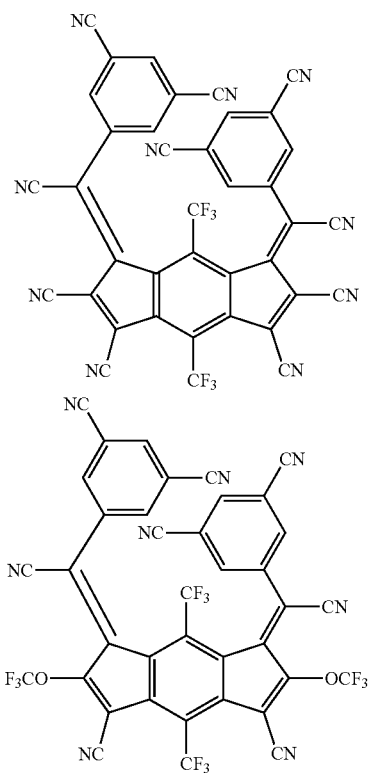
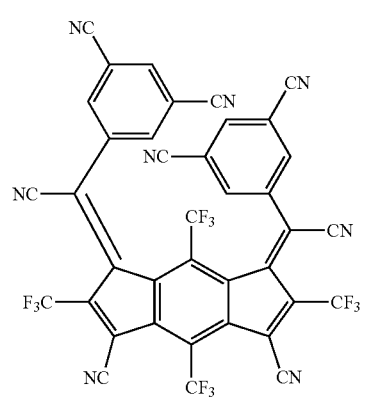
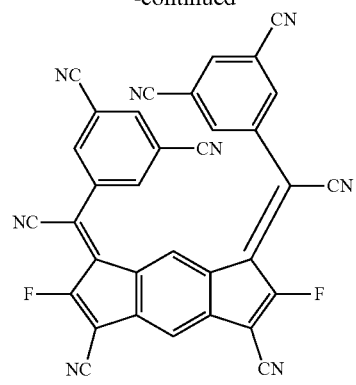
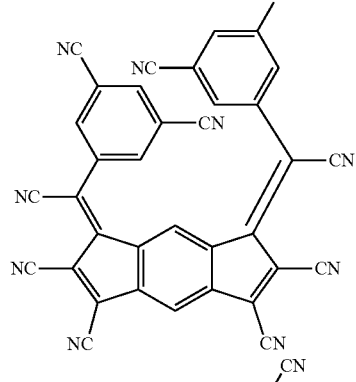
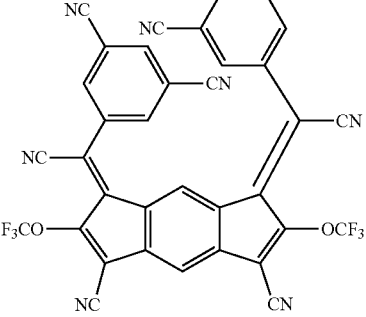
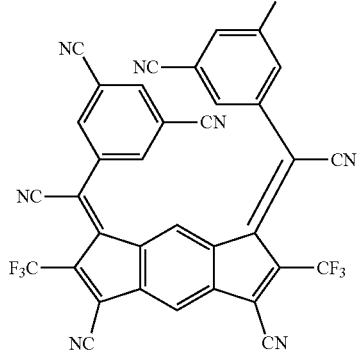
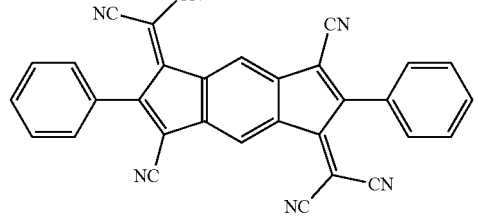

-continued
| 37 | 38 |
|---|---|
| 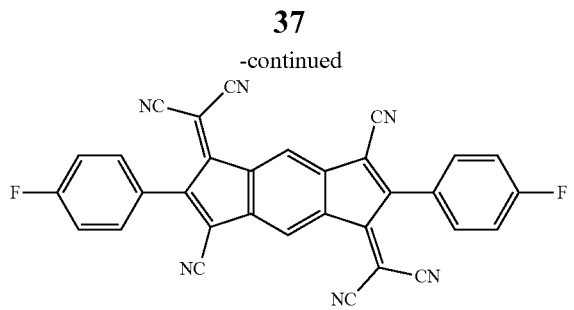 | 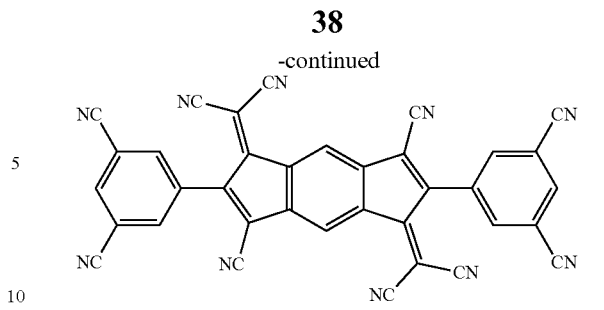 |
| 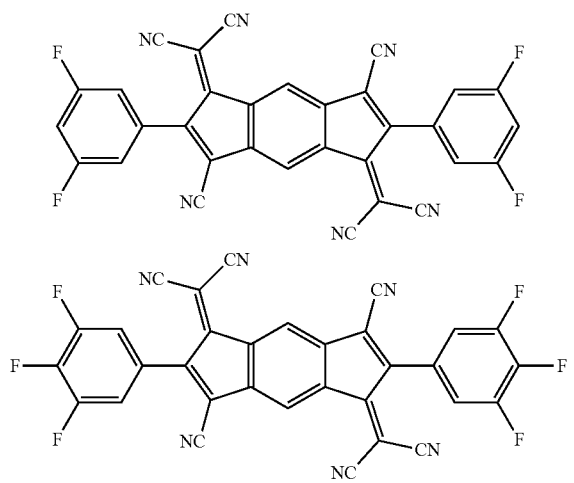 | 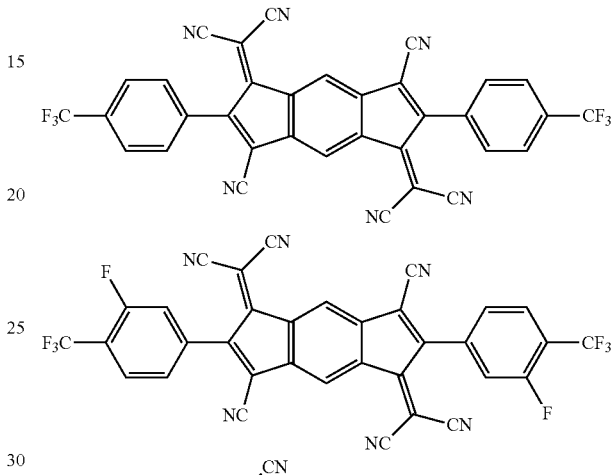 |
| 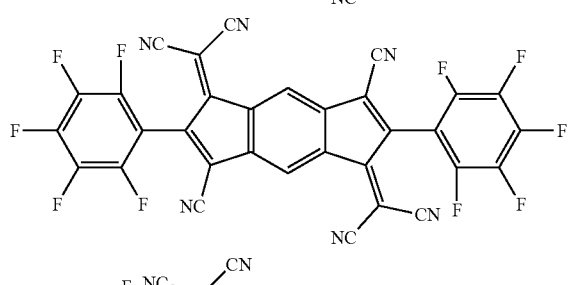 | 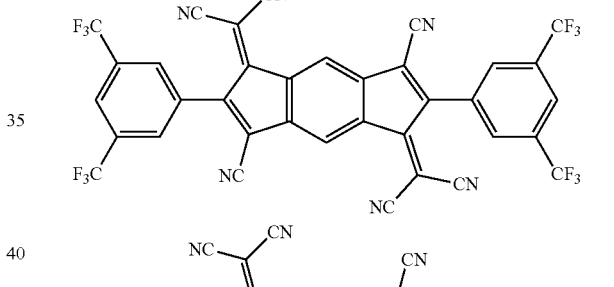 |
| 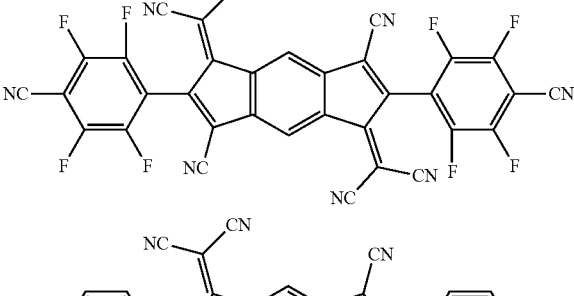 | 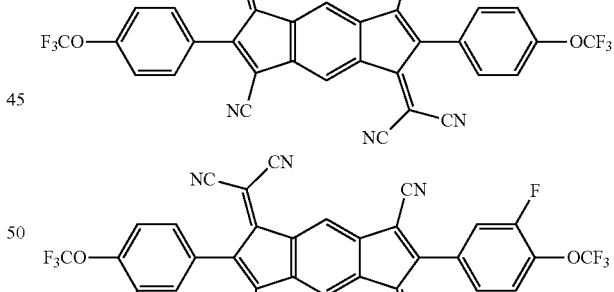 |
| 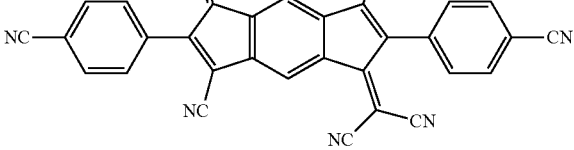 | 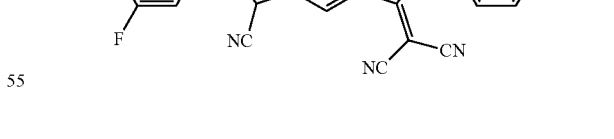 |
| 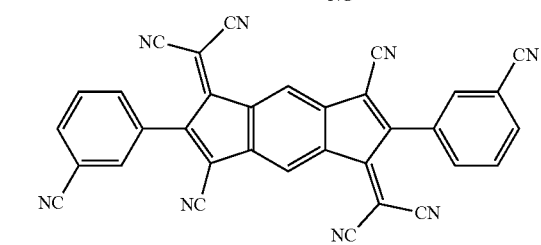 | 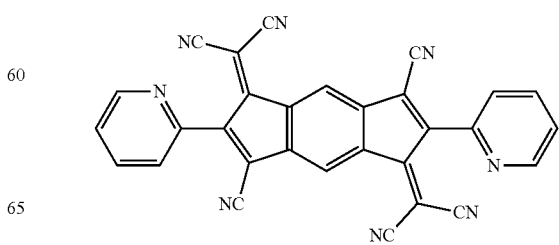 |

39
-continued
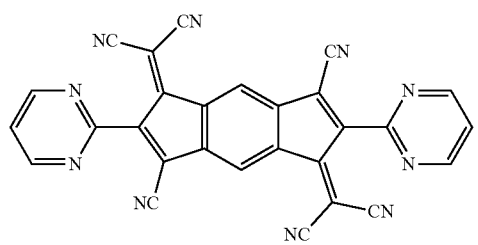
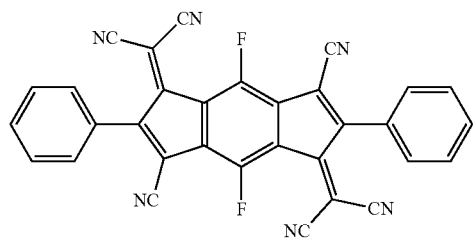
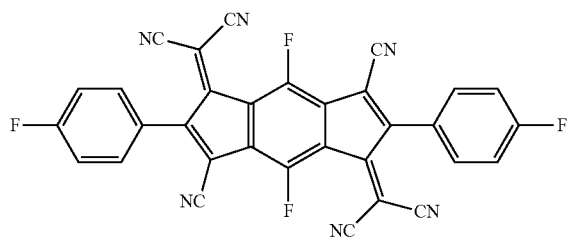
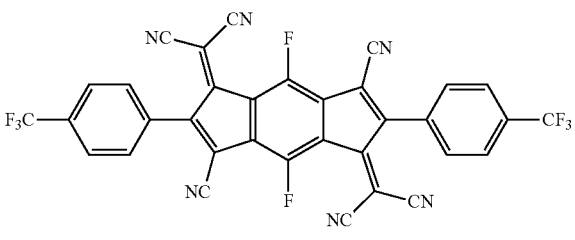
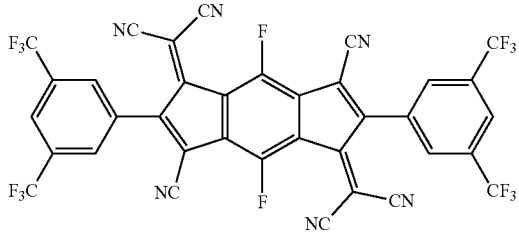
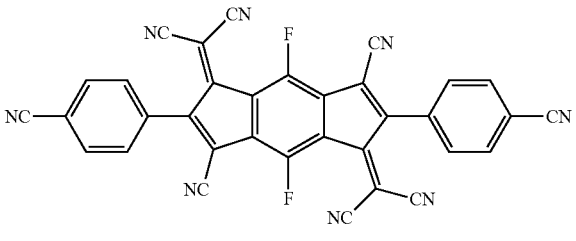
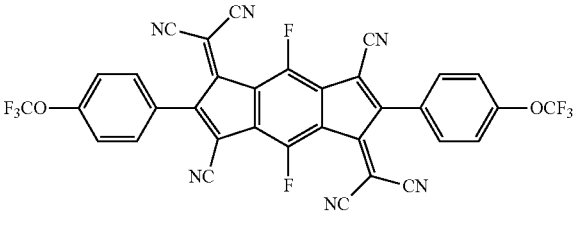
40
-continued
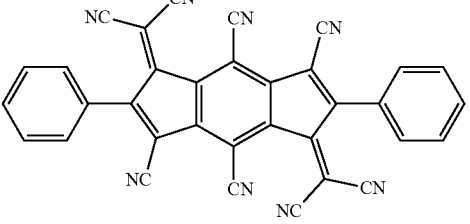
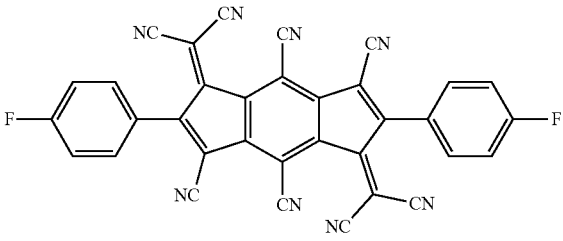
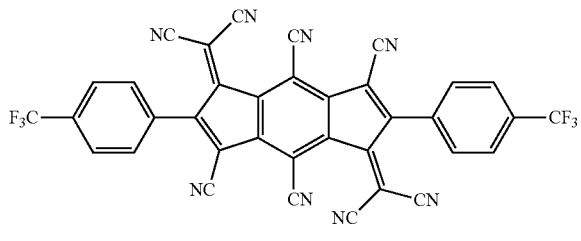
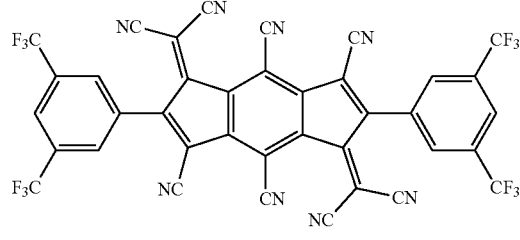
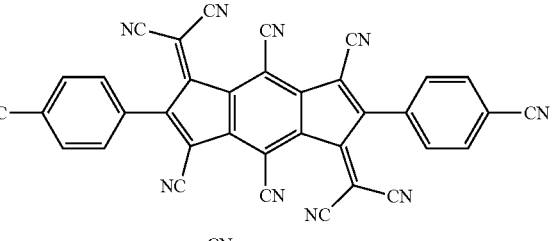
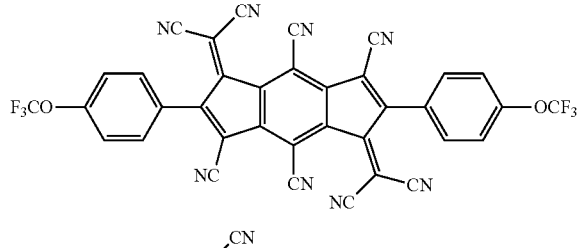
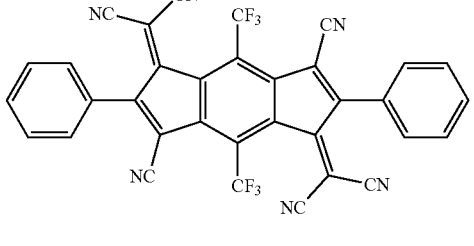

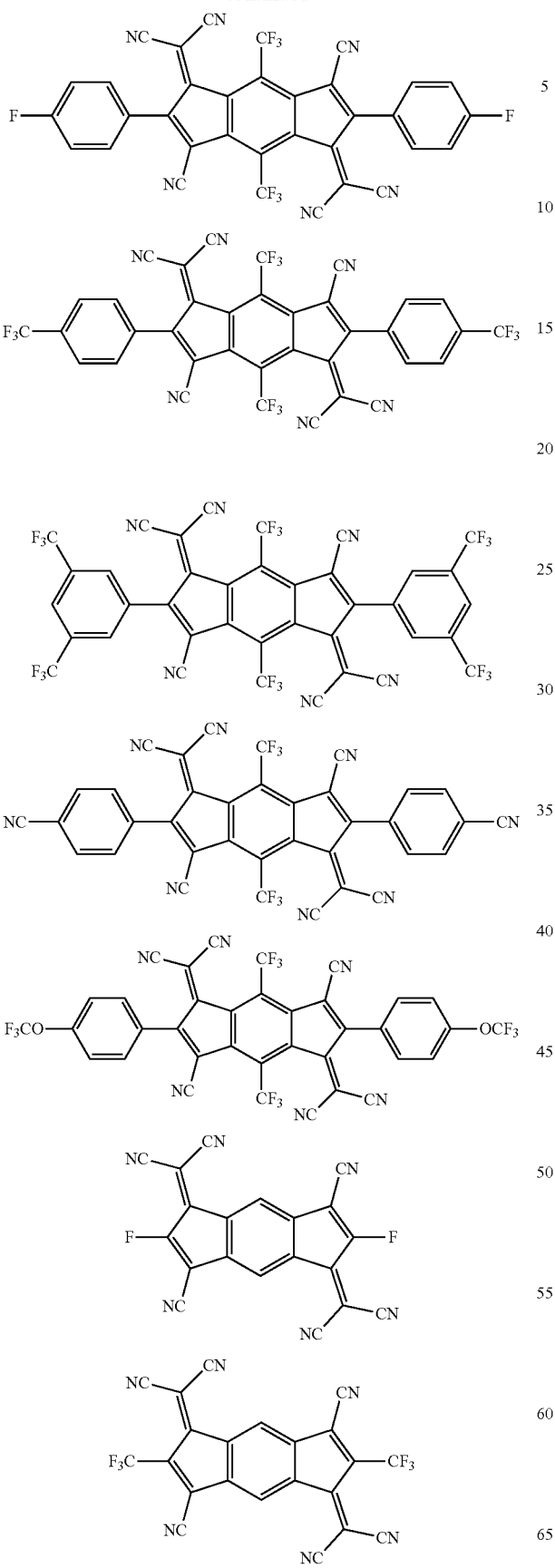
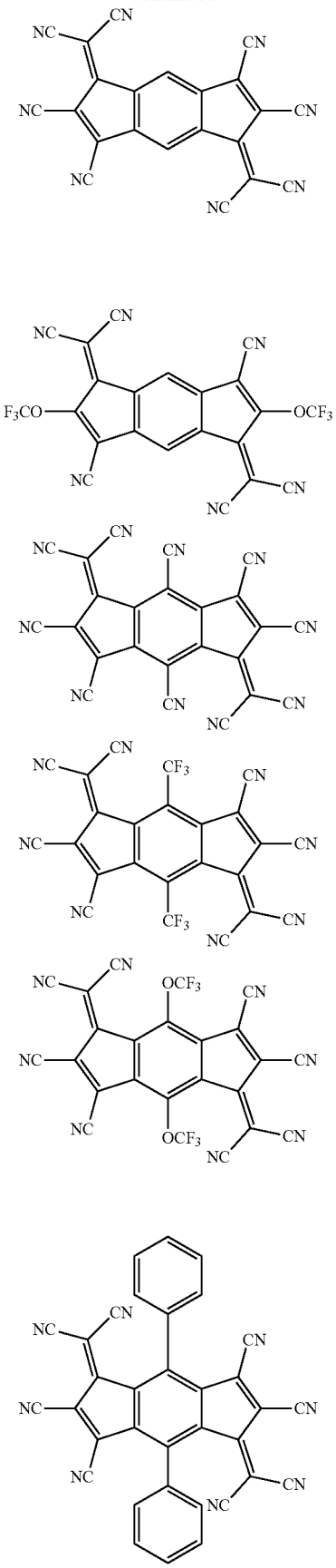

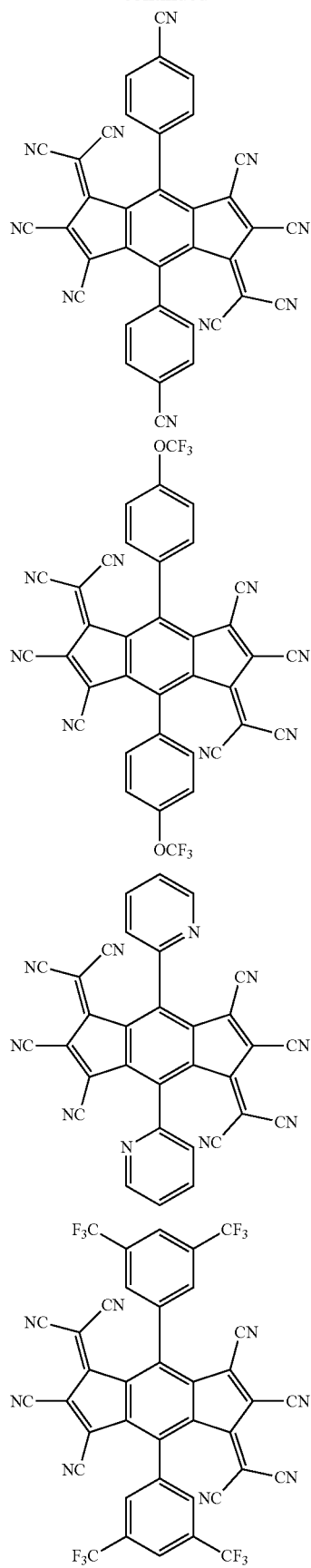
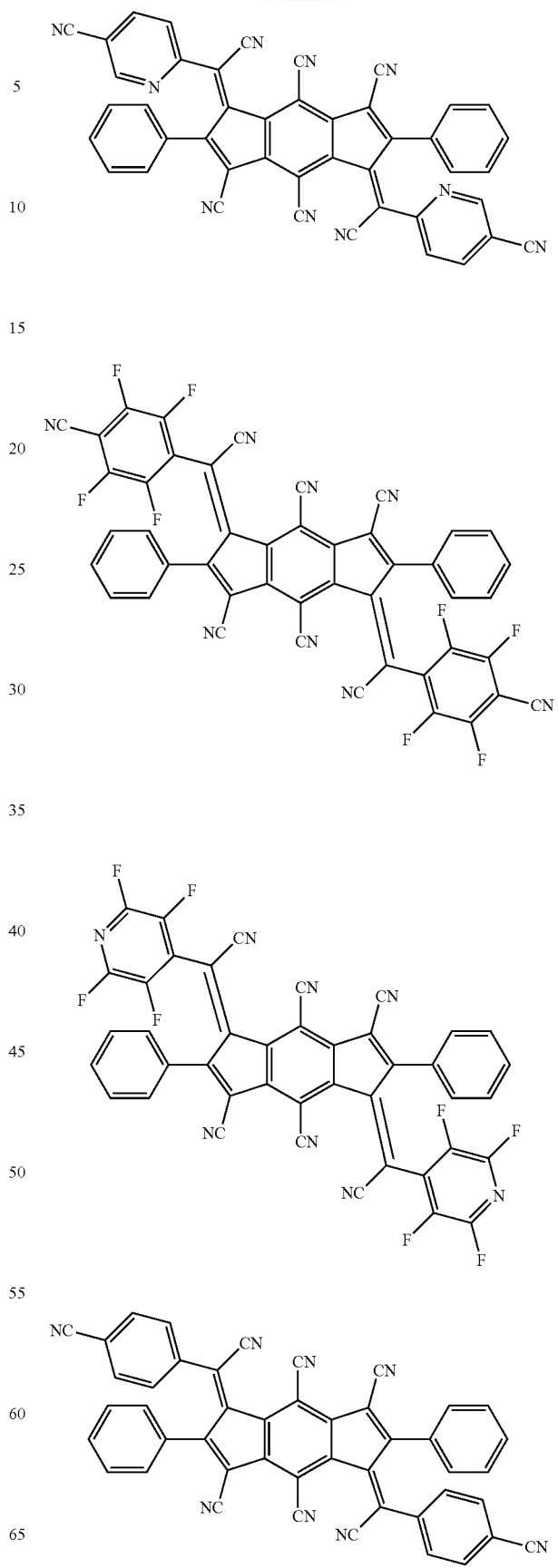

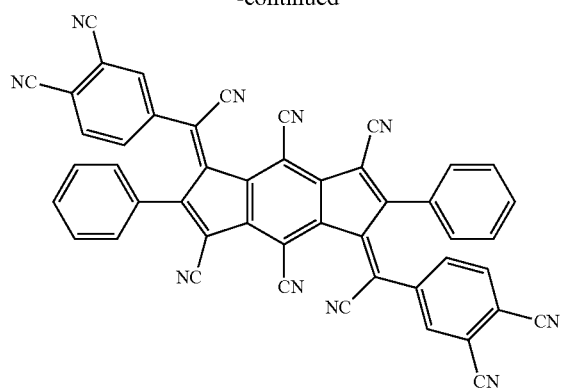
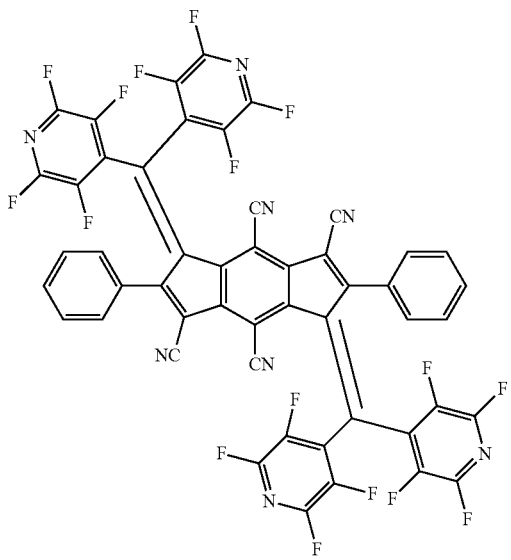
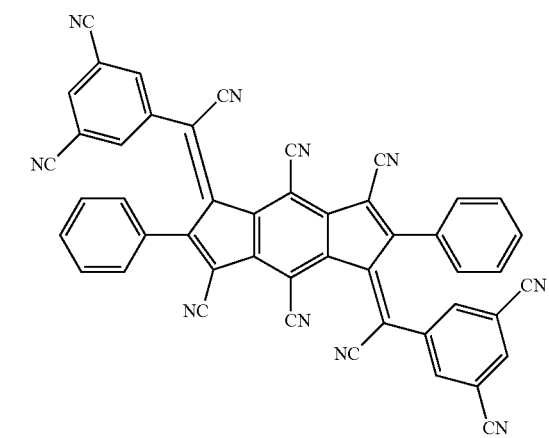
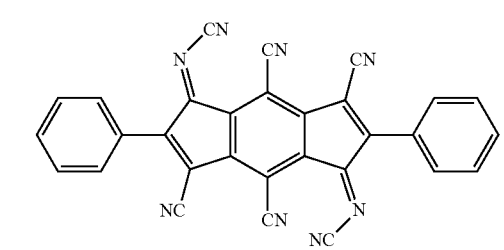
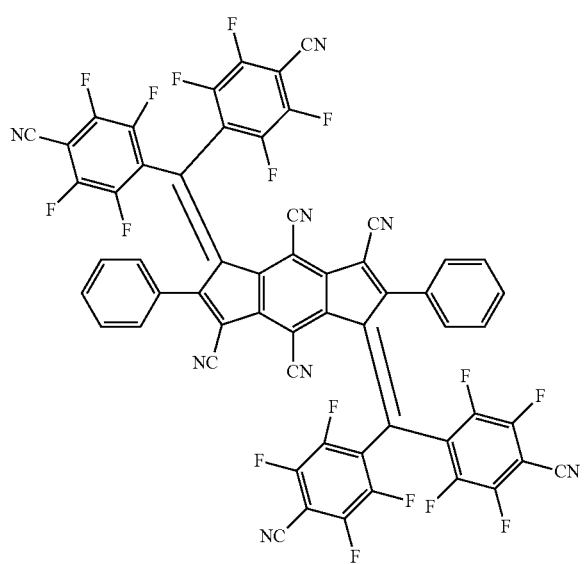
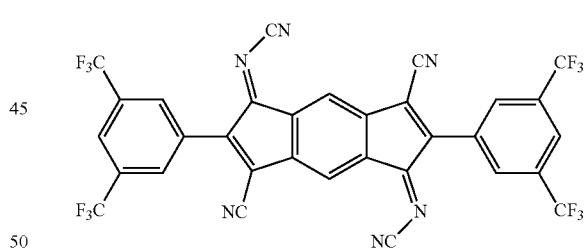
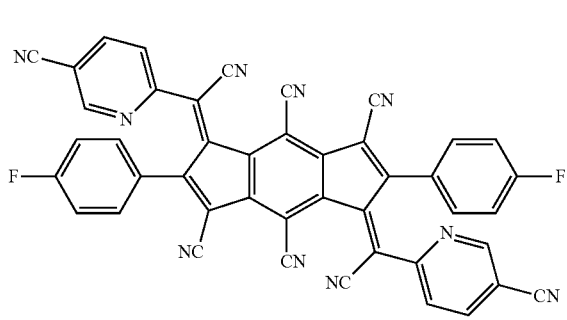

47
-continued
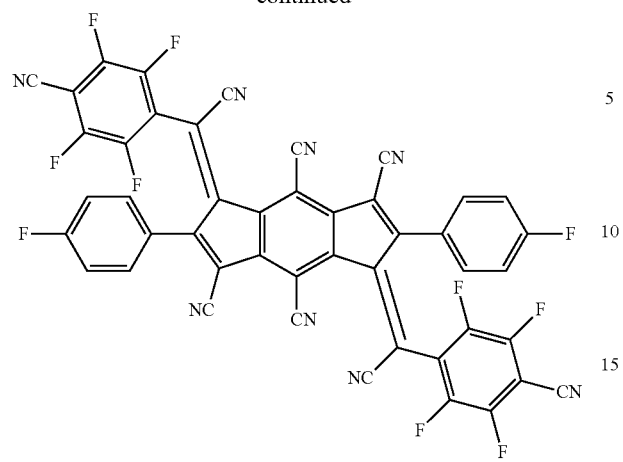
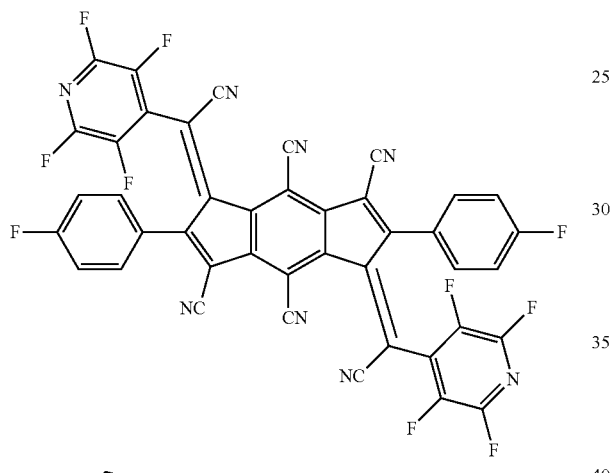
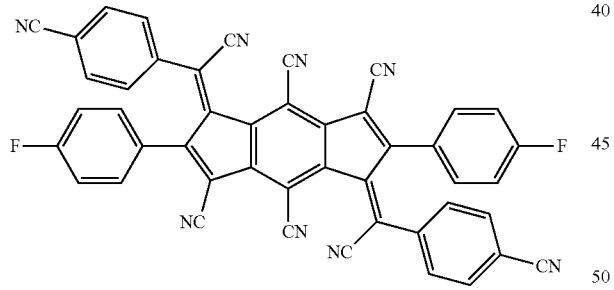
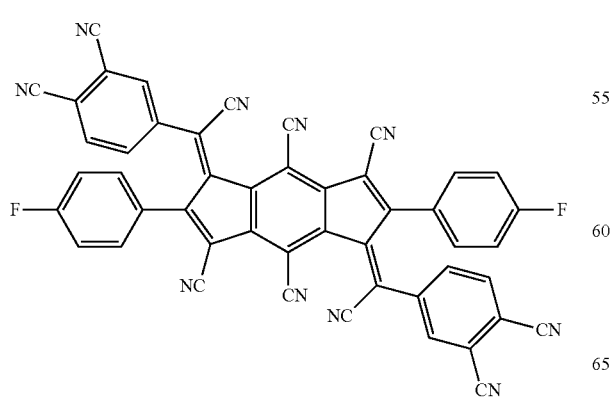
48
-continued
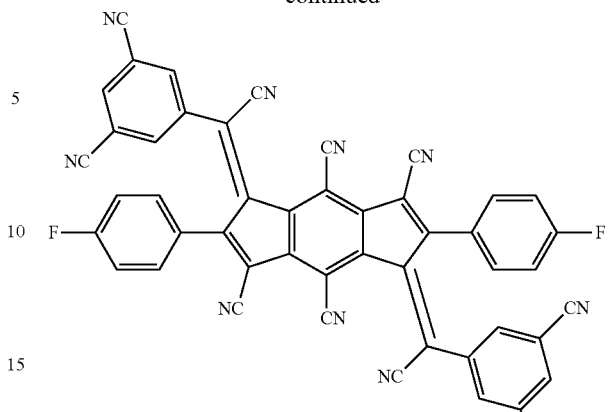
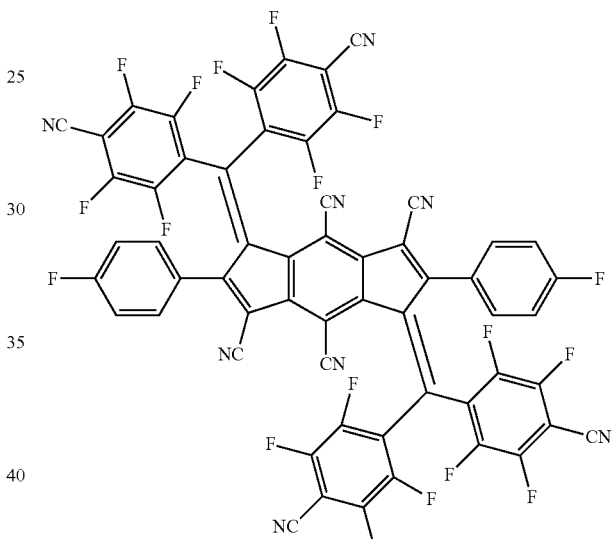
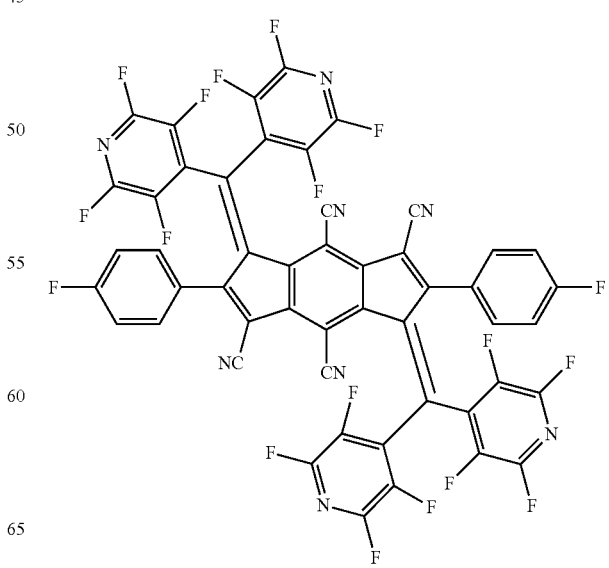

-continued
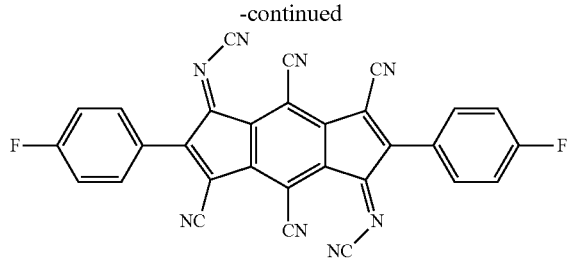
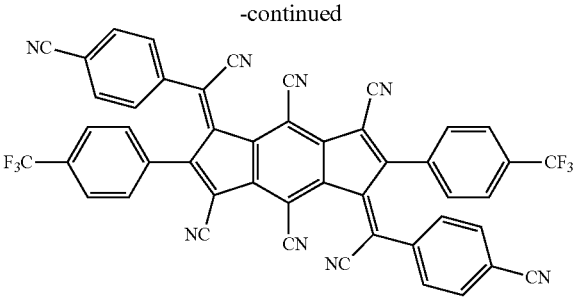
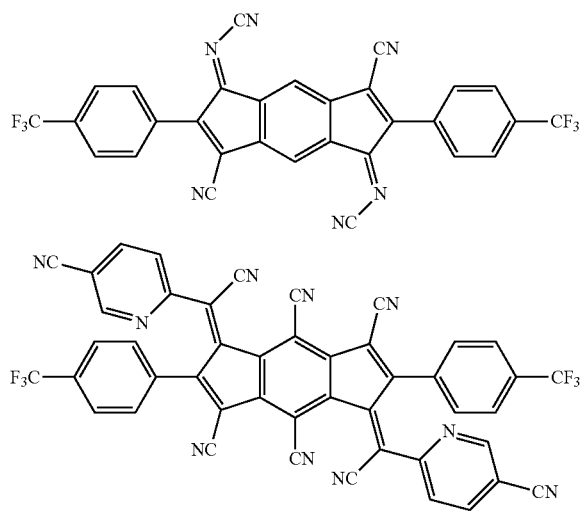
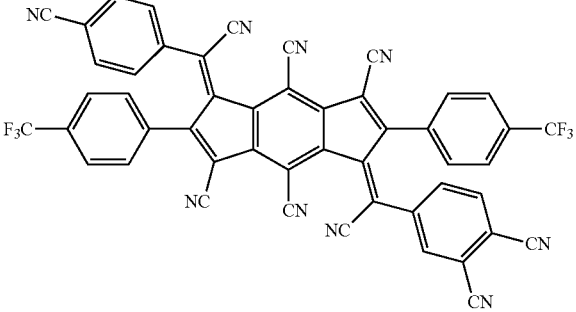
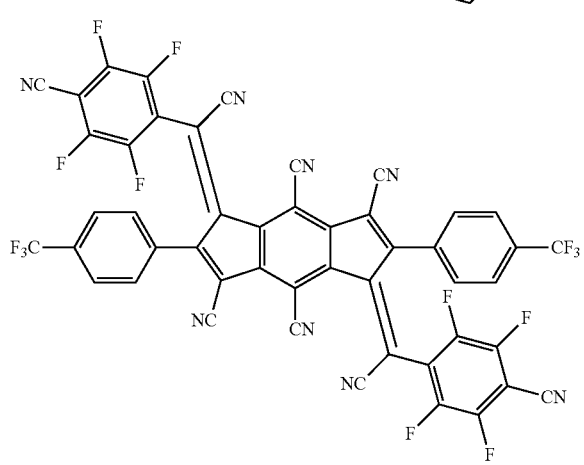
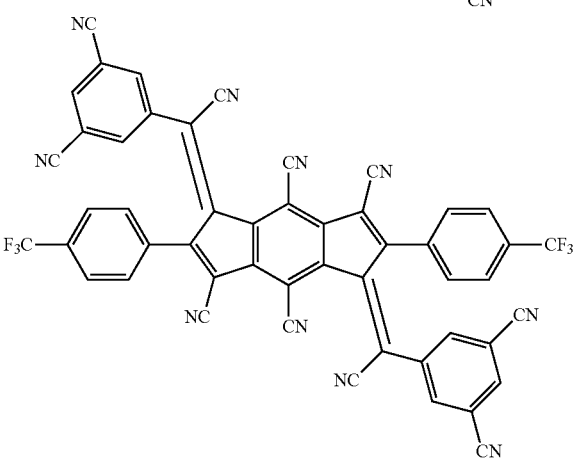
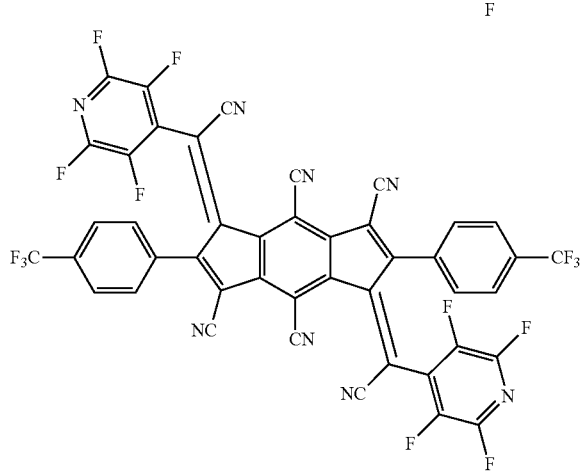
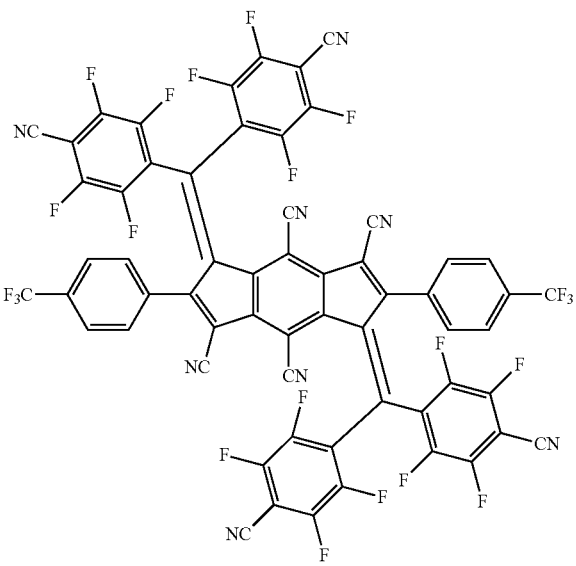

51
-continued
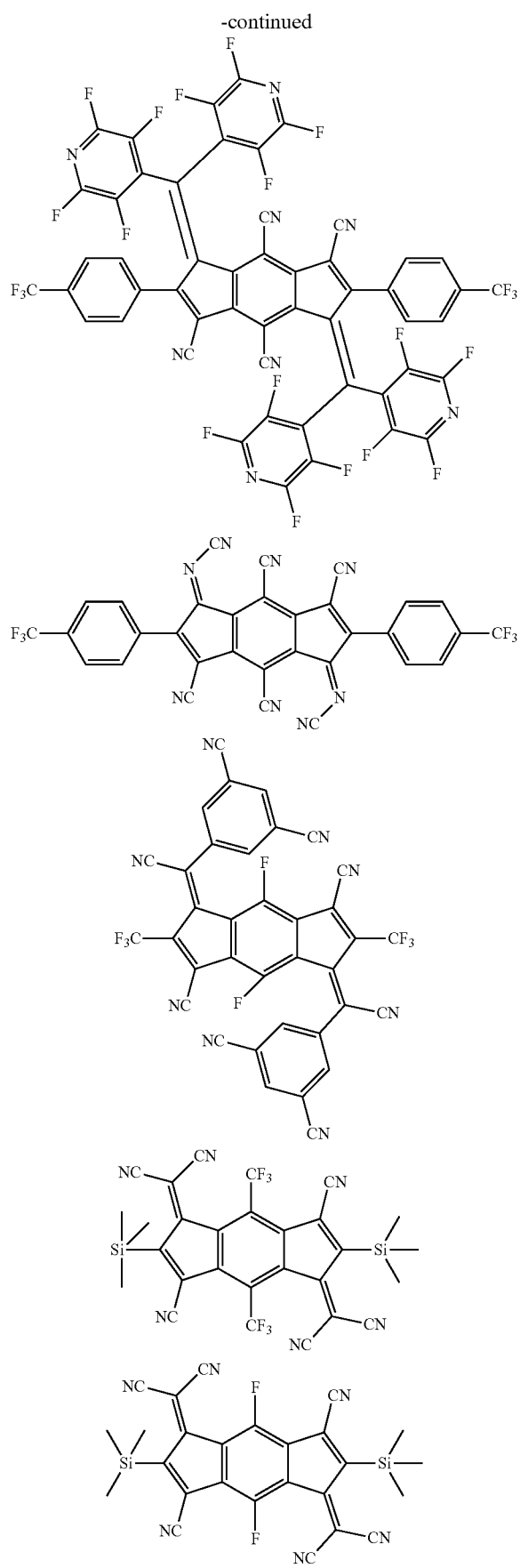
52
-continued
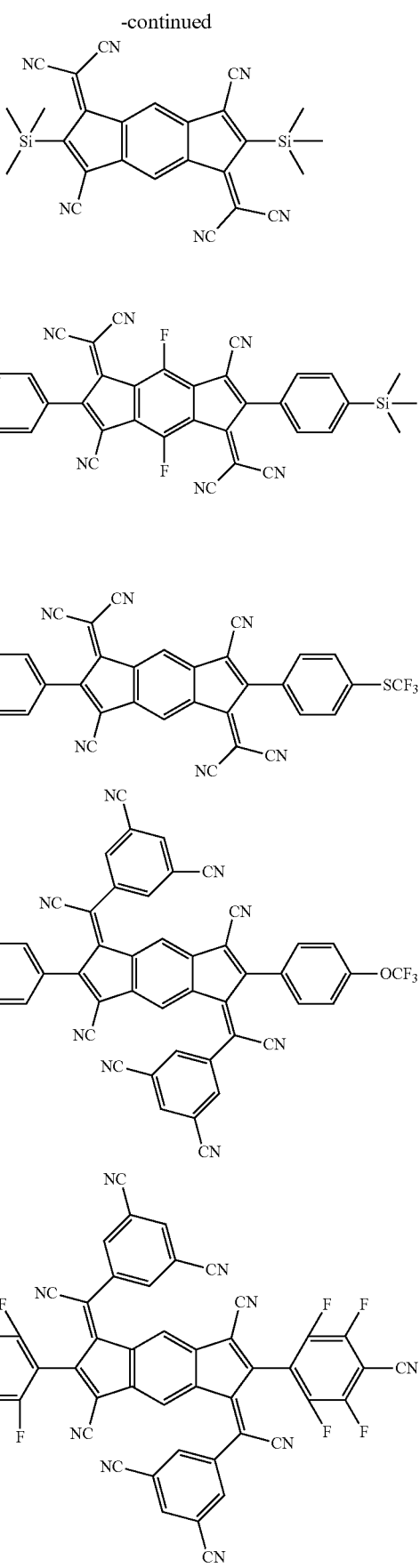

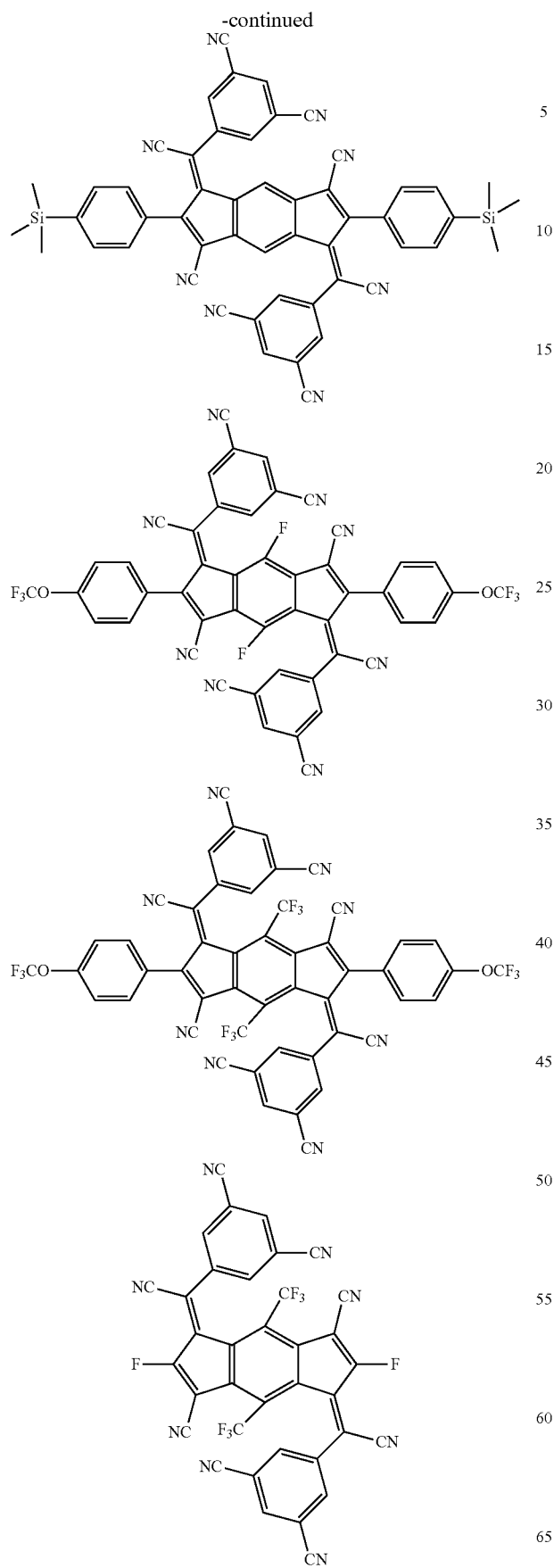
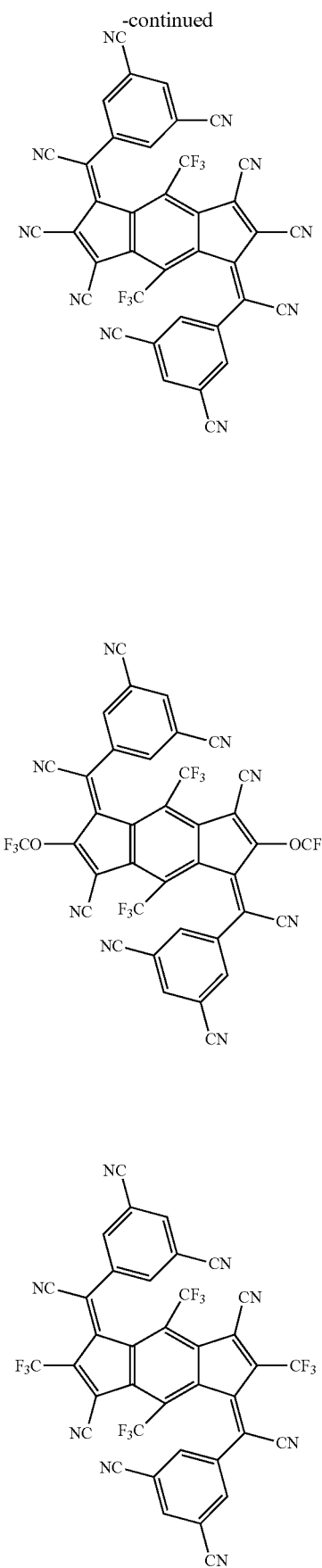

-continued
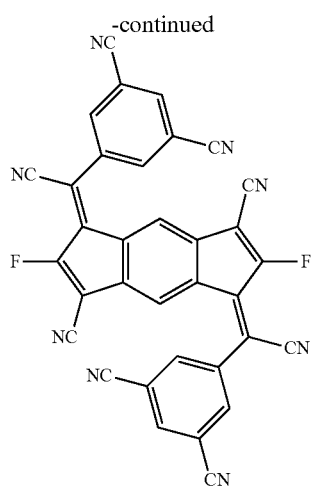
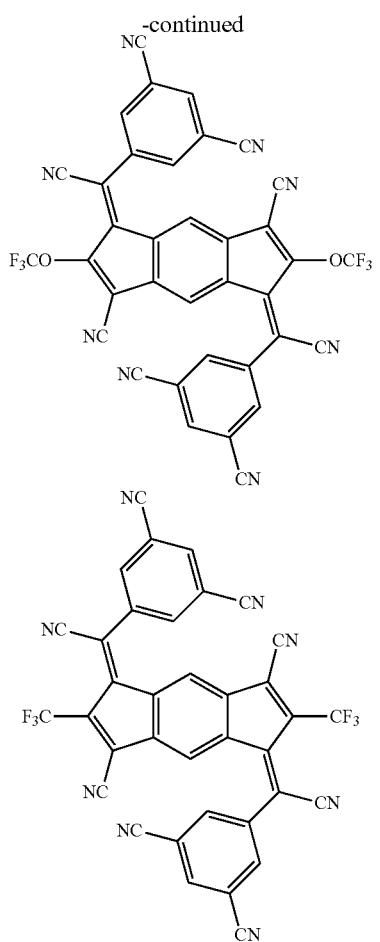
According to an exemplary embodiment of the present specification, Chemical Formula 2 is selected from the following compounds.
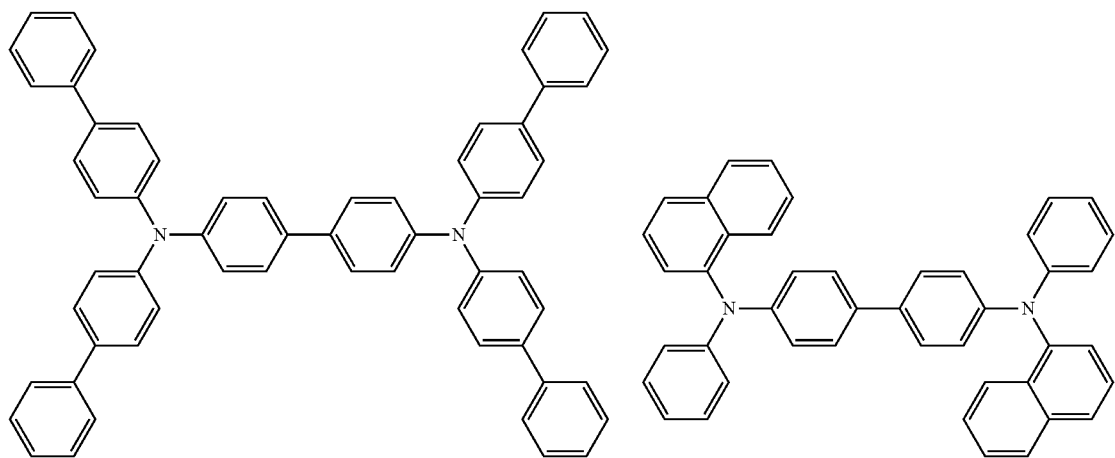

-continued
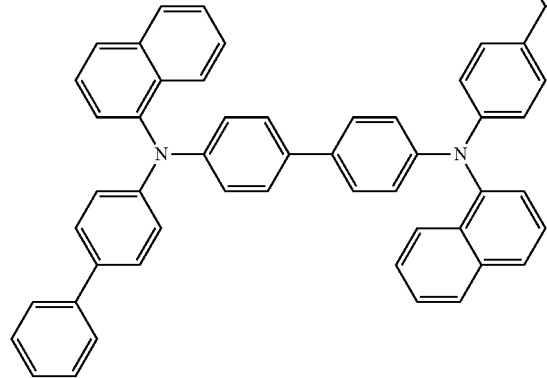
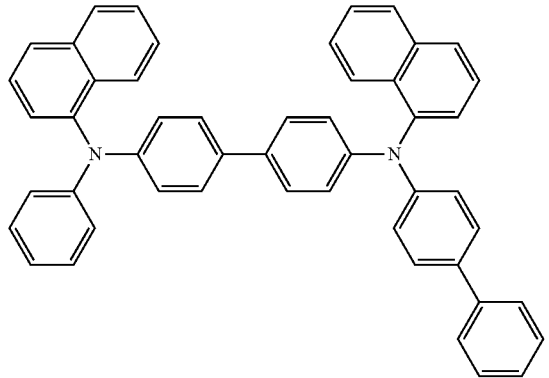
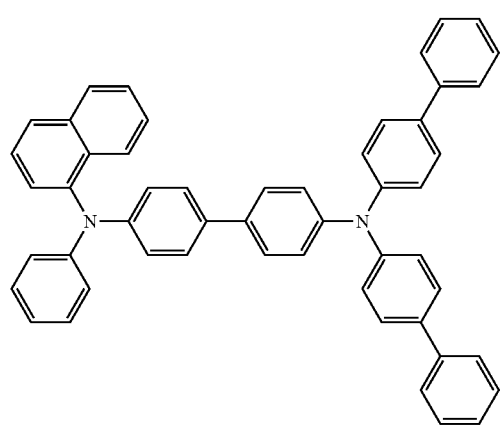
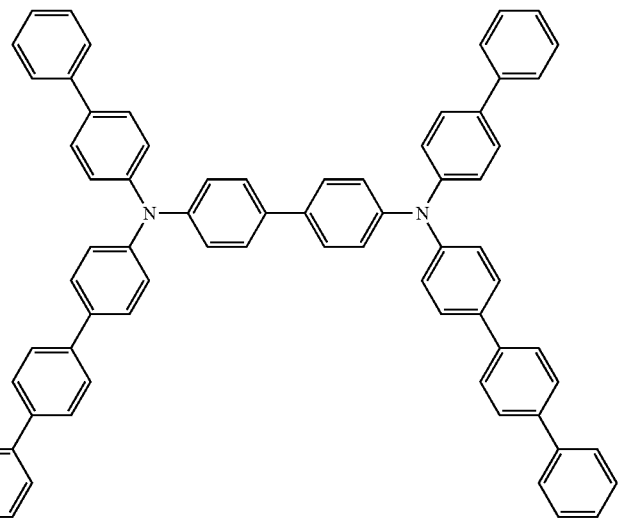
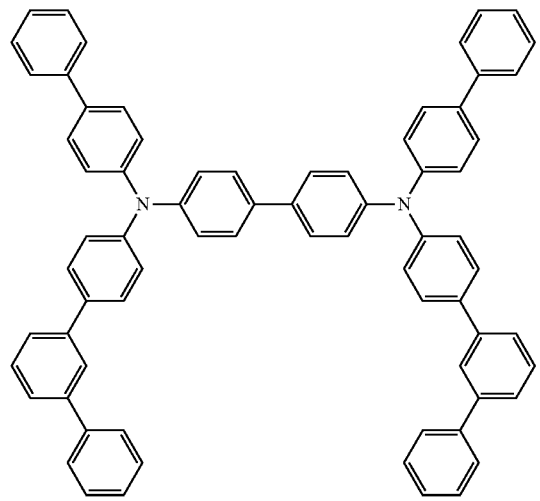
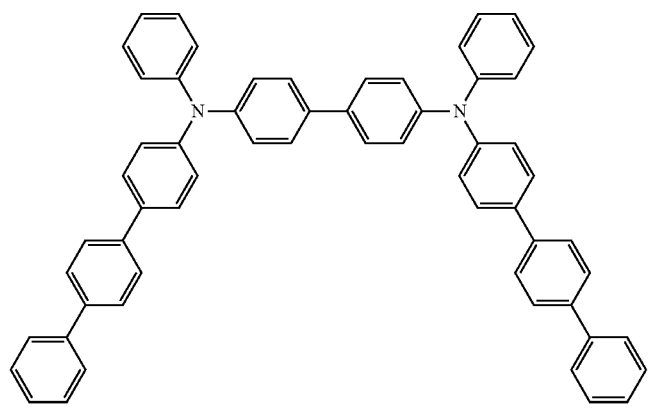

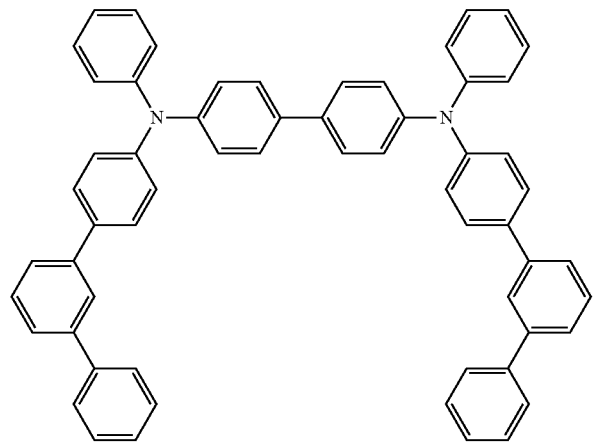
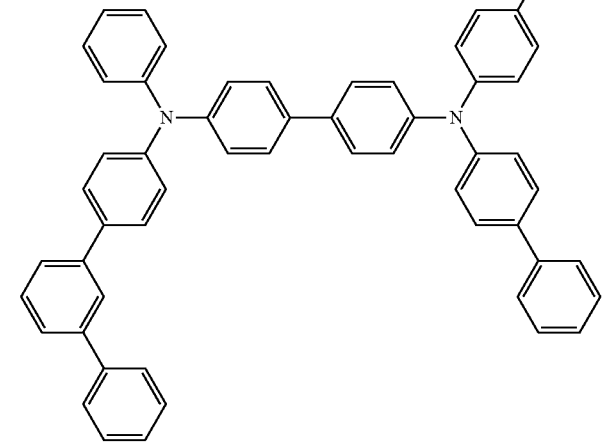
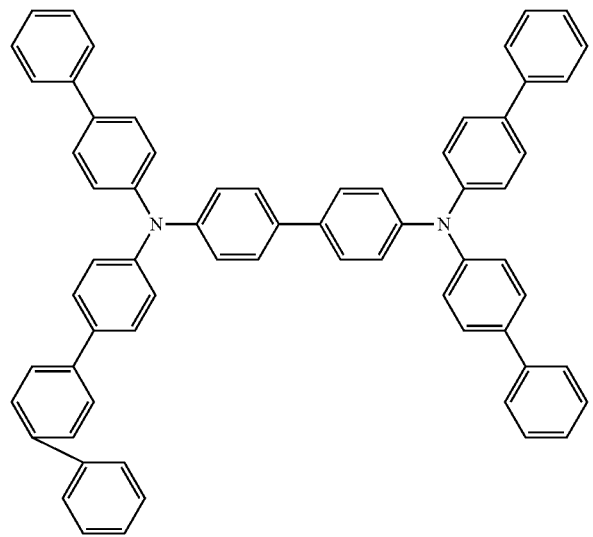
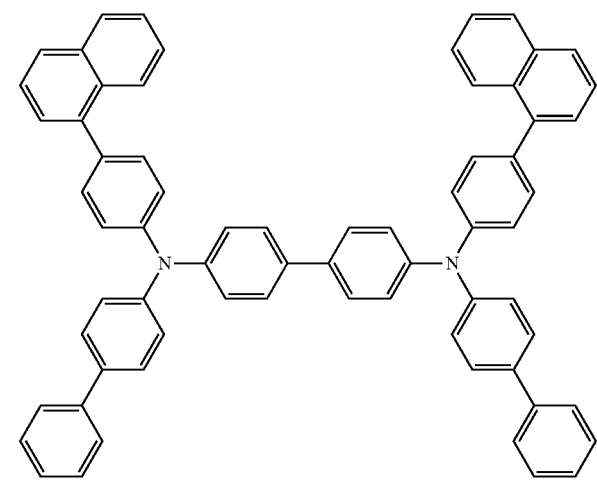
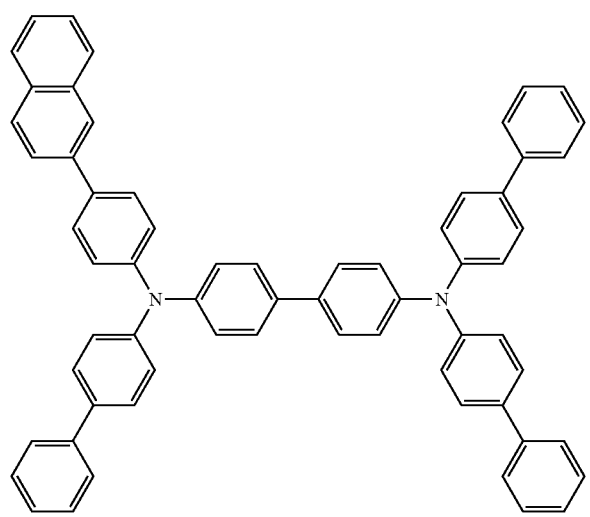
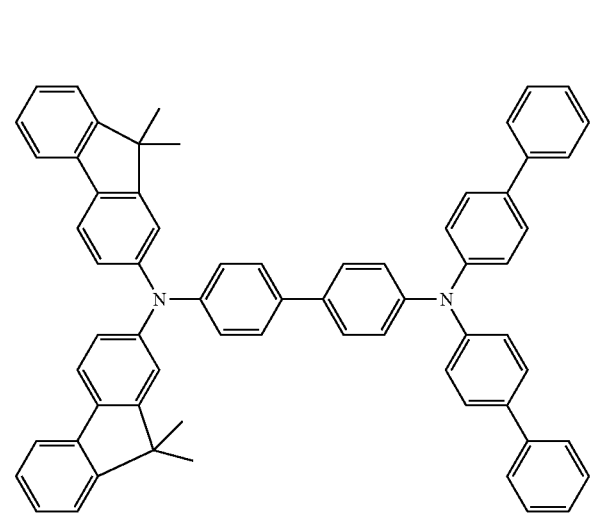

-continued
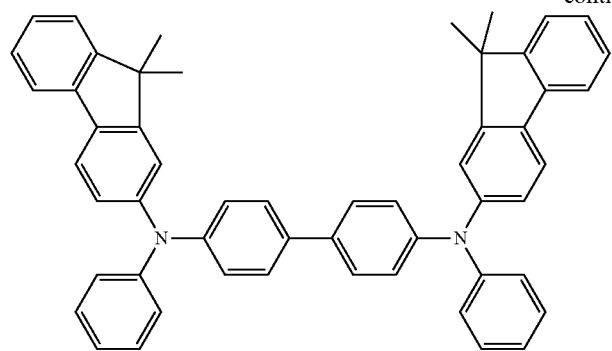
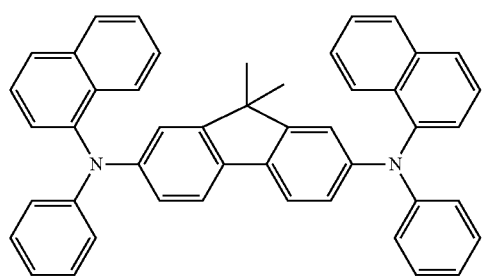
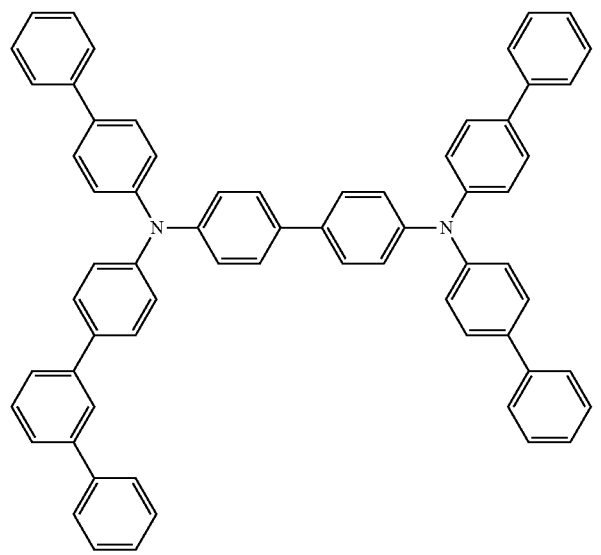
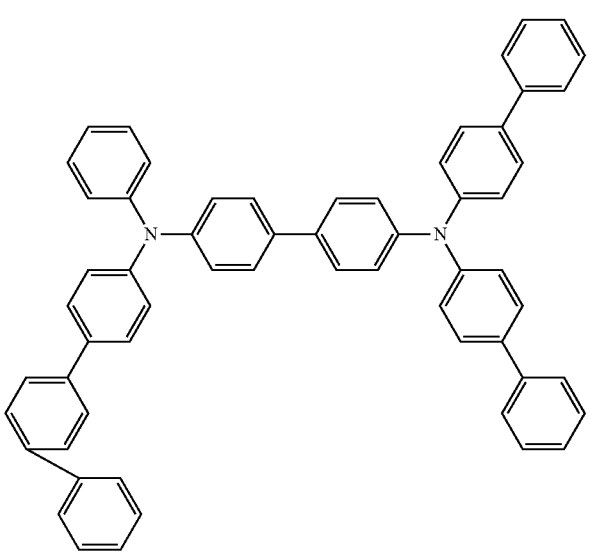
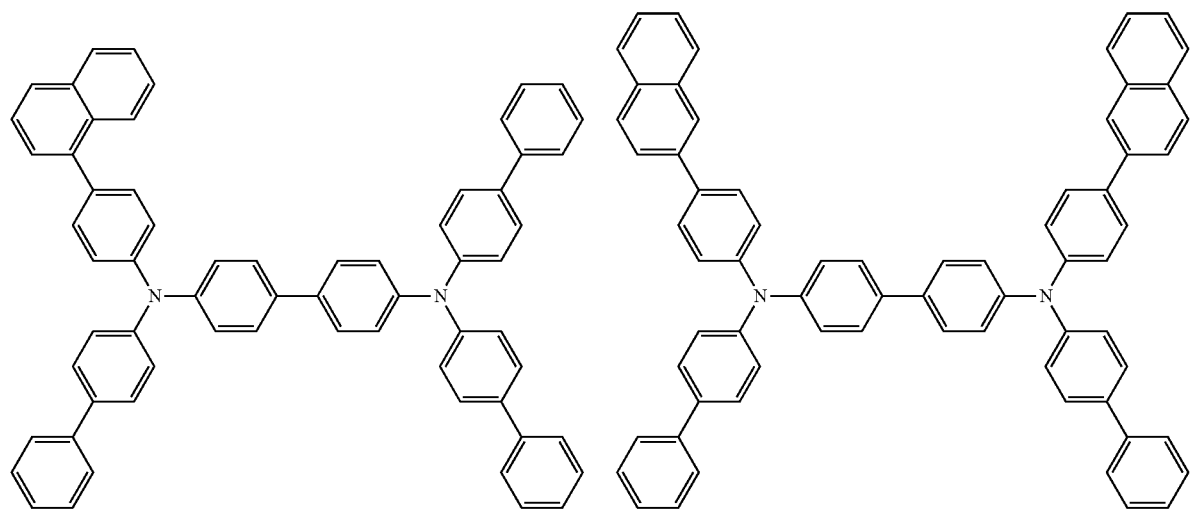

-continued
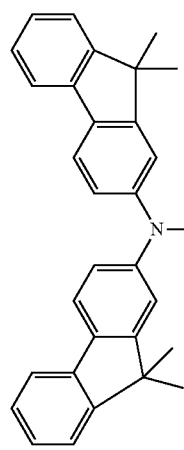 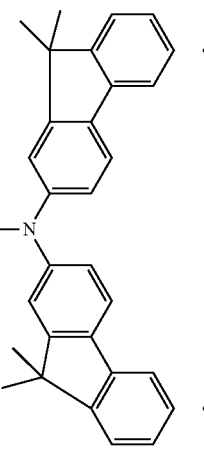
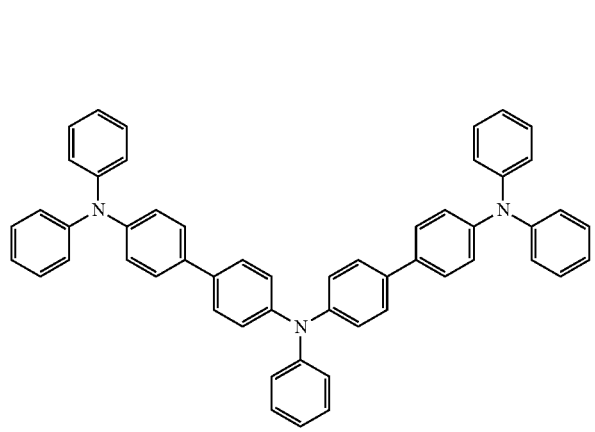 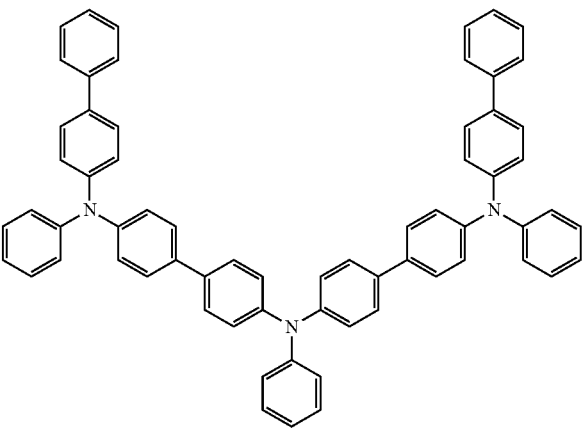
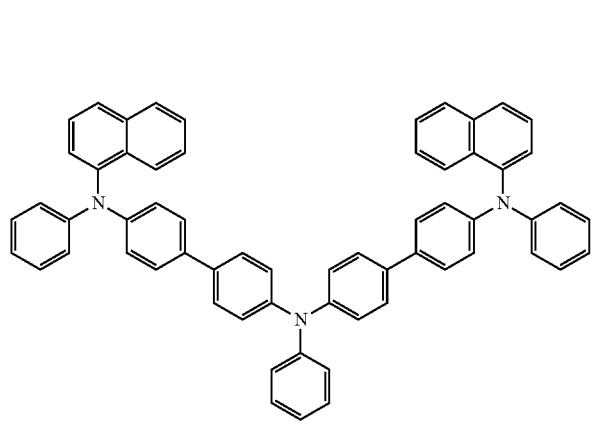 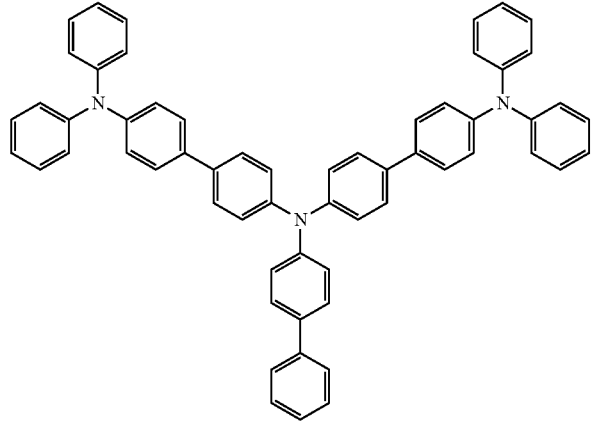

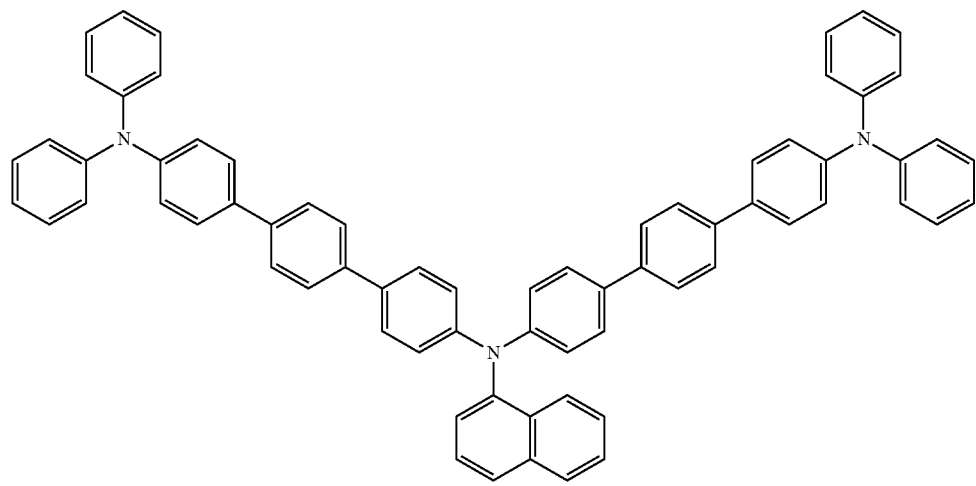
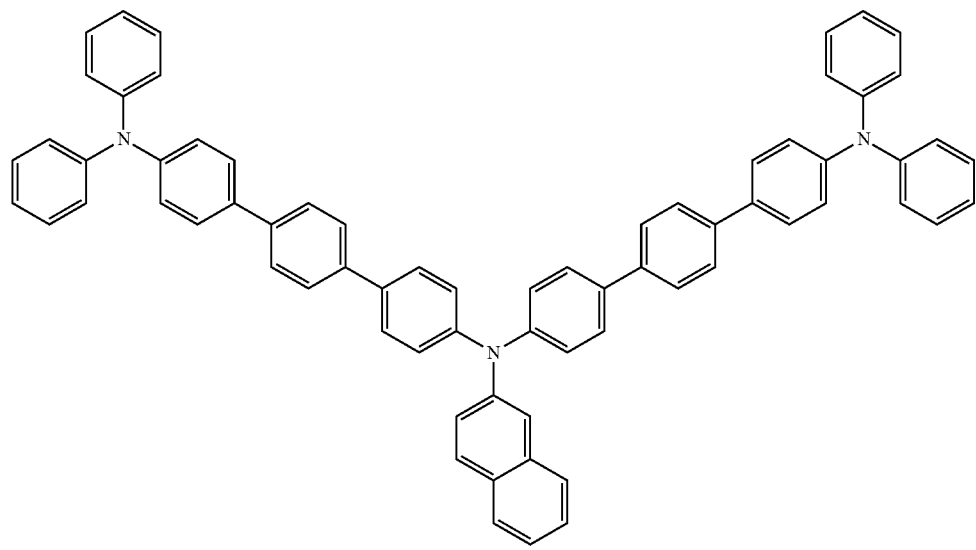
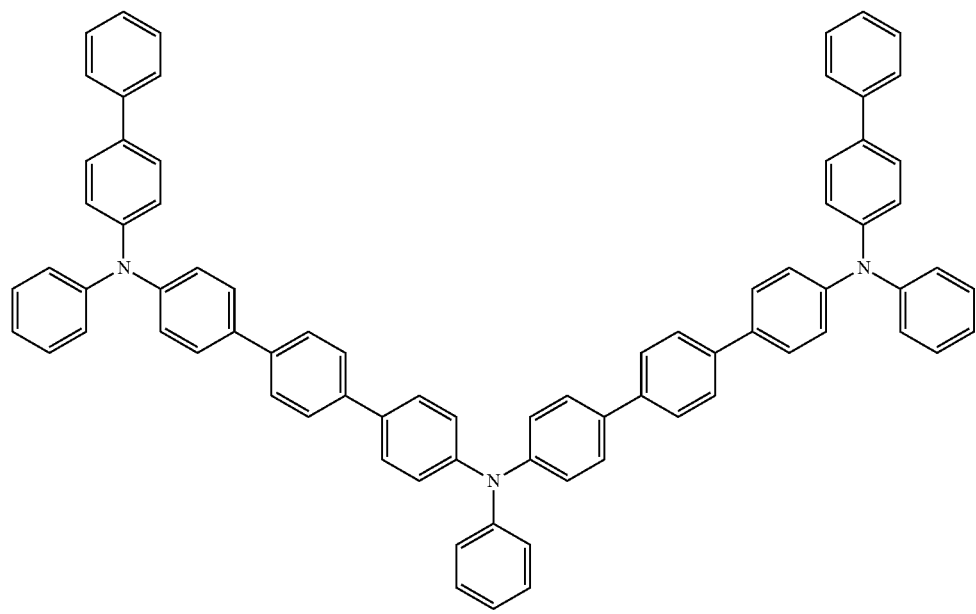

-continued
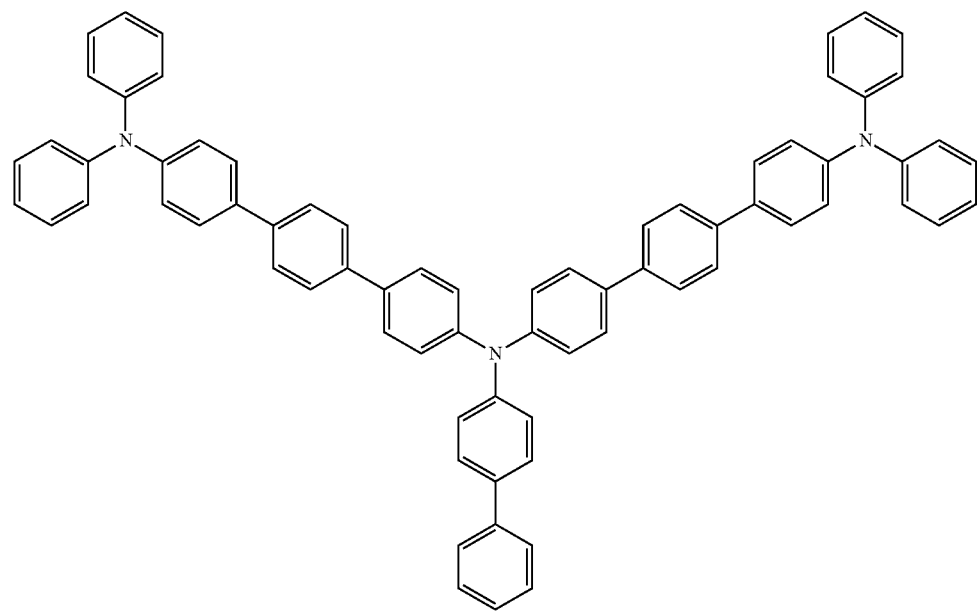
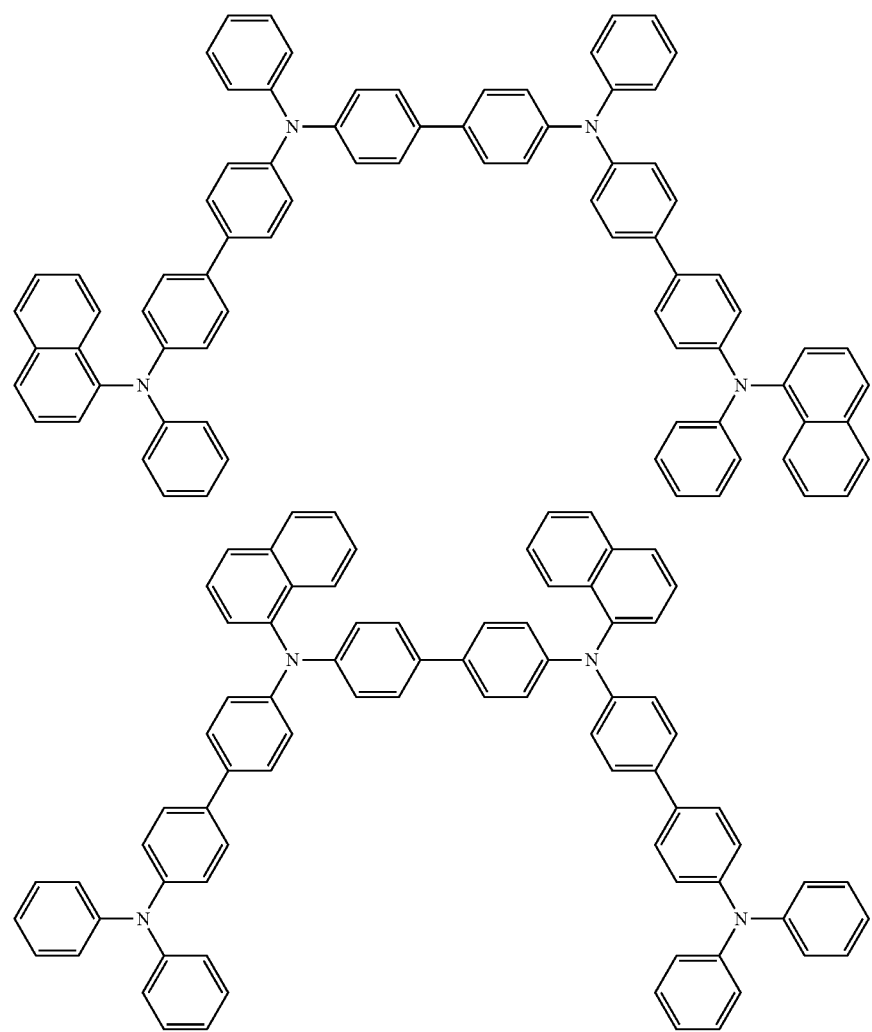

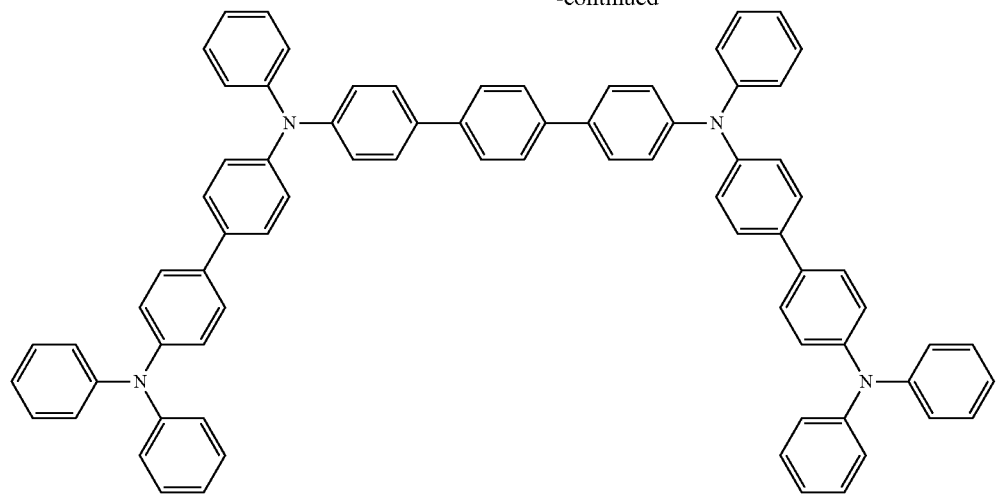
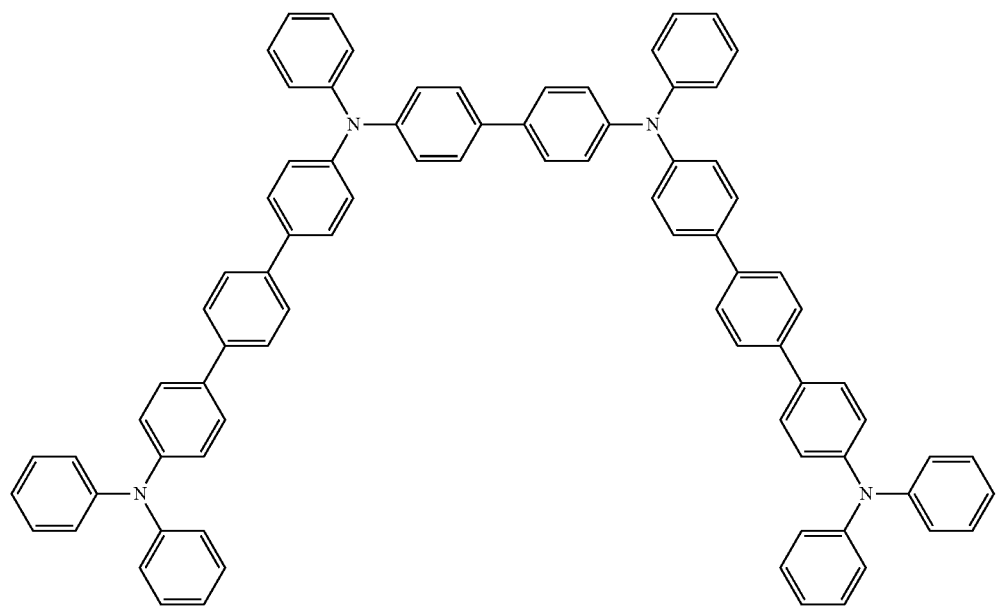
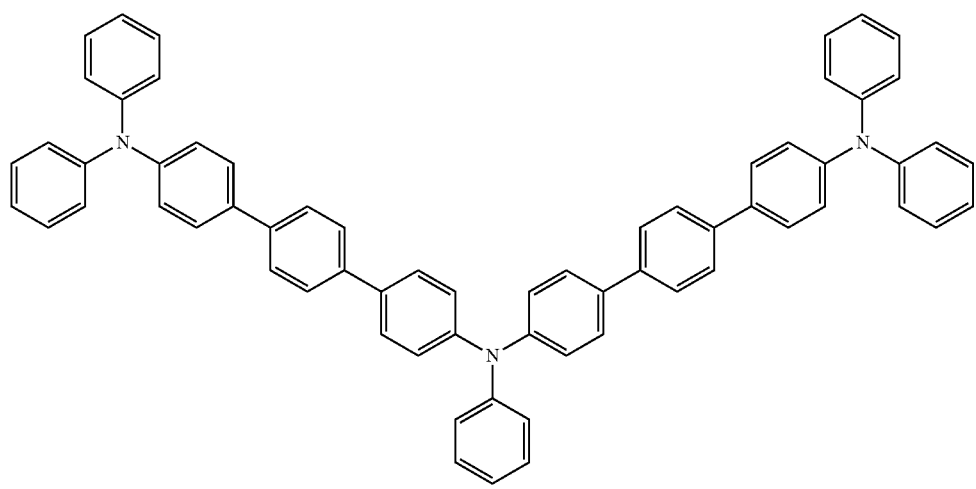

-continued
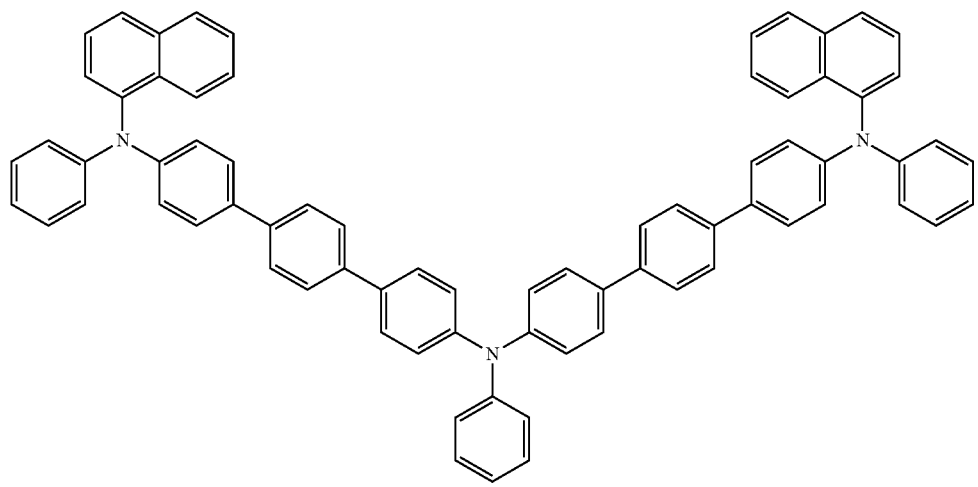
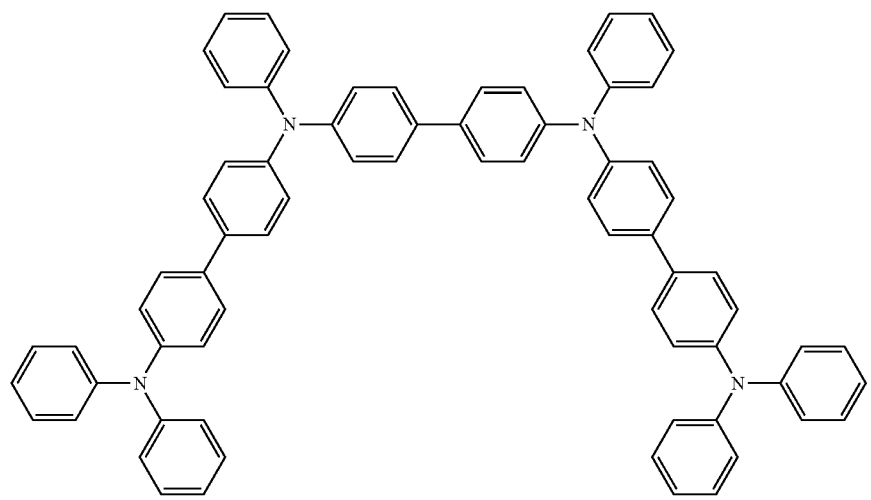
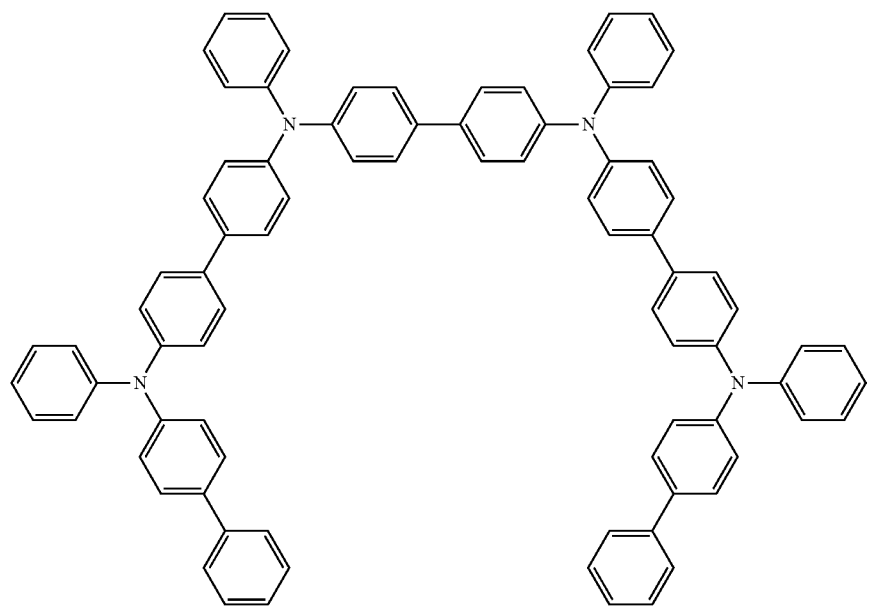

-continued
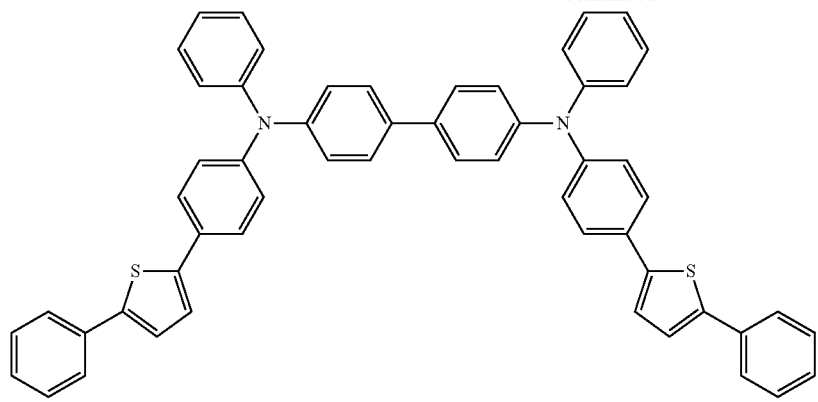
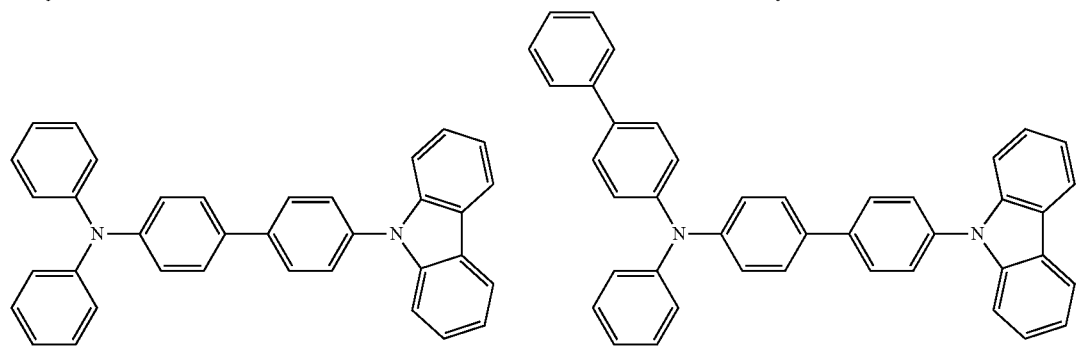
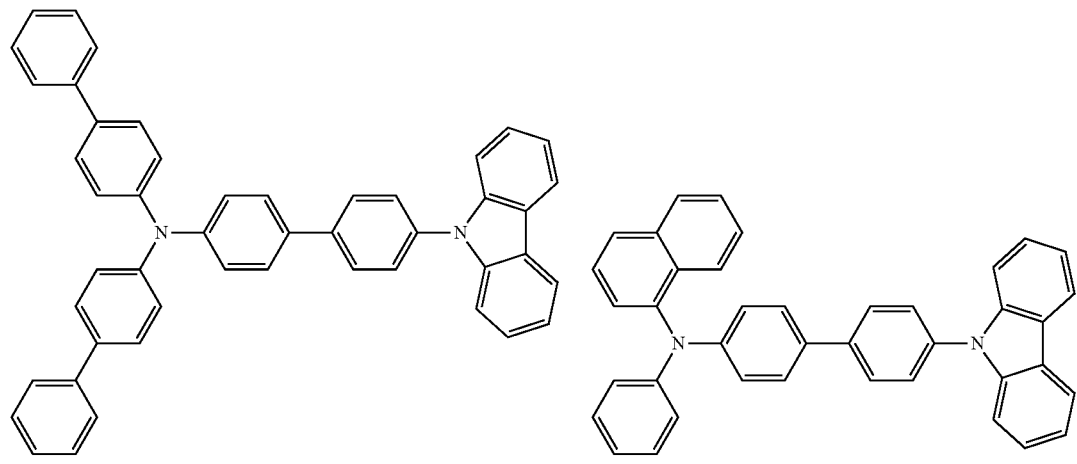
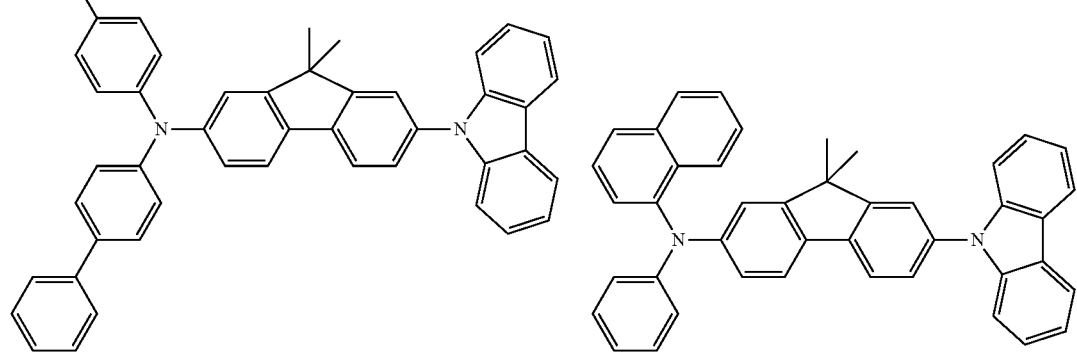

-continued
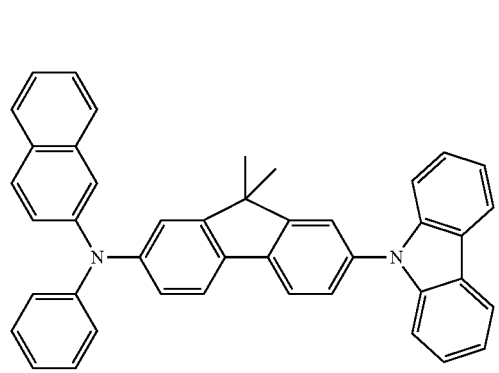
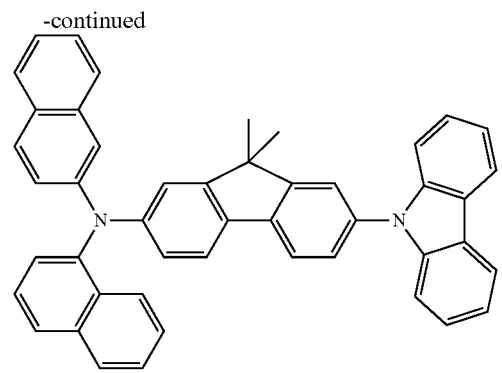
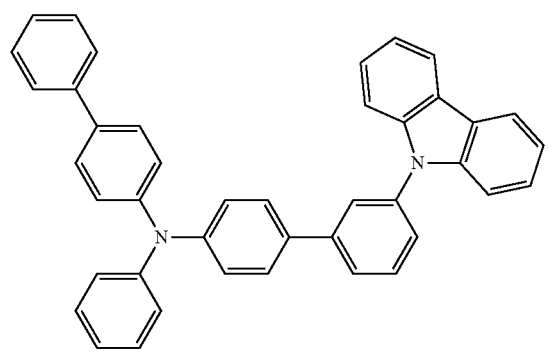
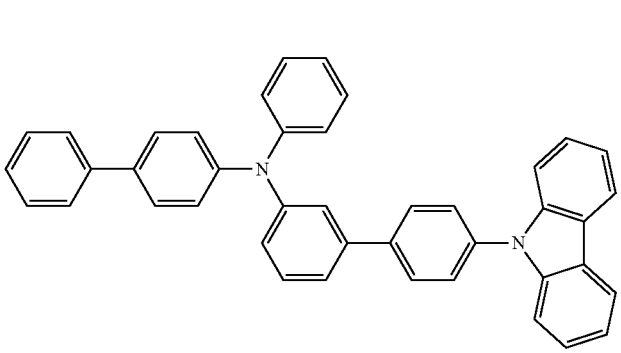
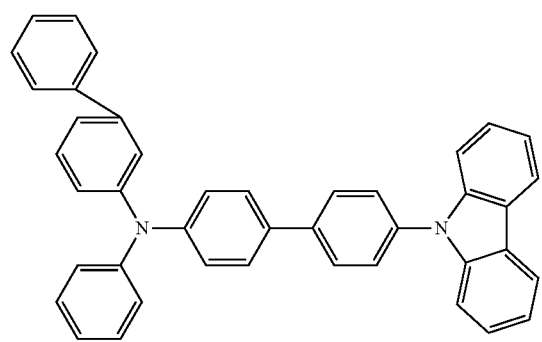
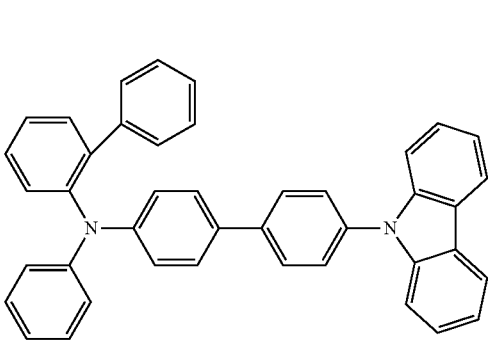
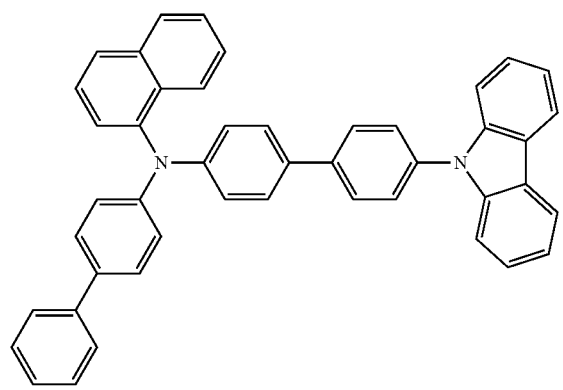
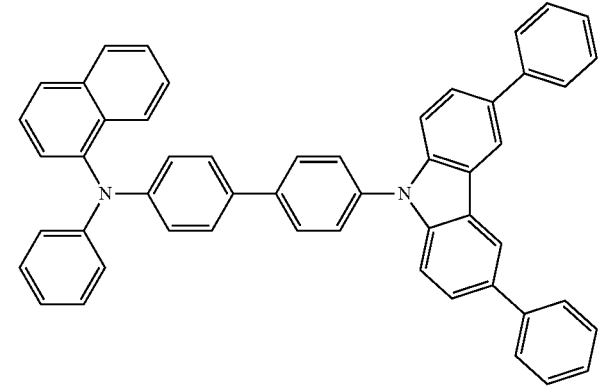

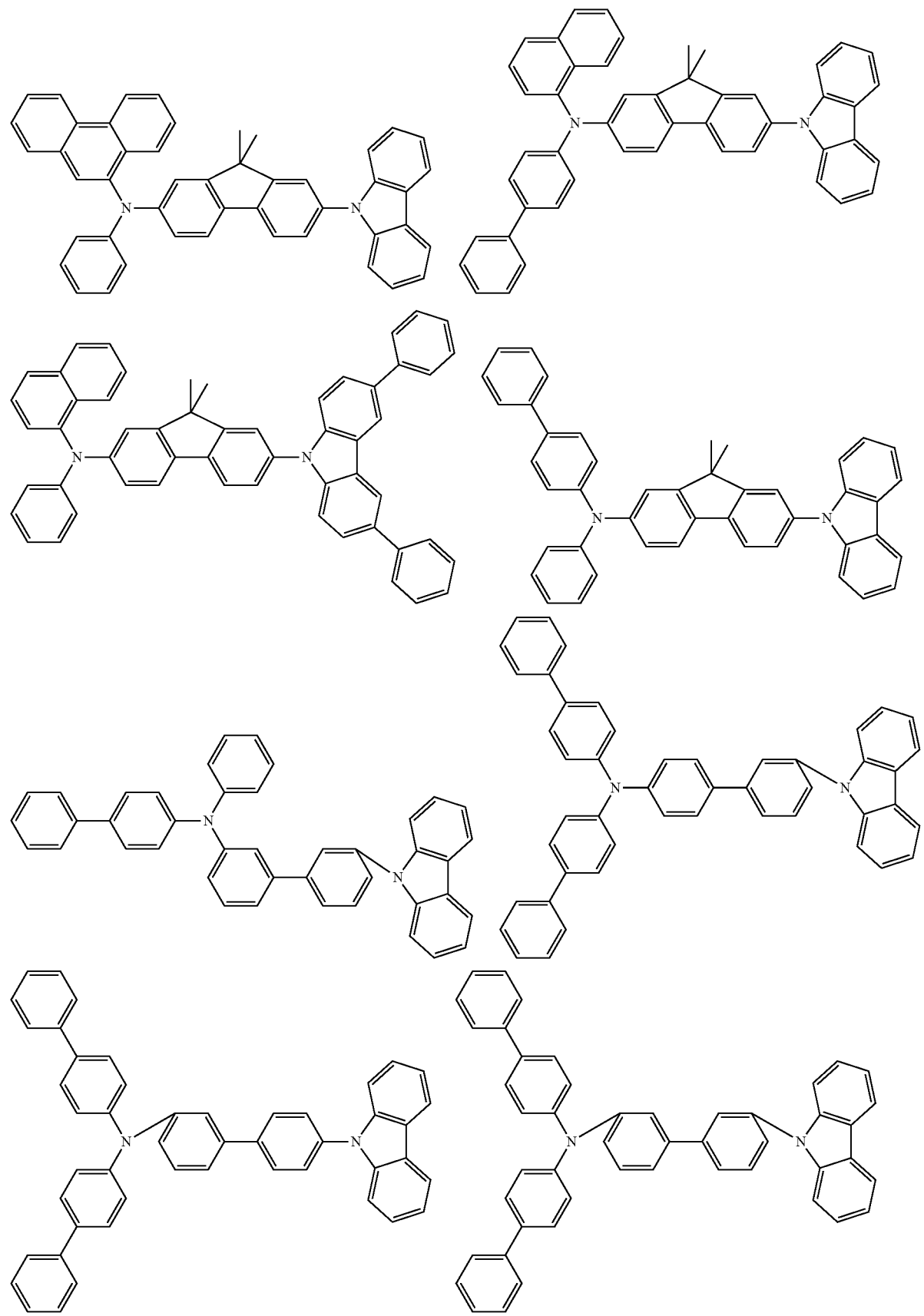

-continued
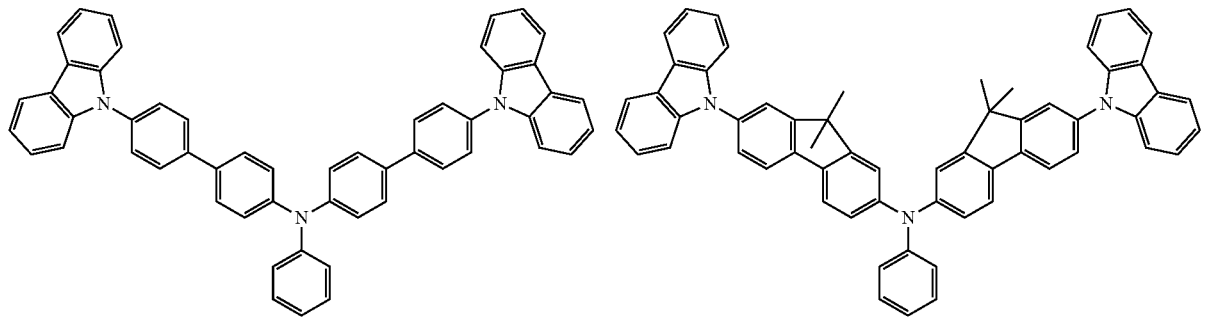
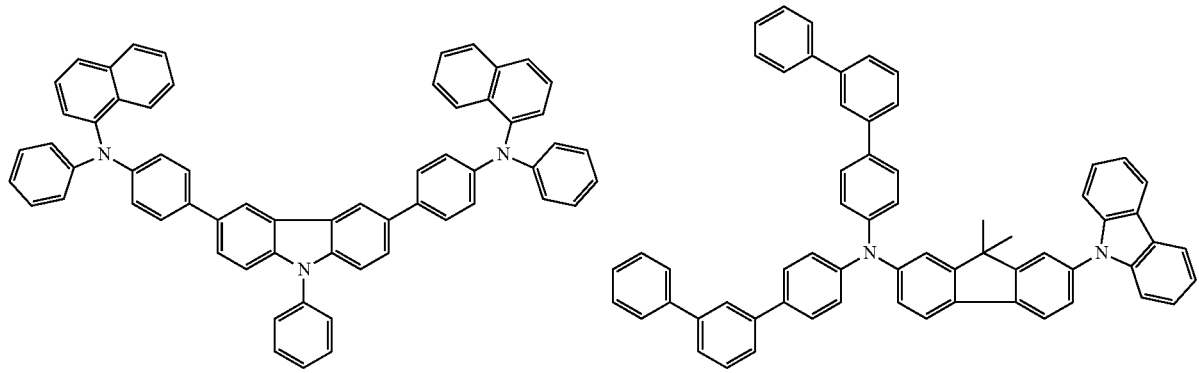
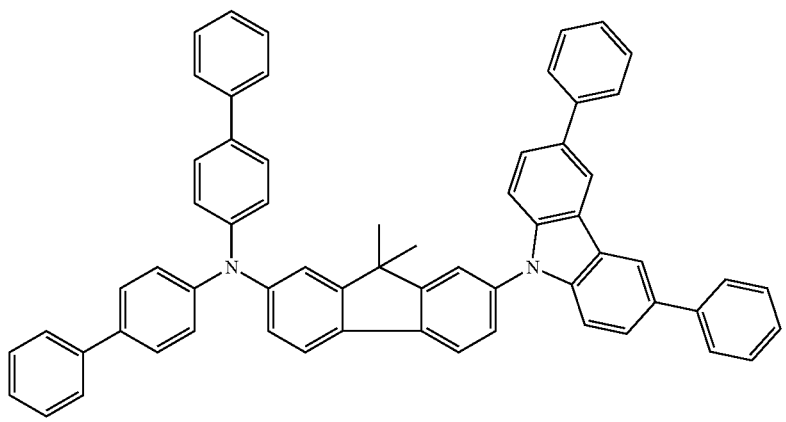
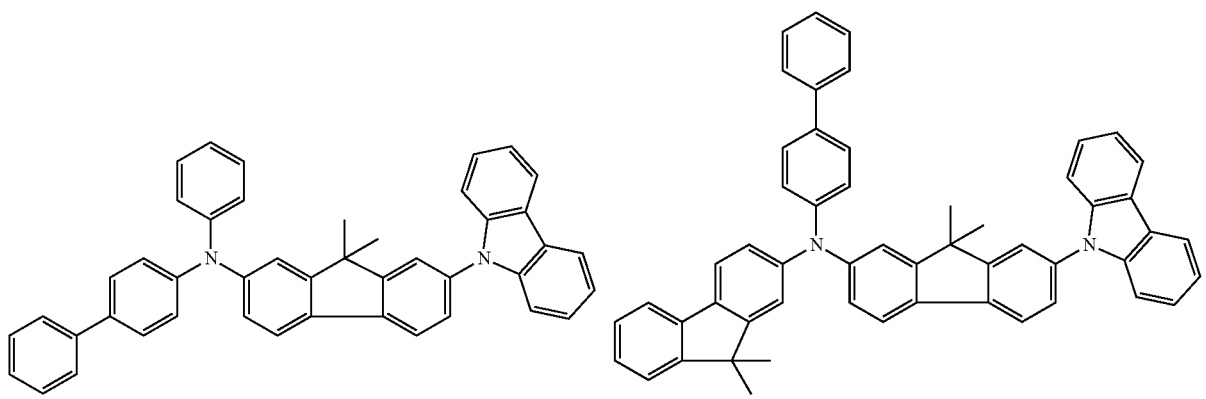

-continued
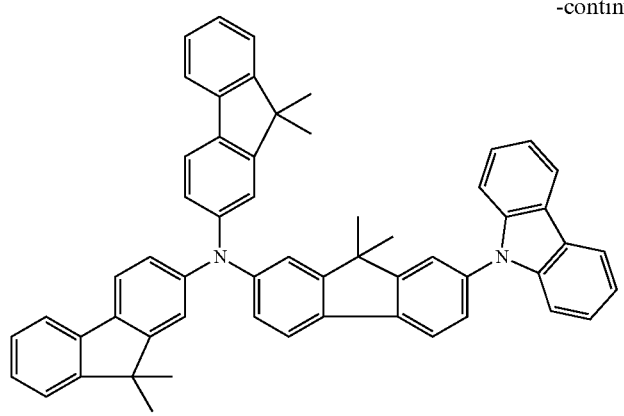
81
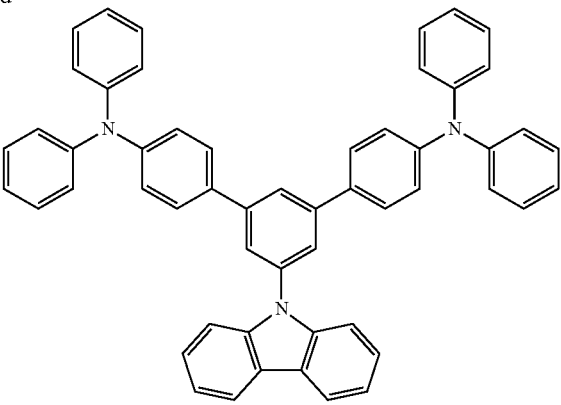
82
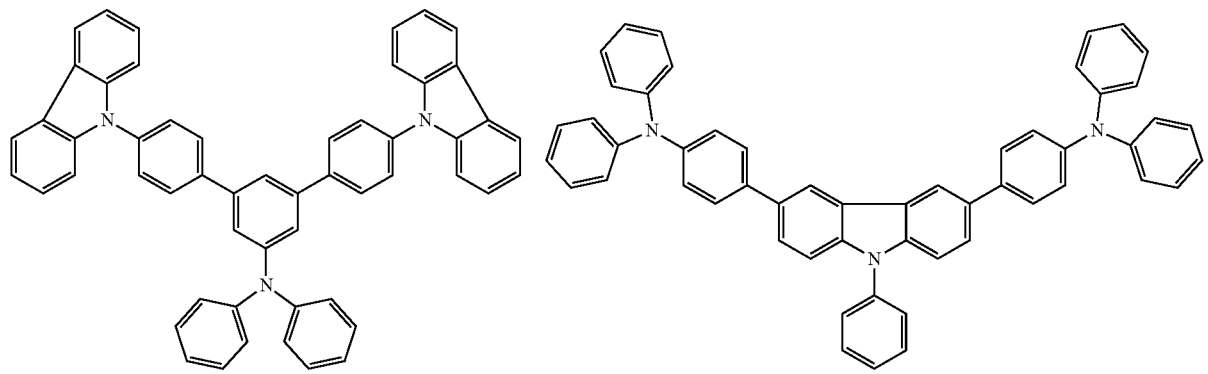
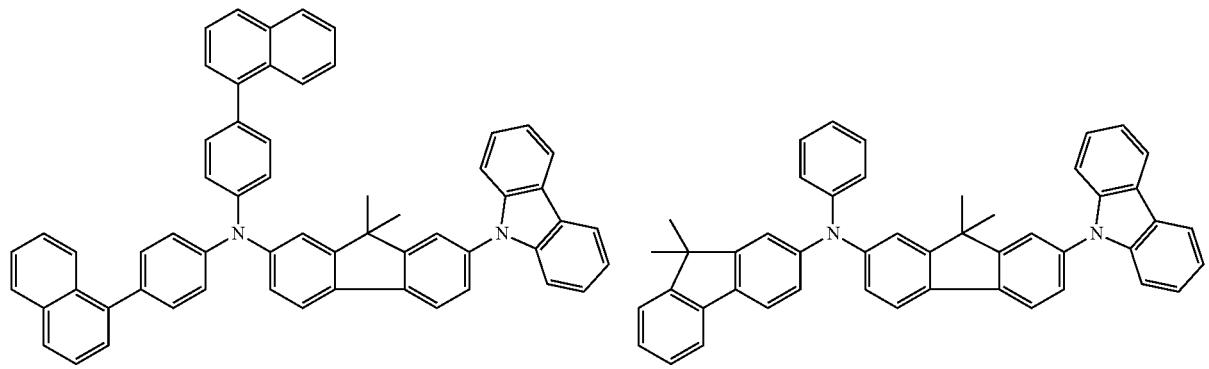
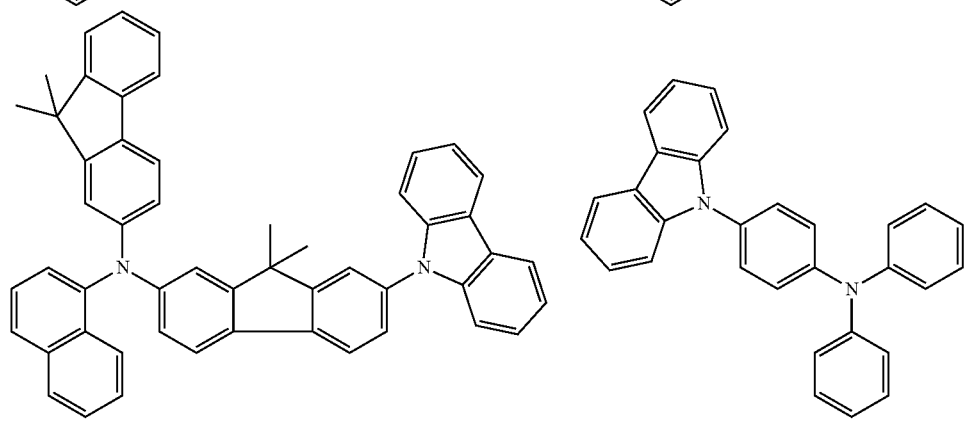

-continued
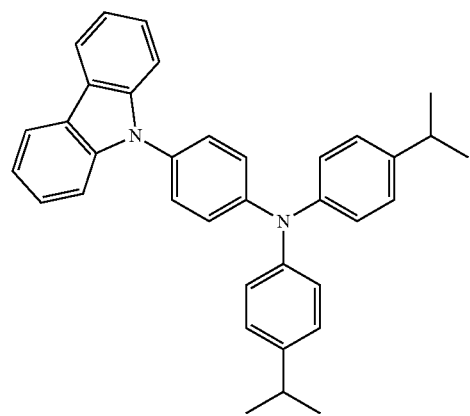
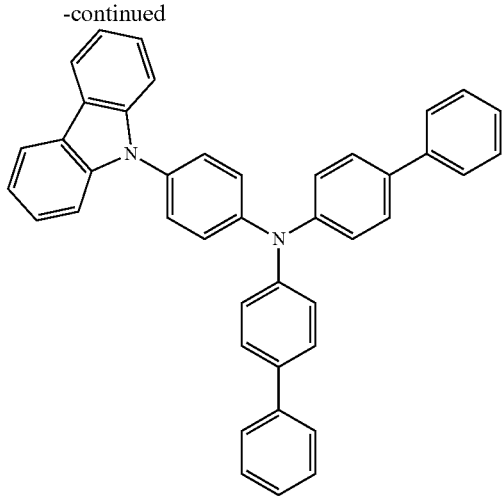
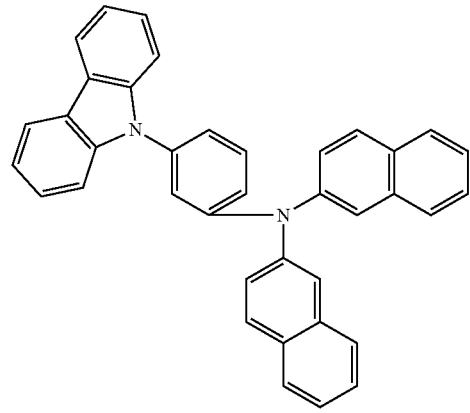
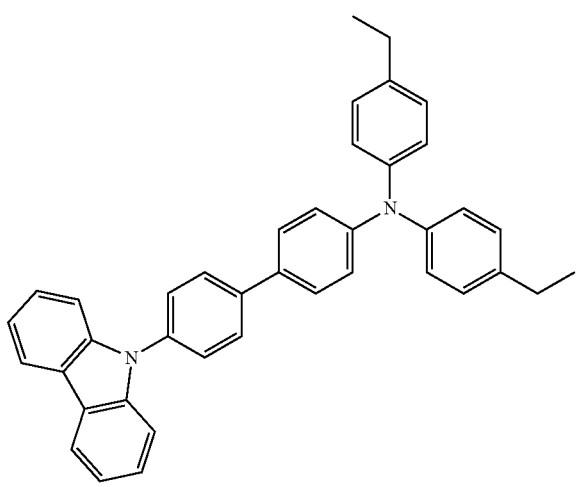
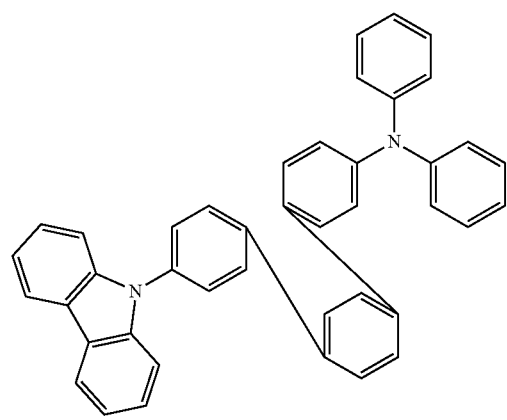
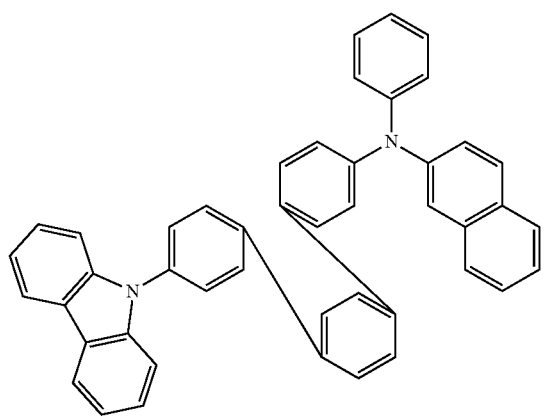

-continued
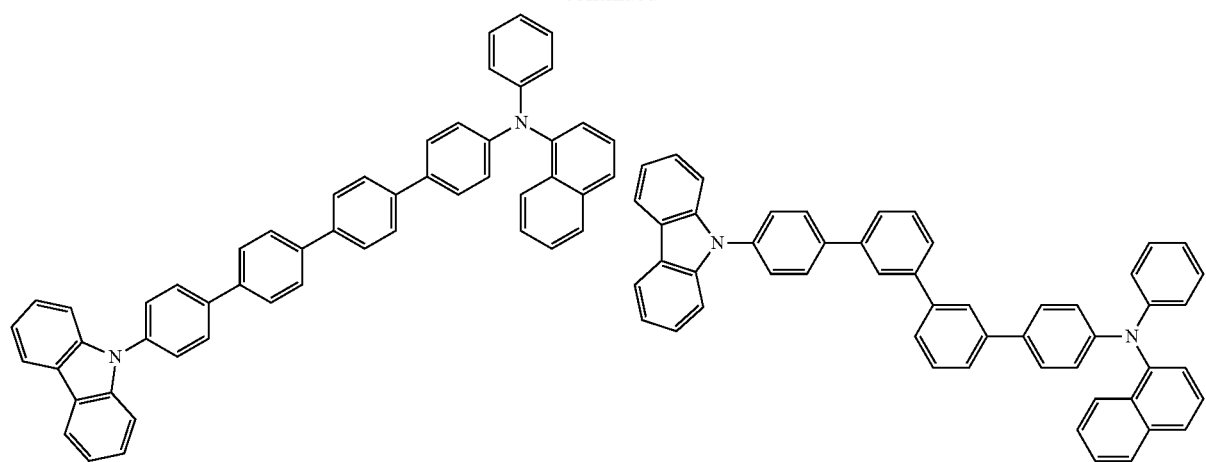
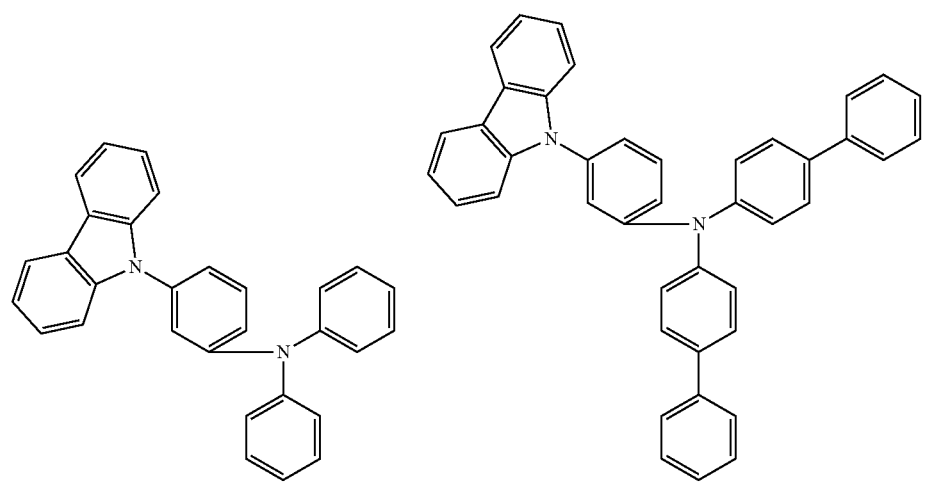
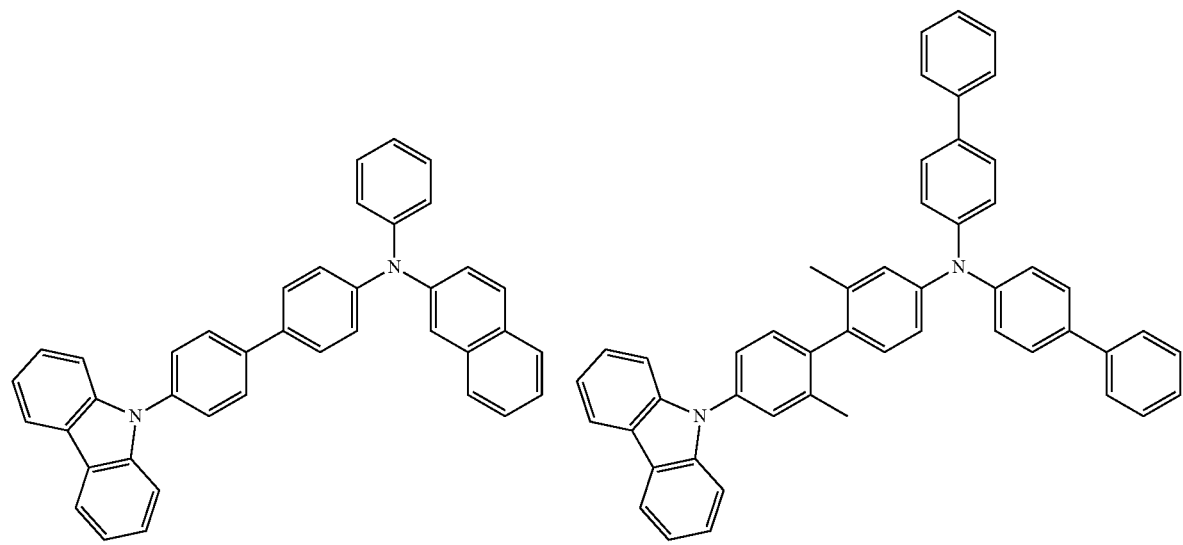

-continued
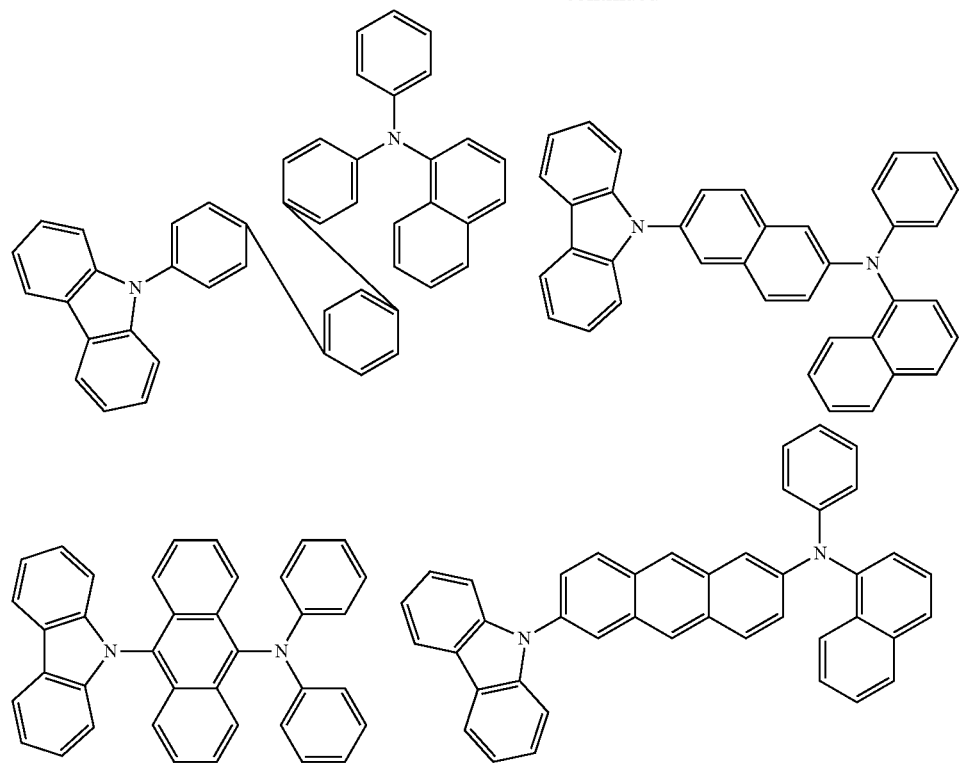
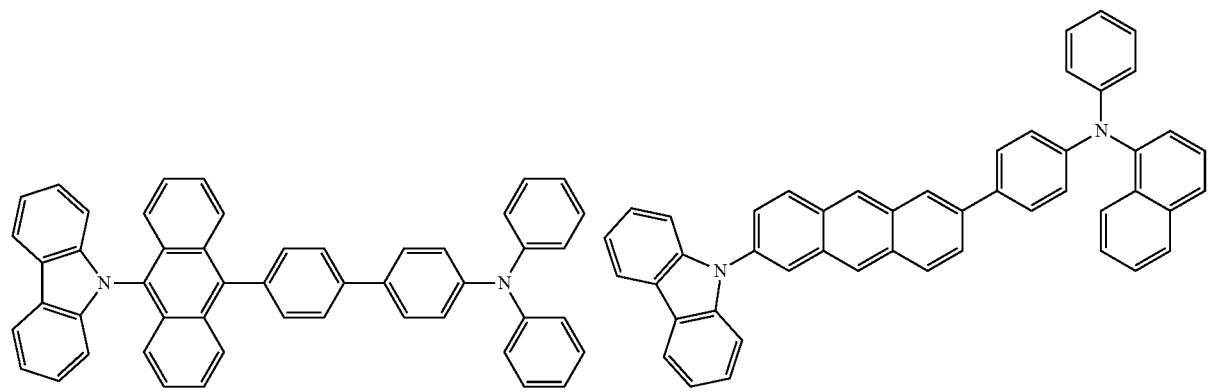
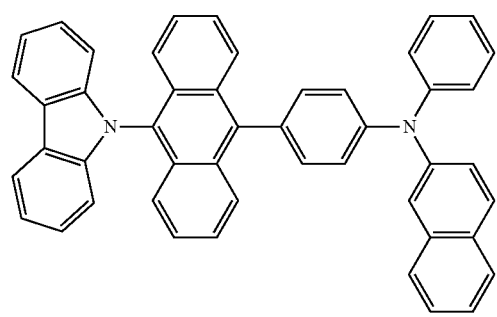 [SMILES: c1ccc(N(c2ccc(-c3c4ccccc4c(-n4c5ccccc5c5ccccc54)c4ccccc34)cc2)c2ccc3ccccc3c2)cc1]

According to an exemplary embodiment of the present specification, Chemical Formula 3 is selected from the following compounds.
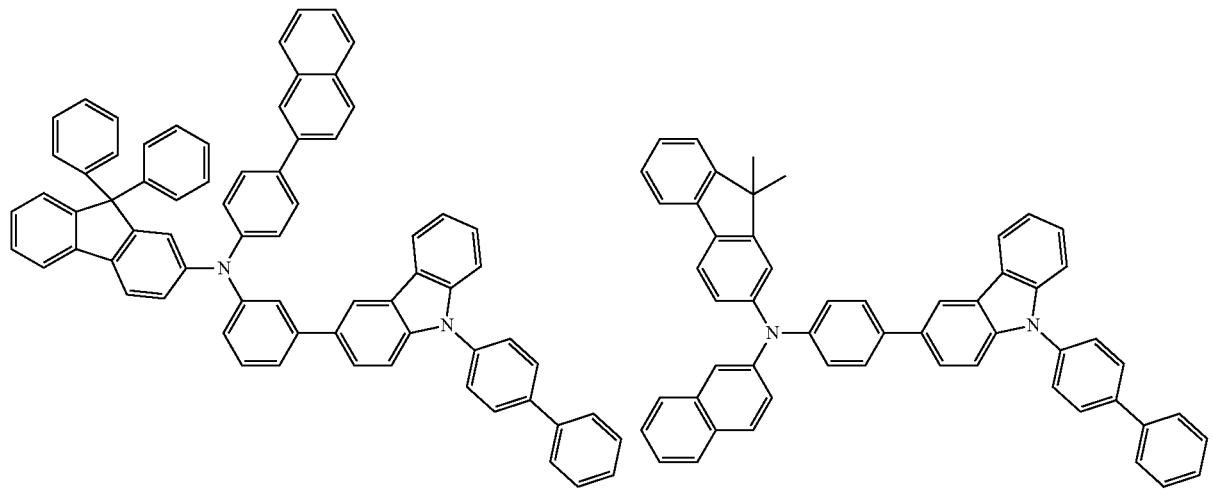
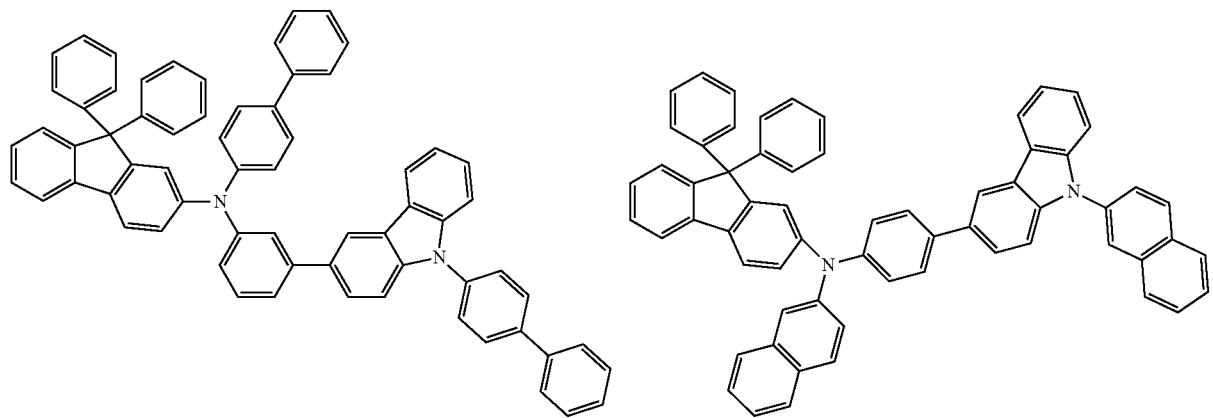
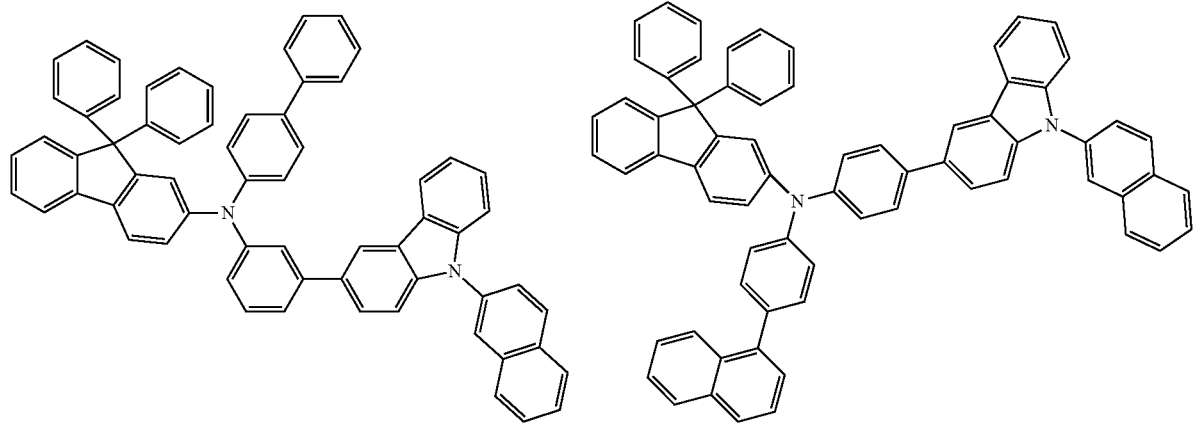

91
92
-continued
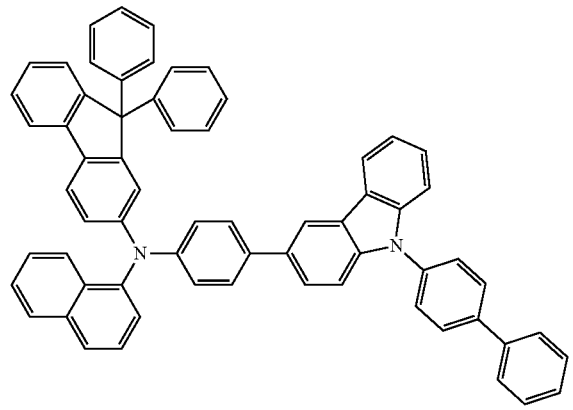
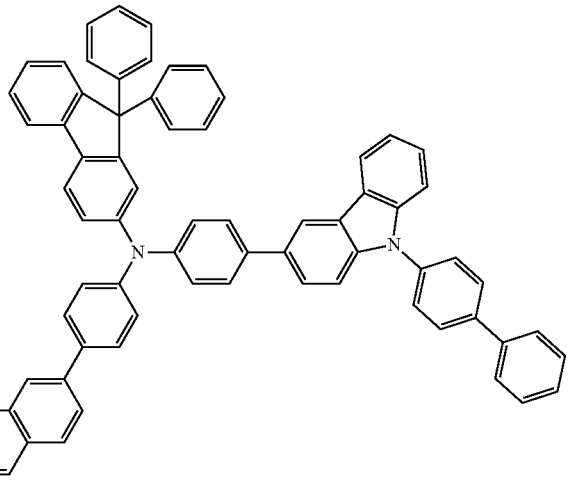
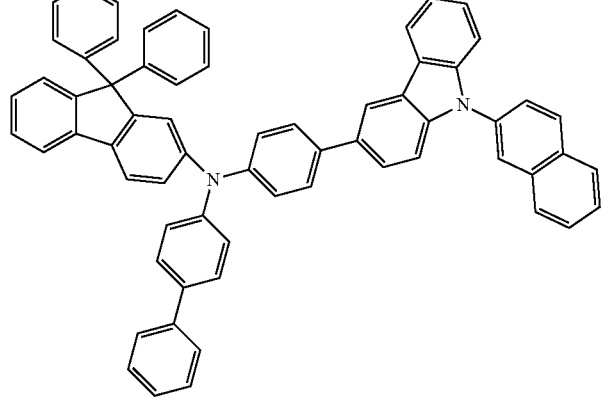
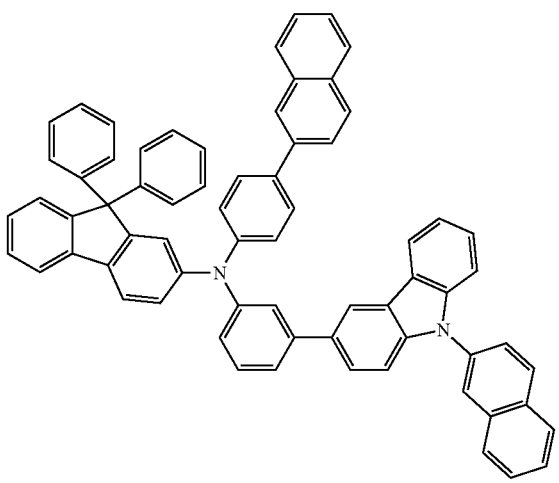
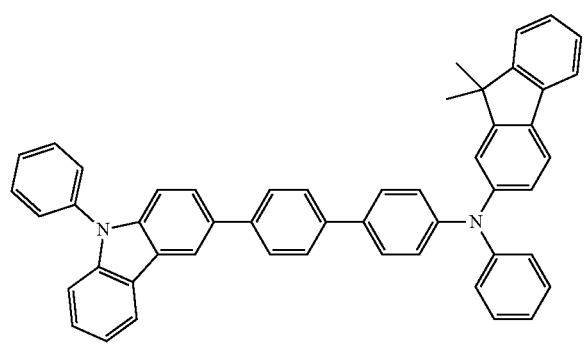
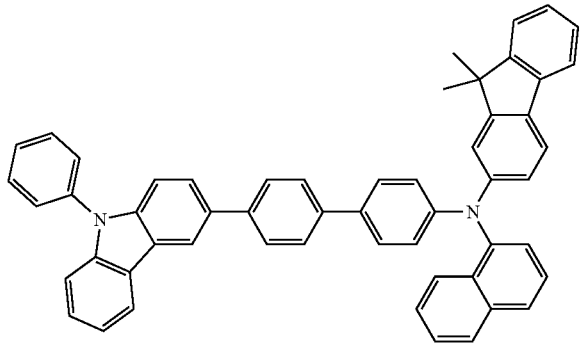

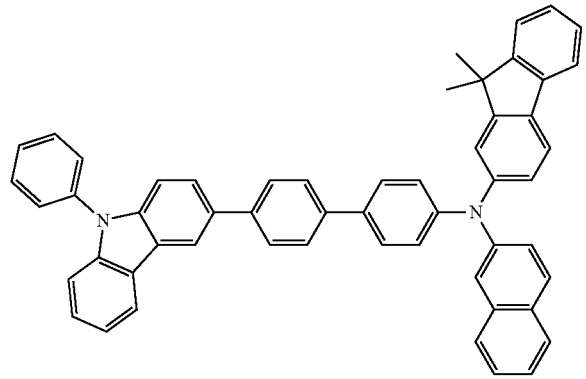
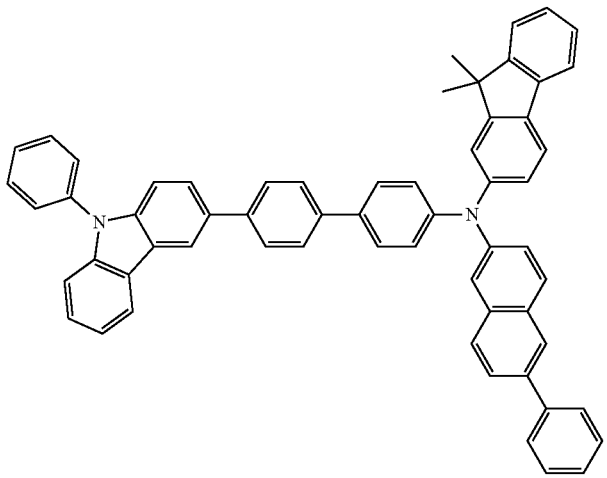
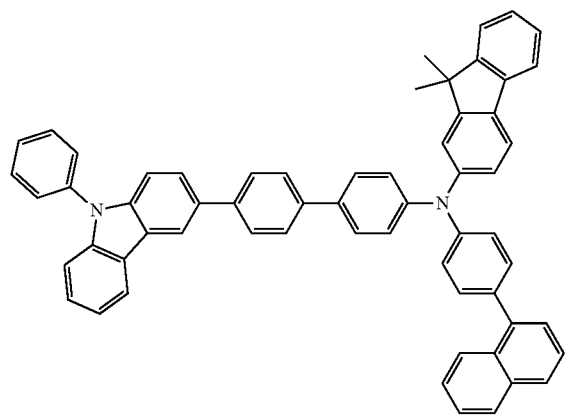
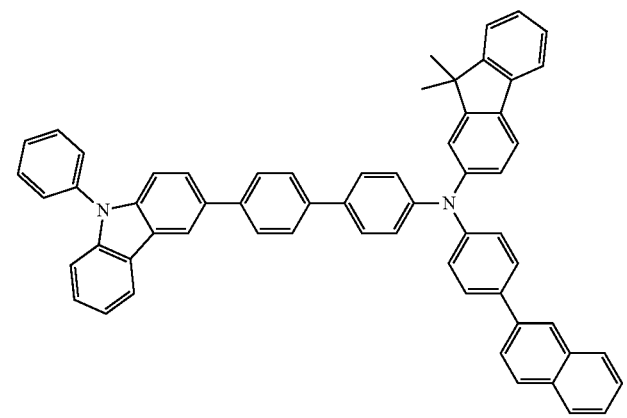
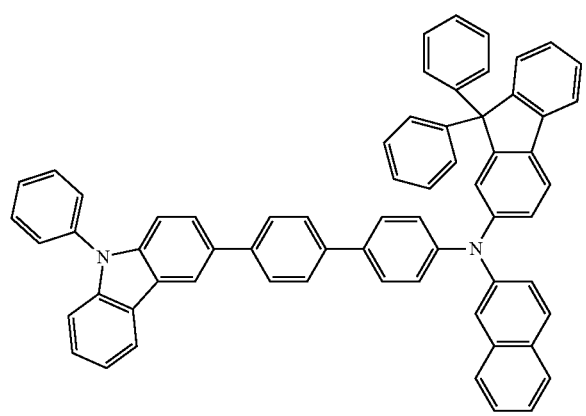
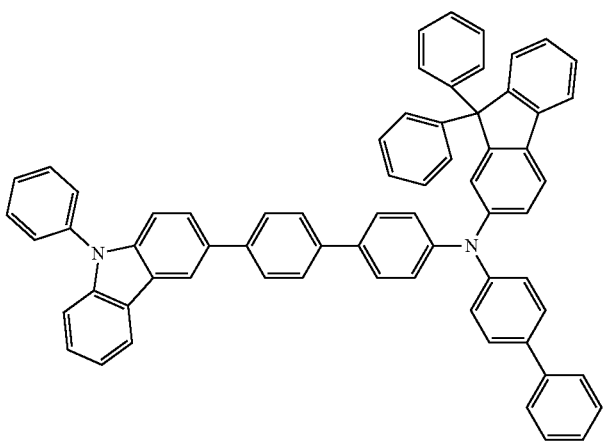

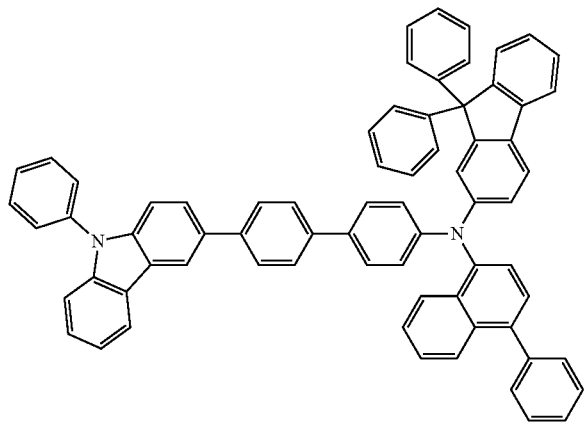
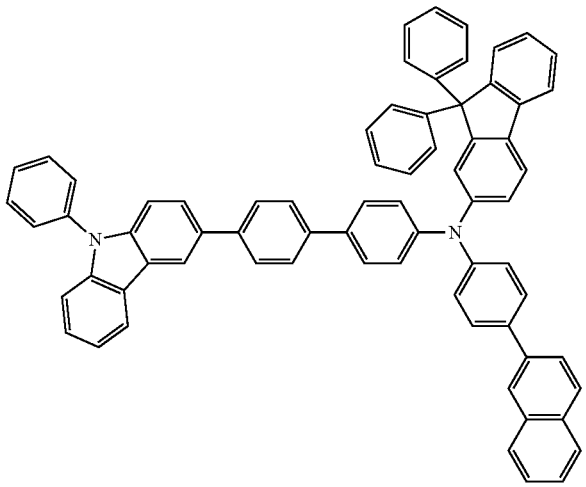
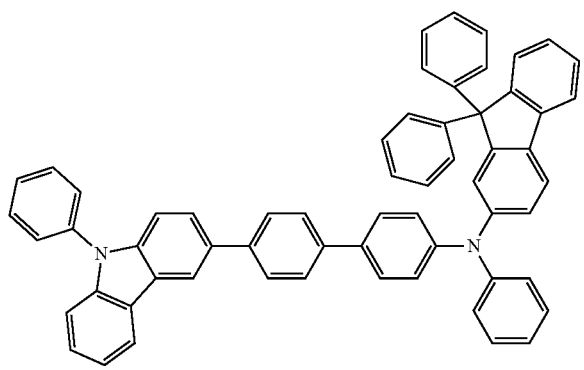
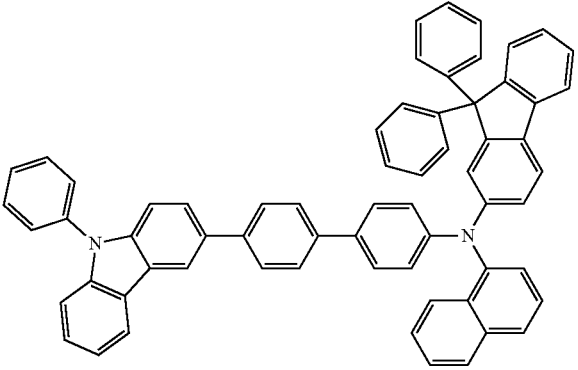
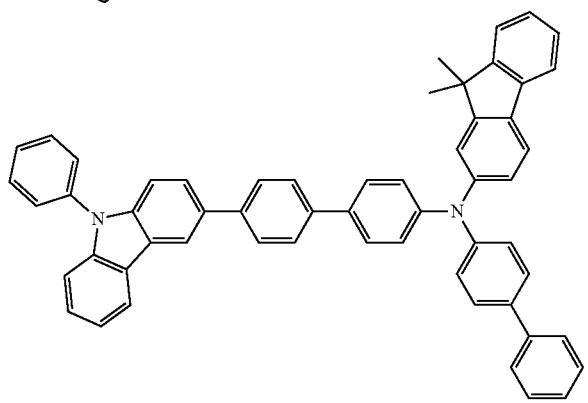
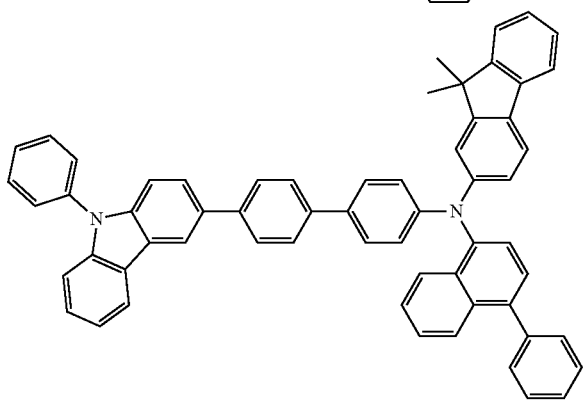
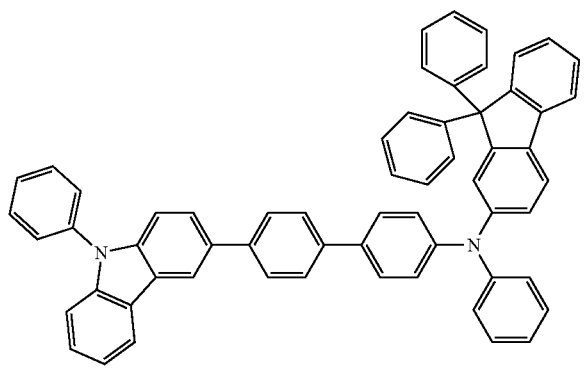
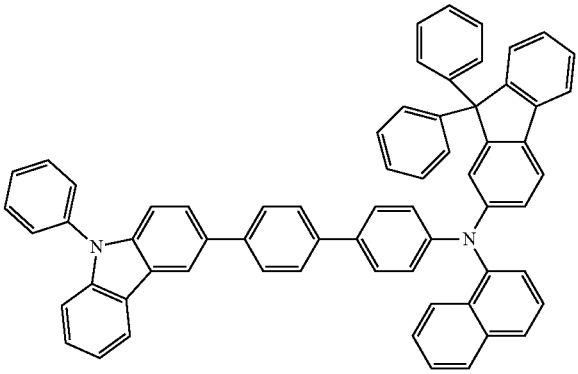

-continued
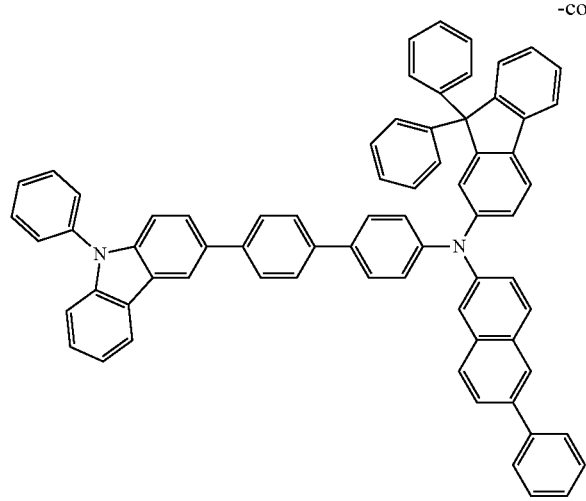
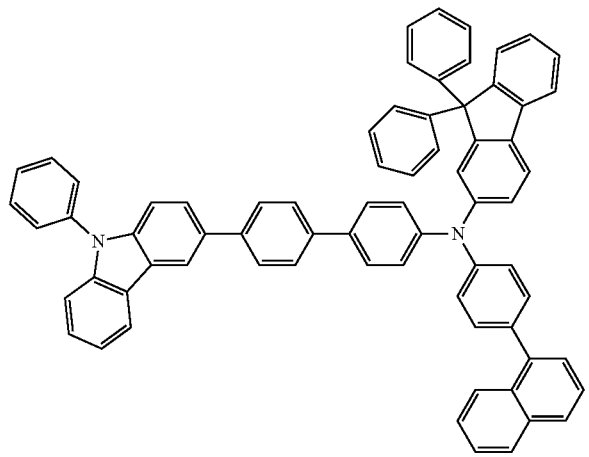
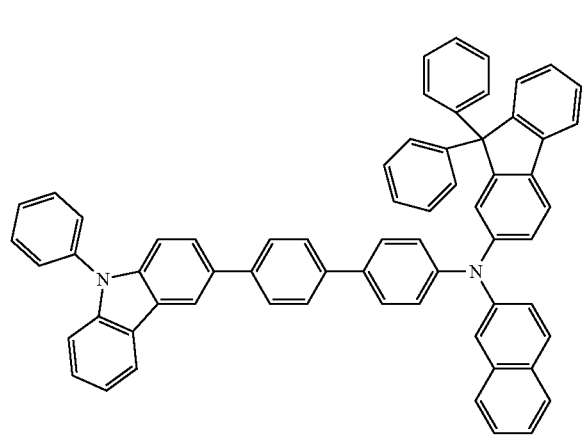
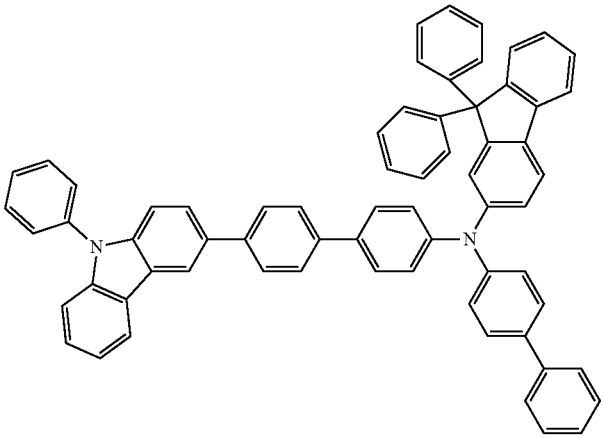
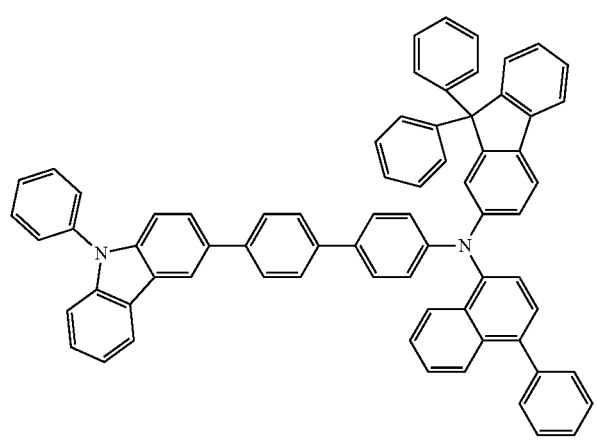
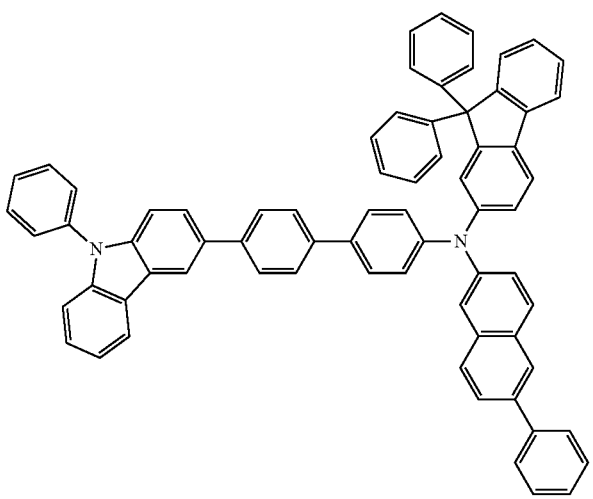

-continued
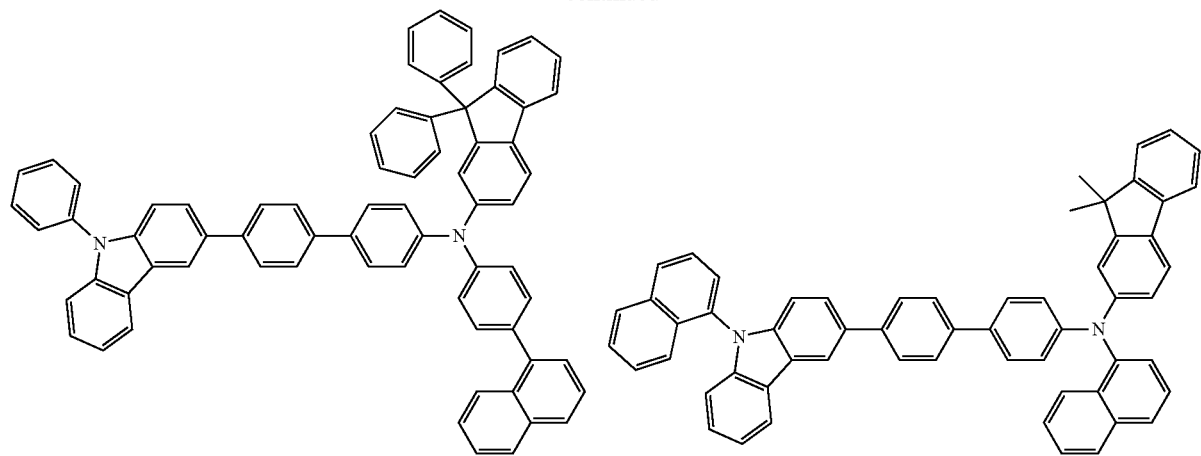
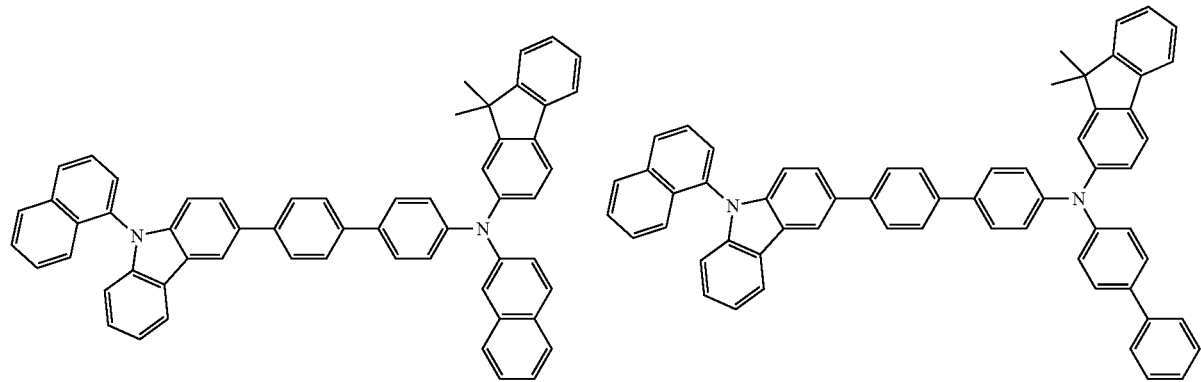
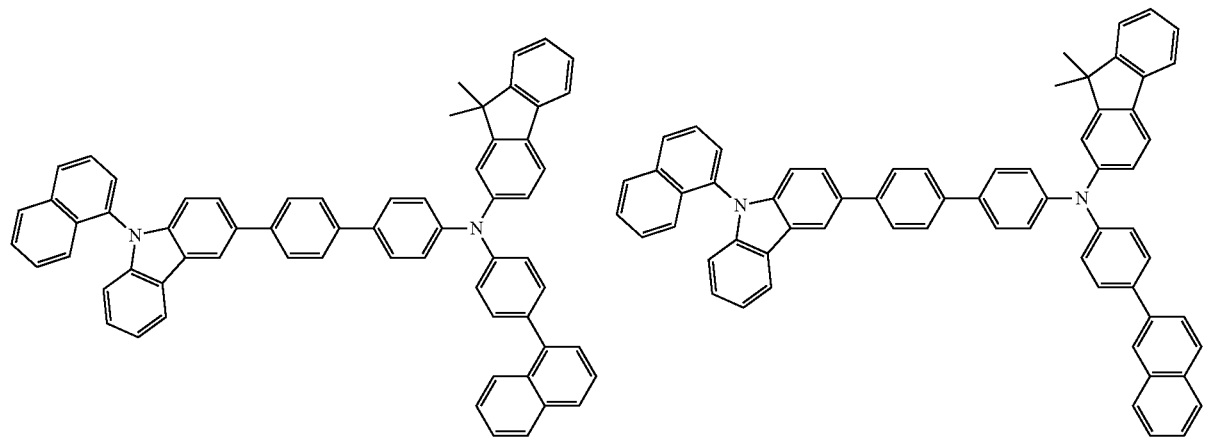
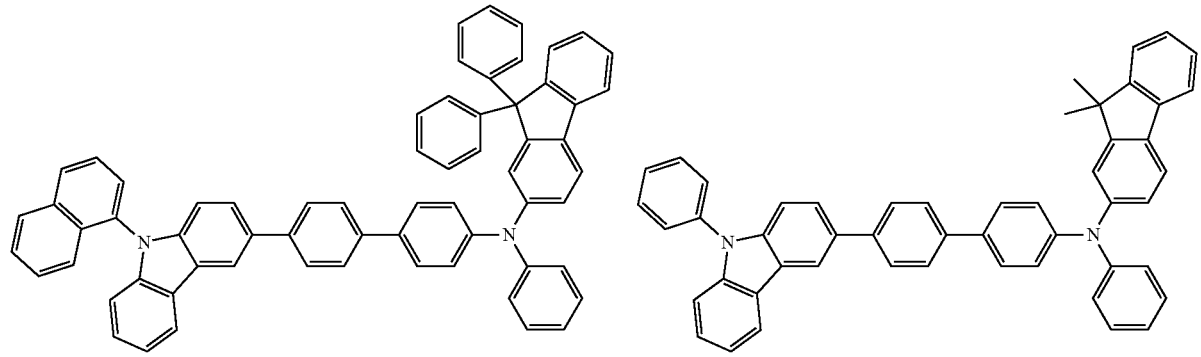

101 102
-continued
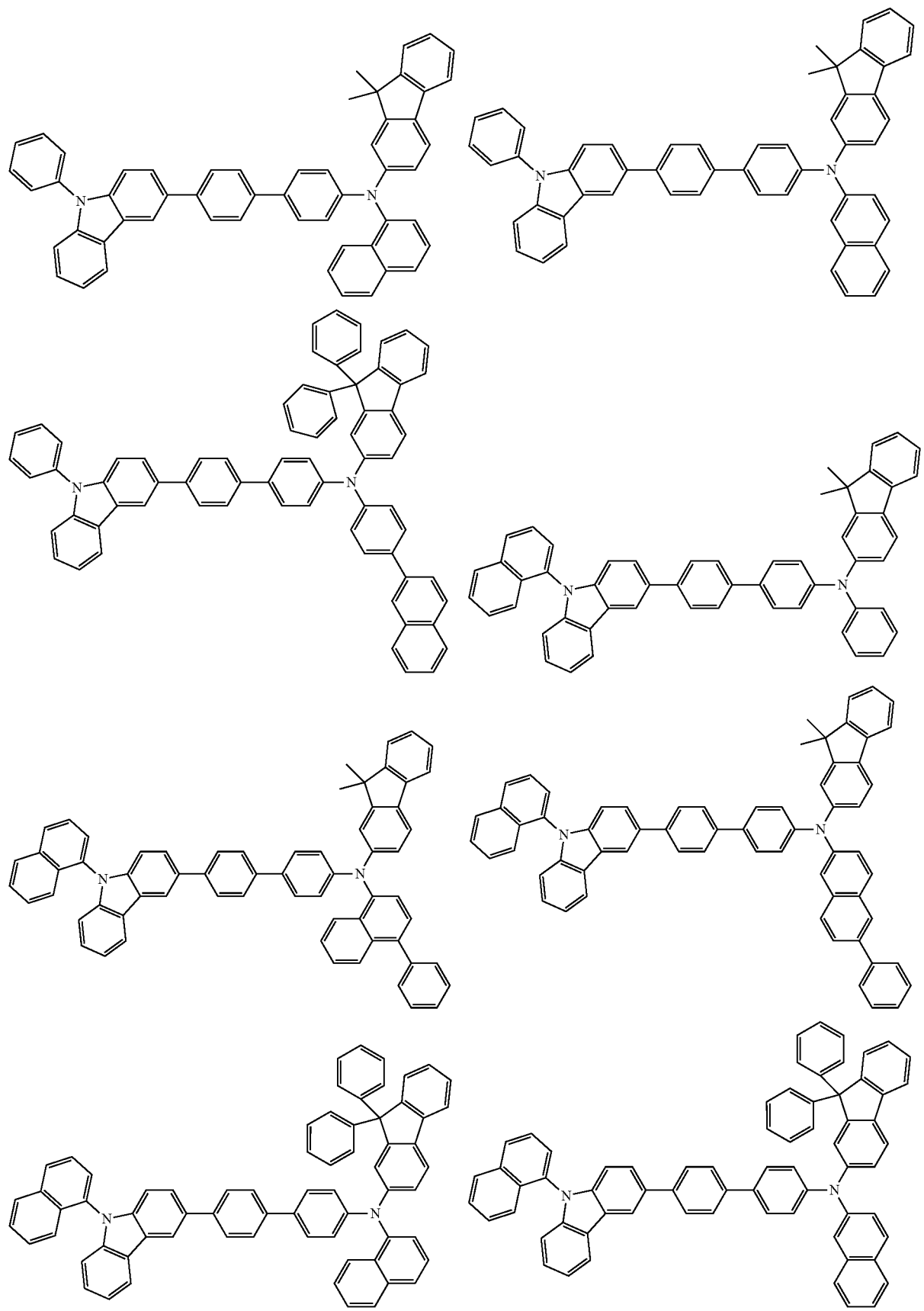

-continued
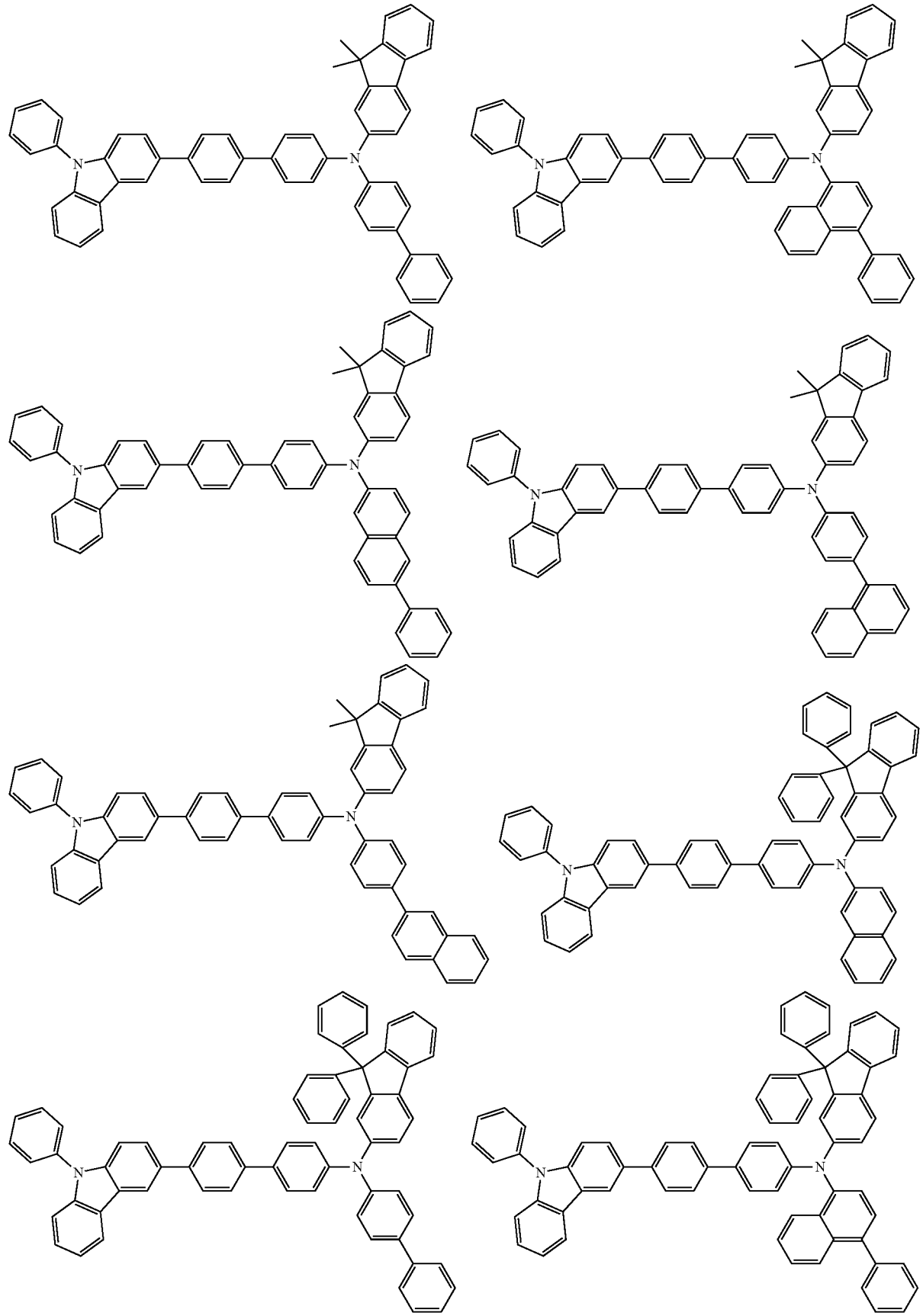

-continued
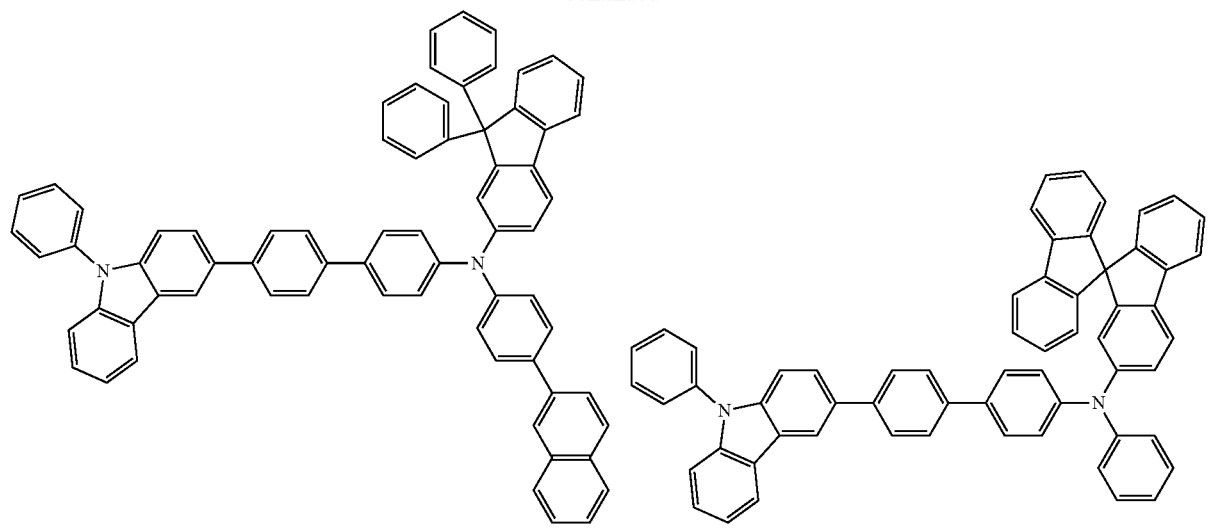
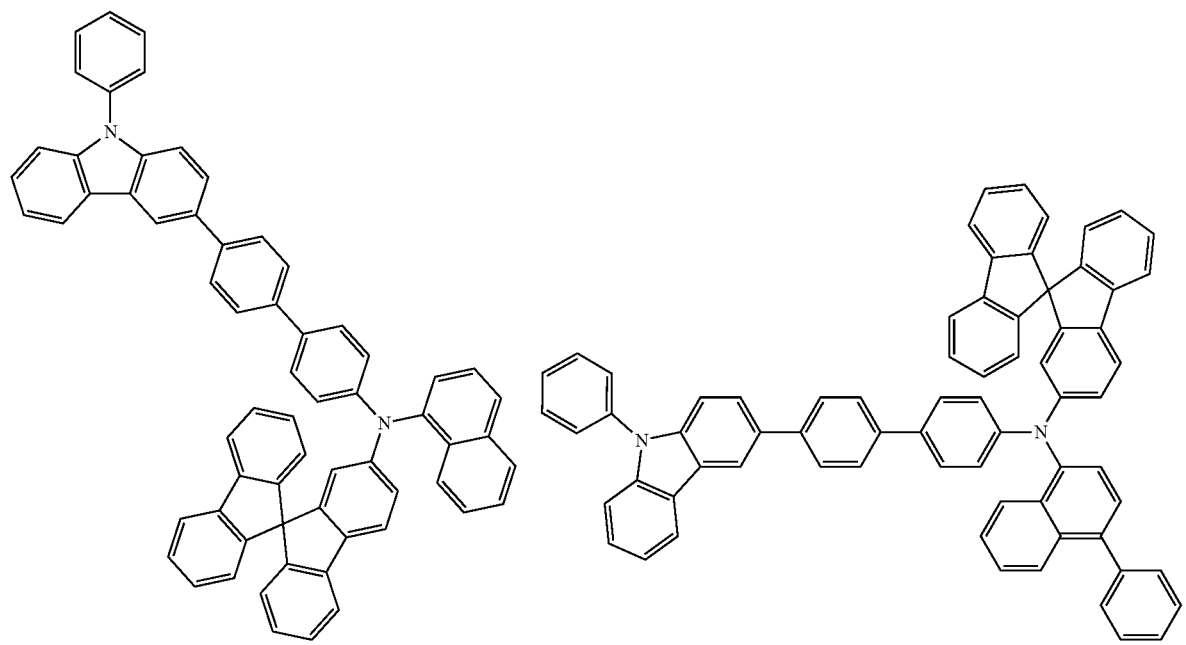
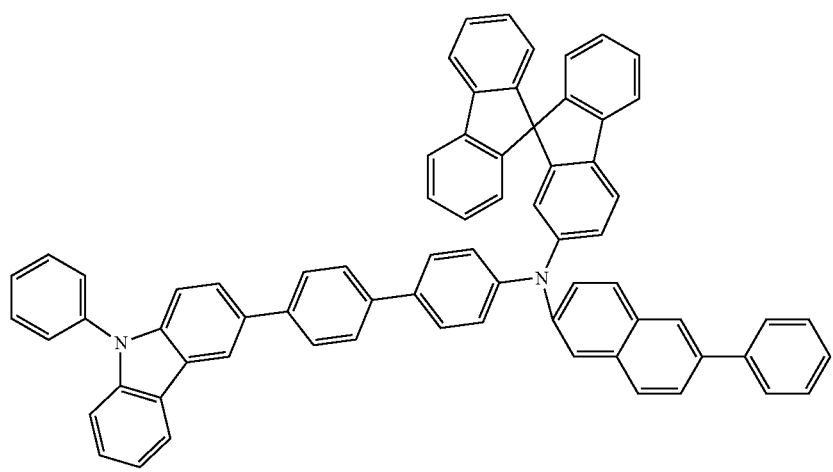

-continued
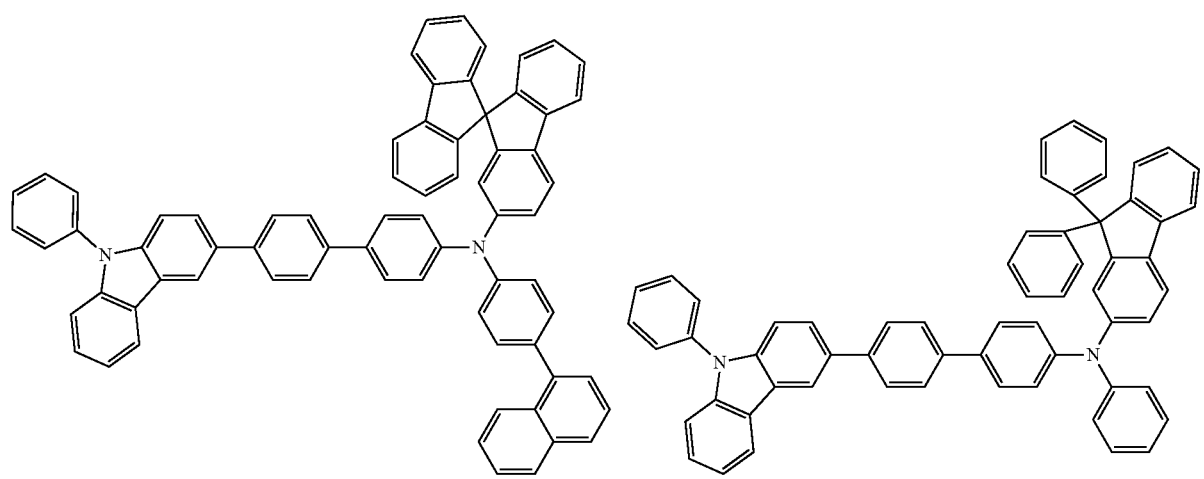
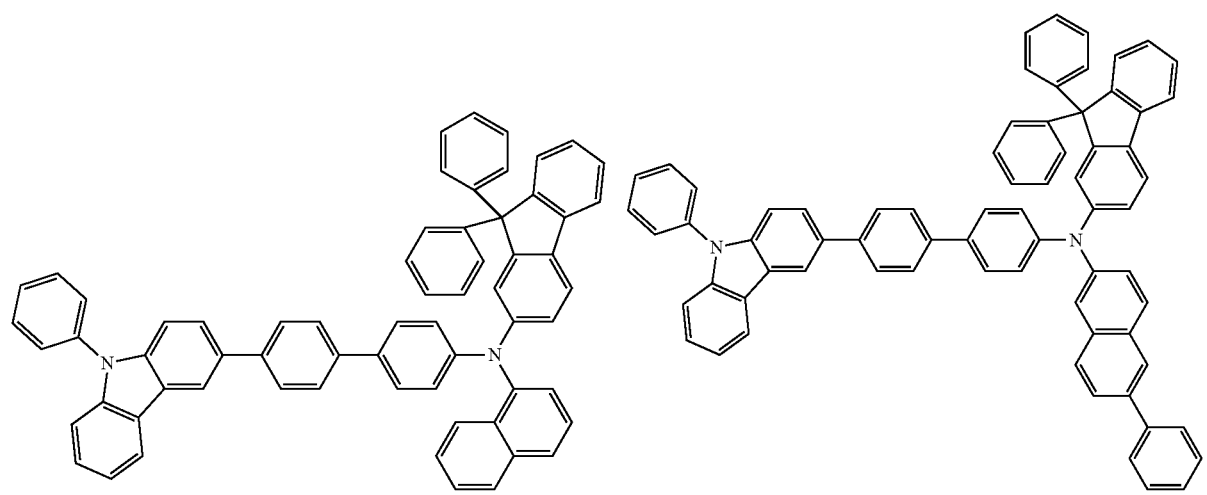
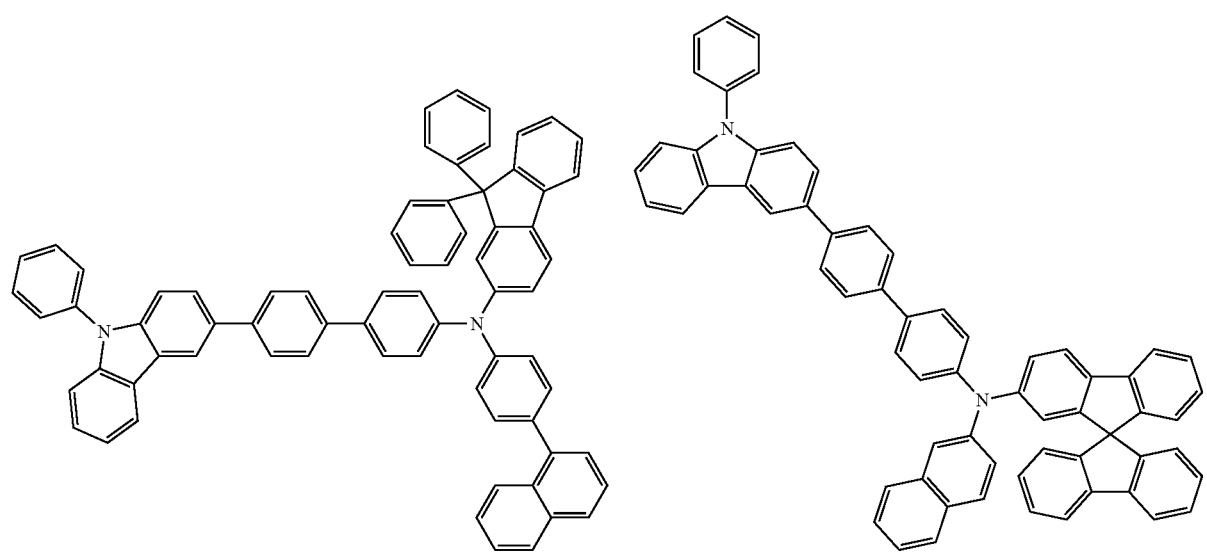

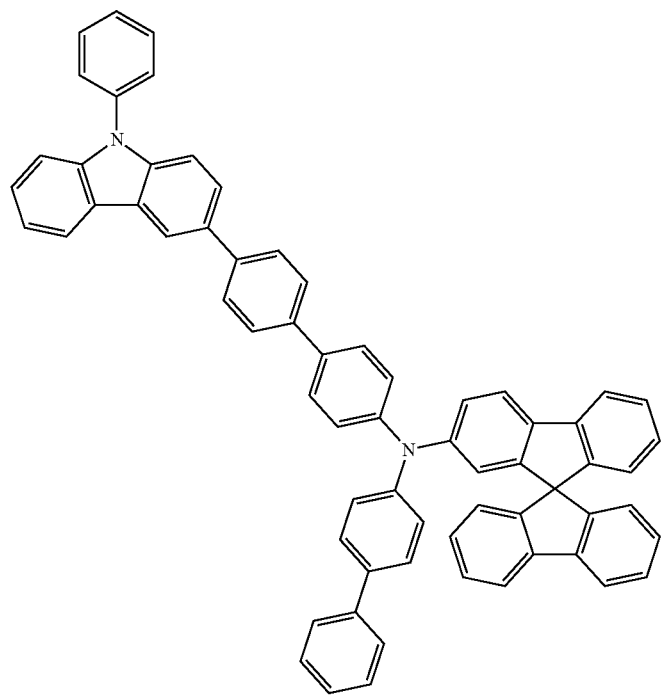
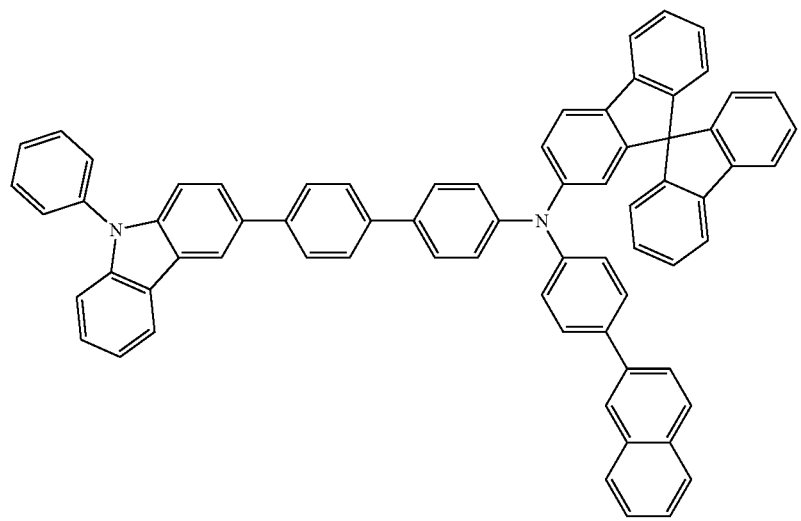
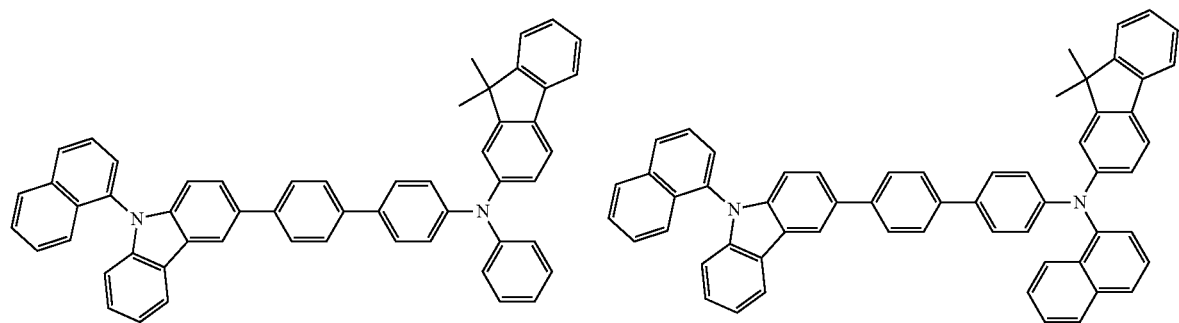

-continued
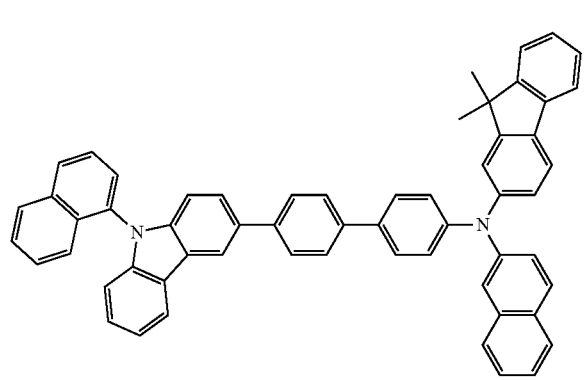 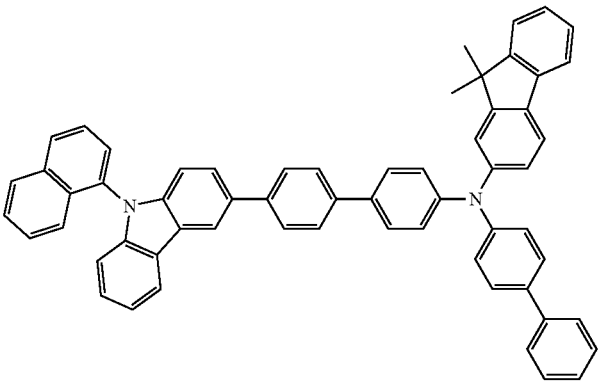
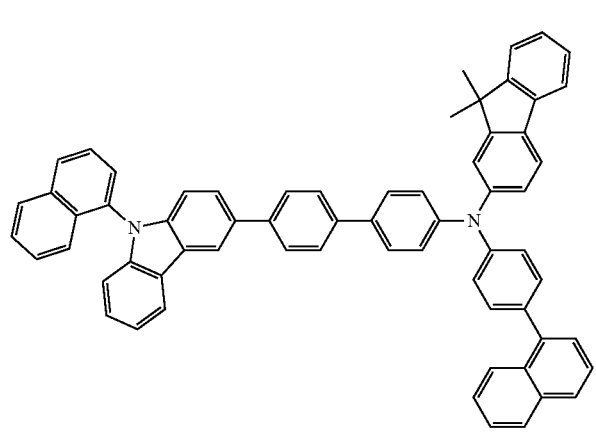 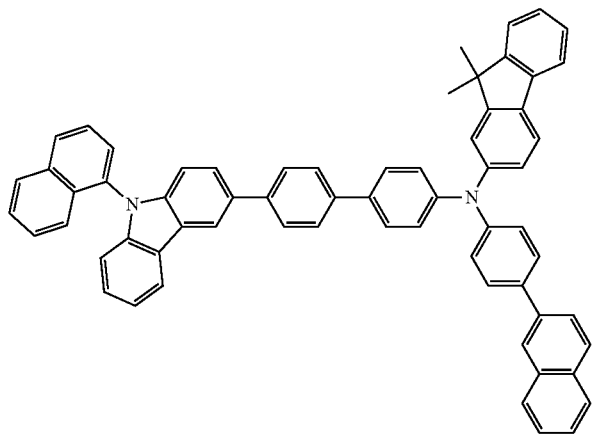
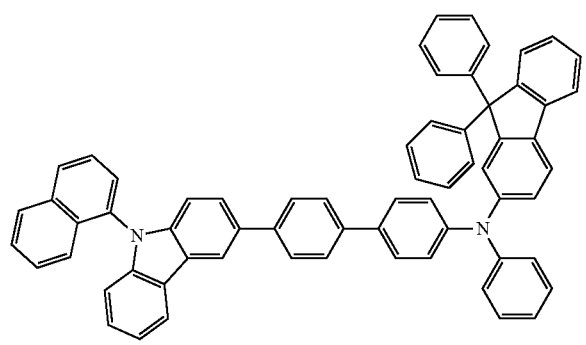 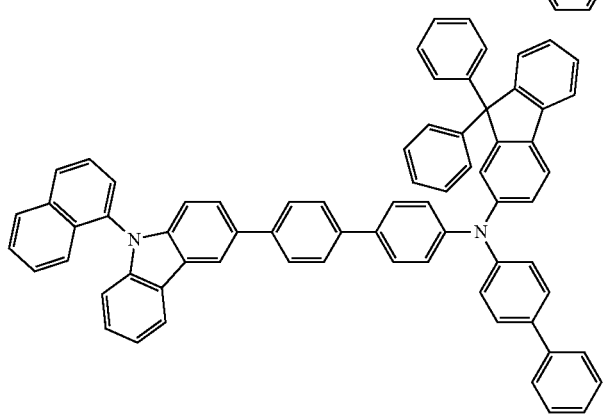
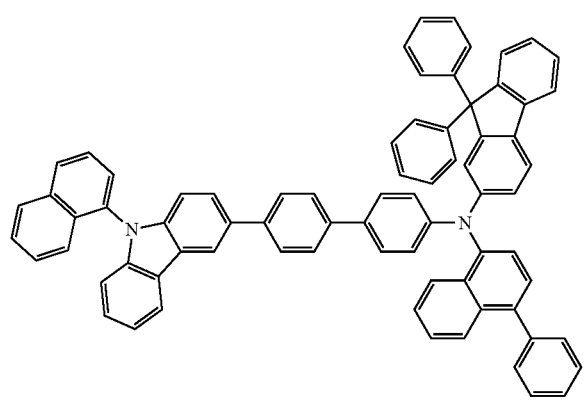 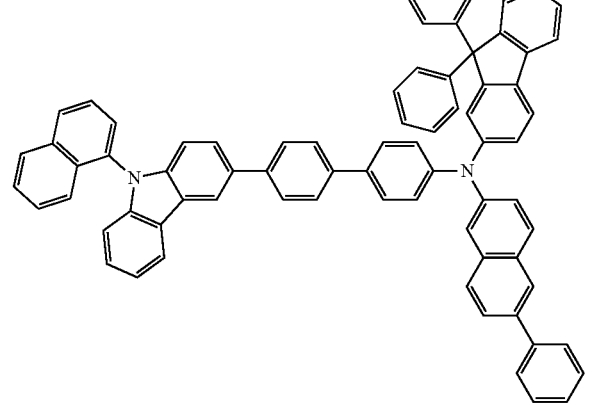

-continued
| 113 | 114 |
|---|---|
| 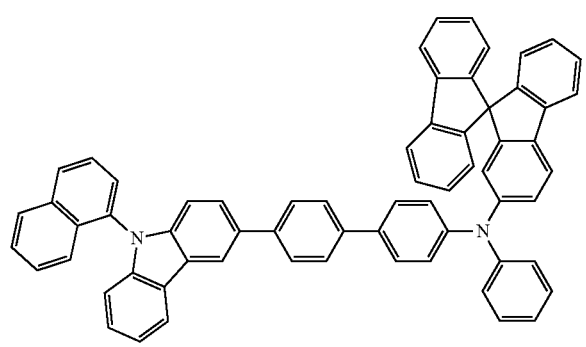 | 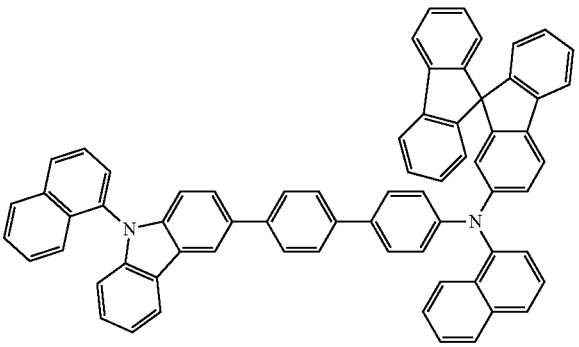 |
| 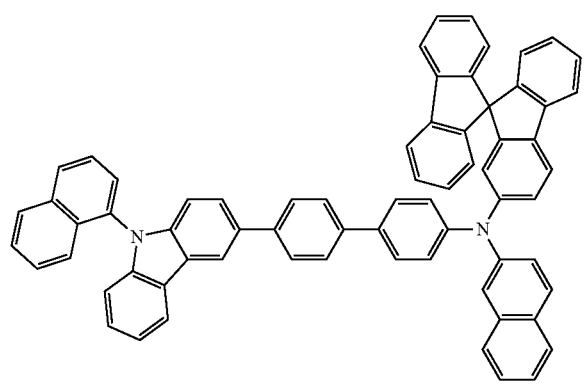 | 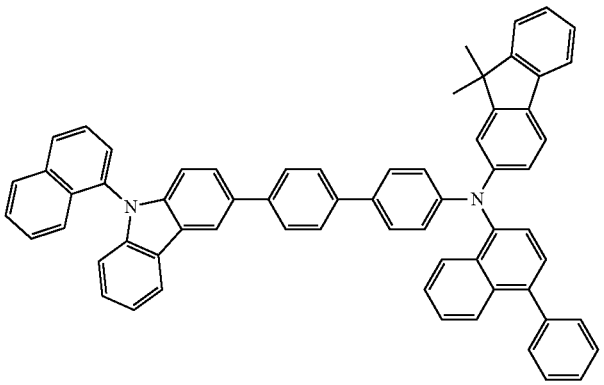 |
| 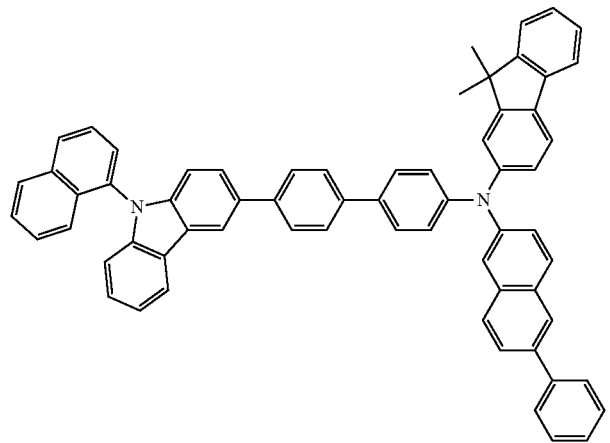 | 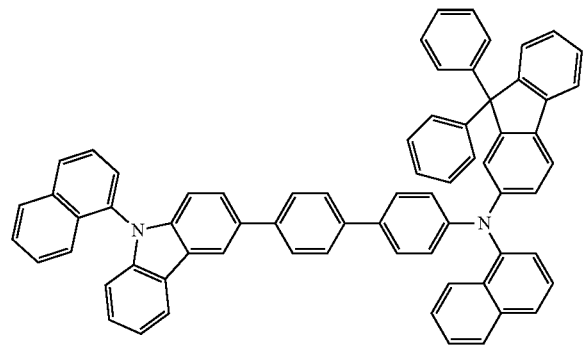 |
| 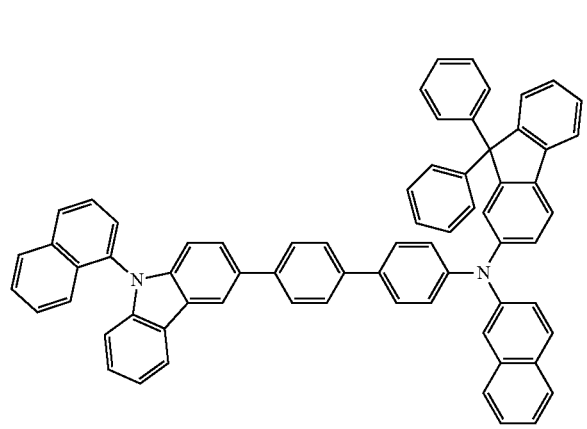 | 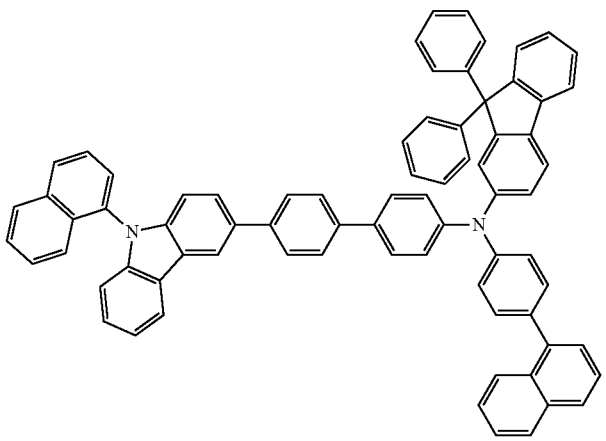 |

-continued
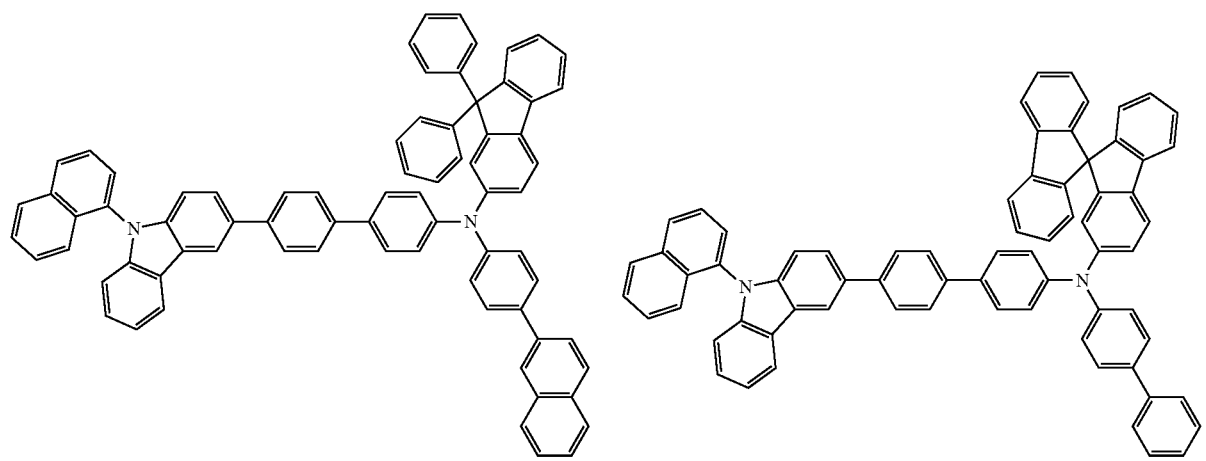
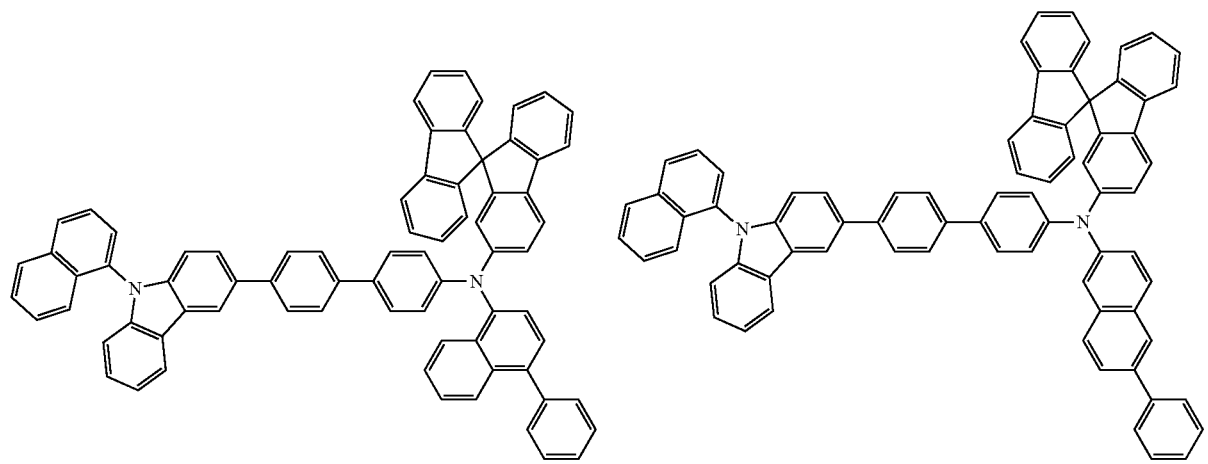
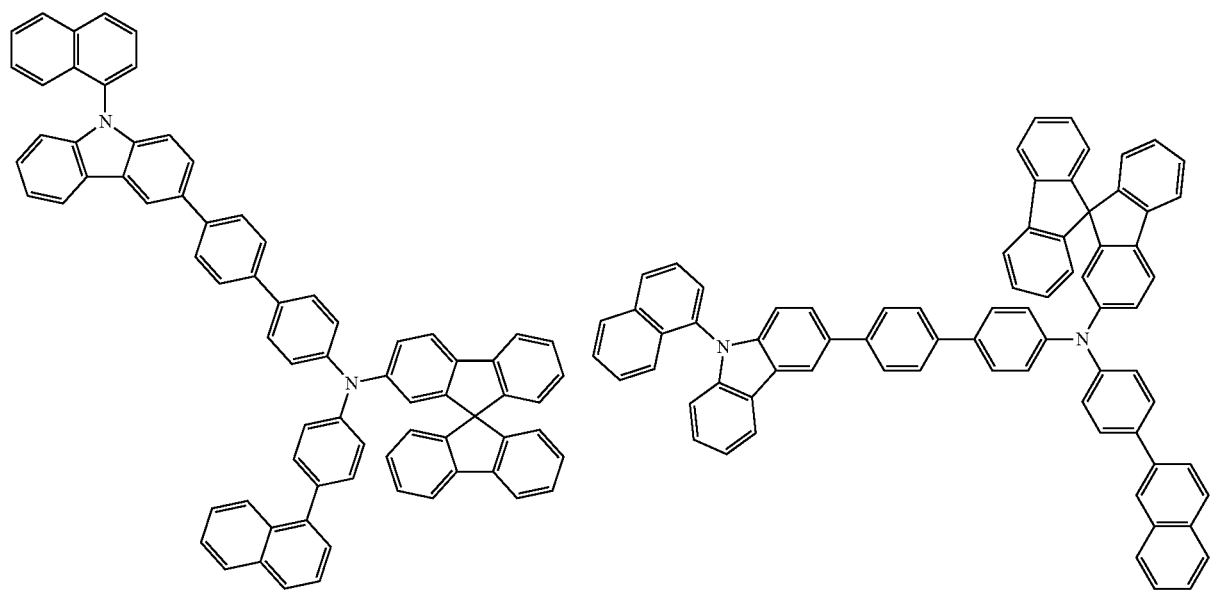

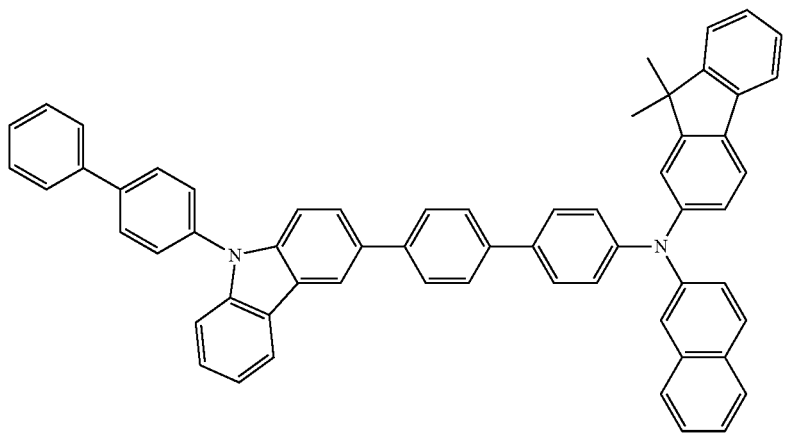
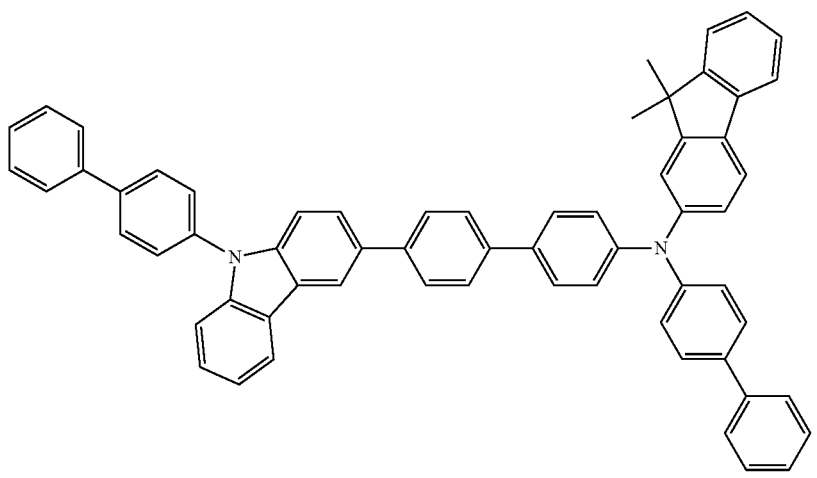
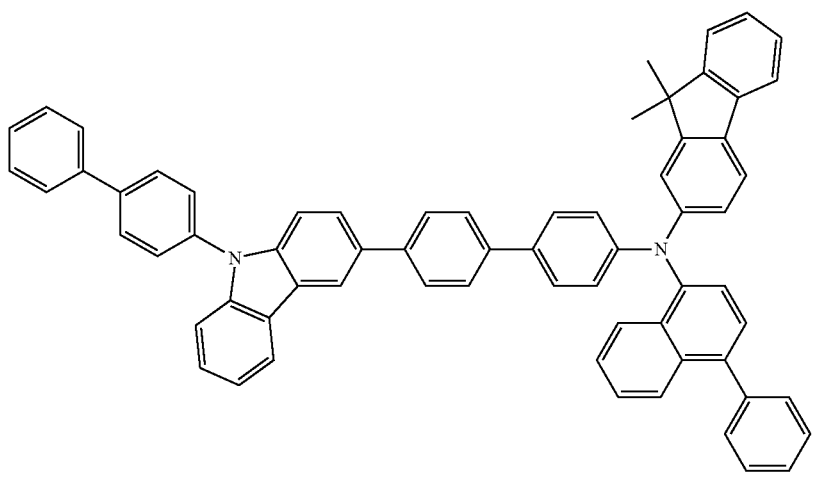

-continued
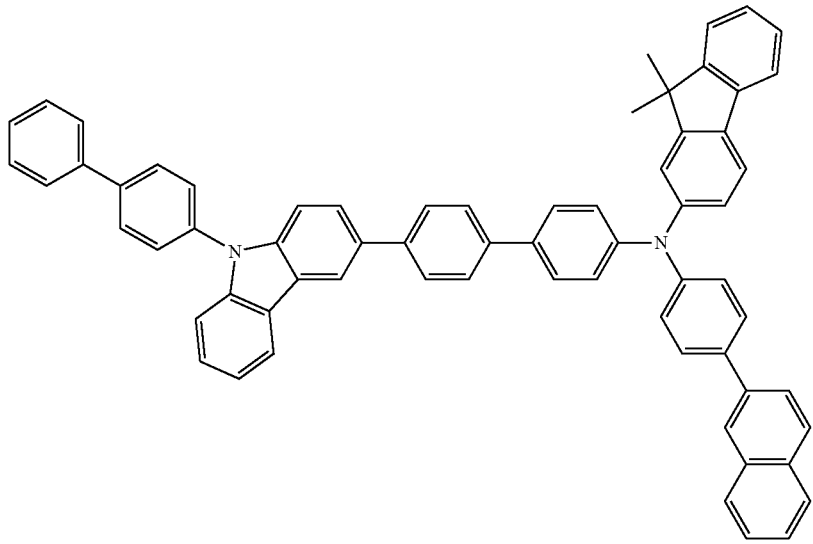
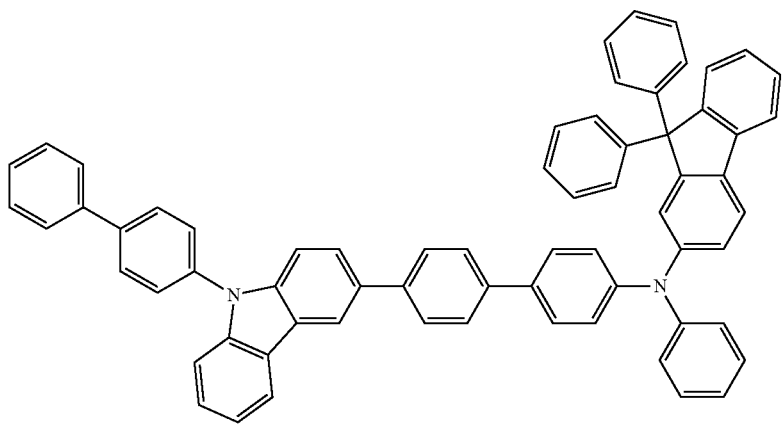
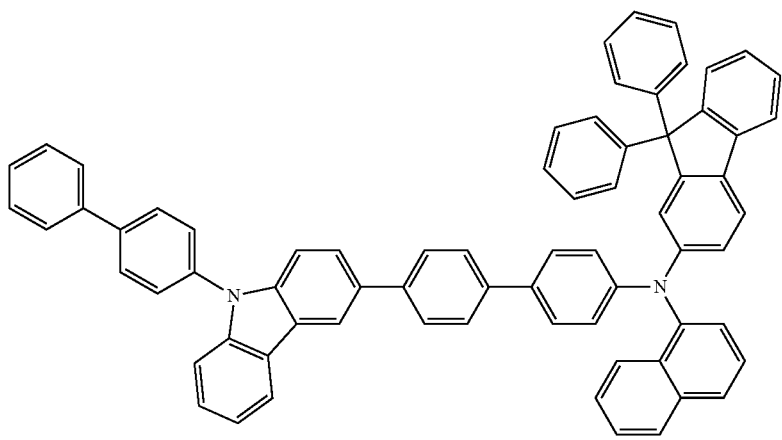

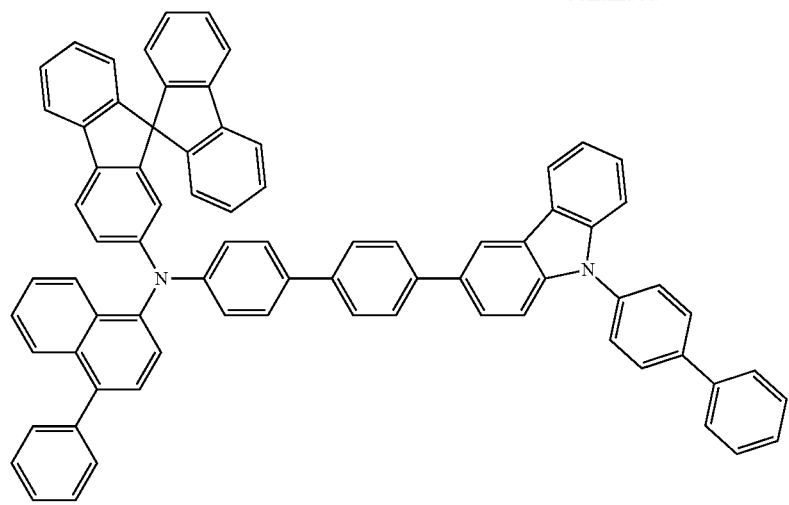
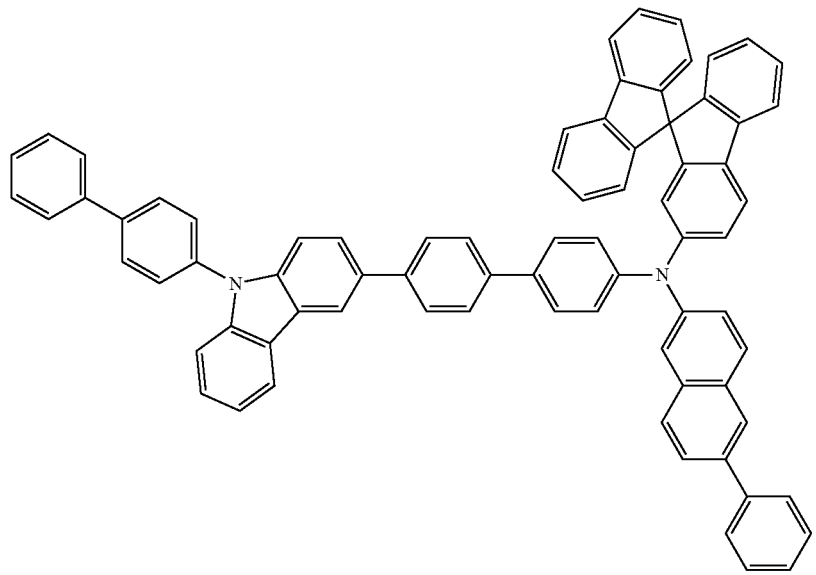
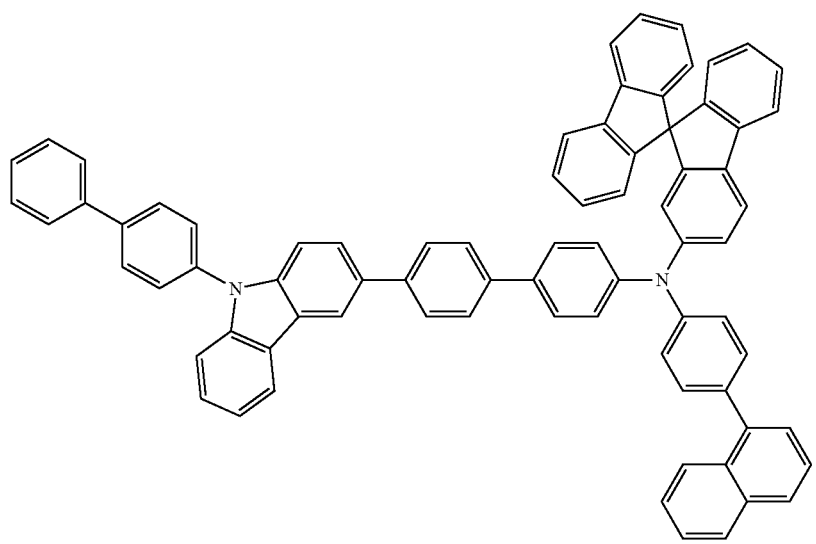

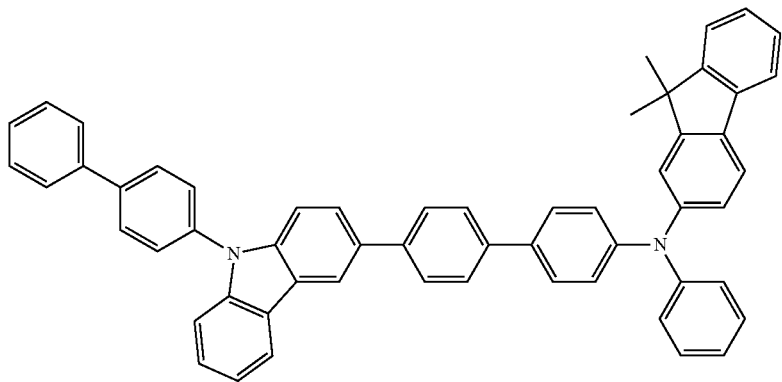
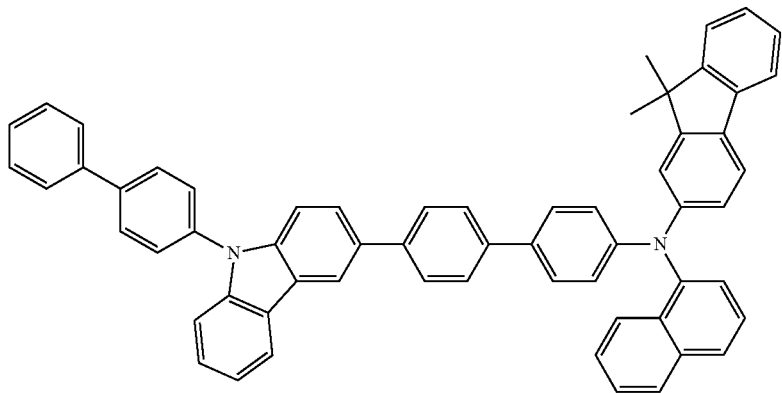
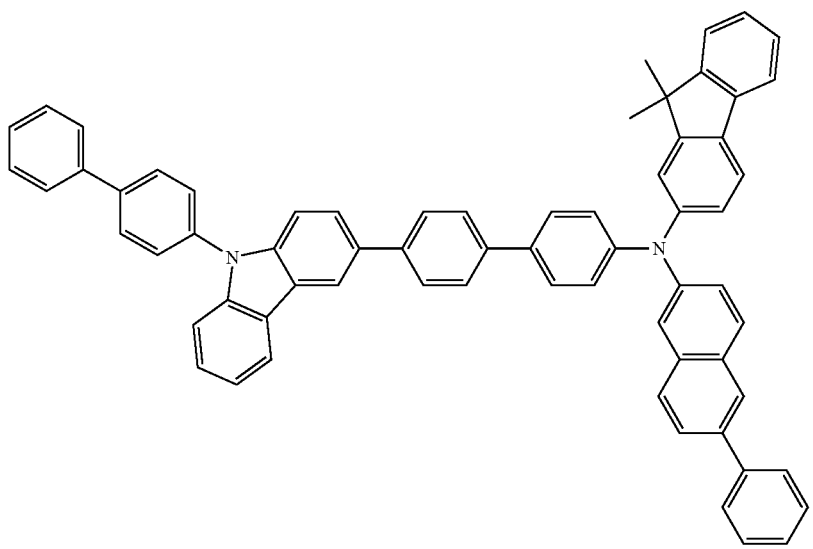

-continued
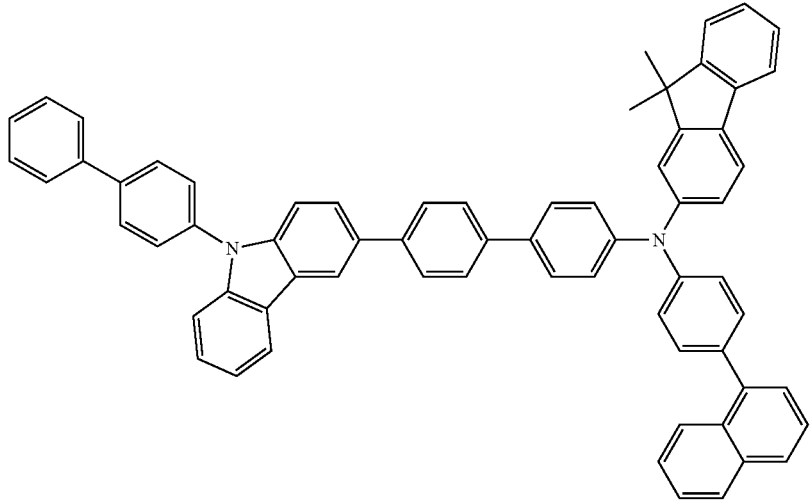
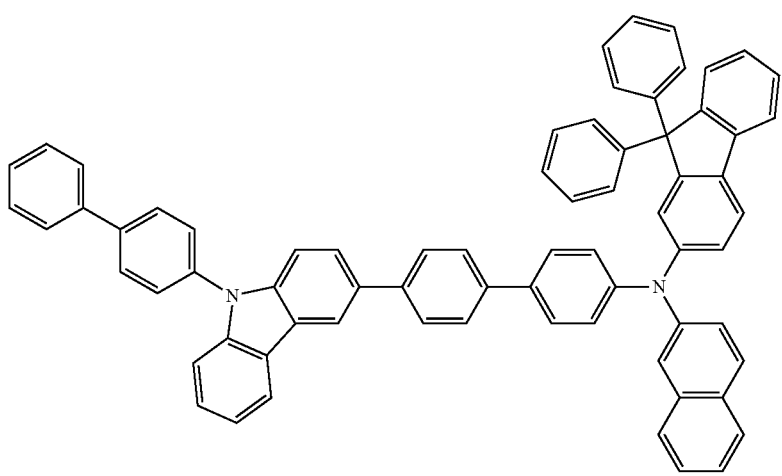
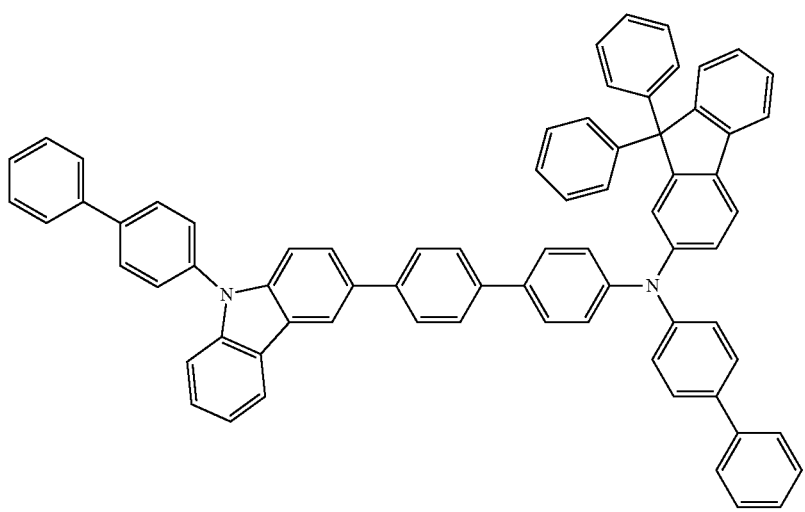

-continued
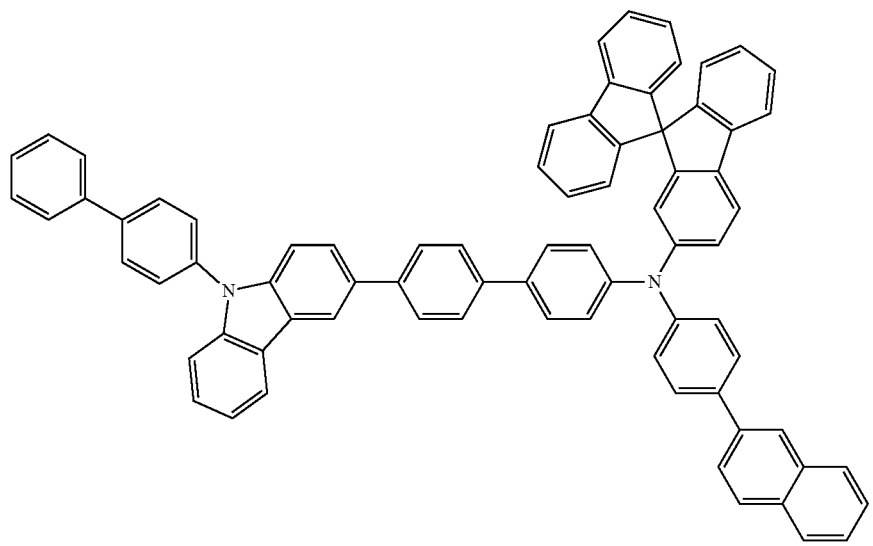
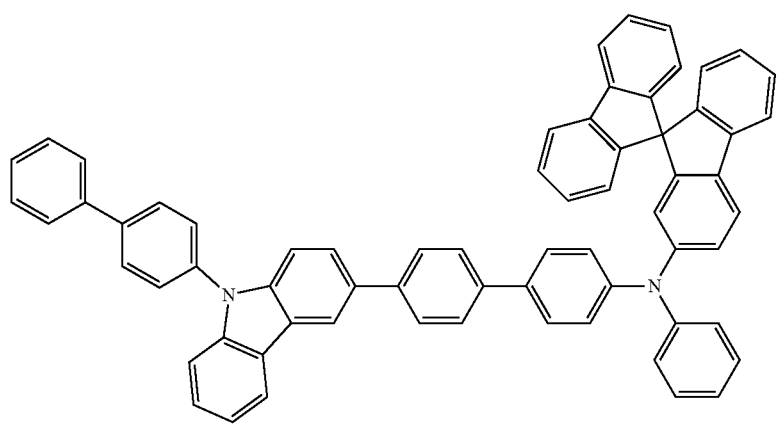
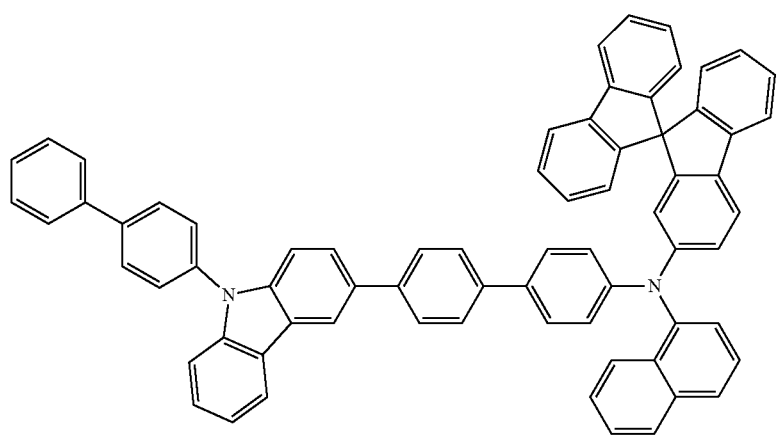

-continued
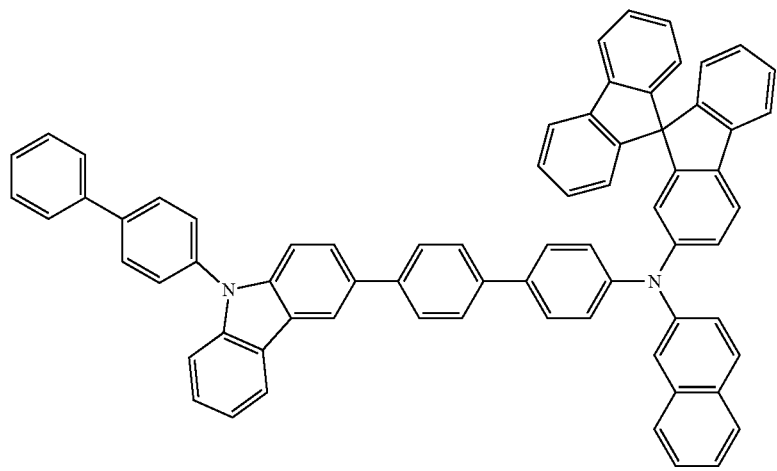
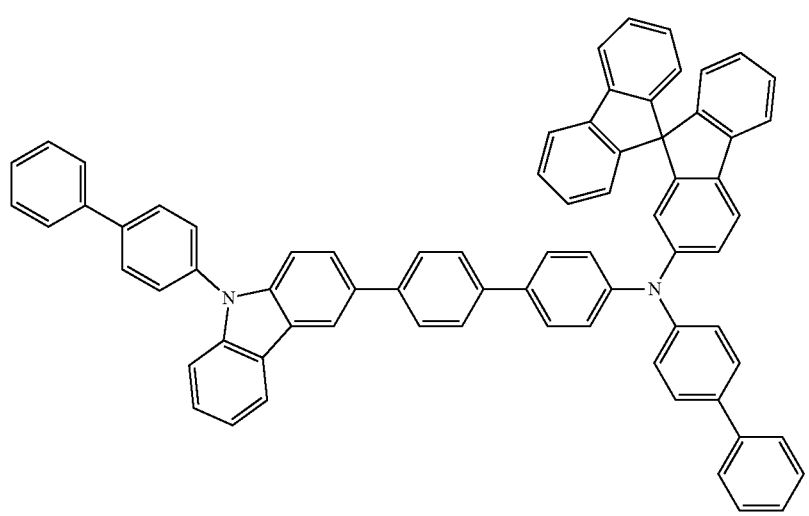
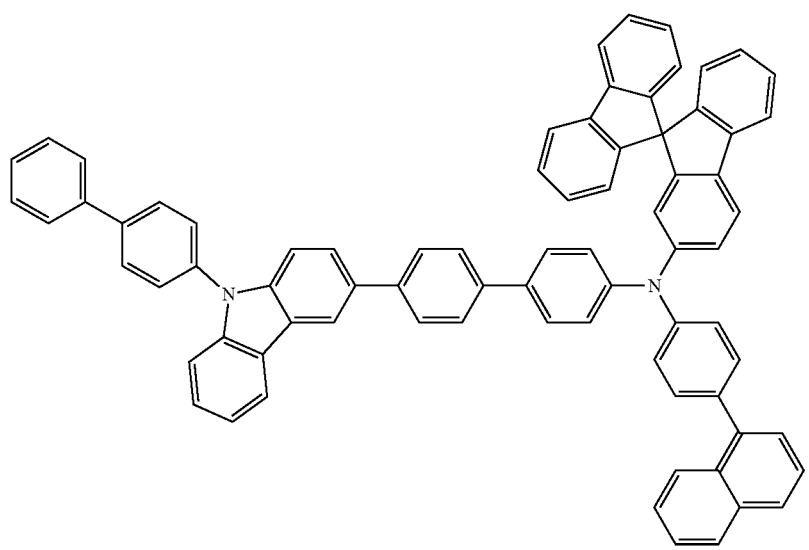

-continued
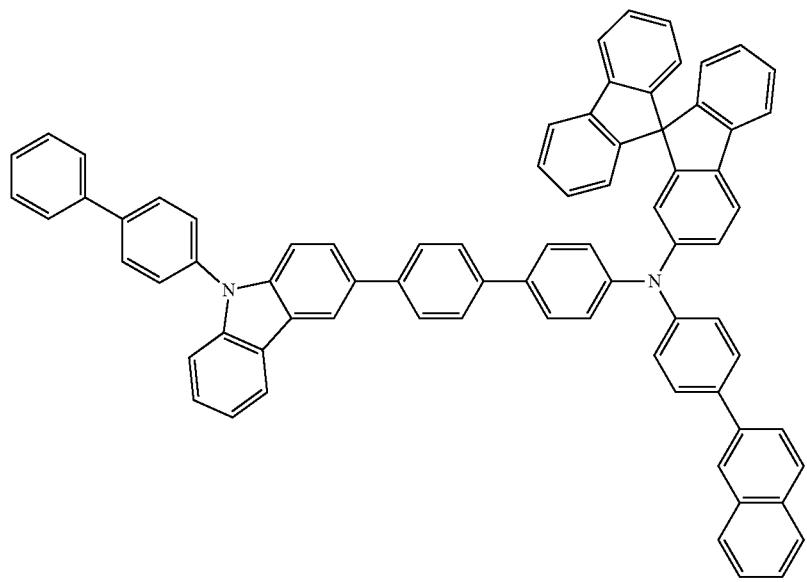
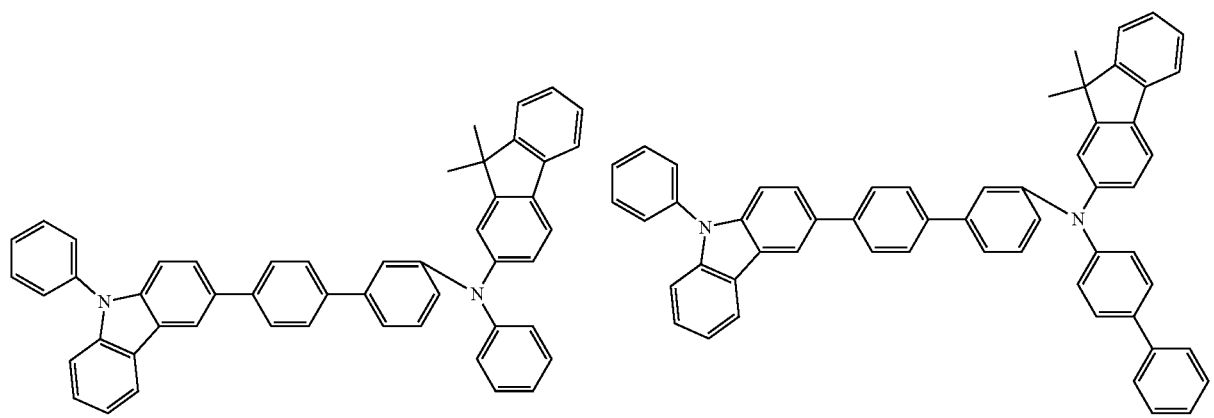
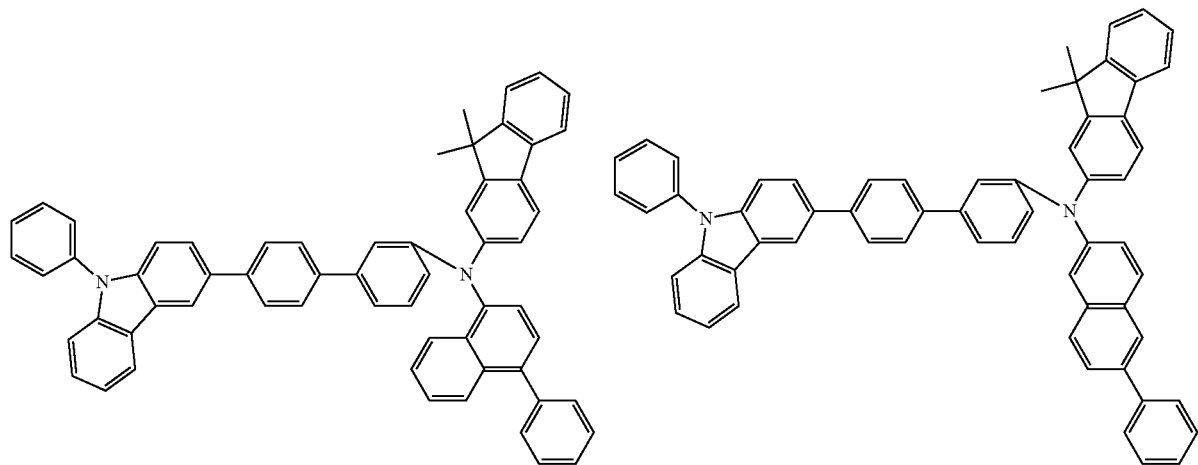

-continued
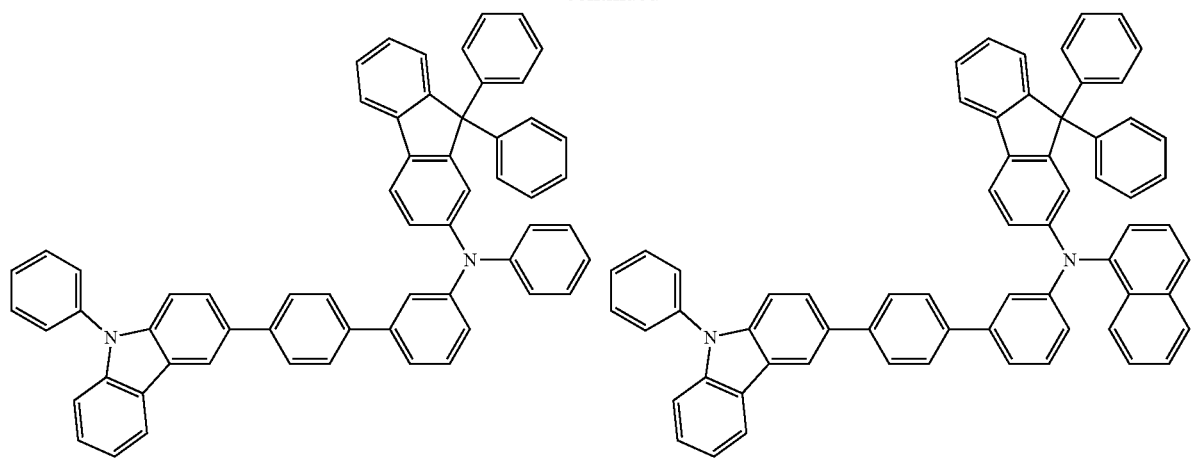
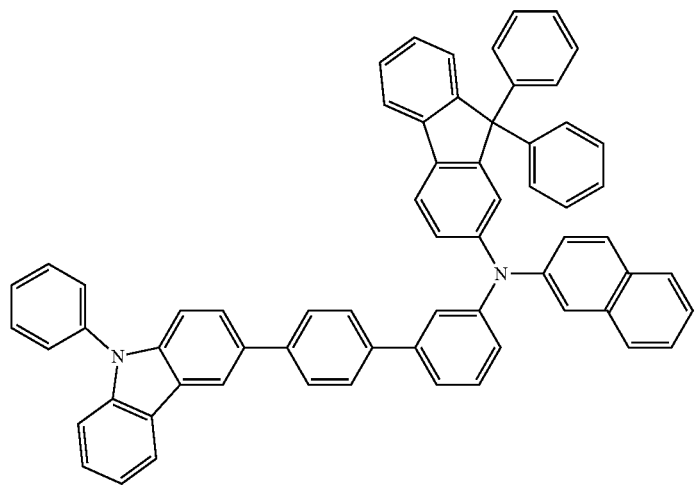
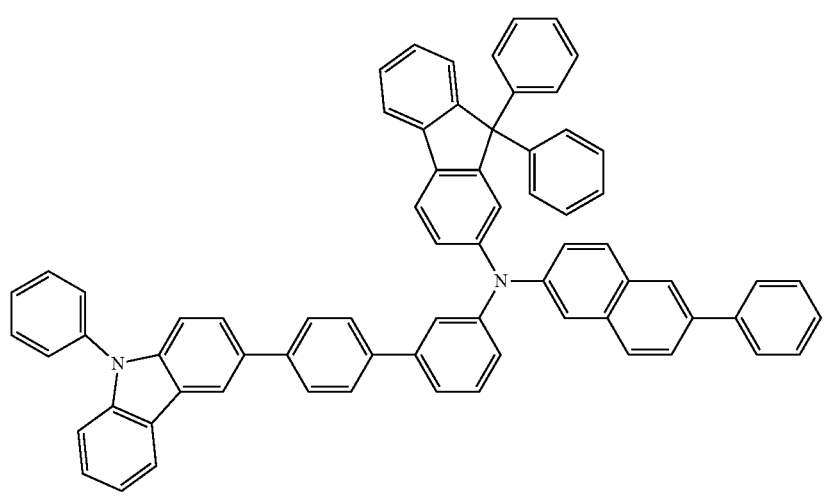

-continued
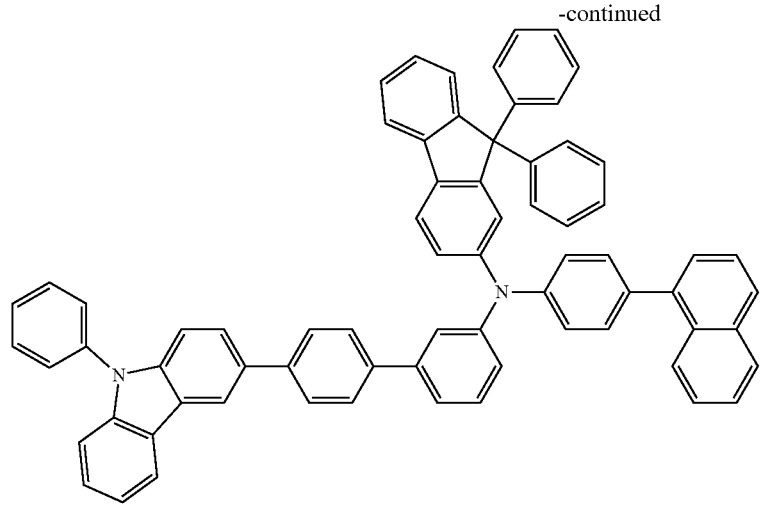
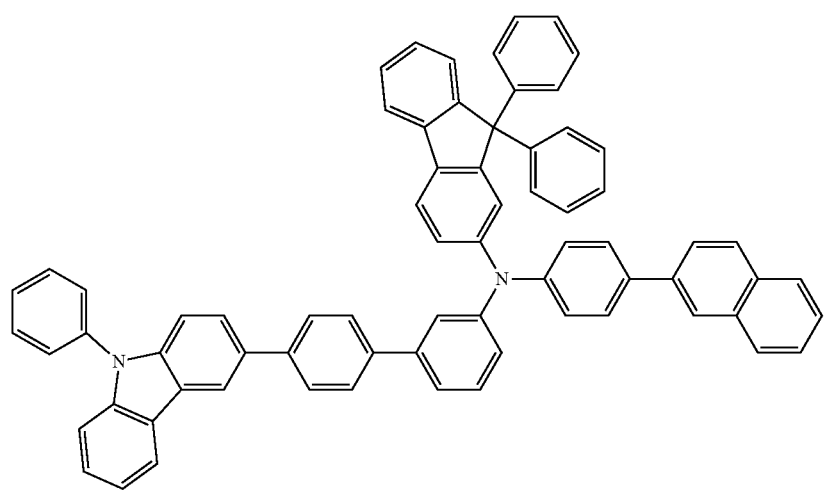
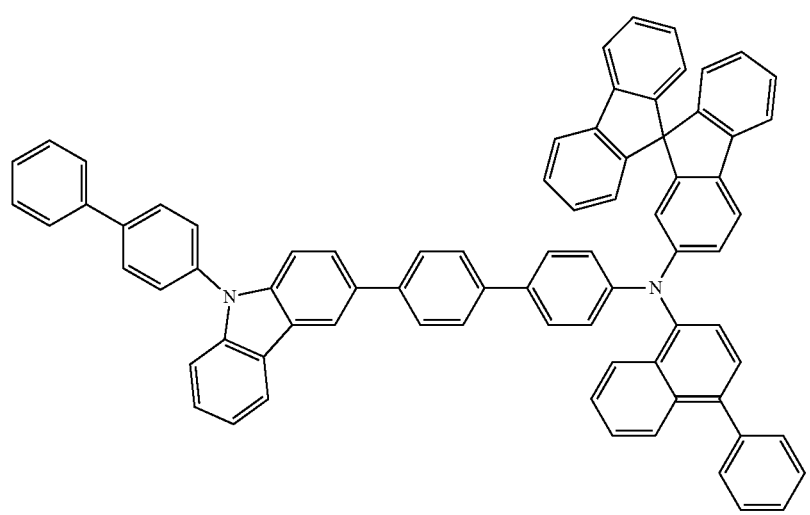

-continued
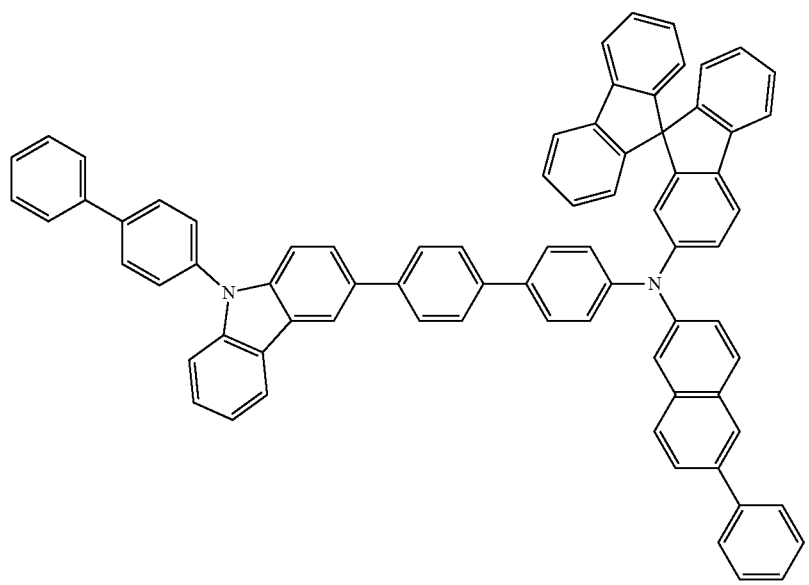
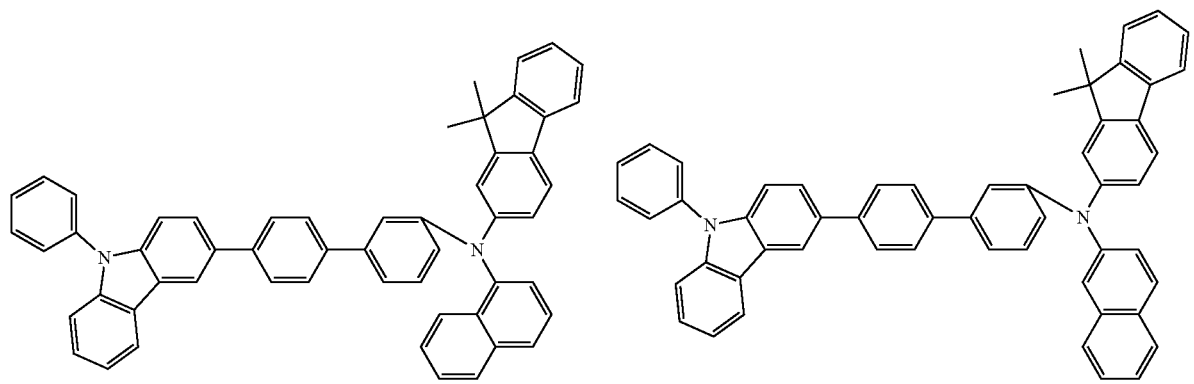
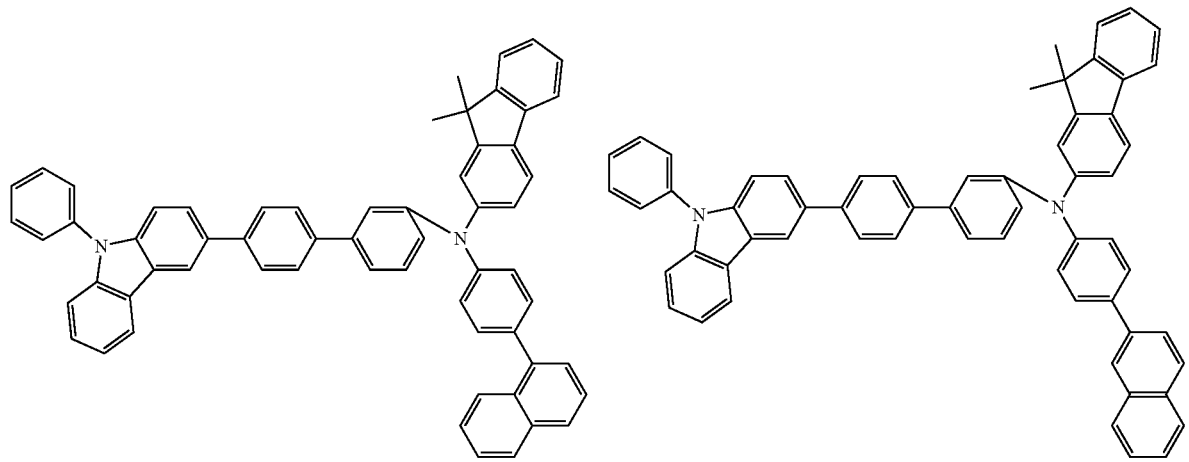

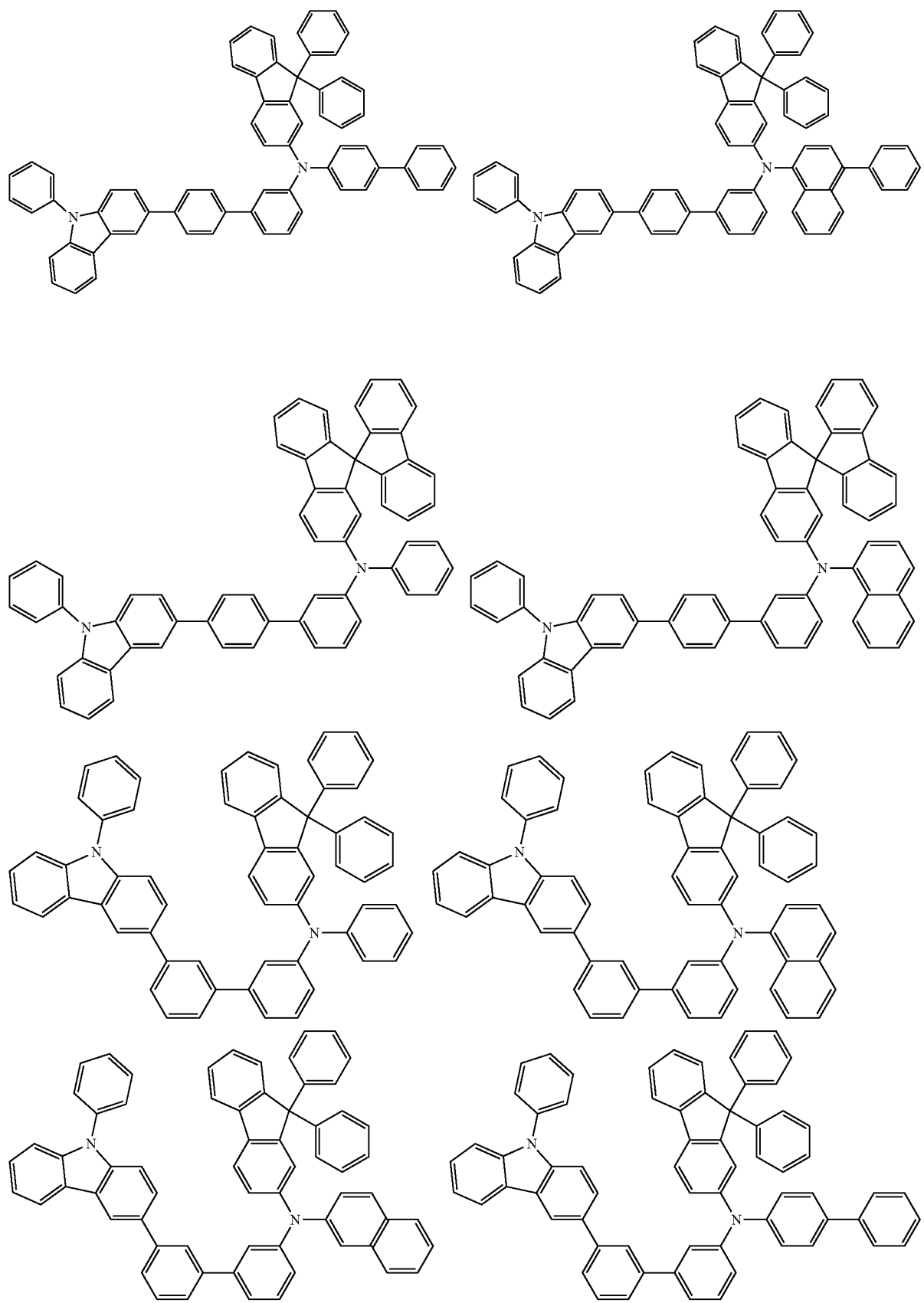

141 142
-continued
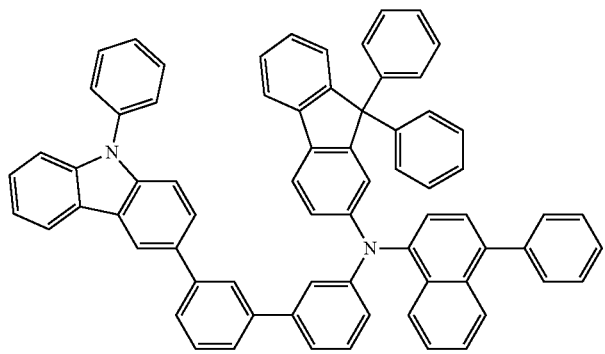
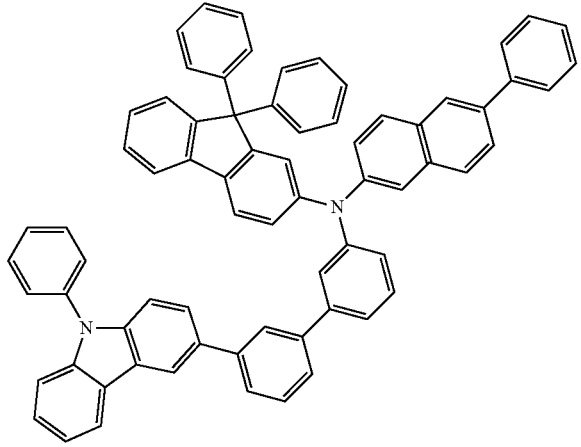
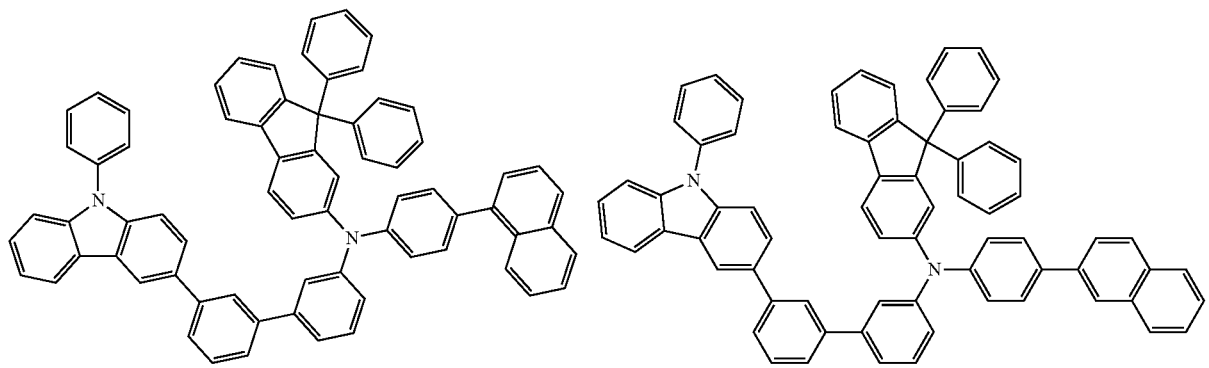
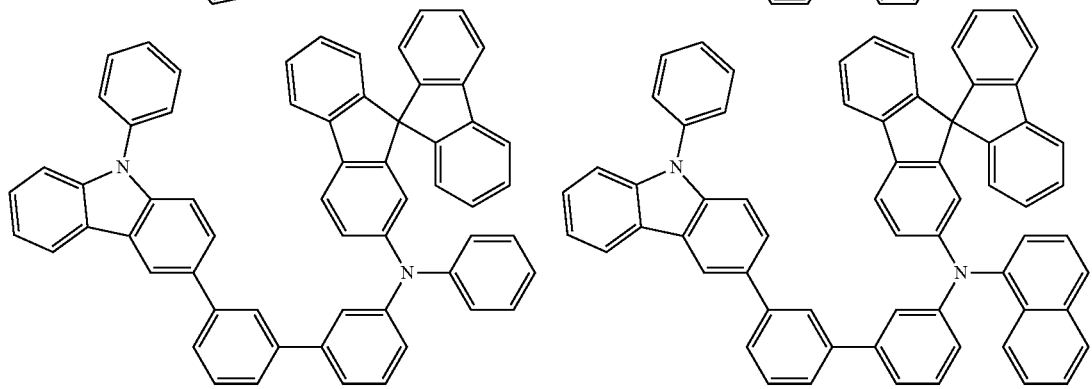
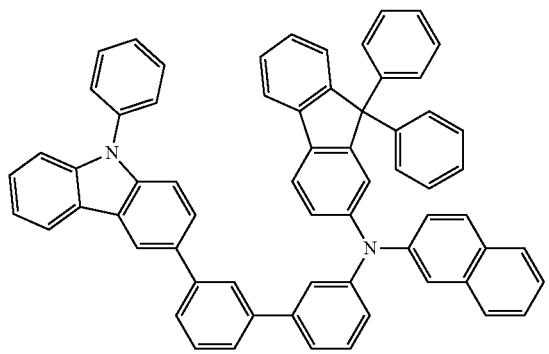
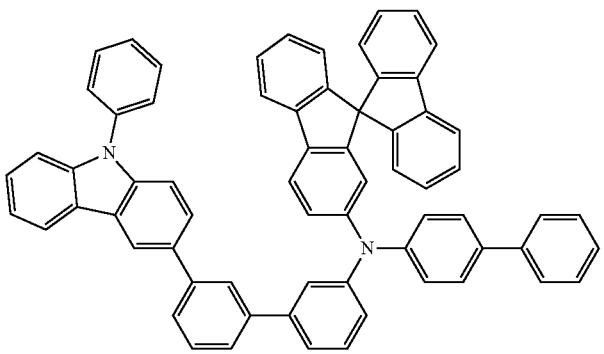

143 144
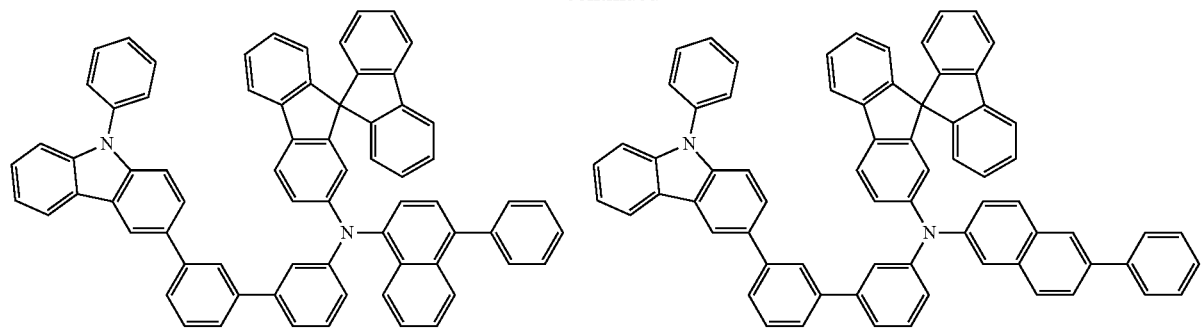
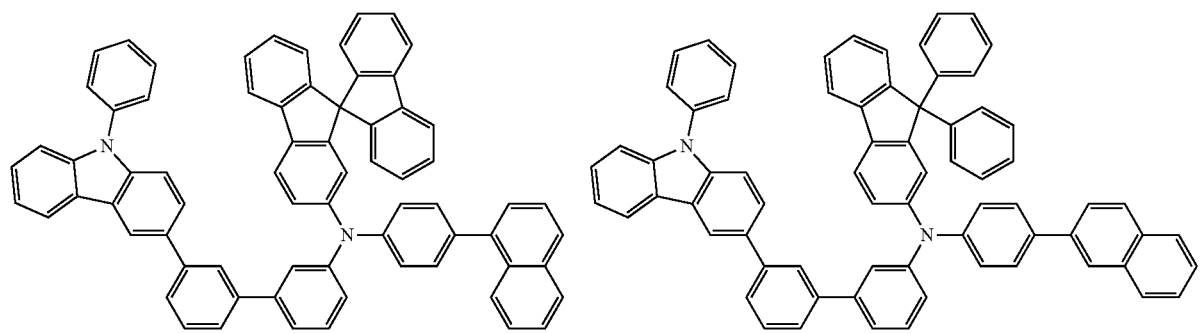
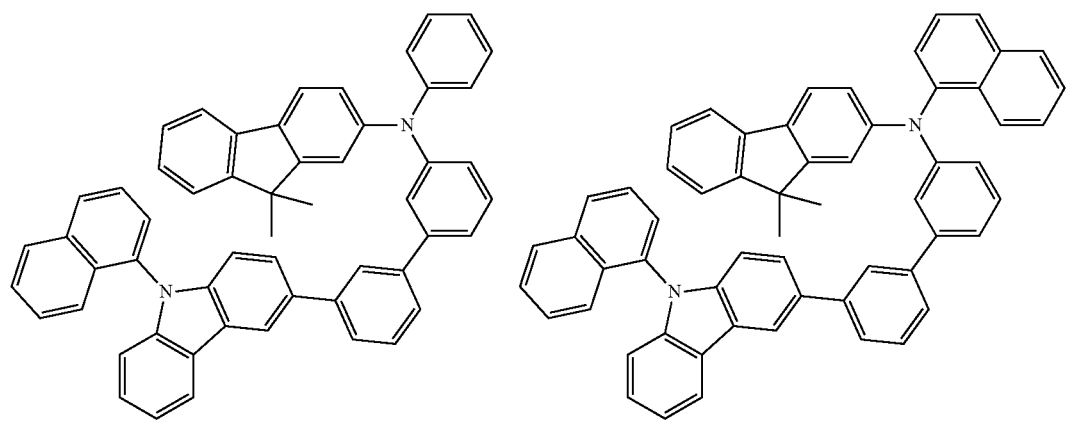
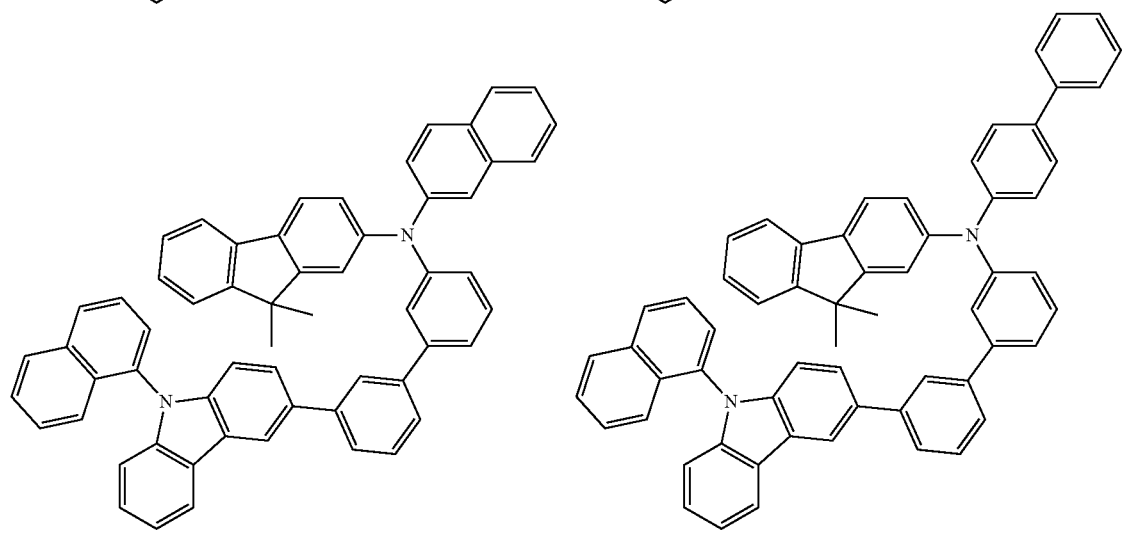

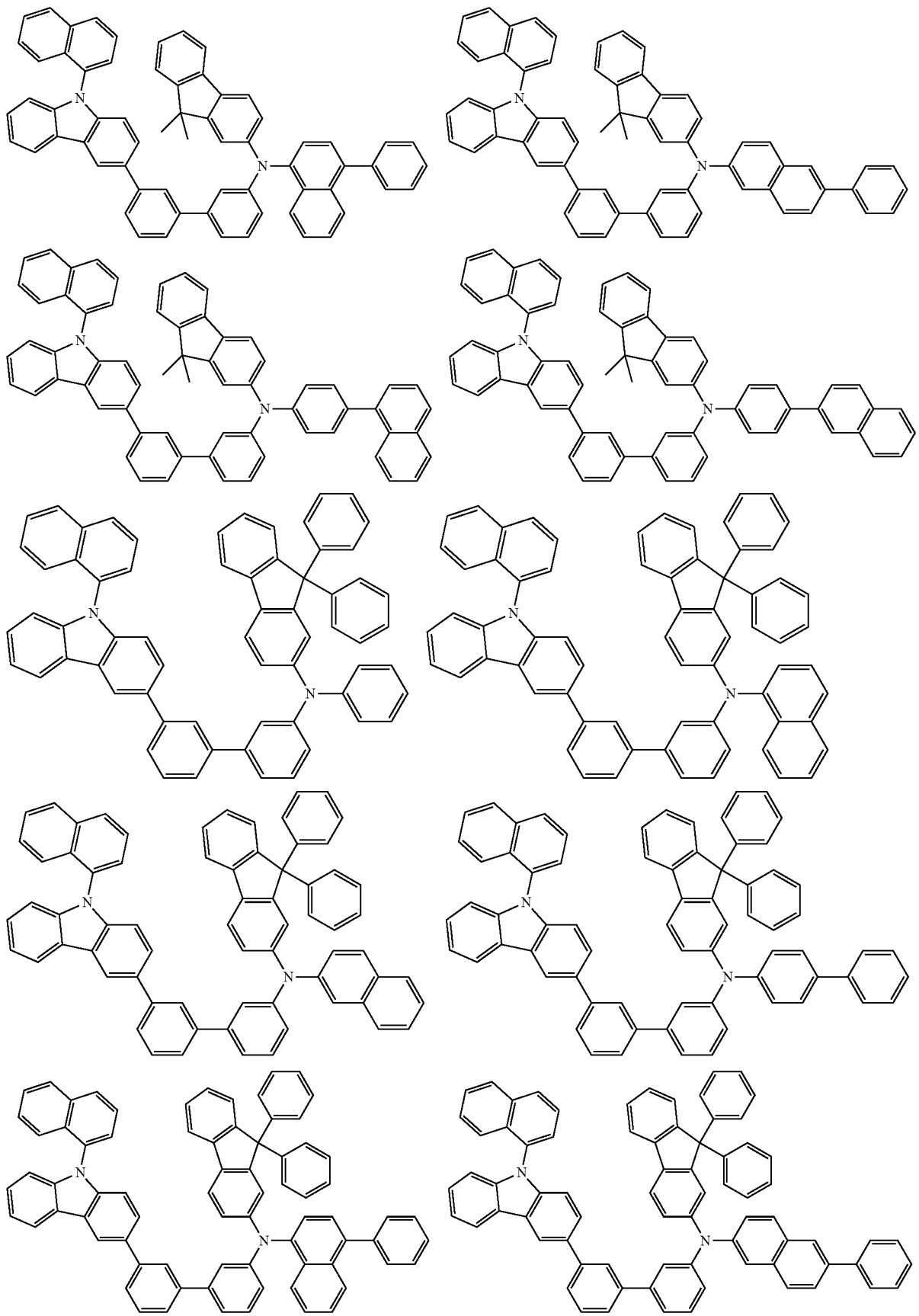

147 148
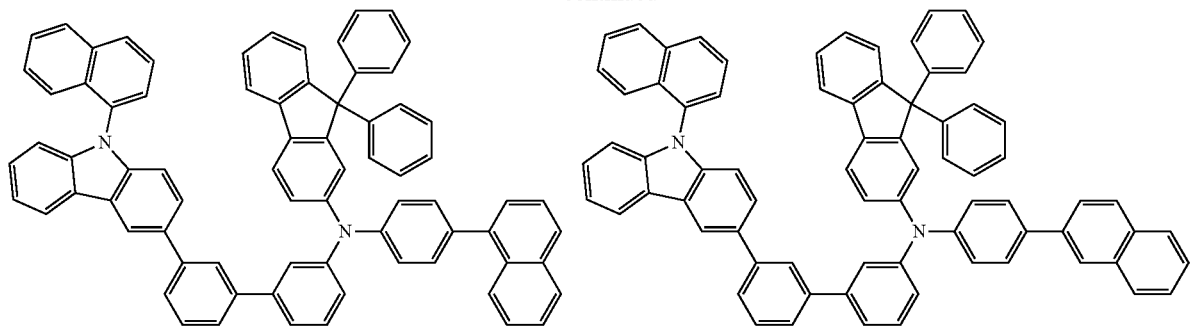
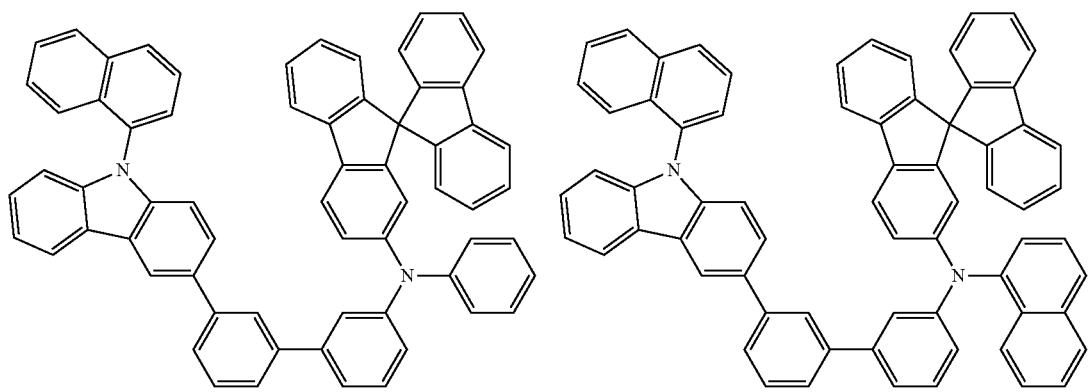
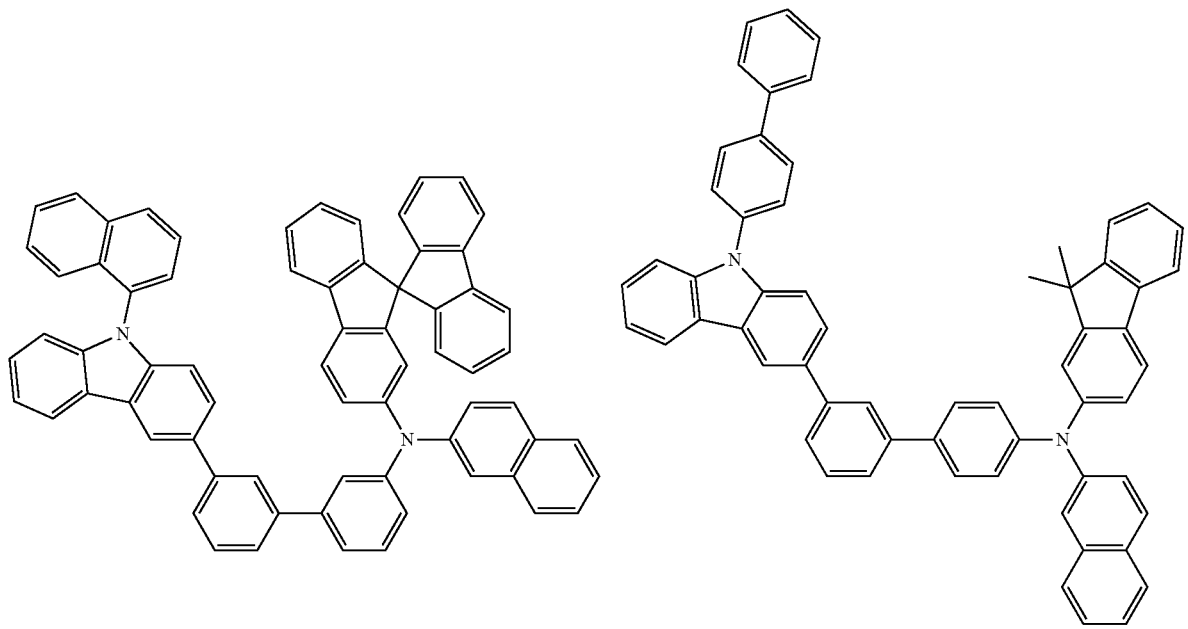

-continued
149
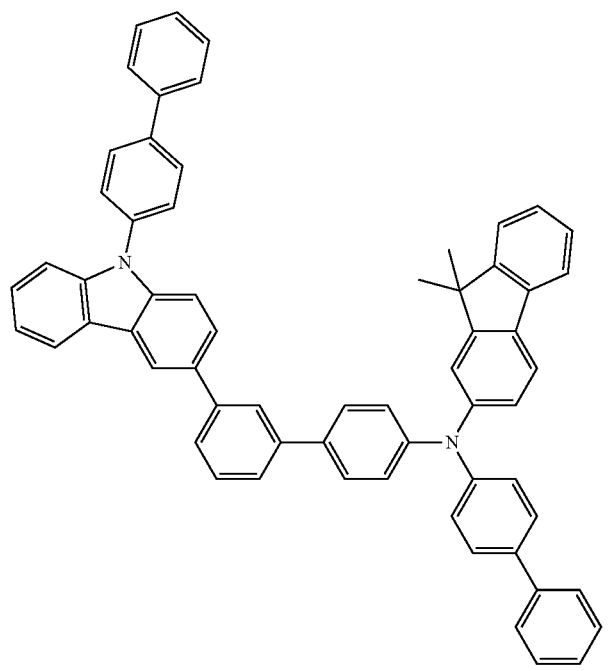
150
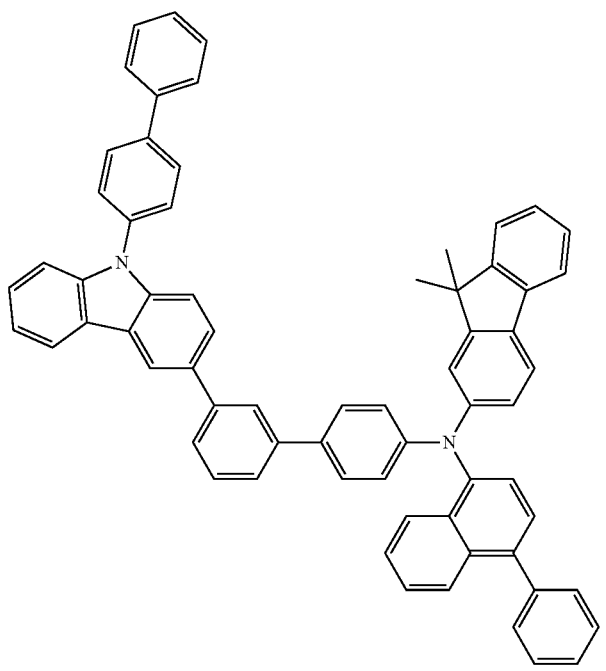
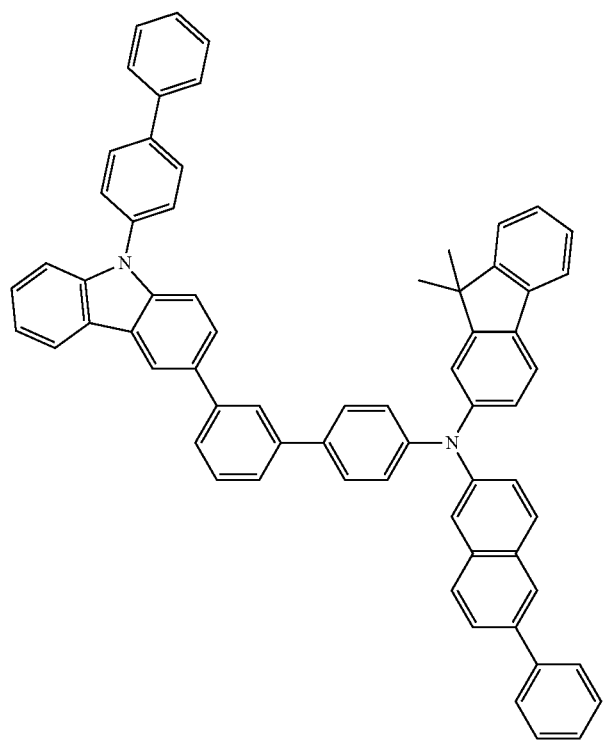
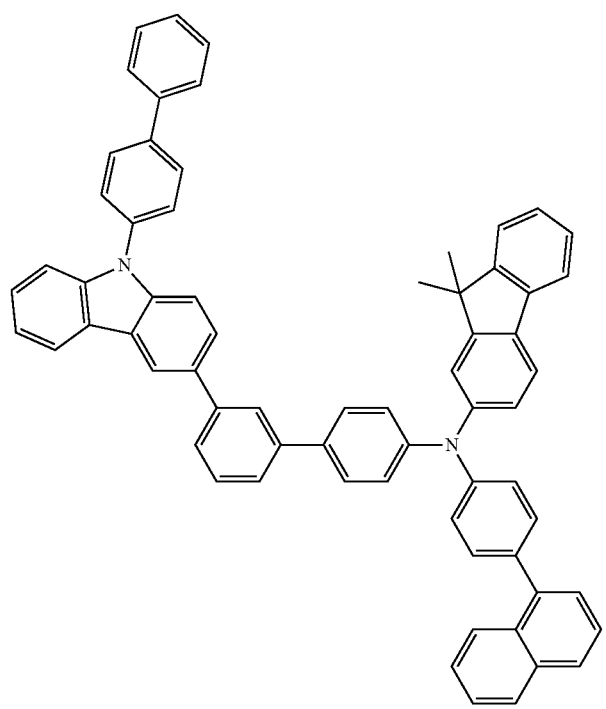

-continued
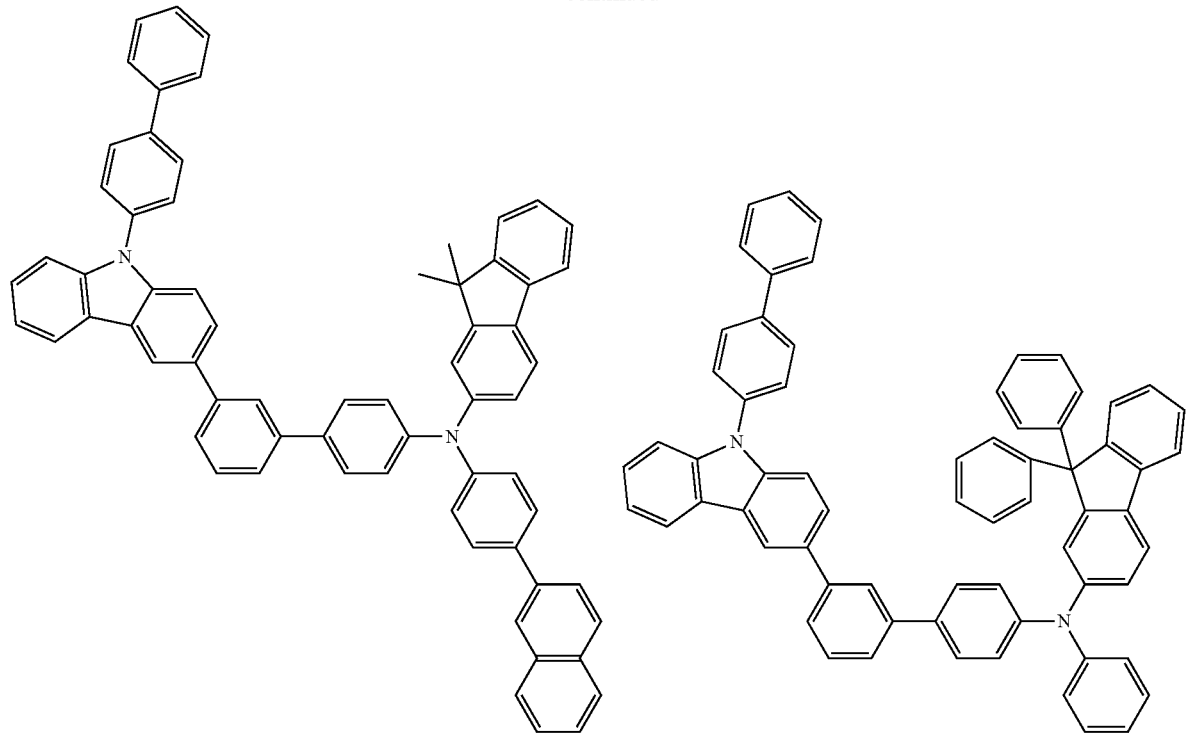
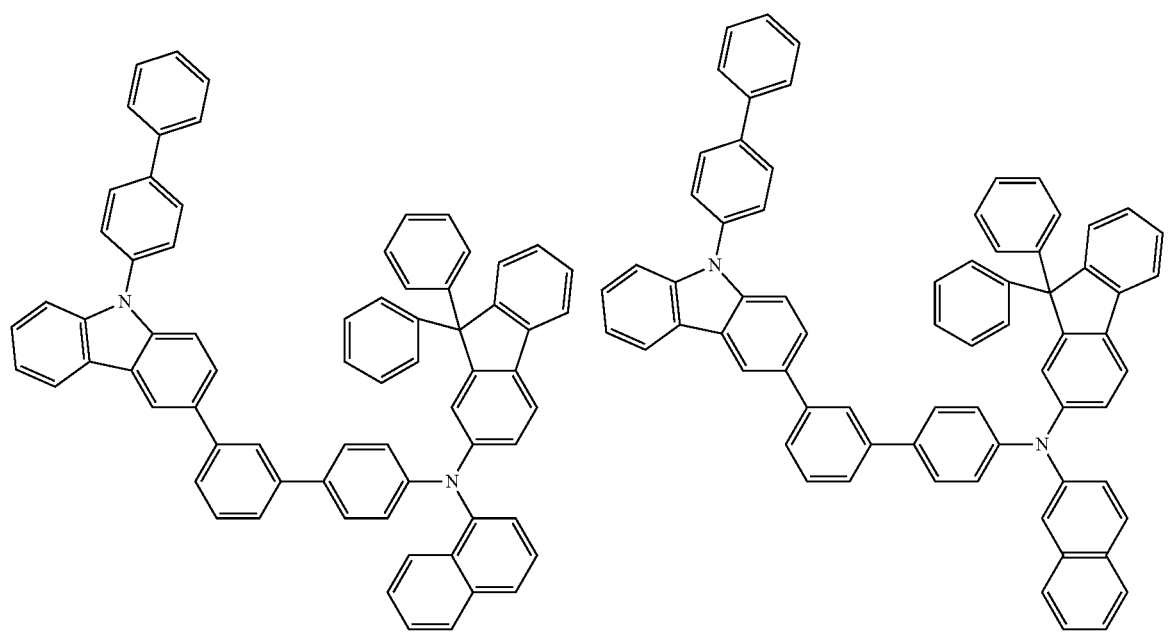

-continued
153
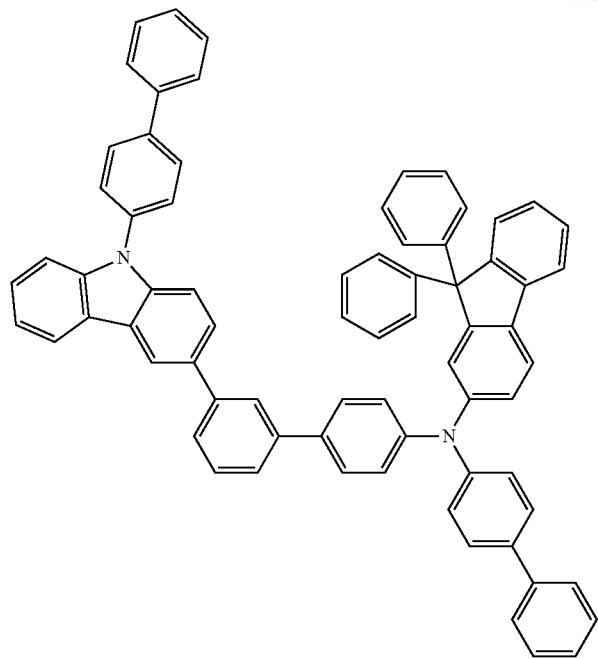
154
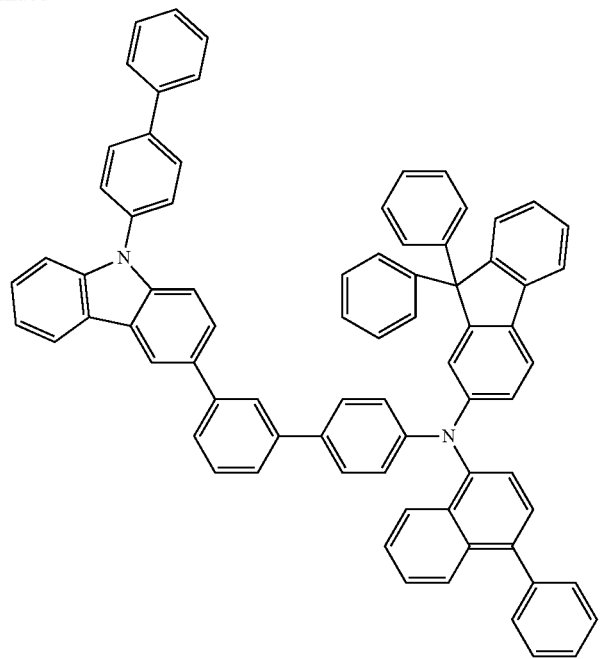
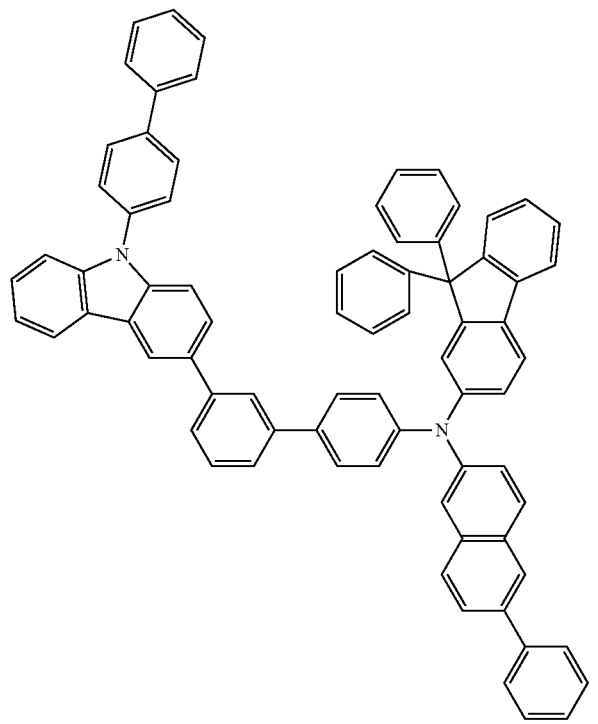
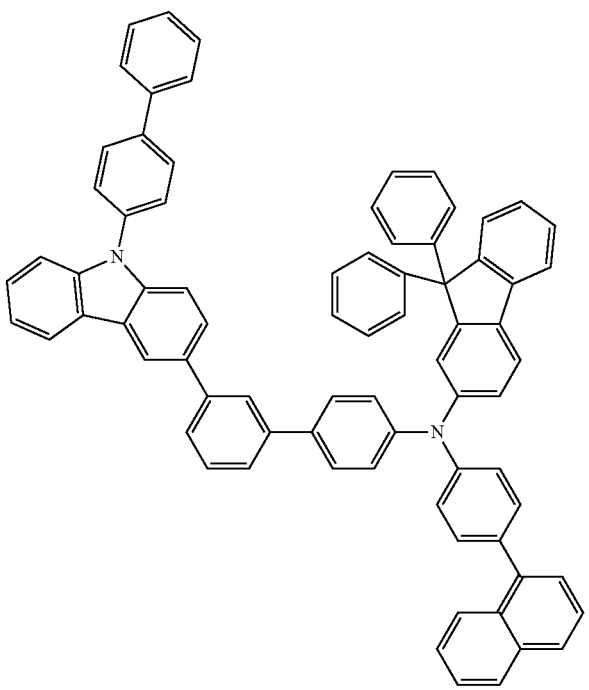

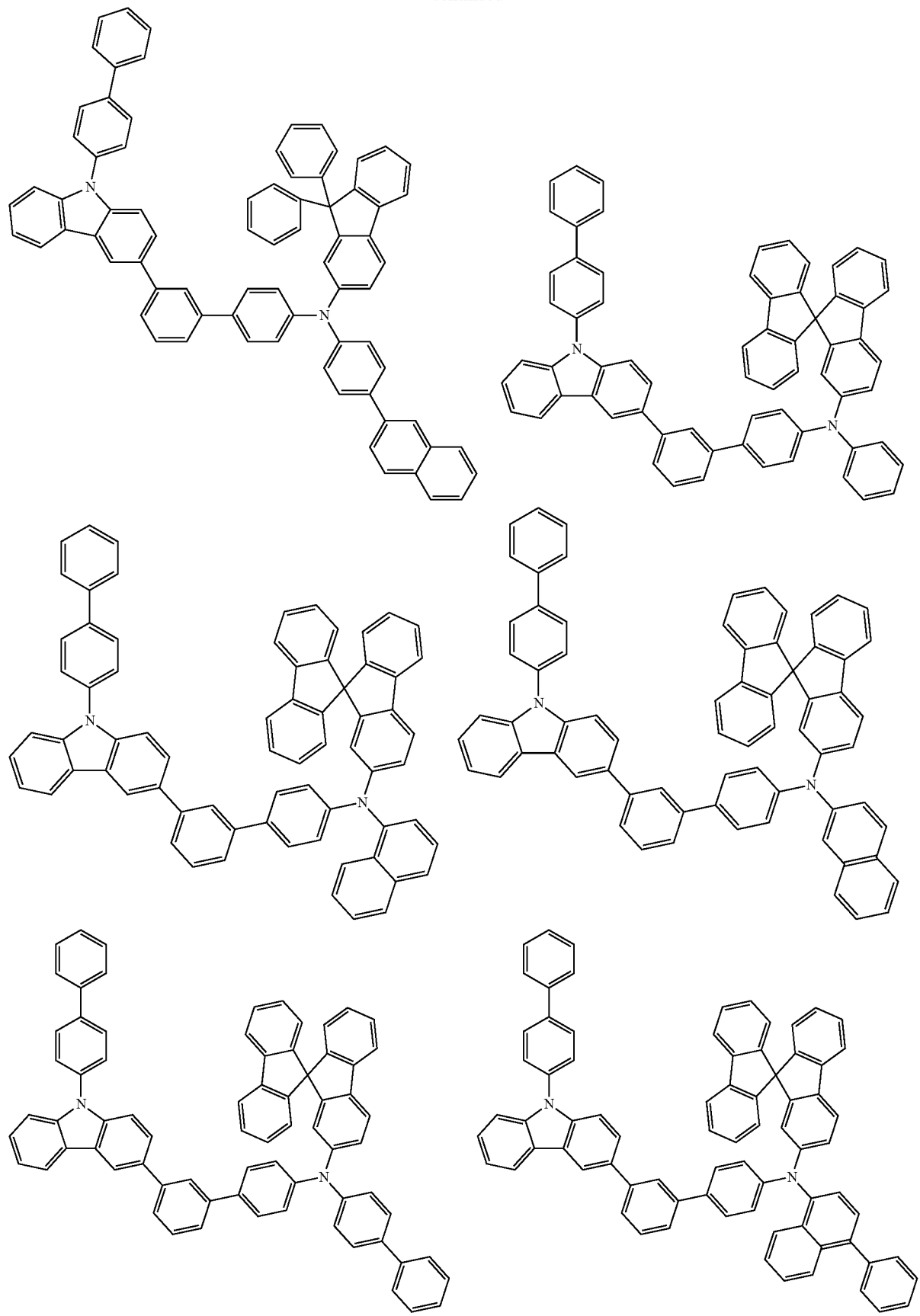

-continued
157 158
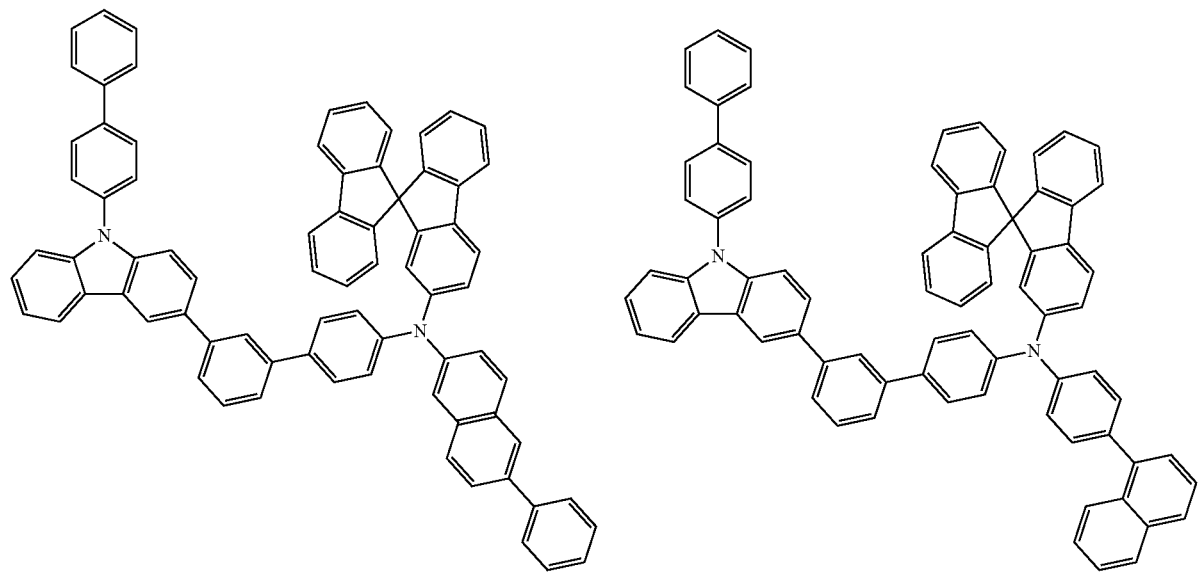
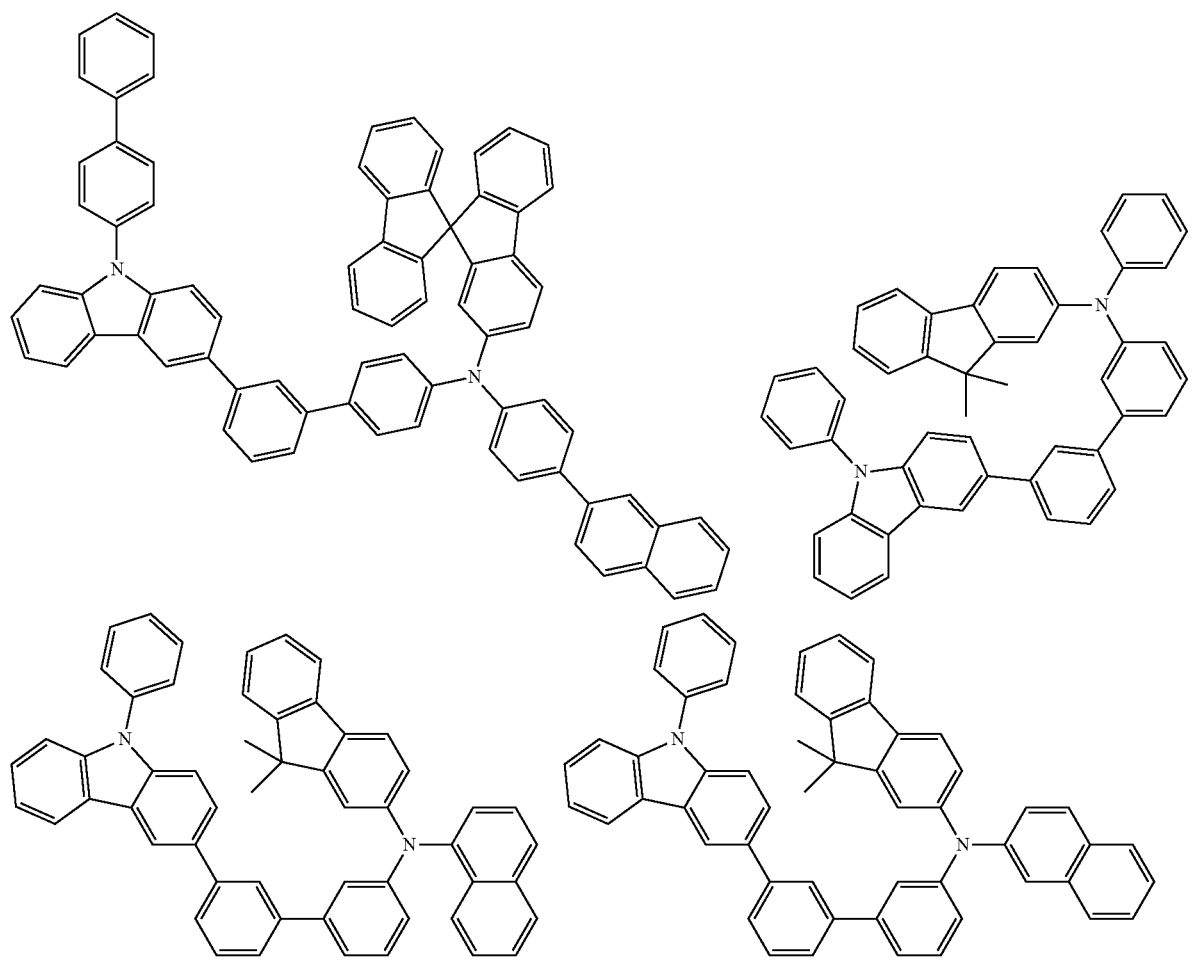

159 160
-continued
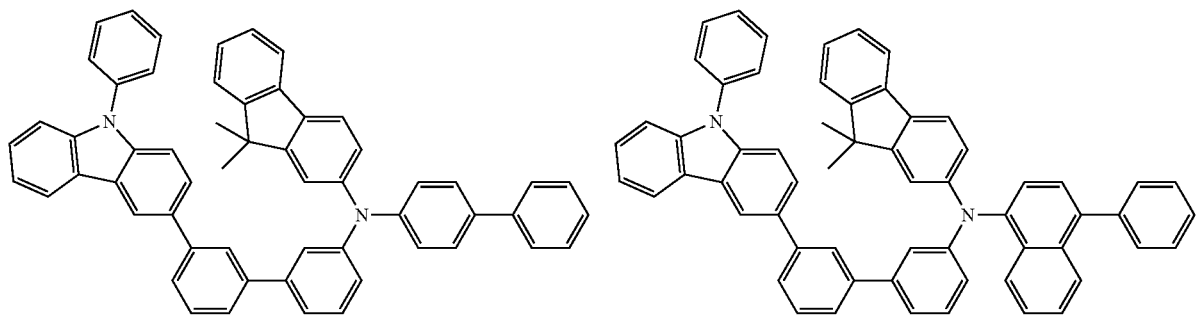
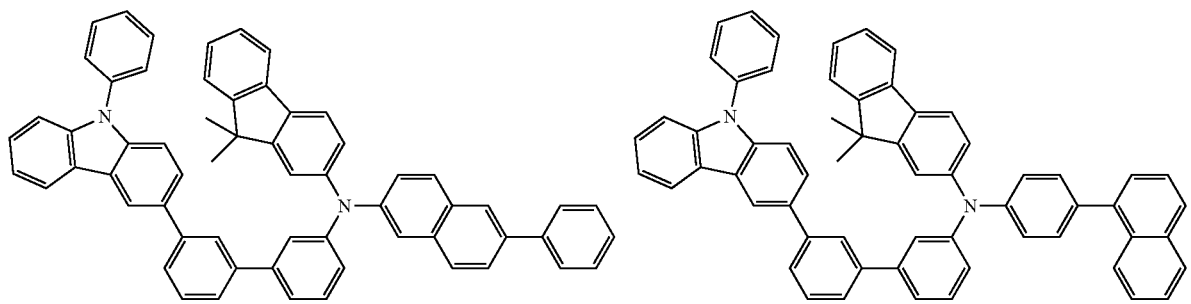
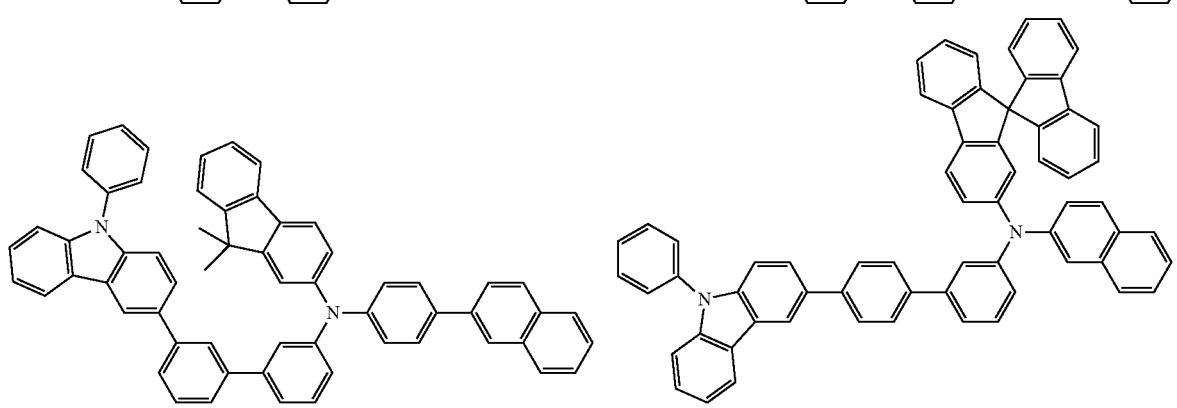
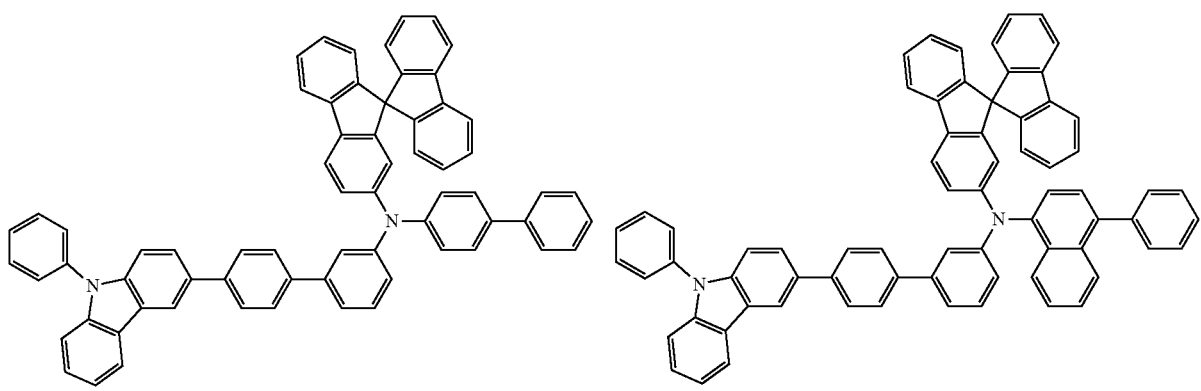

-continued
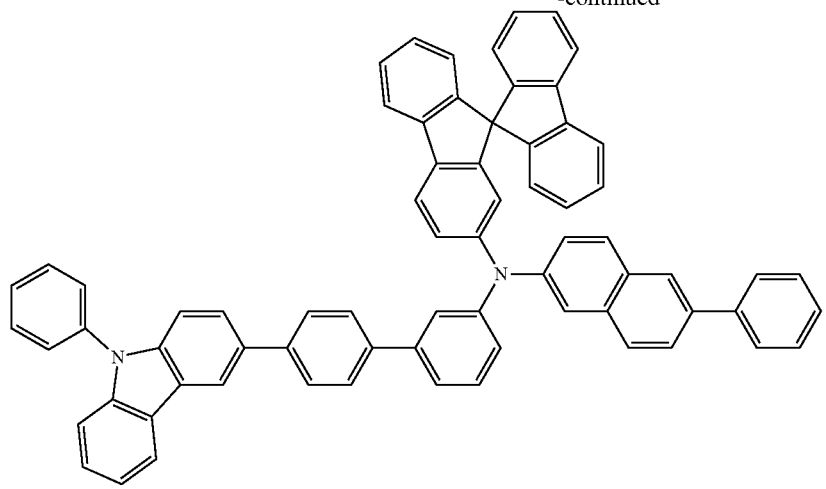
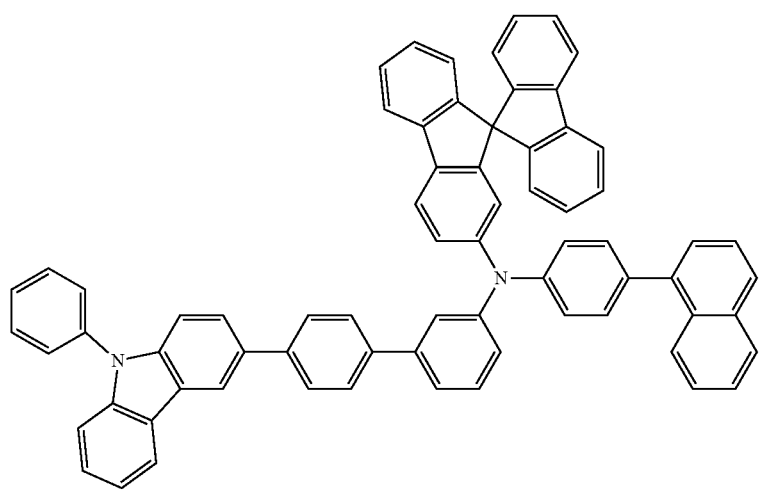
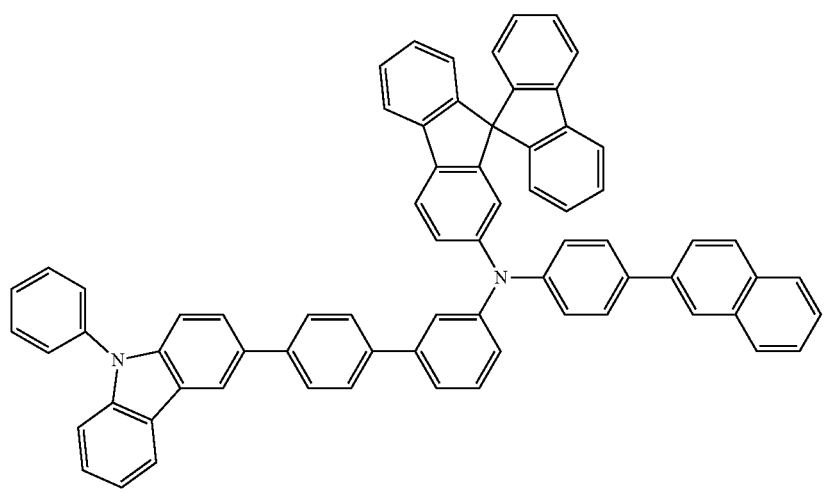

-continued
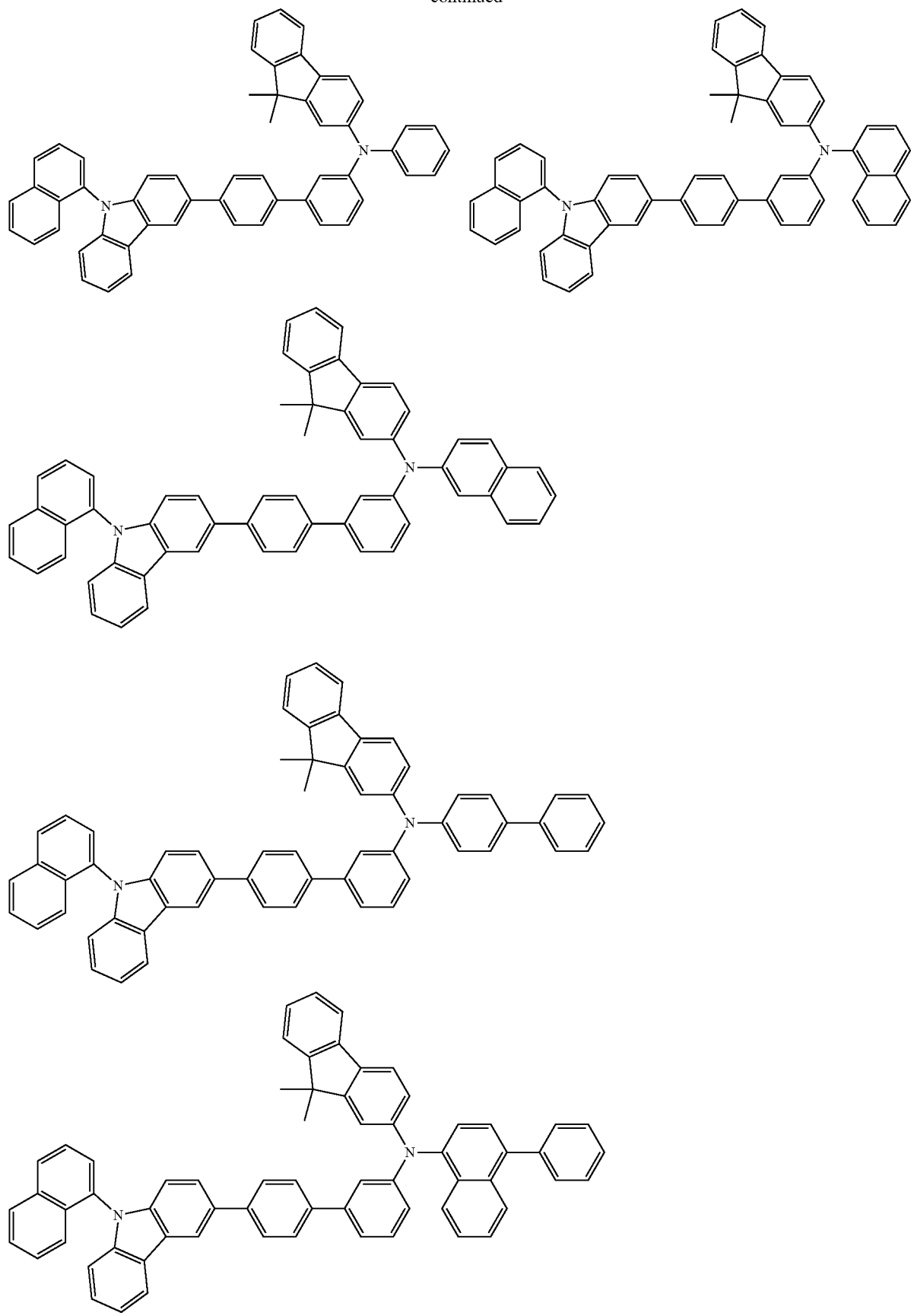

-continued
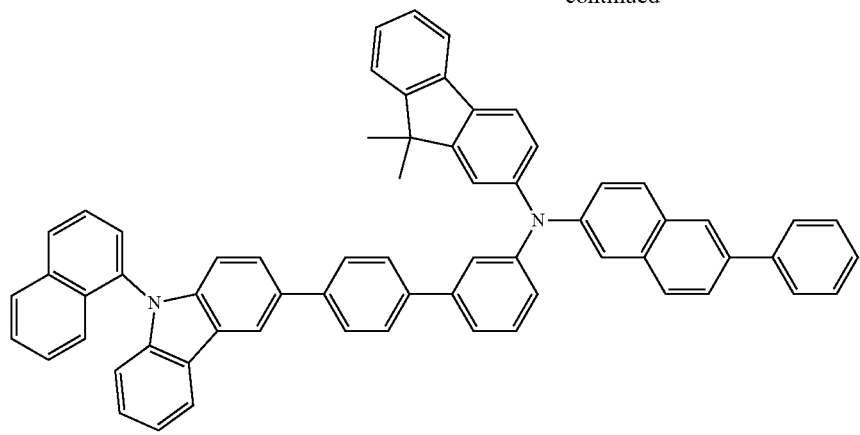
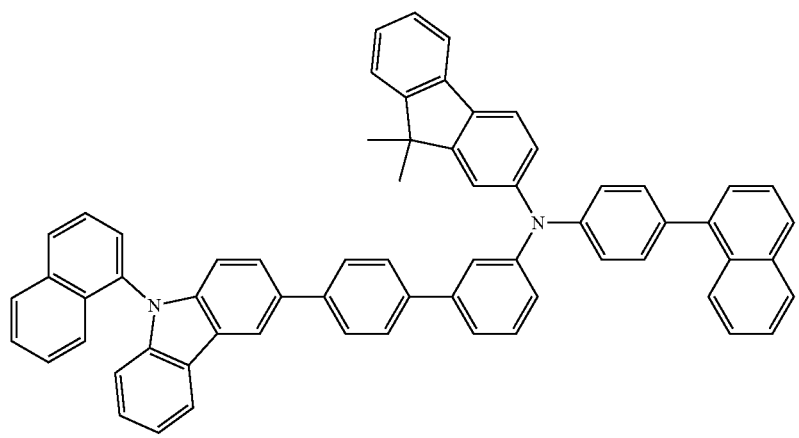
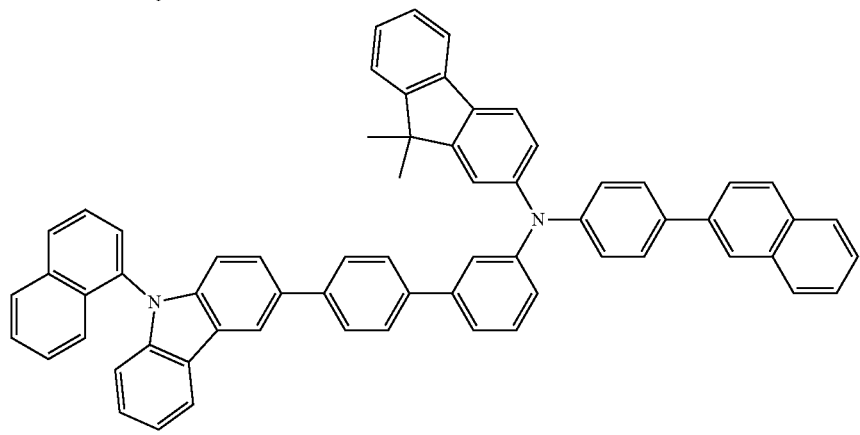
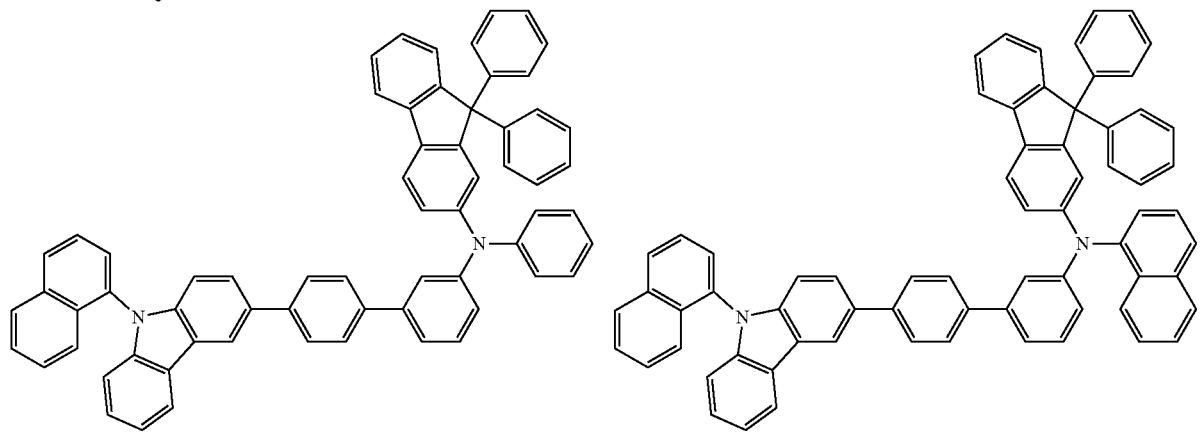

-continued
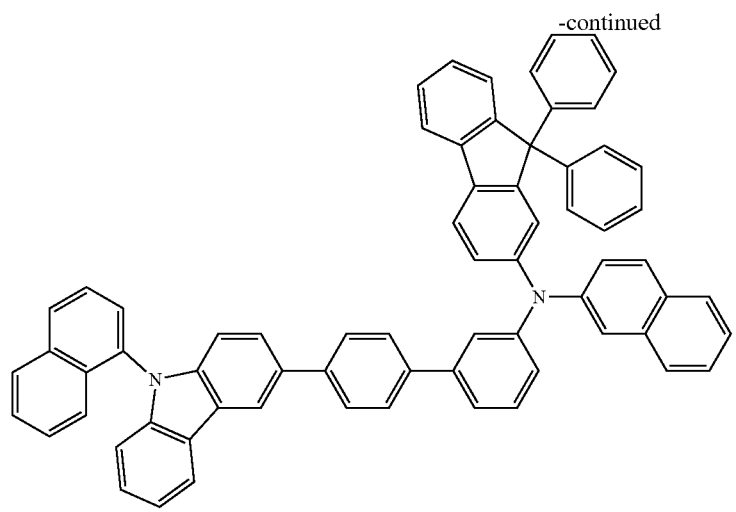
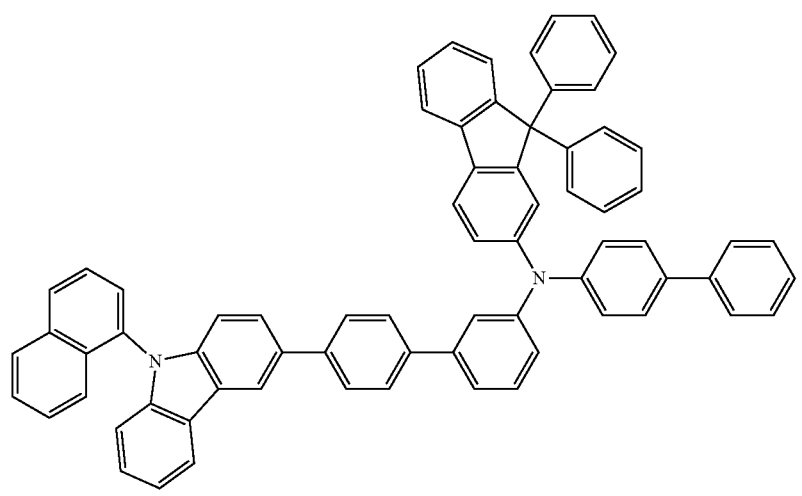
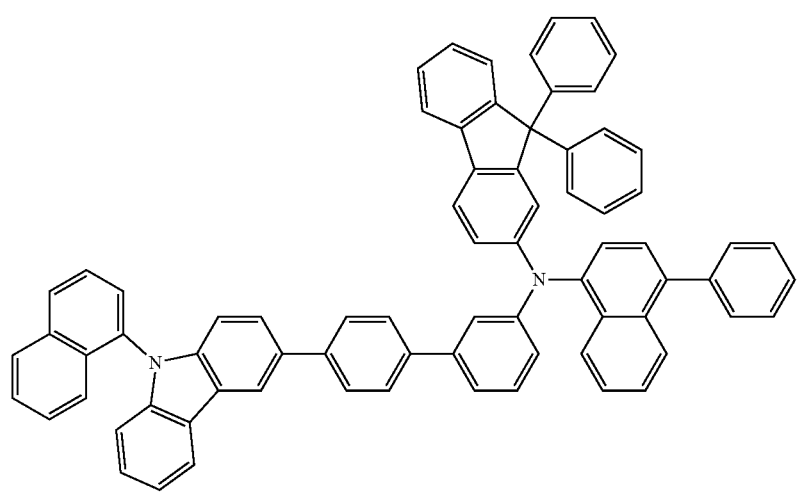

-continued
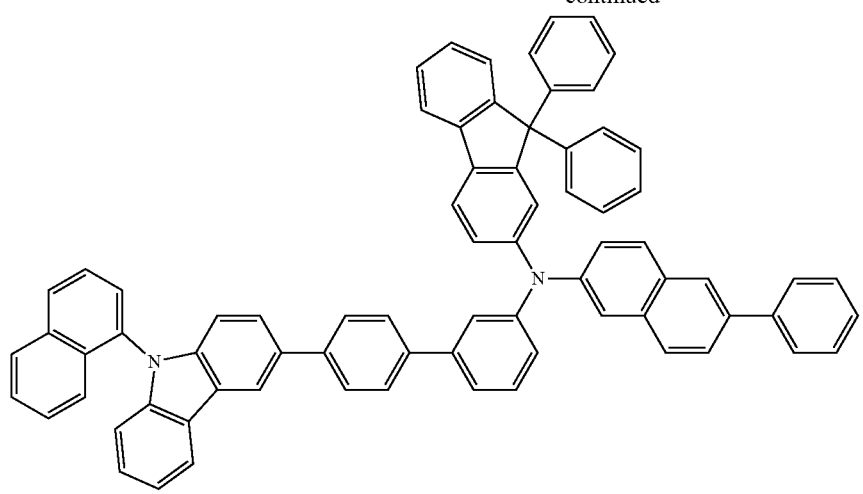
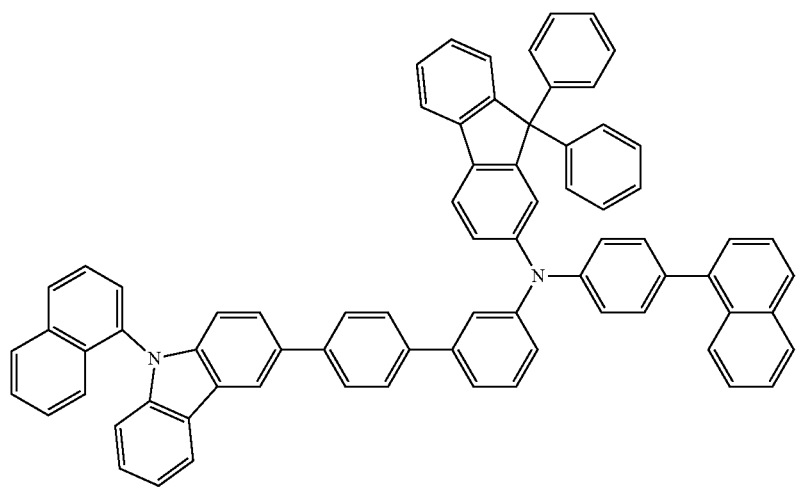
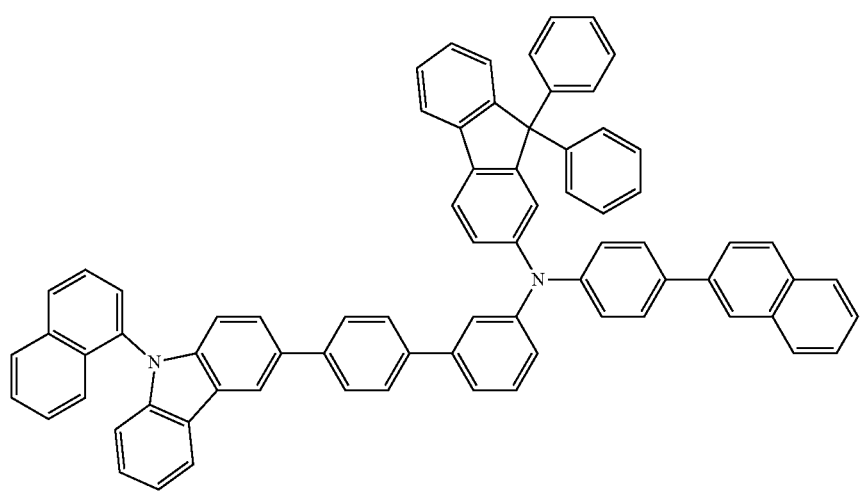

-continued
171
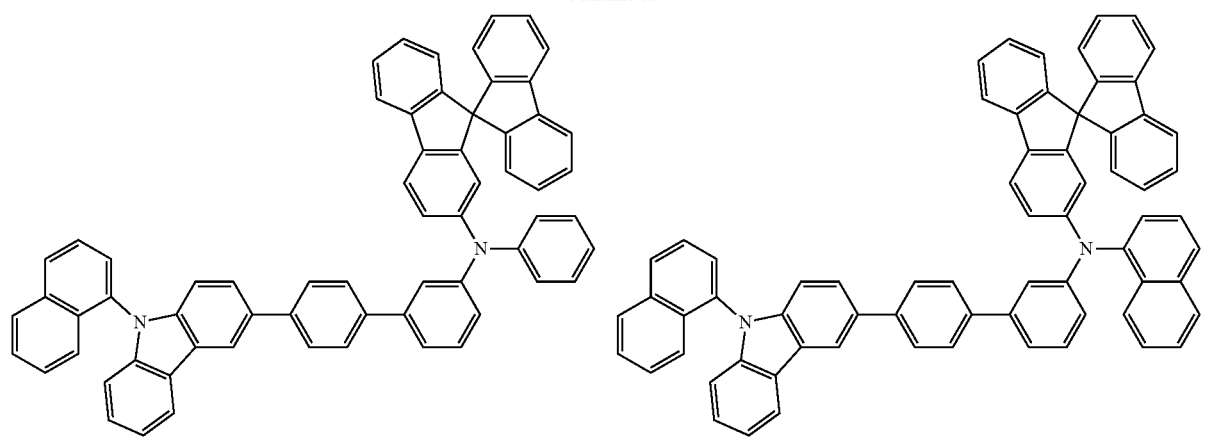
172
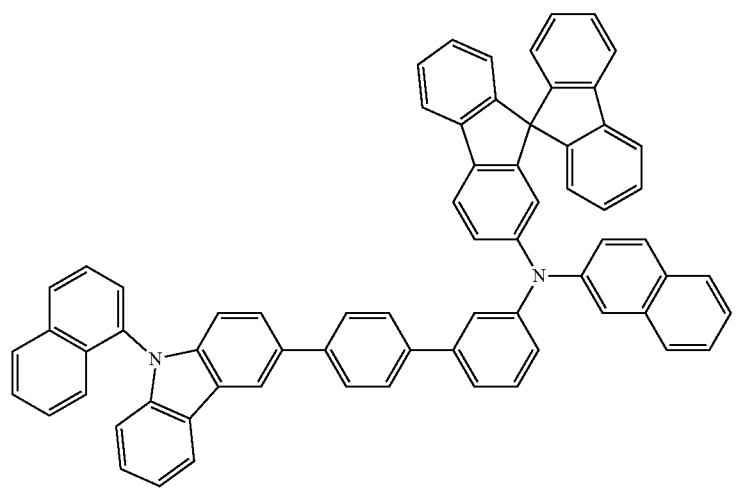
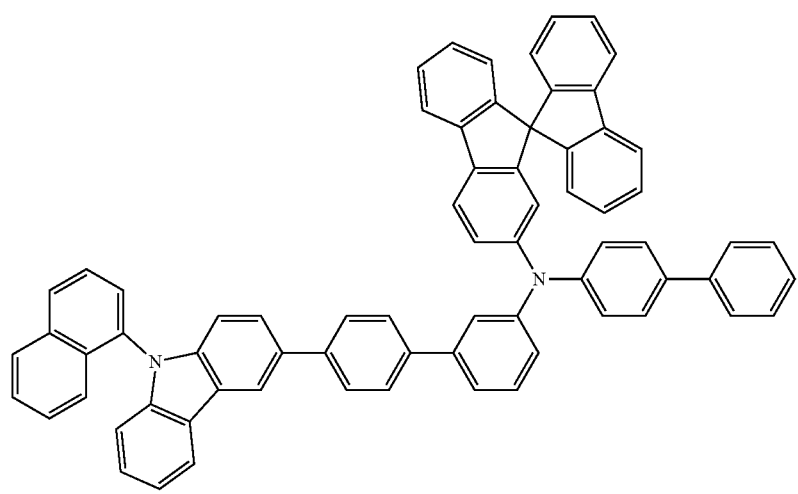

-continued
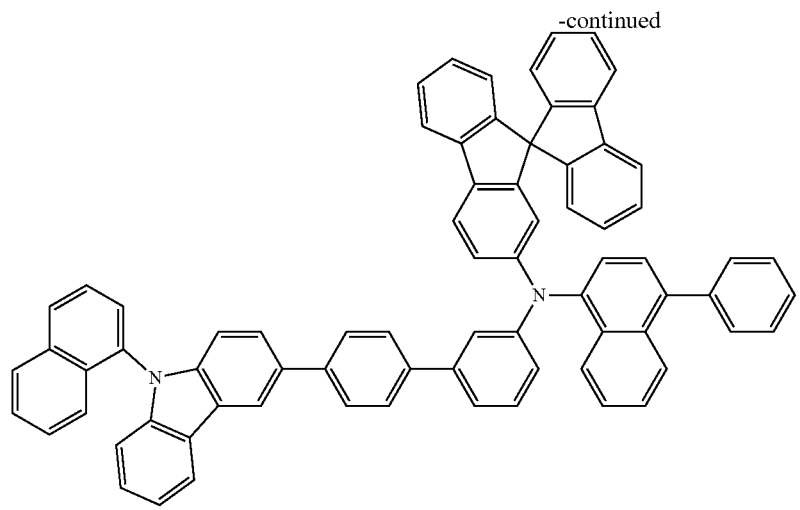
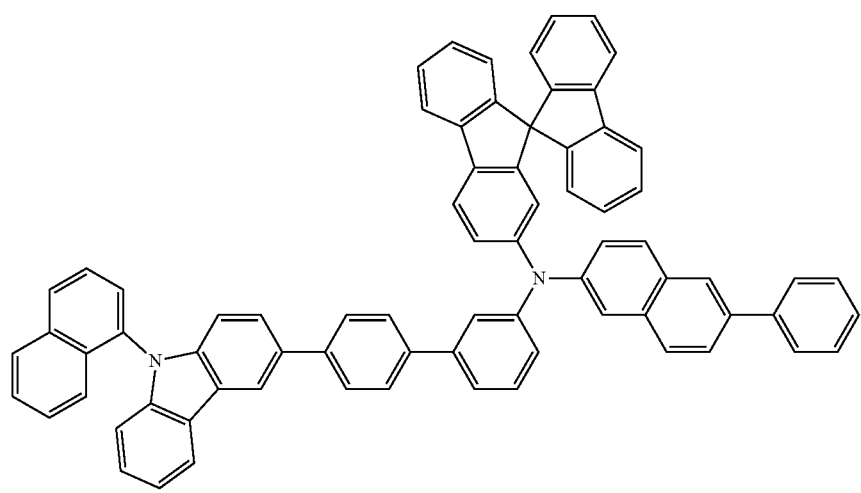
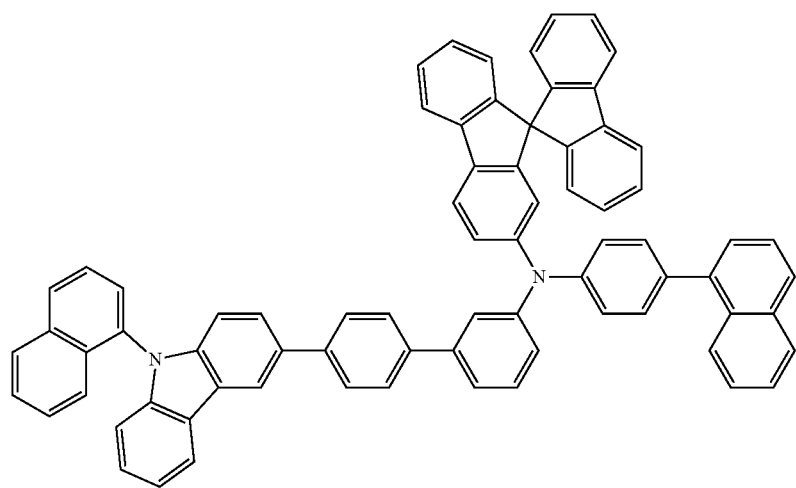

-continued
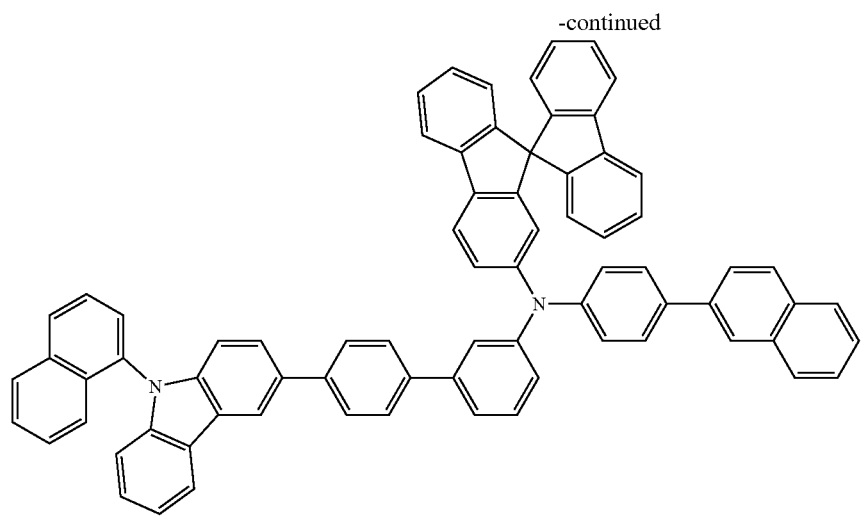
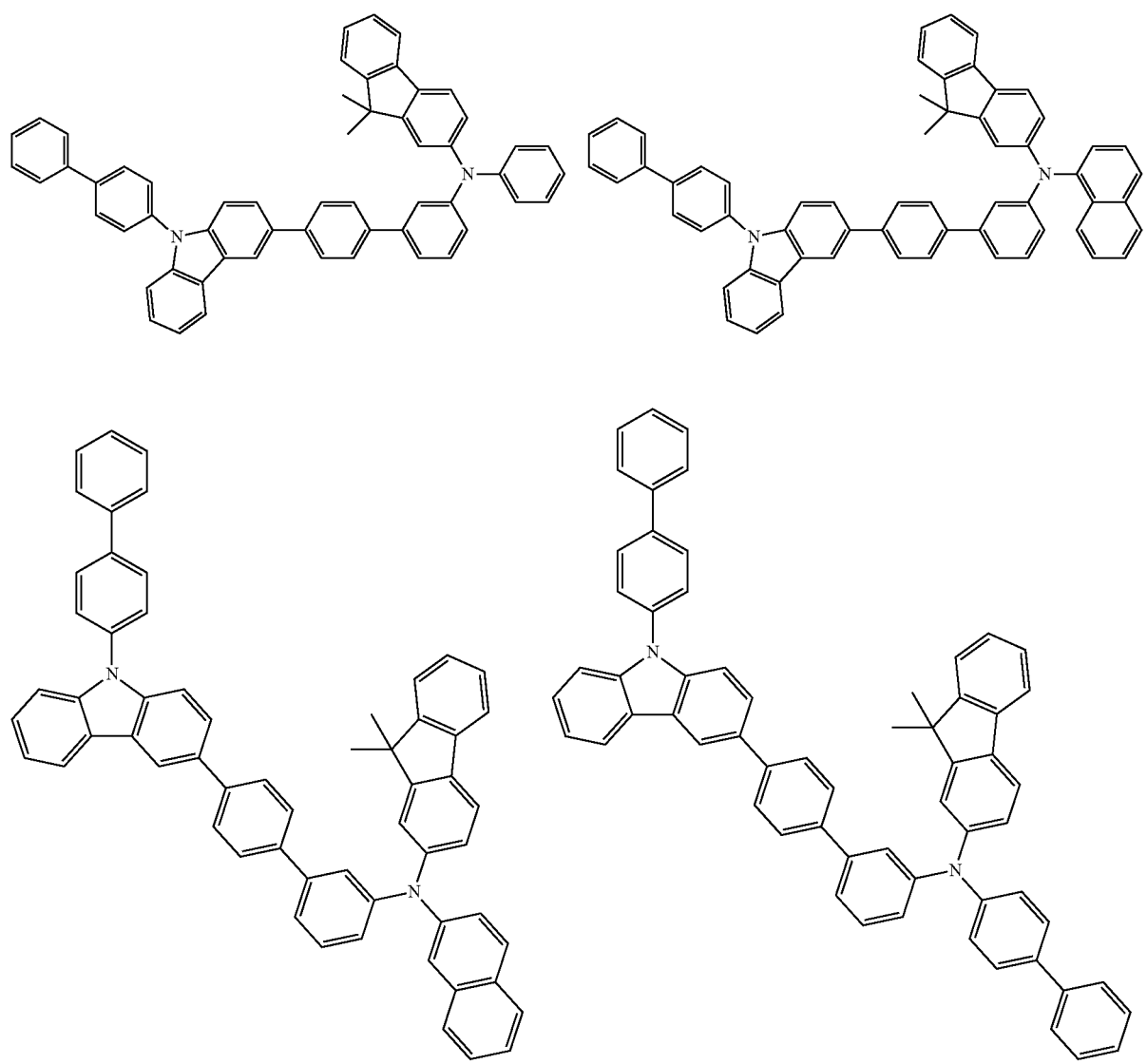

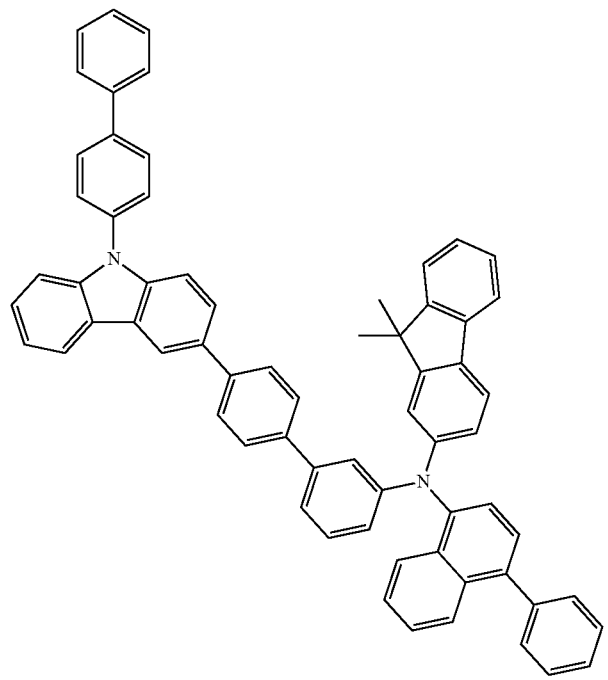
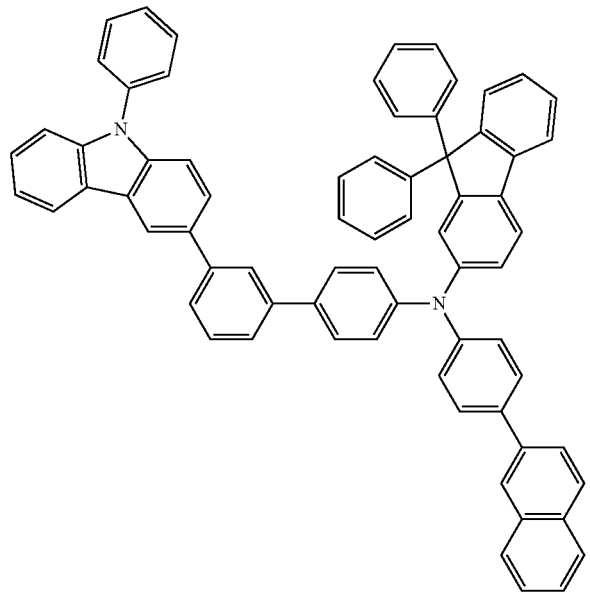
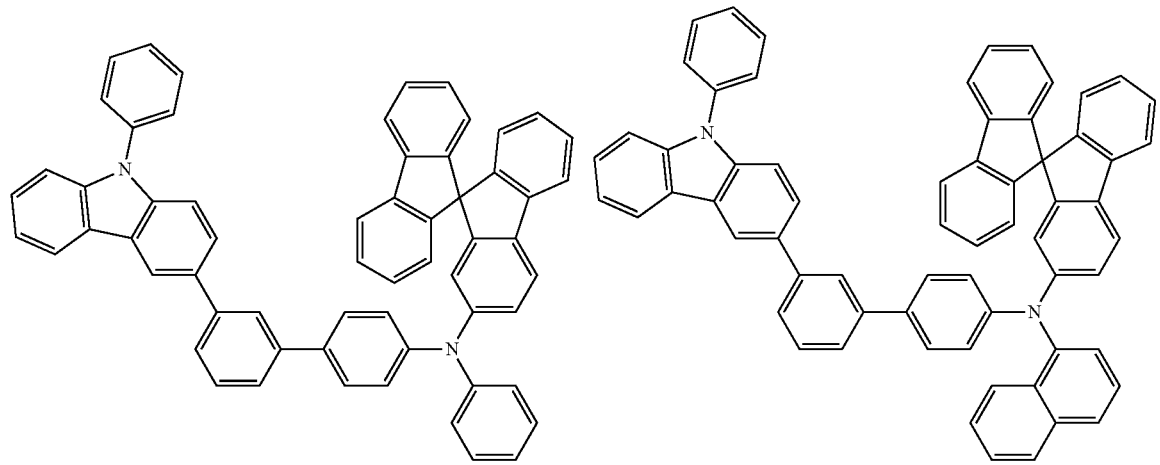
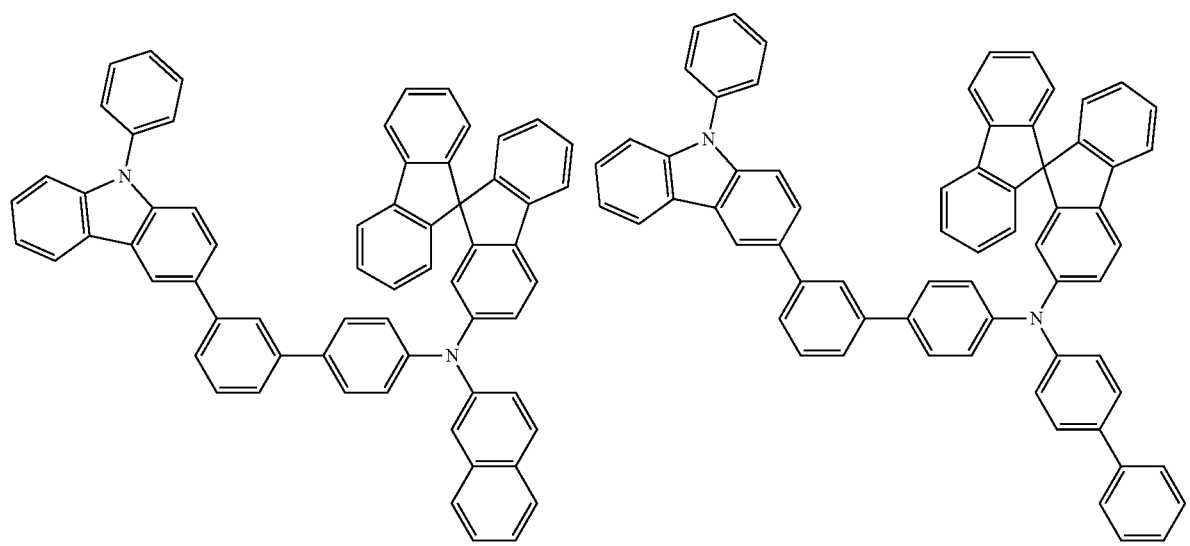

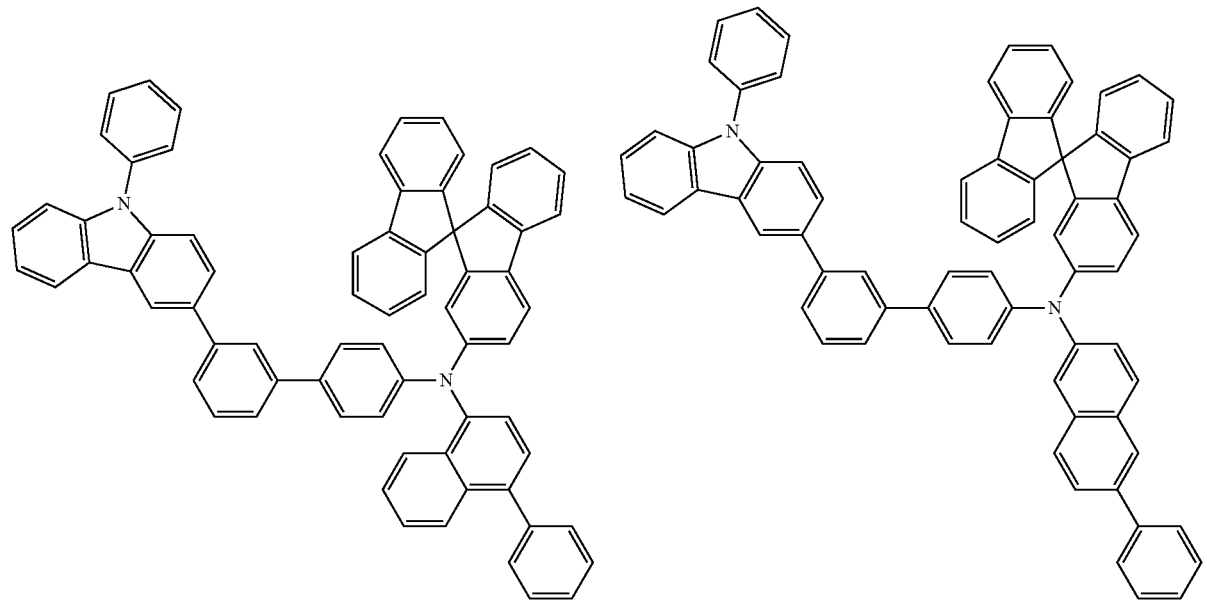
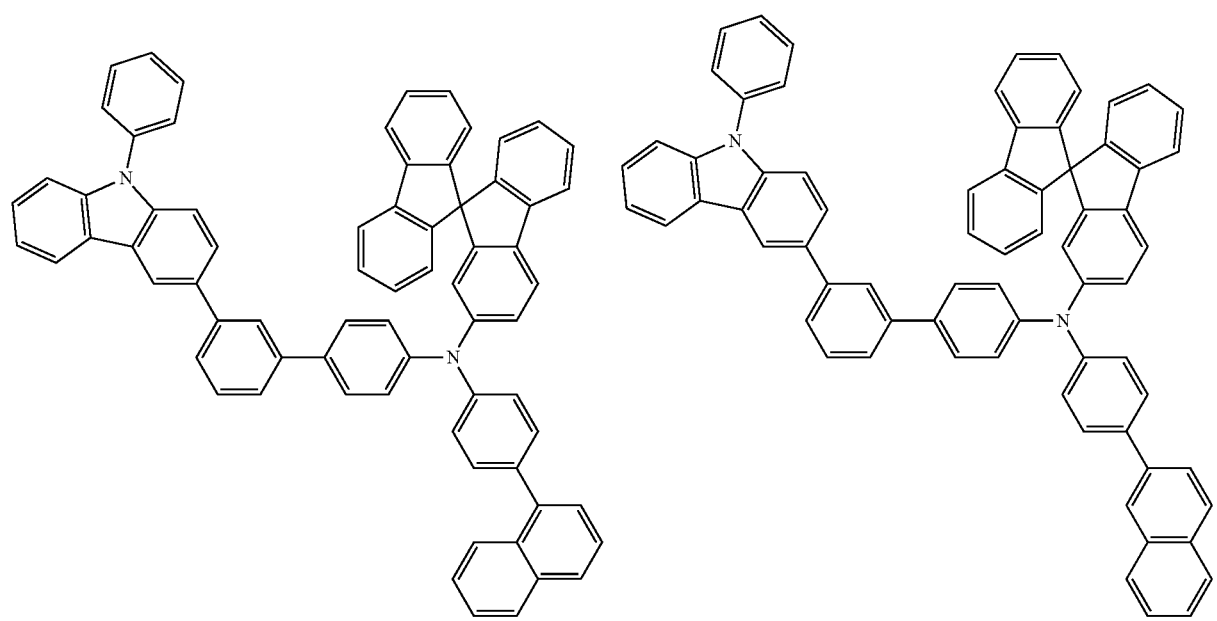
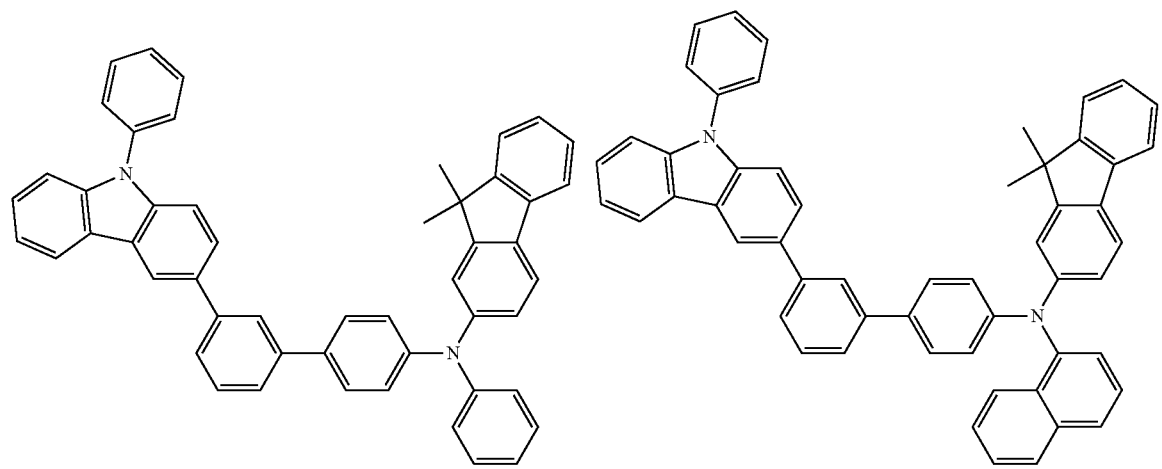

-continued
| 181 | 182 |
|---|---|
| 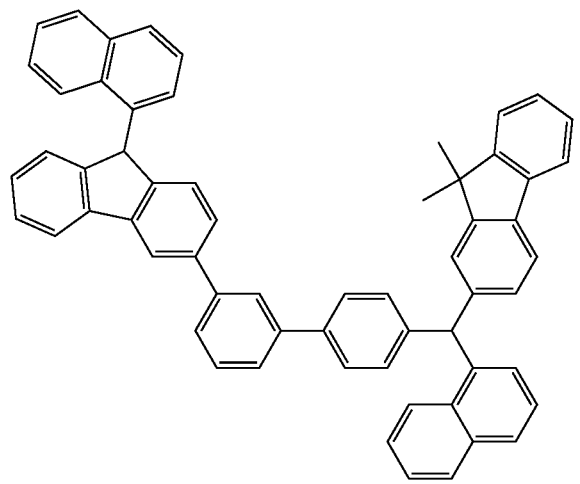 | 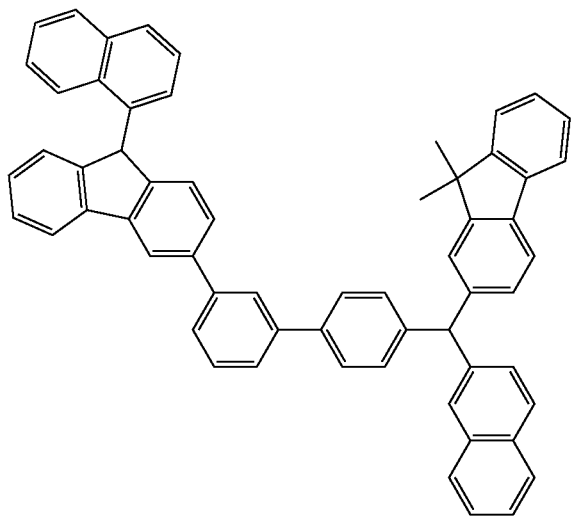 |
| 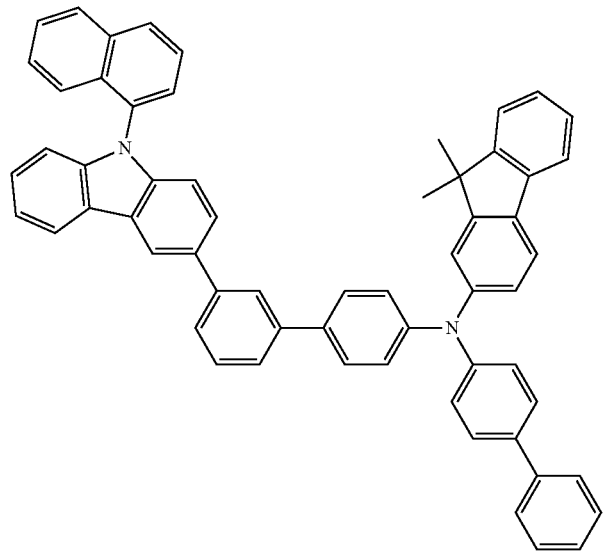 | 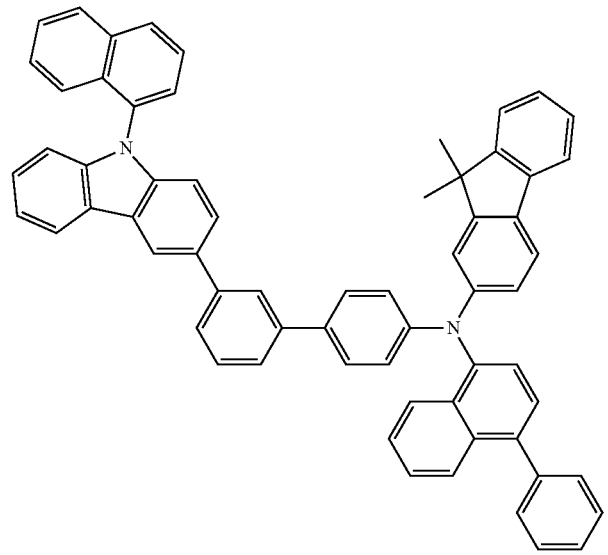 |
| 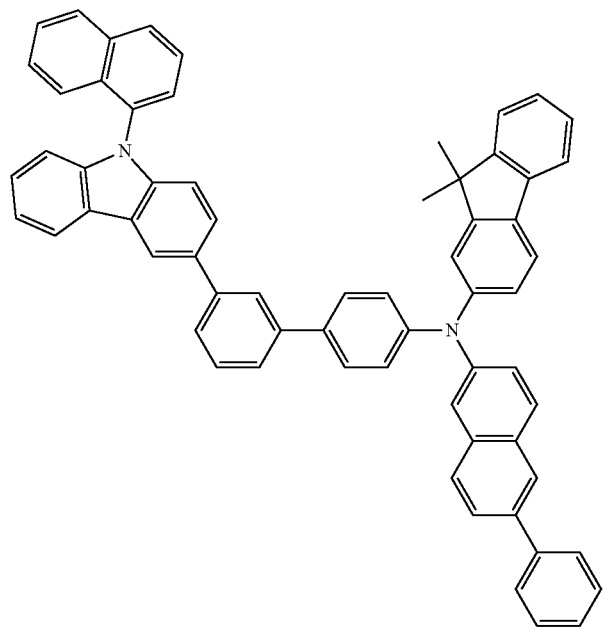 | 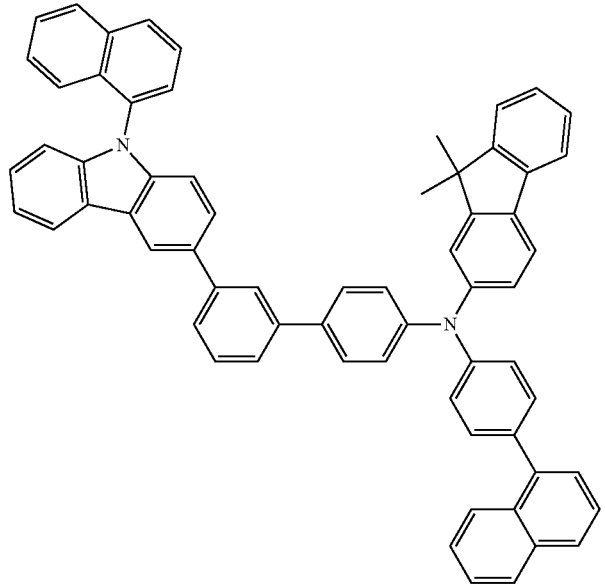 |

-continued
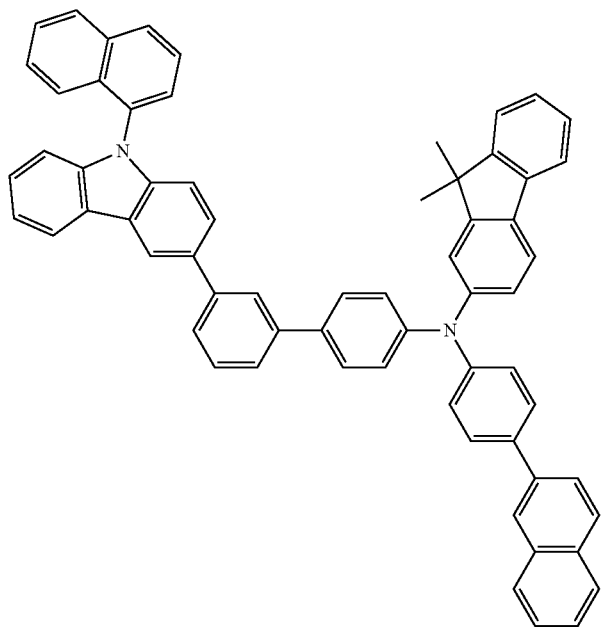
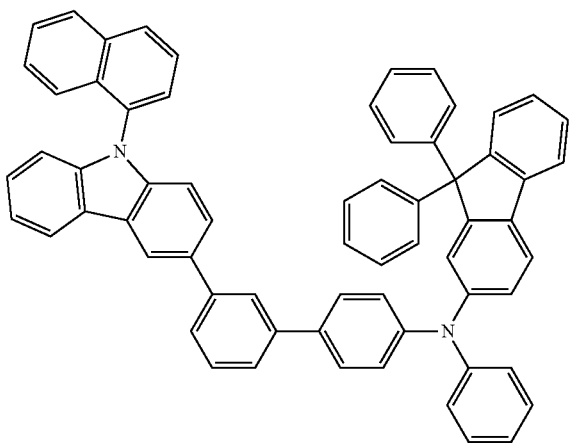
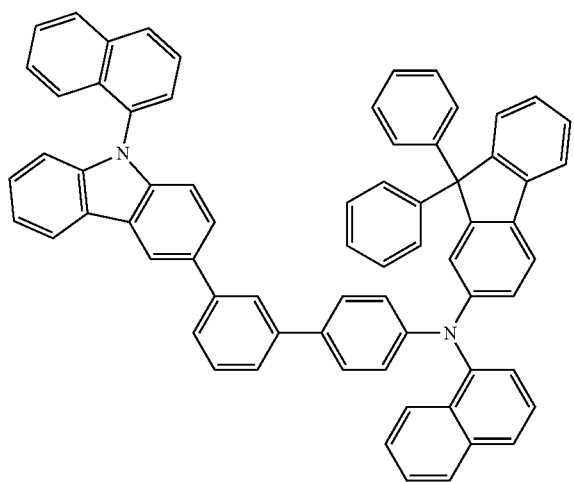
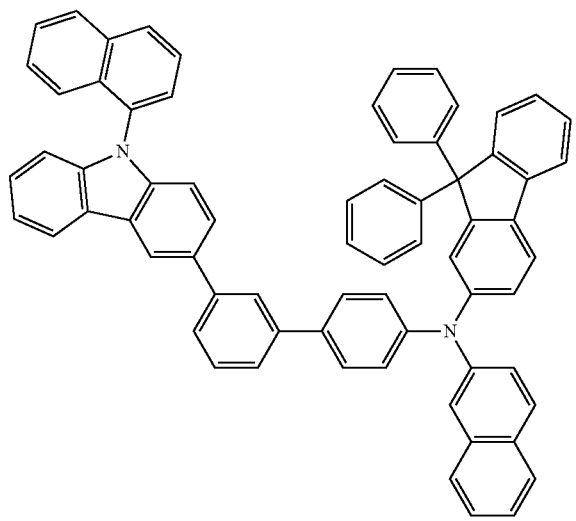
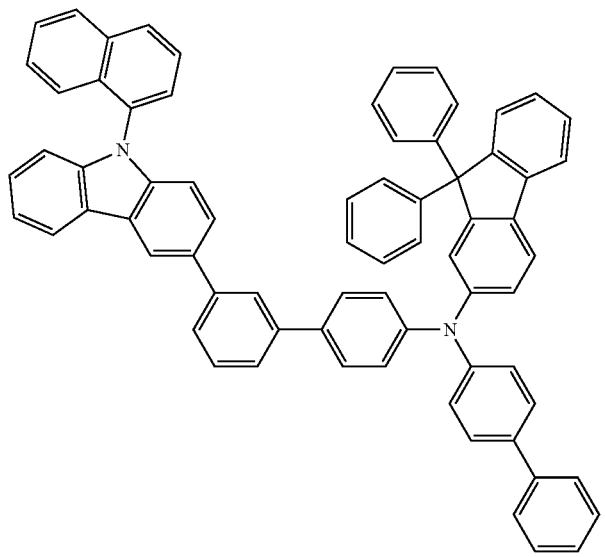
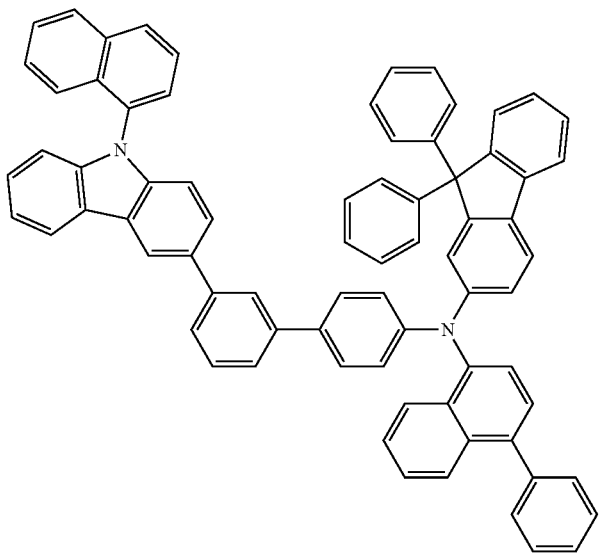

-continued
185
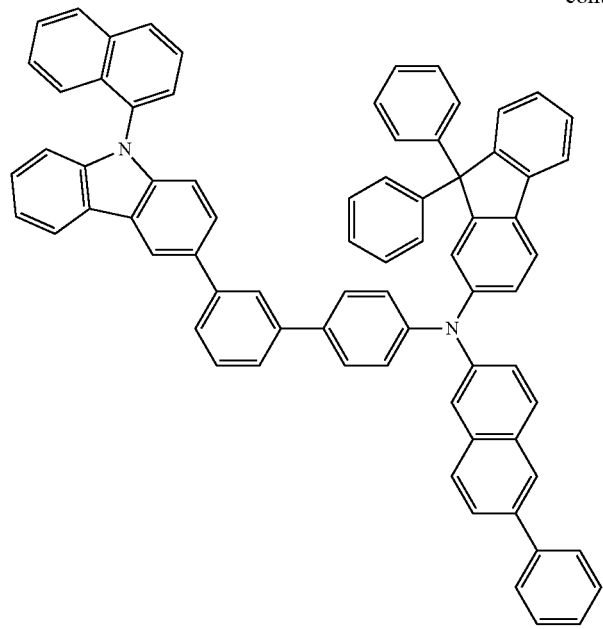
186
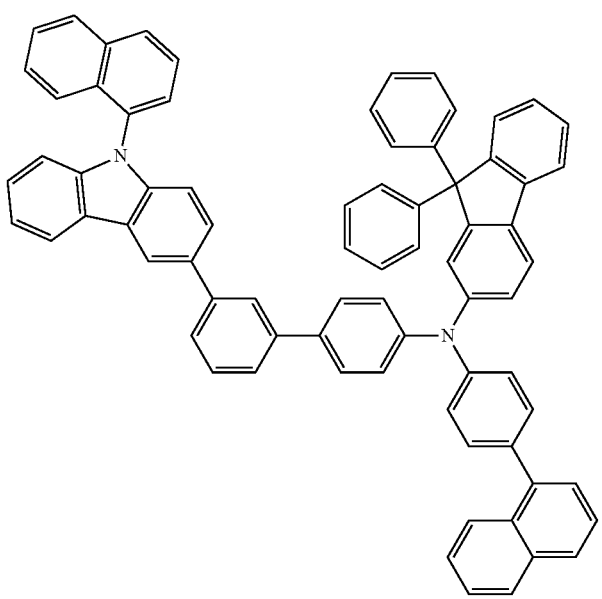
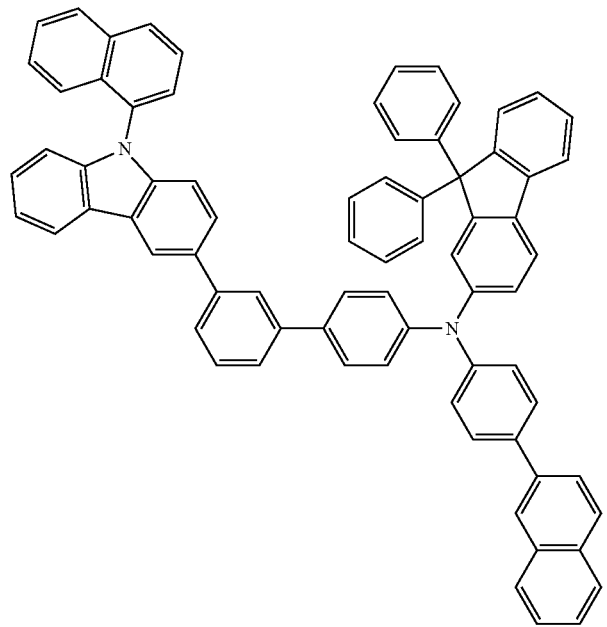
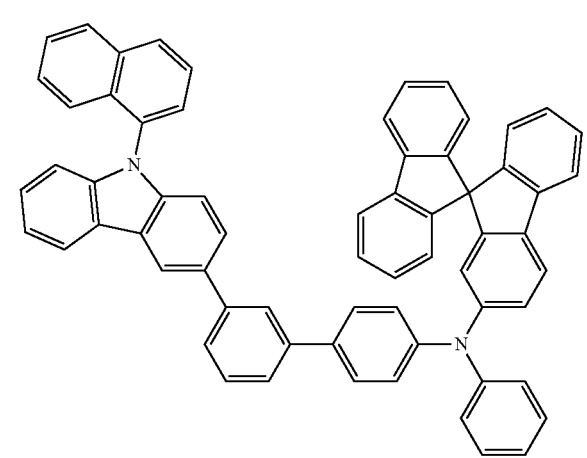

-continued
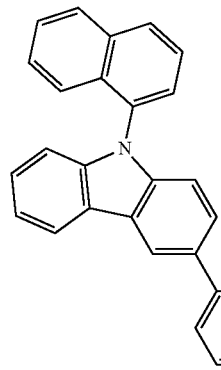 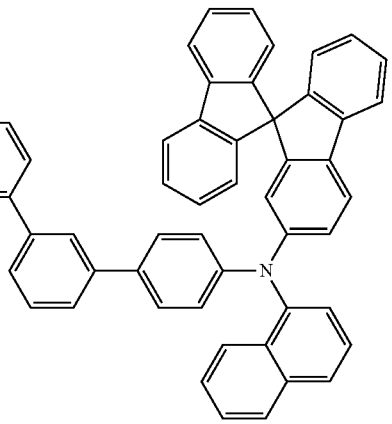 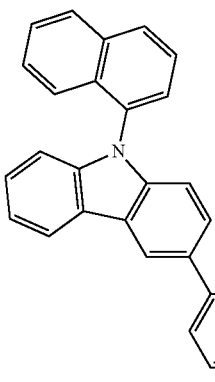 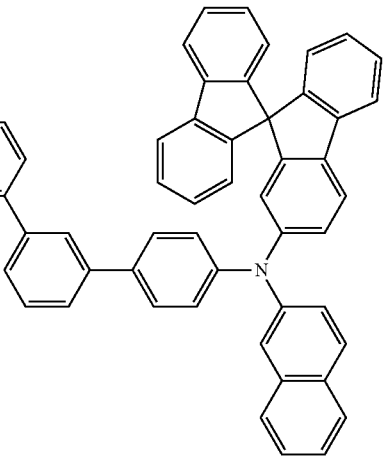
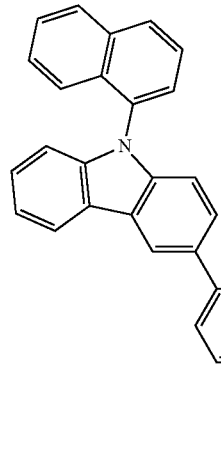 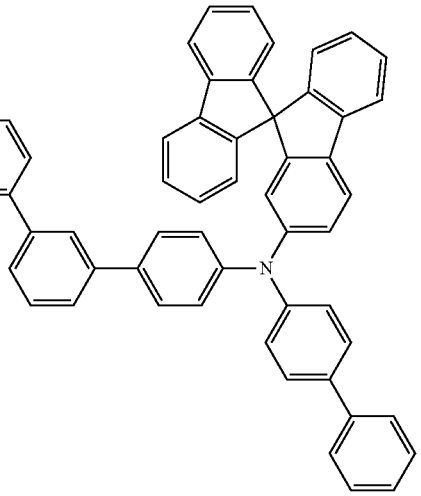 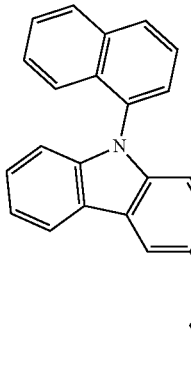 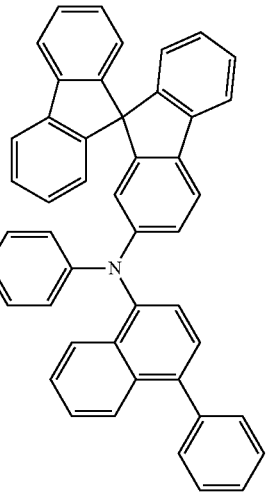
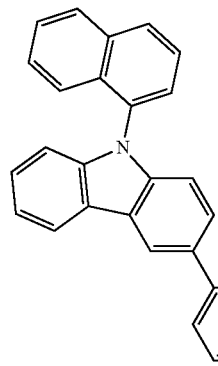 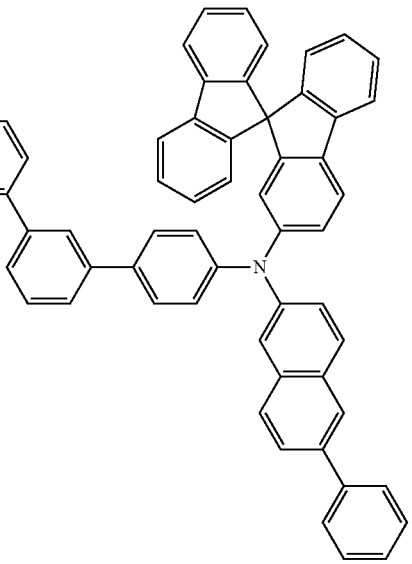 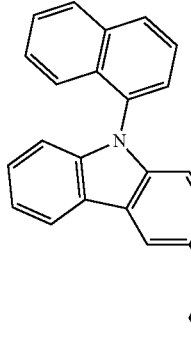 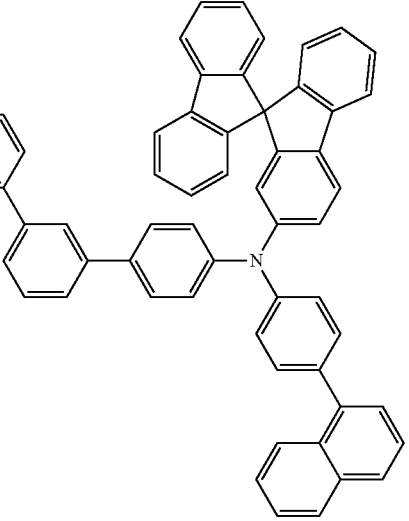

189
190
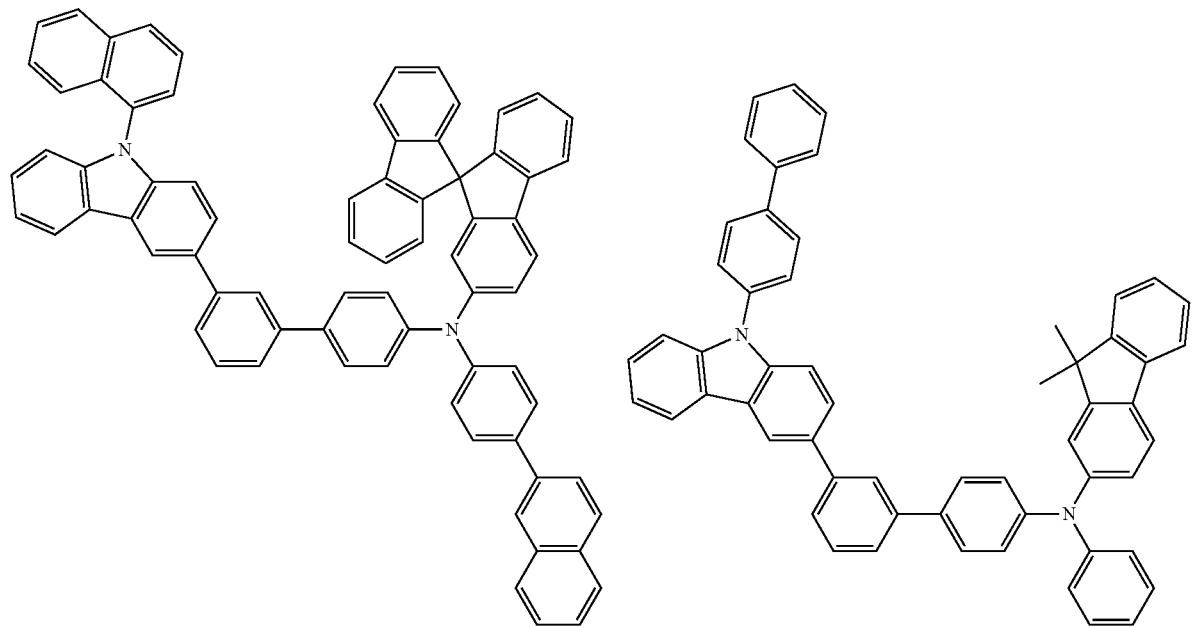
-continued
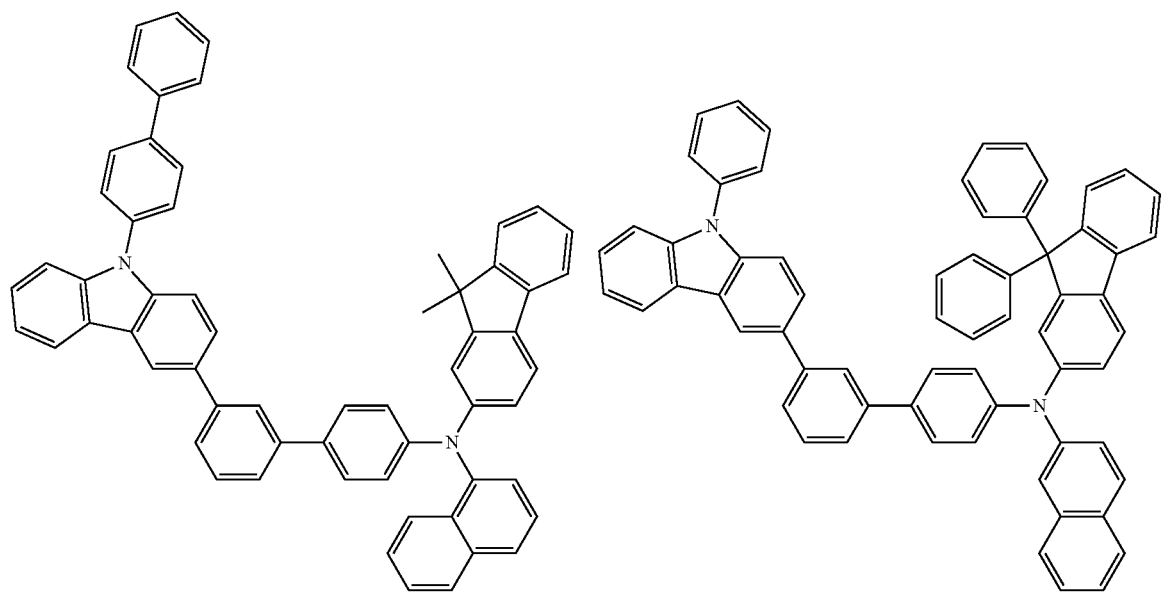

191 192
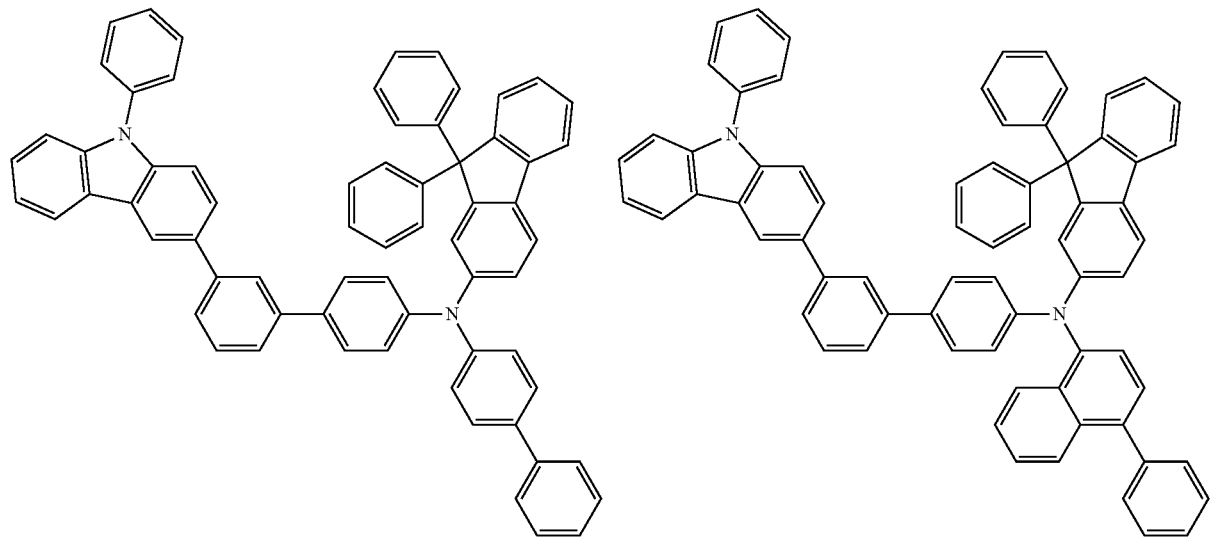
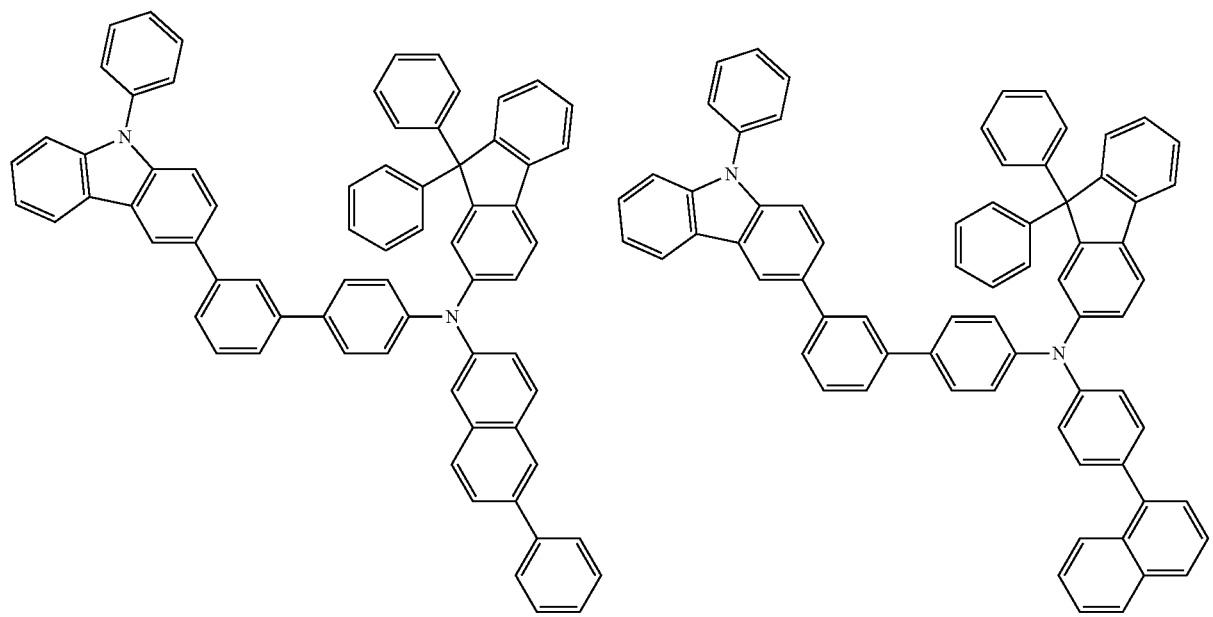

-continued
193
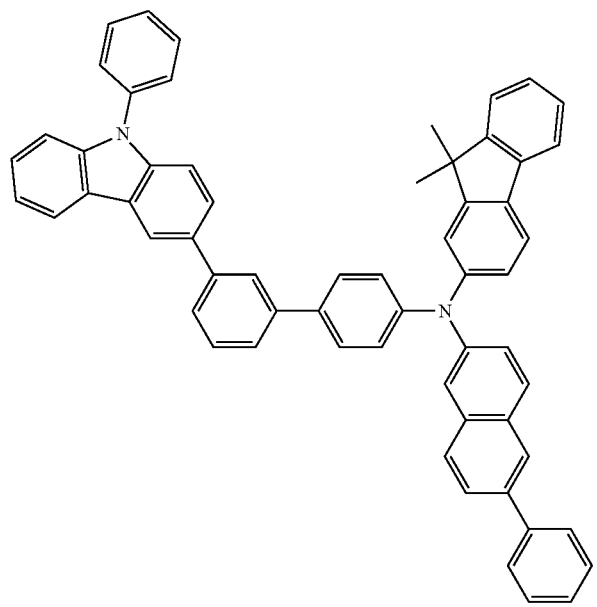
194
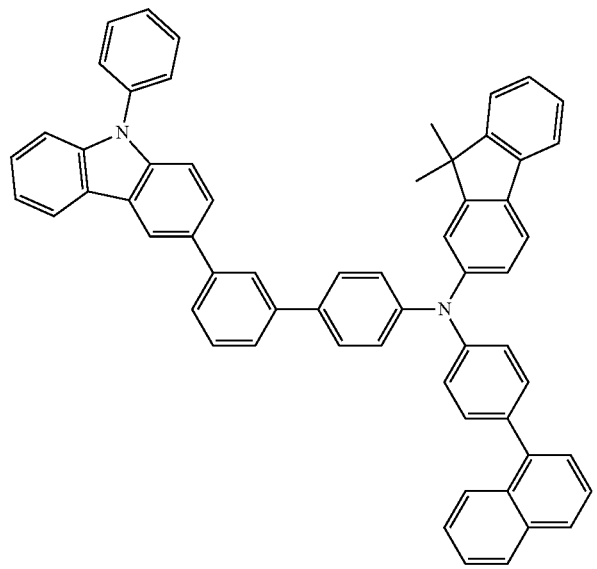
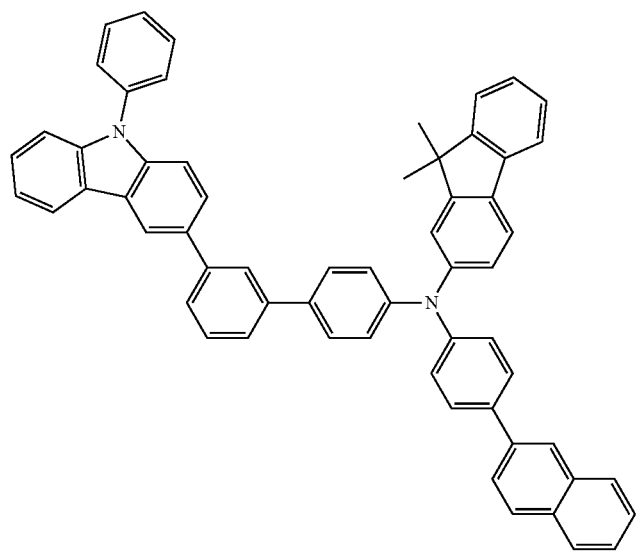
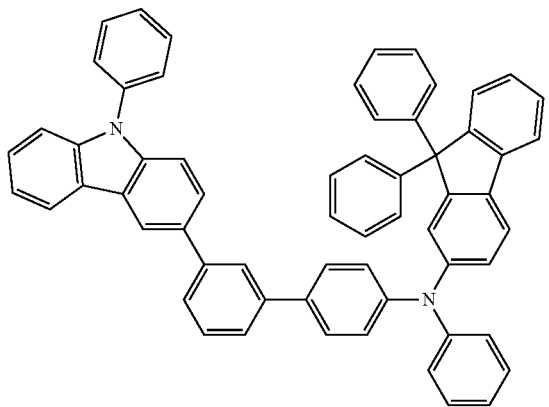
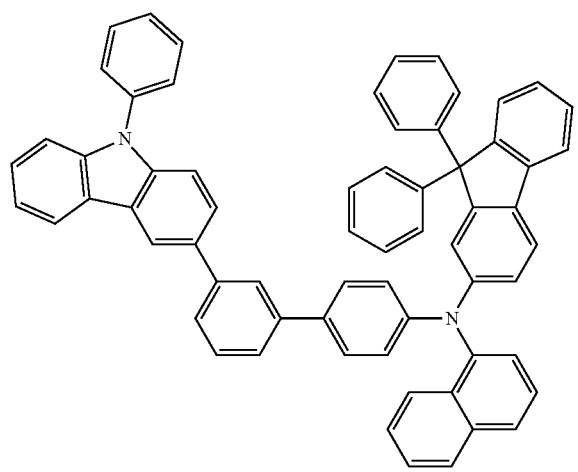
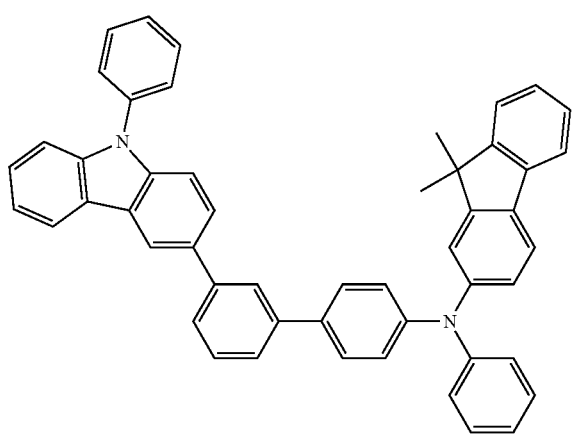

195
196
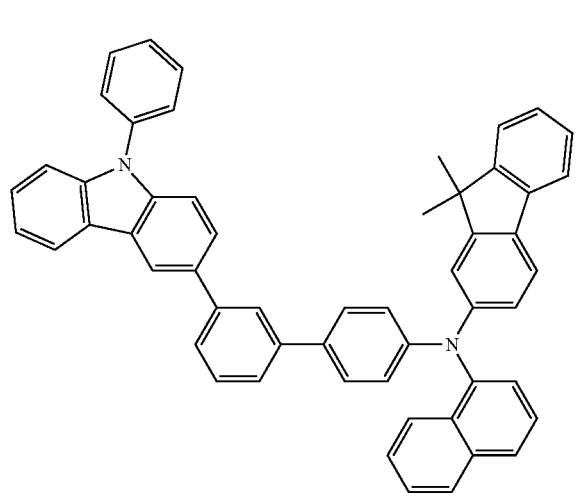
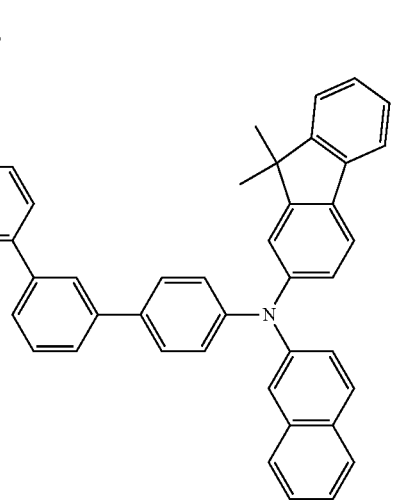
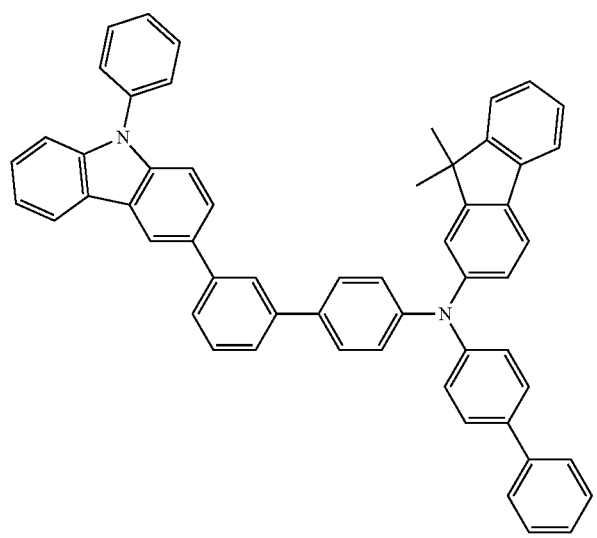
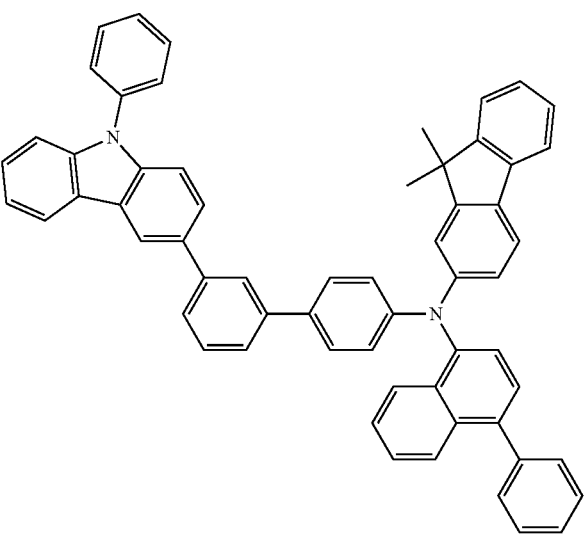

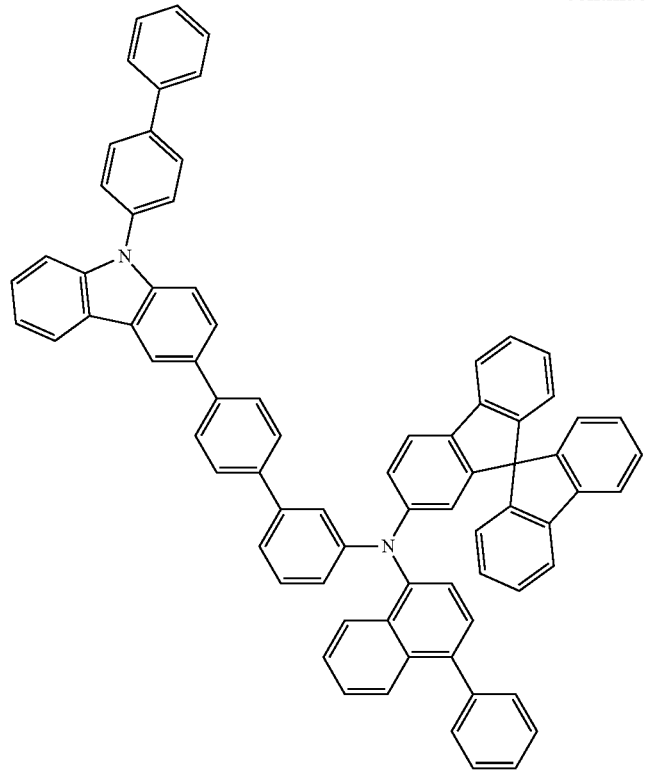
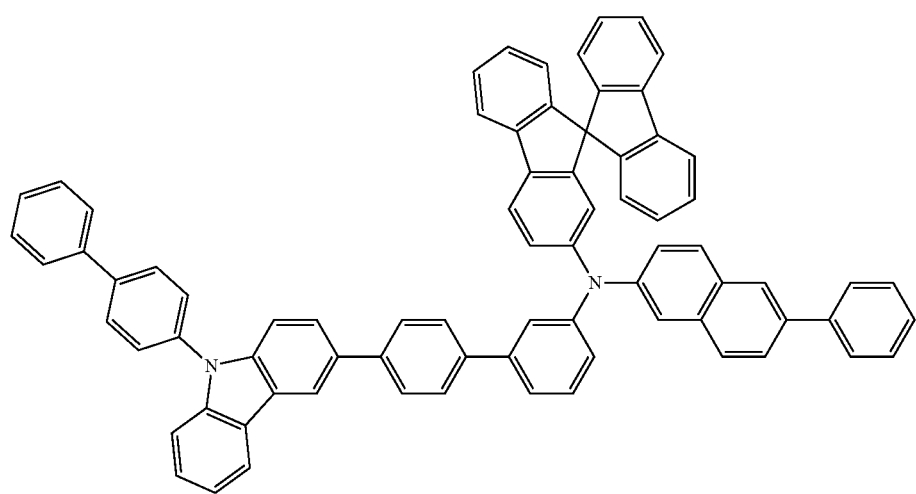

-continued
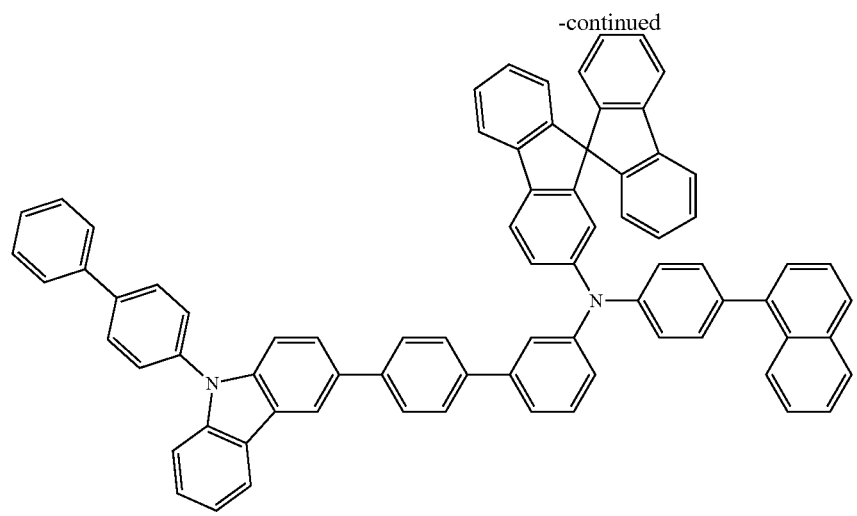
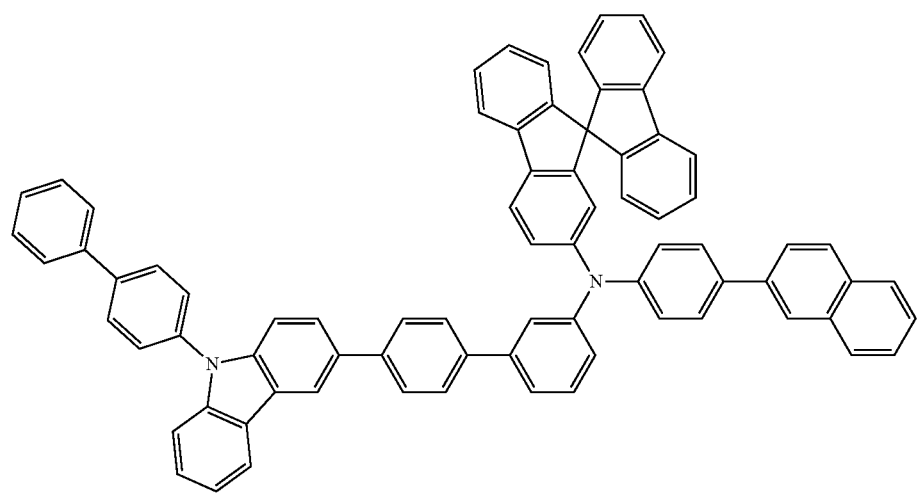
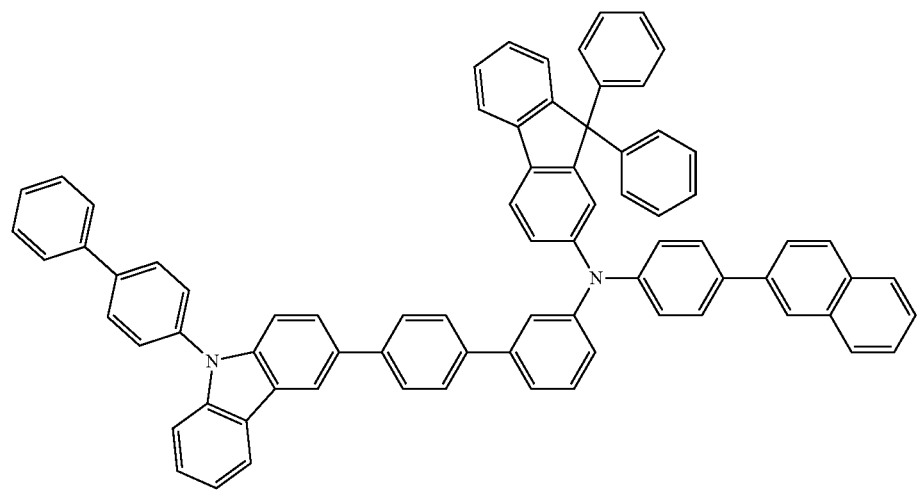

201 202
-continued
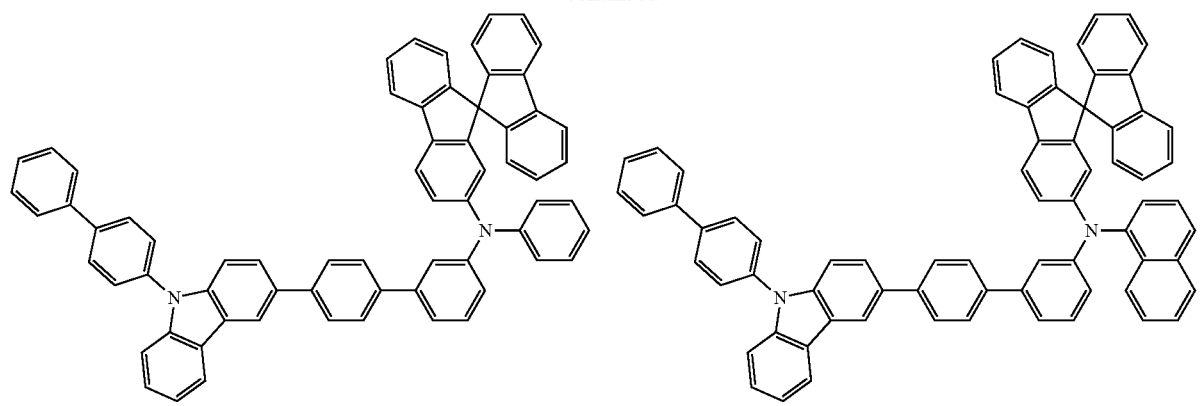
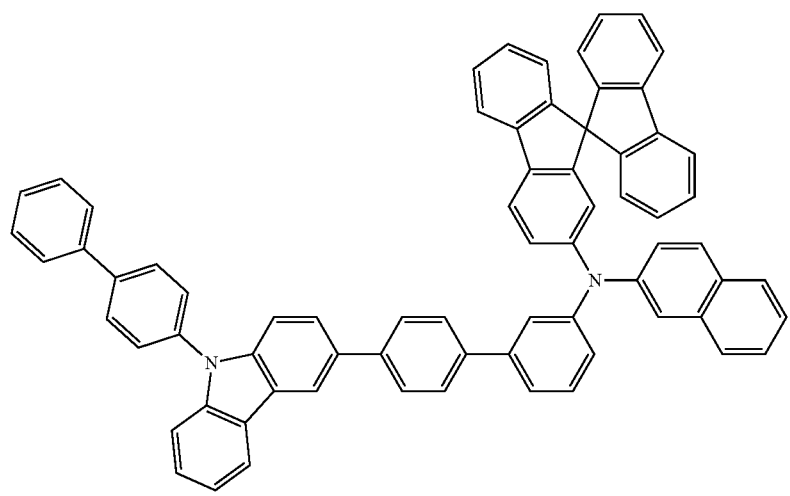
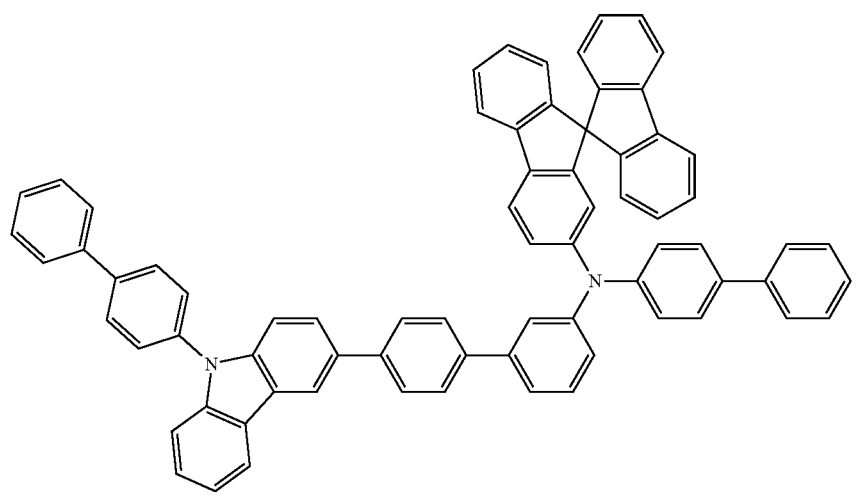

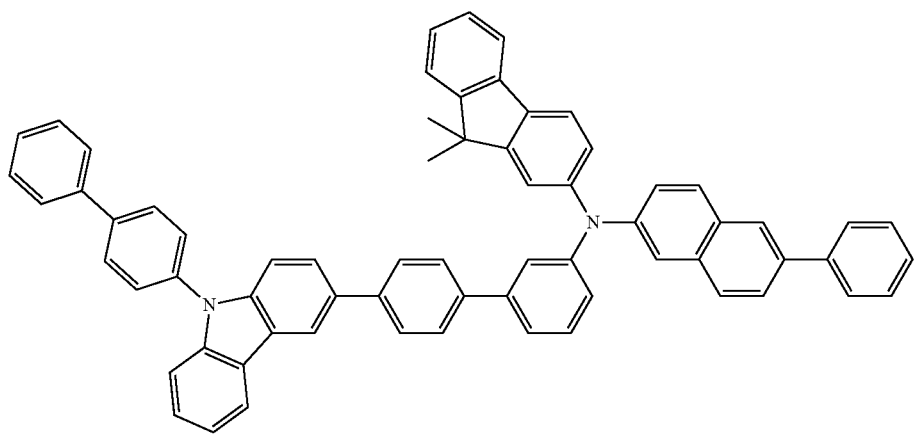
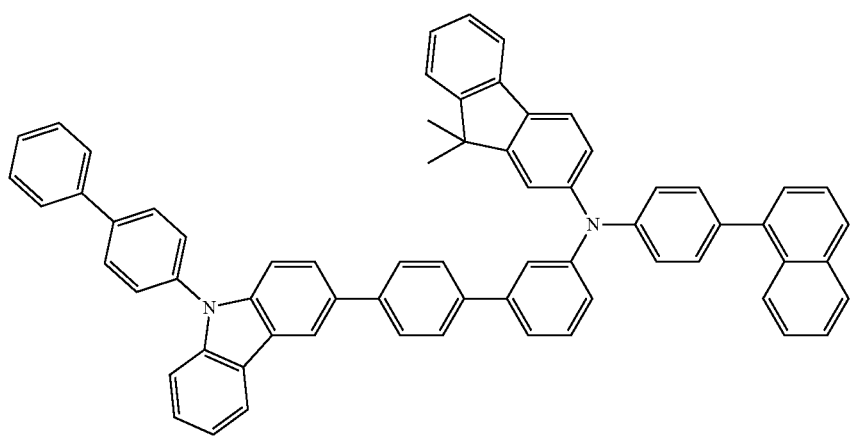
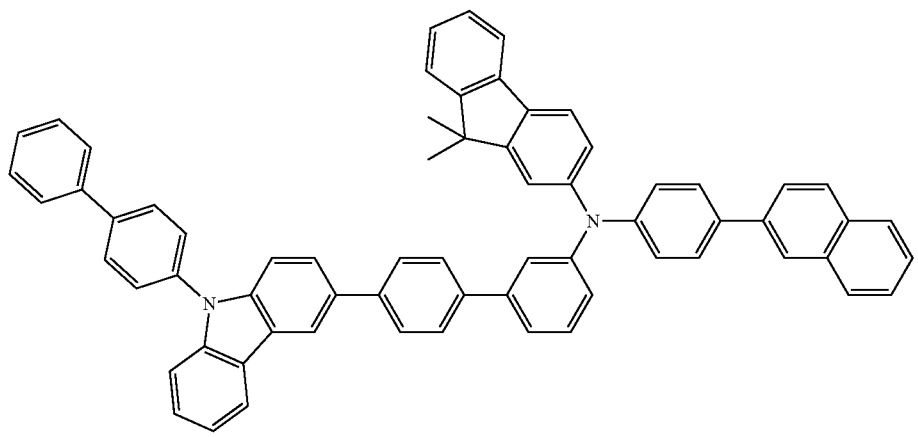

-continued
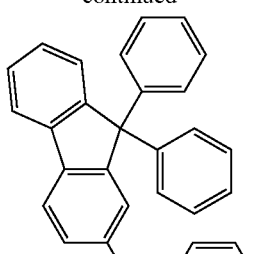
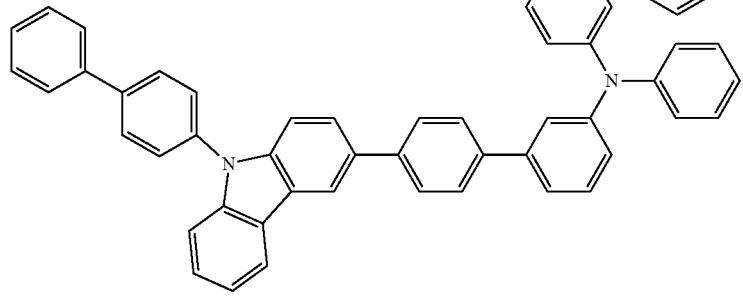
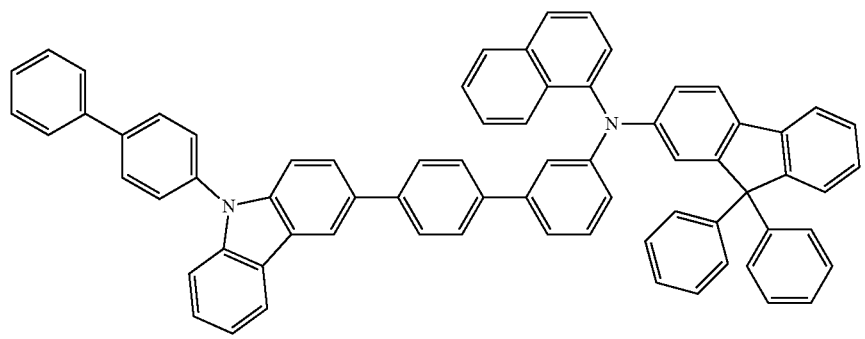
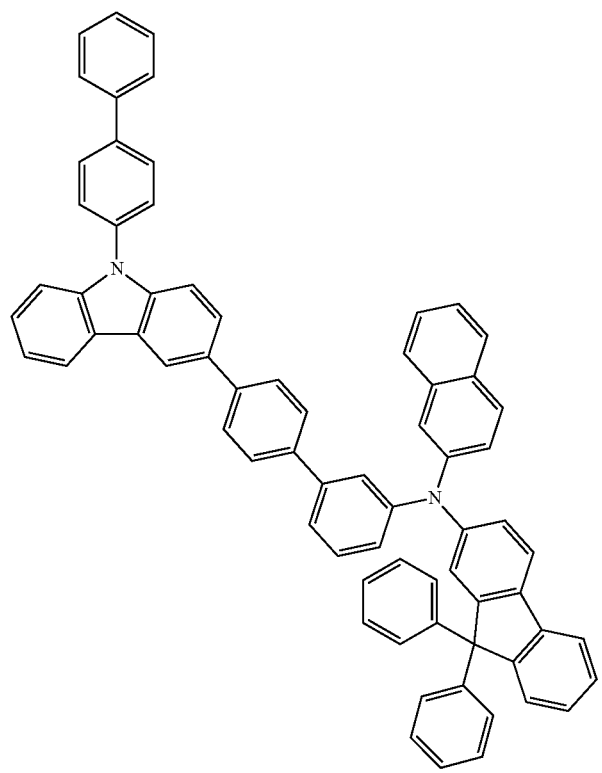
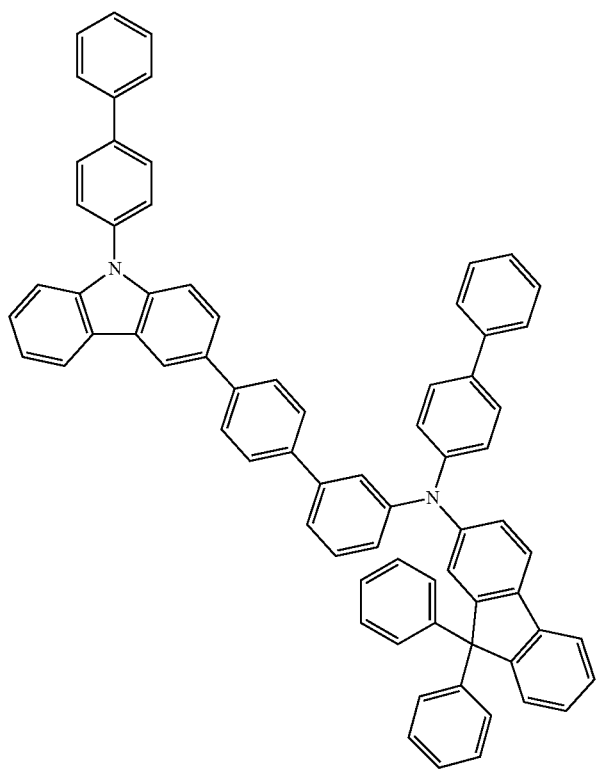

-continued
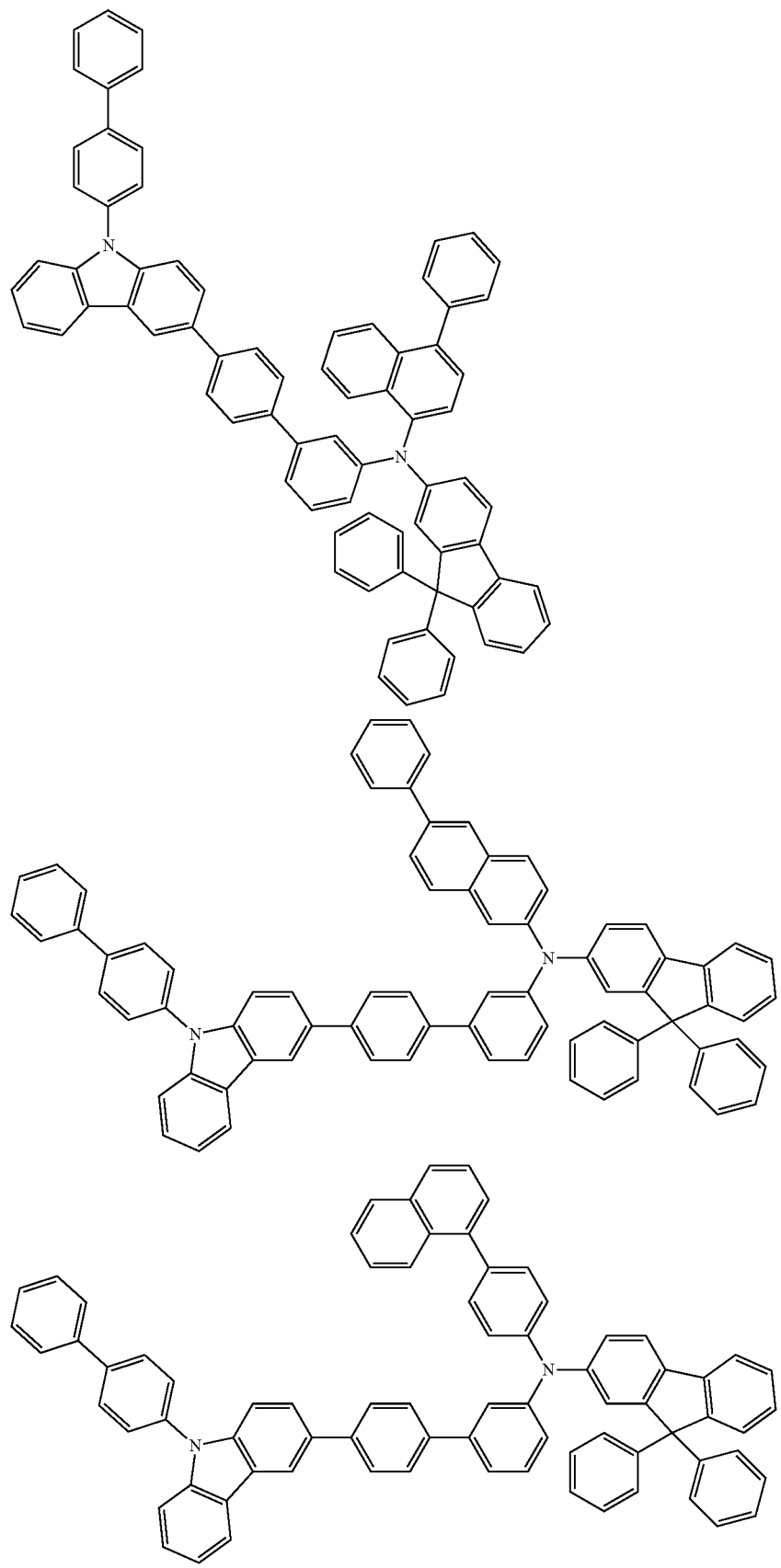

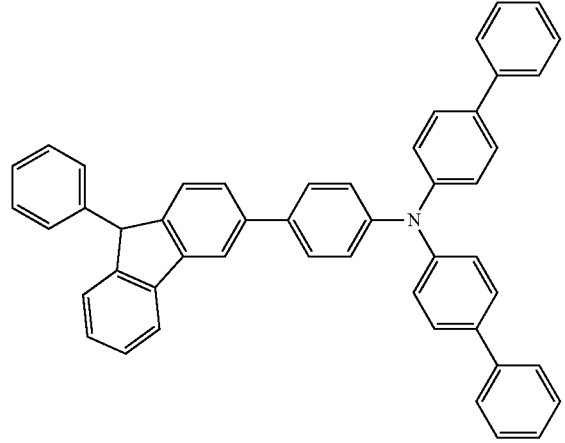
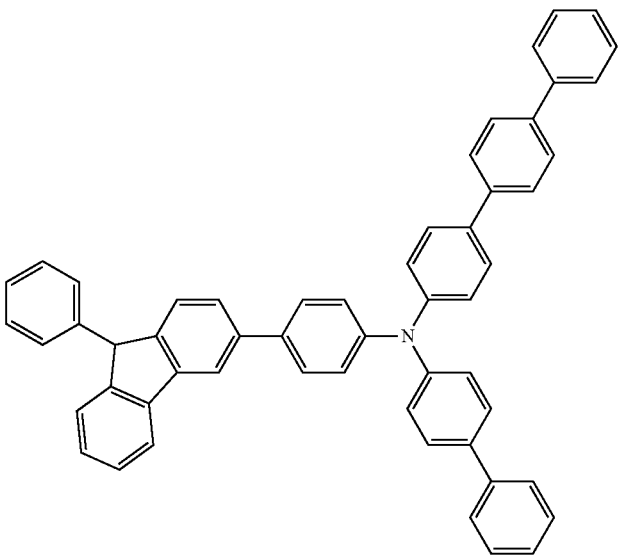
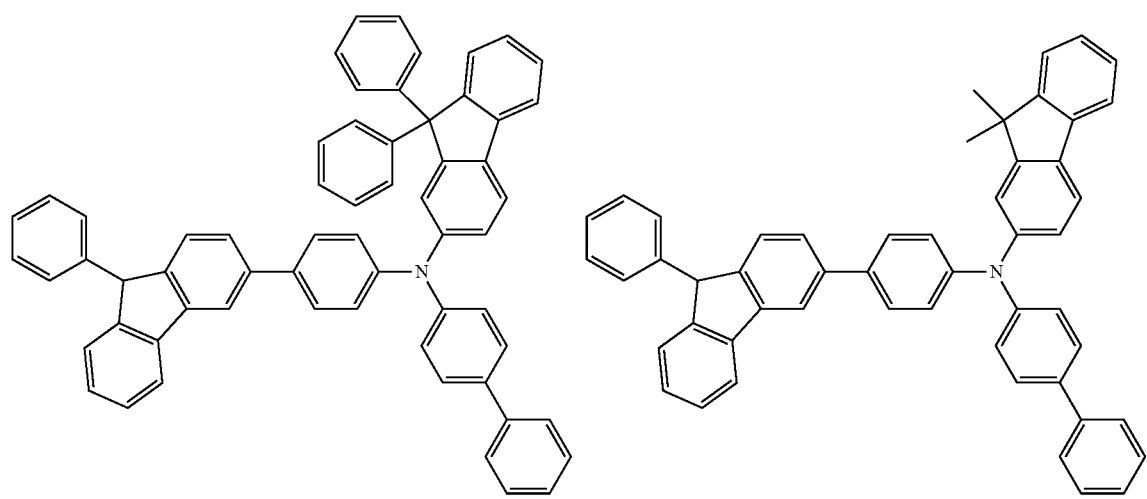
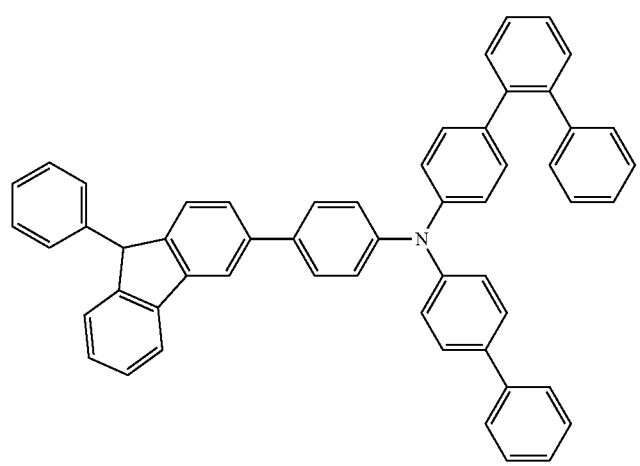

According to an exemplary embodiment of the present specification, Chemical Formula 4 is selected from the following compounds.
(B114)
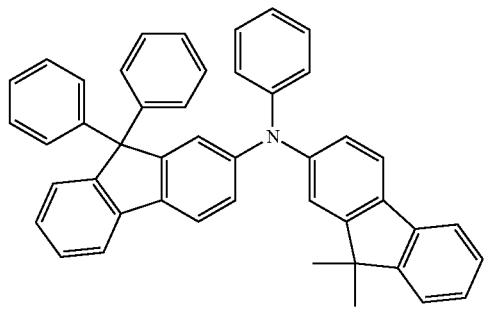
(B115)
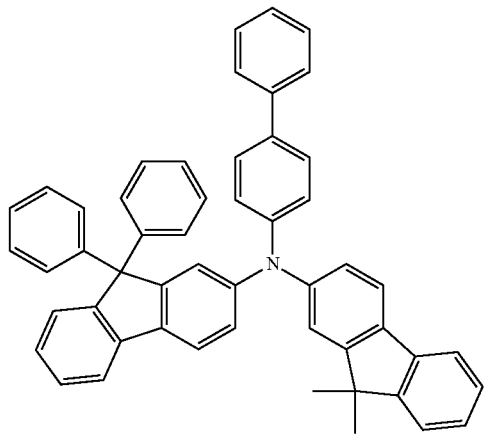
(B116)
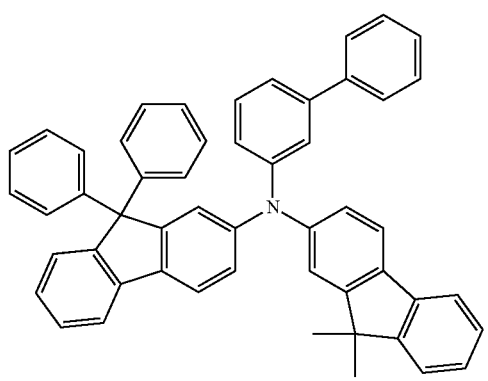
(B117)
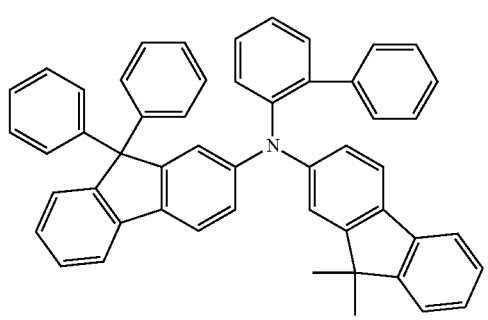
(B118)
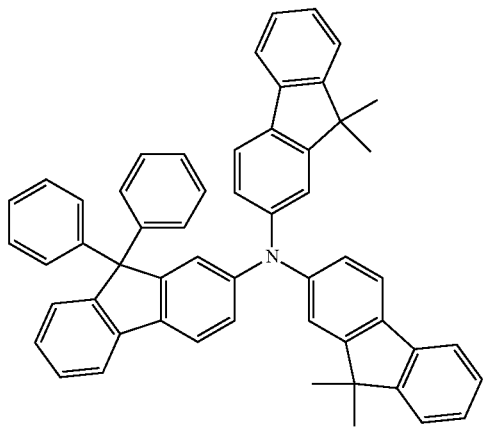
(B119)
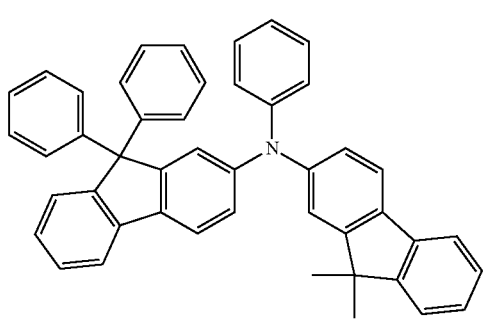
(B120)
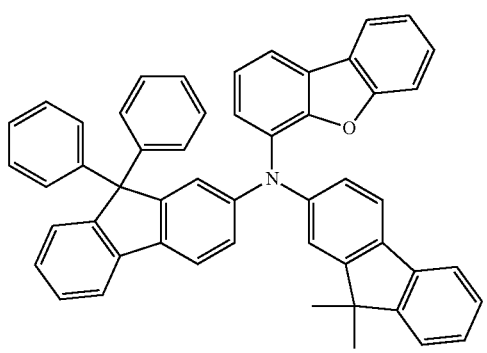
(B121)
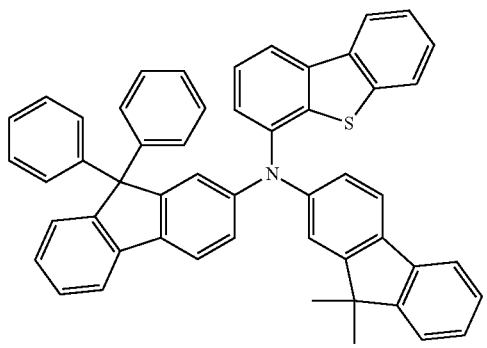

(B122)
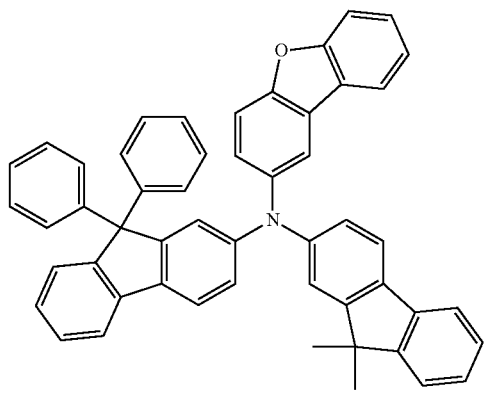
(B123)
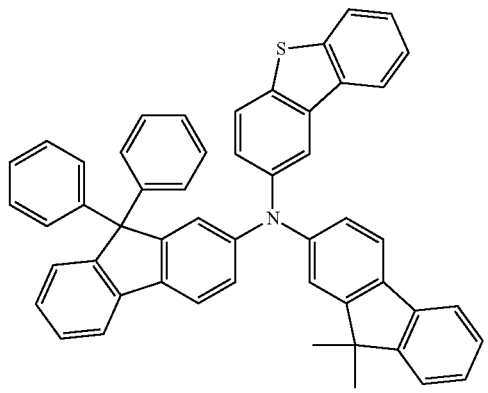
(B124)
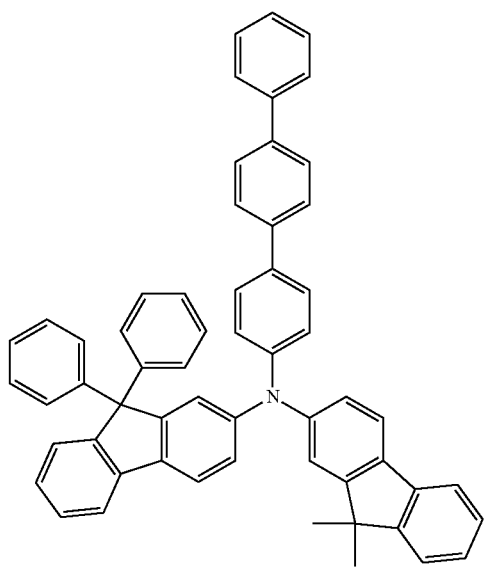
(B125)
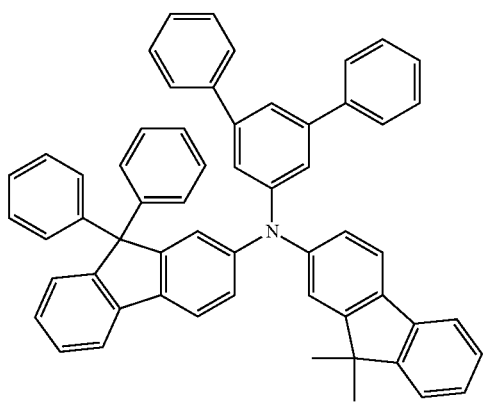
(B126)
(B127)
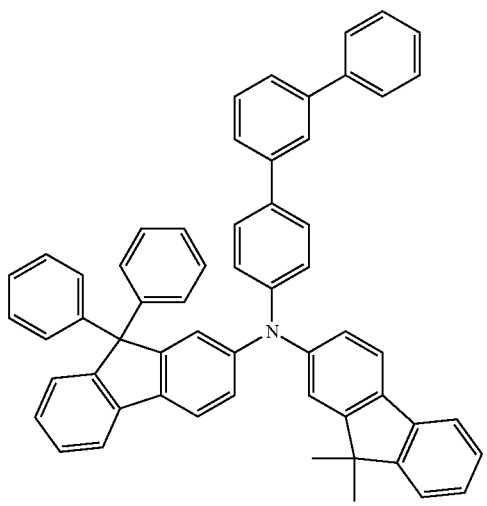

(B128)
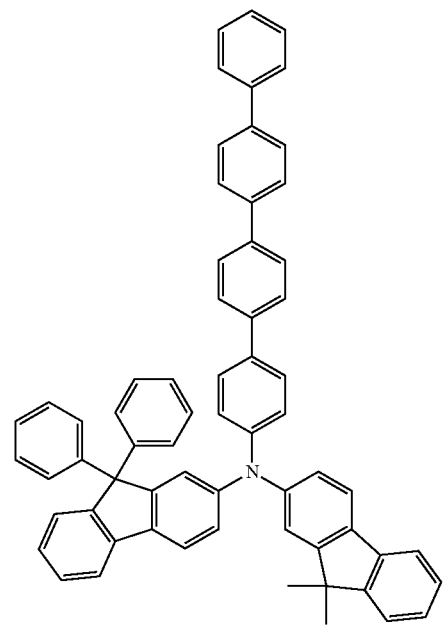
(B129)
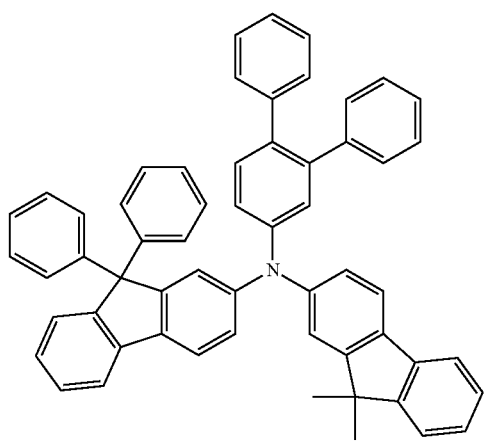
(B130)
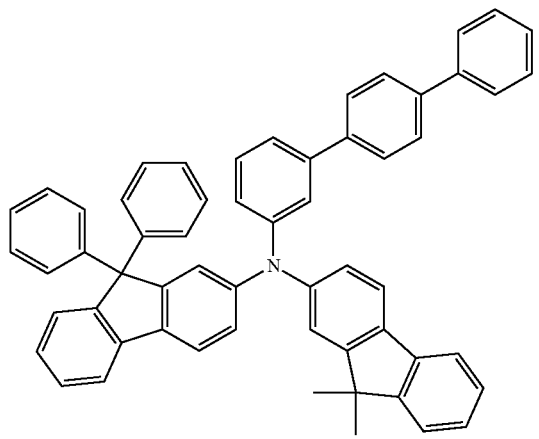
(B131)
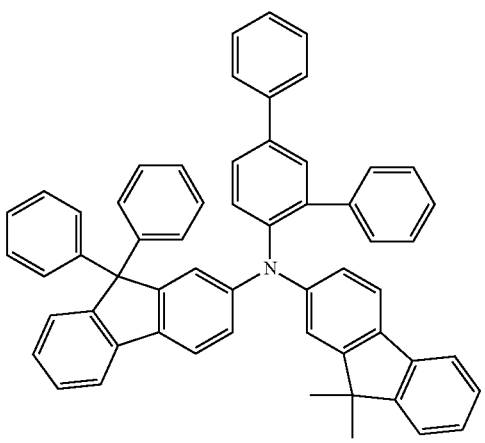
(B132)
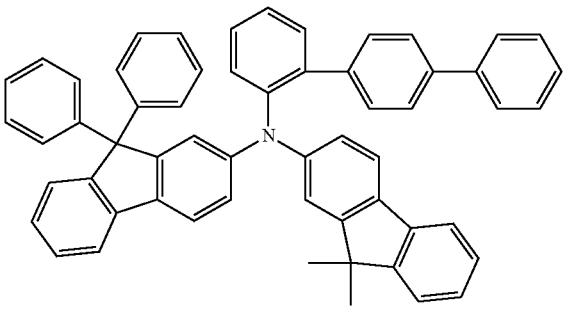
(B133)
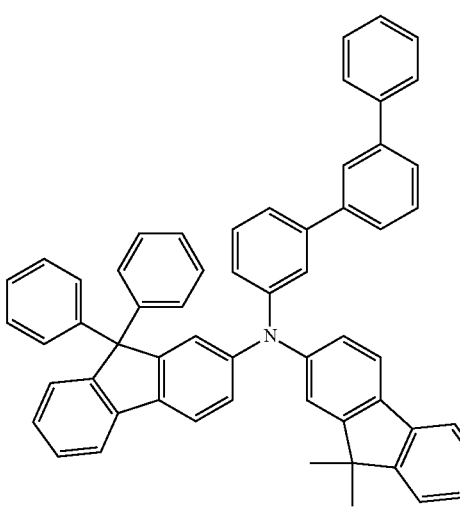

(B134)
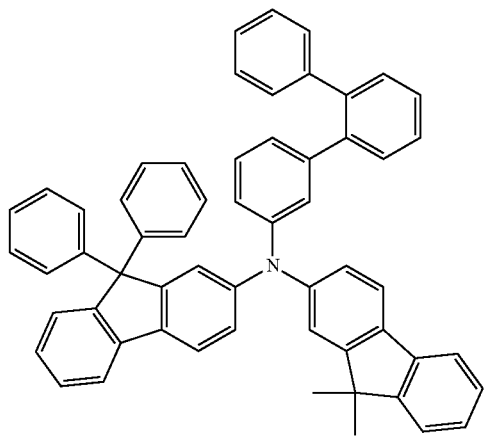
(B135)
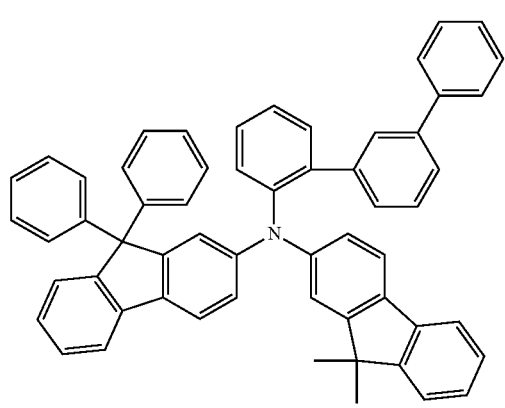
(B136)
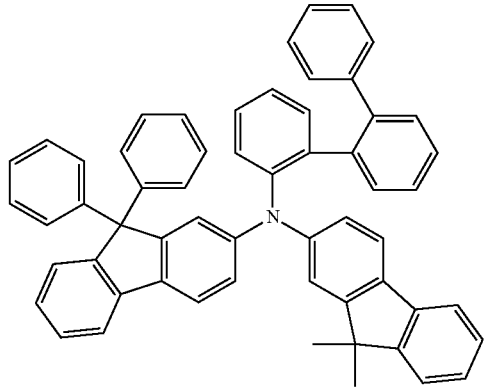
(B137)
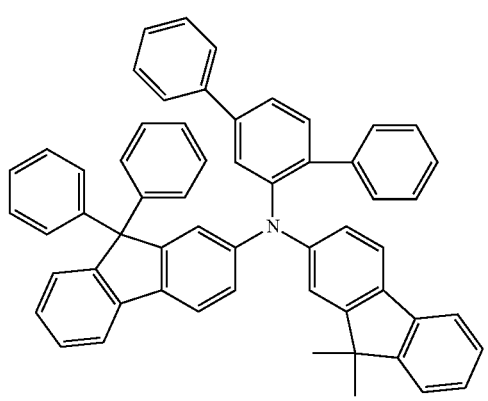
(B138)
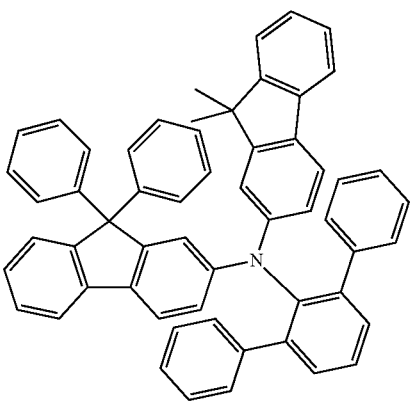
(B139)
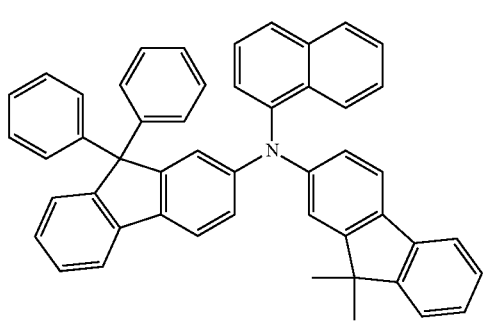
(B140)
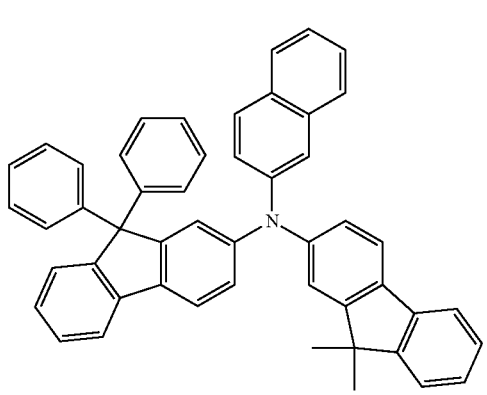
(B141)
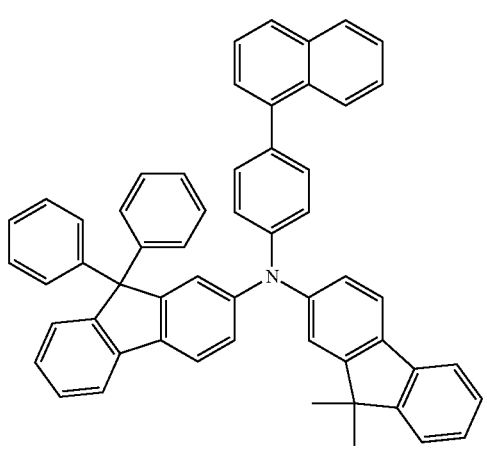

(B142)
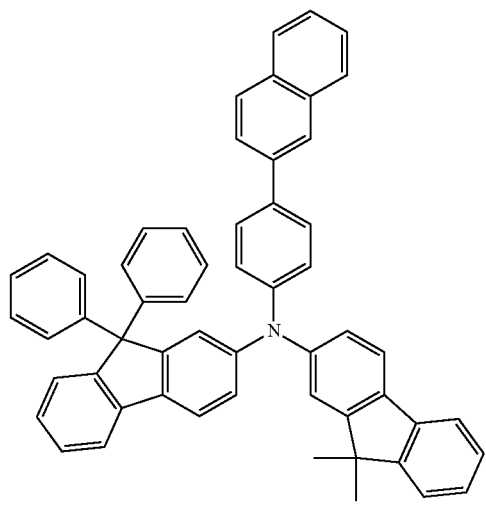
(B145)
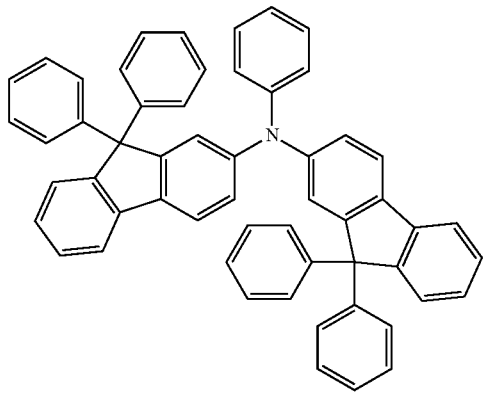
(B143)
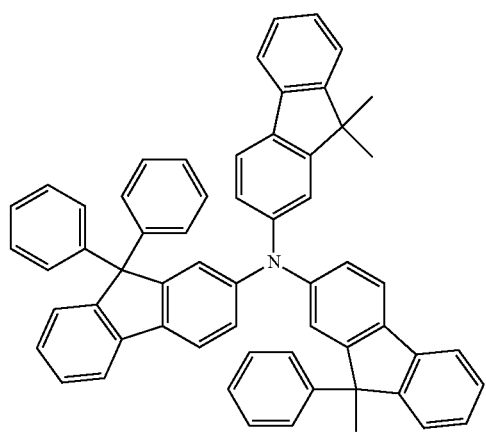
(B146)
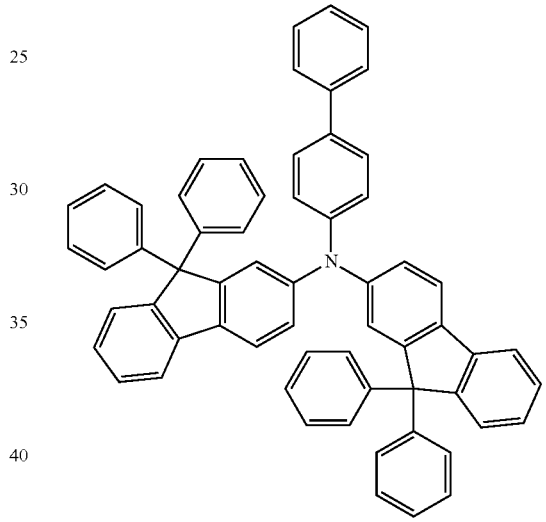
(B144)
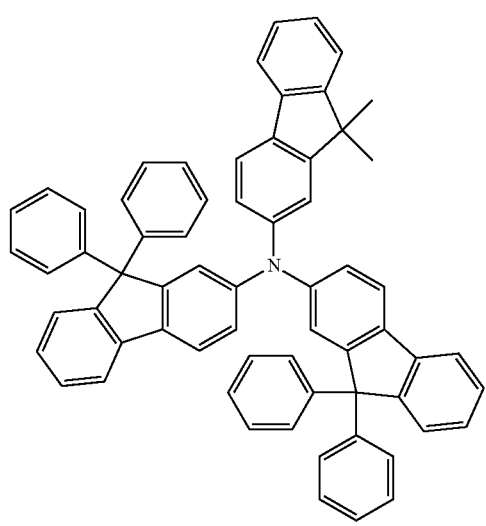
(B147)
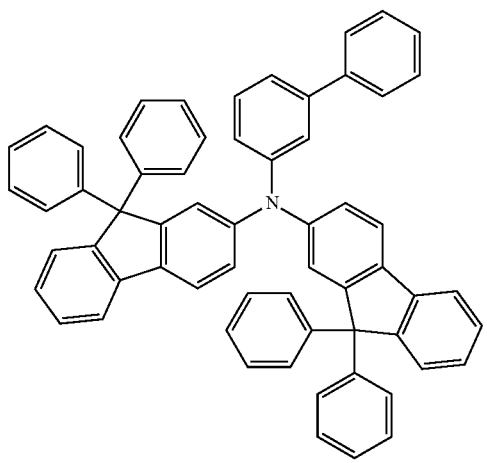

-continued
(B148)
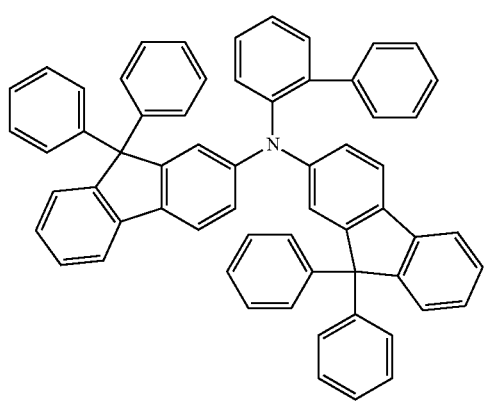
(B149)
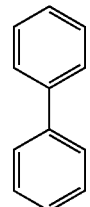
(B150)
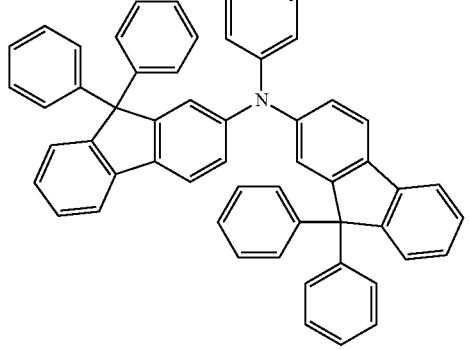
-continued
(B151)
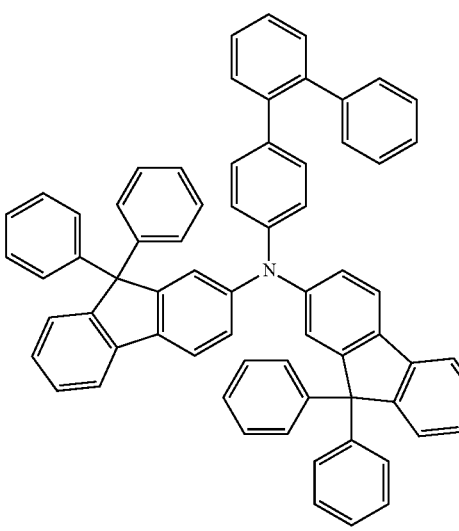
(B152)
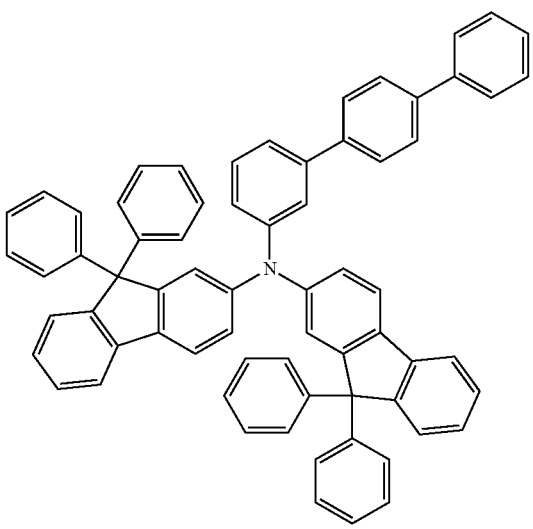

(B153)
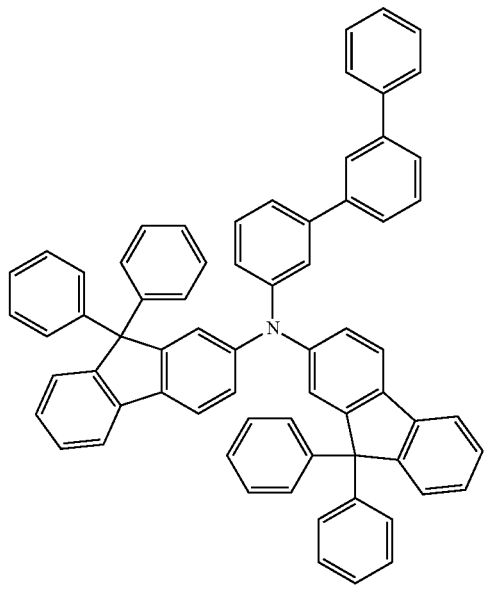
(B154)
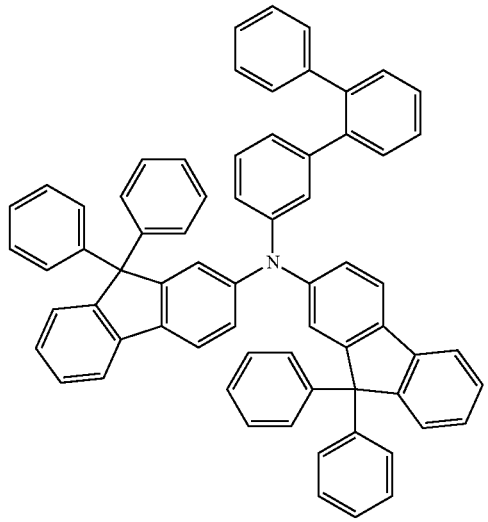
(B155)
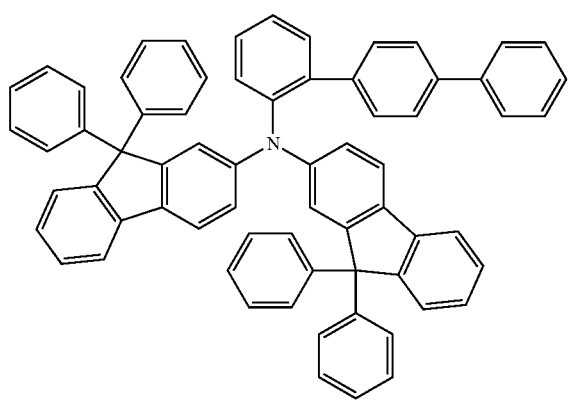
(B156)
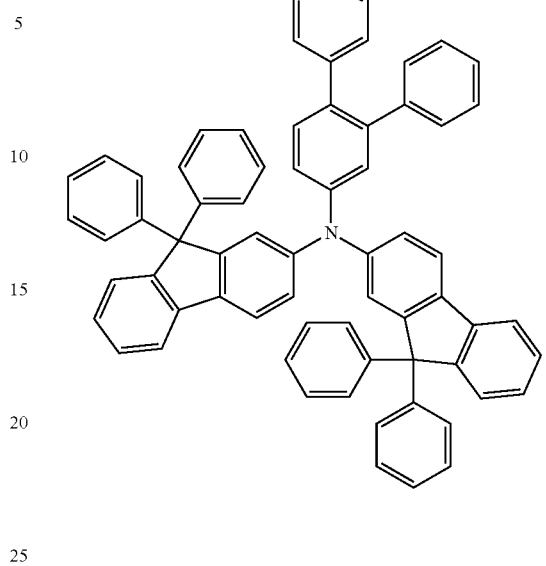
(B157)
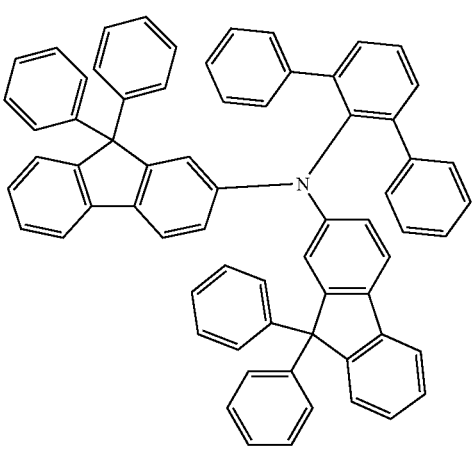
(B158)

(B159)
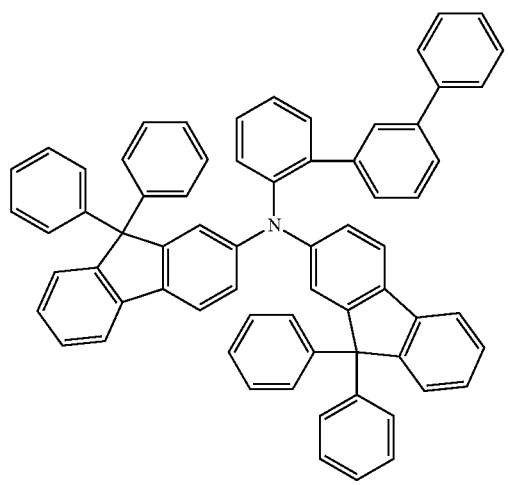
(B160)
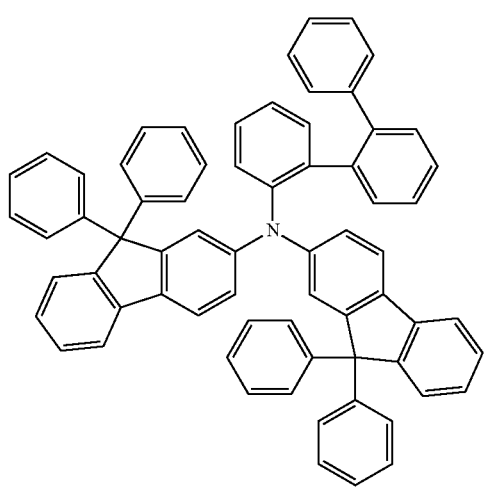
(B161)
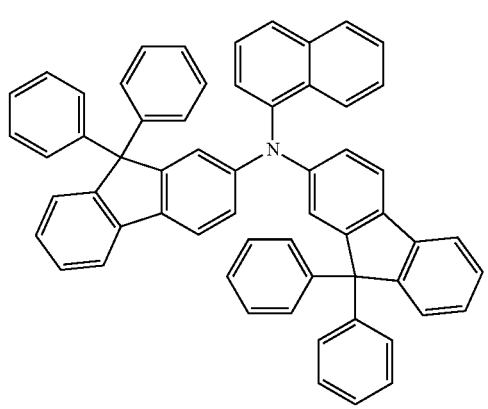
(B162)
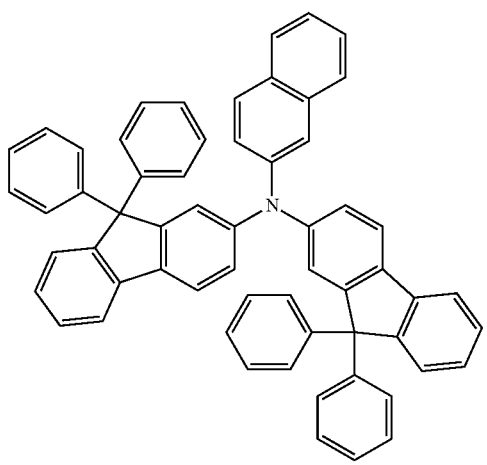
(B163)
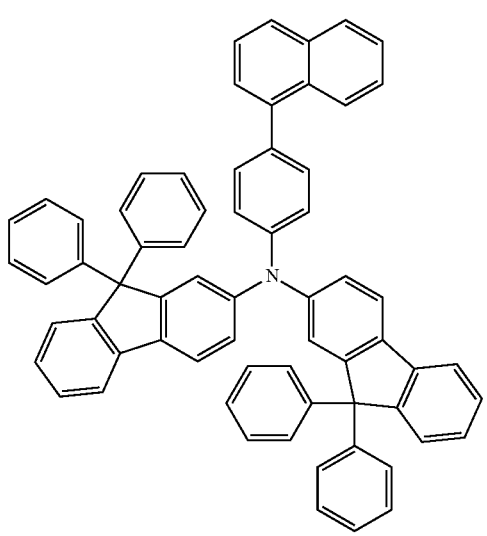
(B164)
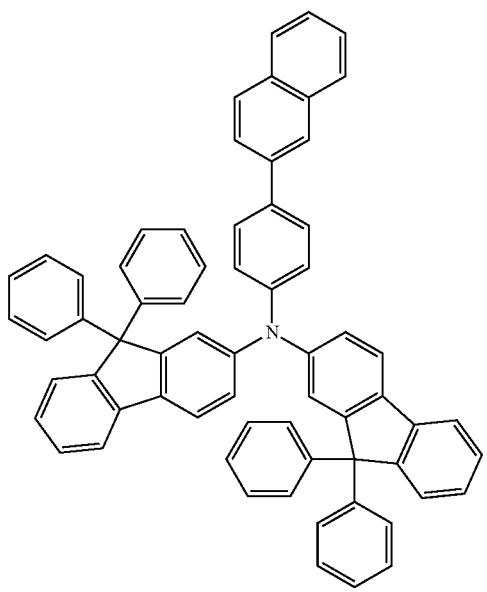

(B165)
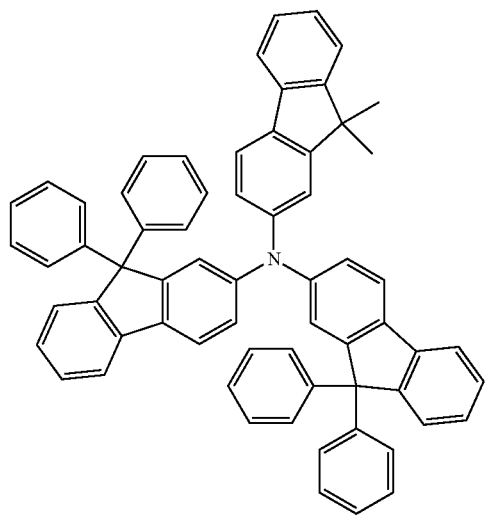
(B168)
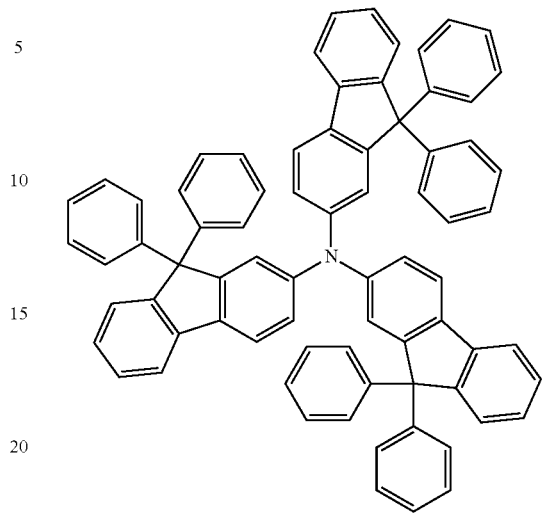
(B166)
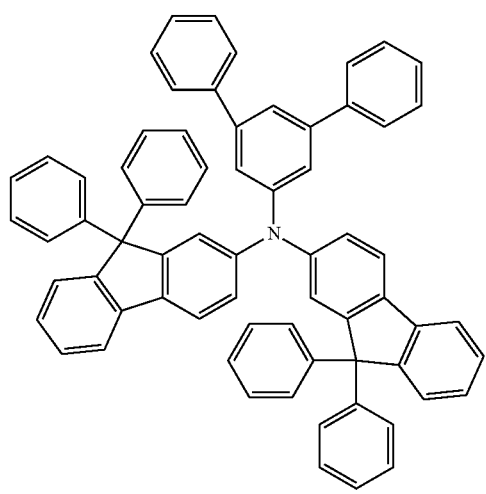
(B169)
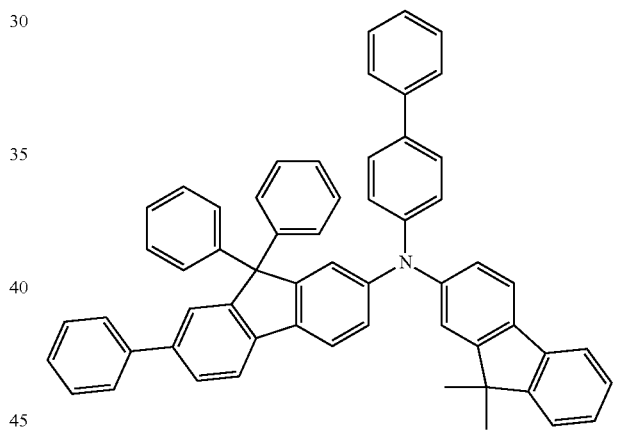
(B167)
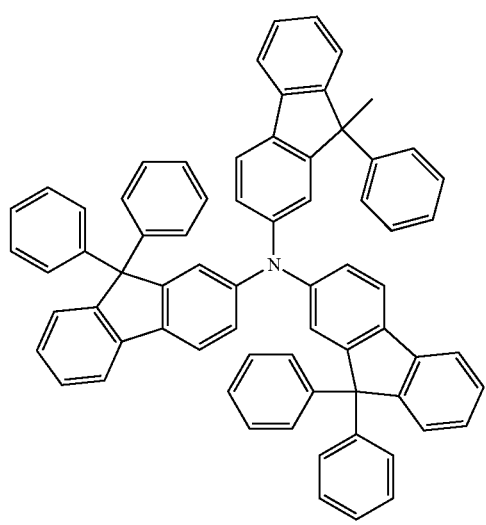
(B170)
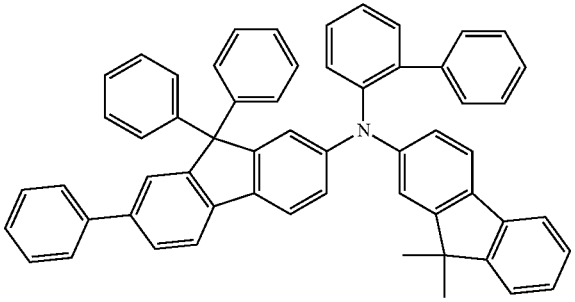

-continued
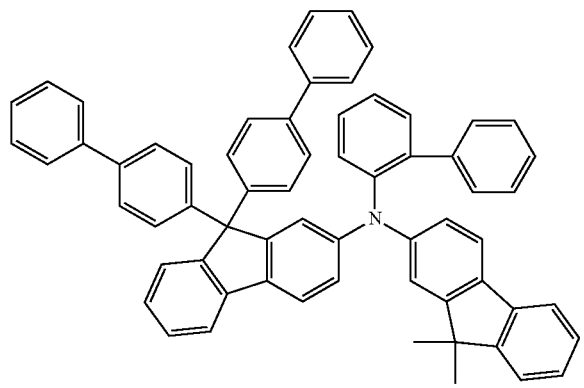
(B1171)
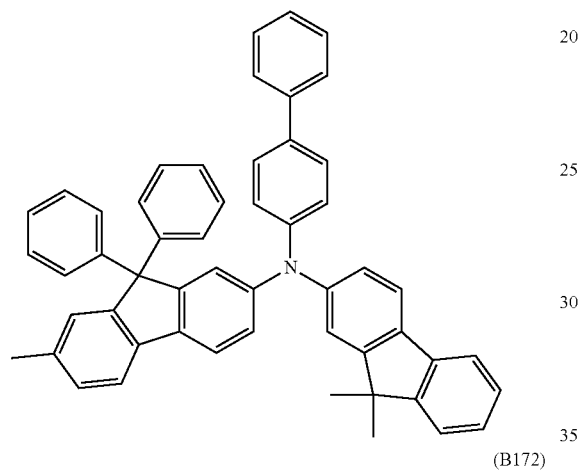
(B172)
(B173)
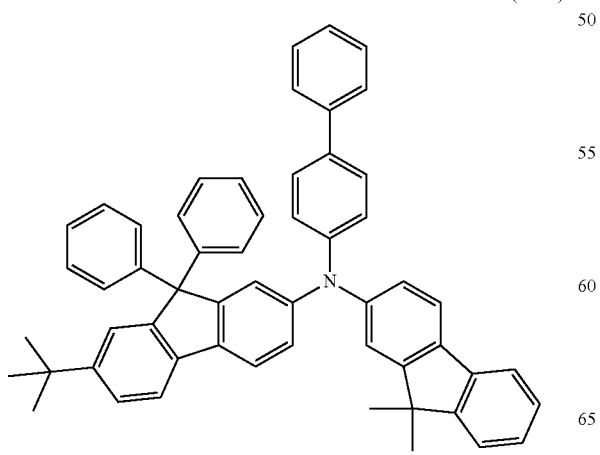
-continued
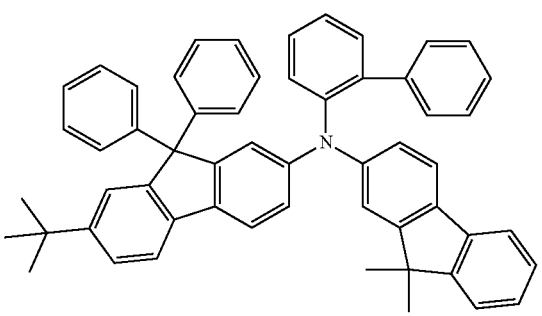
(B174)
(B175)
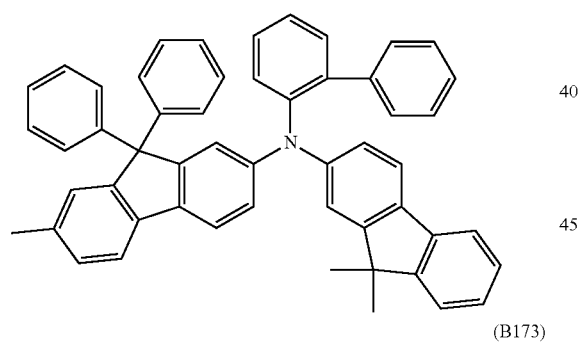
(B176)
(B177)
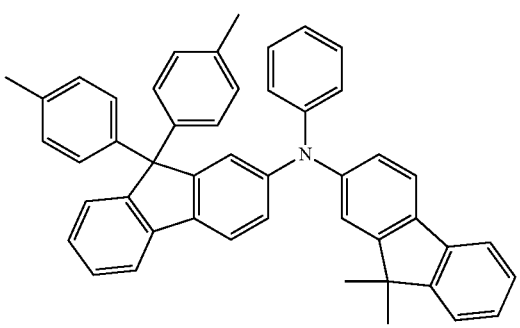

(B178)
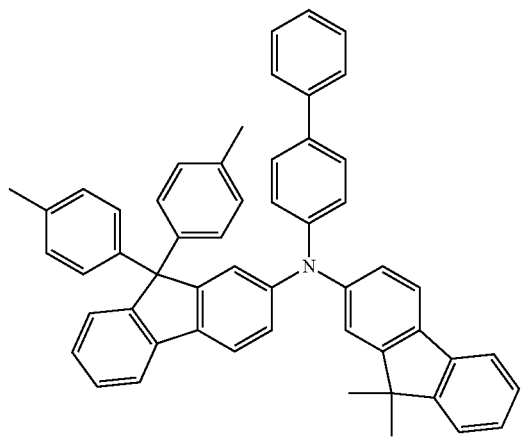
(B179)
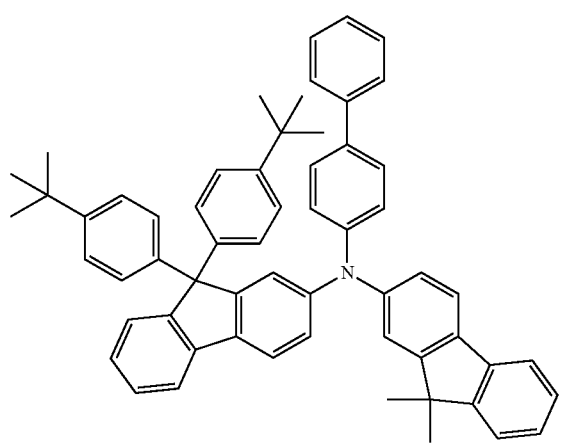
(B180)
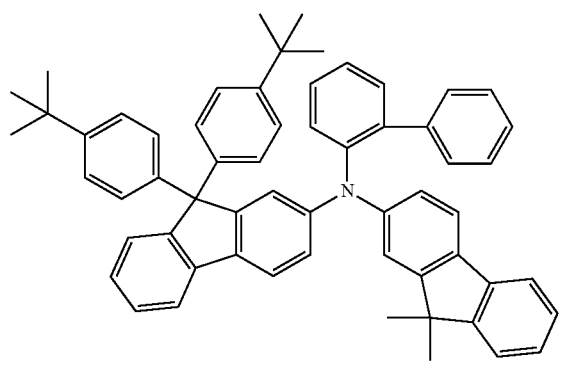
(B181)
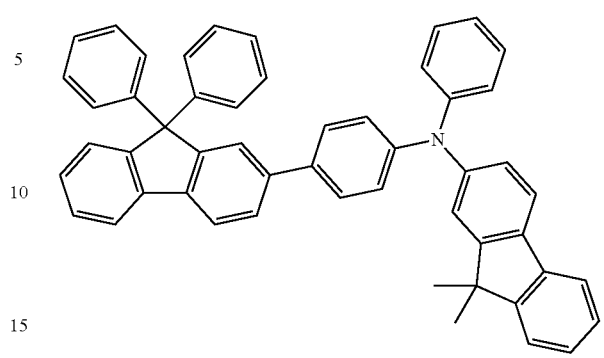
(B182)
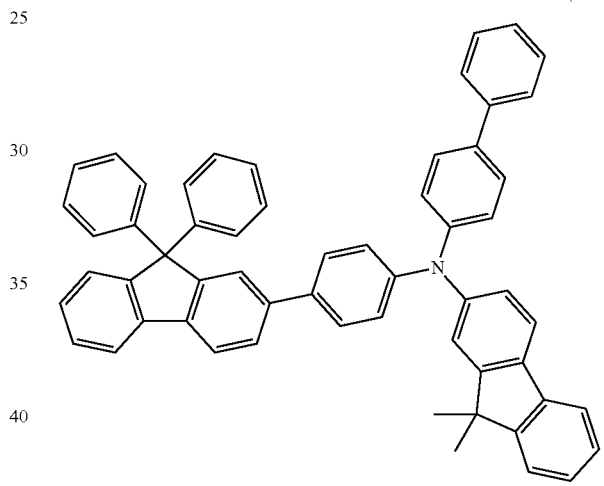
(B183)
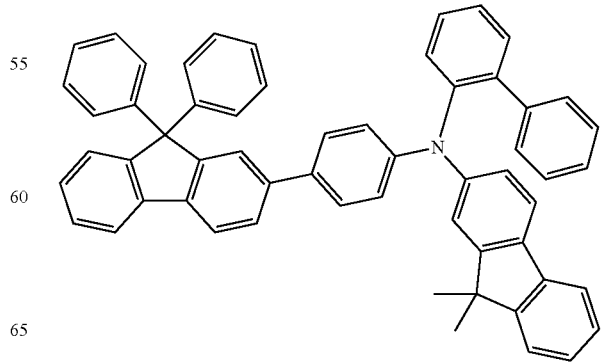

-continued
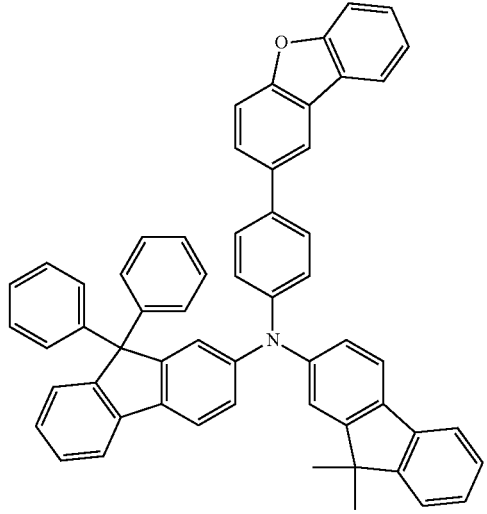
(B184)
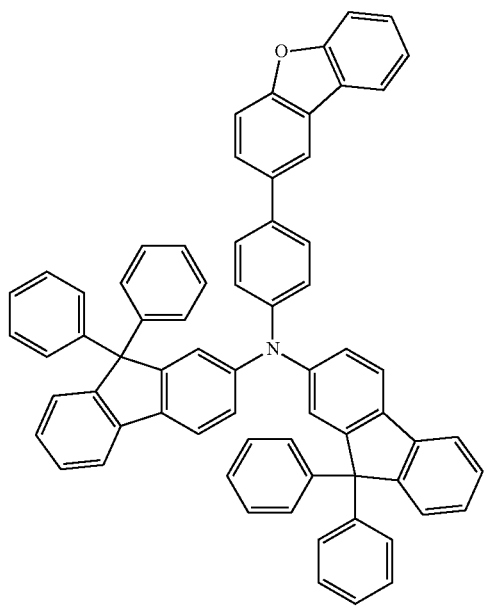
(B185)
-continued
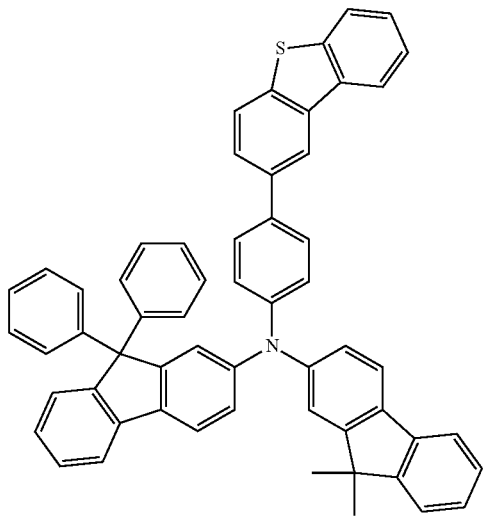
(B186)
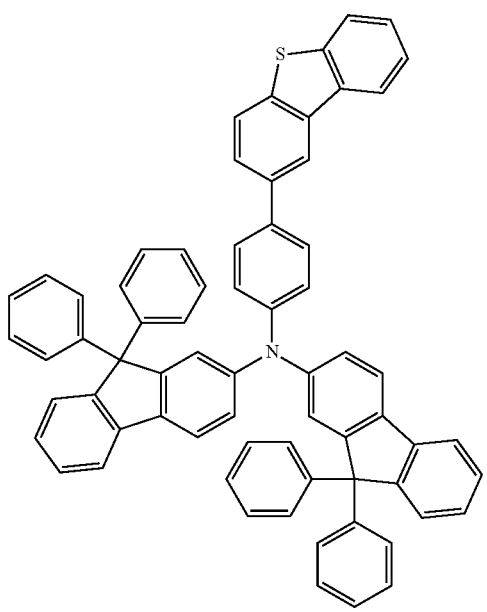
(B187)
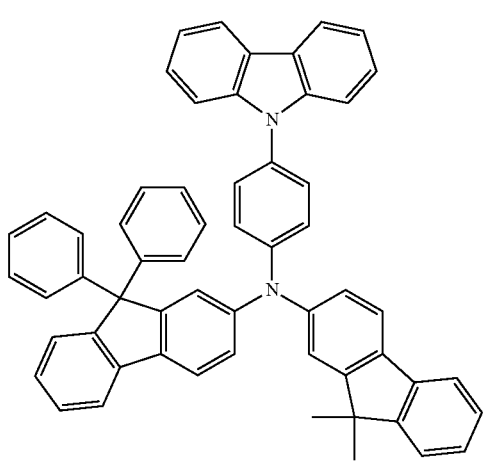
(B188)

(B189)
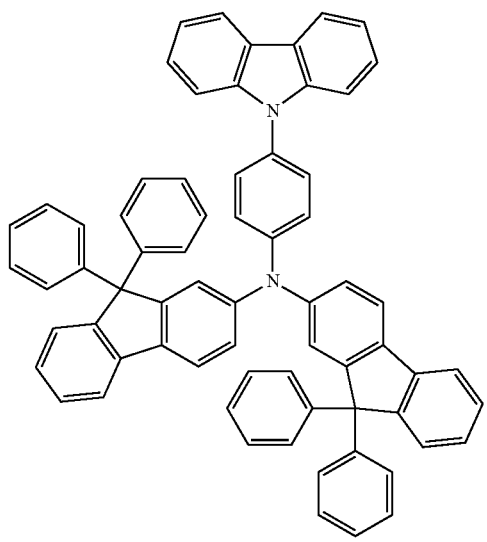
(B192)
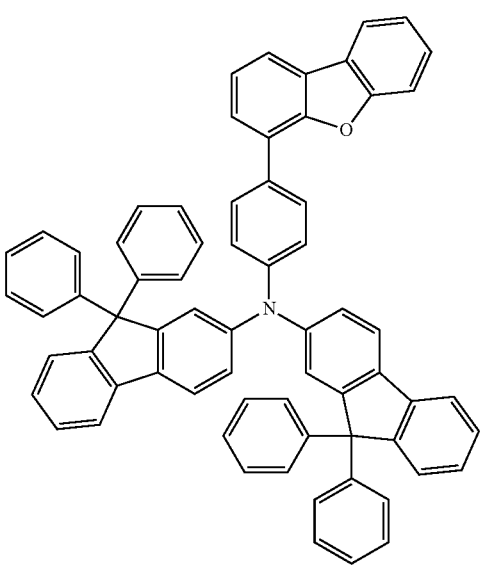
(B190)
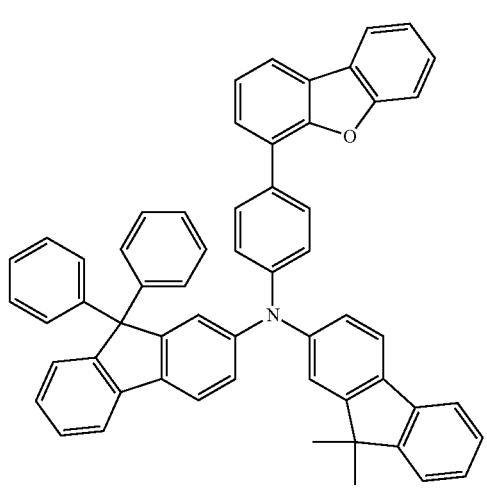
(B193)
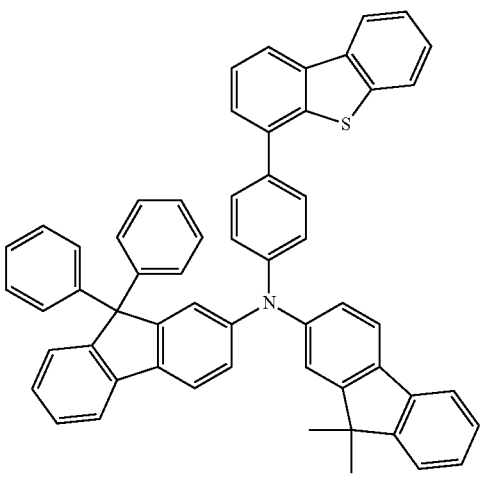
(B191)
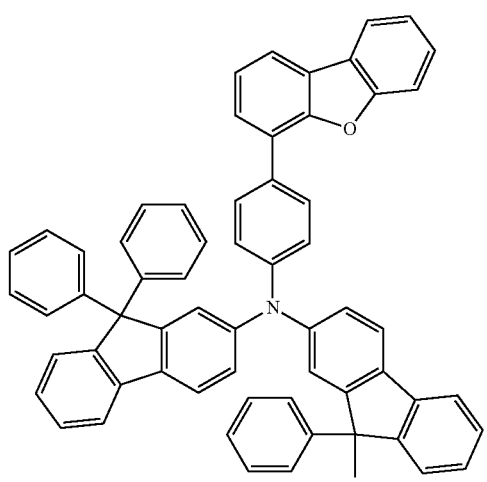
(B194)
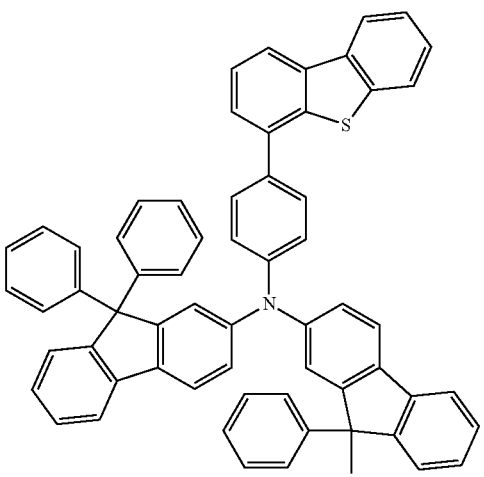

(B195)
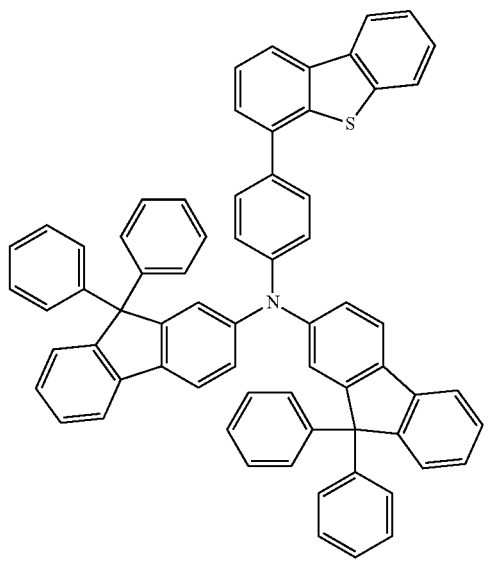
(B196)
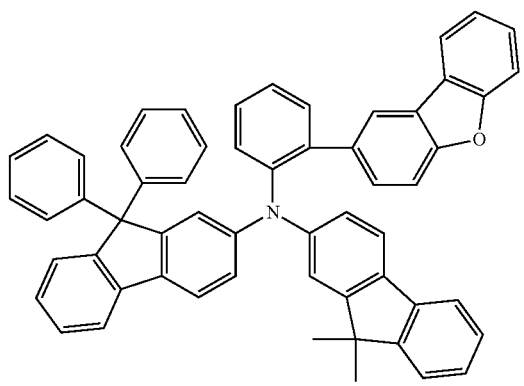
(B197)
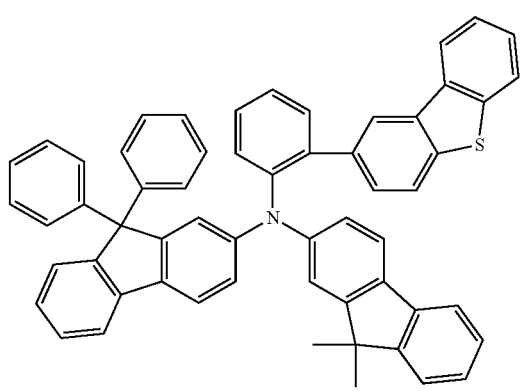
(B198)
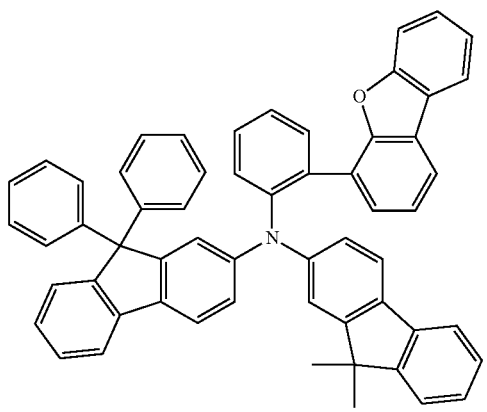
(B199)
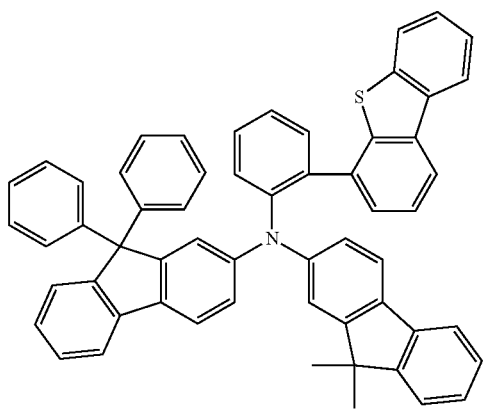
(B200)
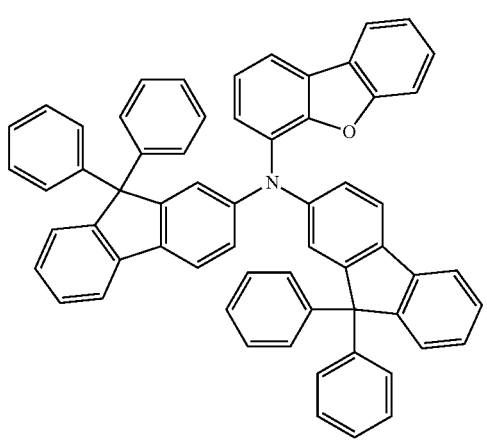

-continued
(B201)
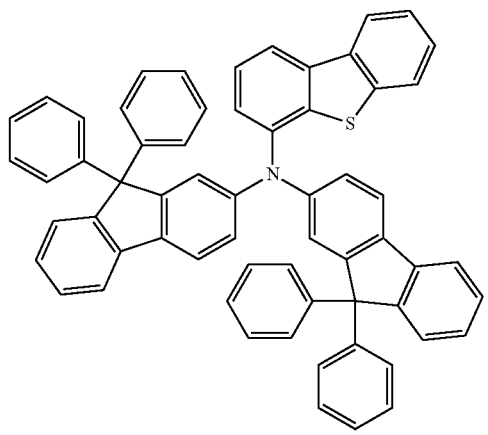
(B204)
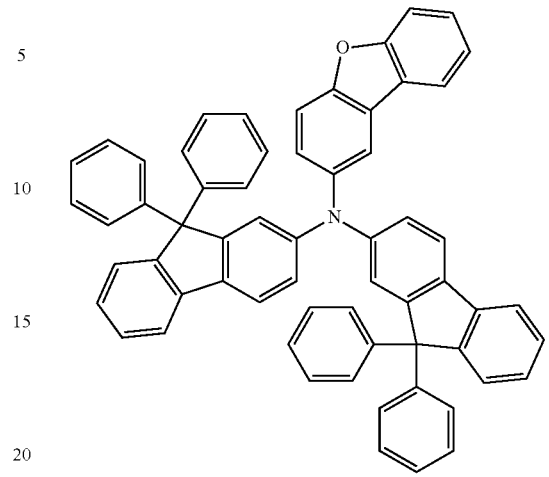
(B202)
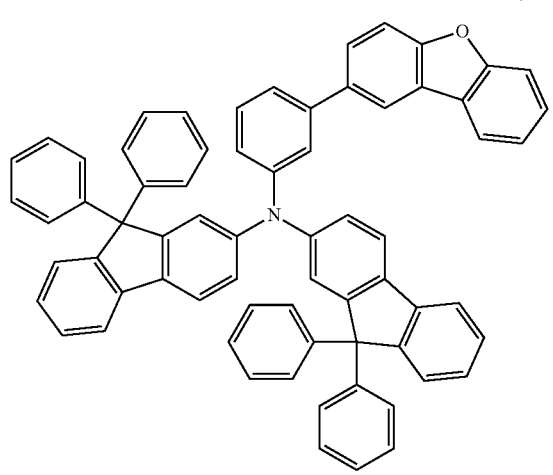
(B205)
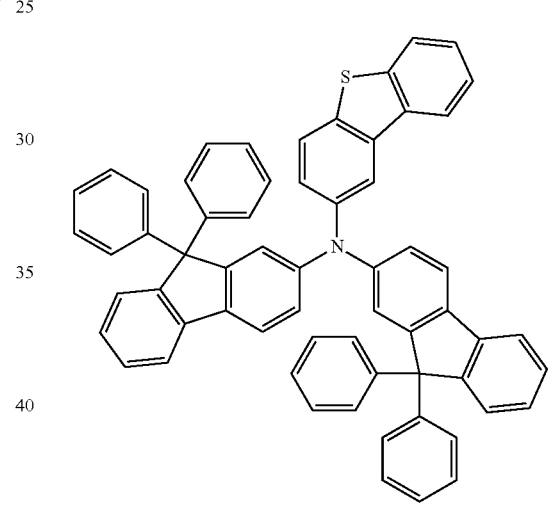
(B203)
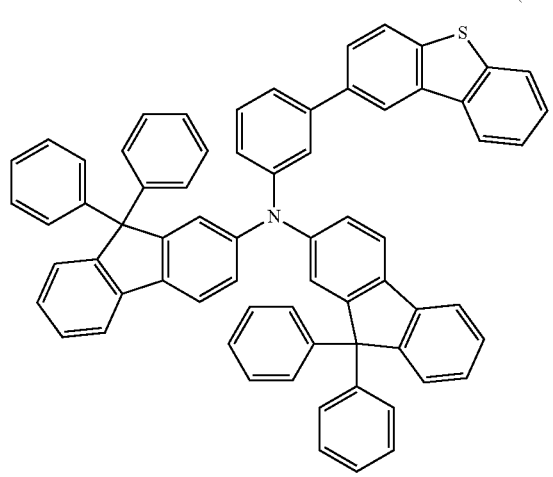
(B206)
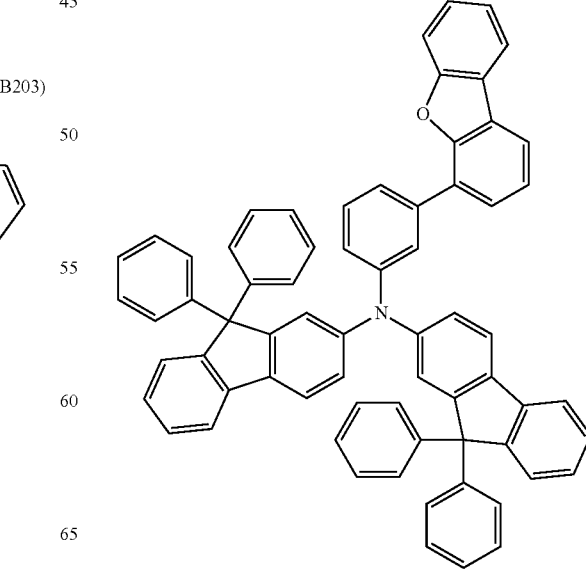

(B207)
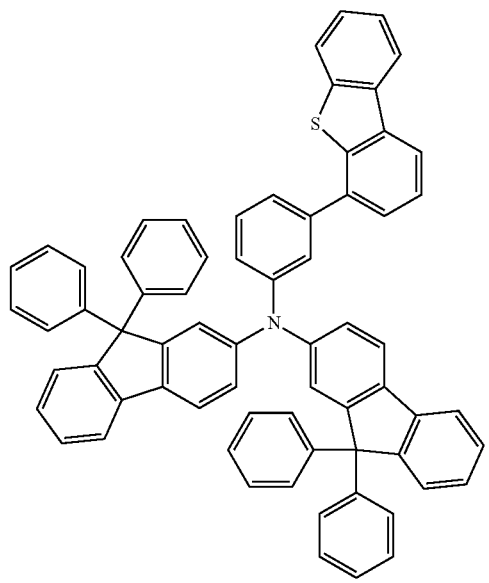
(B208)
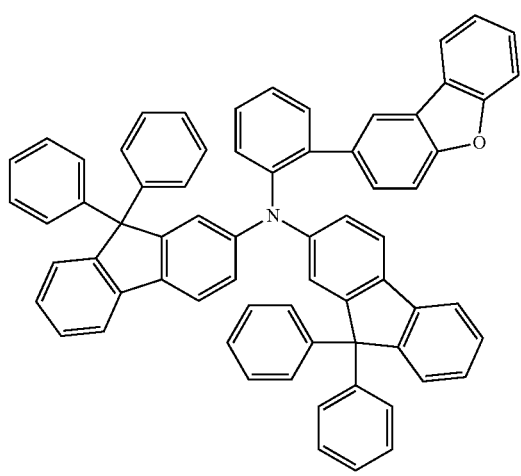
(B209)
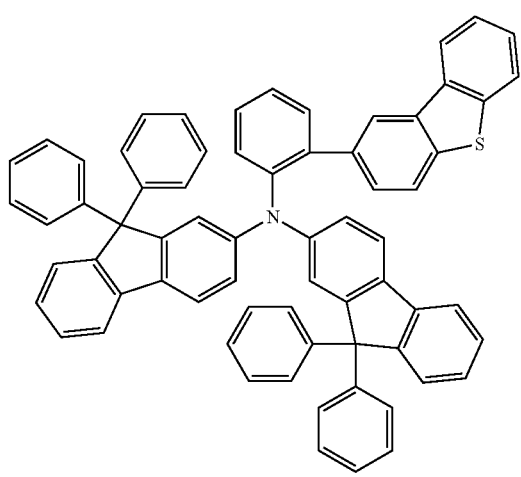
(B210)
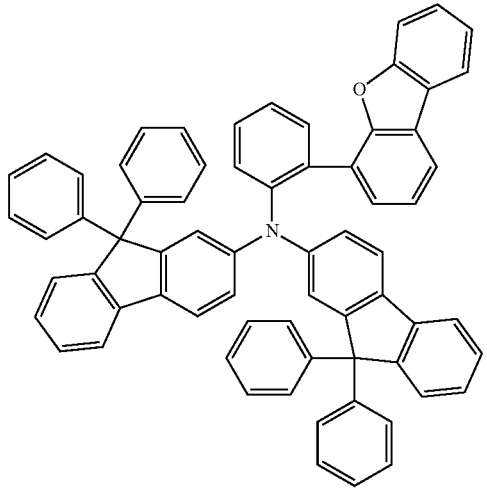
(B211)
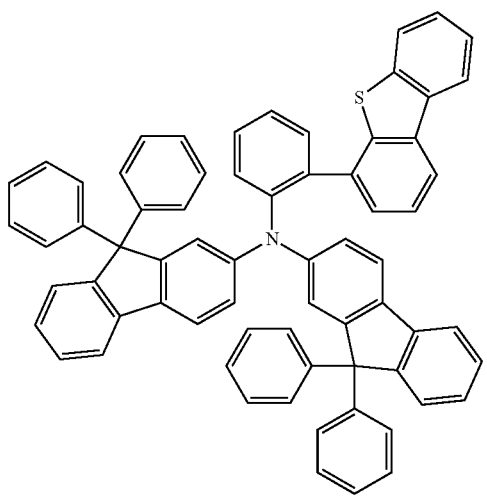
(B212)
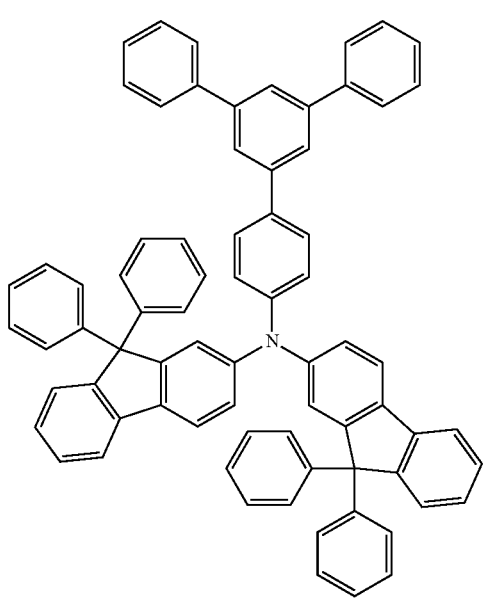

(B213)
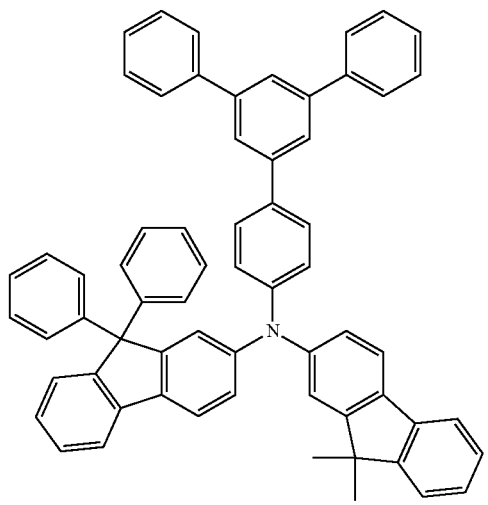
(B216)
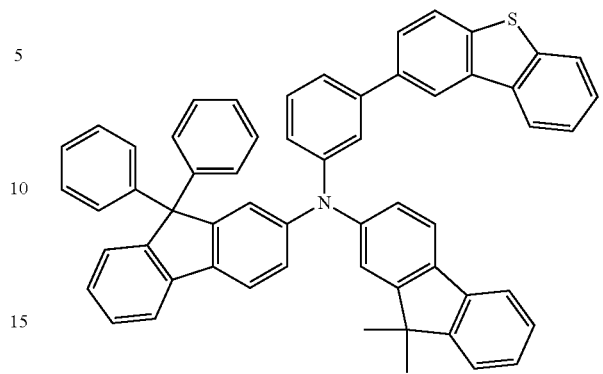
(B214)
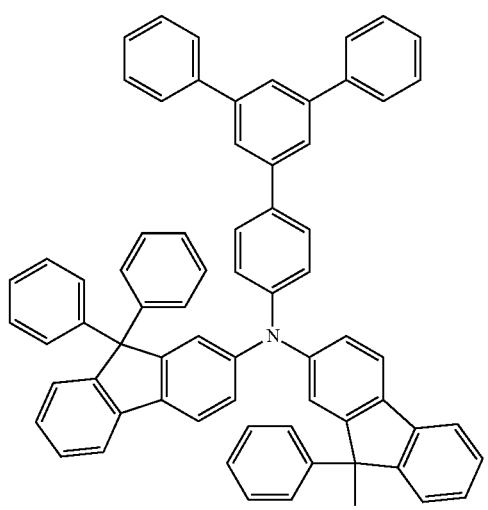
(B217)
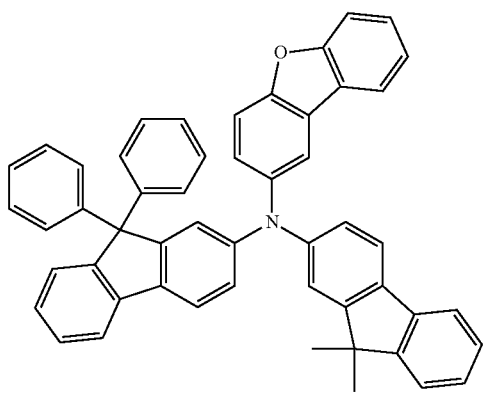
(B215)
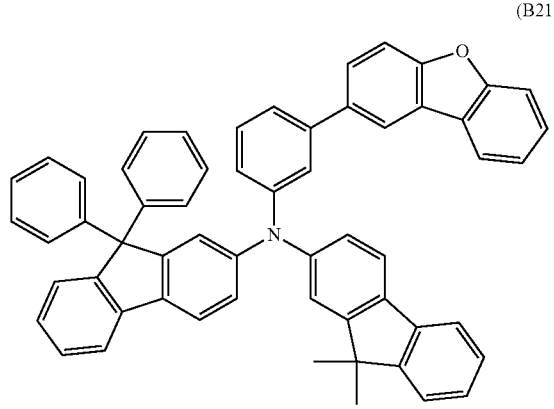
(B218)
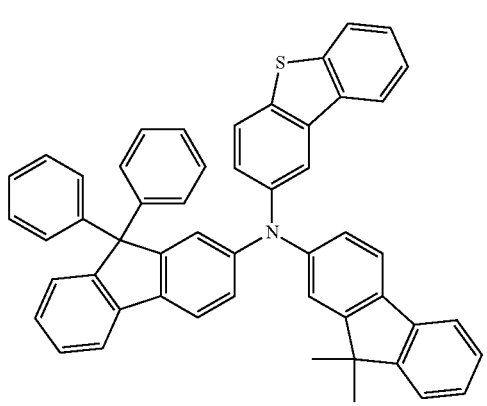

-continued
(B219)
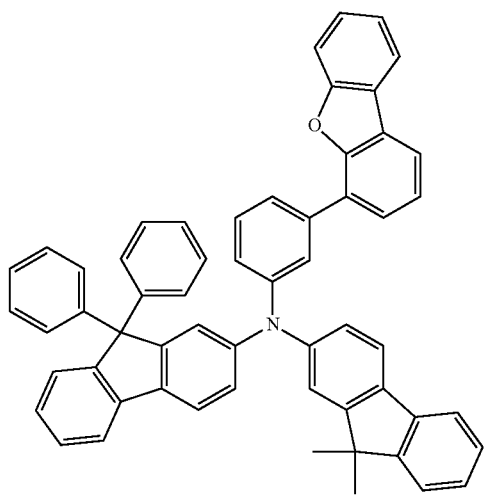
(B220)
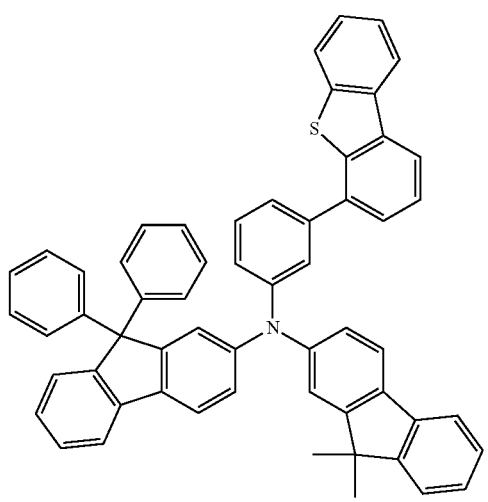
(B221)
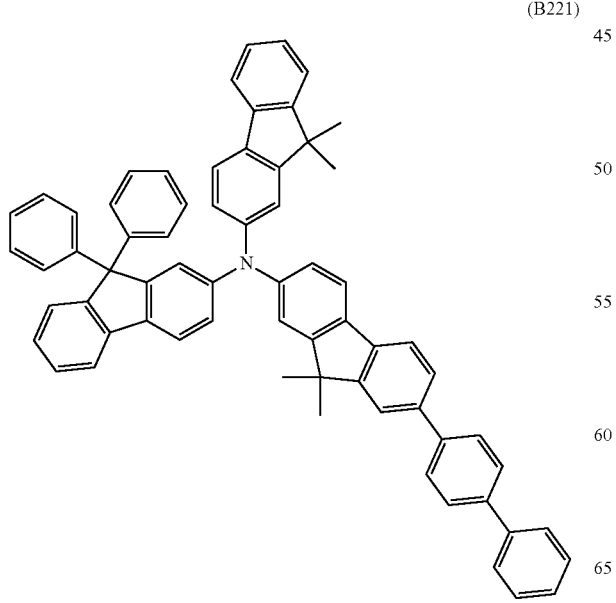
(B222)
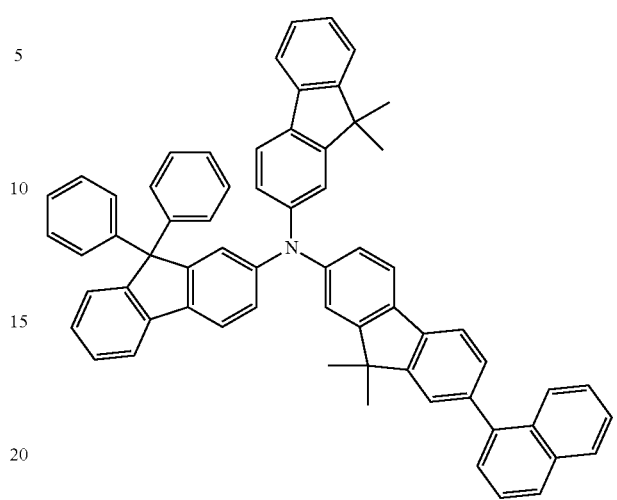
(B223)
(B1224)

-continued
(B225)
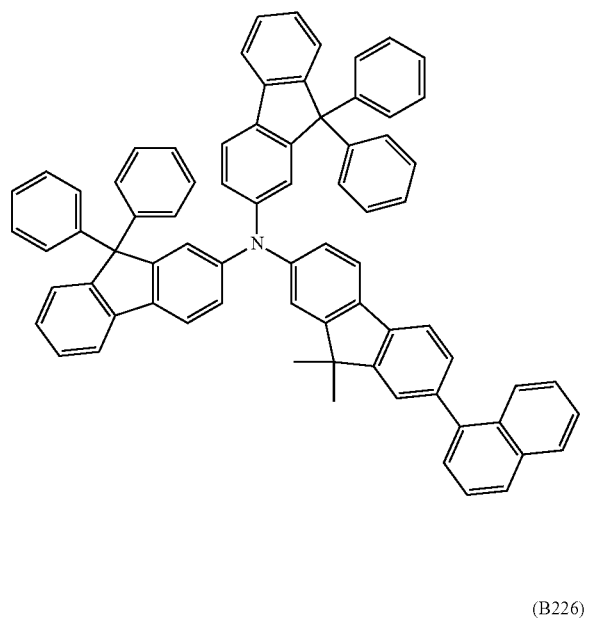
(B228)
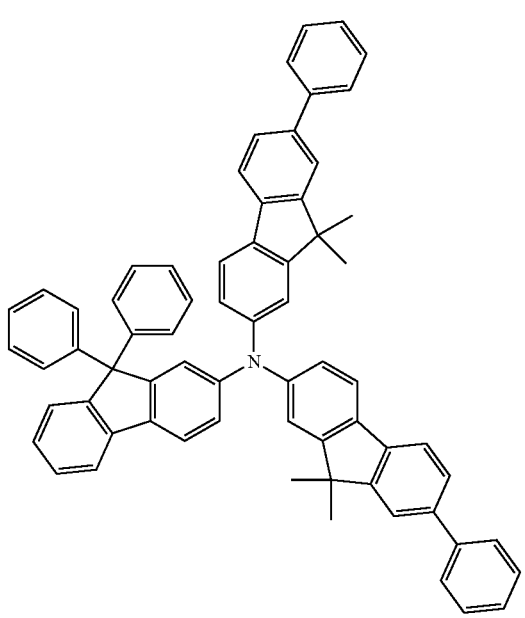
(B226)
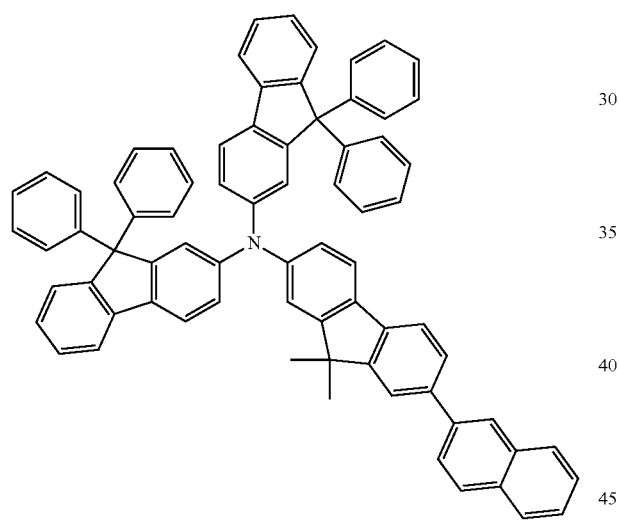
(B227)
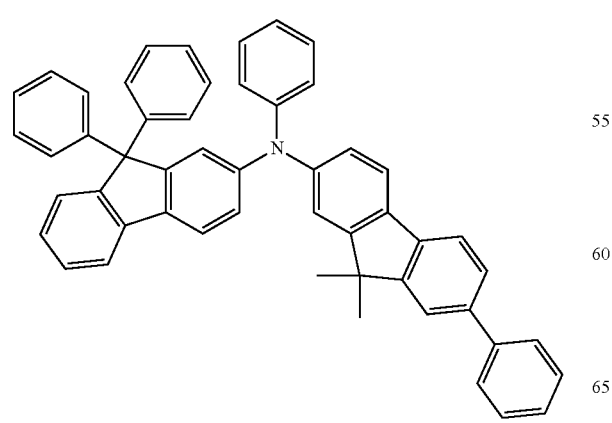
(B229)
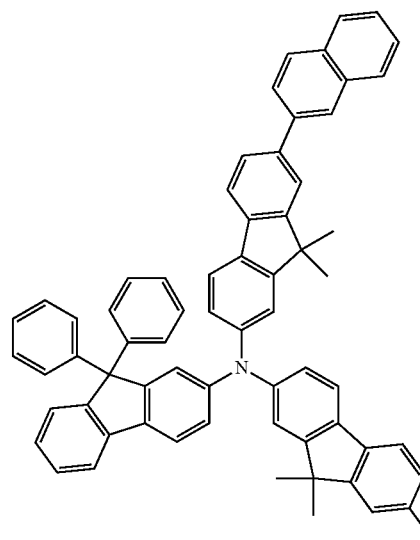

(B230)
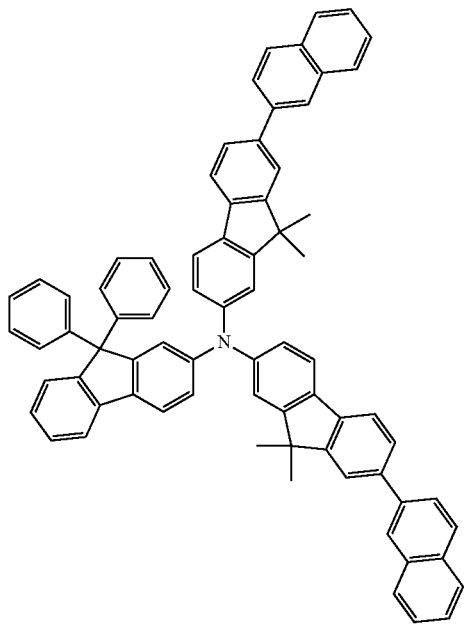
(B231)
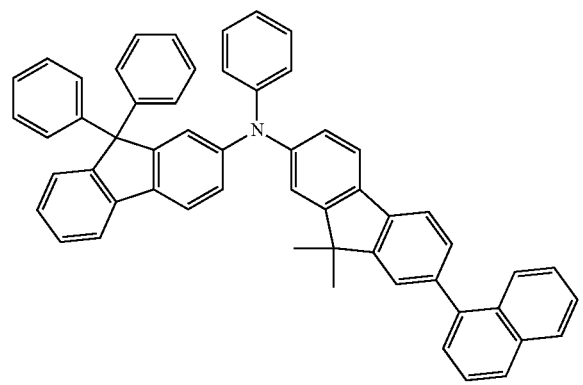
(B232)
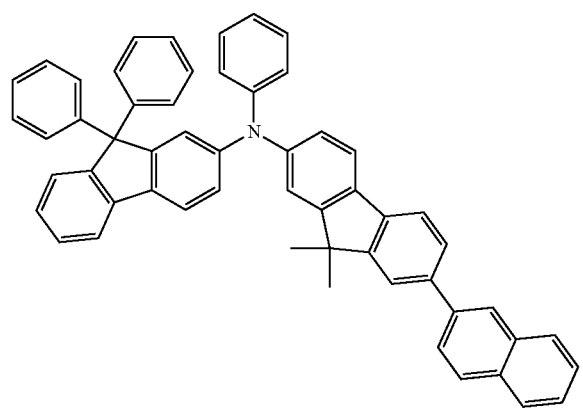
(B233)
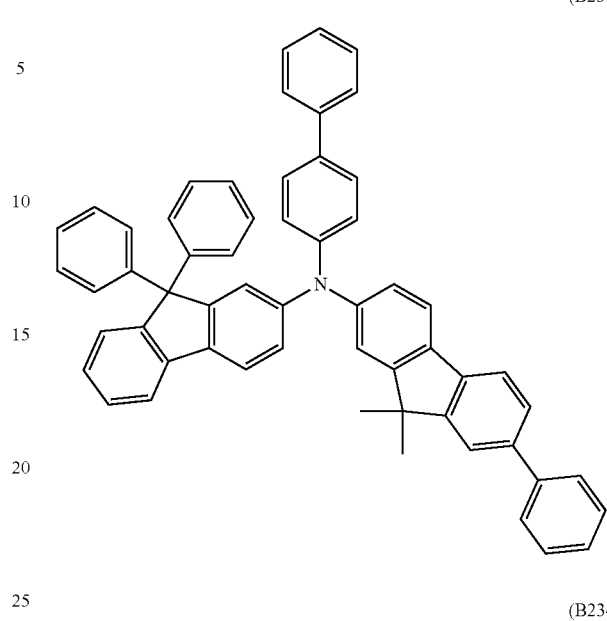
(B234)
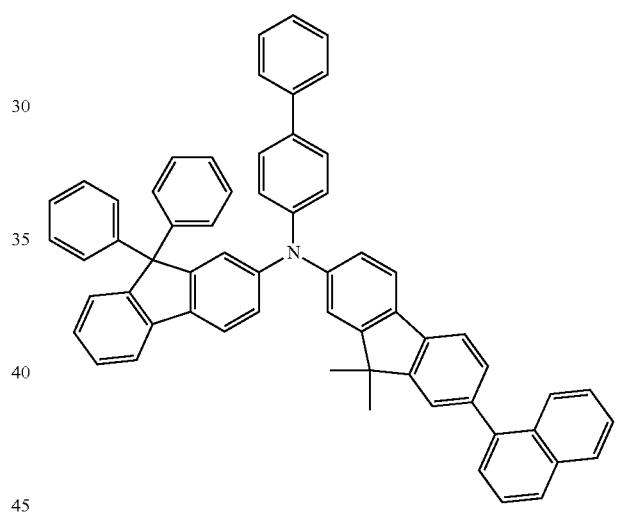
(B235)
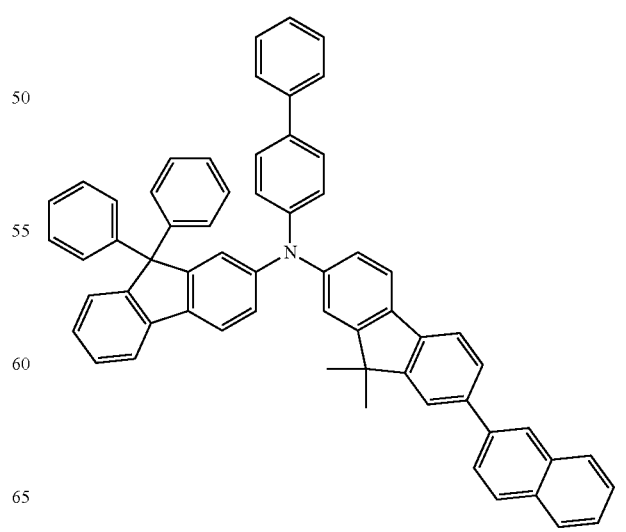

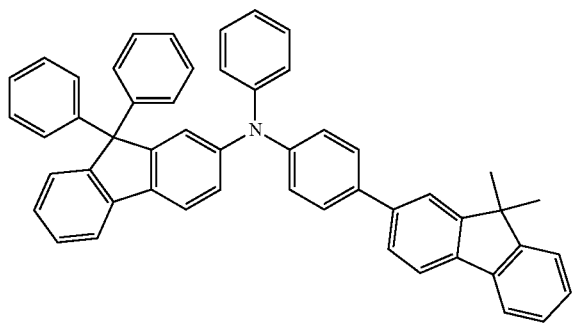
(B236)
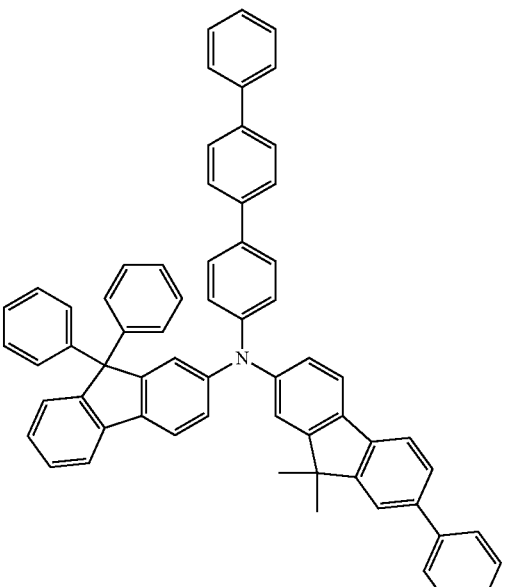
(B240)
(B237)
(B241)
(B238)
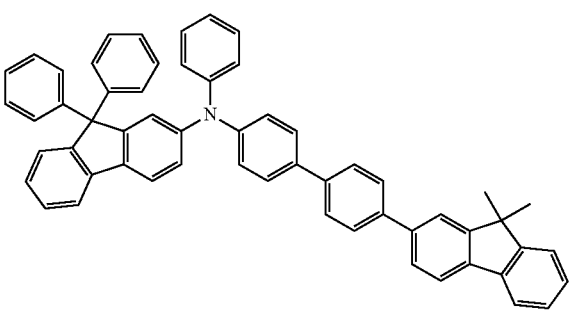
(B242)
(B239)
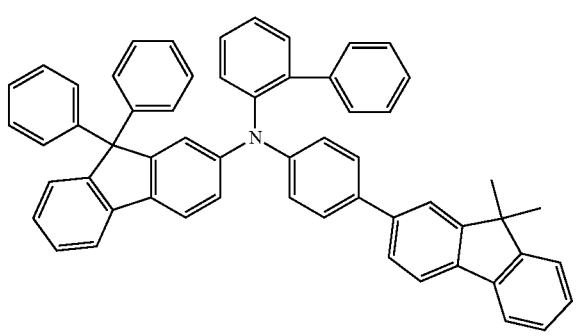

(B243)
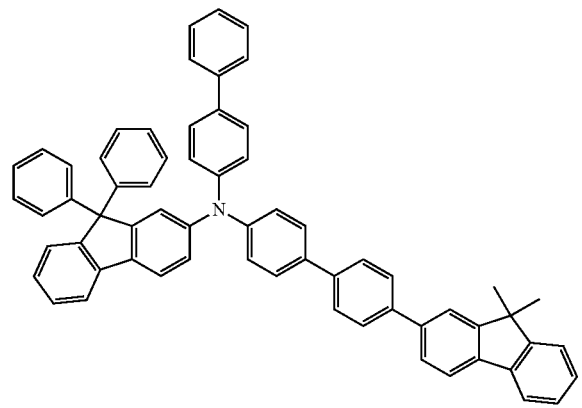
(B266)
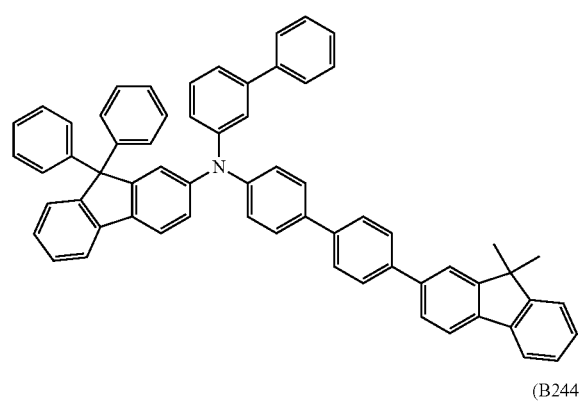
(B244)
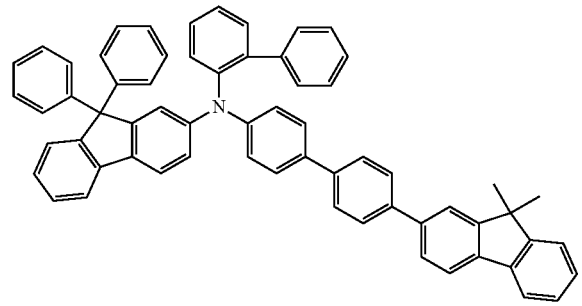
(B245)
(B246)
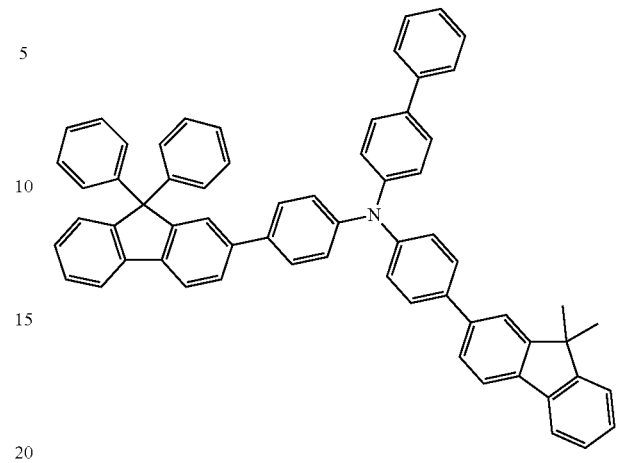
(B247)
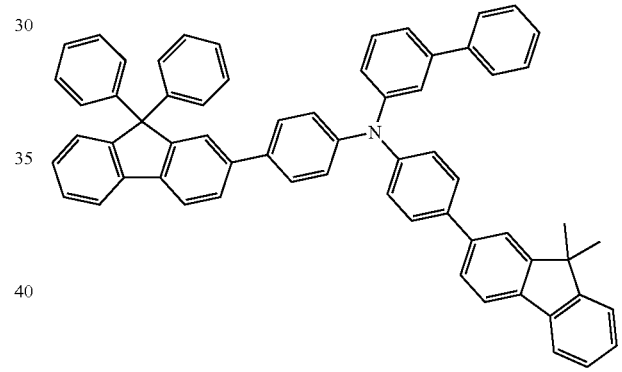
(B248)
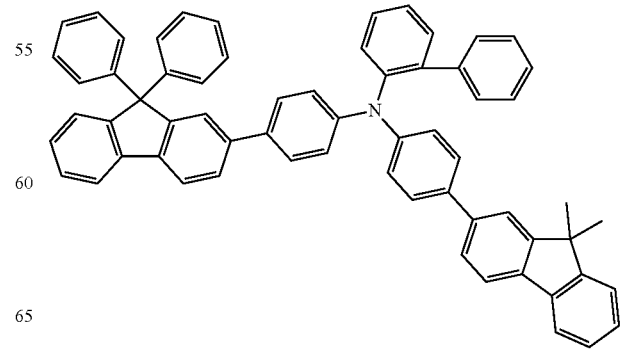

255
-continued
(B249)
(B250)
(B251)
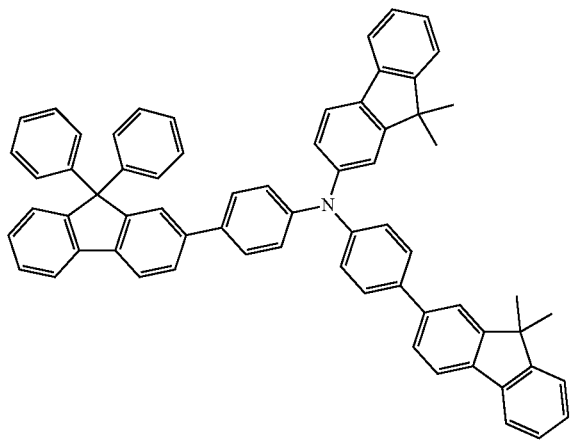
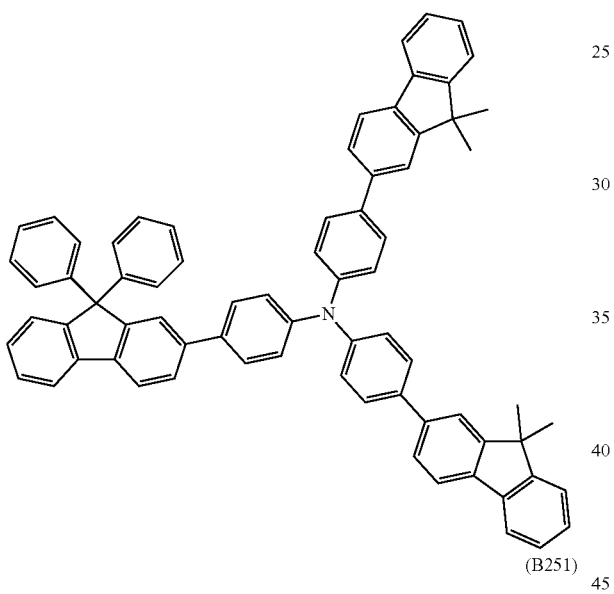
256
-continued
(B252)
(B253)
(B254)
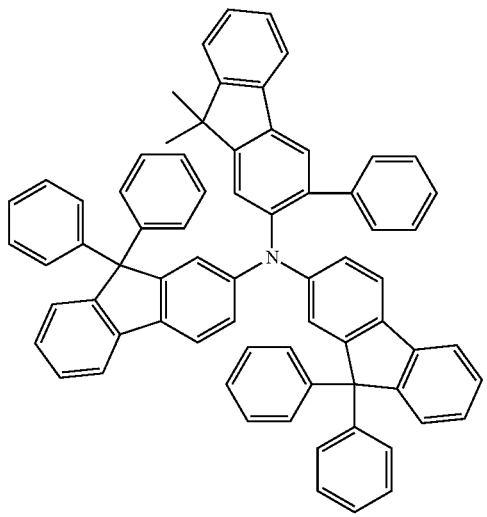
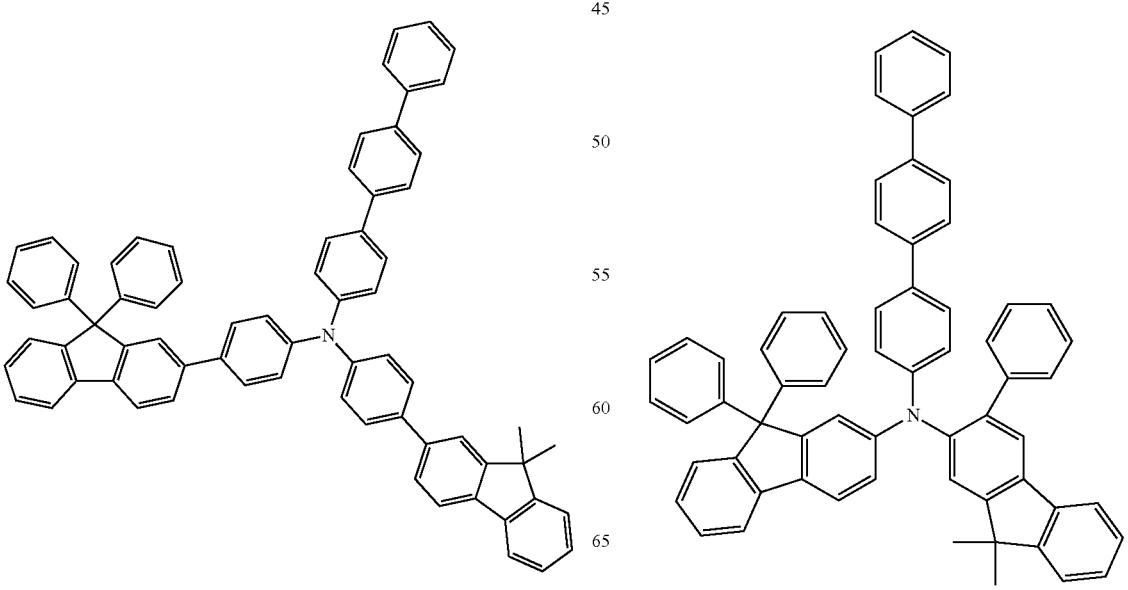

(B255)
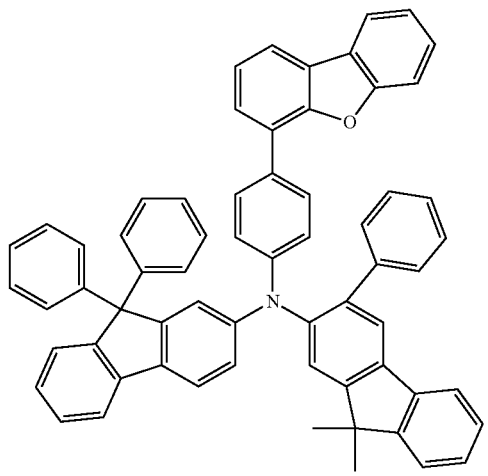
(B256)
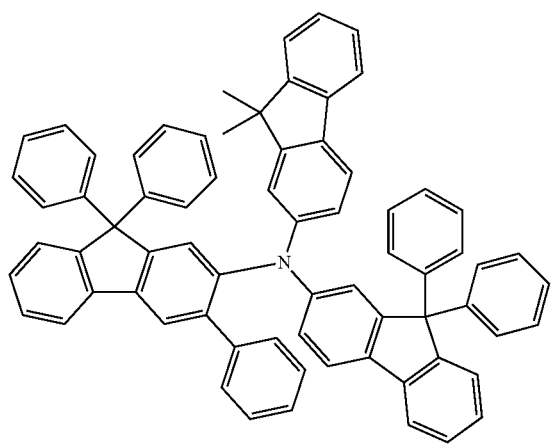
(B257)
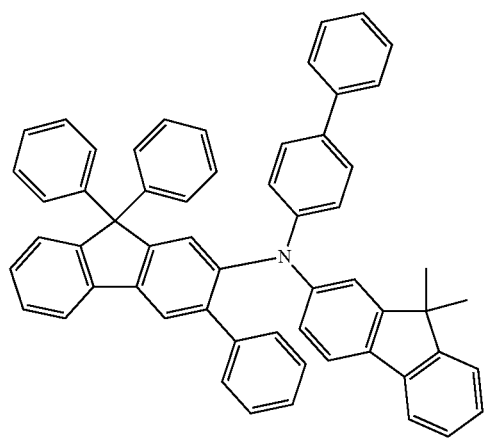
(B258)
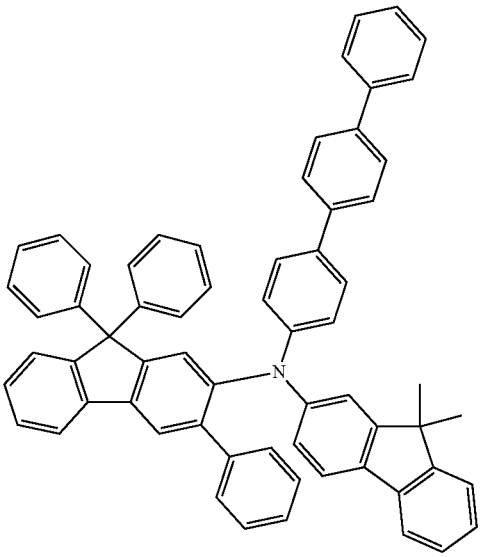
(B259)
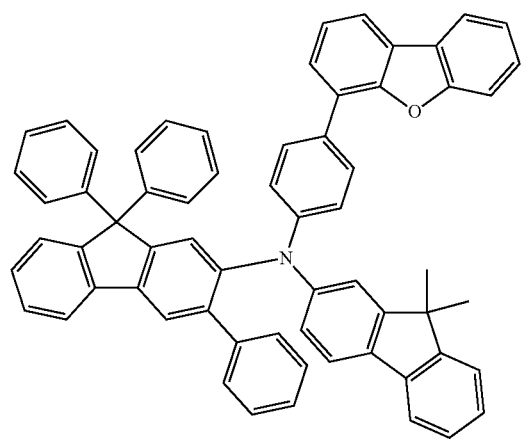
(B260)
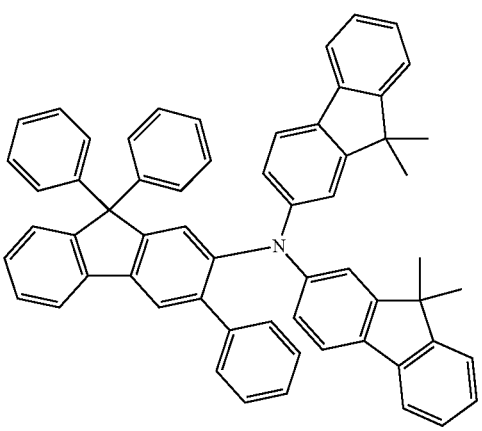

(B261)

(B262)

(B263)

(B264)

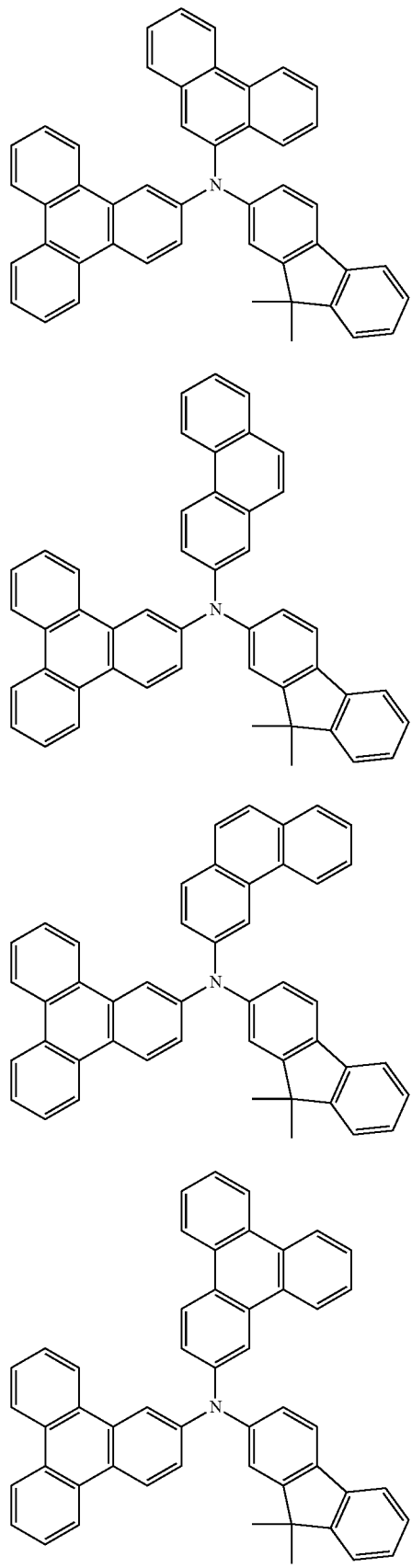

(B265)

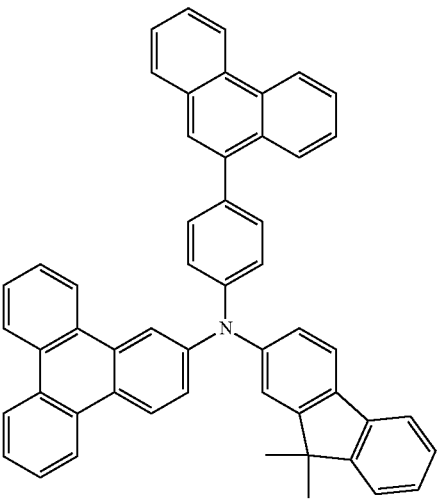

The organic light emitting device of the present specification can be manufactured by materials and methods known in the art, except that the p-type charge injection layer, the p-type charge generation layer, or the layer which simultaneously injects and generates p-type charges includes: the compound of Chemical Formula 1; and one or more of the compounds of Chemical Formulae 2 to 4.

As the anode material, materials having a high work function are usually preferred so as to facilitate the injection of holes into an organic material layer. Specific examples of the anode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al and Mg/Ag; and the like, but are not limited thereto.

The hole injection layer is a layer which injects holes from an electrode, and a hole injection material is preferably a compound which has a capability of transporting holes and thus has an effect of injecting holes at an anode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transporting material is suitably a material having high hole mobility which can accept holes from an anode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which can improve the lifetime and efficiency of the device by preventing electrons injected from an electron injection layer from passing through a light emitting layer and entering a hole injection layer, and can be formed at an appropriate portion between the light emitting layer and the hole injection layer by using publicly-known materials, if necessary.

In the present specification, the light emitting layer can include a material which can emit light in a visible light region by accepting and recombining holes and electrons. As a material for the light emitting layer, a material known in the art can be used. For example, as the material for the light emitting layer, it is possible to use a material having high quantum efficiency for fluorescence or phosphorescence. Specific examples of the material for the light emitting layer include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. Examples of the host material include fused aromatic ring derivatives, or hetero ring-containing compounds, and the like. Specific examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

Examples of the dopant material include aromatic amine derivatives, styrylamine compounds, boron complexes, fluoranthene compounds, metal complexes, and the like.

Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complexes include iridium complexes, platinum complexes, and the like, but are not limited thereto.

The hole blocking layer is a layer which can improve the lifetime and efficiency of the device by preventing holes injected from a hole injection layer from passing through a light emitting layer and entering an electron injection layer, and can be formed at an appropriate portion between the light emitting layer and the electron injection layer by using publicly-known materials, if necessary.

The electron transport layer is a layer which accepts electrons from an electron injection layer and transports the electrons to a light emitting layer, and an electron transporting material is suitably a material having high electron mobility which can proficiently accept electrons from a cathode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a cathode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxy-quinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification can be a top emission type, a bottom emission type, or a dual emission type according to the materials to be used.

An exemplary embodiment of the present specification provides a display device including the organic light emitting device.

MODE FOR INVENTION

Hereinafter, the present specification will be described in detail with reference to Examples for specifically describing the present specification. However, the Examples according to the present specification can be modified in various forms, and it is not interpreted that the scope of the present specification is limited to the Examples described below in detail. The Examples of the present specification are provided to more completely explain the present specification to a person with ordinary skill in the art.

<Measurement of Electric Conductivity>

The electric conductivities of the following compounds were measured, and are shown in the following Table 1. The electric conductivities of the following compounds were measured under measurement conditions of 25° C. and a voltage of 100 V to 200 V by using the 4-point probe in FIG. 4, and the van der Pauw equation.

Compound 1-1

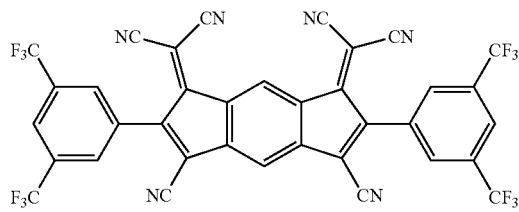

Compound 2-1

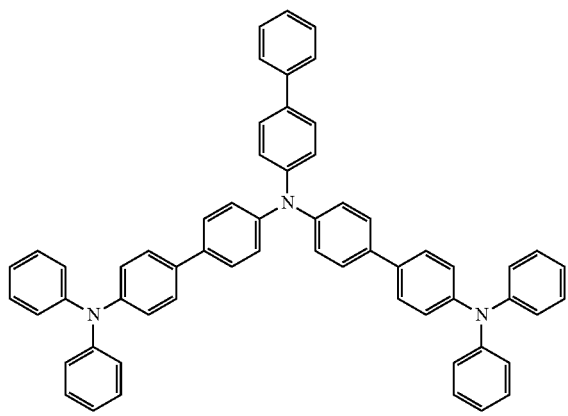

Compound 4-1

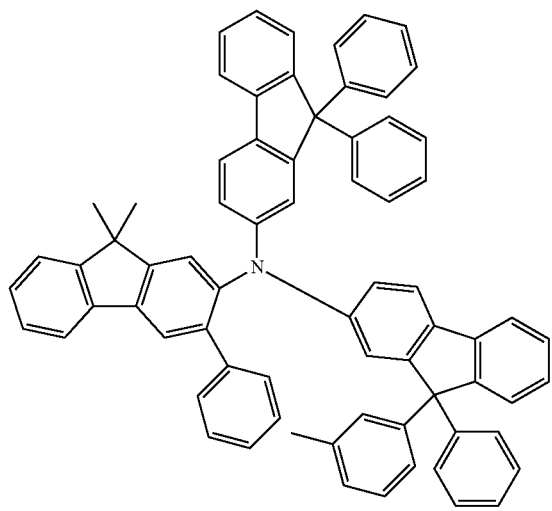

-continued

Comparative Example Compound 1

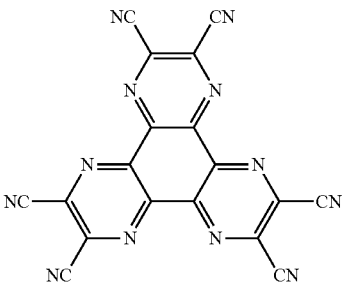

TABLE 1

| | | Electric conductivity (S/cm) |
|---|---|---|
| Comparative Example 1-1 | Comparative Example Compound 1 | $2.04 \times 10^{-7}$ |
| Comparative Example 1-2 | Compound 1-1 | $6.70 \times 10^{-9}$ |
| Comparative Example 1-3 | Compound 4-1 | $2.10 \times 10^{-8}$ |
| Comparative Example 1-4 | Compound 2-1 | $3.99 \times 10^{-7}$ |
| Comparative Example 1-5 | Compound 1-1 (10 wt %) + Compound 4-1 (90 wt %) | $8.38 \times 10^{-8}$ |
| Comparative Example 1-6 | Comparative Example Compound 1 (30 wt %) + Compound 4-1 (70 wt %) | $2.80 \times 10^{-8}$ |
| Example 1-1 | Compound 1-1 (30 wt %) + Compound 4-1 (70 wt %) | $1.45 \times 10^{-6}$ |
| Example 1-2 | Compound 1-1 (30 wt %) + Compound 2-1 (70 wt %) | $7.03 \times 10^{-5}$ |

According to Table 1, it can be seen that according to an exemplary embodiment of the present specification, the case of including the compound of Chemical Formula 1 and the compound of Chemical Formula 4 and the case of including the compound of Chemical Formula 1 and the compound of Chemical Formula 2 have electric conductivity of $1 \times 10^{-6}$ S/cm or more, and the case of using Comparative Example Compound 1, the compound of Chemical Formula 1, the compound of Chemical Formula 2, or the compound of Chemical Formula 4 alone has electric conductivity of less than $1 \times 10^{-7}$ S/cm.

<Manufacture of Organic Light Emitting Device>

Comparative Example 2-1

ITO as an anode was formed to have a thickness of 1,350 Å on a glass substrate by a sputtering method, a p-type charge injection layer was formed to have a thickness of 100 Å by a thermal vacuum deposition using Comparative Example Compound 1, a first hole transport layer was formed to have a thickness of 800 Å thereon by a thermal vacuum deposition using the following HTL1, and then a second hole generation layer was formed to have a thickness of 100 Å by using the following HTL2. A light emitting layer was formed to have a thickness of 250 Å thereon by using the following BH and BD at a weight ratio of 25:1, and an electron transport layer was formed to have a thickness of 300 Å by using the following ETL1 and ETL2 at a weight ratio of 1:1.

Finally, a cathode was formed to have a thickness of 10 Å and 800 Å by using LiF and Al, respectively, thereby manufacturing a blue organic light emitting device.

[HTL1]

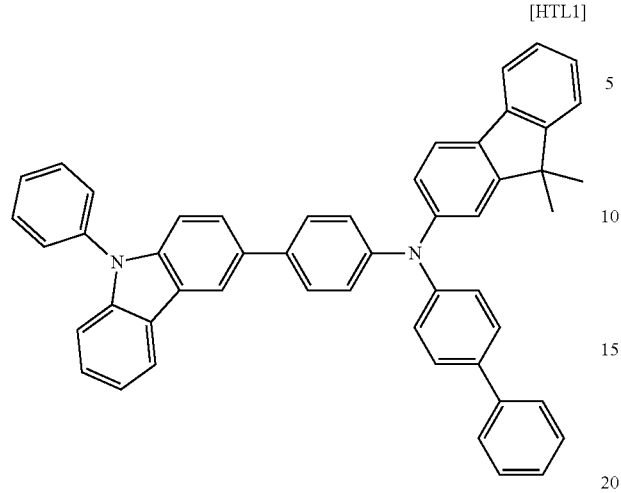

[HTL2]

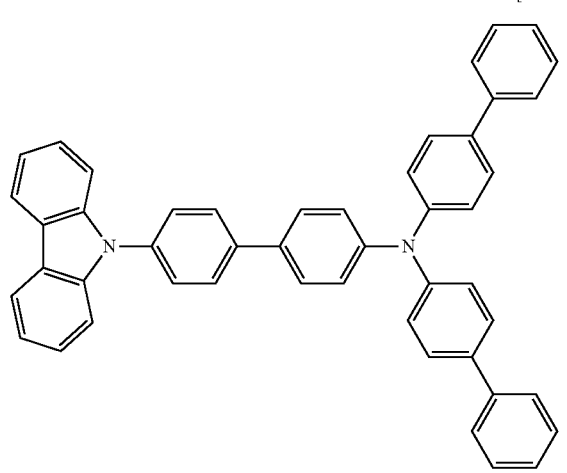

[BH]

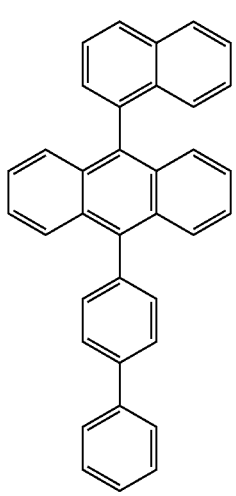

[BD]

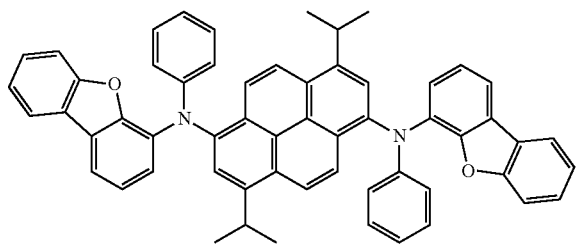

[ETL1]

[ETL2]

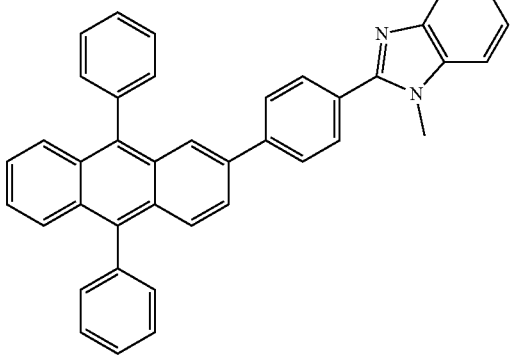

Comparative Example 2-2

A blue organic light emitting device was manufactured in the same manner as in Comparative Example 2-1, except that as the p-type charge injection layer, Compound 1-1 (10 wt %) and Compound 4-1 (90 wt %) were co-deposited instead of Comparative Example Compound 1.

Example 2-1

A blue organic light emitting device was manufactured in the same manner as in Comparative Example 2-1, except that as the p-type charge injection layer, Compound 1-1 (30 wt %) and Compound 4-1 (70 wt %) were co-deposited instead of Comparative Example Compound 1.

The results of the organic light emitting devices manufactured by Comparative Examples 2-1 and 2-2 and Example 2-1 are shown in the following Table 2. The results are data on the voltage, the efficiency, and the light emitting color. The lifetime was expressed as the time for reaching 95% when the initial photoelectric current value was defined as 100%.

TABLE 2

|  | IVL | | | | | | LifeTime |
|---|---|---|---|---|---|---|---|
|  | Voltage (10 mA/cm$^2$) | cd/A | lm/w | QE | CIE-x | CIE-y | Voltage (100 mA/cm$^2$) | 95% |
| Comparative Example 2-1 | 9.58 | 4.21 | 1.38 | 5.32 | 0.139 | 0.099 | 13.35 | 36 |
| Comparative Example 2-2 | 4.61 | 7.88 | 5.37 | 9.94 | 0.140 | 0.098 | 6.30 | 140 |
| Example 2-1 | 3.96 | 7.55 | 5.98 | 9.46 | 0.140 | 0.099 | 5.47 | 200 |

Example 3-1

ITO as an anode was formed to have a thickness of 1,350 Å on a glass substrate by a sputtering method, a hole injection layer was formed to have a thickness of 70 Å by a thermal vacuum deposition using the following HIL and MgF$_2$ at a weight ratio of 10:3, a first hole transport layer was formed to have a thickness of 850 Å thereon by a thermal vacuum deposition using HTL1, and then a second hole transport layer was formed to have a thickness of 100 Å by using HTL2. A first light emitting layer was formed to have a thickness of 200 Å thereon by using BH and BD at a weight ratio of 25:1, and a first electron transport layer was formed to have a thickness of 100 Å by using ETL1.

A first n-type charge generation layer was formed to have a thickness of 185 Å on the first electron transport layer by using the following NCGL and Li, and a first p-type charge generation layer was formed to have a thickness of 80 Å by co-depositing Compound 1-1 (30 wt %) and Compound 4-1 (70 wt %).

A third hole transport layer was formed to have a thickness of 150 Å on the first p-type charge generation layer by using HTL3, a second light emitting layer was formed to have a thickness of 400 Å thereon by using an Ir complex dopant and the following YGH1 and YGH2 hosts, and a second electron transport layer was formed to have a thickness of 240 Å by using ETL2.

A second n-type charge generation layer was formed to have a thickness of 200 Å on the second electron transport layer by using NCGL and Li, and a second p-type charge generation layer was formed to have a thickness of 100 Å by co-depositing Compound 1-1 (30 wt %) and Compound 4-1 (70 wt %).

A fourth hole transport layer was formed to have a thickness of 700 Å on the second p-type charge generation layer by using HTL1, a fifth hole transport layer was formed to have a thickness of 100 Å by using HTL2, a light emitting layer was formed to have a thickness of 250 Å thereon by using BH and BD at a weight ratio of 25:1, and then a third electron transport layer was formed to have a thickness of 300 Å by using the following ETL1 and ETL2 at a weight ratio of 1:1.

Finally, a cathode was formed to have a thickness of 10 Å and 800 Å by using LiF and Al, respectively, thereby manufacturing a white organic light emitting device.

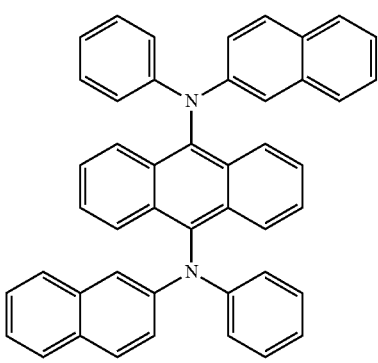

[HIL]

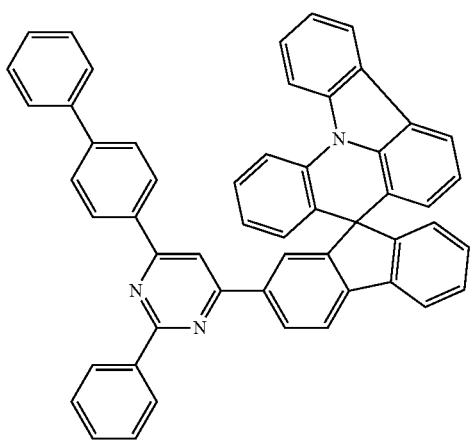

[ETL1]

-continued

[NCGL]

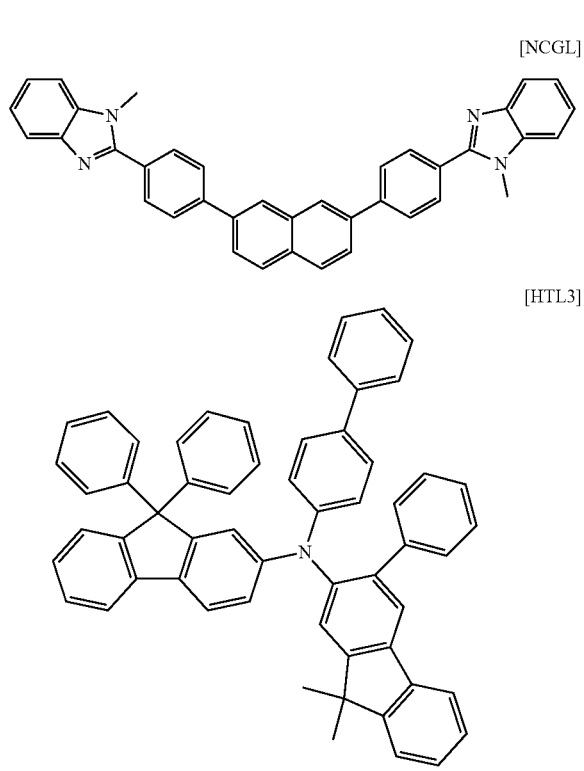

[HTL3]

[YGH1]

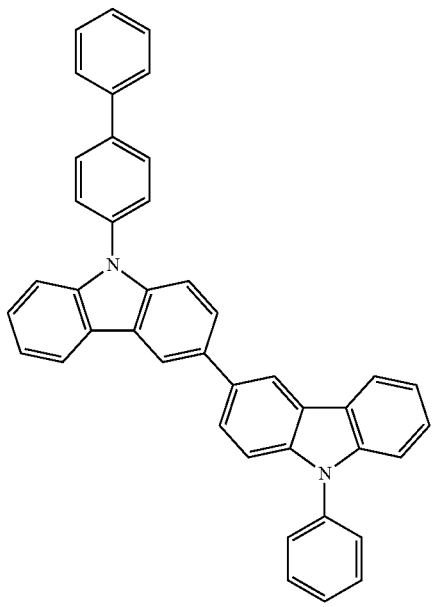

-continued

[YGH2]

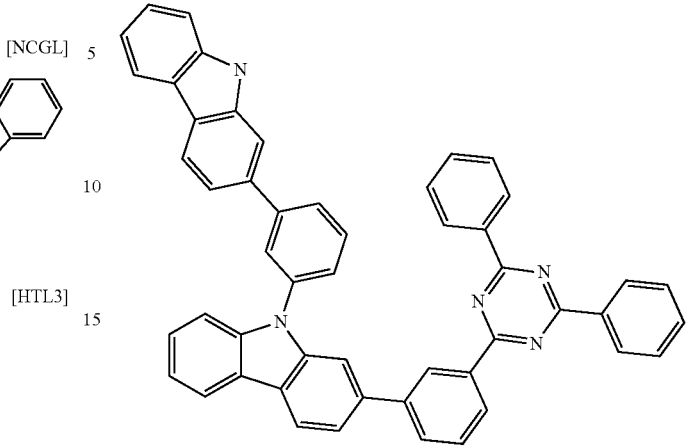

Example 3-2

A white organic light emitting device was manufactured in the same manner as in Example 3-1, except that as the second p-type charge generation layer, Compound 1-1 (30 wt %) and Compound 2-1 (70 wt %) were co-deposited instead of Compound 1-1 (30 wt %) and Compound 4-1 (70 wt %).

Comparative Example 3-1

A white organic light emitting device was manufactured in the same manner as in Example 3-1, except that as the second p-type charge generation layer, Comparative Example Compound 1 was deposited instead of Compound 1-1 (30 wt %) and Compound 4-1 (70 wt %).

Comparative Example 3-2

A white organic light emitting device was manufactured in the same manner as in Example 3-1, except that as the second p-type charge generation layer, Compound 1-1 (10 wt %) and Compound 4-1 (90 wt %) were co-deposited instead of Compound 1-1 (30 wt %) and Compound 4-1 (70 wt %).

The results of the organic light emitting devices manufactured by Examples 3-1 and 3-2 and Comparative Examples 3-1 and 3-2 are shown in the following Table 3. The results are data on the voltage, the efficiency, and the light emitting color. The lifetime was expressed as the time for reaching 95% when the initial photoelectric current value was defined as 100%.

TABLE 3

| | IVL | | | | | | | LifeTime |
|---|---|---|---|---|---|---|---|---|
| | Voltage (10 mA/cm$^2$) | cd/A | lm/w | QE | CIE-x | CIE-y | Voltage (100 mA/cm$^2$) | 95% |
| Example 3-1 | 11.07 | 78.46 | 22.26 | 37.52 | 0.264 | 0.294 | 14.49 | 490 |
| Example 3-2 | 11.03 | 79.21 | 22.57 | 37.07 | 0.261 | 0.294 | 13.93 | 400 |

TABLE 3-continued

| | IVL | | | | | | | |
|---|---|---|---|---|---|---|---|---|
| | Voltage (10 mA/cm$^2$) | cd/A | lm/w | QE | CIE-x | CIE-y | Voltage (100 mA/cm$^2$) | LifeTime 95% |
| Comparative Example 3-1 | 16.27 | 76.24 | 14.72 | 34.22 | 0.282 | 0.319 | >20 | 295 |
| Comparative Example 3-2 | 12.98 | 76.68 | 18.56 | 35.43 | 0.272 | 0.306 | 17.01 | 410 |

From the results in Tables 2 and 3, it can be confirmed that the organic light emitting devices including the compound of Chemical Formula 1 and the compound of Chemical Formula 4 or the compound of Chemical Formula 1 and the compound of Chemical Formula 2 according to an exemplary embodiment of the present specification as the p-type charge injection layer or the p-type charge generation layer can improve the light emitting efficiency, the driving voltage, and the lifetime characteristics as compared to the organic light emitting device including Comparative Example Compound 1 alone as the p-type charge injection layer or the p-type charge generation layer. Further, it can be confirmed that the case where the weight ratio of the compound of Chemical Formula 1 and the compound of Chemical Formula 4 or the compound of Chemical Formula 1 and the compound of Chemical Formula 2 is a weight ratio of 30:70 can improve the light emitting efficiency, the driving voltage, and the lifetime characteristics as compared to the case where the weight ratio thereof is 10:90.

The invention claimed is:

1. An organic light emitting device comprising:
an anode;
a cathode provided to face the anode; and
one or more light emitting units provided between the anode and the cathode,
wherein the organic light emitting device includes a charge generation layer provided between the anode and the one light emitting unit, or between the two light emitting units adjacent to each other among the light emitting units,
the charge generation layer comprises a p-type charge injection layer, a p-type charge generation layer, or a layer which simultaneously injects and generates p-type charges, and
the p-type charge injection layer, the p-type charge generation layer, or the layer which simultaneously injects and generates p-type charges has electric conductivity of $1\times10^{-6}$ S/cm or more,
wherein the p-type charge injection layer, the p-type charge generation layer, or the layer which simultaneously injects and generates p-type charges comprises:
a compound of the following Chemical Formula 1-1 or 1-2; and
one or more of compounds of the following Chemical Formulae 2 to 4 at a weight ratio of 20:80 to 80:20:

[Chemical Formula 1-1]

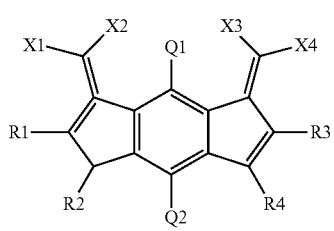

-continued

[Chemical Formula 1-2]

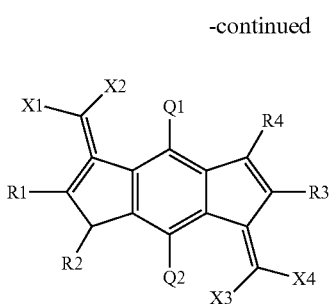

wherein in Chemical Formula 1-1 or 1-2:
X1 to X4 are the same as or different from each other, and are each independently hydrogen, a nitrile group, a nitro group, a halogen group, a carboxyl group, a carbonyl group, a substituted or unsubstituted haloalkyl group, a substituted or unsubstituted alkyl group, a substituted or unsubstituted alkoxy group, a substituted or unsubstituted aryloxy group, a substituted or unsubstituted heteroaryloxy group, a substituted or unsubstituted aryl group, or a substituted or unsubstituted heteroaryl group, or adjacent groups are optionally bonded to each other to form a substituted or unsubstituted ring;
R1 and R3 are the same as or different from each other, and are each independently hydrogen, a nitrile group, a halogen group, a substituted or unsubstituted haloalkyl group, a substituted or unsubstituted haloalkoxy group, a substituted or unsubstituted halothioalkoxy group, a substituted or unsubstituted ether group, a substituted or unsubstituted alkoxy group, a substituted or unsubstituted thioalkoxy group, a substituted or unsubstituted silyl group, a substituted or unsubstituted heteroaryl group, a substituted or unsubstituted aryl group selected from the group consisting of a biphenyl group, a terphenyl group, a naphthyl group, an anthracenyl group, a phenanthryl group, a triphenyl group, a pyrenyl group, a phenalenyl group, a perylenyl group, a chrysenyl group, and a fluorenyl group, or a phenyl group substituted with one or more selected from the group consisting of a halogen group, a nitrile group, a haloalkyl group, a haloalkoxy group, a halothioalkoxy group, and a silyl group substituted with an alkyl group;
R2 and R4 are the same as or different from each other, and are each independently hydrogen, a nitrile group, a halogen group, a substituted or unsubstituted haloalkyl group, a substituted or unsubstituted haloalkoxy group, a substituted or unsubstituted halothioalkoxy group, a substituted or unsubstituted ether group, a substituted or unsubstituted alkyl group, a substituted or unsubstituted alkoxy group, a substituted or unsubstituted thioalkoxy group, a substituted or unsubstituted silyl group, a substituted or unsubstituted aryl group, or a substituted or unsubstituted heteroaryl group; and Q1 and Q2 are the same as or different from each other, and are each independently hydrogen; a halogen group; a nitrile group; a substituted or unsubstituted haloalkyl group; a substituted or unsubstituted haloalkoxy group; an aryl group that is unsubstituted or substituted with one or more selected from the group consisting of a nitrile group, a haloalkyl group, and a haloalkoxy group; or a substituted or unsubstituted heteroaryl group;

[Chemical Formula 2]

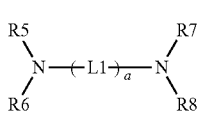

wherein in Chemical Formula 2:

L1 is a substituted or unsubstituted arylene group or a substituted or unsubstituted heteroarylene group;

R5 to R8 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group, or adjacent groups are optionally bonded to each other to form a substituted or unsubstituted ring;

a is an integer from 1 to 10; and when a is 2 or more, two or more L1s are the same as or different from each other;

[Chemical Formula 3]

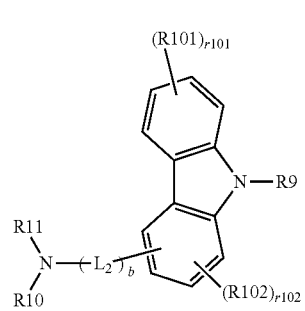

wherein in Chemical Formula 3:

L2 is a substituted or unsubstituted arylene group;

R9 to R11 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;

R101 and R102 are the same as or different from each other, and are each independently hydrogen, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;

b is an integer from 1 to 10;

when b is 2 or more, two or more L2s are the same as or different from each other;

r101 is an integer from 1 to 4;

r102 is an integer from 1 to 3; and when r101 and r102 are each 2 or more, two or more structures in the parenthesis are the same as or different from each other;

[Chemical Formula 4]

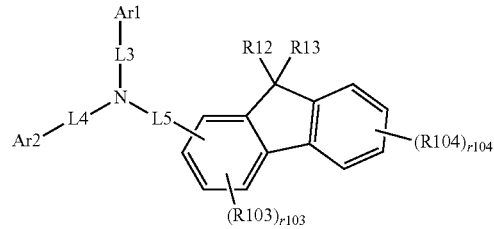

wherein in Chemical Formula 4:

L3 to L5 are the same as or different from each other, and are each independently a direct bond, a substituted or unsubstituted arylene group, or a substituted or unsubstituted heteroarylene group;

Ar1 is a substituted or unsubstituted aryl group or a substituted or unsubstituted heteroaryl group;

Ar2 is a substituted or unsubstituted aryl group;

R12, R13, R103, and R104 are the same as or different from each other, and are each independently hydrogen, deuterium, a nitrile group, a nitro group, a hydroxy group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group, or adjacent groups are bonded to each other to form a substituted or unsubstituted ring;

r103 is an integer from 1 to 3;

r104 is an integer from 1 to 4; and when r103 and r104 are each 2 or more, two or more structures in the parenthesis are the same as or different from each other.

2. The organic light emitting device of claim 1, wherein the p-type charge injection layer, the p-type charge generation layer, or the layer which simultaneously injects and generates p-type charges is formed by co-depositing the compound of Chemical Formula 1-1 or 1-2 and one or more of the compounds of Chemical Formulae 2 to 4.

3. The organic light emitting device of claim 2, wherein the co-deposition comprises:
the compound of Chemical Formula 1-1 or 1-2; and
one or more of the compounds of Chemical Formulae 2 to 4 at a weight ratio of 20:80 to 80:20.

4. An organic light emitting device, comprising:
an anode;
a cathode provided to face the anode; and
one or more light emitting units provided between the anode and the cathode,
wherein the organic light emitting device includes a charge generation layer provided between the anode and the one light emitting unit, or between the two light emitting units adjacent to each other among the light emitting units,
the charge generation layer comprises a p-type charge injection layer, a p-type charge generation layer, or a layer which simultaneously injects and generates p-type charges, and
the p-type charge injection layer, the p-type charge generation layer, or the layer which simultaneously injects and generates p-type charges has electric conductivity of $1 \times 10^{-6}$ S/cm or more,
wherein the p-type charge injection layer, the p-type charge generation layer, or the layer which simultaneously injects and generates p-type charges comprises:
a compound selected from among the following compounds:

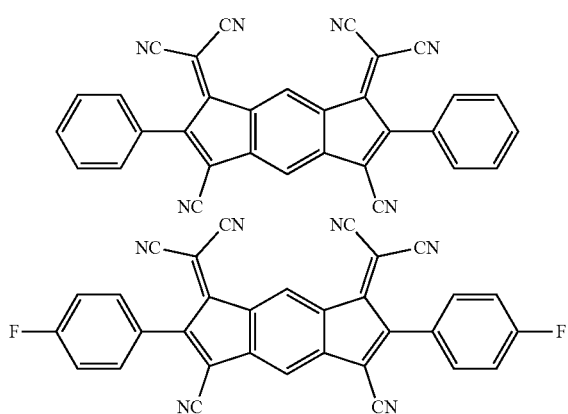

-continued

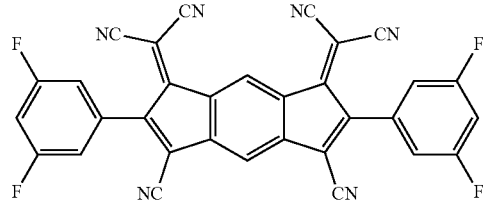

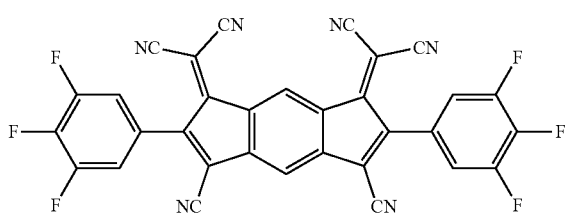

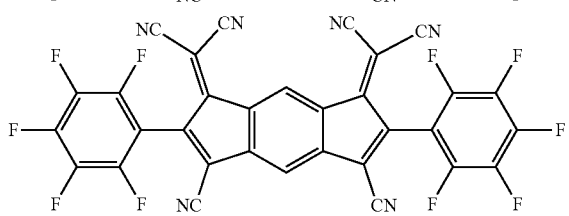

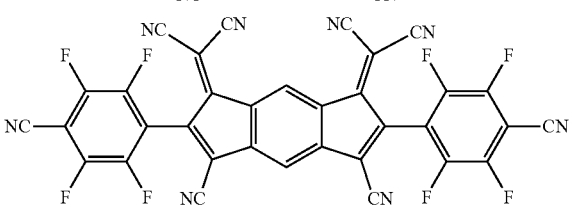

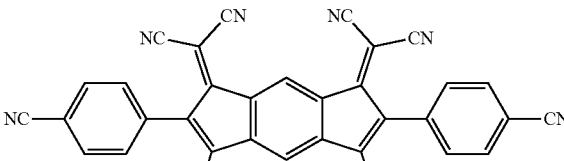

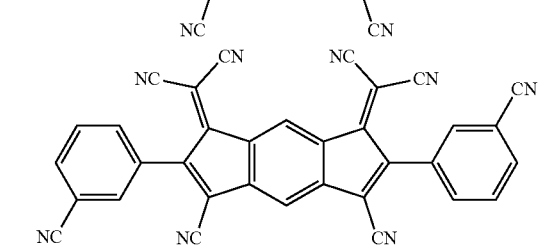

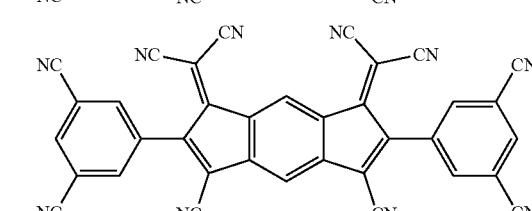

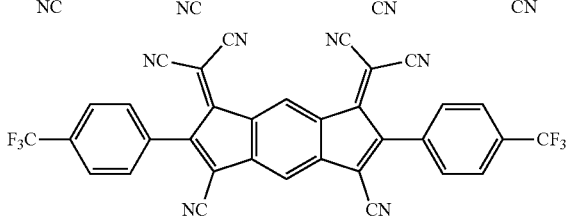

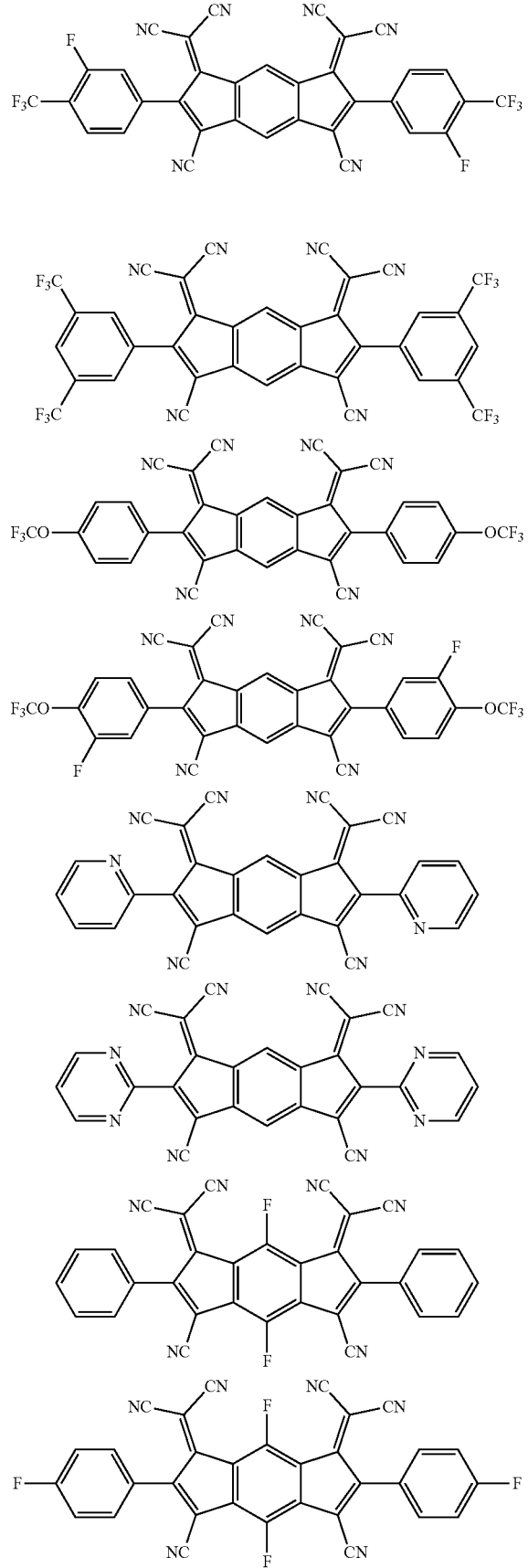
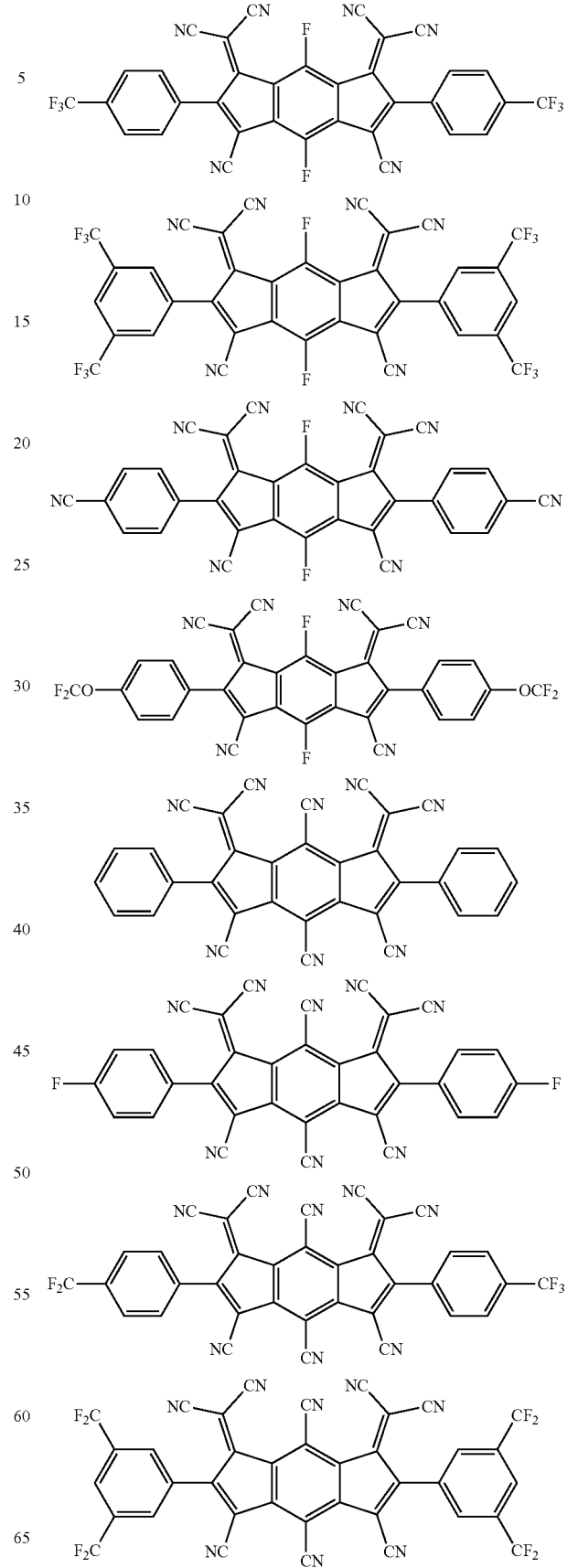

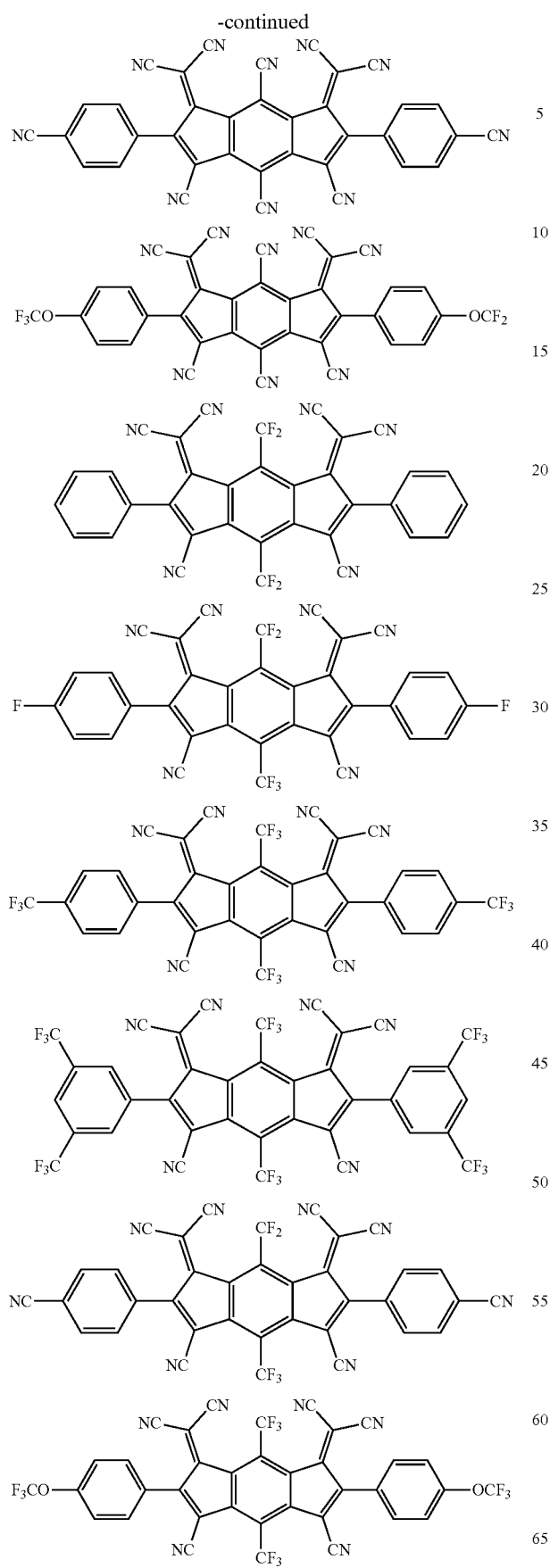
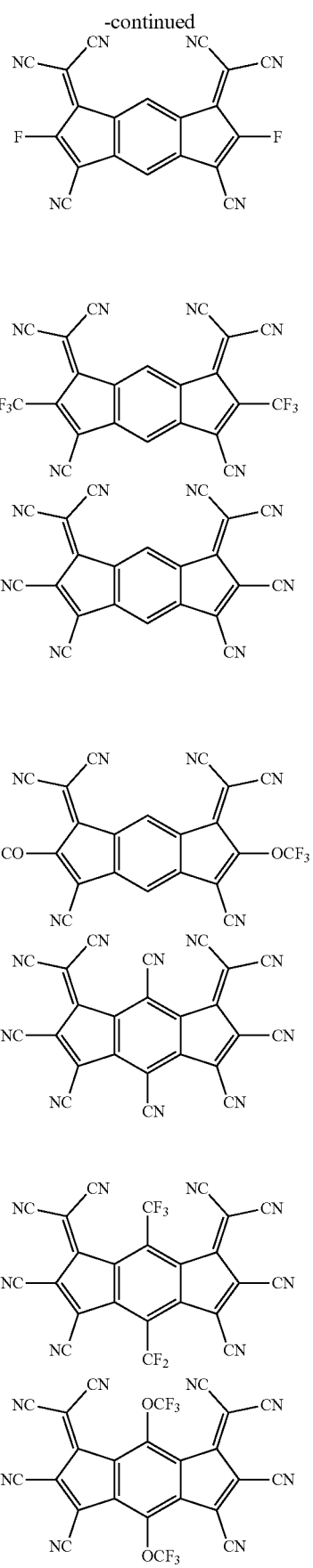

281
-continued
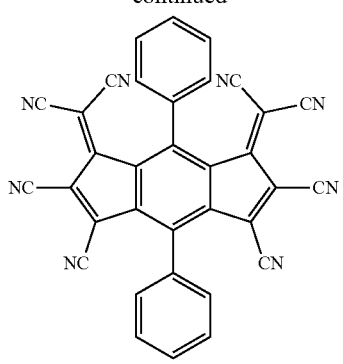
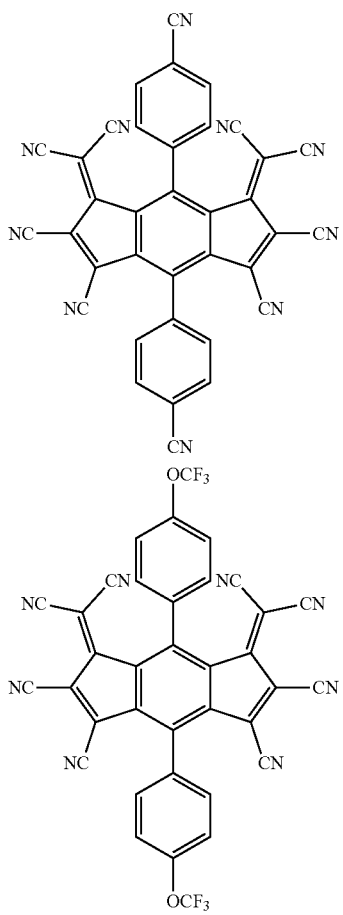
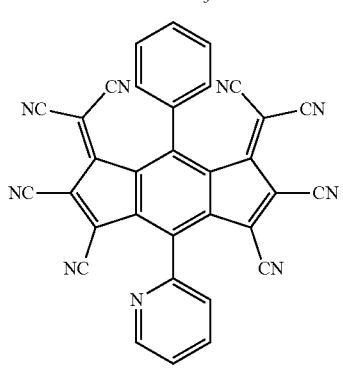
282
-continued
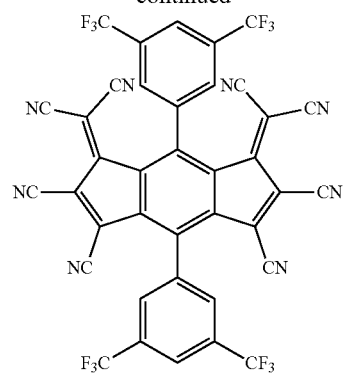
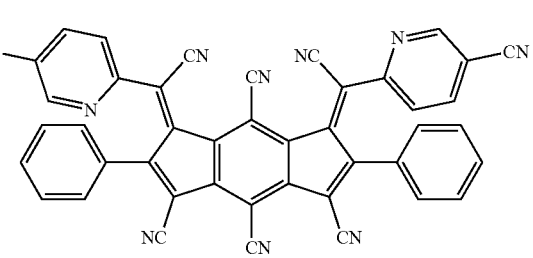
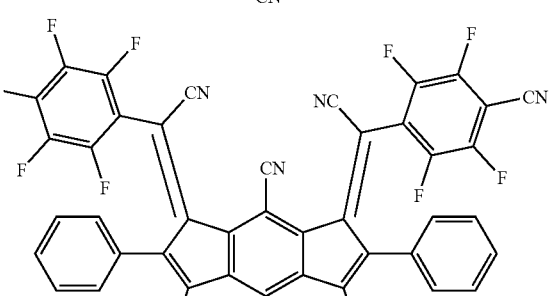
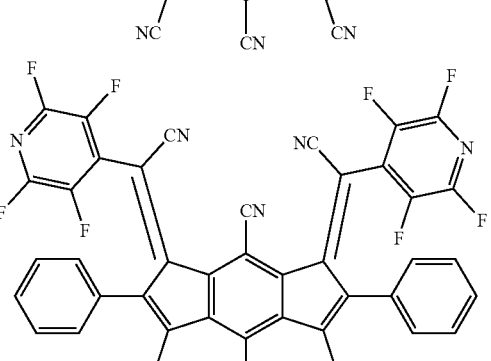
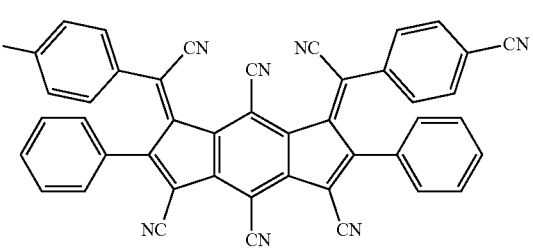

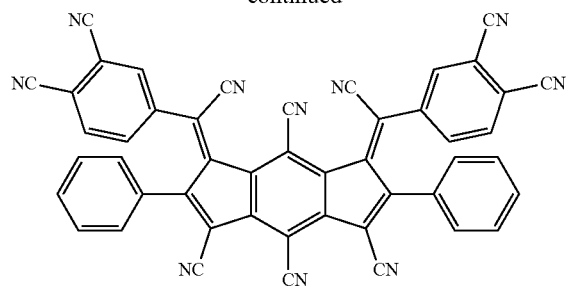
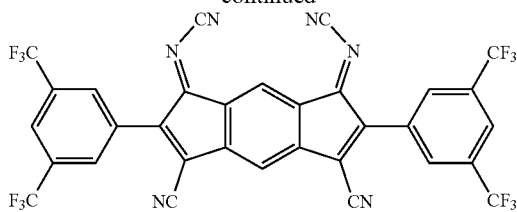
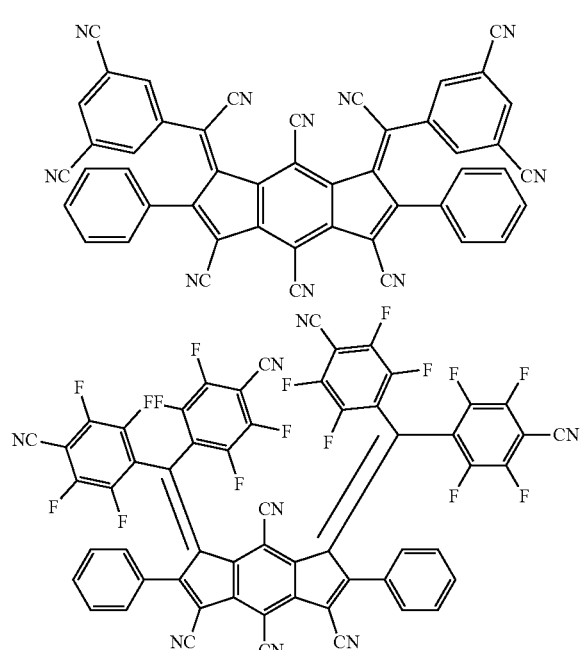
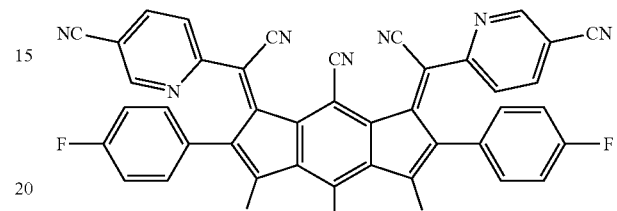
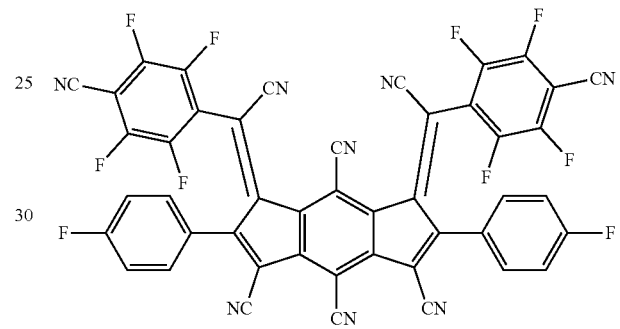
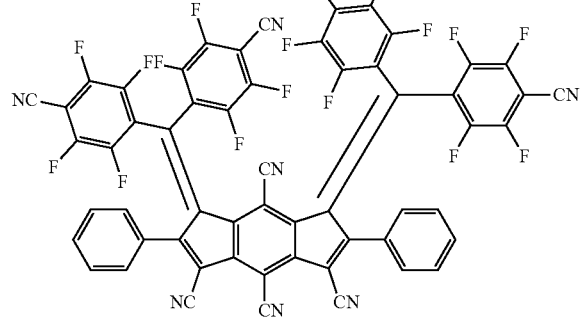
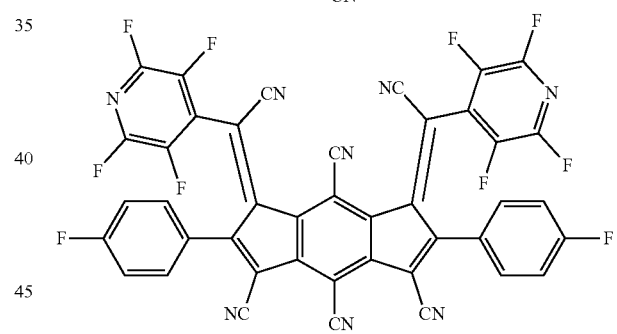
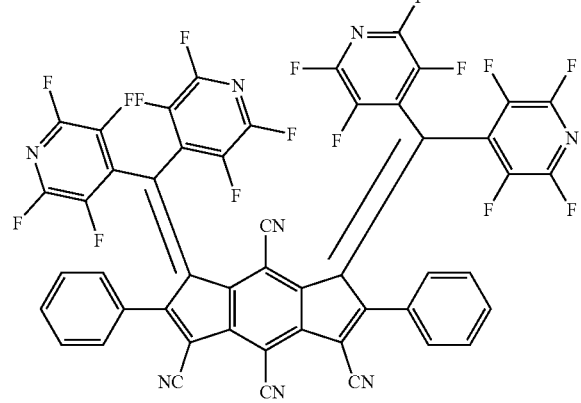
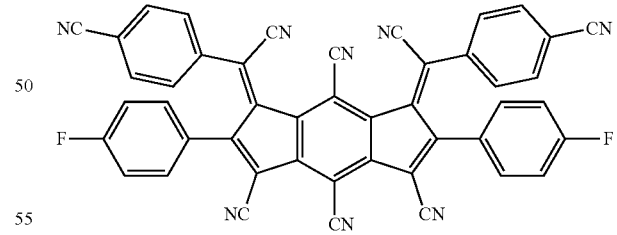
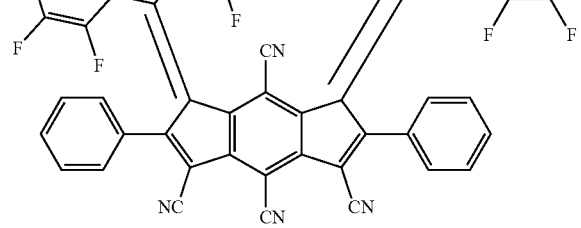
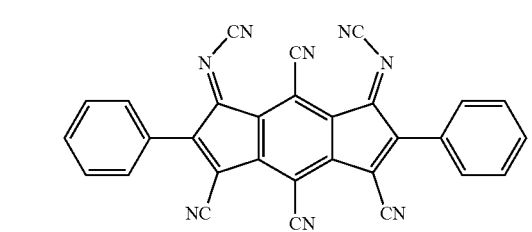
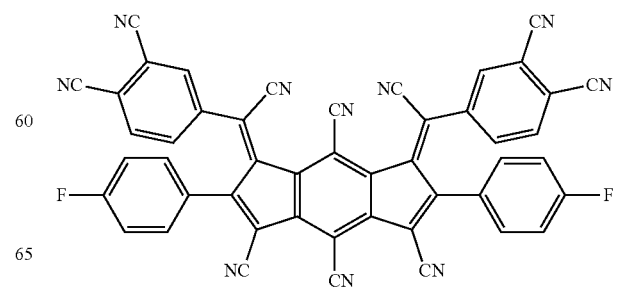

285
-continued
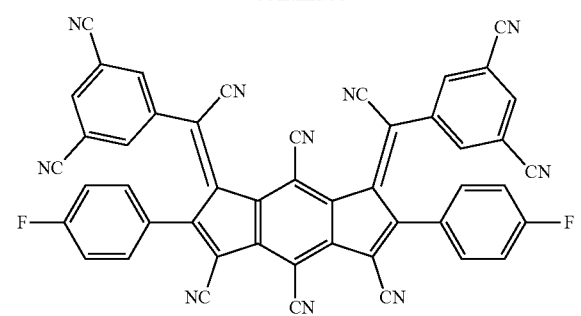
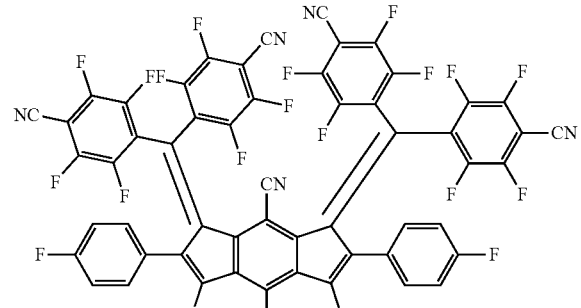
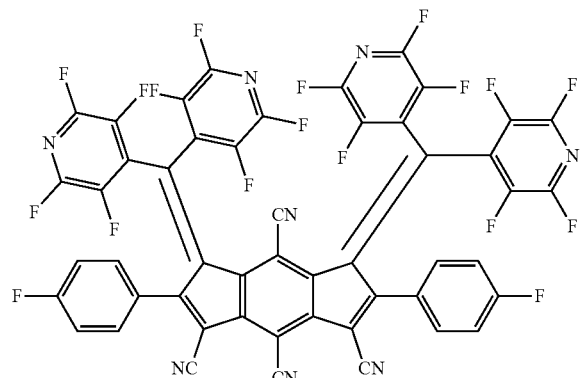
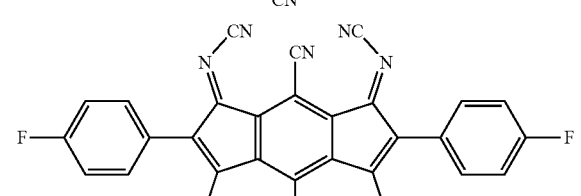
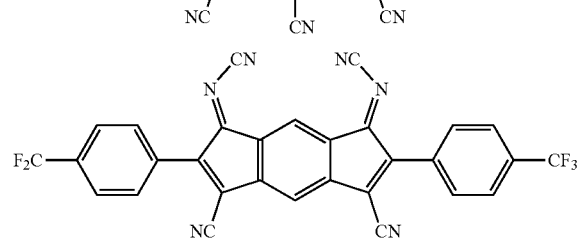
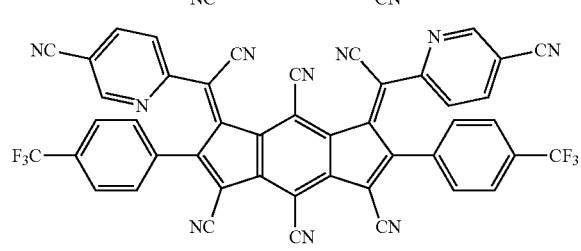
286
-continued
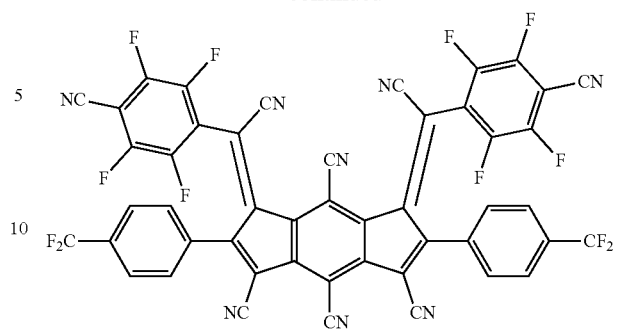
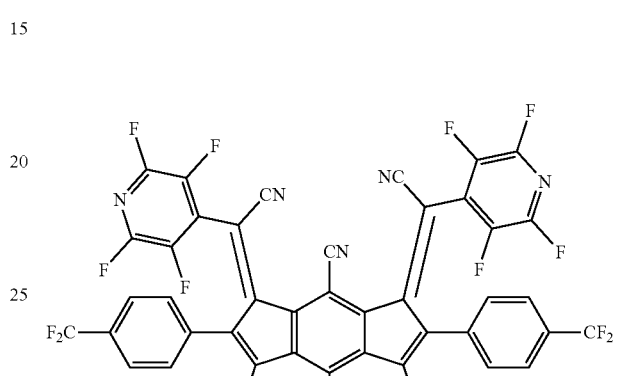
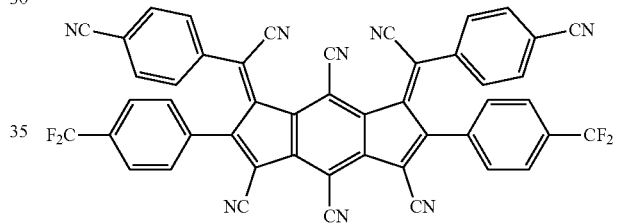
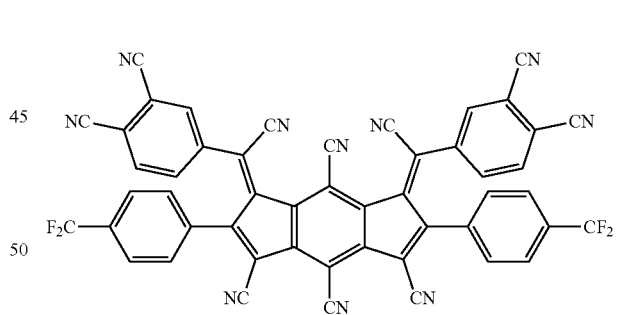
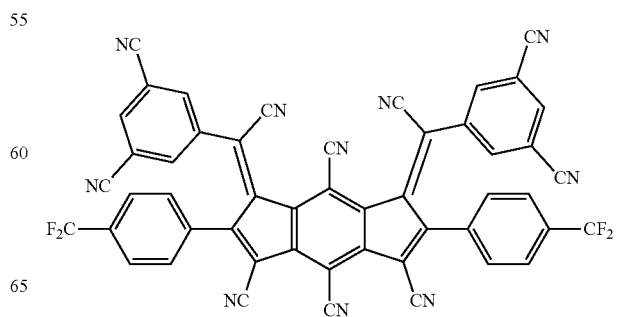

287
-continued
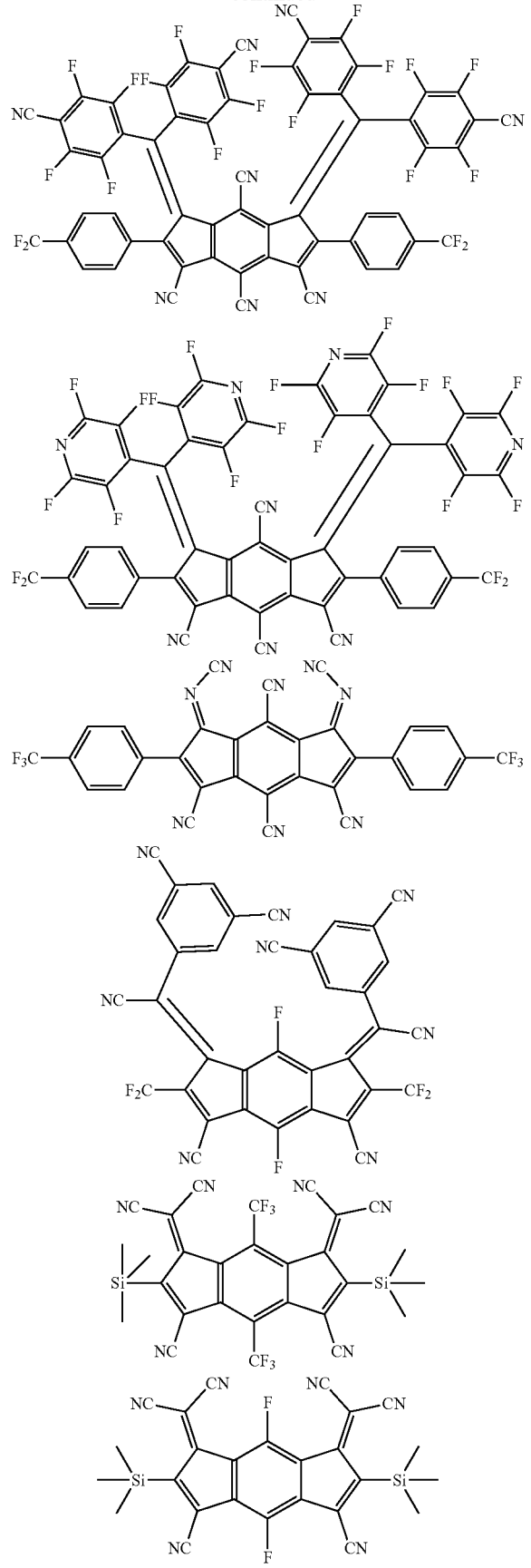
288
-continued
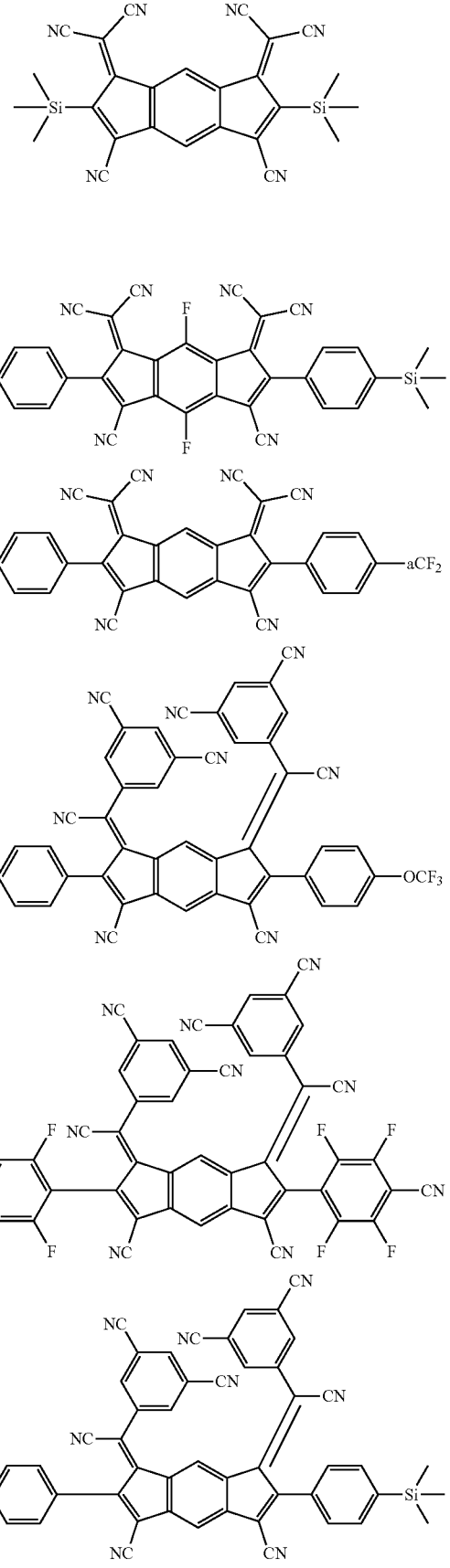

289
-continued
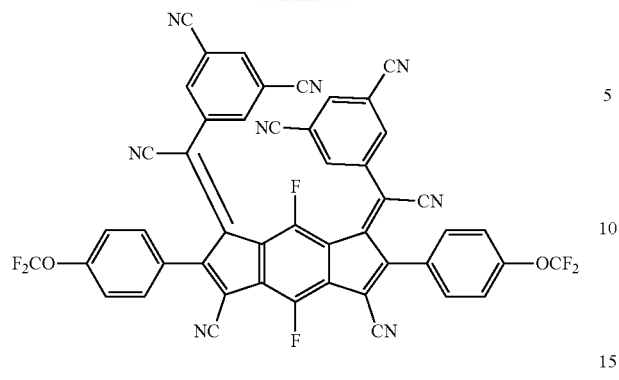
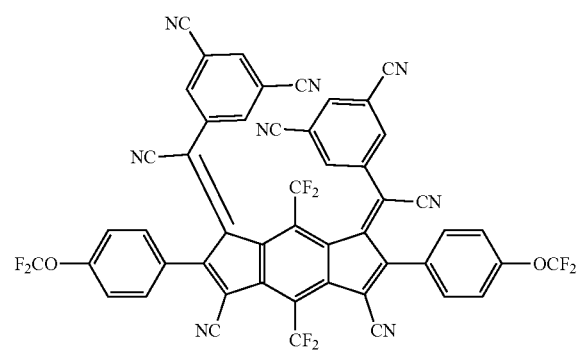
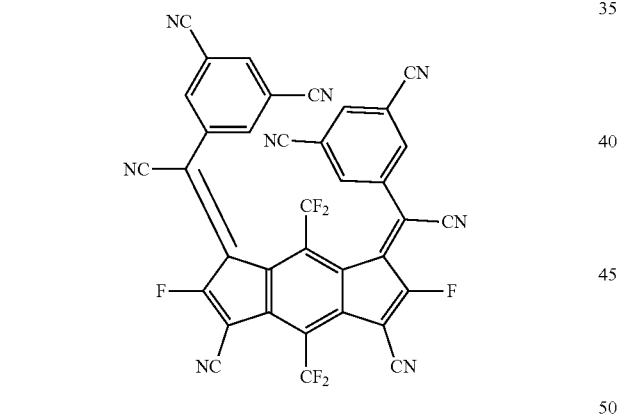
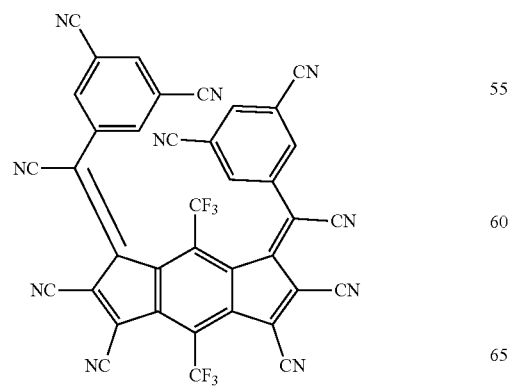
290
-continued
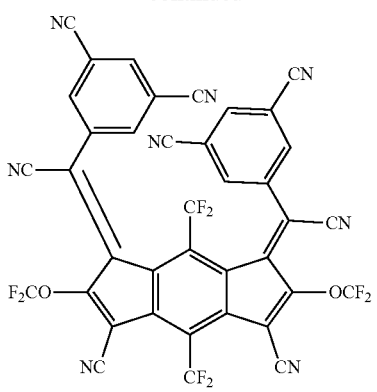
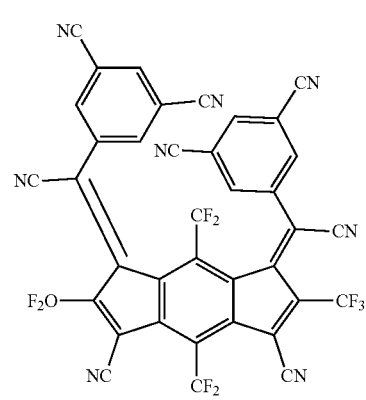
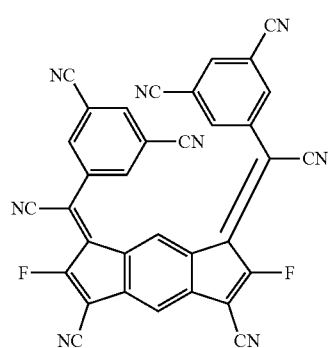
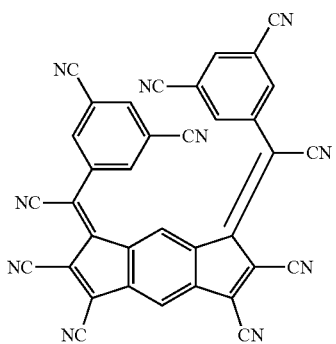

291
-continued
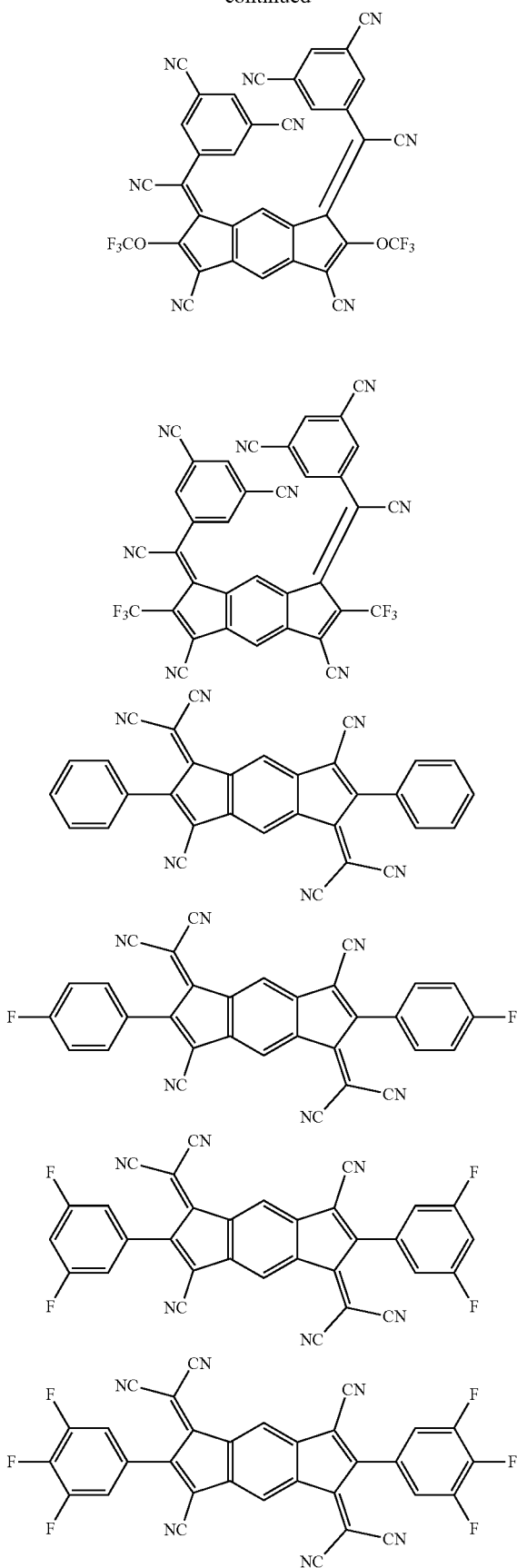
292
-continued
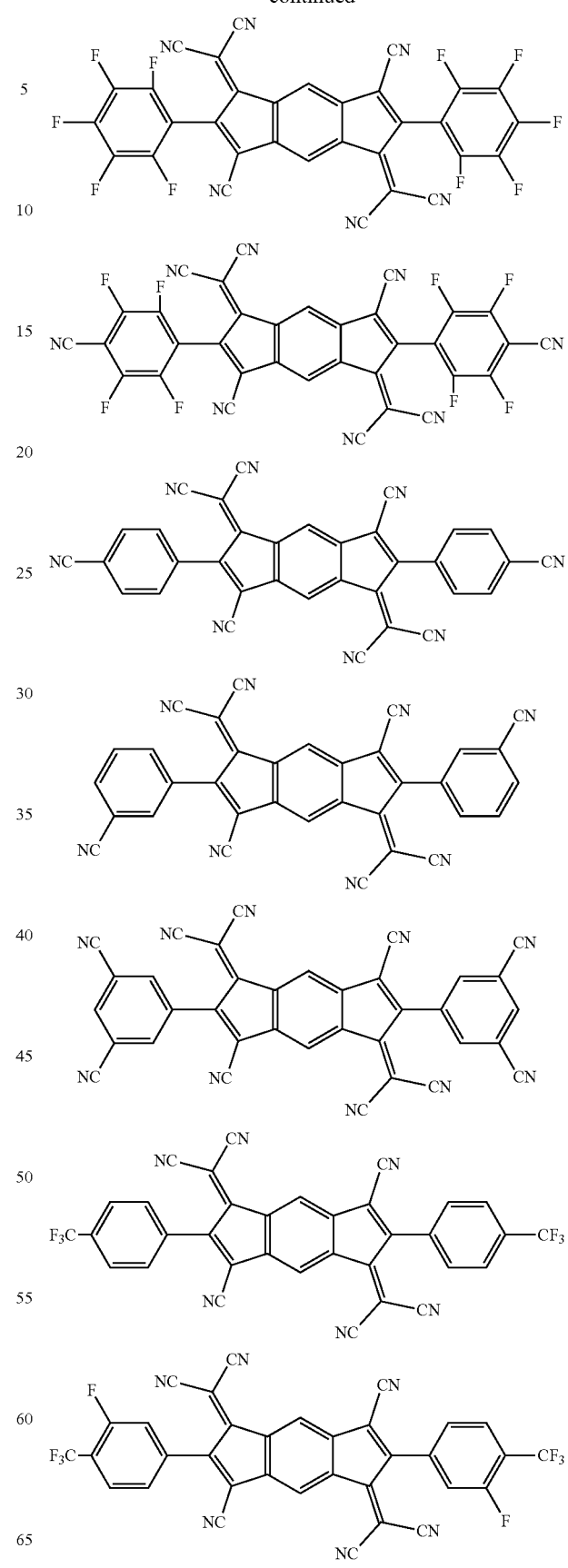

293
-continued
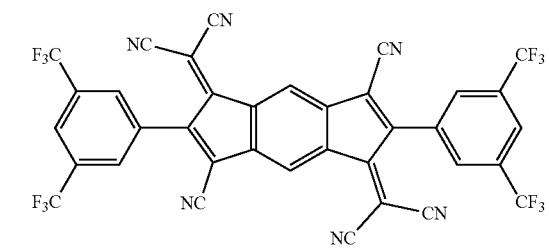
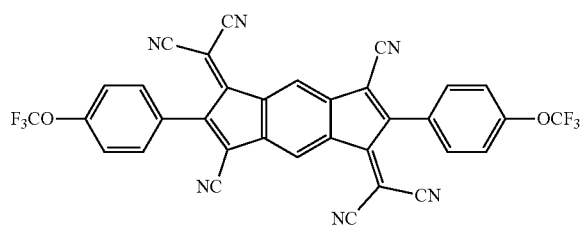
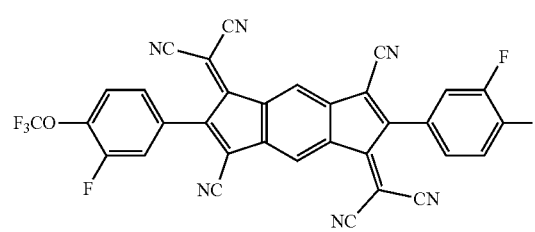
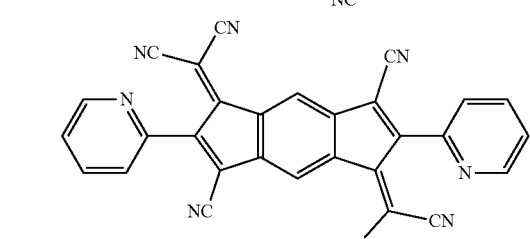
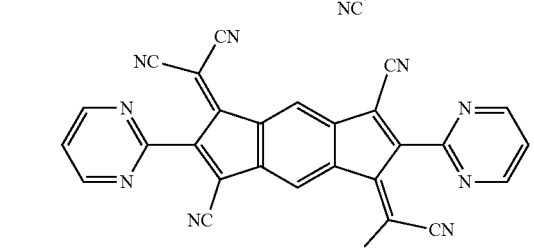
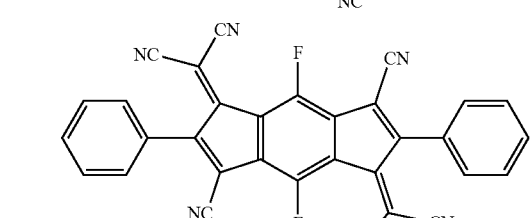
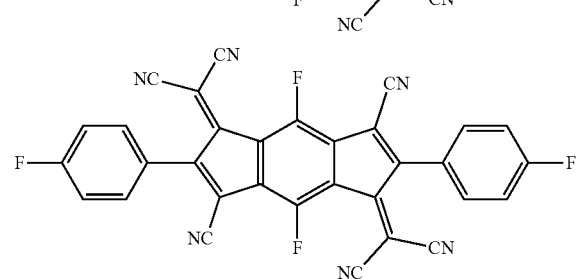
294
-continued
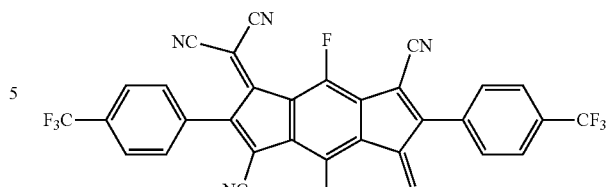
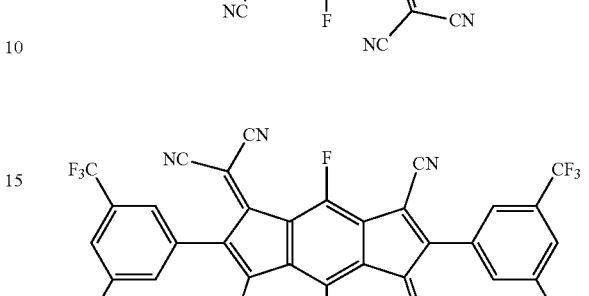
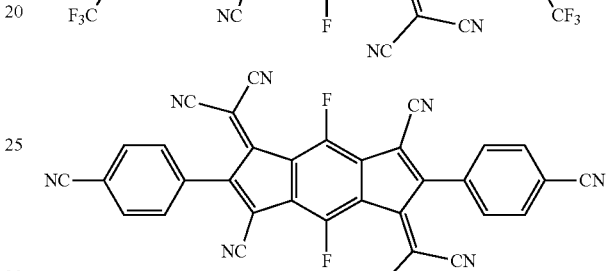
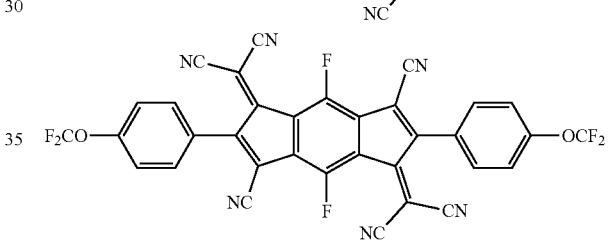
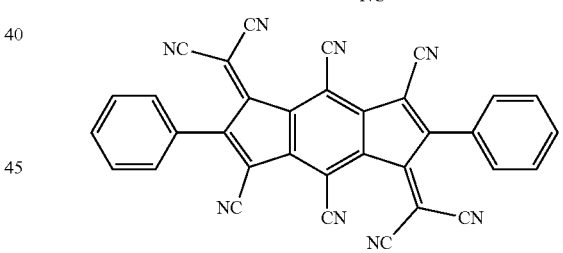
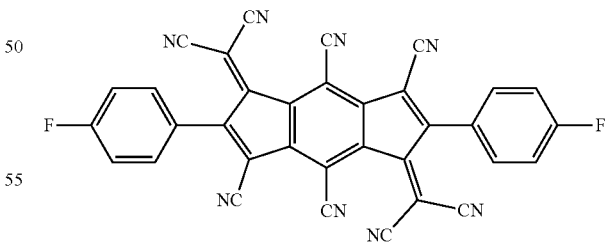
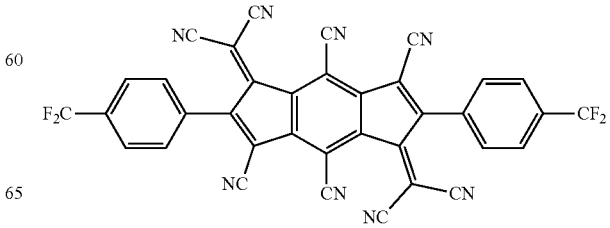

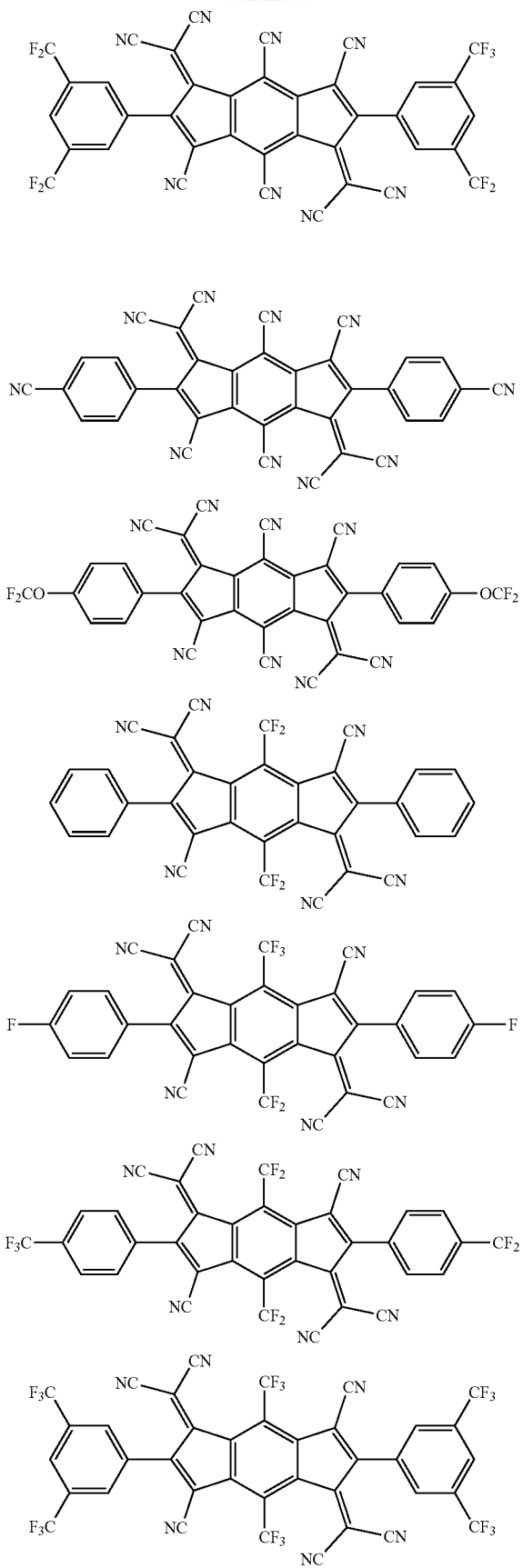
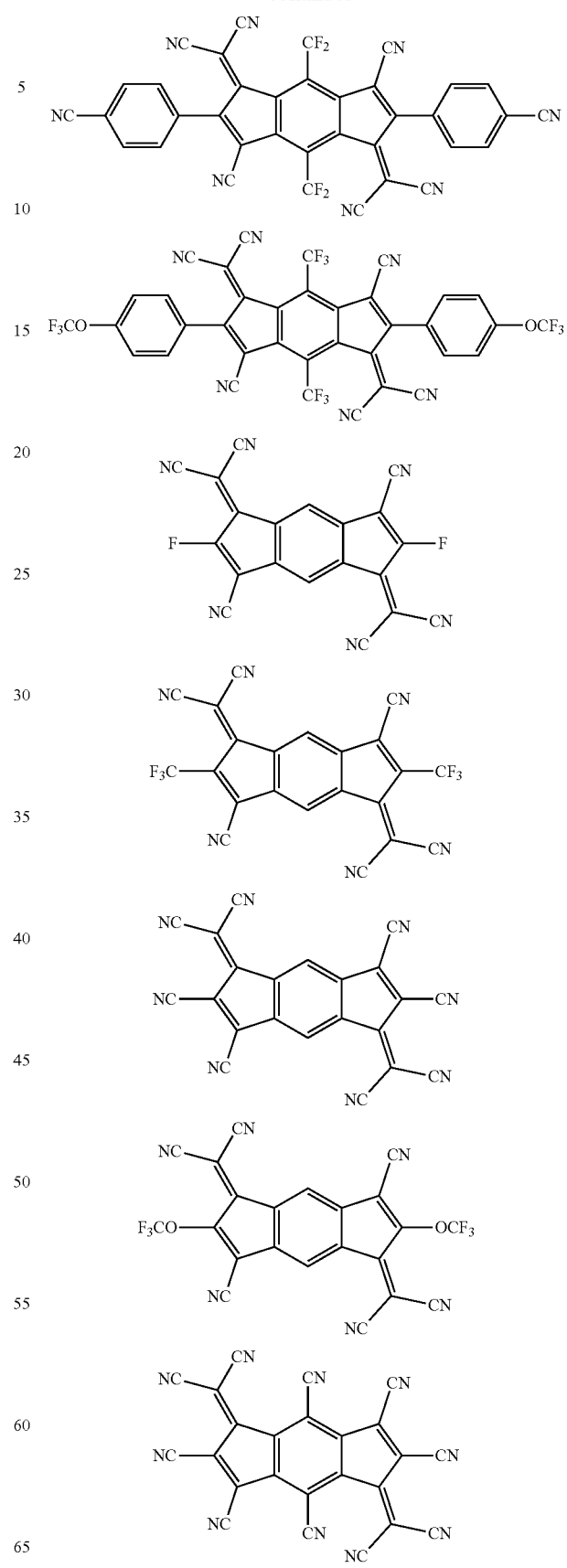

297
-continued
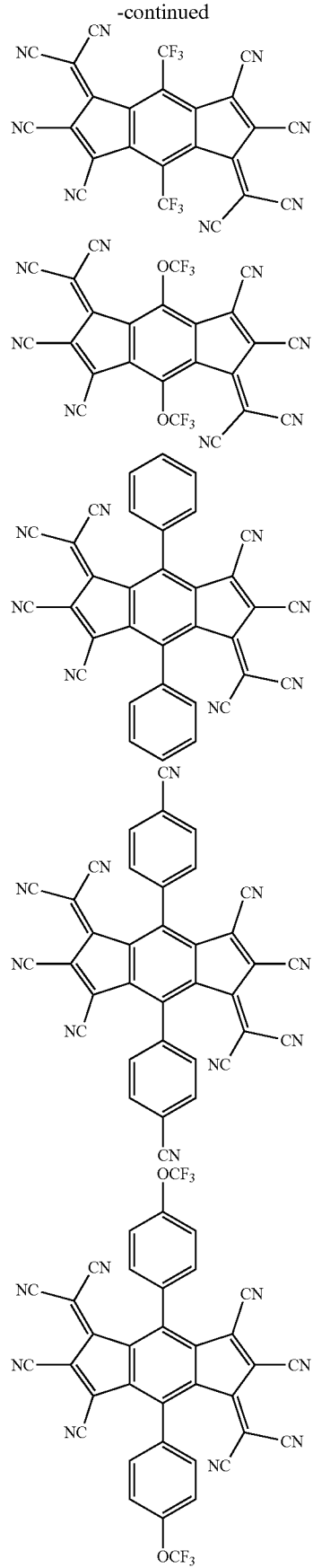
298
-continued
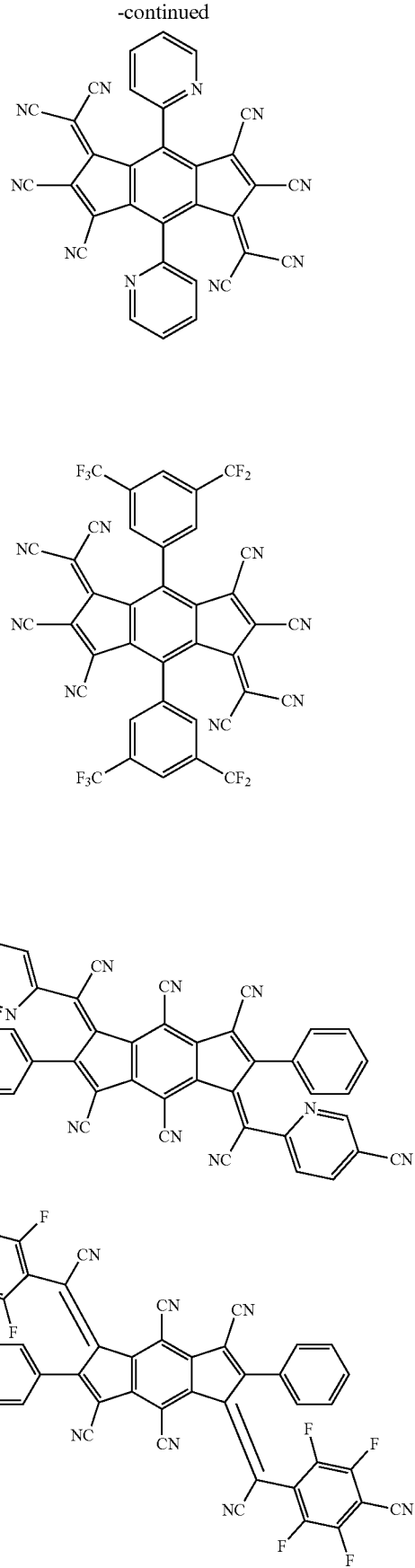

299
-continued
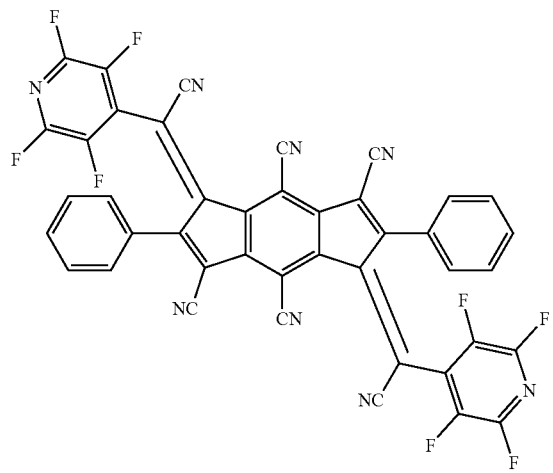
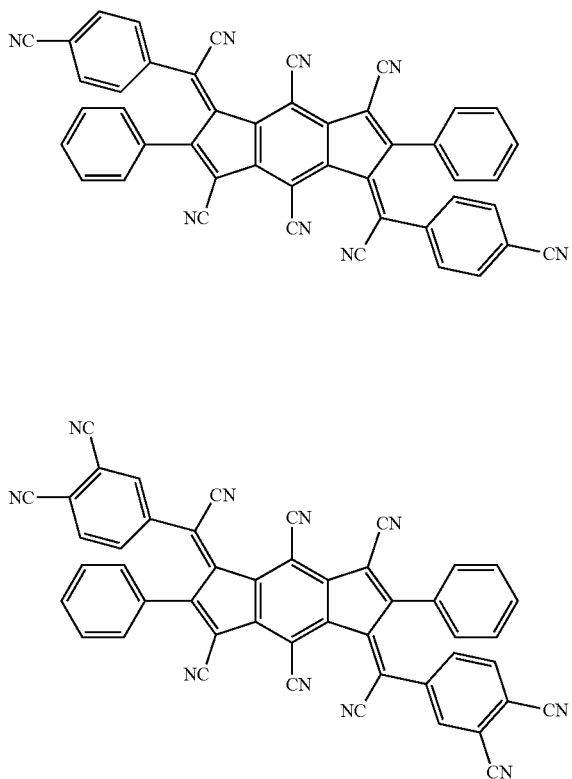
300
-continued
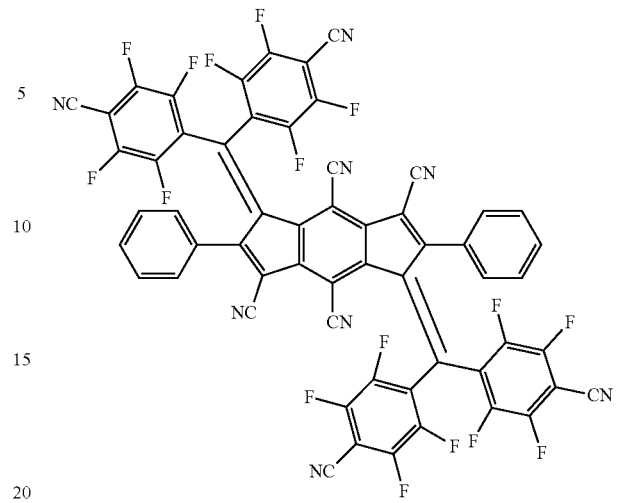
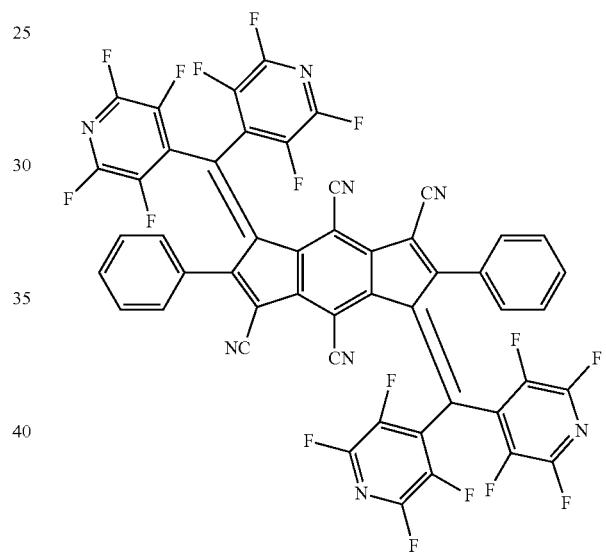
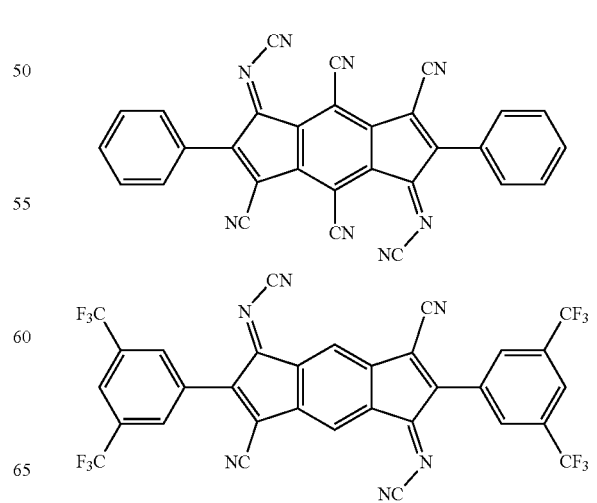

301
-continued
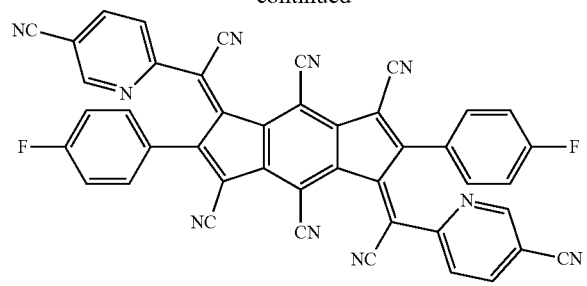
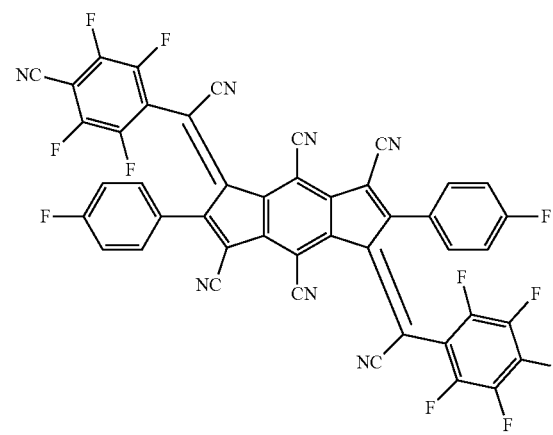
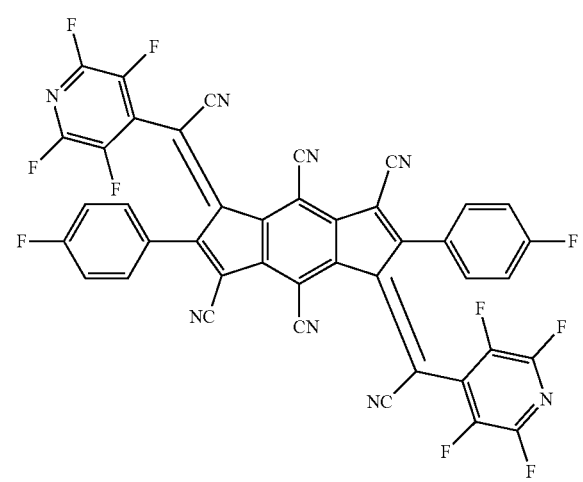
302
-continued
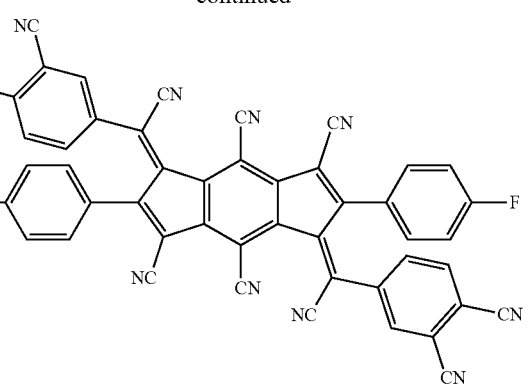
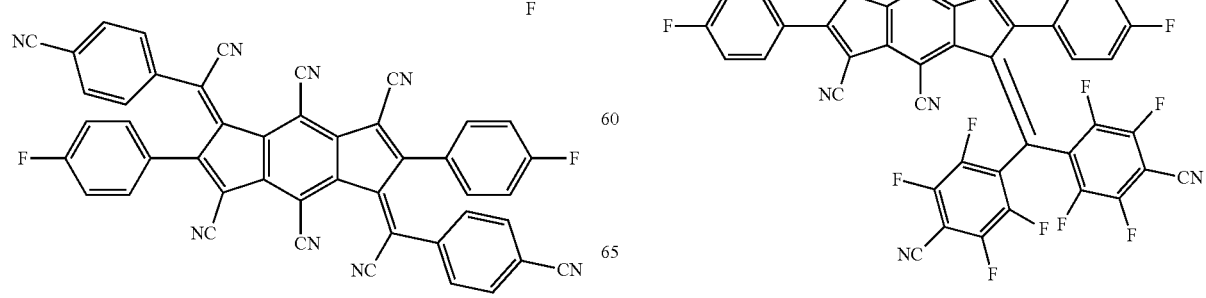

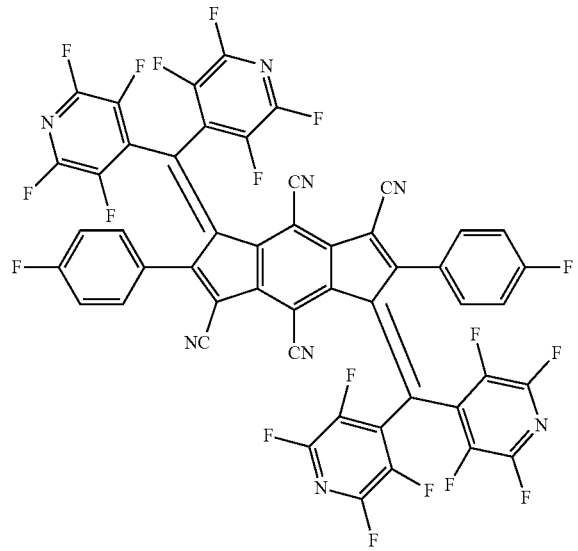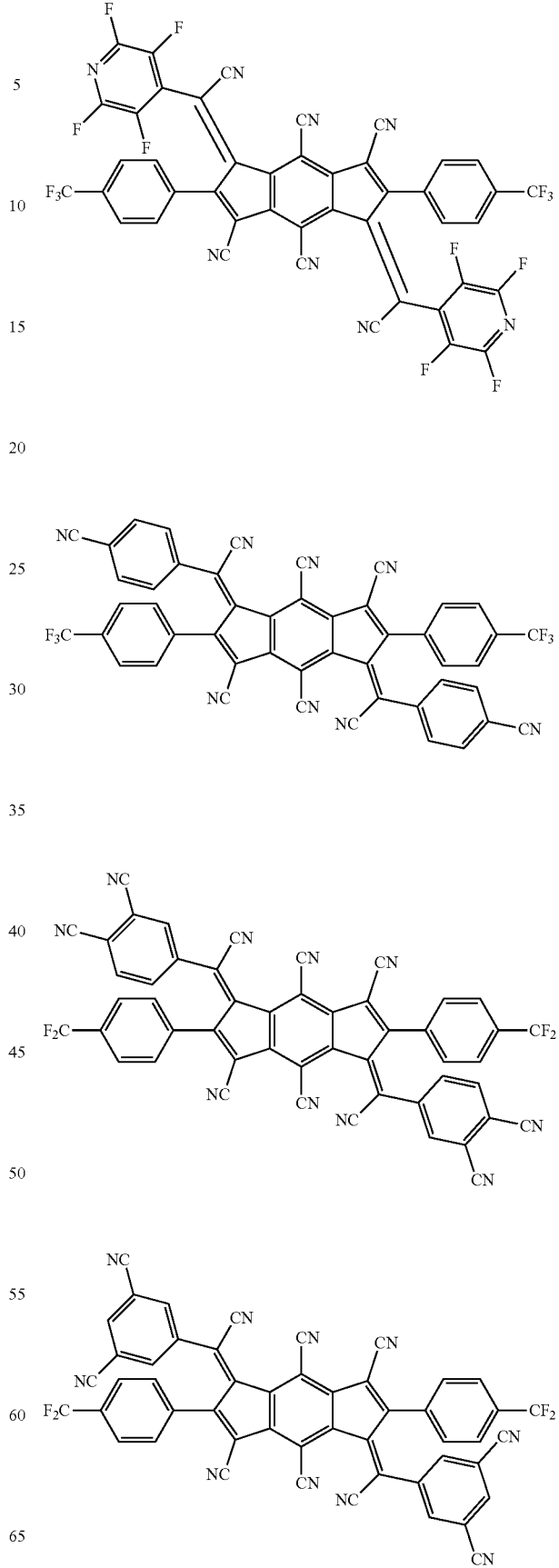

305
-continued
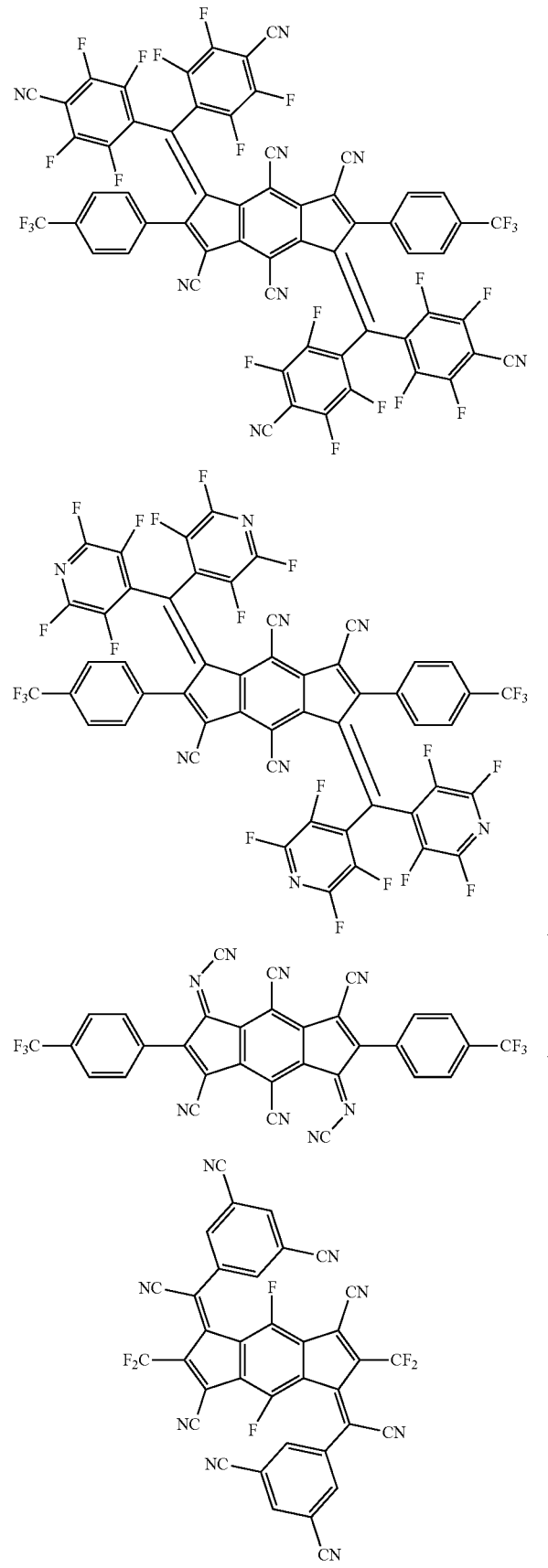
306
-continued
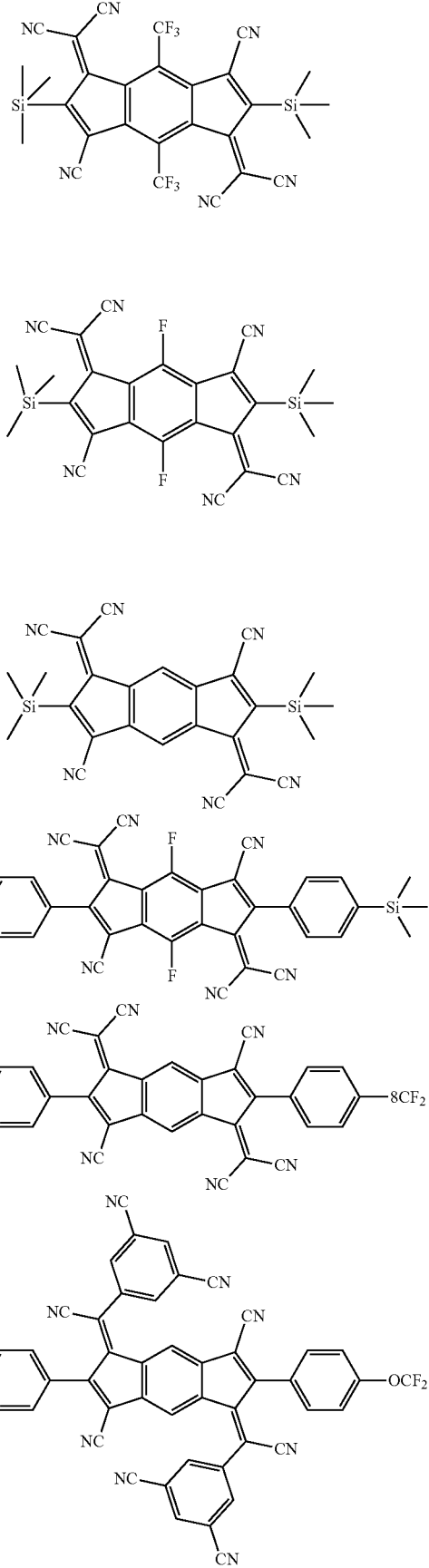

307
-continued
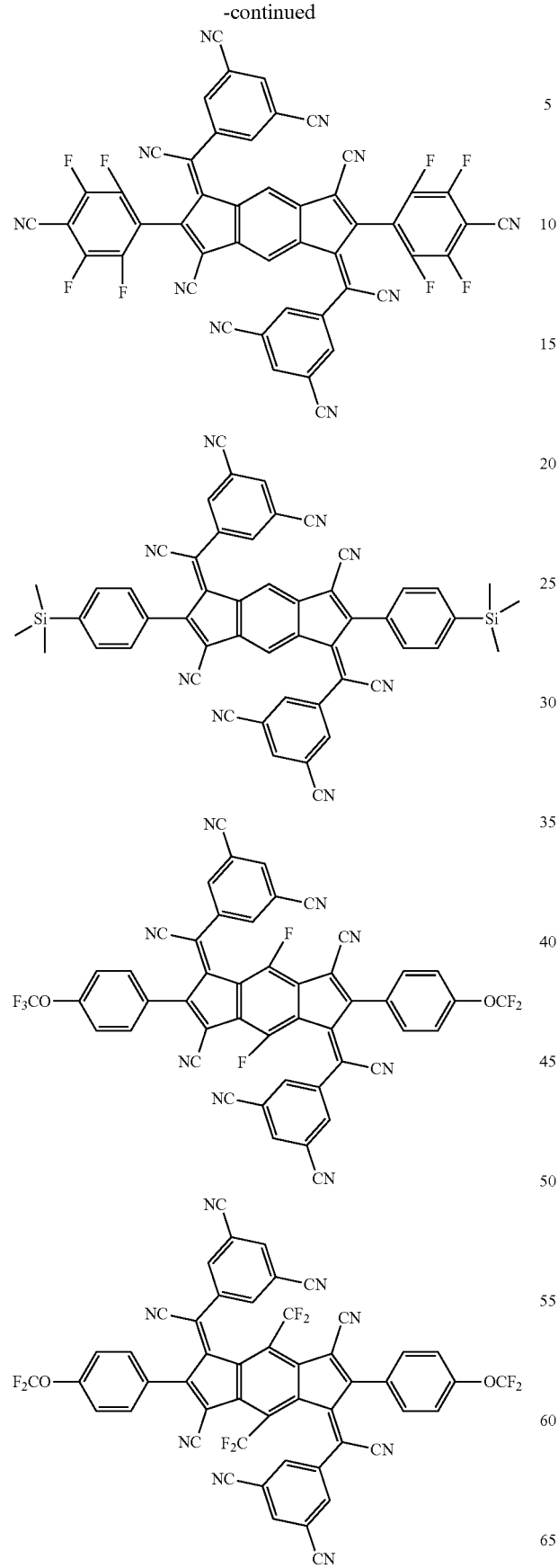
308
-continued
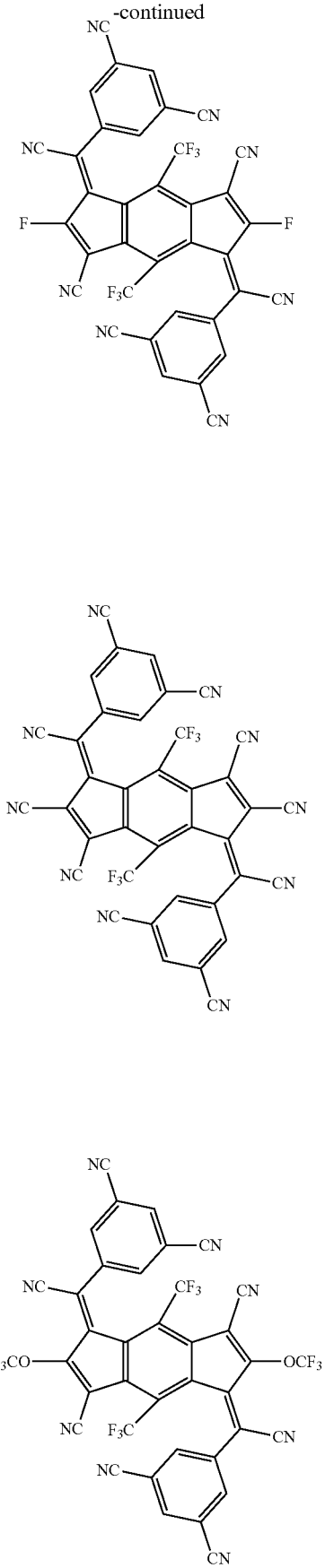

-continued

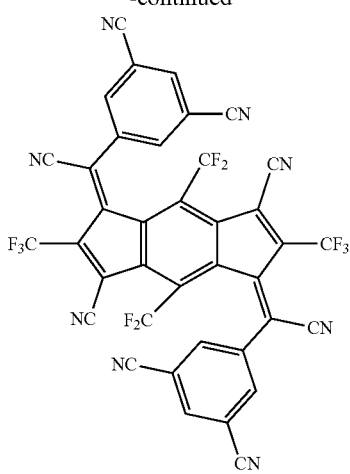

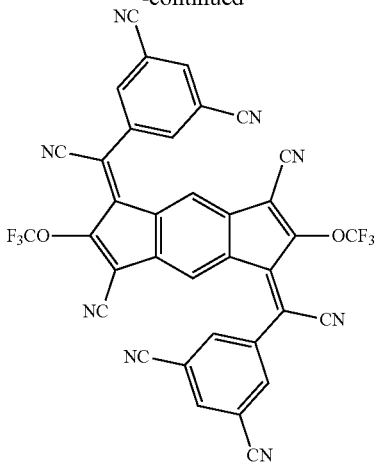

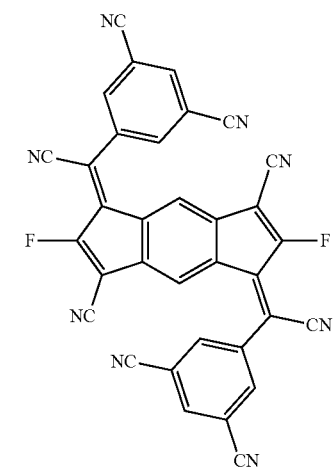

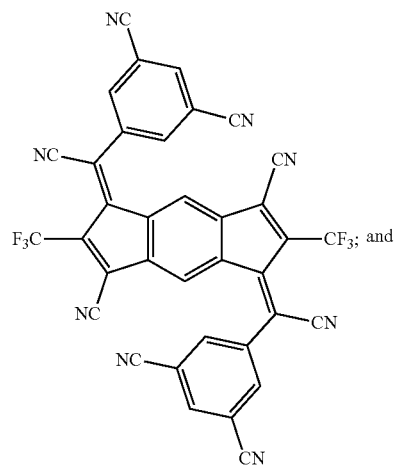 [SMILES: N#CC1=C(C(F)(F)F)/C(=C(\C#N)c2cc(C#N)cc(C#N)c2)c2cc3c(cc21)/C(=C(/C#N)c1cc(C#N)cc(C#N)c1)C(C(F)(F)F)=C3C#N] and

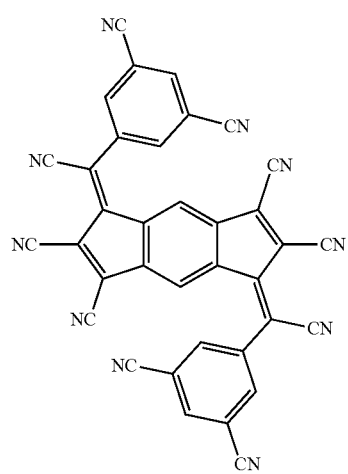

one or more of compounds of the following Chemical Formulae 2 to 4 at a weight ratio of 20:80 to 80:20:

[Chemical Formula 2]

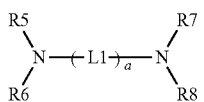

wherein in Chemical Formula 2:
L1 is a substituted or unsubstituted arylene group or a substituted or unsubstituted heteroarylene group;
R5 to R8 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group, or adjacent groups are optionally bonded to each other to form a substituted or unsubstituted ring;

a is an integer from 1 to 10; and when a is 2 or more, two or more L1s are the same as or different from each other;

[Chemical Formula 3]

wherein in Chemical Formula 3:

L2 is a substituted or unsubstituted arylene group;

R9 to R11 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;

R101 and R102 are the same as or different from each other, and are each independently hydrogen, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;

b is an integer from 1 to 10;

when b is 2 or more, two or more L2s are the same as or different from each other;

r101 is an integer from 1 to 4;

r102 is an integer from 1 to 3; and when r101 and r102 are each 2 or more, two or more structures in the parenthesis are the same as or different from each other;

[Chemical Formula 4]

wherein in Chemical Formula 4:

L3 to L5 are the same as or different from each other, and are each independently a direct bond, a substituted or unsubstituted arylene group, or a substituted or unsubstituted heteroarylene group;

Ar1 is a substituted or unsubstituted aryl group or a substituted or unsubstituted heteroaryl group;

Ar2 is a substituted or unsubstituted aryl group;

R12, R13, R103, and R104 are the same as or different from each other, and are each independently hydrogen, deuterium, a nitrile group, a nitro group, a hydroxy group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group, or adjacent groups are bonded to each other to form a substituted or unsubstituted ring;

r103 is an integer from 1 to 3;

r104 is an integer from 1 to 4; and when r103 and r104 are each 2 or more, two or more structures in the parenthesis are the same as or different from each other.

5. The organic light emitting device of claim 1, wherein the compound of Chemical Formula 2 is selected from among the following compounds:

313
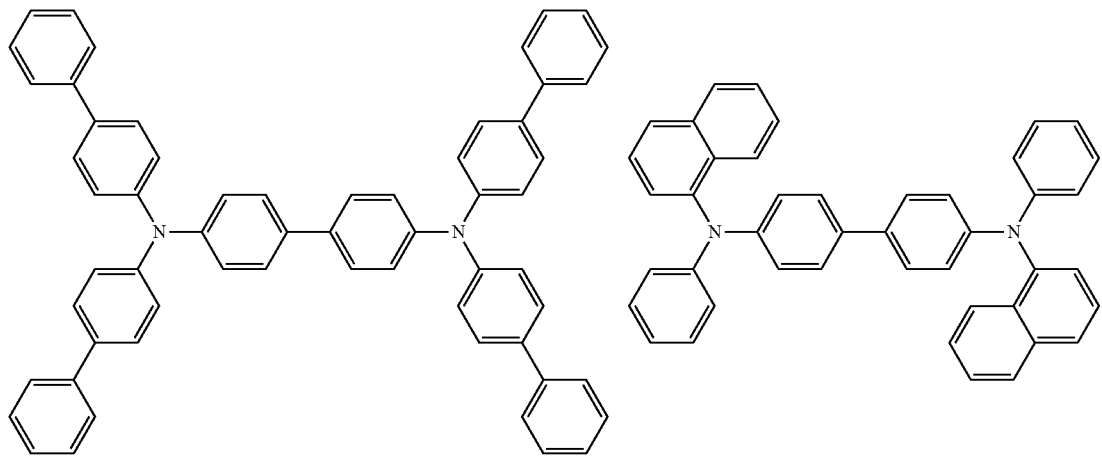
314
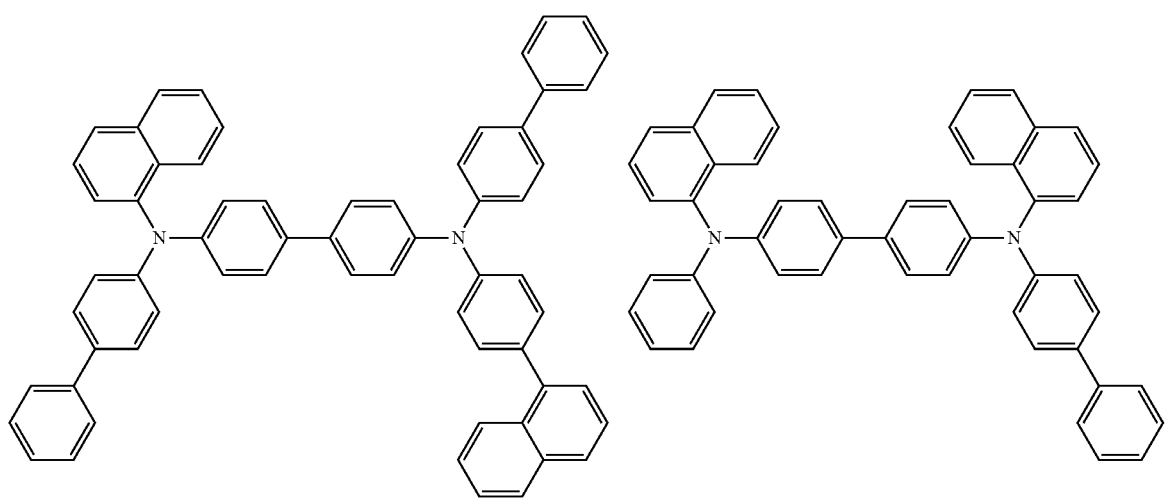
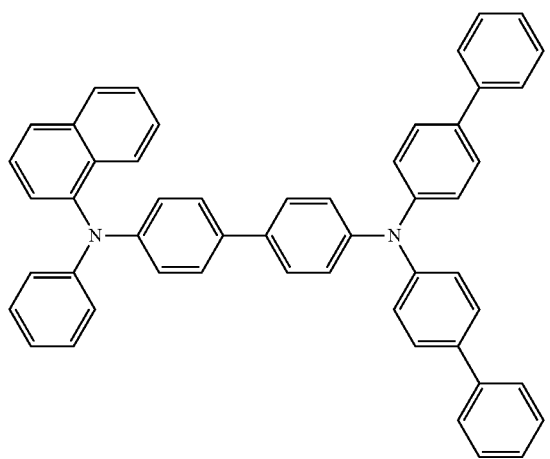

-continued
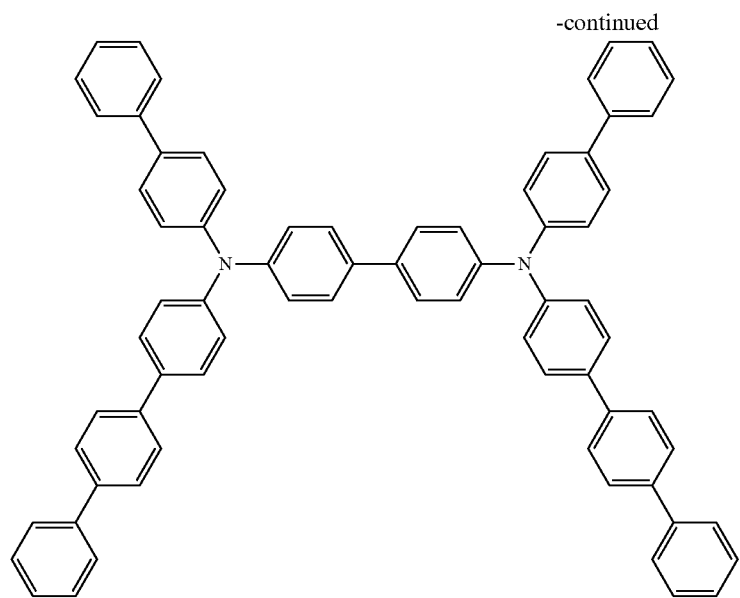
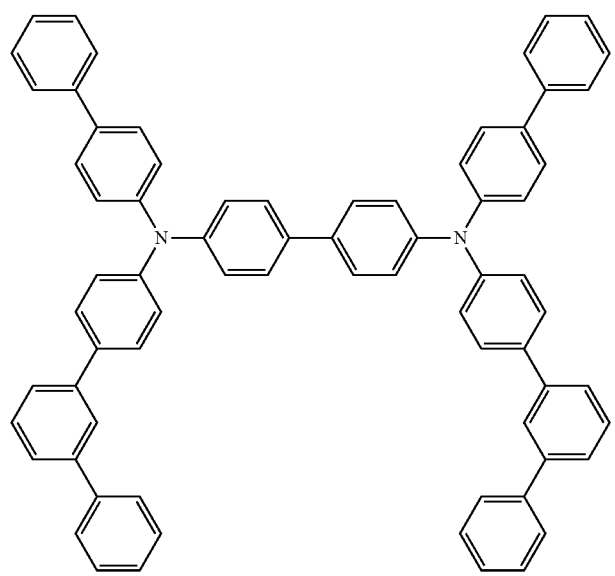
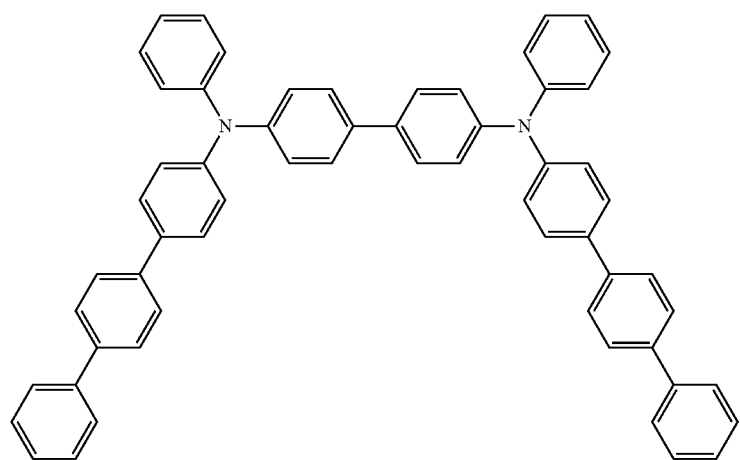

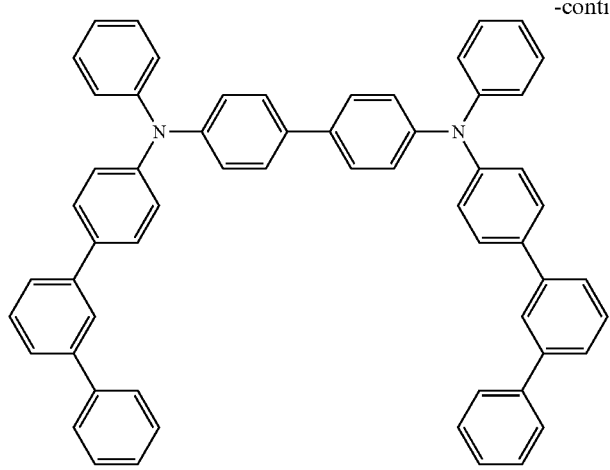
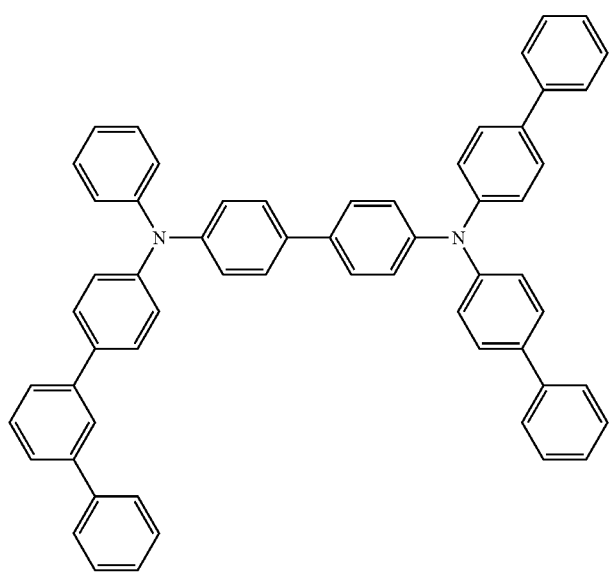
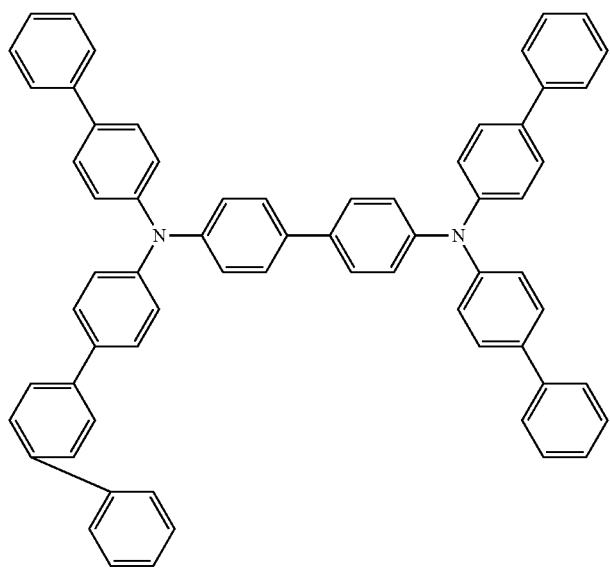

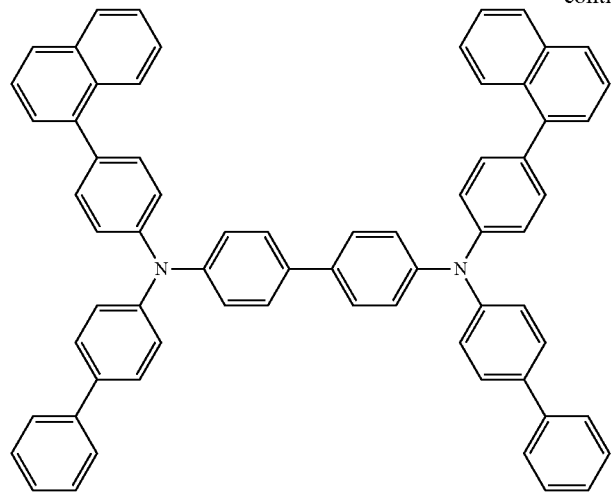
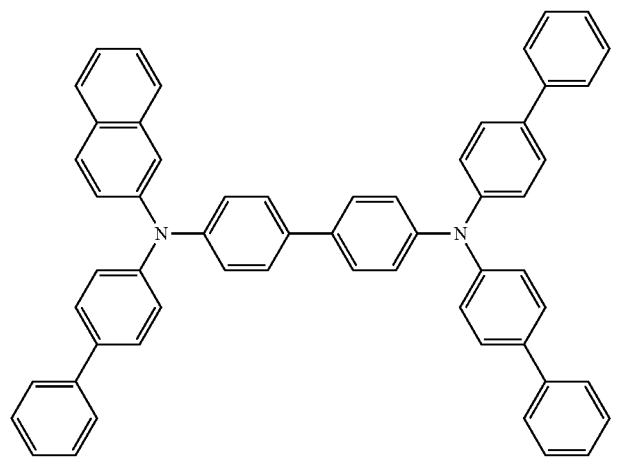
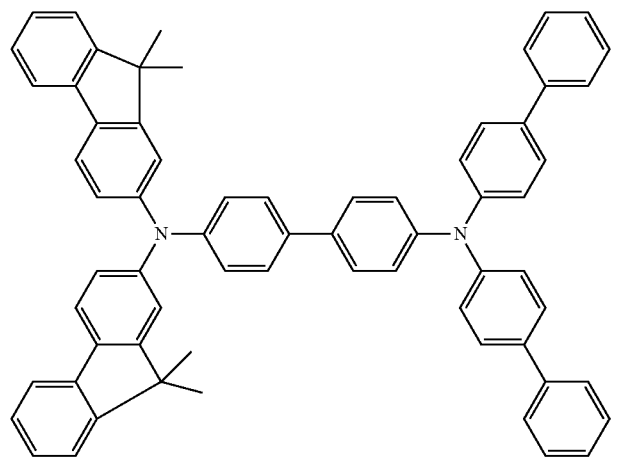

-continued
321
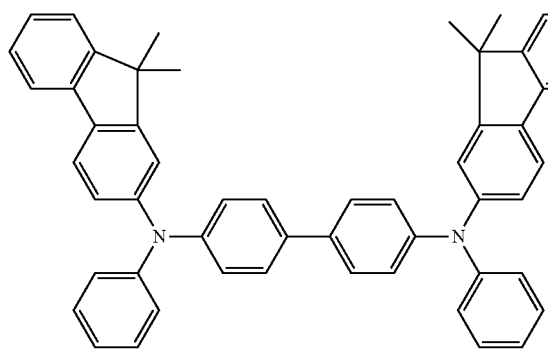
322
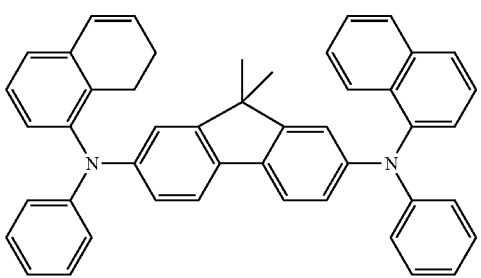
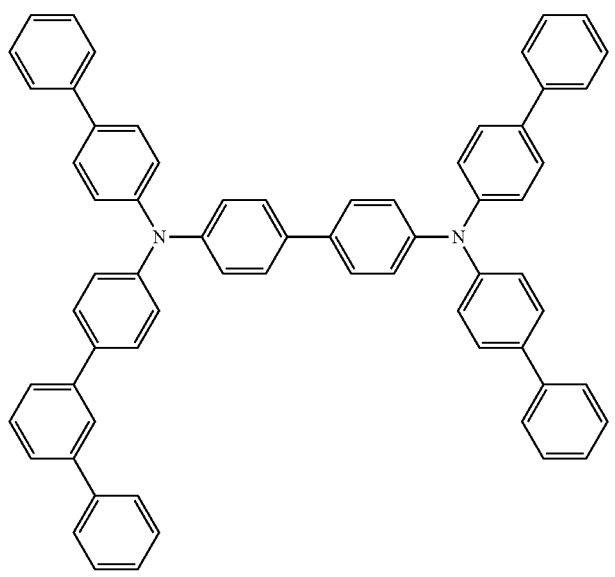
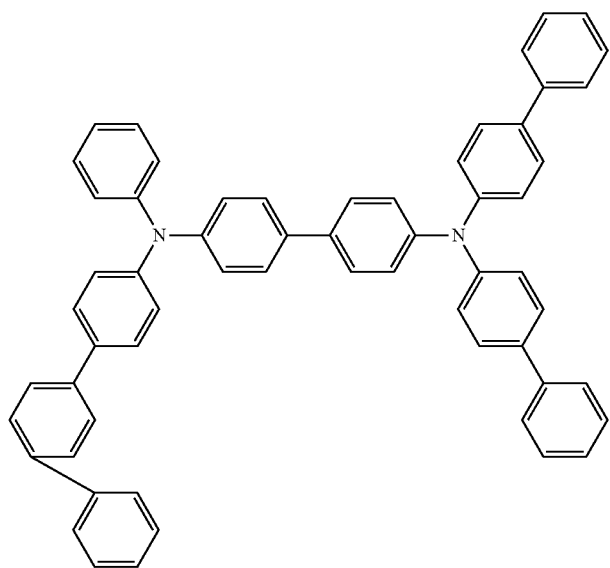

-continued
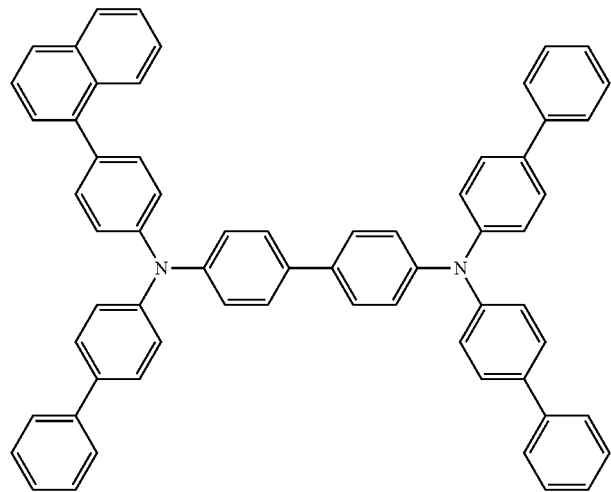
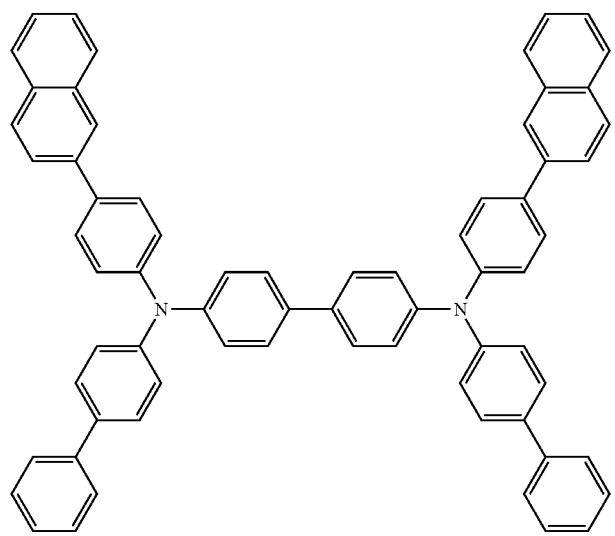
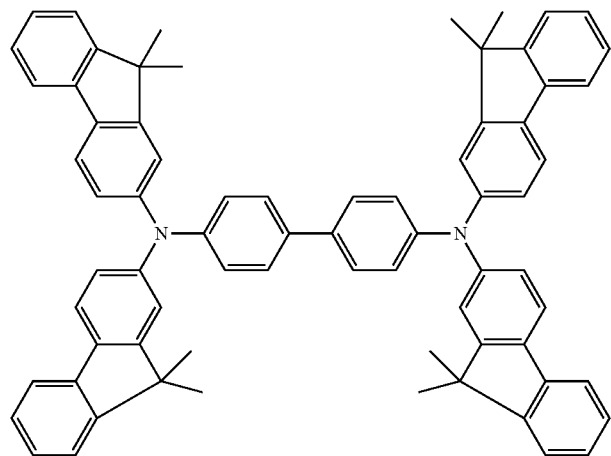

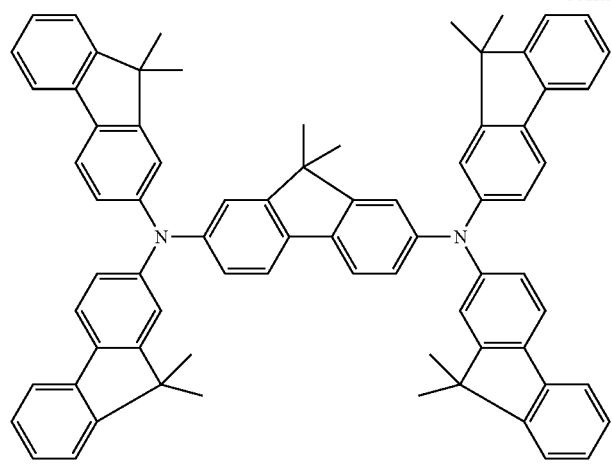
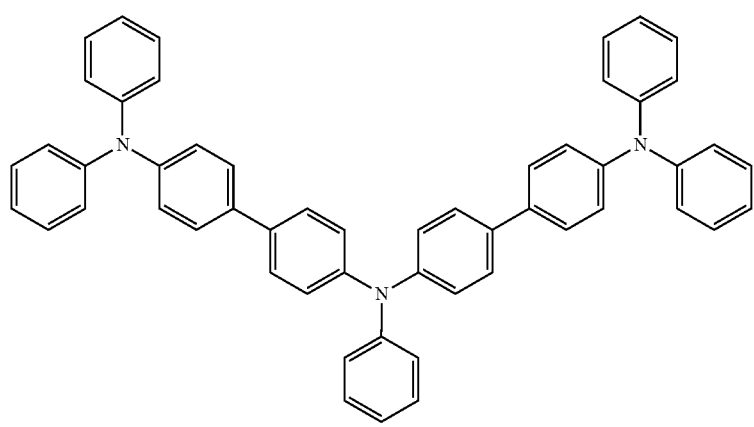
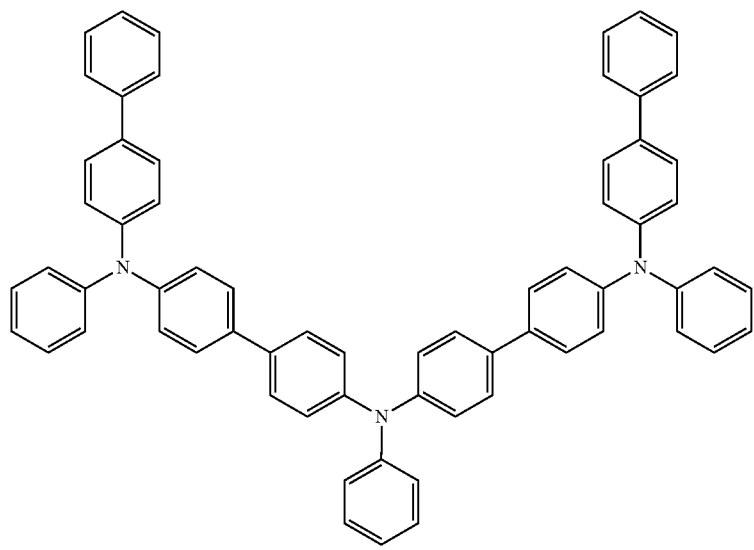

-continued
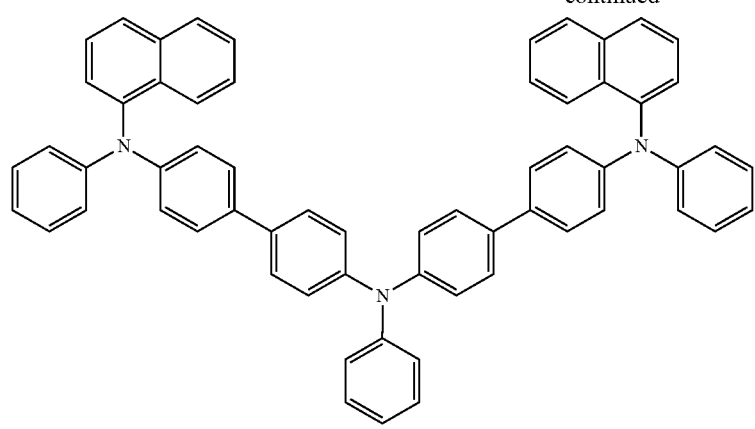
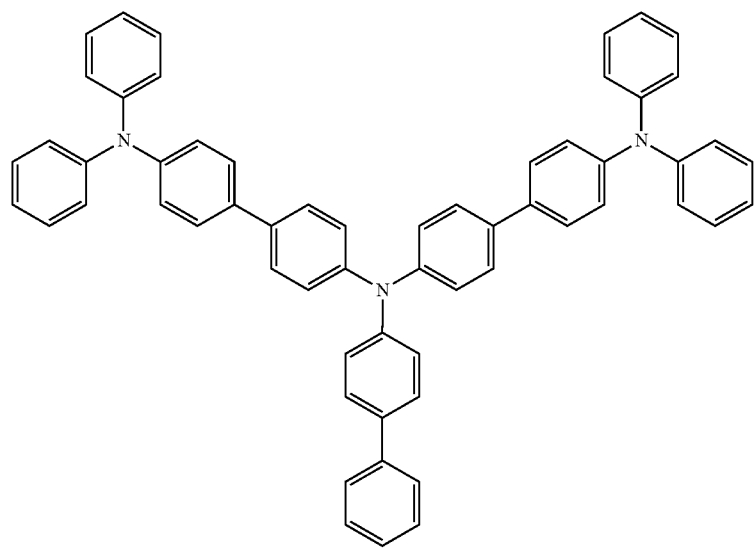
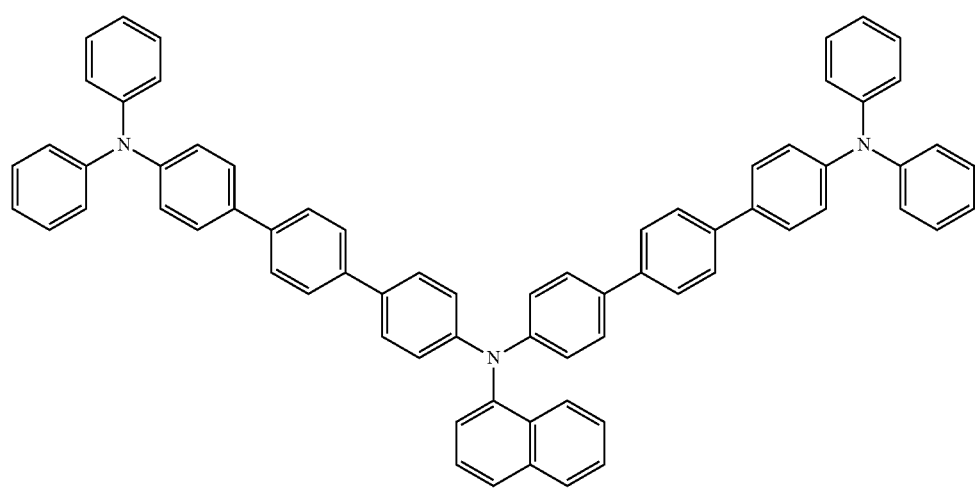

-continued
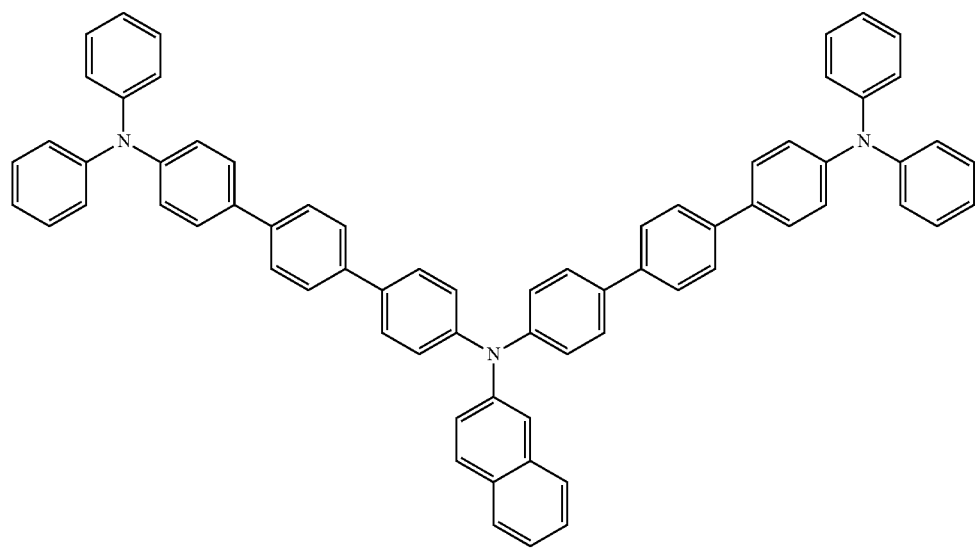
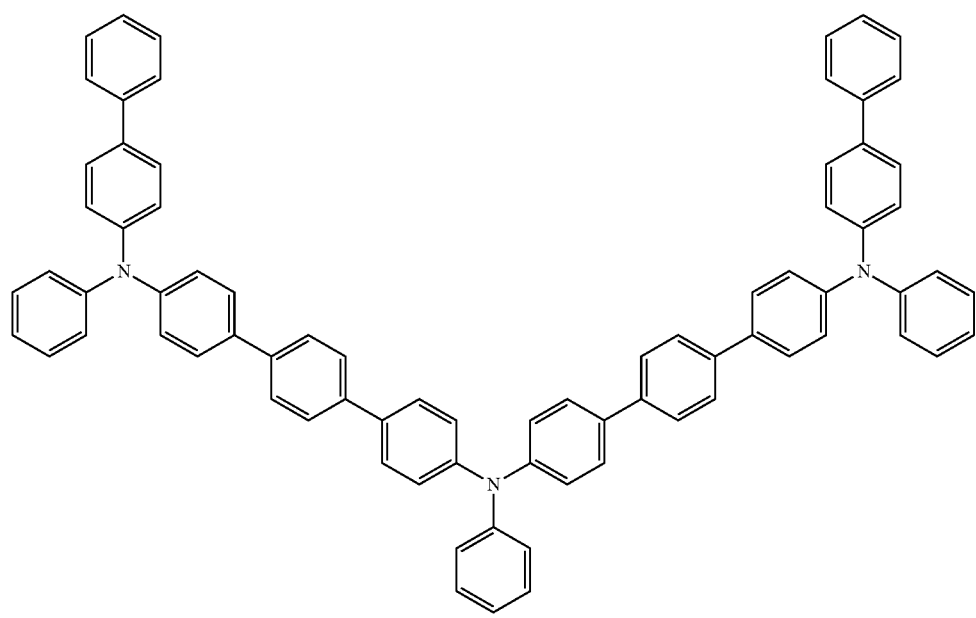

331 332
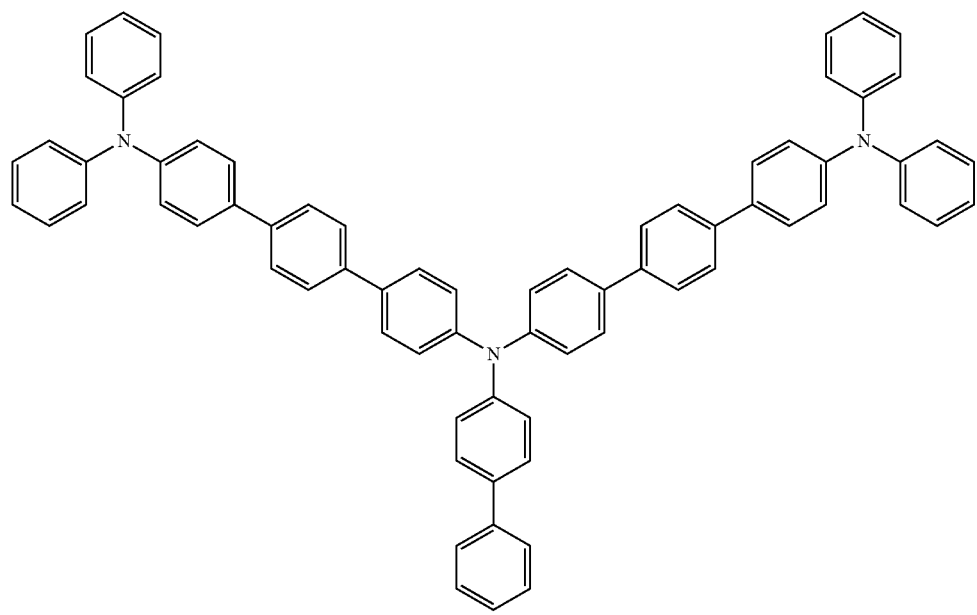
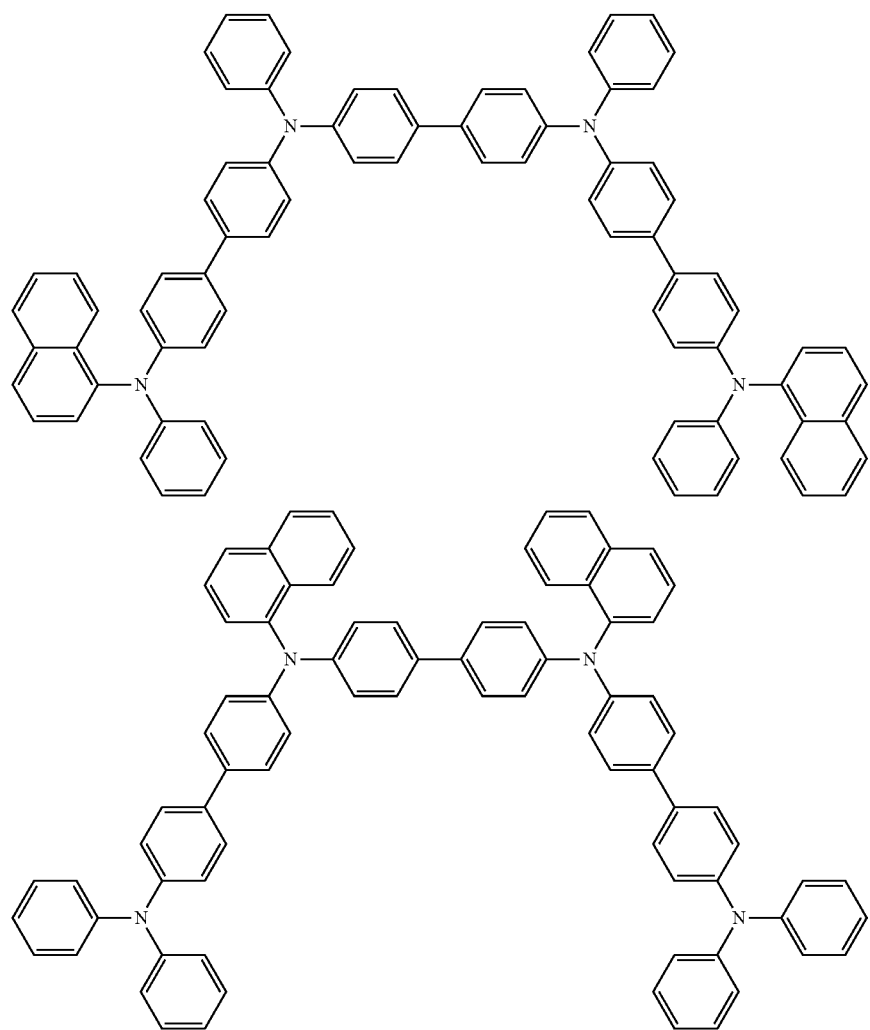

-continued
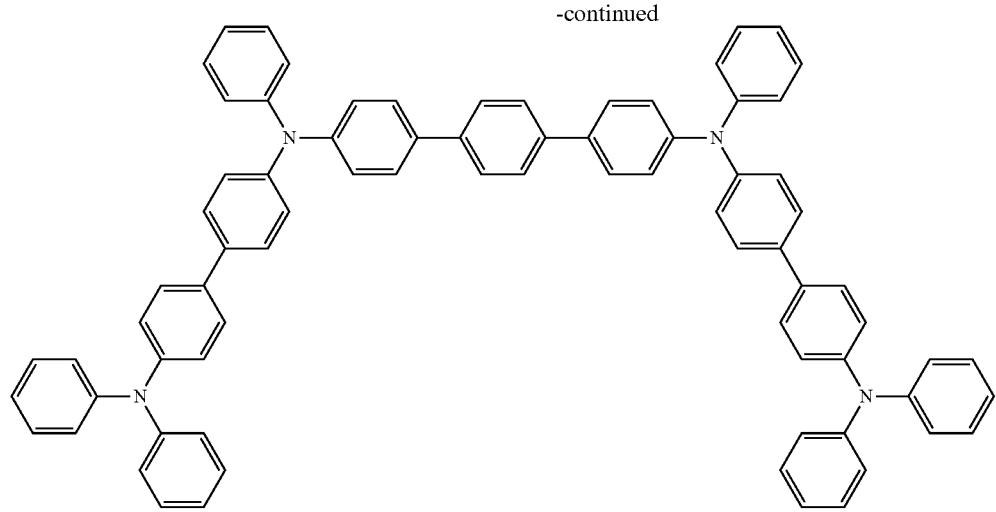
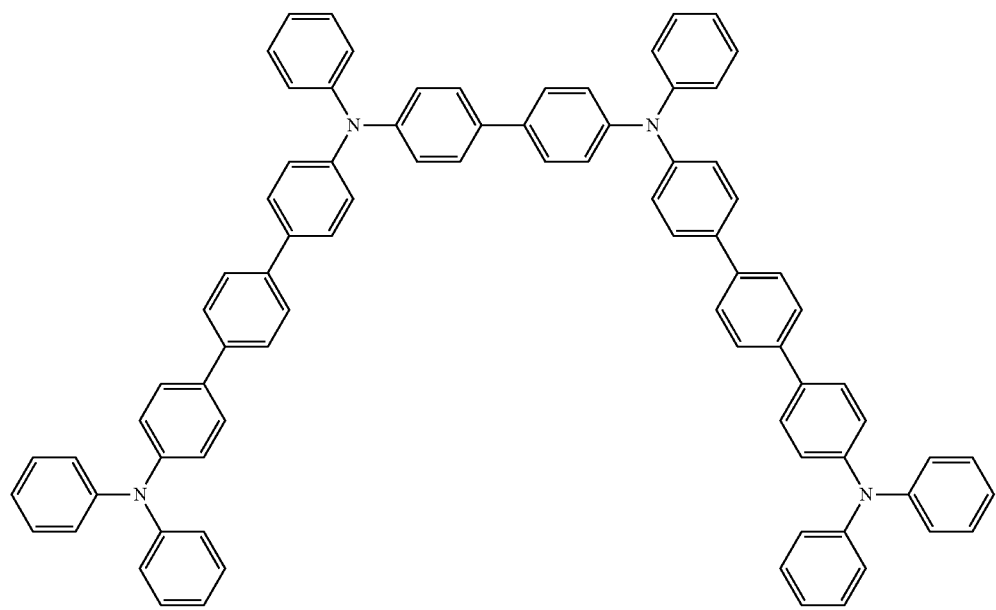
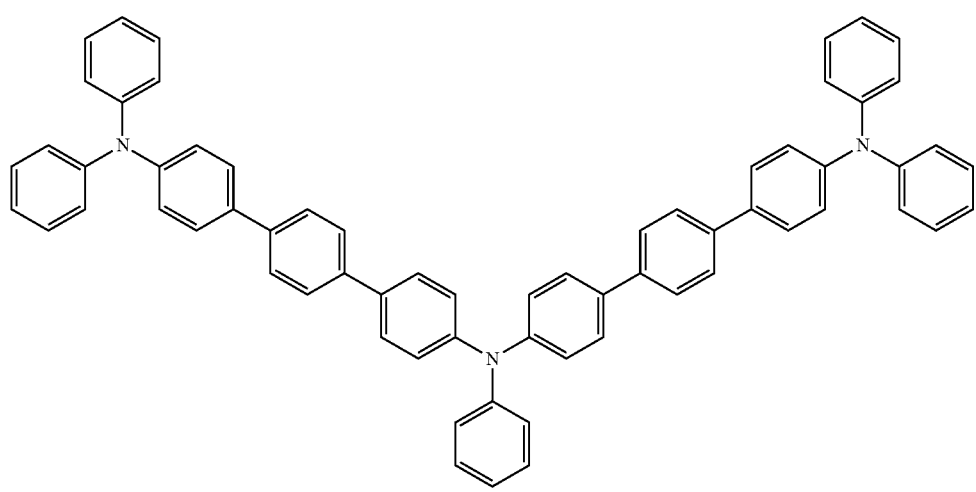

335
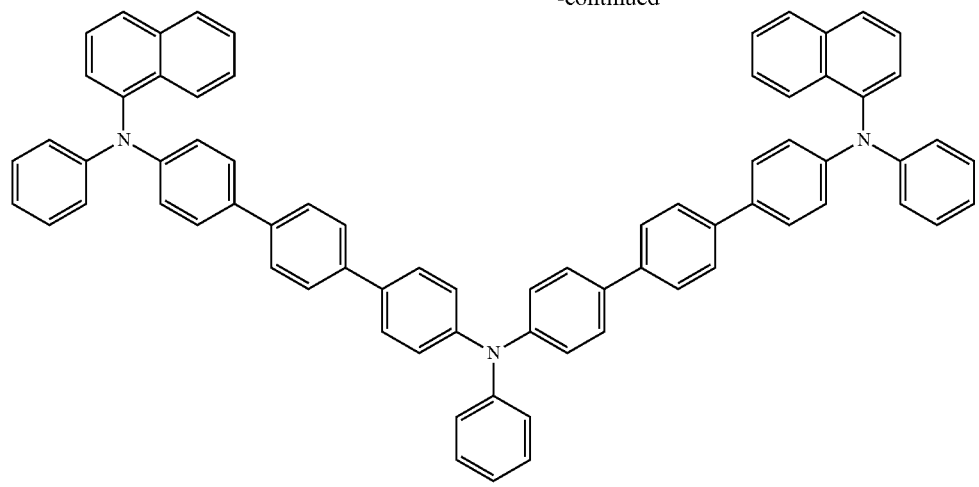
336
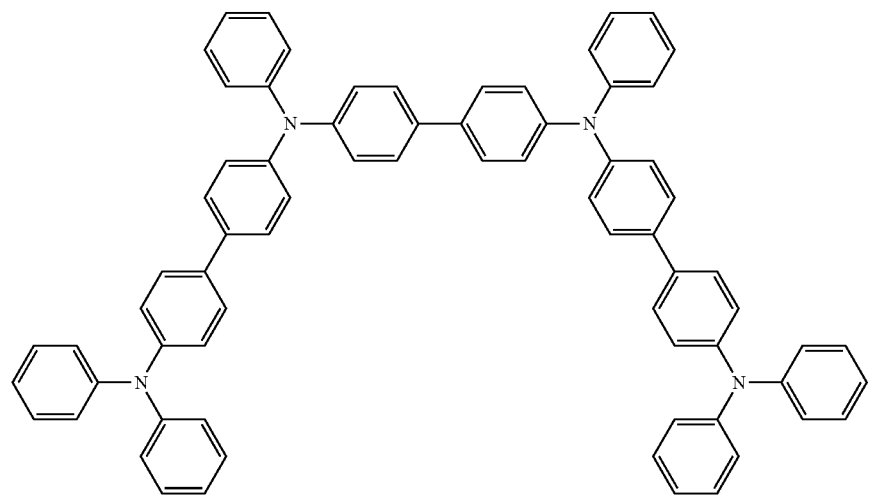
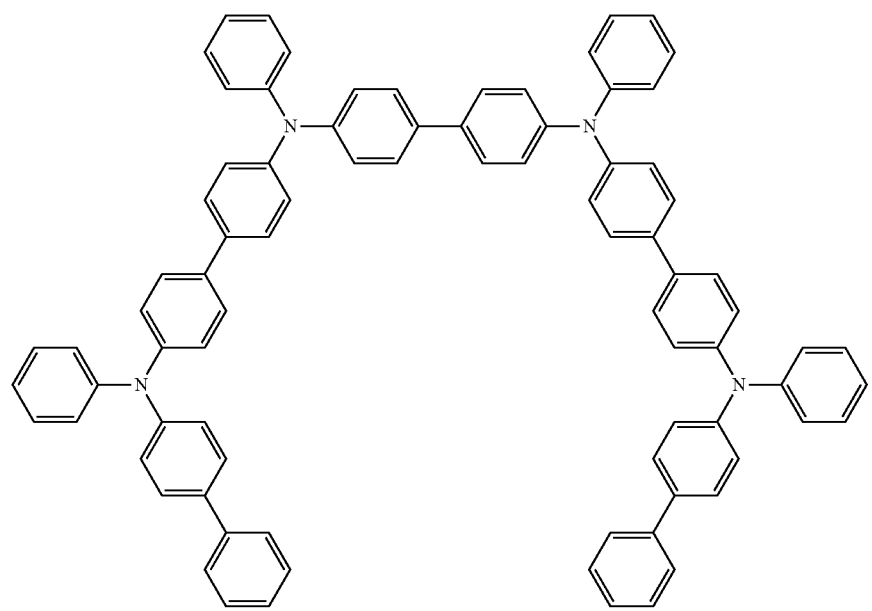

-continued
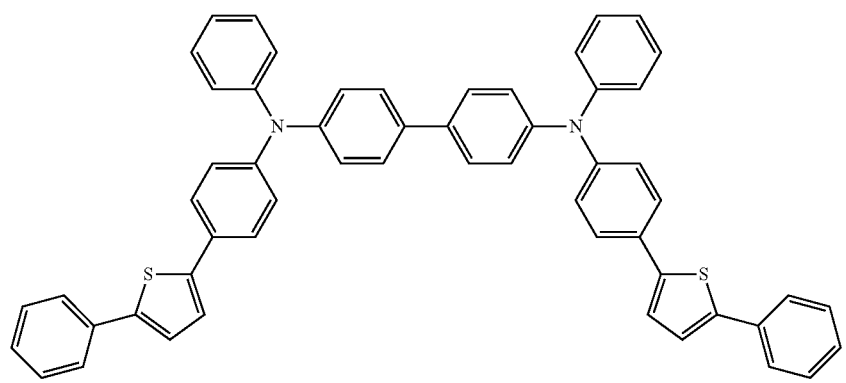
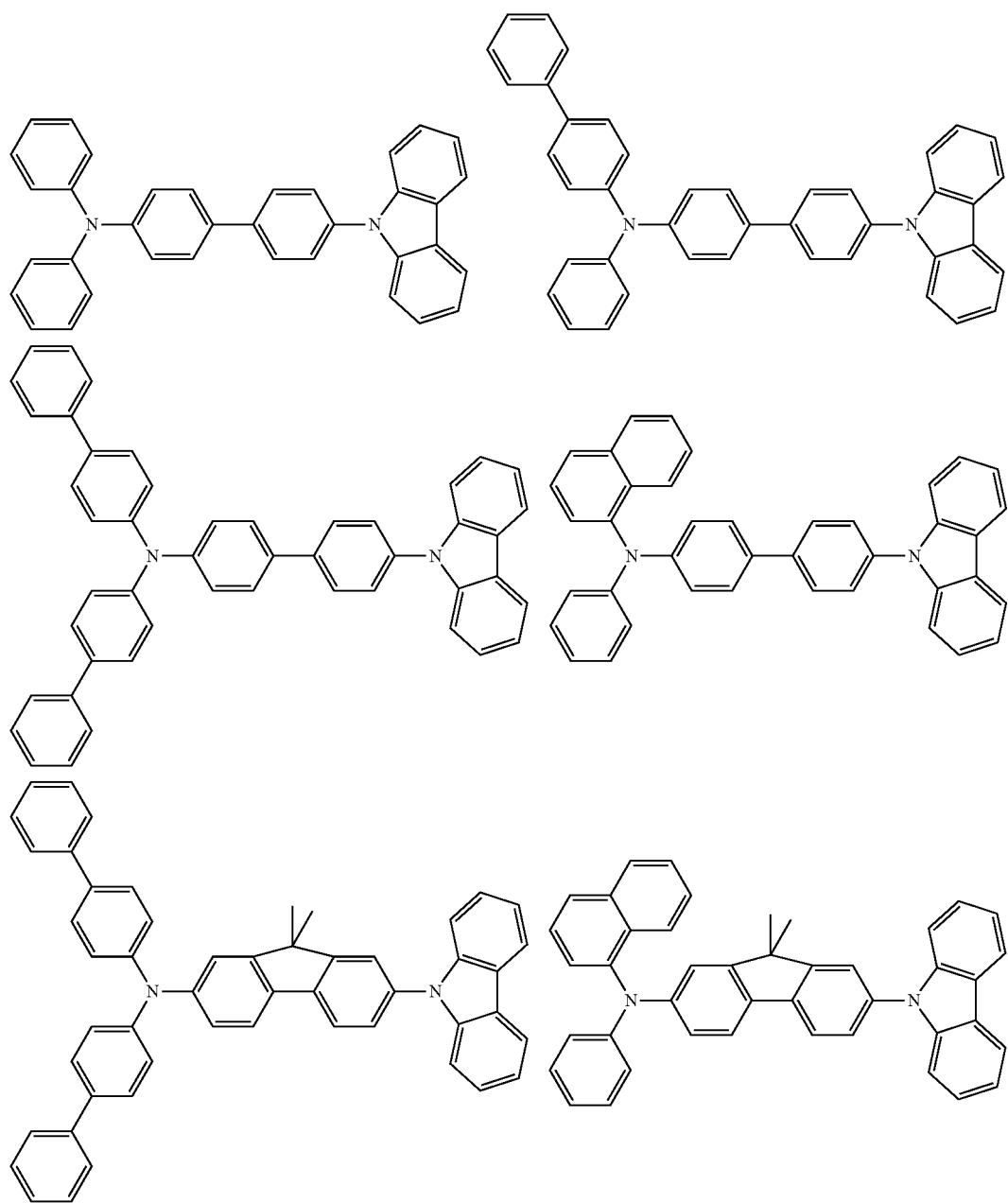

-continued
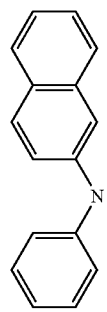 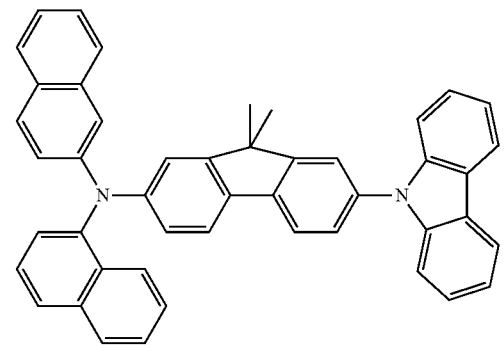
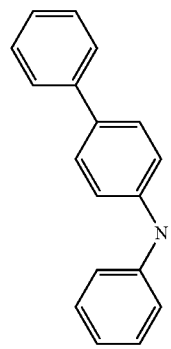 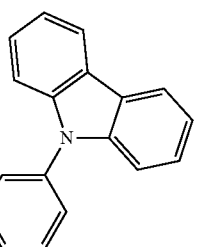 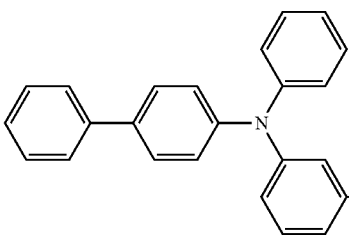 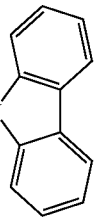
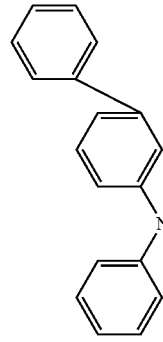 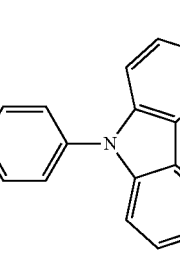 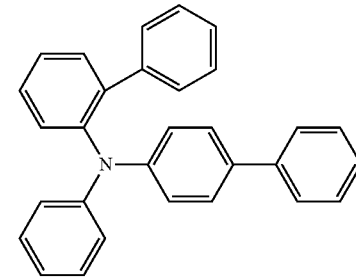 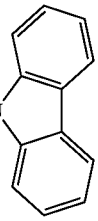
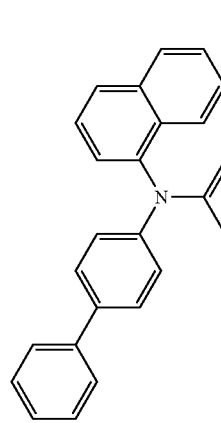 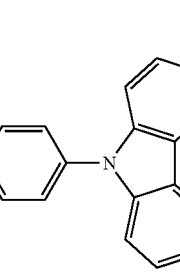  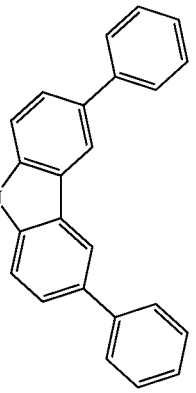

341 342
-continued
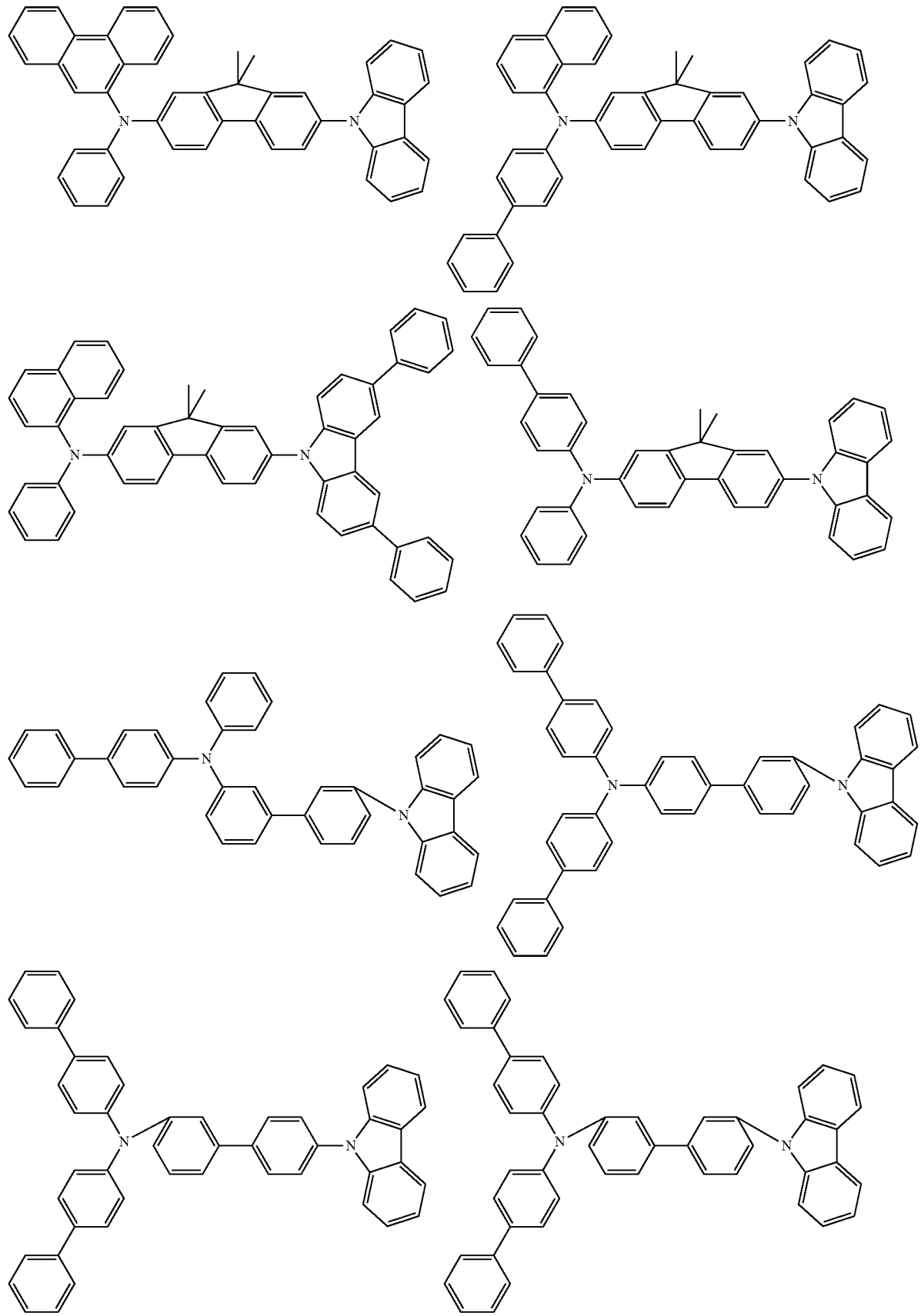

-continued
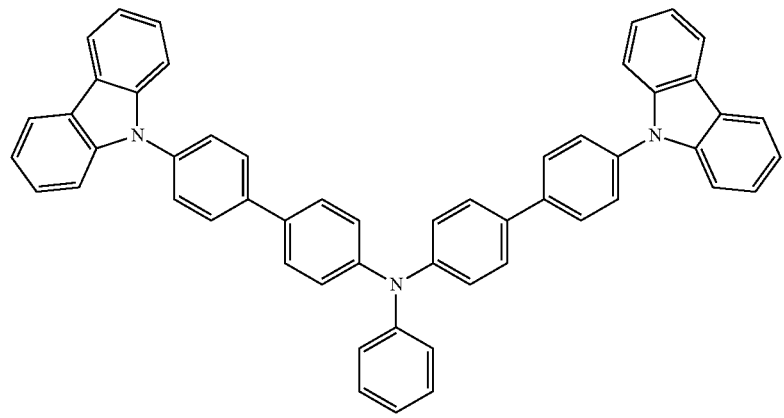
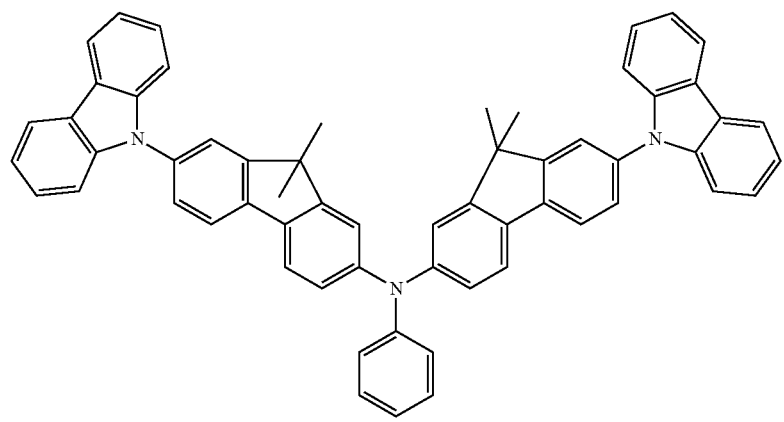
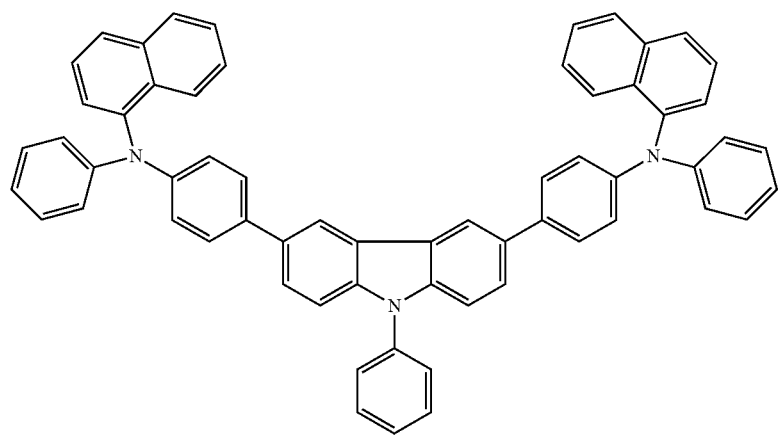

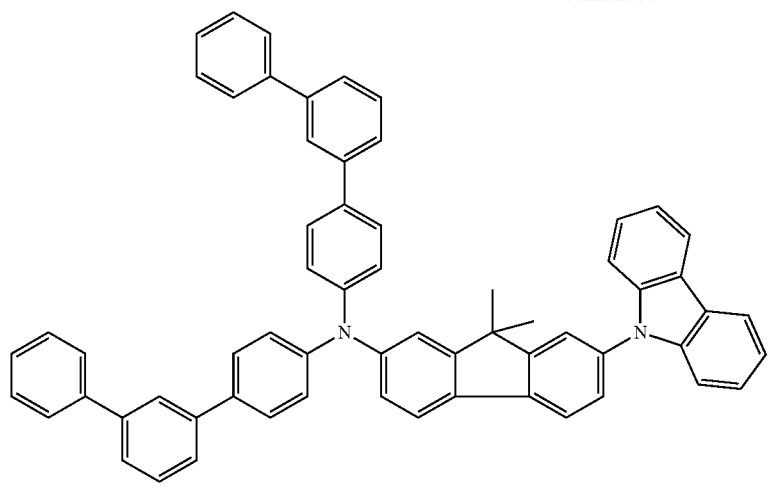
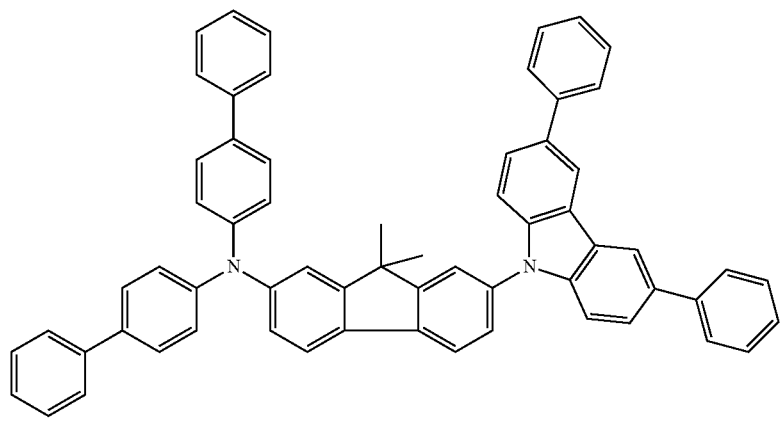
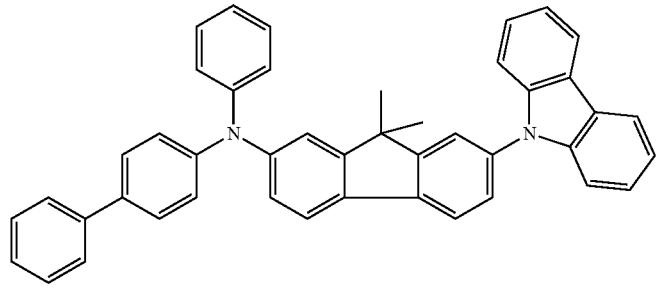
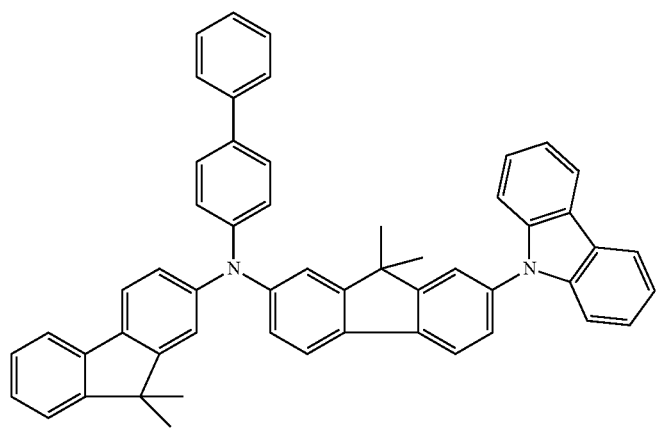

-continued
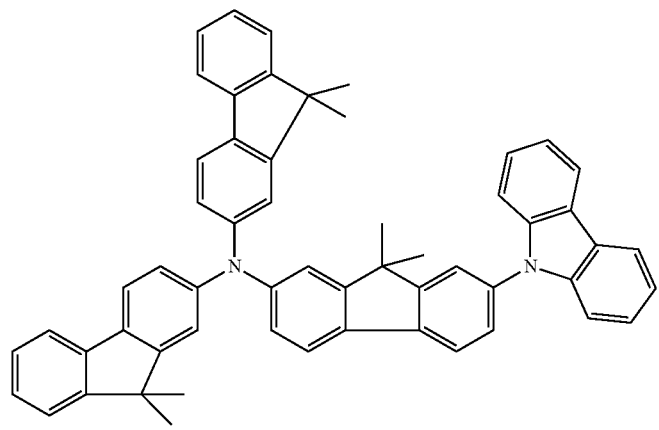
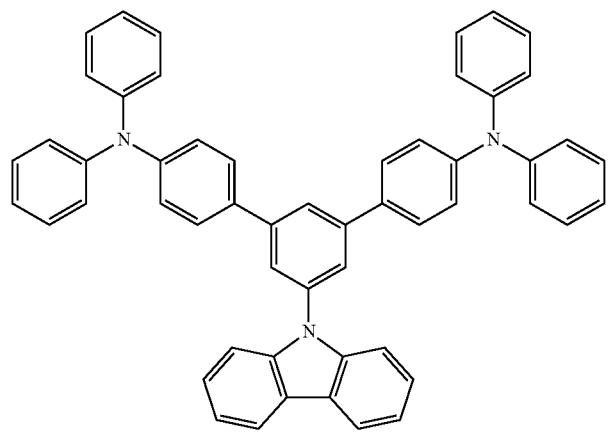
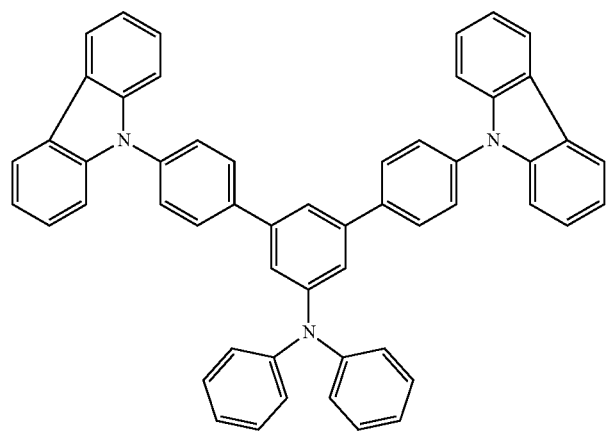
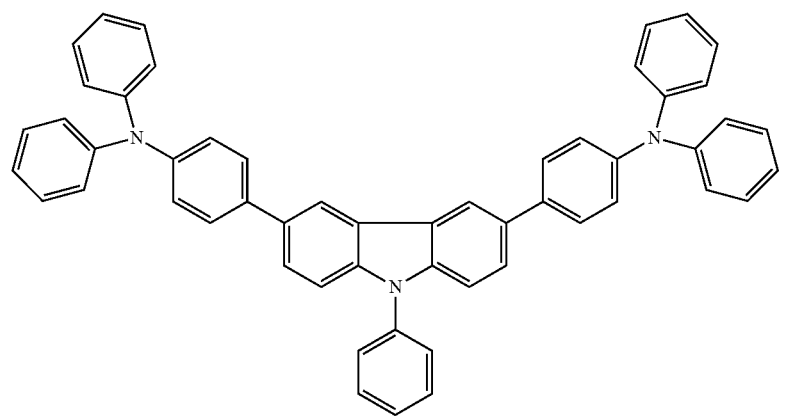

-continued
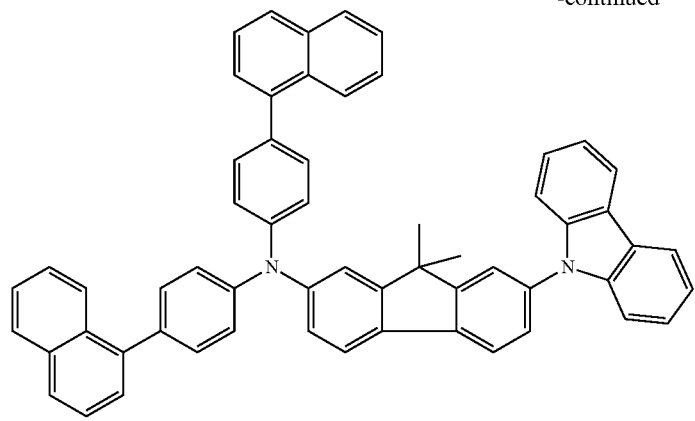
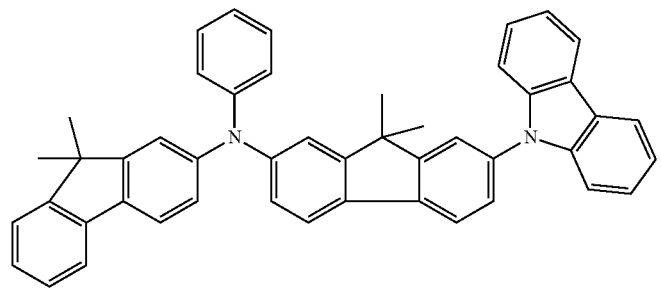
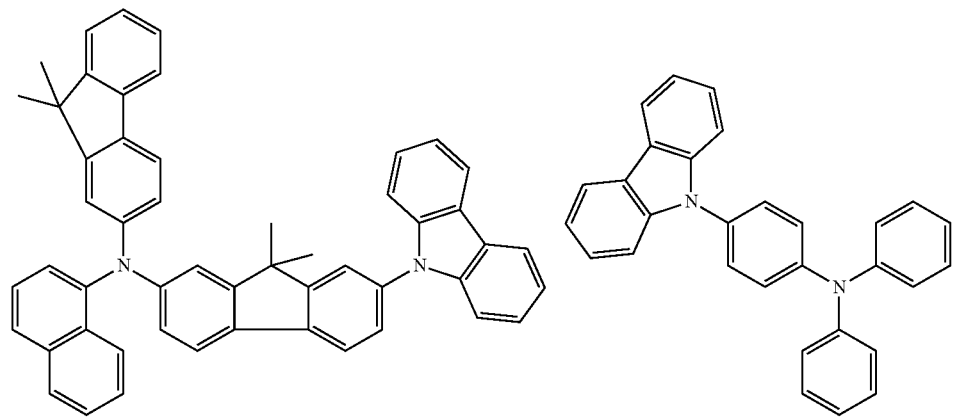
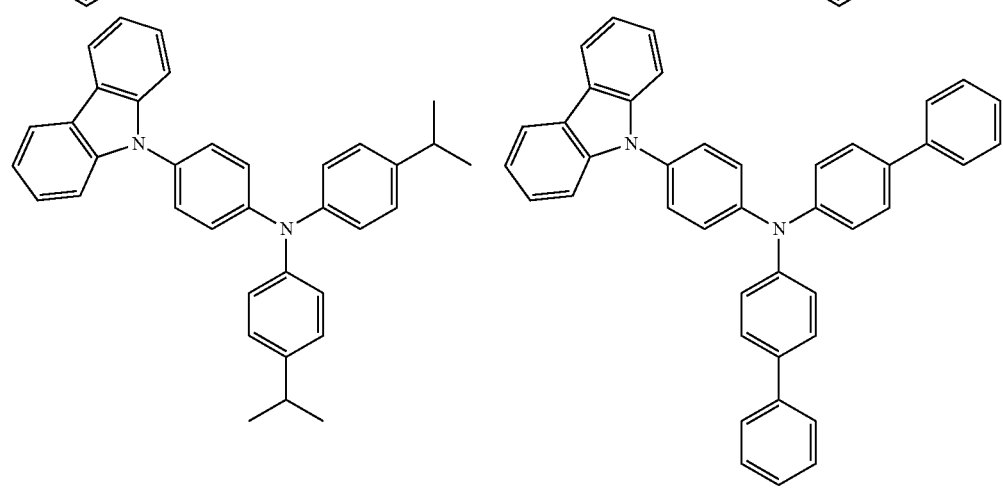

-continued
351
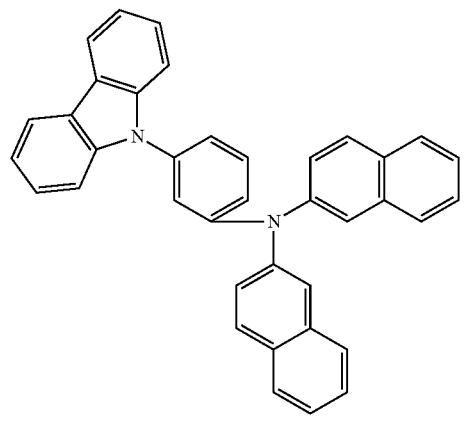
352
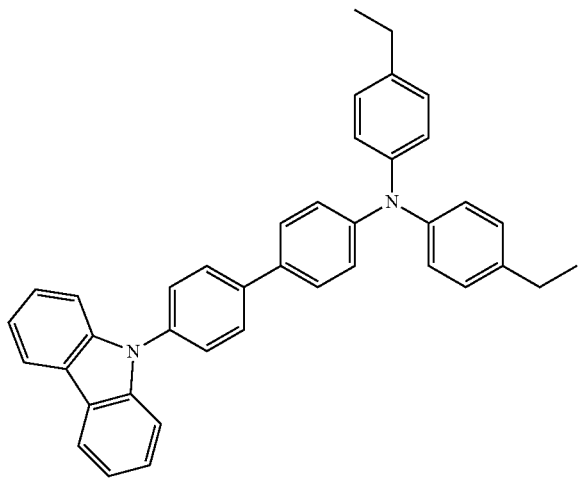
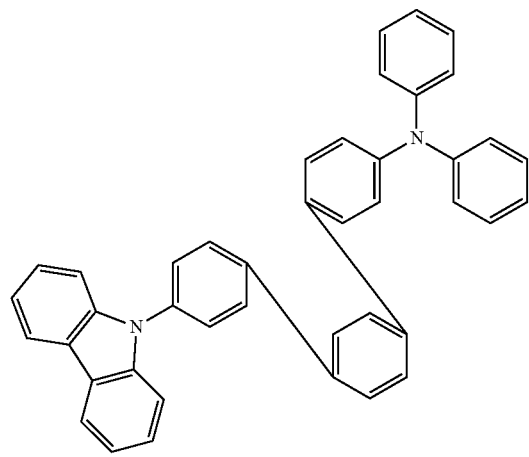
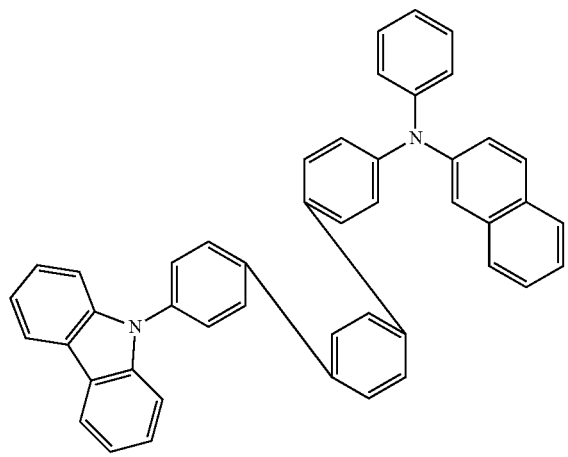
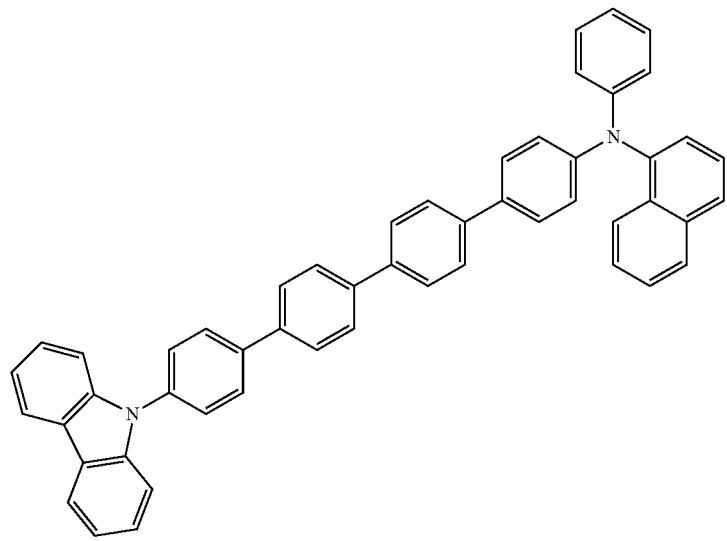

353
354
-continued
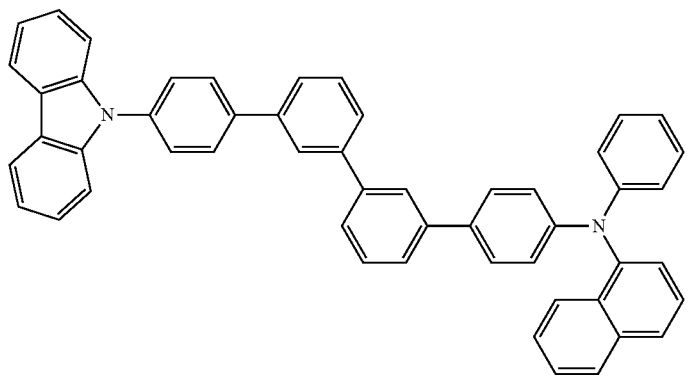
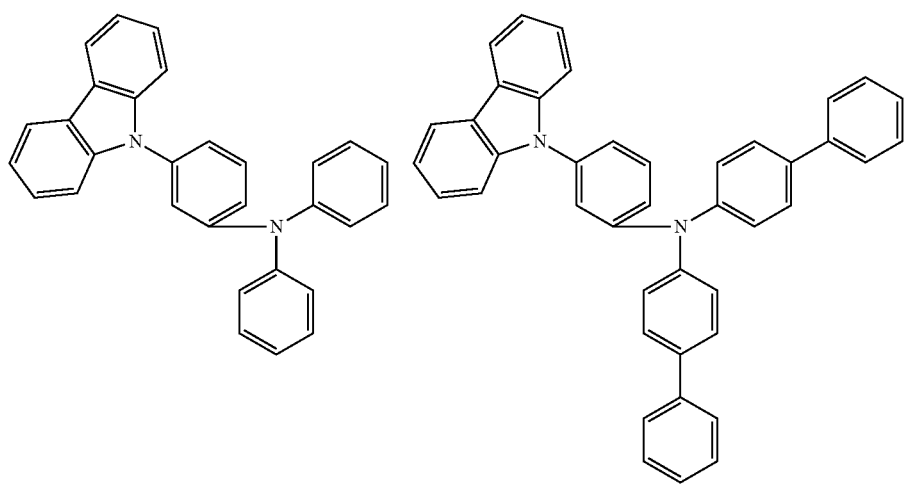
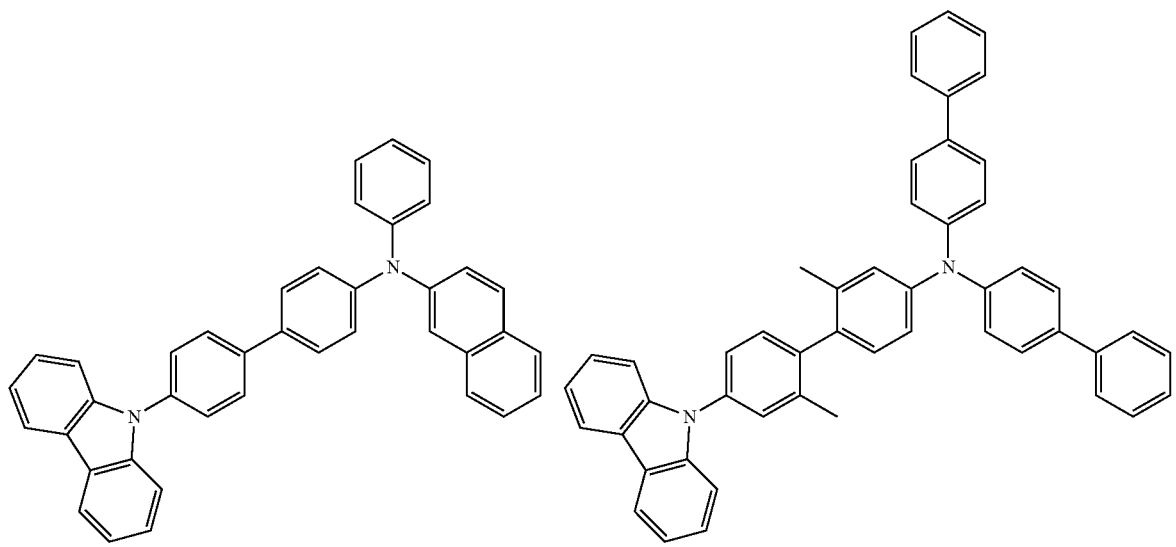

-continued
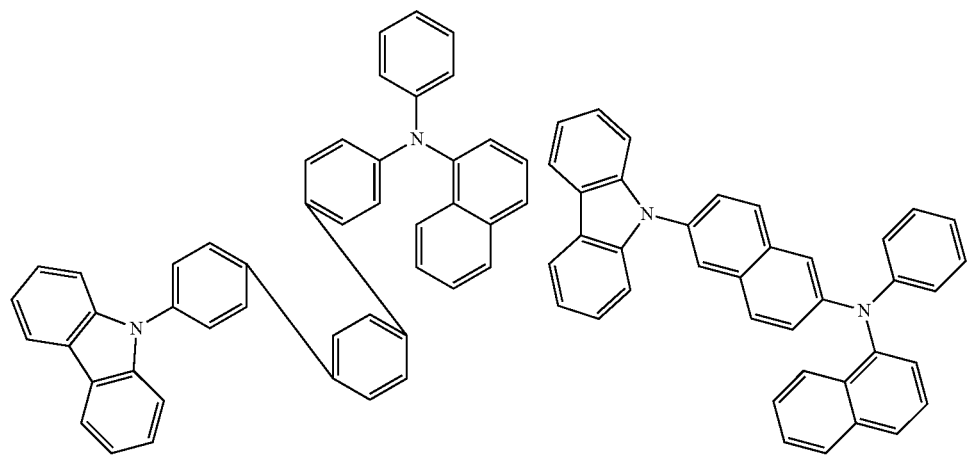
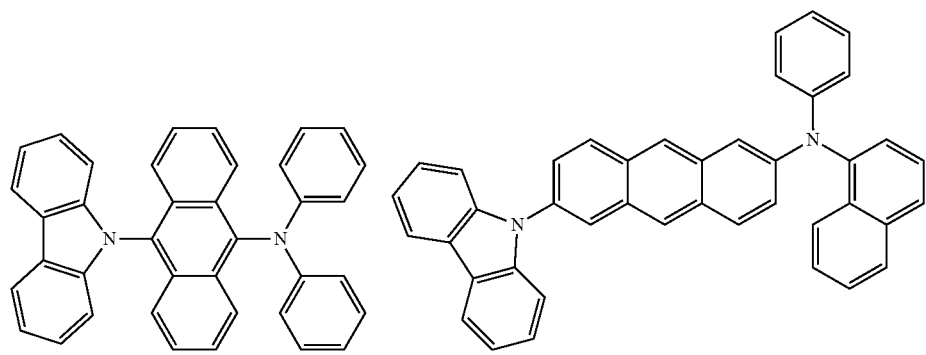
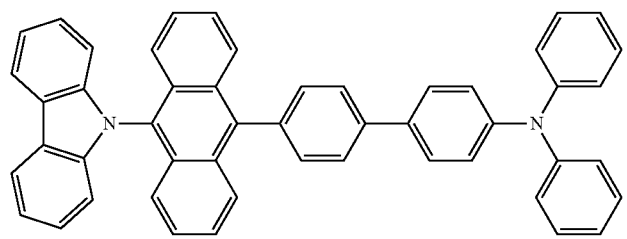
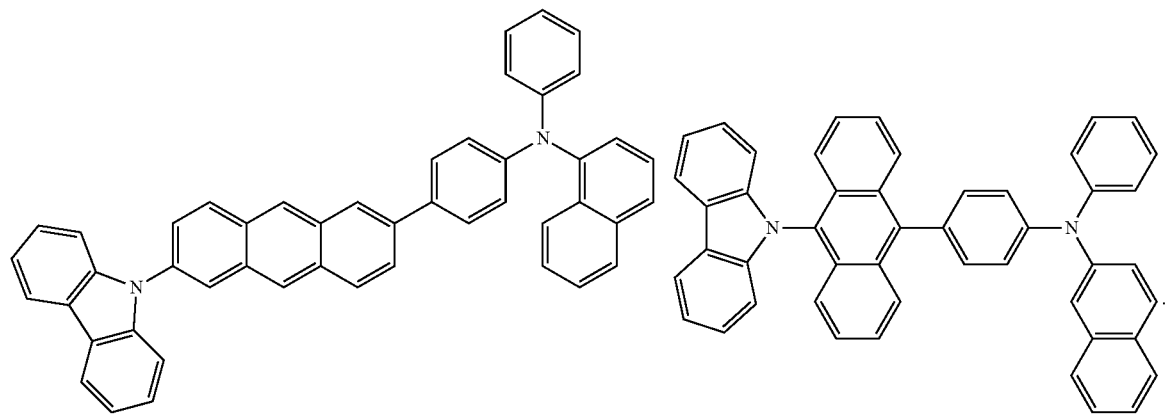

6. The organic light emitting device of claim 1, wherein the compound of Chemical Formula 3 is selected from among the following compounds:
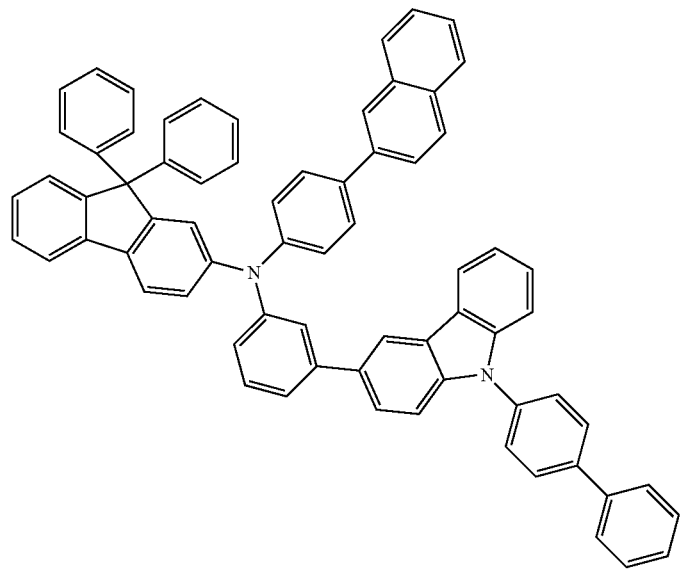
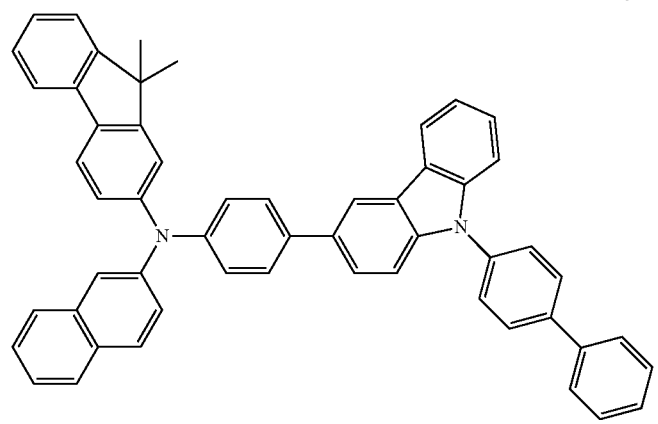
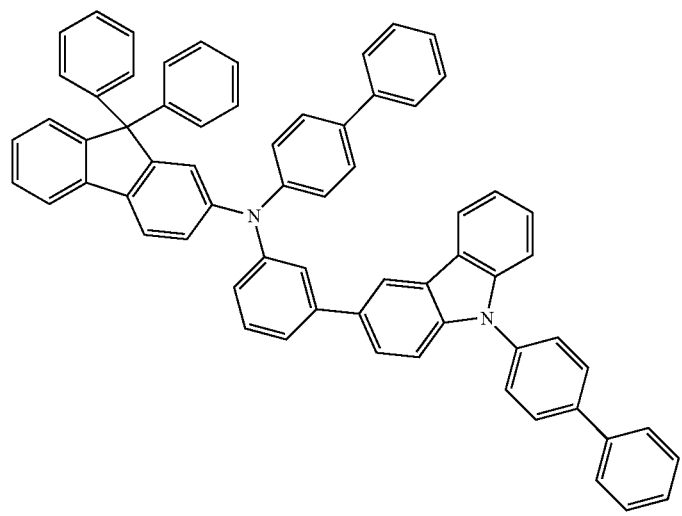

-continued
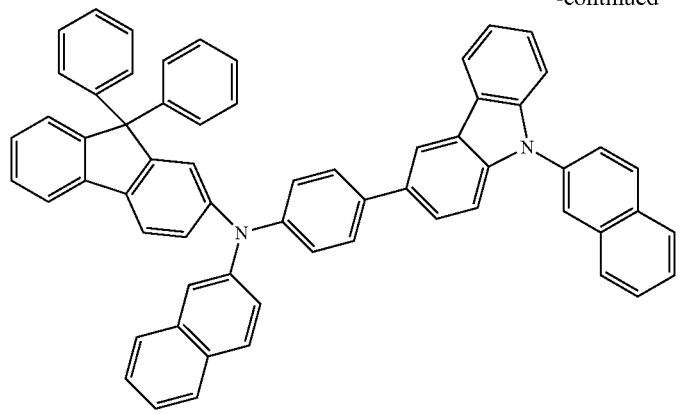
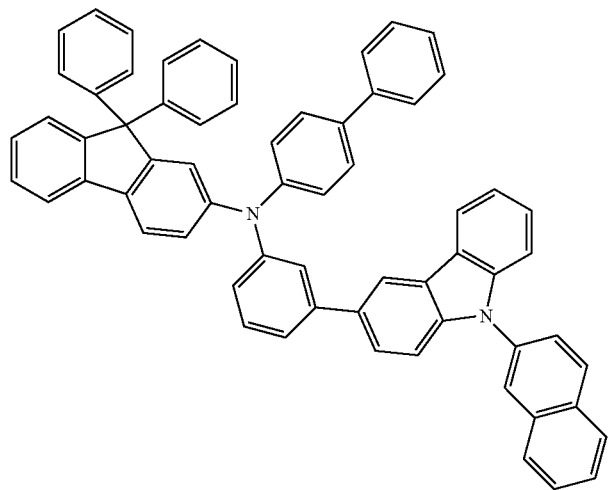
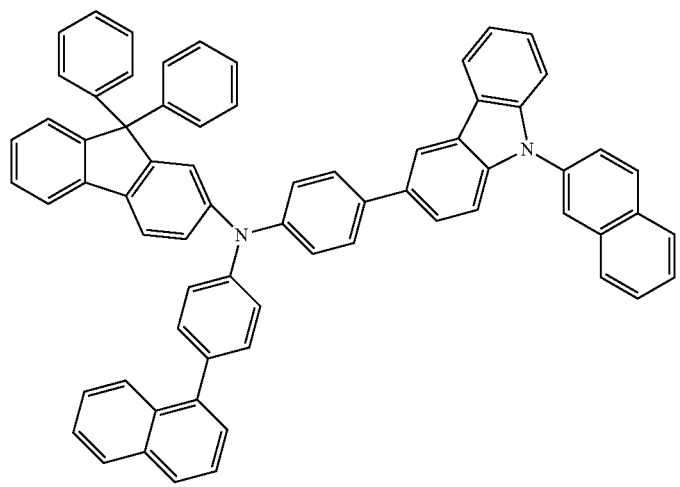

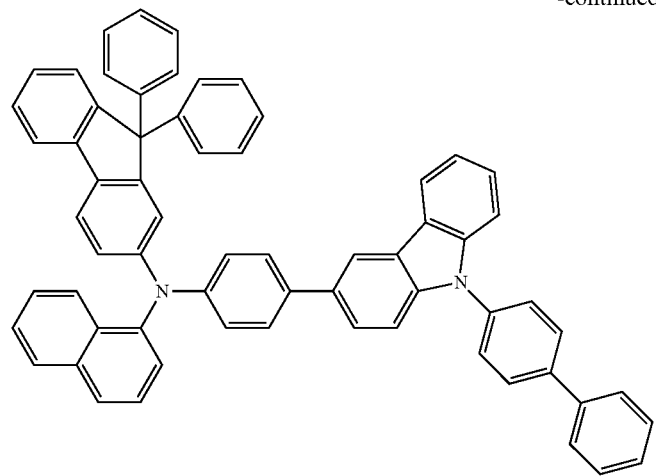
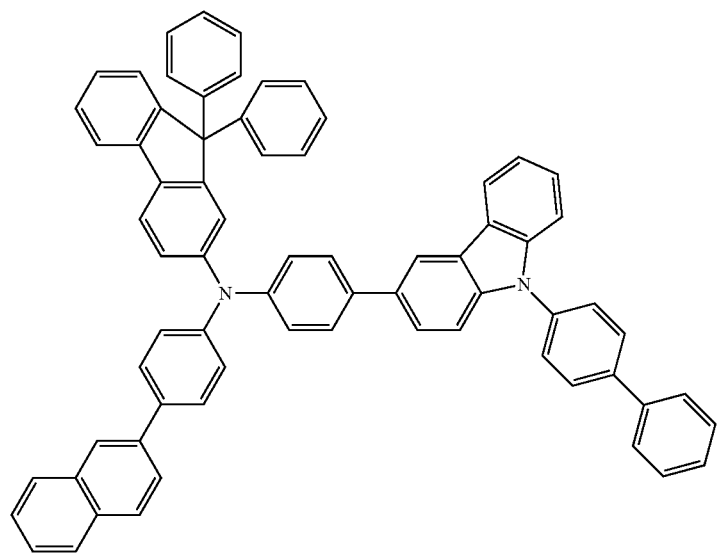
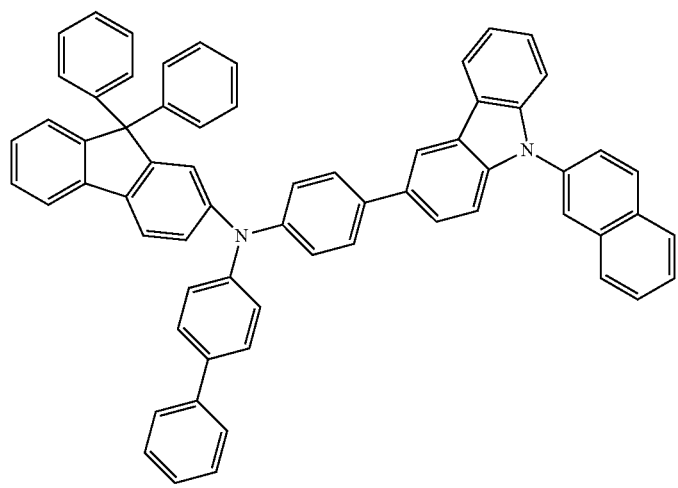

-continued
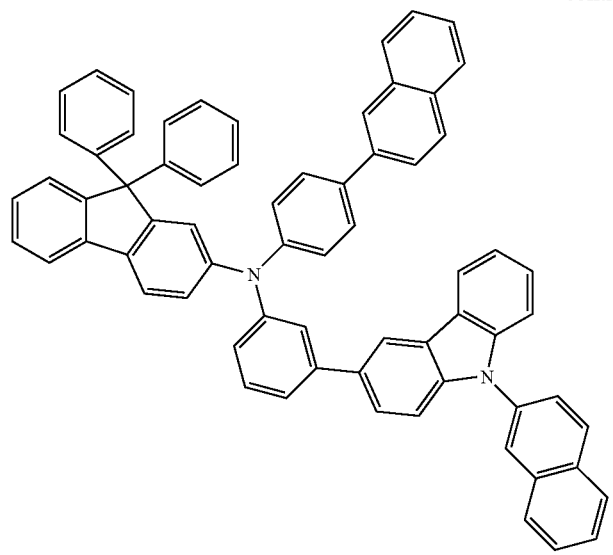
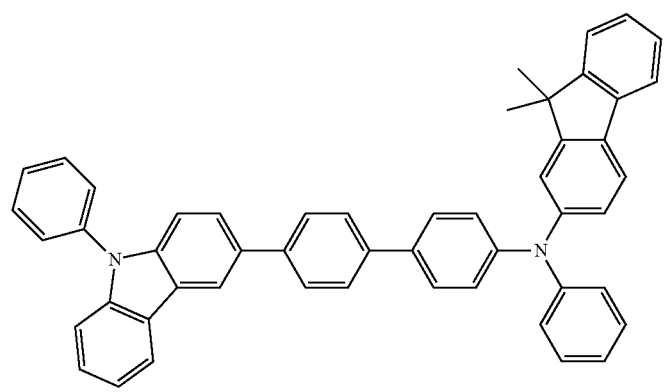
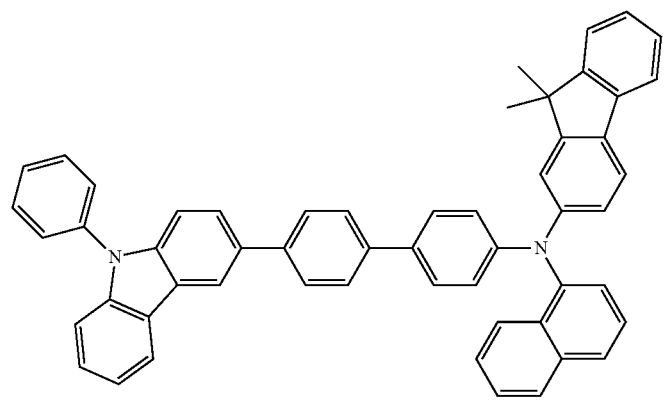

-continued
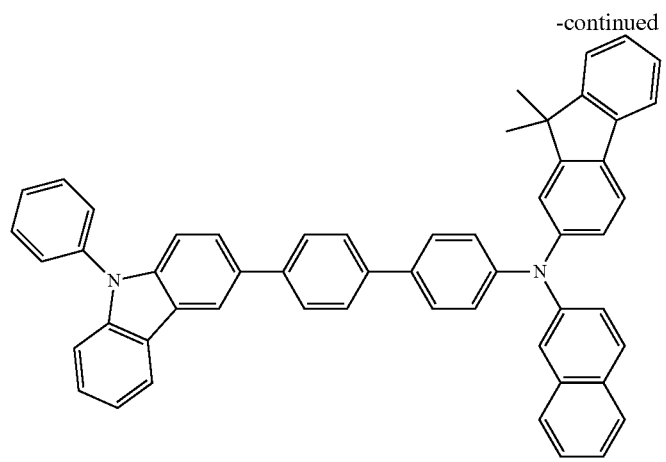
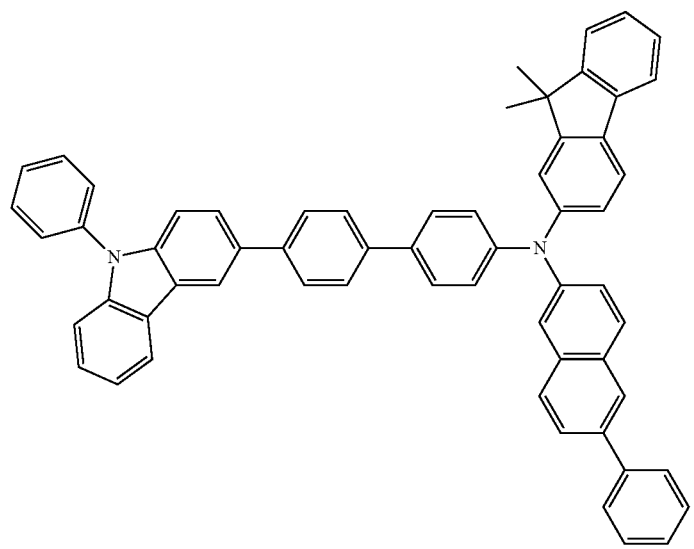
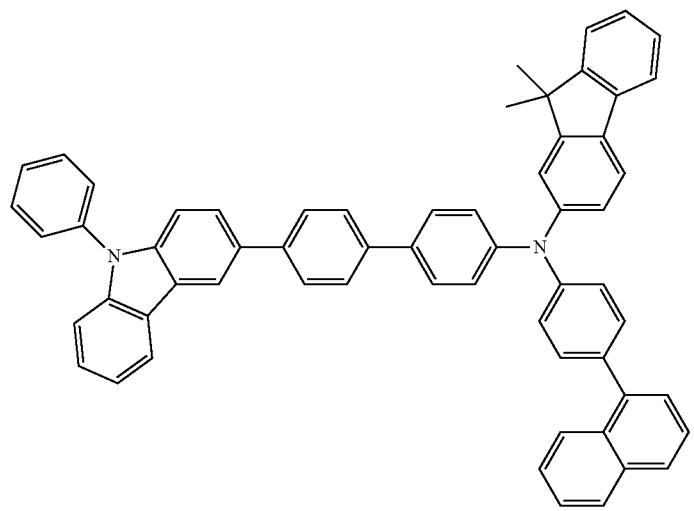

-continued
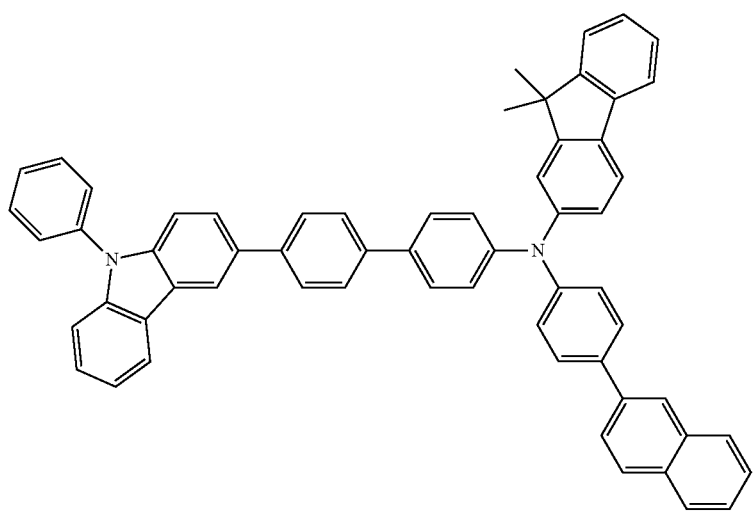

-continued
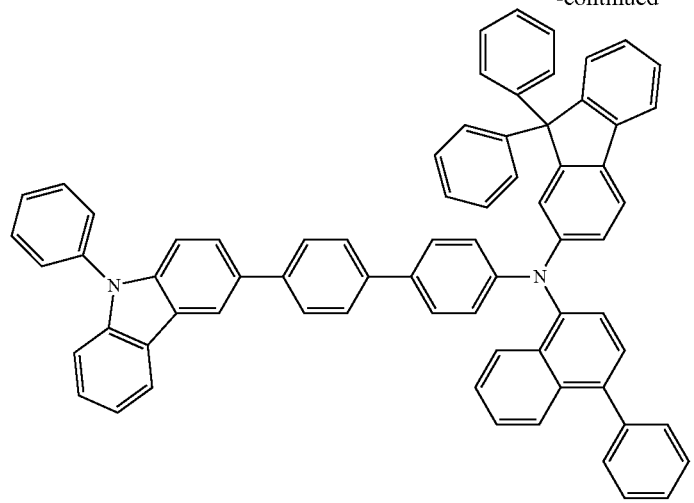
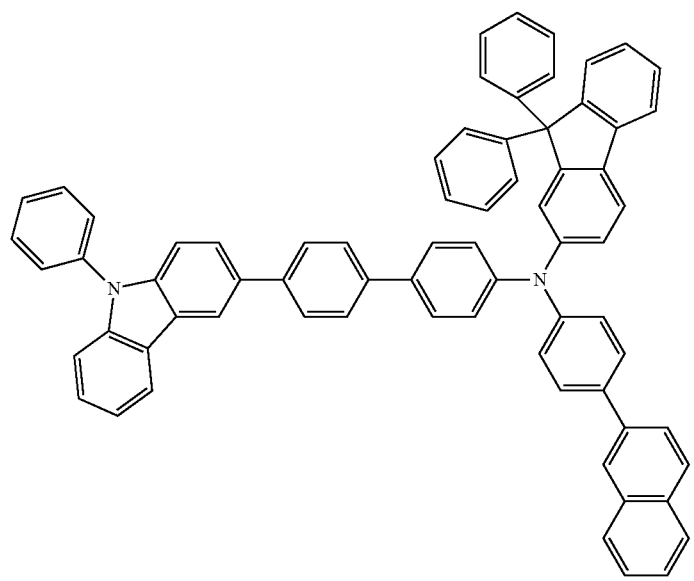
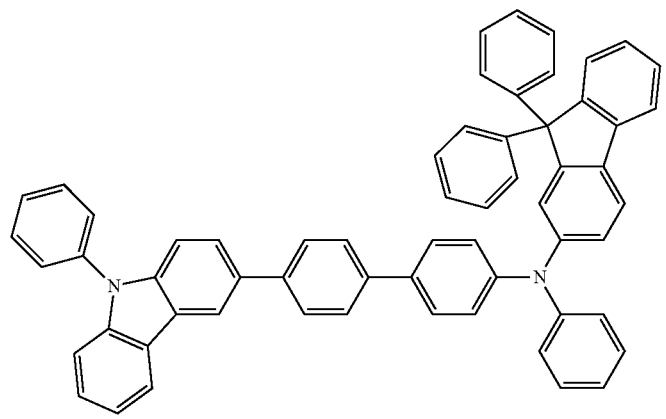

-continued
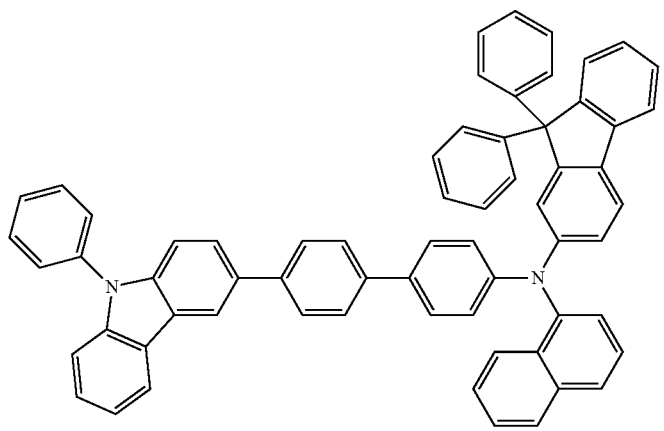
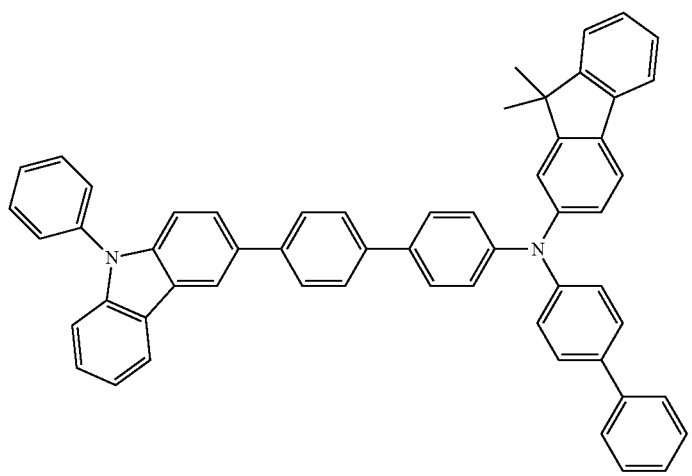
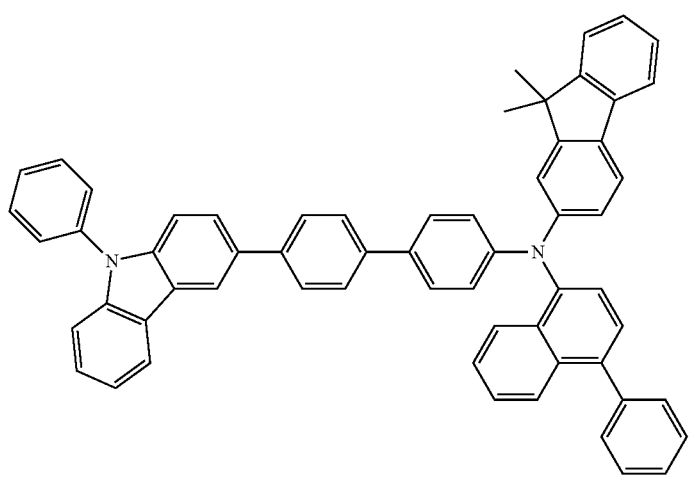

-continued
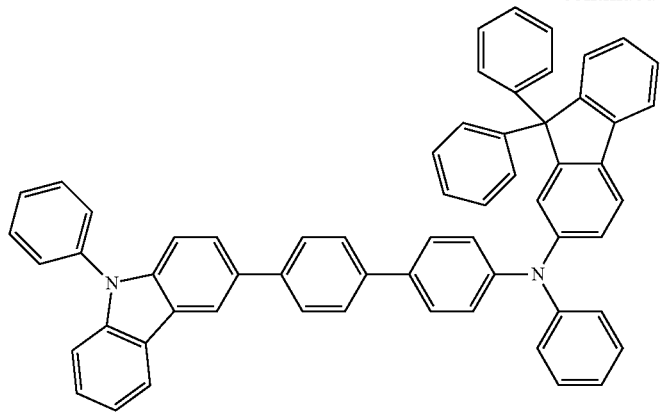
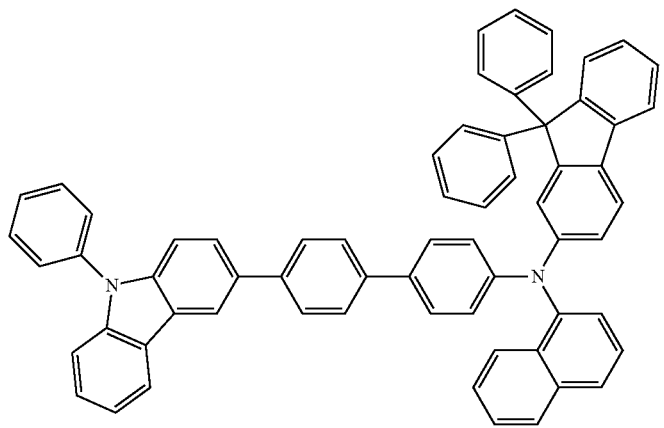
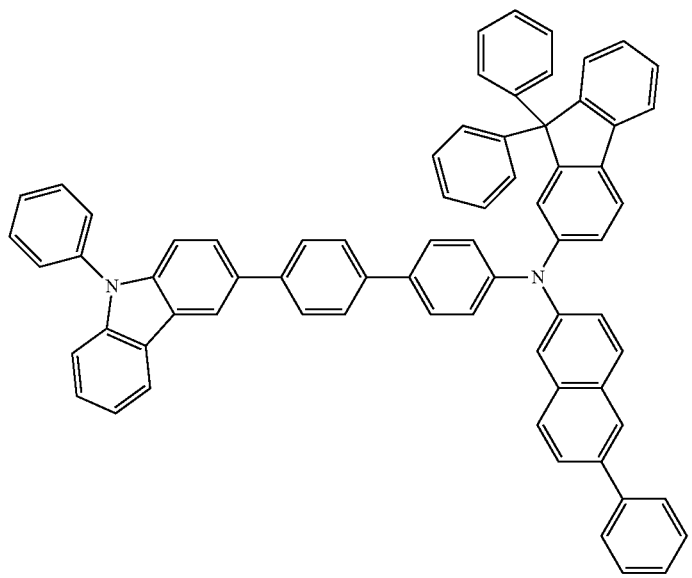

-continued
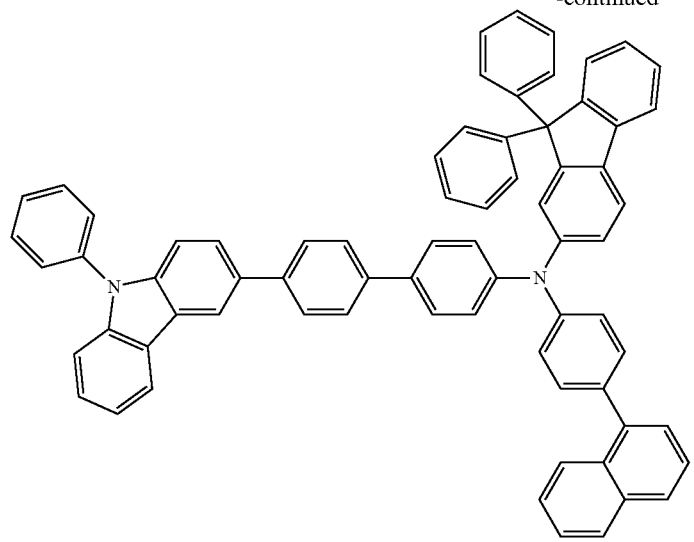
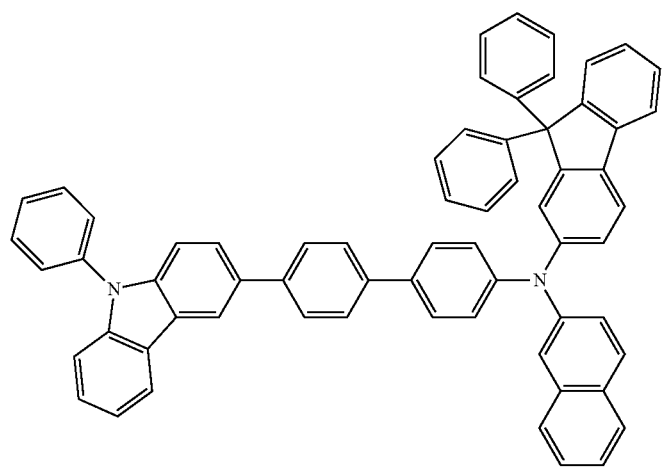
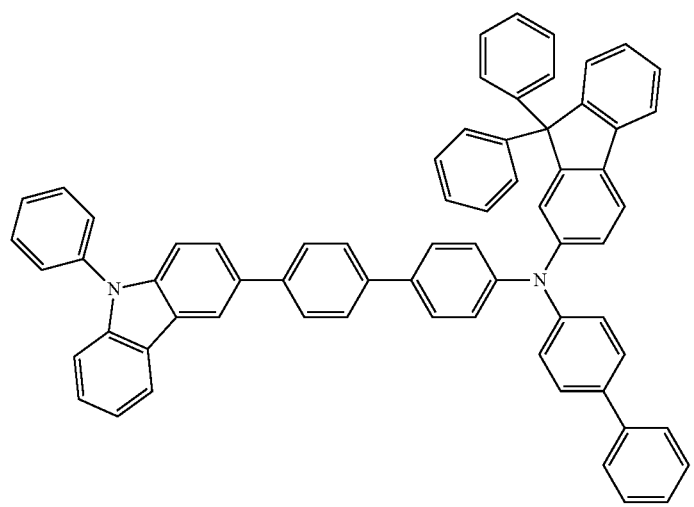

-continued
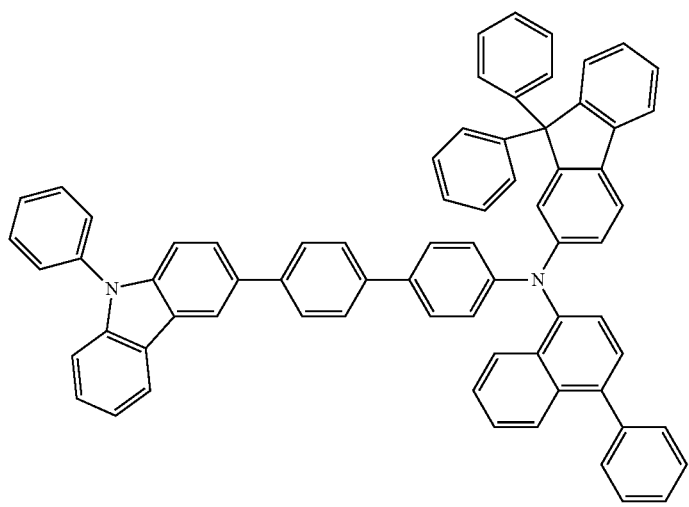
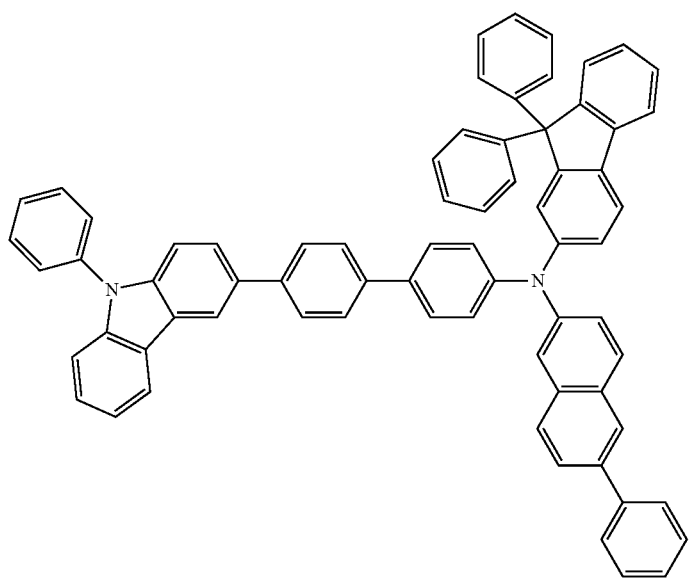
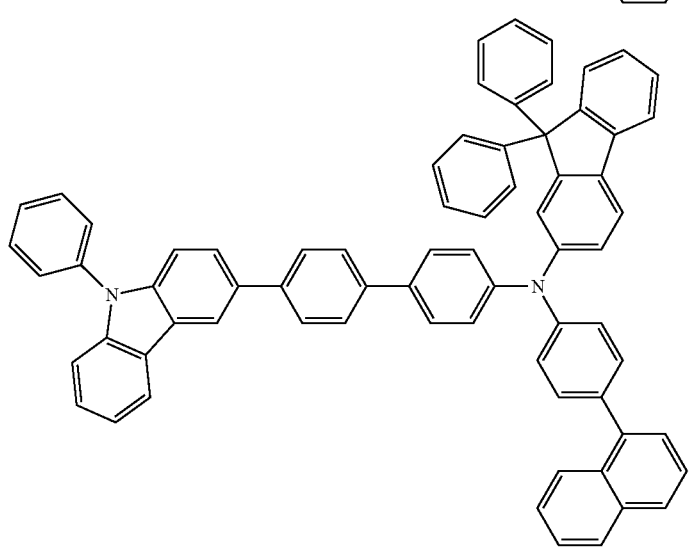

-continued
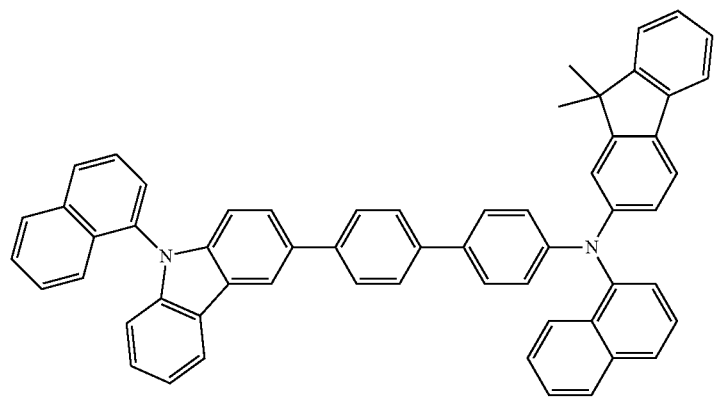
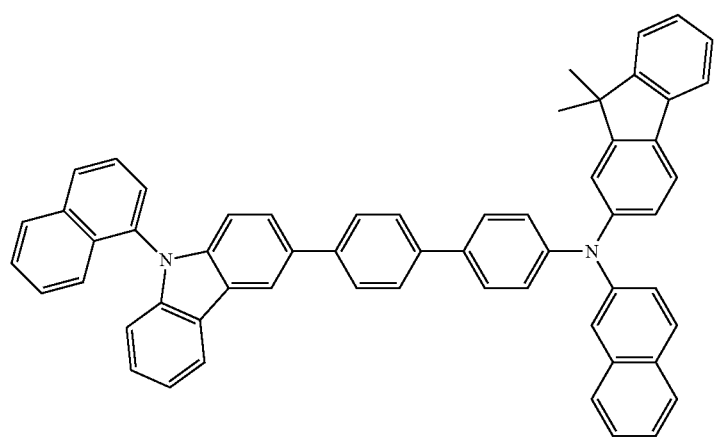
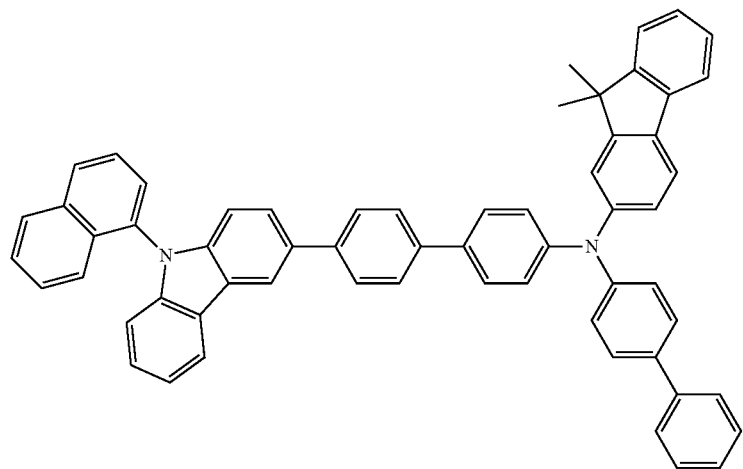

-continued
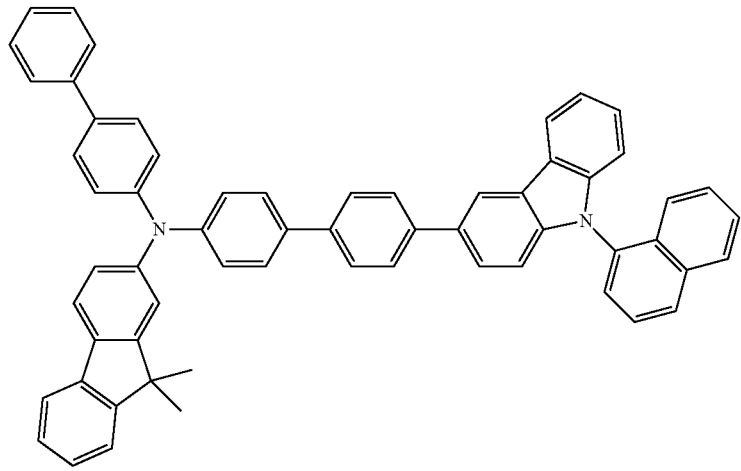
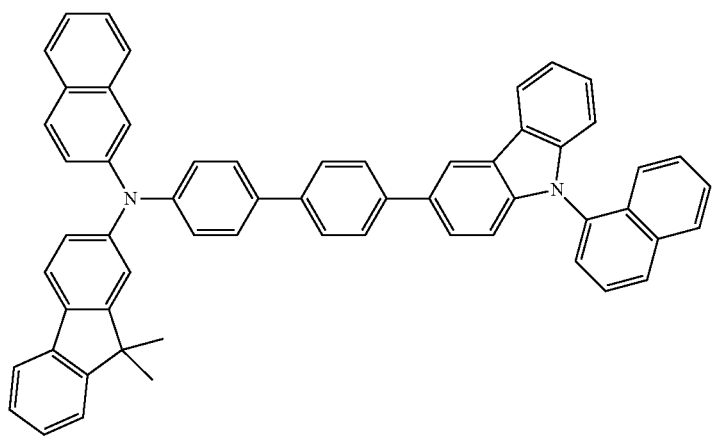
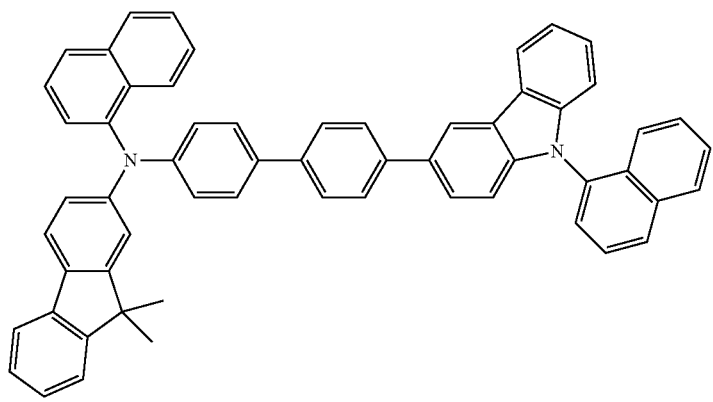

-continued
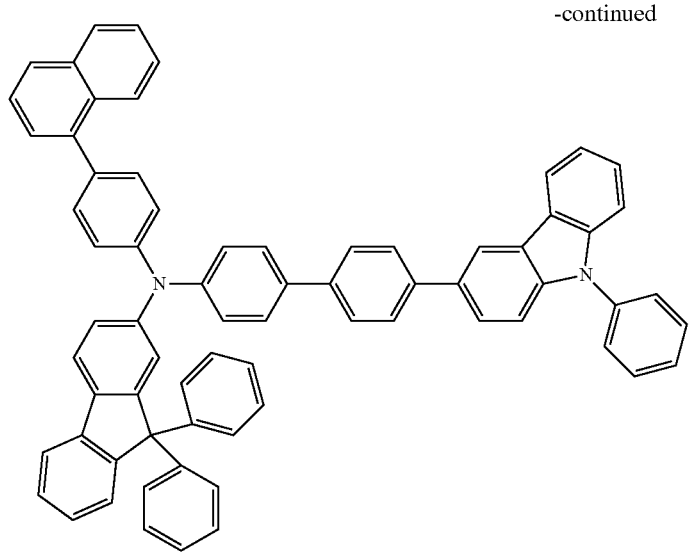
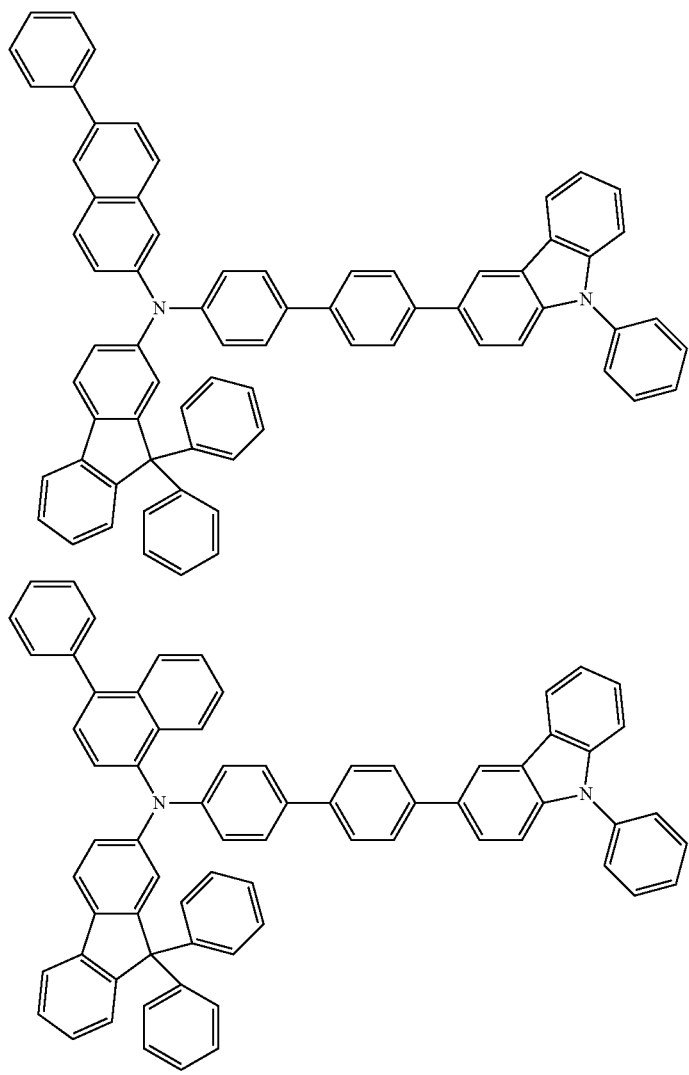

-continued
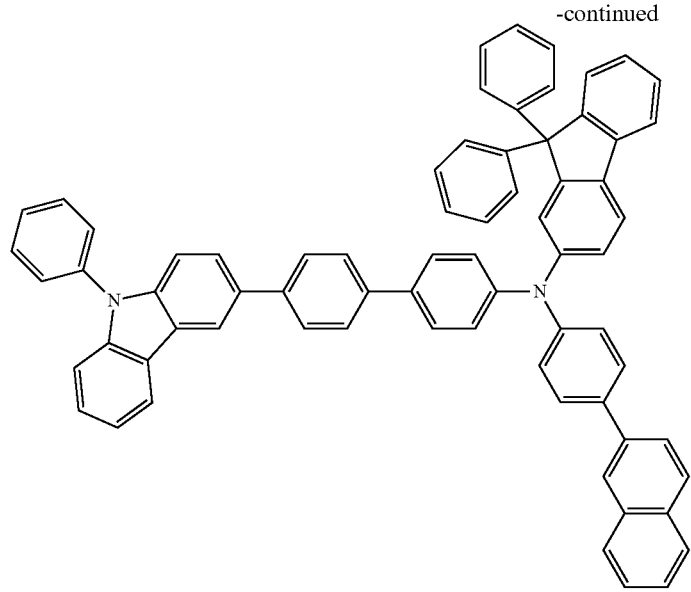
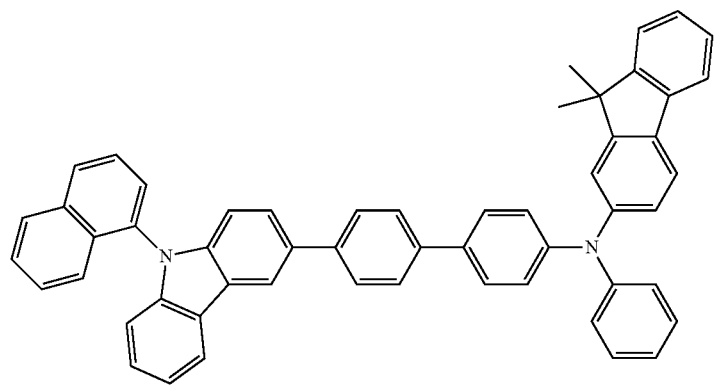
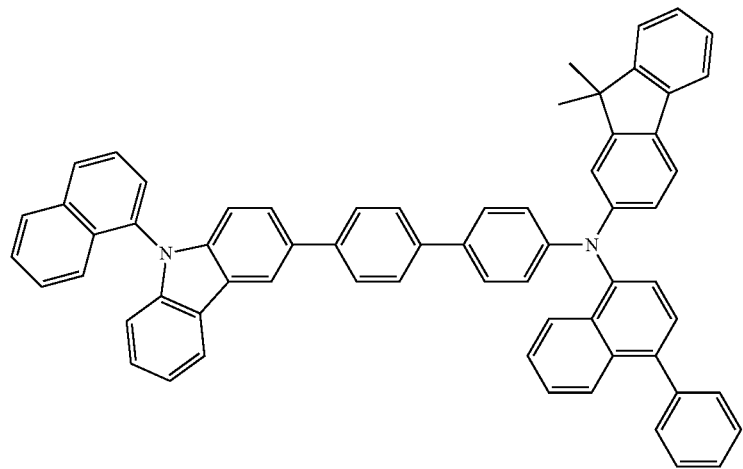

-continued
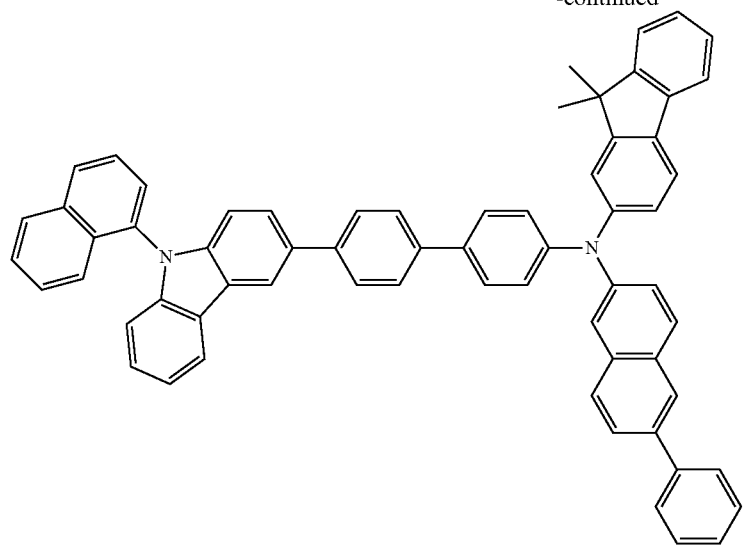
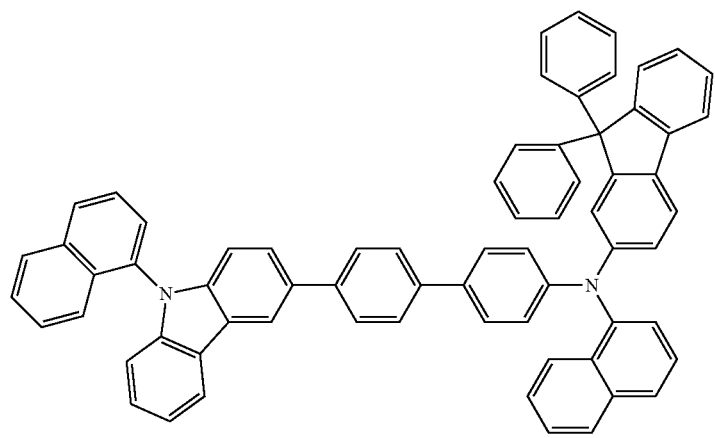
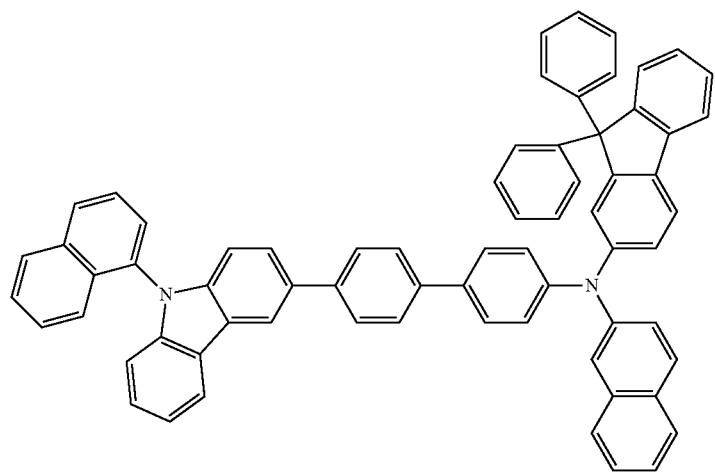

-continued
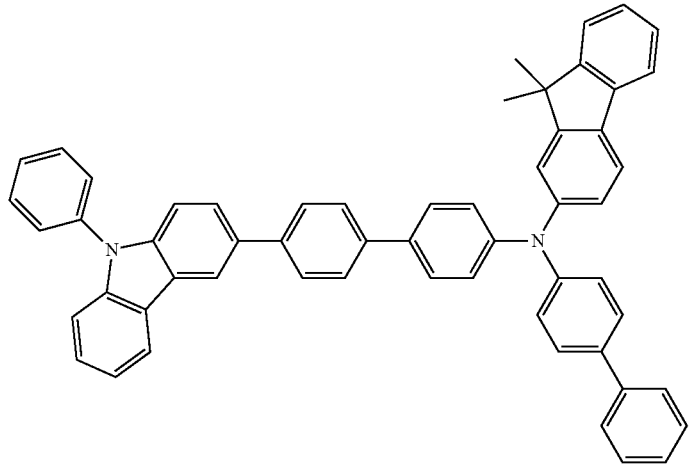
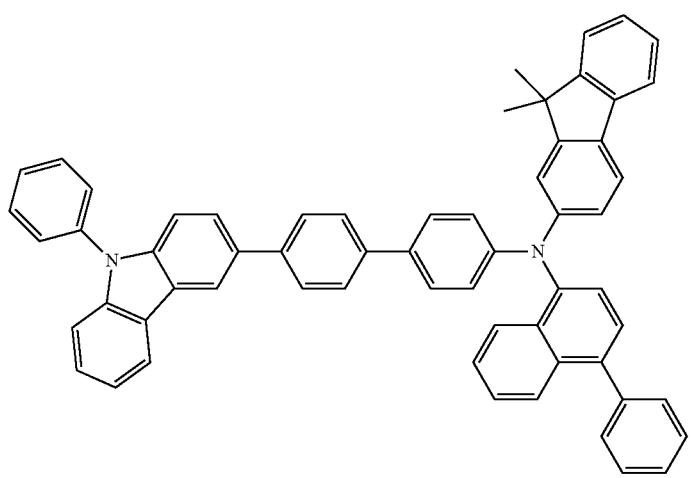
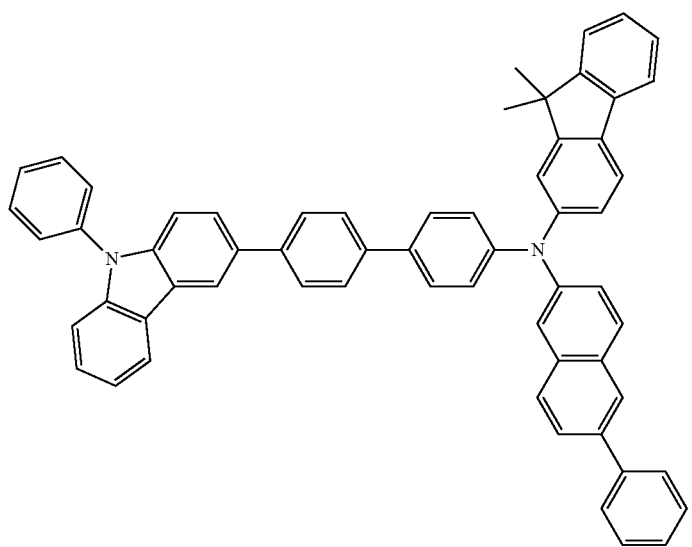

-continued
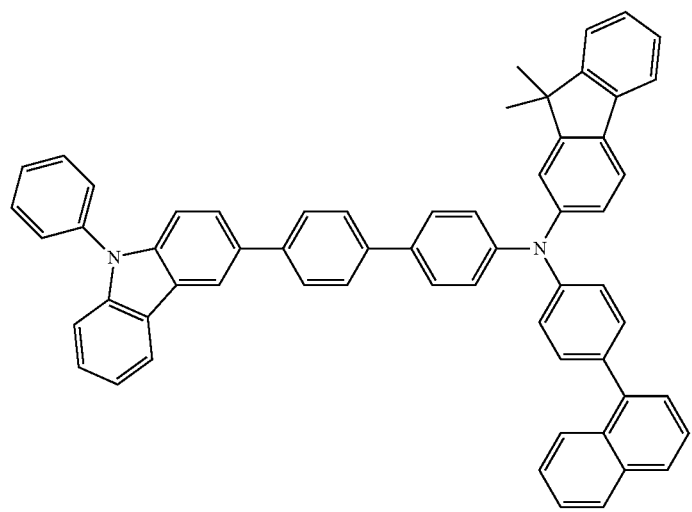
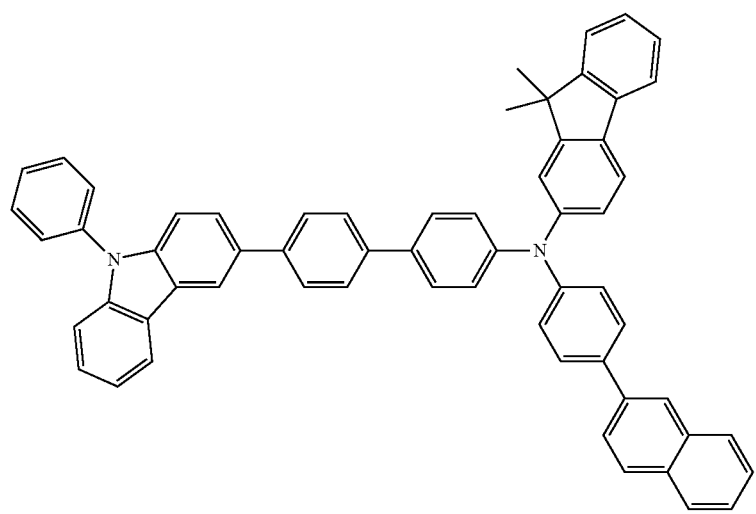
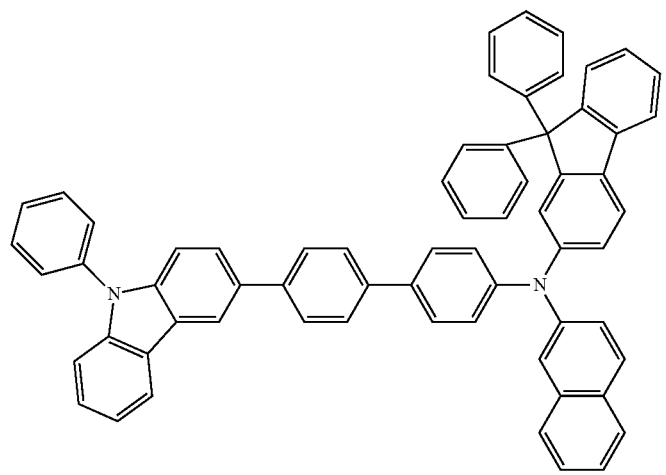

-continued
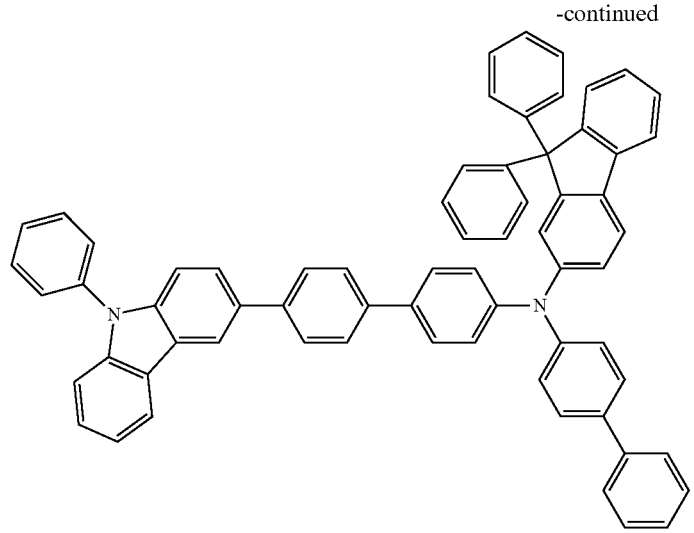
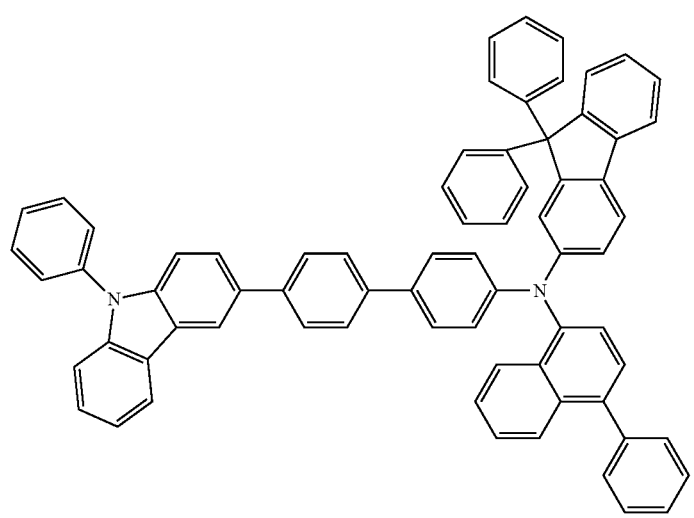
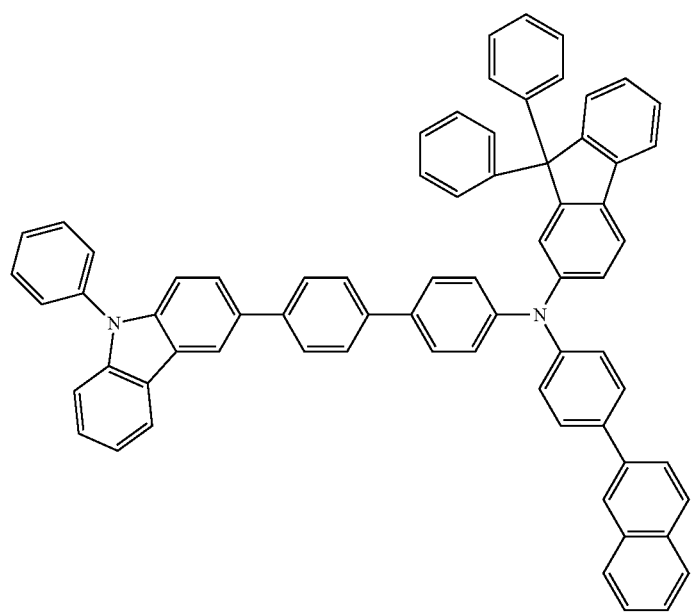

-continued
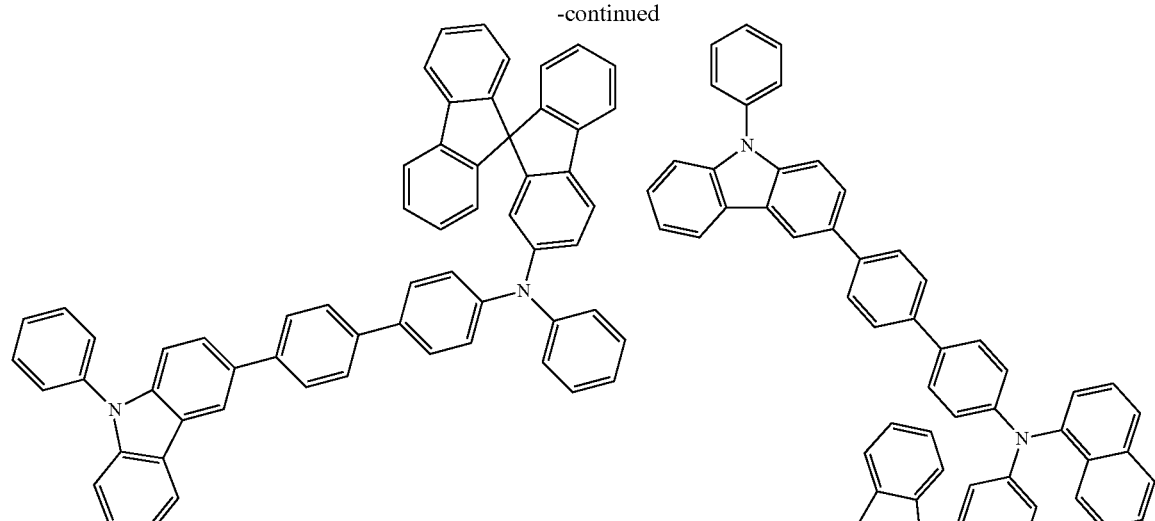
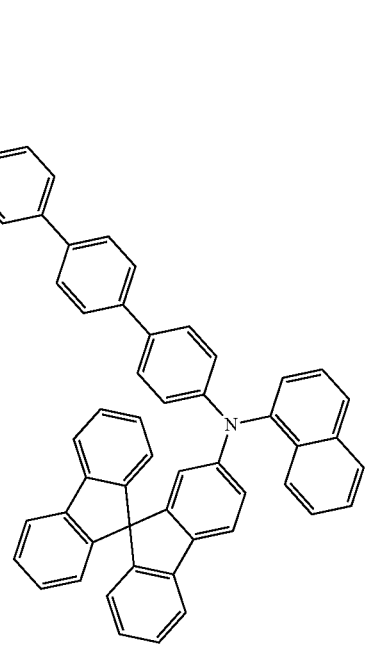
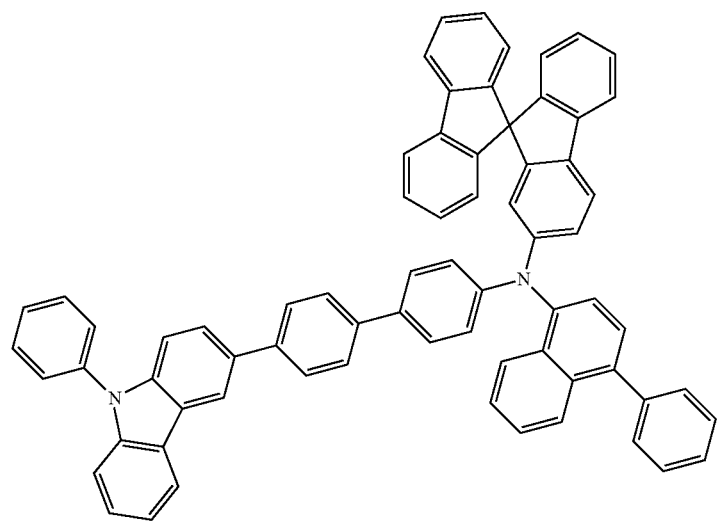
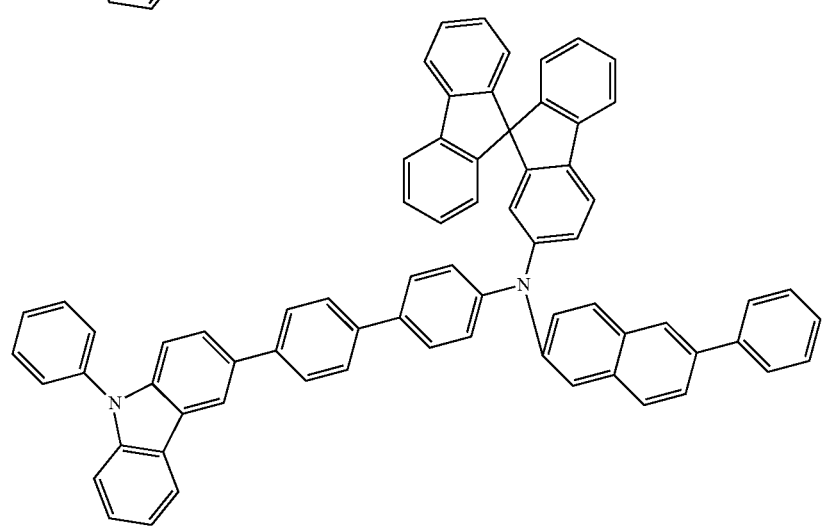

-continued
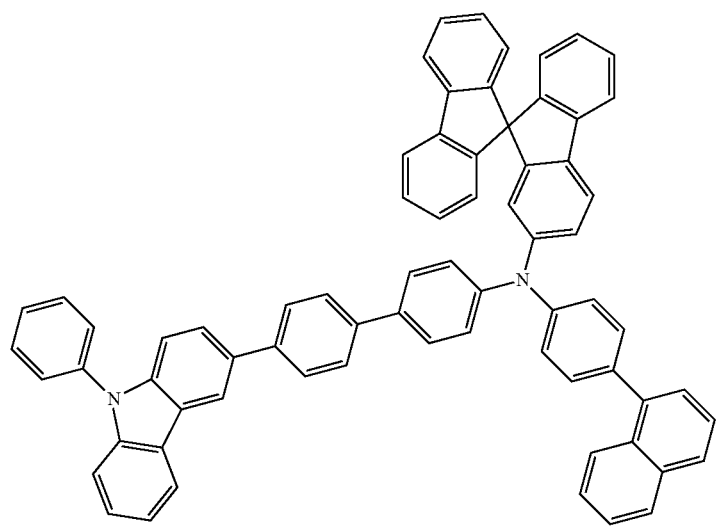
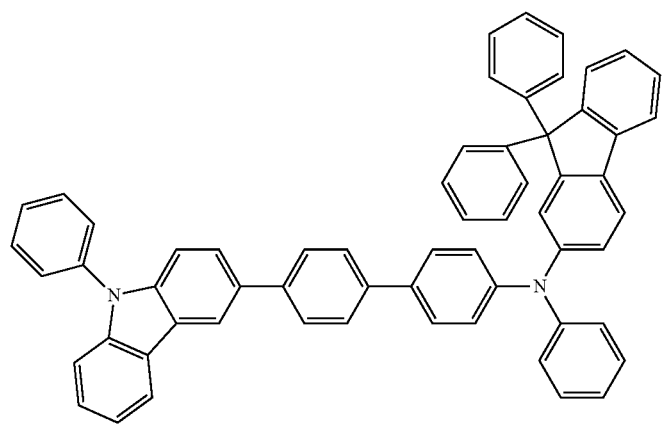
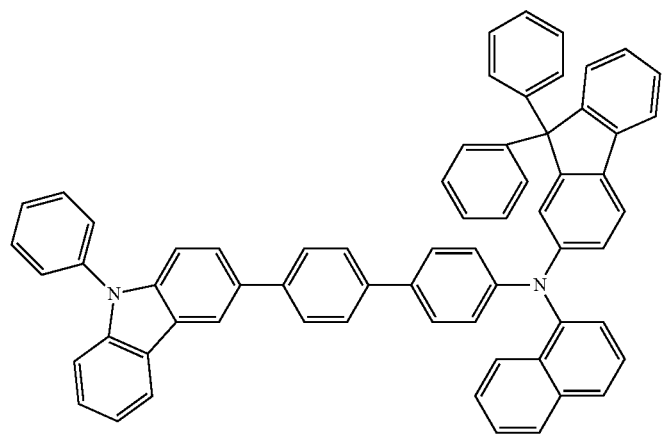

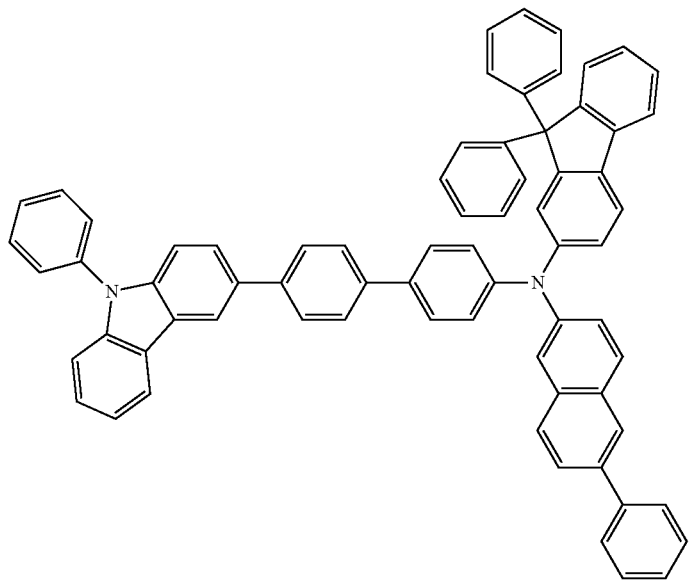
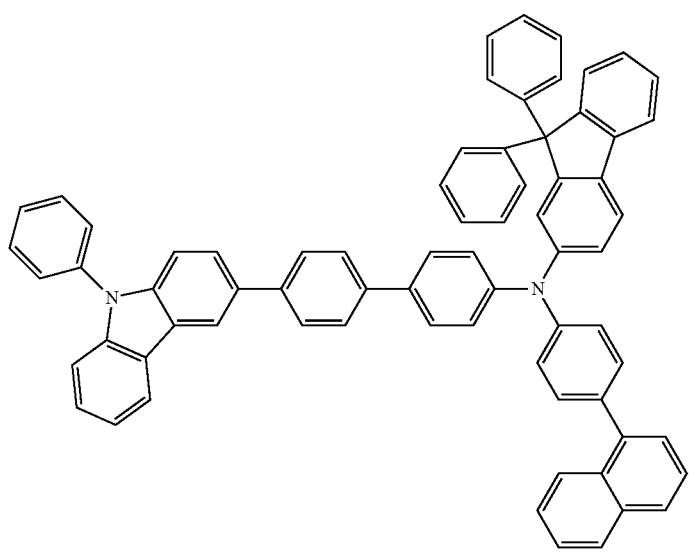

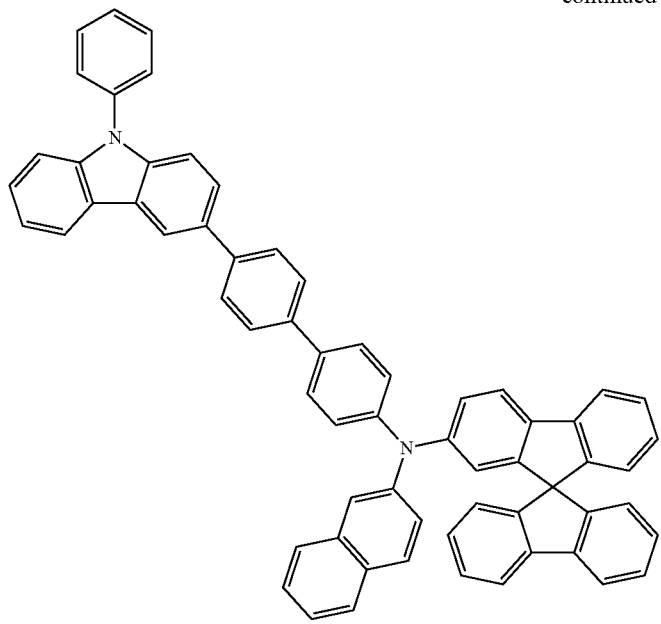
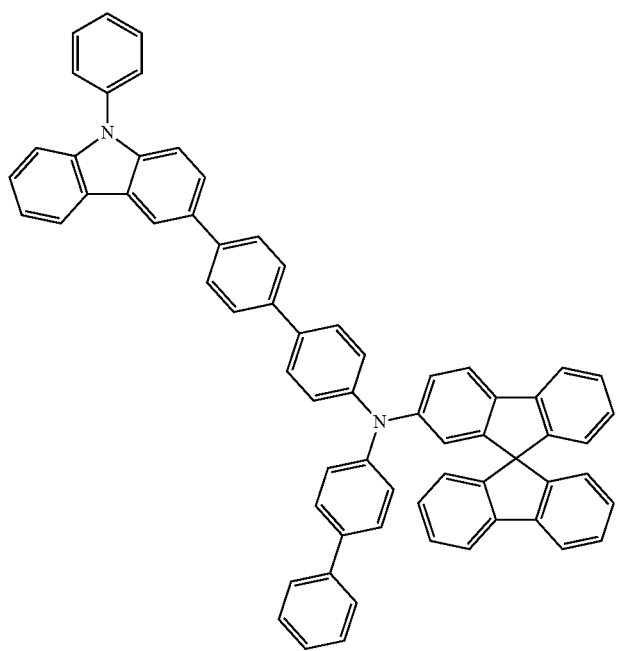

-continued
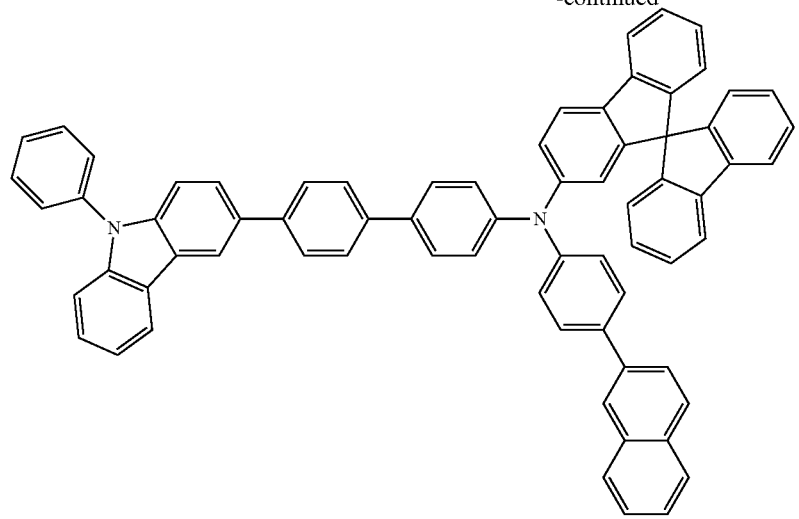
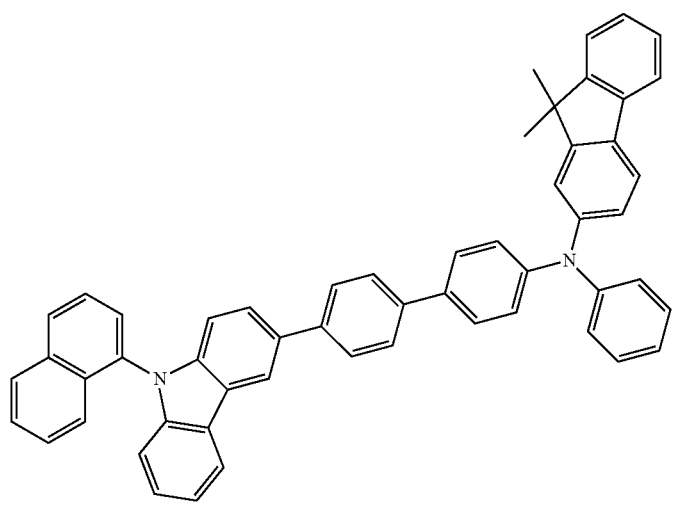
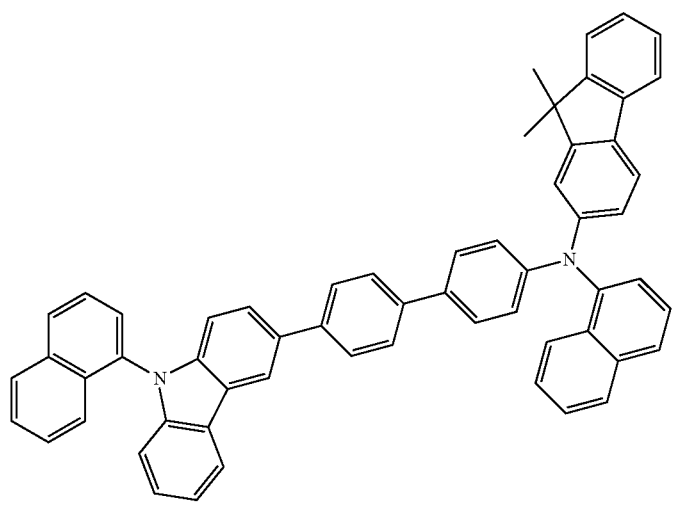

-continued
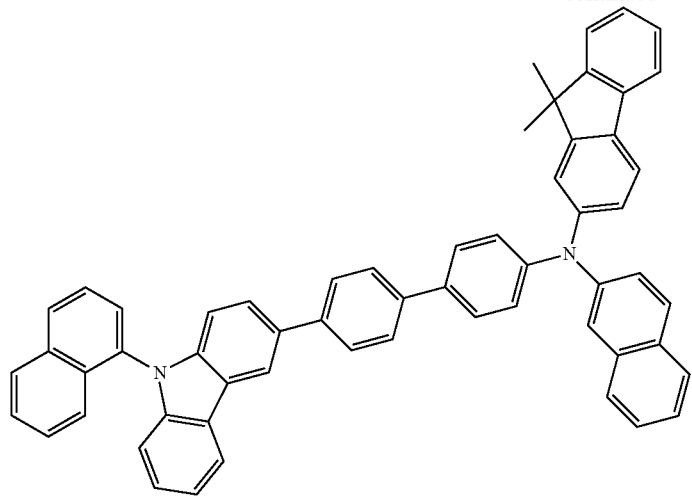
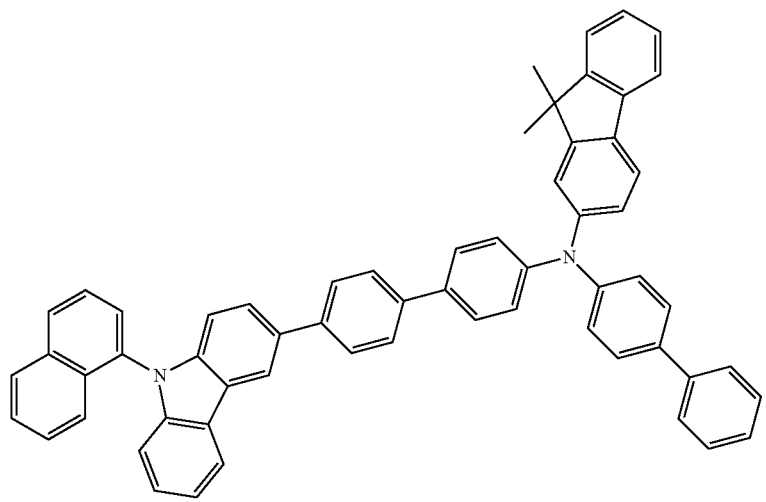
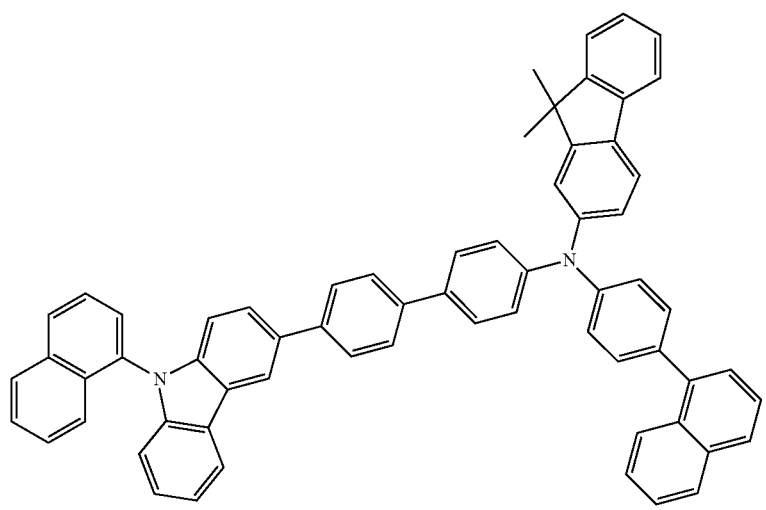

-continued
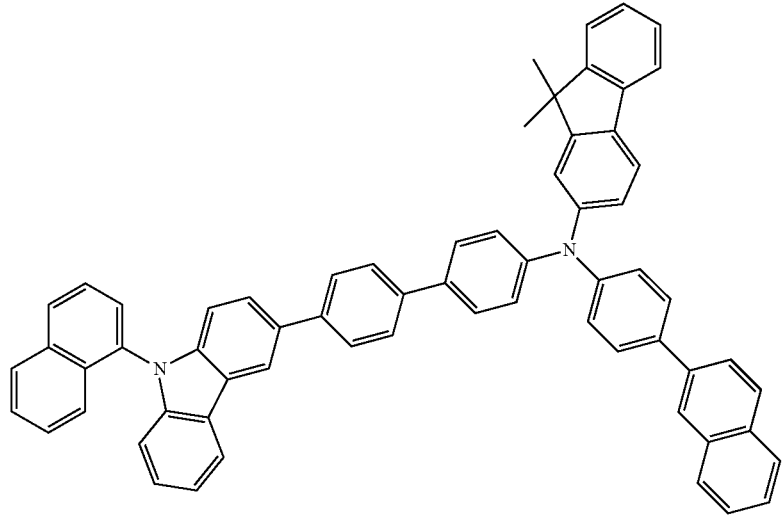
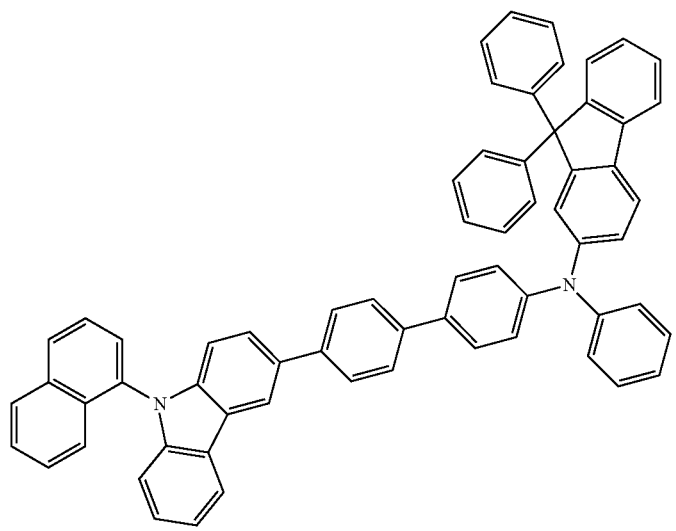
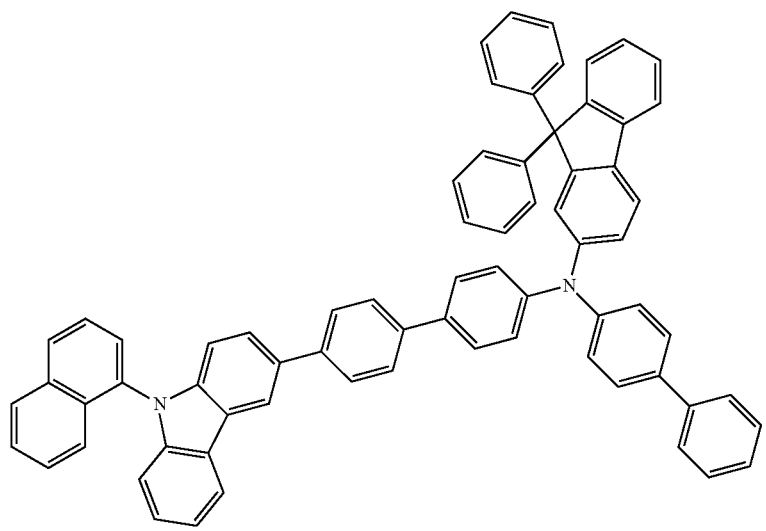

-continued
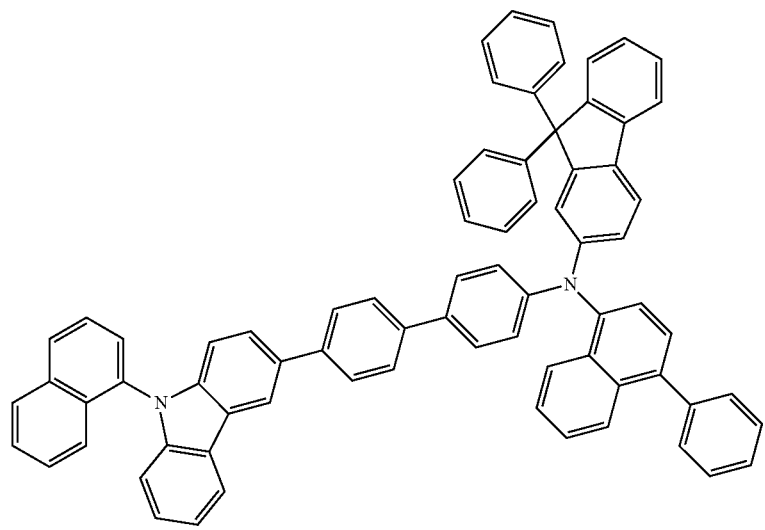
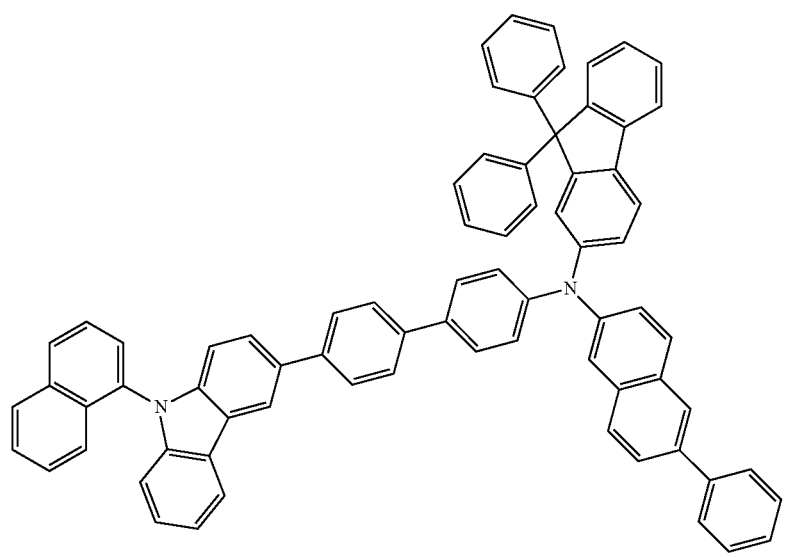
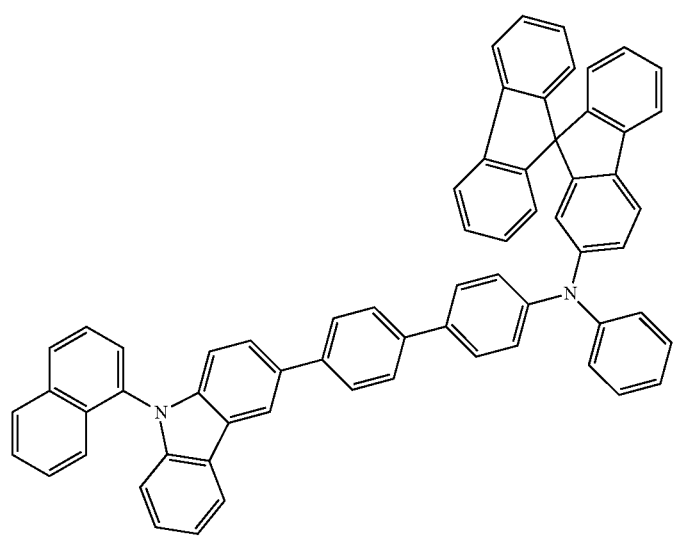

-continued
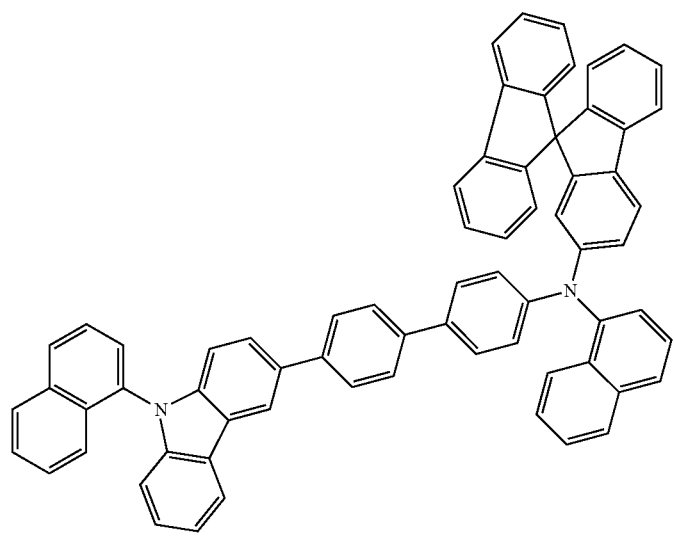
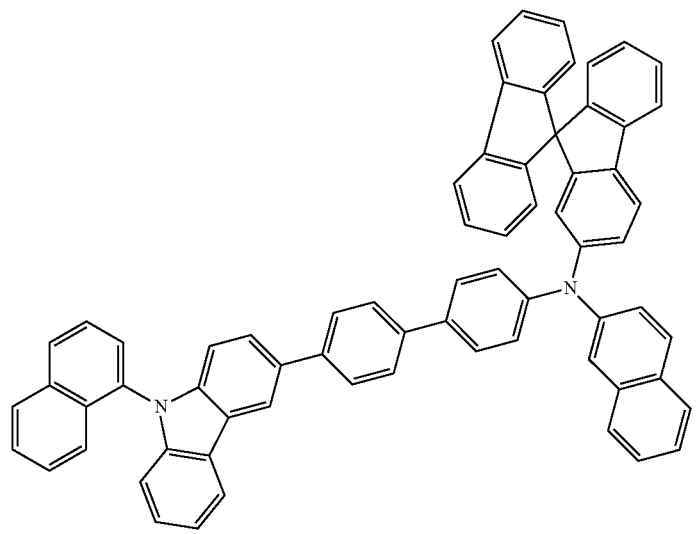
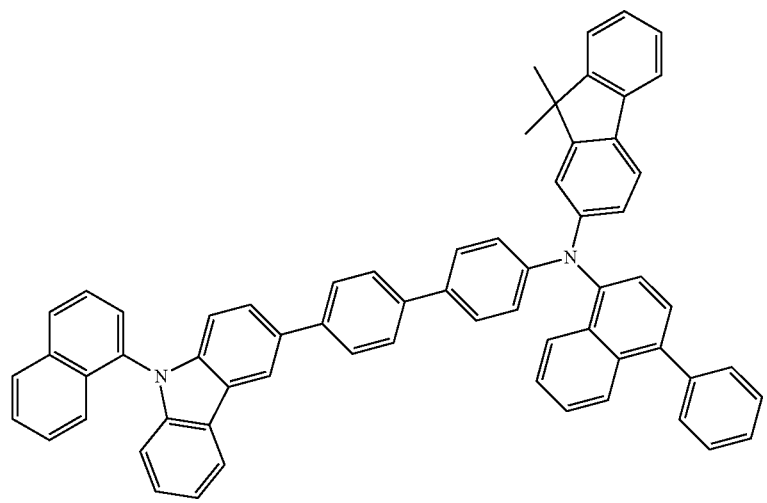

-continued
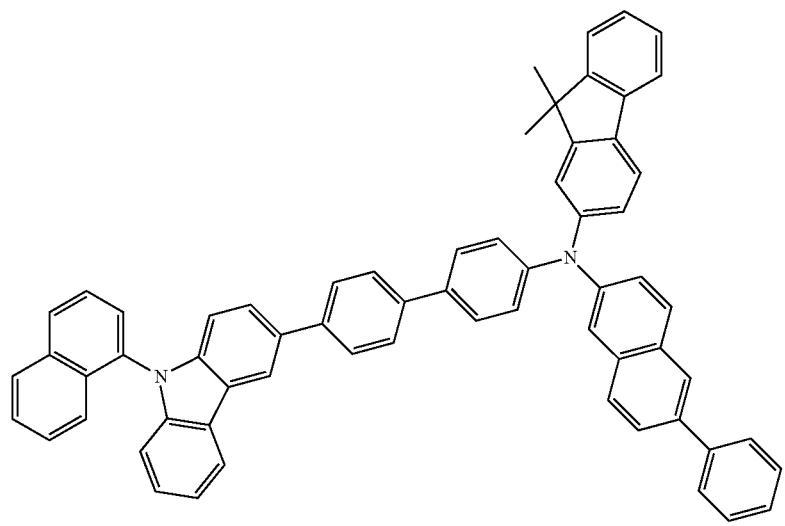
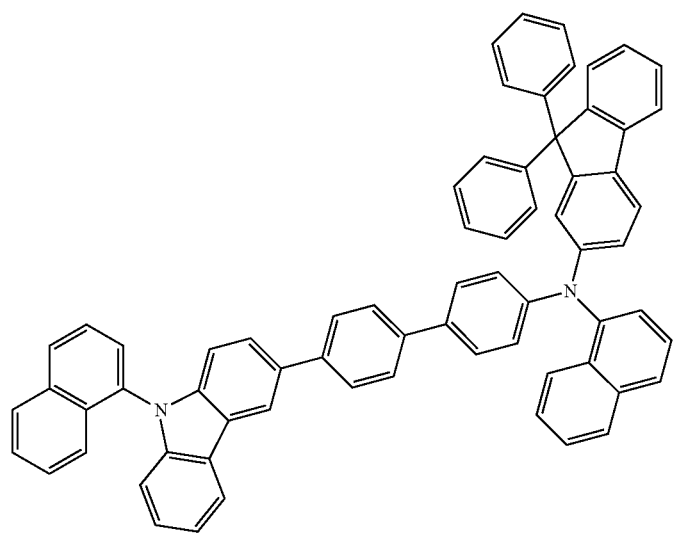
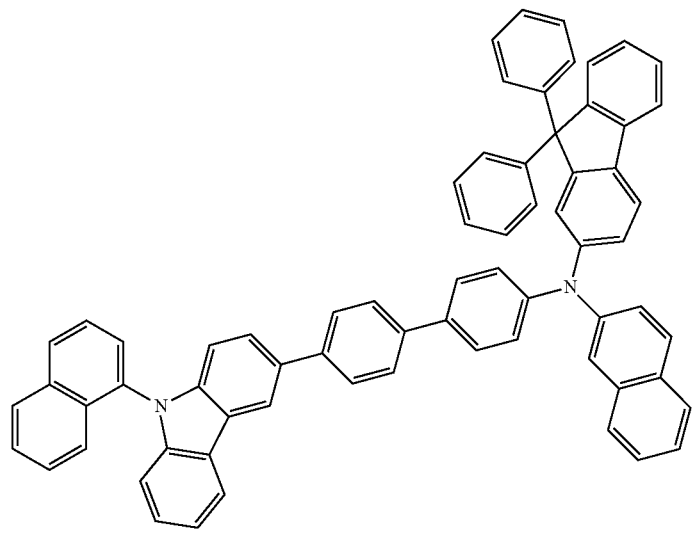

-continued
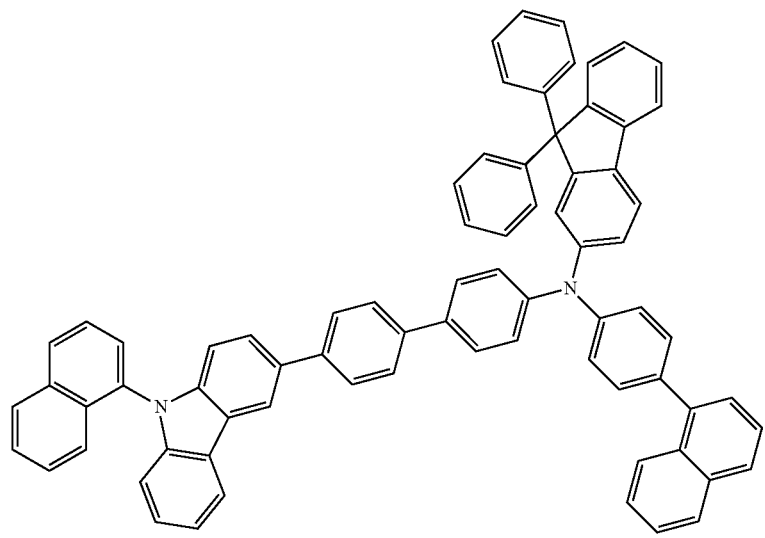
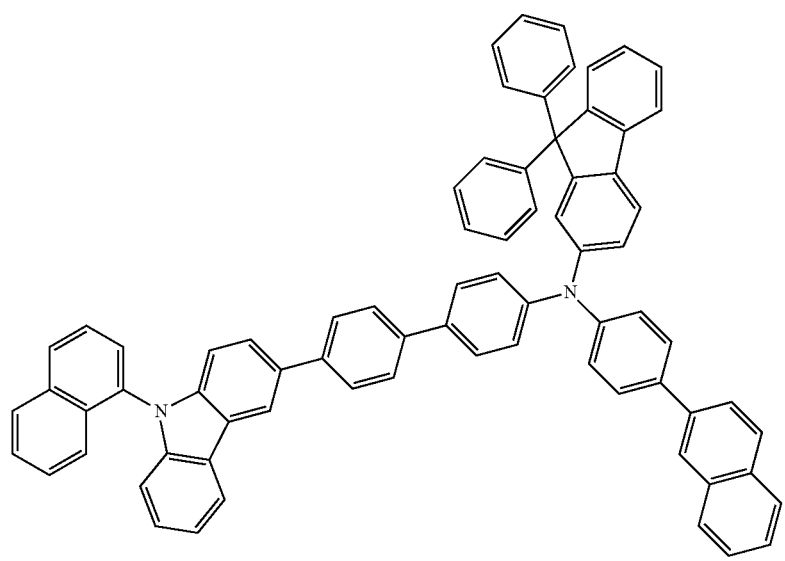
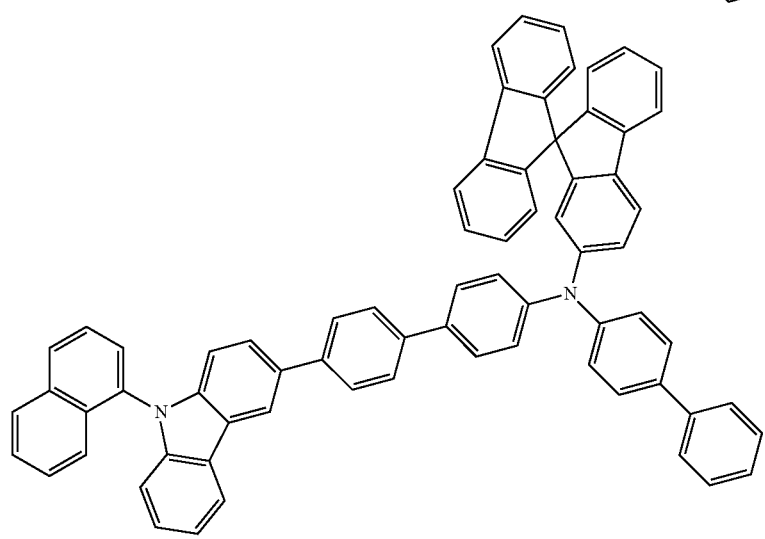

-continued
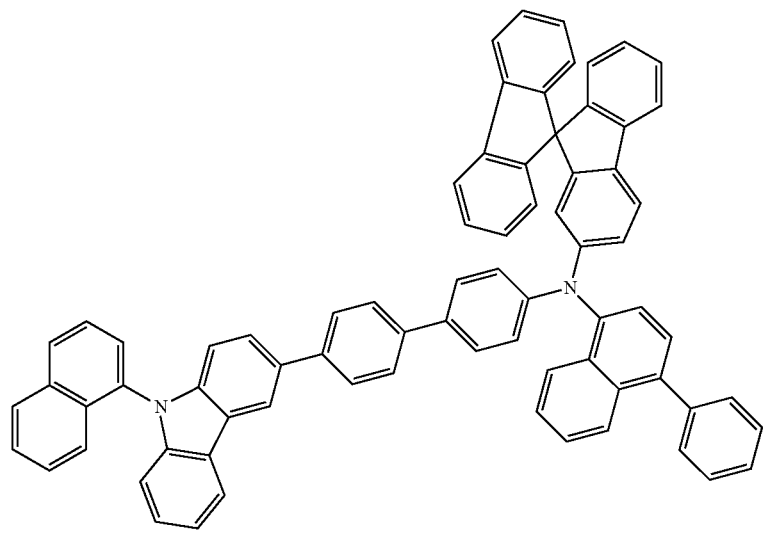
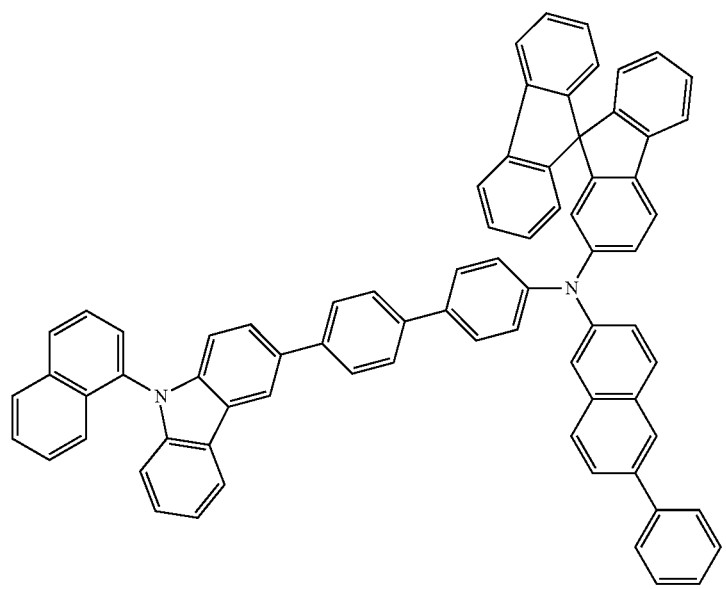

-continued

-continued
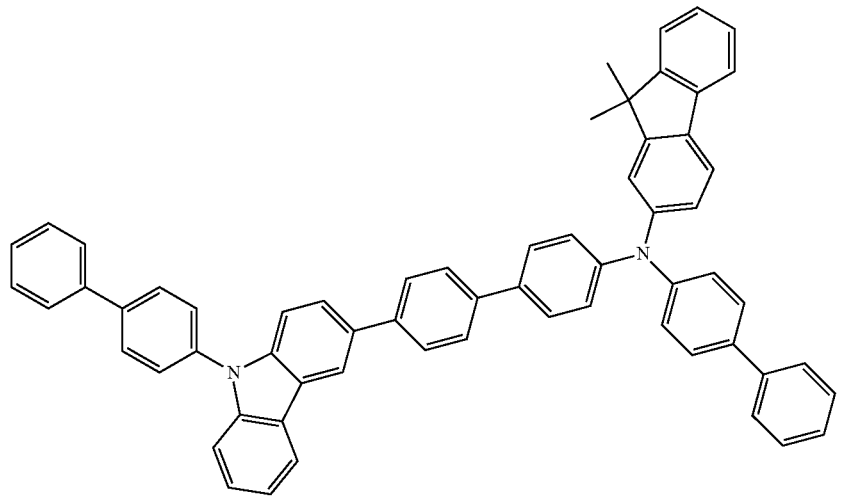
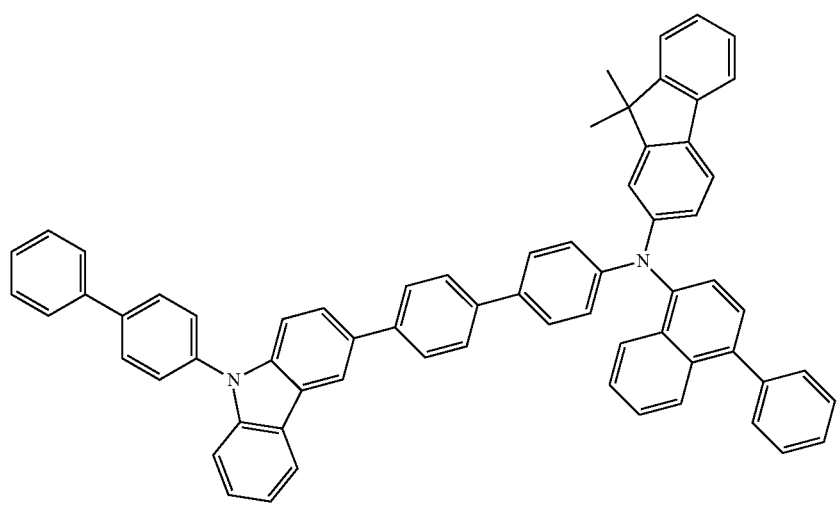
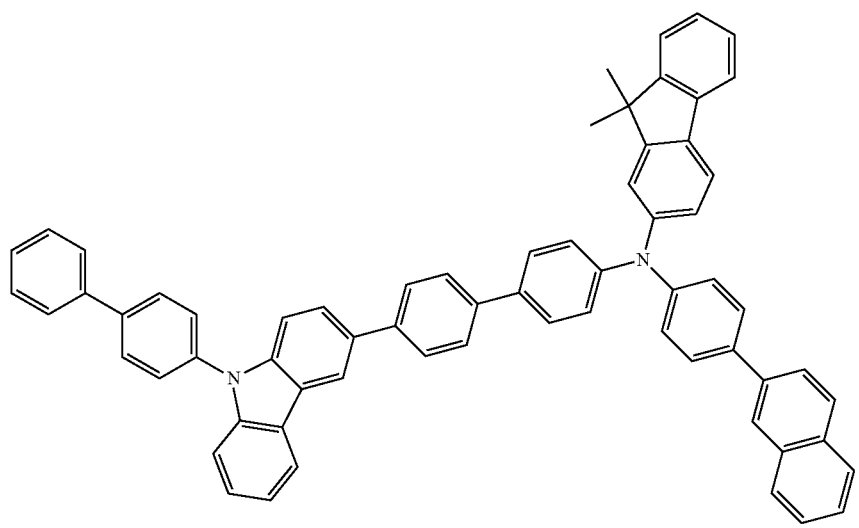

-continued
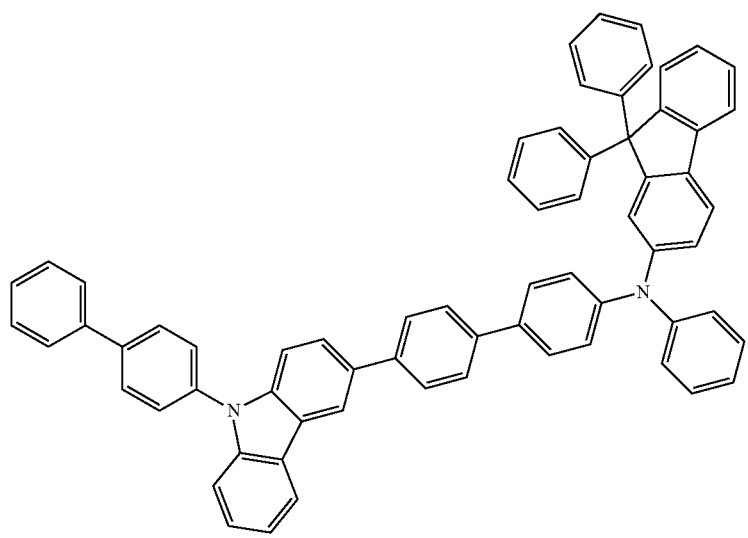
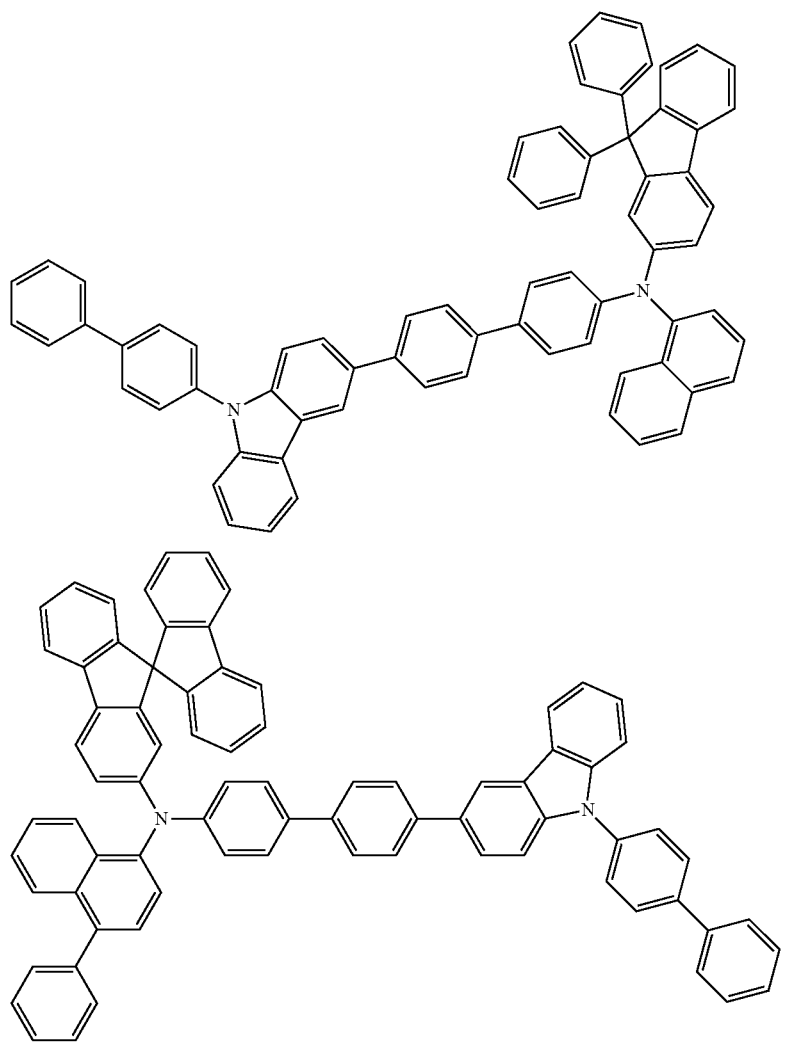

-continued
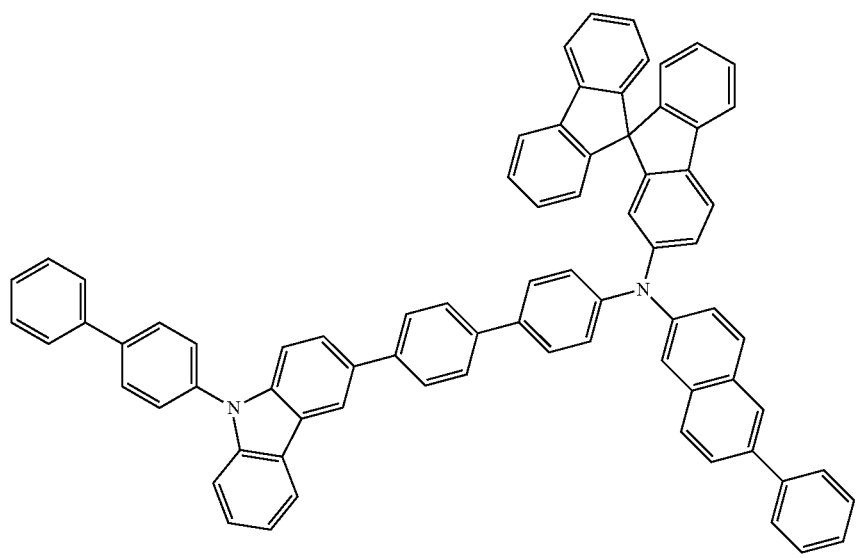
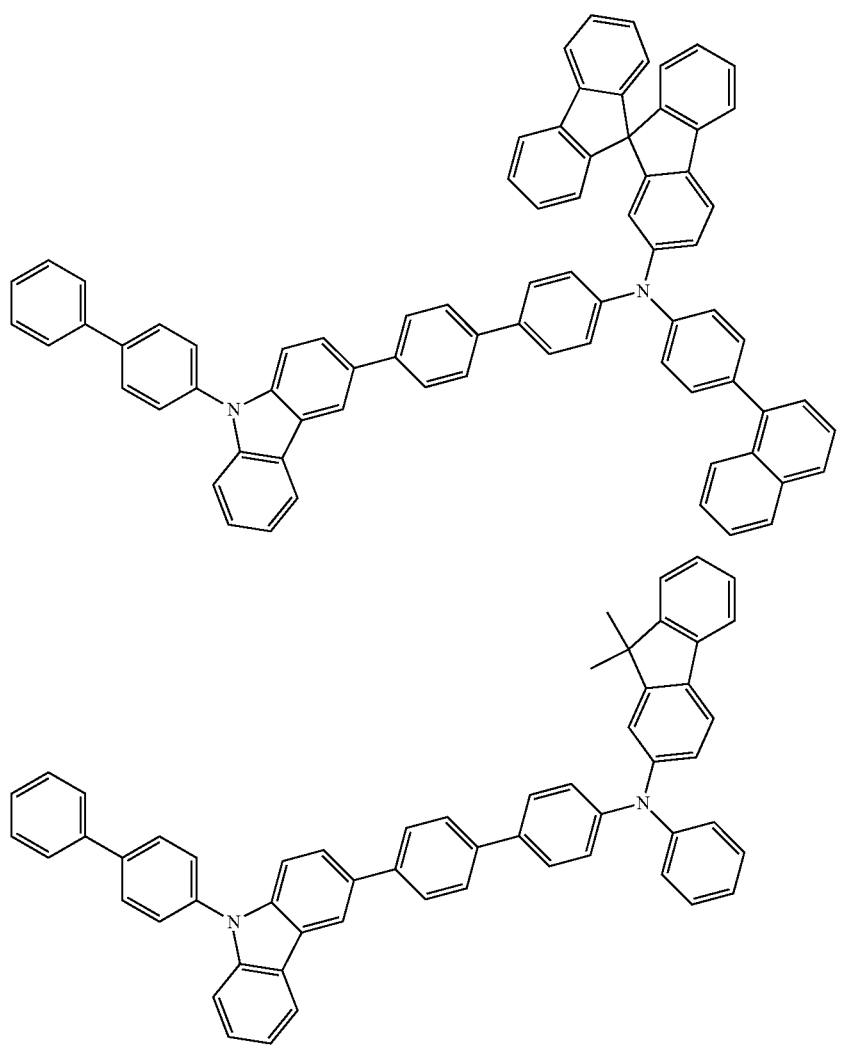

-continued
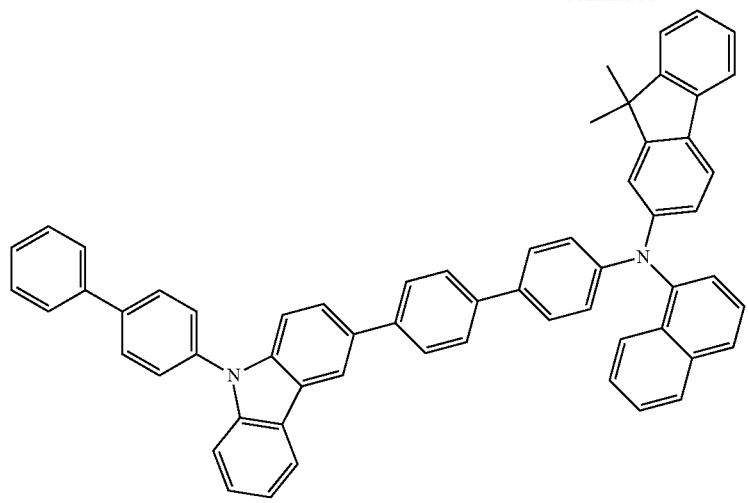
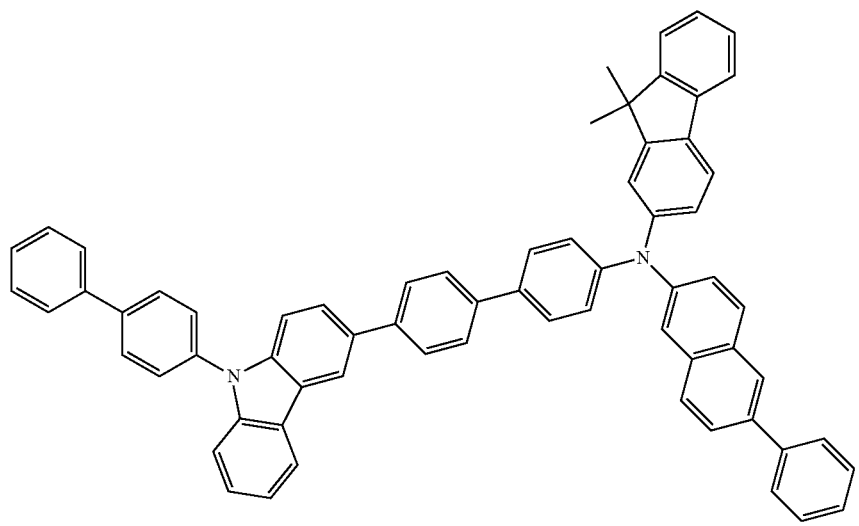
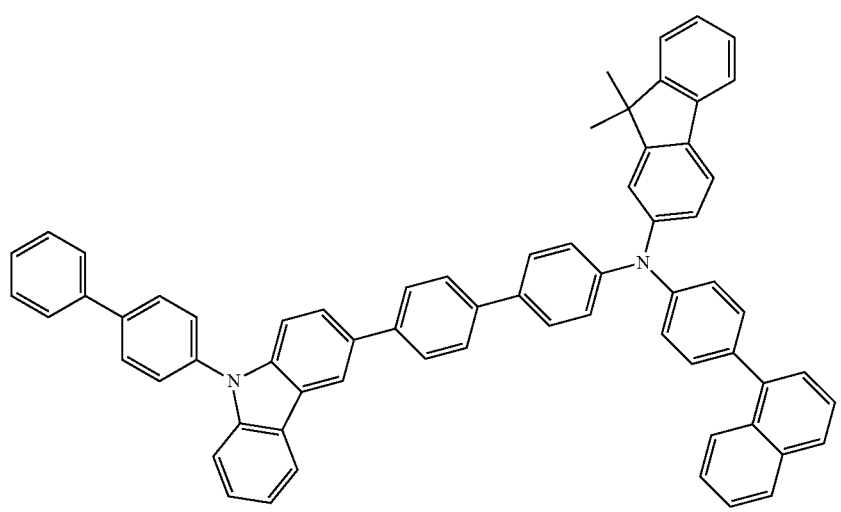

-continued
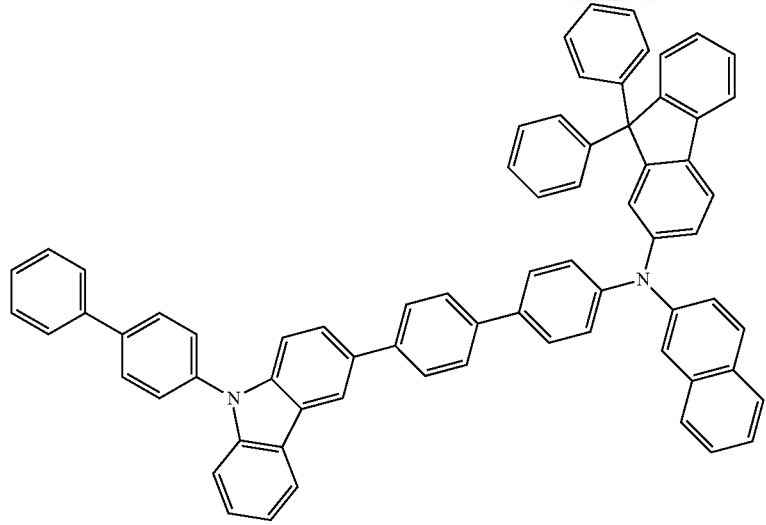
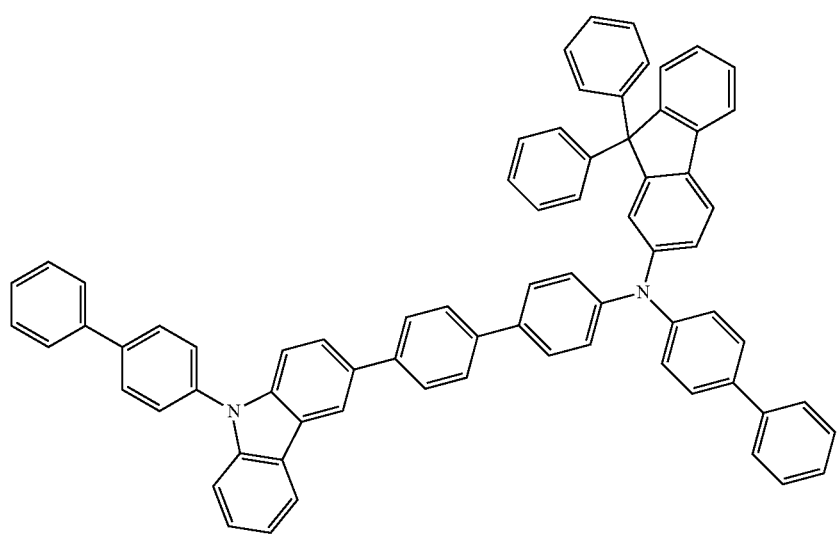
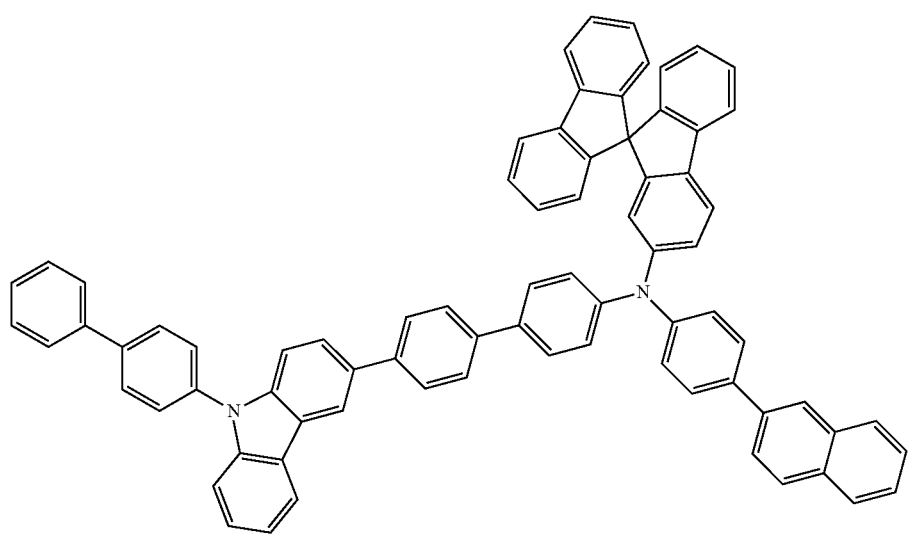

-continued
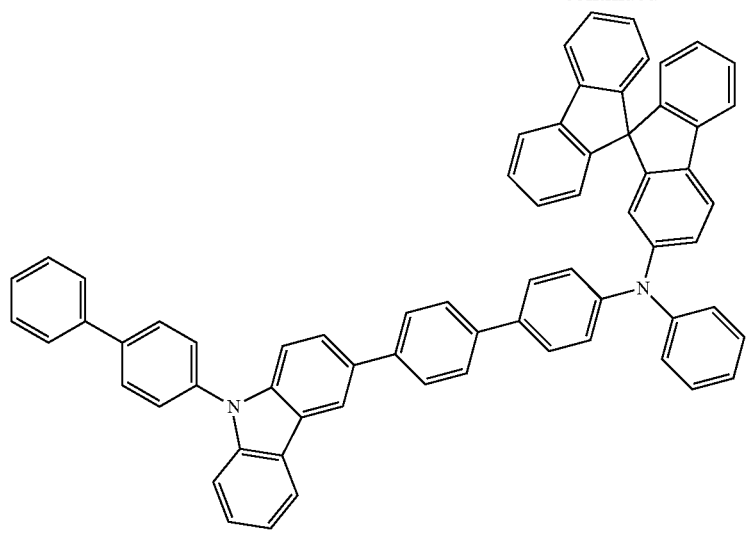
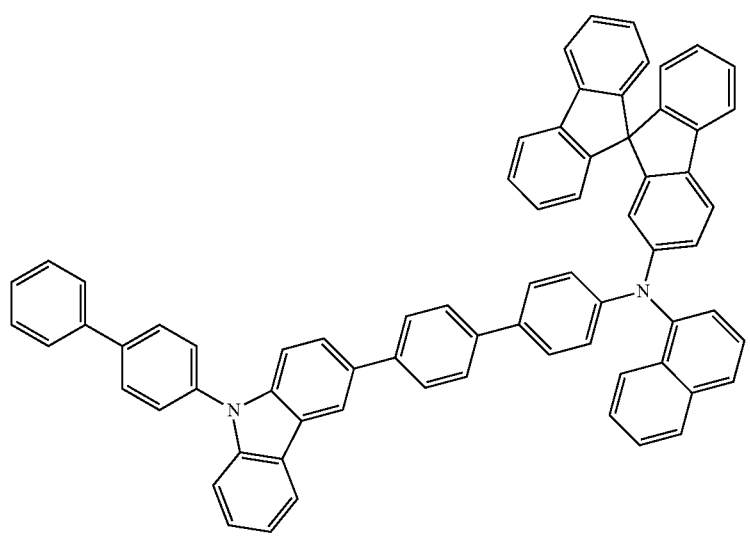
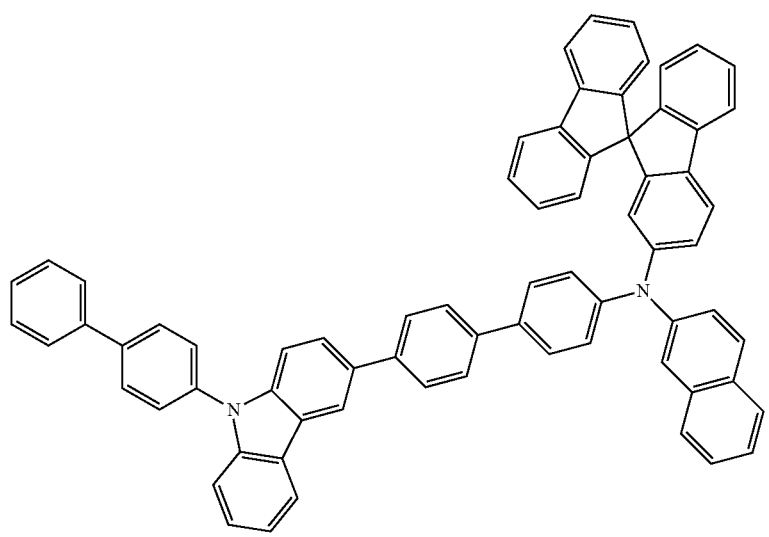

-continued
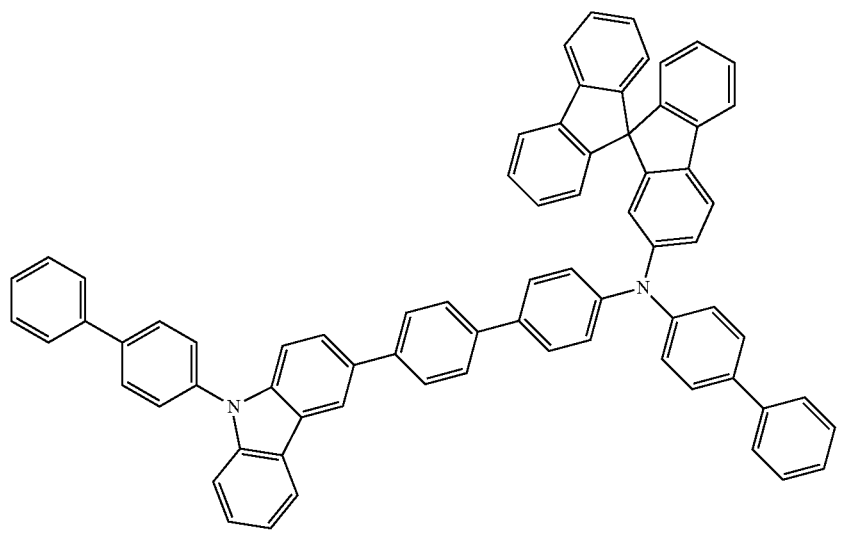
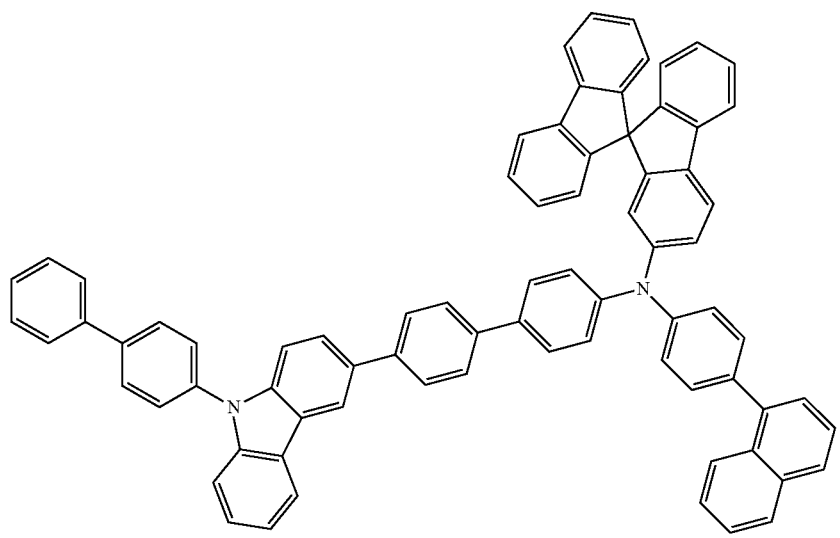
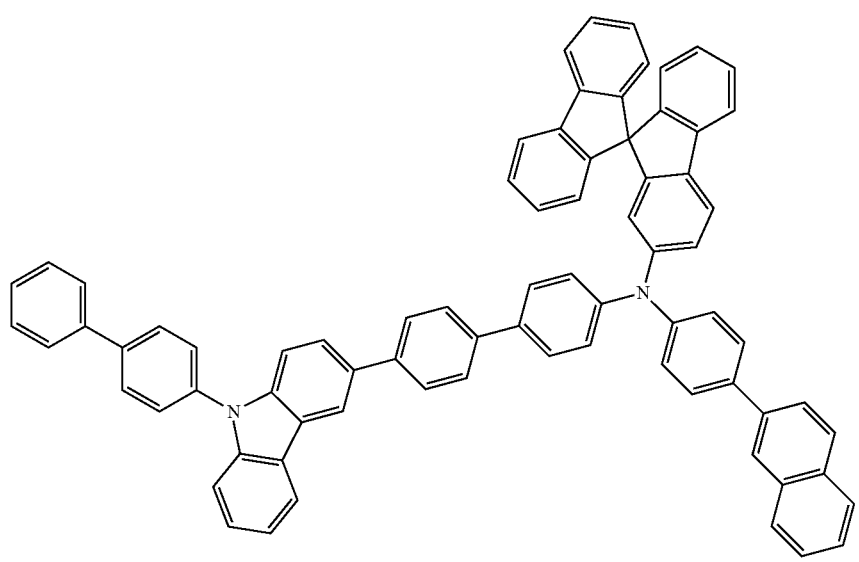

-continued
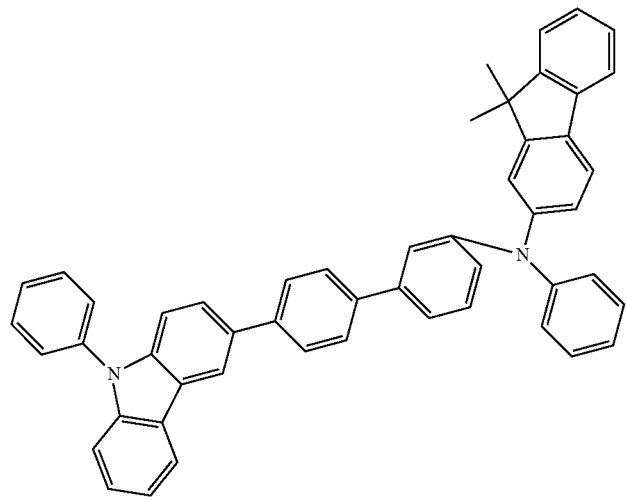
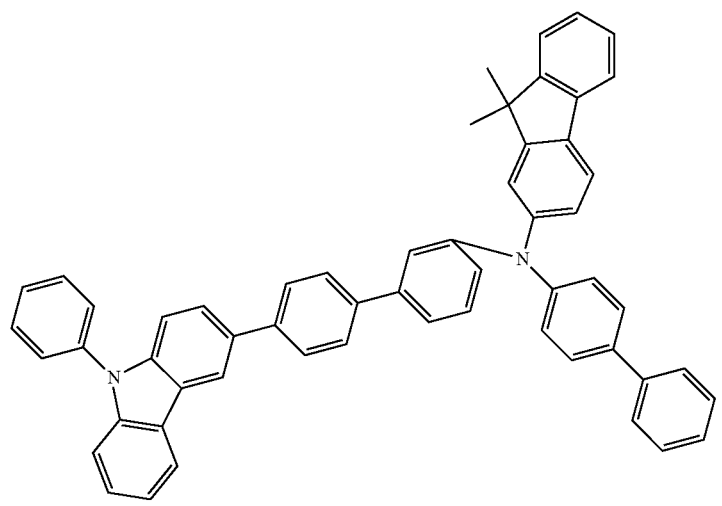
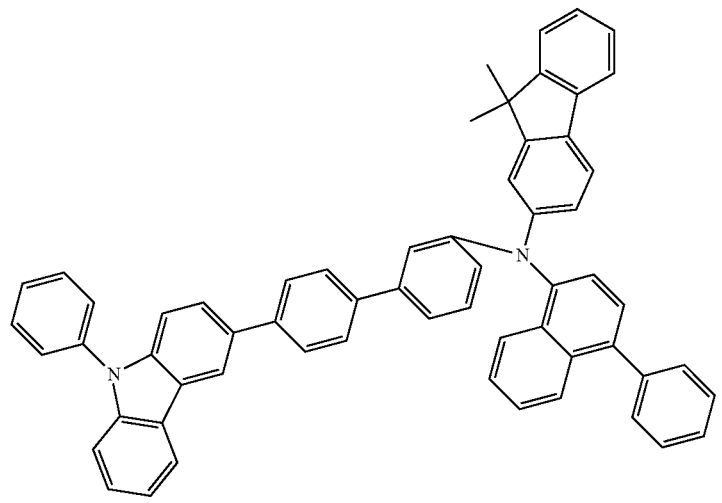

-continued
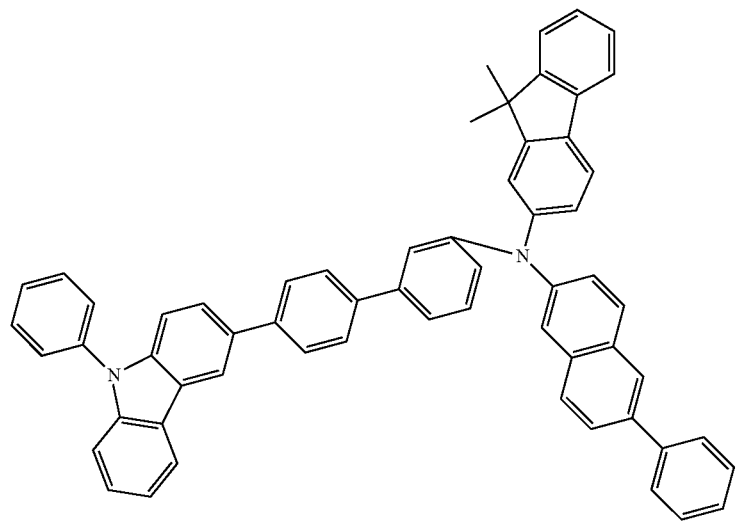
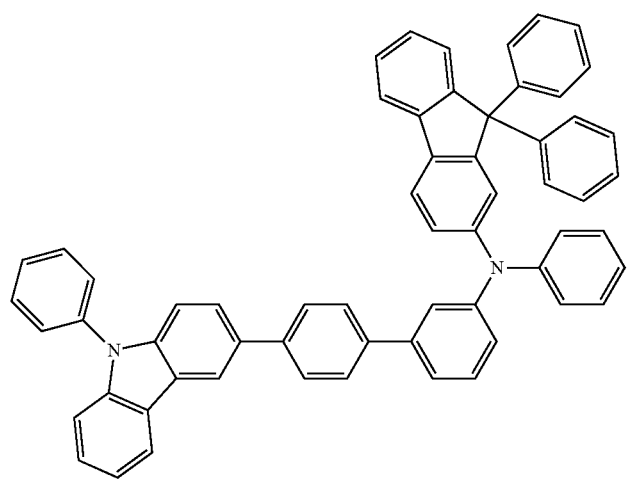
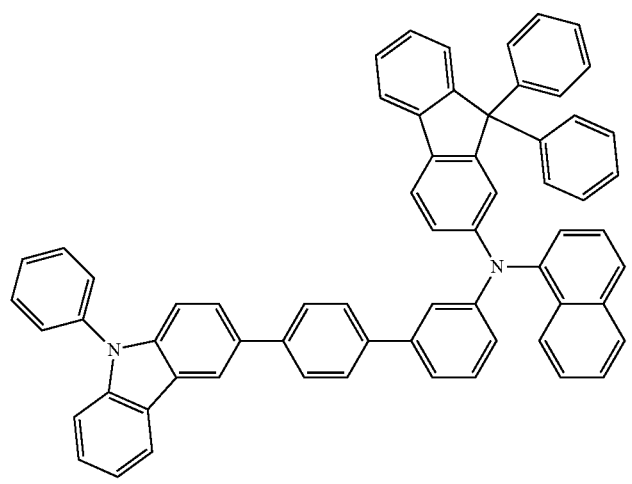

-continued
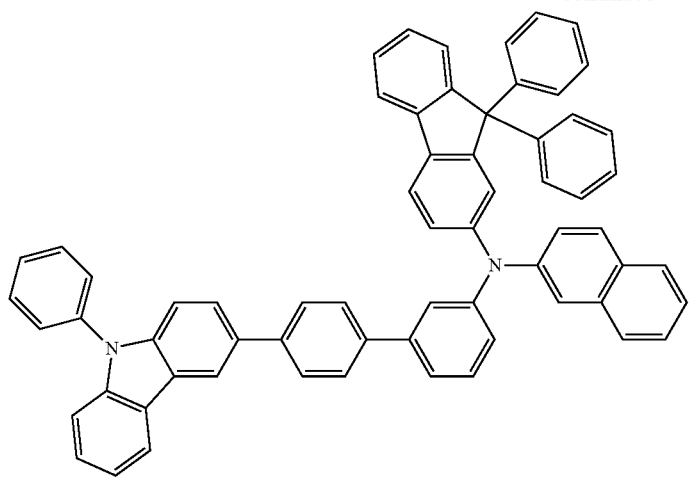
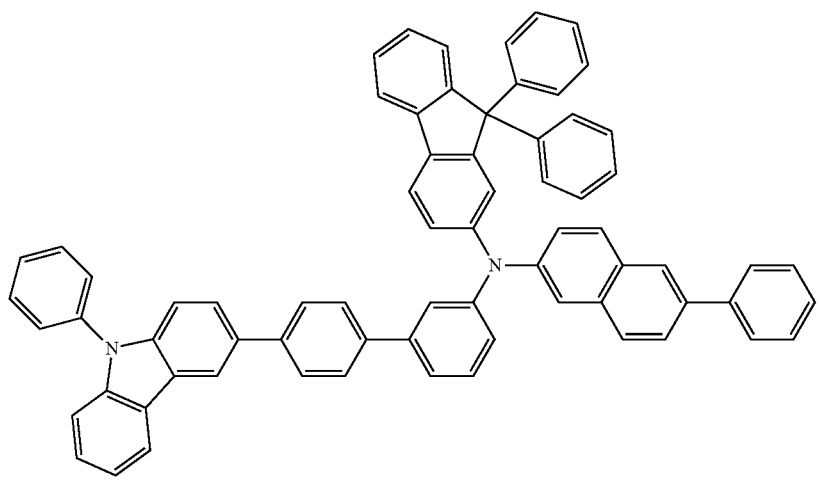
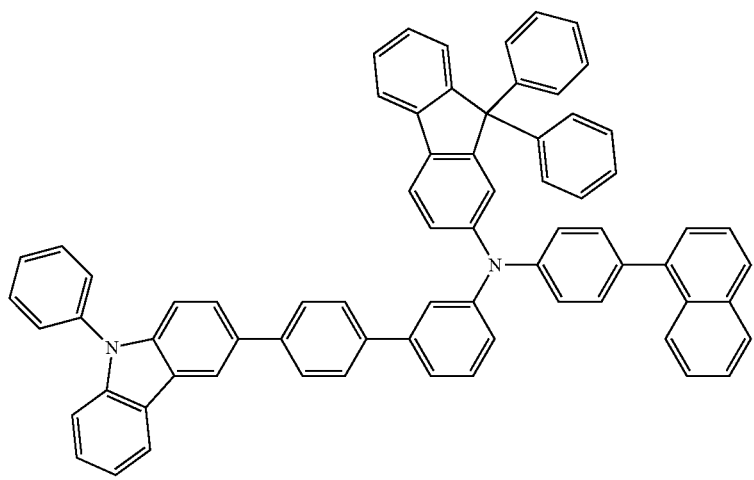

-continued
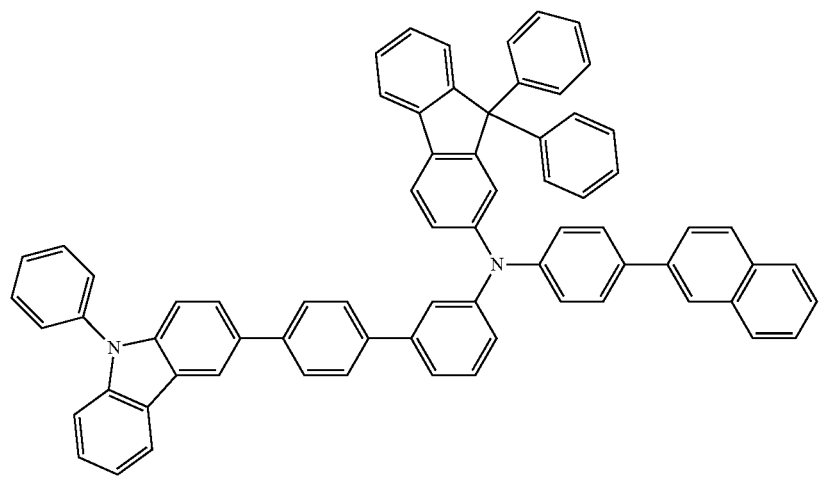
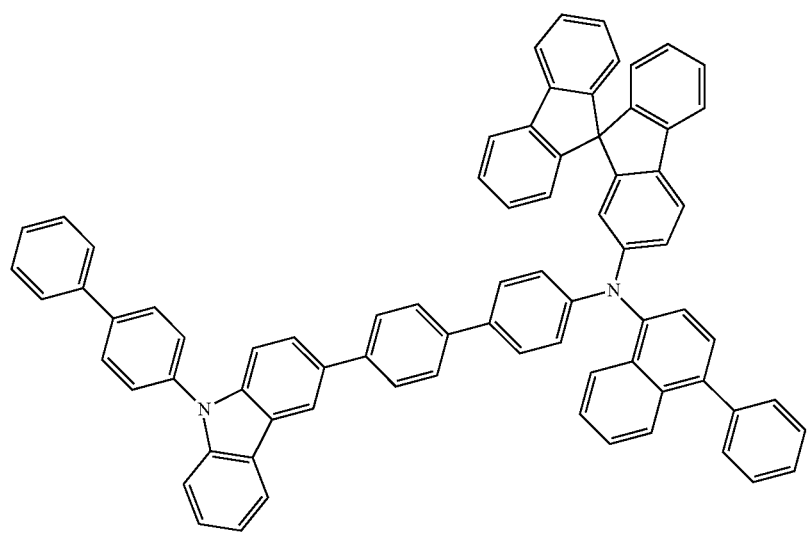
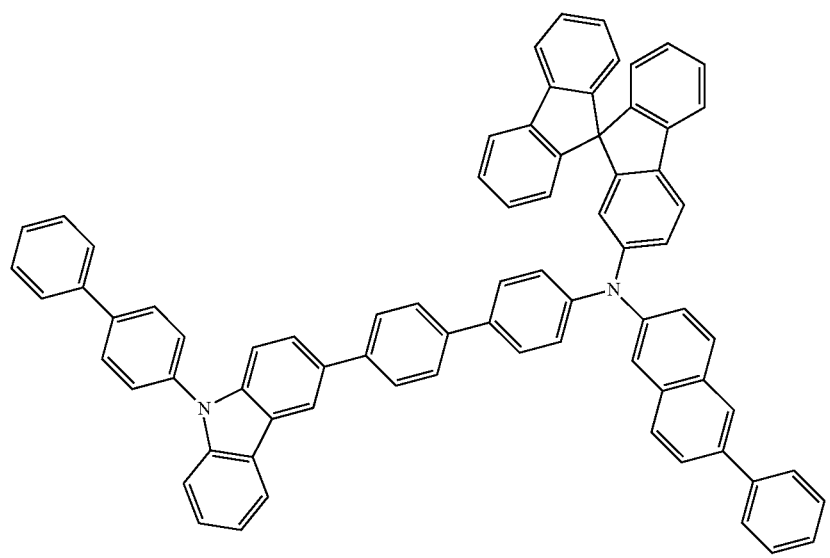

-continued
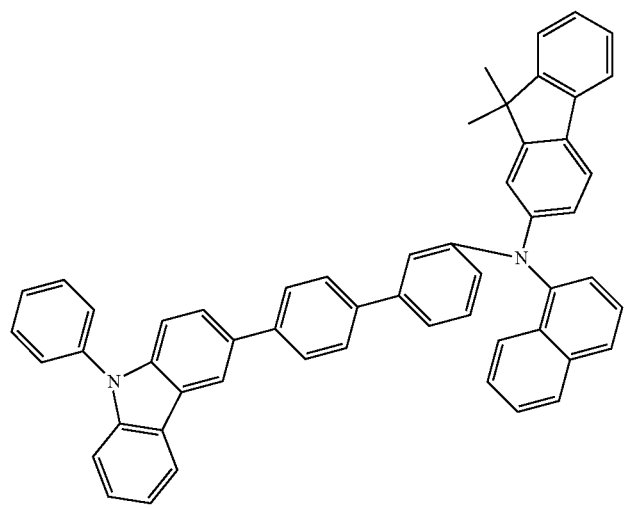
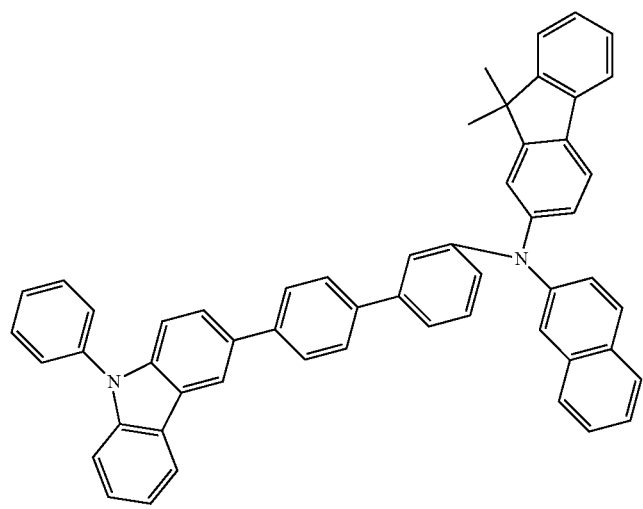
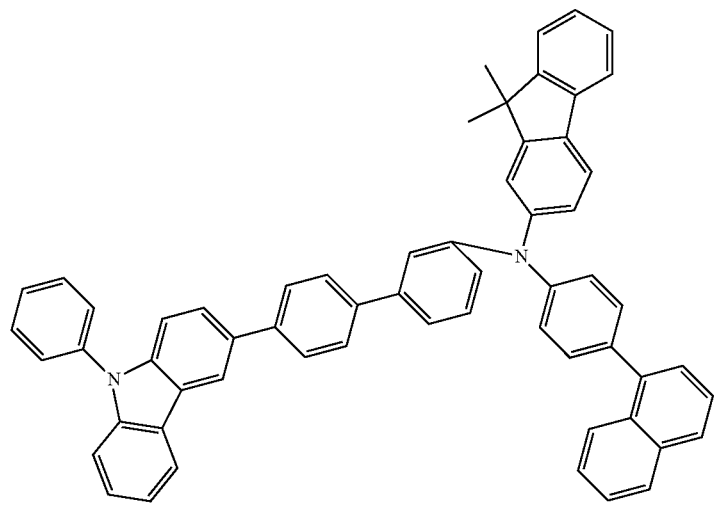

-continued
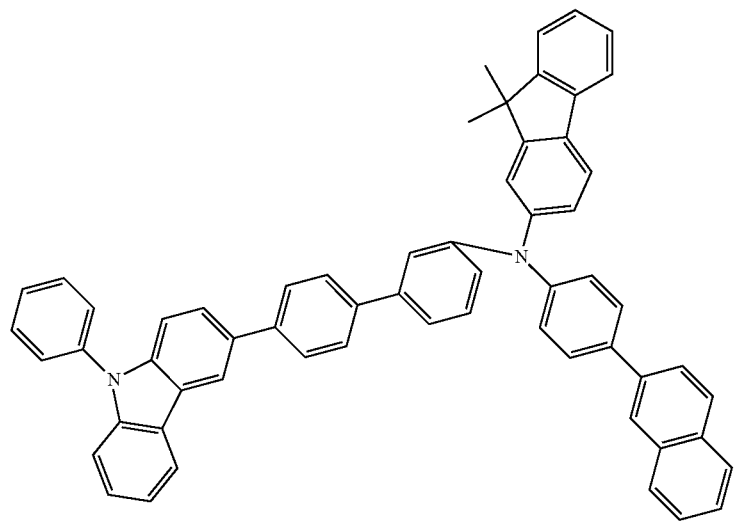
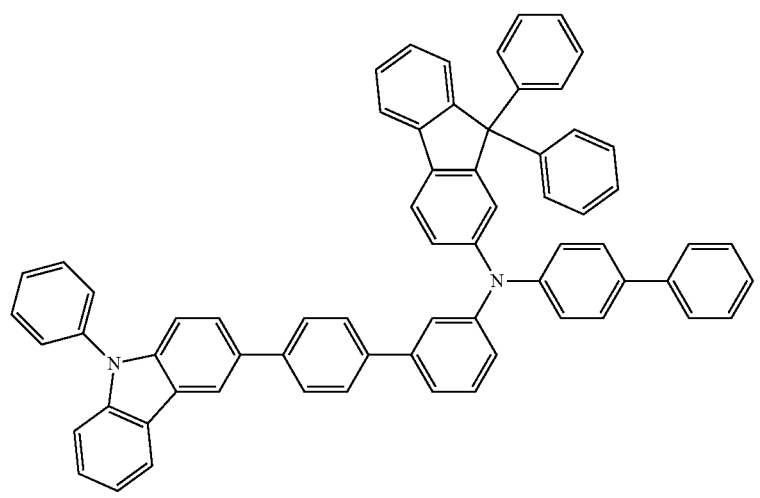
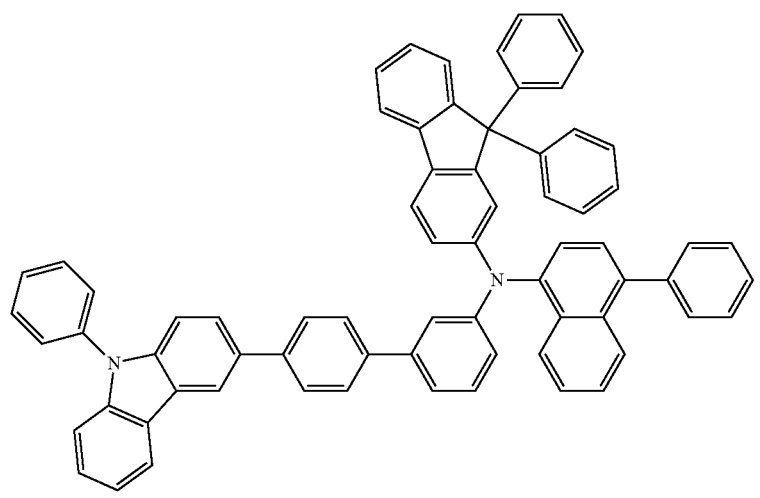

-continued
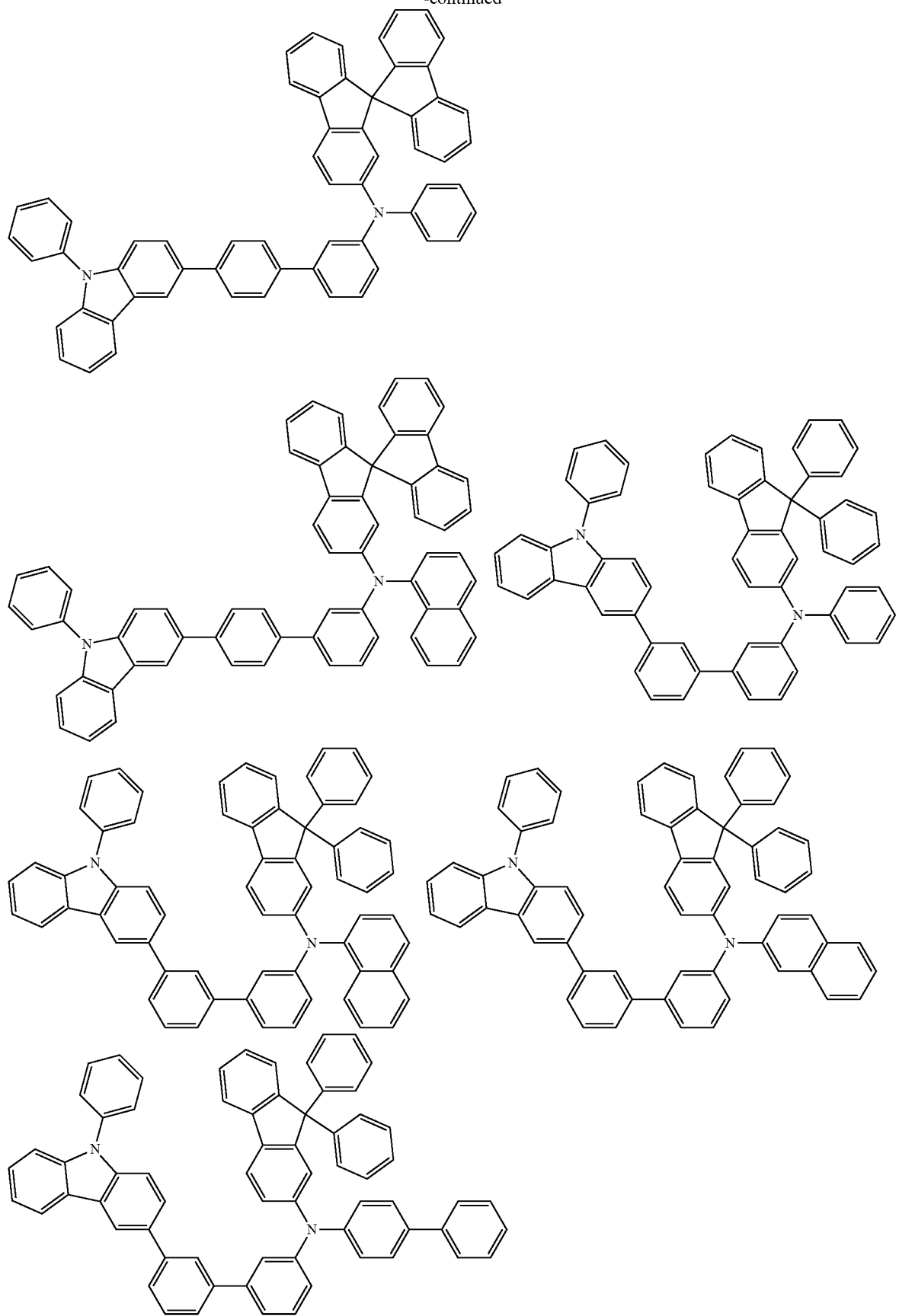

-continued
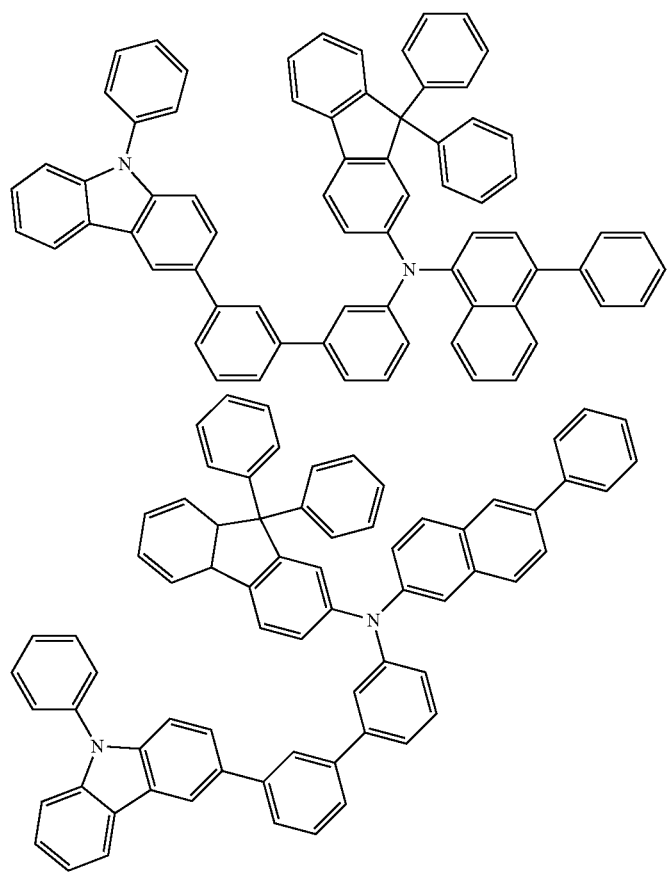
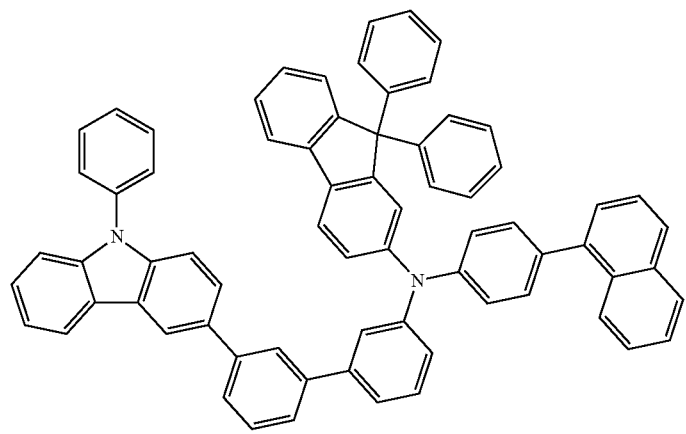
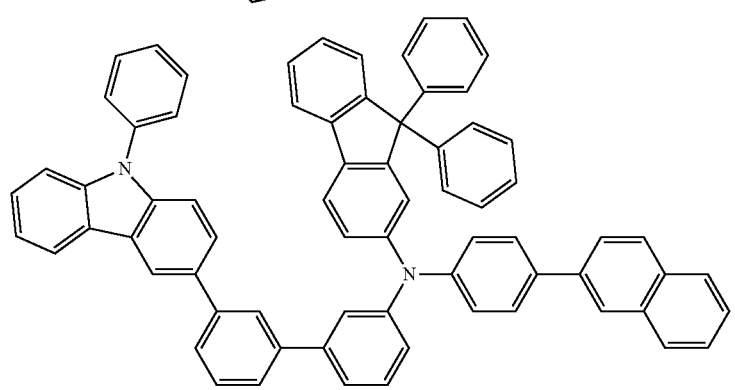

451 452
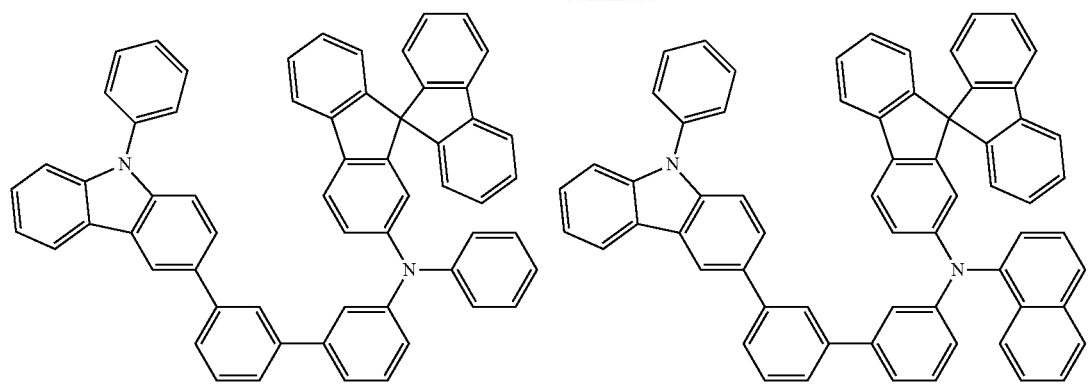
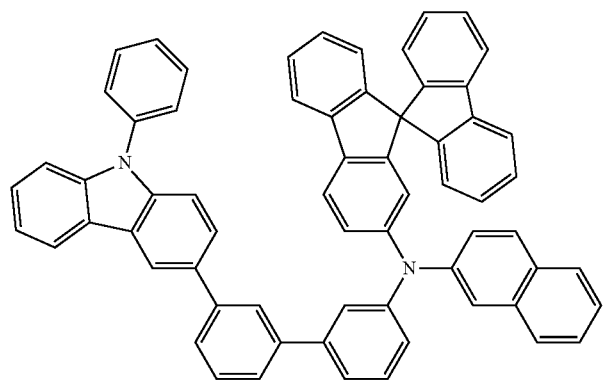
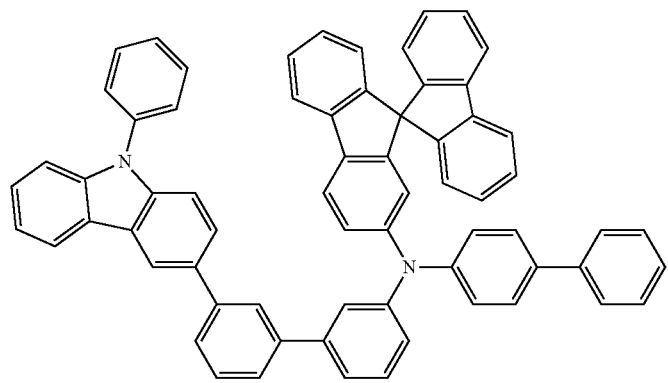
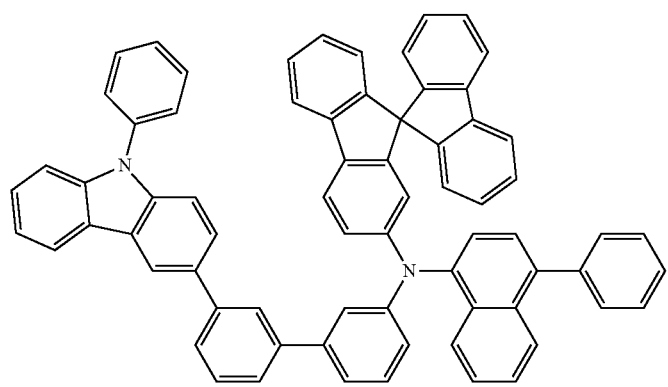

453 454
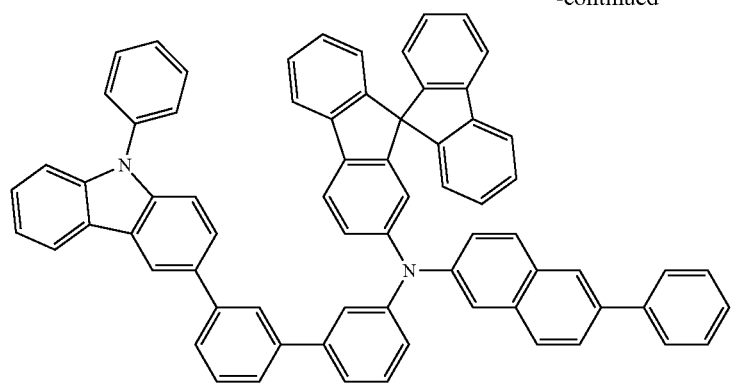
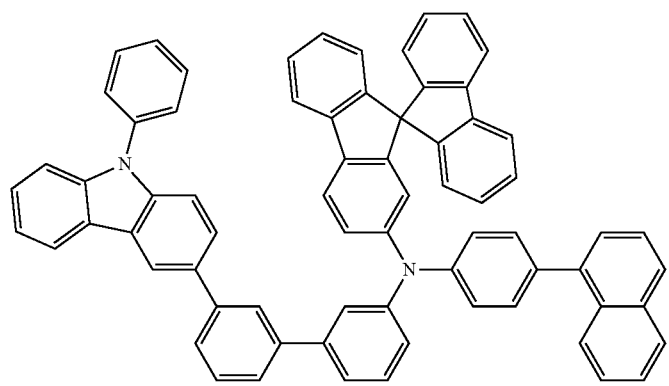
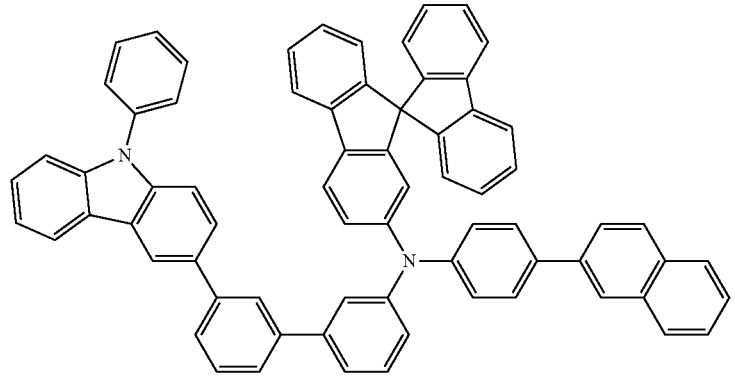
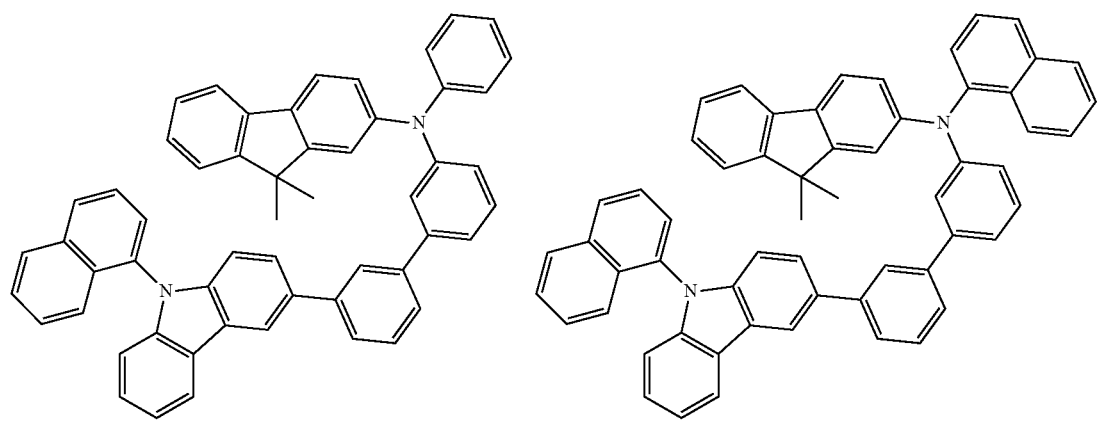

-continued
455
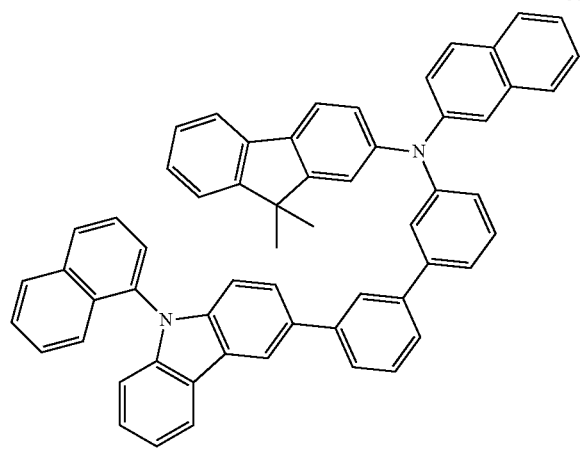
456
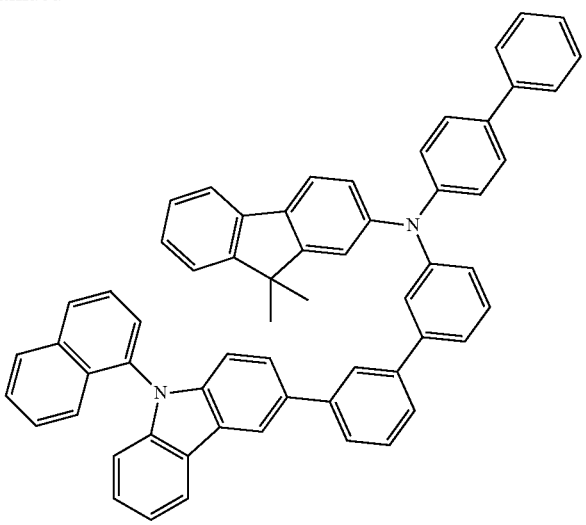
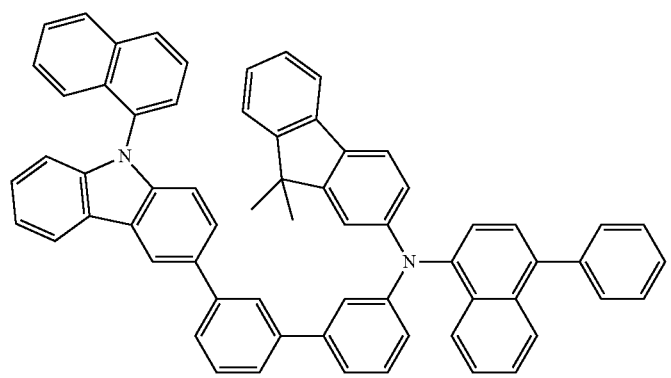
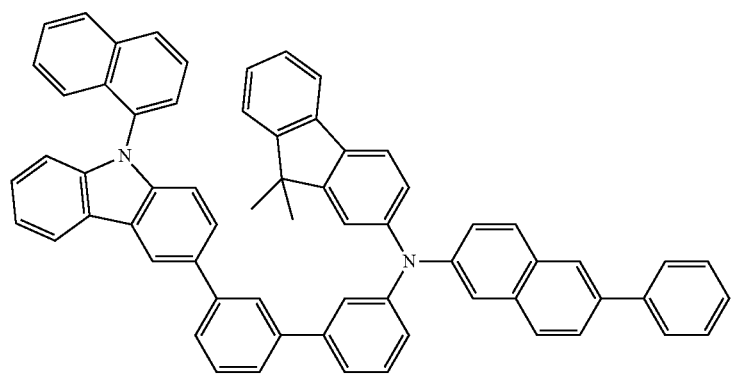
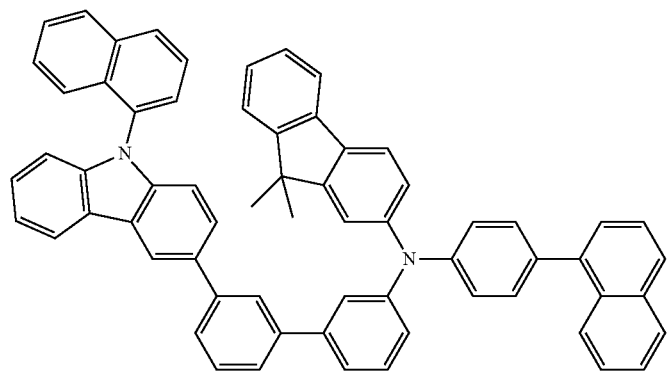

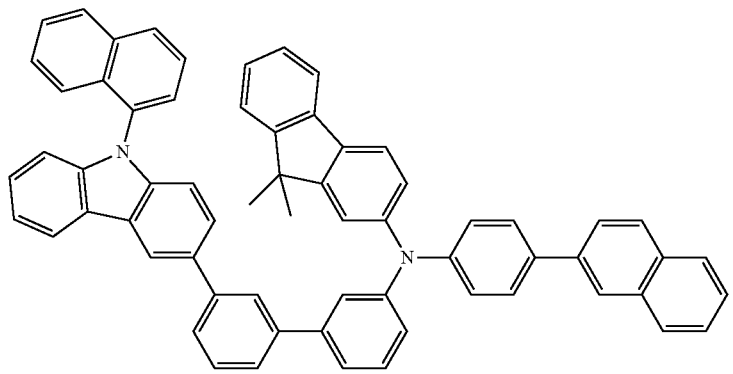
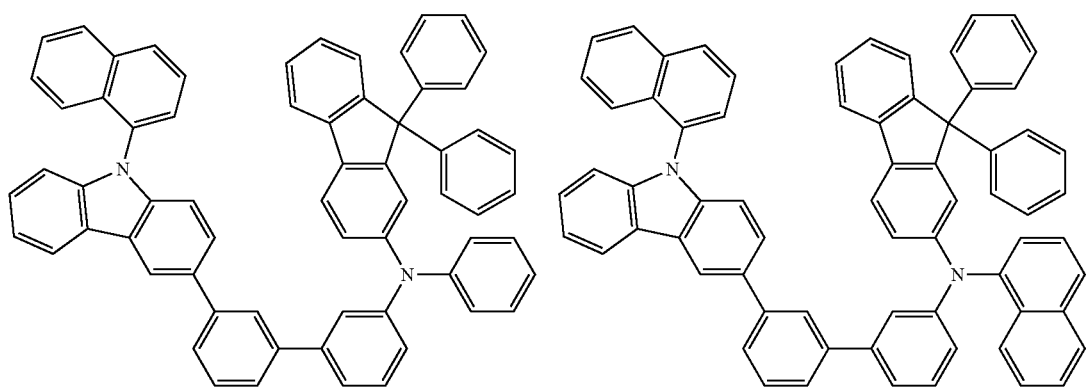
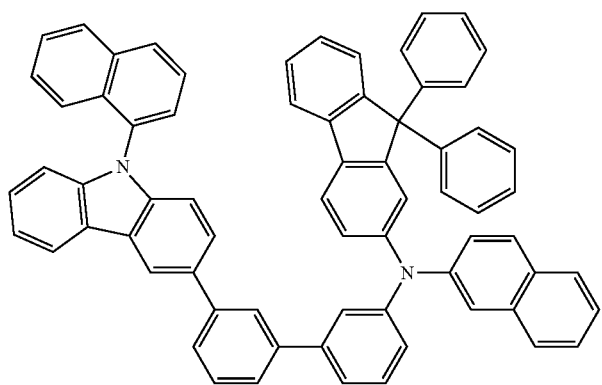
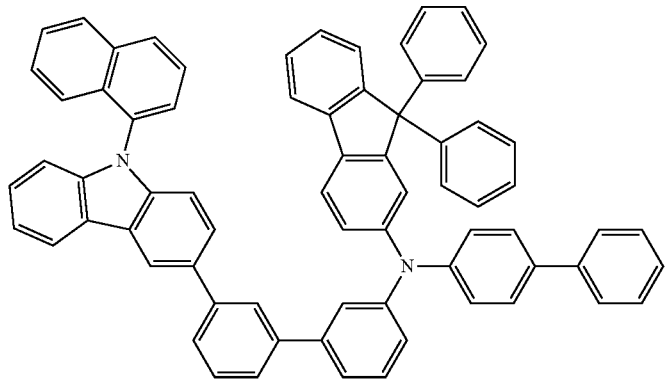

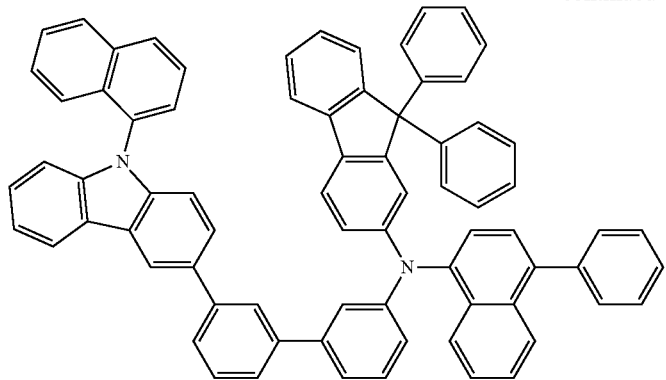
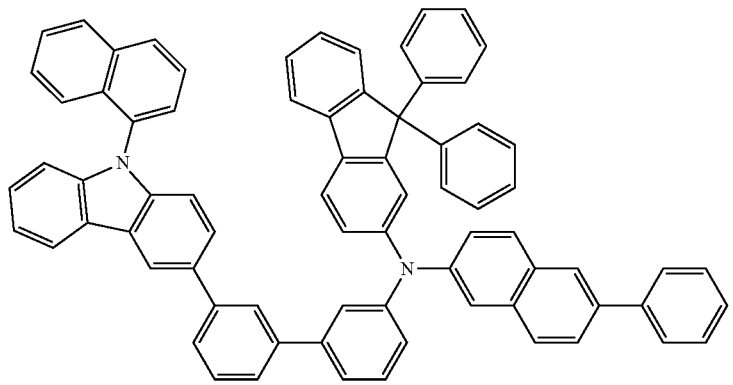
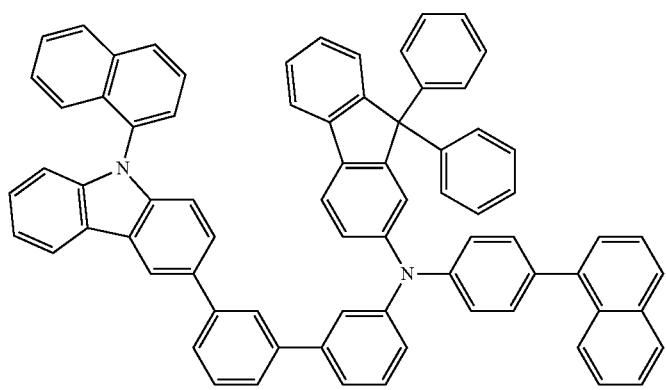
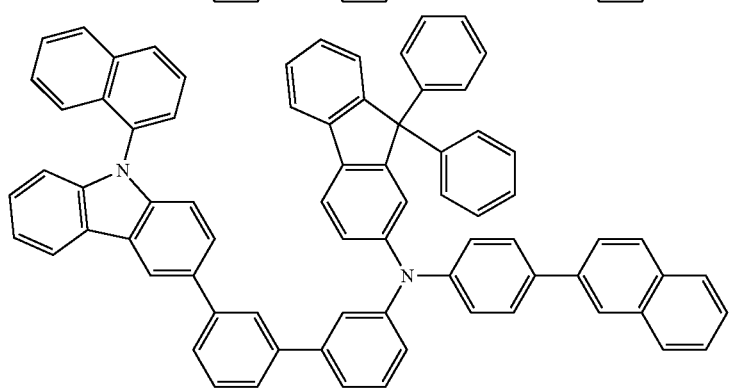

461 462
-continued
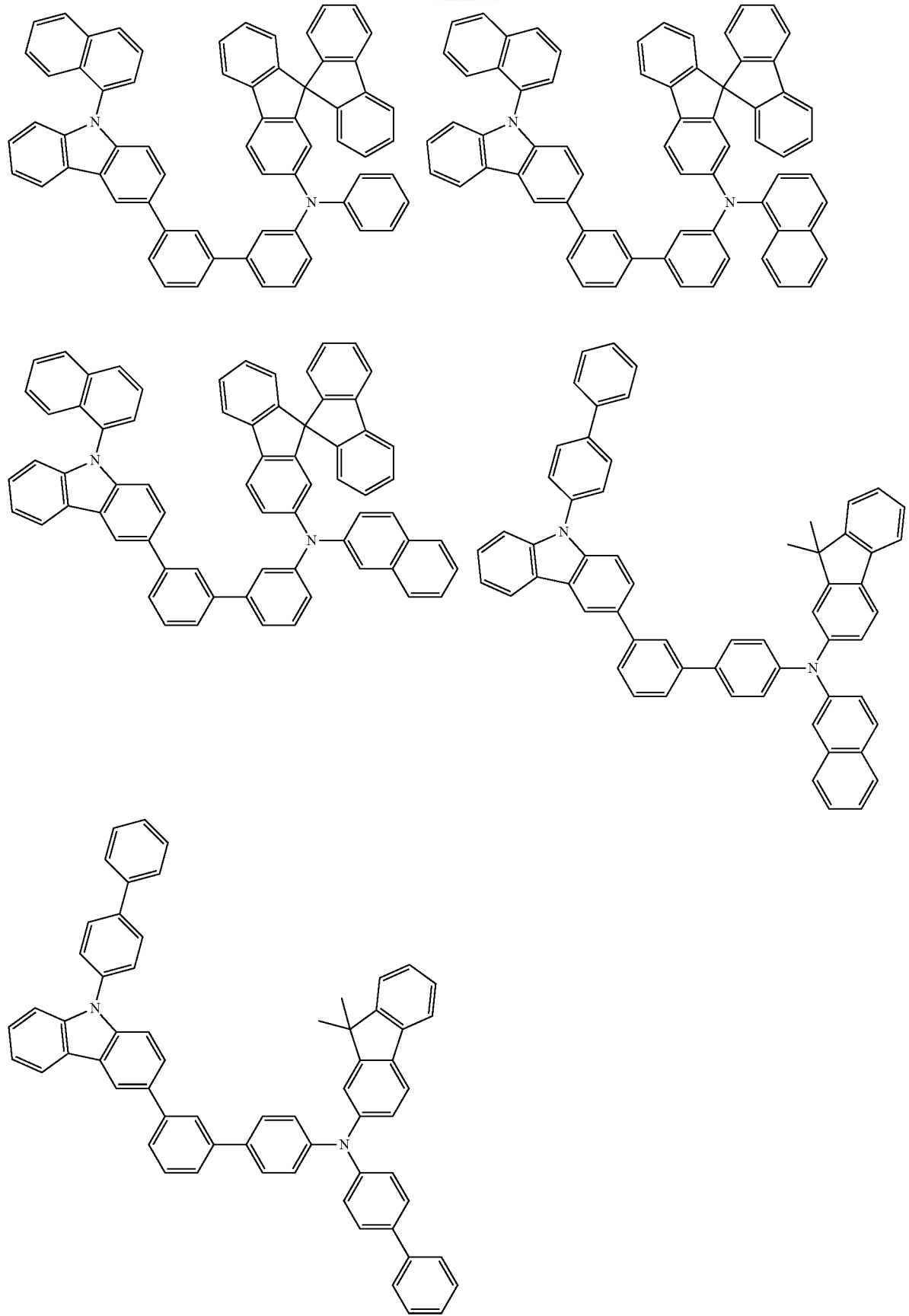

-continued
463
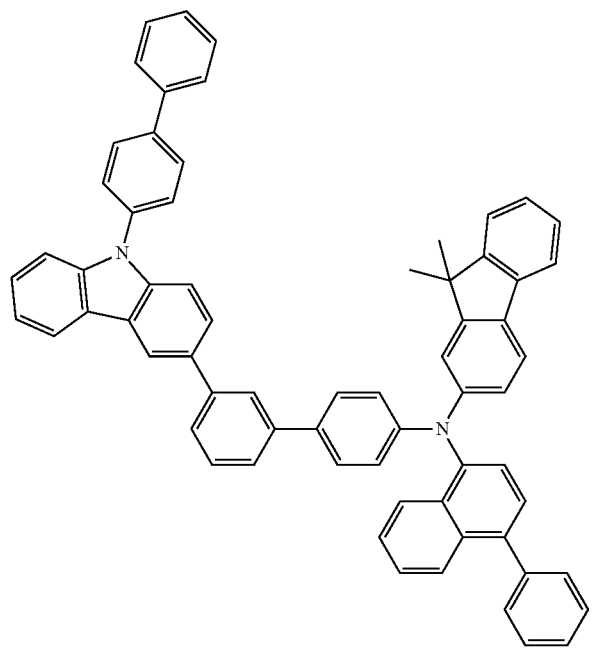
464
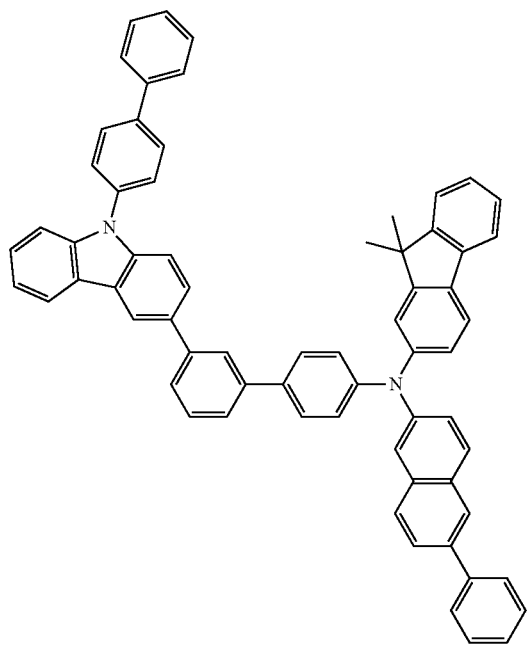
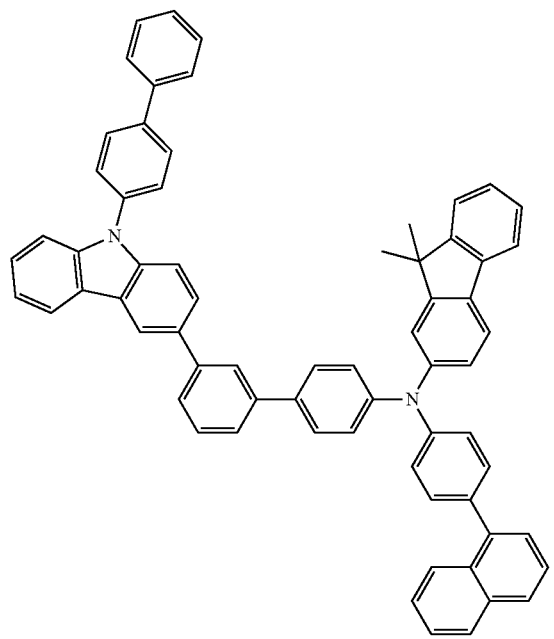
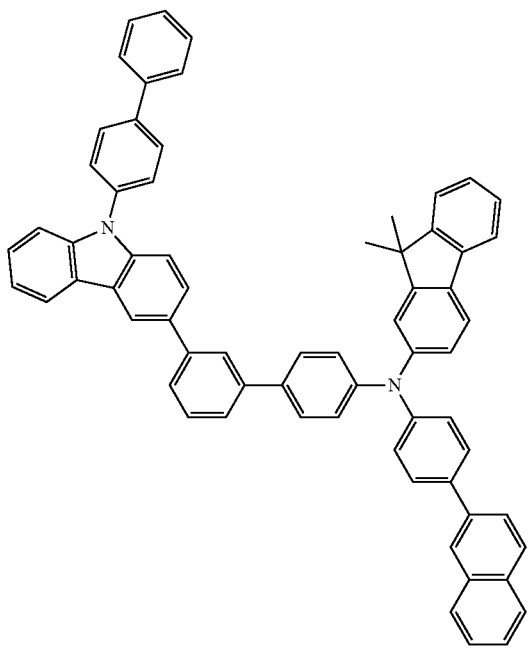

-continued
465
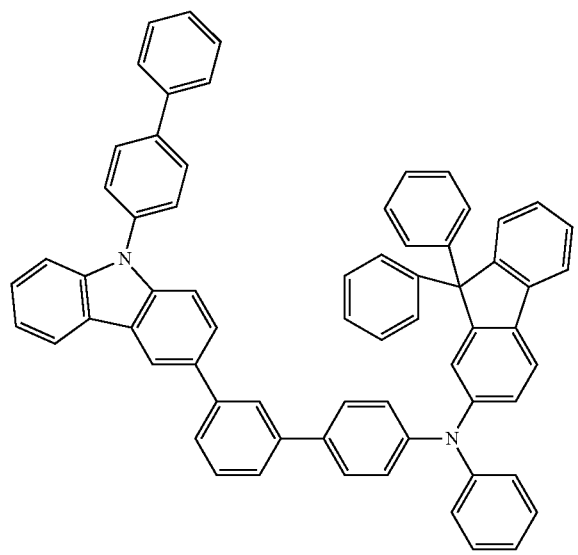
466
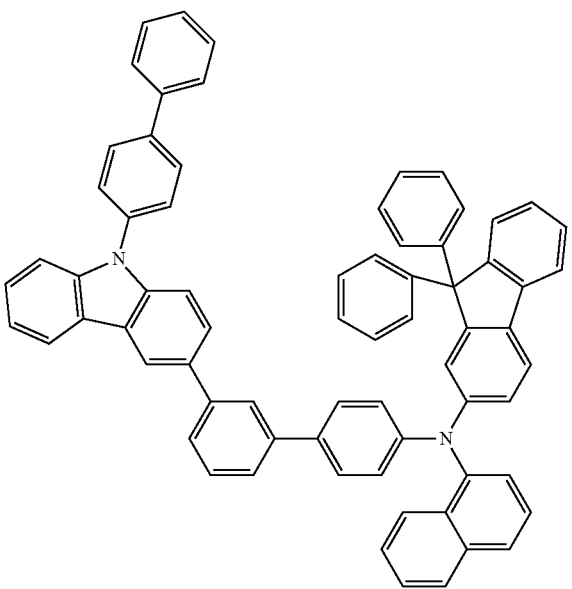
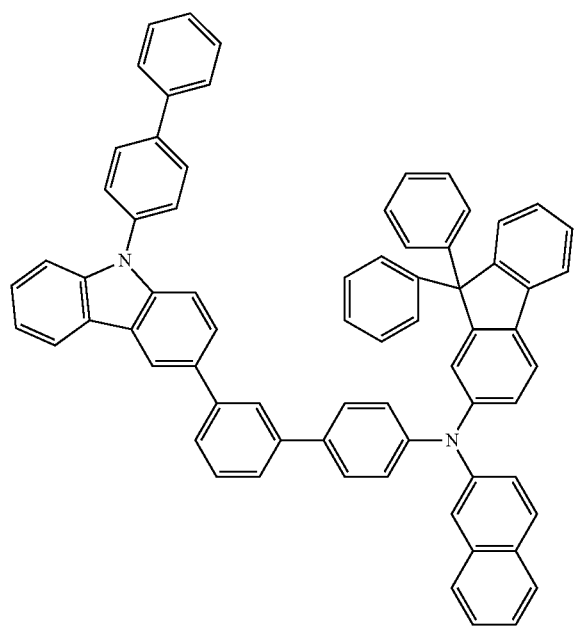
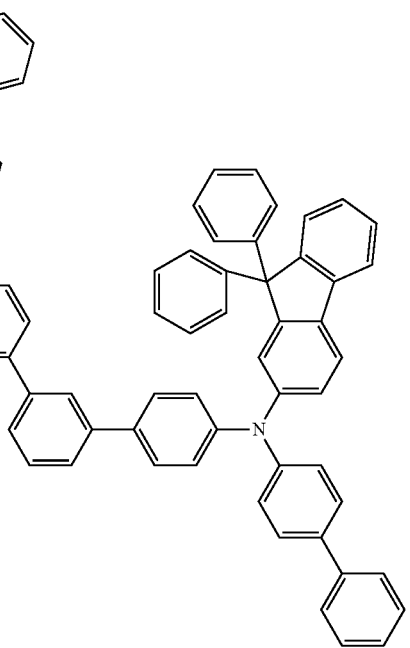

-continued
467
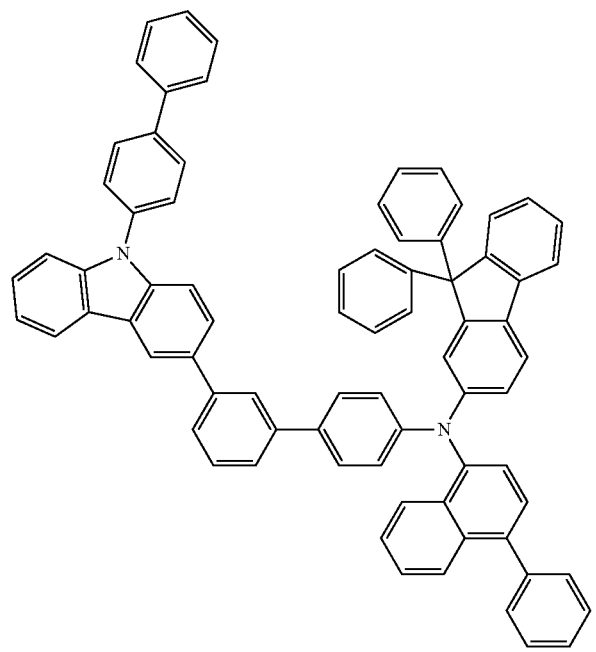
468
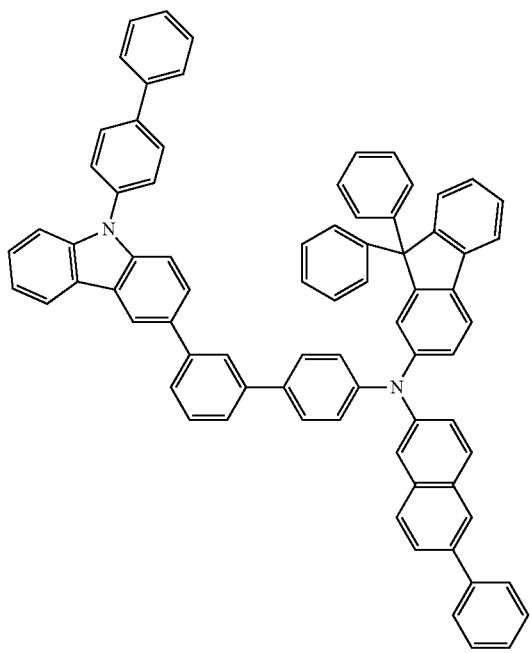
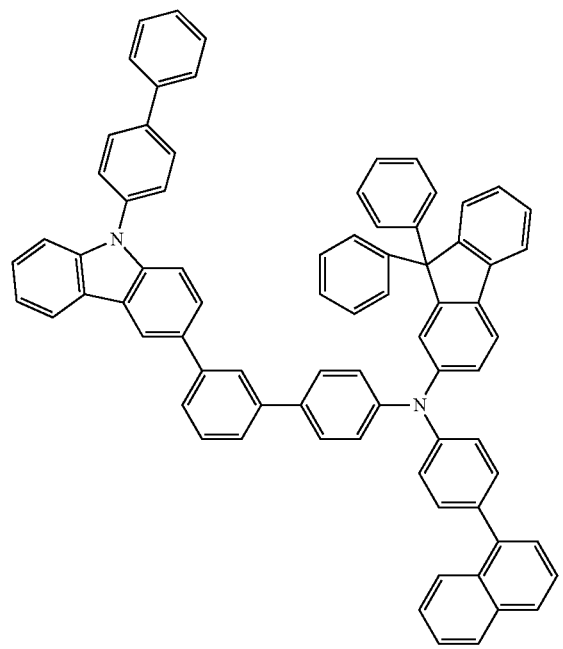
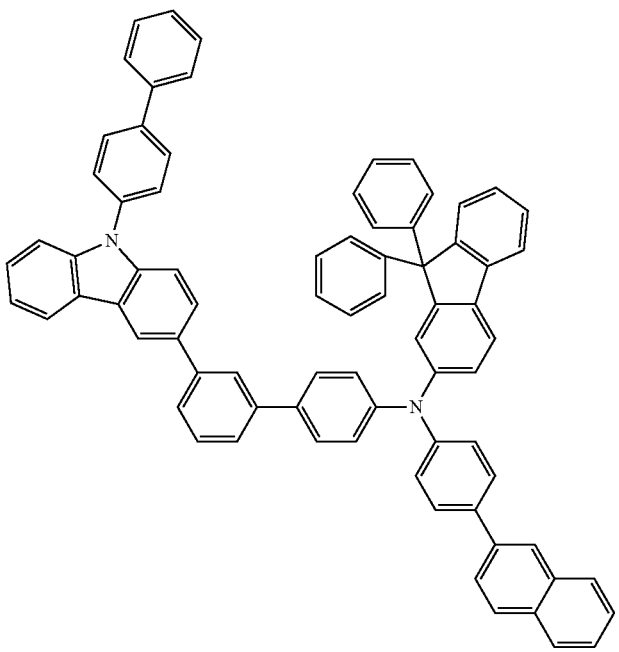

-continued
| 469 | 470 |
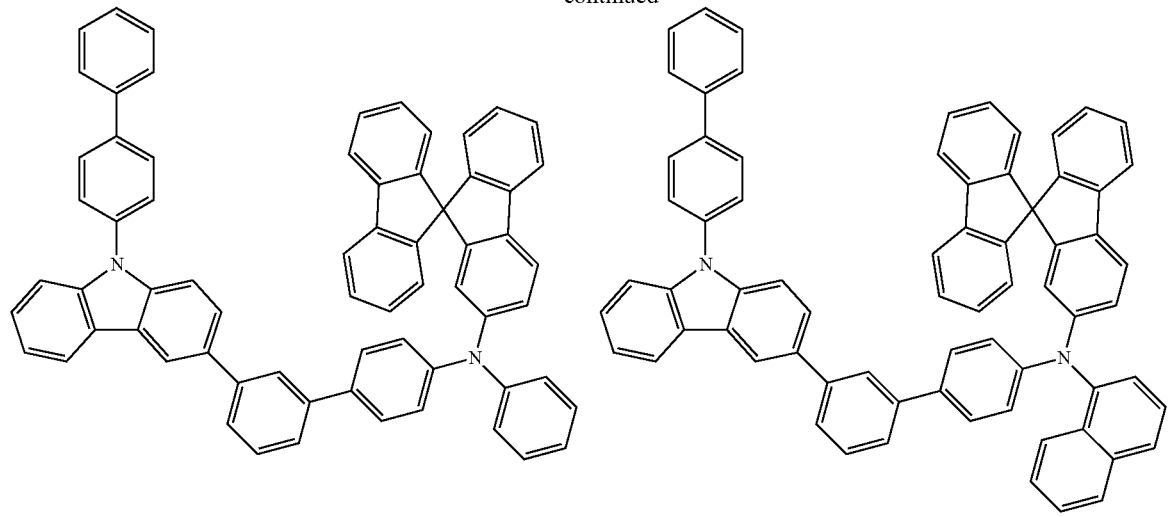
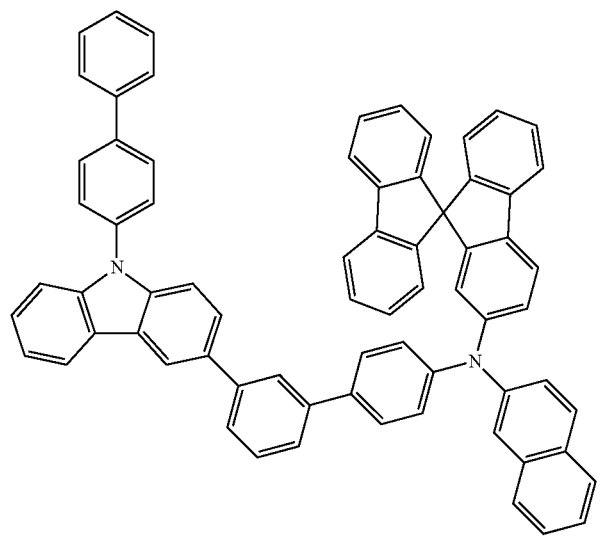
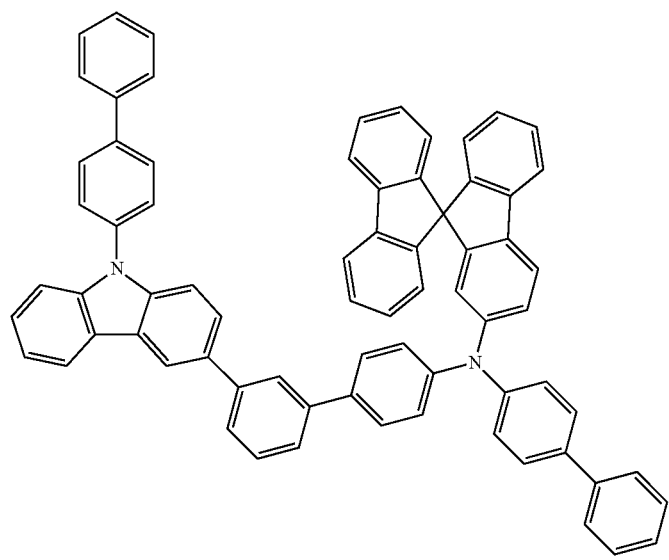

-continued
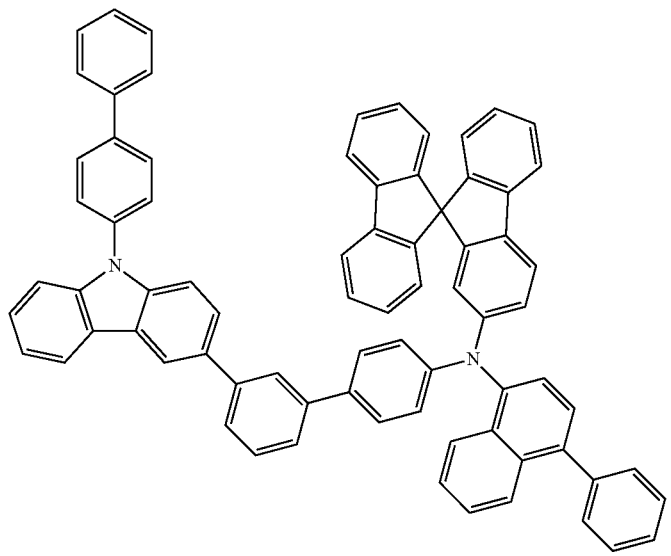
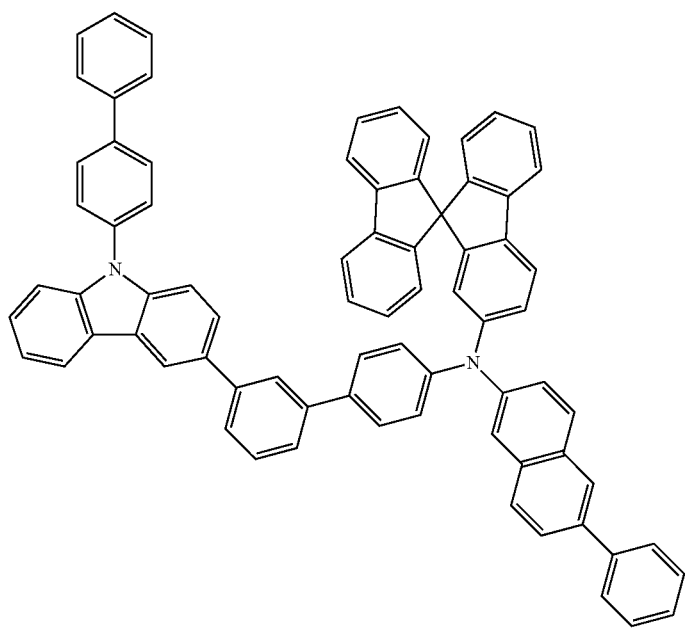

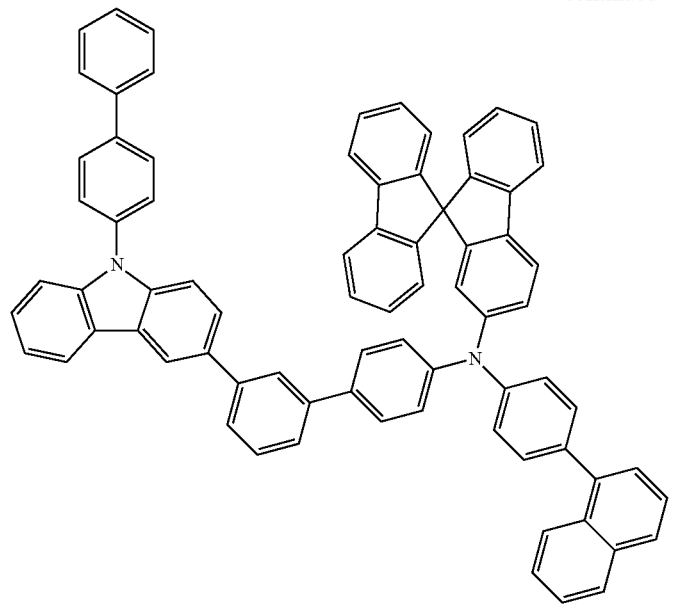
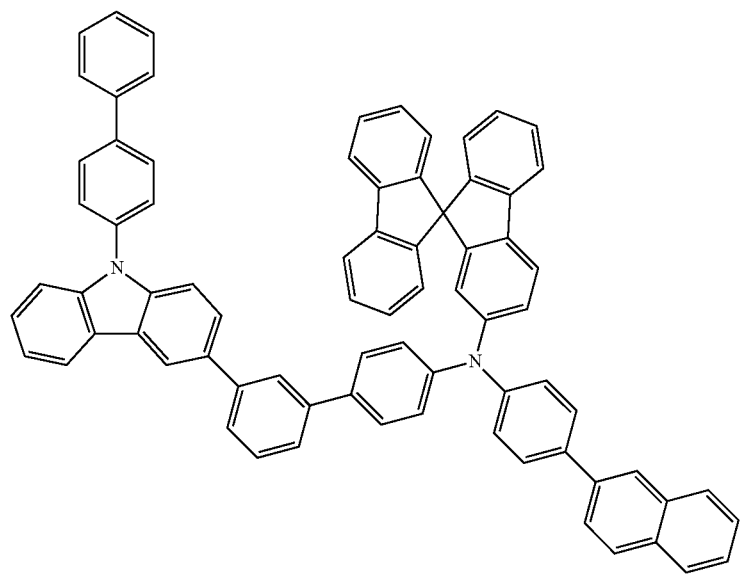
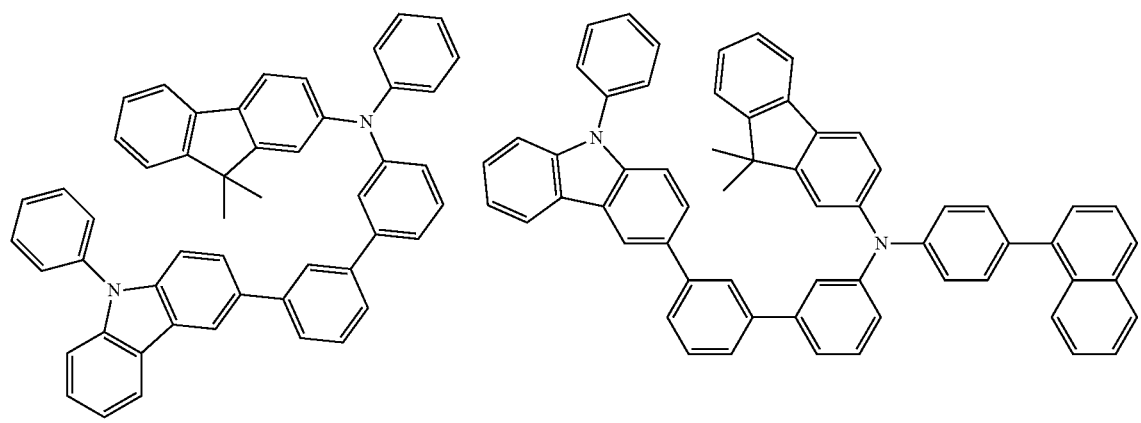

-continued
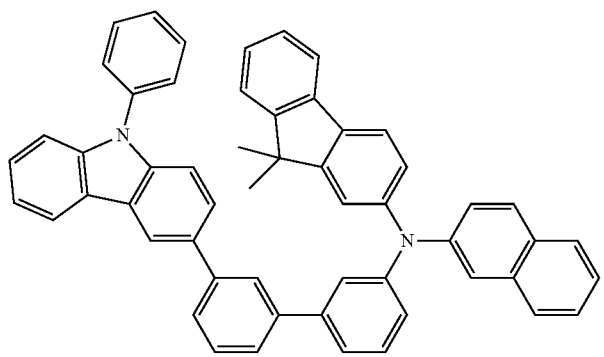
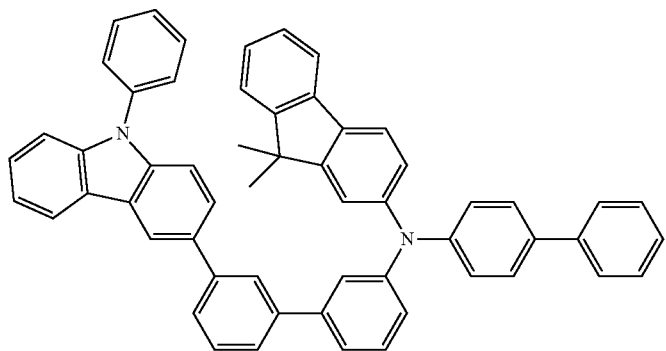
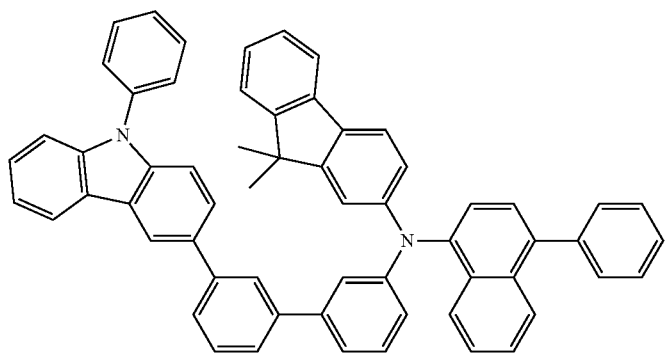
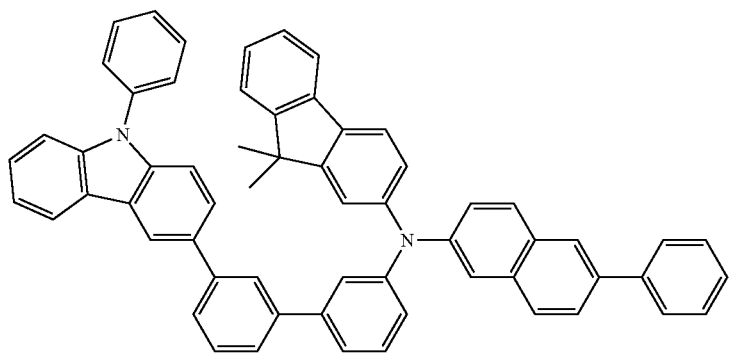

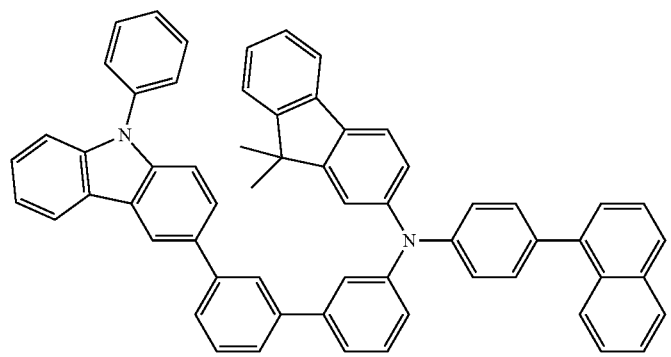
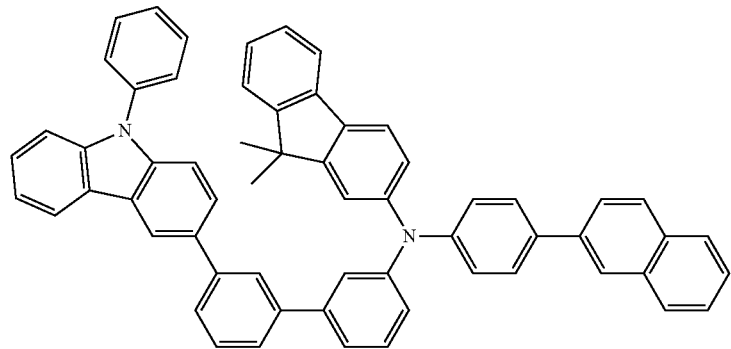
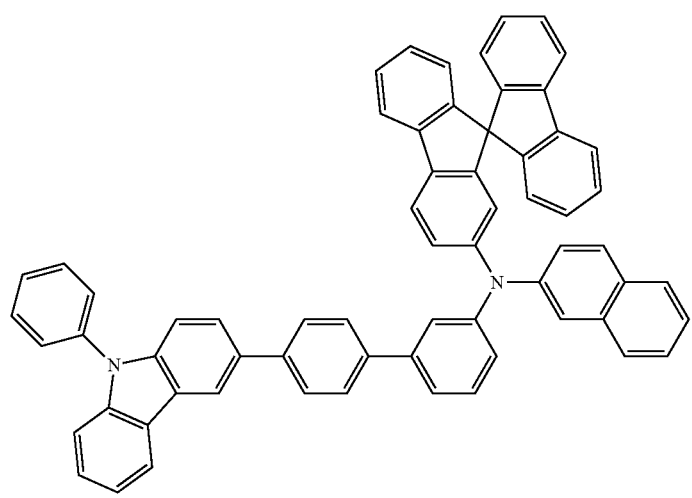
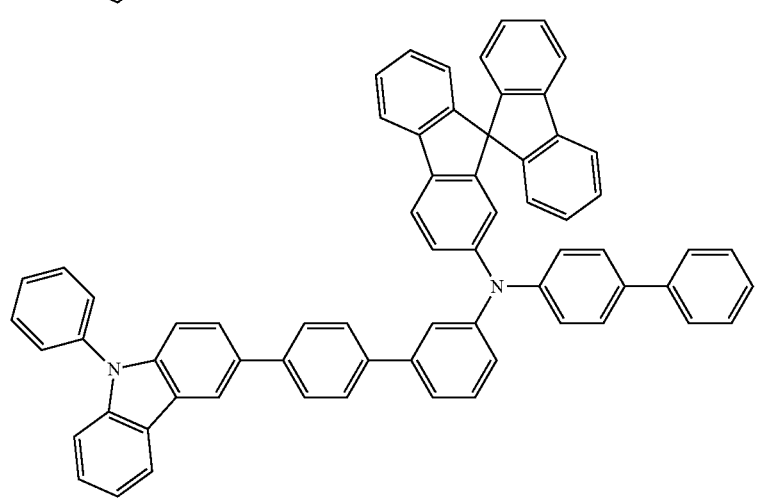

-continued
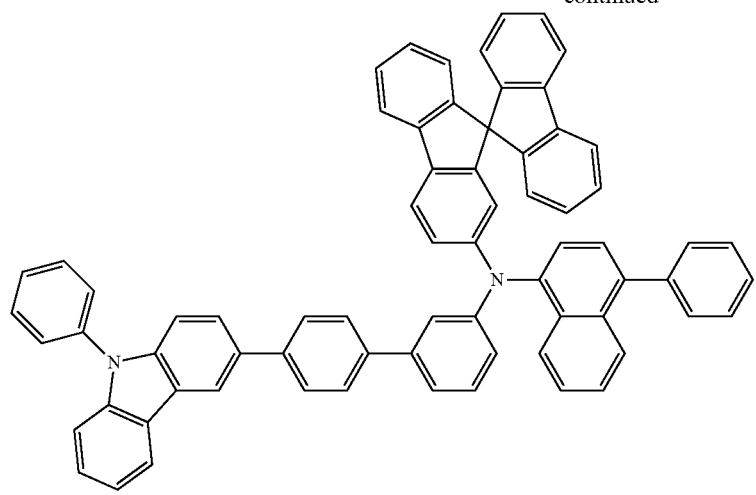
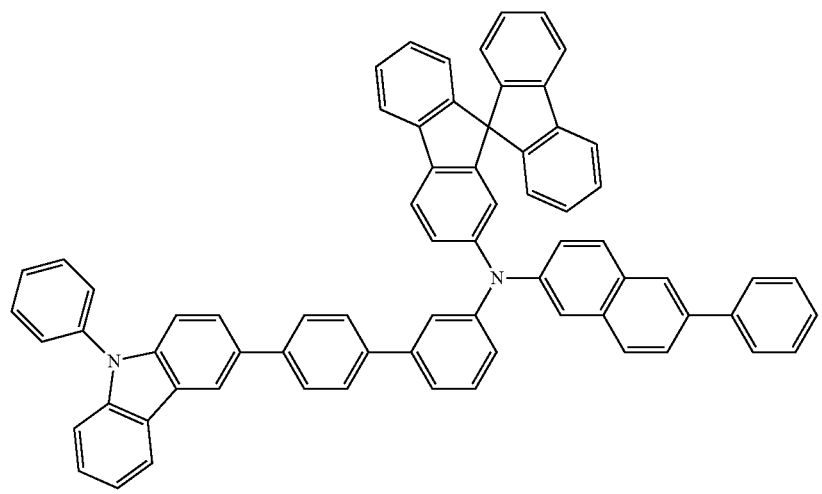
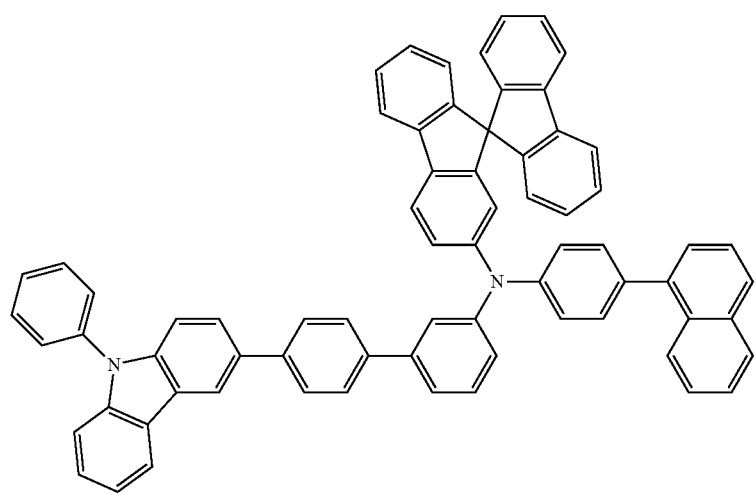

-continued
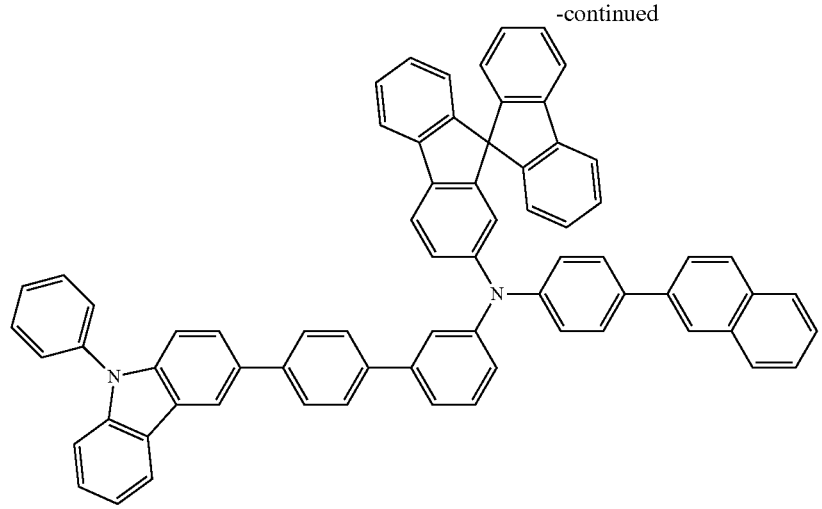
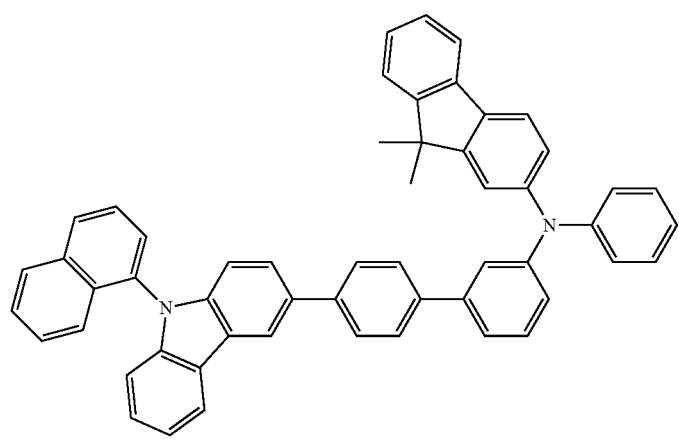
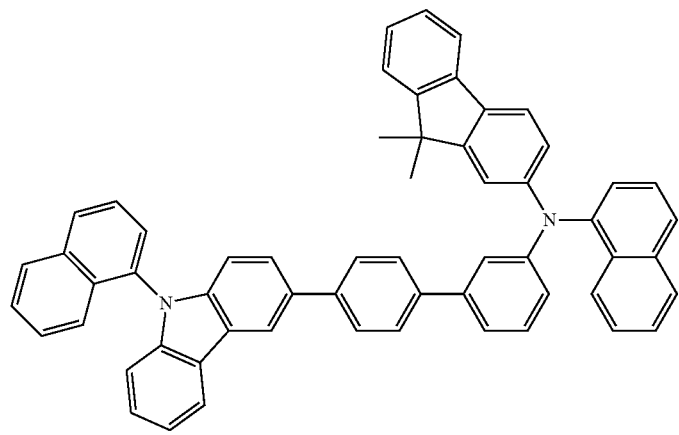

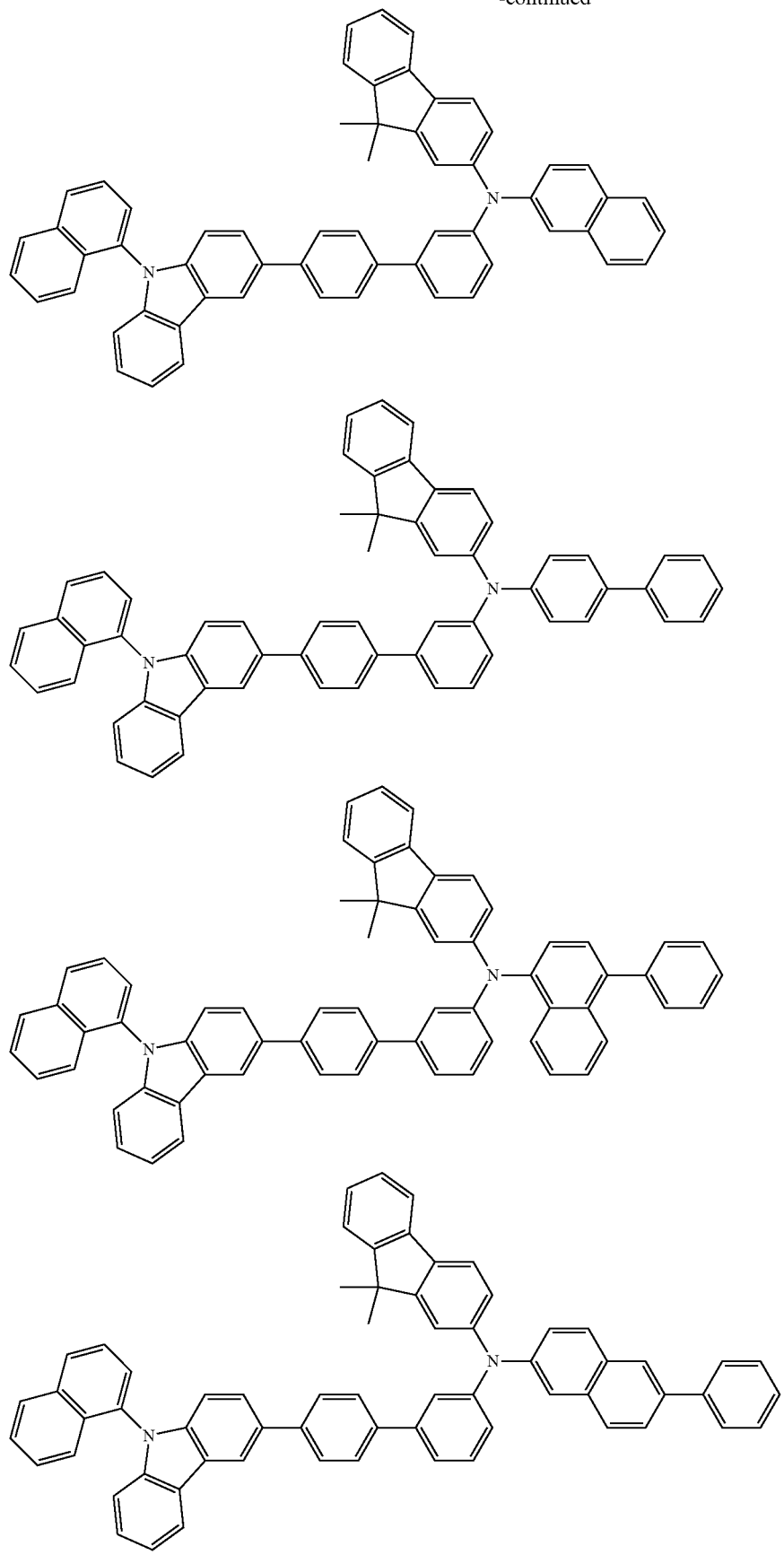

-continued
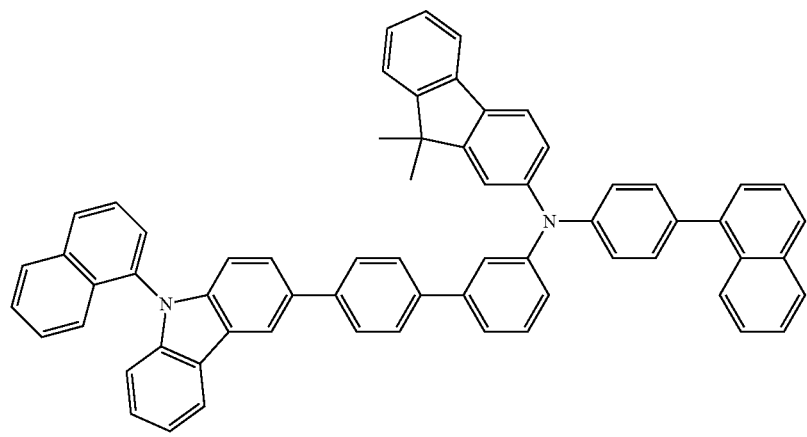
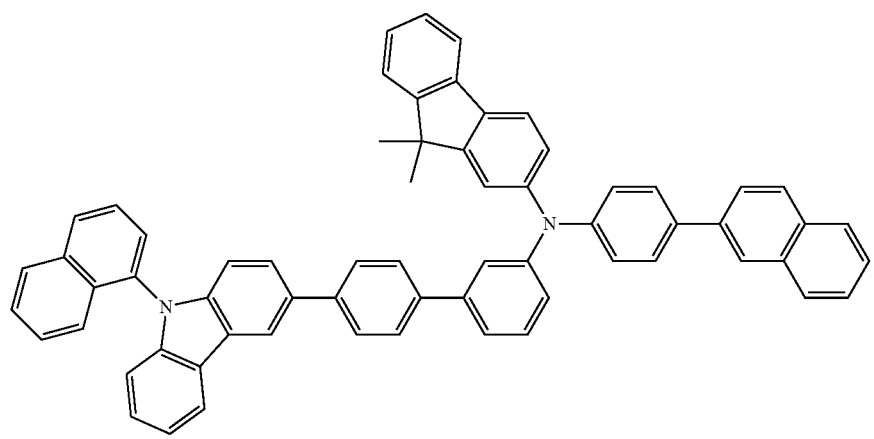
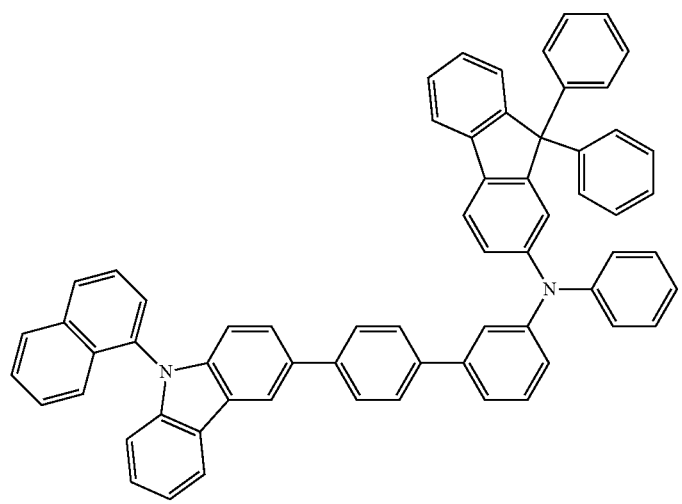

-continued
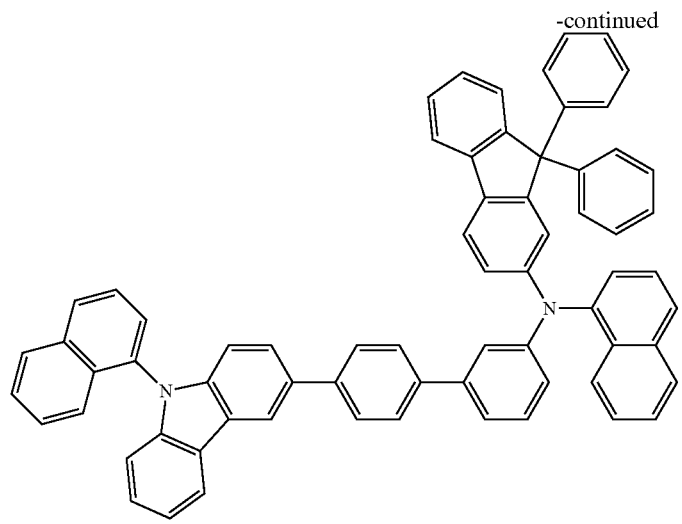
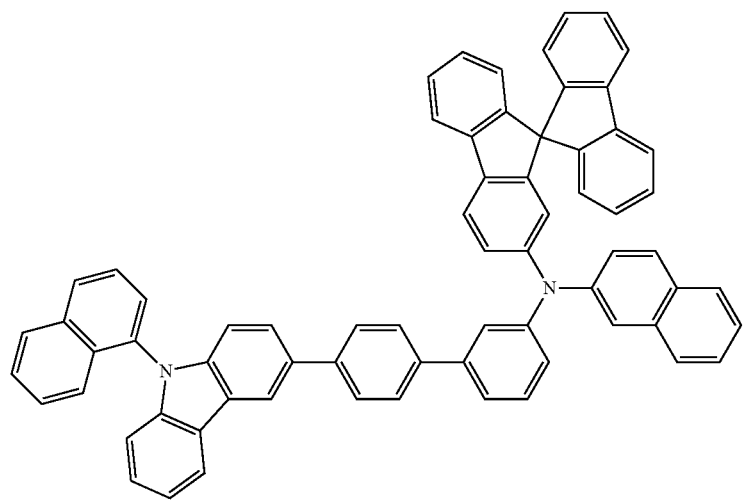
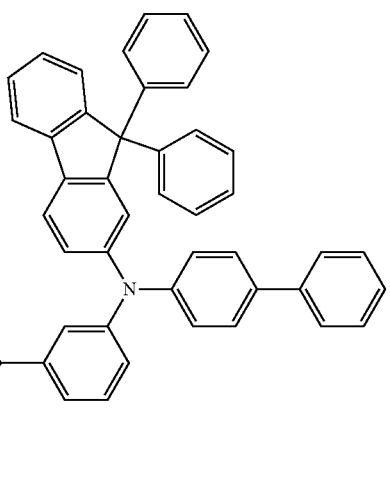

-continued
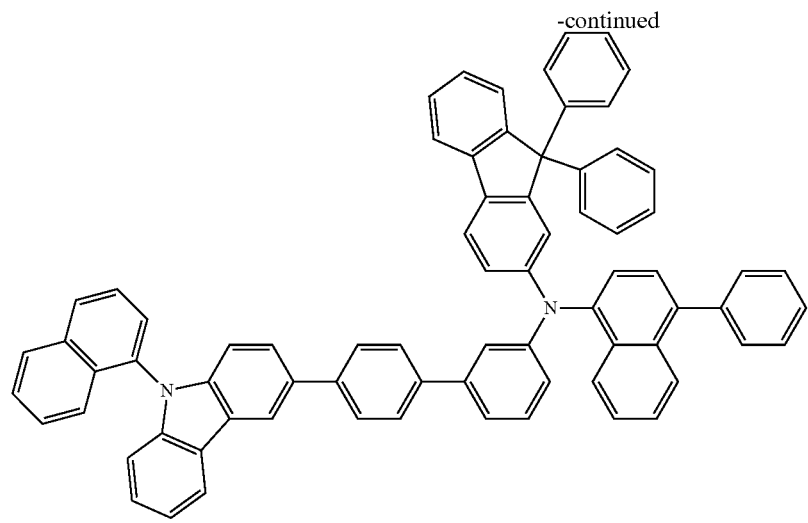
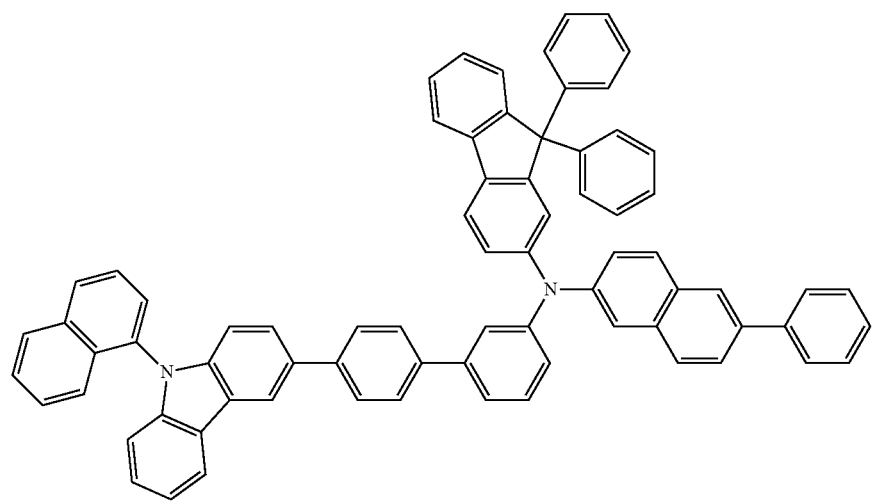
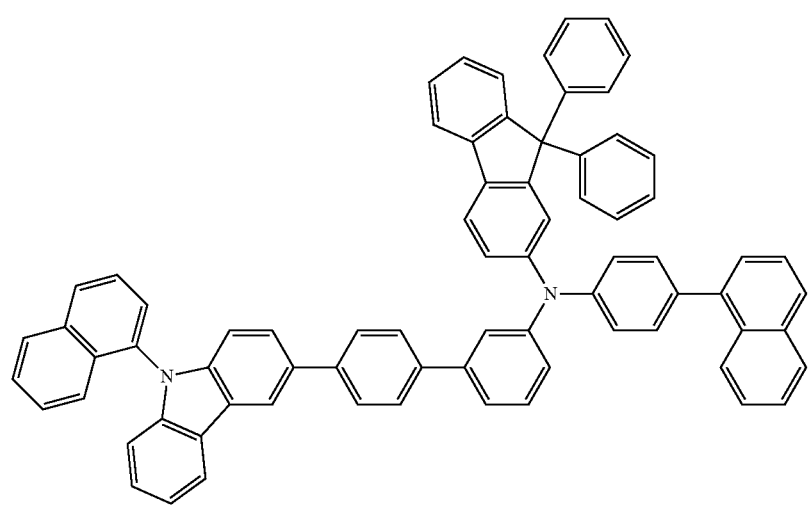

-continued
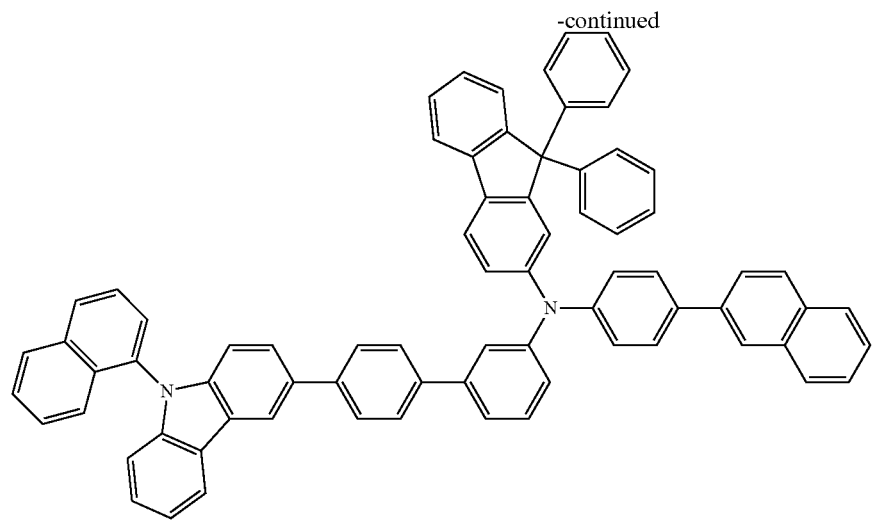
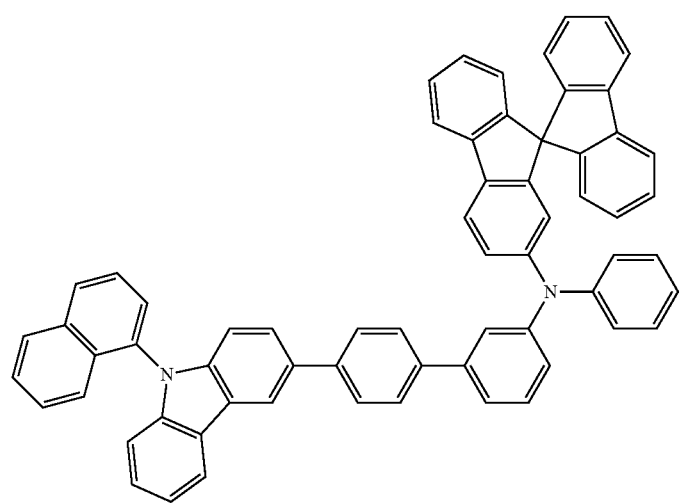
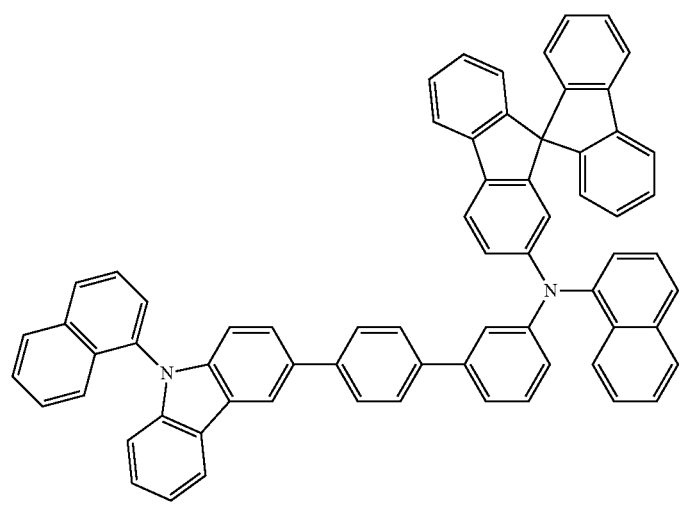

-continued
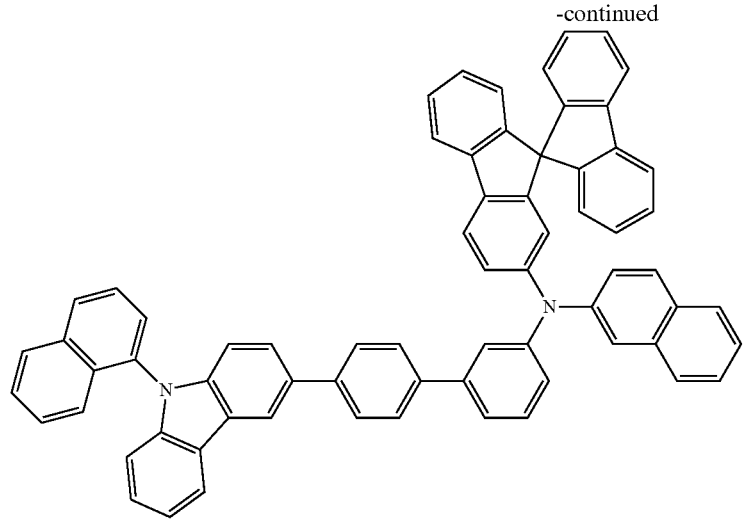
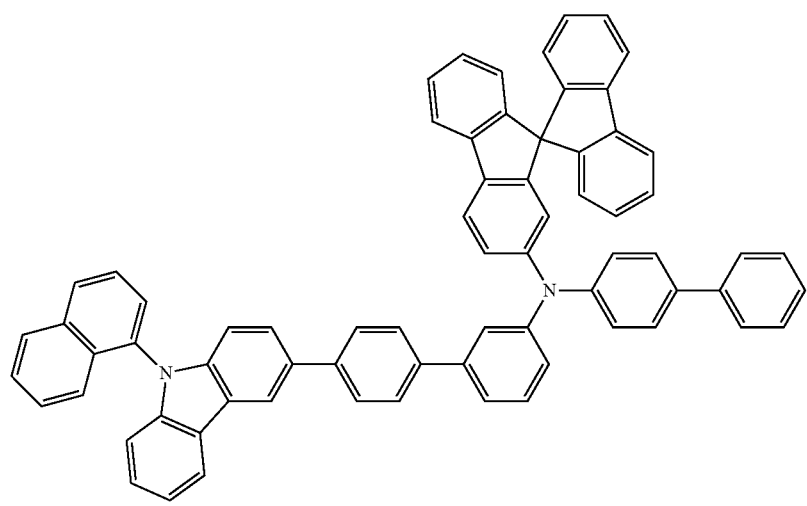
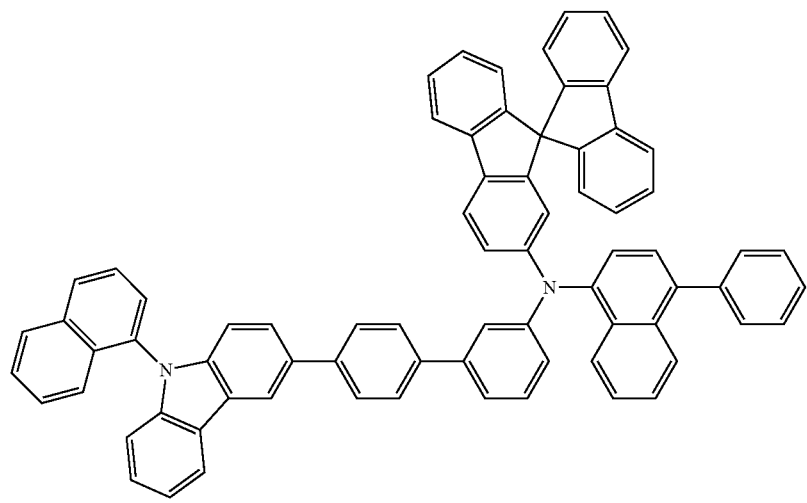

-continued
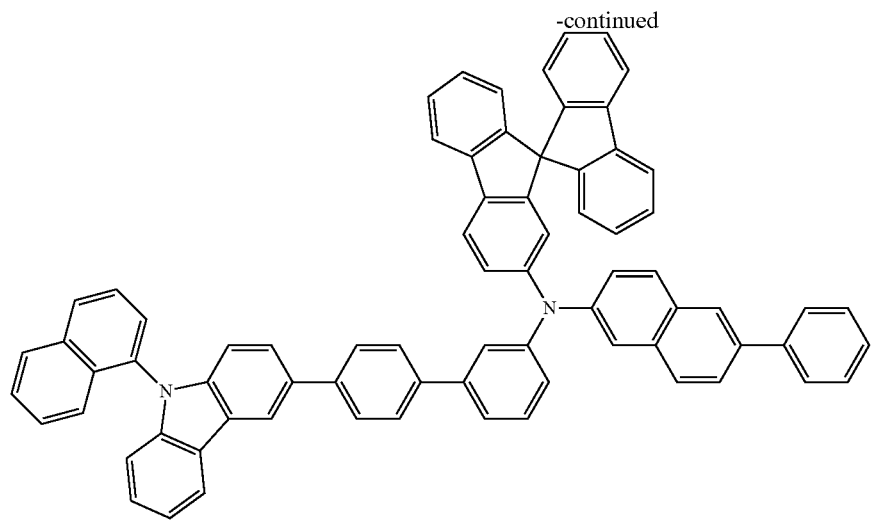
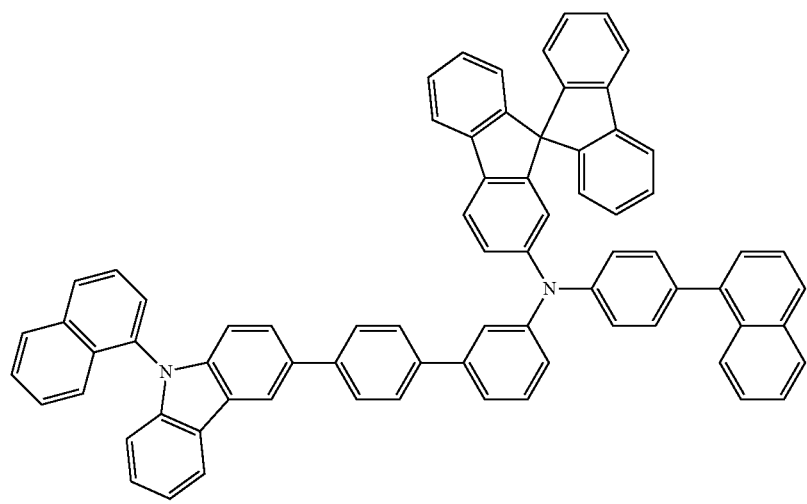
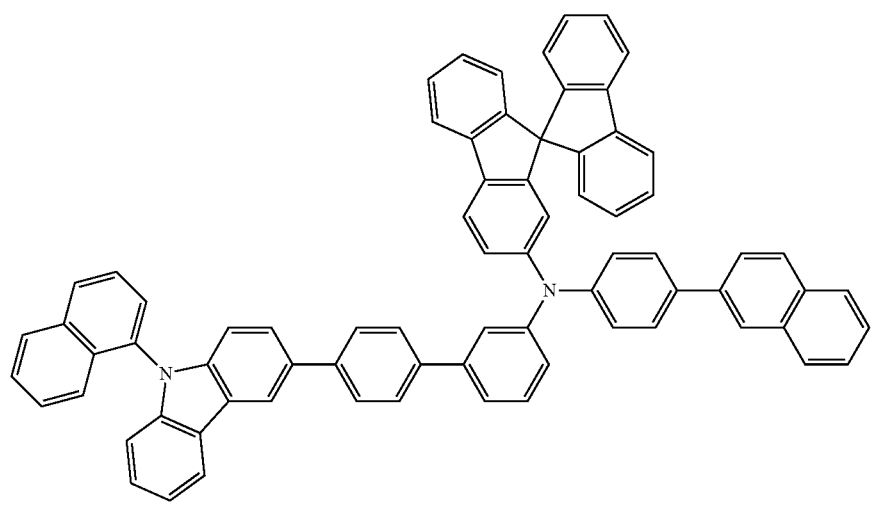

-continued
497
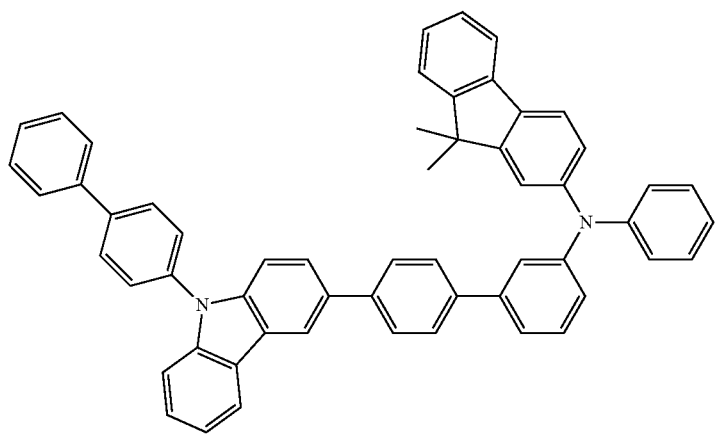
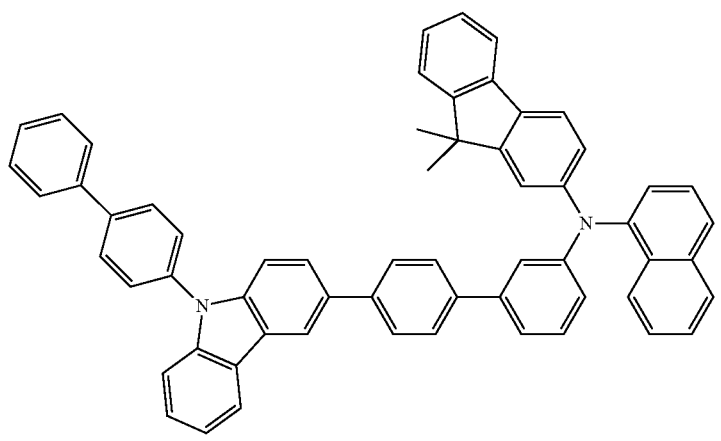
498
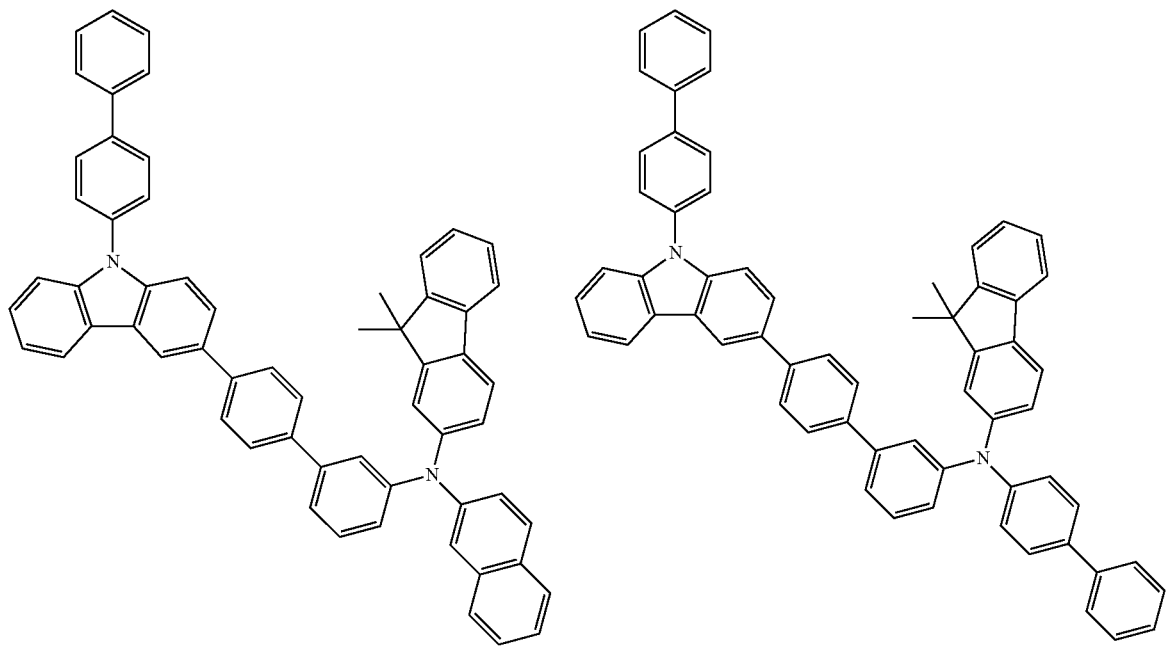

499
500
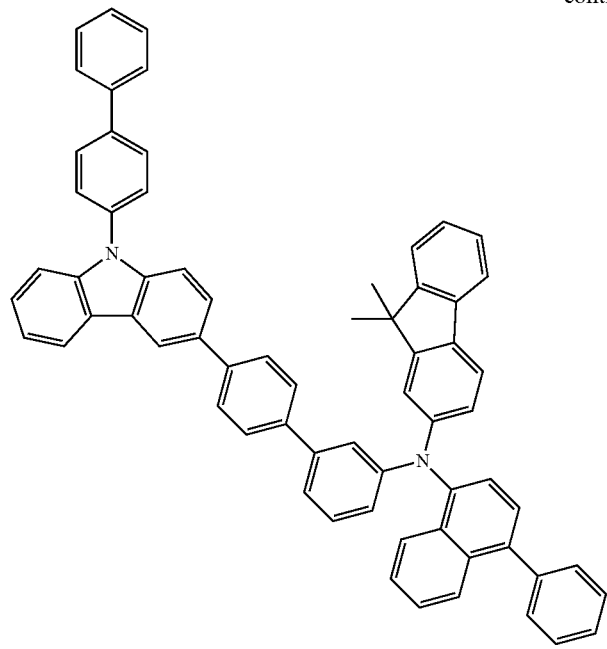
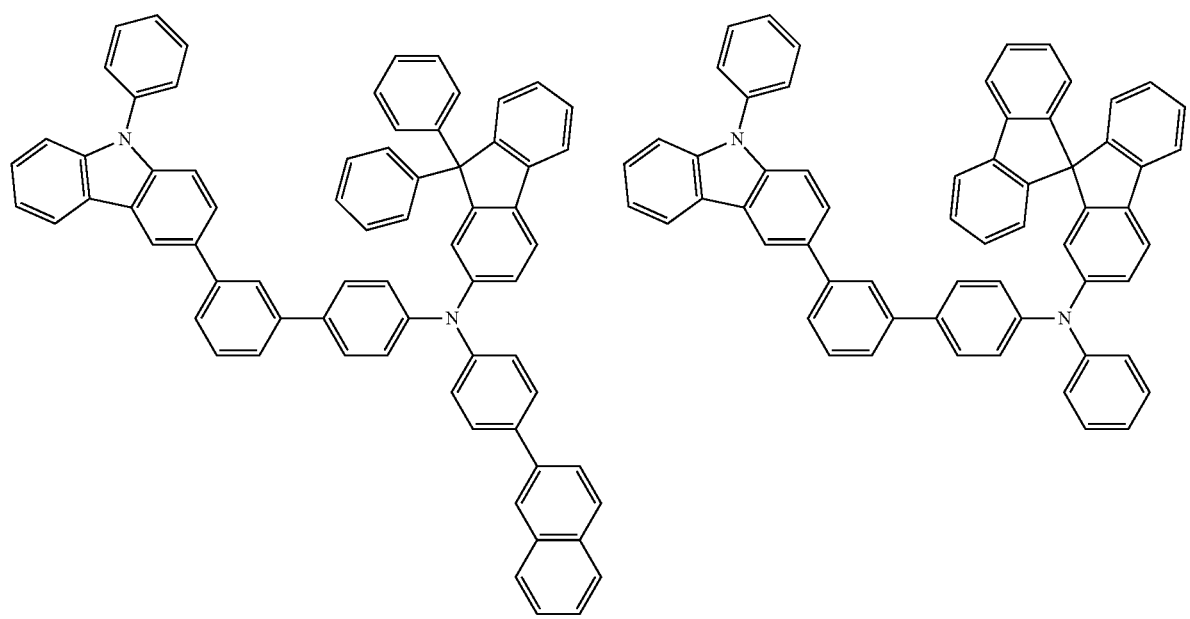

-continued
501
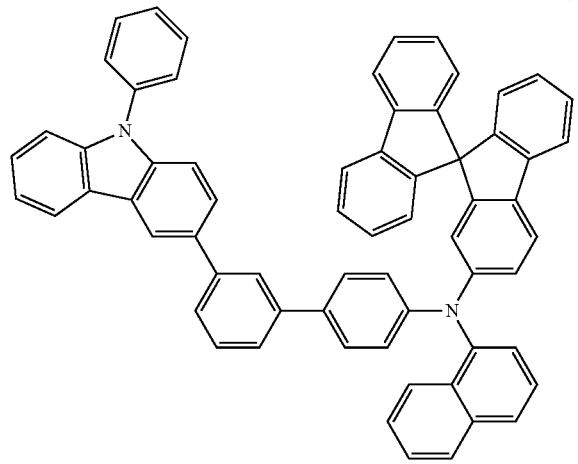
502
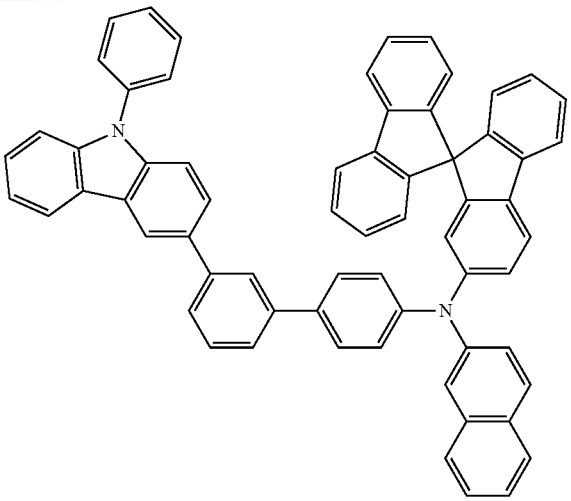
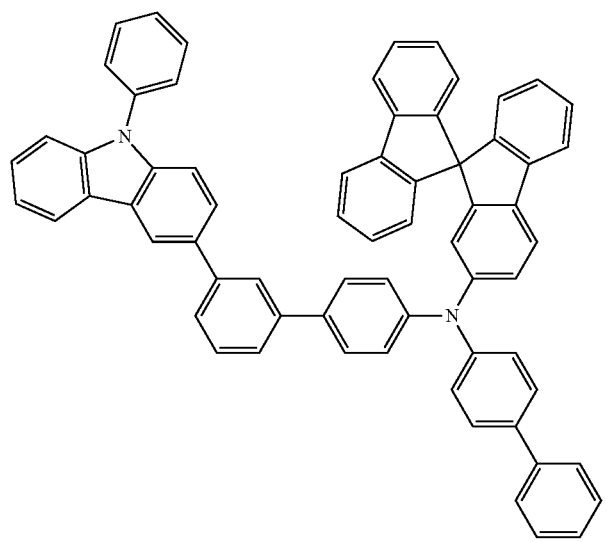
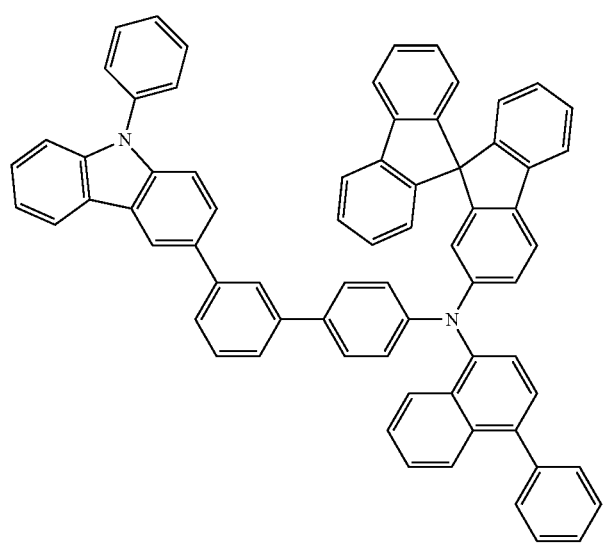

-continued
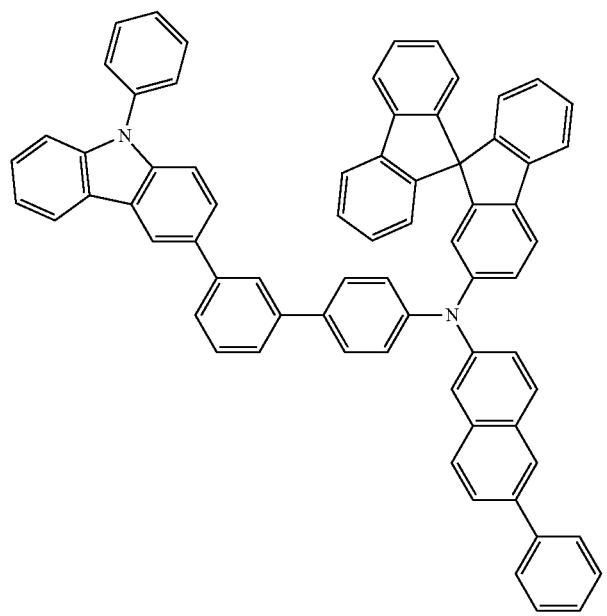
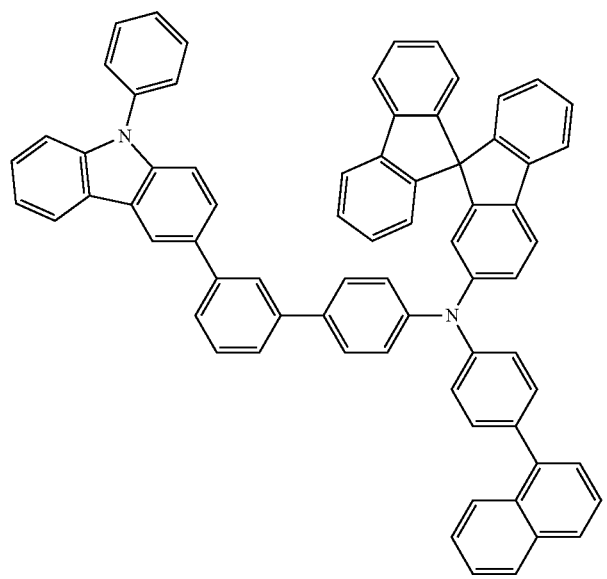
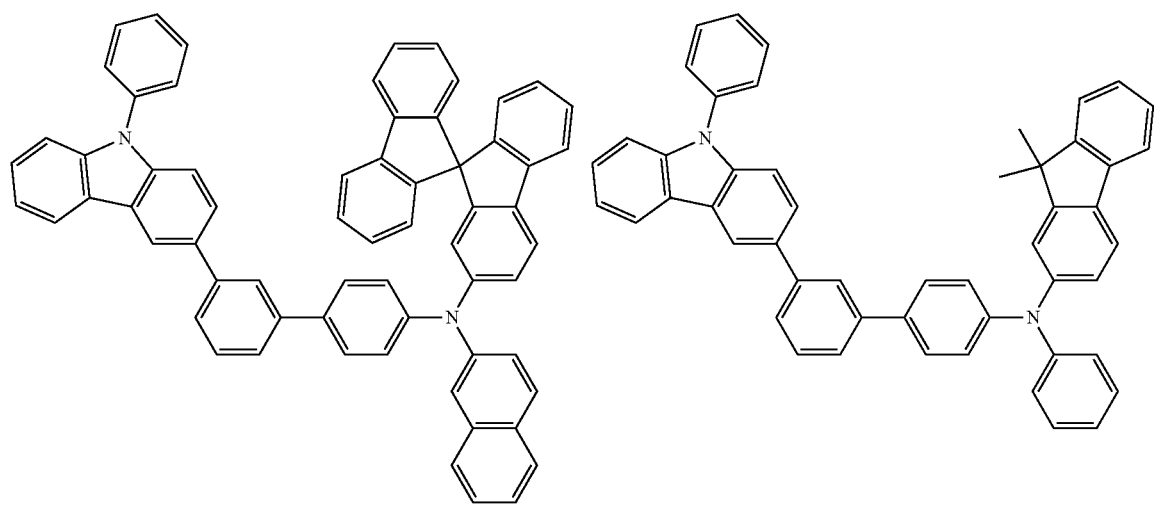

-continued
505
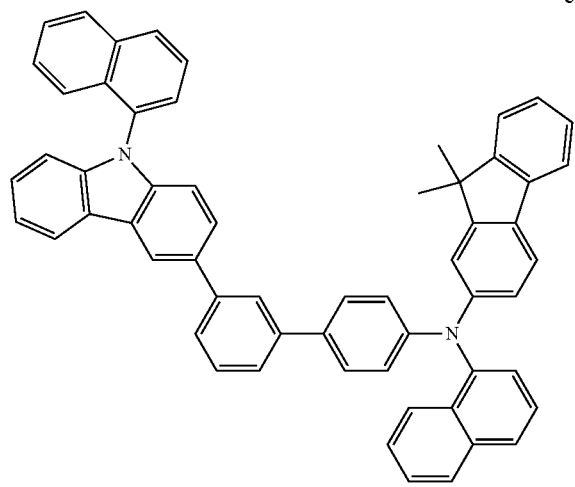
506
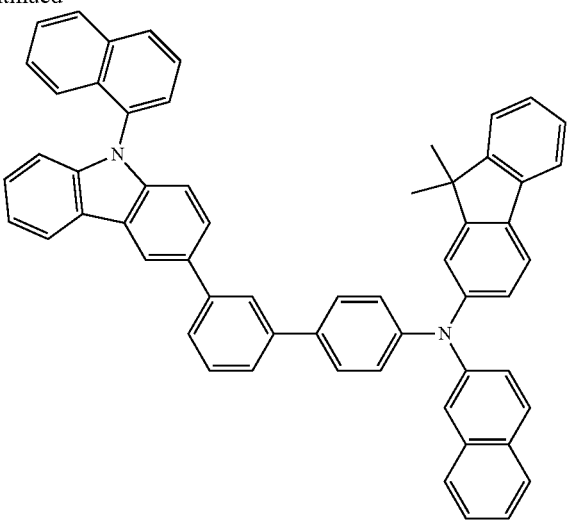
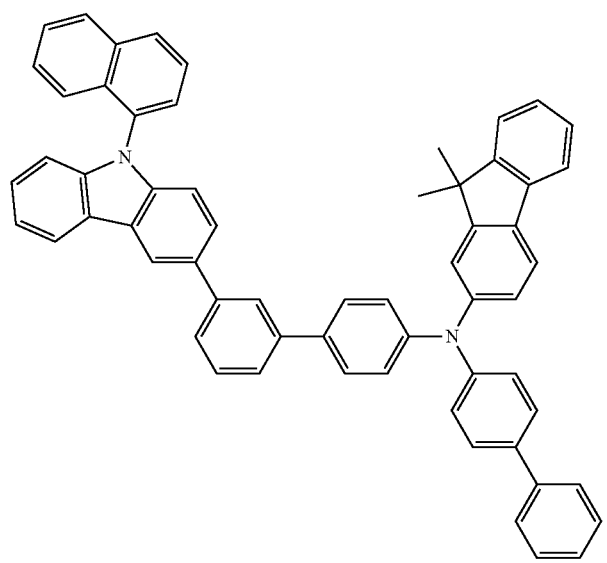
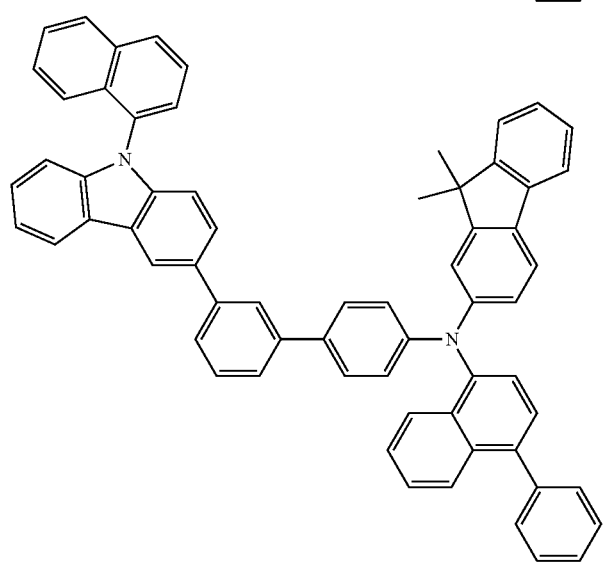

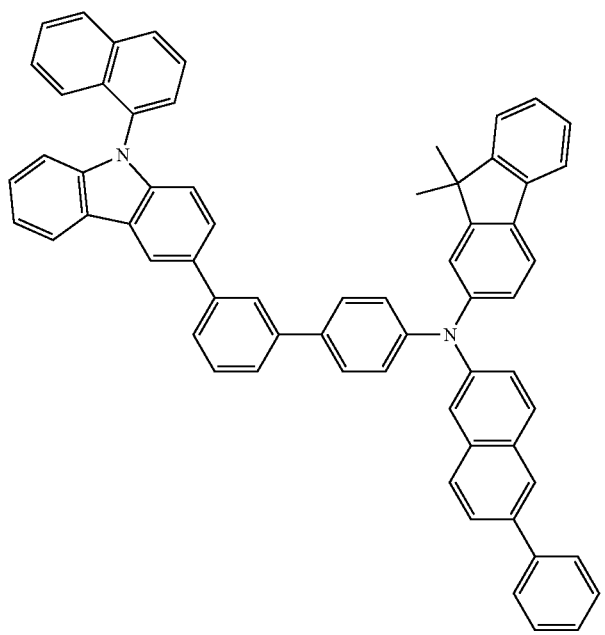
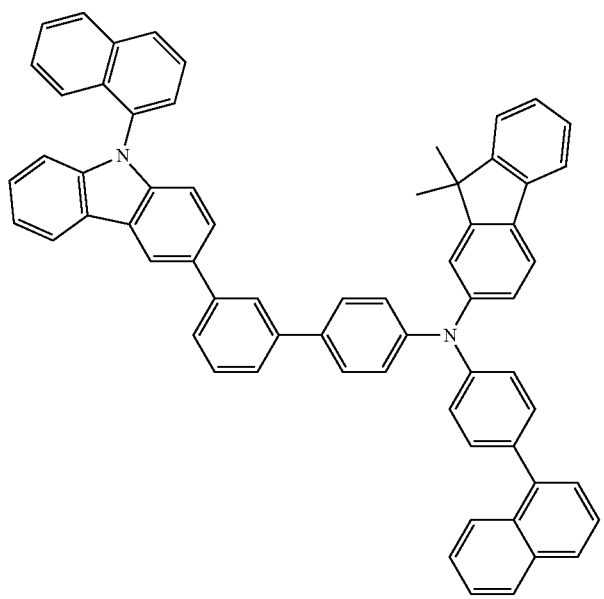

509
510
-continued
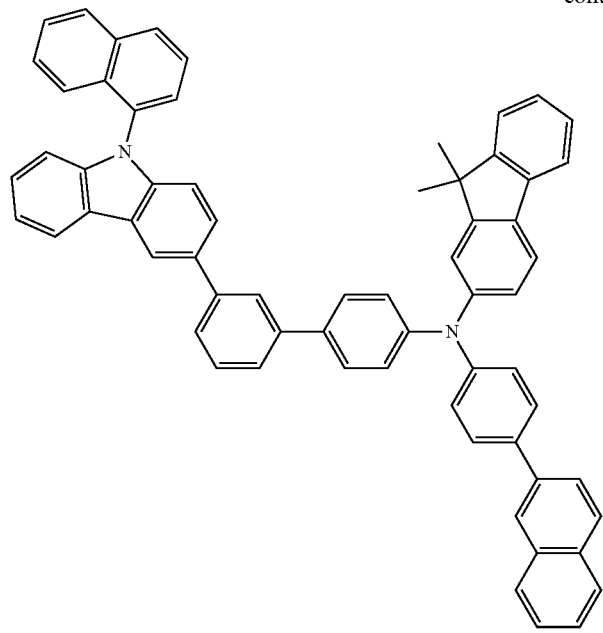
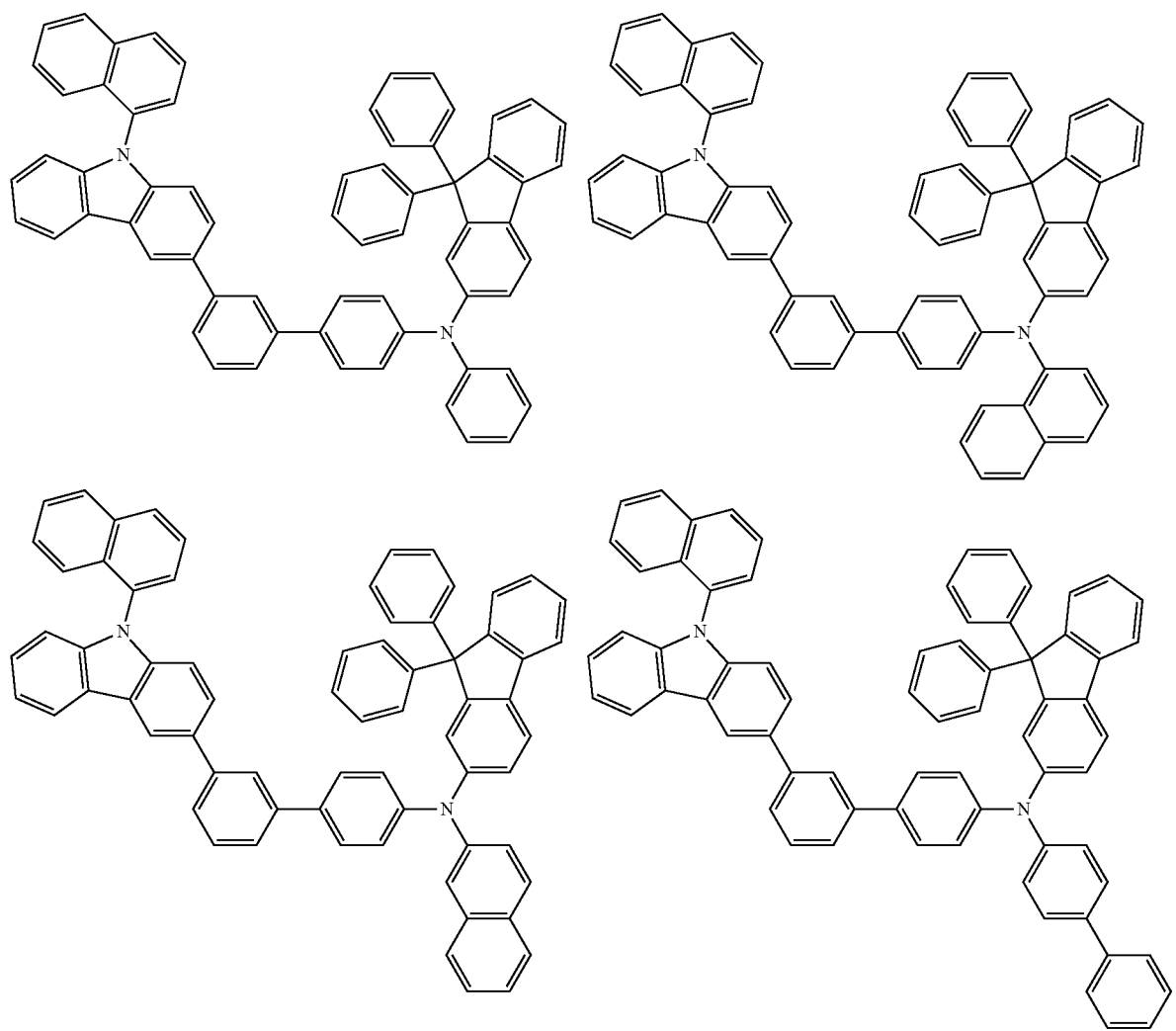

-continued
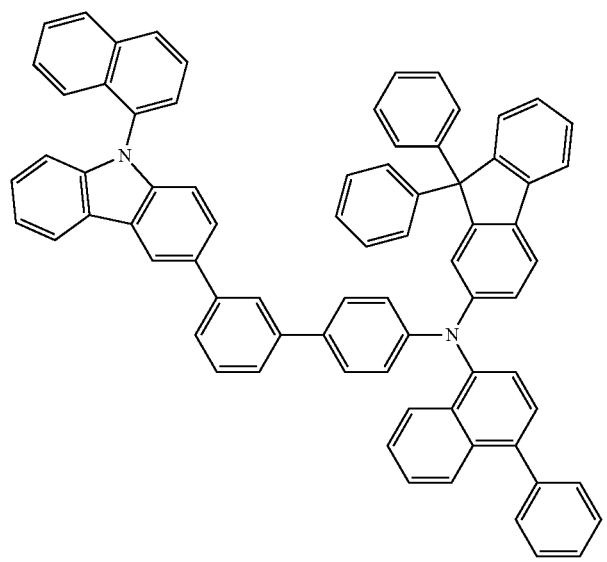
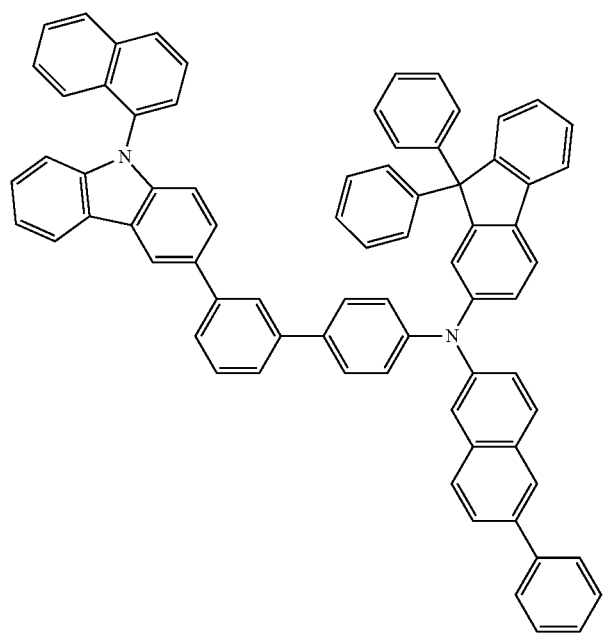

513
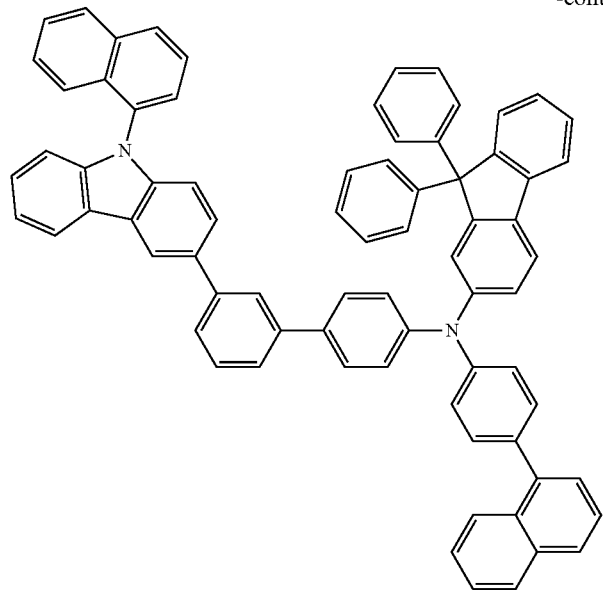
514
-continued
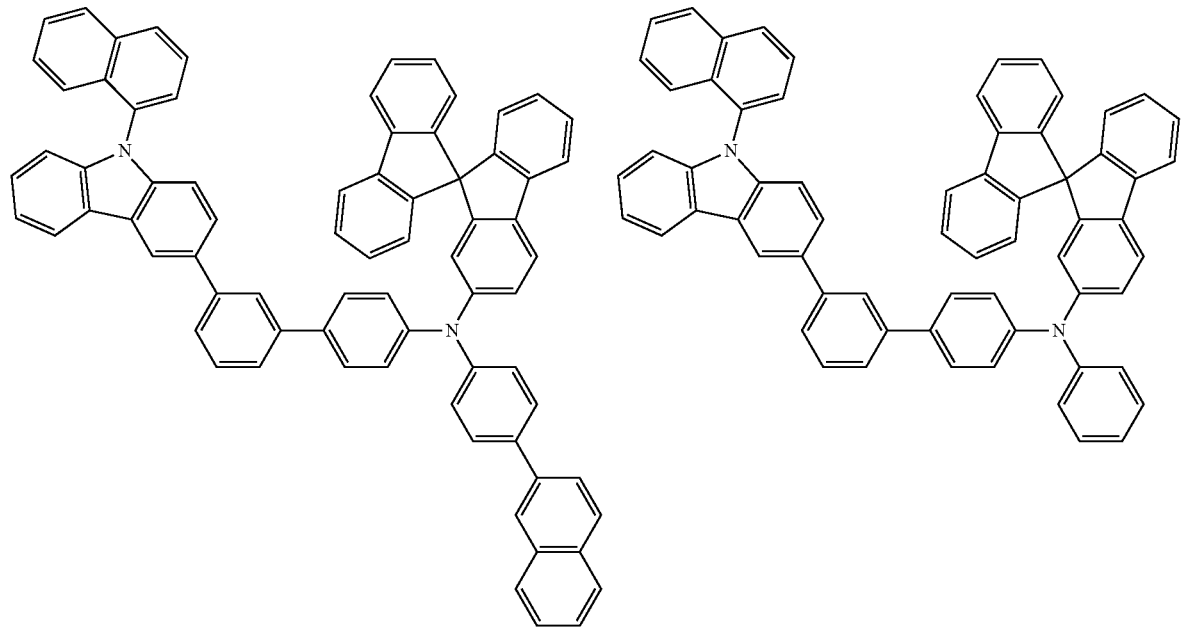
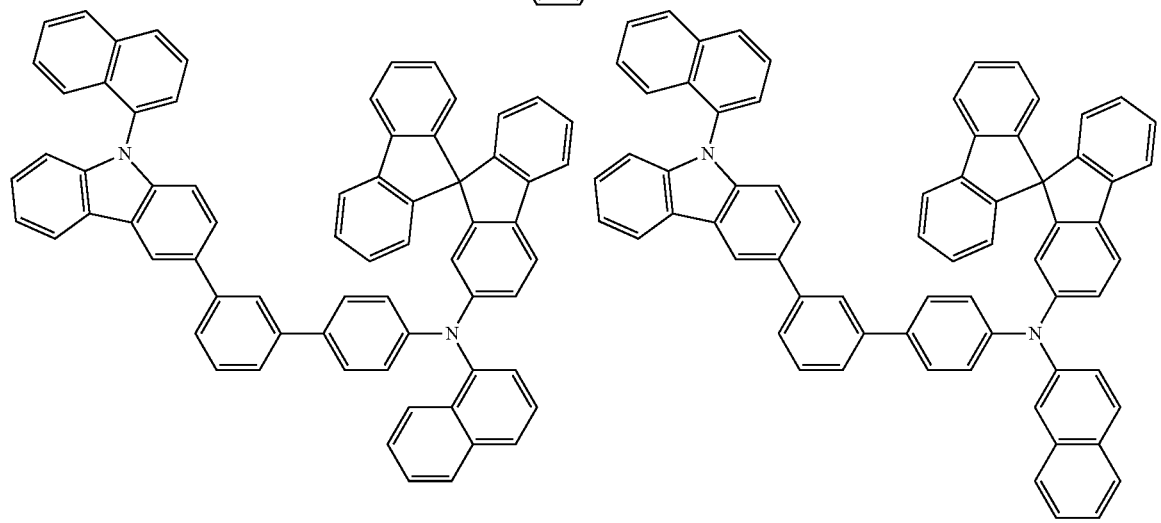

-continued
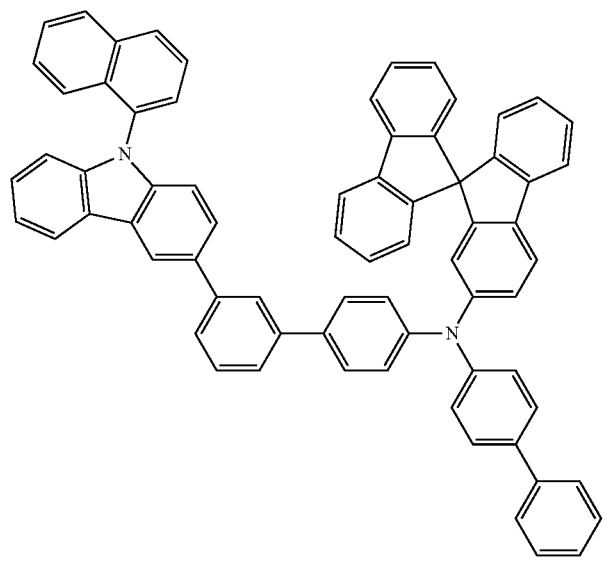
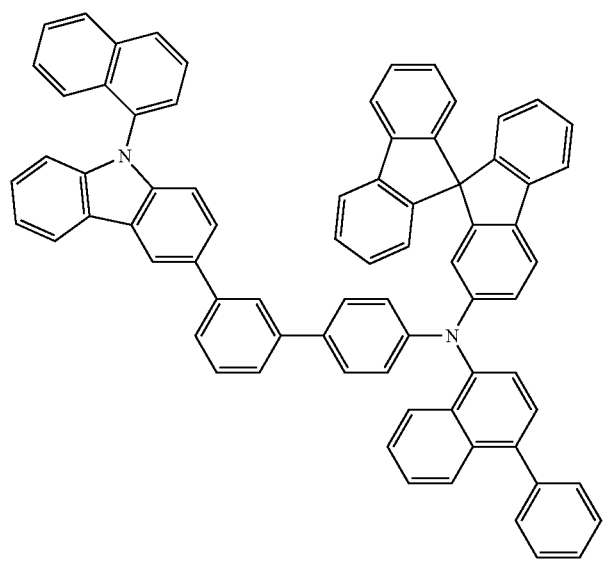

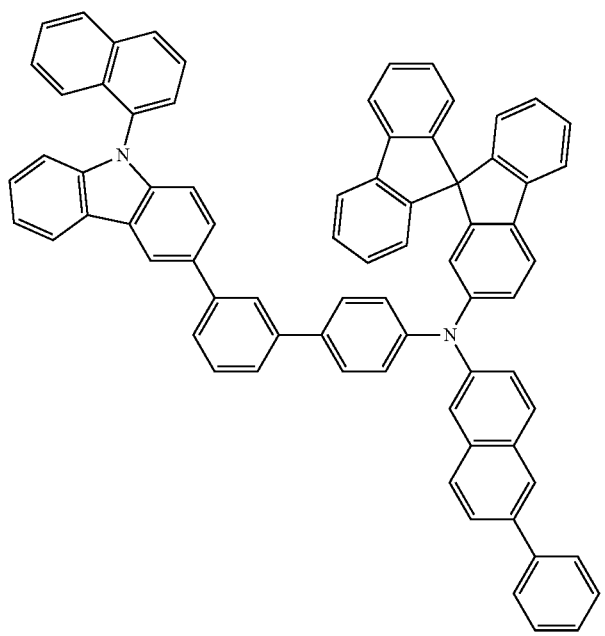
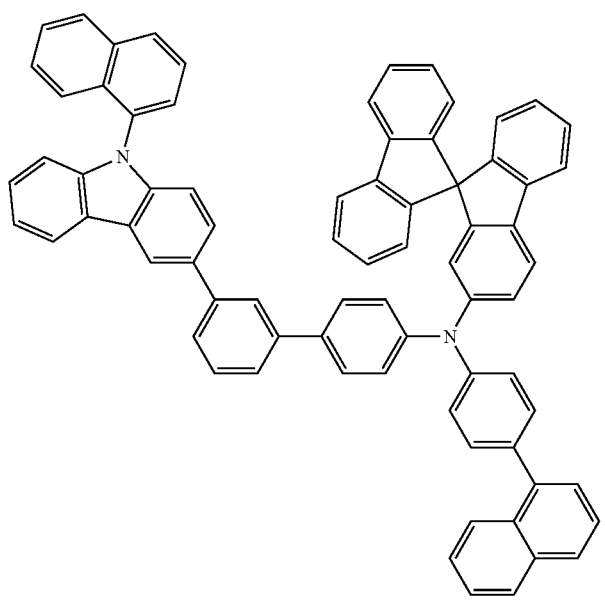

519 520
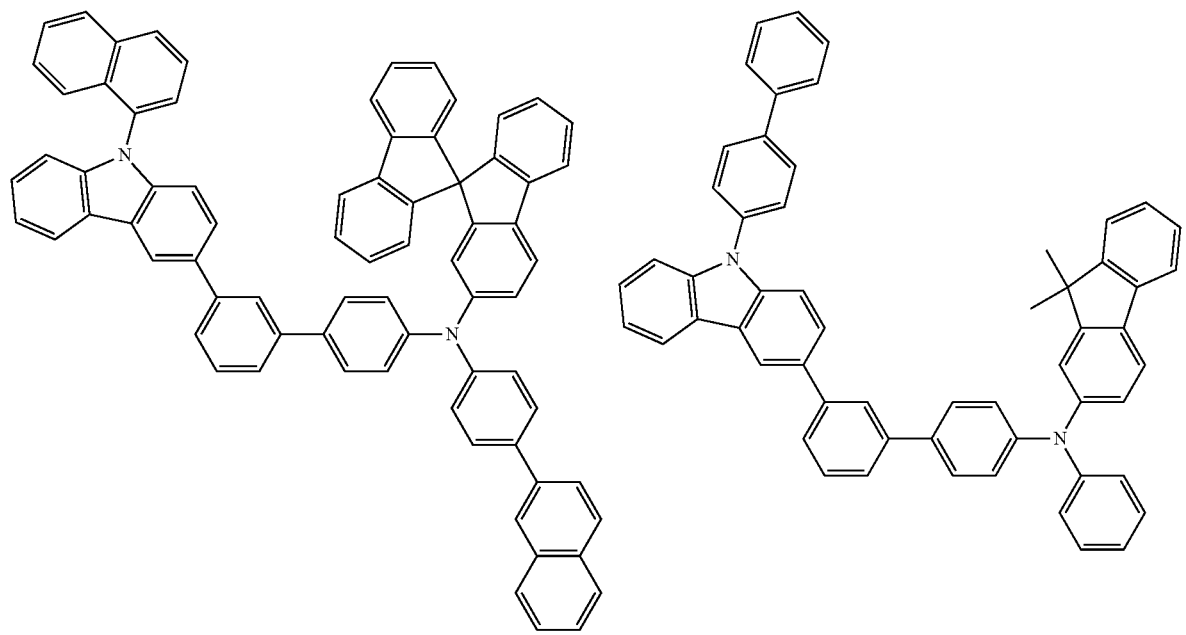
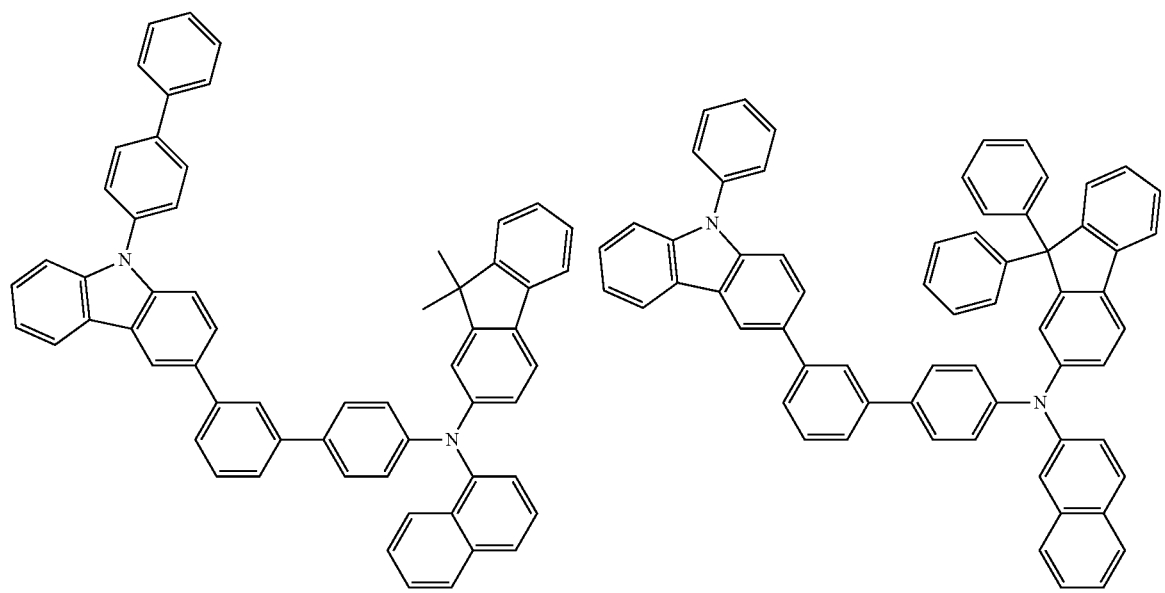

-continued
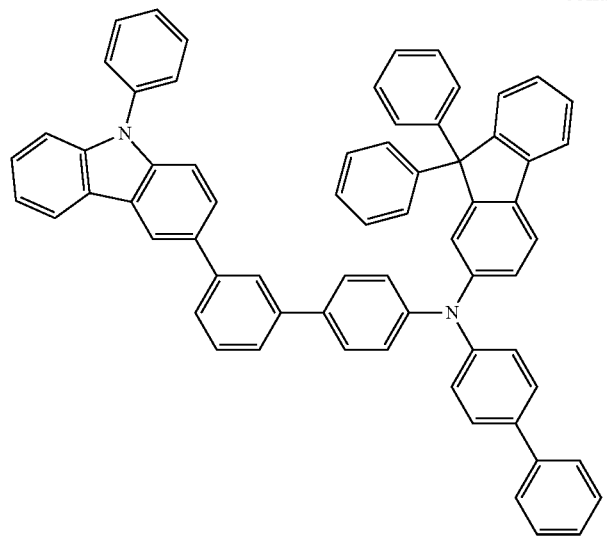
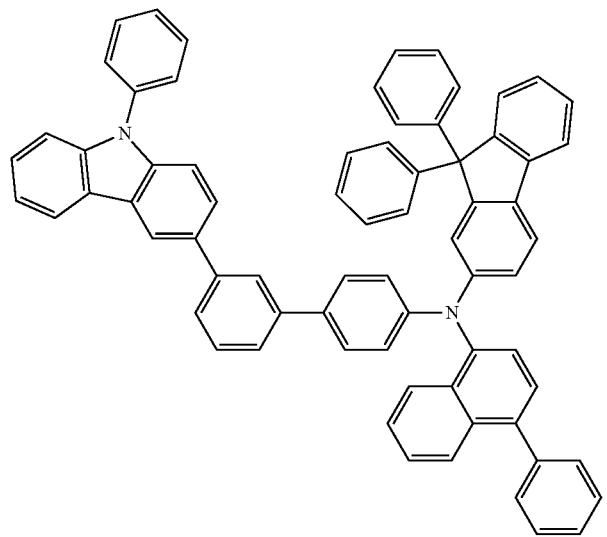
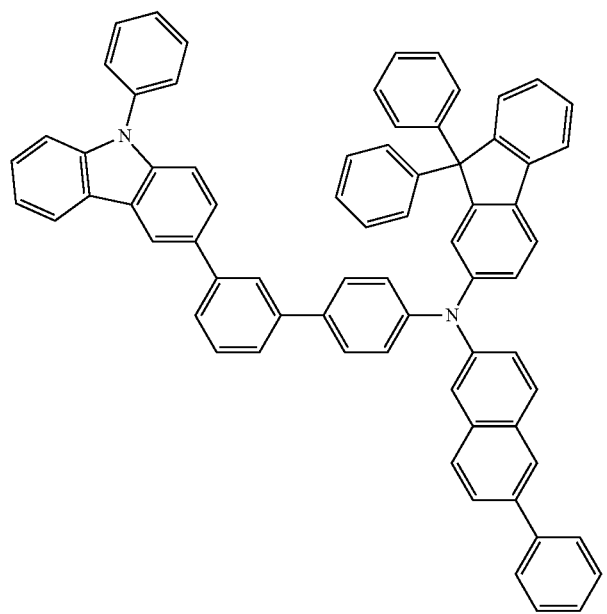

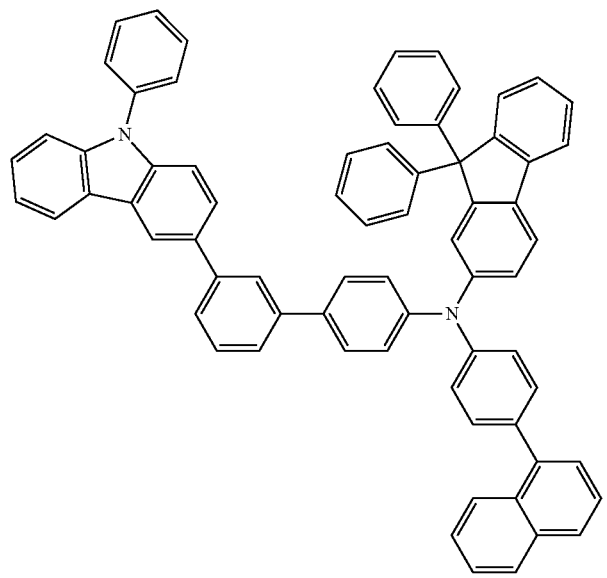
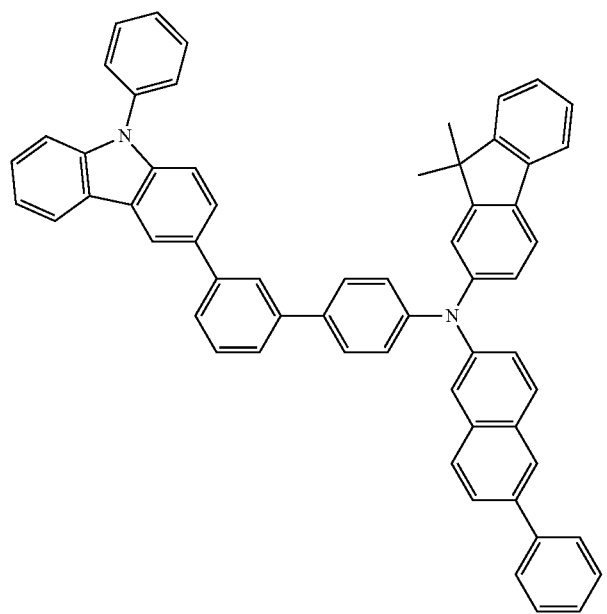

525
-continued
526
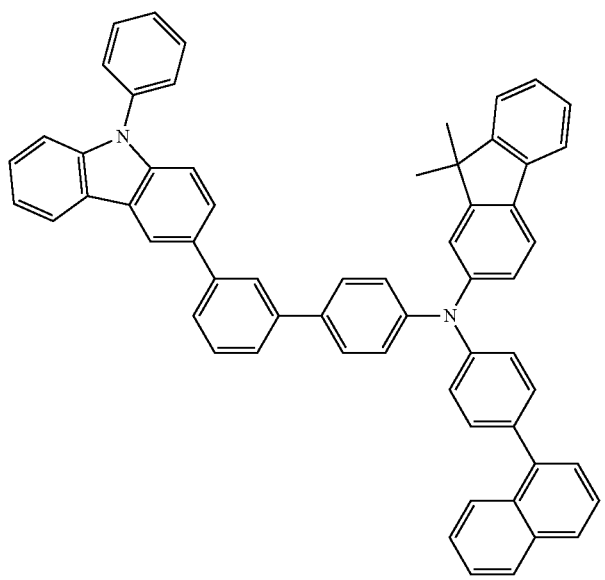
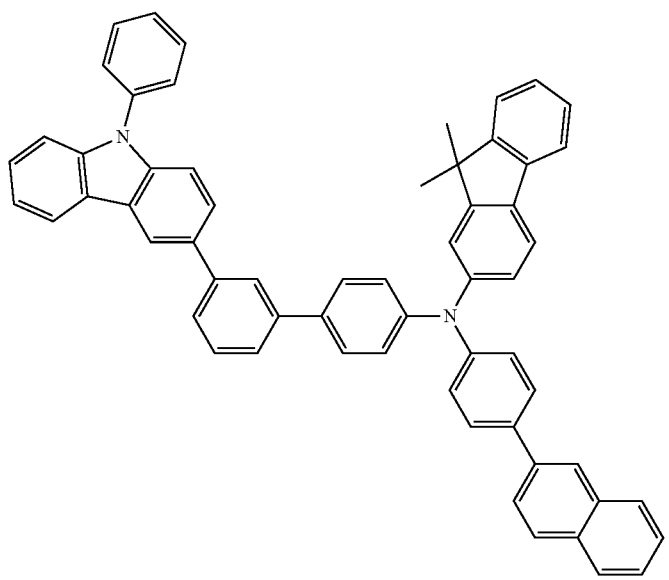
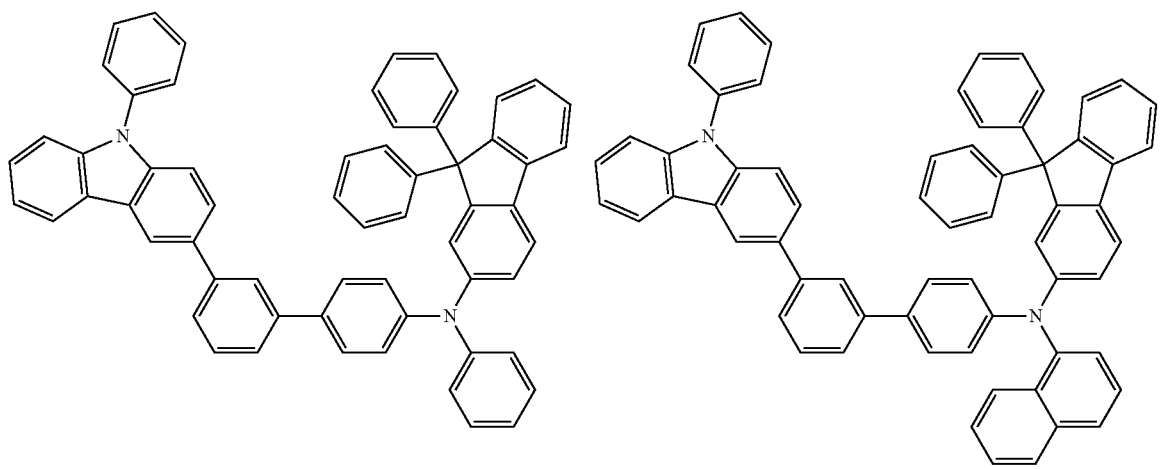

-continued
527 528
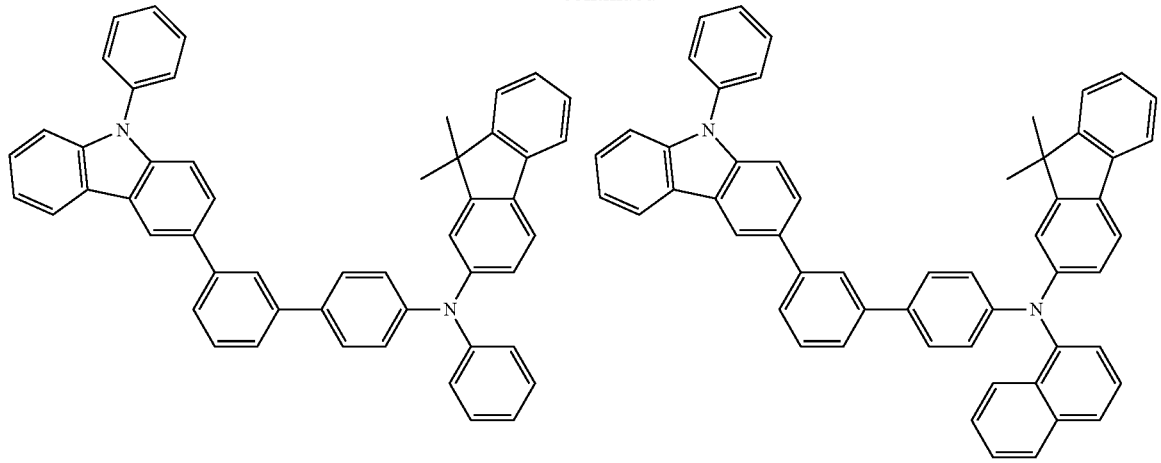
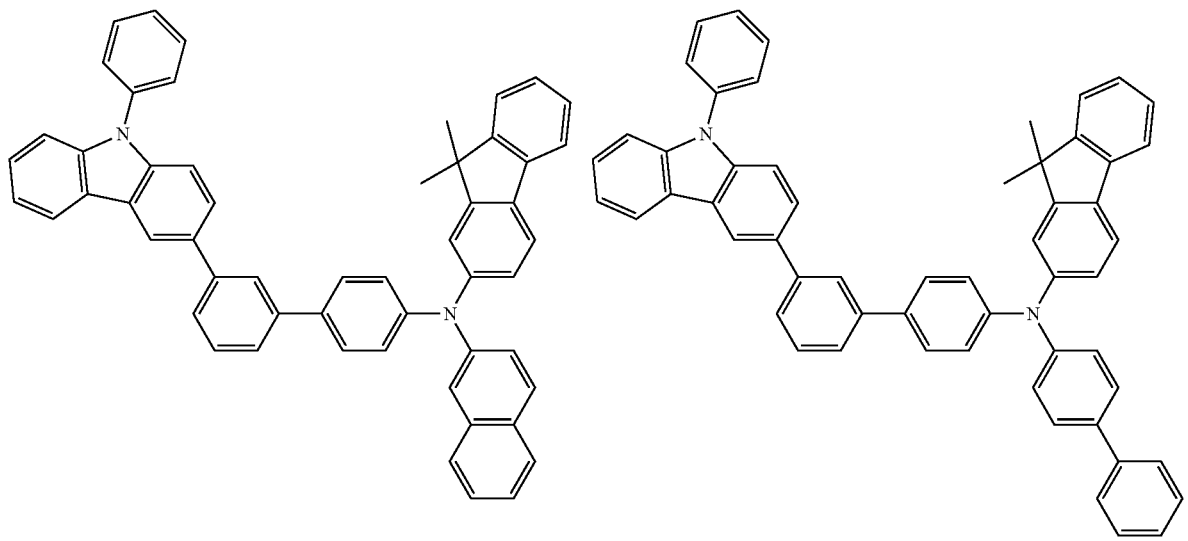
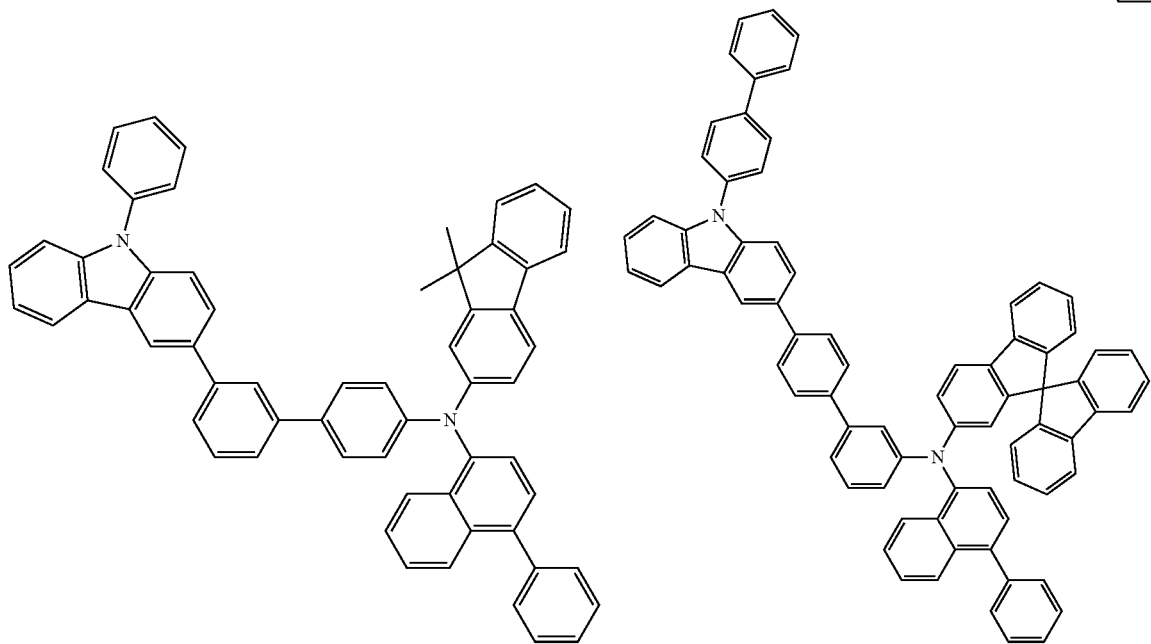

-continued
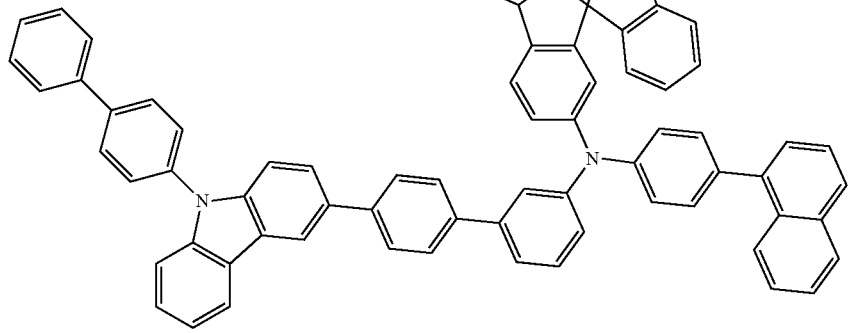
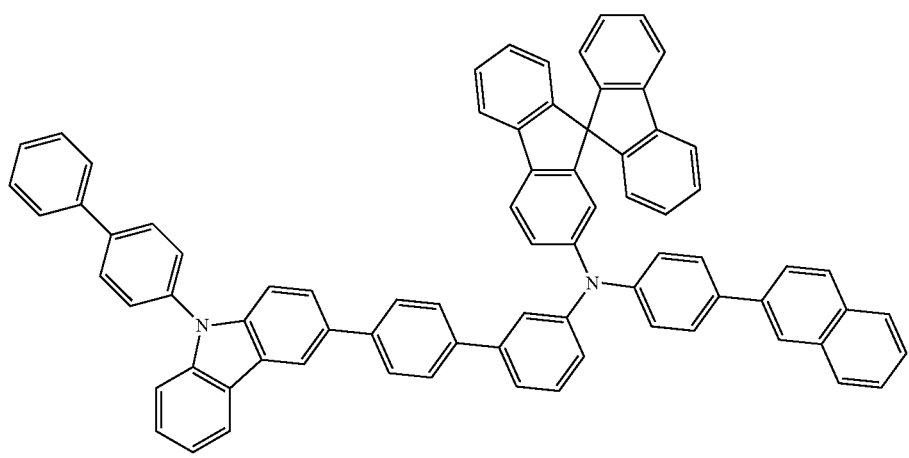
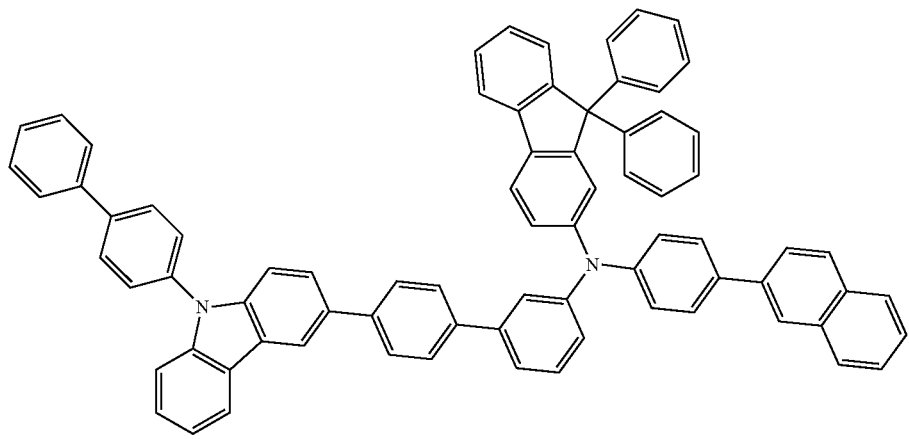

-continued
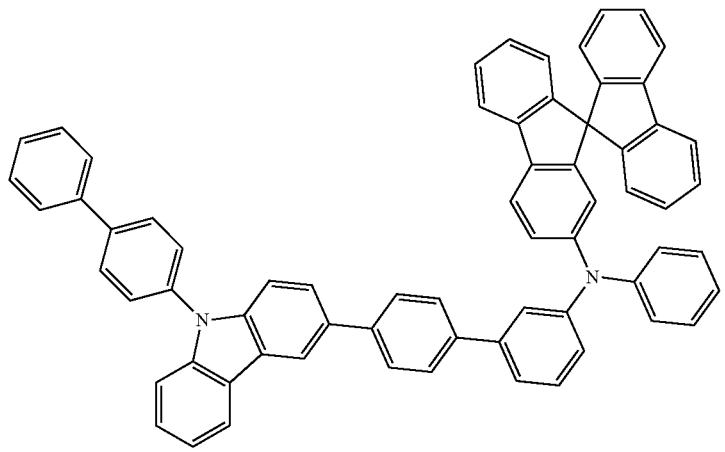
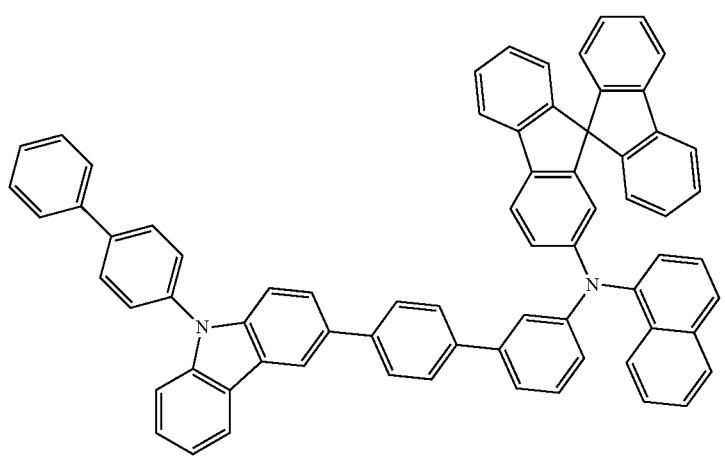
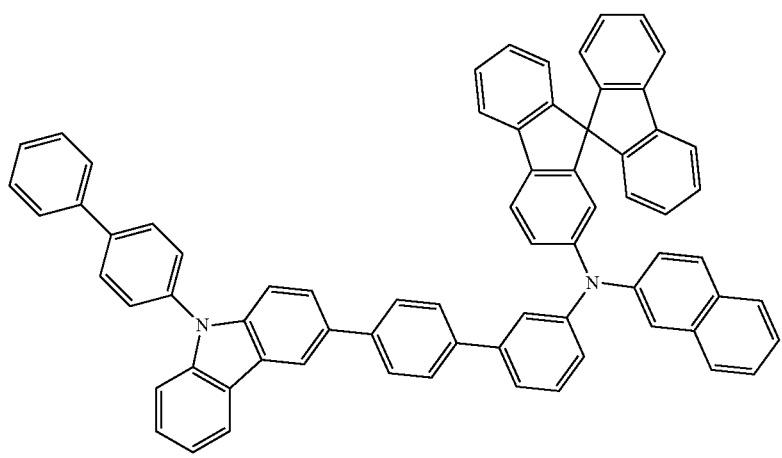

-continued
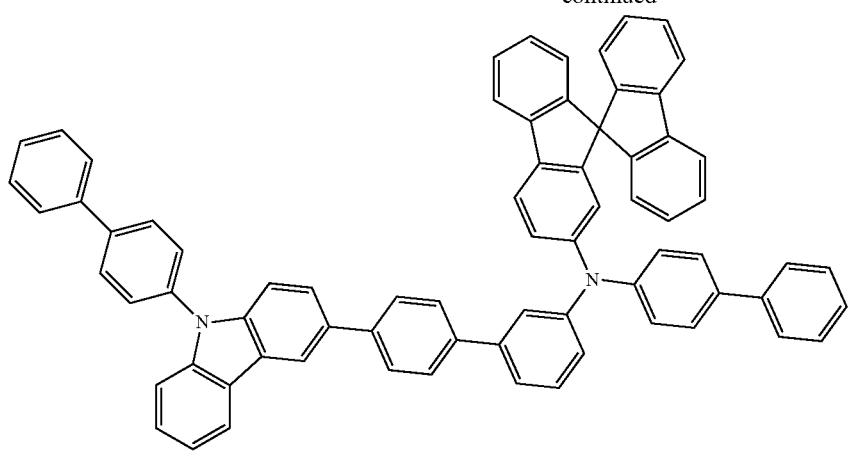
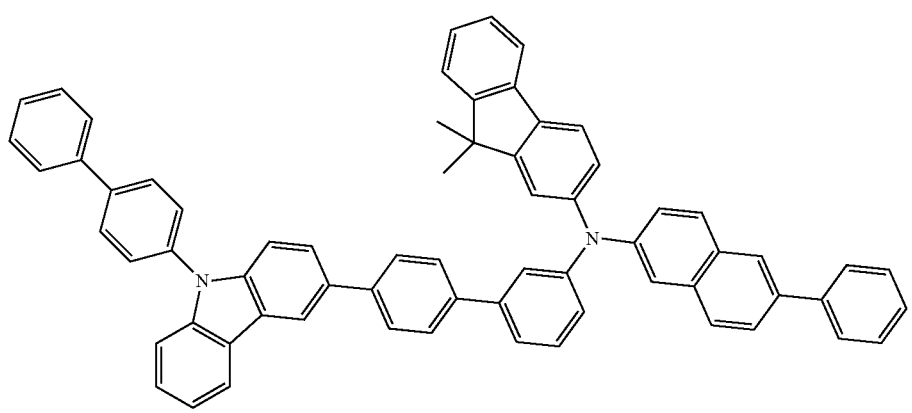
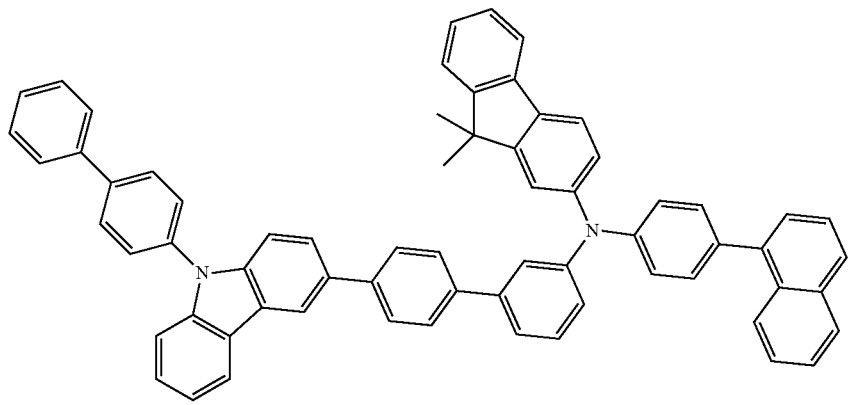
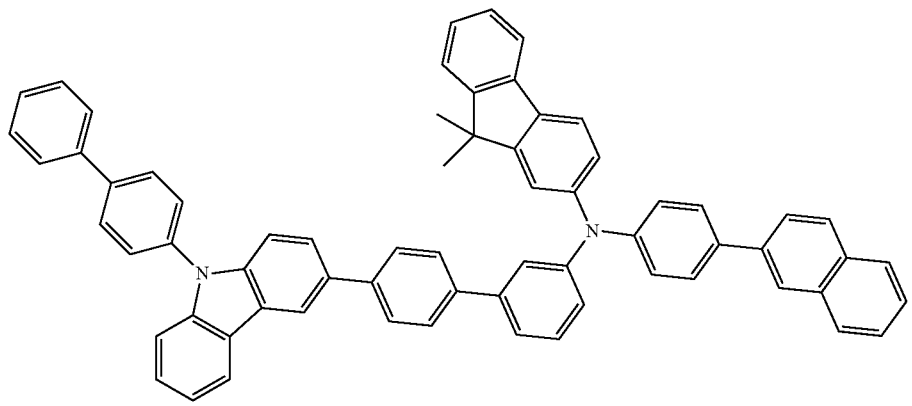

-continued
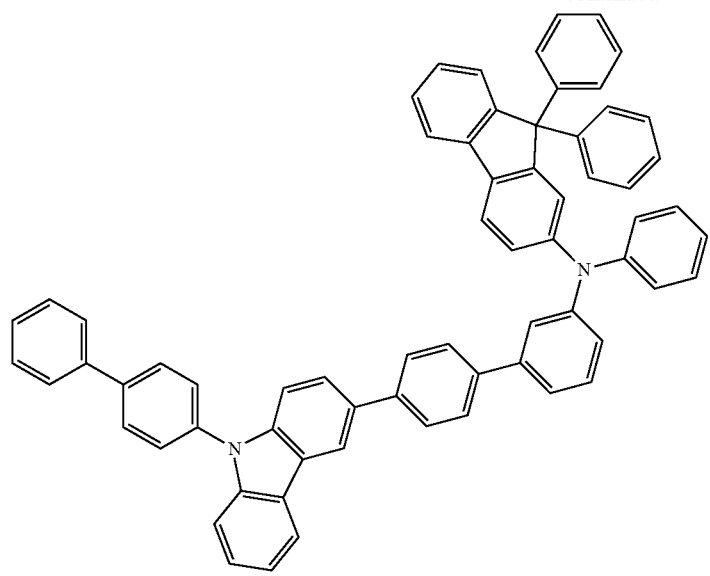
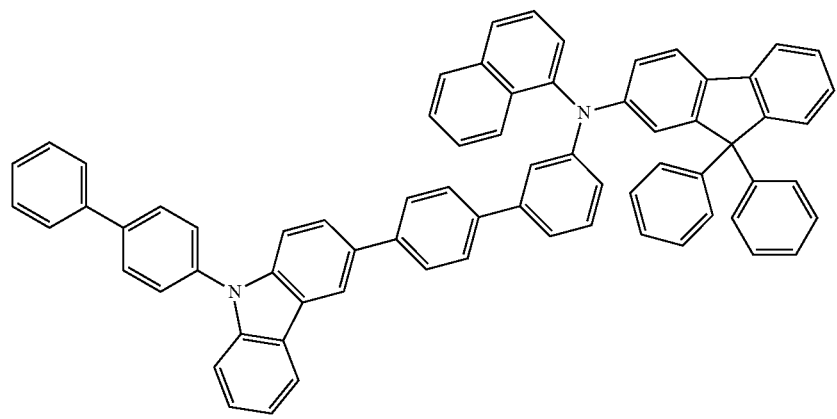
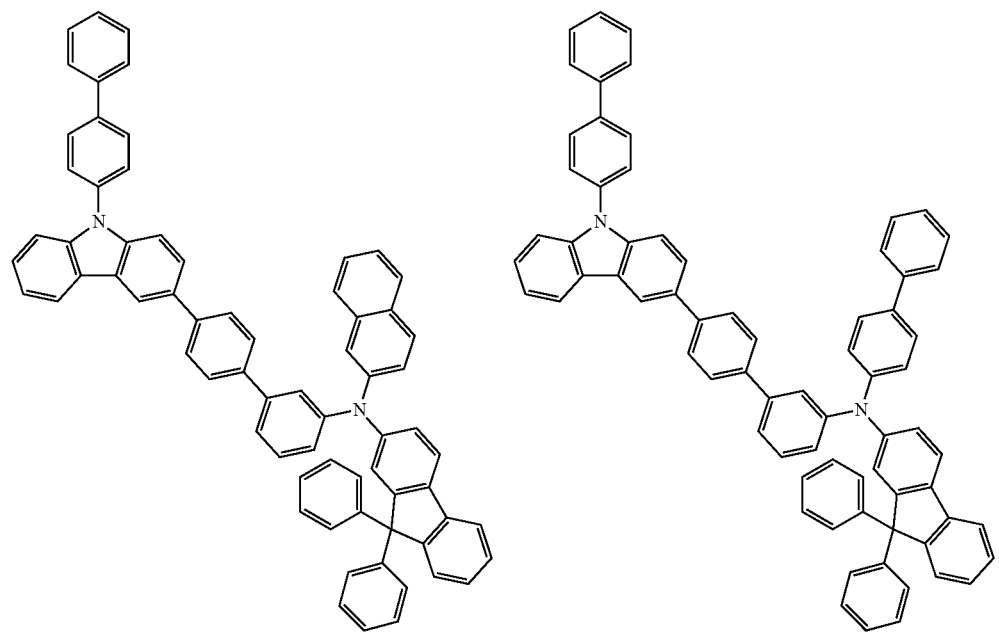

-continued
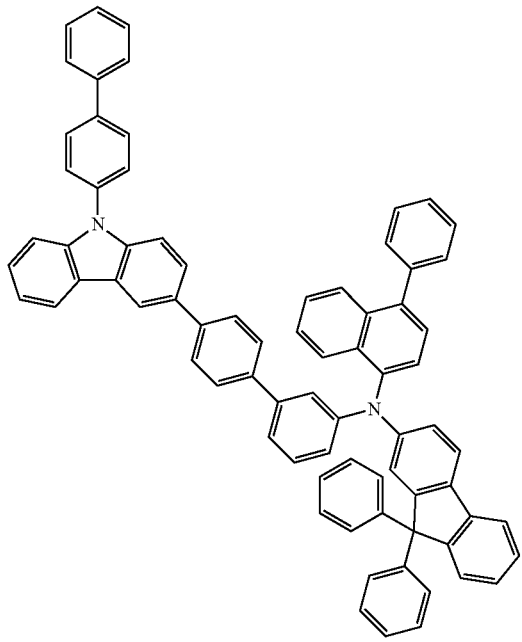
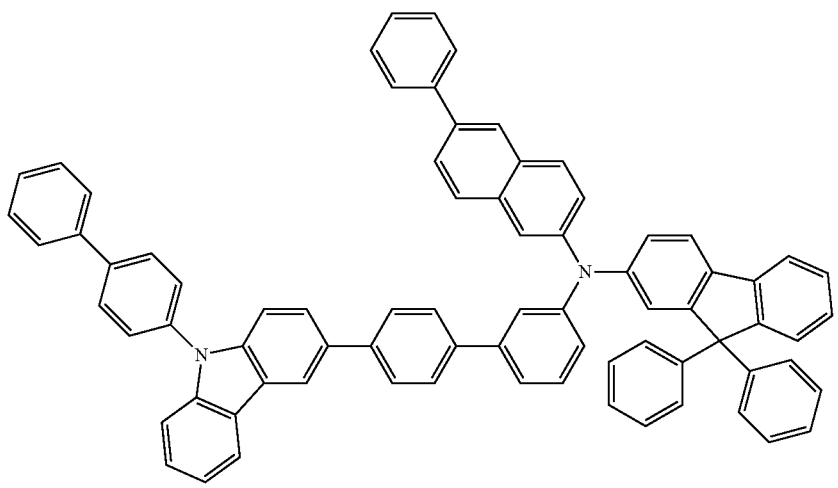
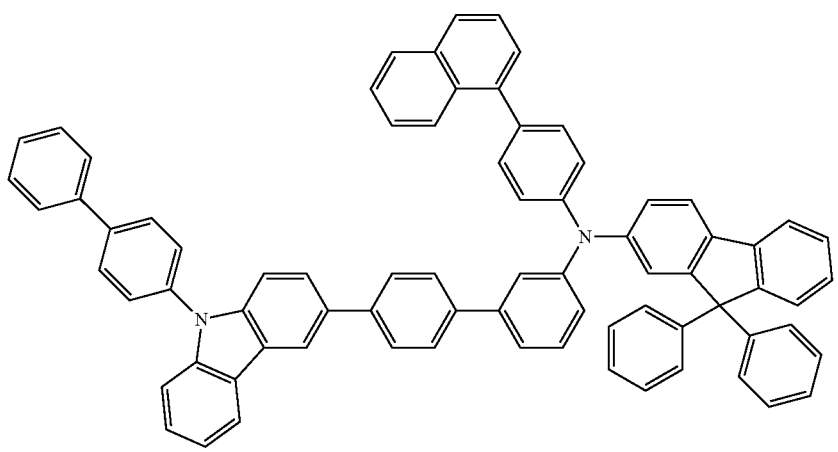

-continued
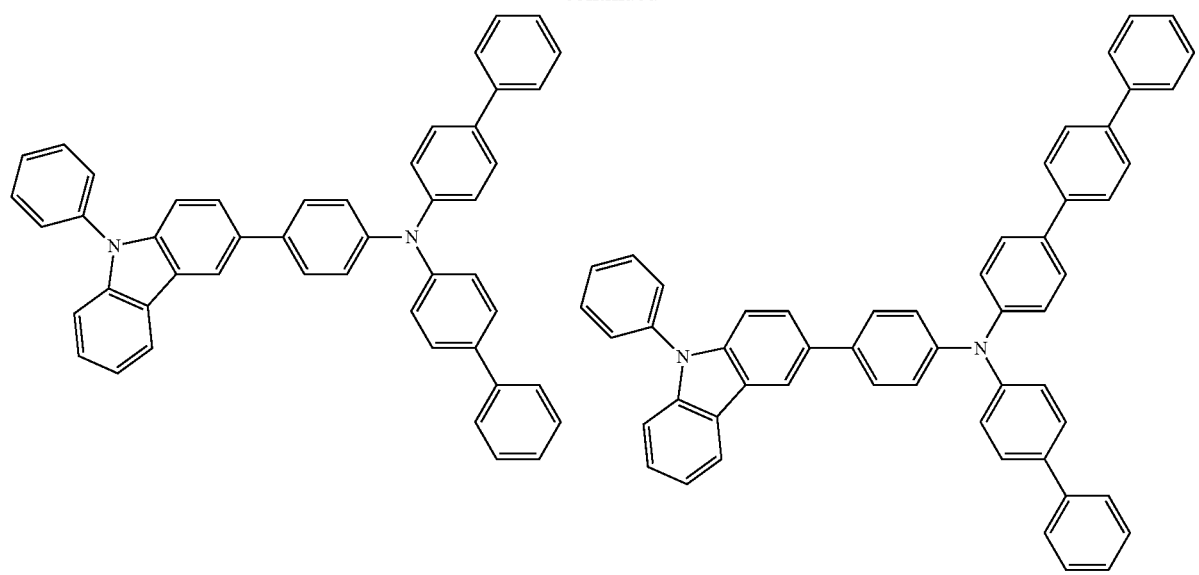
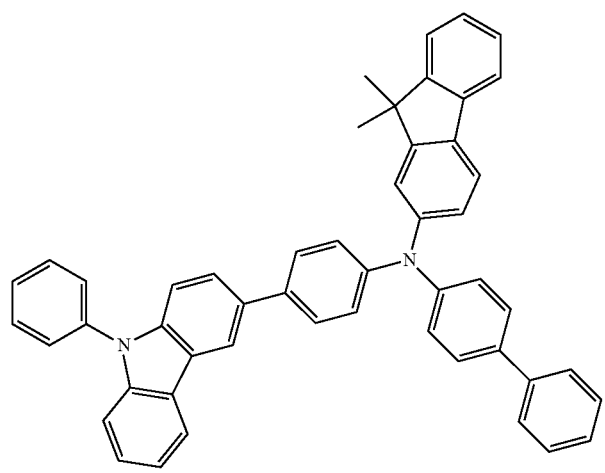
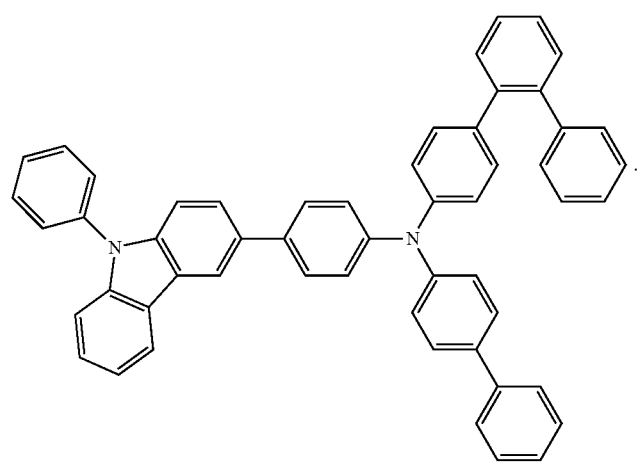

7. The organic light emitting device of claim 1, wherein the compound of Chemical Formula 4 is selected from the following compounds:
(B114)
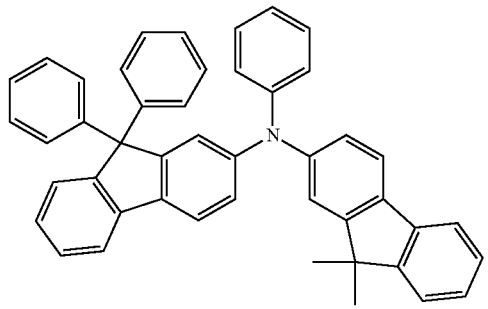
(B115)
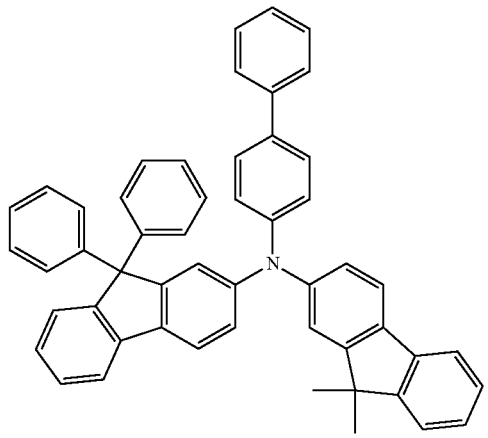
(B116)
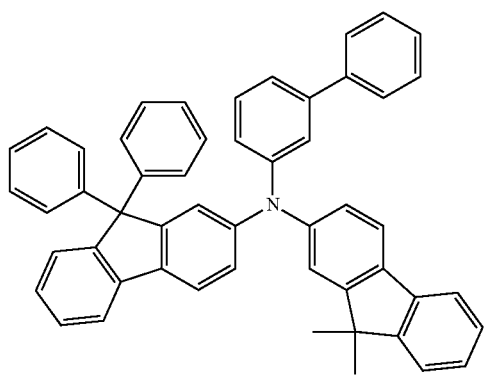
(B117)
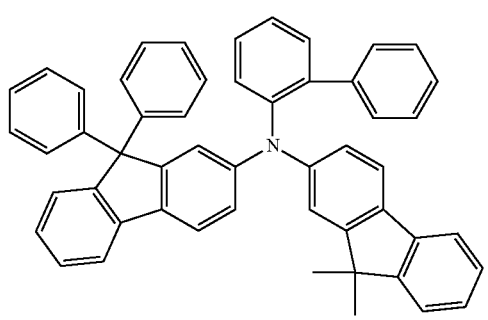
-continued
(B118)
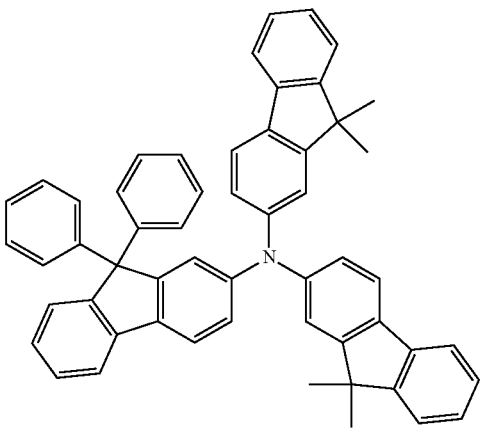
(B120)
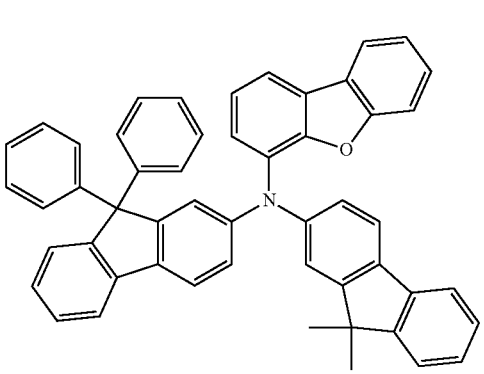
(B121)
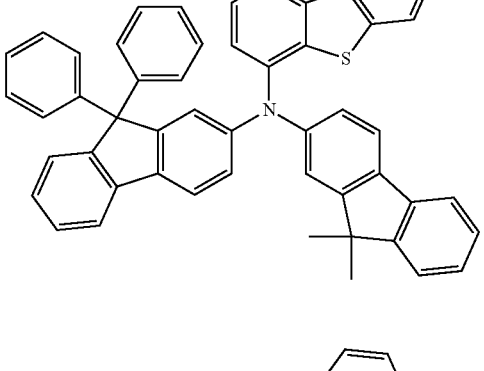
(B122)
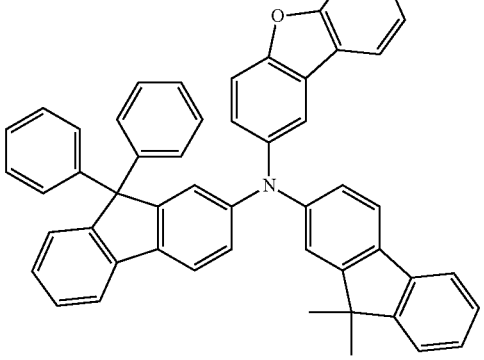

(B123)
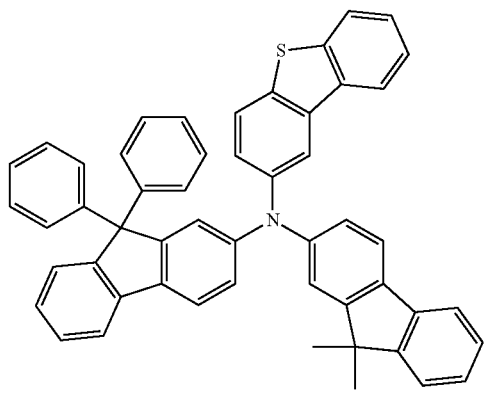
(B124)
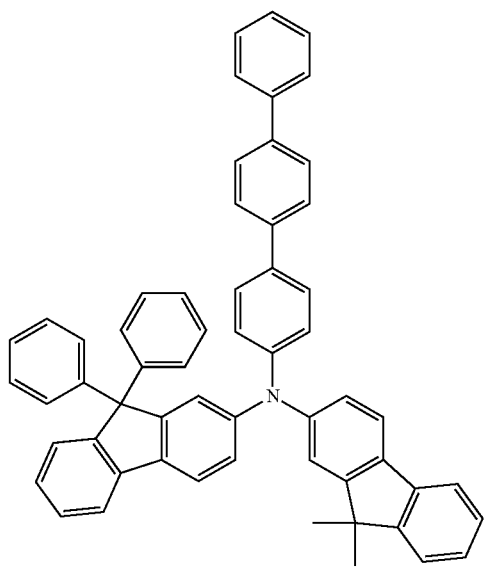
(B125)
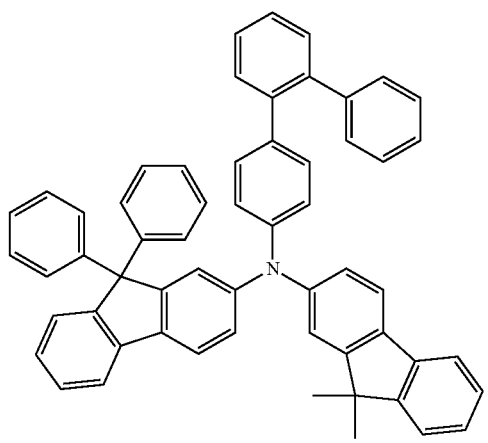
(B126)
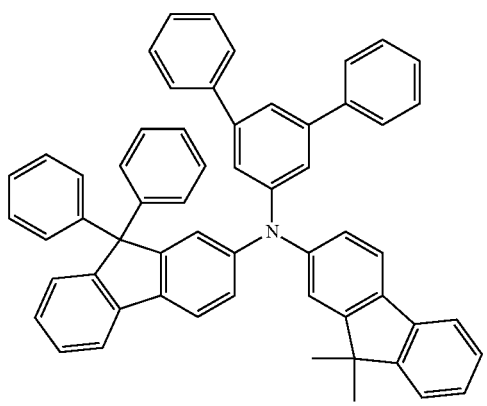
(B127)
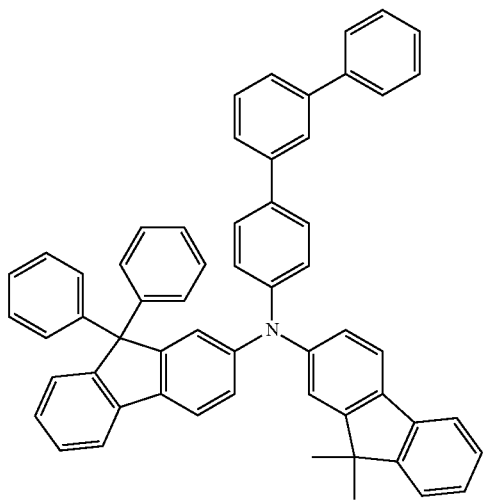
(B128)
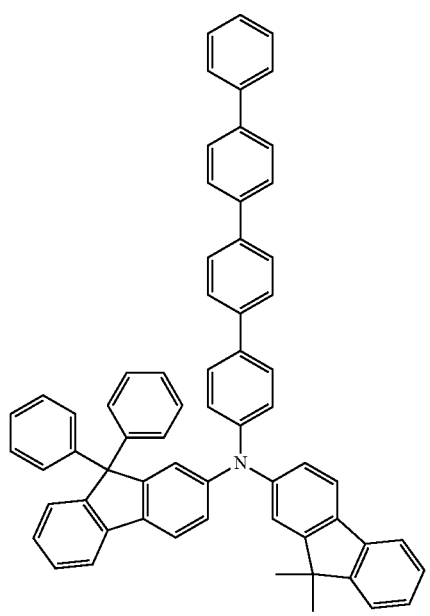

(B129)
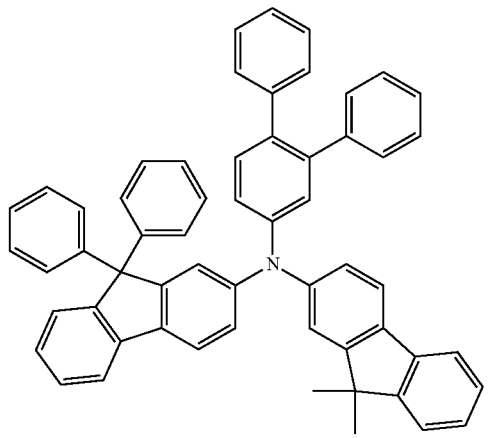
(B130)
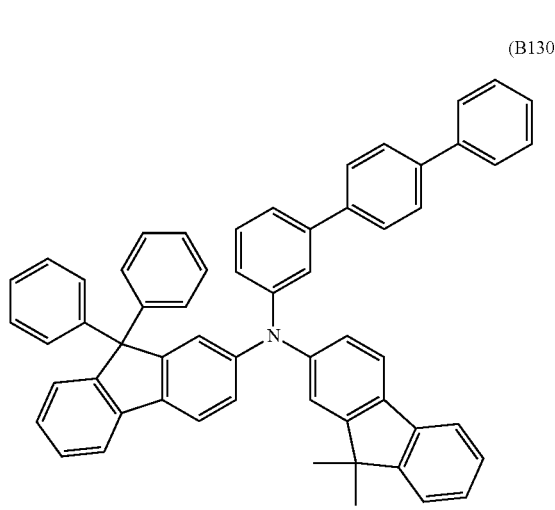
(B131)
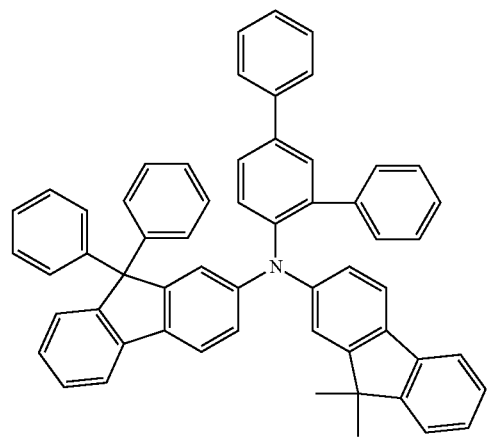
(B132)
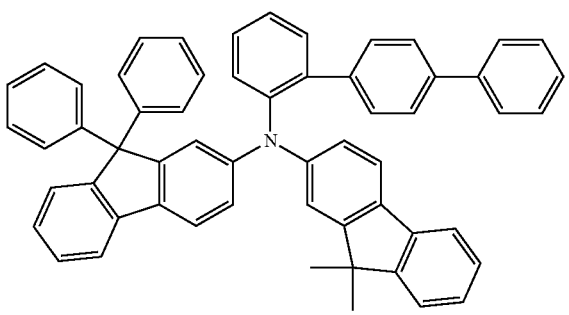
(B133)
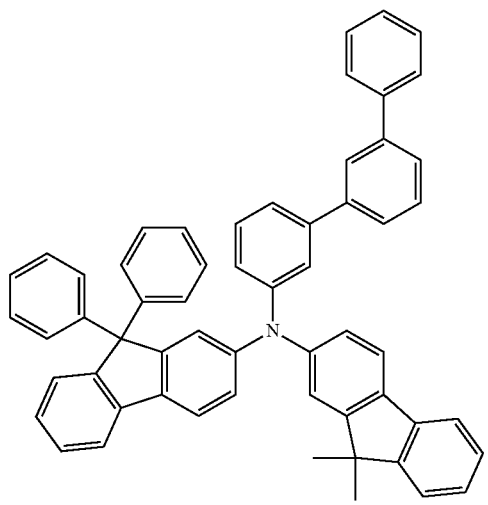
(B134)
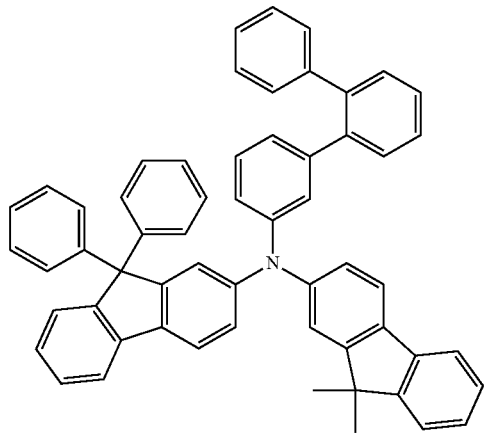

-continued
(B135)
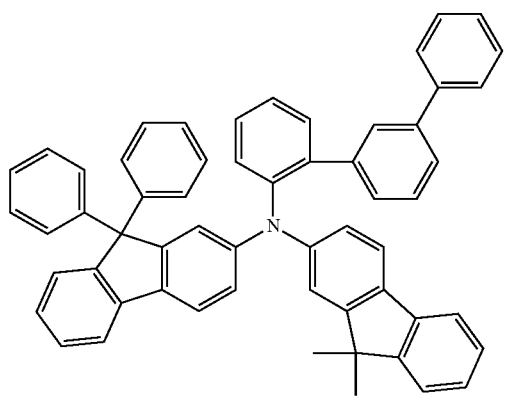
(B136)
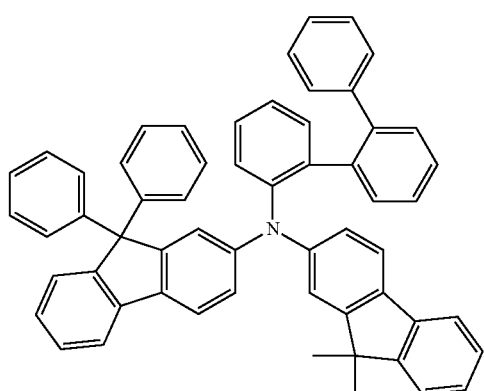
(B137)
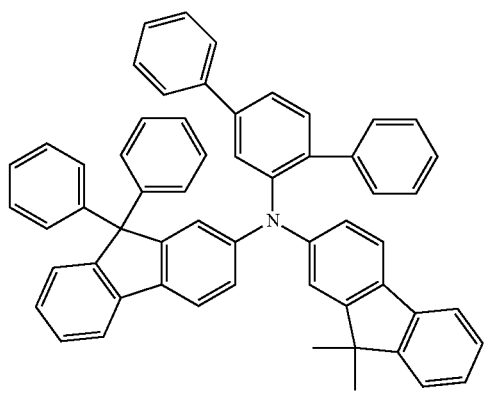
(B138)
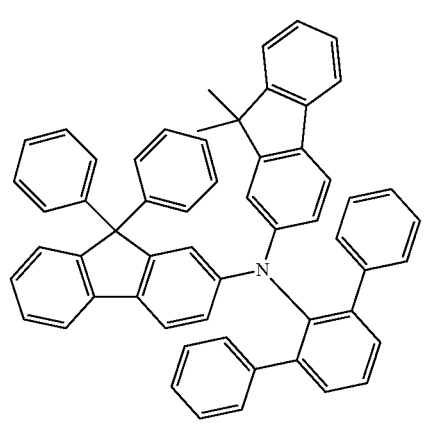
-continued
(B139)
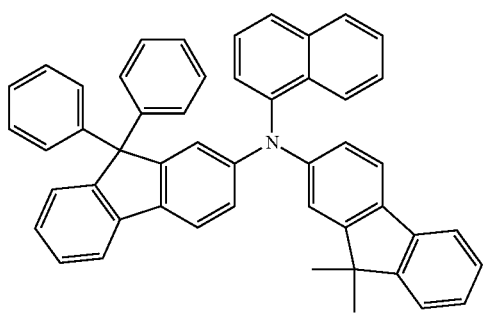
(B140)
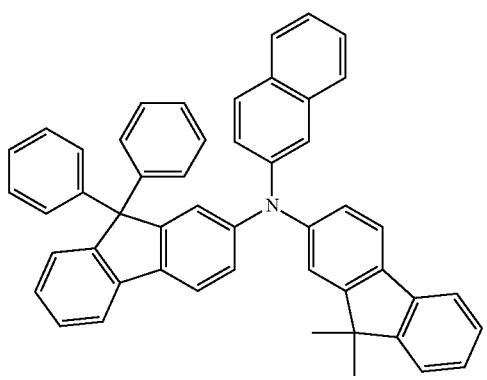
(B141)
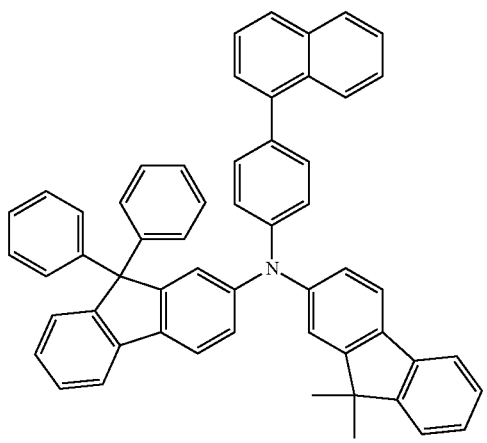

-continued
(B142)
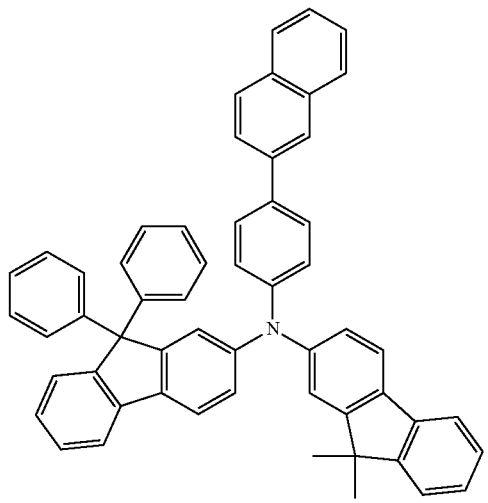
(B143)
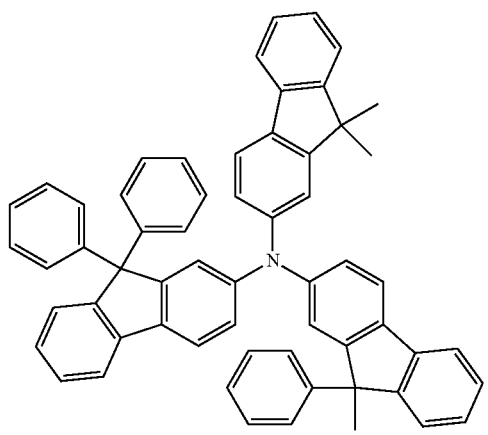
(B144)
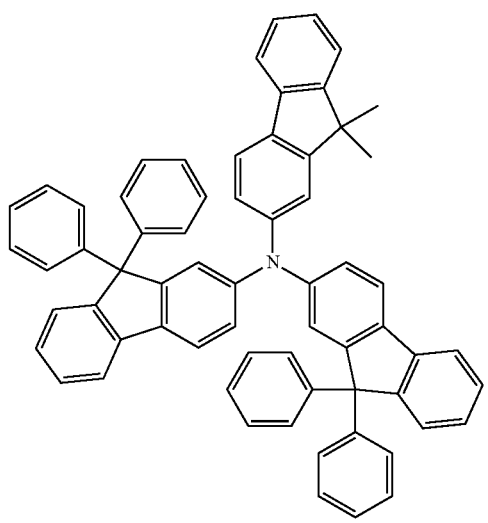
-continued
(B145)
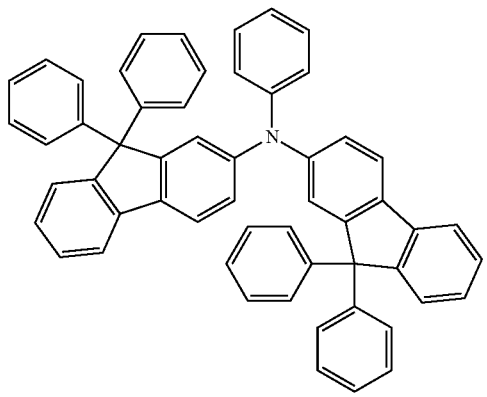
(B146)
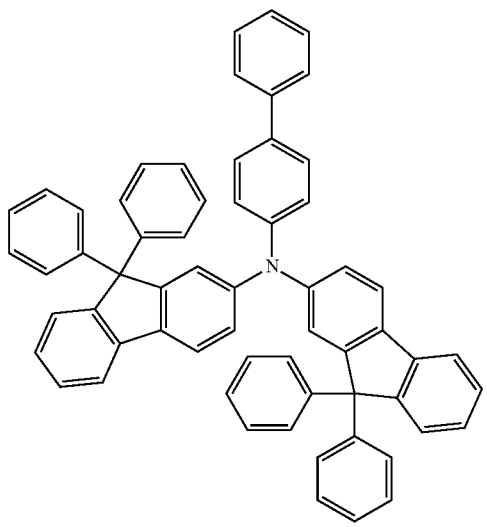
(B147)
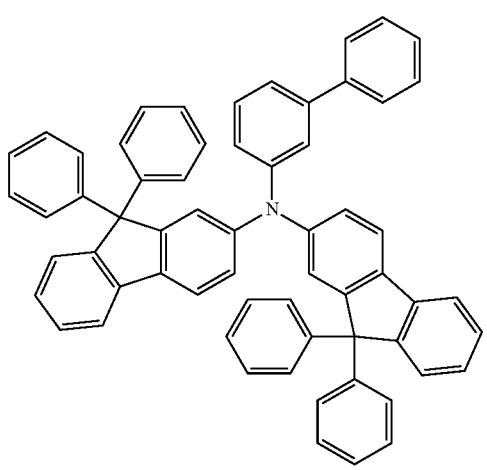

-continued
(B148)
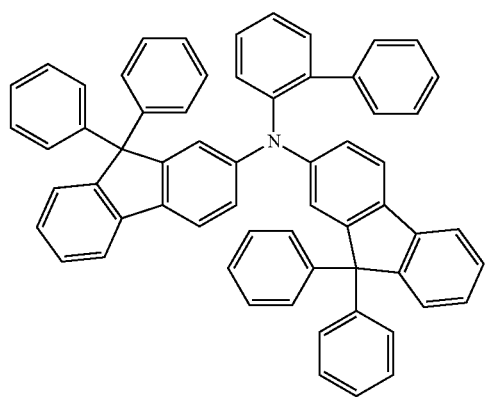
(B149)
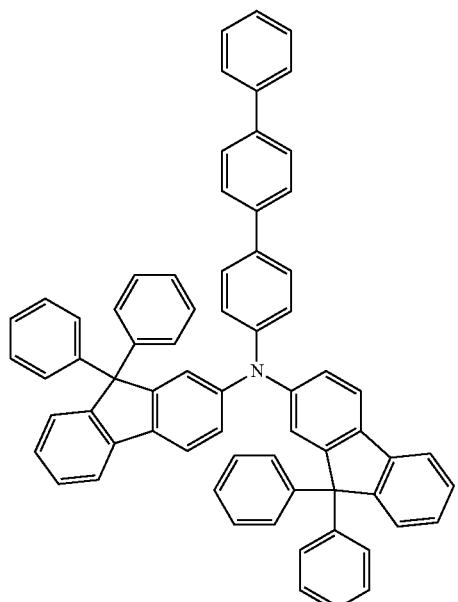
(B150)
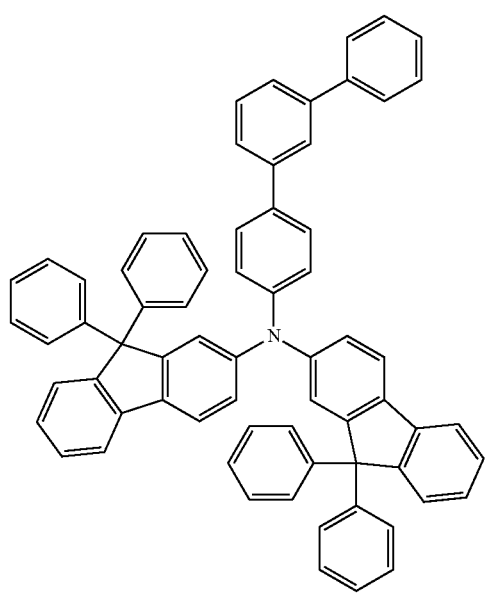
-continued
(B151)
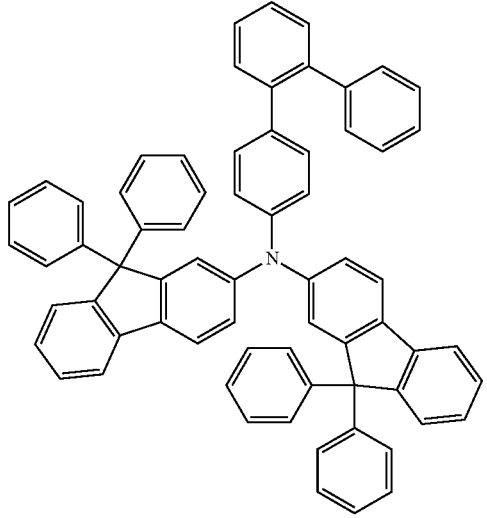
(B152)
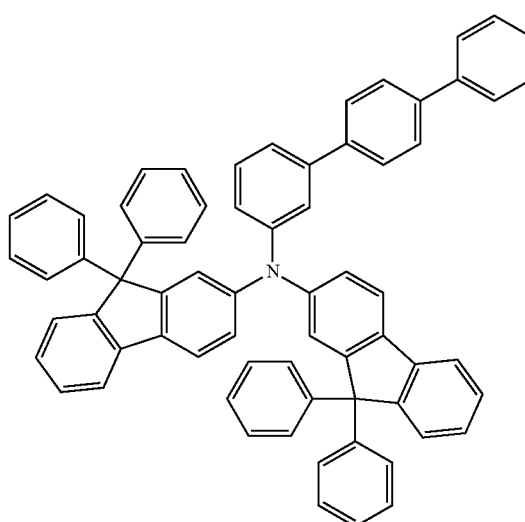
(B153)
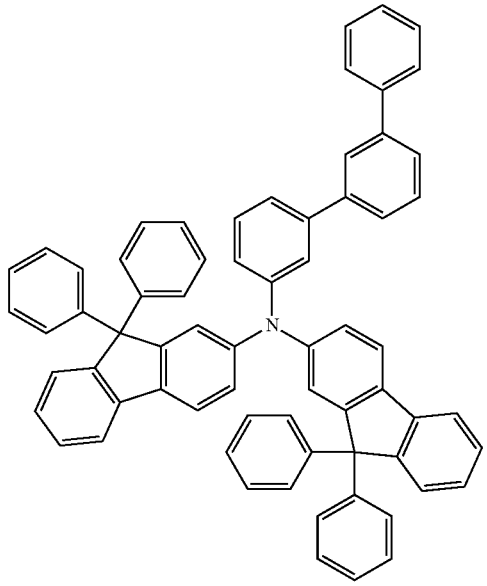

-continued
(B154)
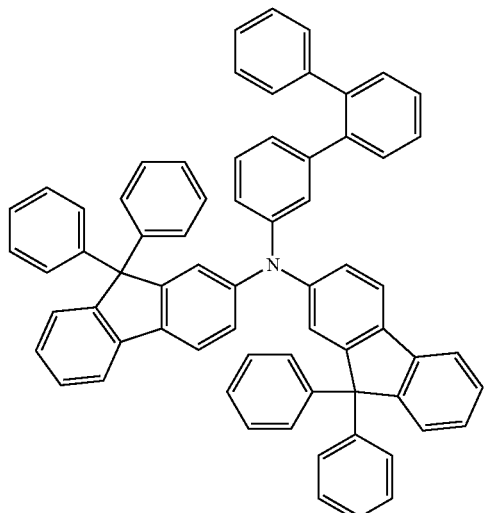
(B155)
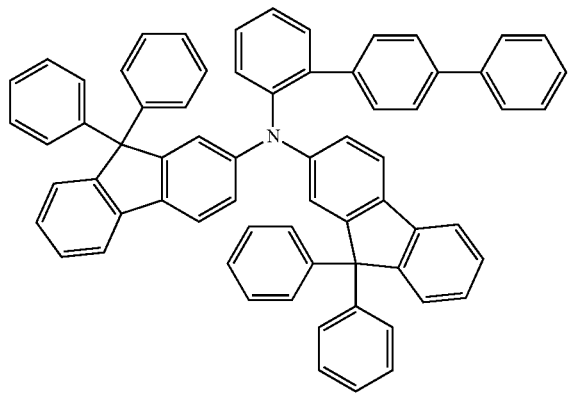
(B156)
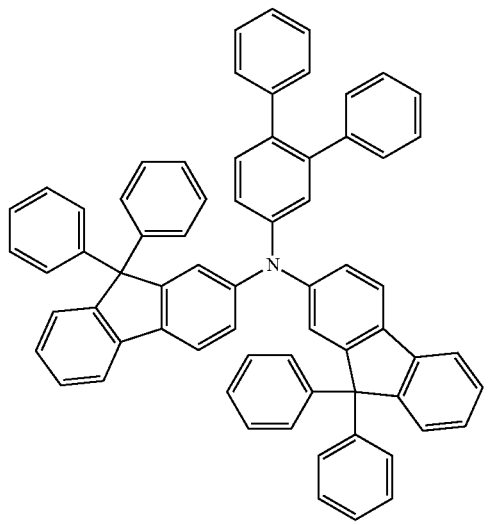
-continued
(B157)
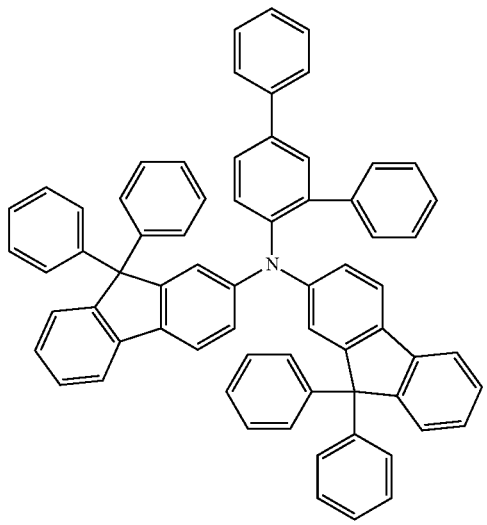
(B158)
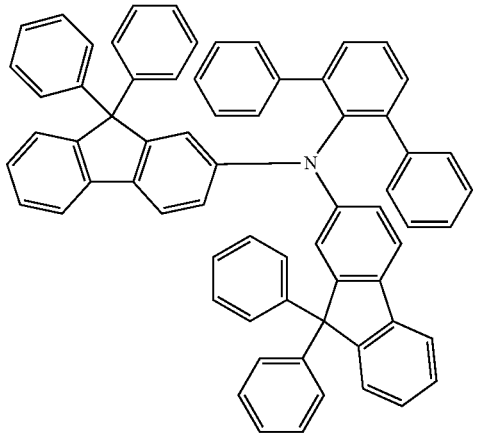
(B159)
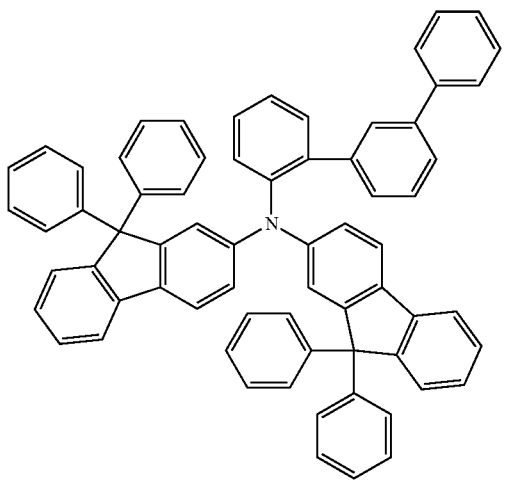

(B160)
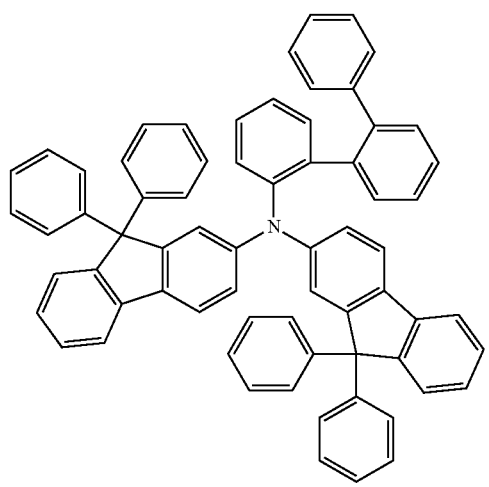
(B161)
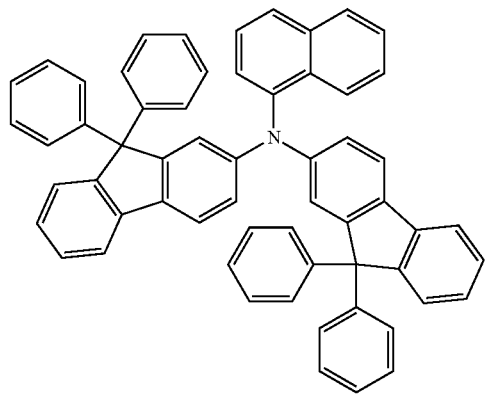
(B162)
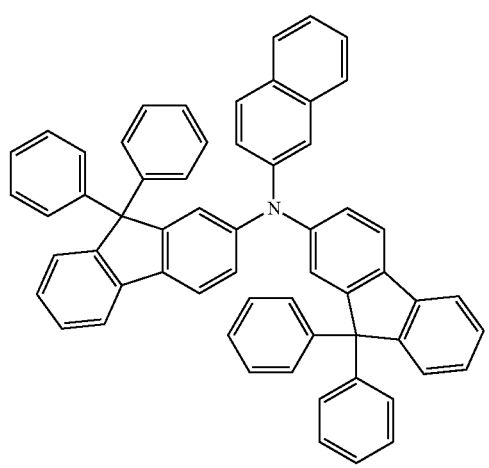
(B163)
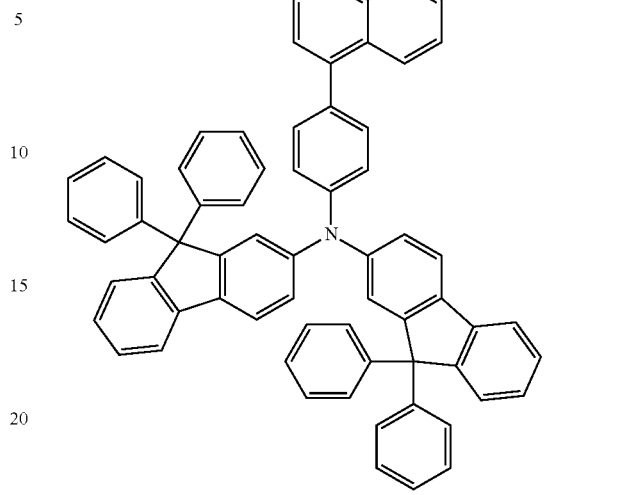
(B164)
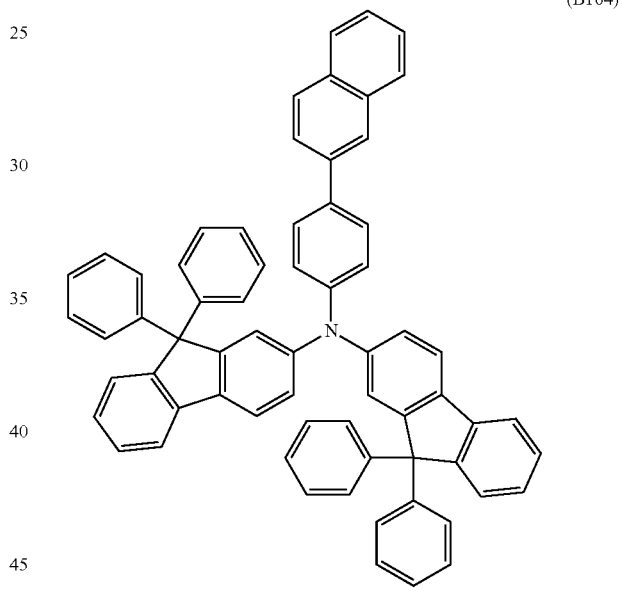
(B165)
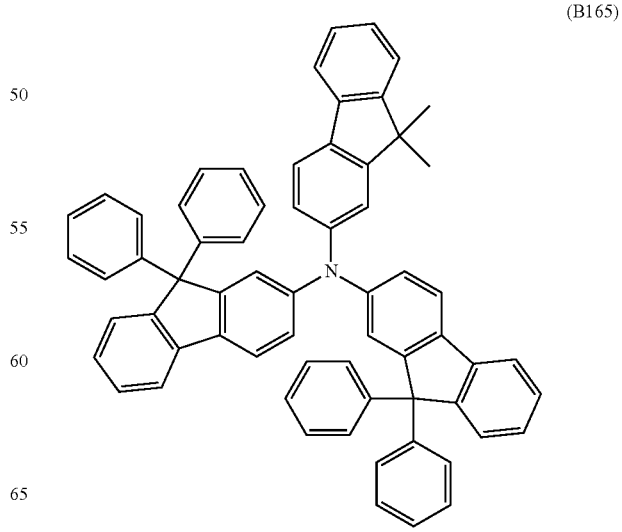

(B166)
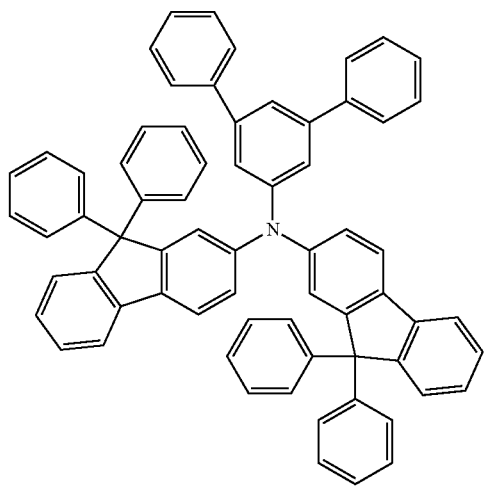
(B167)
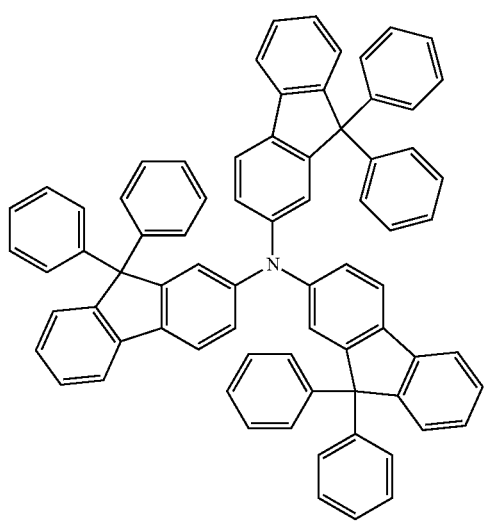
(B168)
(B169)
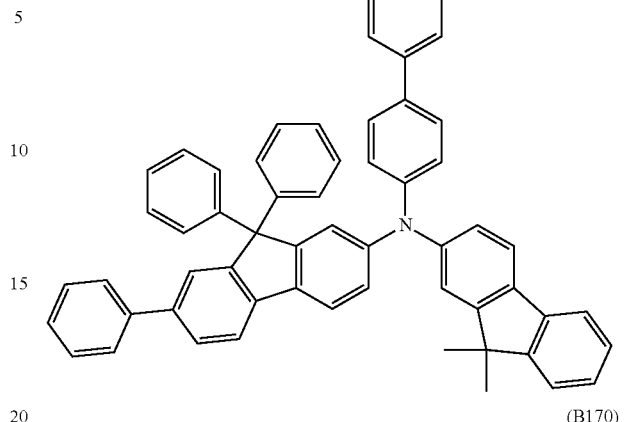
(B170)
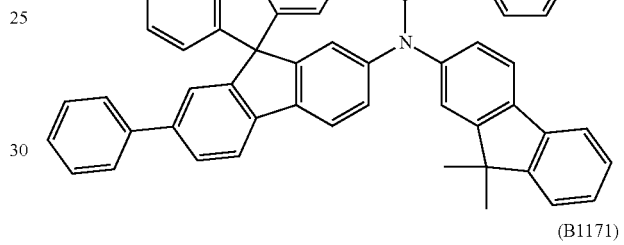
(B1171)
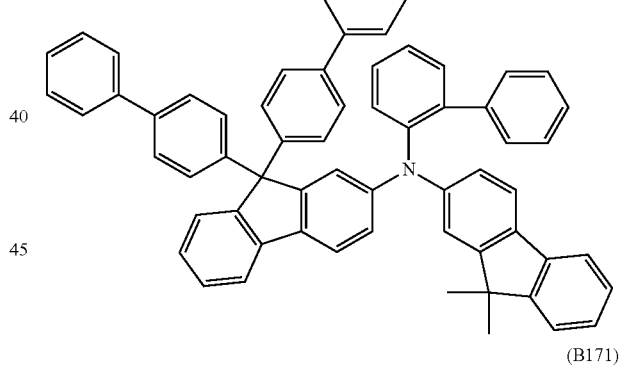
(B171)
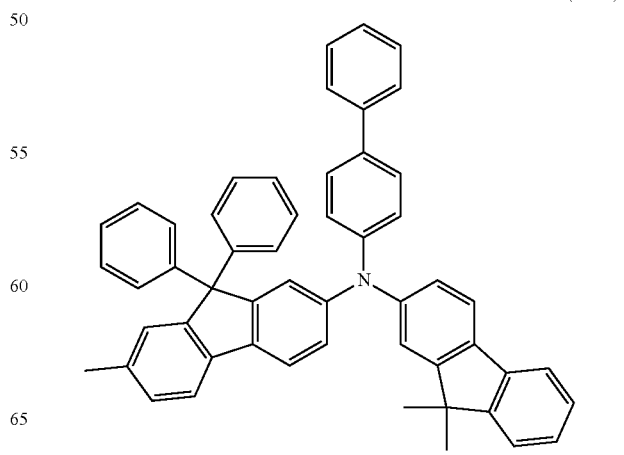

-continued
(B172) 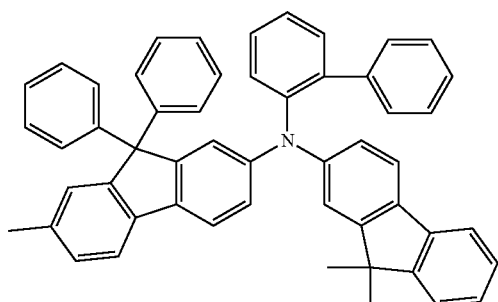
(B173) 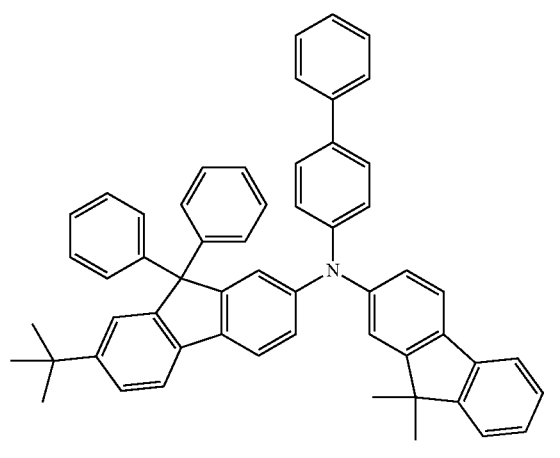
(B174) 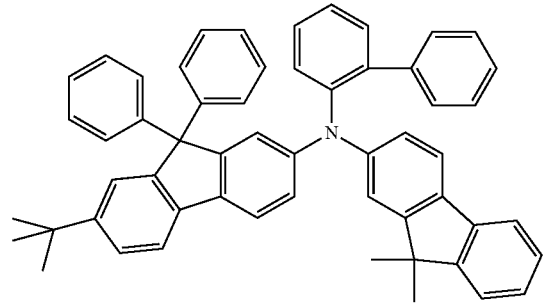
(B175) 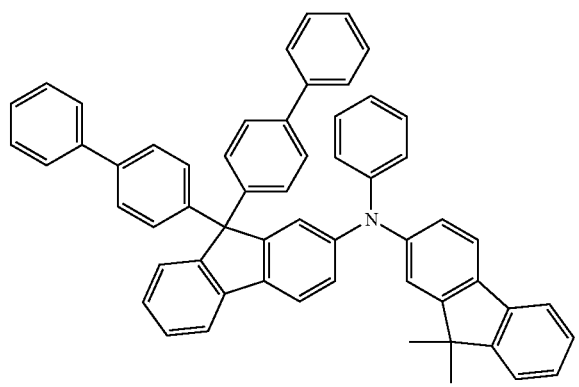
-continued
(B176) 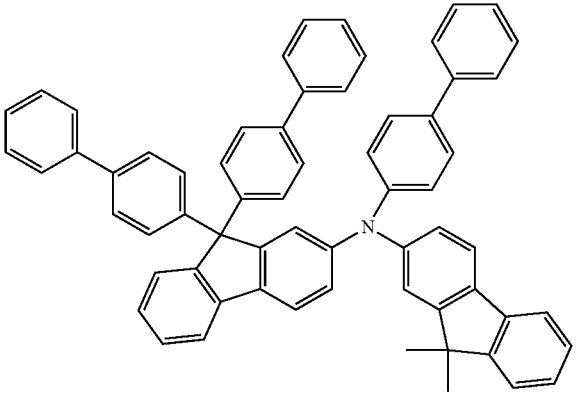
(B177) 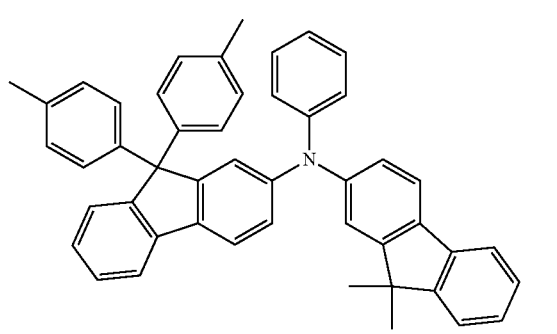
(B178) 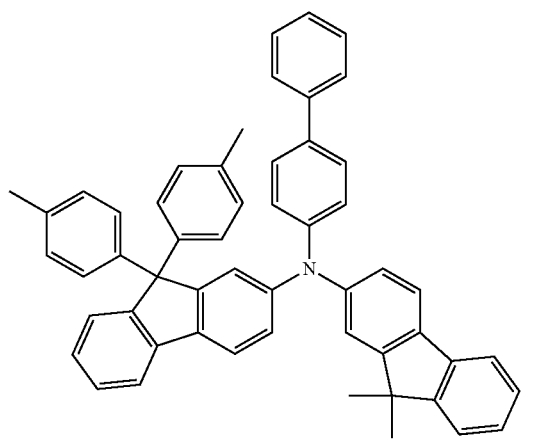

(B179)
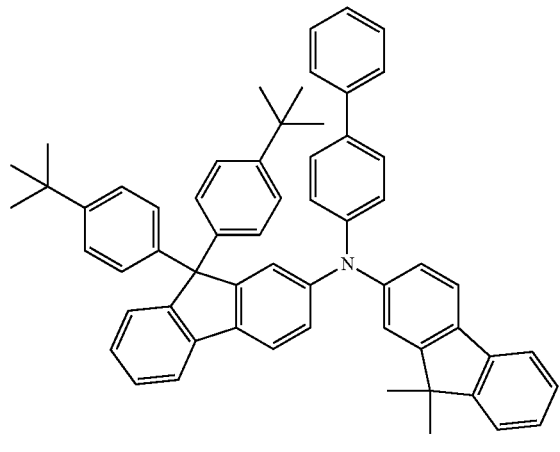
(B180)
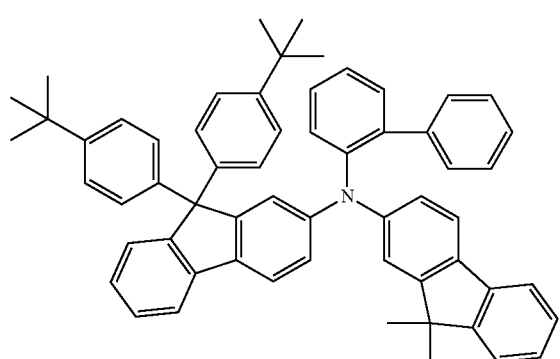
(B181)
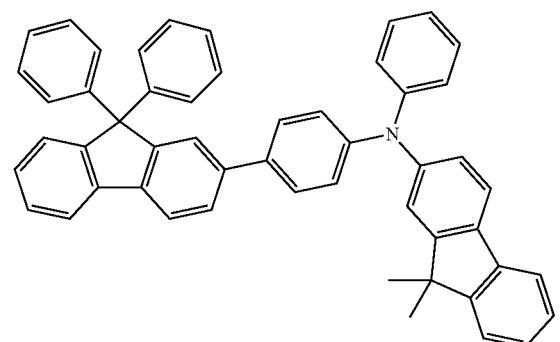
(B182)
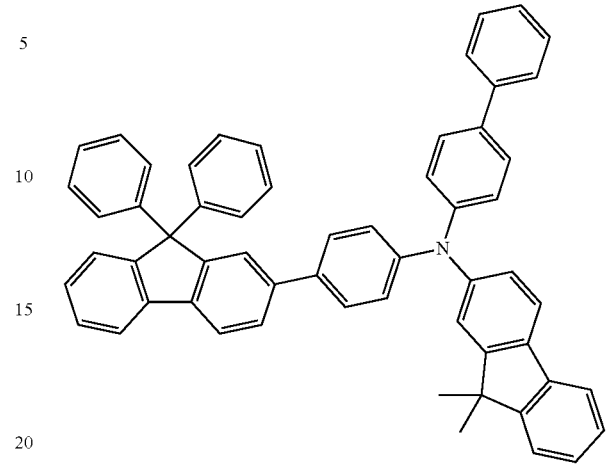
(B183)
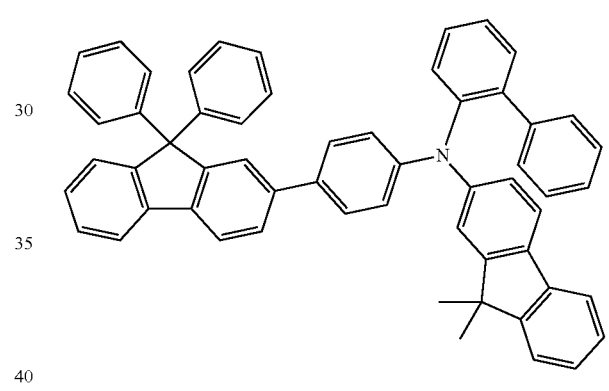
(B184)
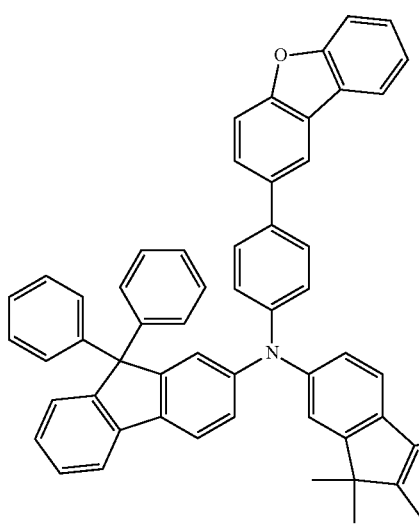

563
-continued
(B185)
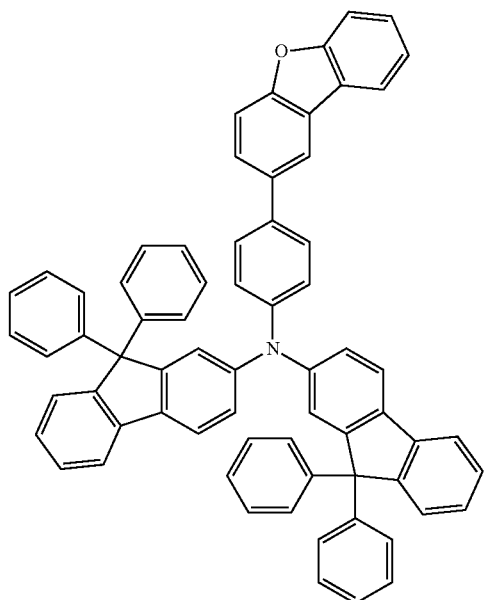
(B186)
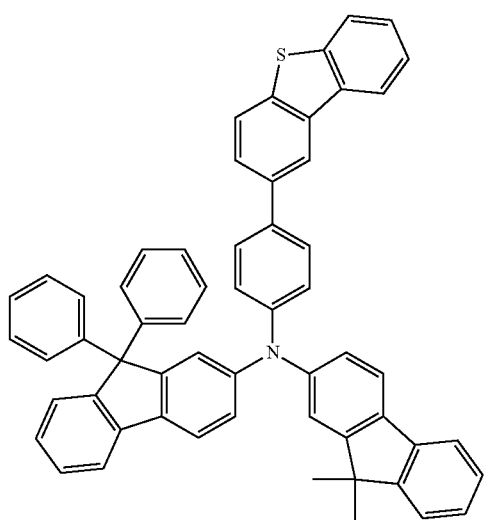
564
-continued
(B187)
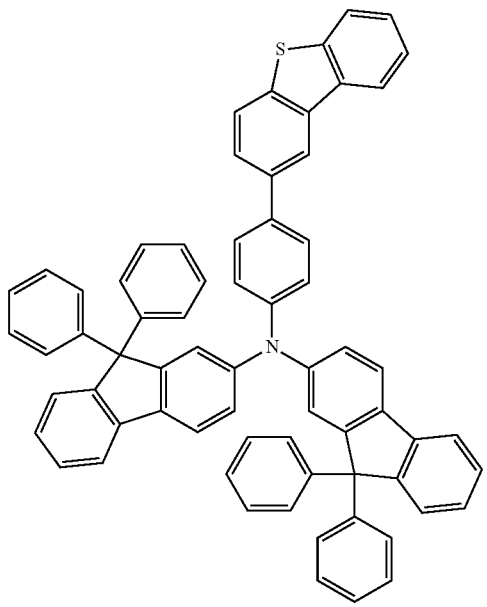
(B188)
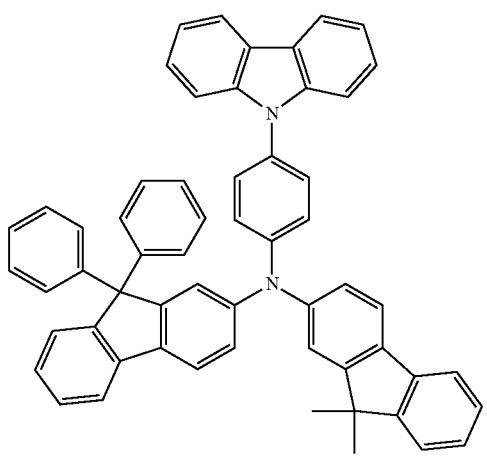
(B189)
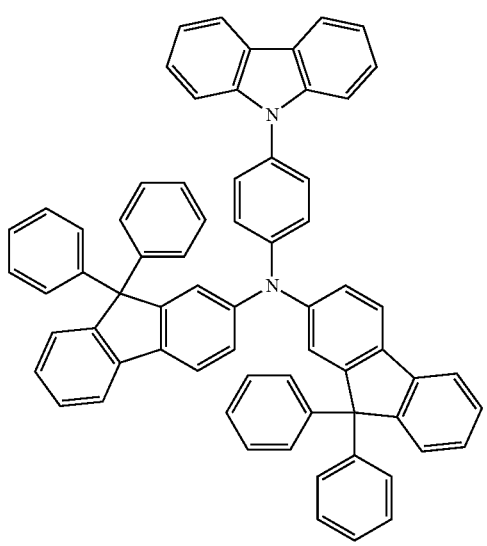

(B190)
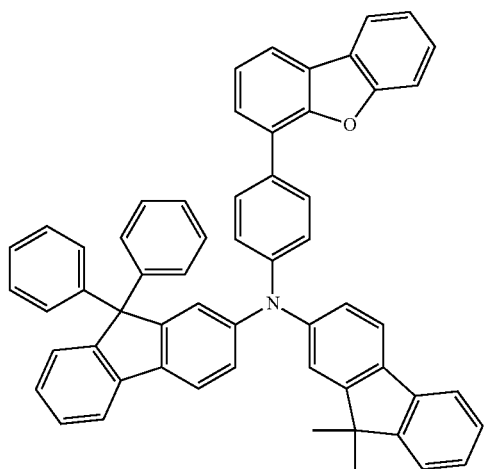
(B191)
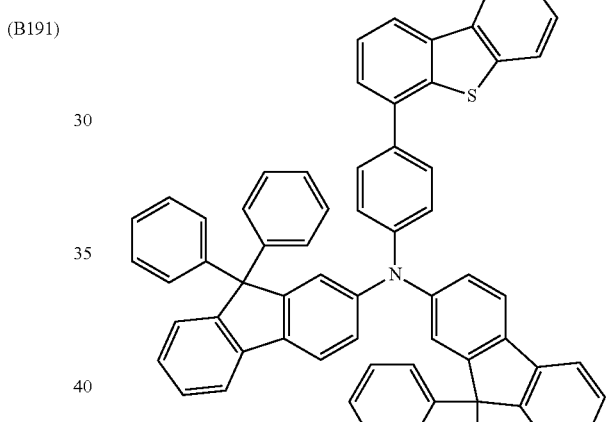
(B192)
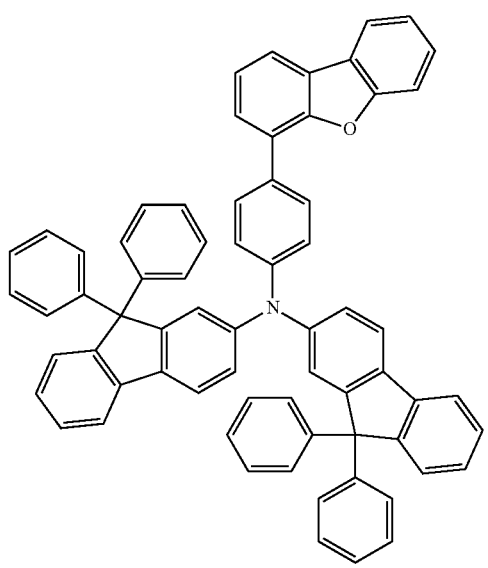
(B193)
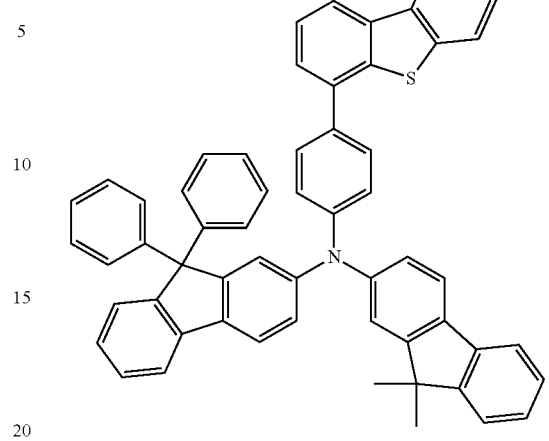
(B194)
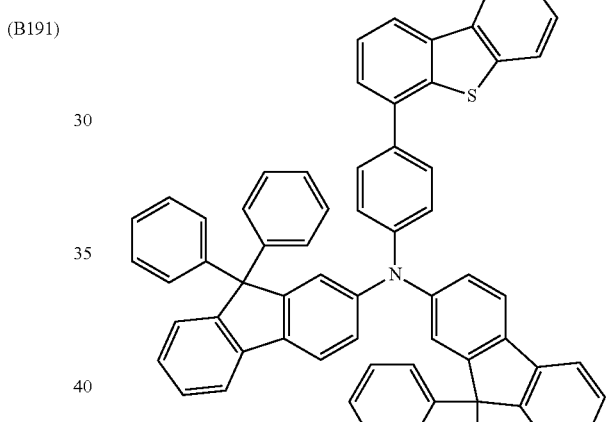
(B195)
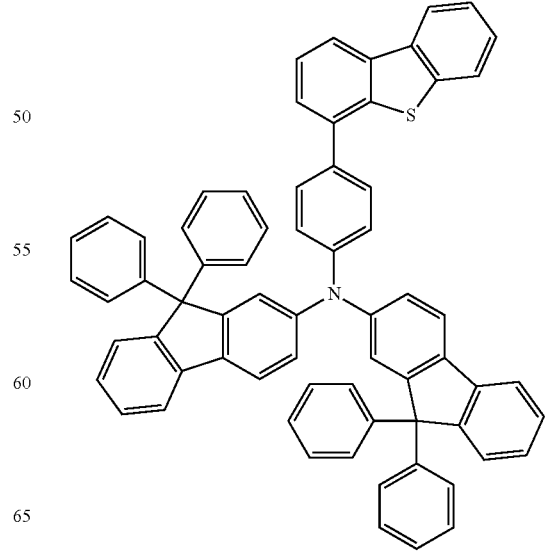

-continued
(B196)
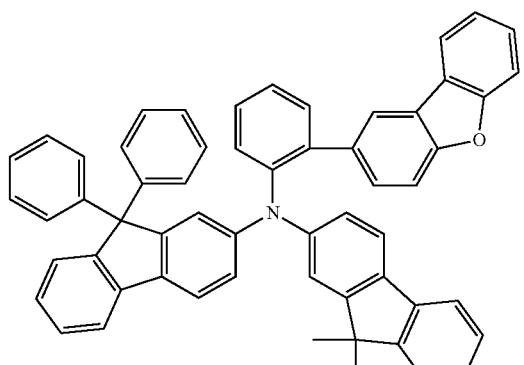
(B197)
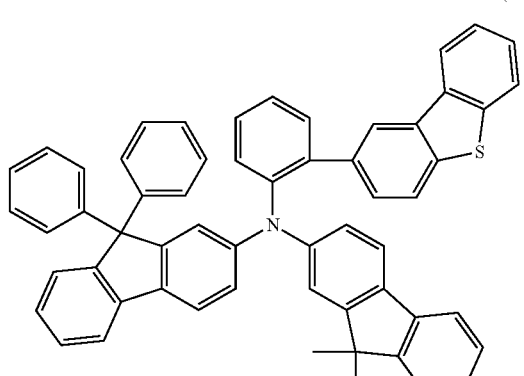
(B198)
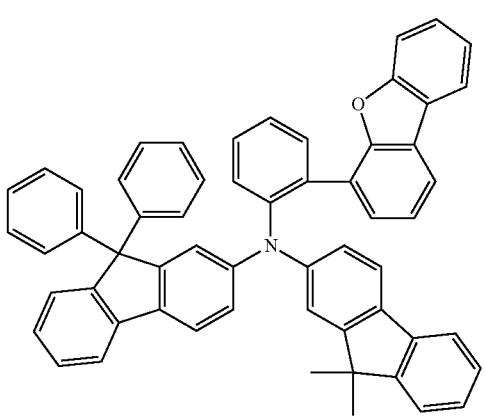
(B199)
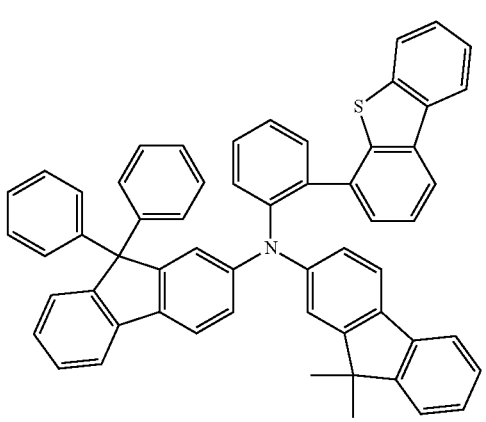
-continued
(B200)
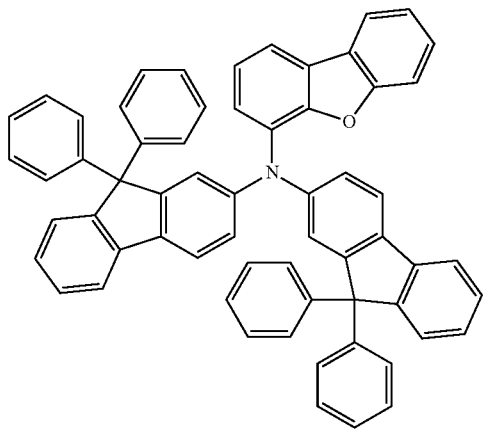
(B201)
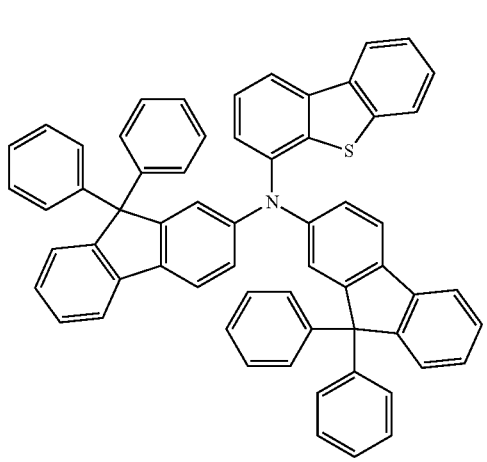
(B202)
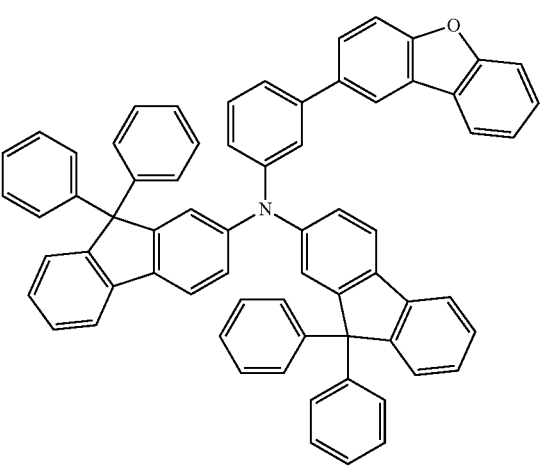

(B203)
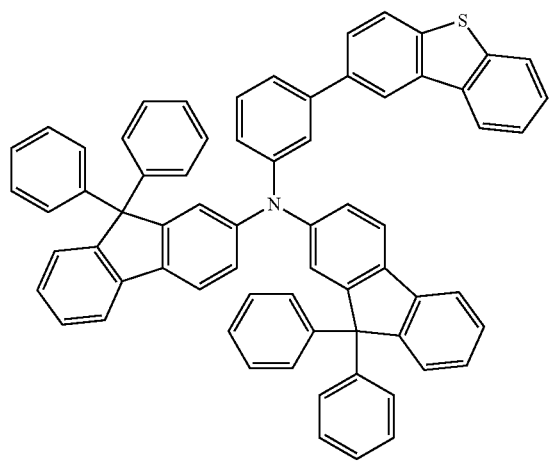
(B204)
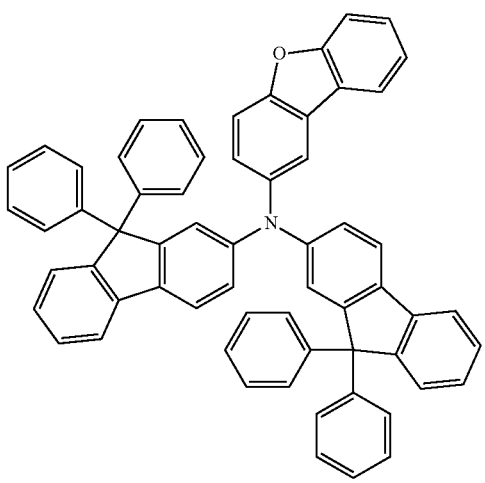
(B205)
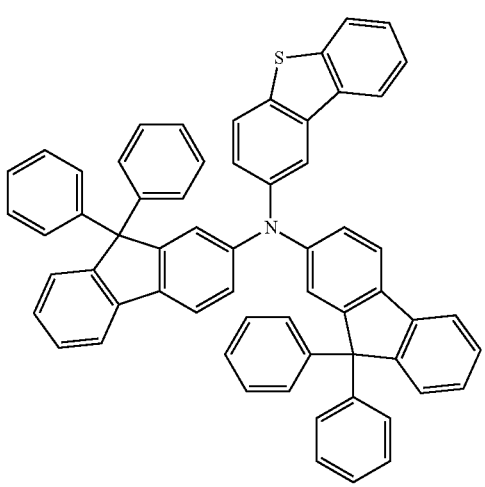
(B206)
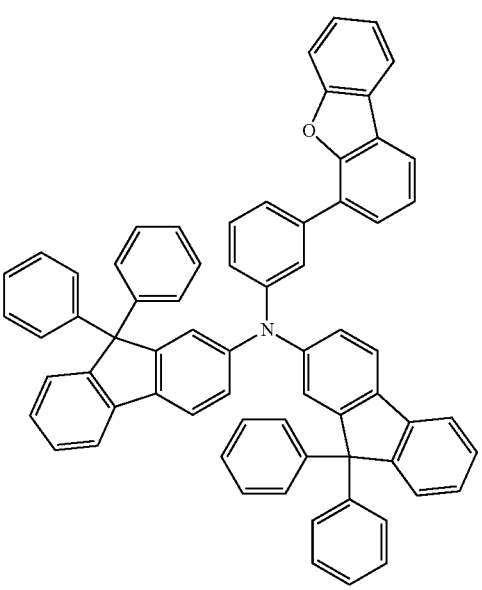
(B207)
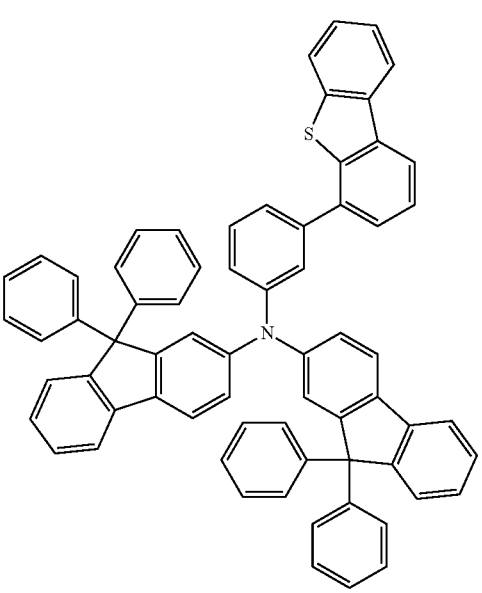

-continued
(B208) 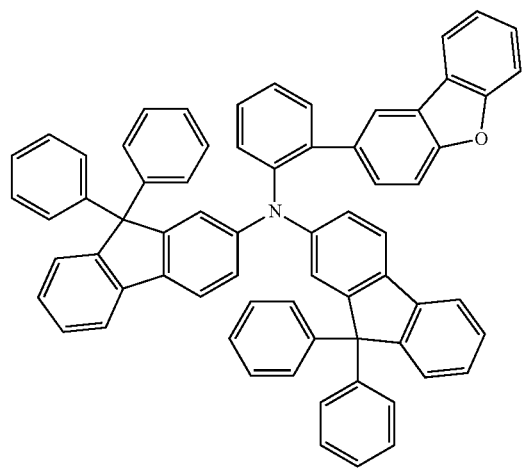
(B211) 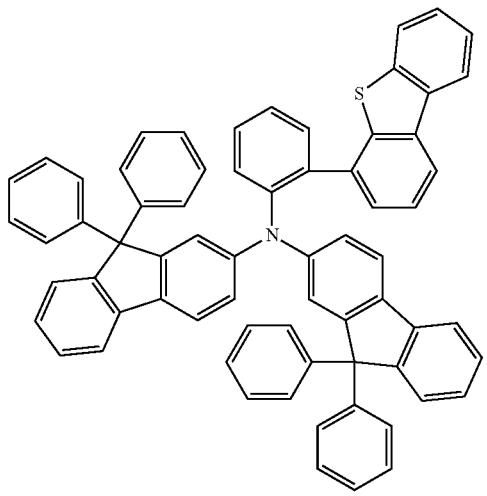
(B209) 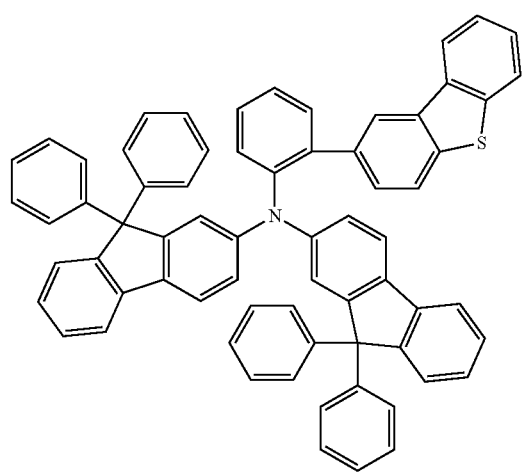
(B212) 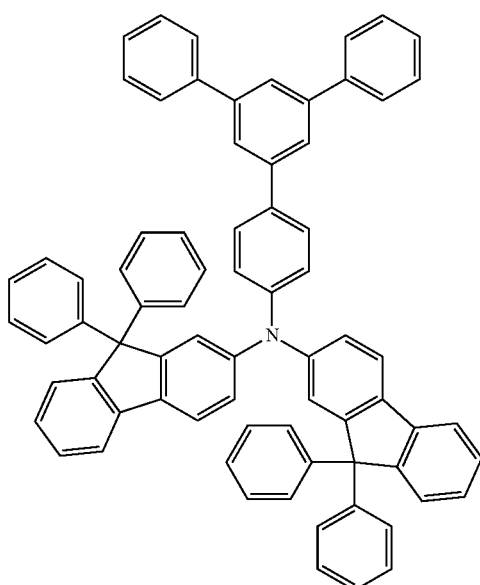
(B210) 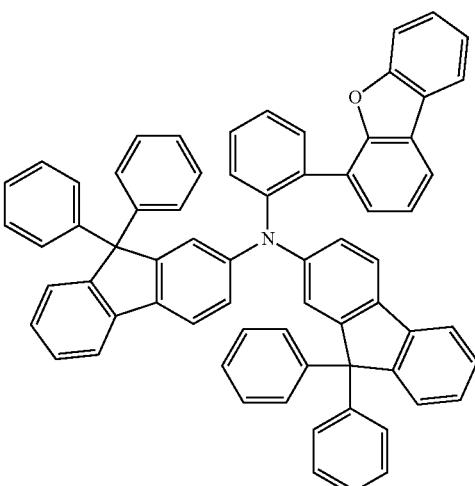
(B213) 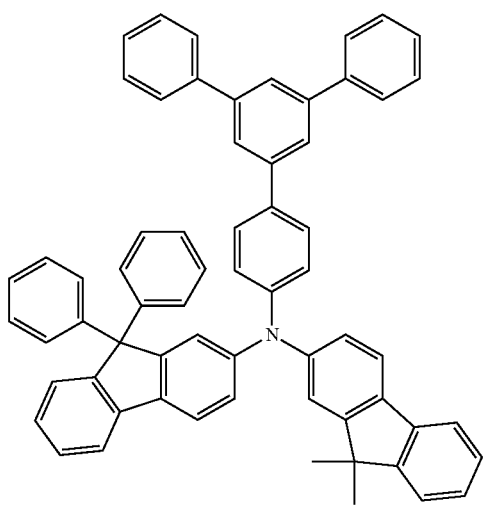

(B214)
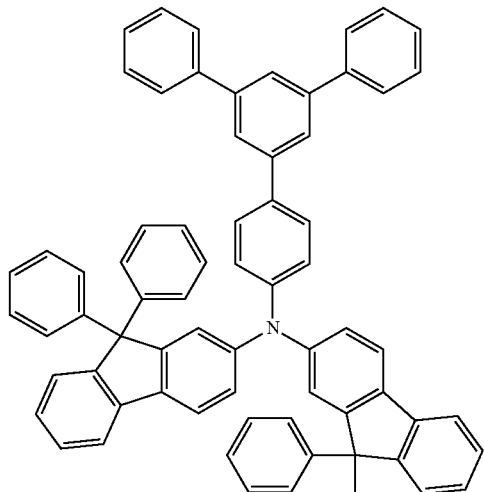
(B215)
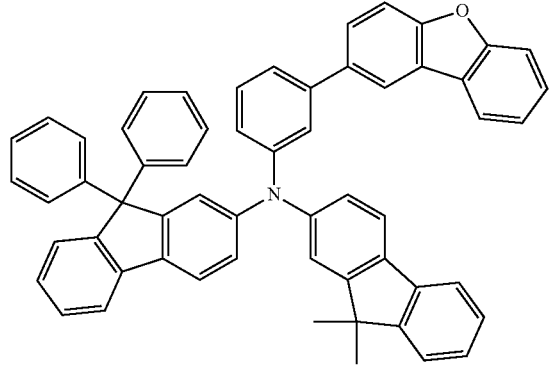
(B216)
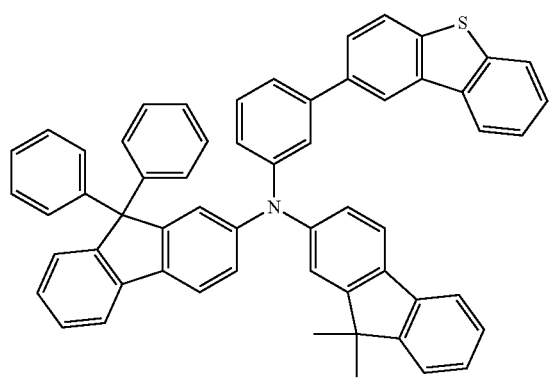
(B217)
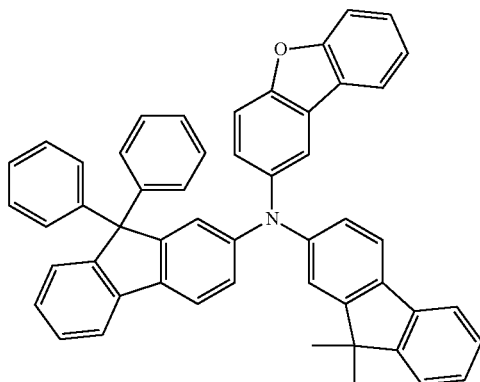
(B218)
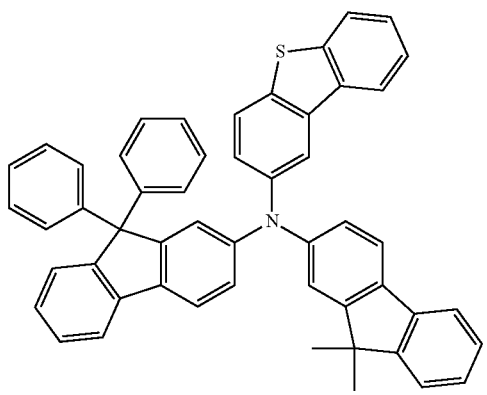
(B219)
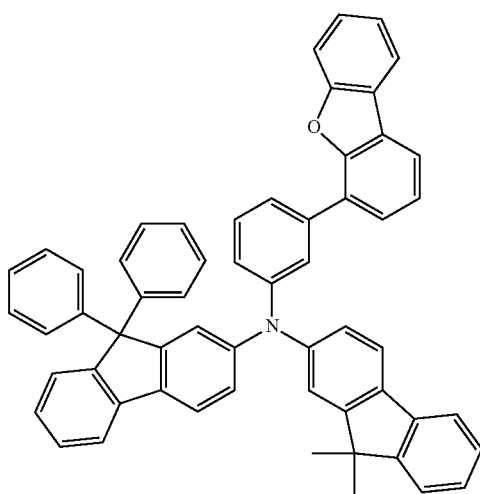

(B220)
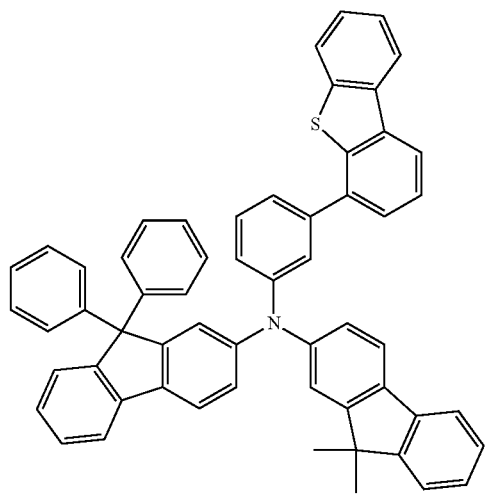
(B223)
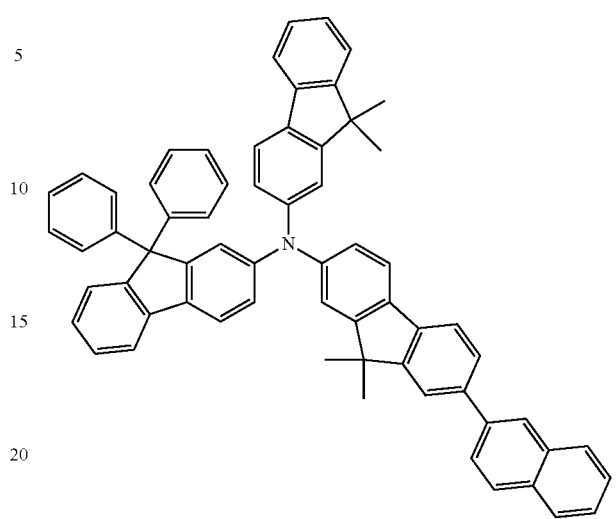
(B221)
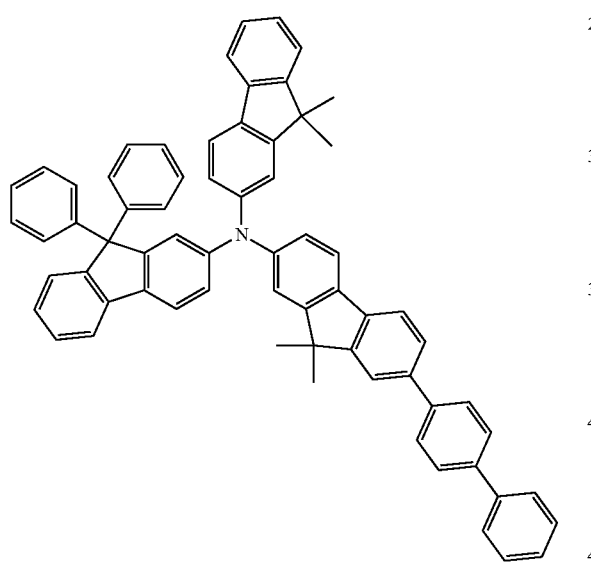
(B1224)
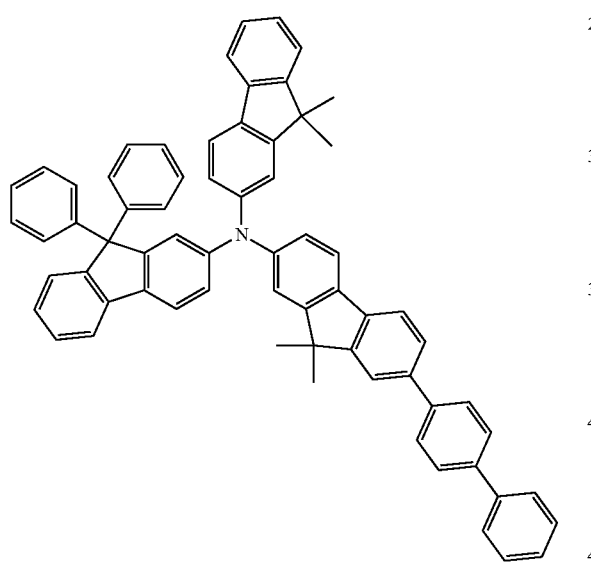
(B222)
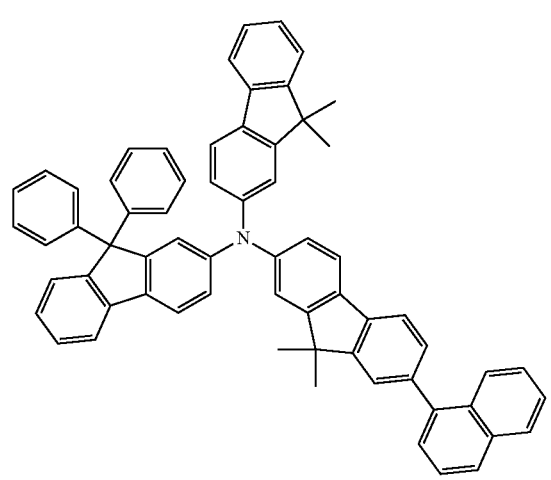
(B225)
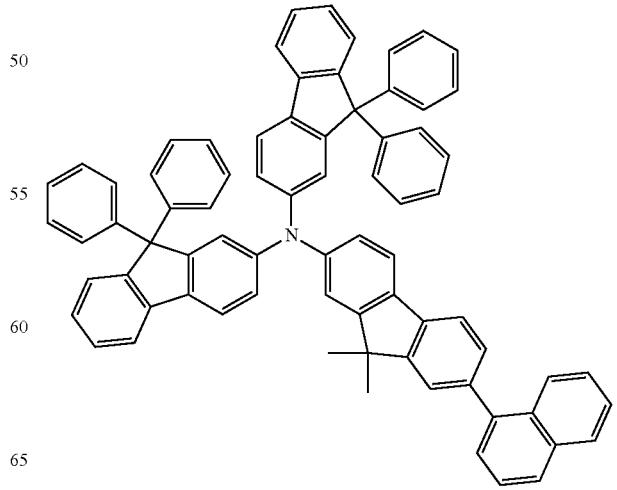

(B226)
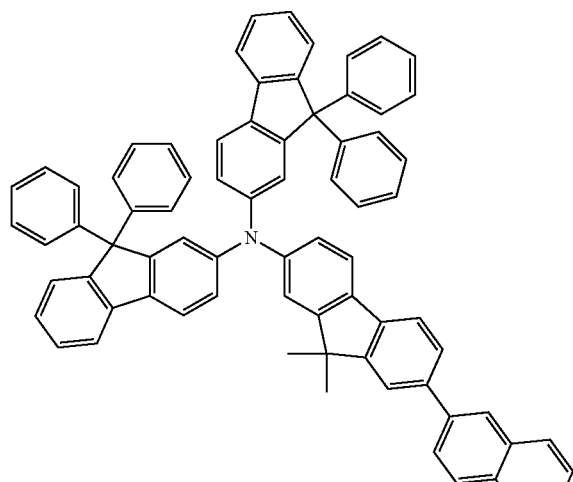
(B227)
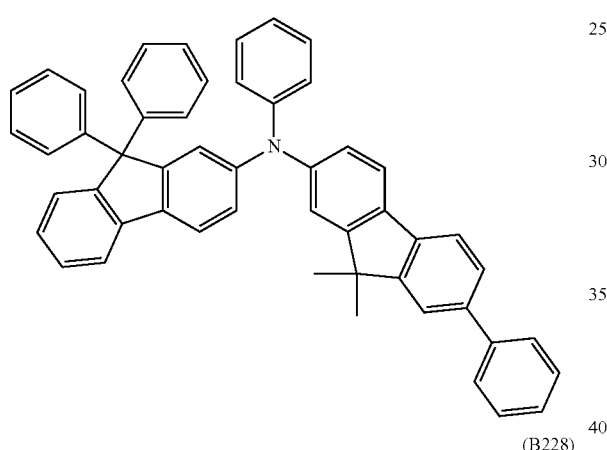
(B228)
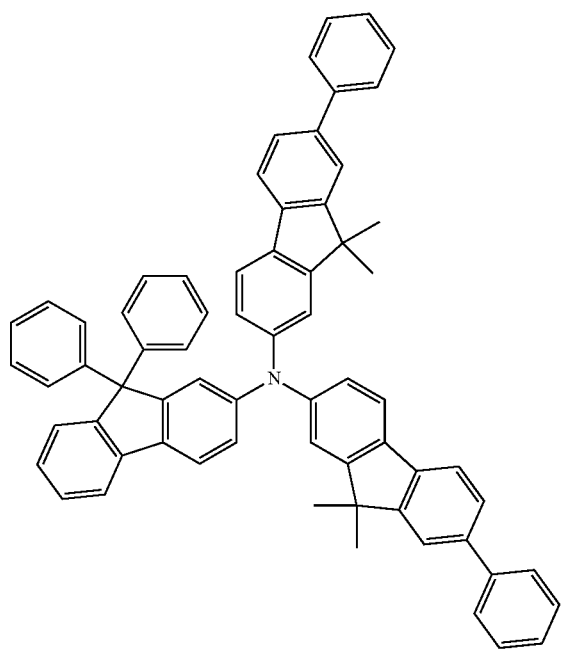
(B229)
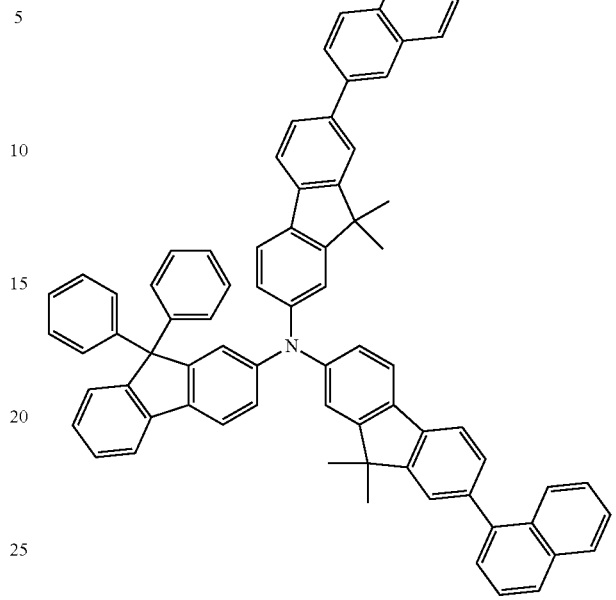
(B230)
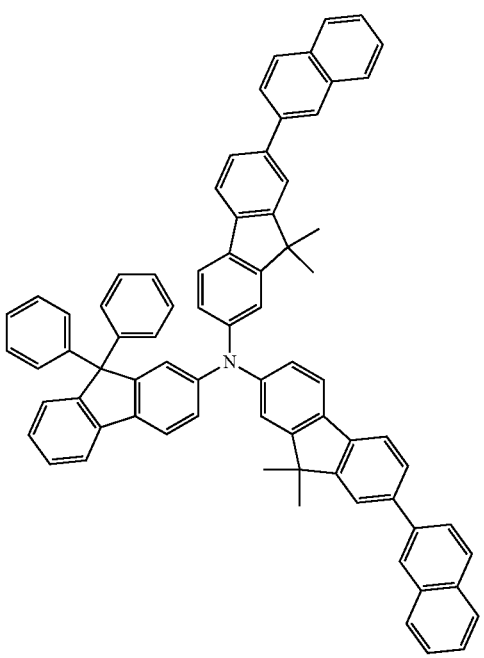

(B231)
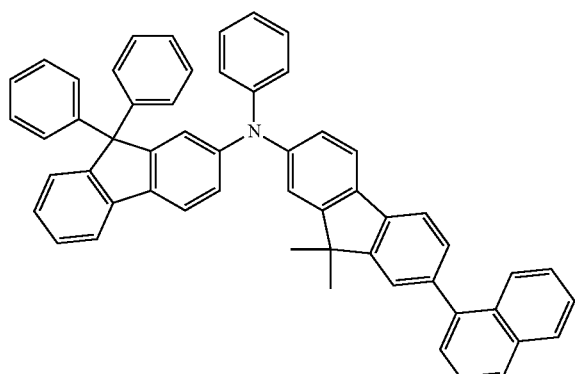
(B232)
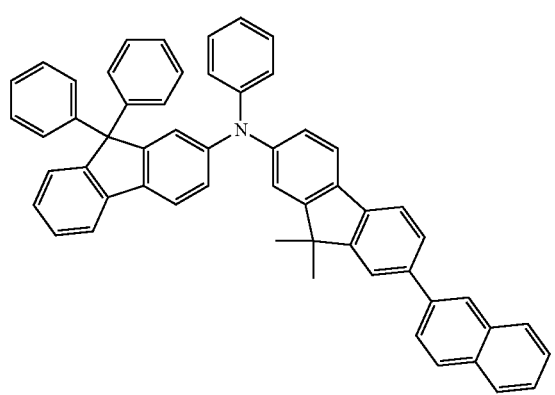
(B233)
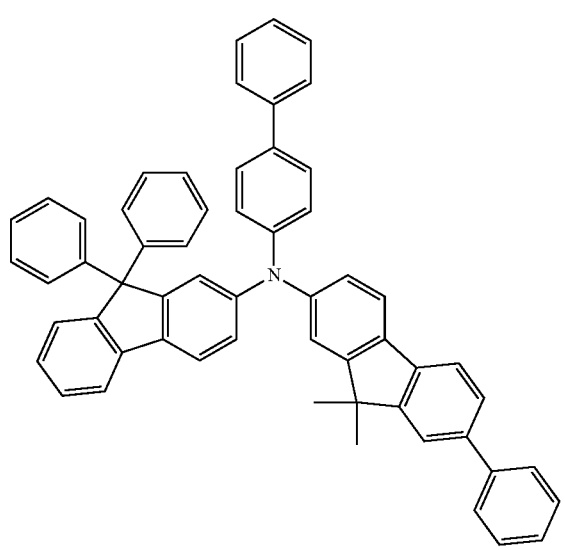
(B234)
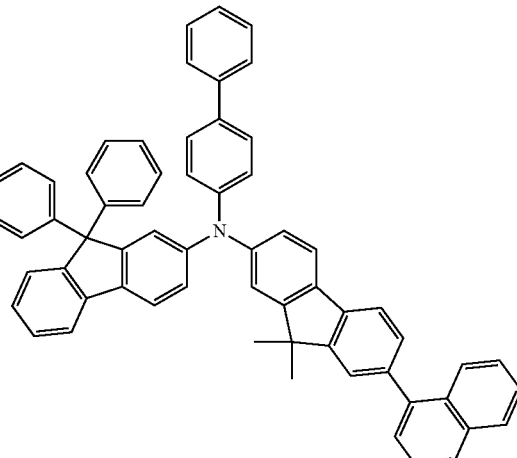
(B235)
(B236)
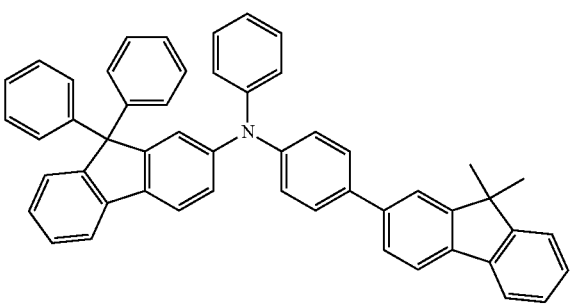

(B237)
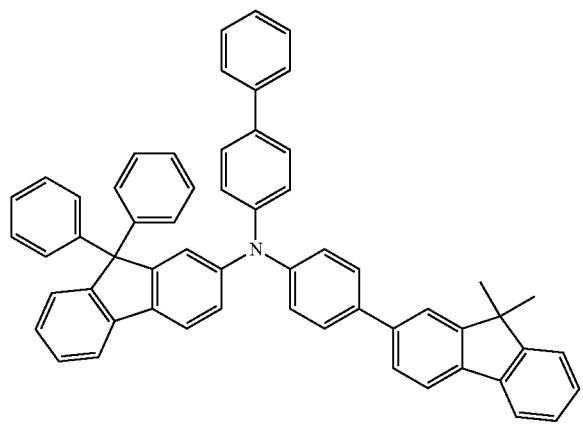
(B238)
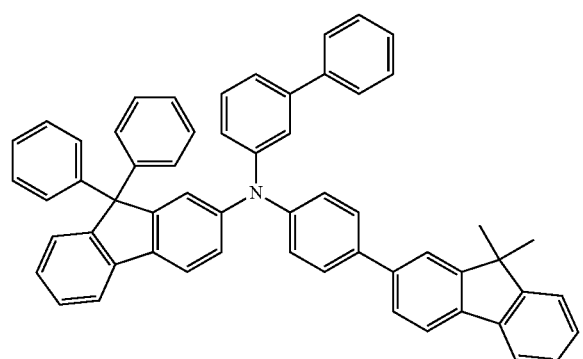
(B239)
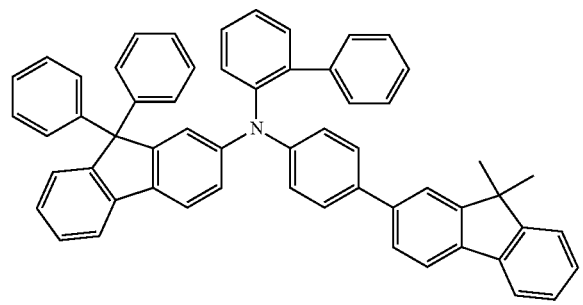
(B240)
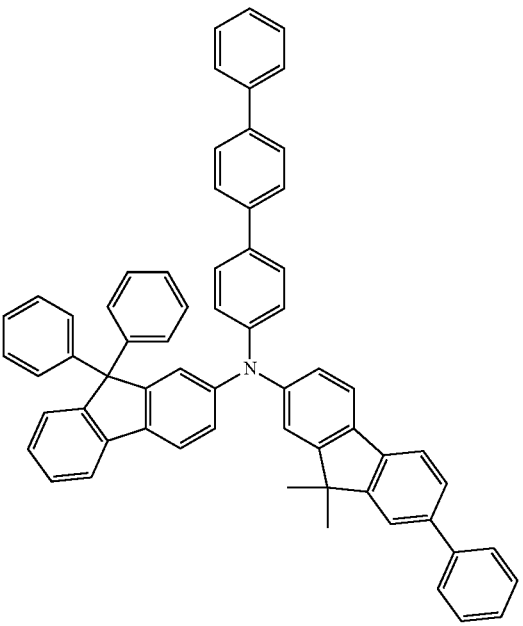
(B241)
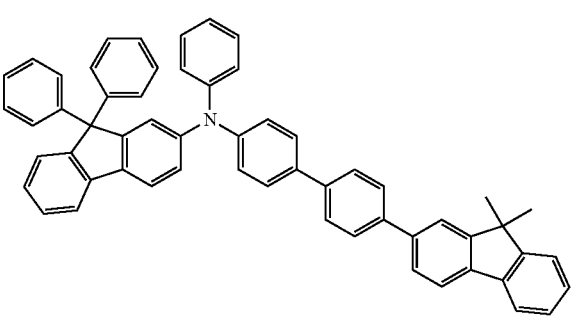
(B242)
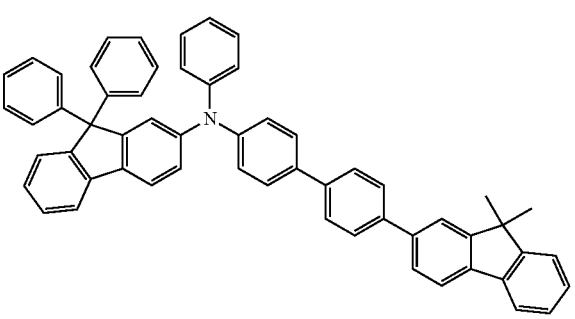

(B243)
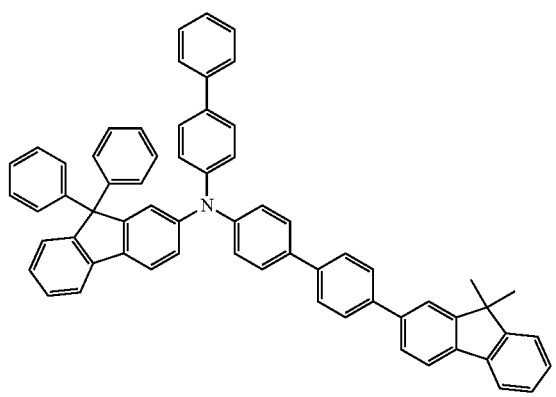
(B266)
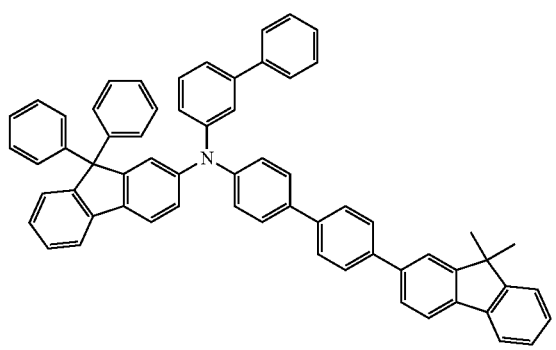
(B244)
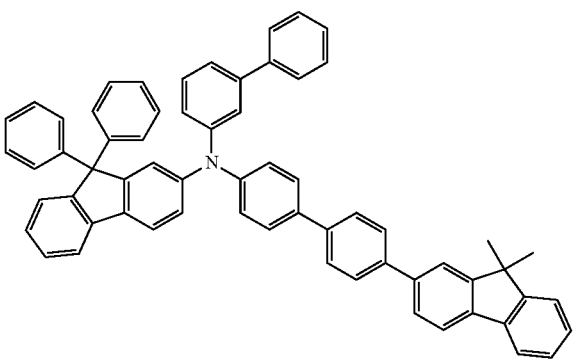
(B245)
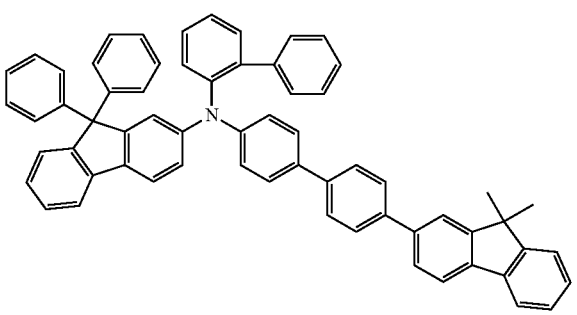
(B246)
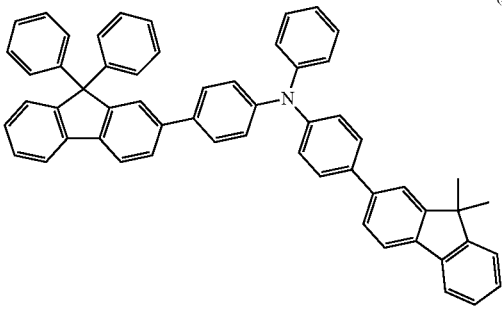
(B247)
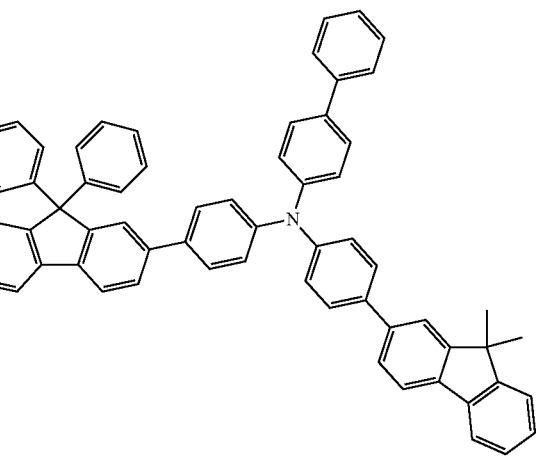
(B248)
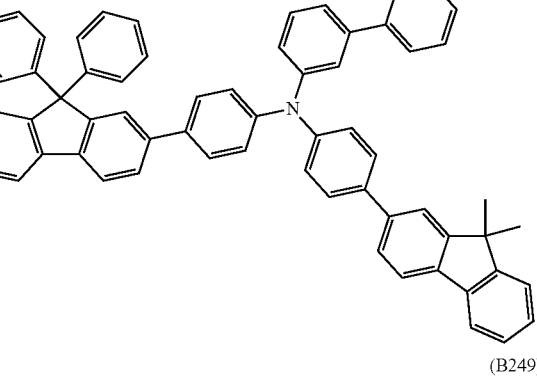
(B249)
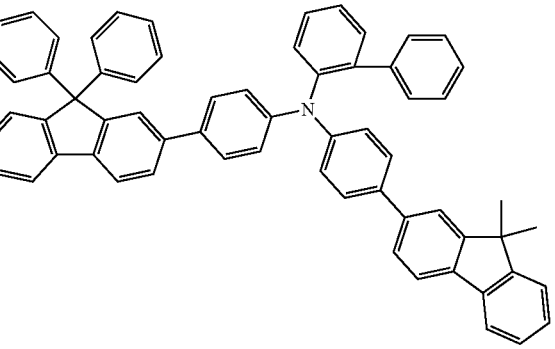

-continued
(B250)
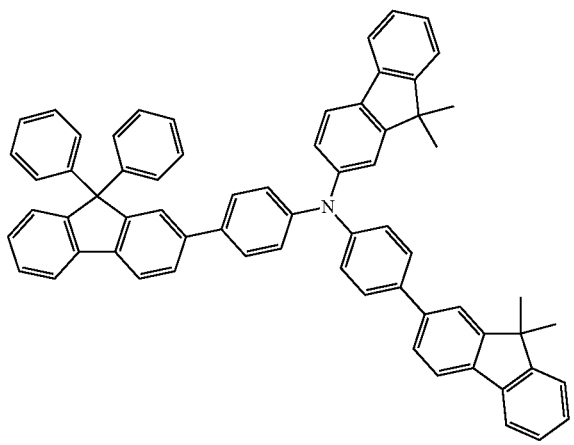
(B252)
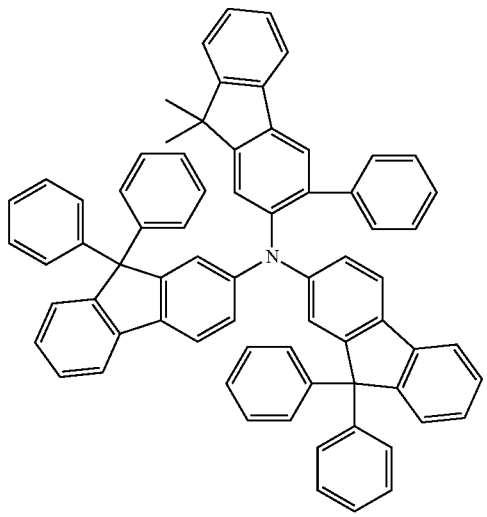
(B250)
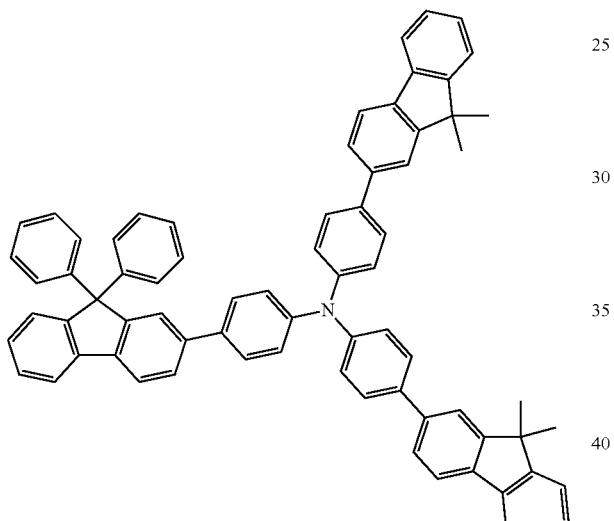
(B253)
(B251)
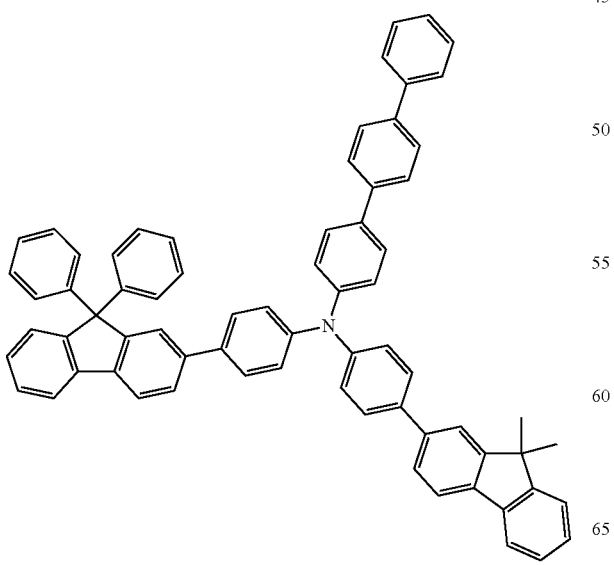
(B254)
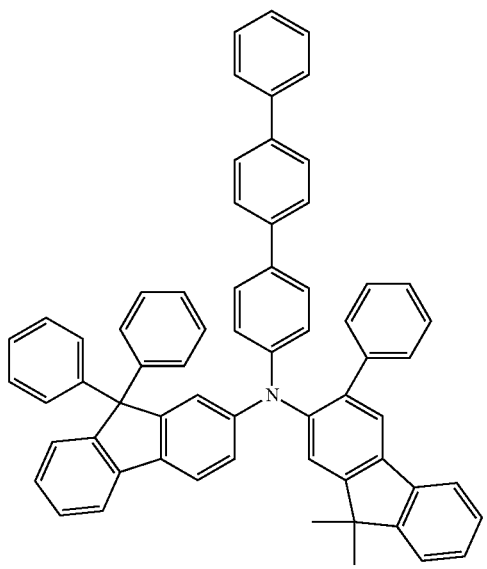

-continued
(B255)
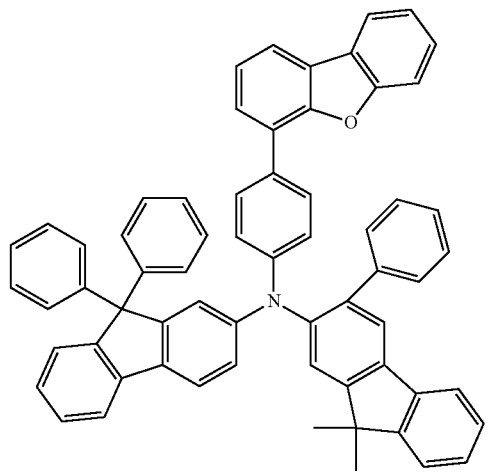
(B256)
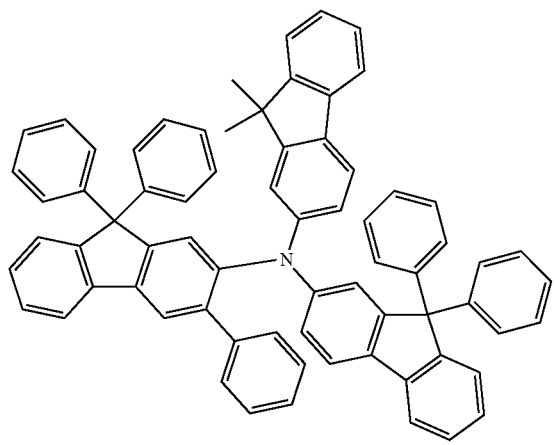
(B257)
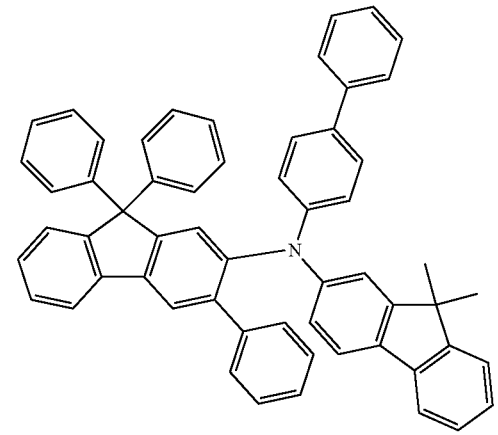
-continued
(B258)
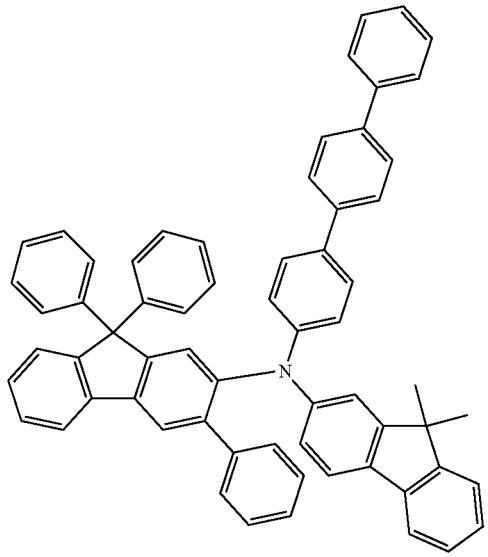
(B259)
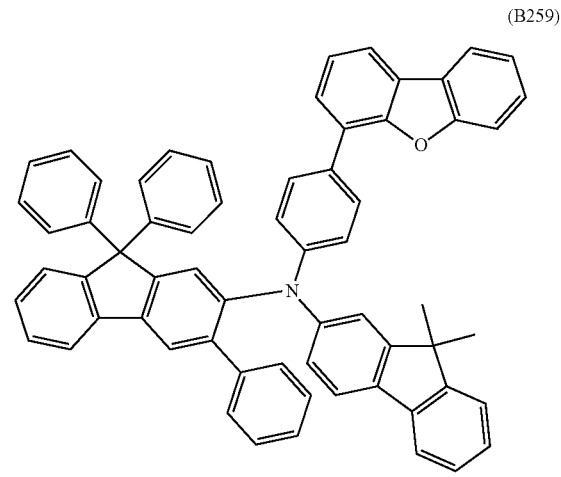
(B260)
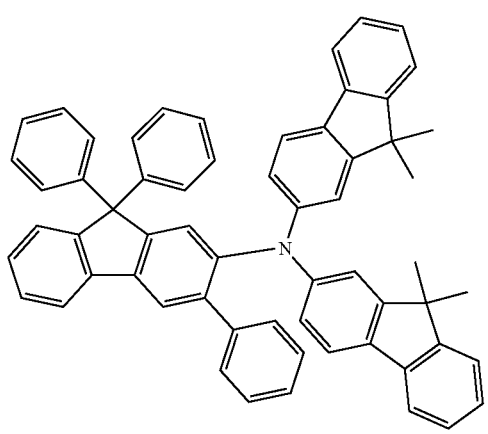

(B261)
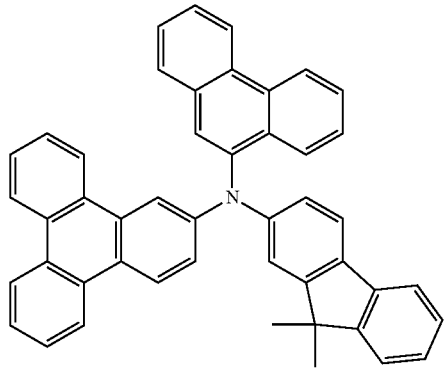
(B262)
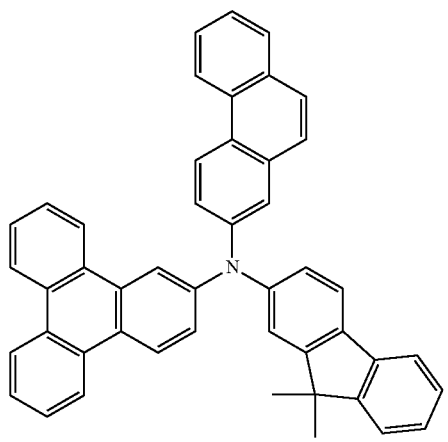
(B263)
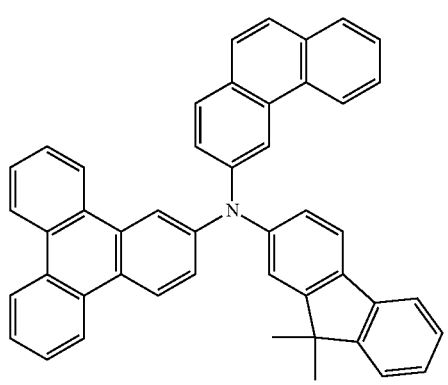
(B264)
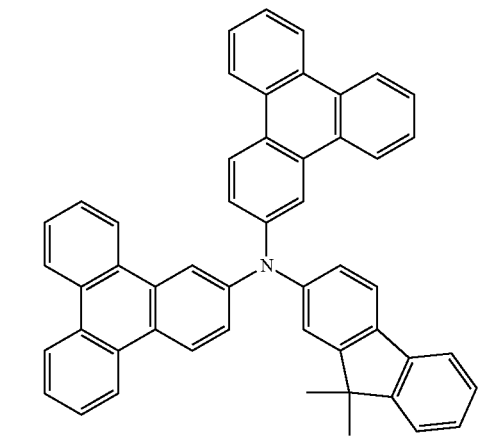
(B265)
8. The organic light emitting device of claim 4, wherein the compound of Chemical Formula 2 is selected from among the following compounds:

591                                         592
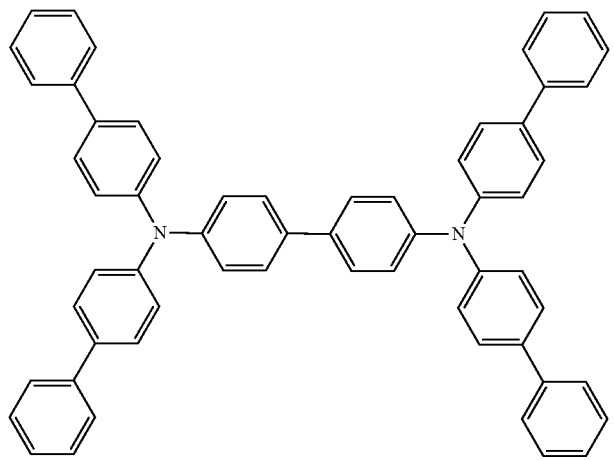
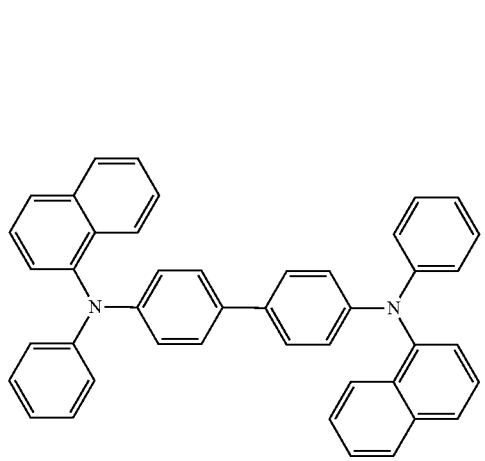
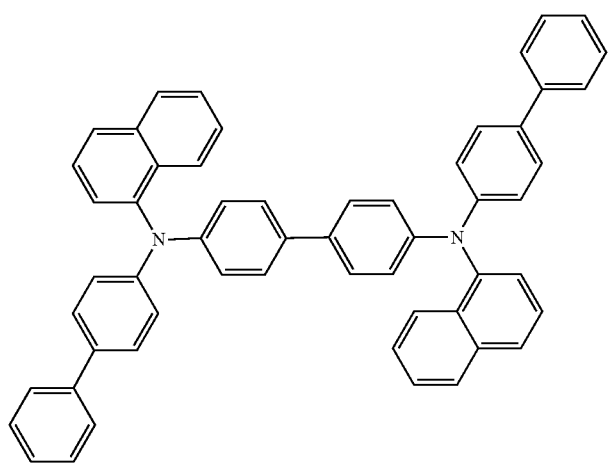
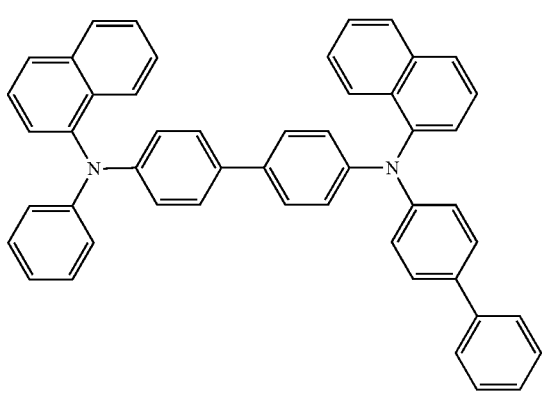
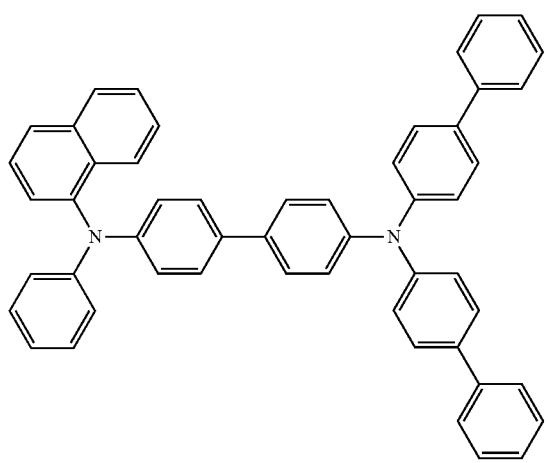

-continued
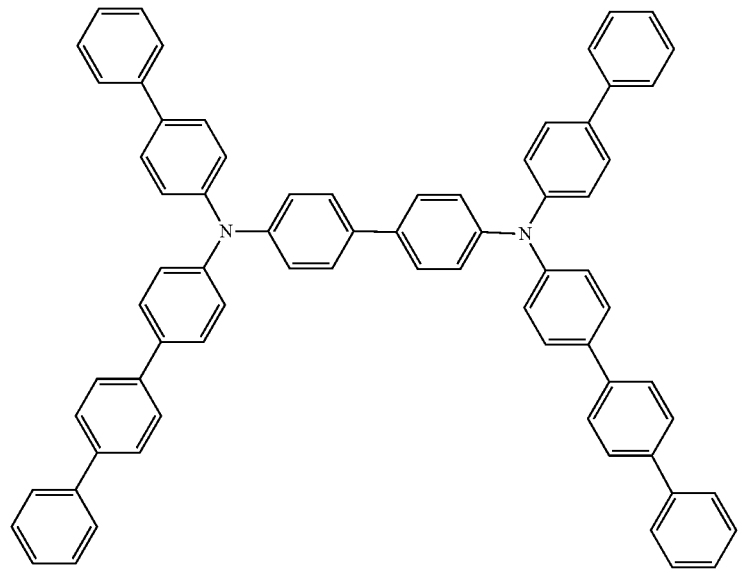
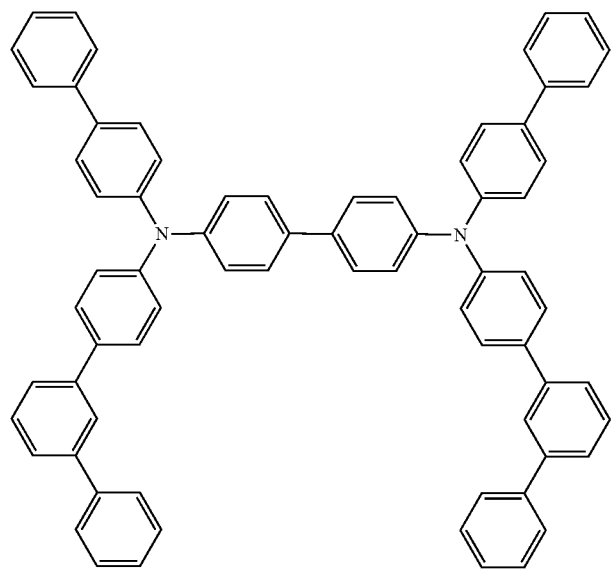
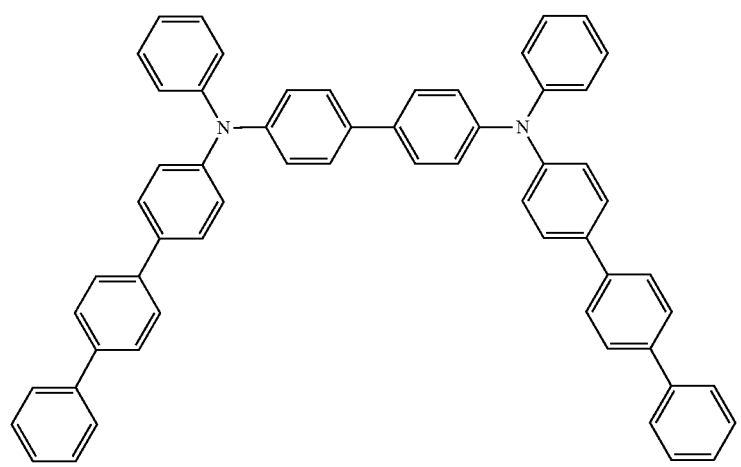

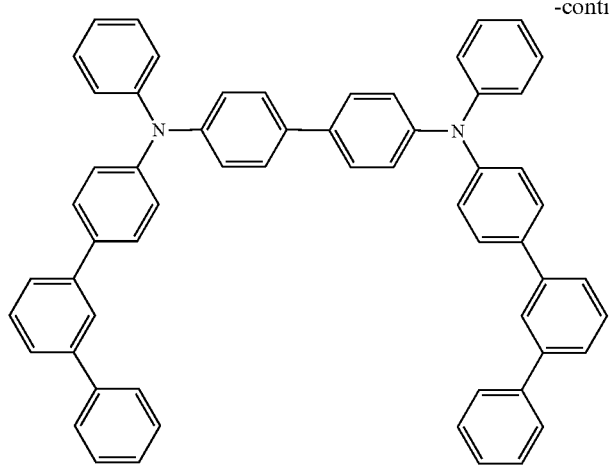
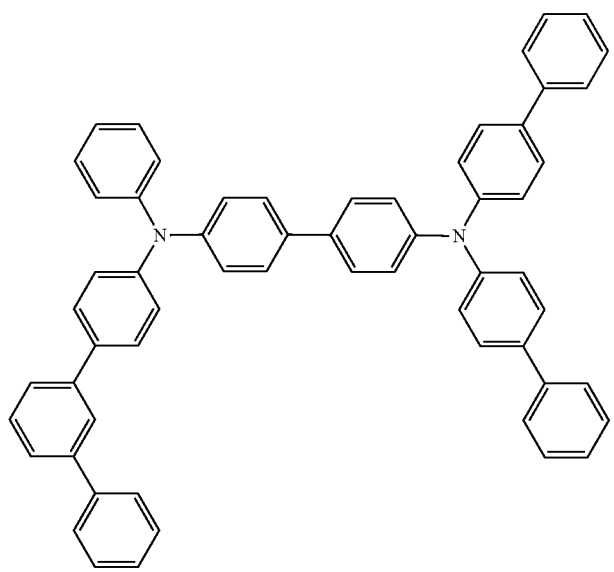
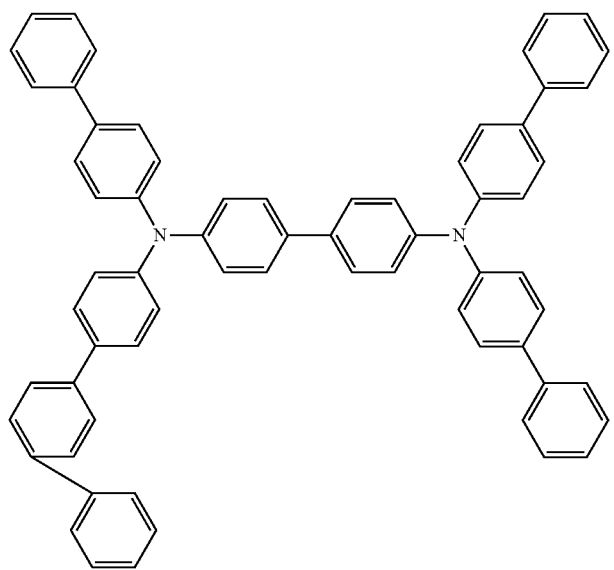

-continued
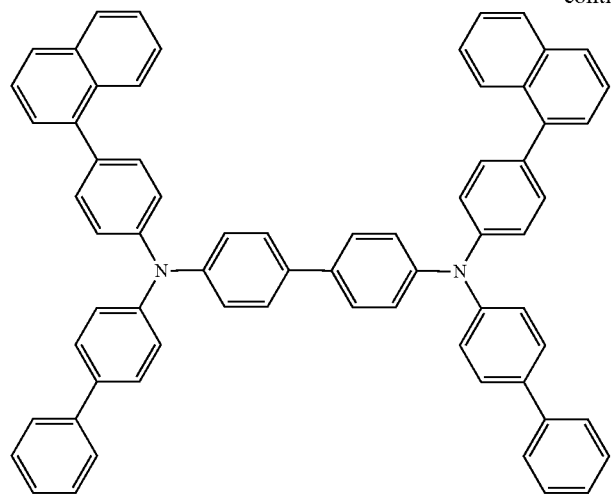
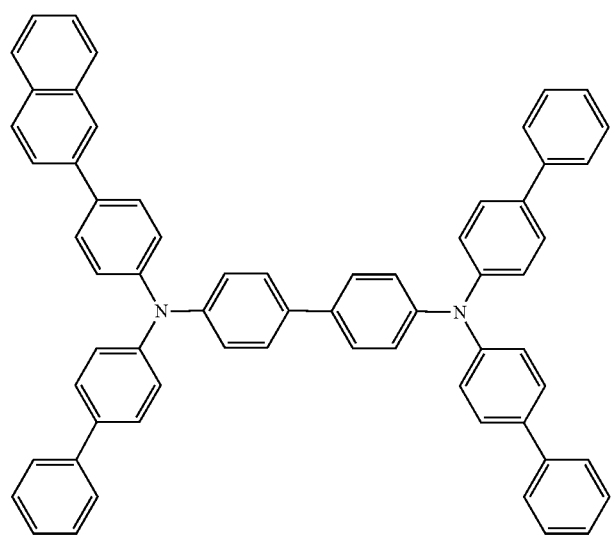
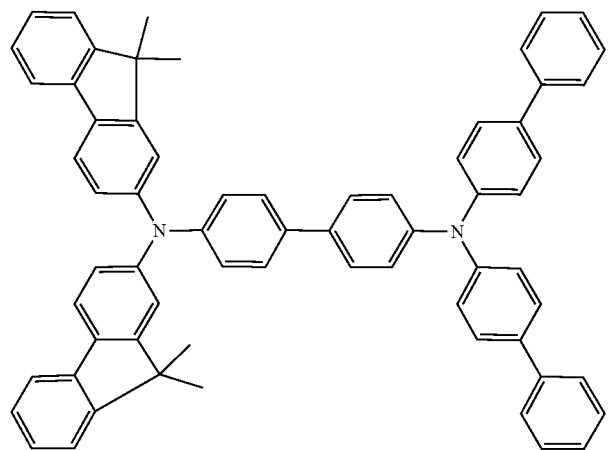

-continued
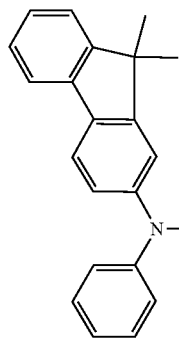
599
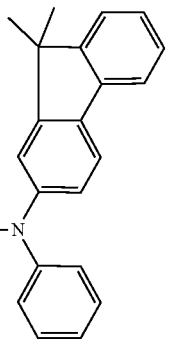
600
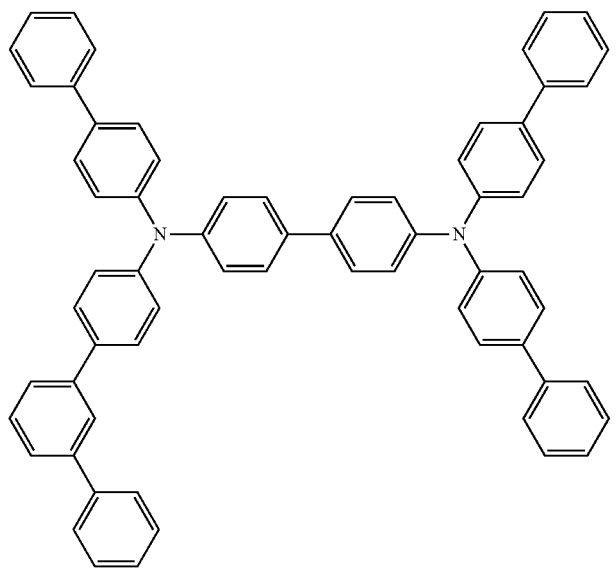
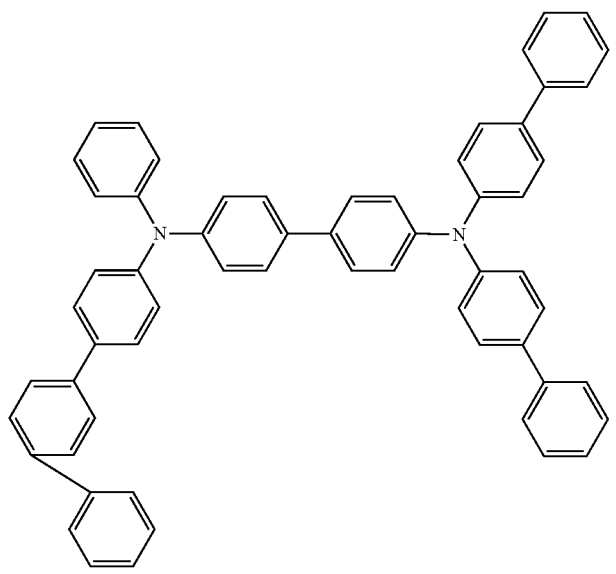

601
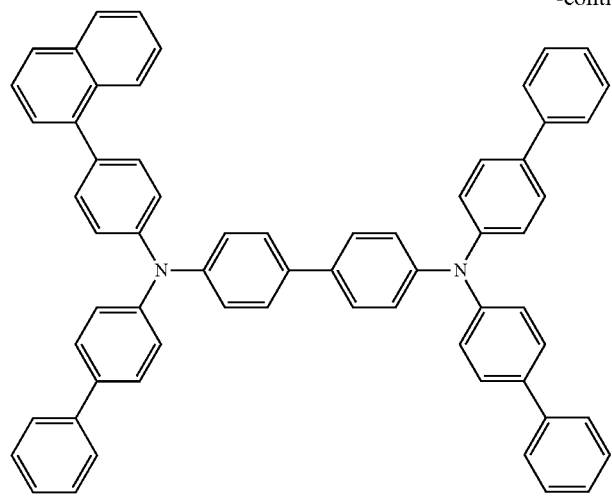
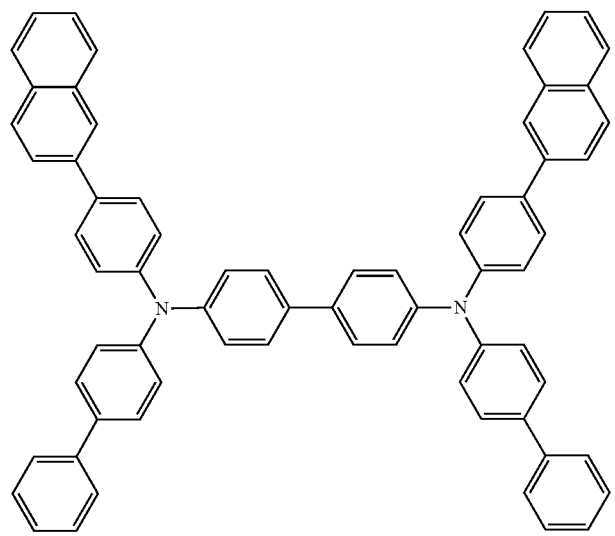
602
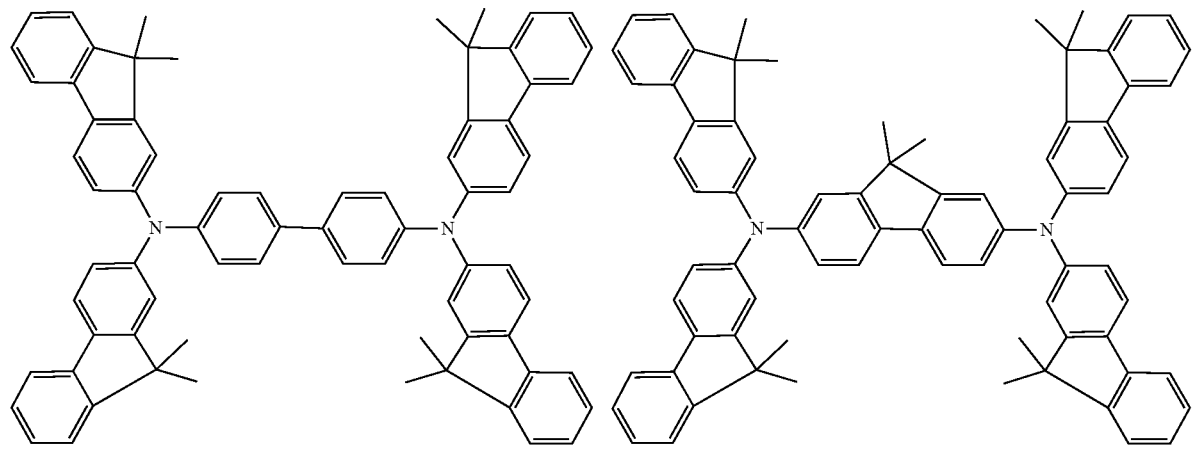

-continued
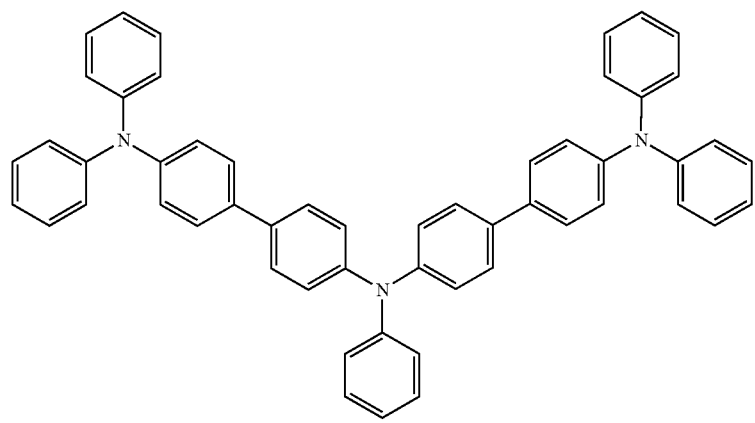
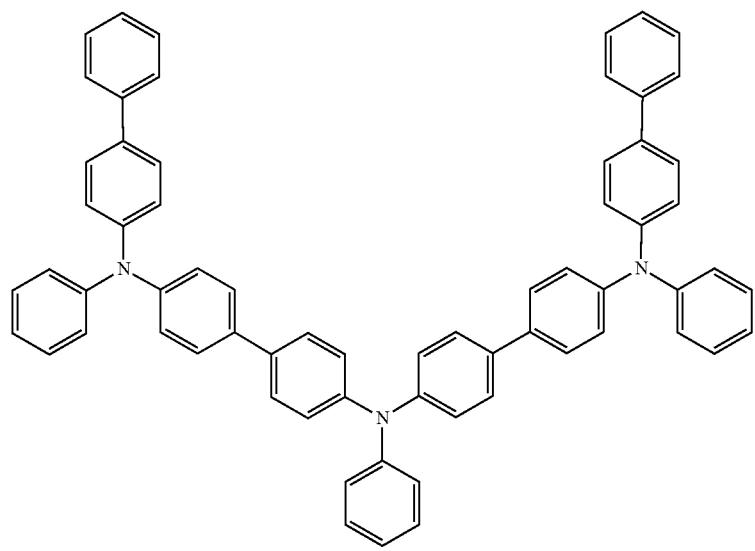
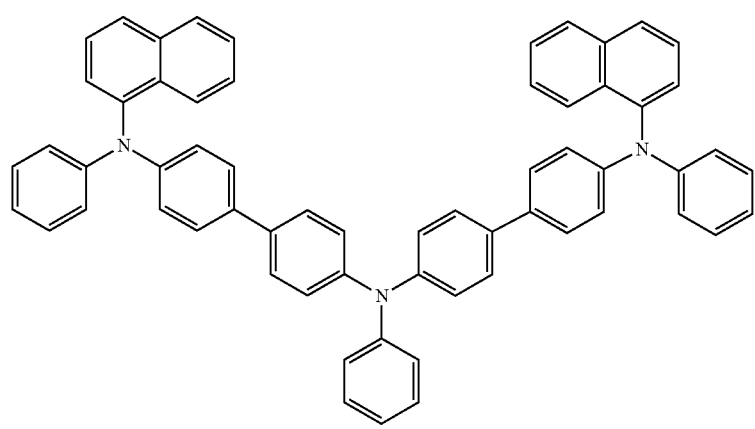

-continued
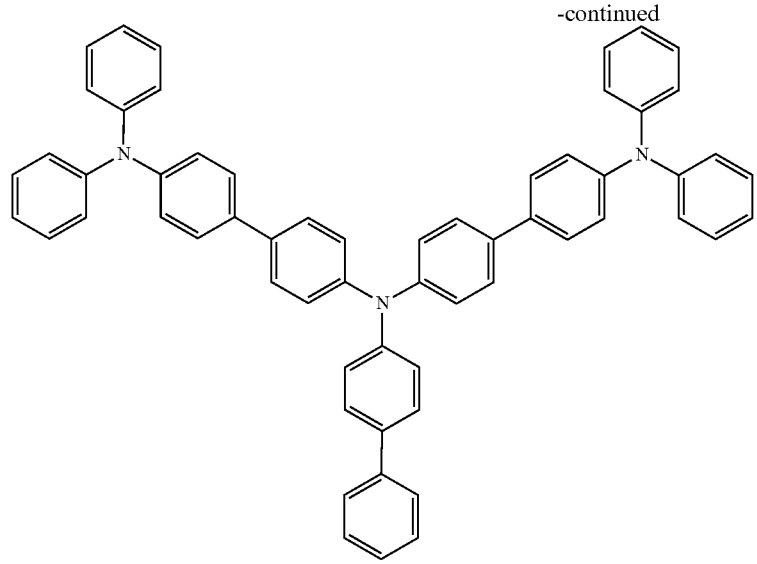
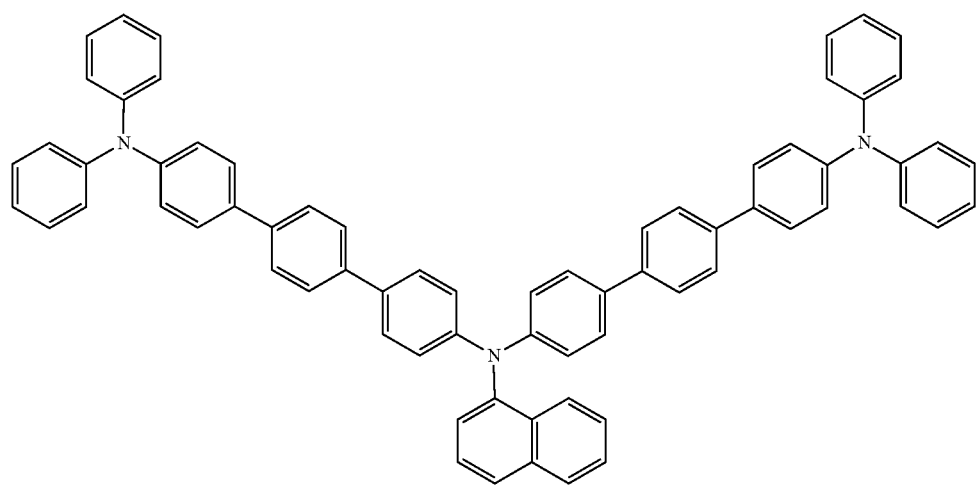
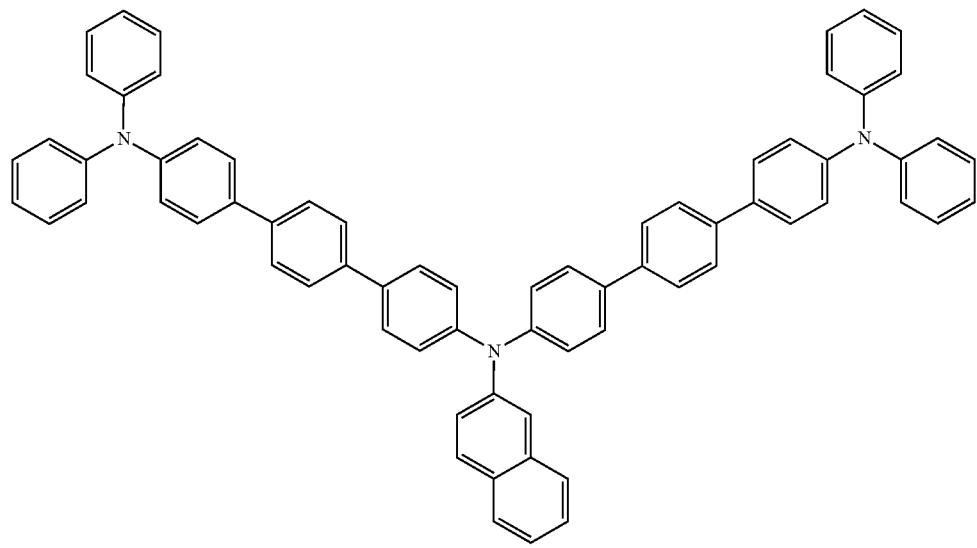

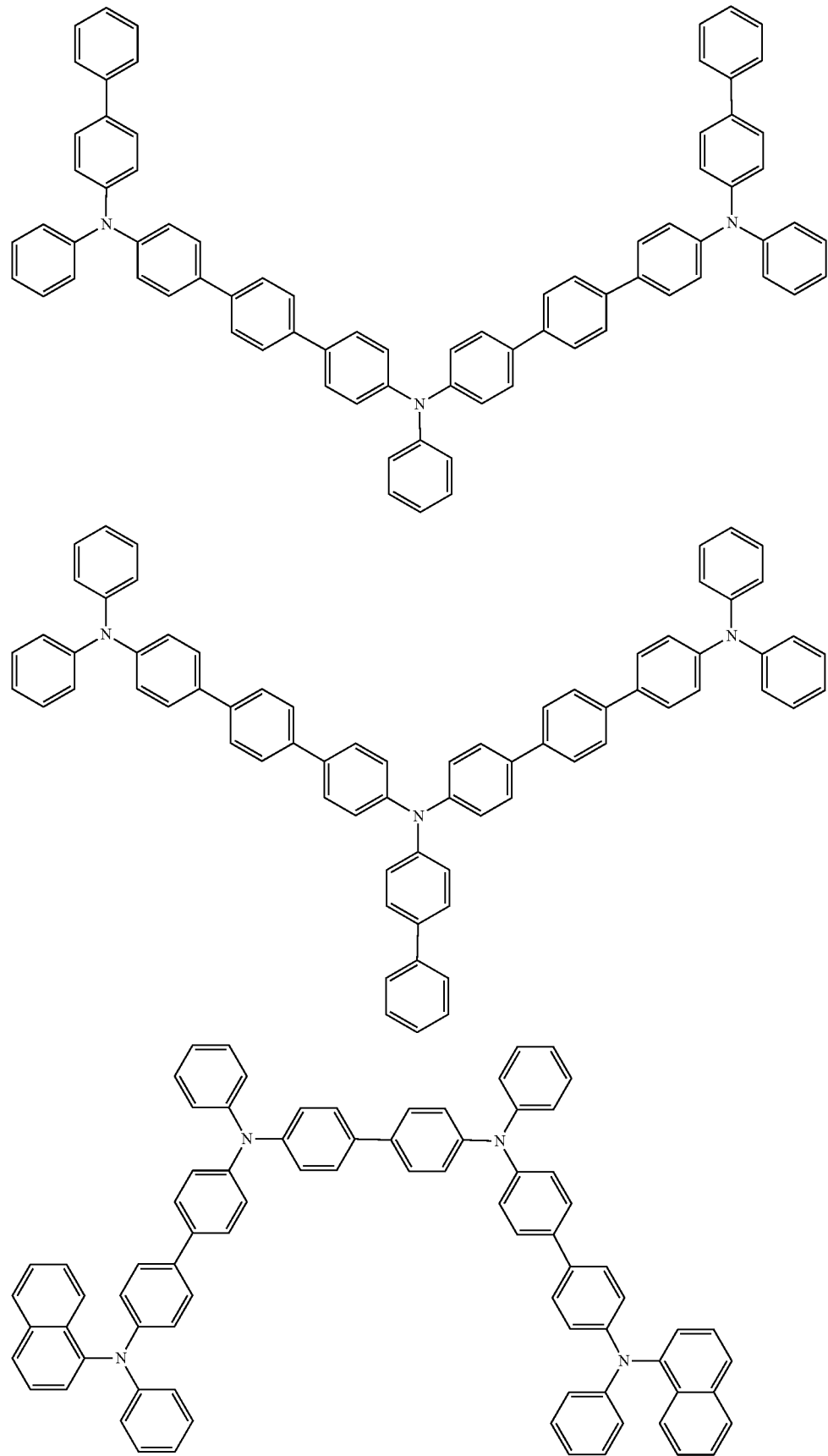

-continued
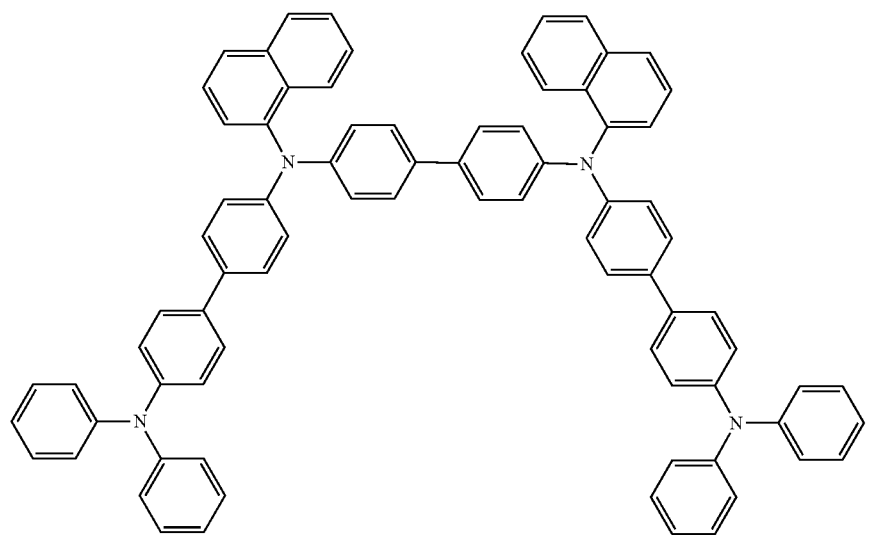
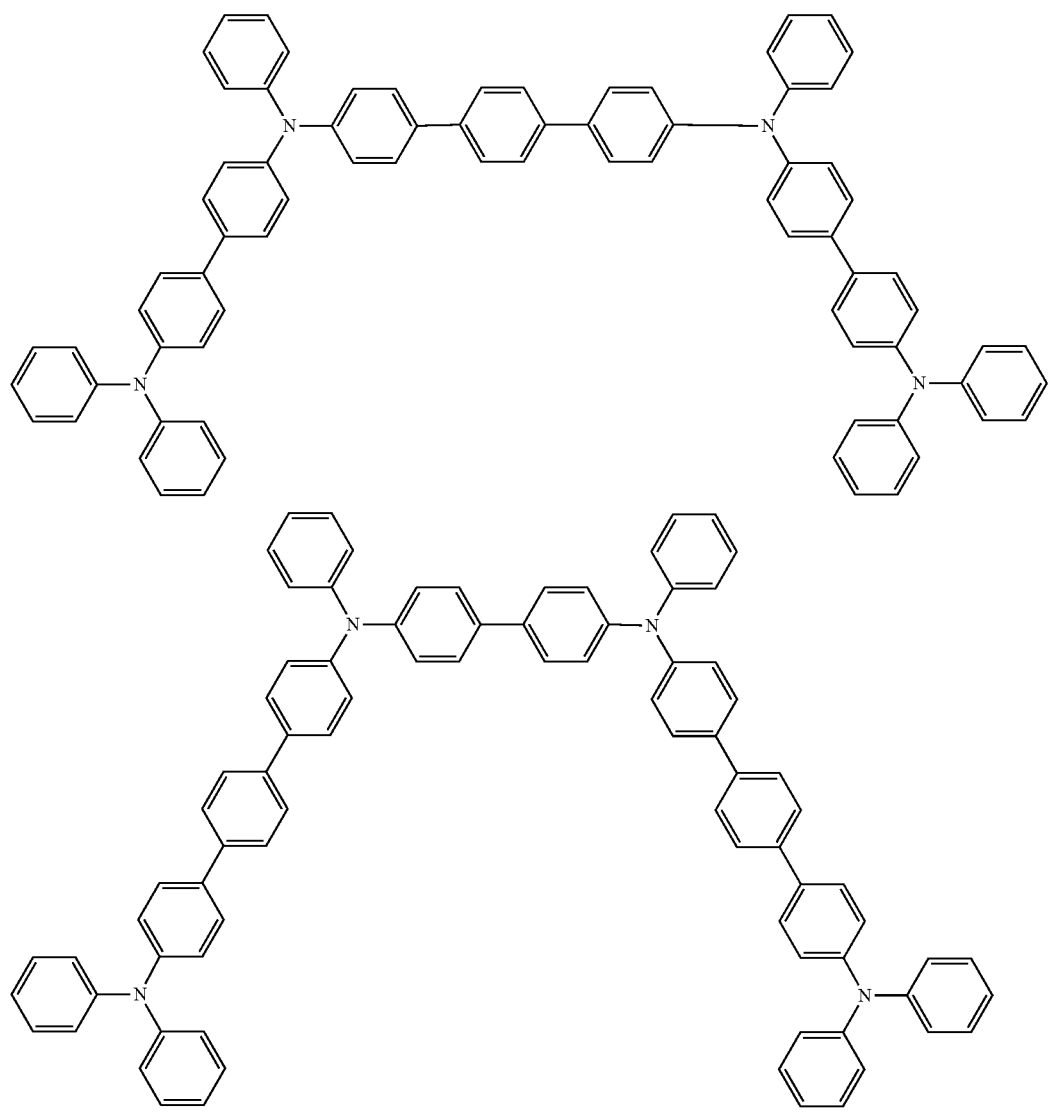

-continued
611
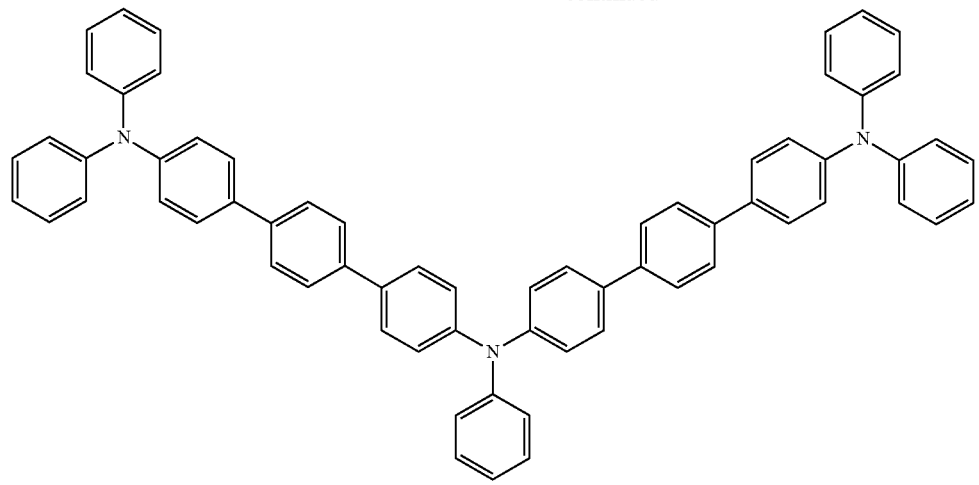
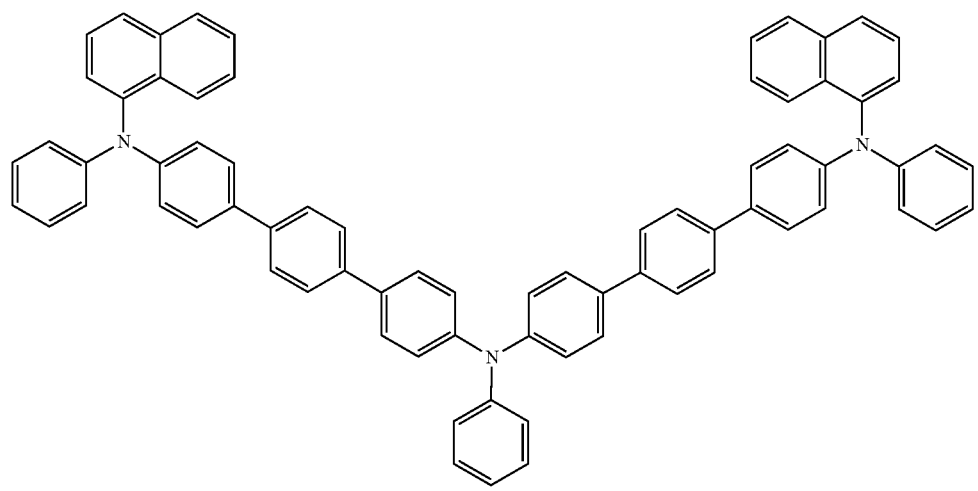
612
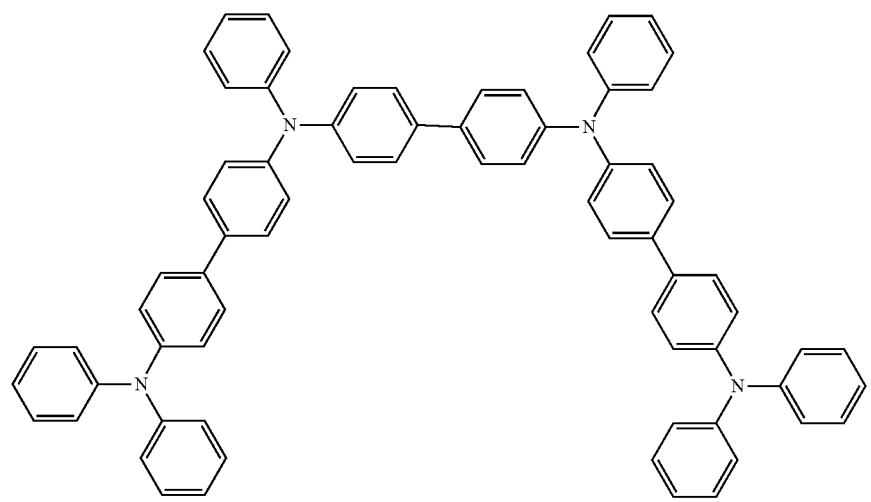

613
-continued
614
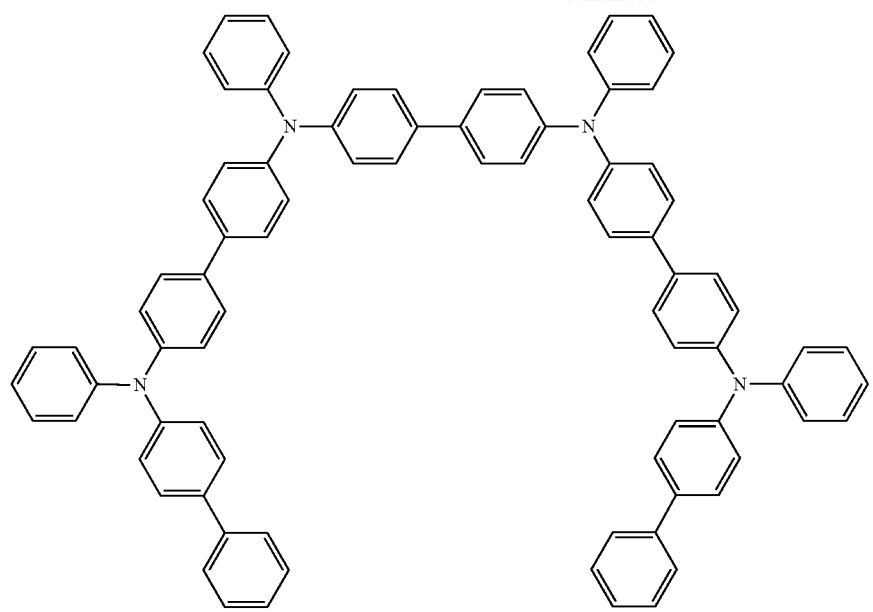
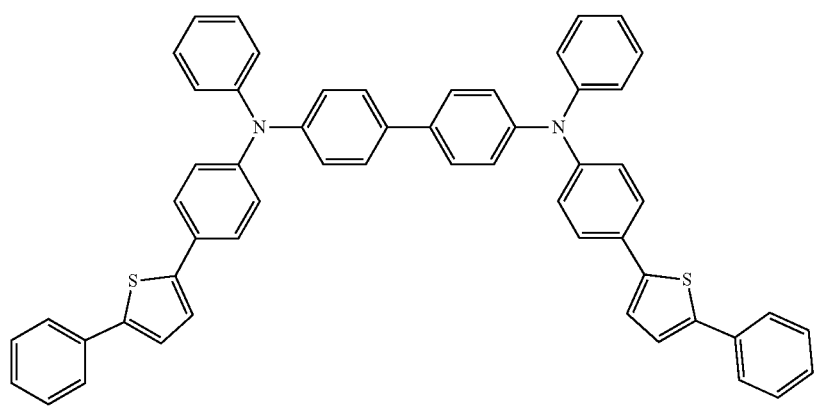
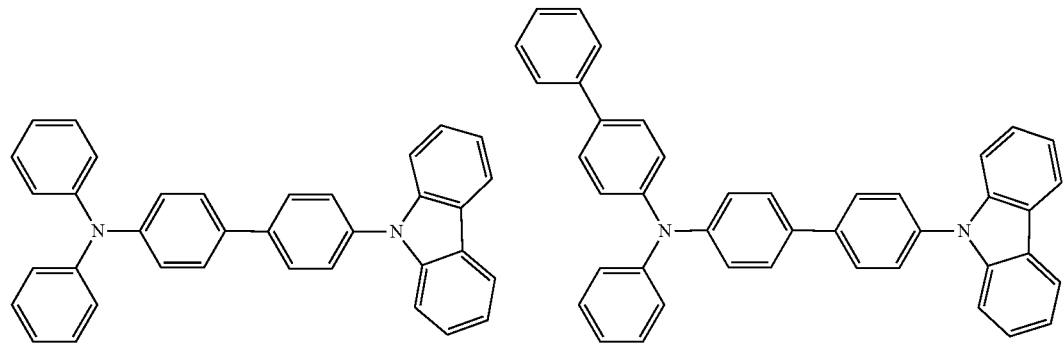

615 616
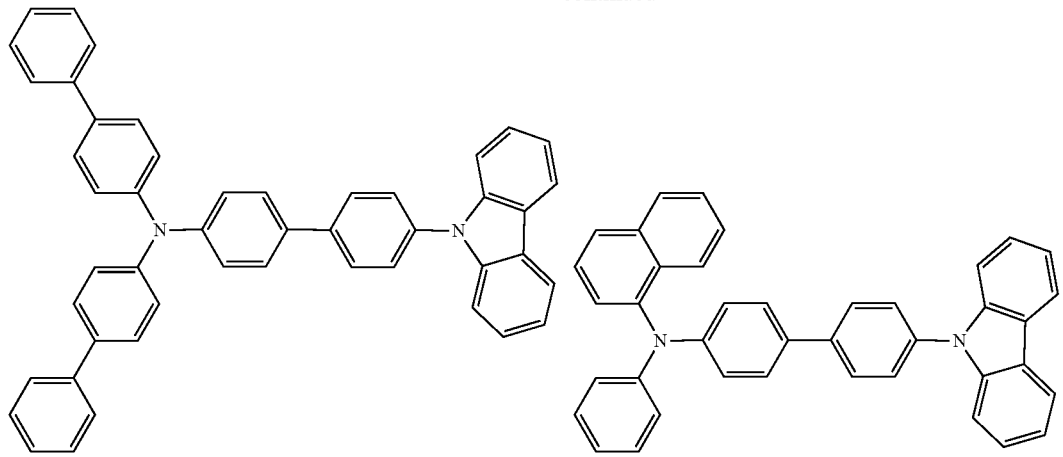
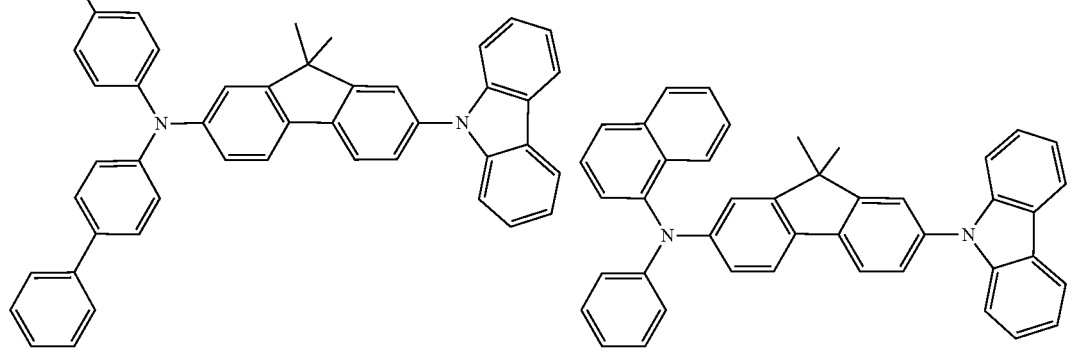
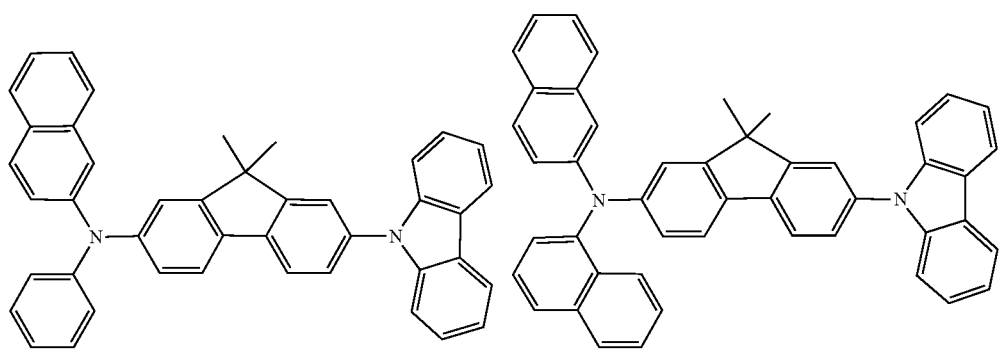
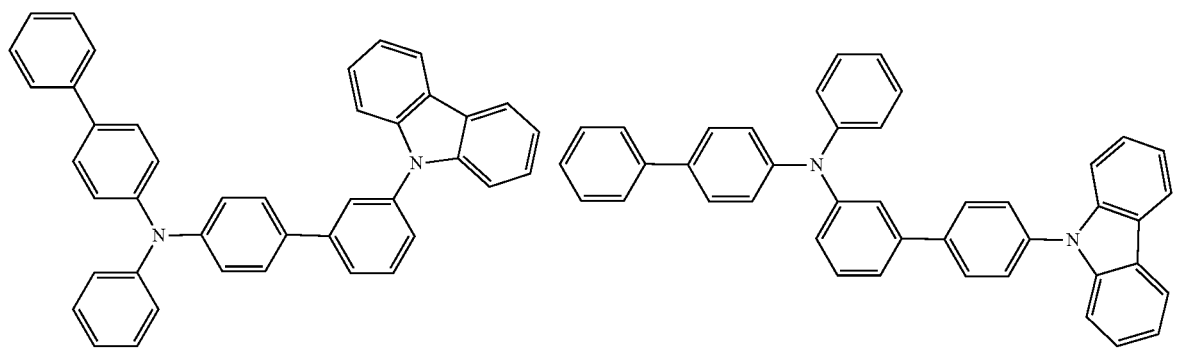

-continued
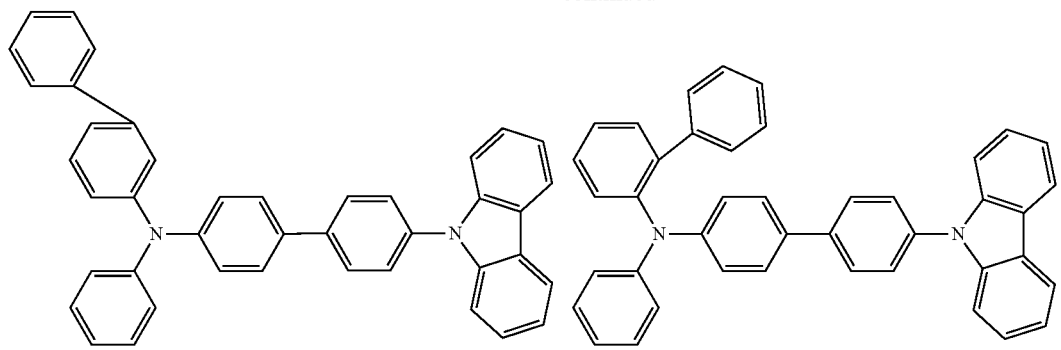
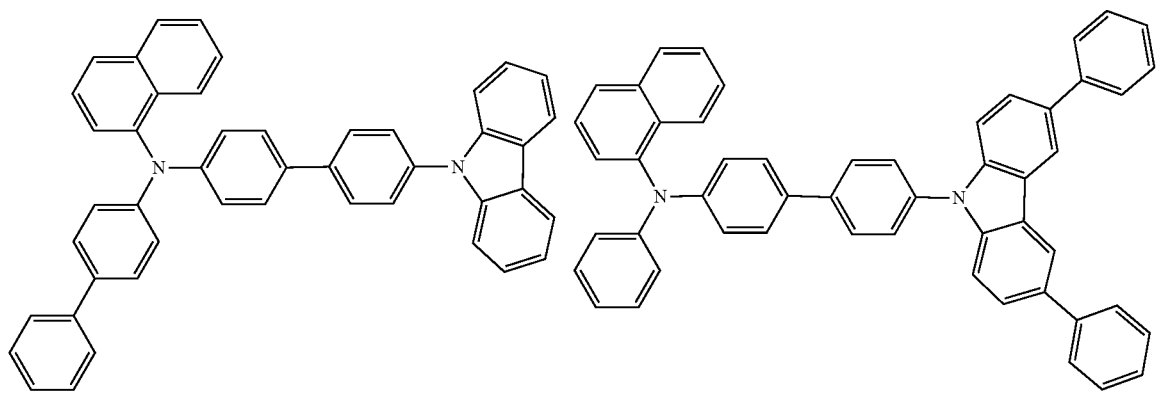
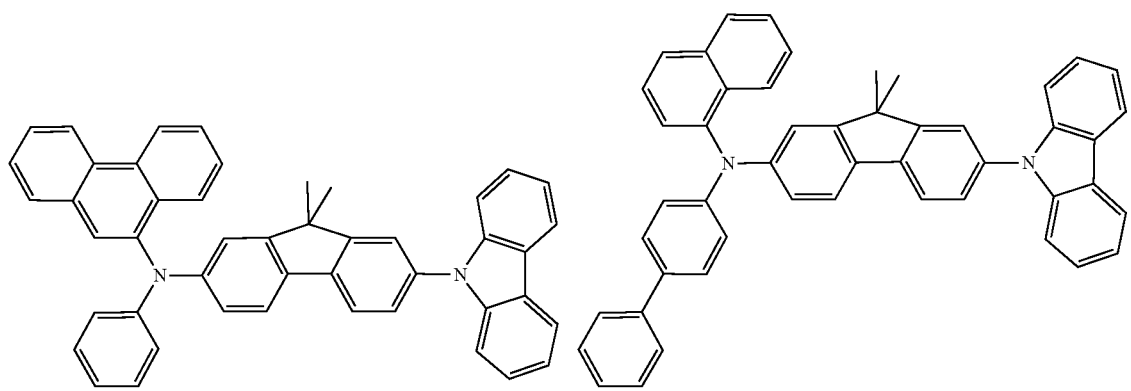
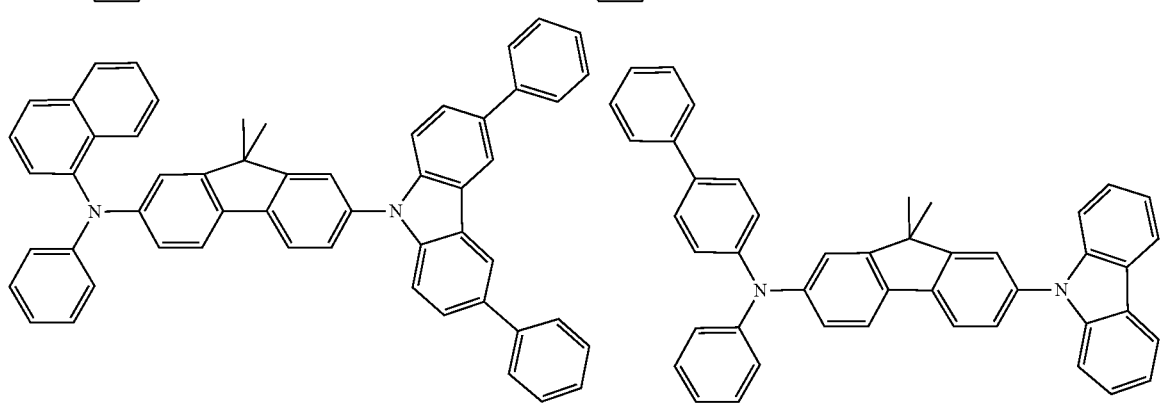

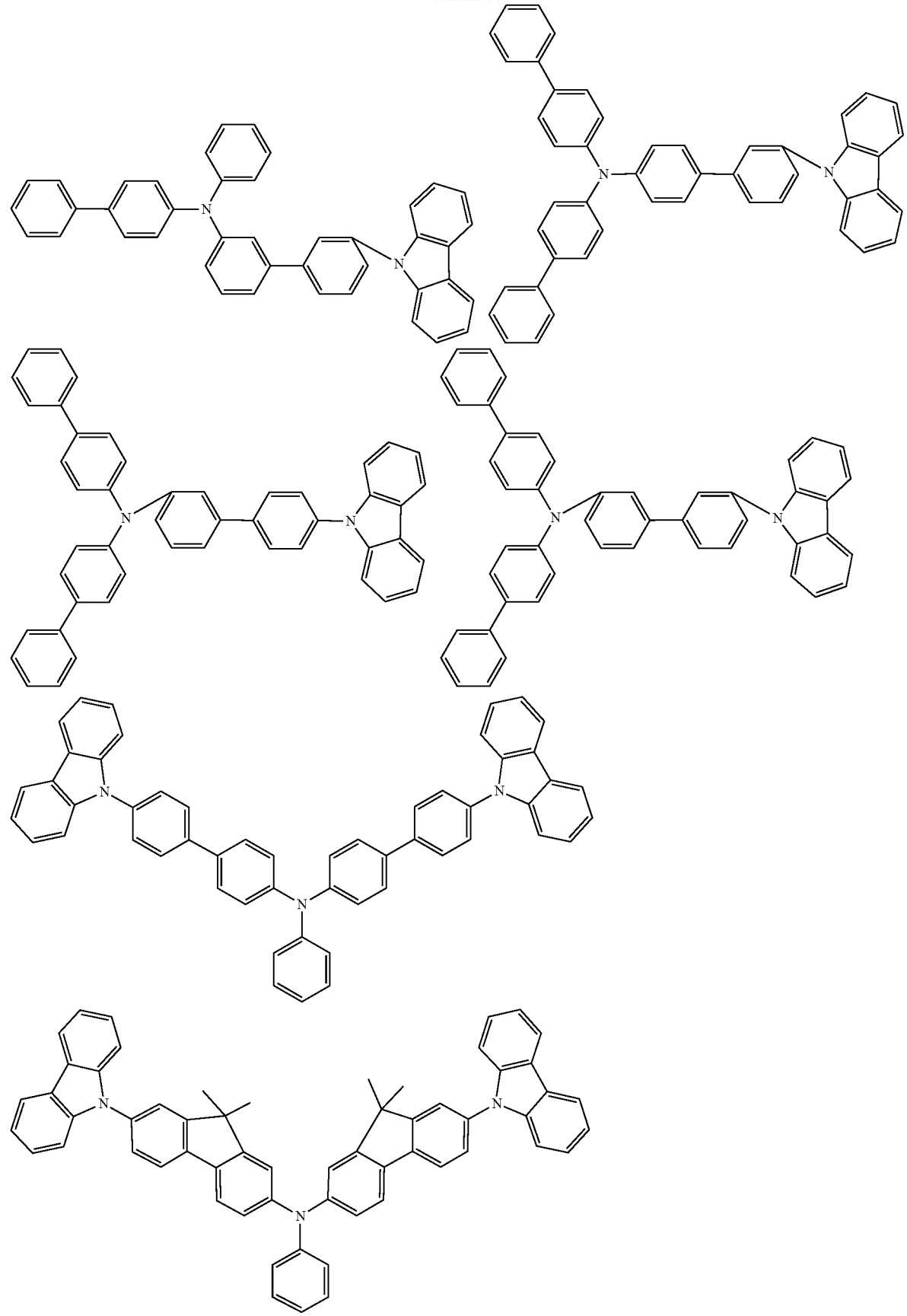

-continued
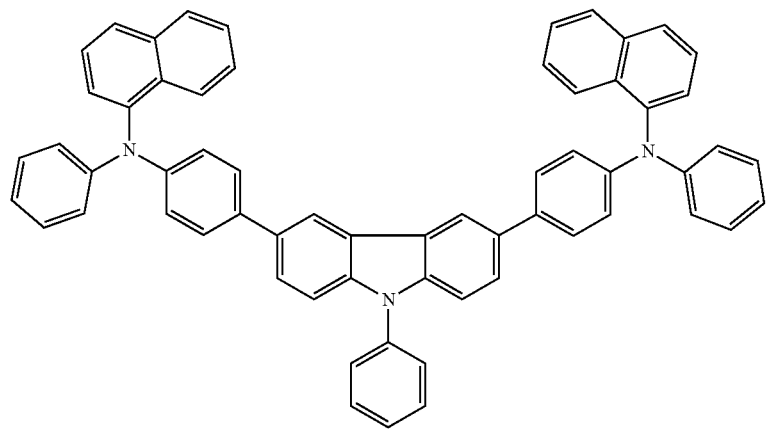
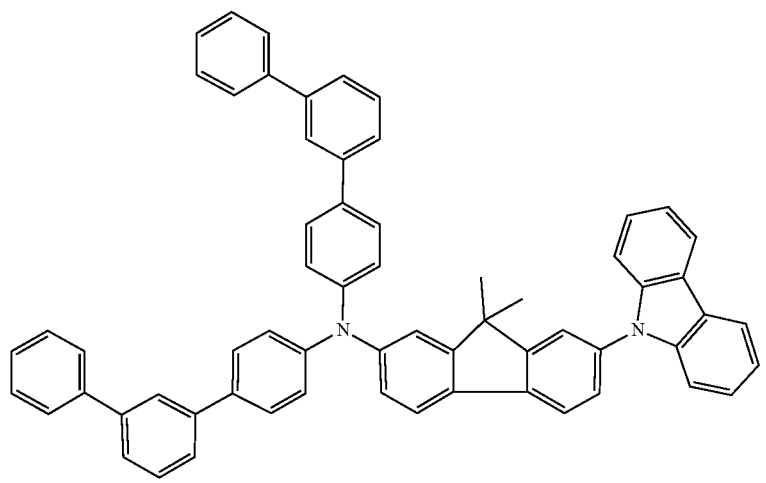
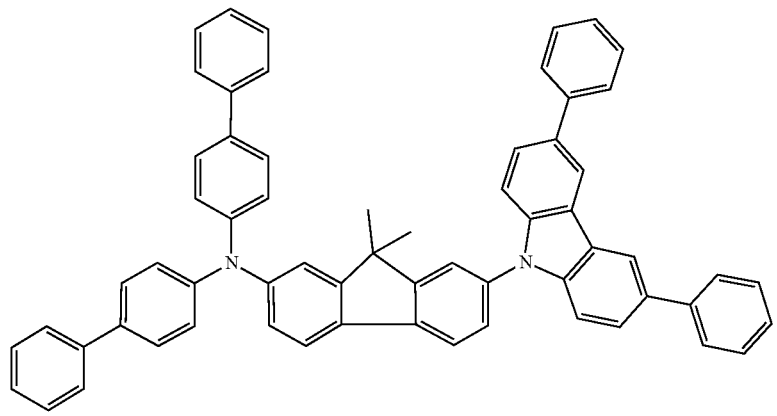
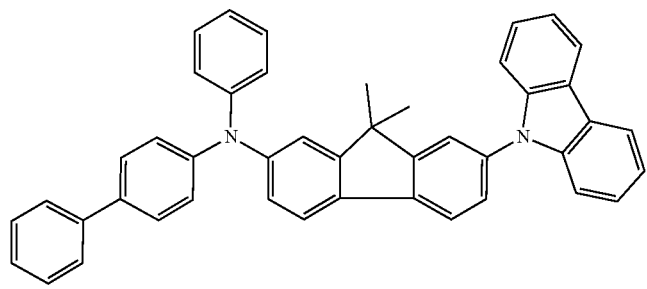

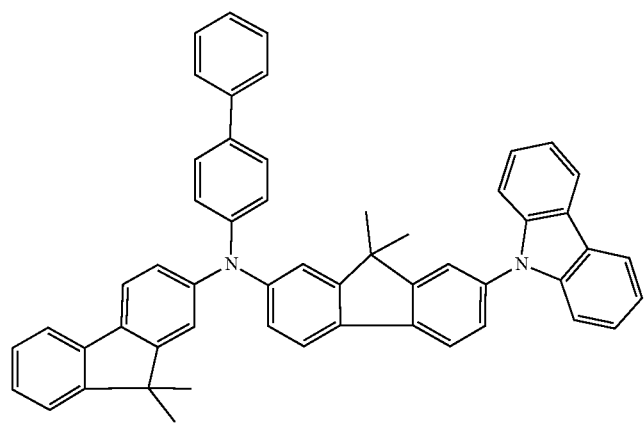
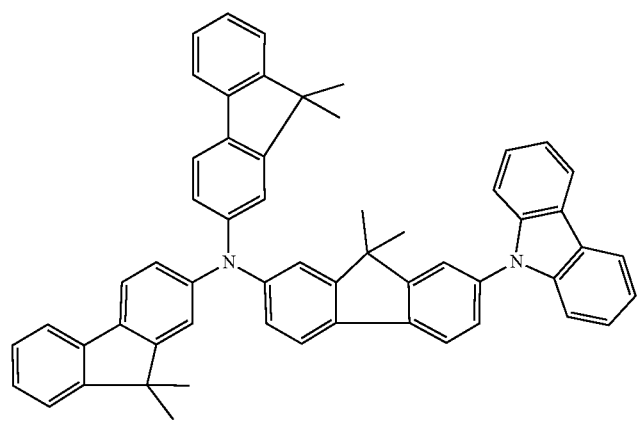
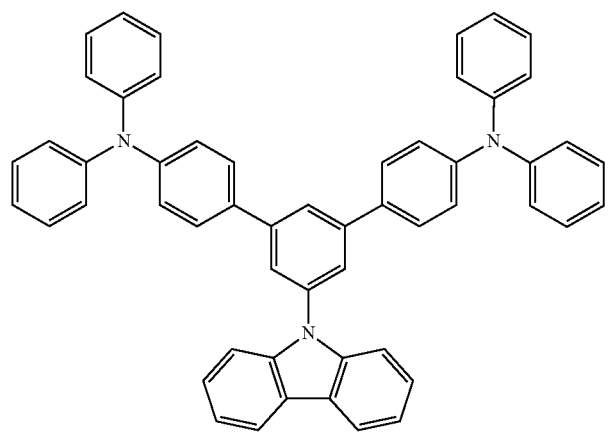
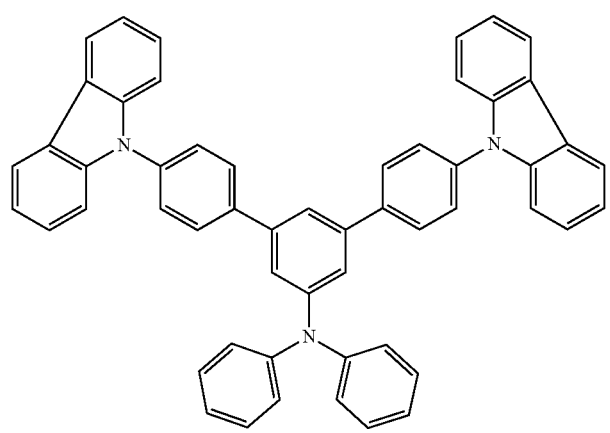

625                                  626
-continued
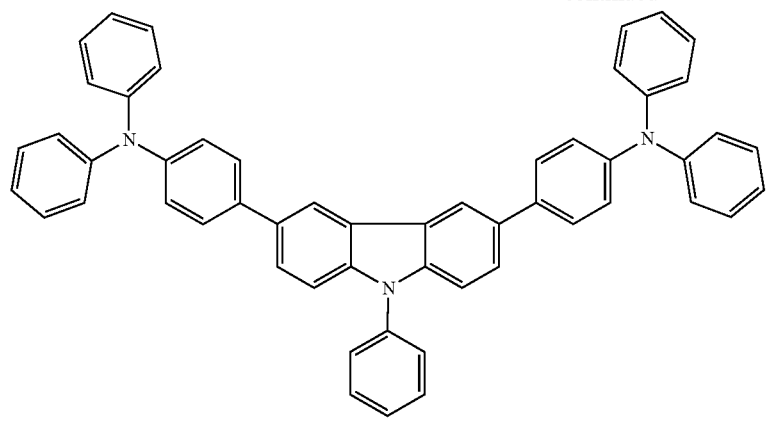
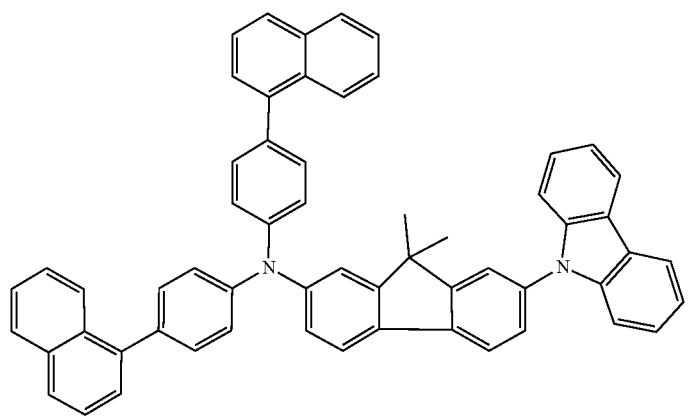
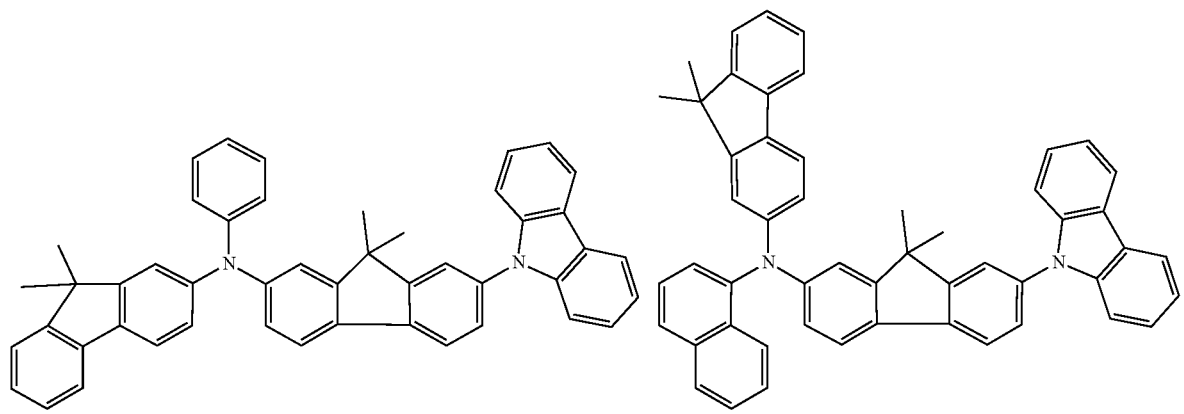
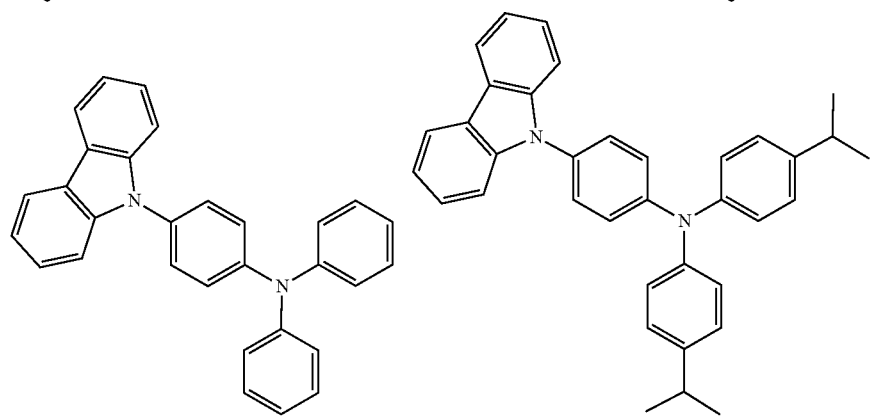

627 628
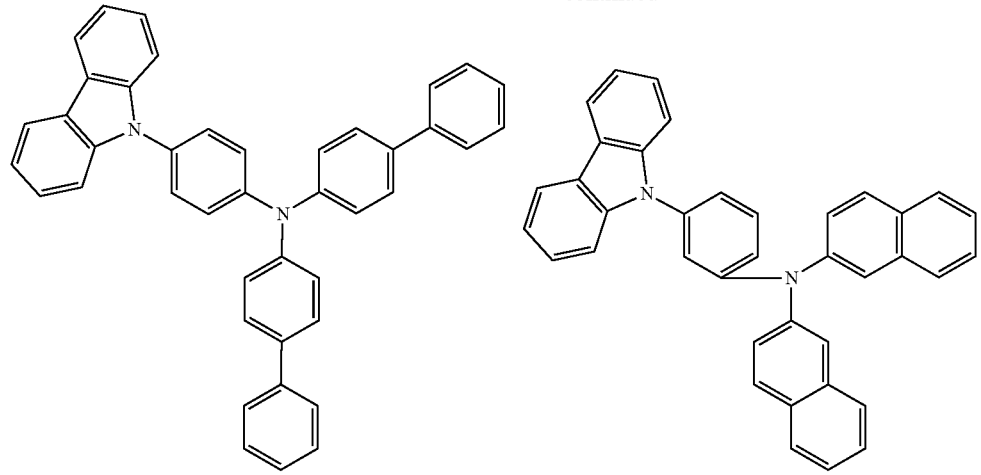
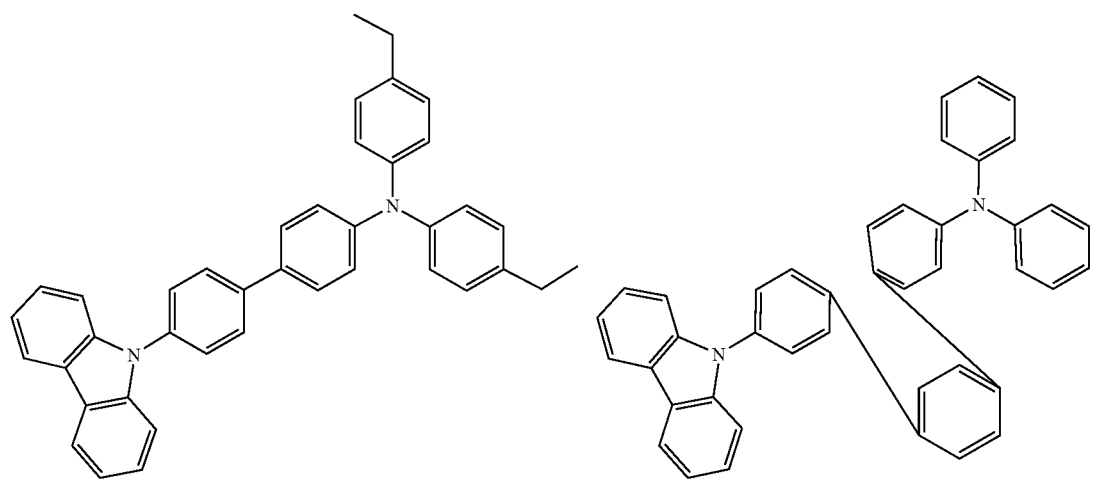
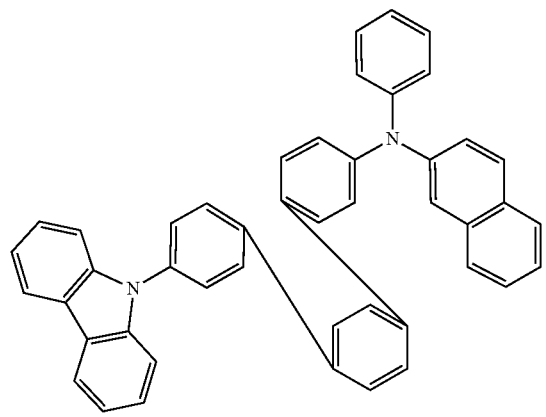

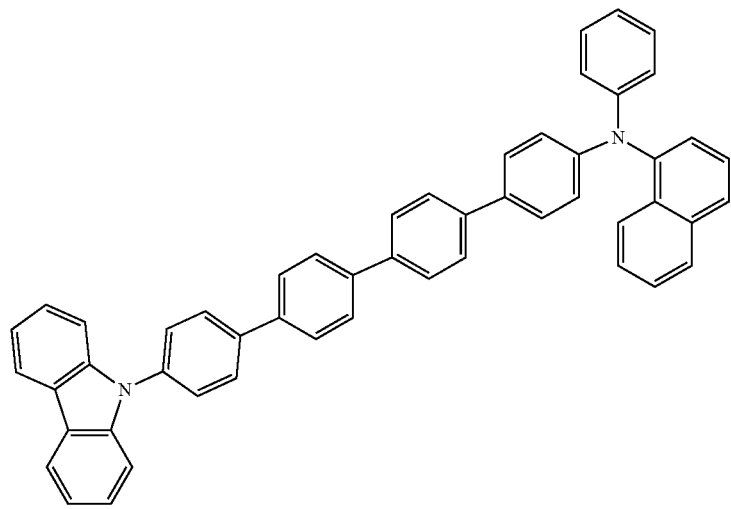
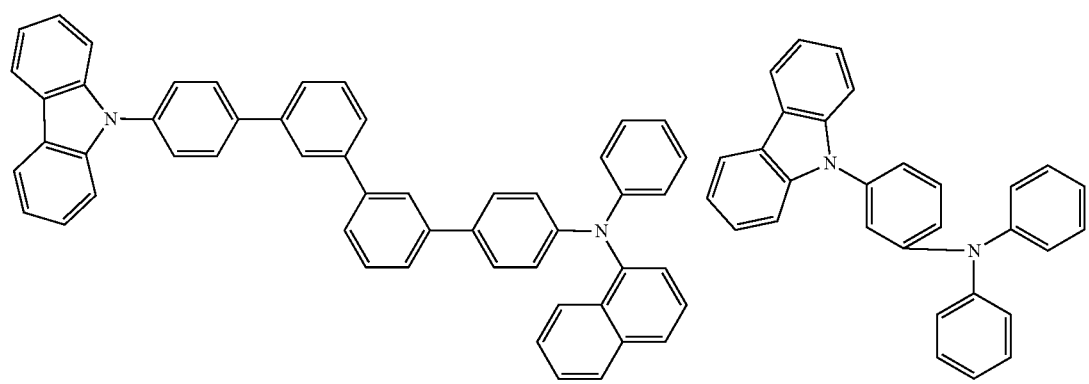
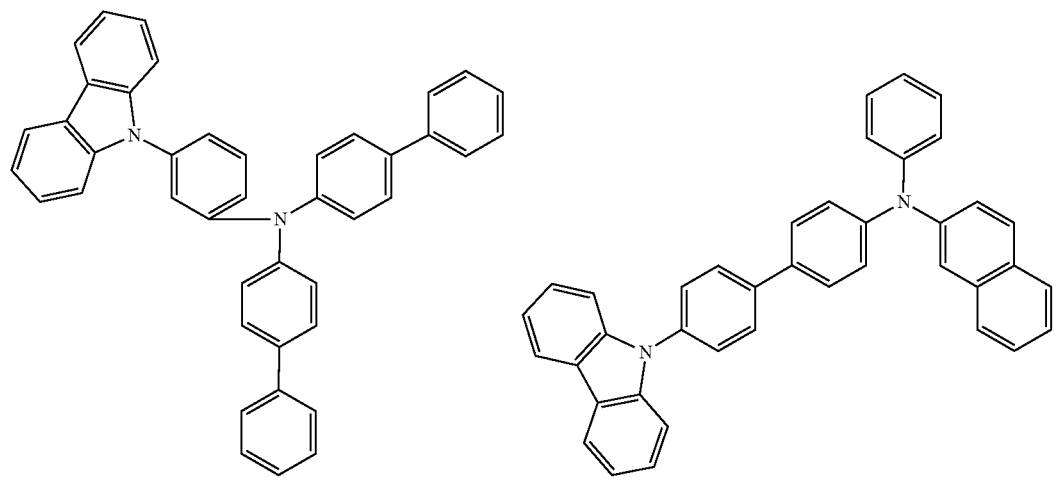

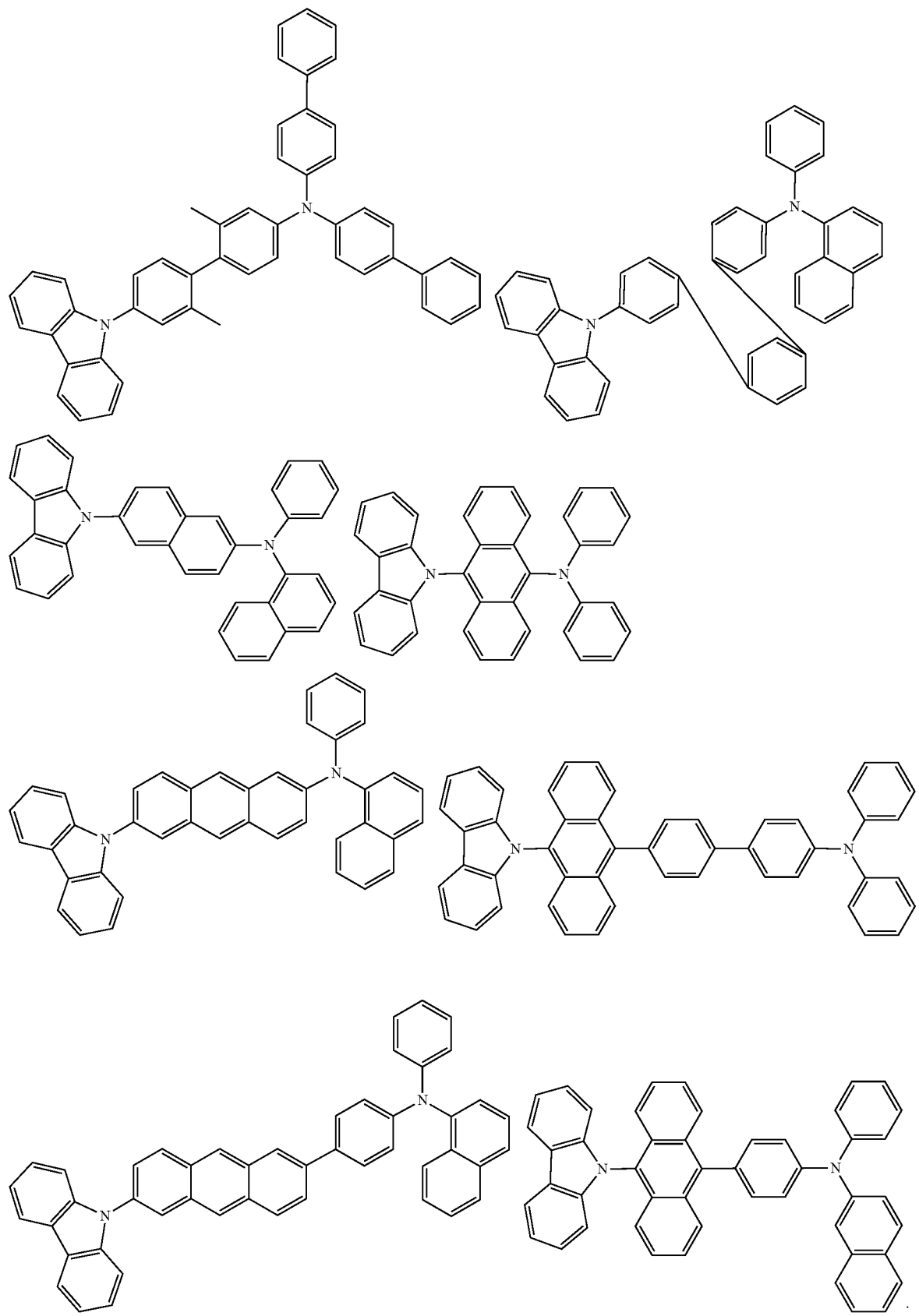

9. The organic light emitting device of claim 4, wherein the compound of Chemical Formula 3 is selected from among the following compounds:
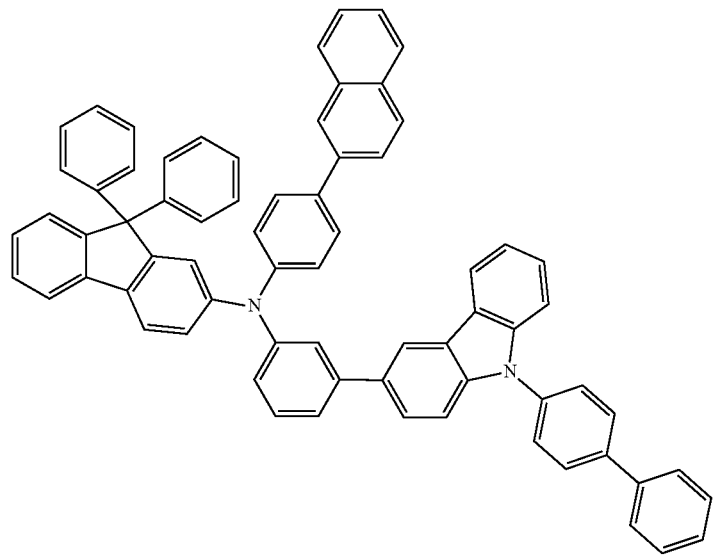
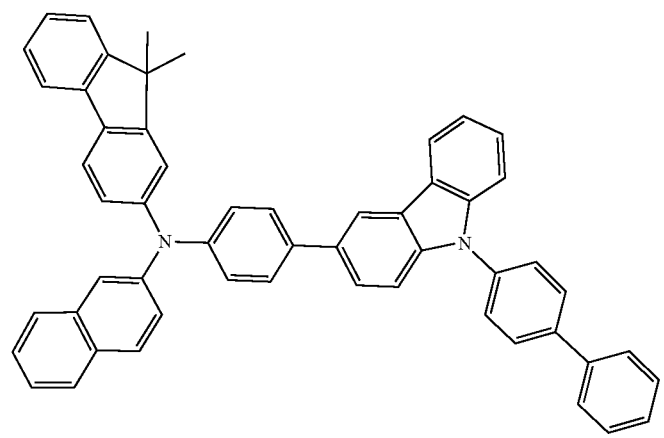
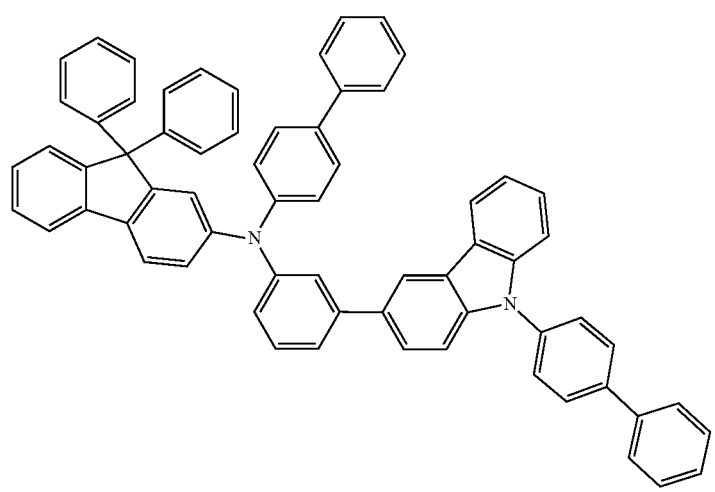

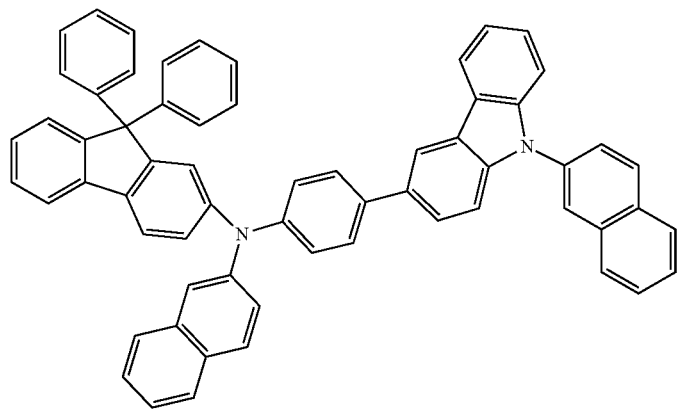
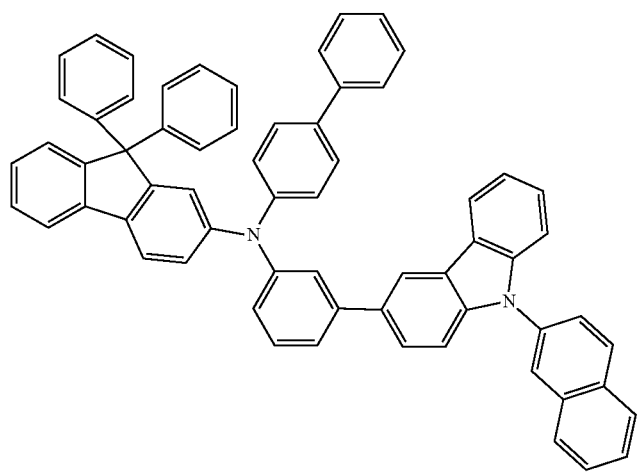
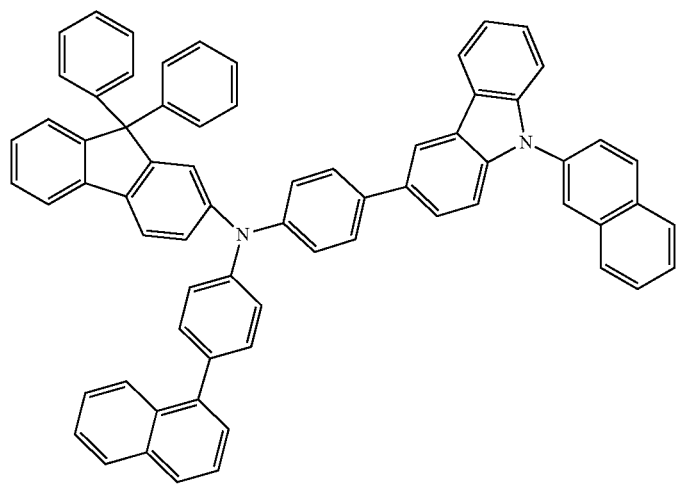

-continued
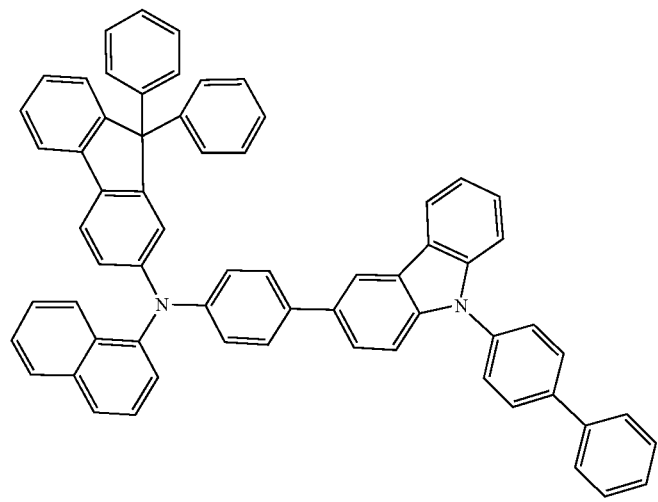
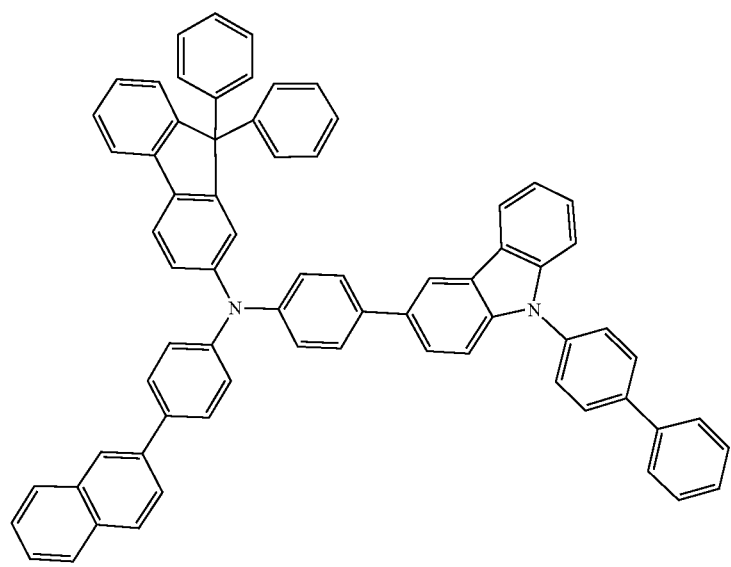
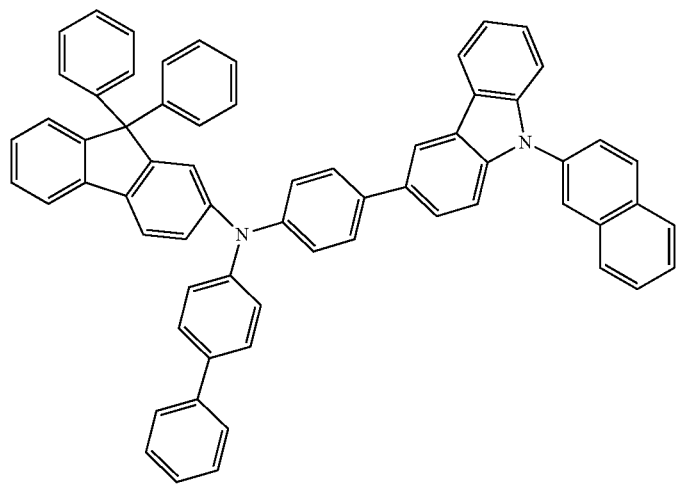

-continued
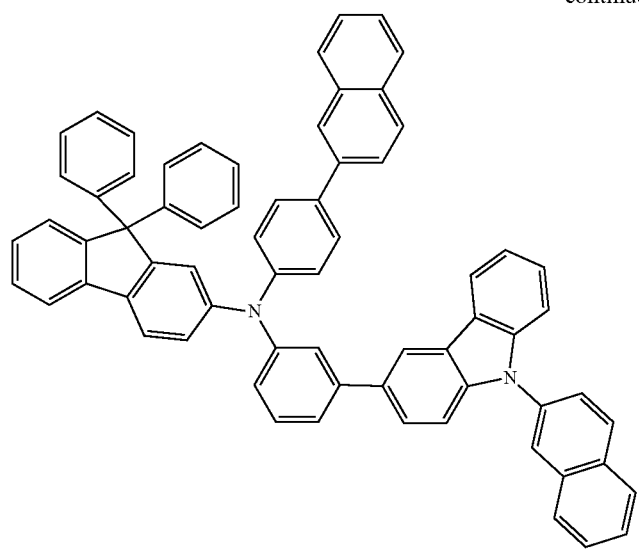
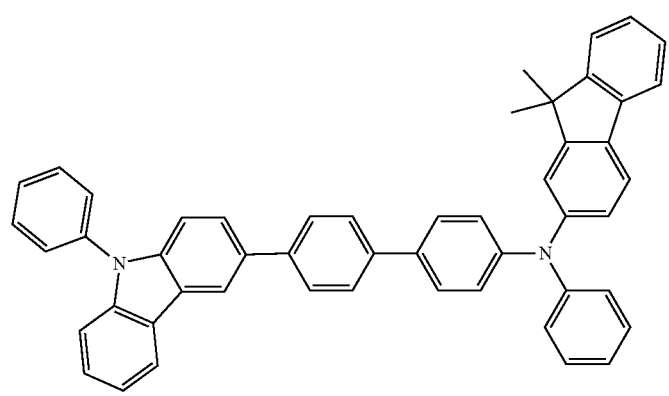
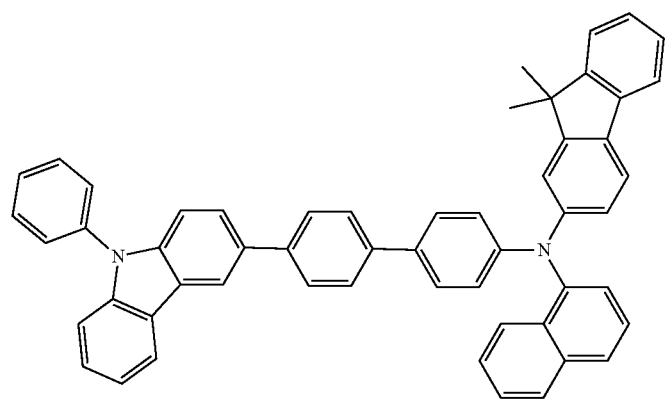

-continued
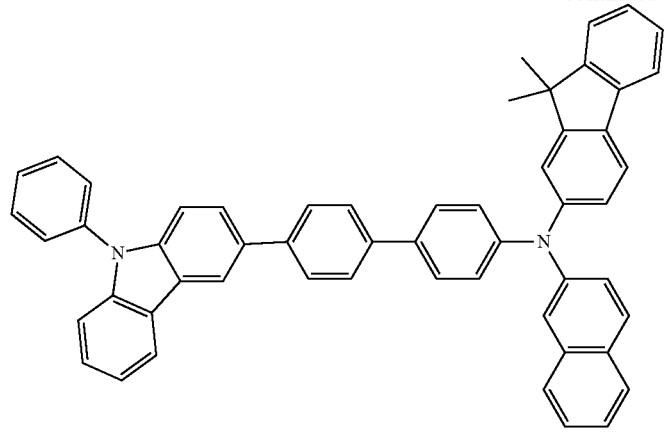
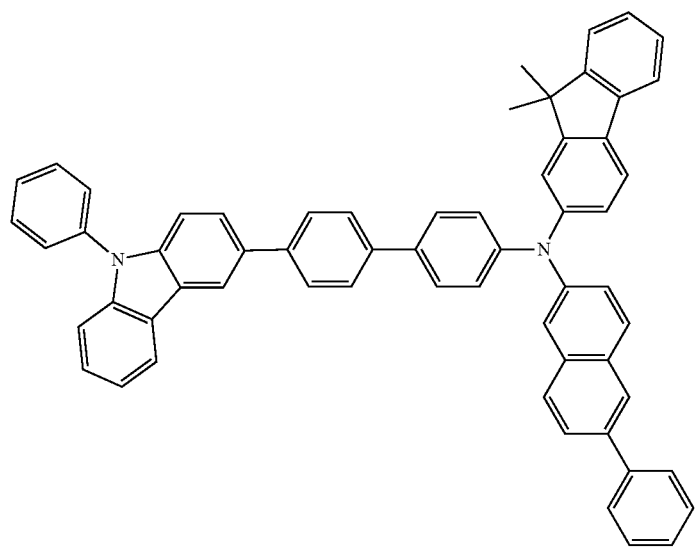
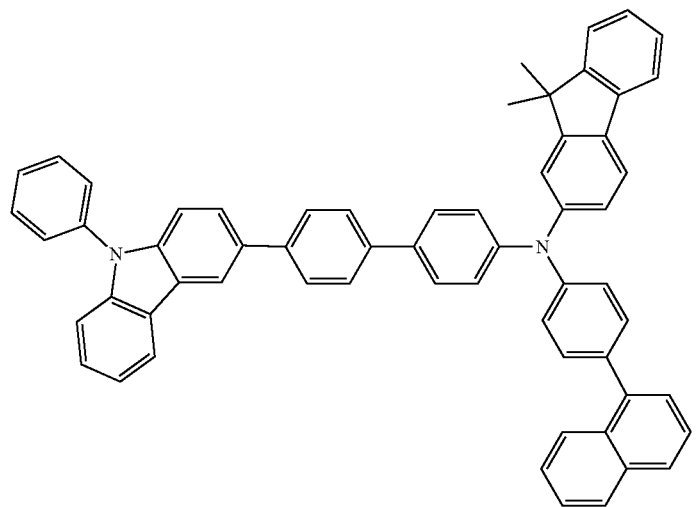

-continued
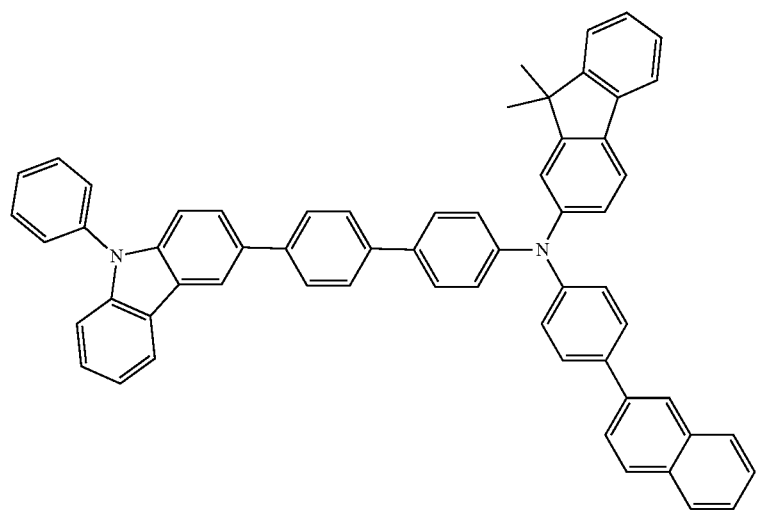
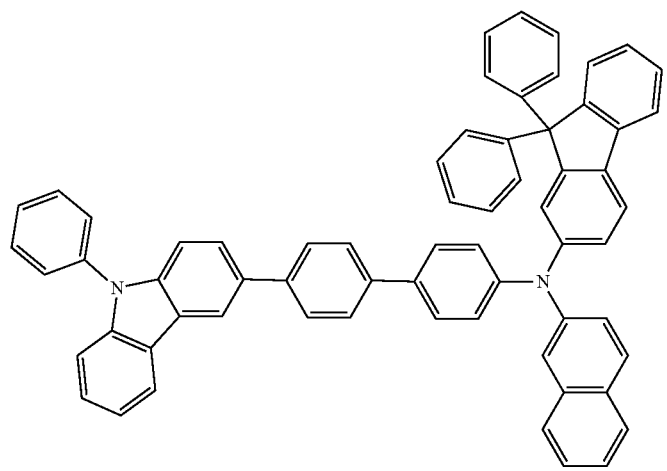
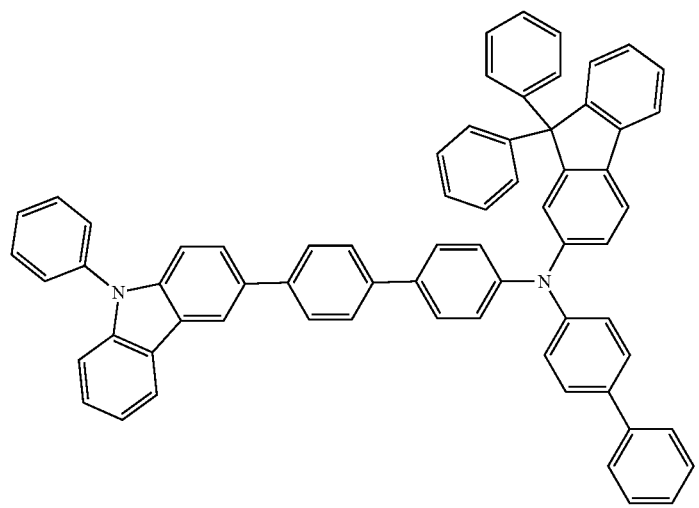

-continued
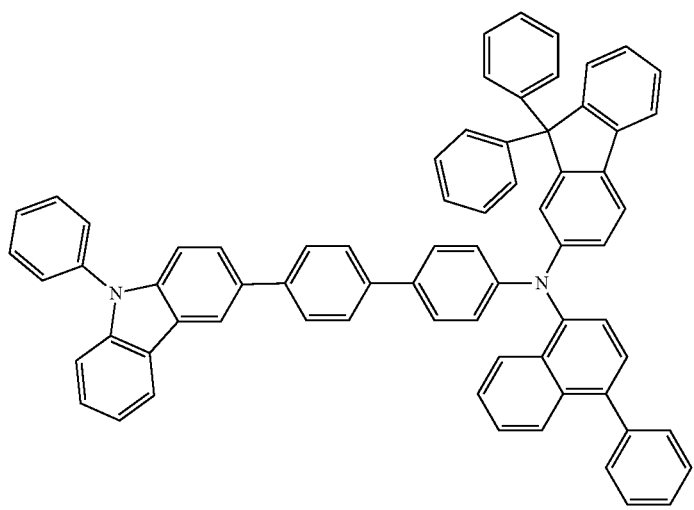
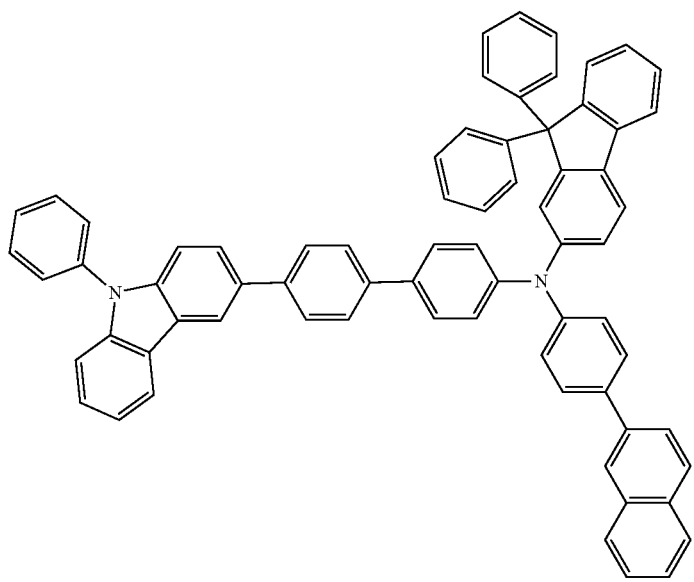
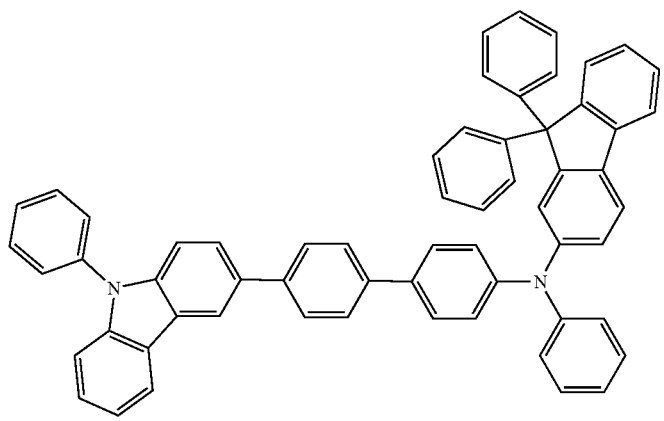

-continued
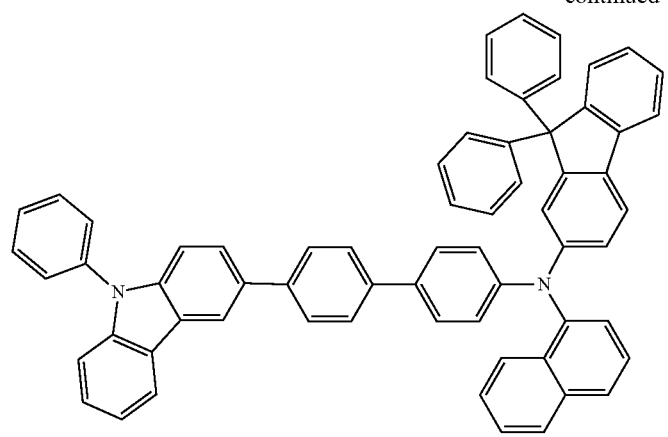
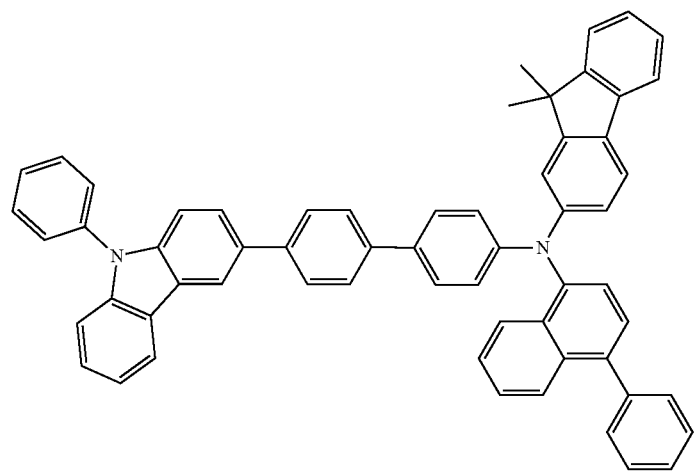

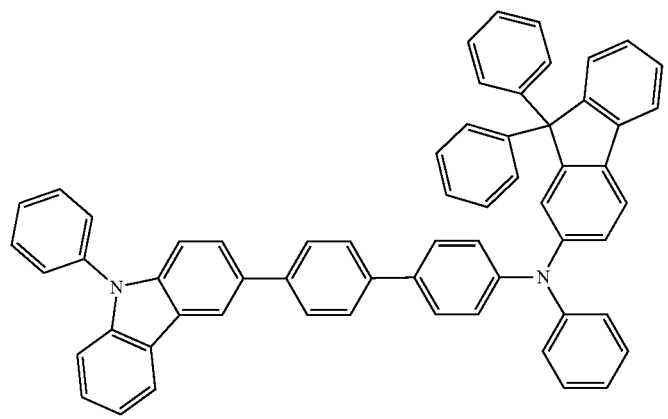
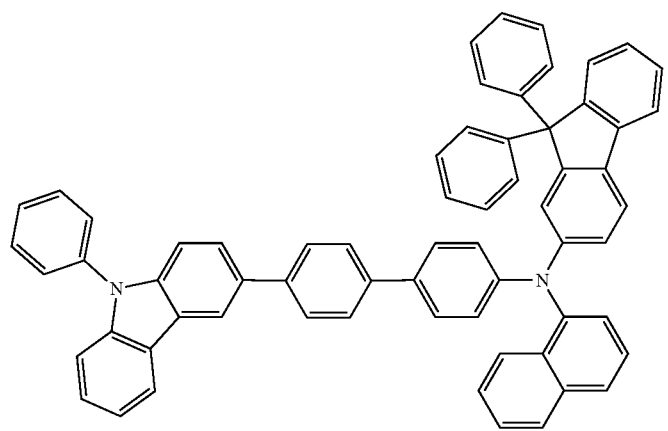
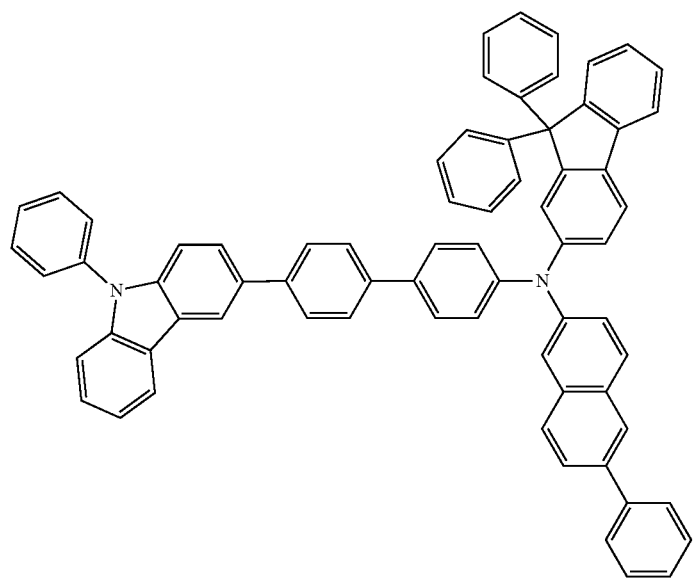

-continued
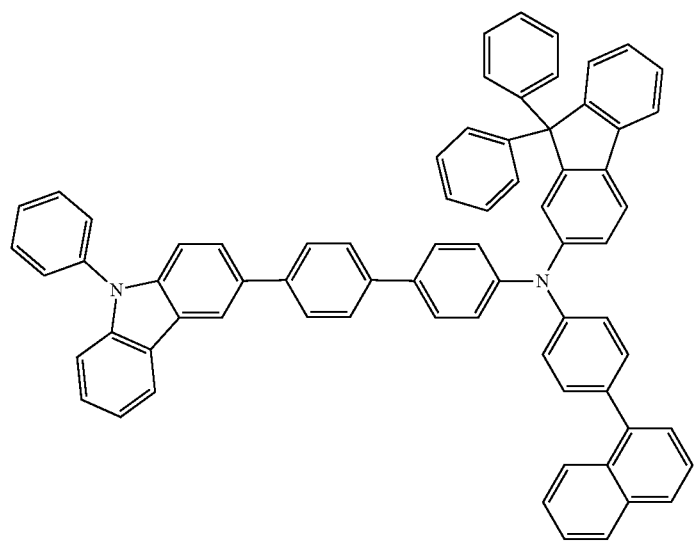
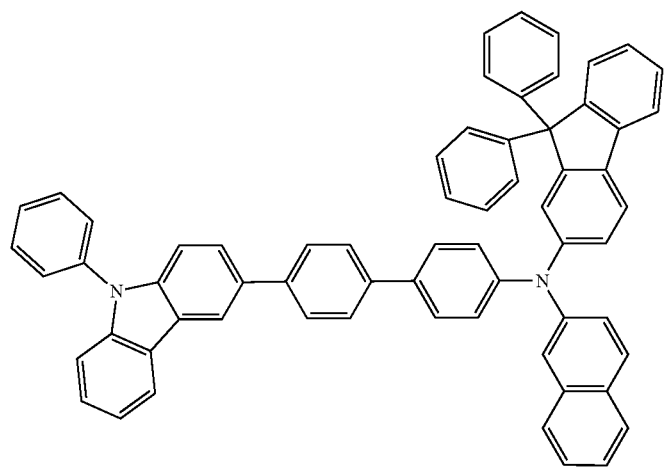
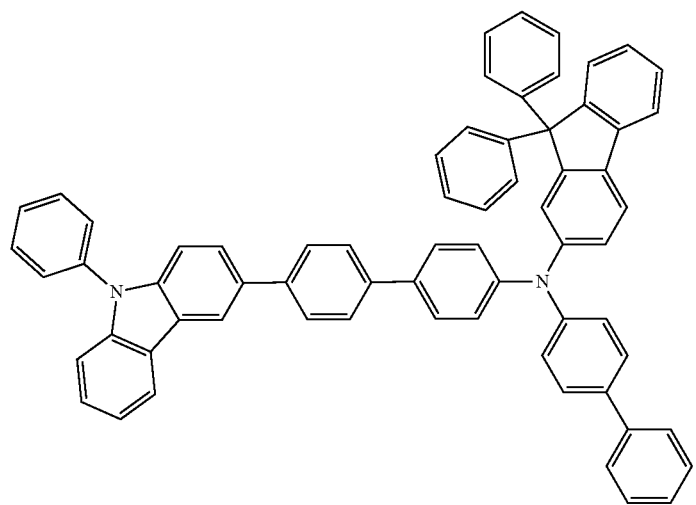

-continued
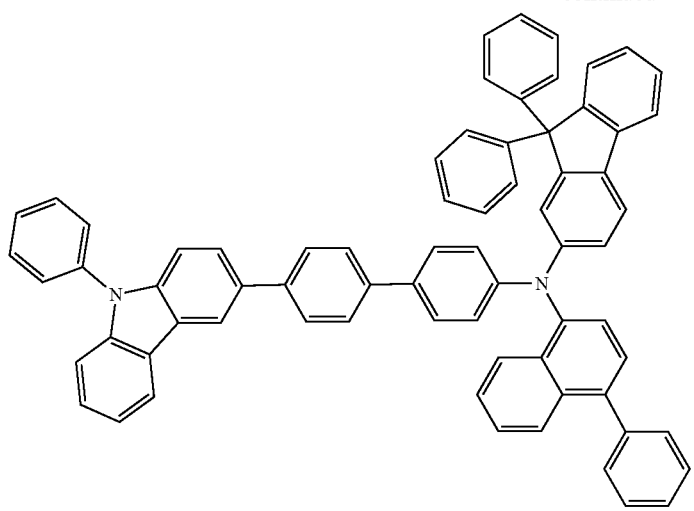
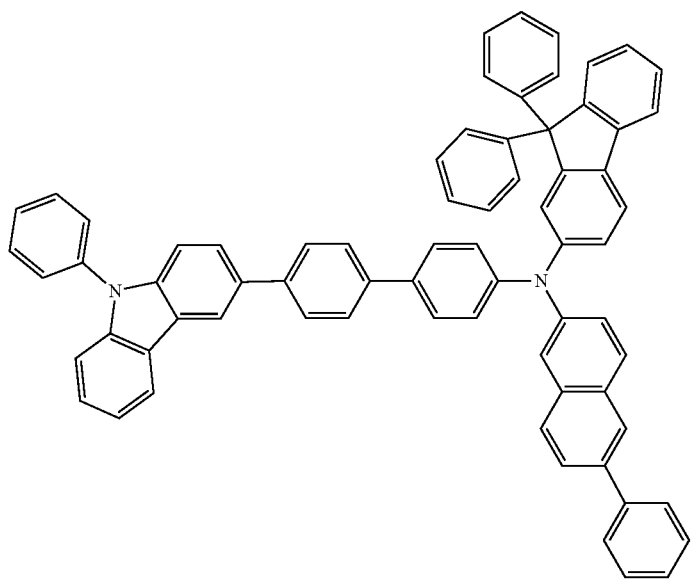
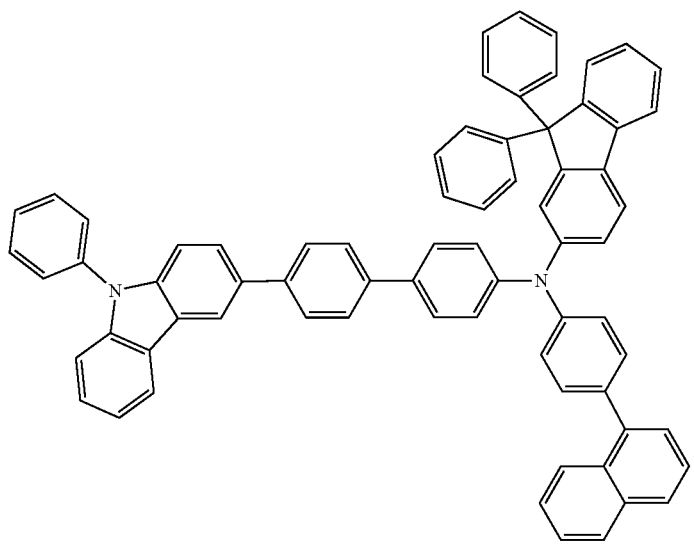

-continued
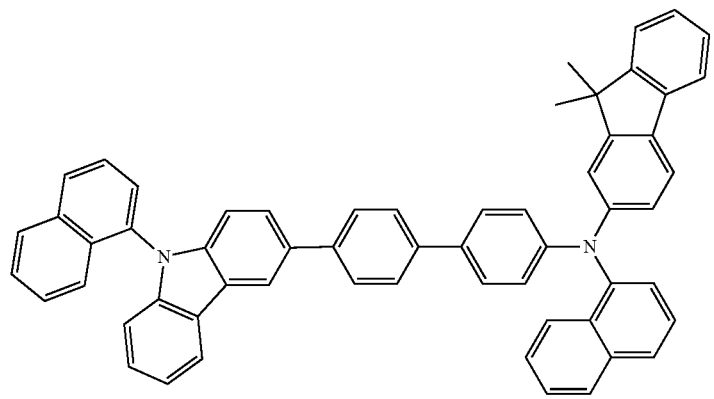
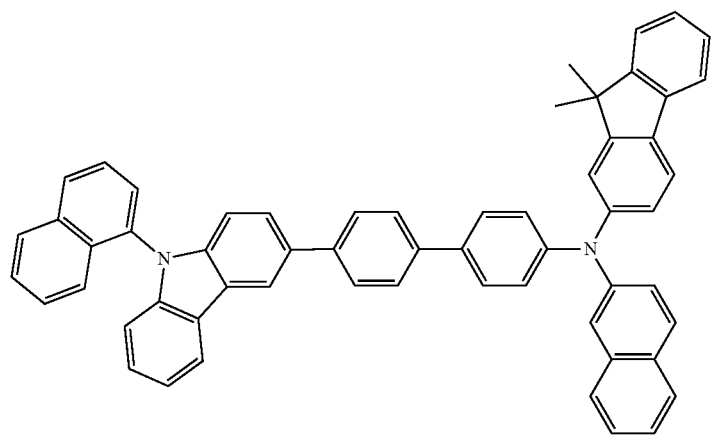
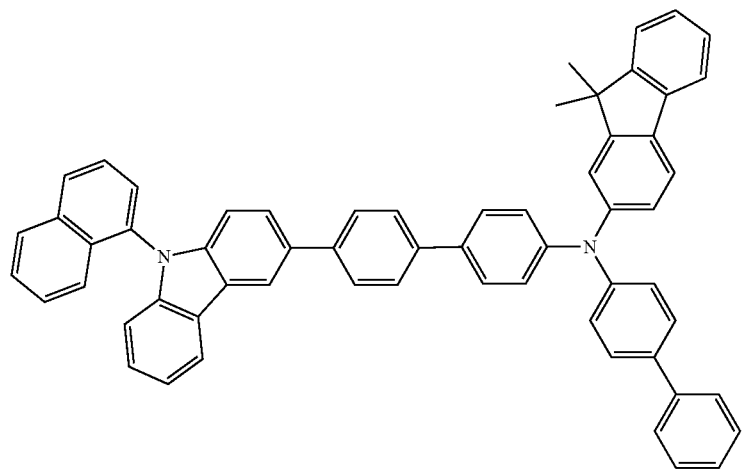

-continued
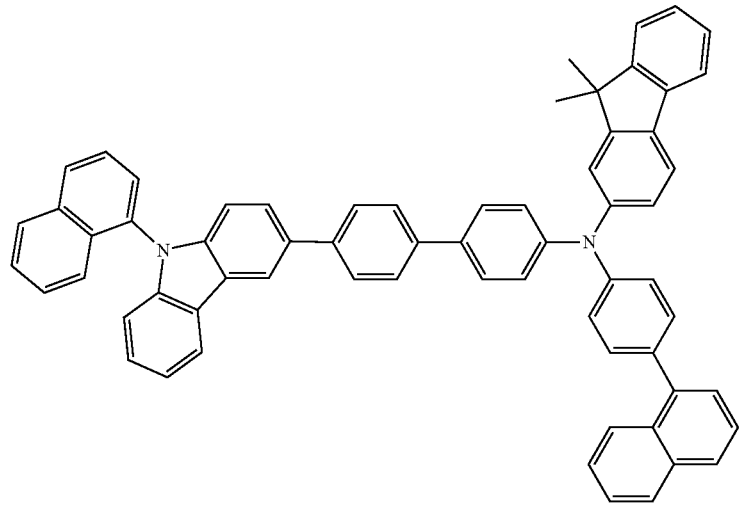
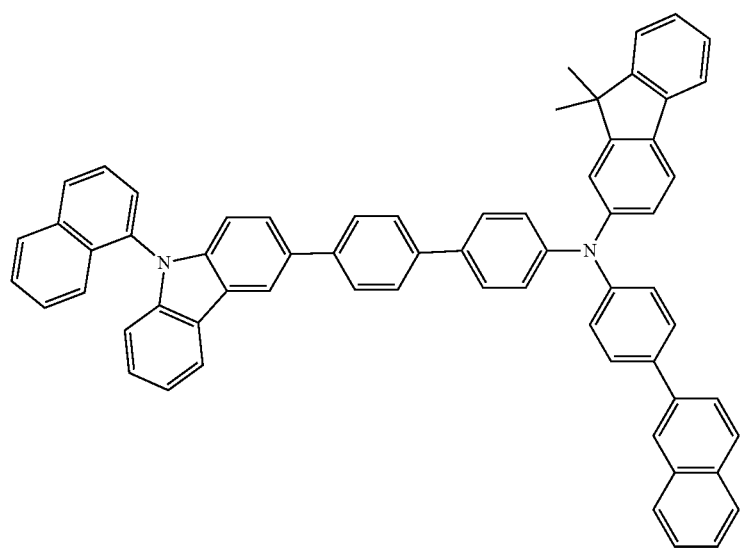
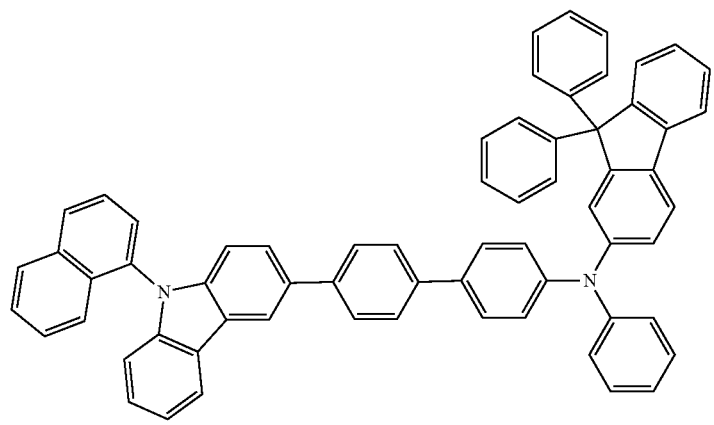

-continued
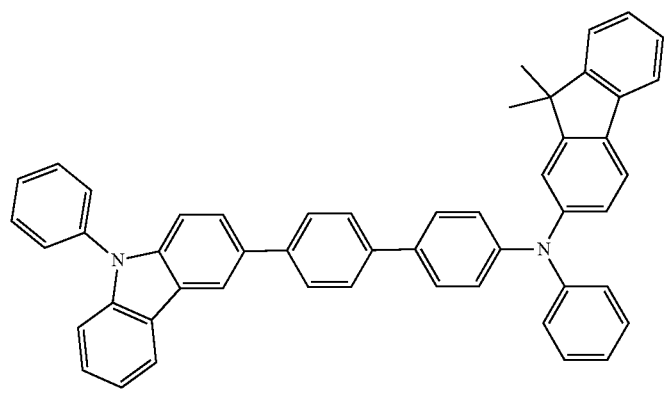
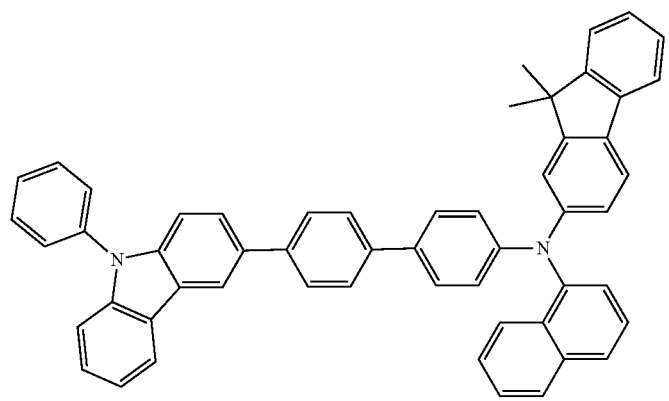
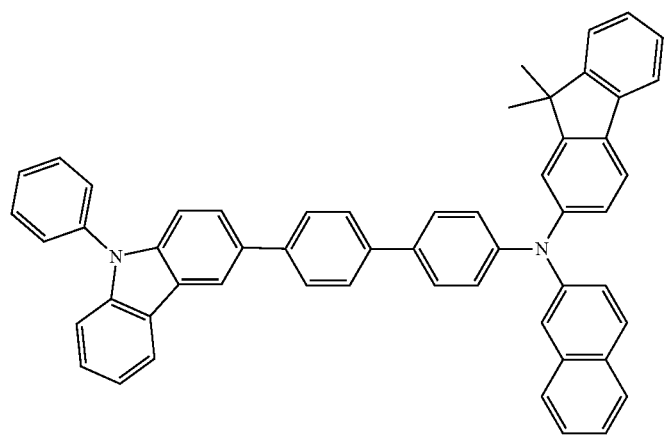

-continued
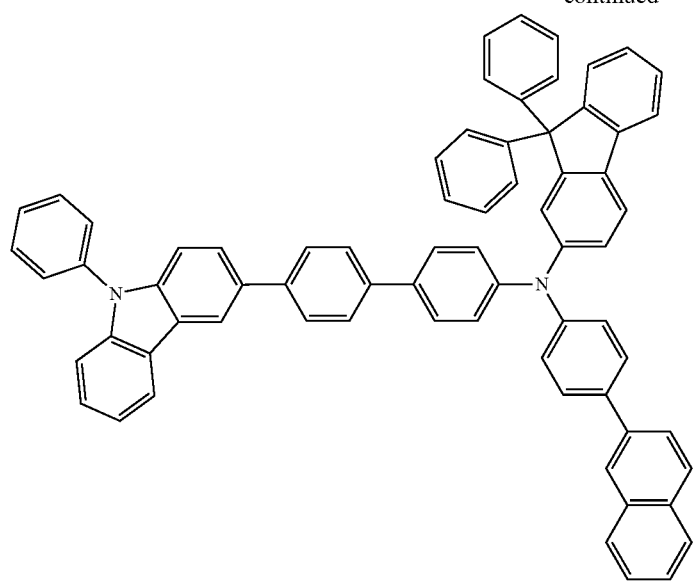
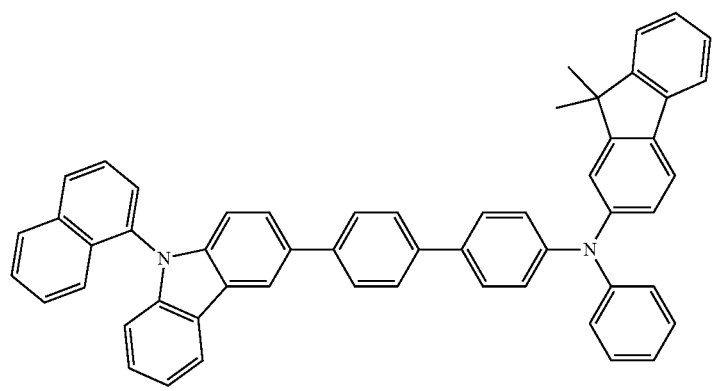
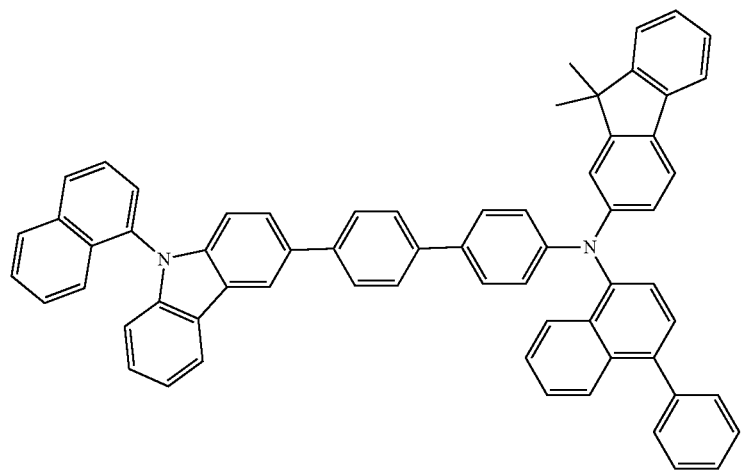

-continued
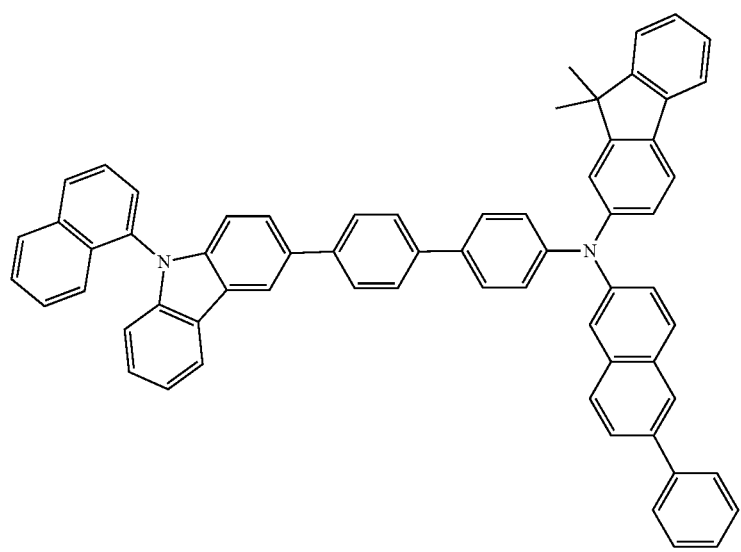
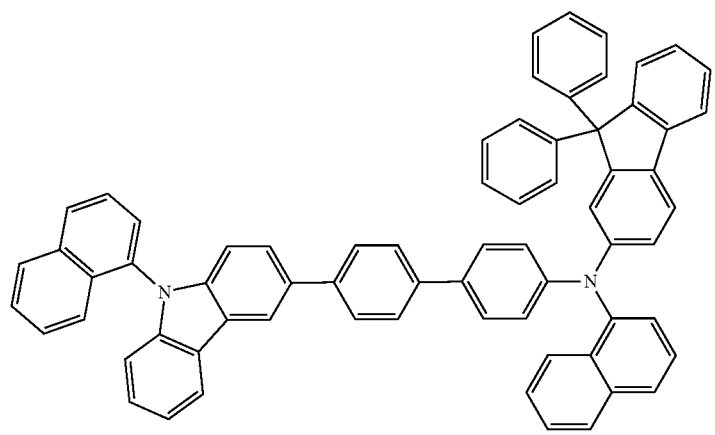
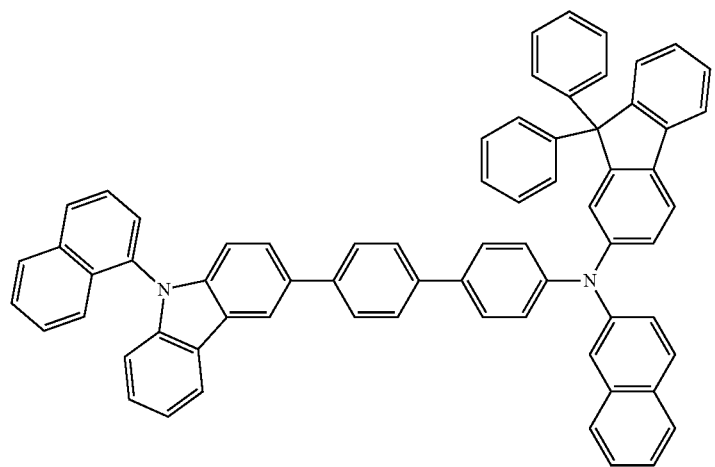

-continued
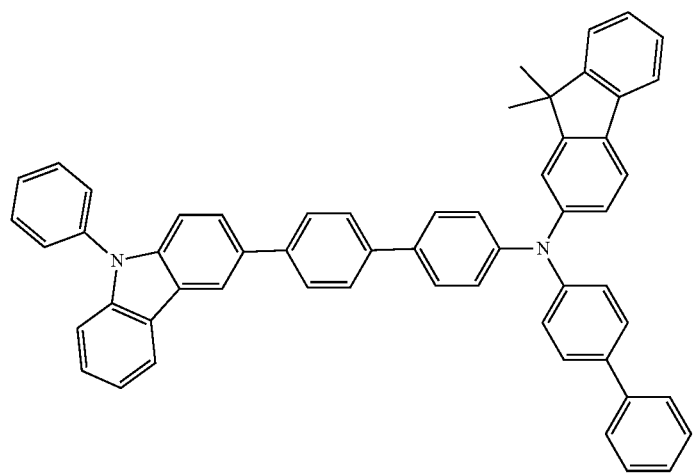
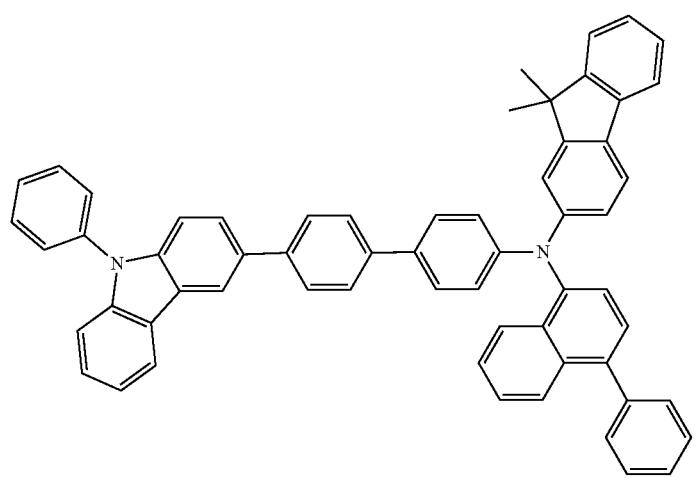
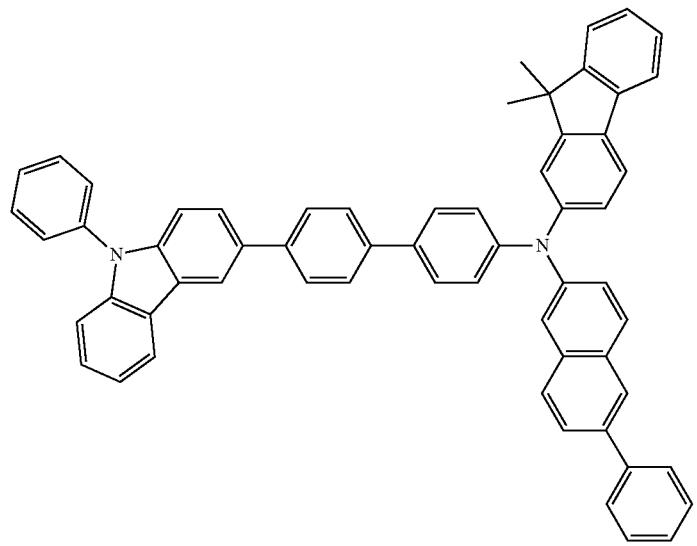

-continued
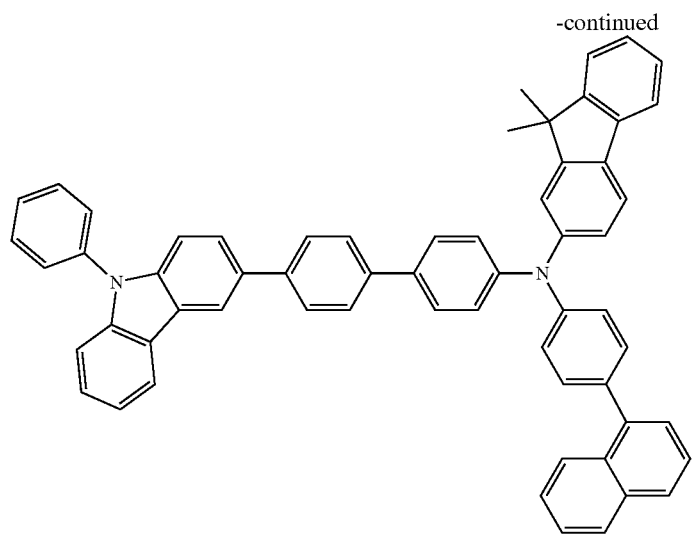
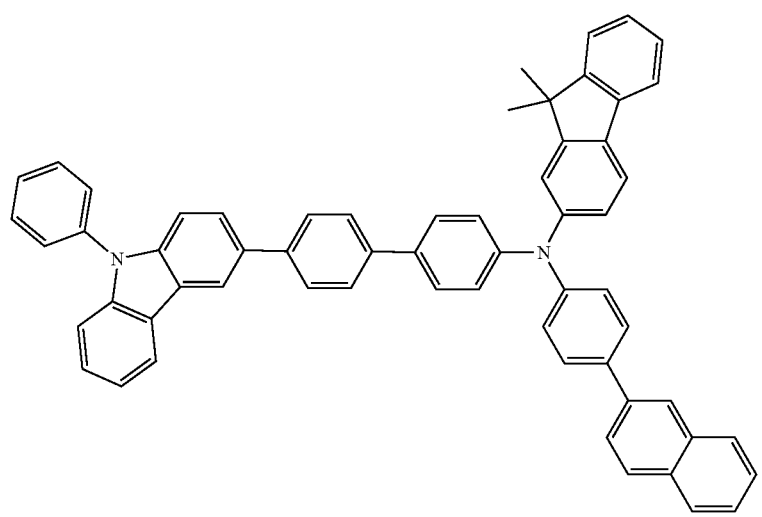
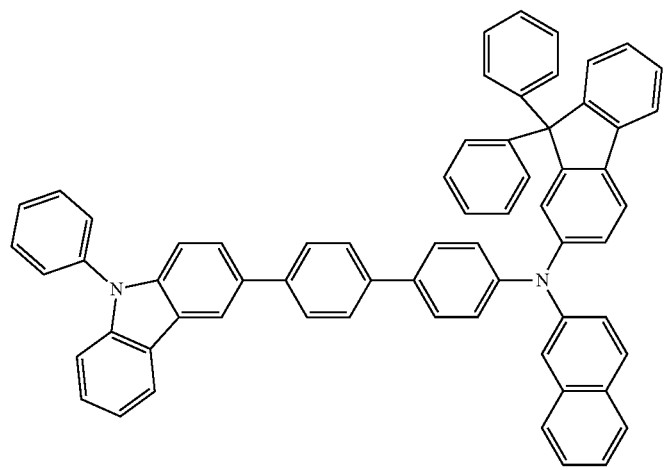

-continued
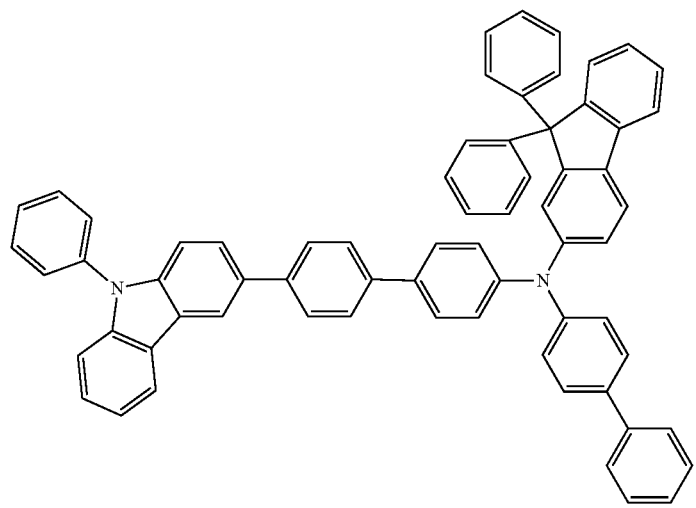
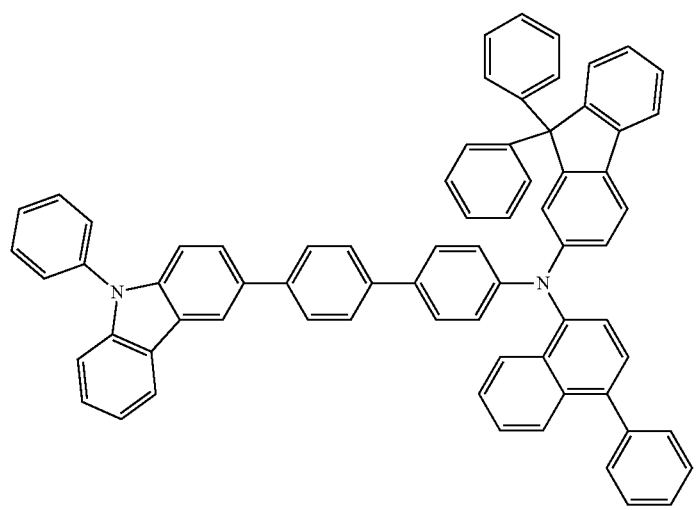
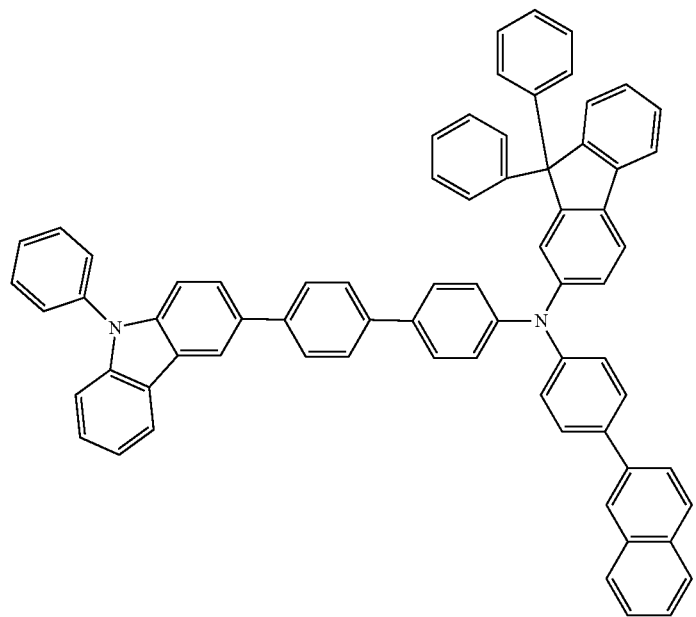

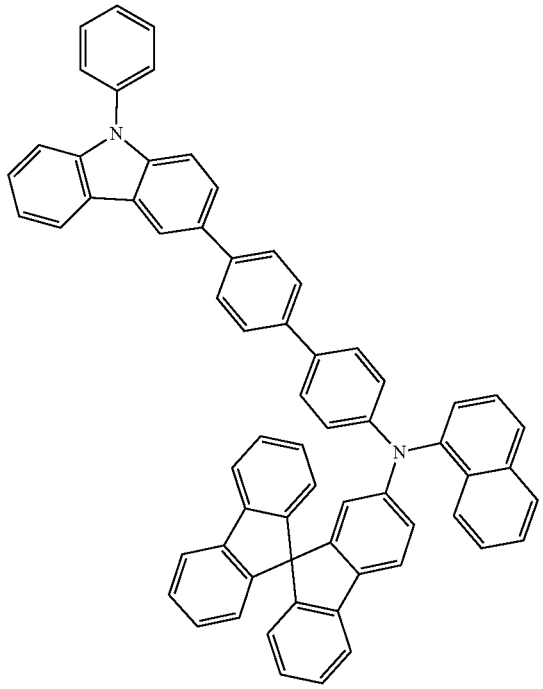
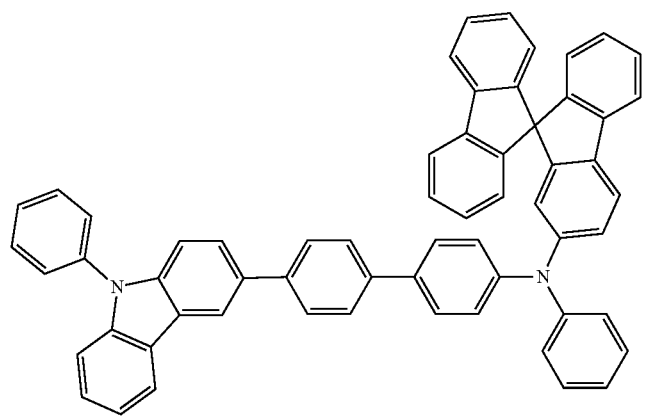
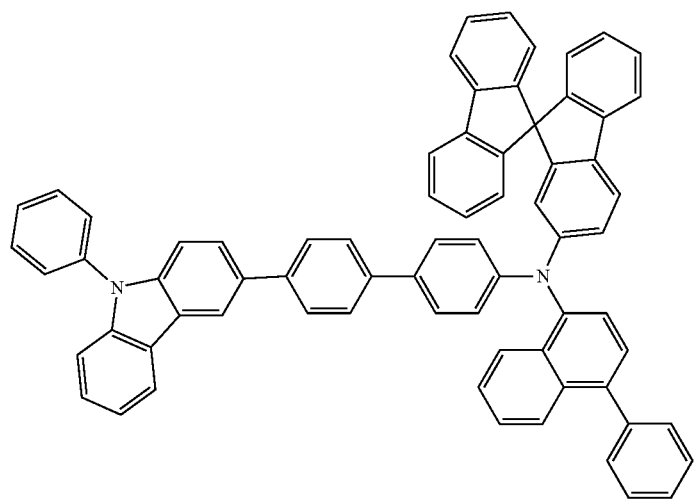
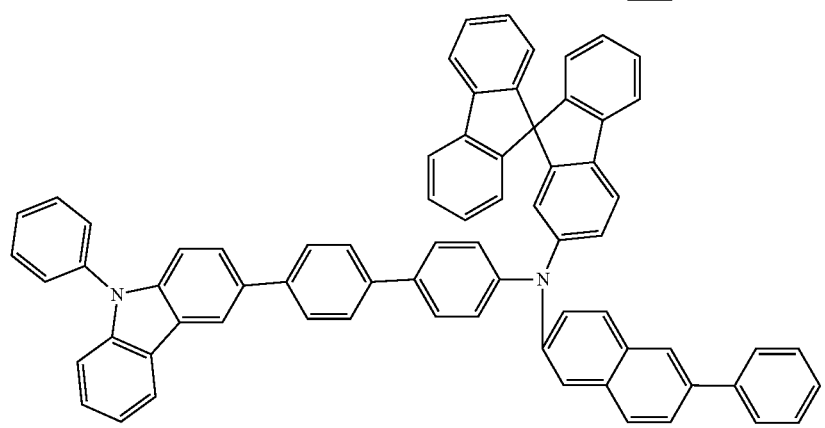

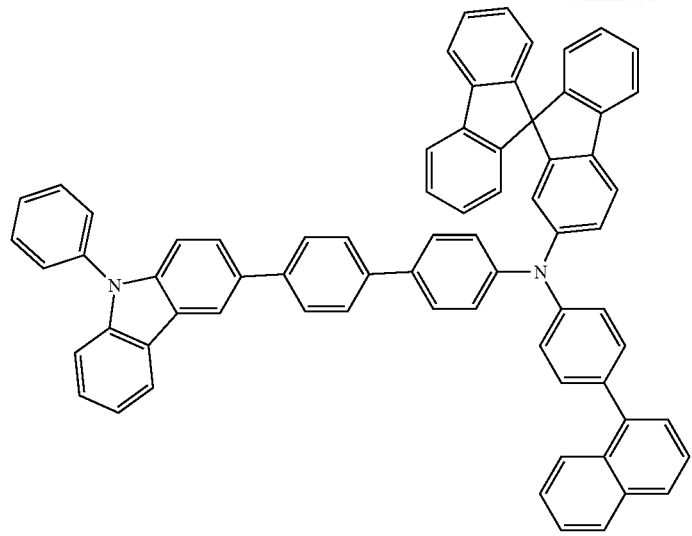
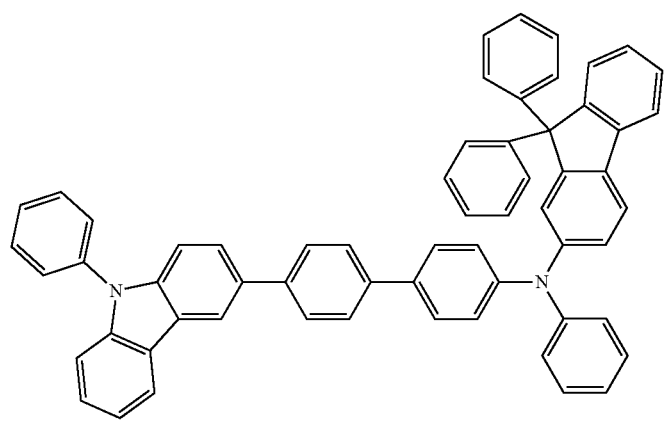
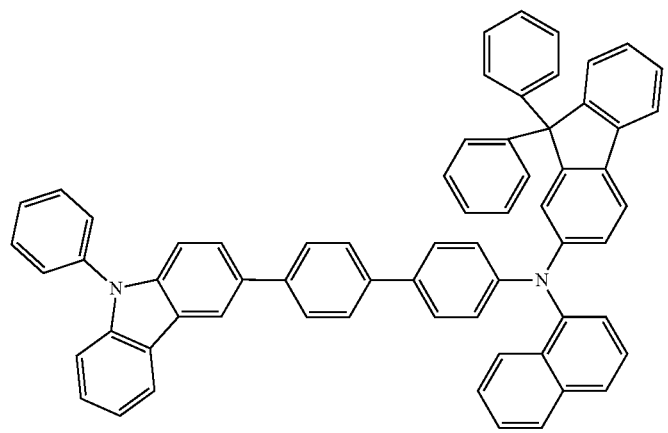

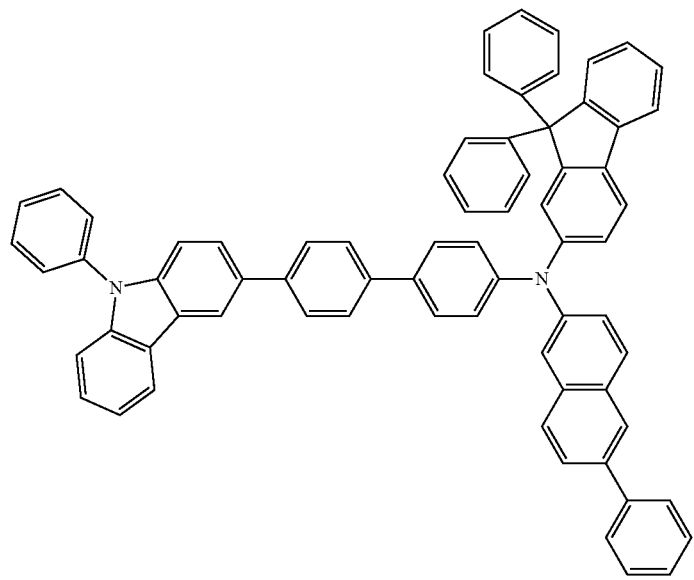
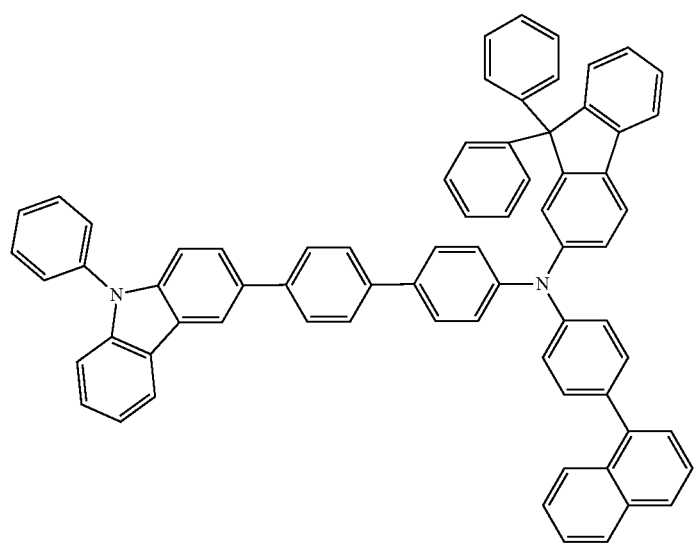

-continued
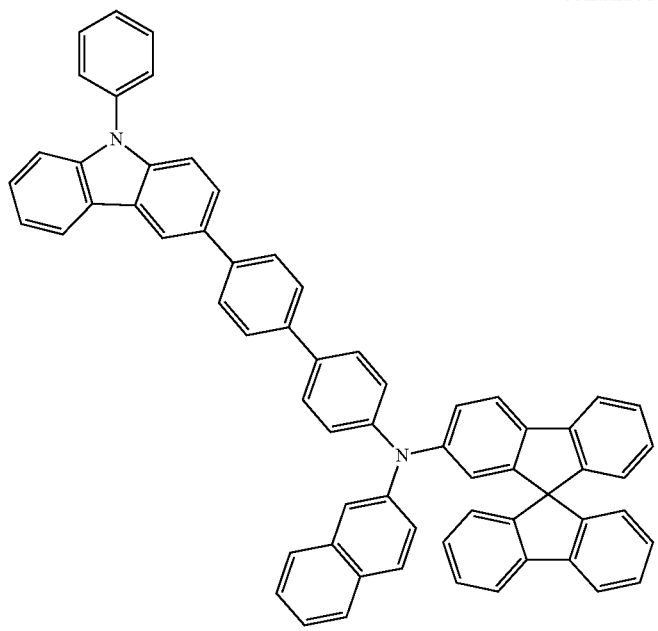
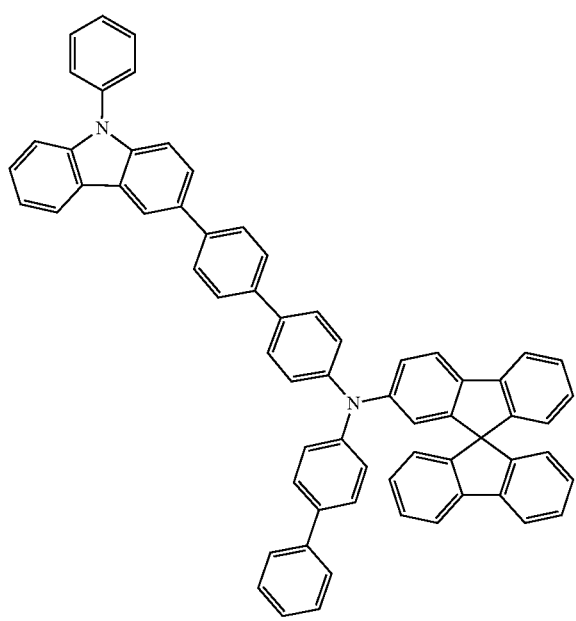

-continued
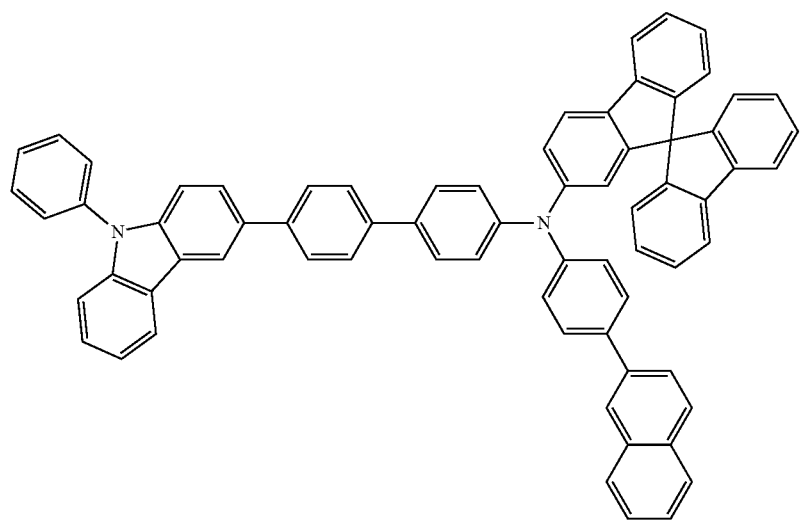
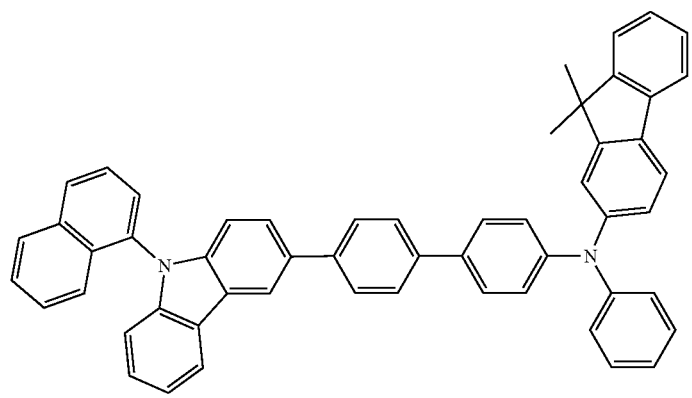
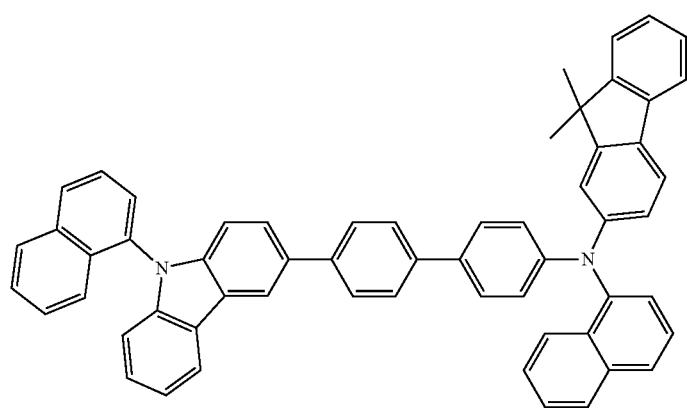

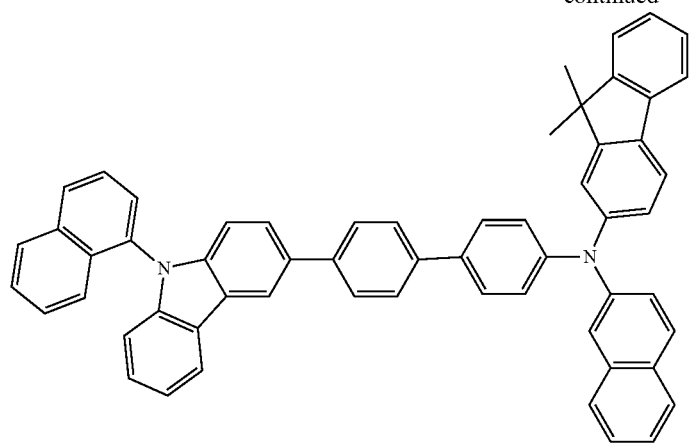
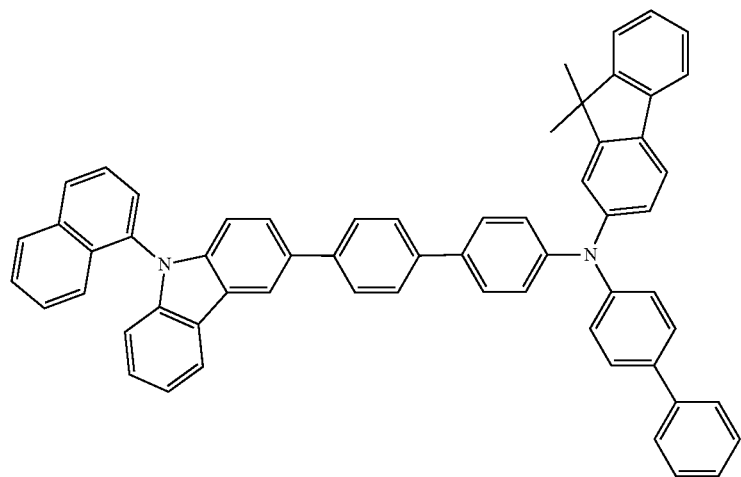
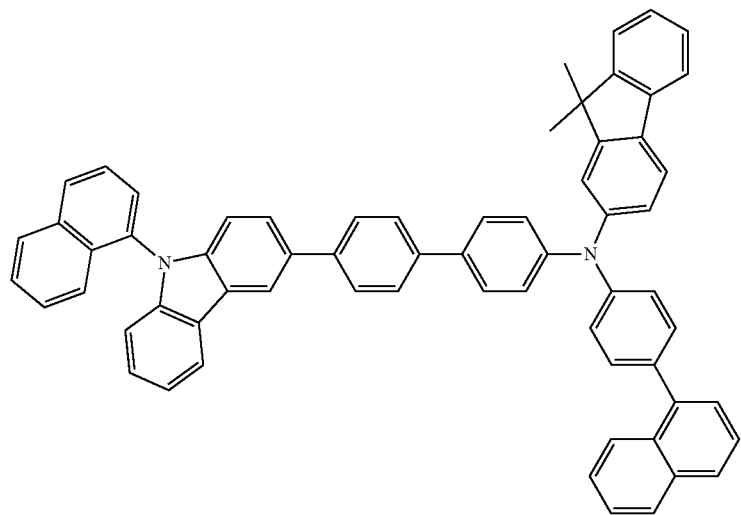

-continued
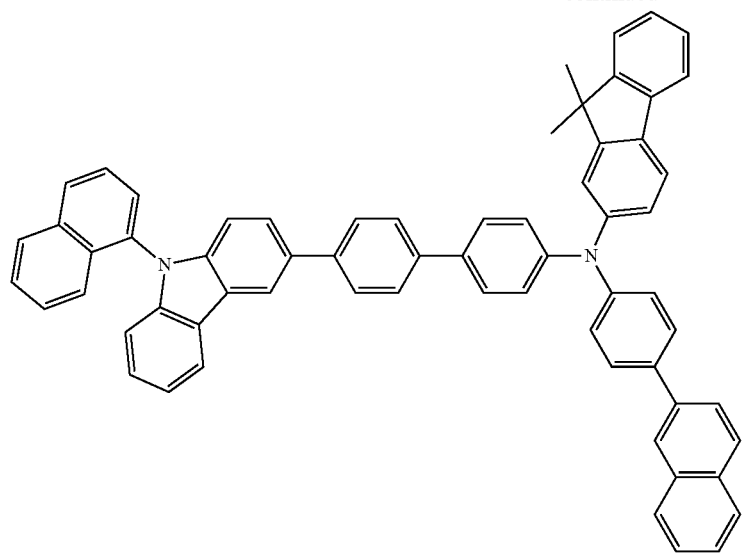
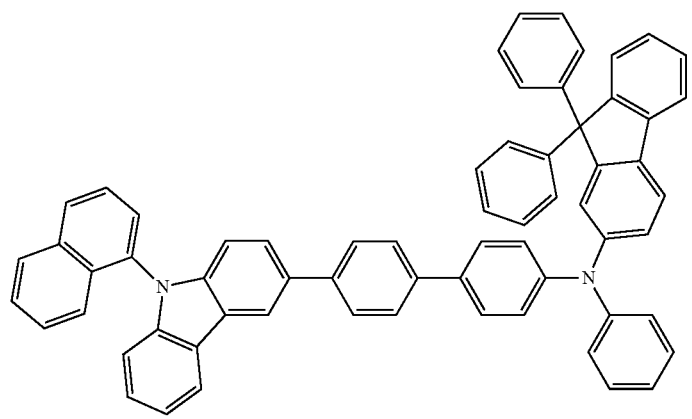
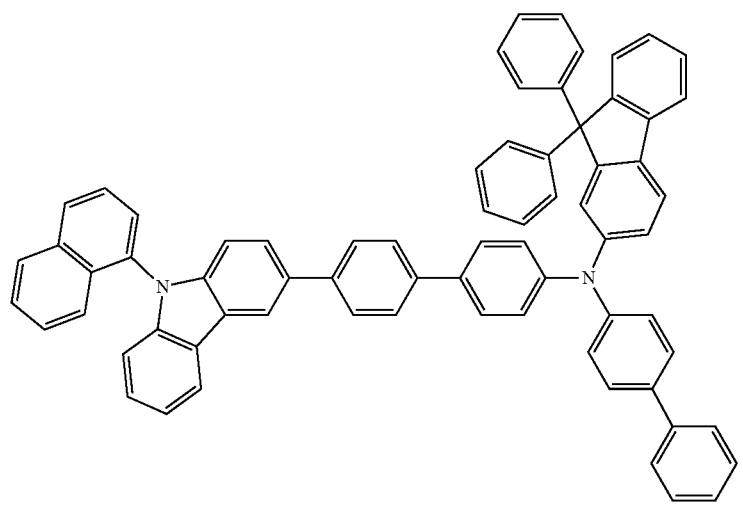

-continued
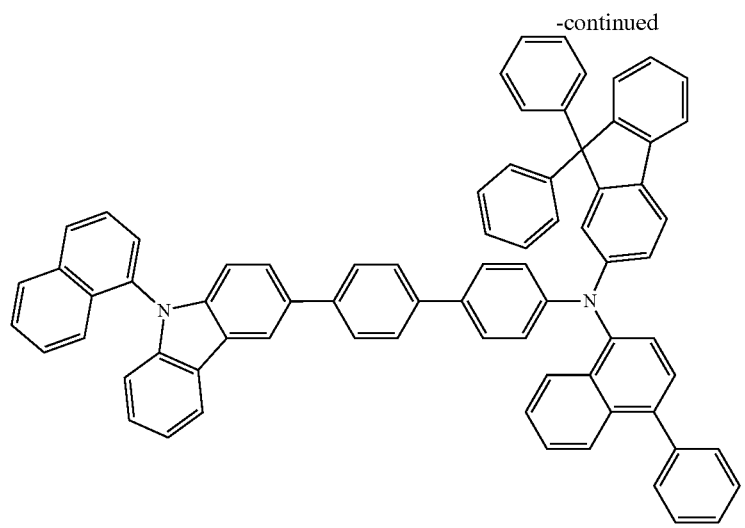
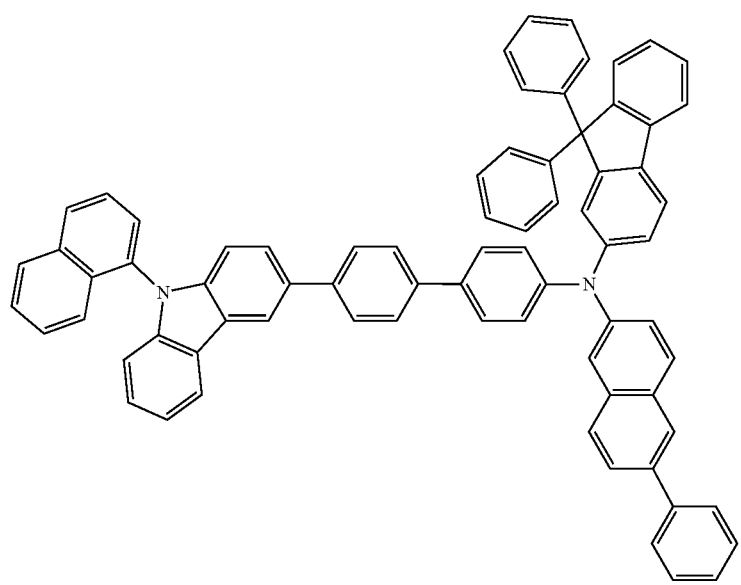
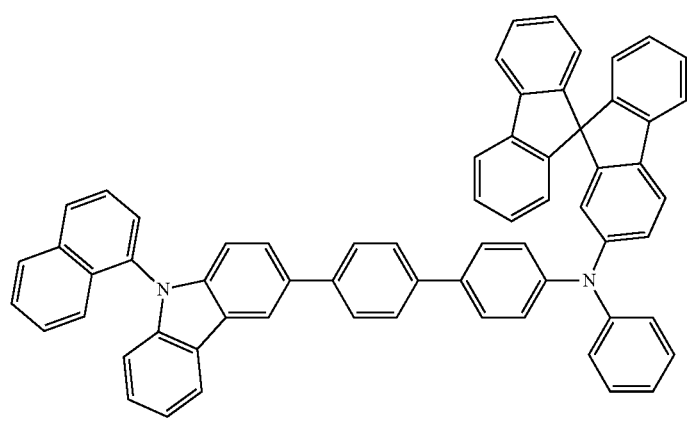

-continued
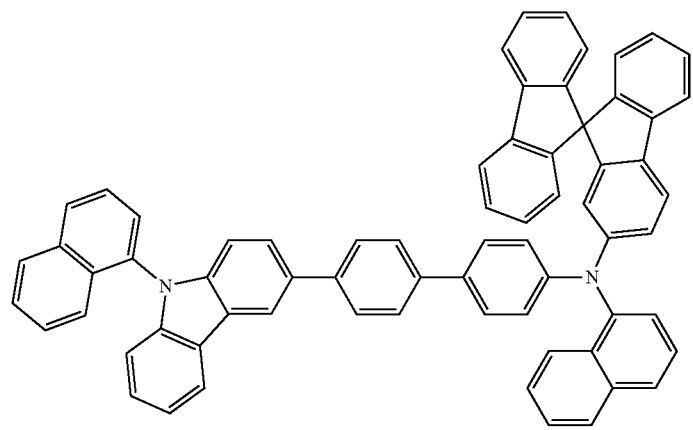
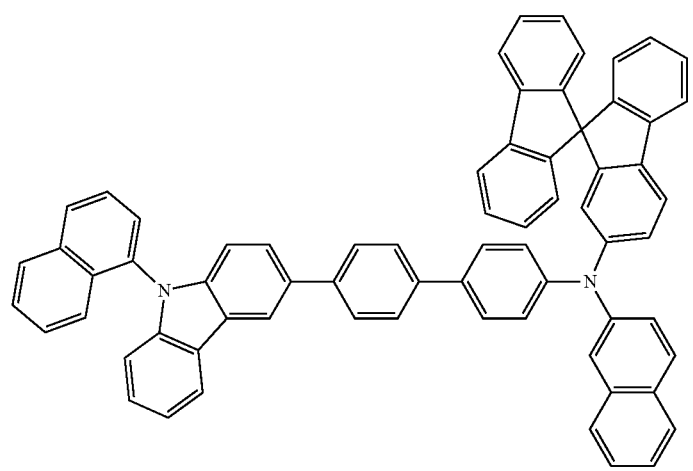
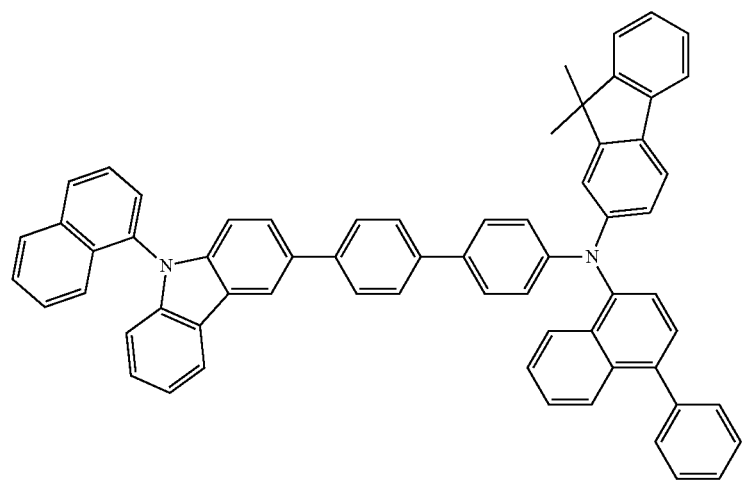

-continued
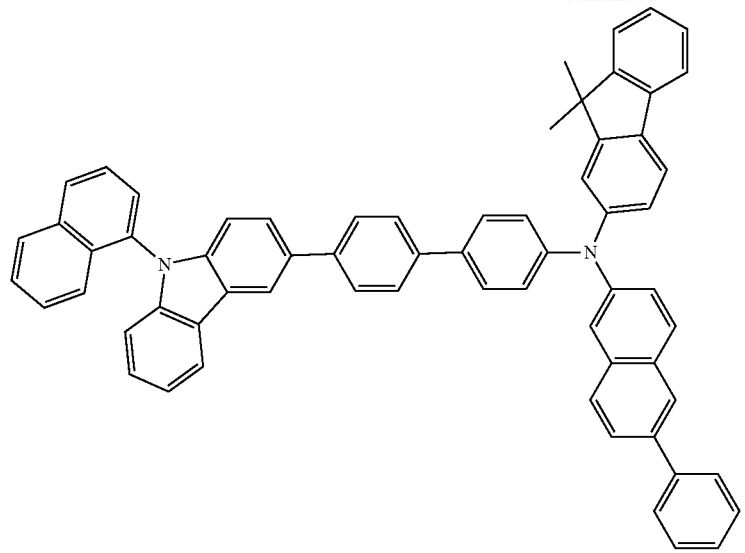
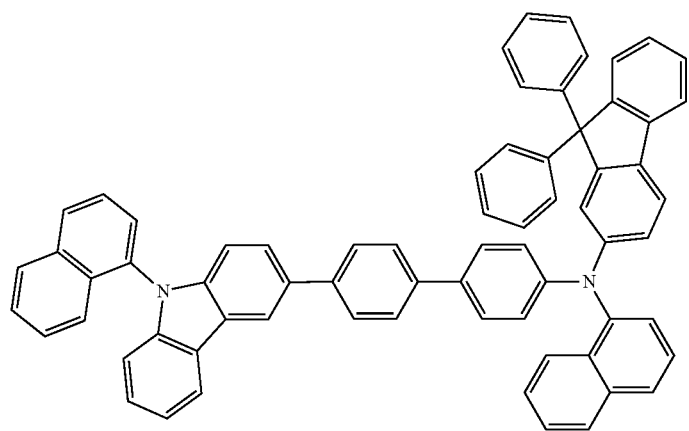
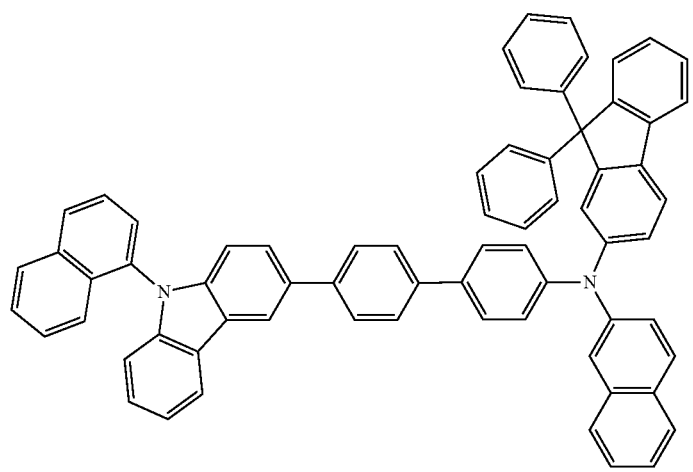

-continued
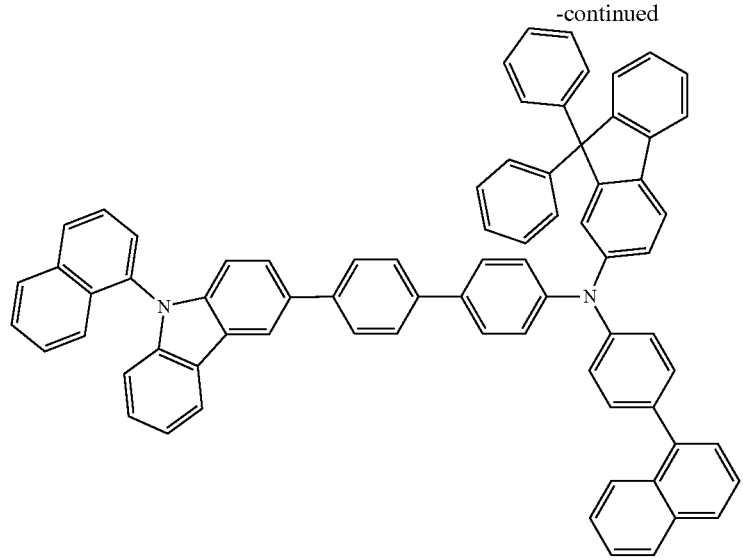
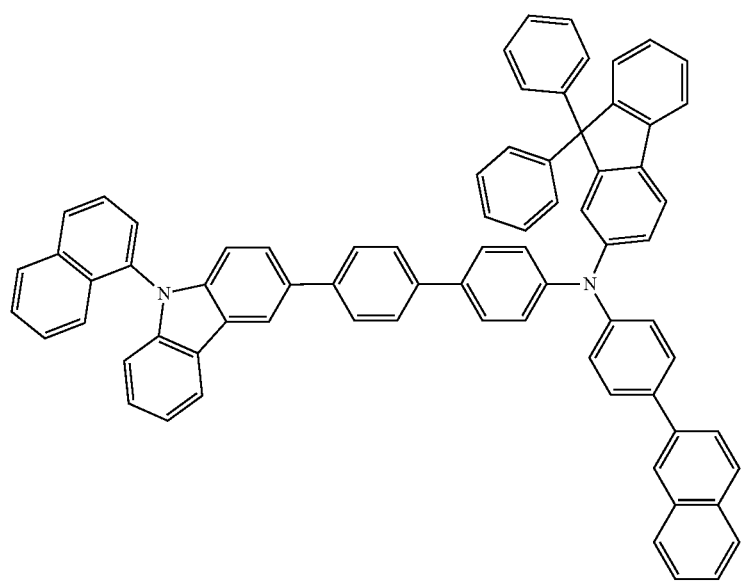
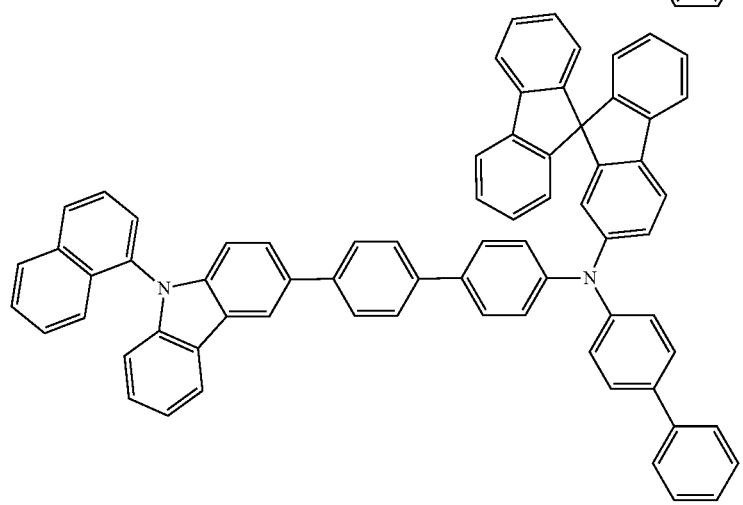

-continued
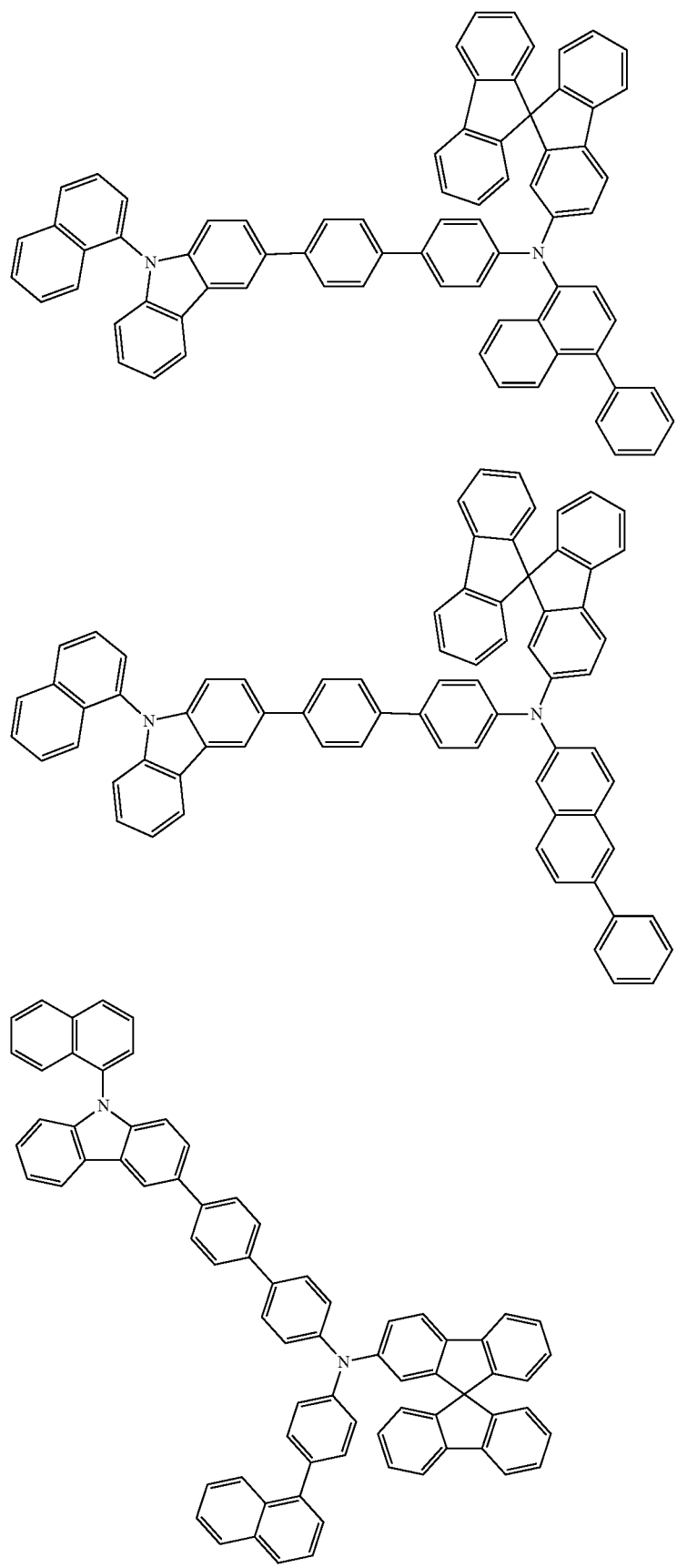

-continued
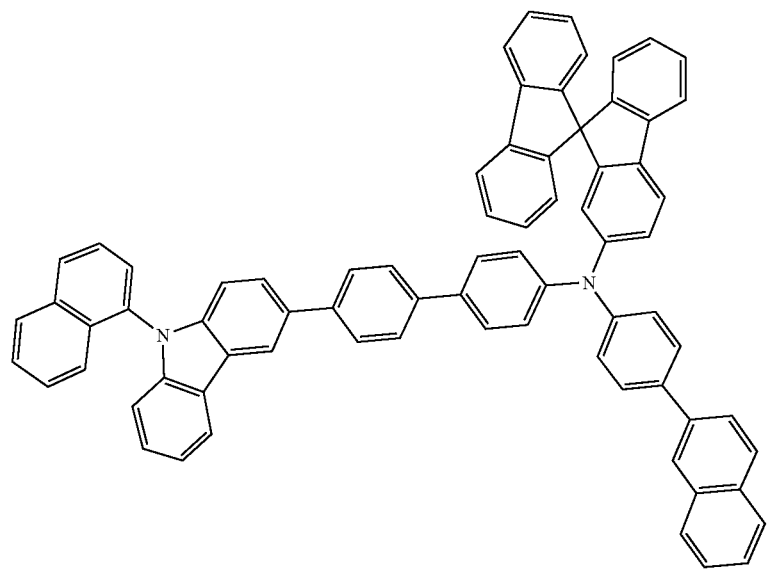
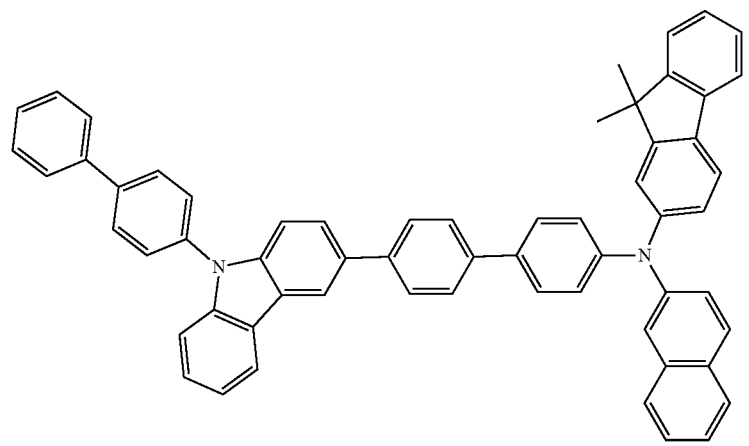
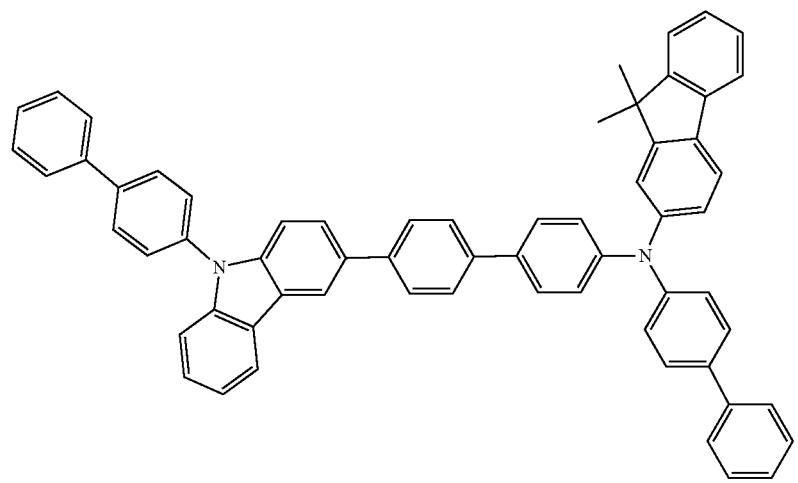

-continued
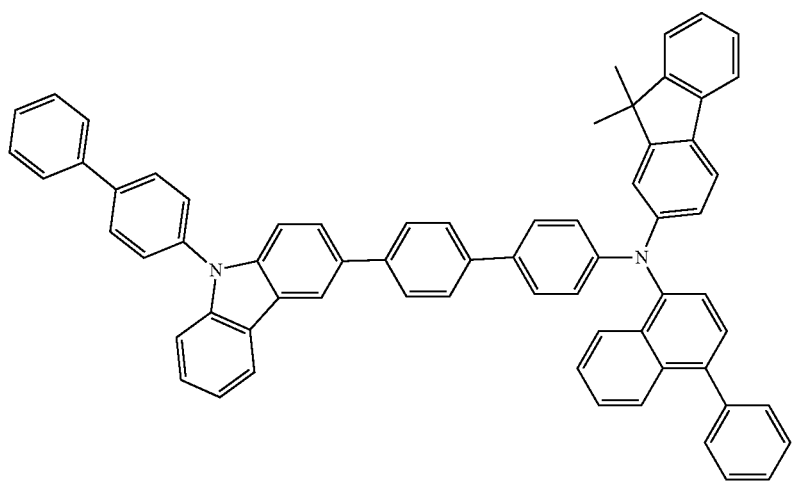
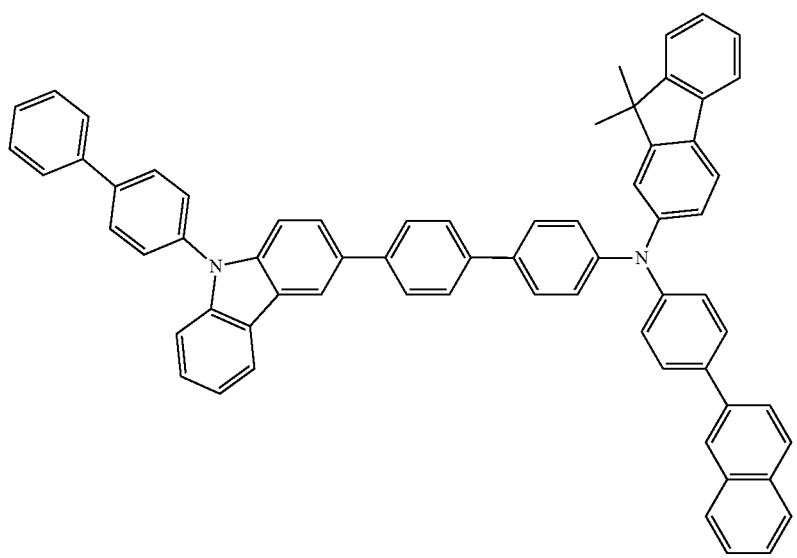
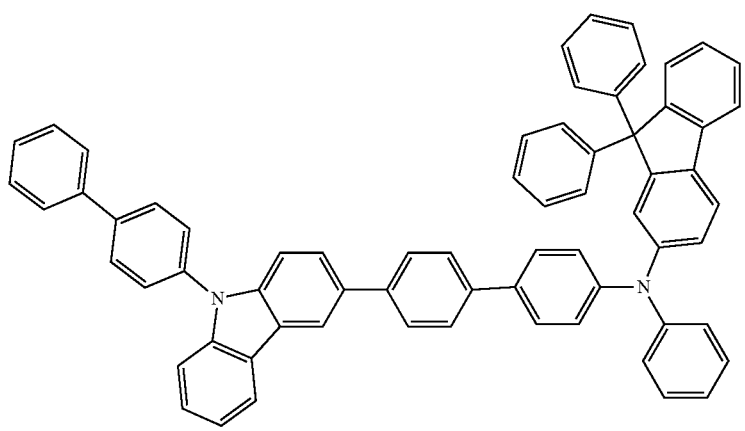

-continued
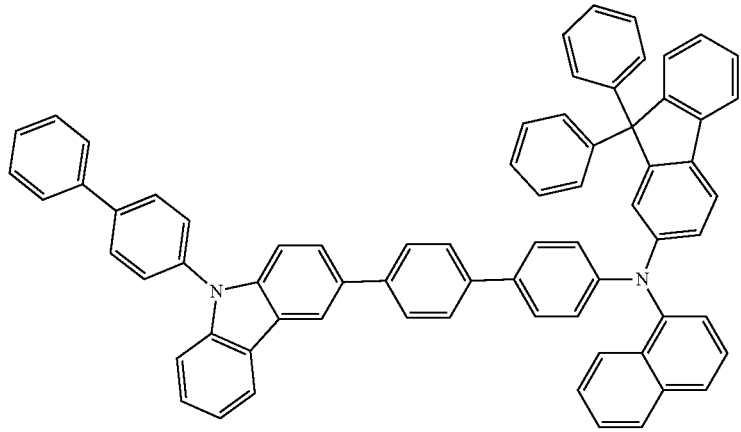
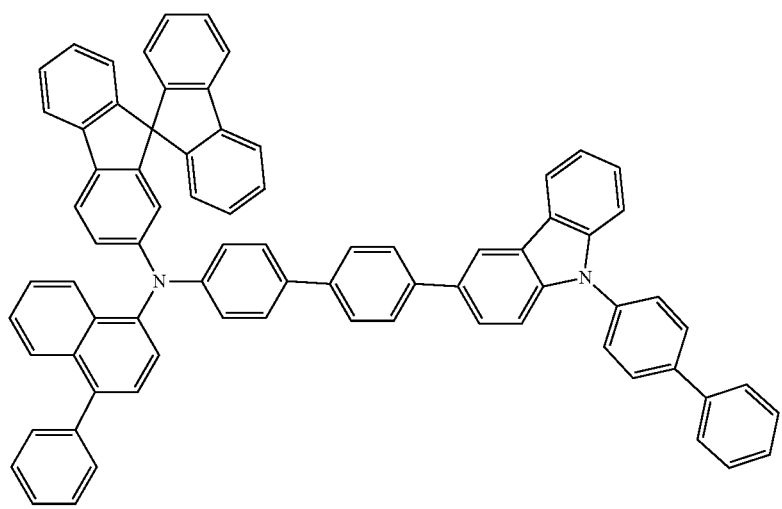
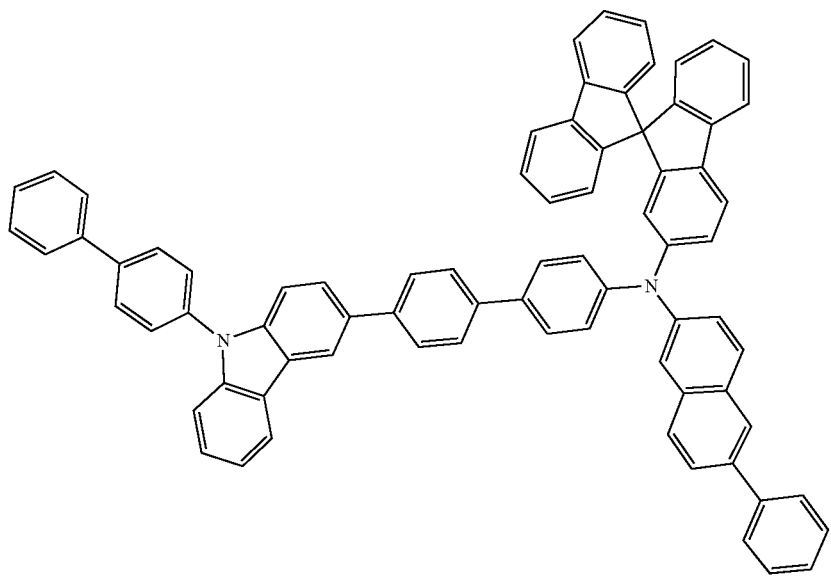

-continued
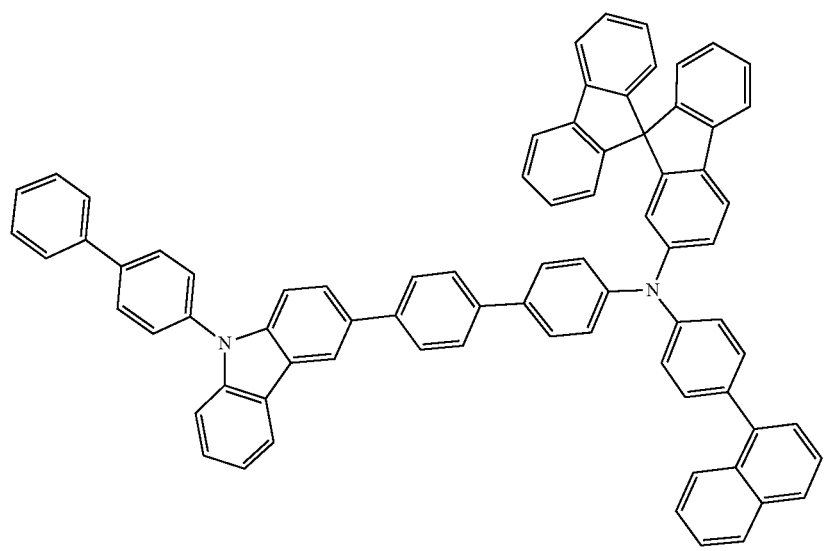
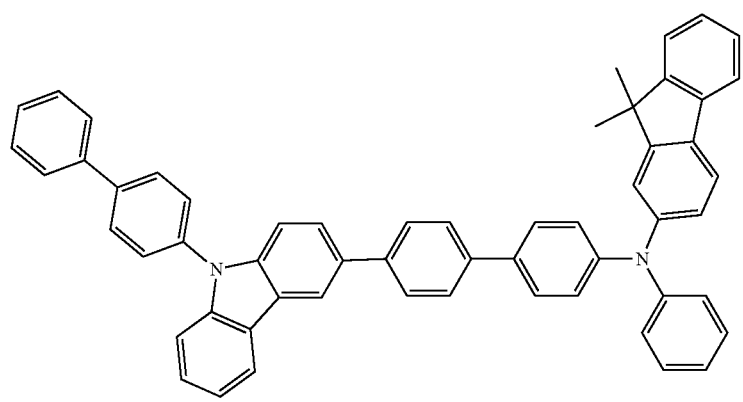
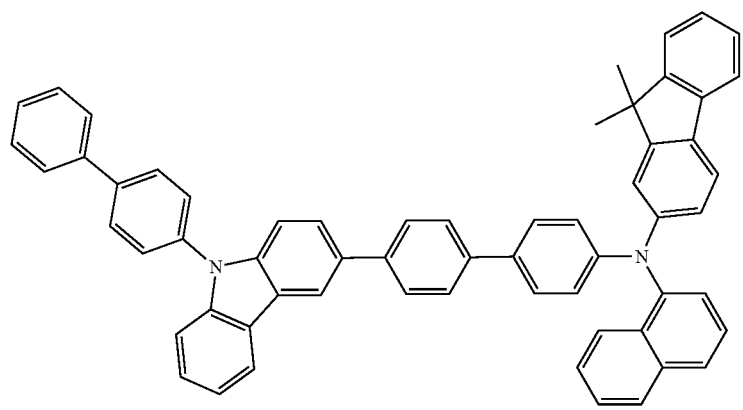

-continued
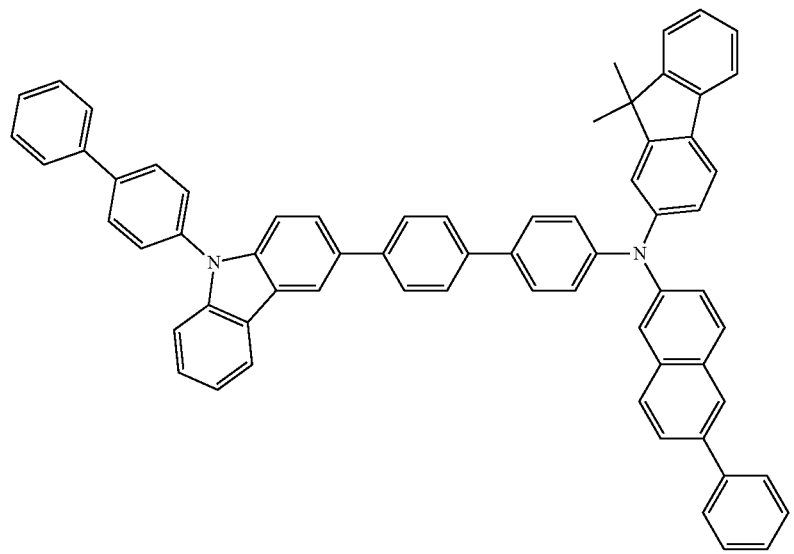
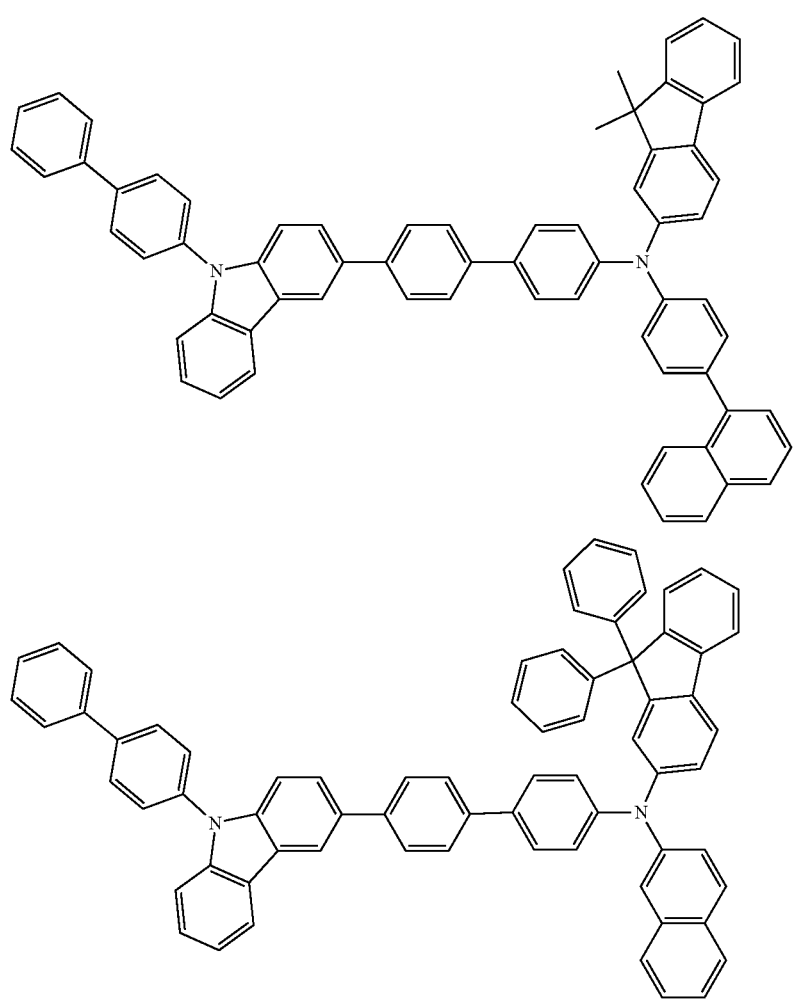

-continued
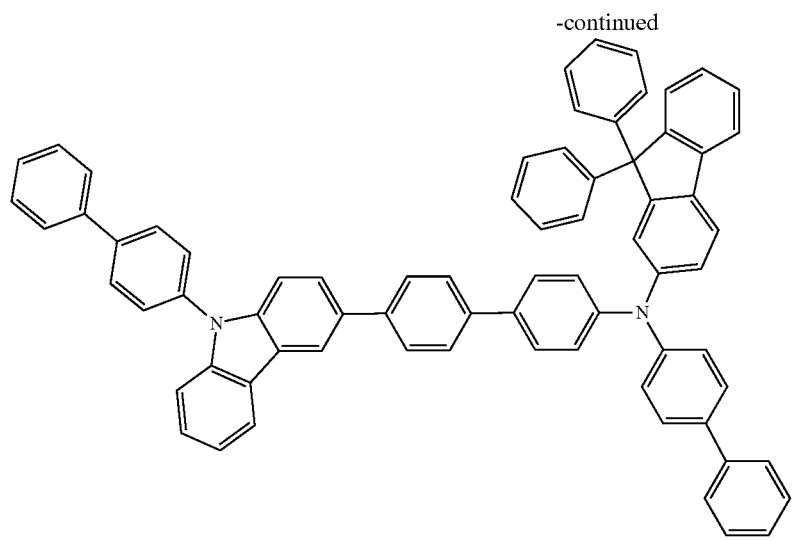
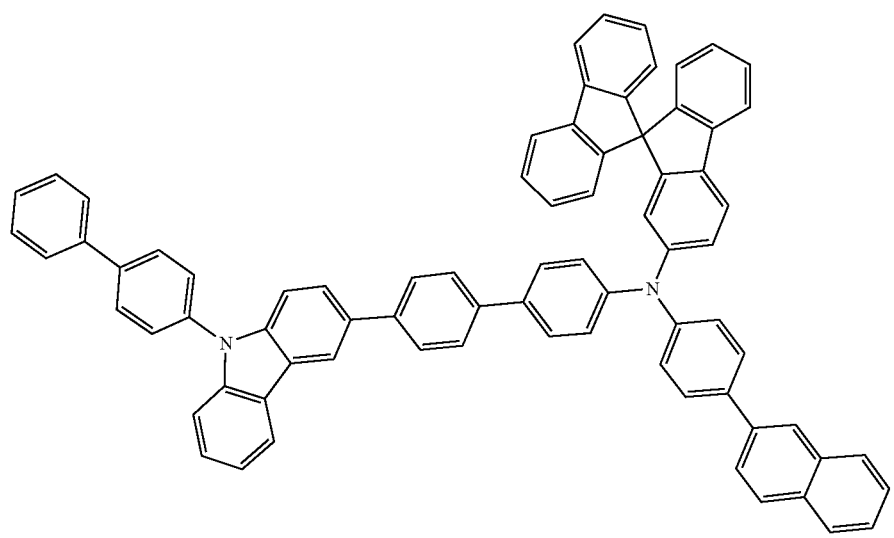
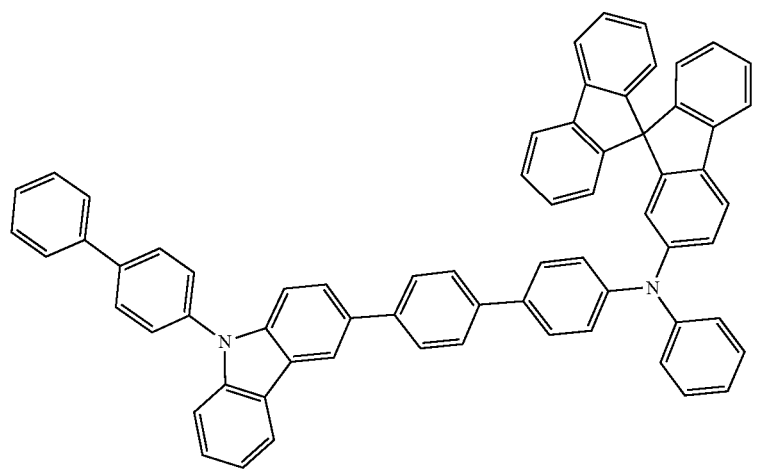

-continued
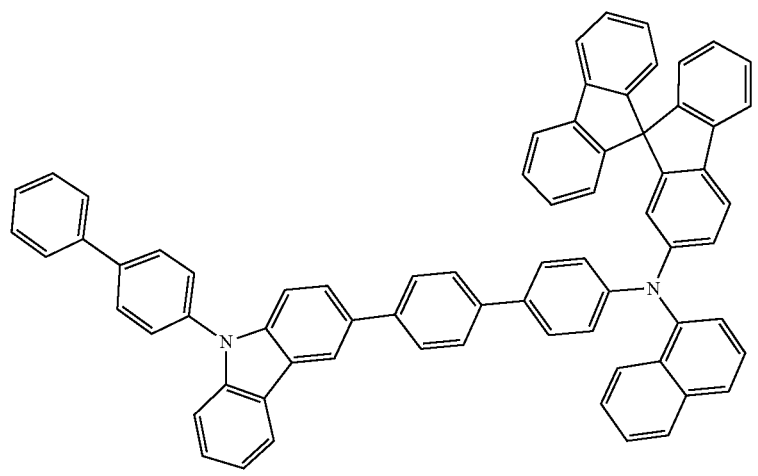
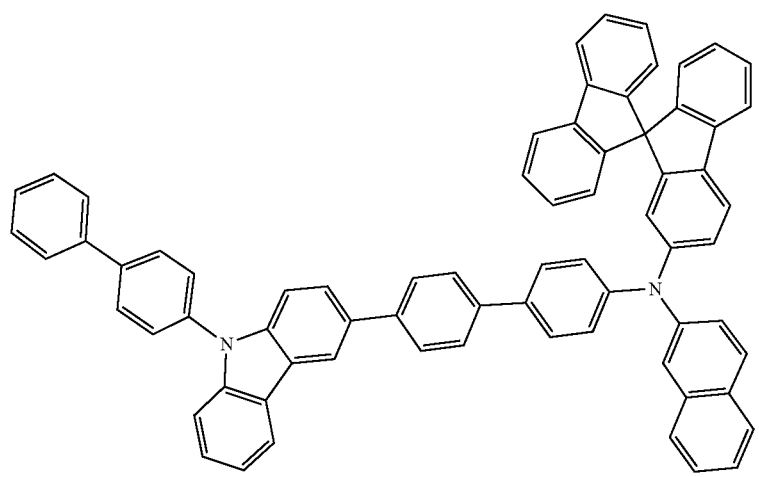
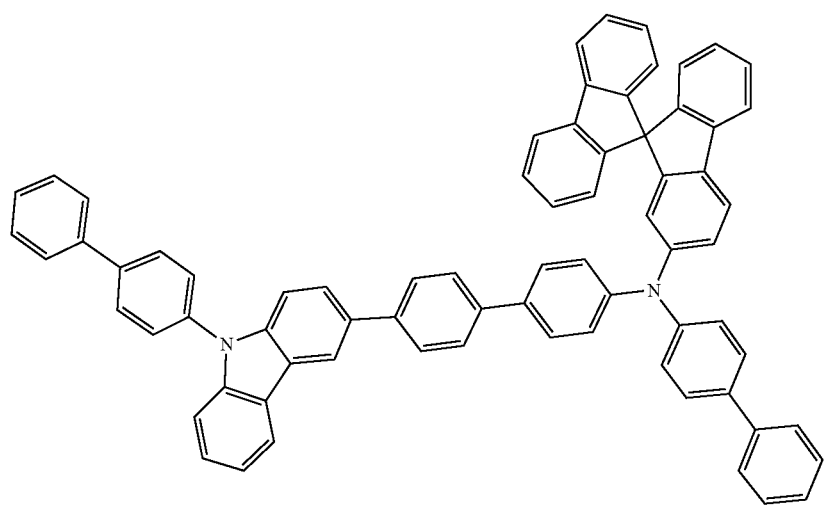

-continued
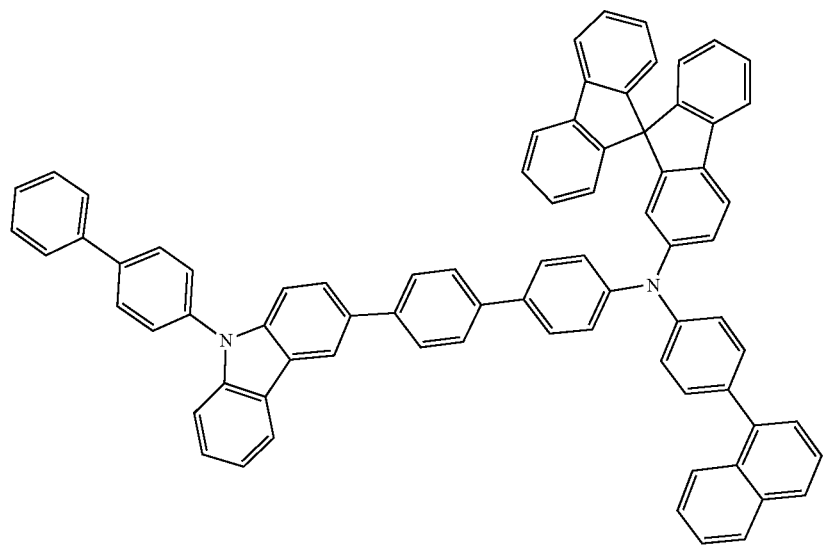
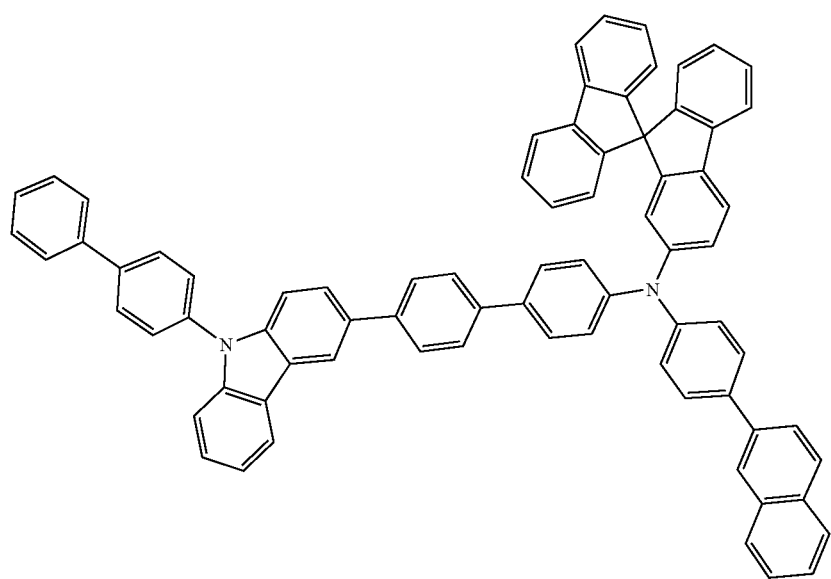
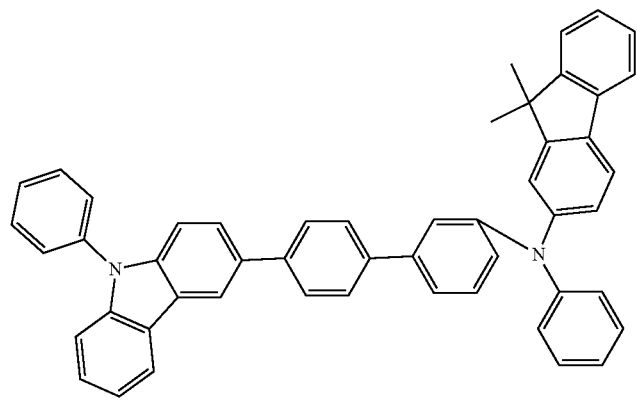

-continued
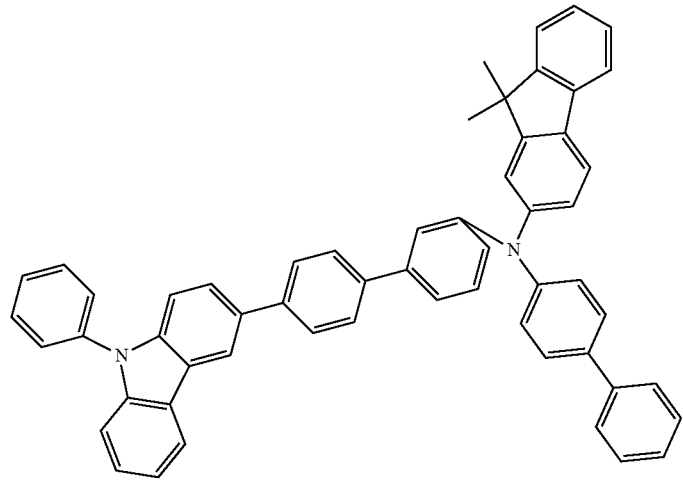
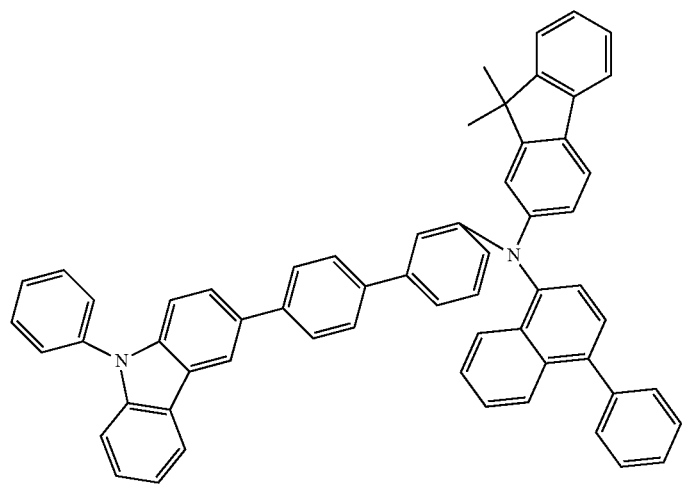
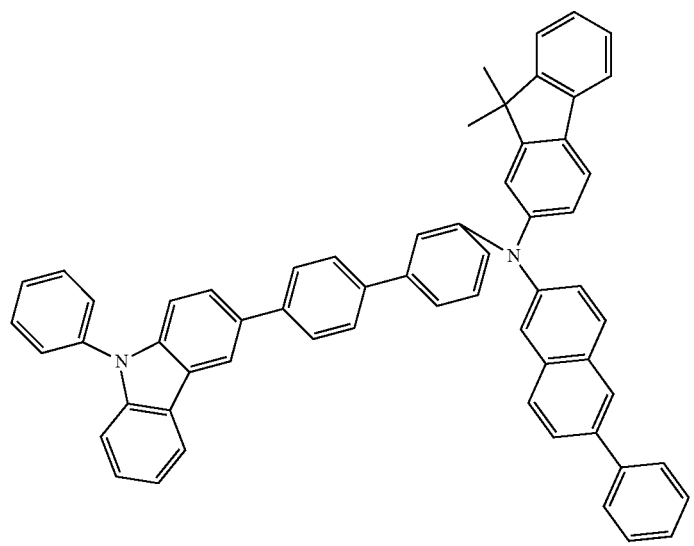

-continued
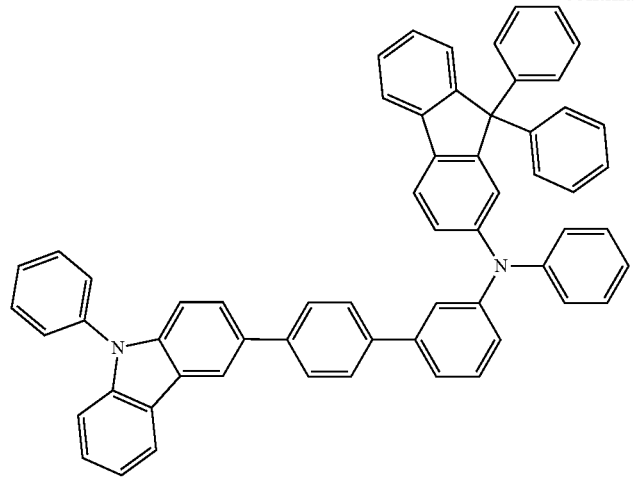
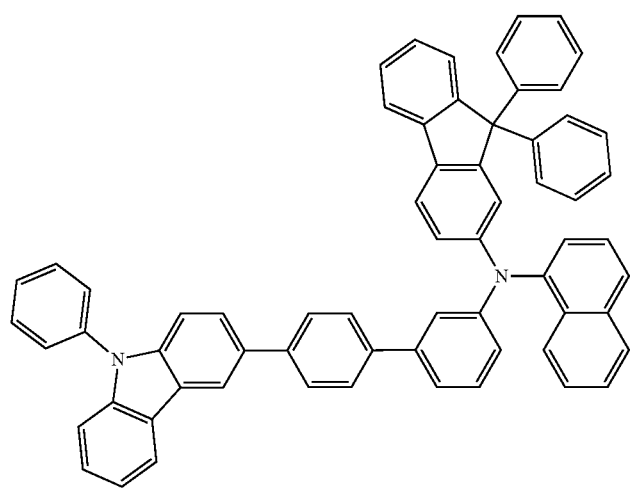
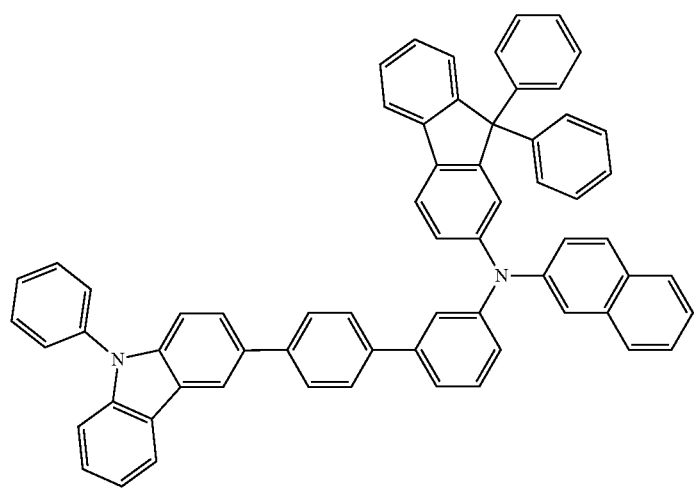

-continued
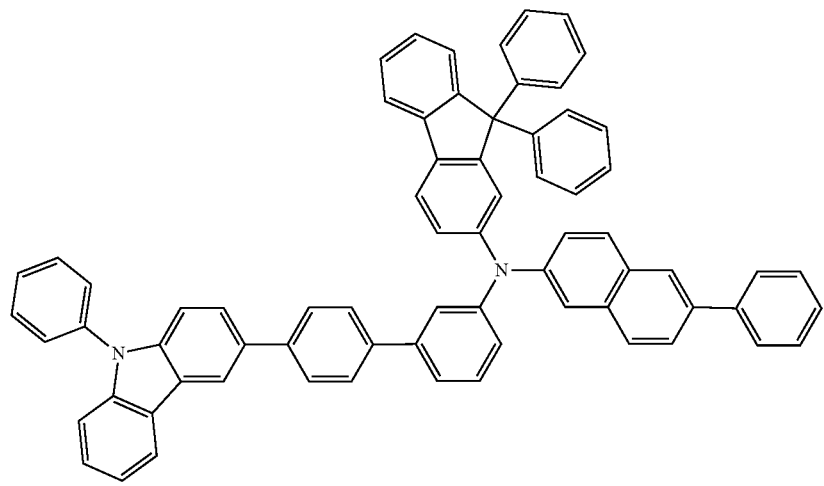
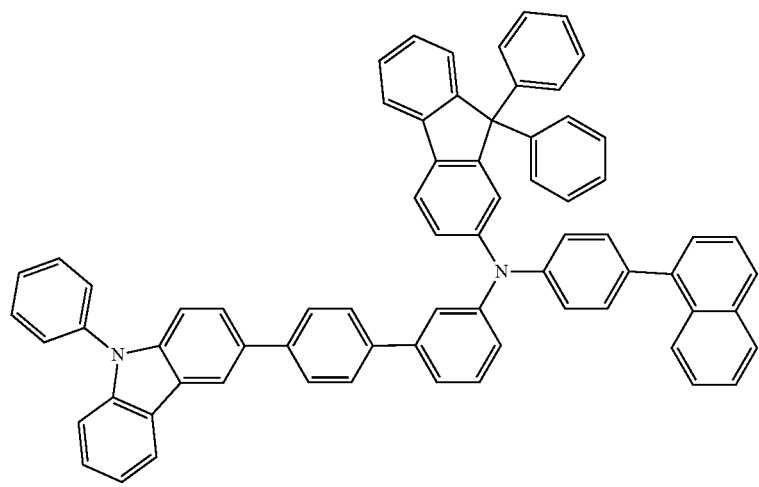
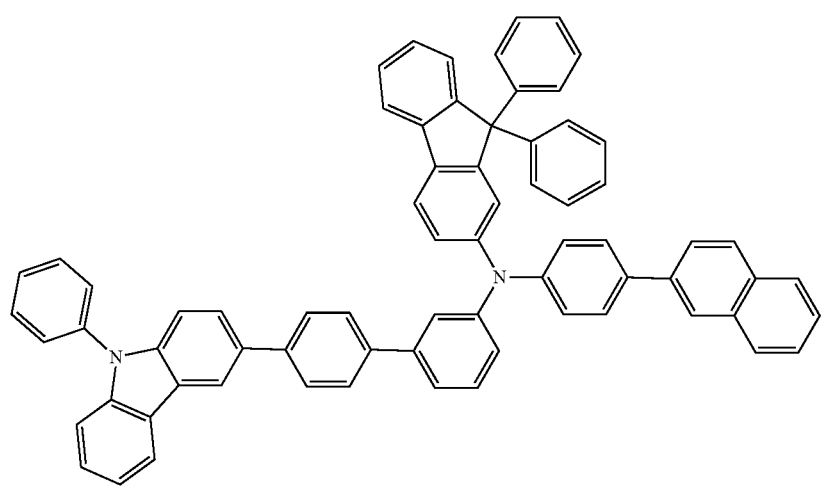

-continued
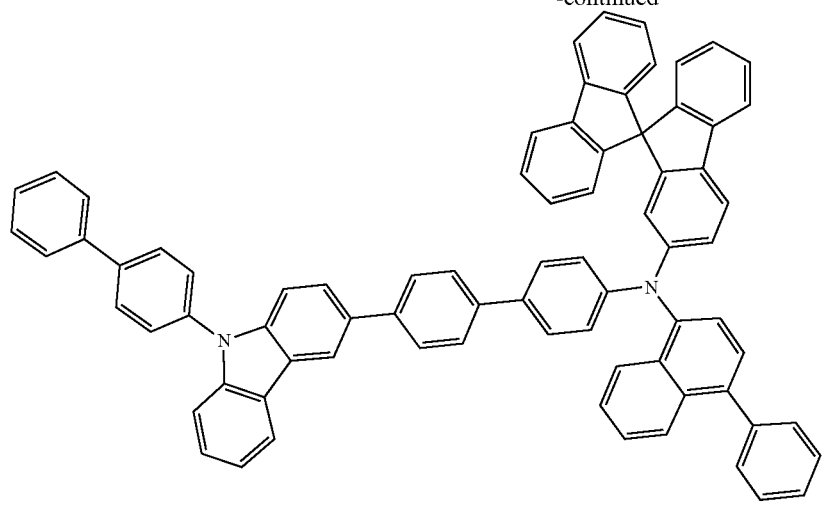
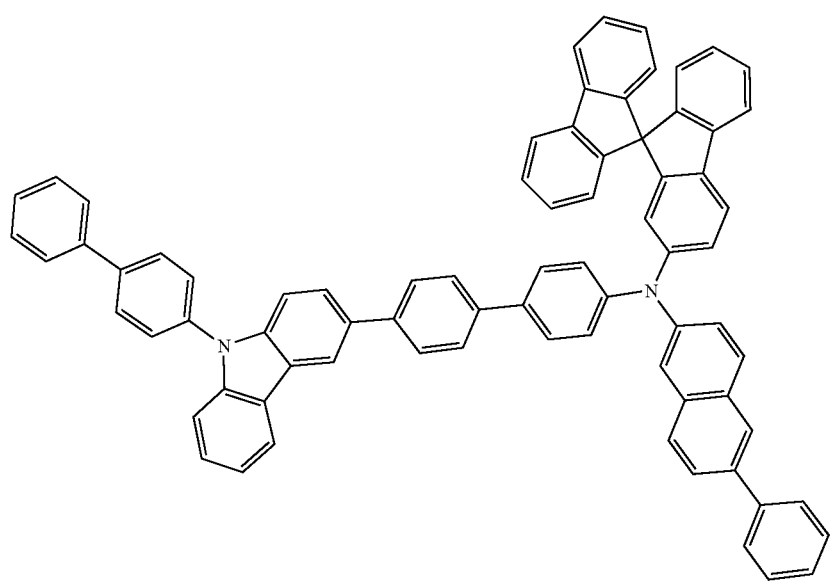
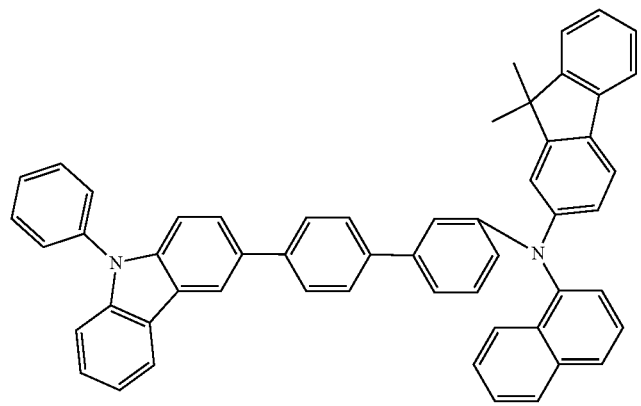

-continued
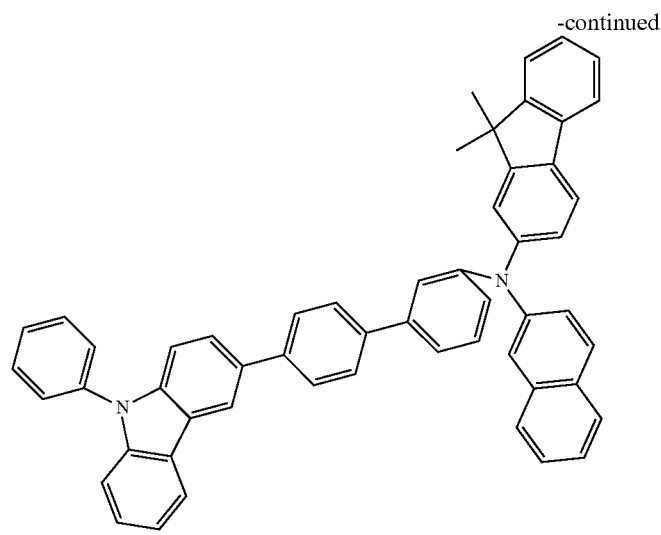
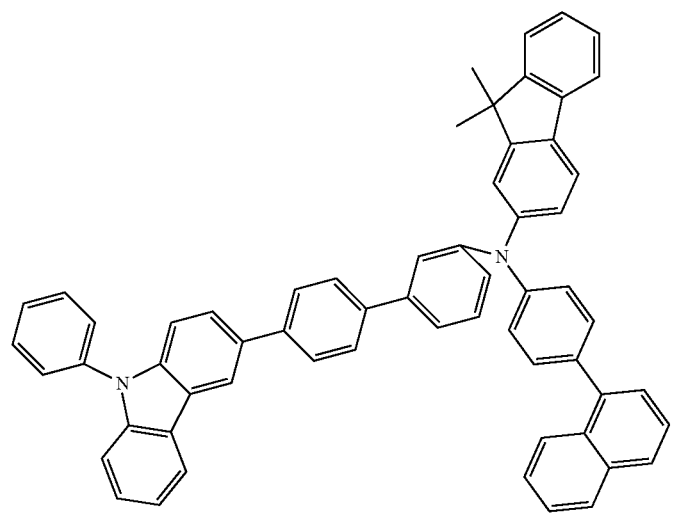
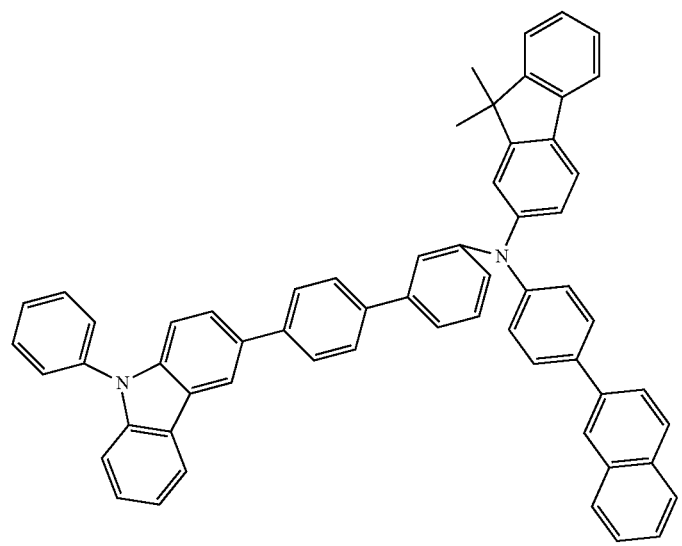

-continued
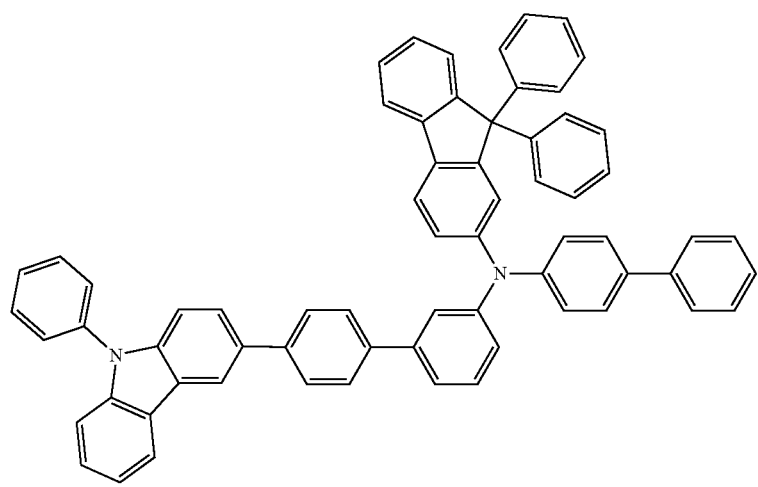
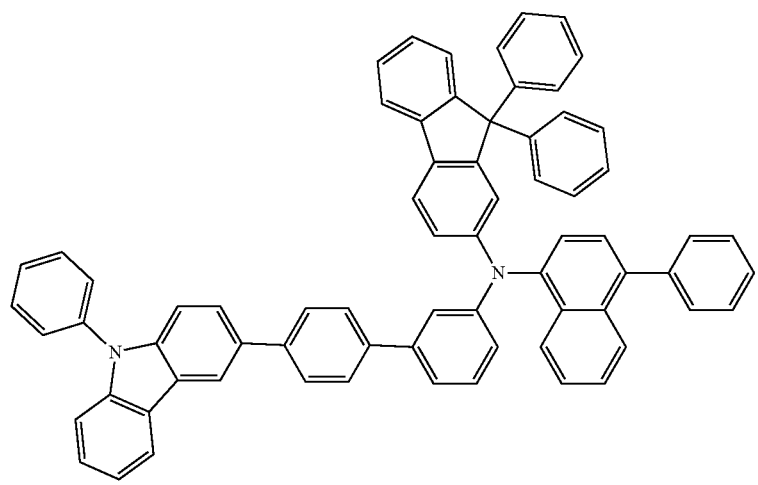
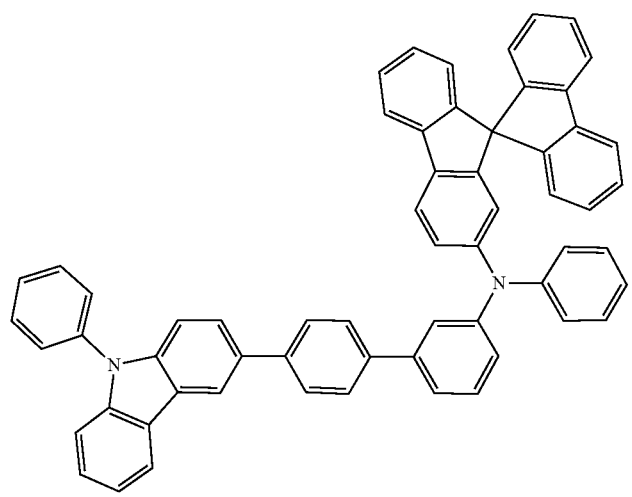

-continued
723
724
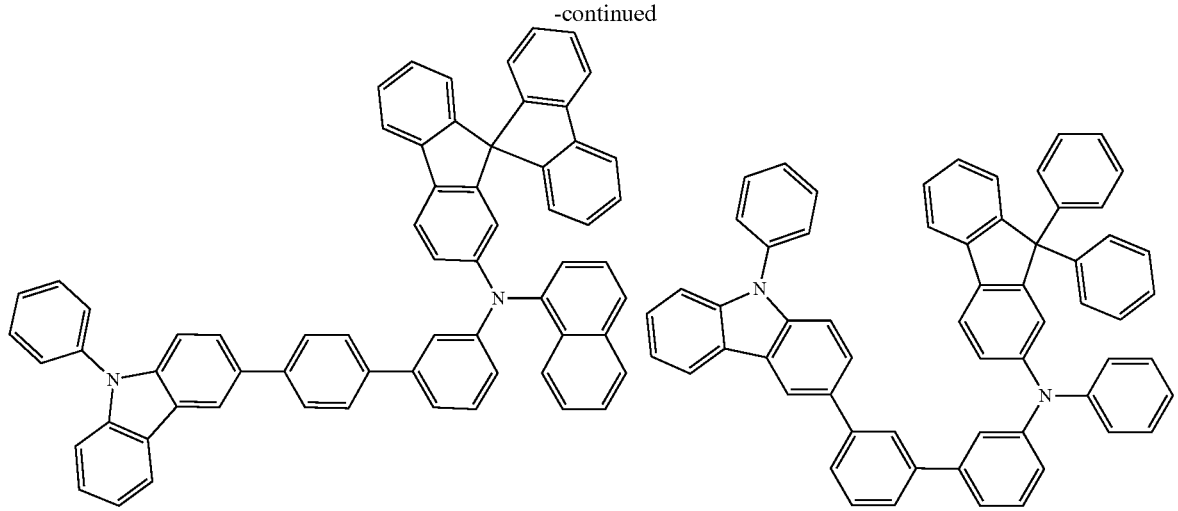
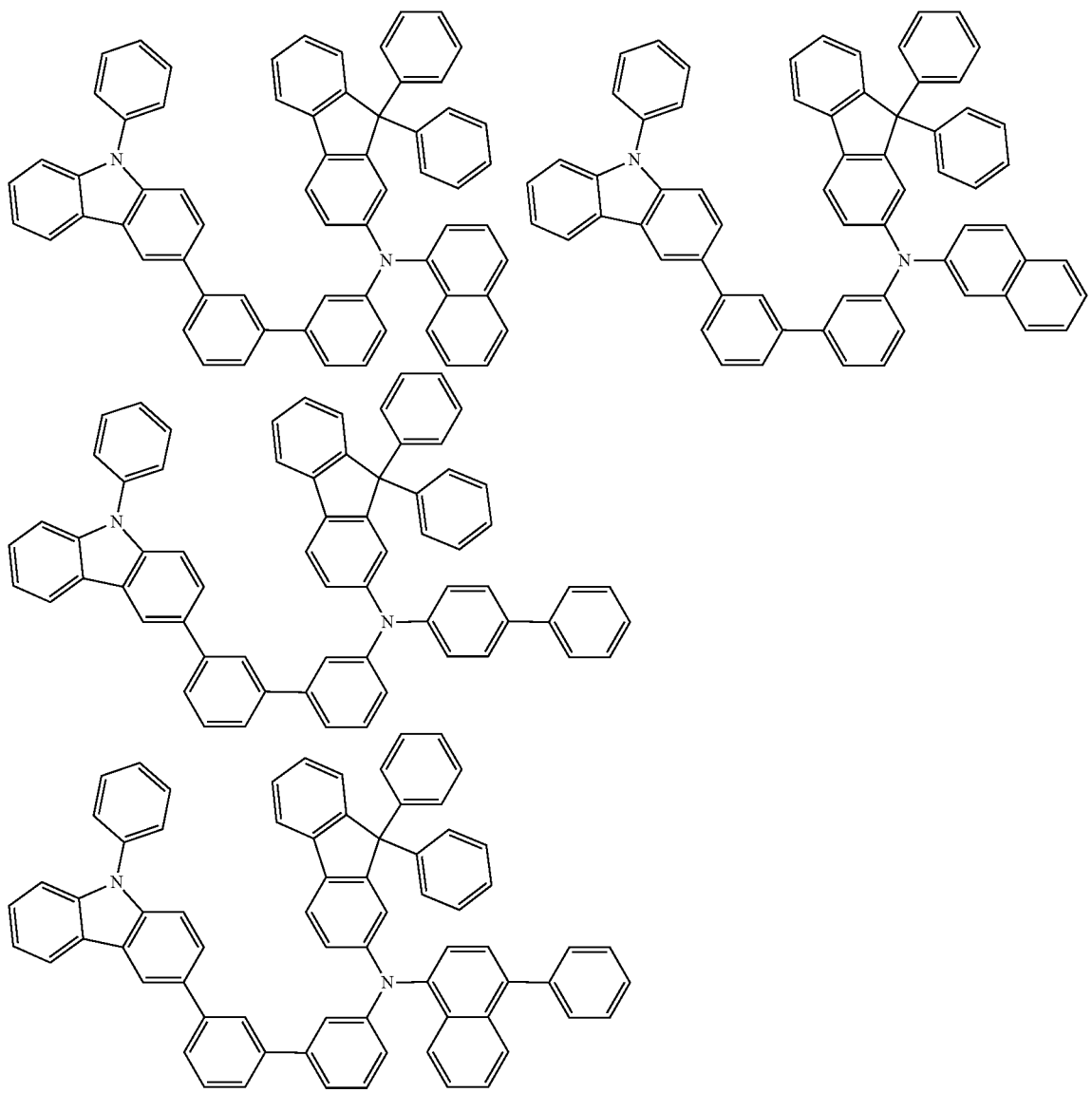

725 726
-continued
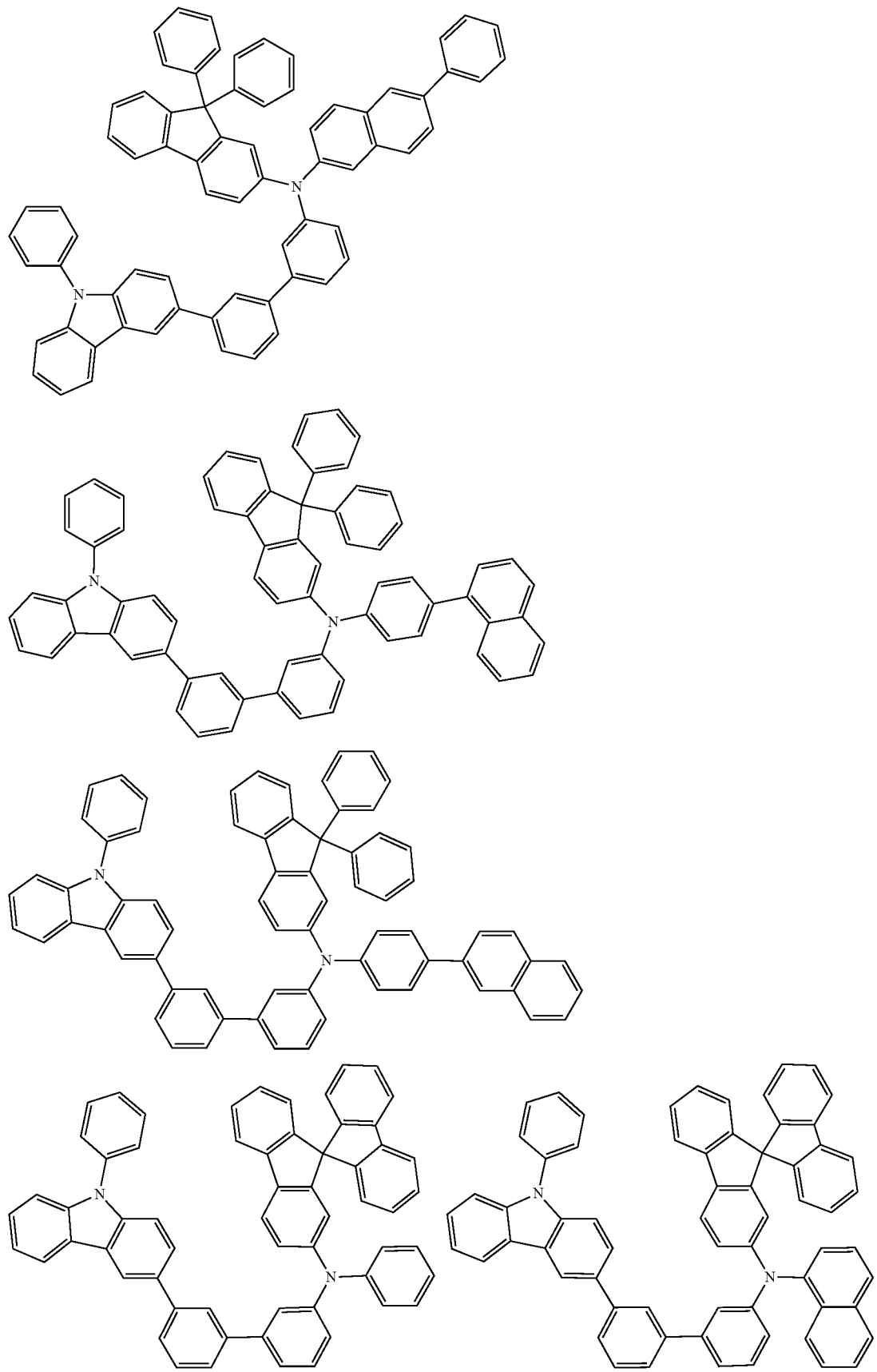

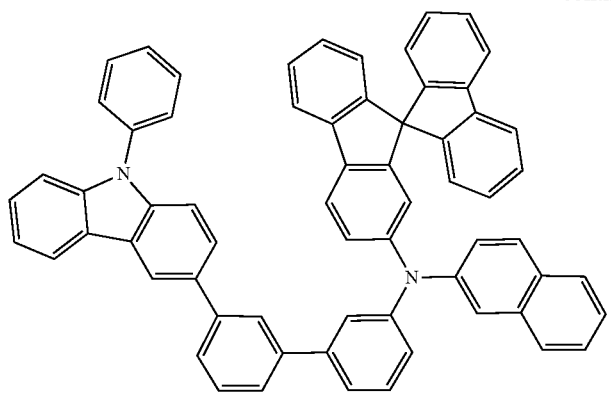
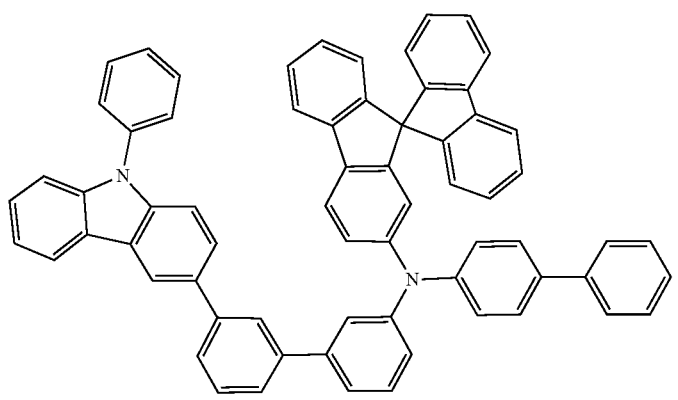
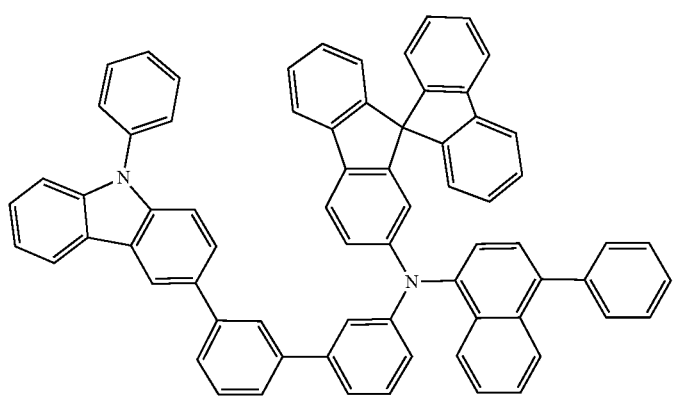
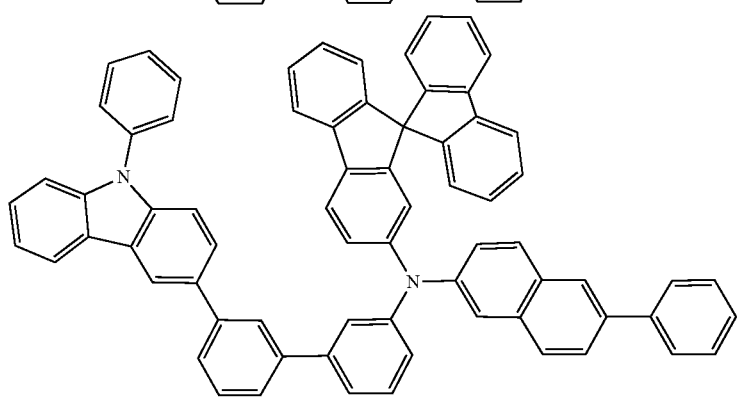

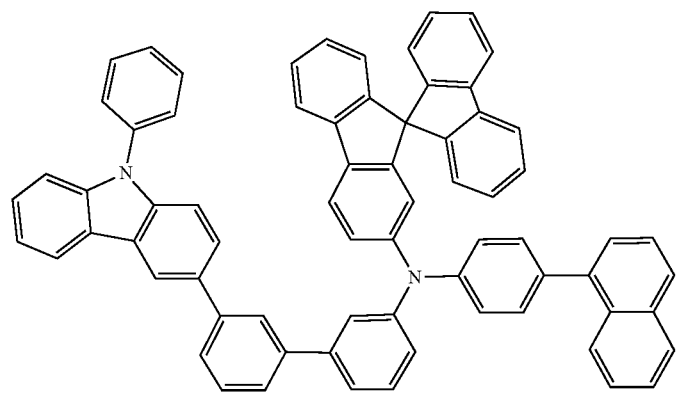
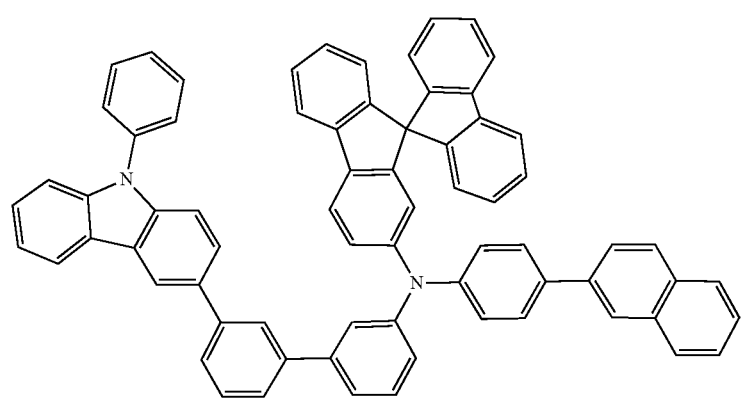
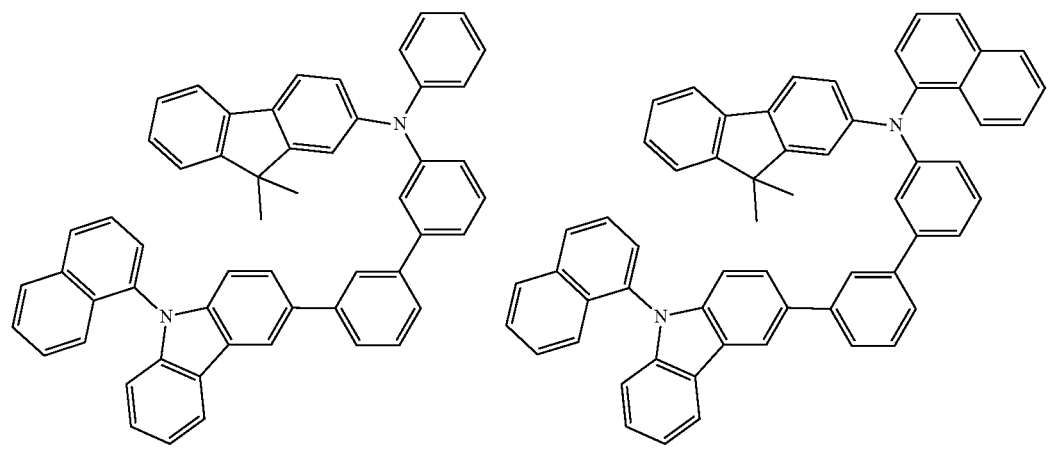

| 731 | 732 |
|---|---|
| 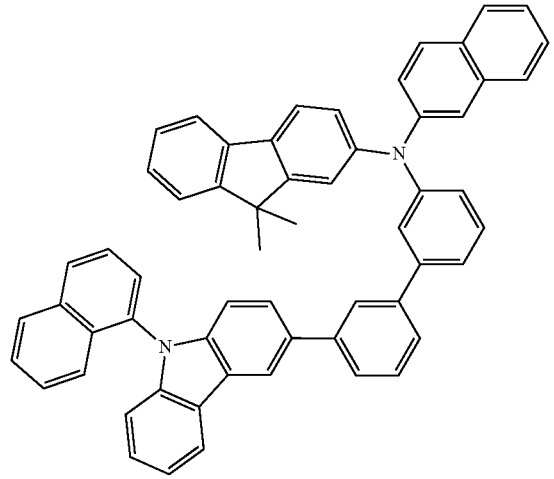 | 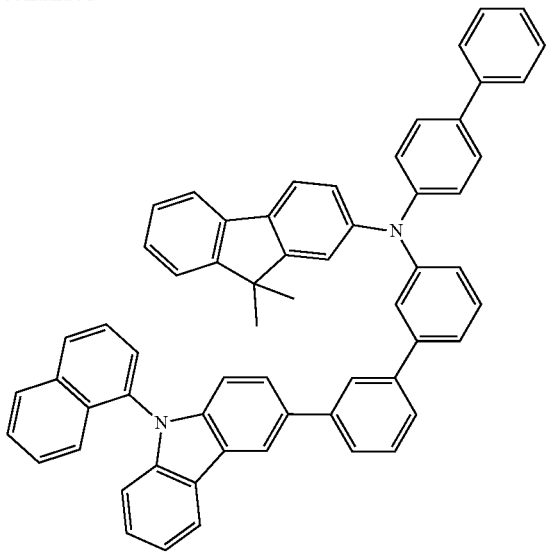 |
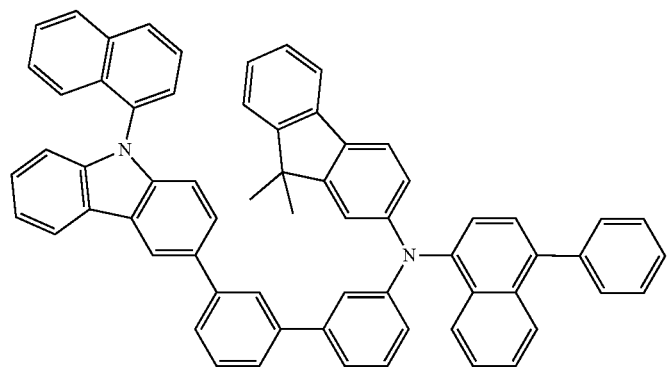
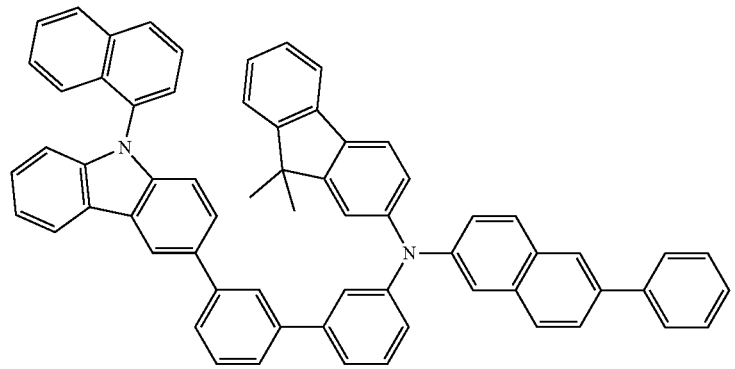
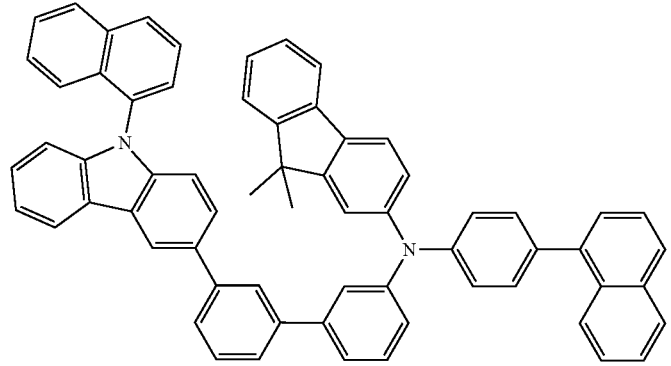

-continued
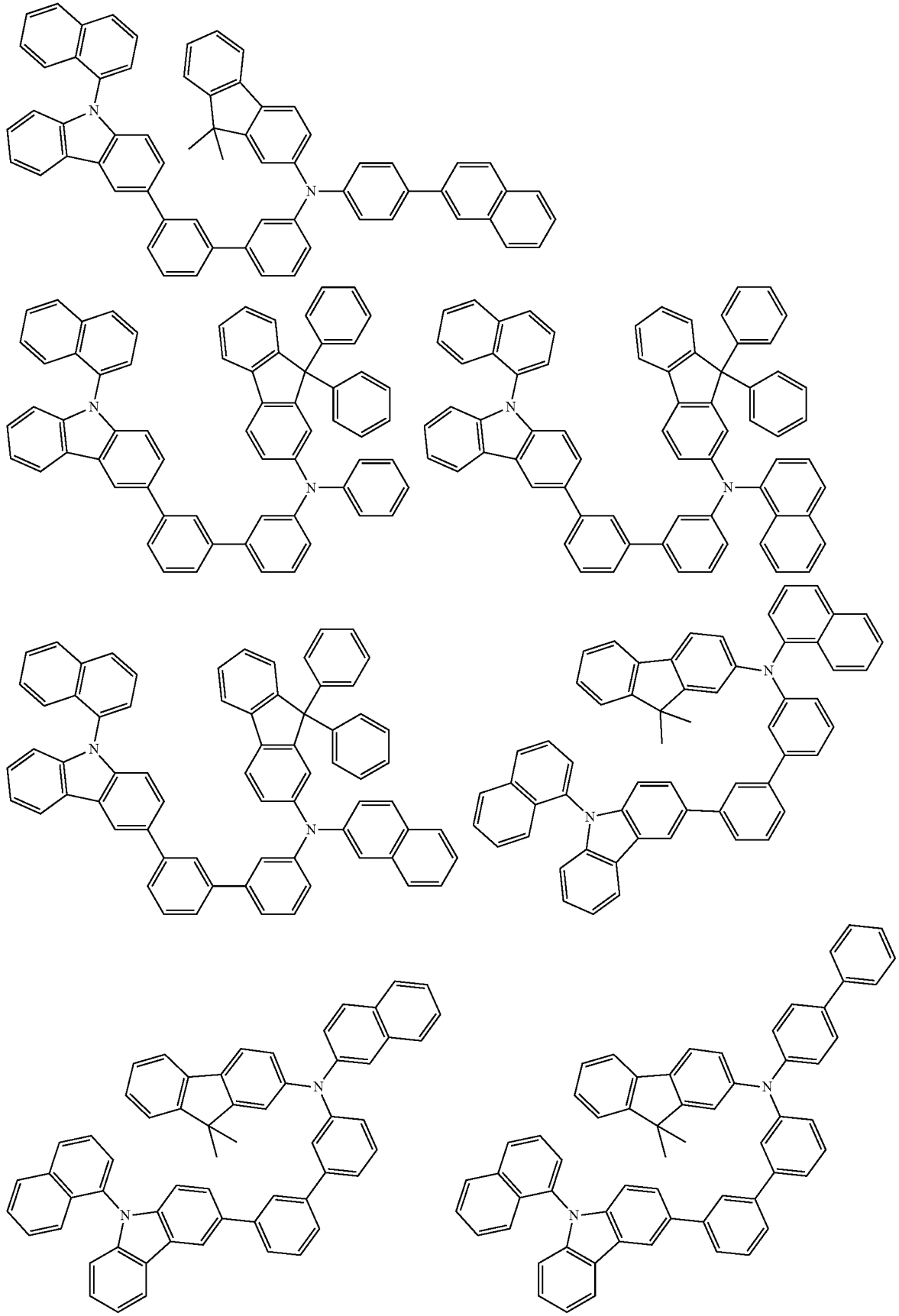

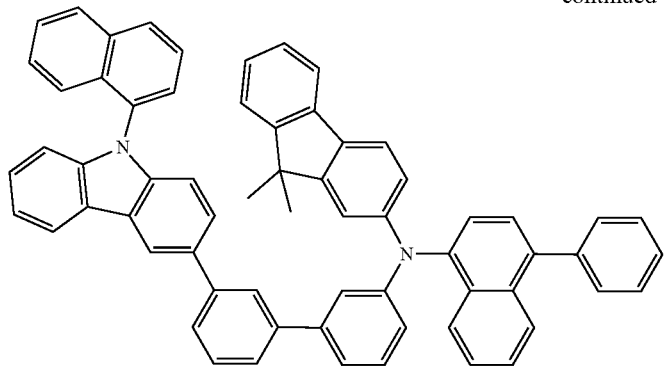
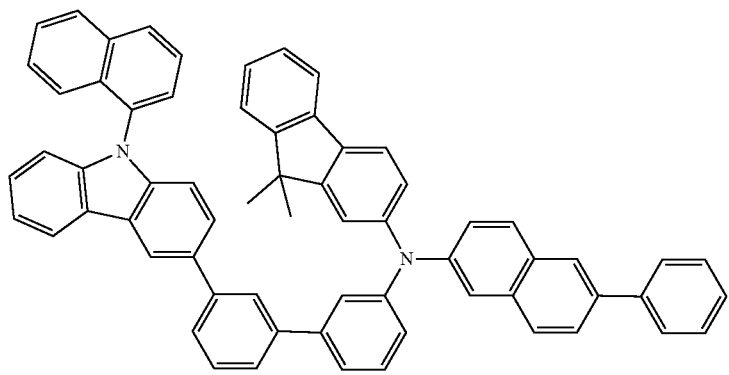
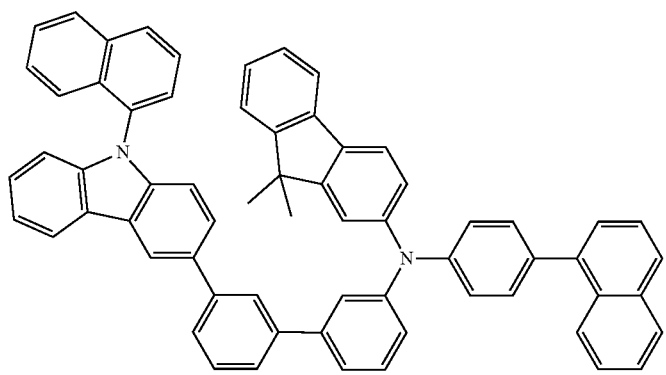
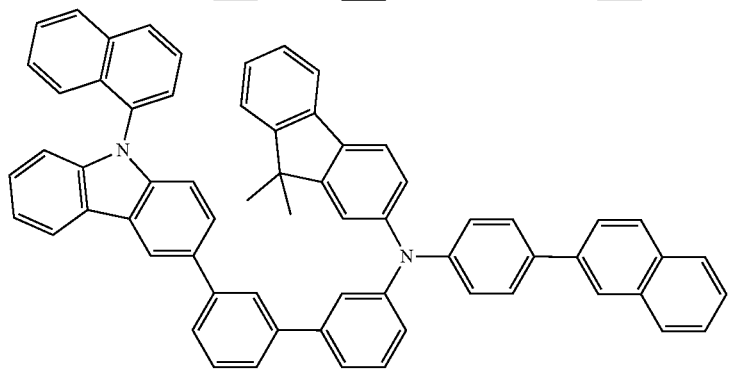

-continued
737 738
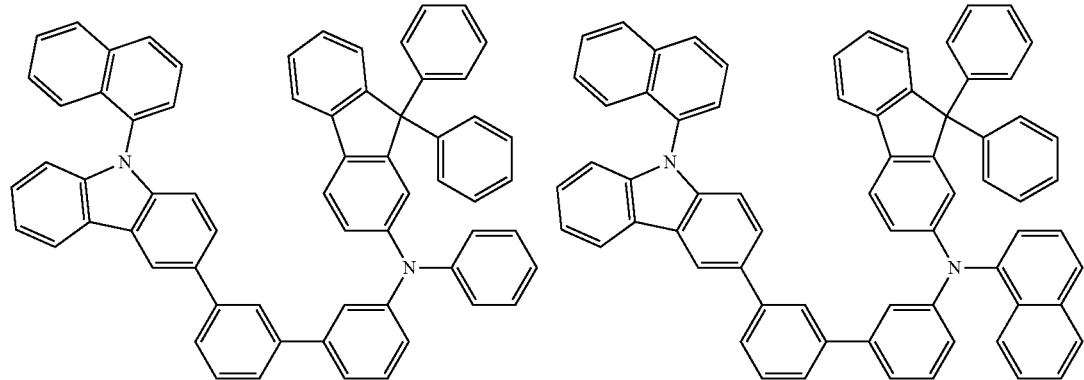
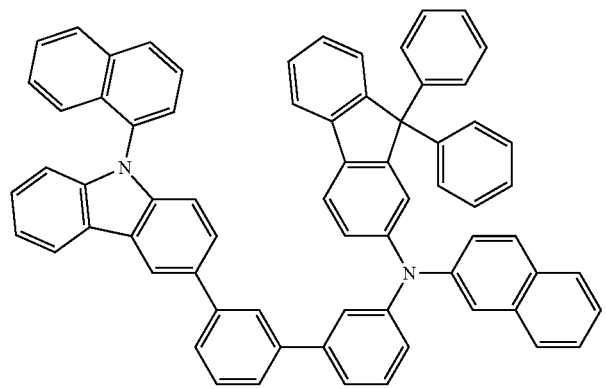
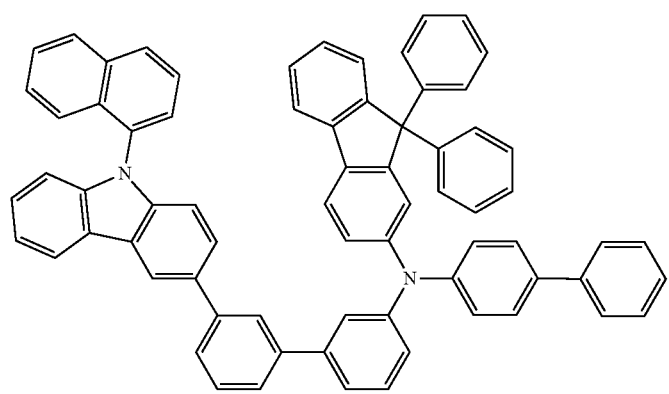
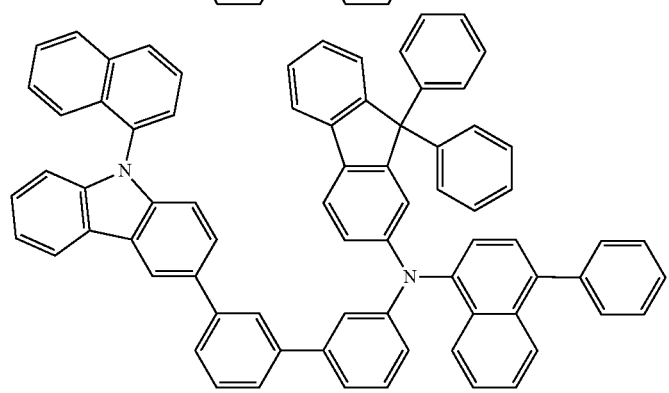

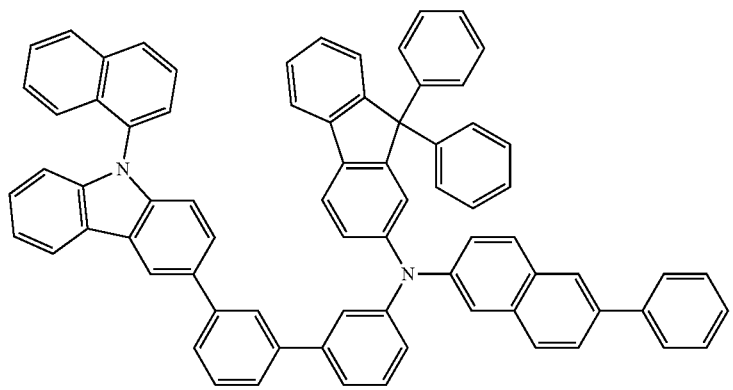
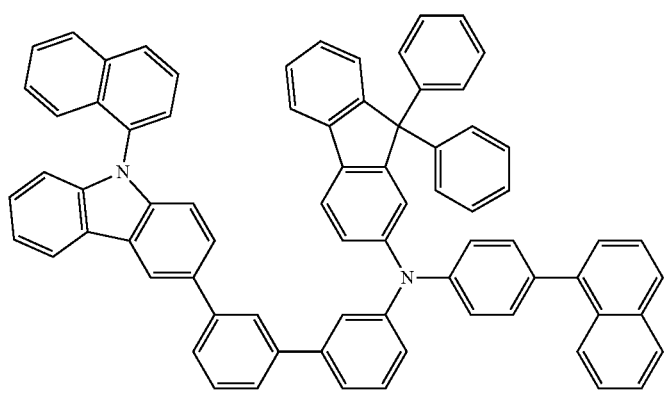
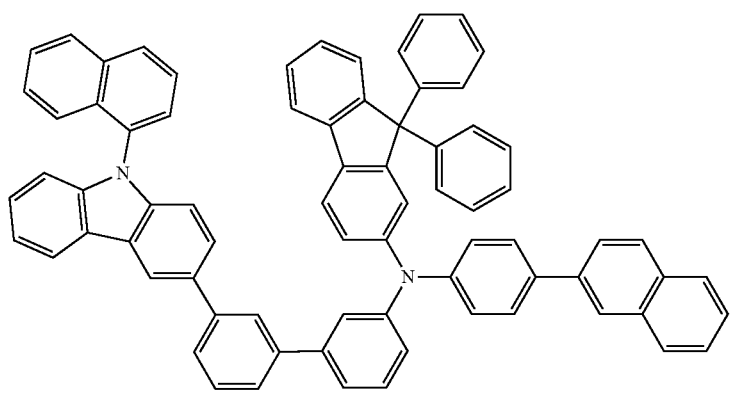
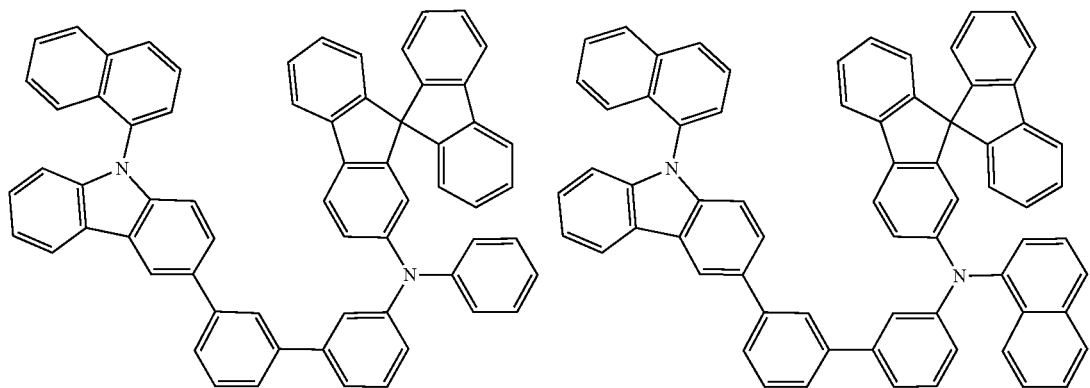

-continued
741
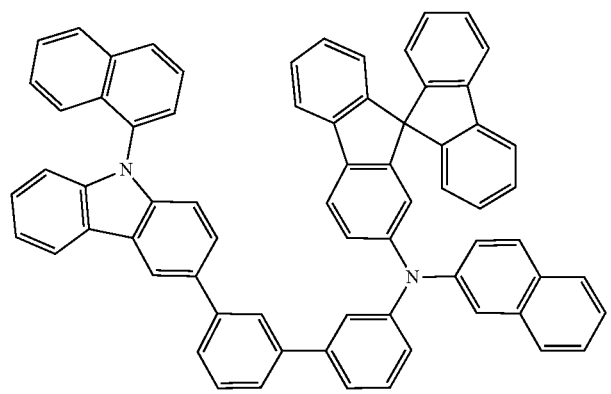
742
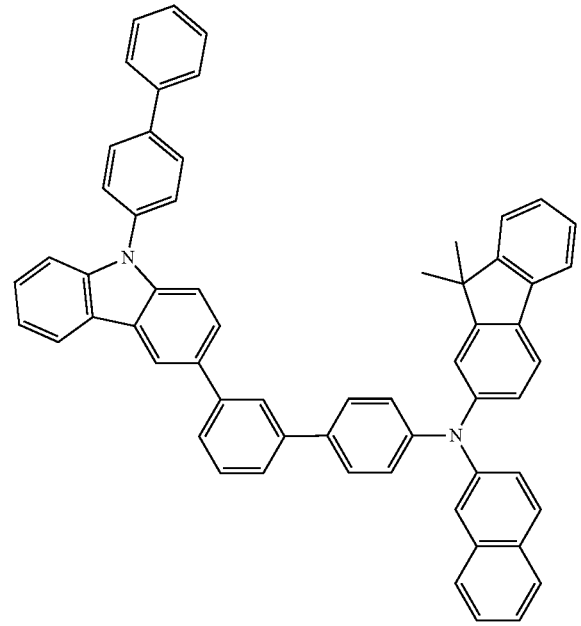
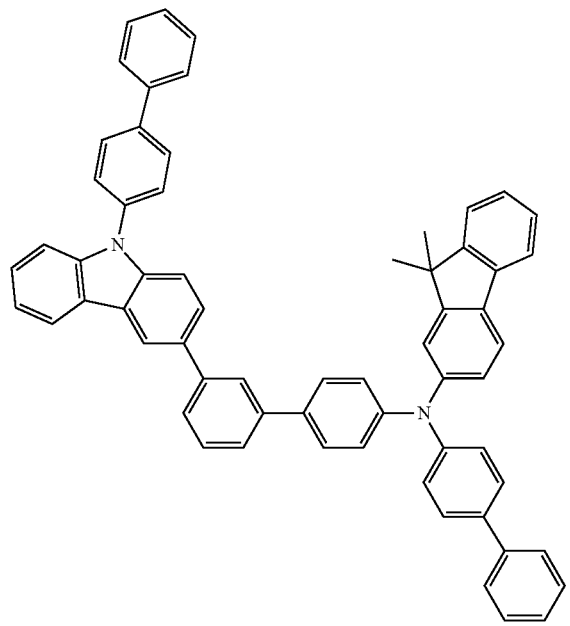
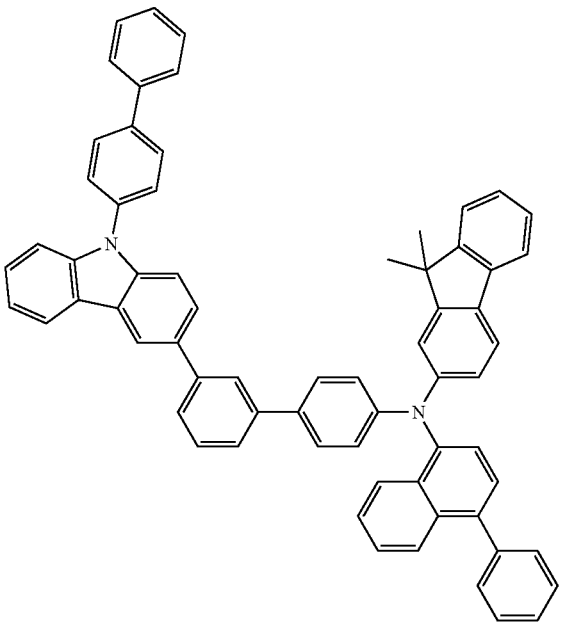

-continued
743
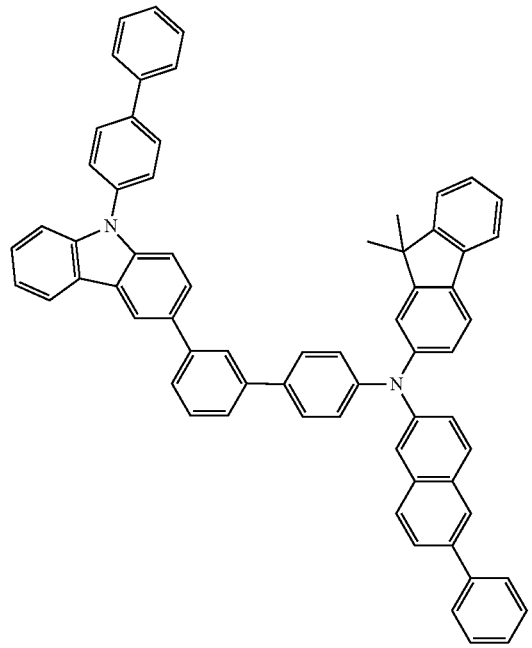
744
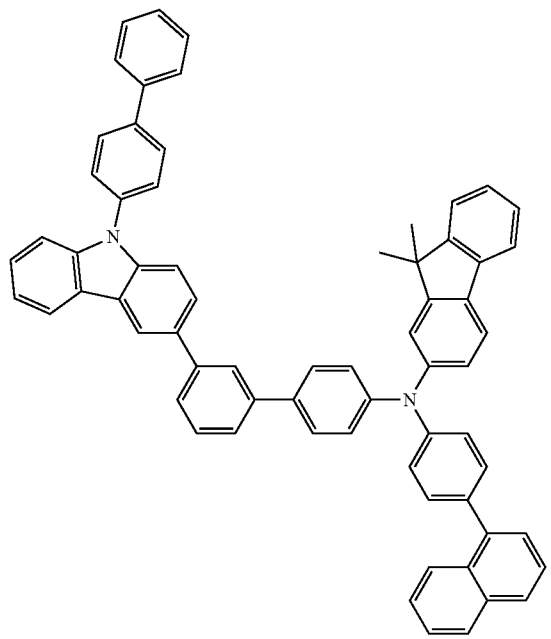
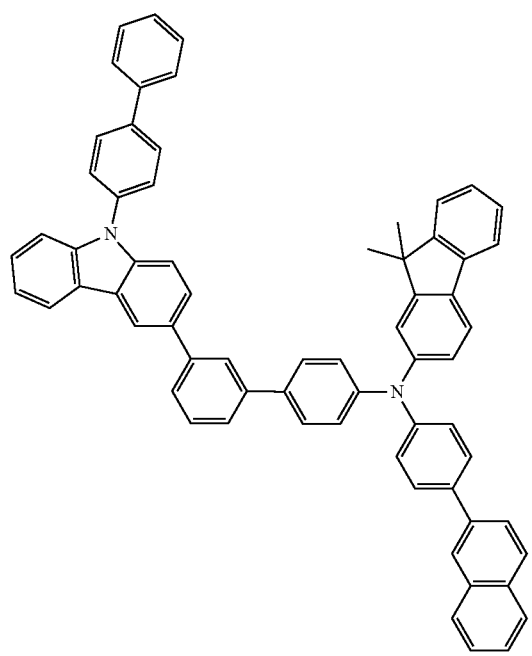
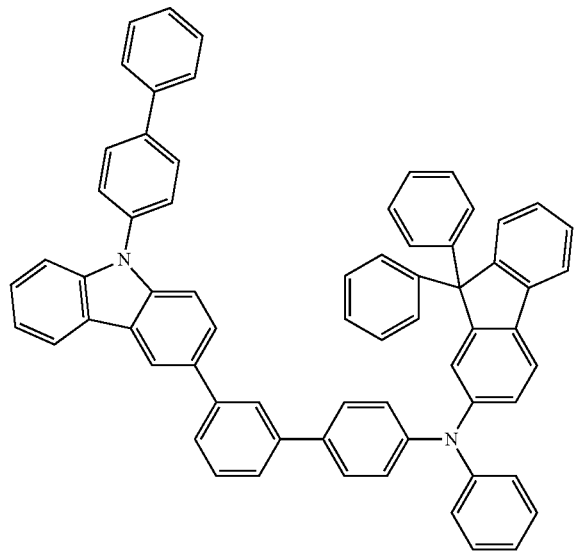

745
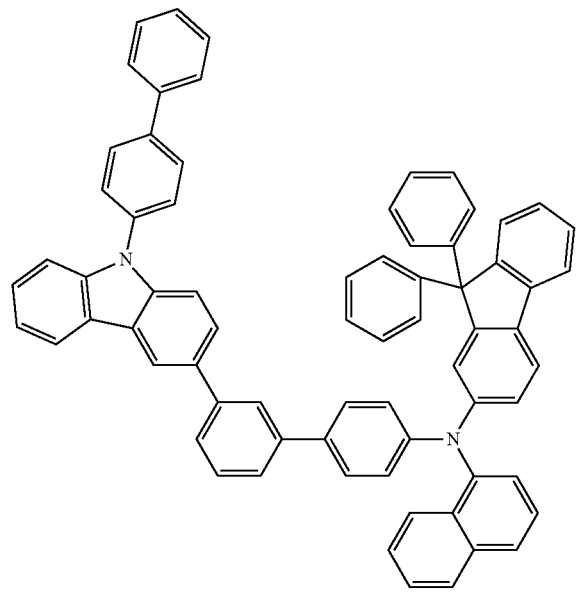
746
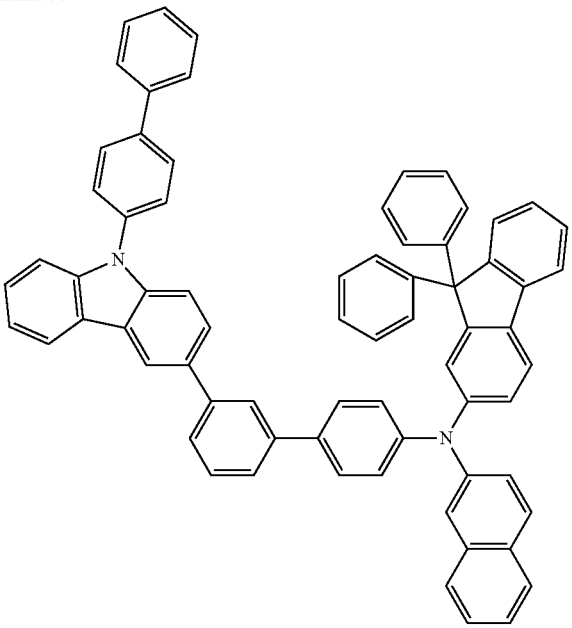
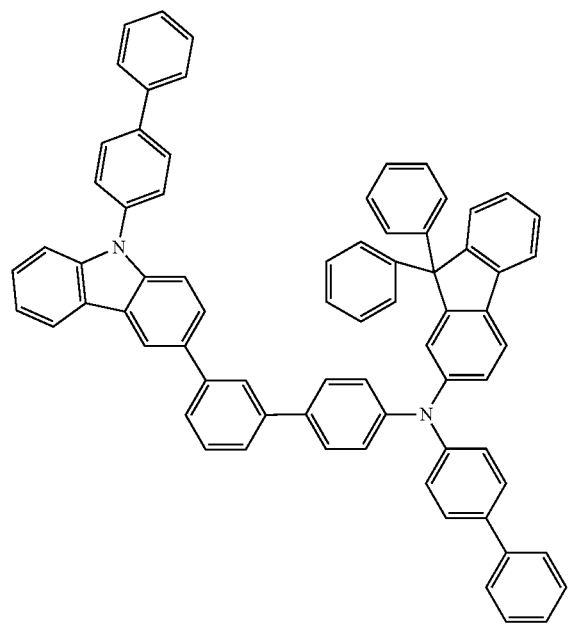
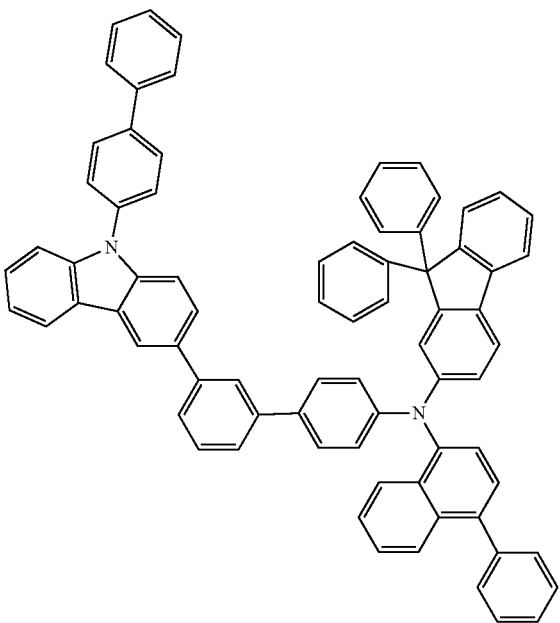

-continued
747
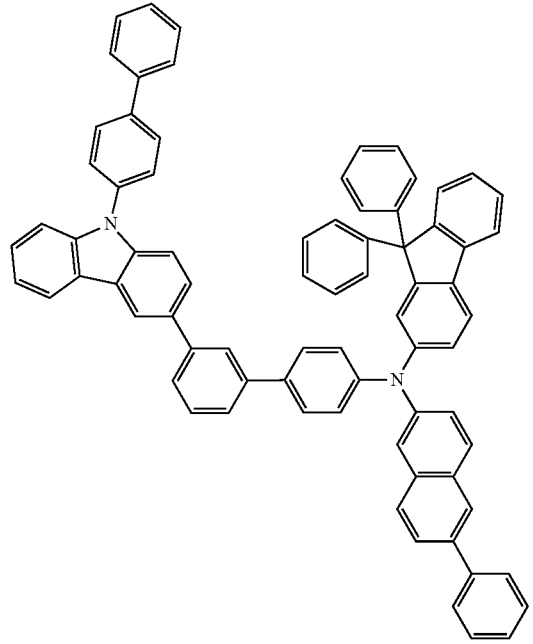
748
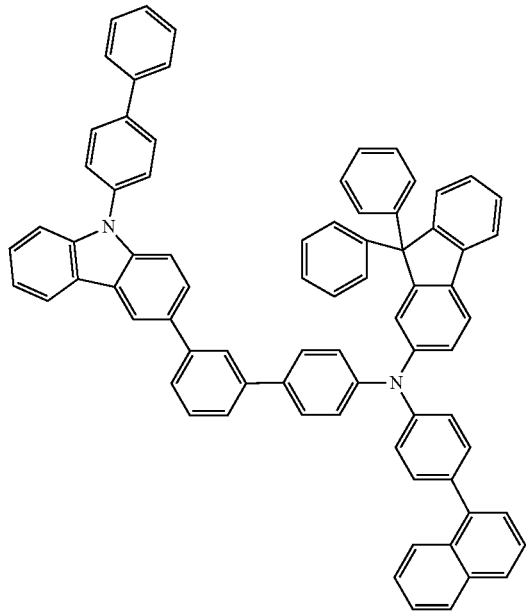
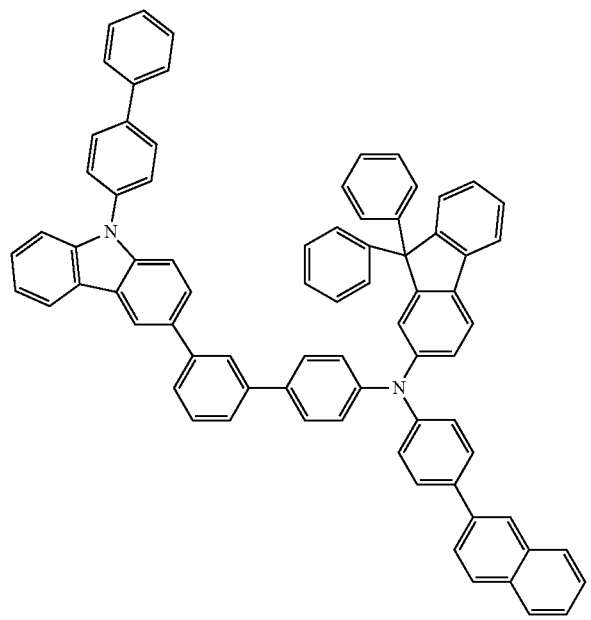
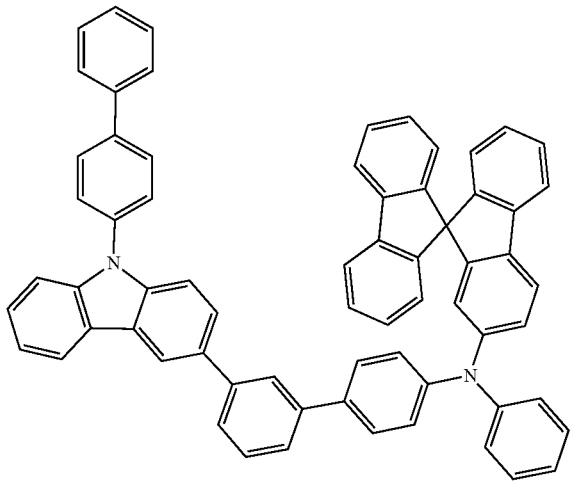

-continued
749
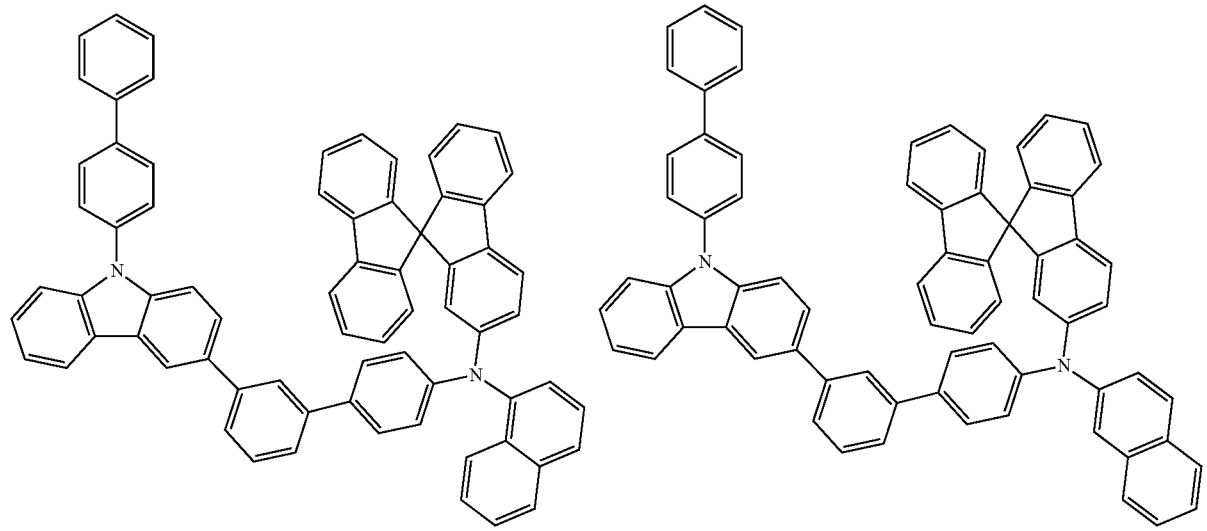
750
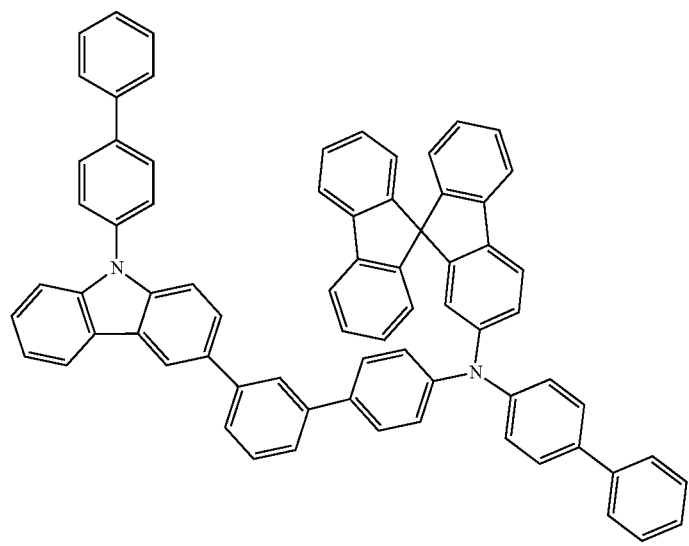
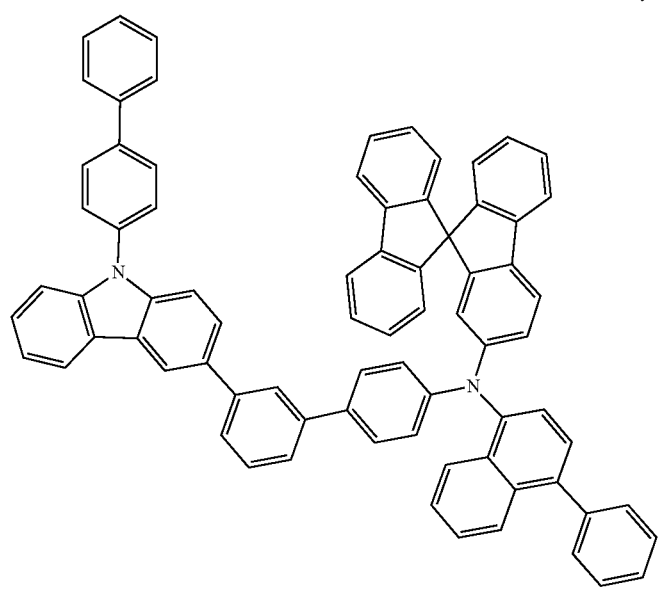

-continued
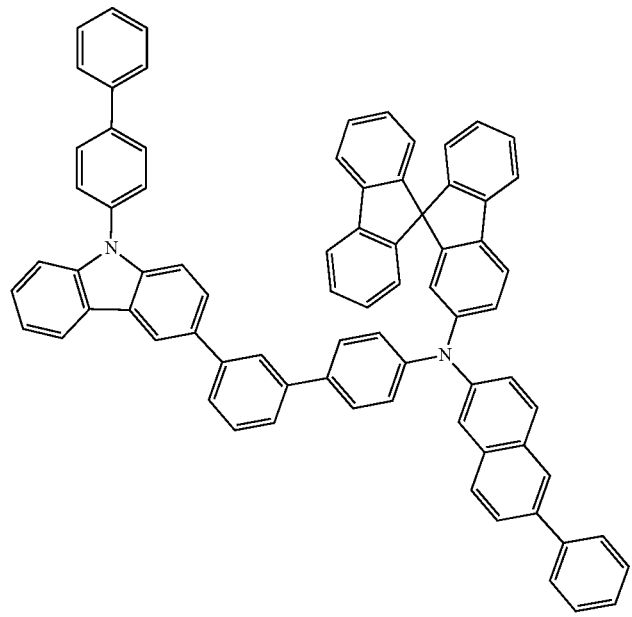
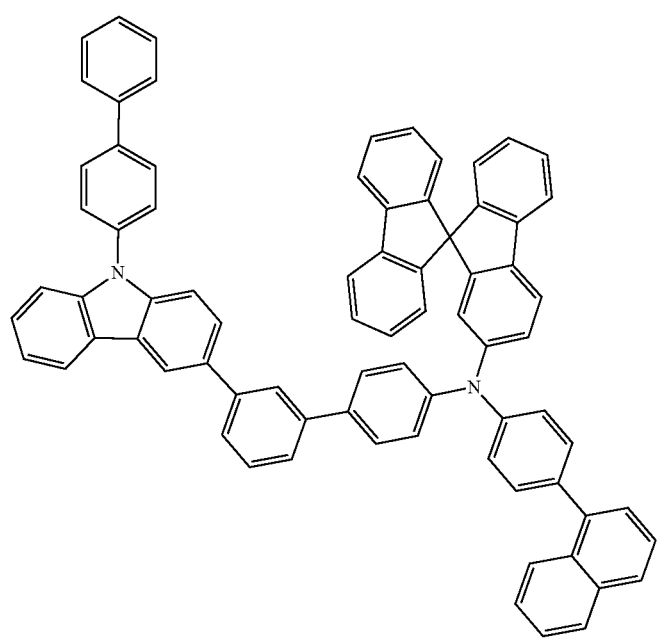

-continued
753
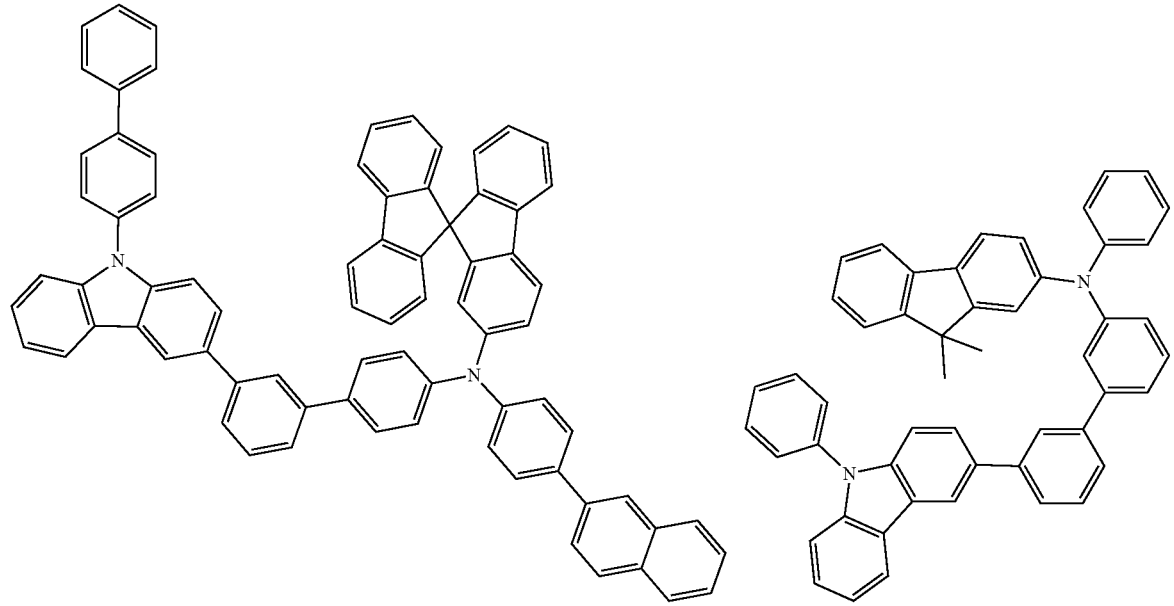
754
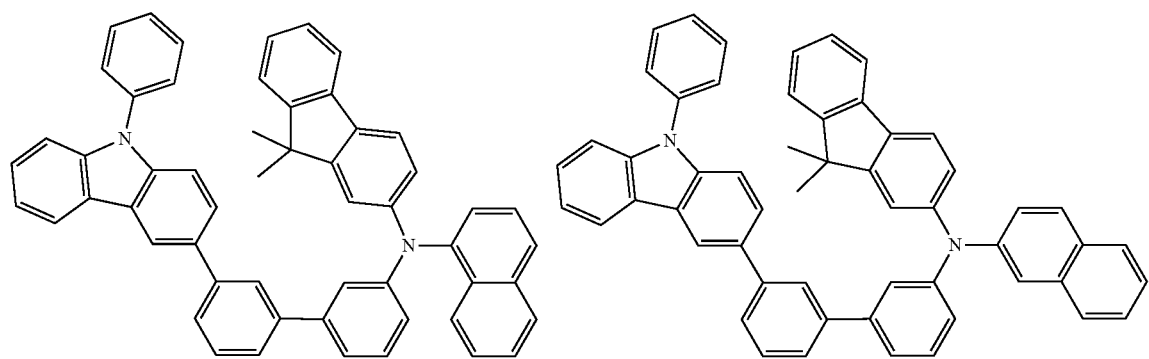
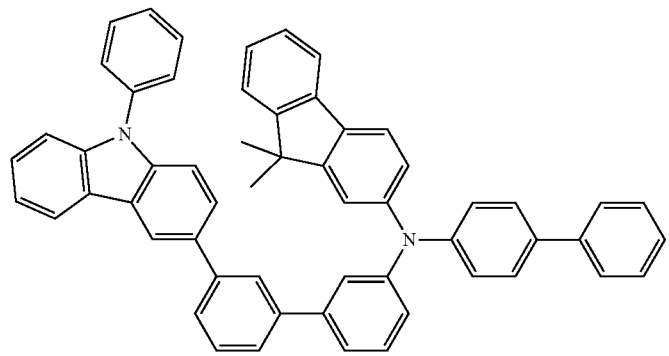
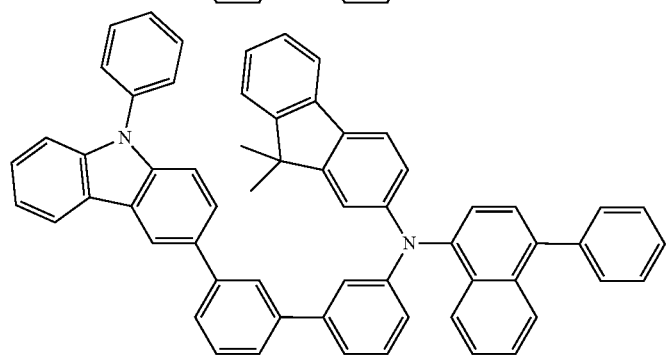

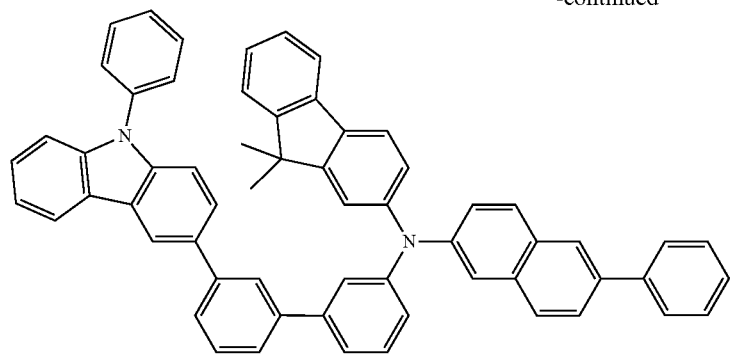
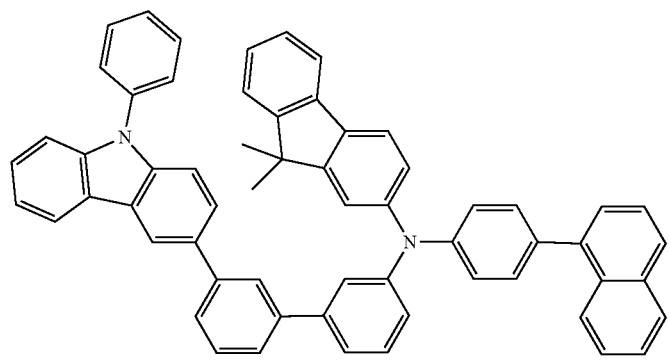
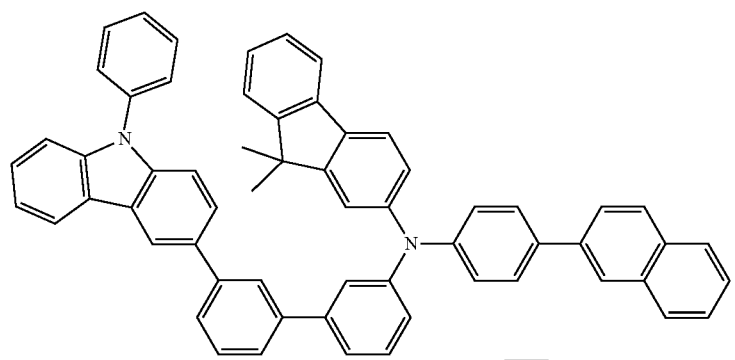
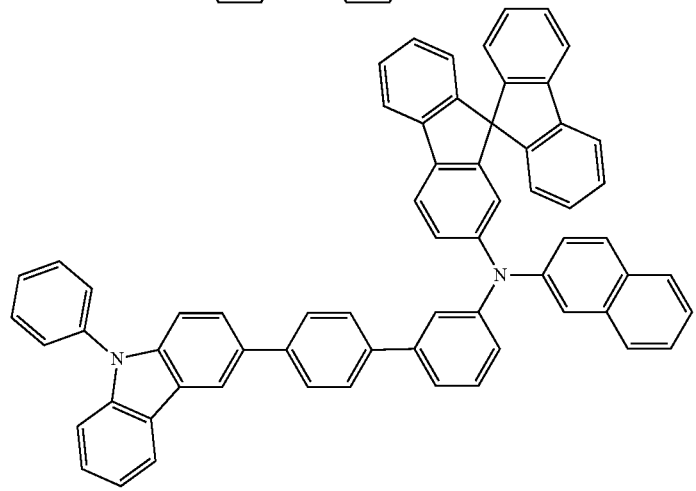

-continued
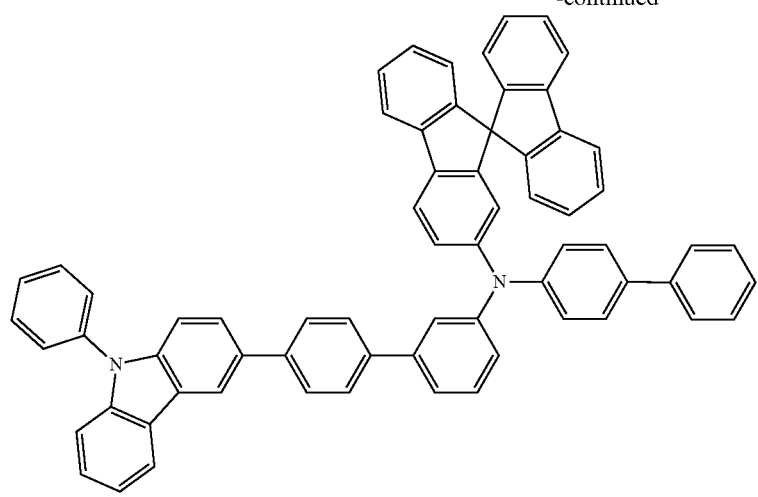
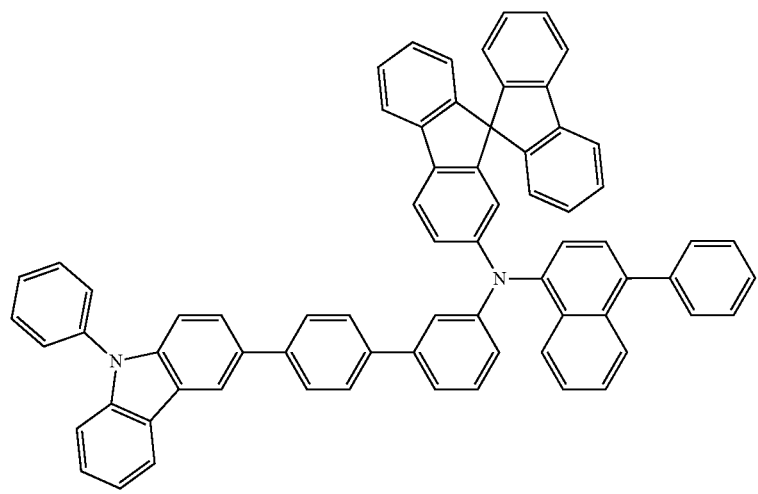
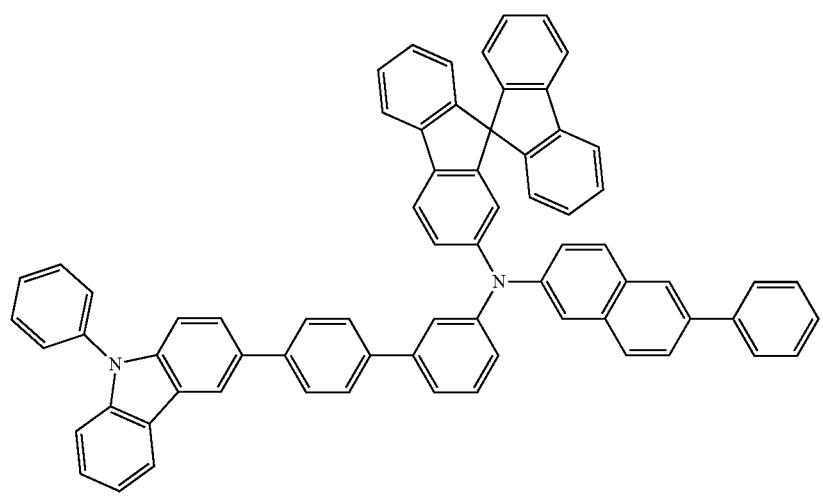

-continued
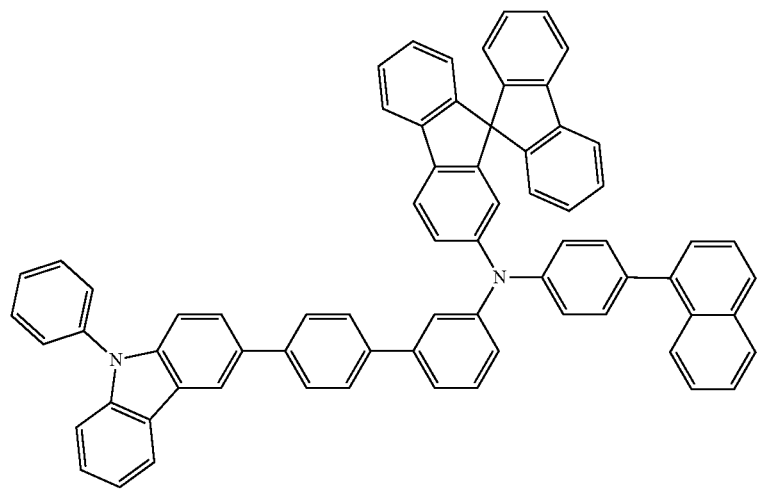
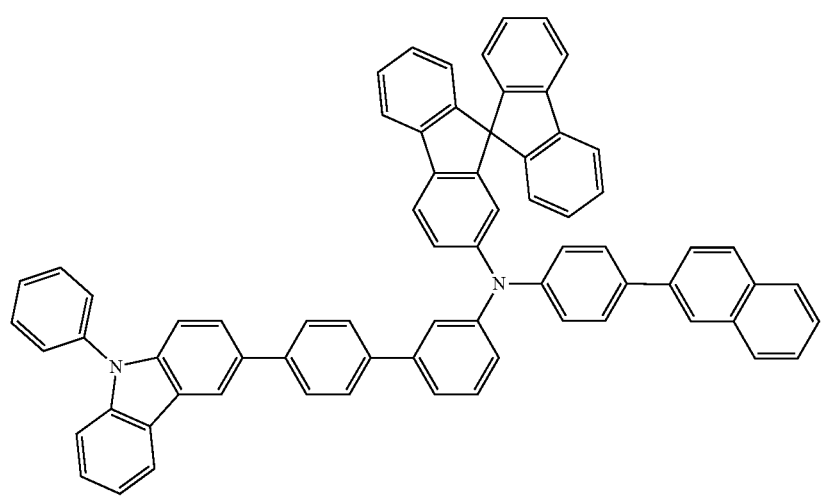
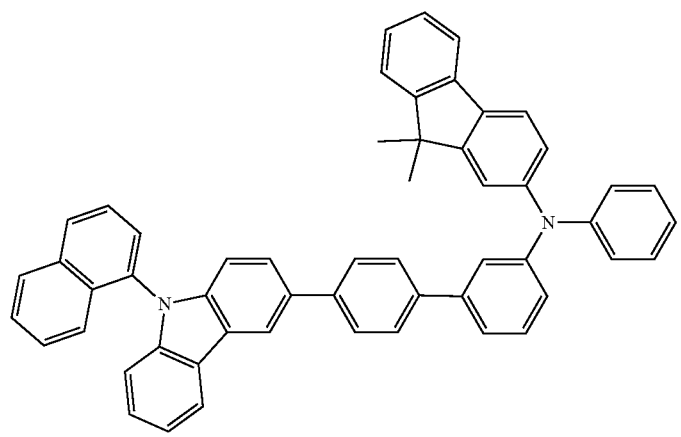

-continued
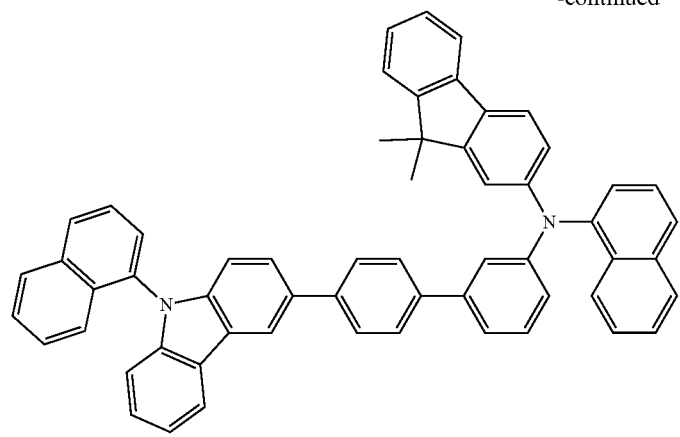
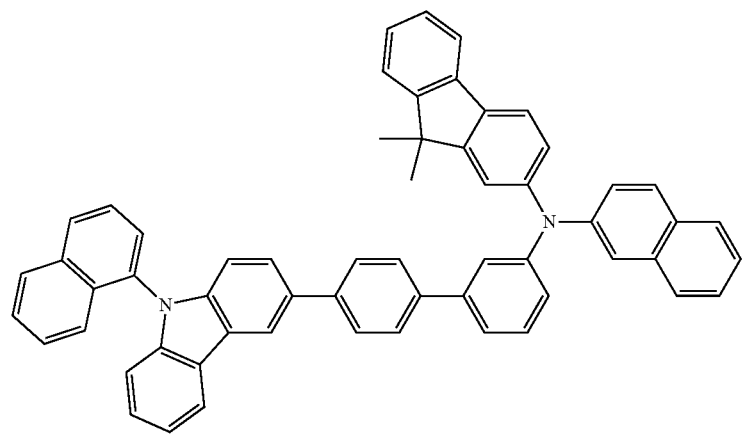
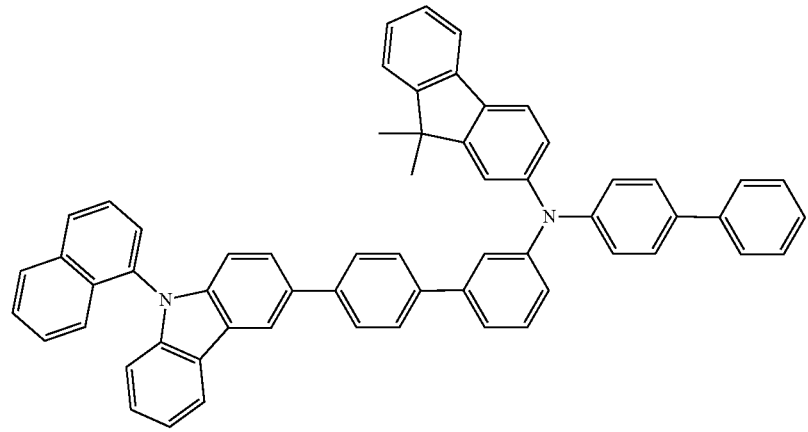
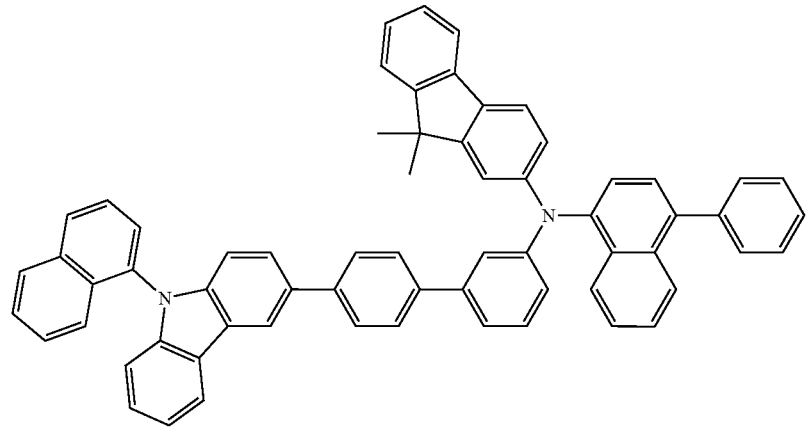

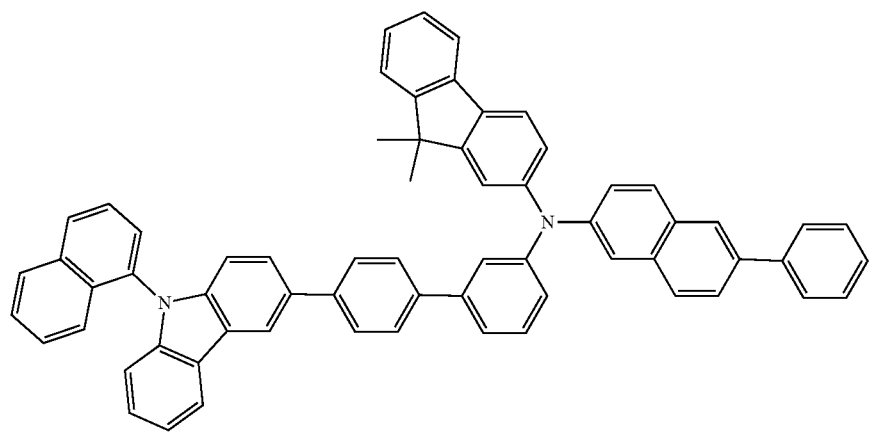
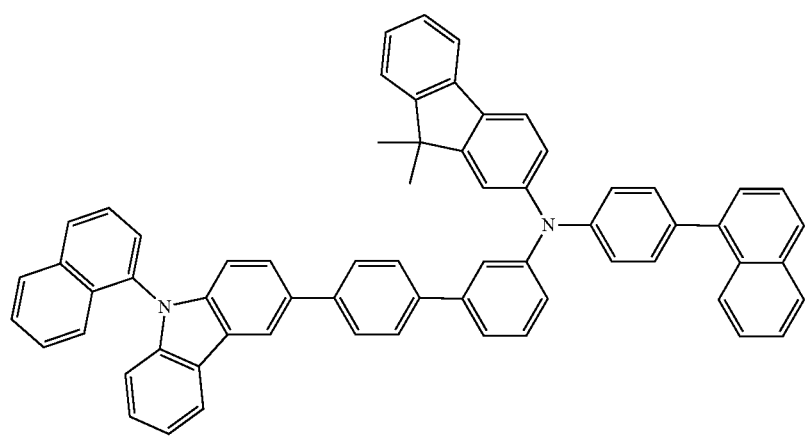
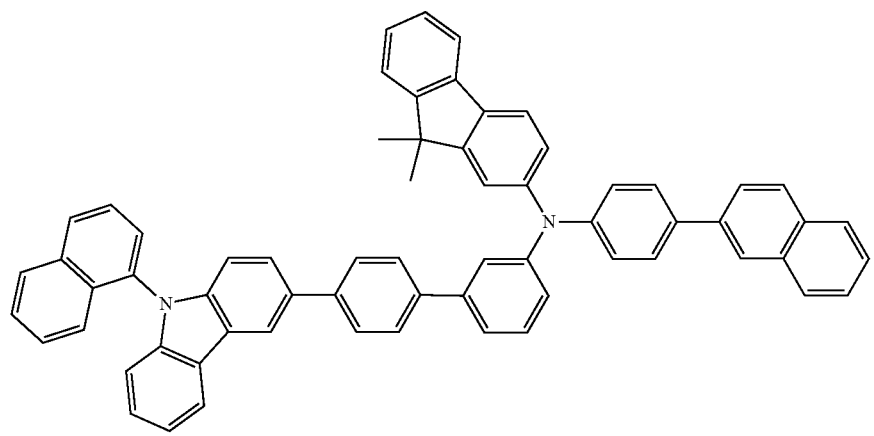

-continued
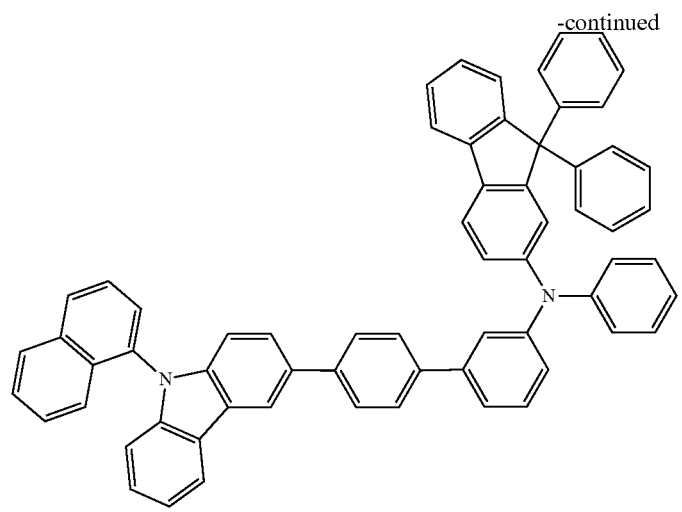
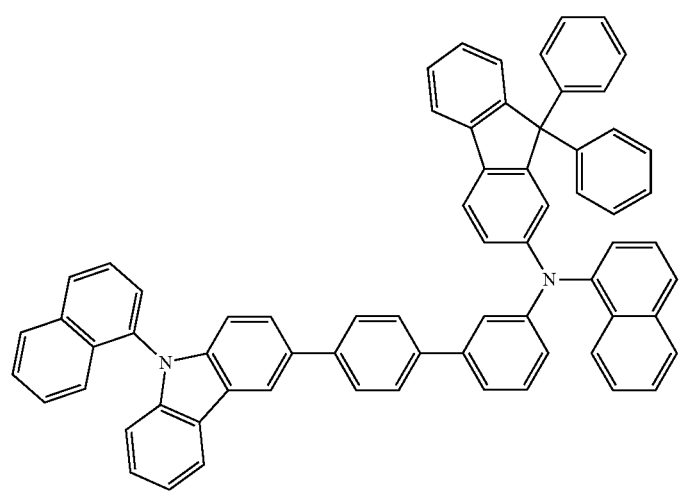
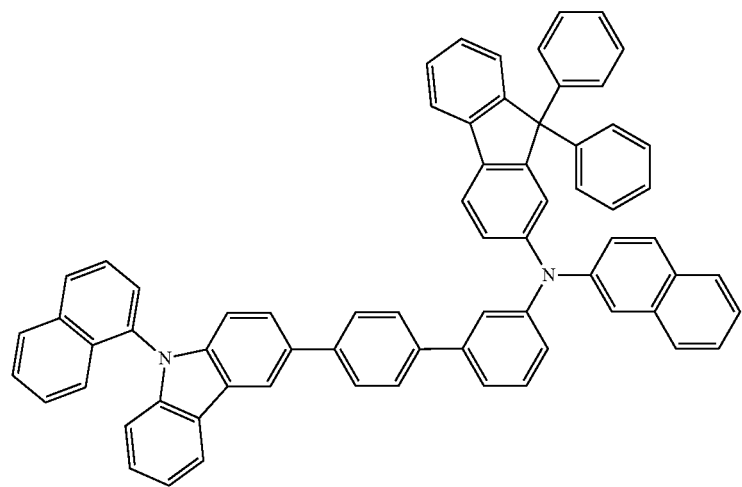

-continued
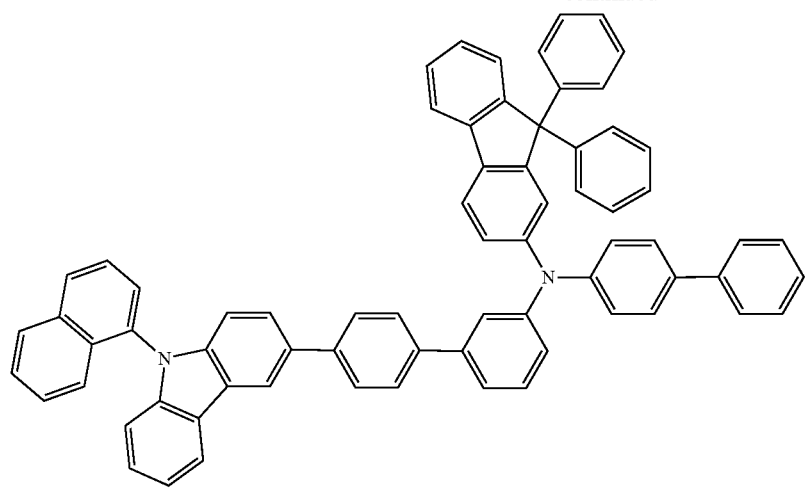
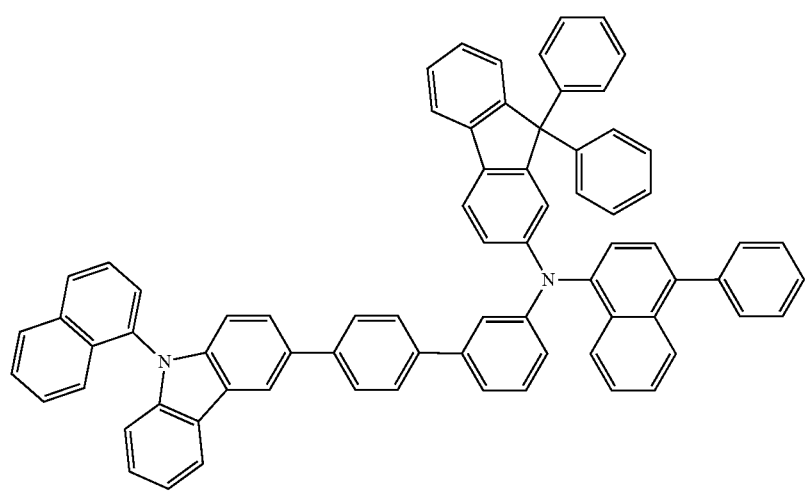
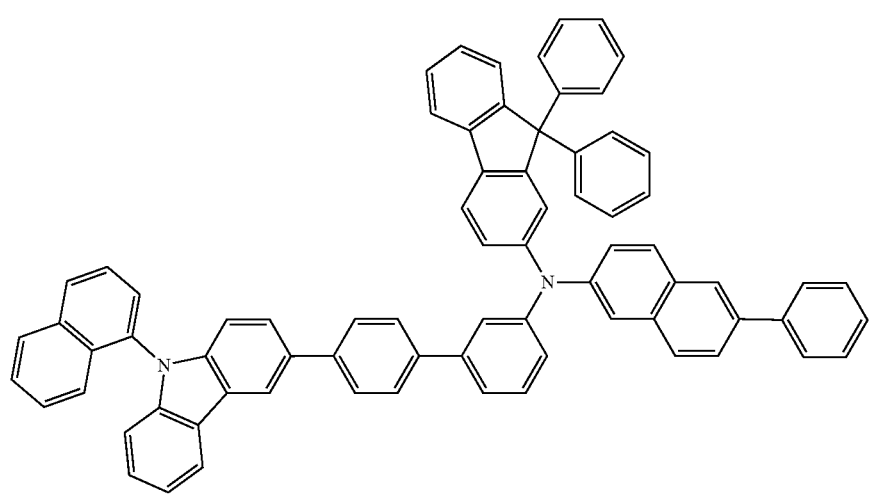

-continued
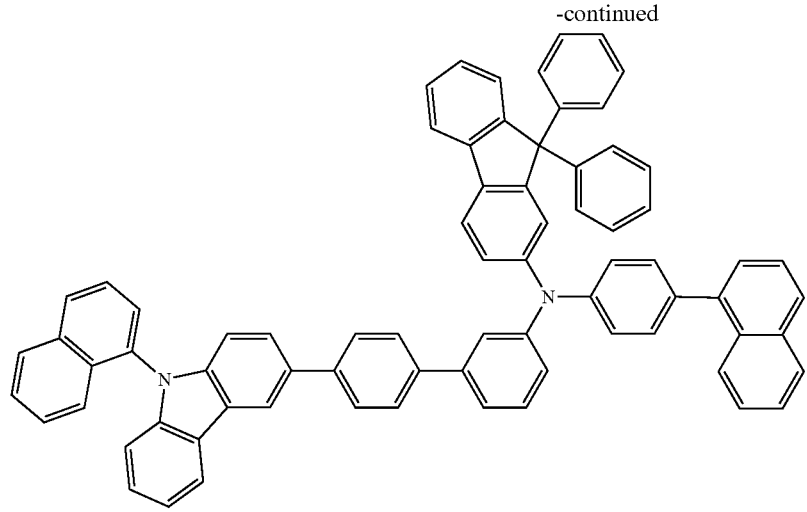
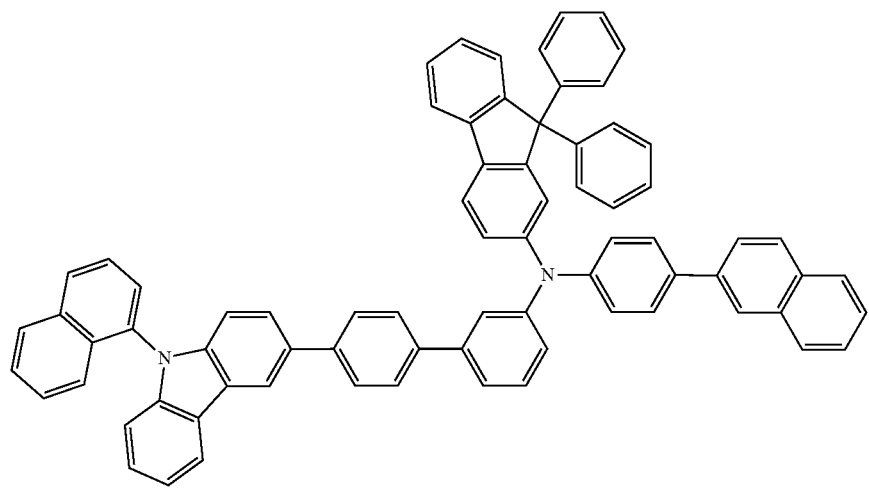
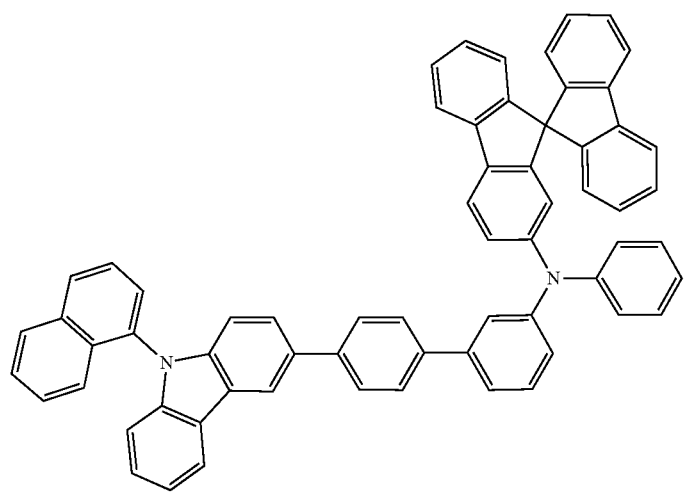

-continued
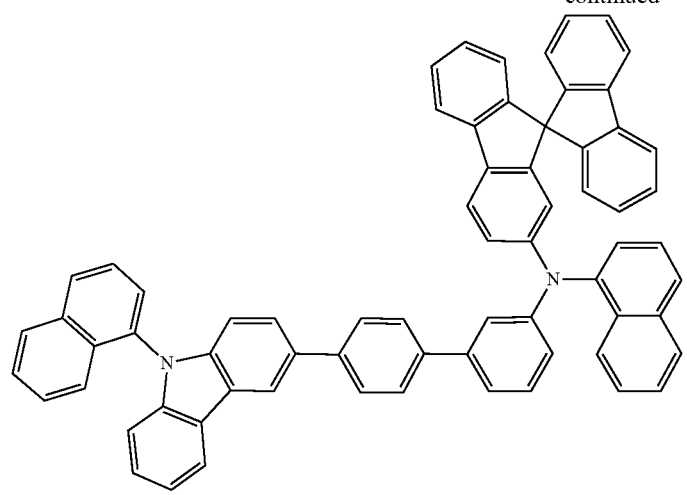
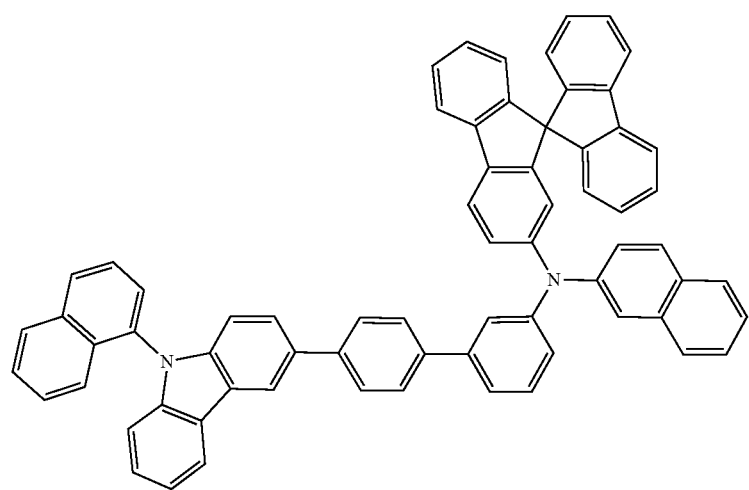
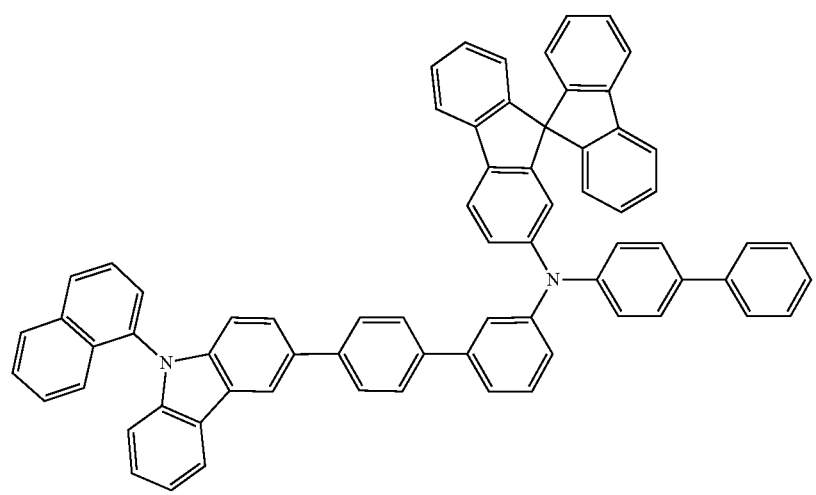

-continued
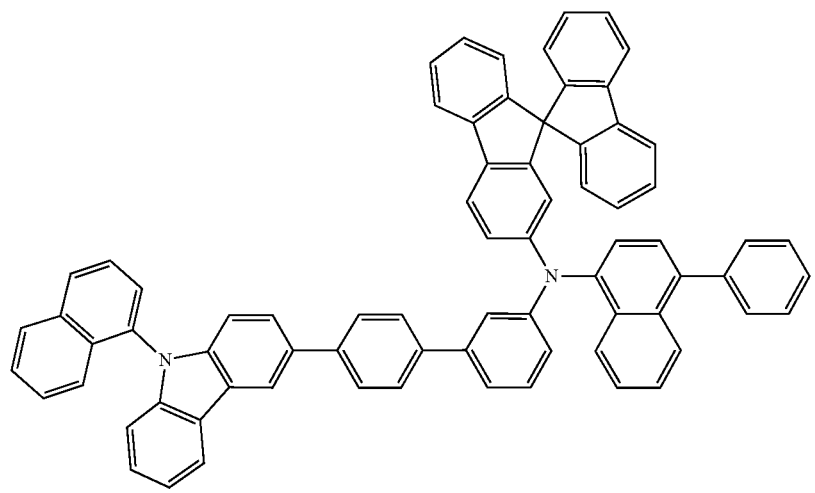
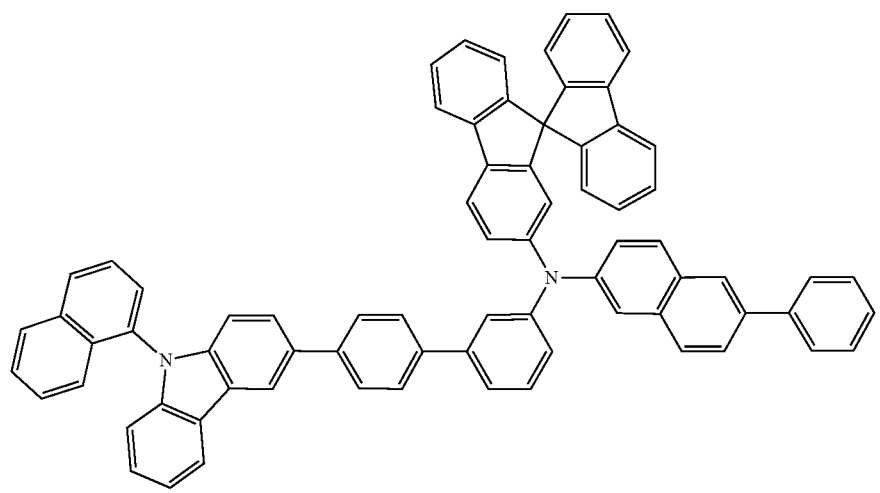
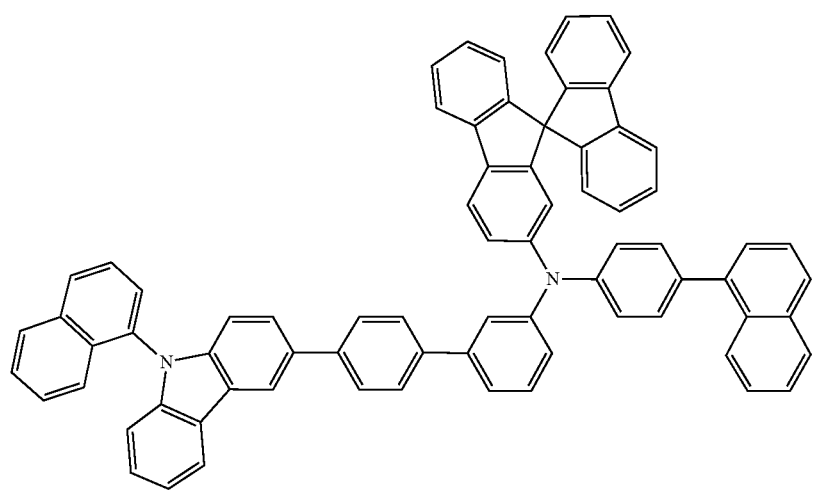

-continued
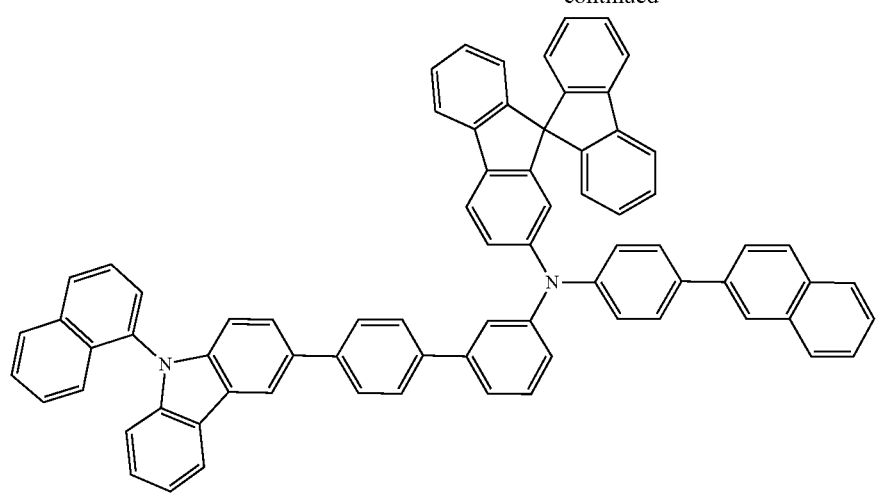
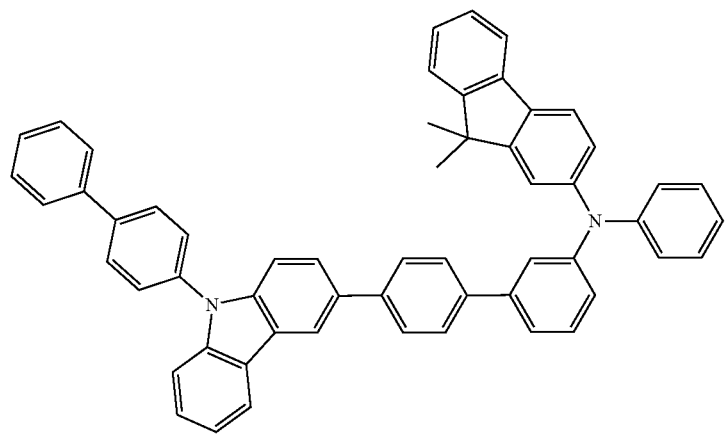
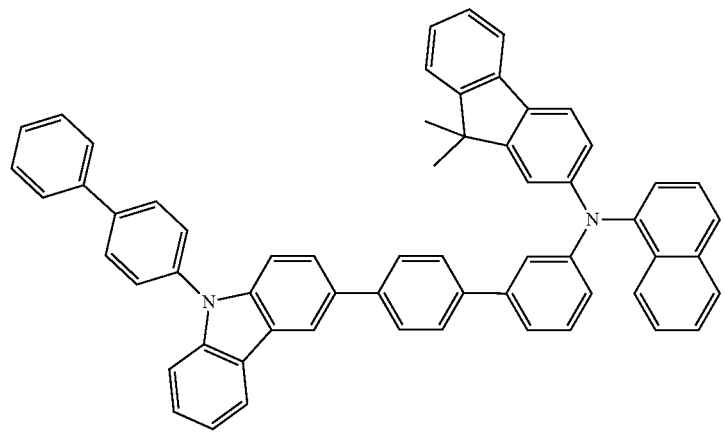

-continued
777
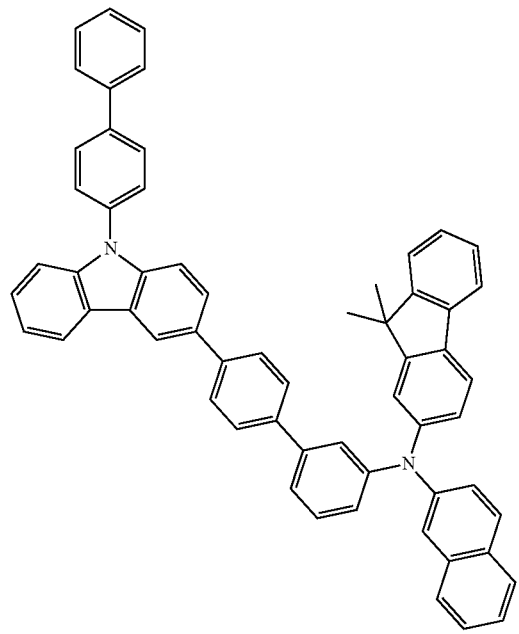
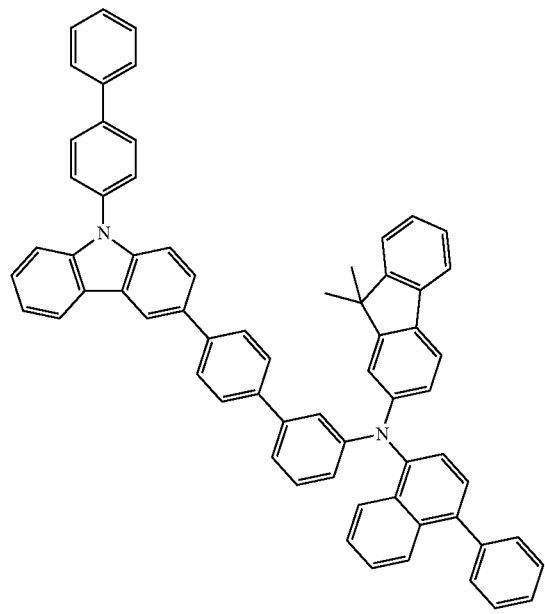
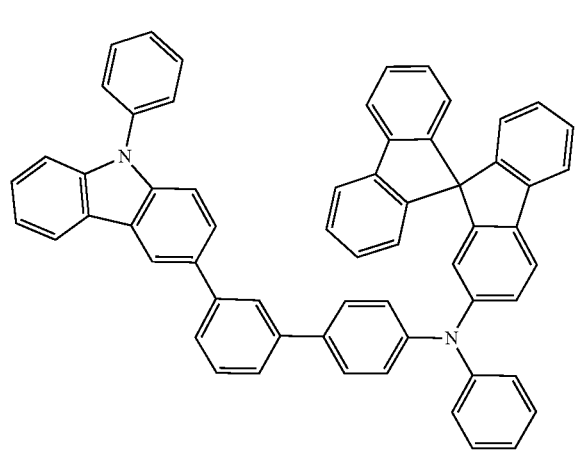
778
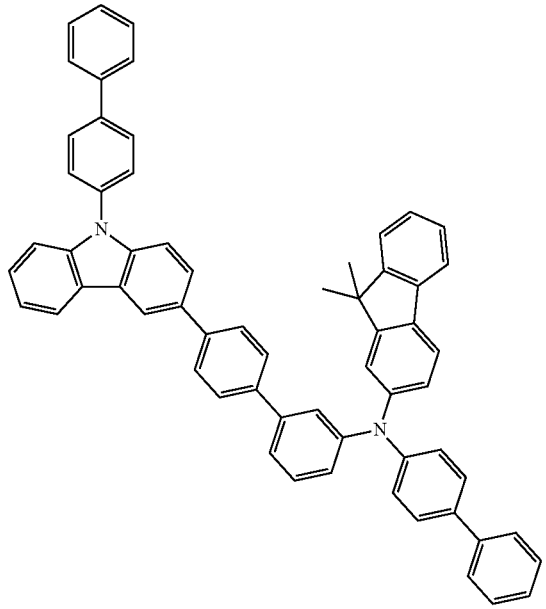
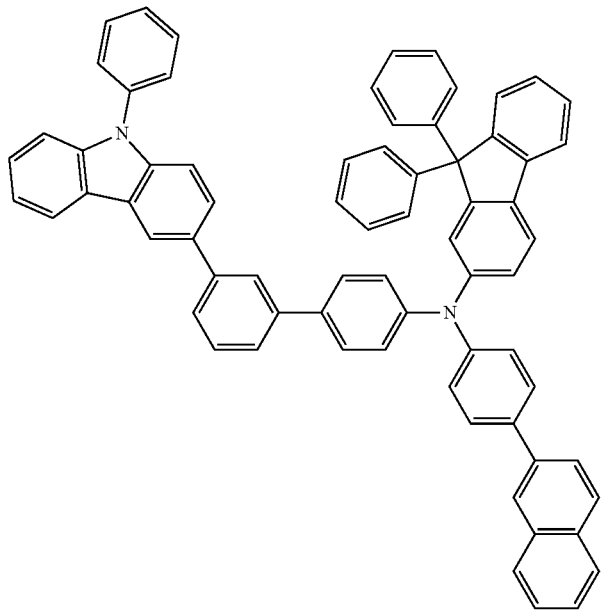
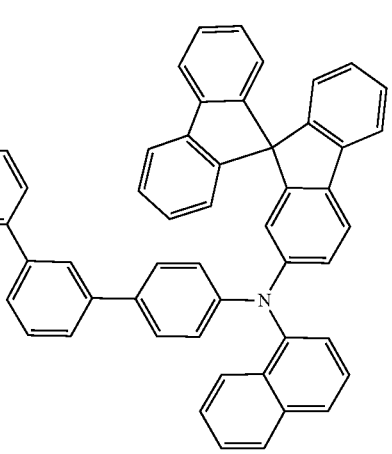

-continued
779
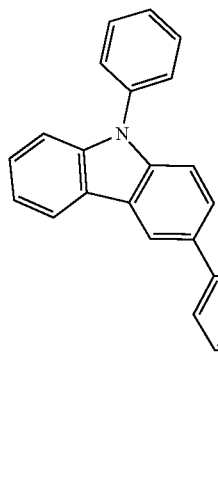
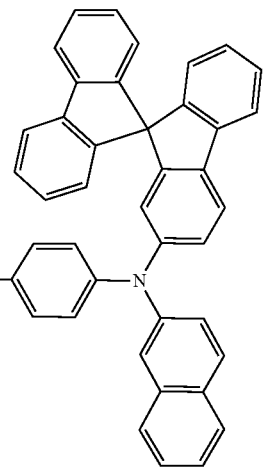
780
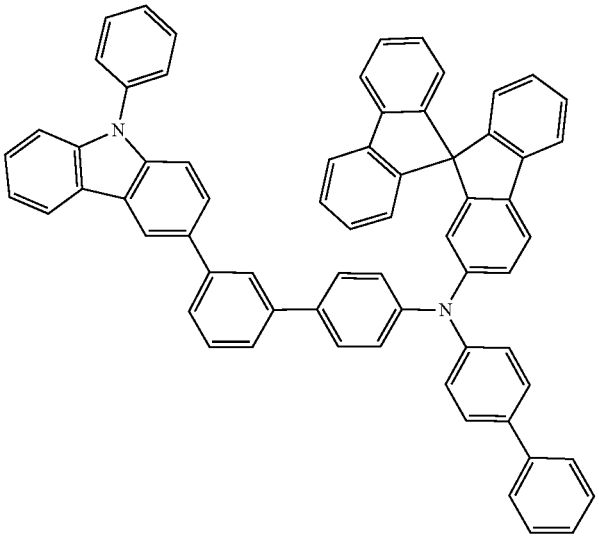
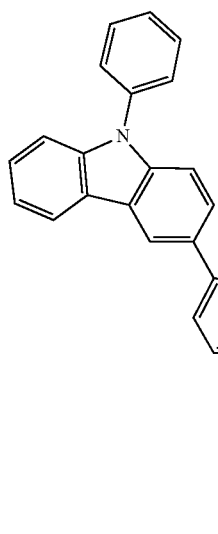
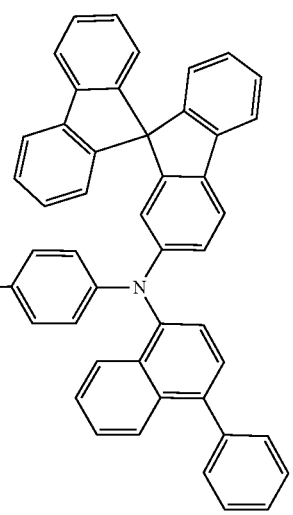
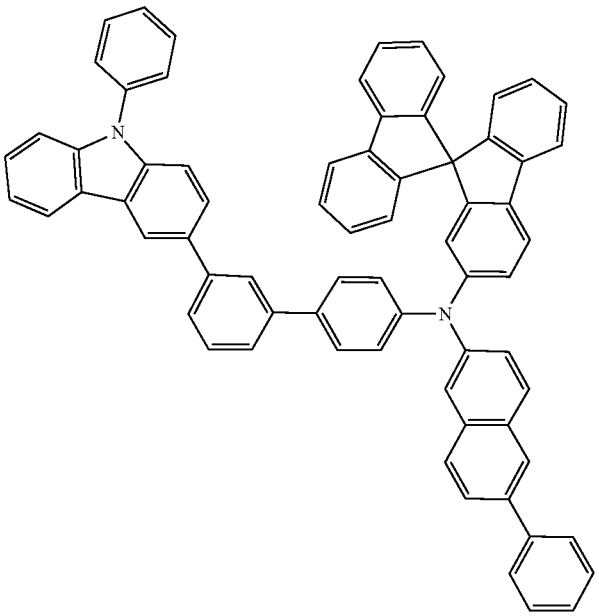
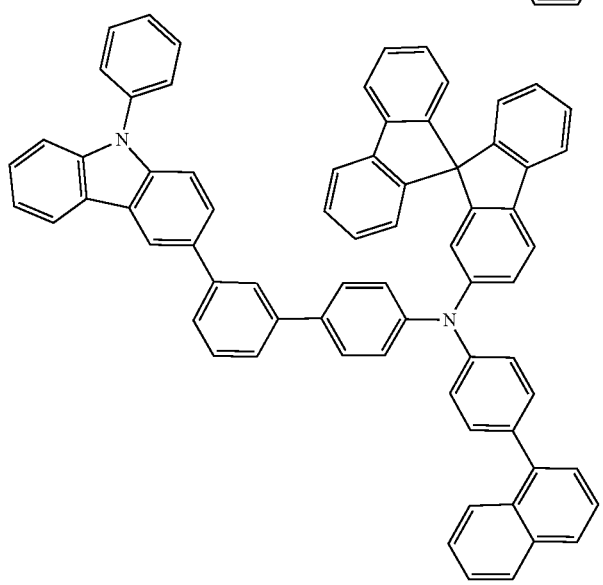

781
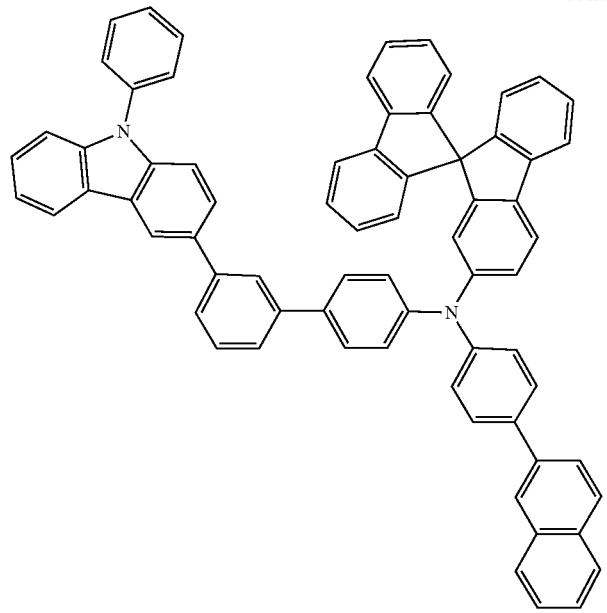
782
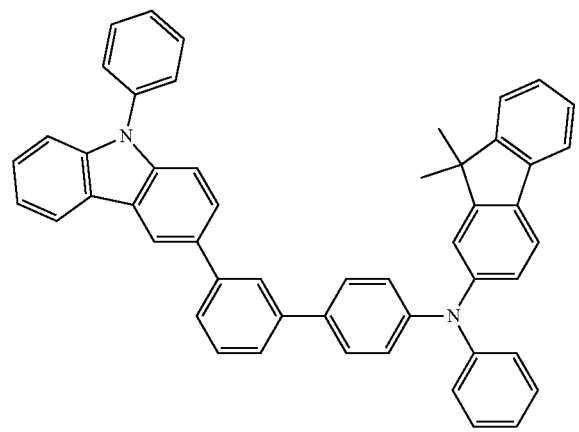
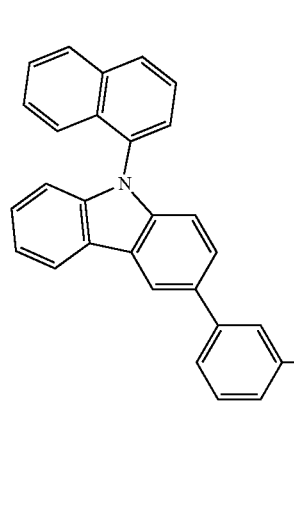
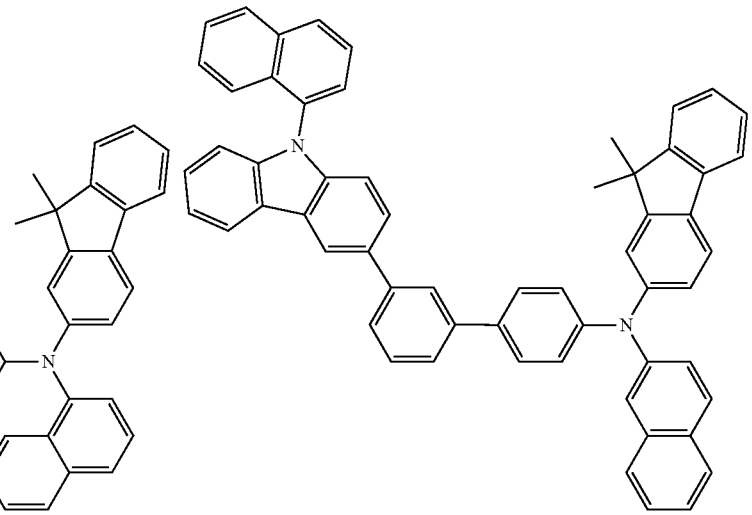
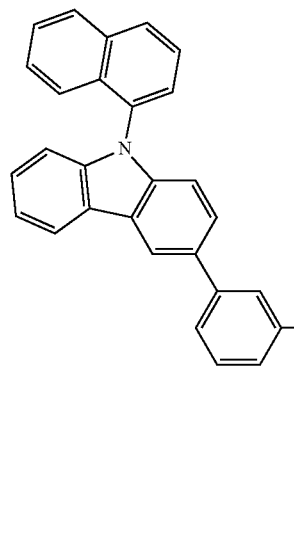
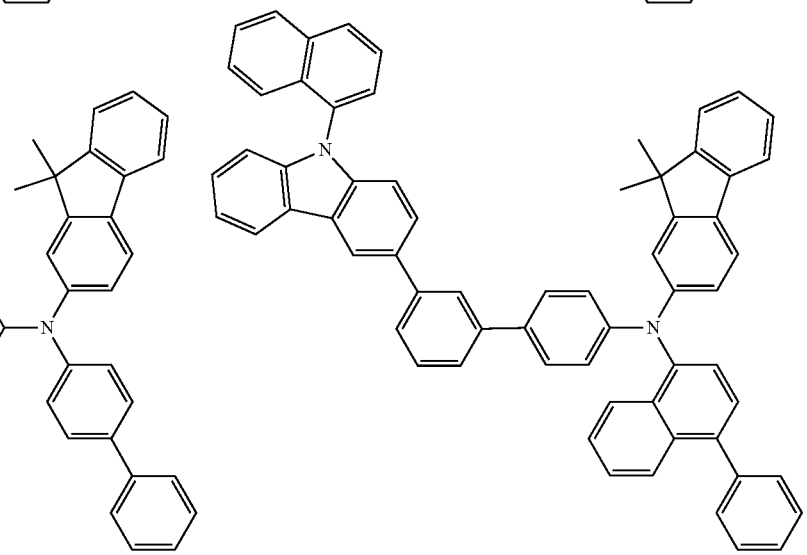

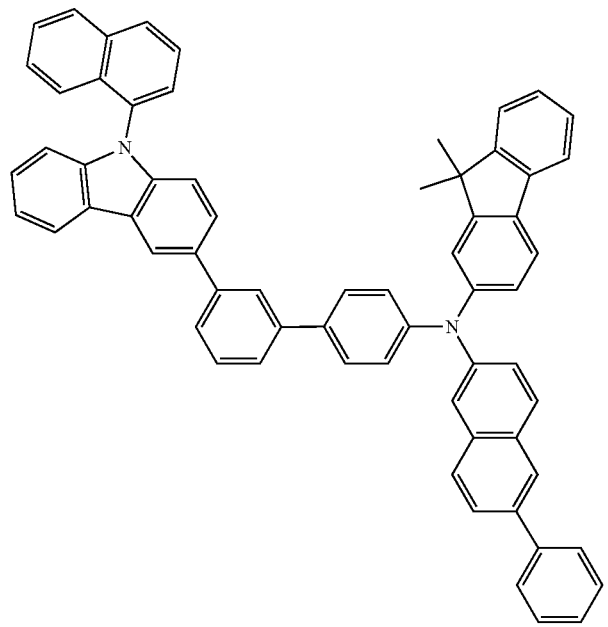
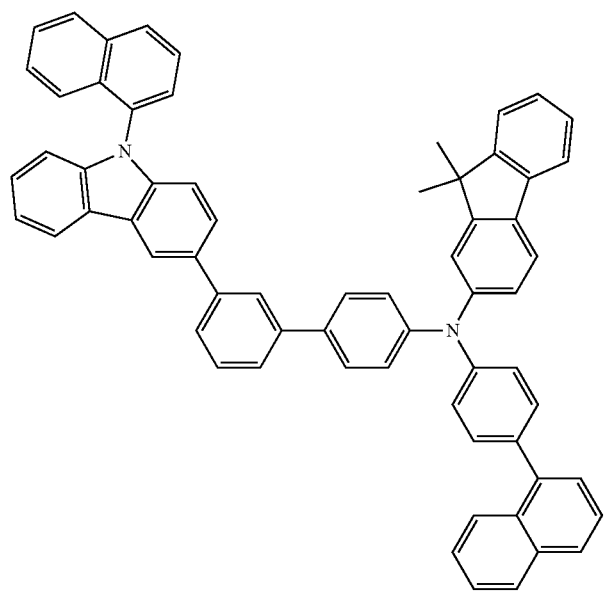

785 786
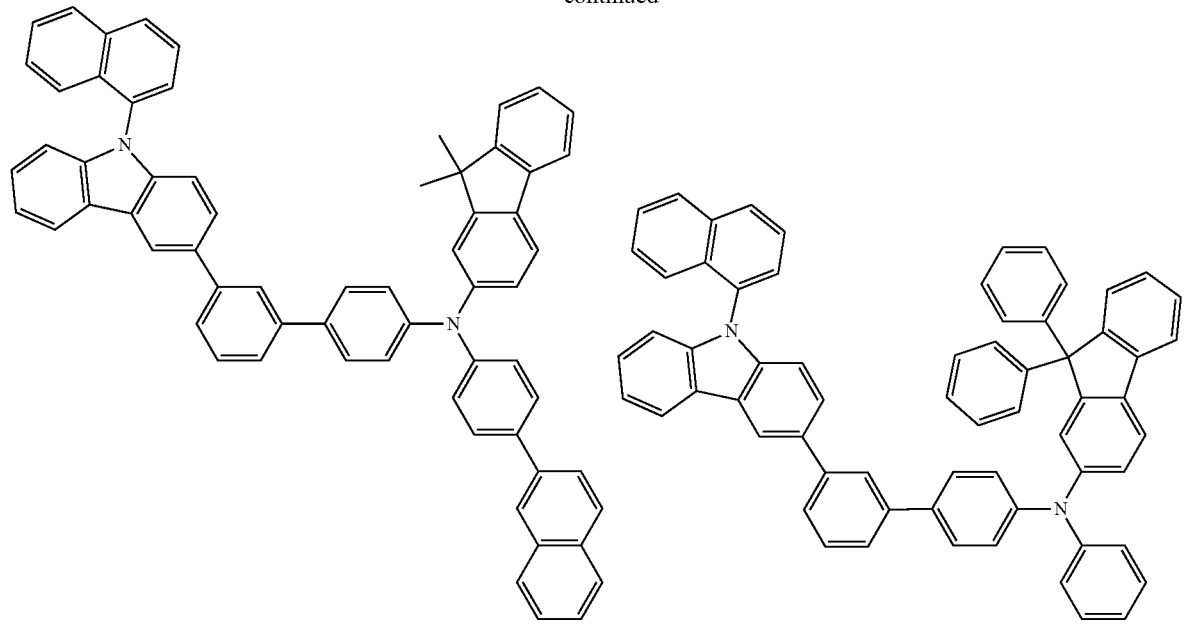
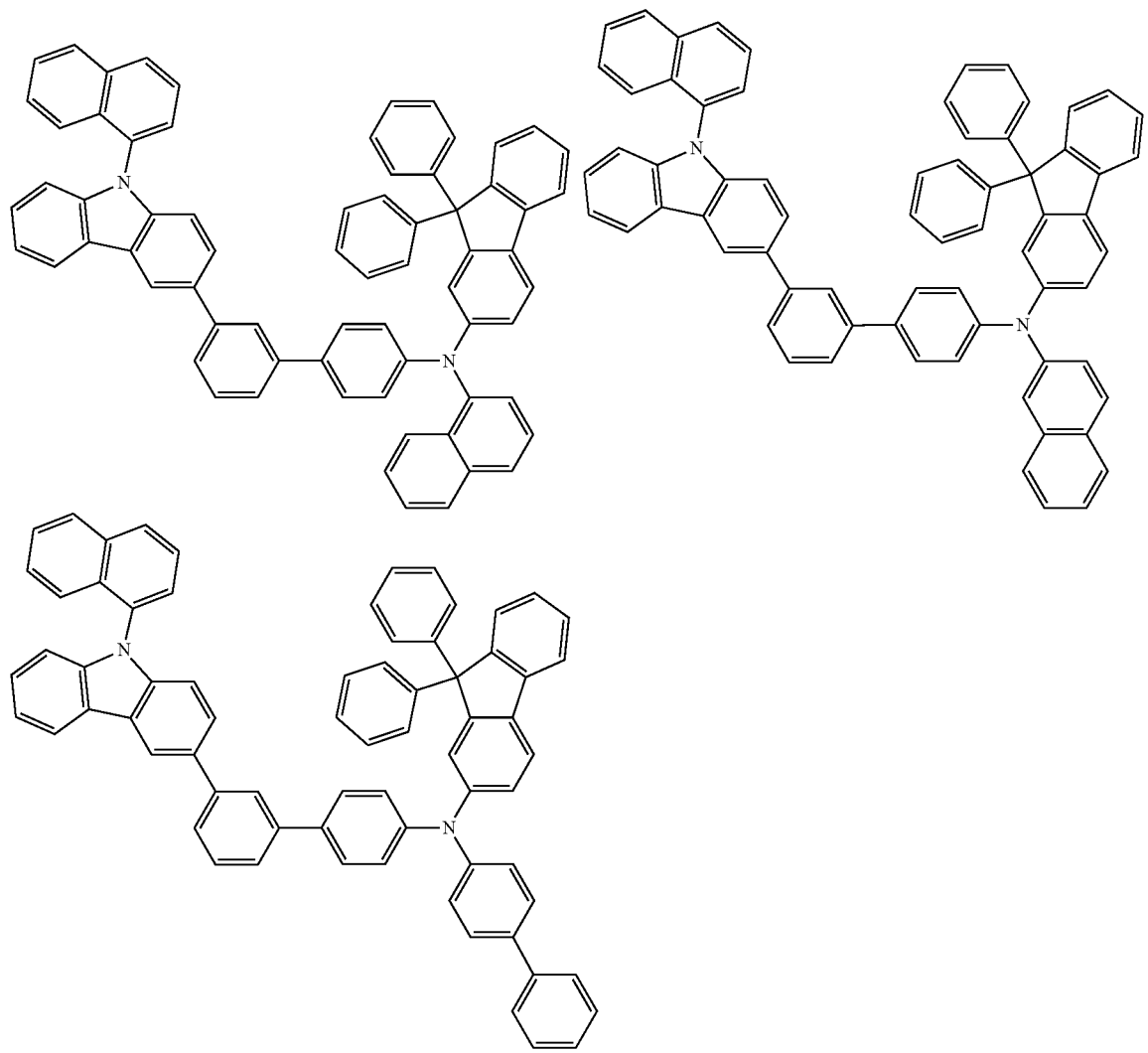

787
788
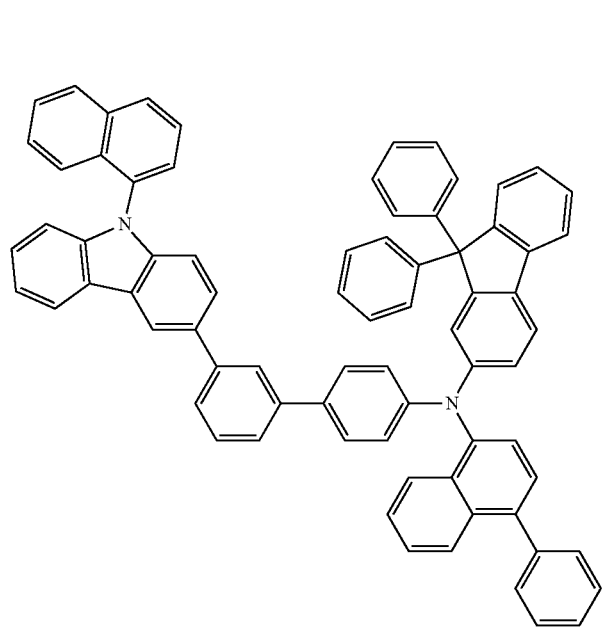
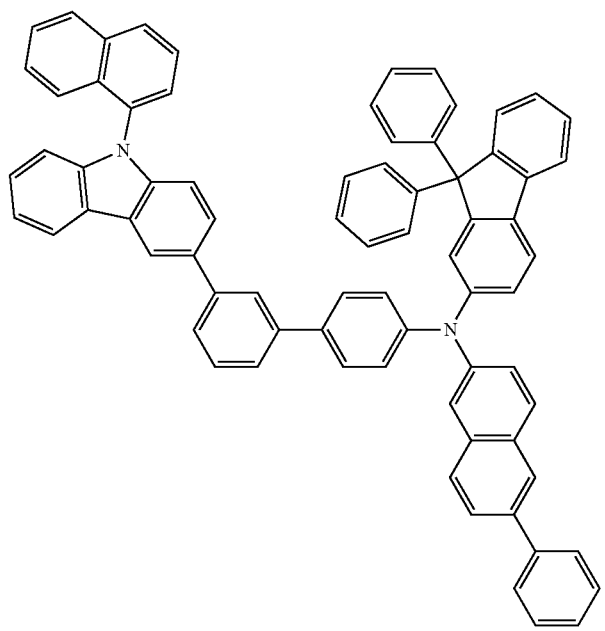
-continued
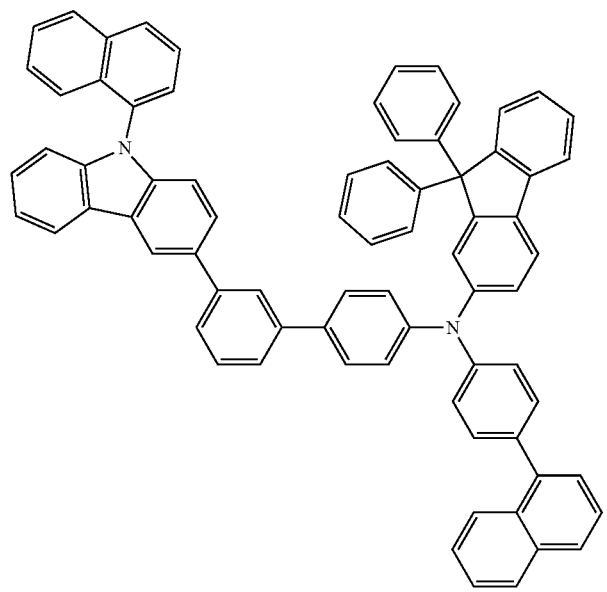

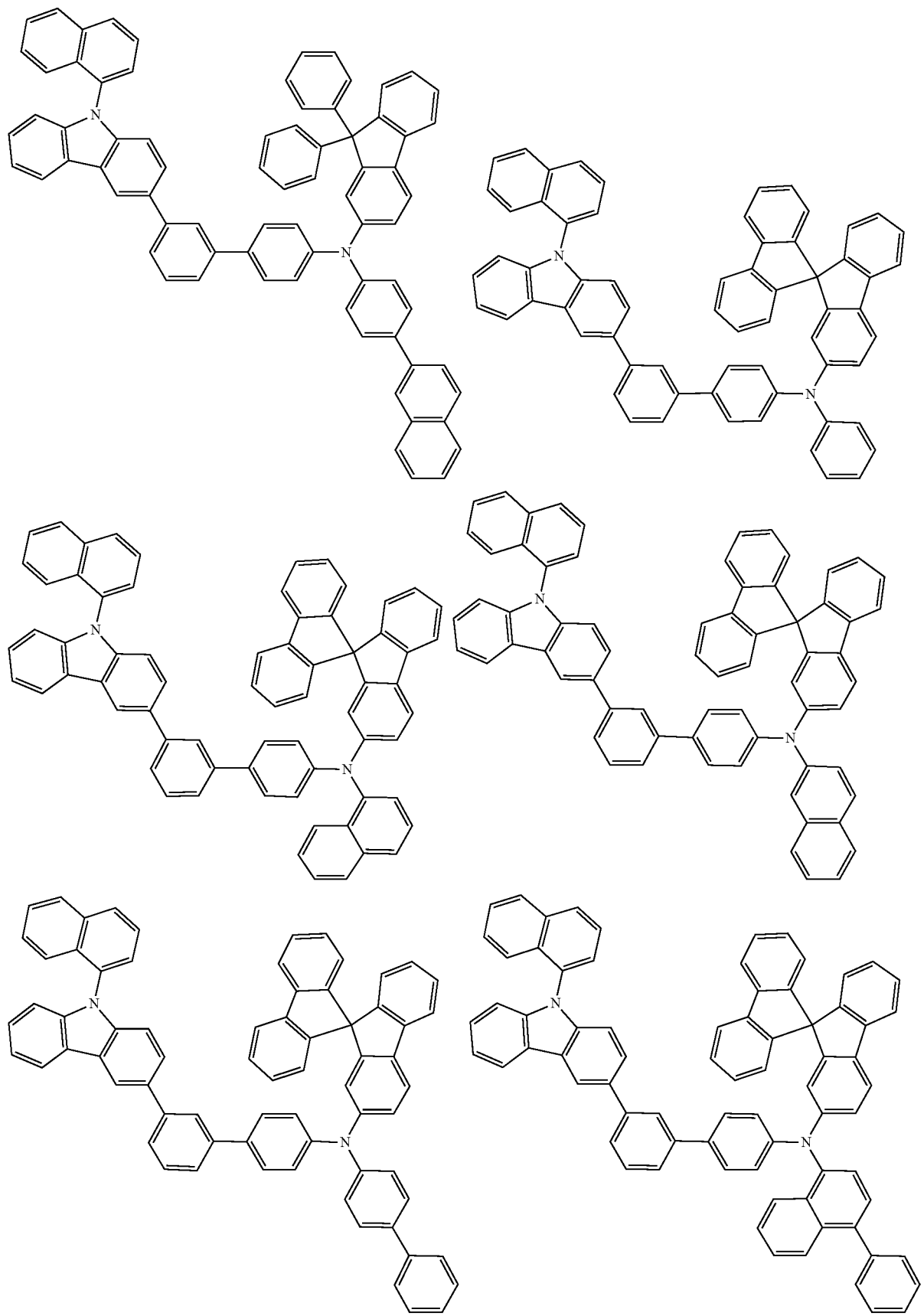

-continued
791
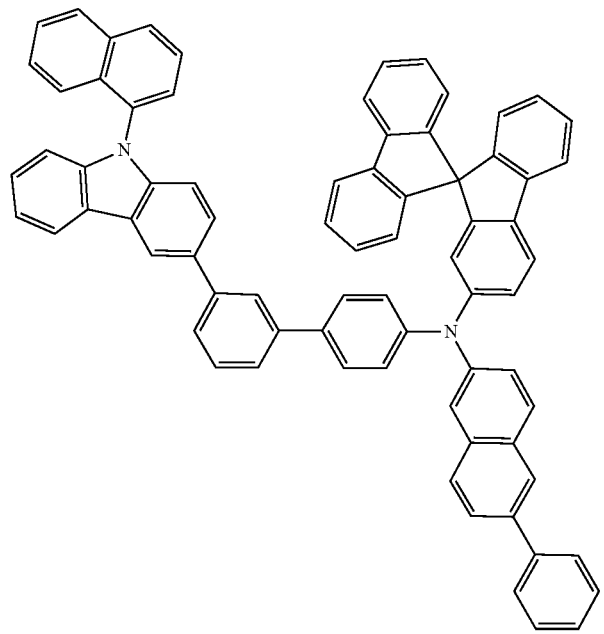
792
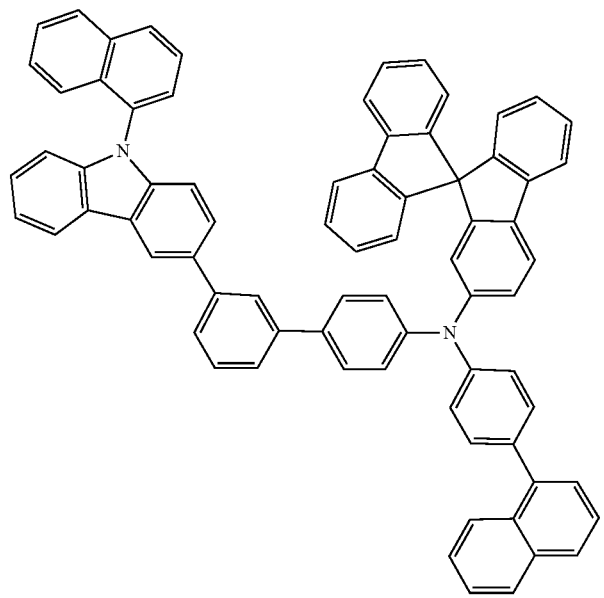
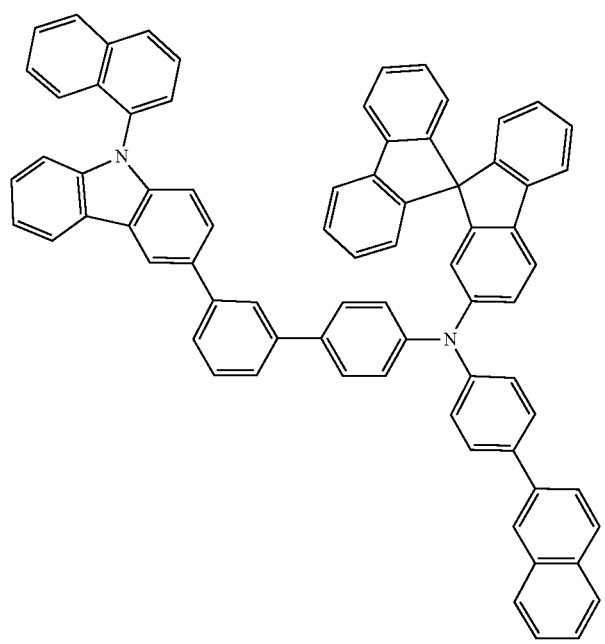
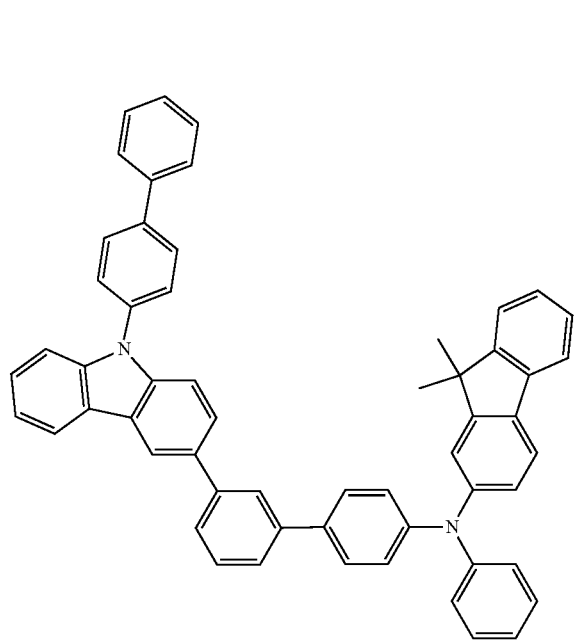

793 794
-continued
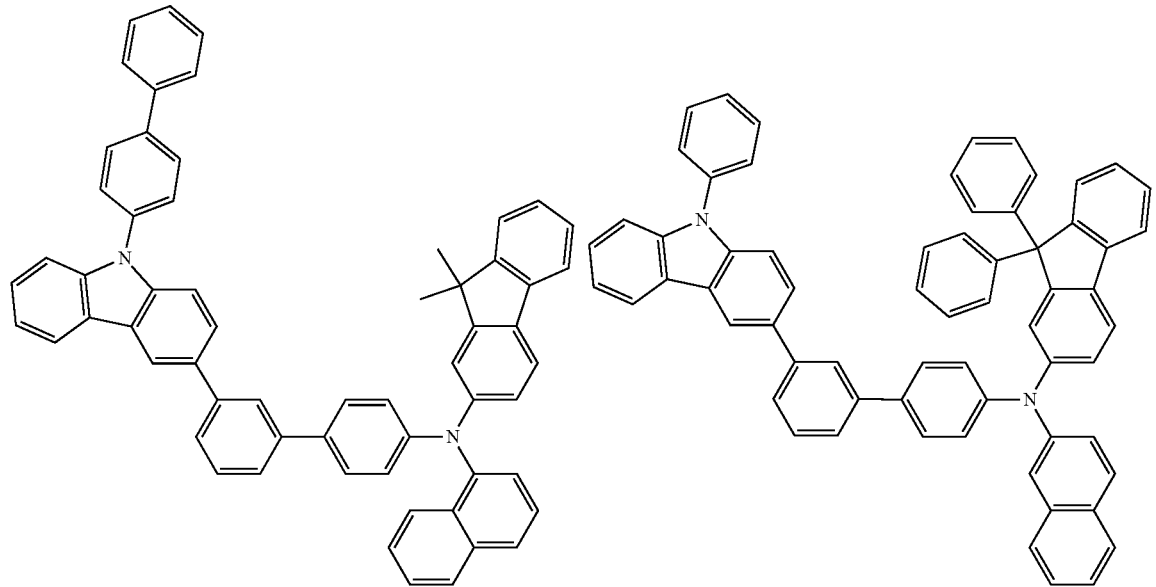
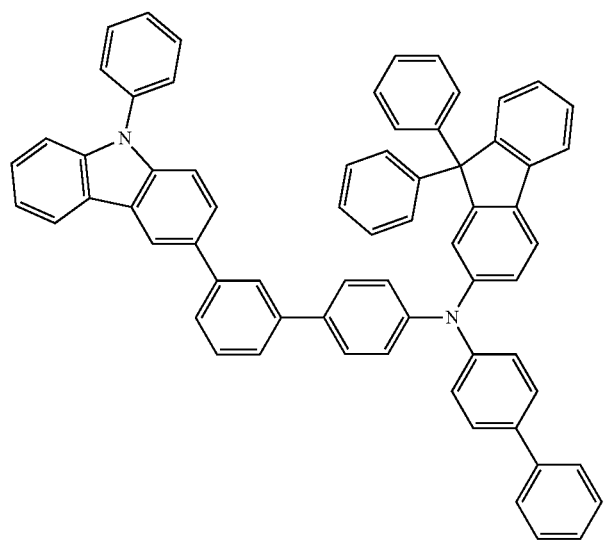
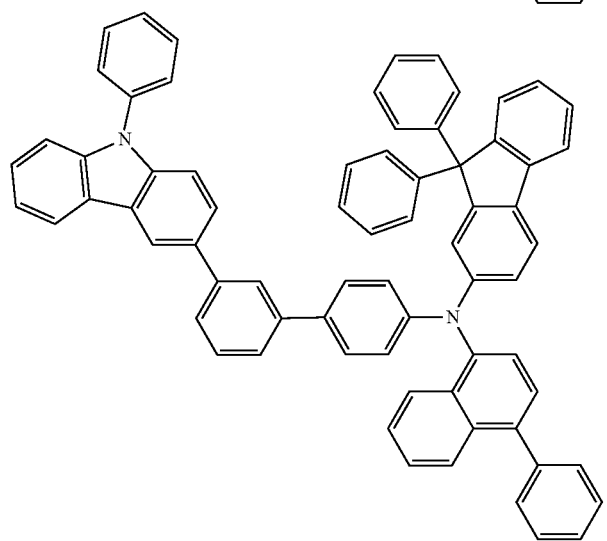

-continued
795
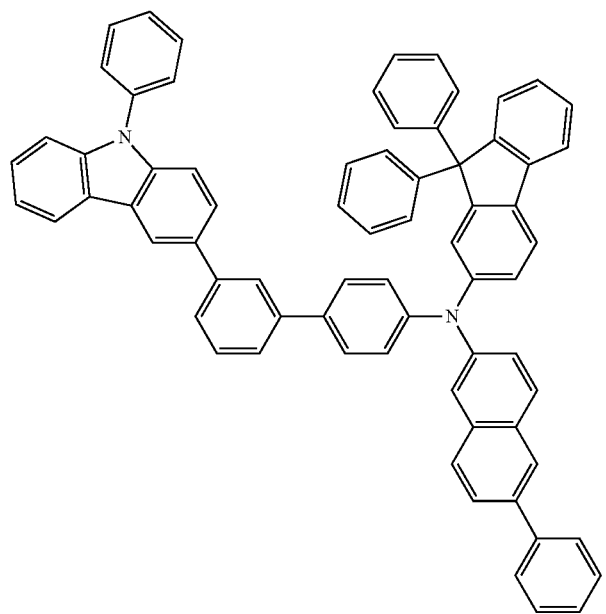
796
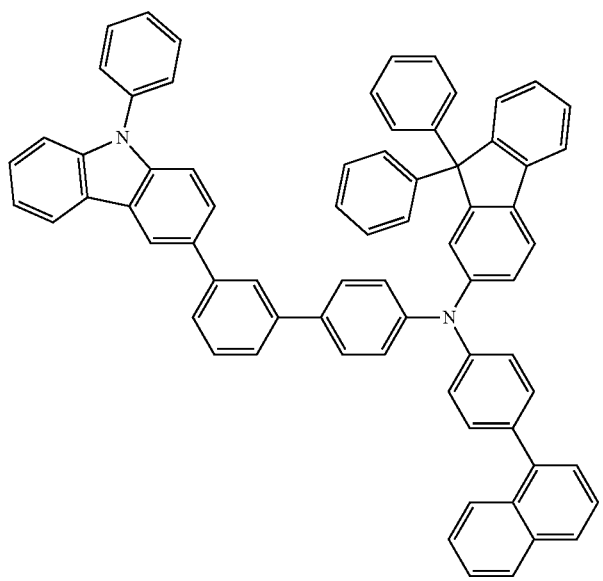
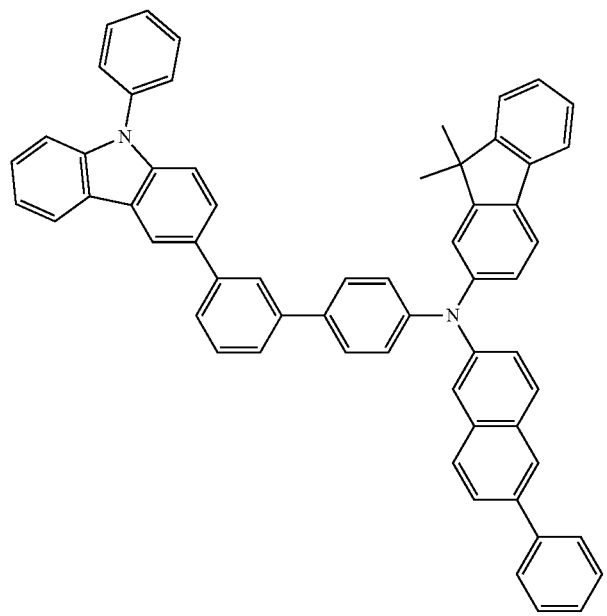
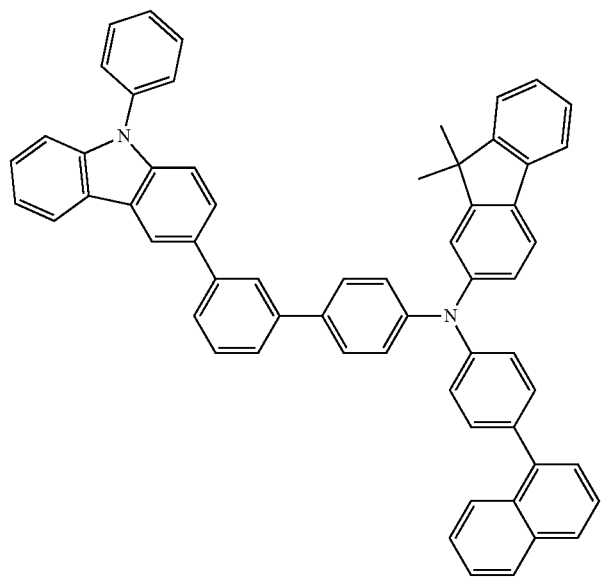

797 798
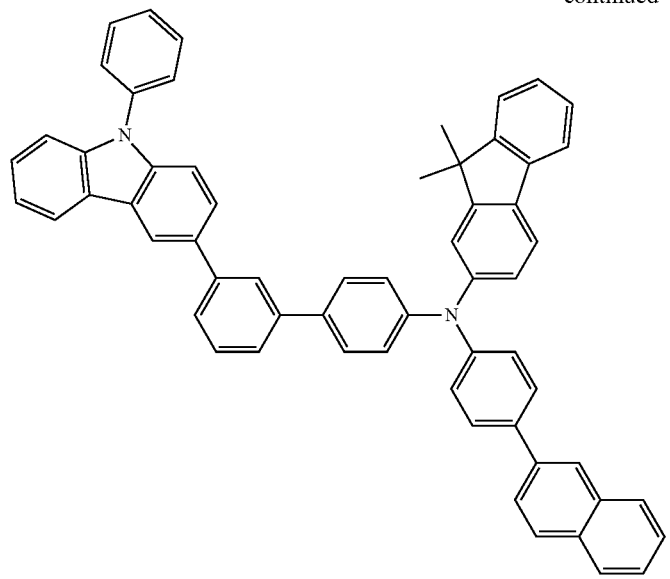
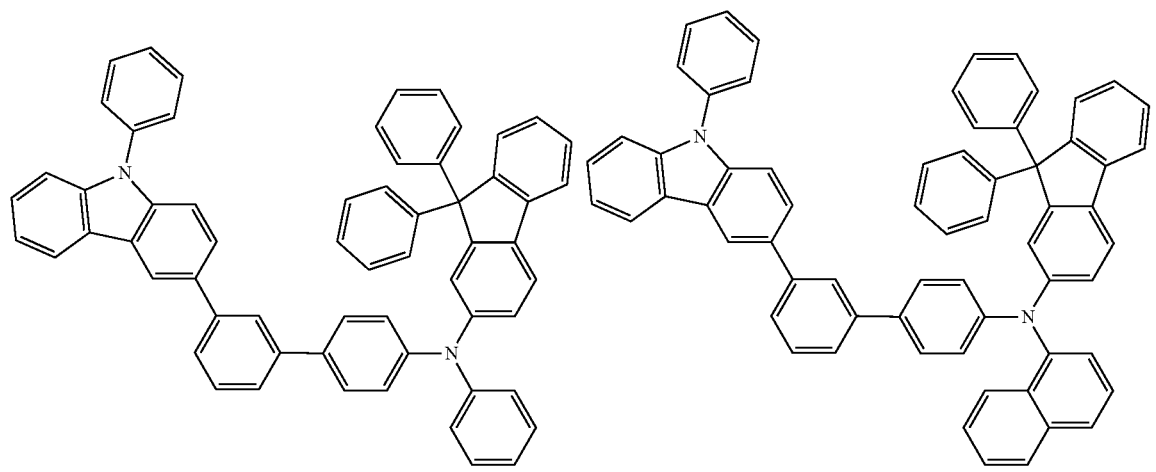
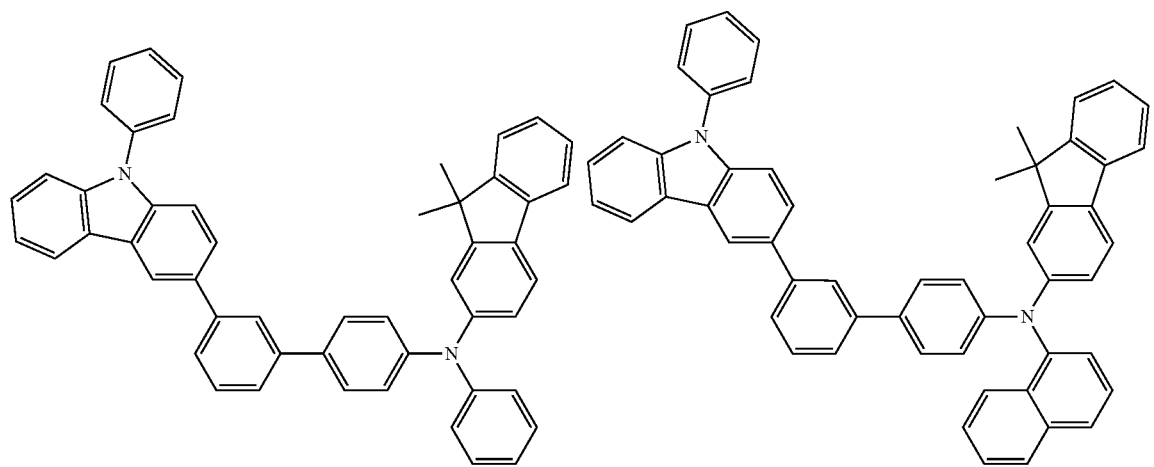

-continued
799
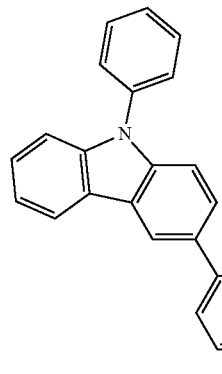
800
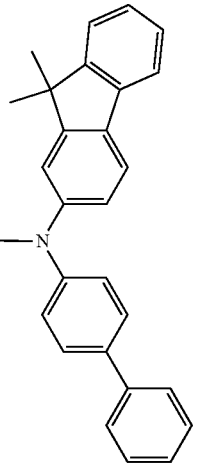
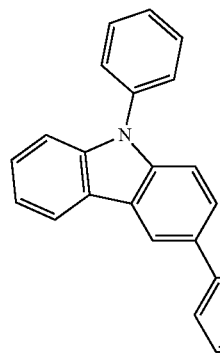
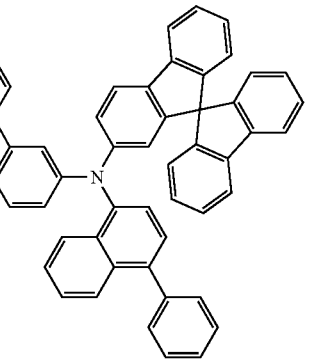
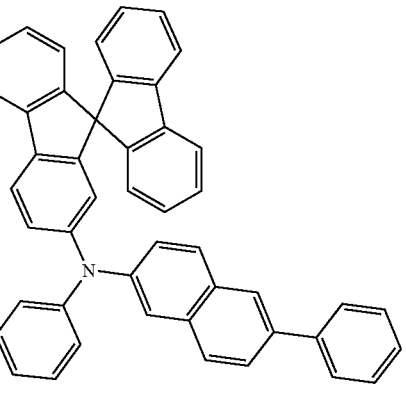

-continued
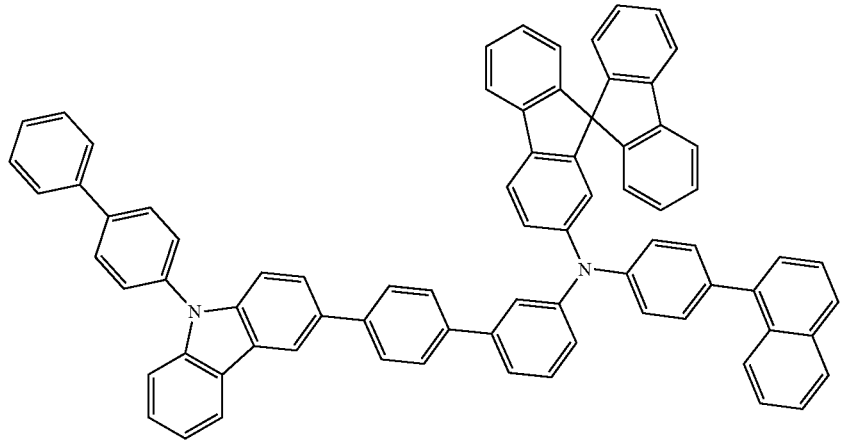
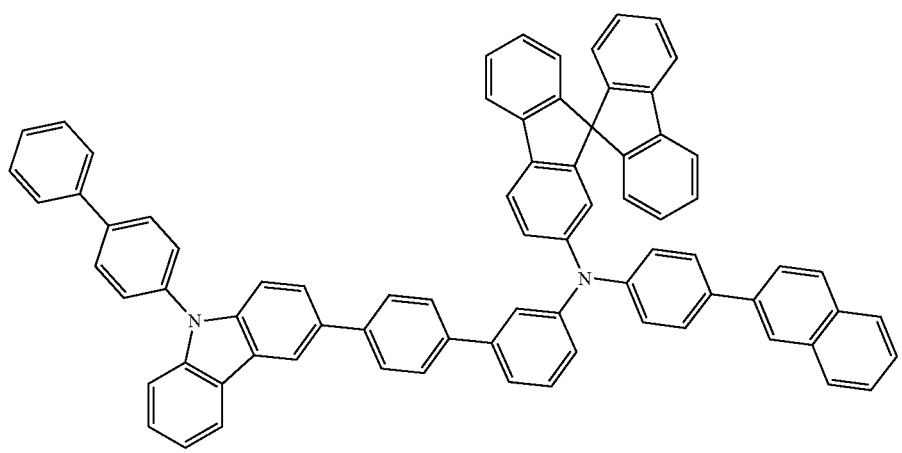
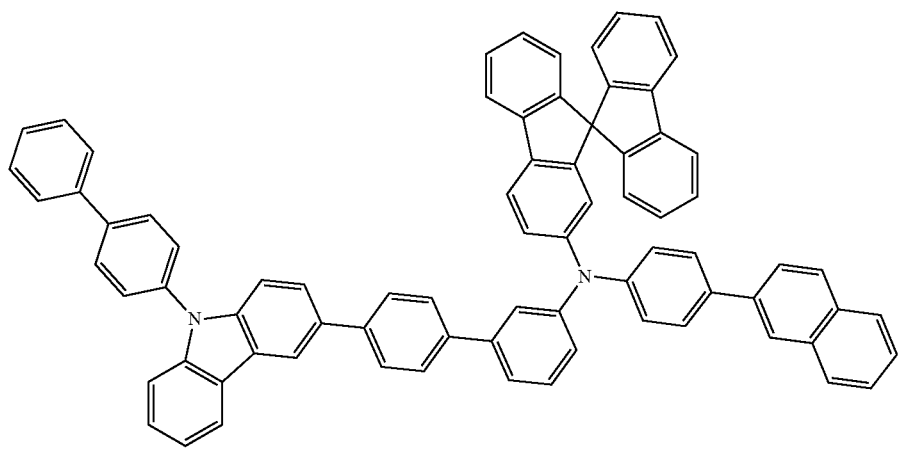

-continued

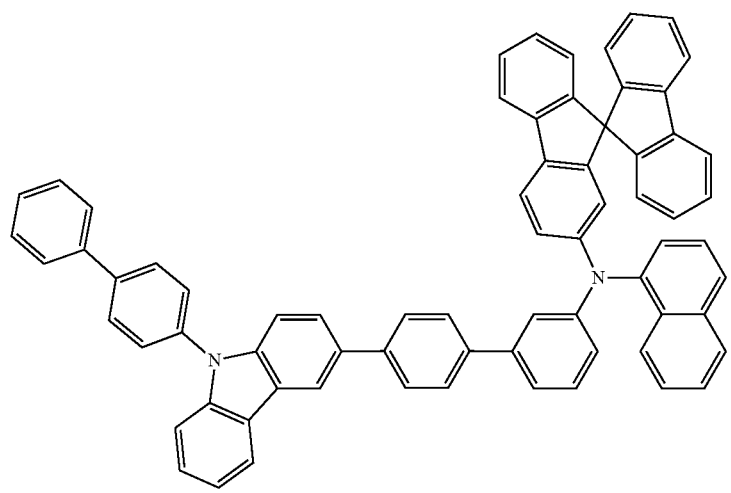
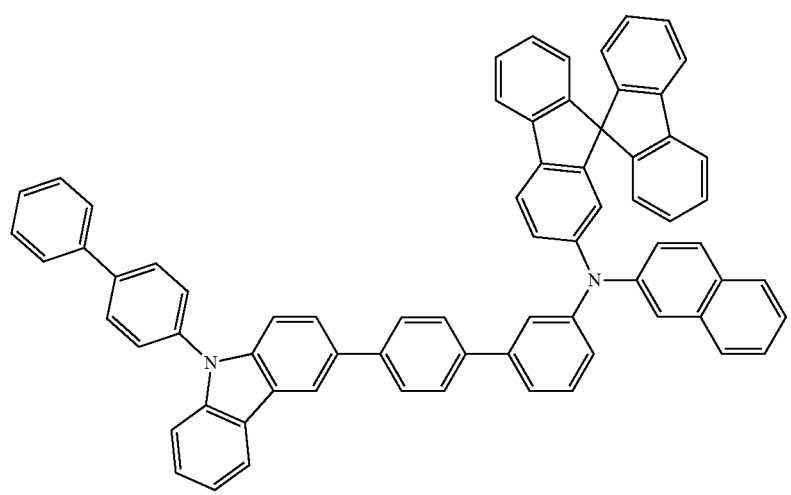

-continued
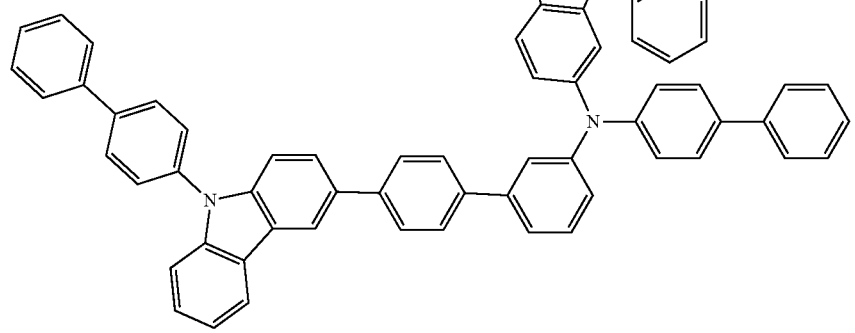
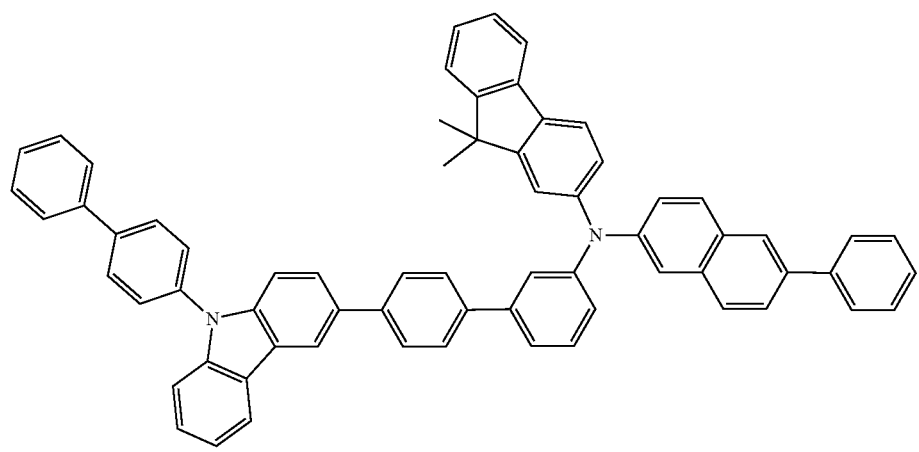
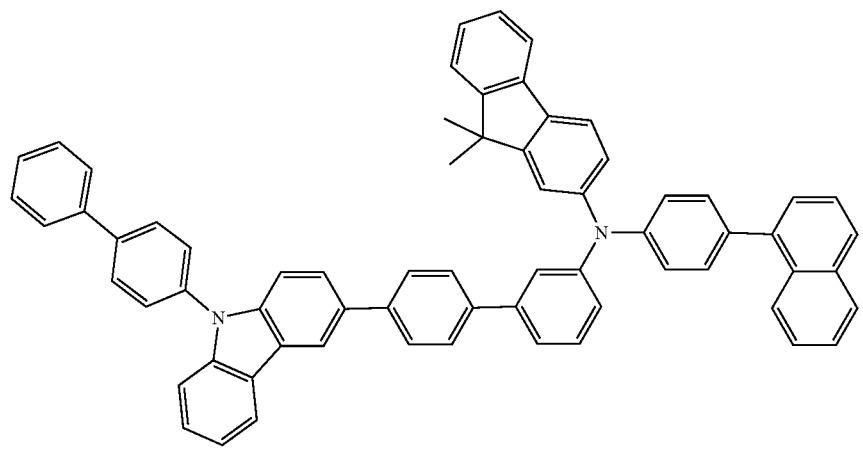

-continued
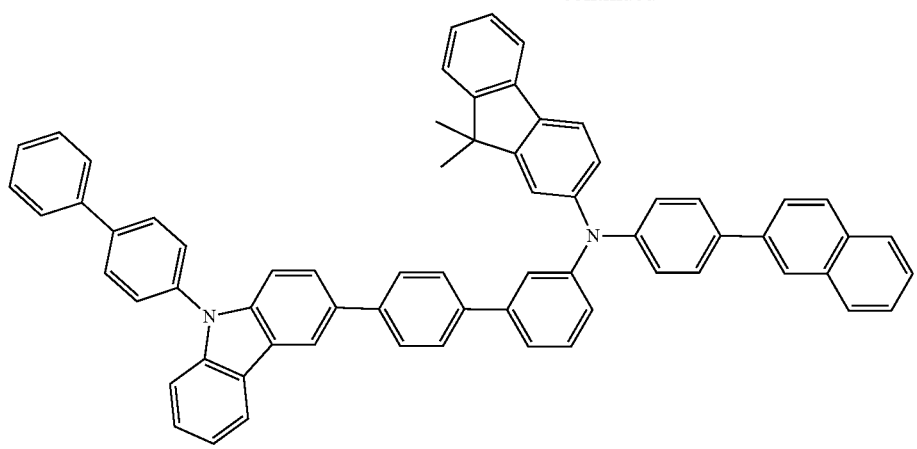
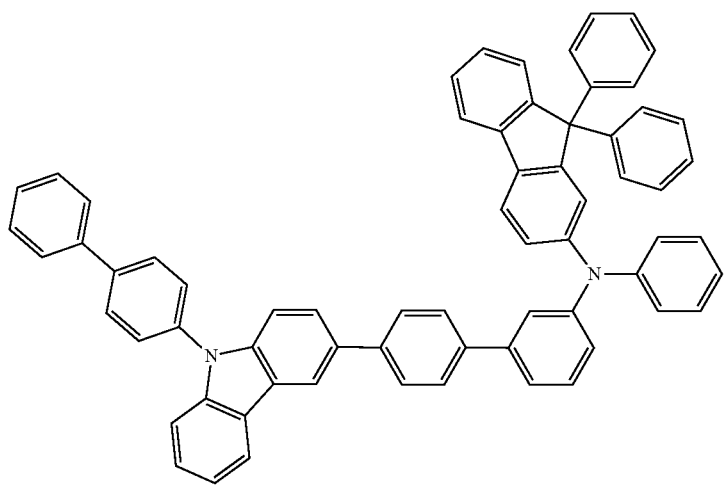
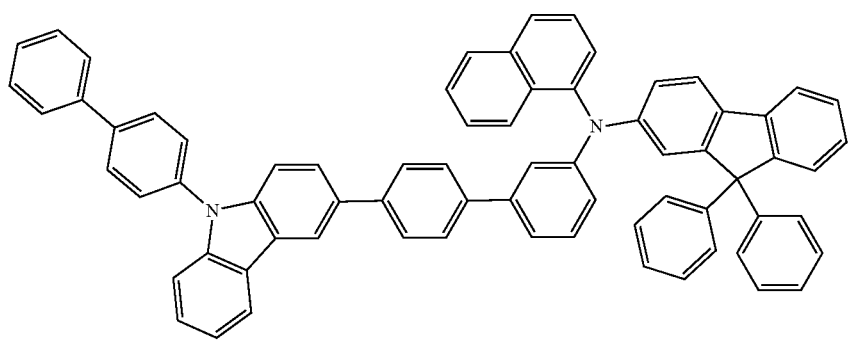

-continued
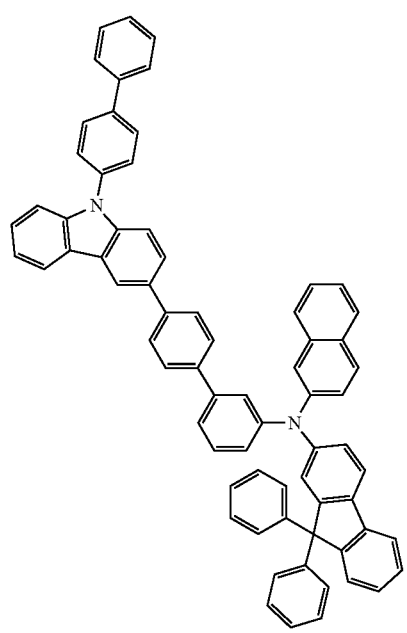
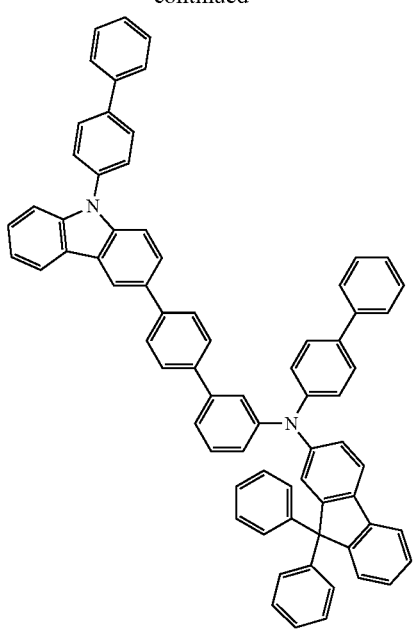
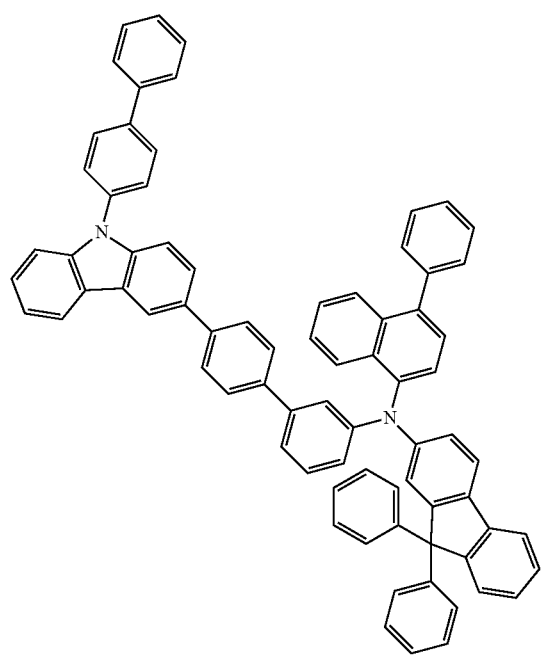

811
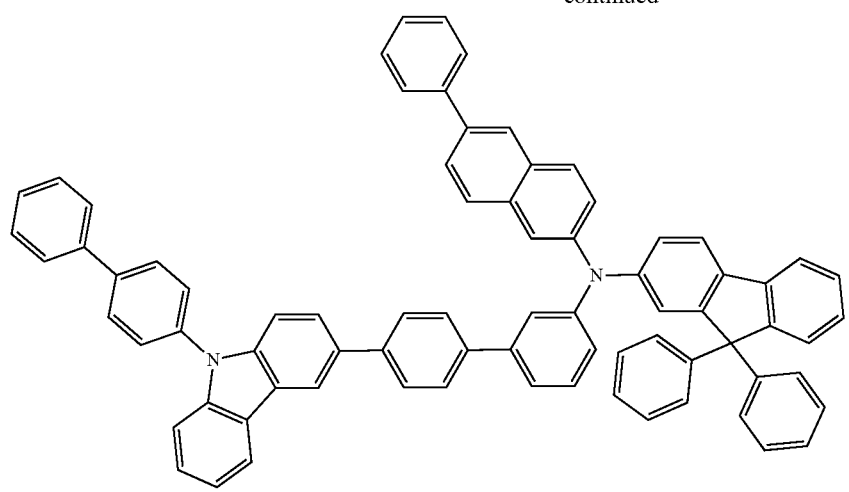
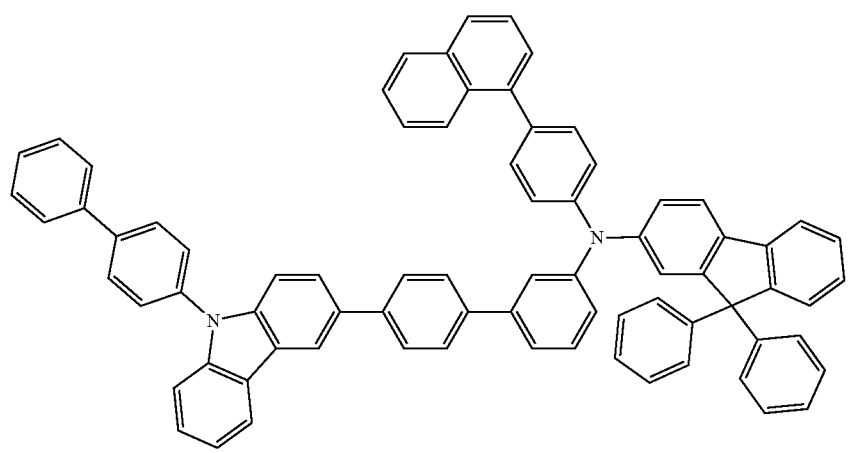
812
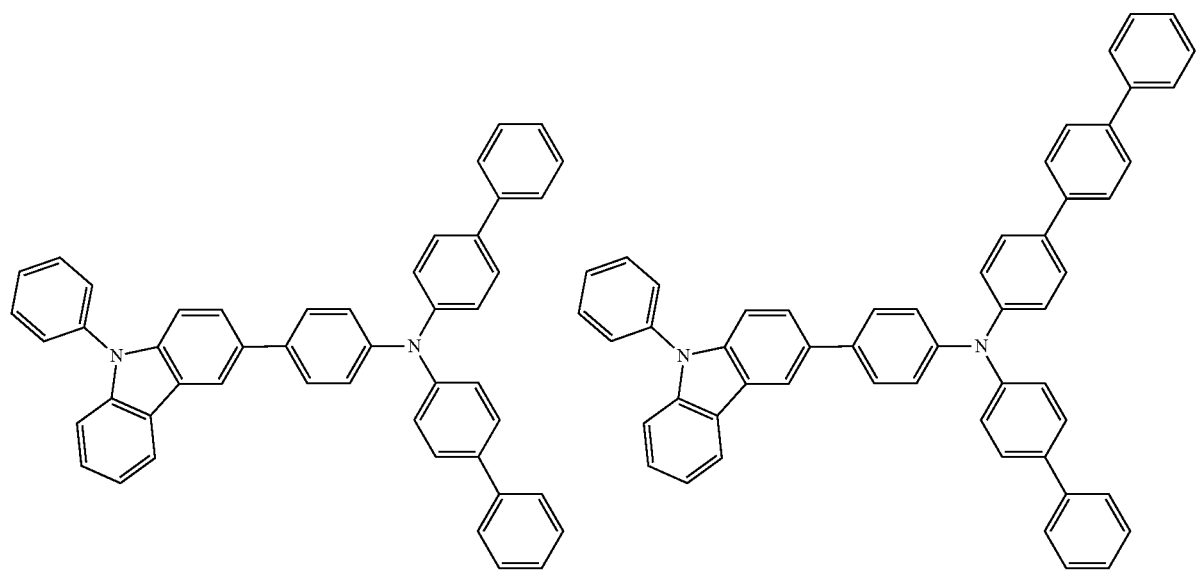

813 814
-continued
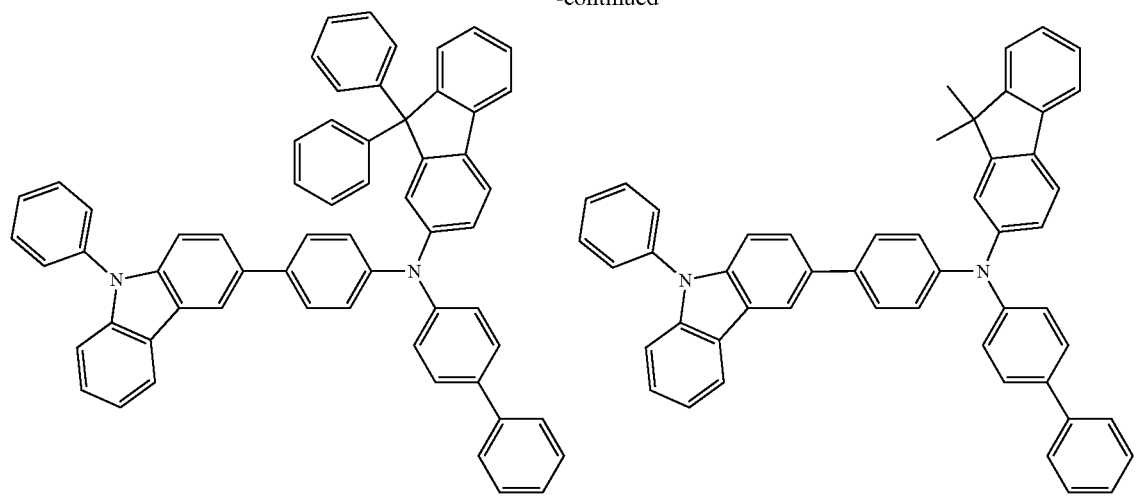
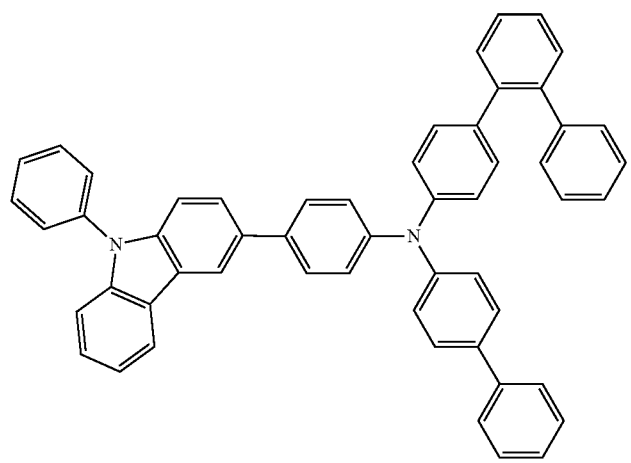
10. The organic light emitting device of claim 4, wherein the compound of Chemical Formula 4 is selected from among the following compounds:
(B114)
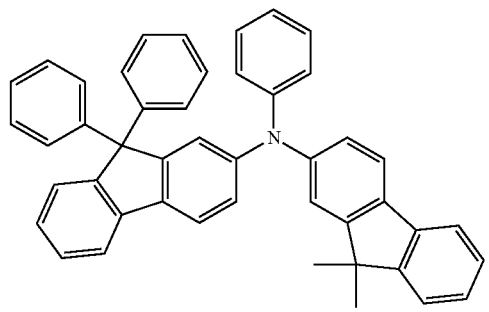
-continued
(B115)
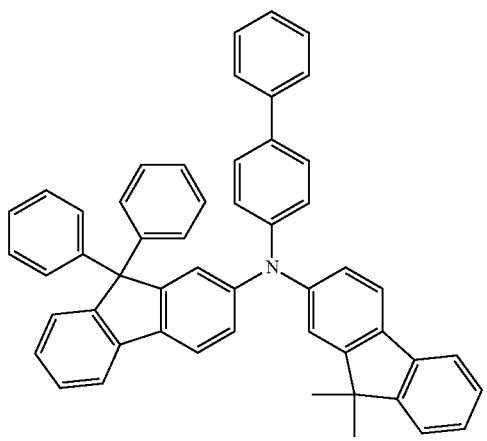

-continued
(B116)
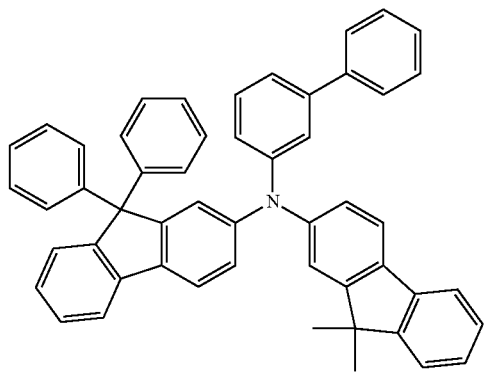
(B117)
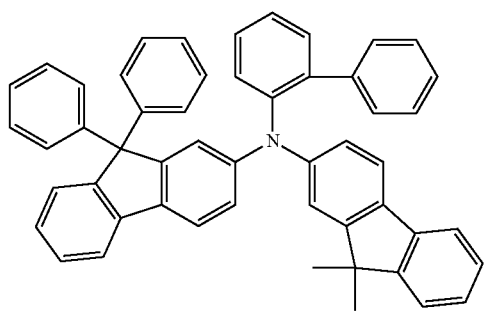
(B118)
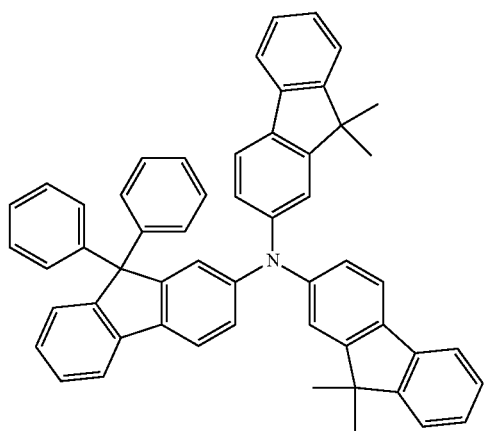
(B120)
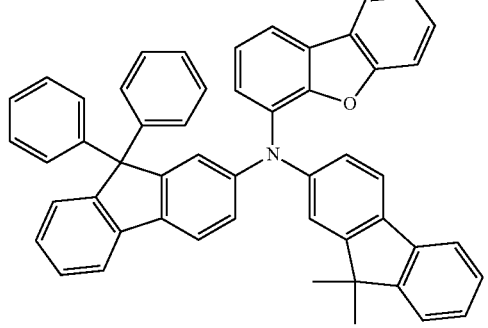
-continued
(B121)
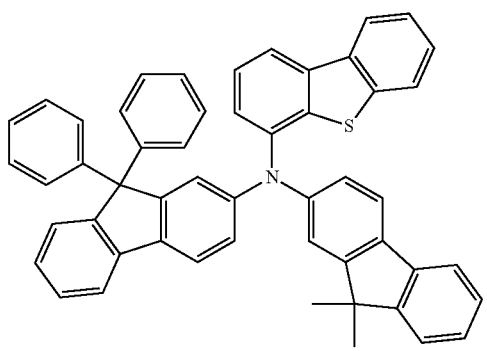
(B122)
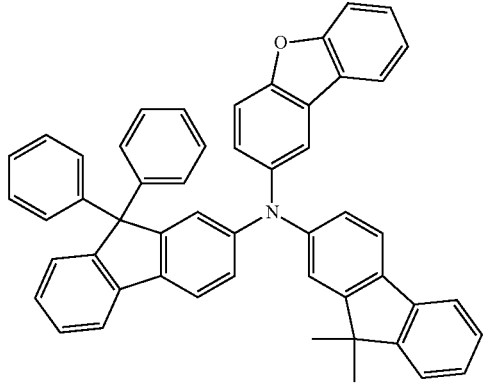
(B123)
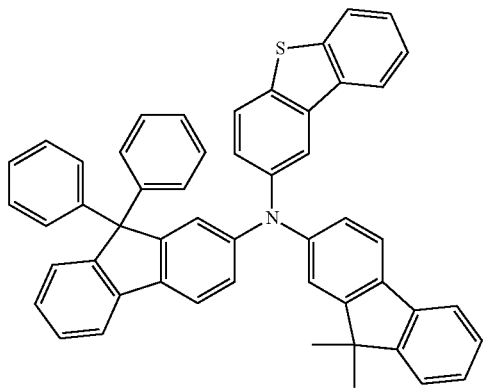

(B124)
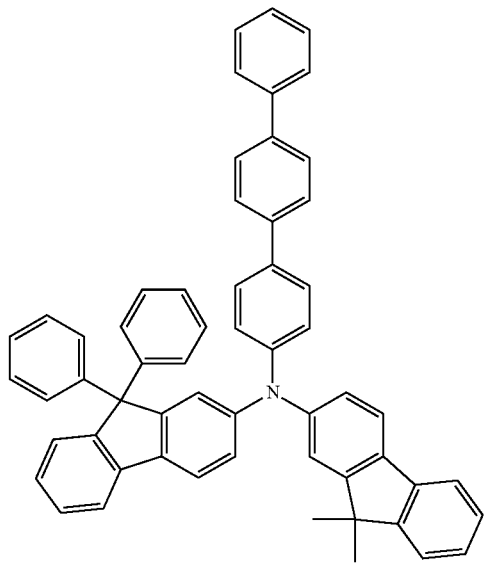
(B125)
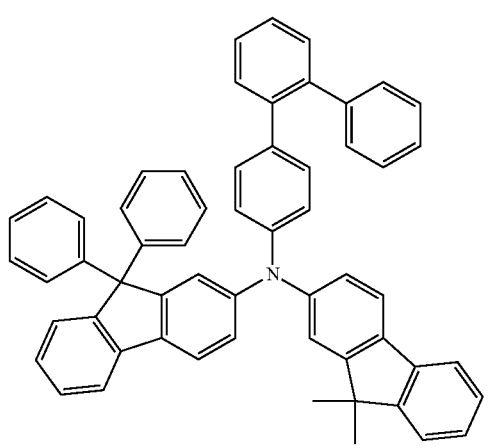
(B126)
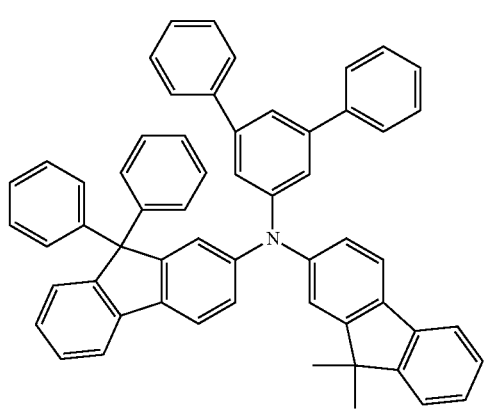
(B127)
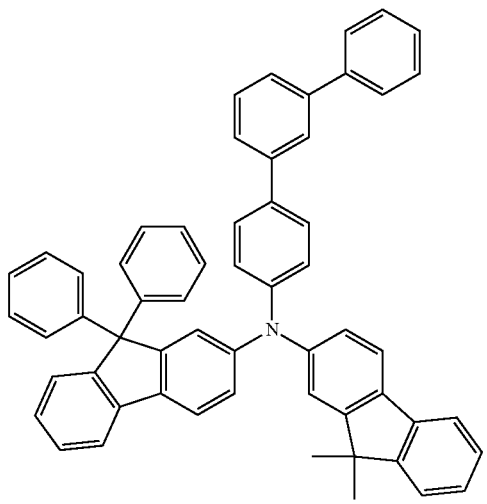
(B128)
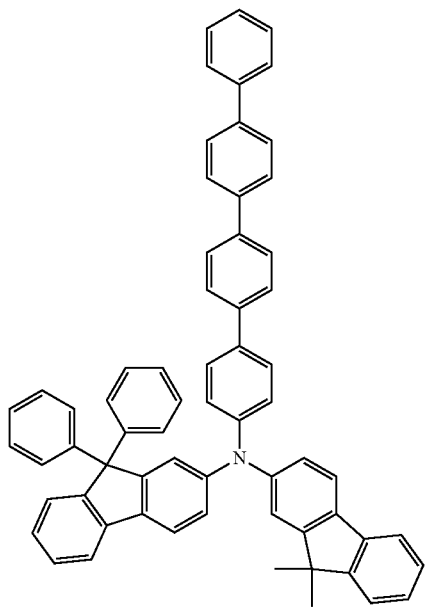
(B129)
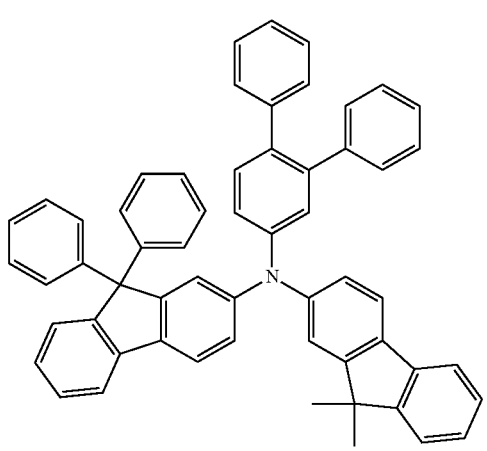

(B130)
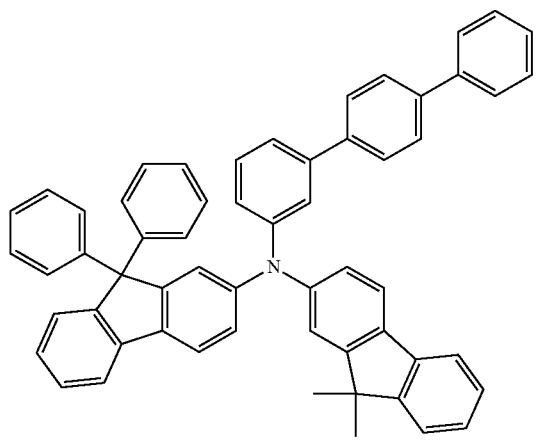
(B131)
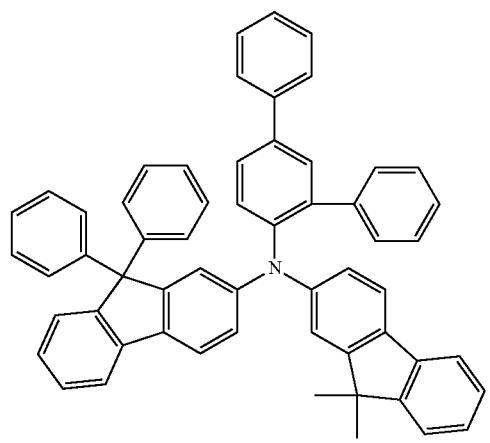
(B132)
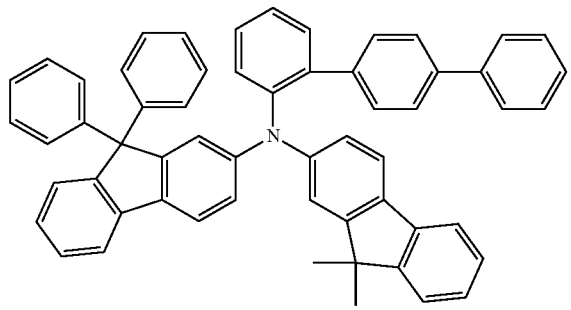
(B133)
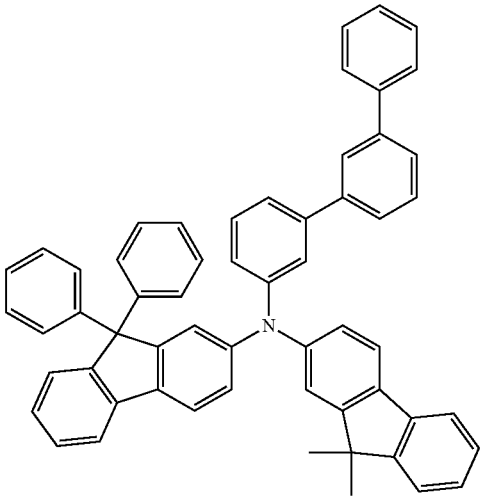
(B134)
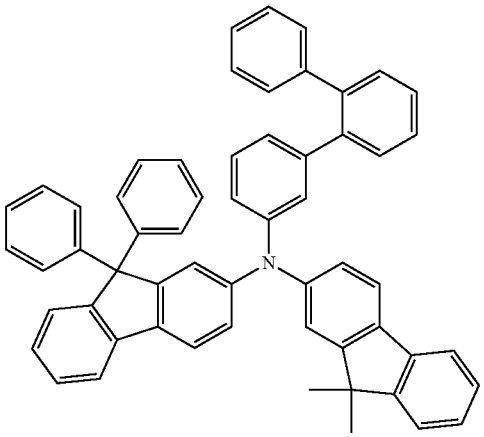
(B135)
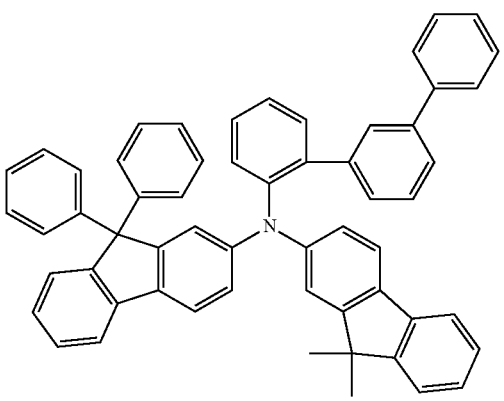

-continued
(B136)
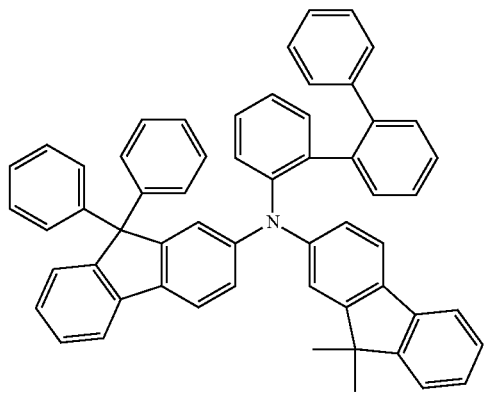
(B137)
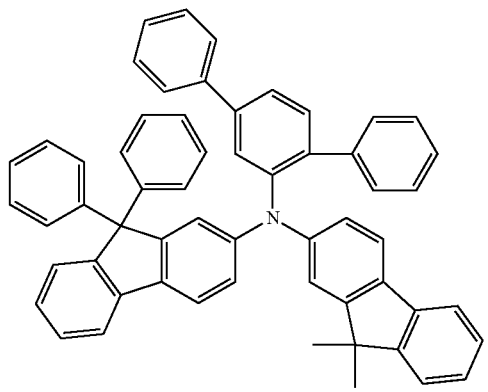
(B138)
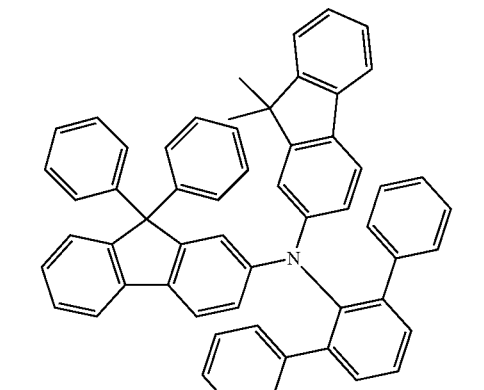
(B139)
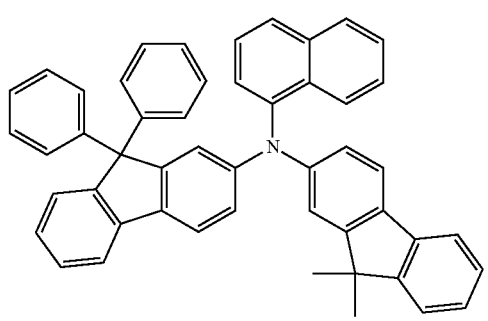
-continued
(B140)
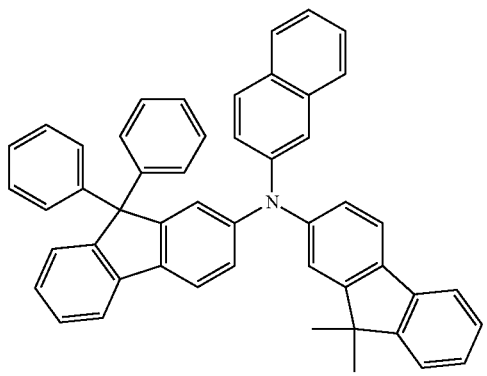
(B141)
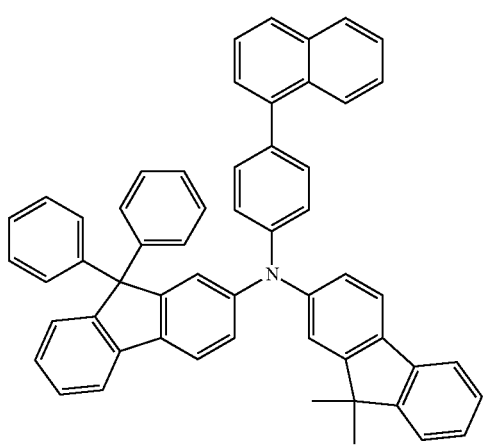
(B142)
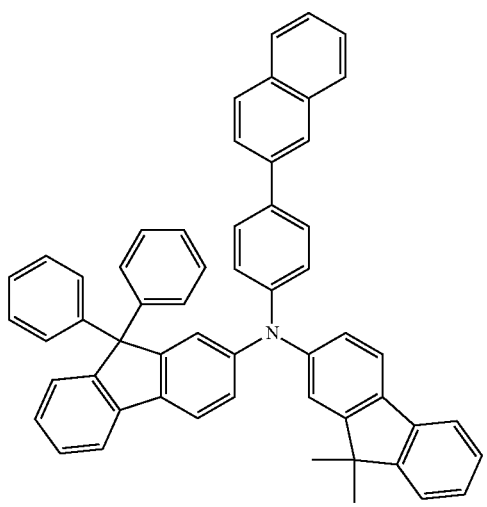

-continued
(B143)
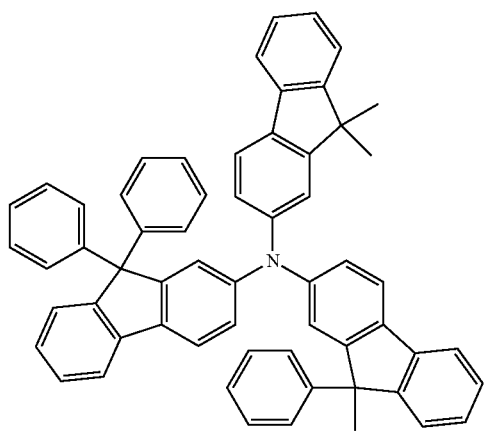
(B144)
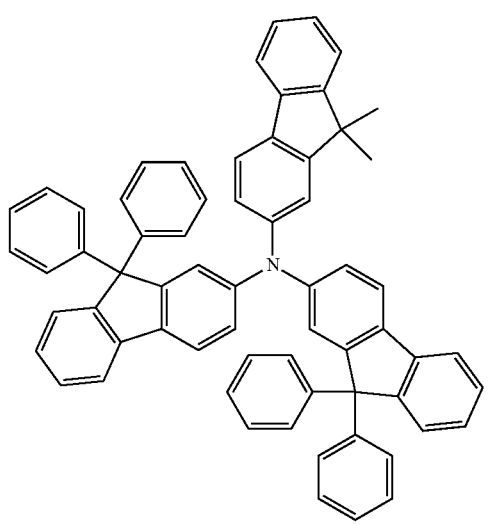
(B145)
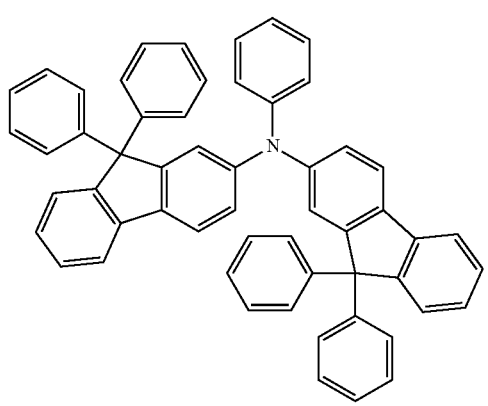
-continued
(B146)
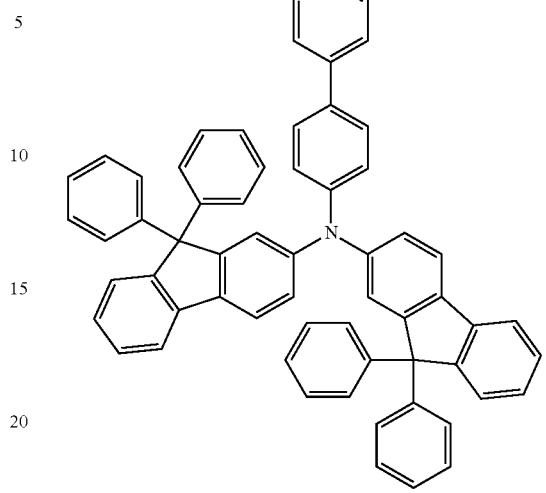
(B147)
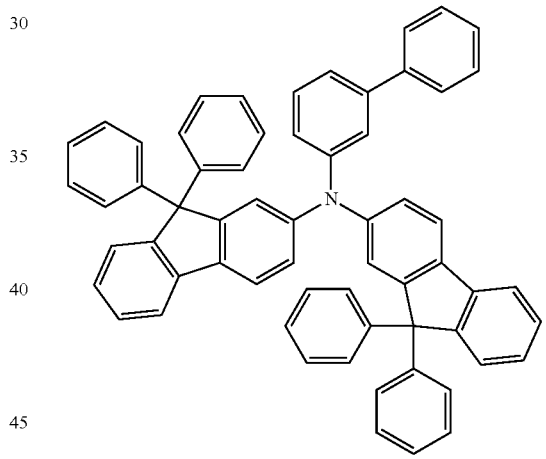
(B148)
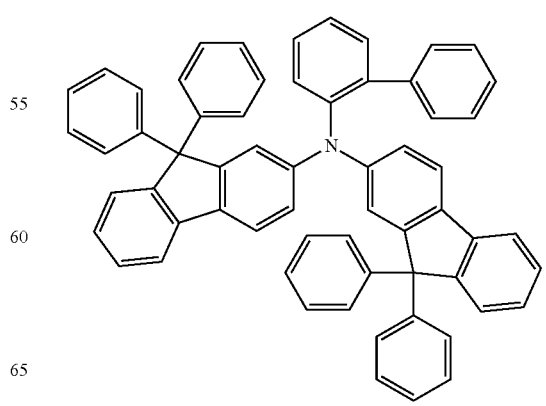

(B149)
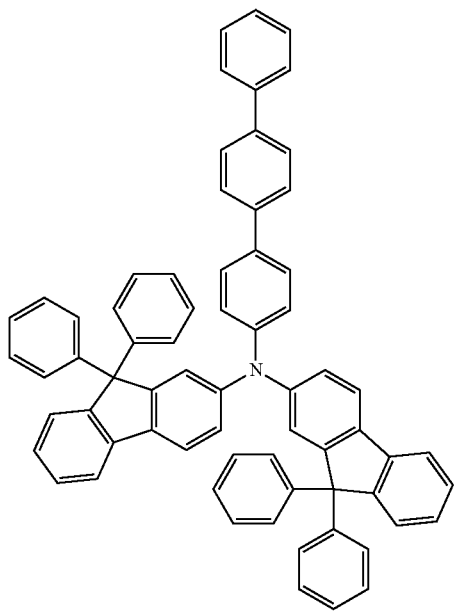
(B150)
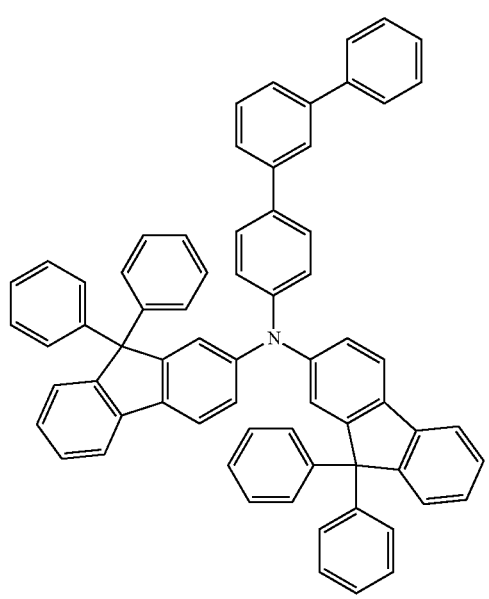
(B151)
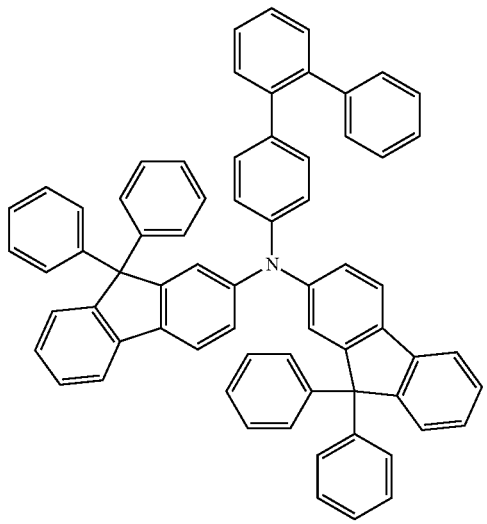
(B152)
(B153)
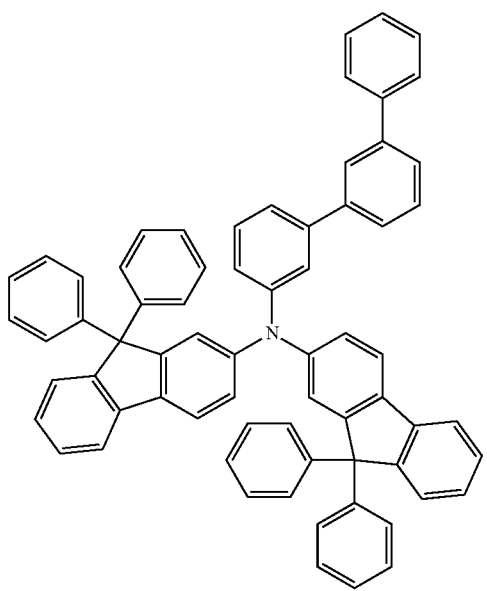

(B154)
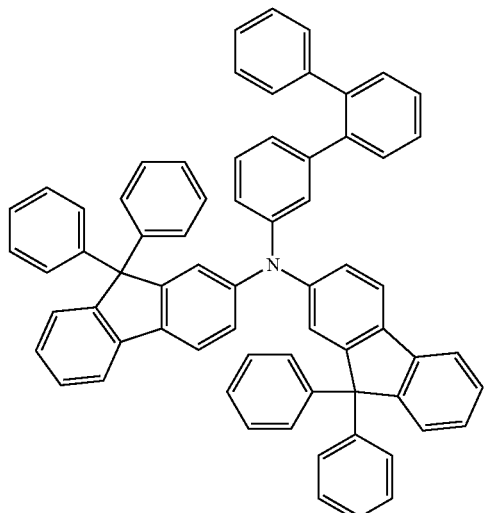
(B155)
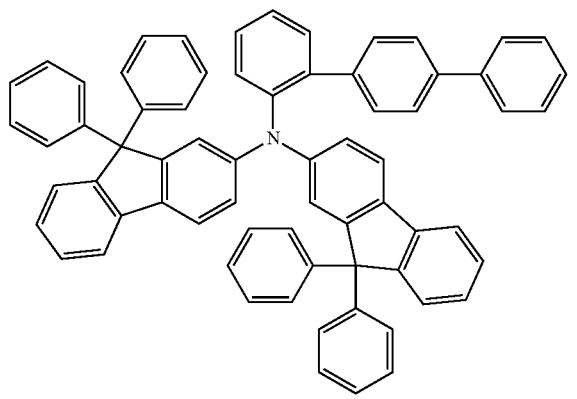
(B156)
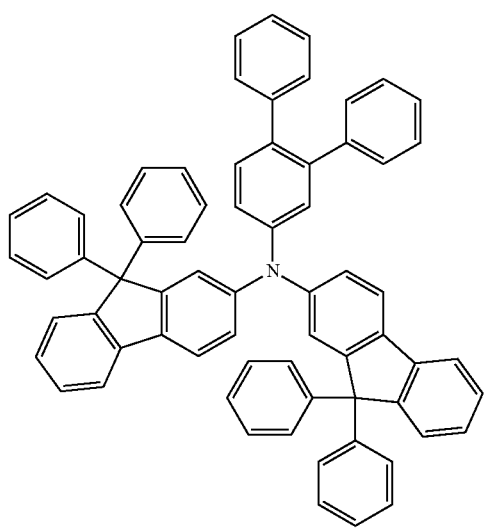
(B157)
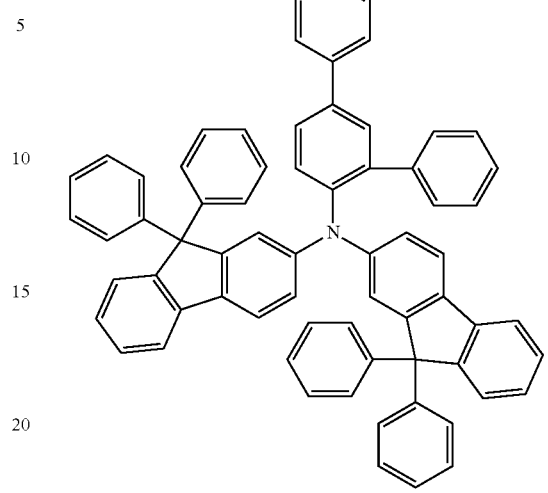
(B158)
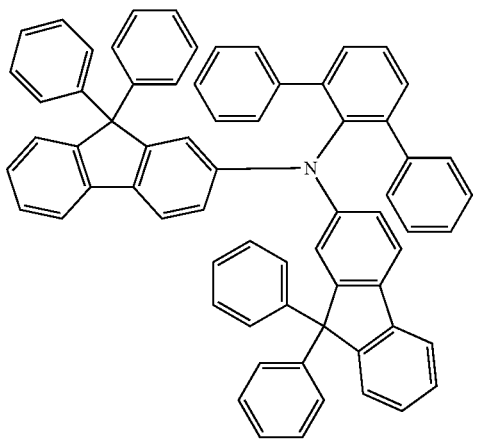
(B159)
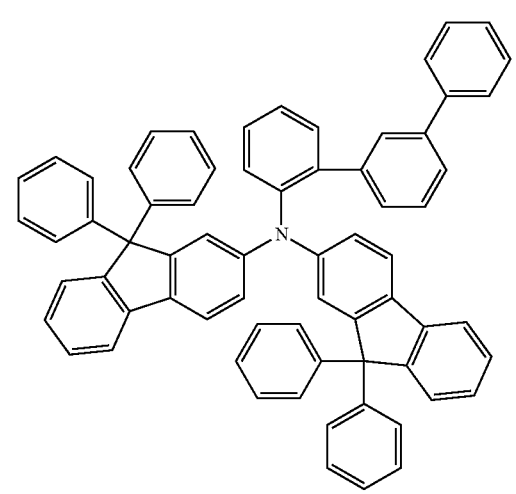

(B160)
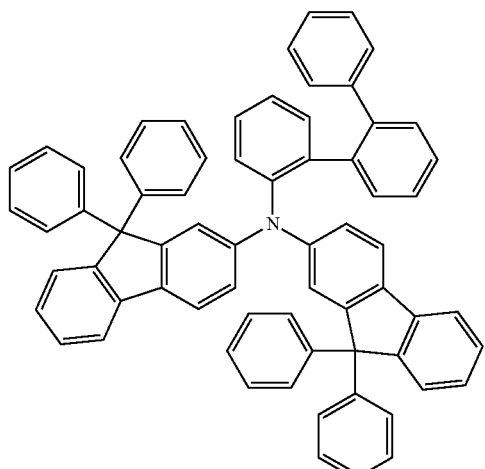
(B161)
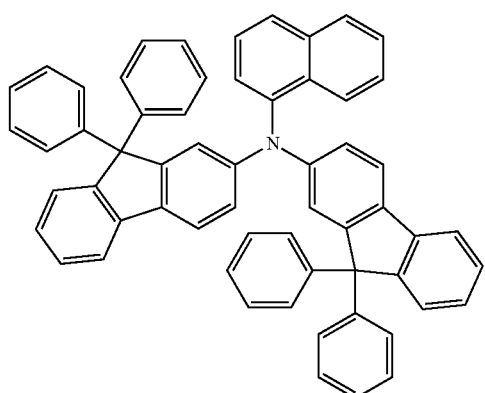
(B162)
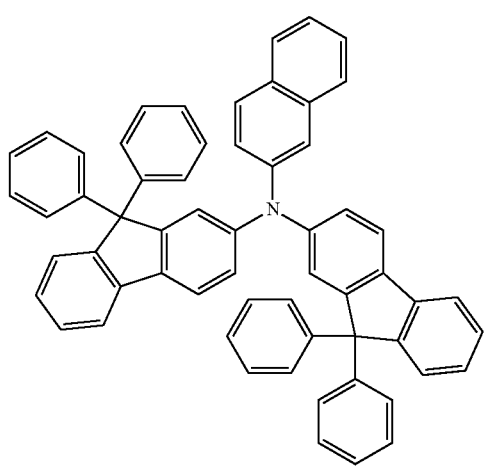
(B163)
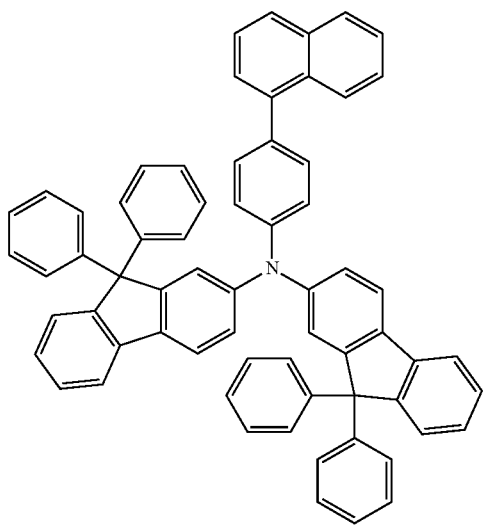
(B164)
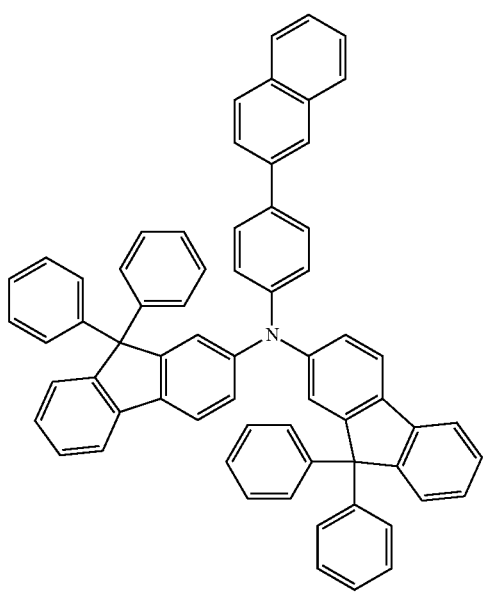
(B165)
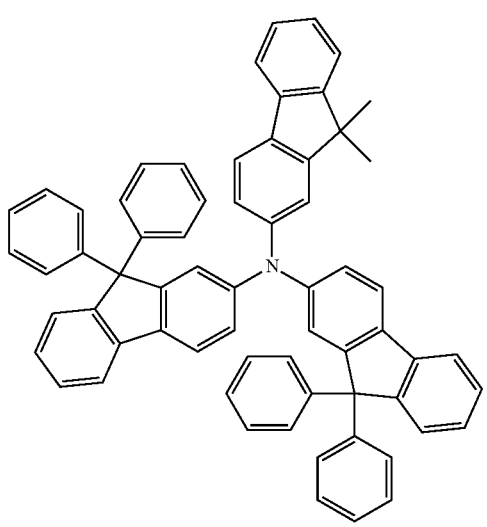

(B166)
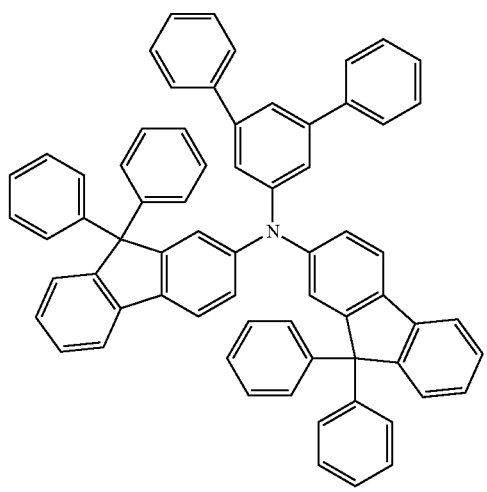
(B167)
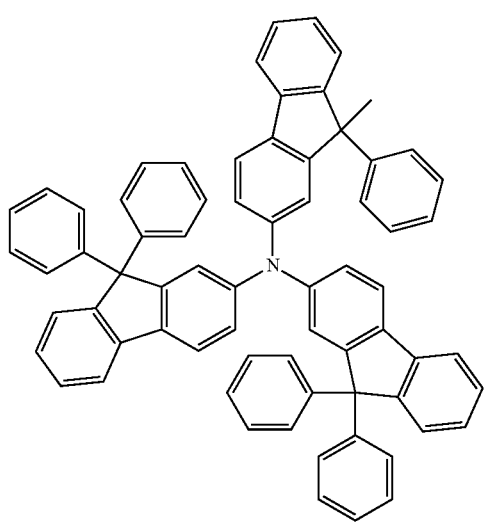
(B168)
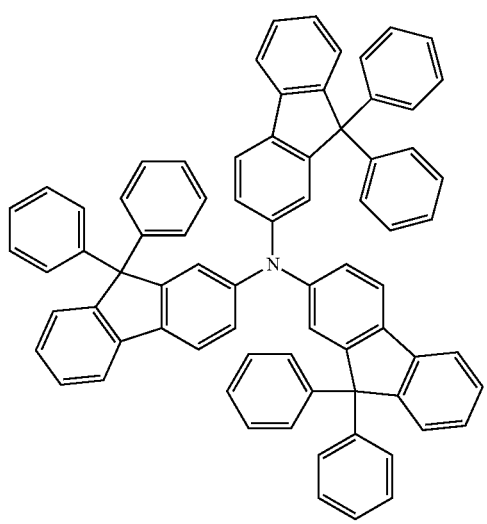
(B169)
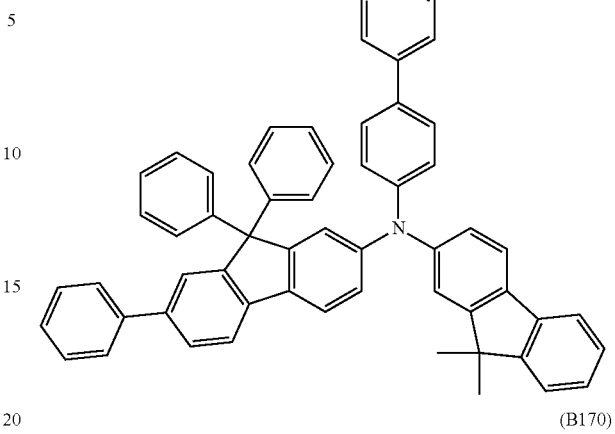
(B170)
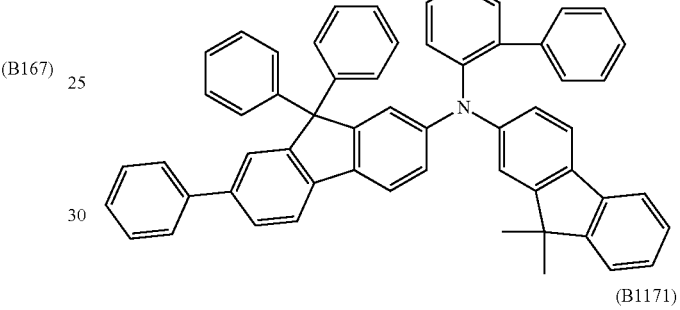
(B1171)
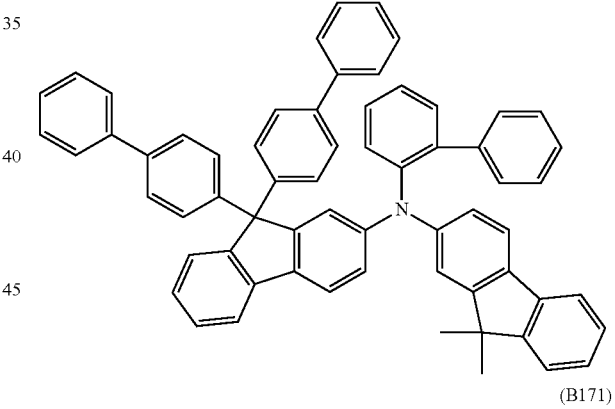
(B171)
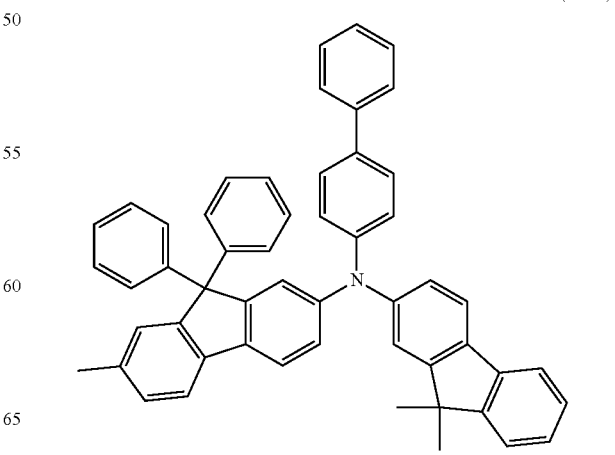

(B172) 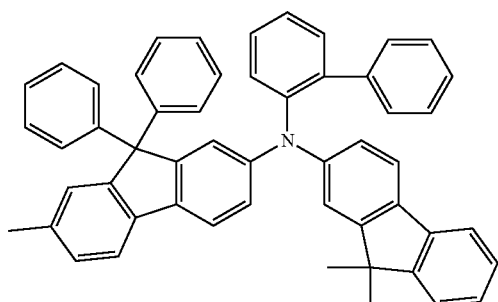
(B173) 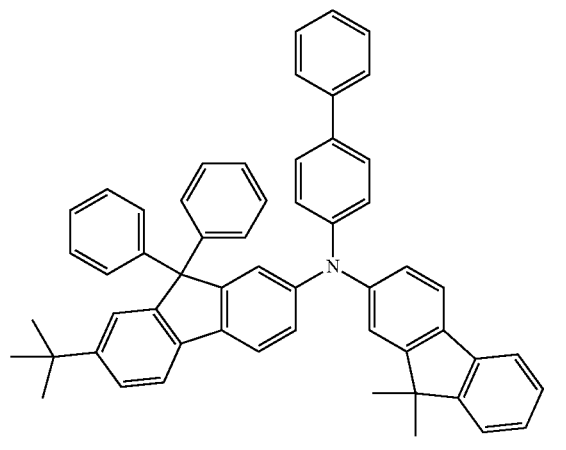
(B174) 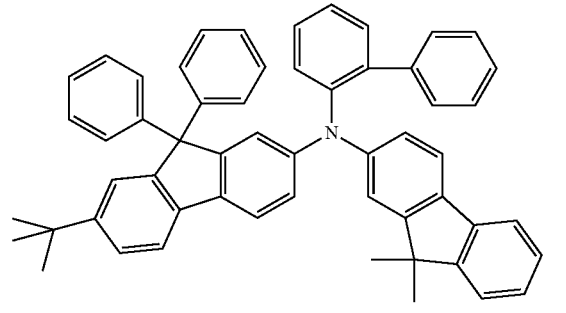
(B175) 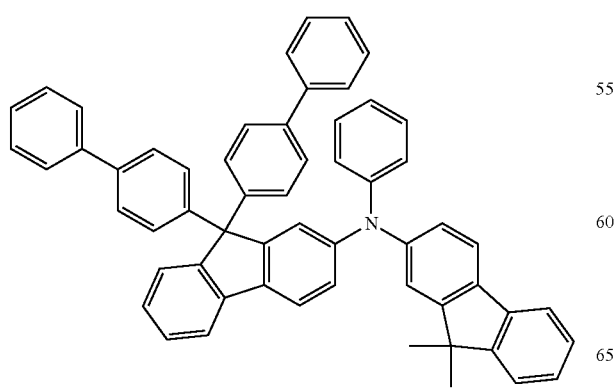
(B176) 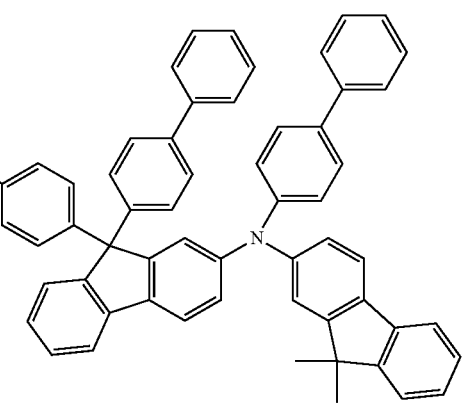
(B177) 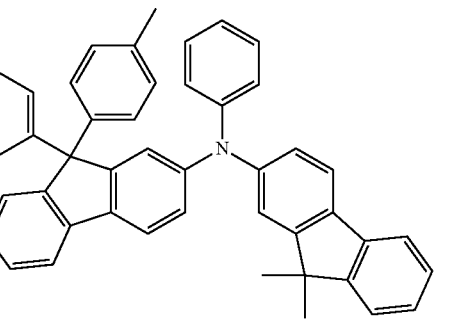
(B178) 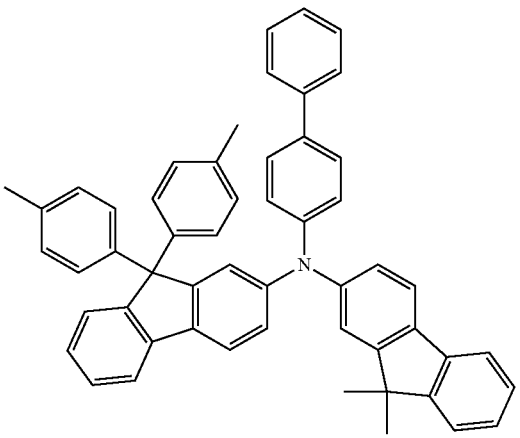

(B179)
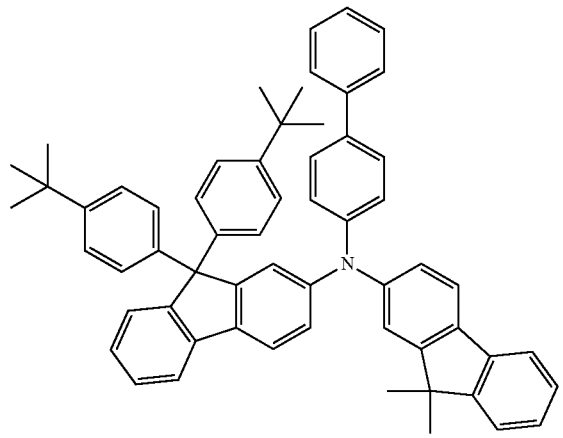
(B180)
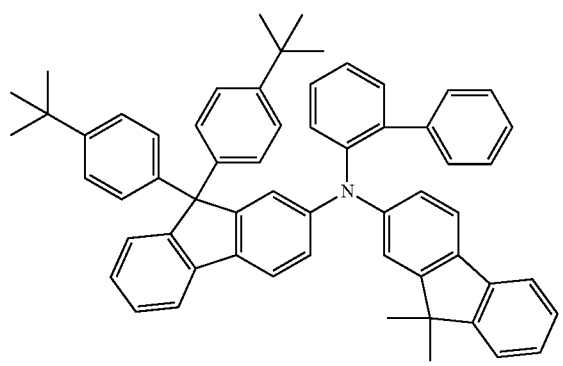
(B181)
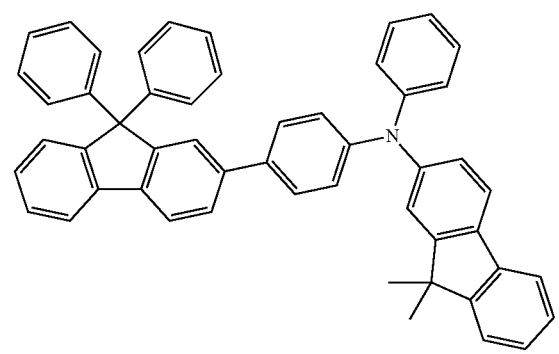
(B182)
(B183)
(B184)

837
-continued
(B185)
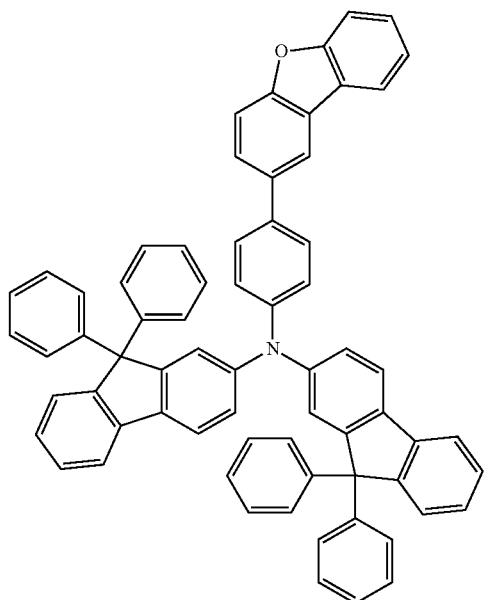
(B186)
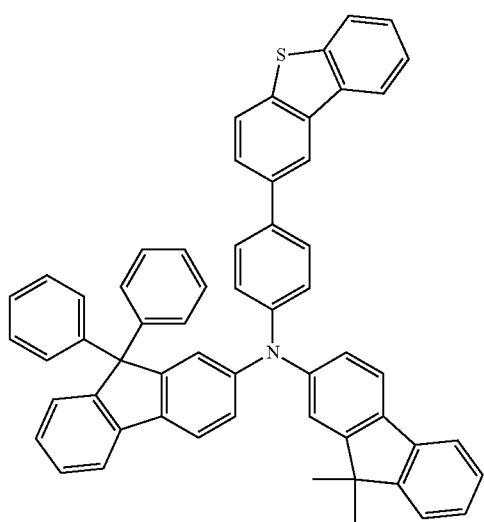
838
-continued
(B187)
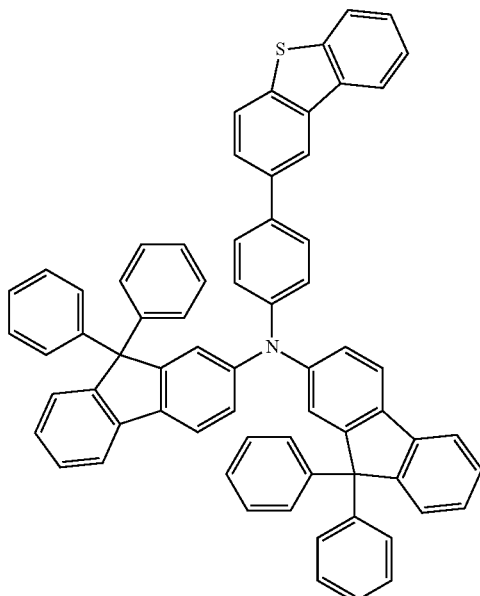
(B188)
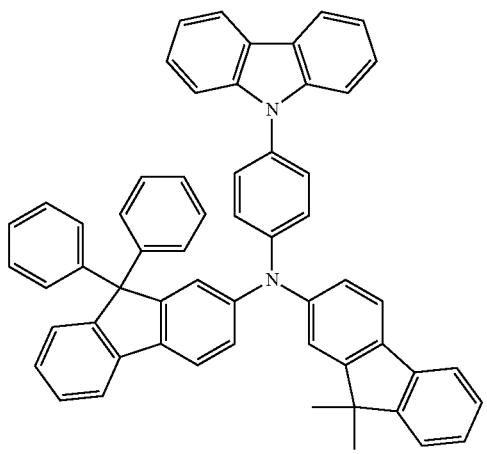
(B189)
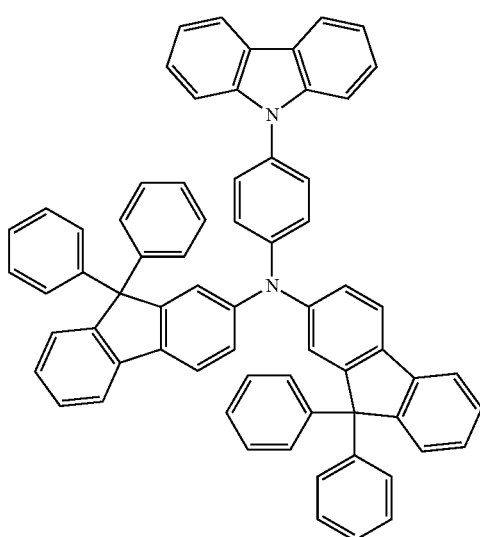

(B190)
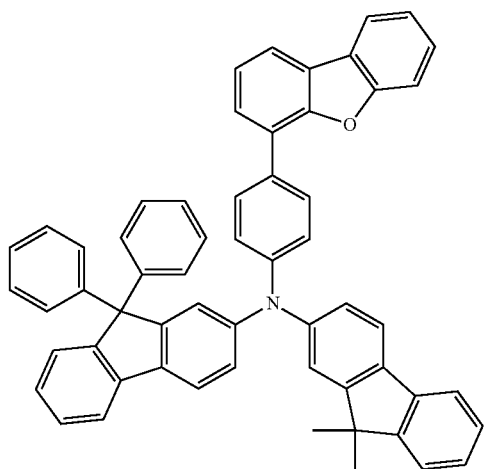
(B193)
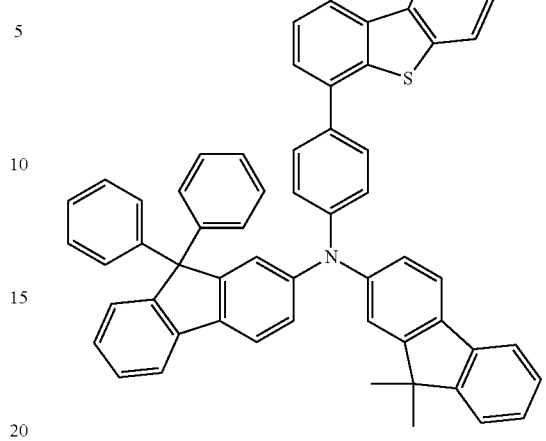
(B191)
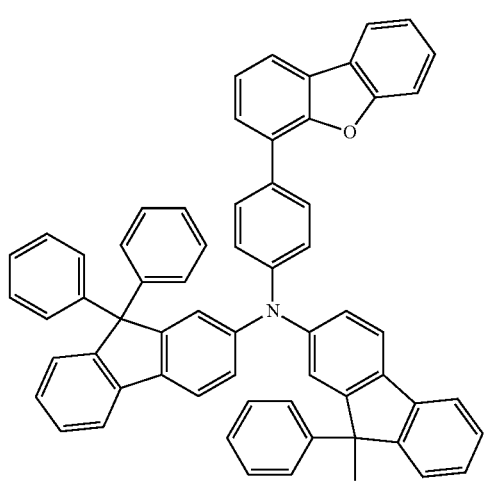
(B194)
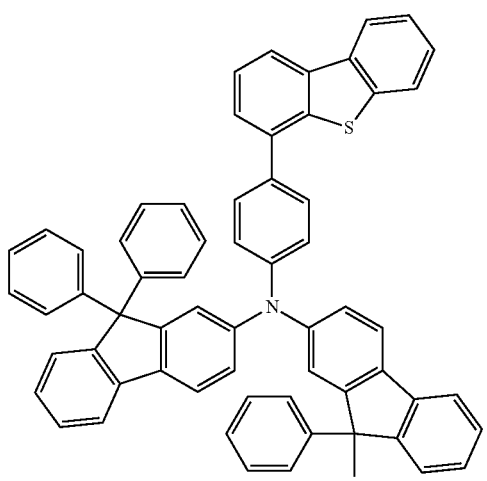
(B192)
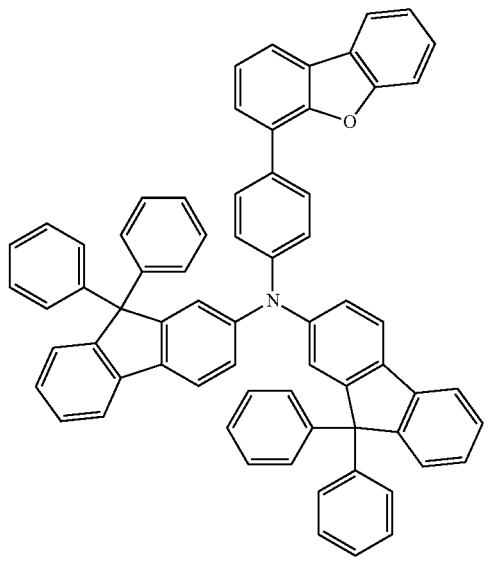
(B195)
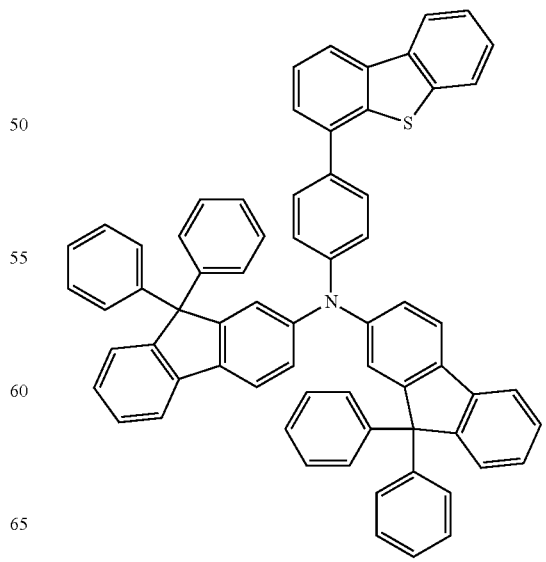

(B196)
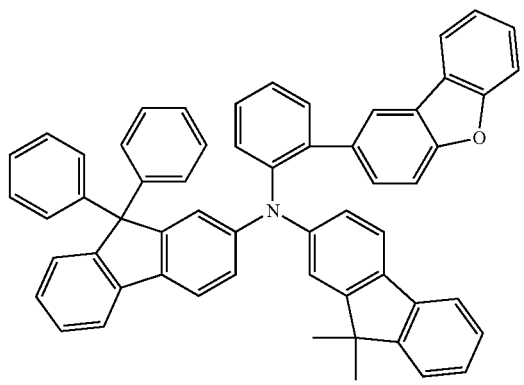
(B197)
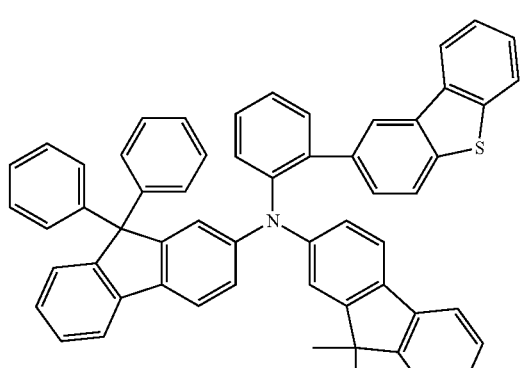
(B198)
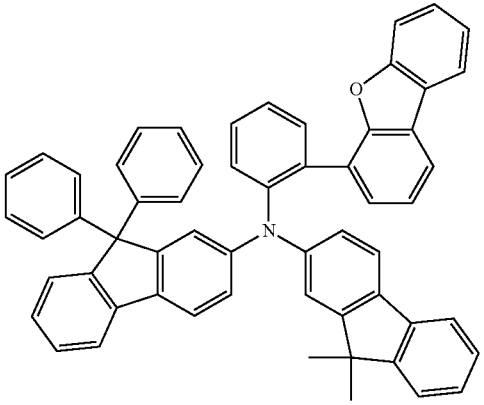
(B199)
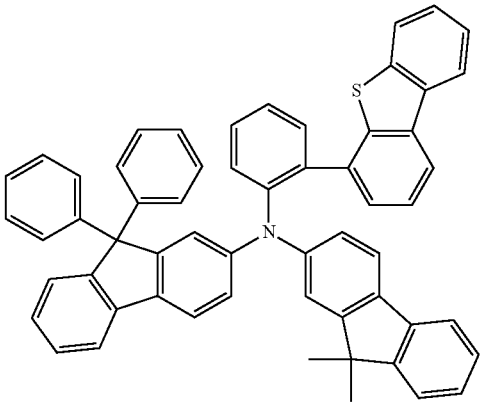
(B200)
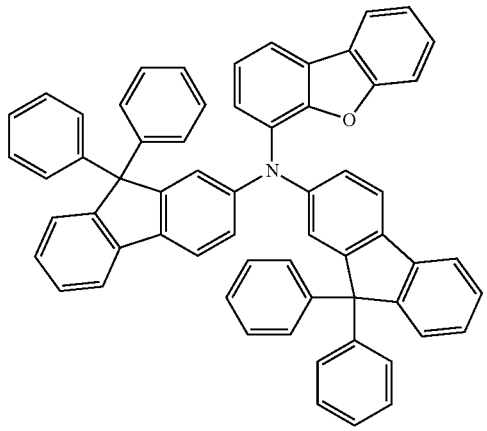
(B201)
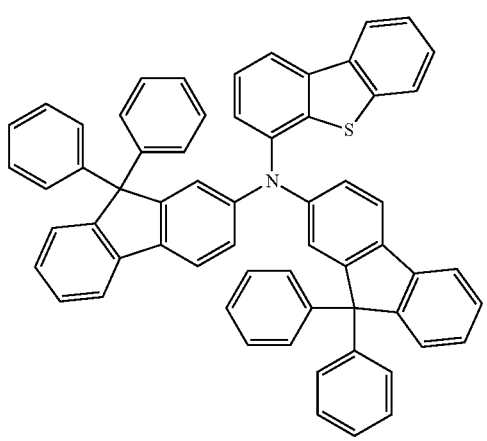
(B202)
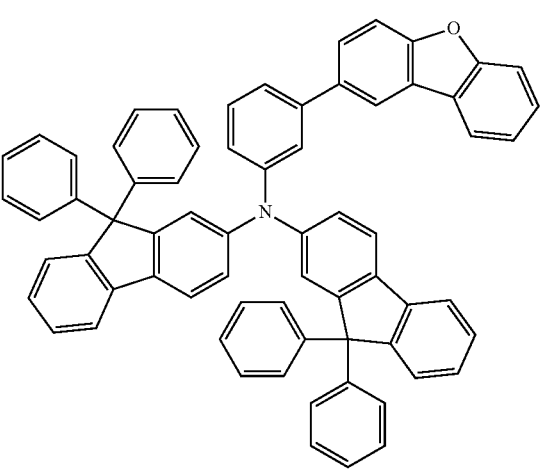

(B203)
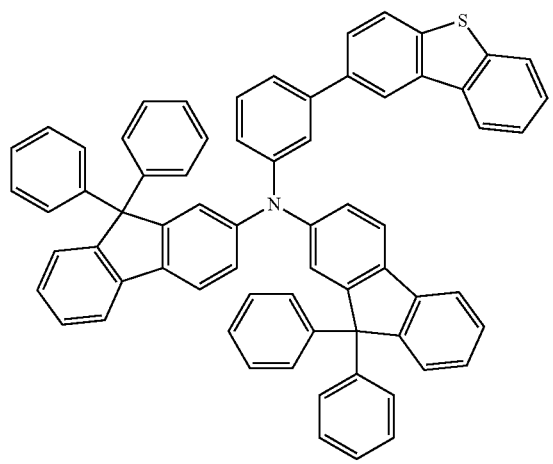
(B204)
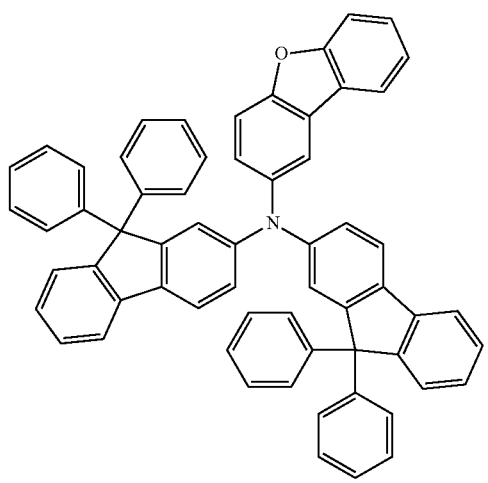
(B205)
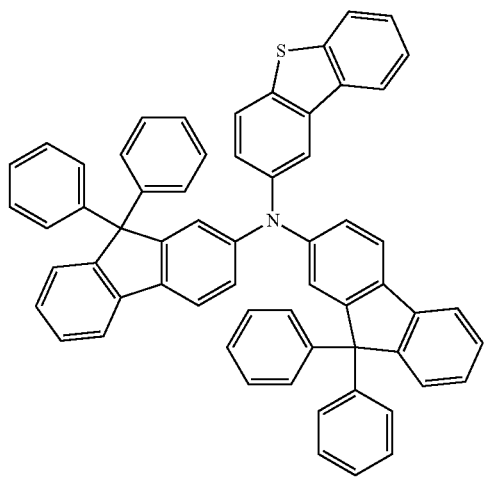
(B206)
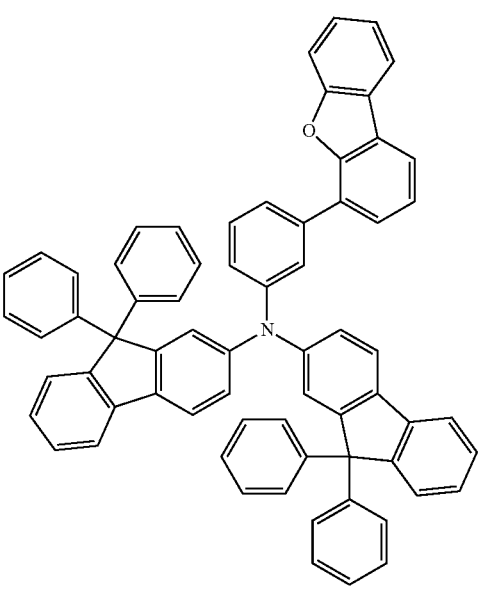
(B207)

(B208)
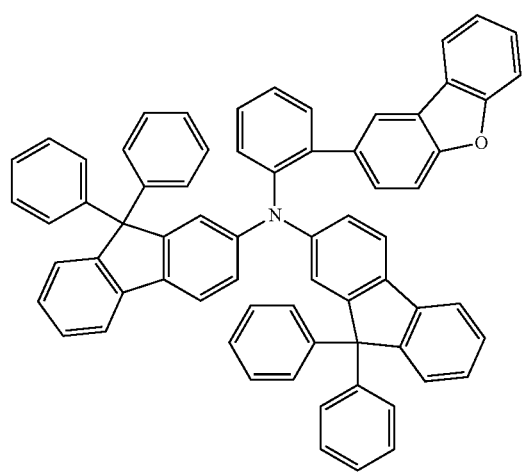
(B209)
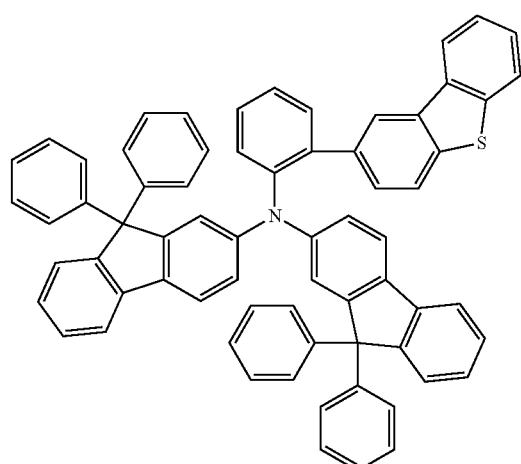
(B210)
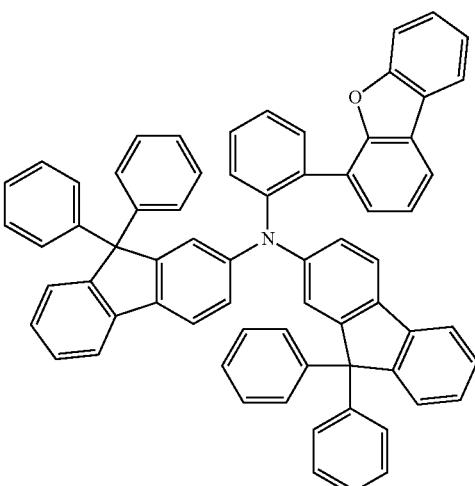
(B211)
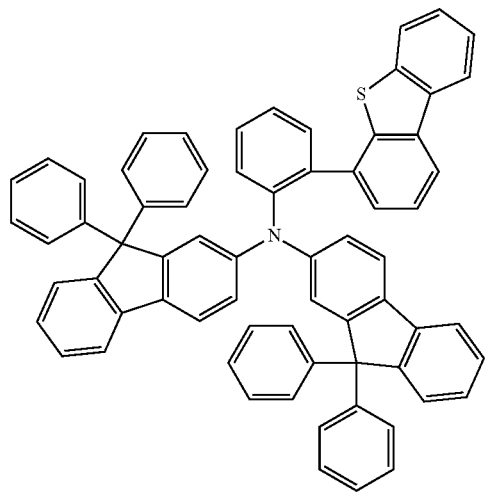
(B212)
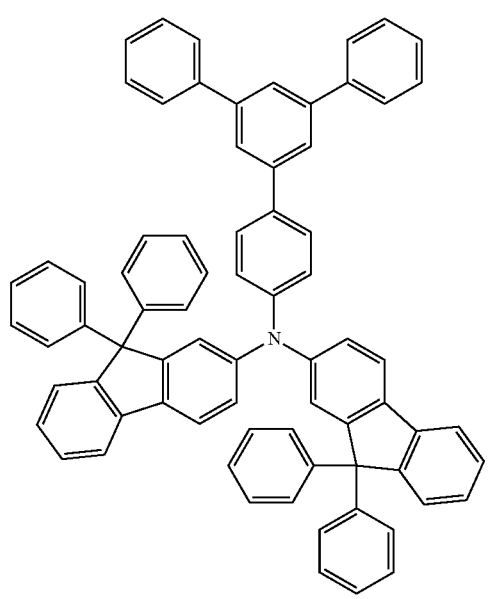
(B213)
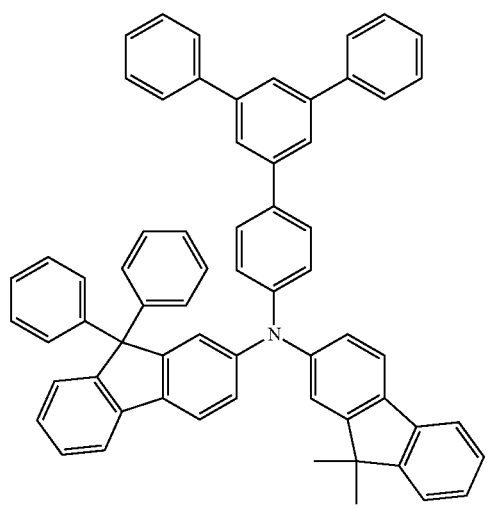

(B214)
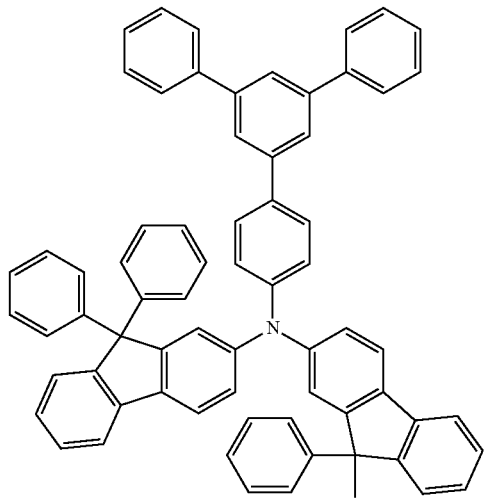
(B215)
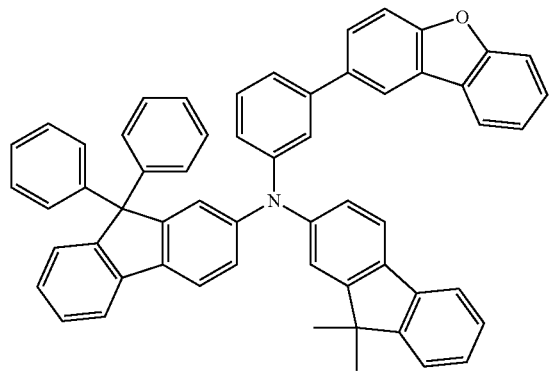
(B216)
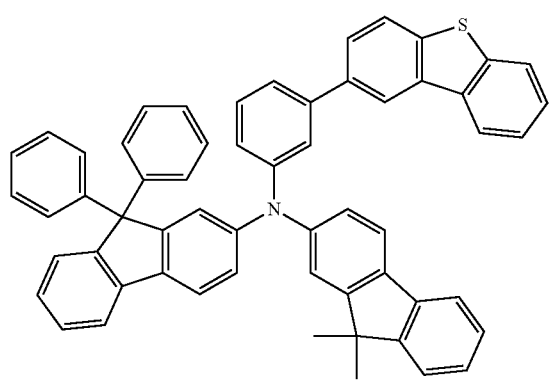
(B217)
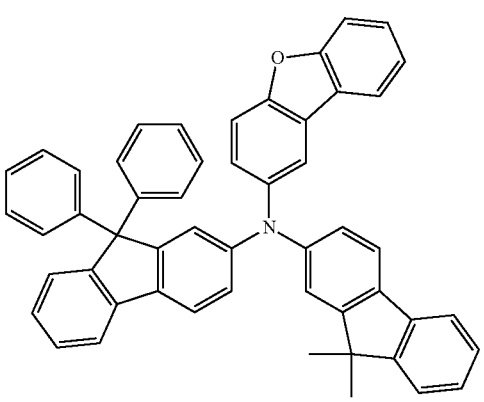
(B218)
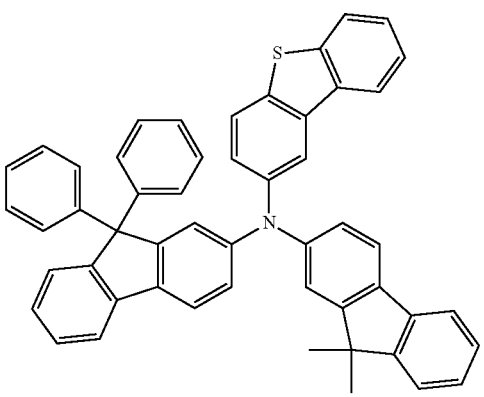
(B219)
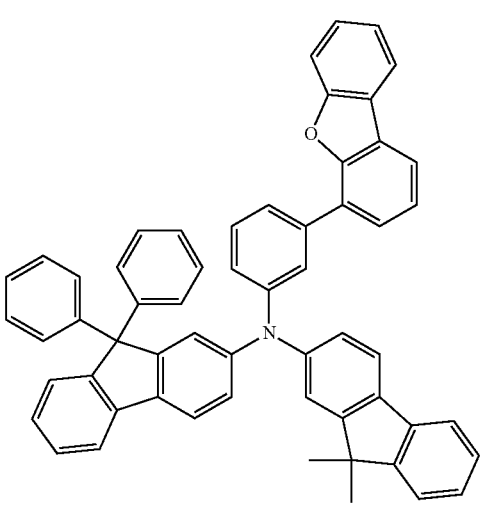

(B220)
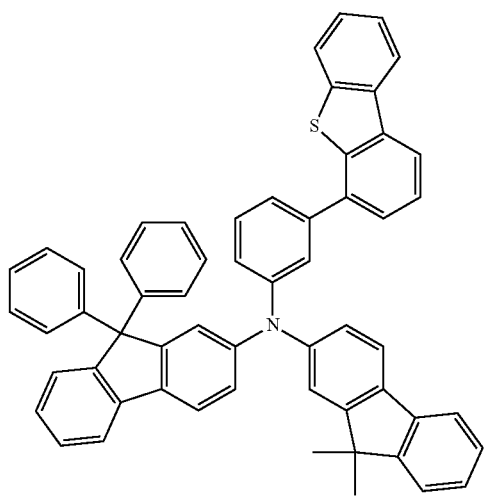
(B221)
(B222)
(B223)
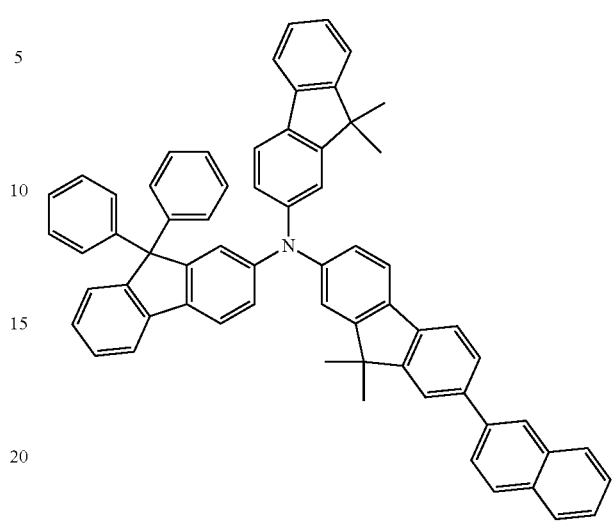
(B1224)
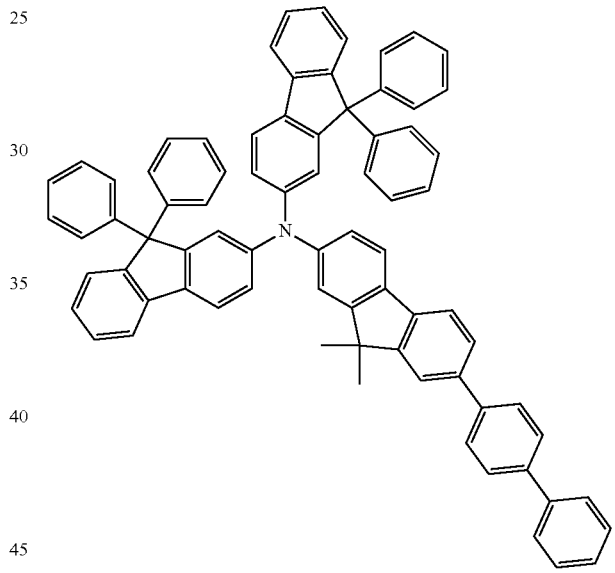
(B225)
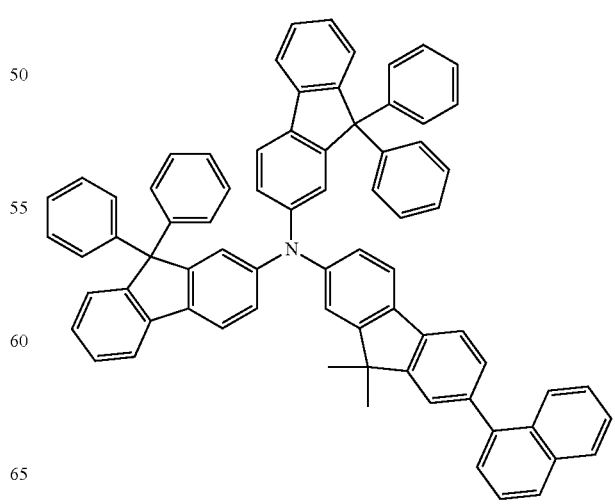

(B226)
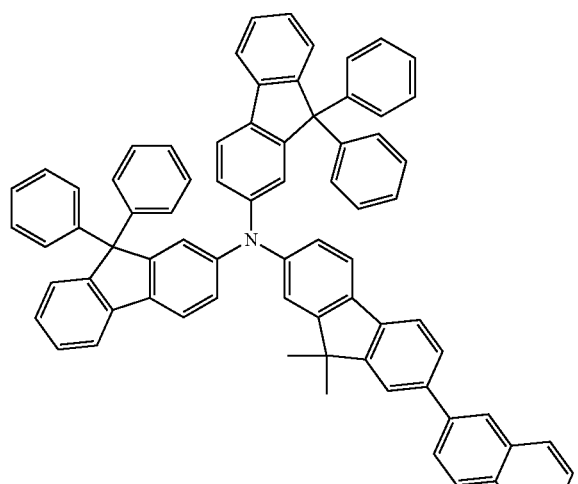
(B227)
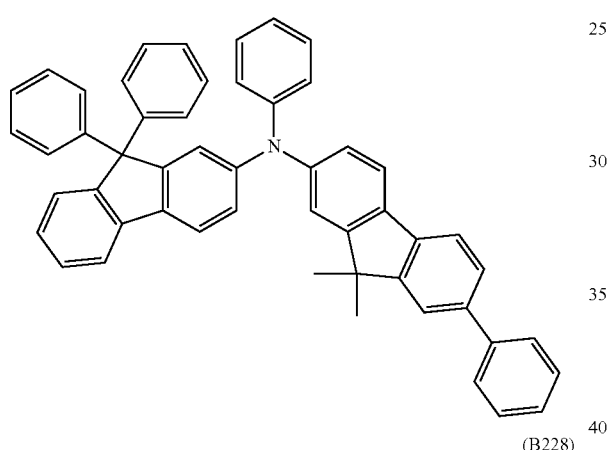
(B228)
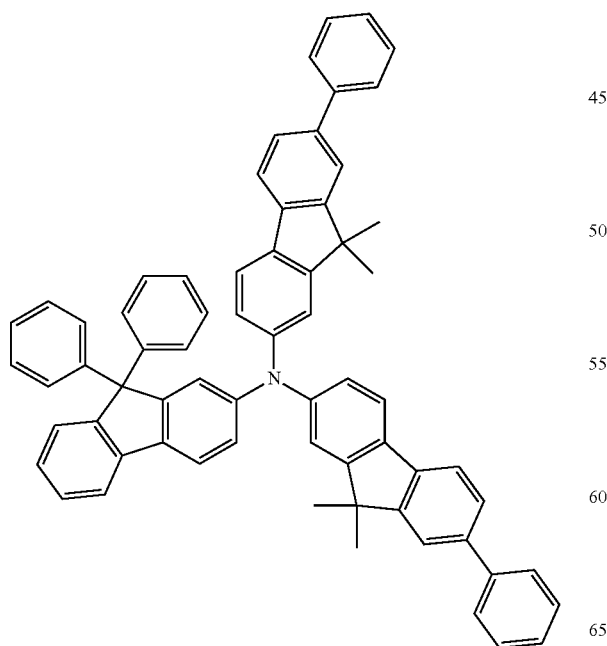
(B229)
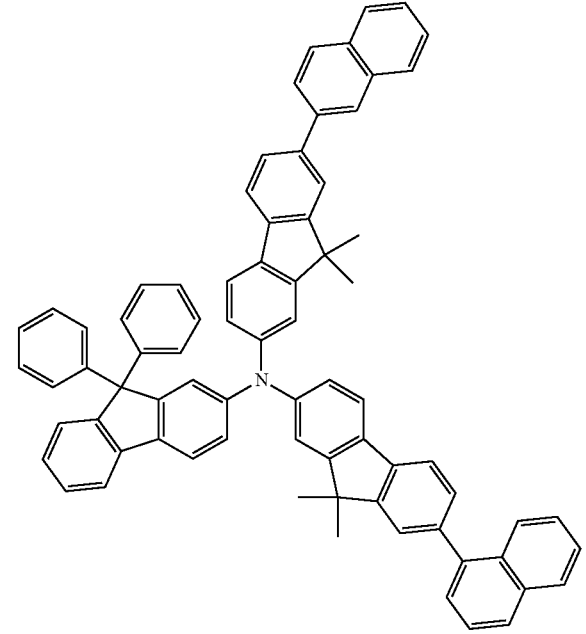
(B230)
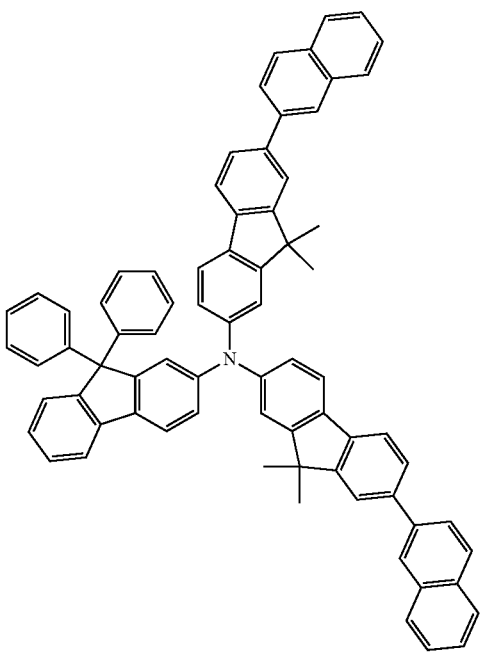

-continued
(B231)
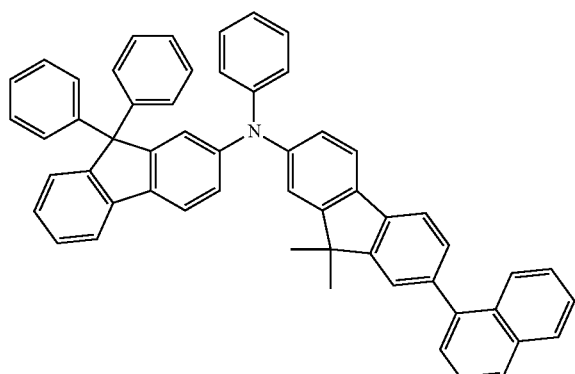
(B232)
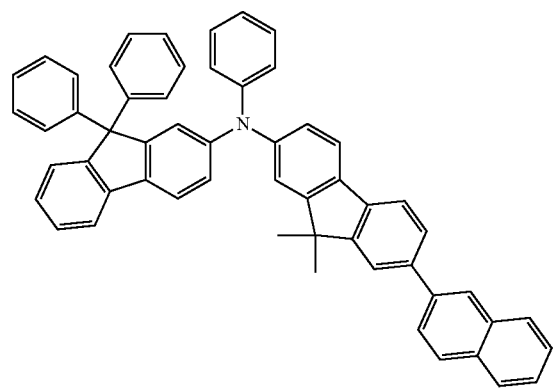
(B233)
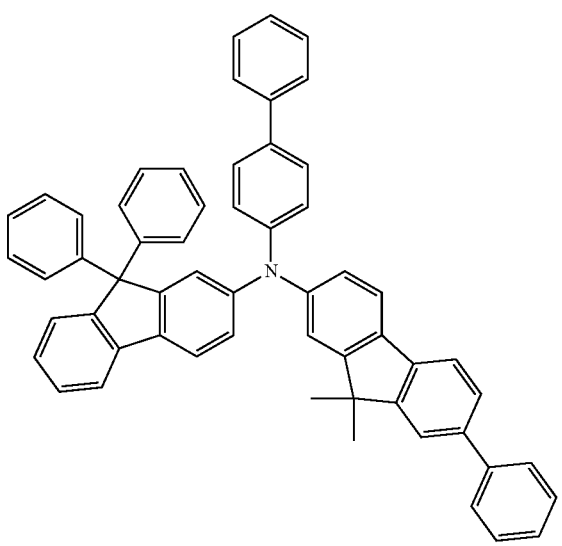
-continued
(B234)
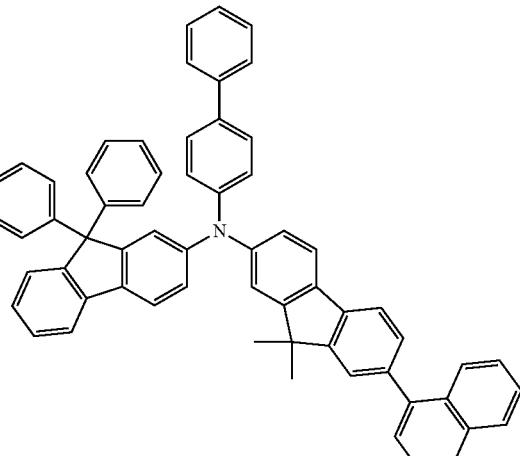
(B235)
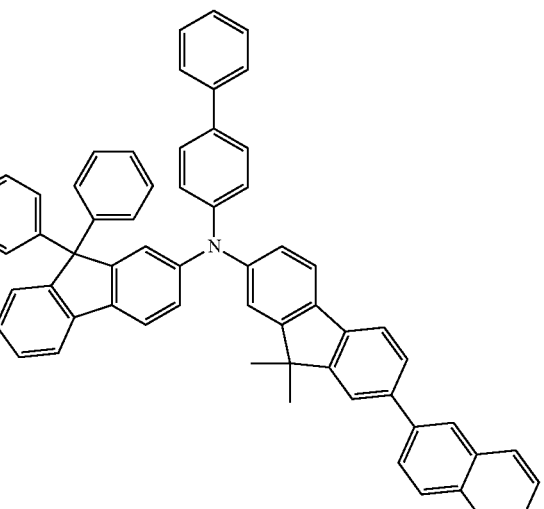
(B236)
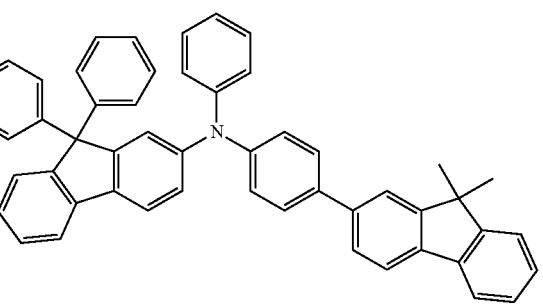

855
-continued
(B237)
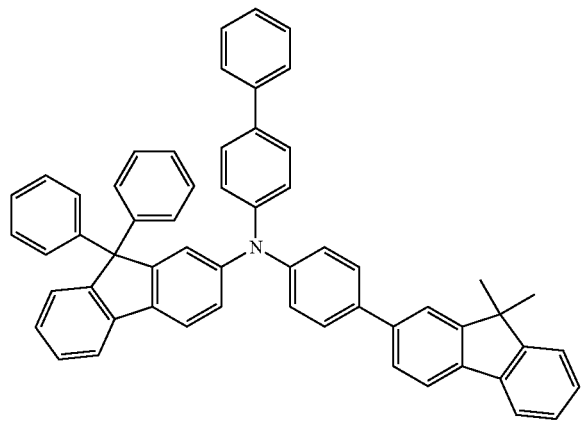
(B238)
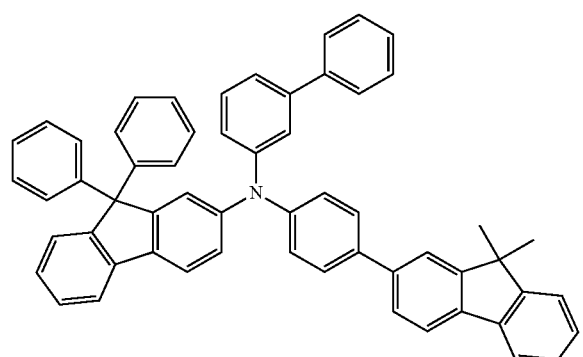
(B239)
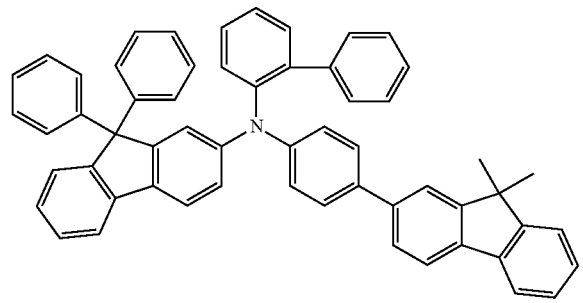
856
-continued
(B240)
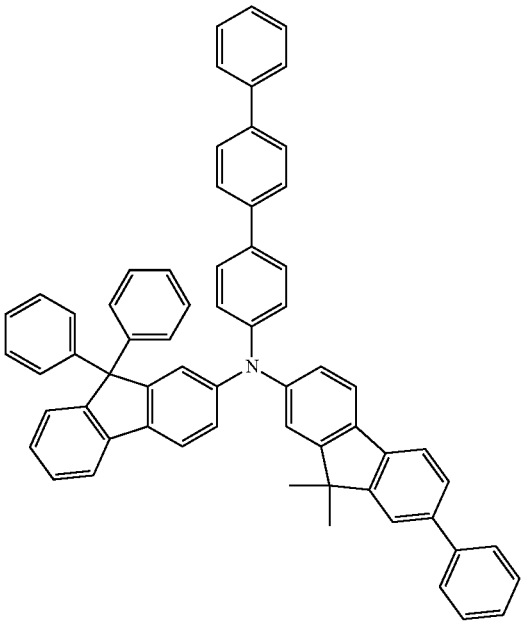
(B241)
(B242)

-continued
(B243)
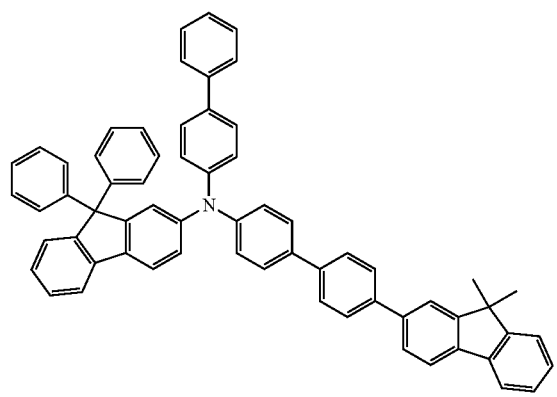
(B266)
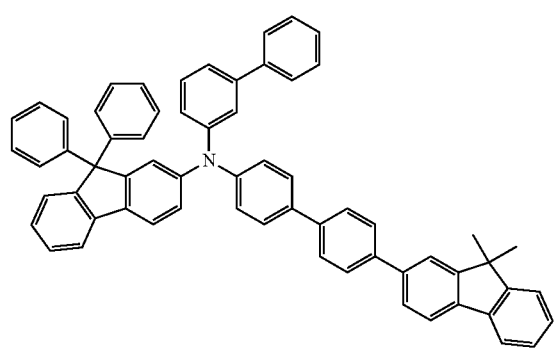
(B244)
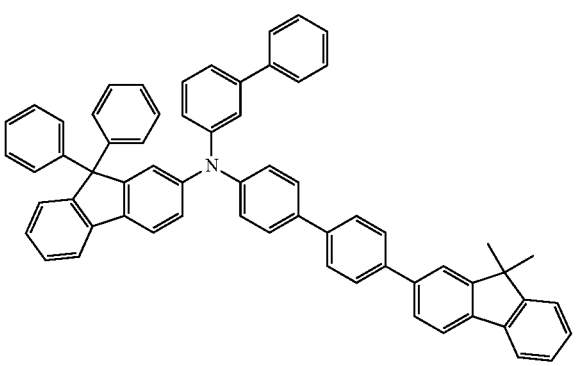
(B245)
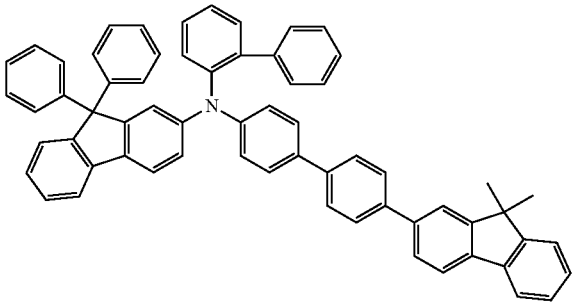
-continued
(B246)
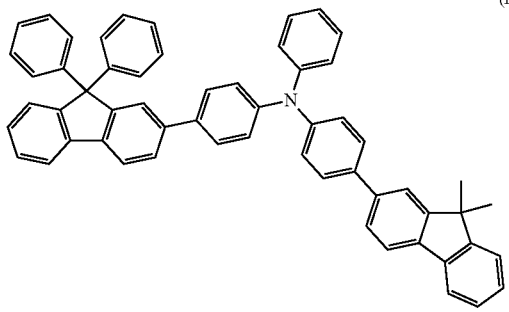
(B247)
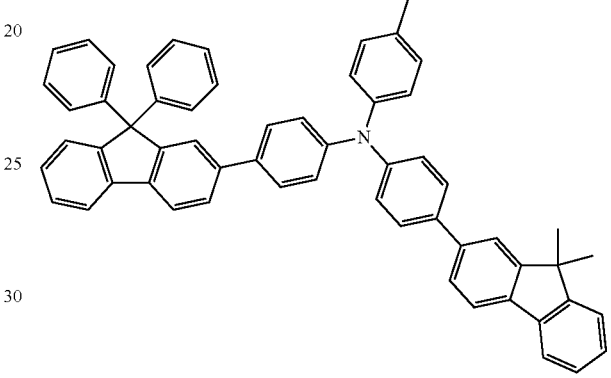
(B248)
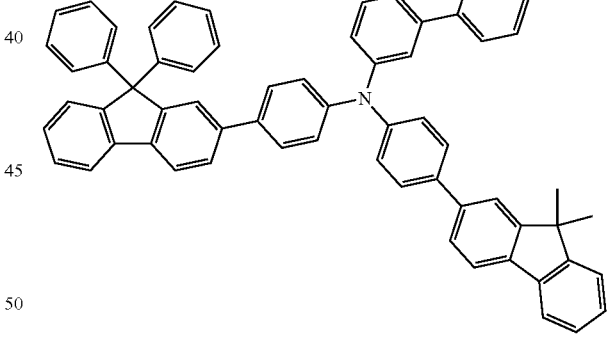
(B249)
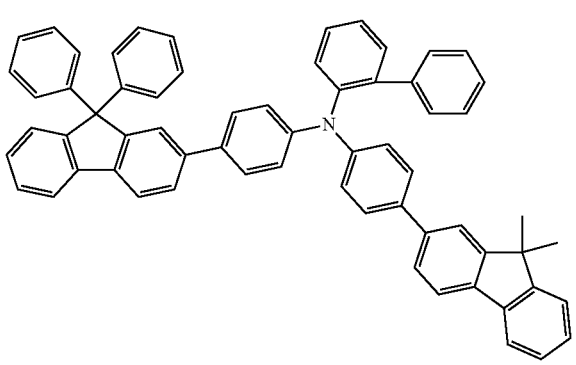

(B250)
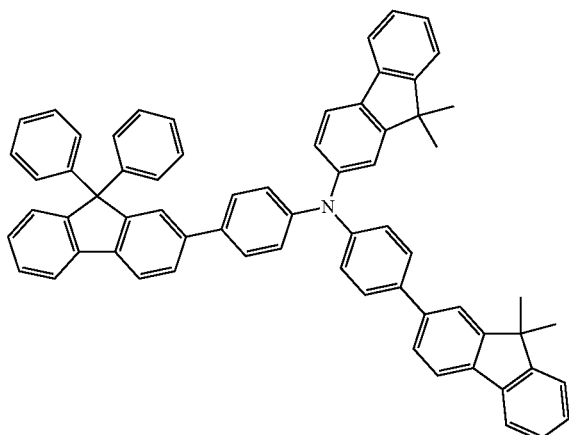
(B252)
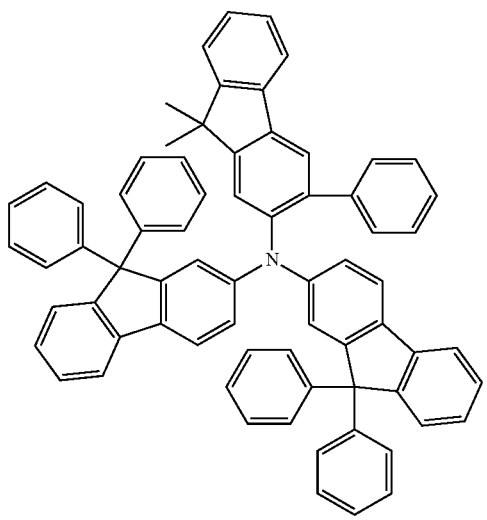
(B250)
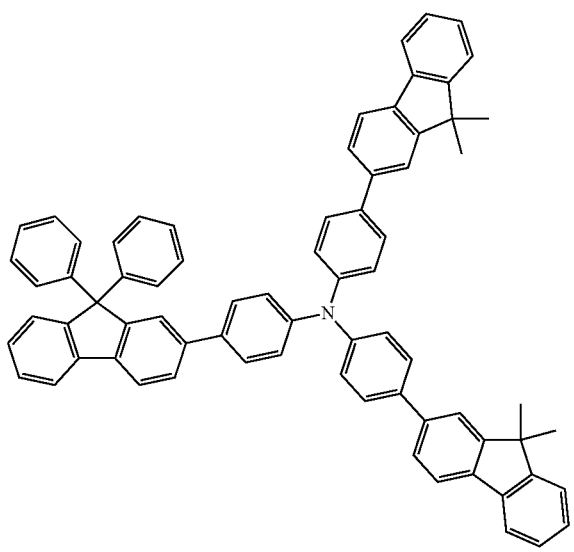
(B253)
(B251)
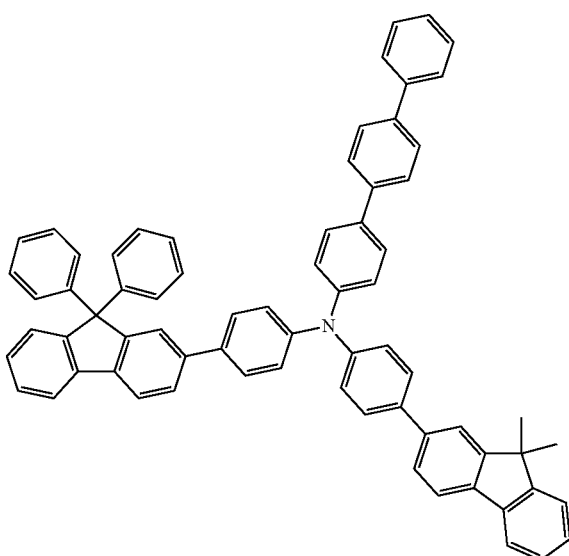
(B254)

(B255)
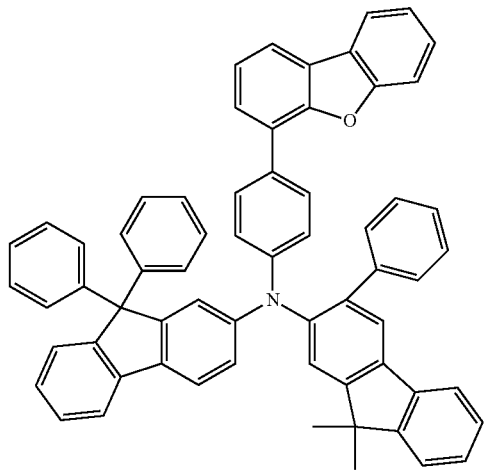
(B256)
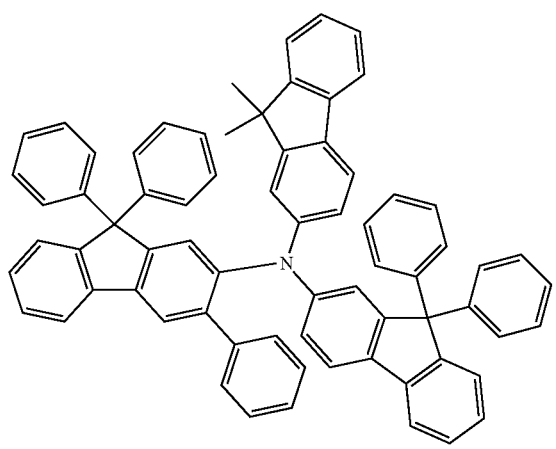
(B257)
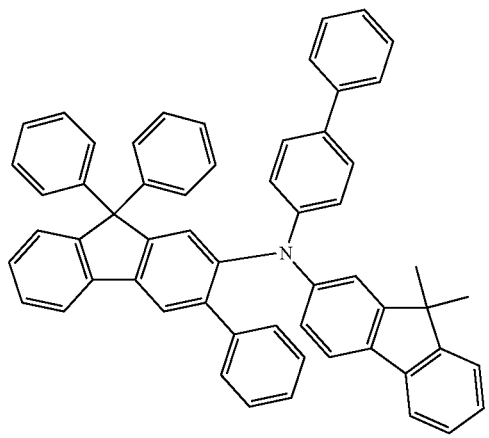
(B258)
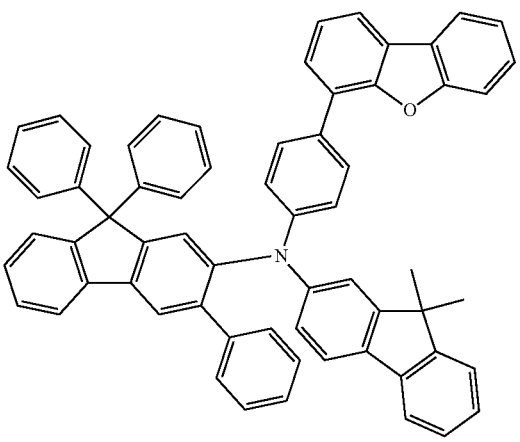
(B259)
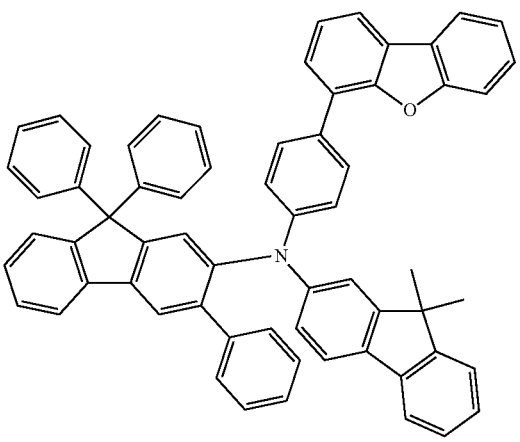
(B260)
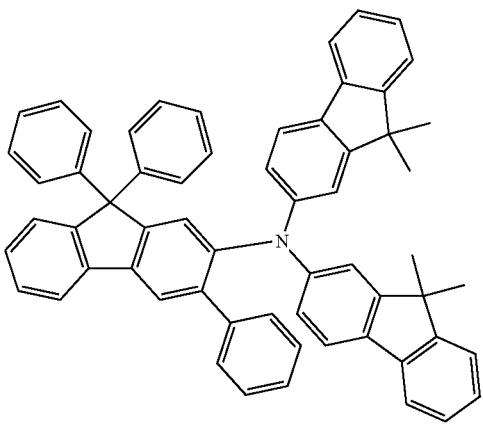

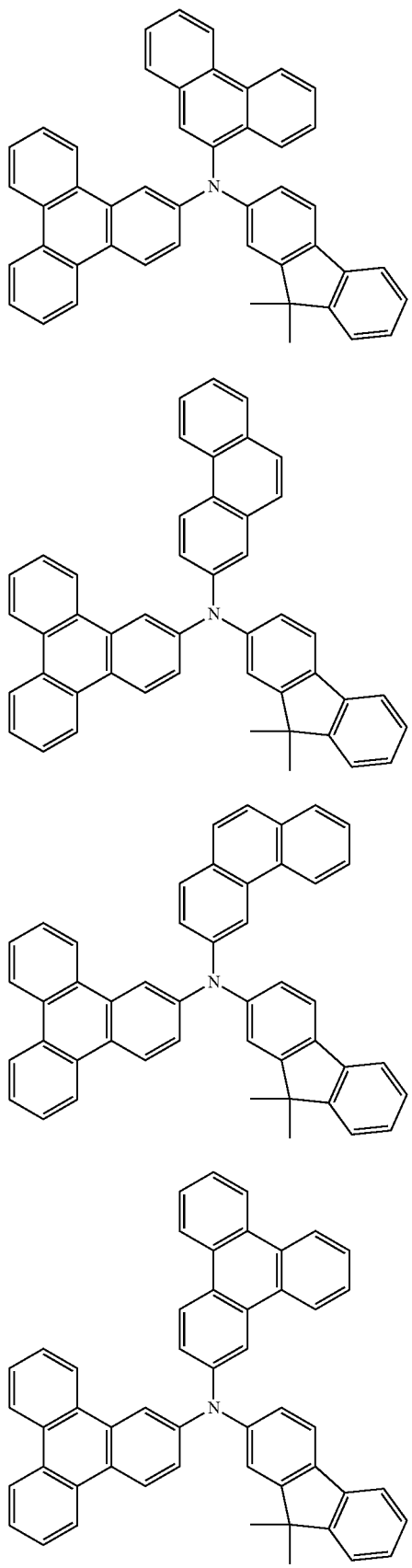

(B261)

(B262)

(B263)

(B264)

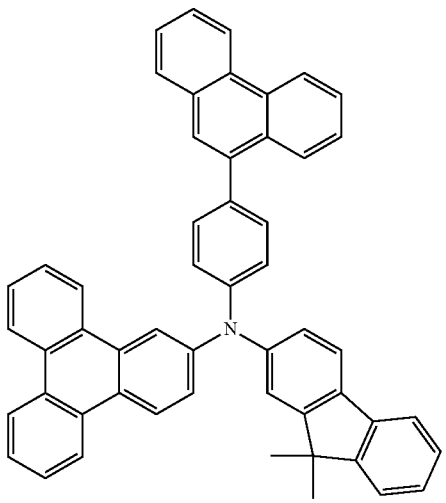

(B265)

11. An organic light emitting device comprising:
an anode;
a cathode provided to face the anode; and
one or more light emitting units provided between the anode and the cathode,
wherein the organic light emitting device includes a charge generation layer provided between the anode and the one light emitting unit, or between the two light emitting units adjacent to each other among the light emitting units,
the charge generation layer comprises a p-type charge injection layer, a p-type charge generation layer, or a layer which simultaneously injects and generates p-type charges, and
the p-type charge injection layer, the p-type charge generation layer, or the layer which simultaneously injects and generates p-type charges has electric conductivity of $1\times10^{-6}$ S/cm or more,
wherein the p-type charge injection layer, the p-type charge generation layer, or the layer which simultaneously injects and generates p-type charges comprises:
a compound of the following Chemical Formula 1-1 or 1-2; and
one or more of compounds of the following Chemical Formulae 2 to 4 at a weight ratio of 20:80 to 80:20:

[Chemical Formula 1-1]

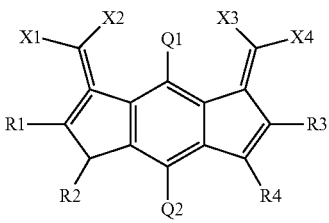

-continued

[Chemical Formula 1-2]

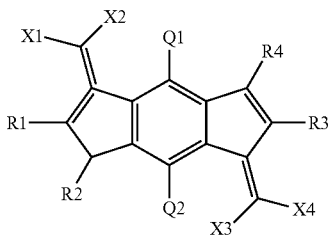

wherein in Chemical Formula 1-1 or 1-2:
X1 to X4 are the same as or different from each other, and are each independently hydrogen, a nitrile group, a nitro group, a halogen group, a carboxyl group, a carbonyl group, a substituted or unsubstituted haloalkyl group, a substituted or unsubstituted alkyl group, a substituted or unsubstituted alkoxy group, a substituted or unsubstituted aryloxy group, a substituted or unsubstituted heteroaryloxy group, a substituted or unsubstituted aryl group, or a substituted or unsubstituted heteroaryl group, or adjacent groups are optionally bonded to each other to form a substituted or unsubstituted ring;
R1 and R3 are the same as or different from each other, and are each independently hydrogen, a nitrile group, a halogen group, a substituted or unsubstituted haloalkyl group, a substituted or unsubstituted haloalkoxy group, a substituted or unsubstituted halothioalkoxy group, a substituted or unsubstituted ether group, a substituted or unsubstituted alkoxy group, a substituted or unsubstituted thioalkoxy group, a substituted or unsubstituted silyl group, a substituted or unsubstituted aryl group, or a substituted or unsubstituted heteroaryl group;
R2 and R4 are the same as or different from each other, and are each independently hydrogen, a nitrile group, a halogen group, a substituted or unsubstituted haloalkyl group, a substituted or unsubstituted haloalkoxy group, a substituted or unsubstituted halothioalkoxy group, a substituted or unsubstituted ether group, a substituted or unsubstituted alkyl group, a substituted or unsubstituted alkoxy group, a substituted or unsubstituted thioalkoxy group, a substituted or unsubstituted silyl group, a substituted or unsubstituted aryl group, or a substituted or unsubstituted heteroaryl group; and
Q1 and Q2 are the same as or different from each other, and are each independently a halogen group; a nitrile group; a substituted or unsubstituted haloalkyl group; a substituted or unsubstituted haloalkoxy group; an aryl group that is unsubstituted or substituted with one or more selected from the group consisting of a nitrile group, a haloalkyl group, and a haloalkoxy group; or a substituted or unsubstituted heteroaryl group;

[Chemical Formula 2]

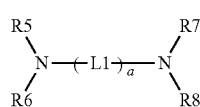

wherein in Chemical Formula 2:
L1 is a substituted or unsubstituted arylene group or a substituted or unsubstituted heteroarylene group;

R5 to R8 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group, or adjacent groups are optionally bonded to each other to form a substituted or unsubstituted ring;
a is an integer from 1 to 10; and
when a is 2 or more, two or more L1 s are the same as or different from each other;

[Chemical Formula 3]

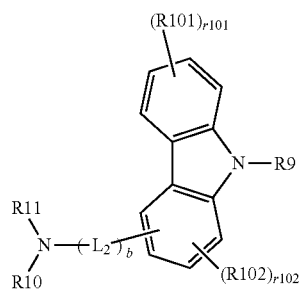

wherein in Chemical Formula 3:
L2 is a substituted or unsubstituted arylene group;
R9 to R11 are the same as or different from each other, and are each independently a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;
R101 and R102 are the same as or different from each other, and are each independently hydrogen, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted arylphosphine group, a substituted or unsubstituted phosphine oxide group, a substituted or unsubstituted aryl group, or a substituted or unsubstituted heteroaryl group;
b is an integer from 1 to 10;
when b is 2 or more, two or more L2s are the same as or different from each other;
r101 is an integer from 1 to 4;
r102 is an integer from 1 to 3; and
when r101 and r102 are each 2 or more, two or more structures in the parenthesis are the same as or different from each other;

[Chemical Formula 4]

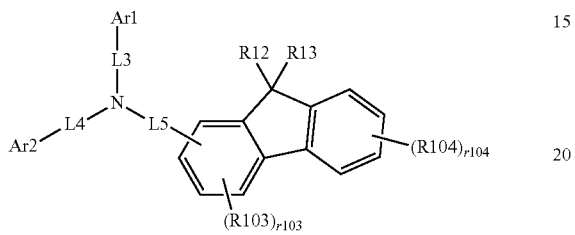

wherein in Chemical Formula 4:
L3 to L5 are the same as or different from each other, and are each independently a direct bond, a substituted or unsubstituted arylene group, or a substituted or unsubstituted heteroarylene group;
Ar1 is a substituted or unsubstituted aryl group or a substituted or unsubstituted heteroaryl group;
Ar2 is a substituted or unsubstituted aryl group;
R12, R13, R103, and R104 are the same as or different from each other, and are each independently hydrogen, deuterium, a nitrile group, a nitro group, a hydroxy group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group, or adjacent groups are bonded to each other to form a substituted or unsubstituted ring;
r103 is an integer from 1 to 3;
r104 is an integer from 1 to 4; and
when r103 and r104 are each 2 or more, two or more structures in the parenthesis are the same as or different from each other.

12. The organic light emitting device of claim 11, wherein the compound of Chemical Formula 2 is selected from among the following compounds:

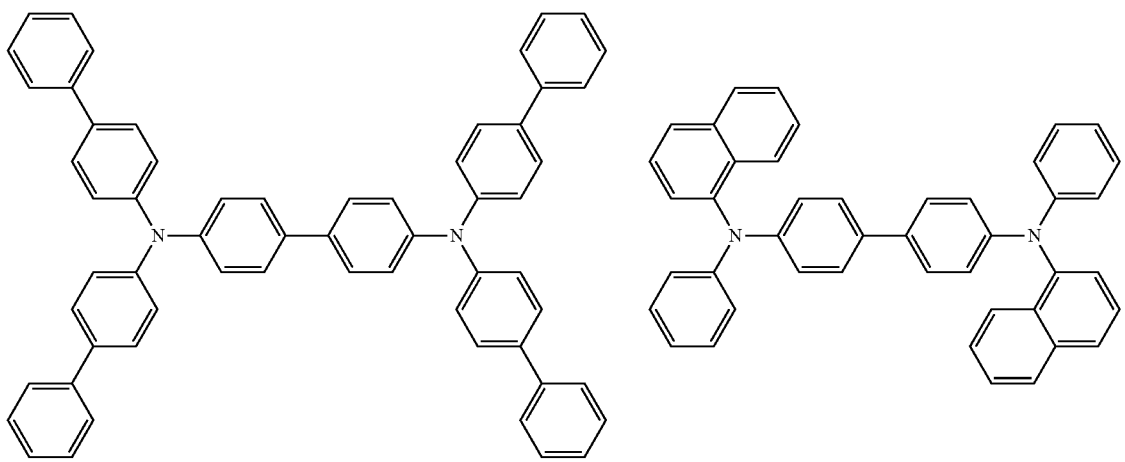

869
870
-continued
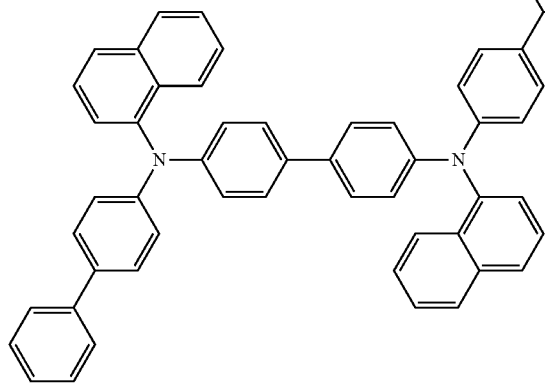 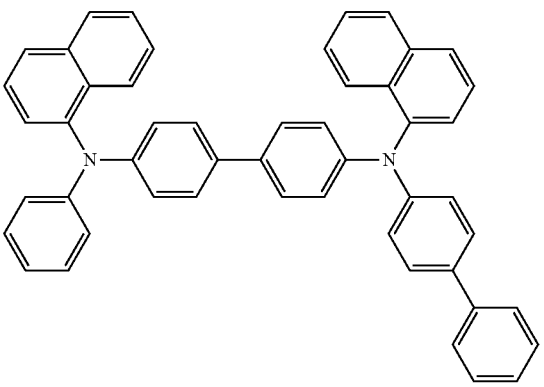
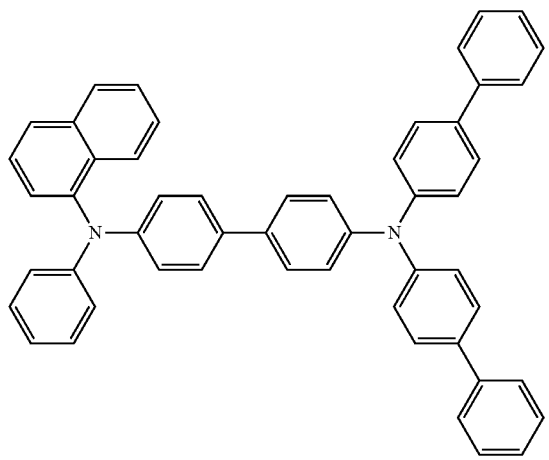
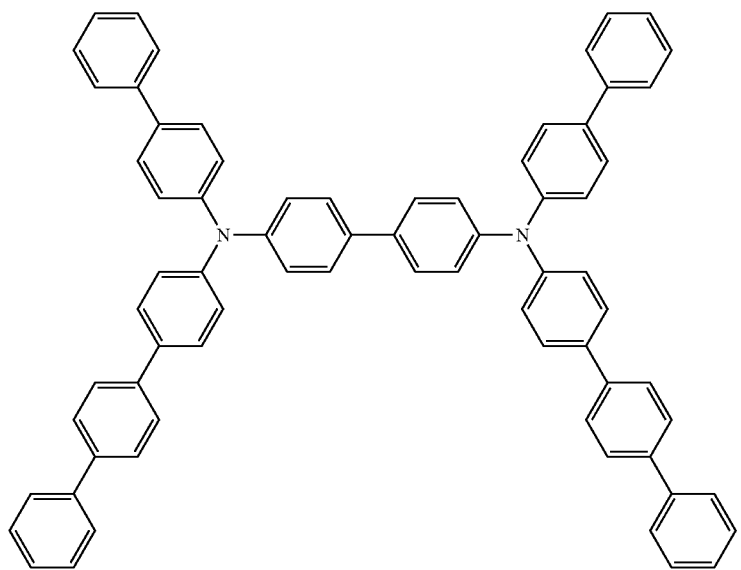

871
-continued
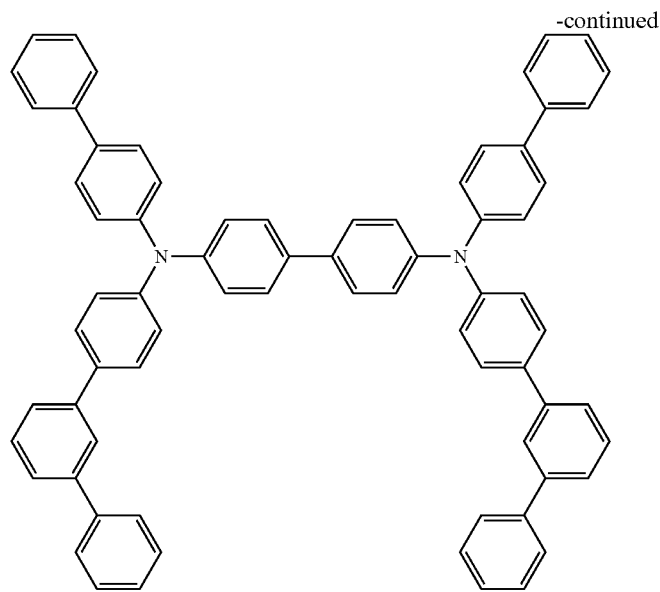
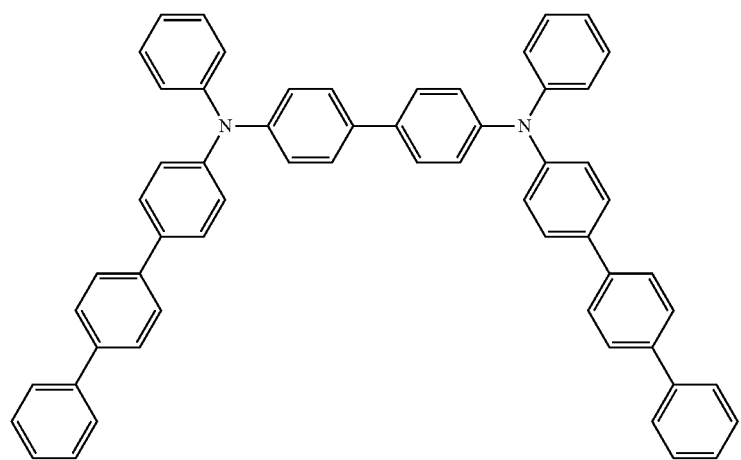
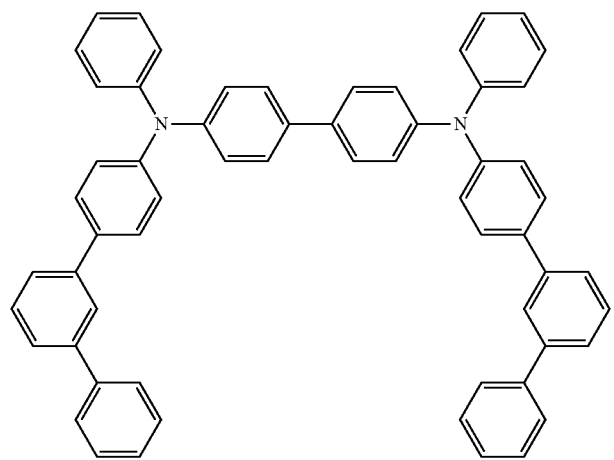
872

-continued
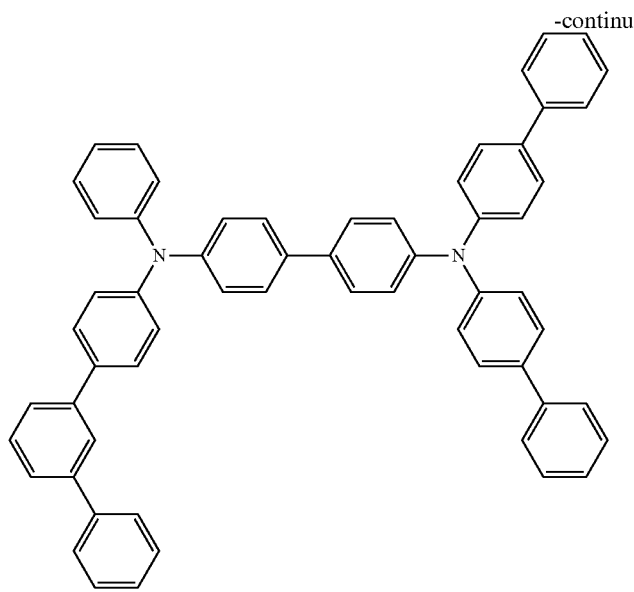
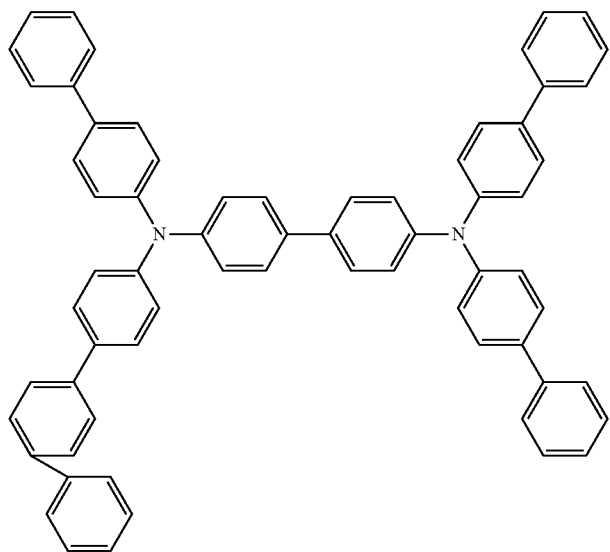
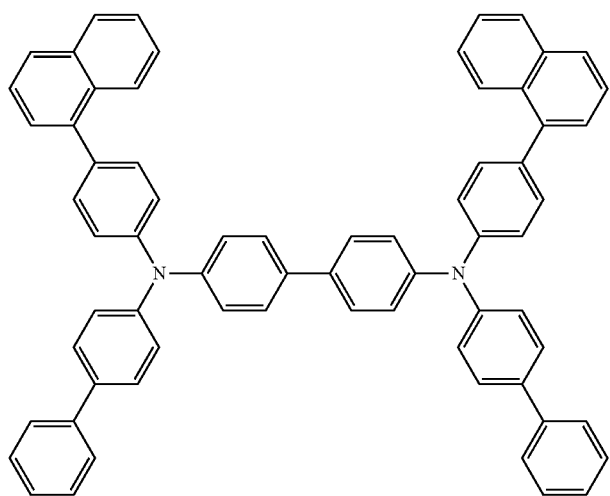

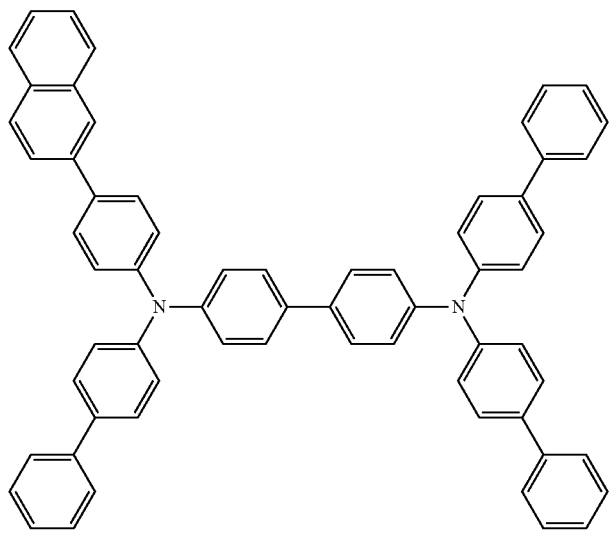
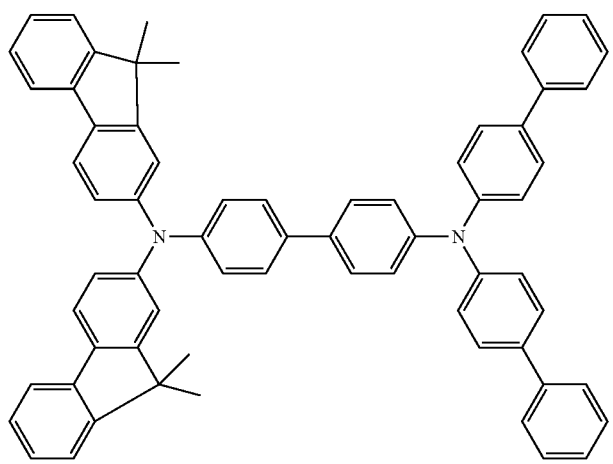
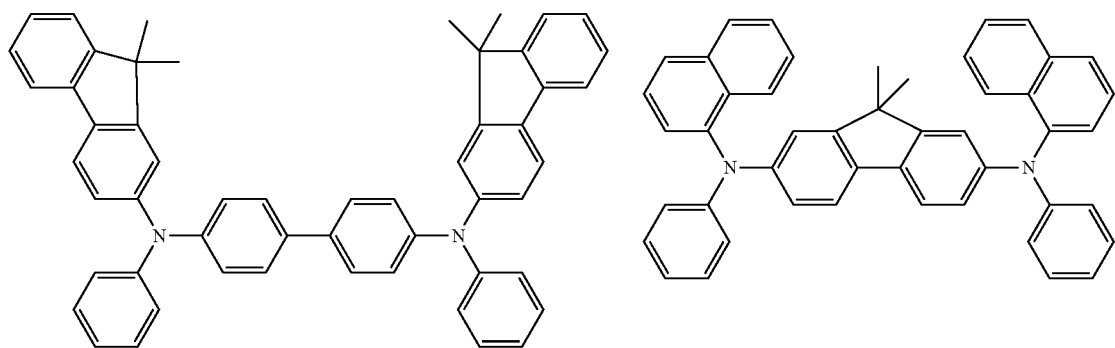

-continued
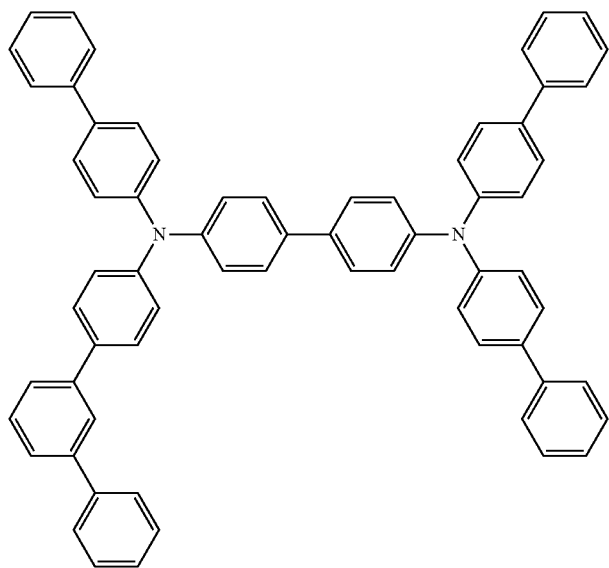
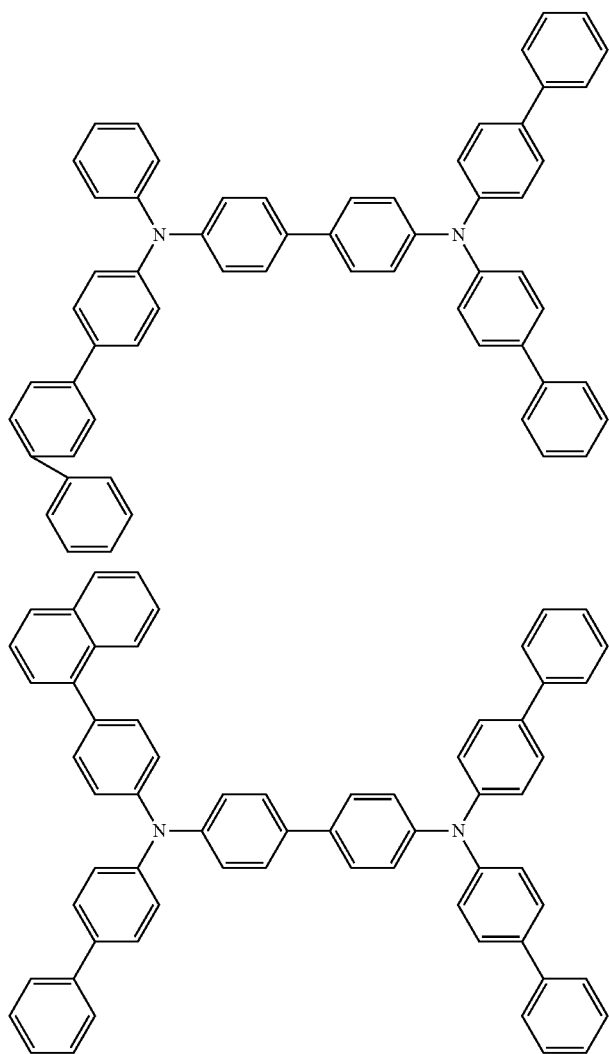

-continued
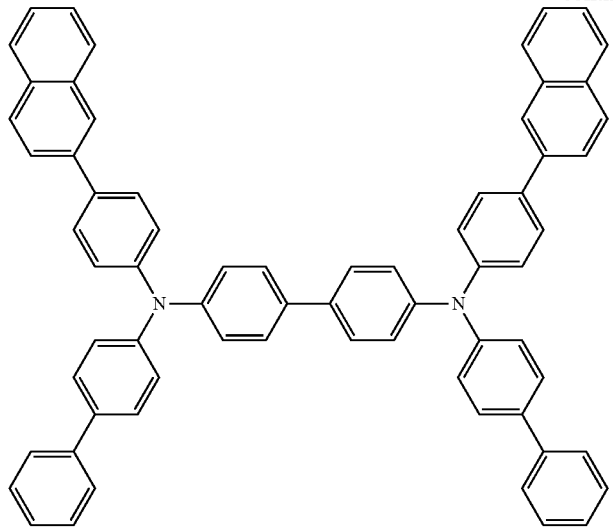
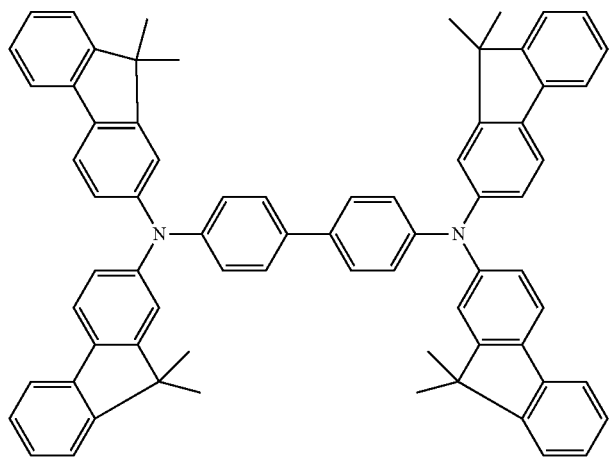
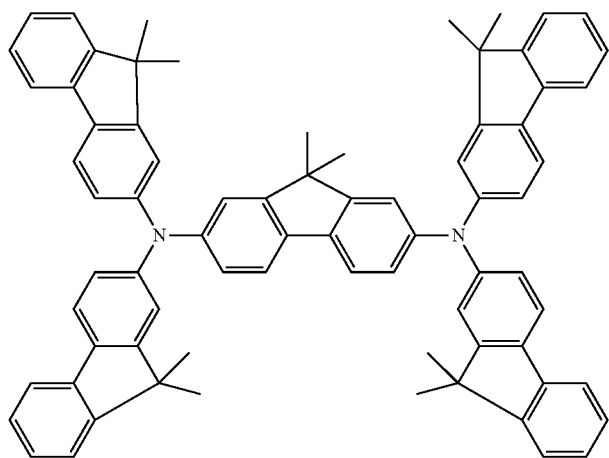

881
-continued
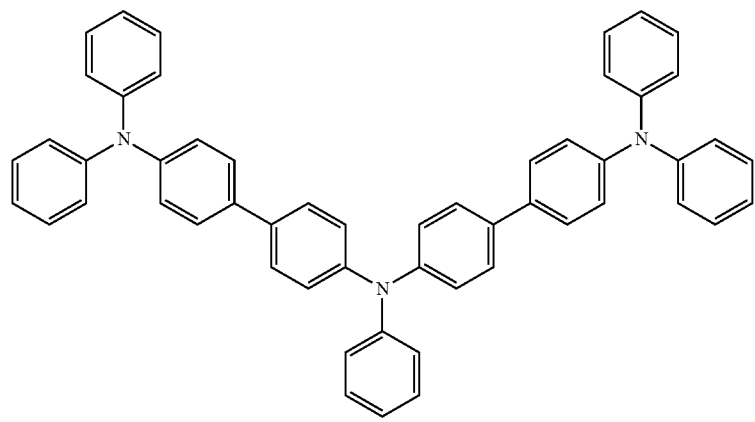
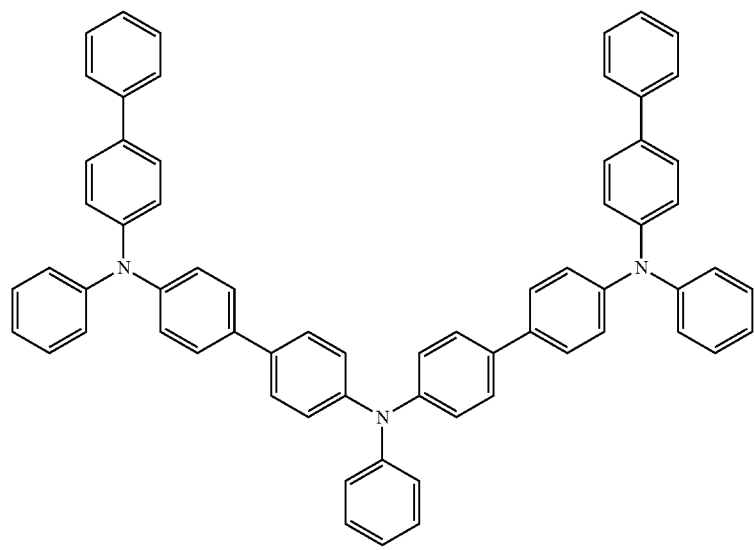
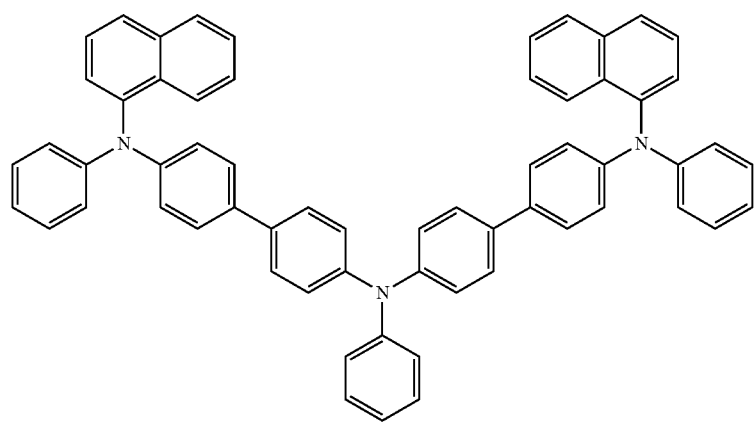
882

-continued
883
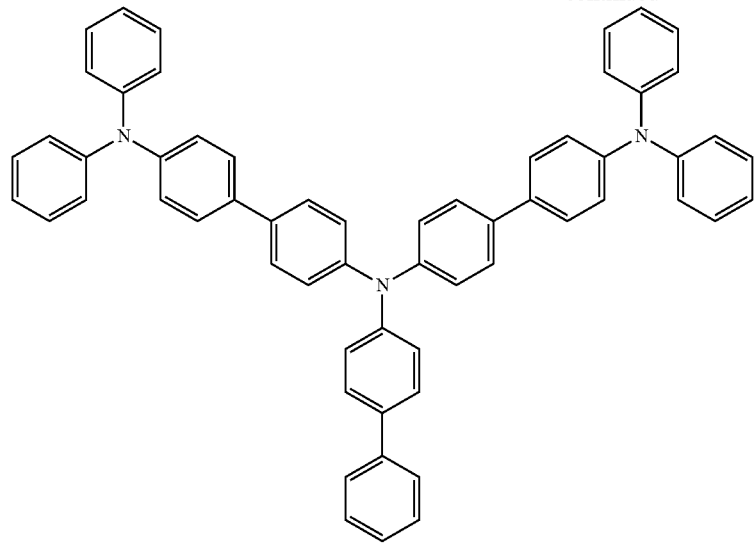
884
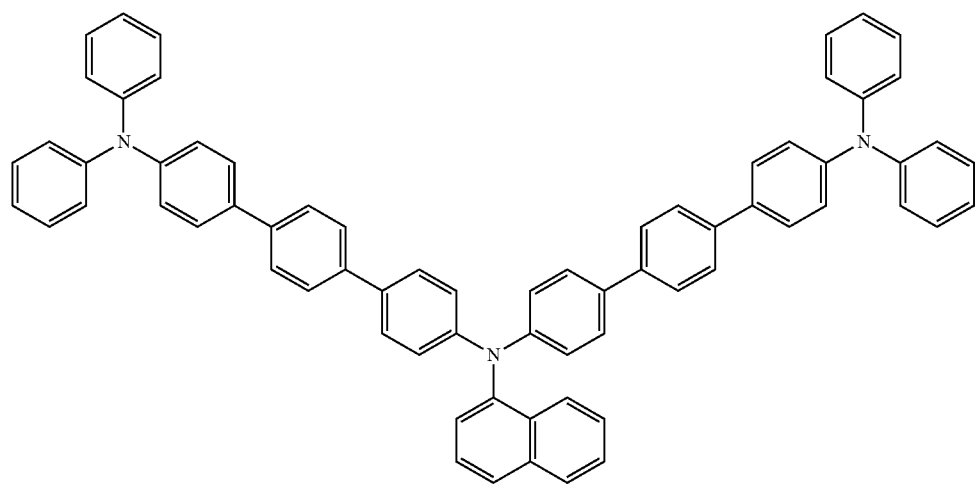
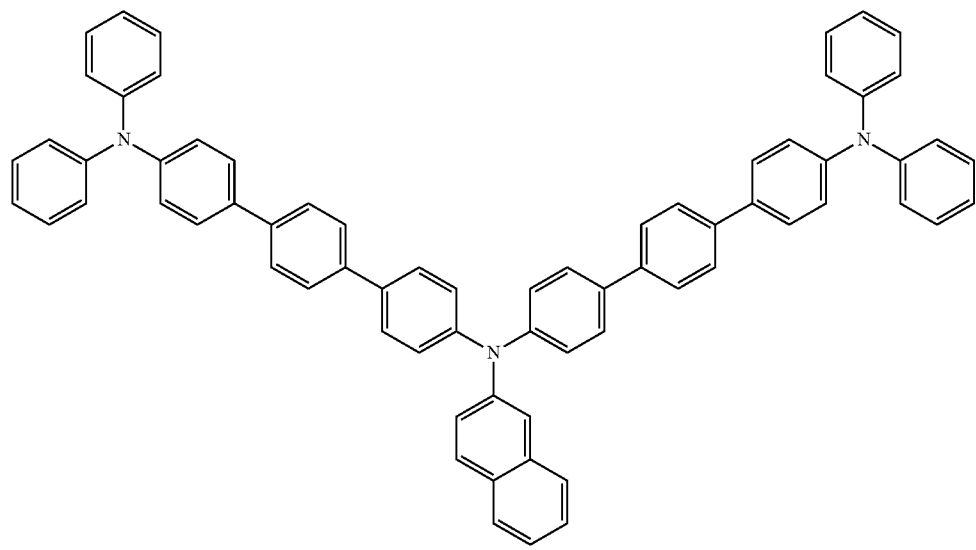

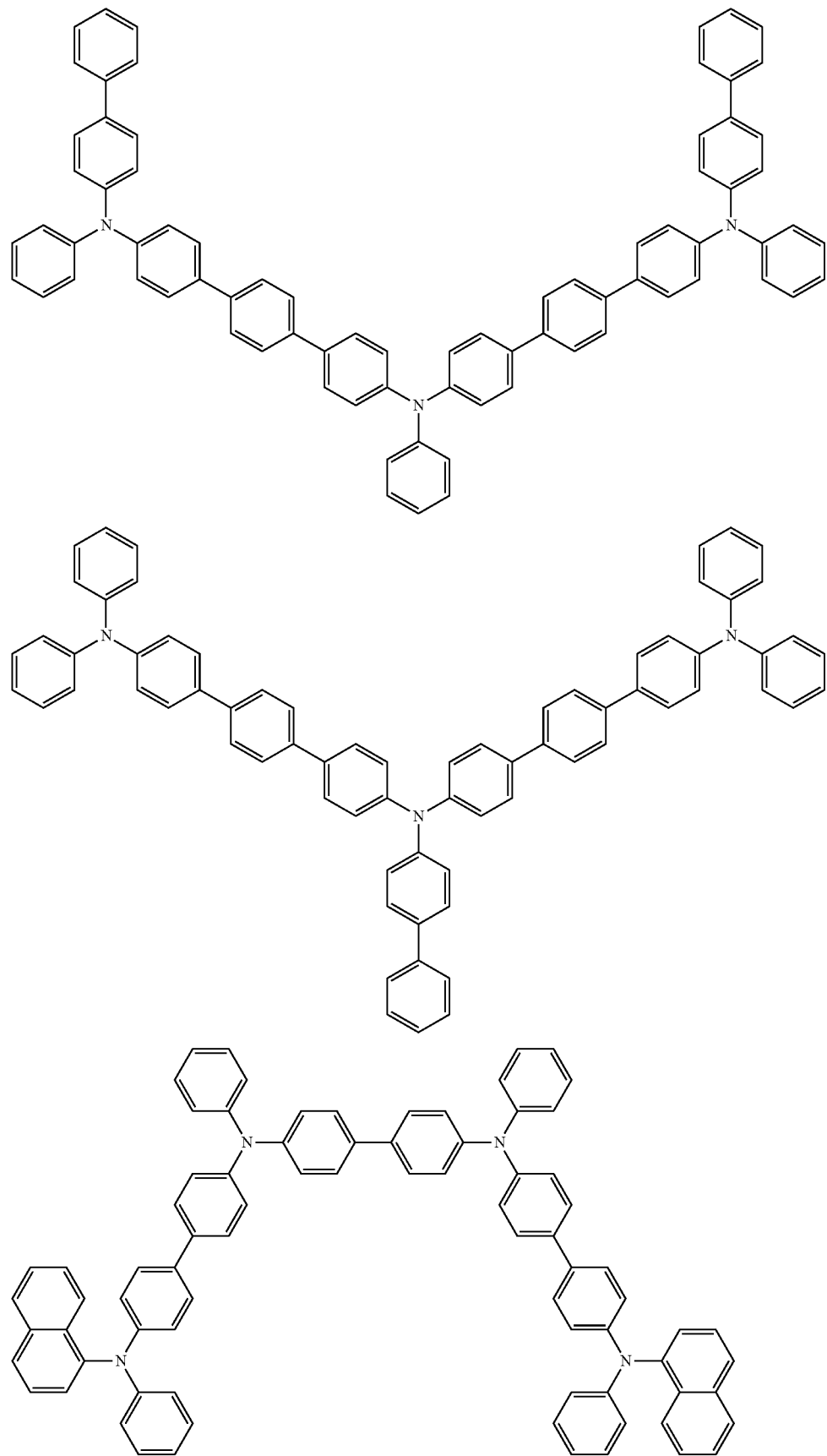

-continued
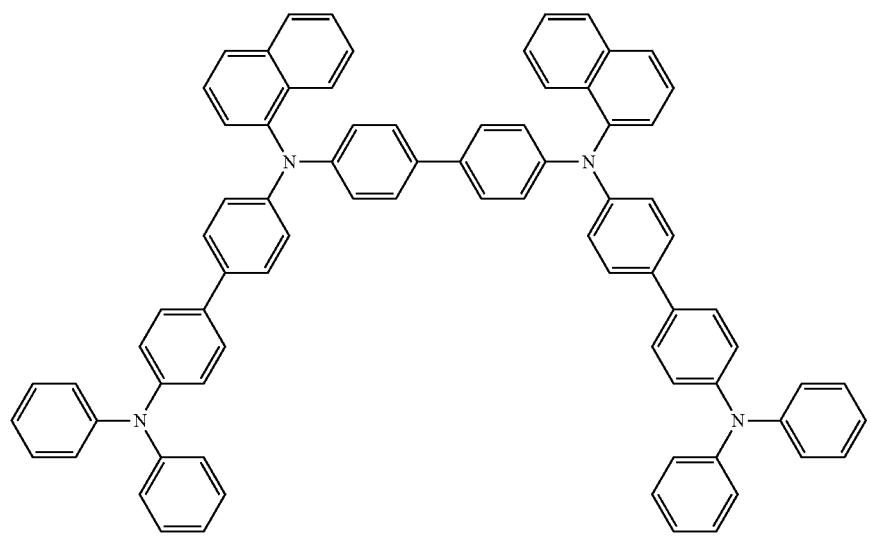
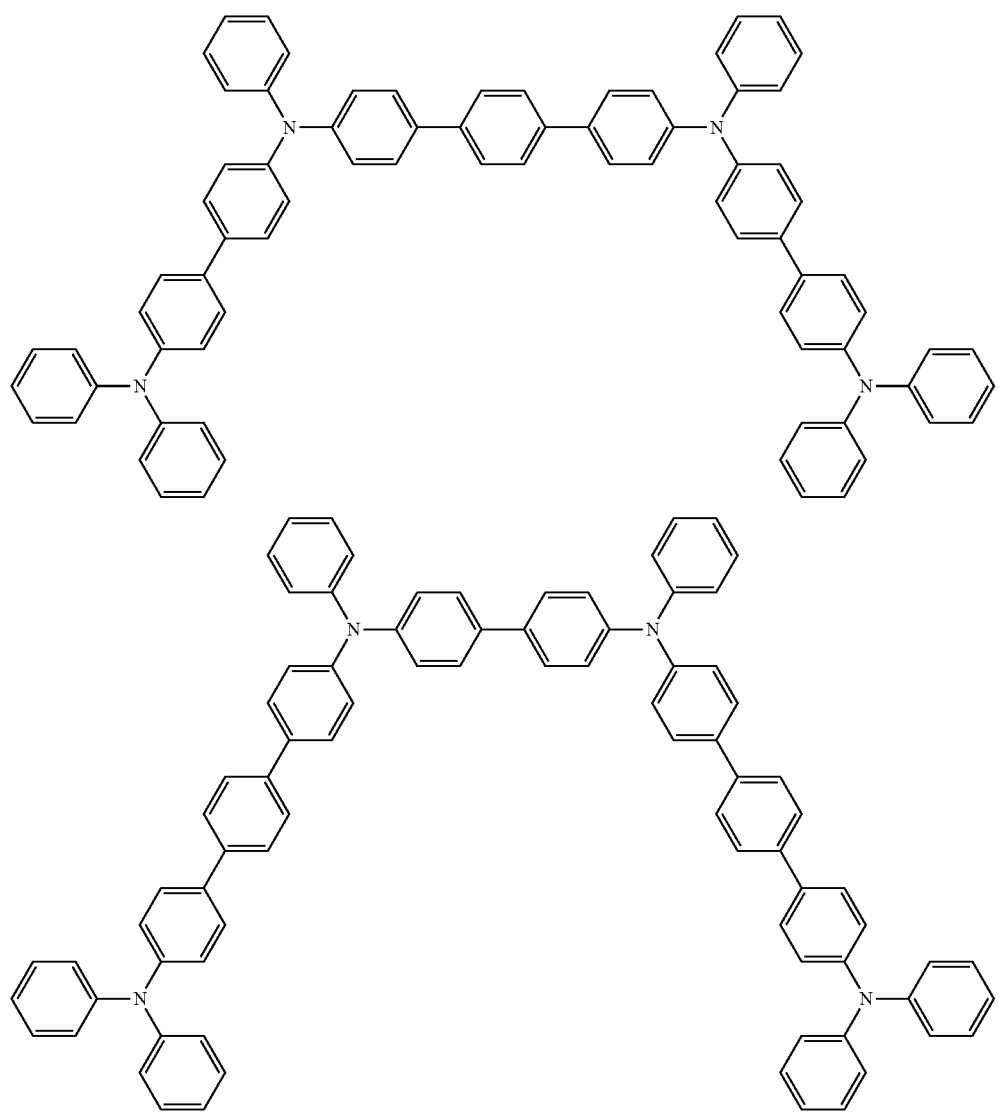

889 890
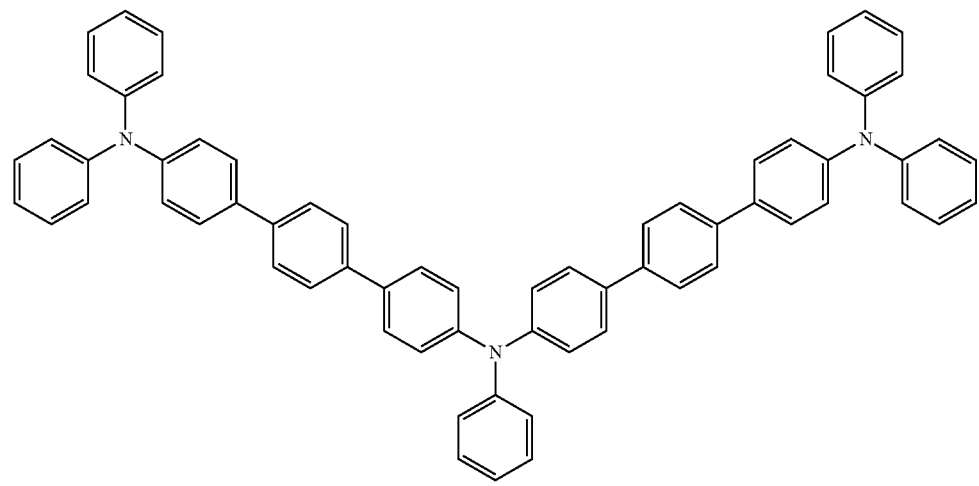
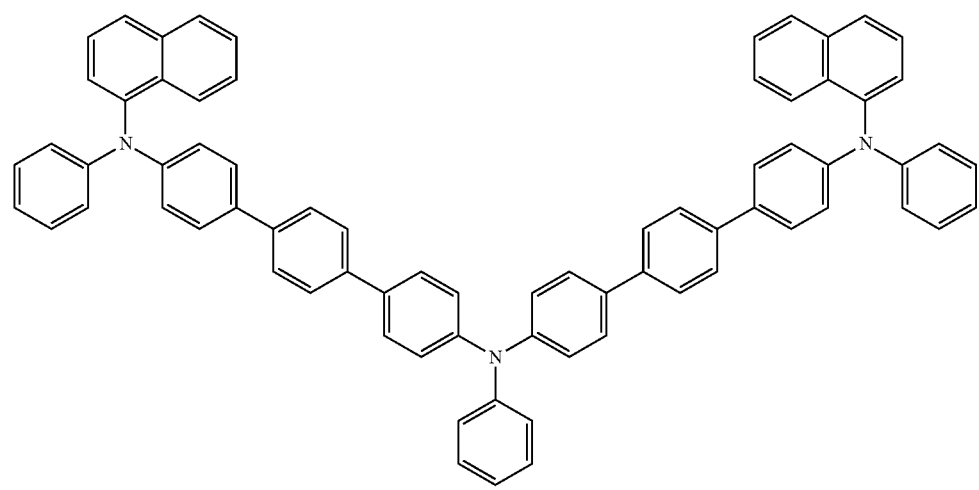
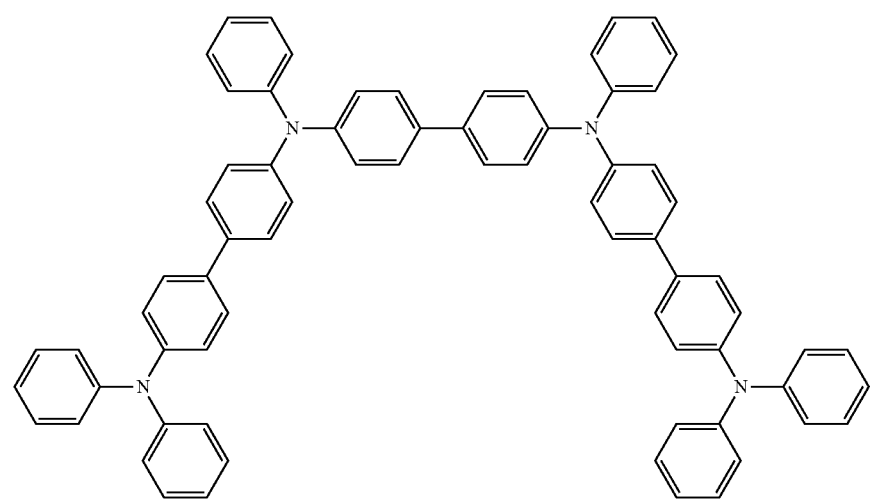

-continued
891
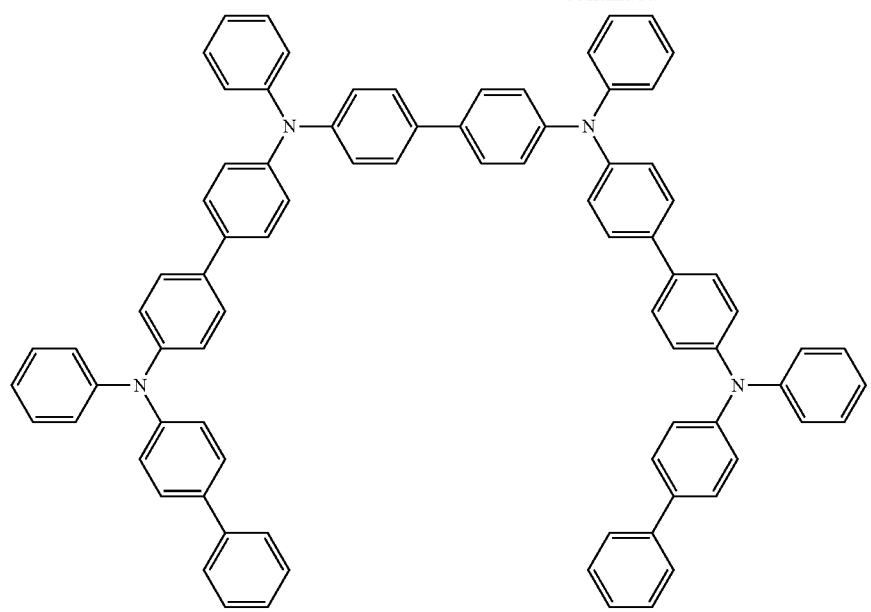
892
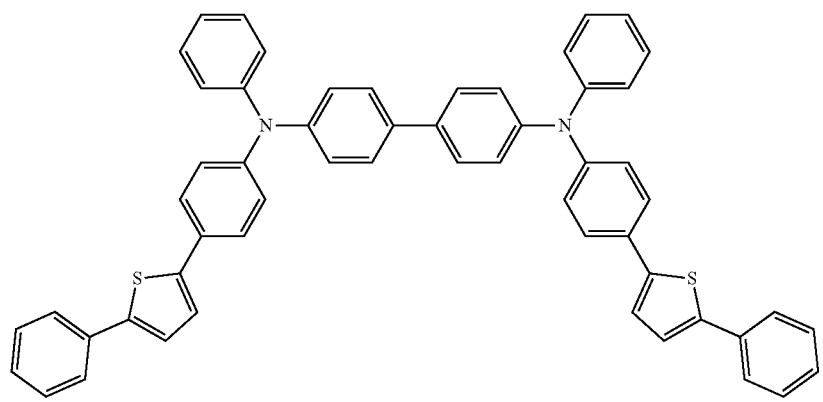
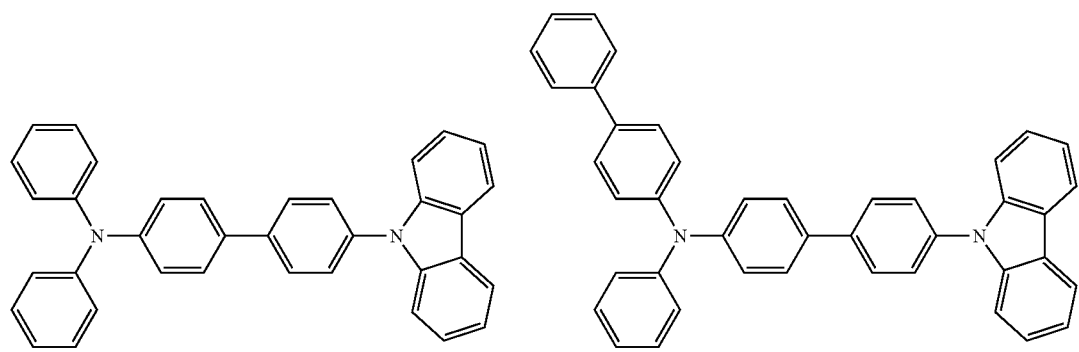

-continued
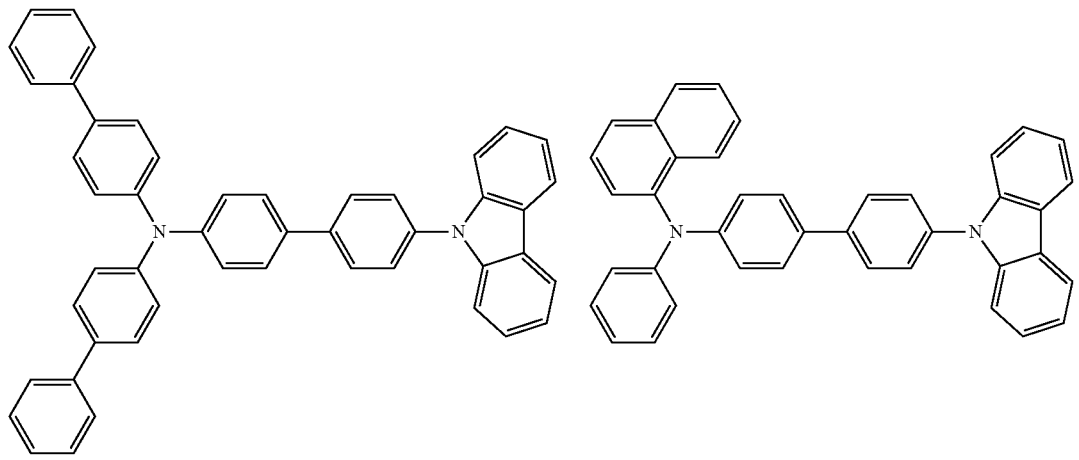
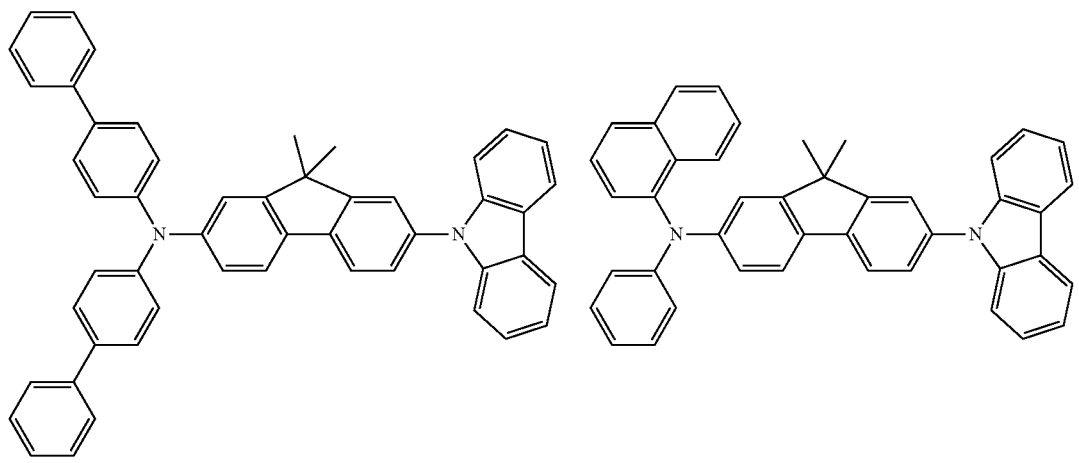
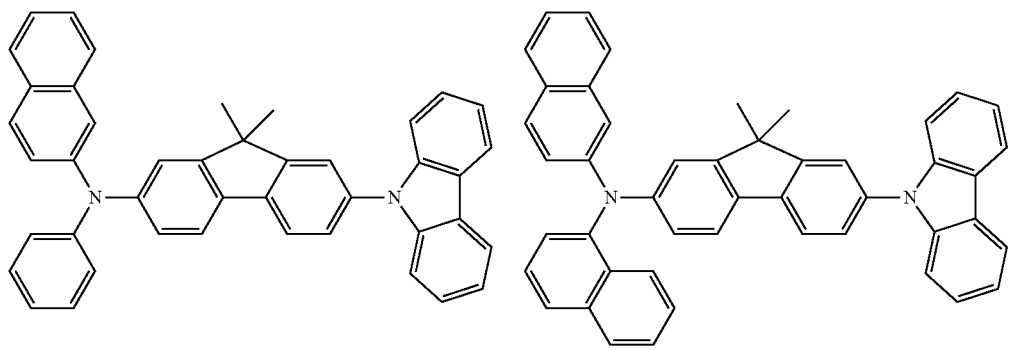
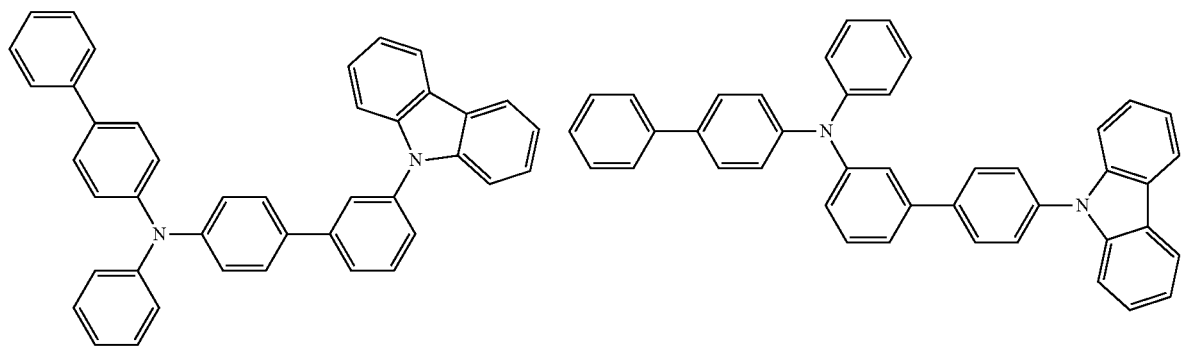

895 896
-continued
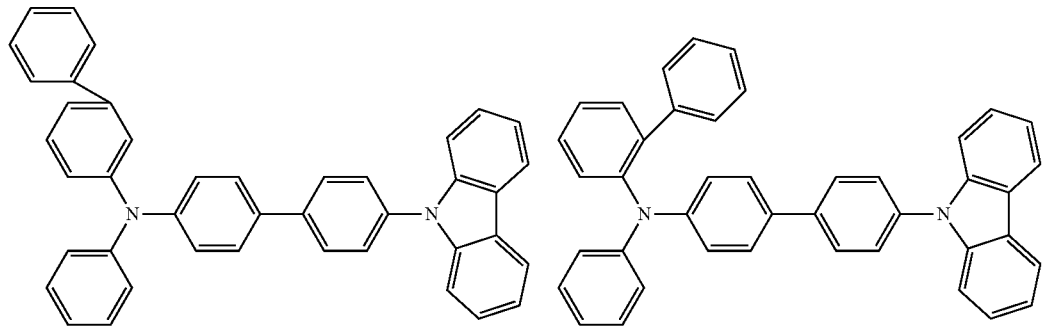
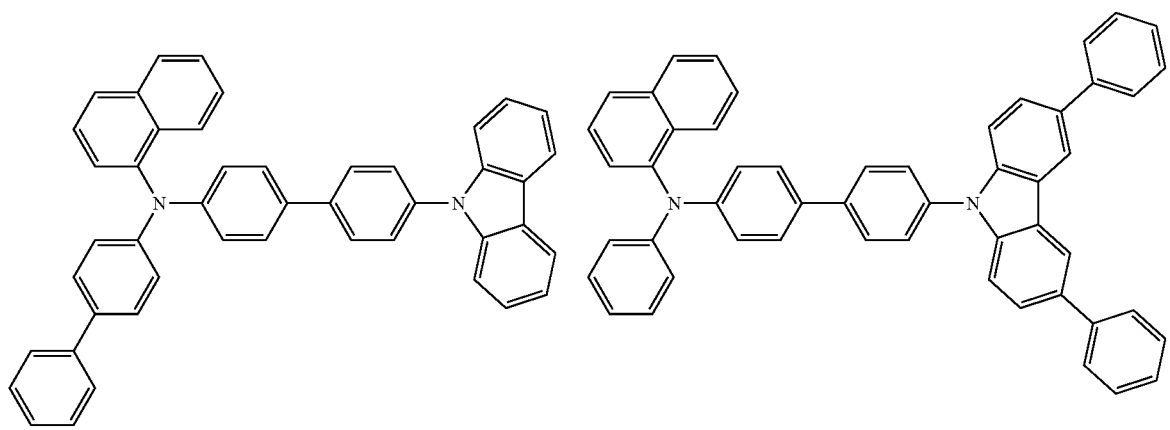
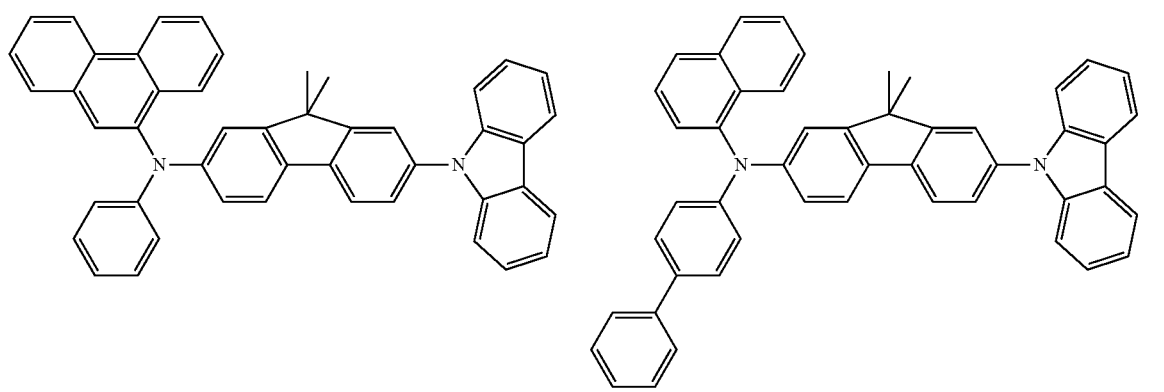
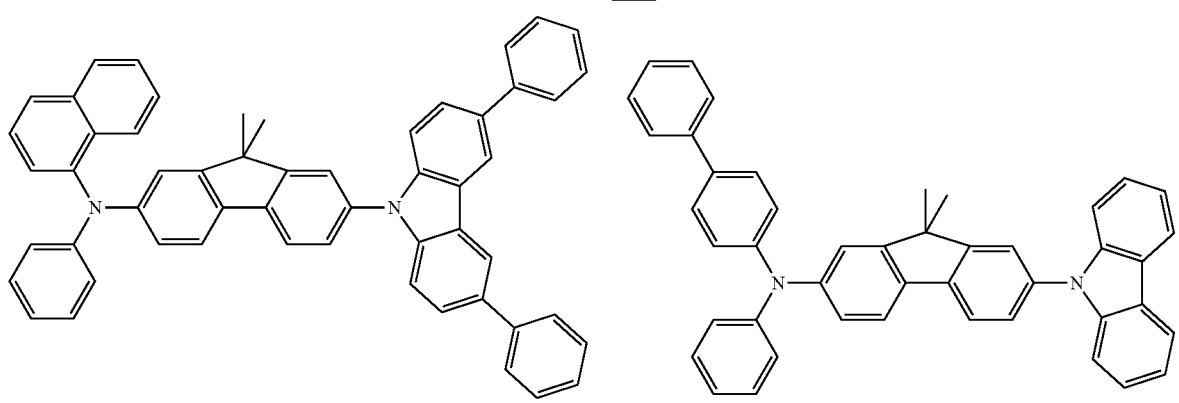

-continued
897 898
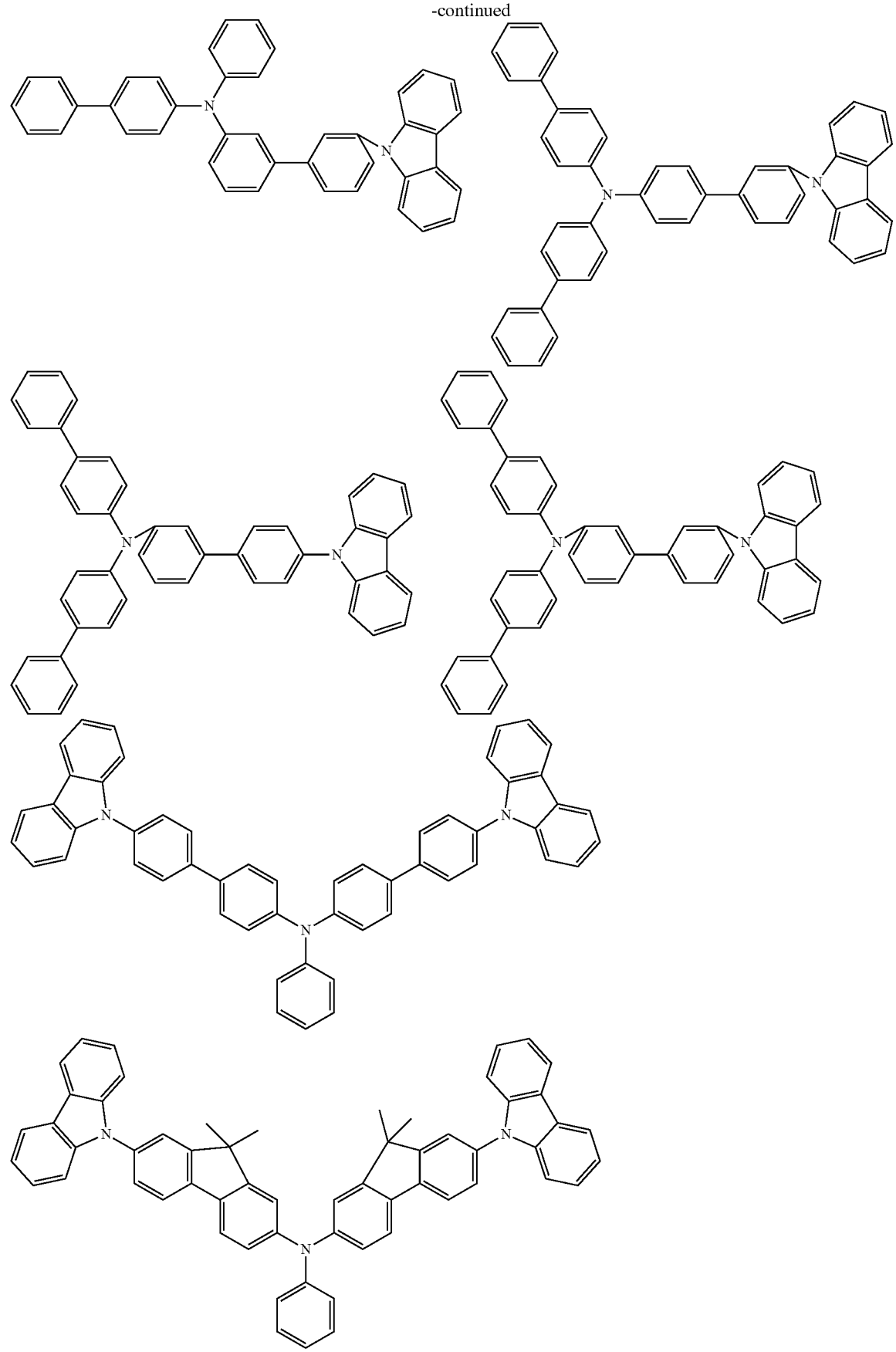

899
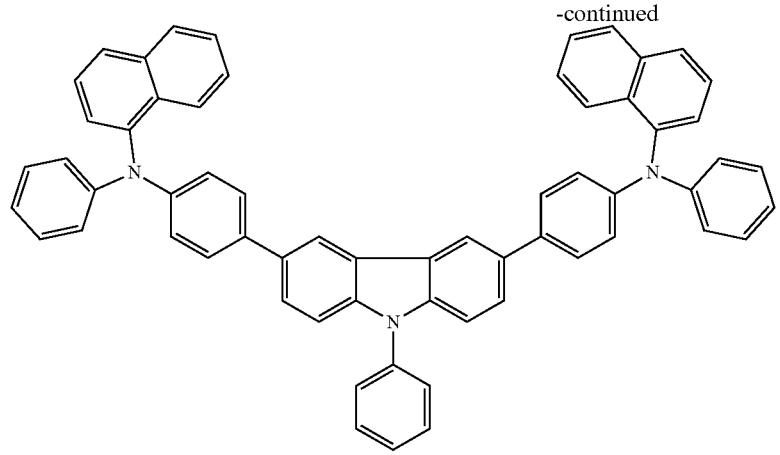
900
-continued
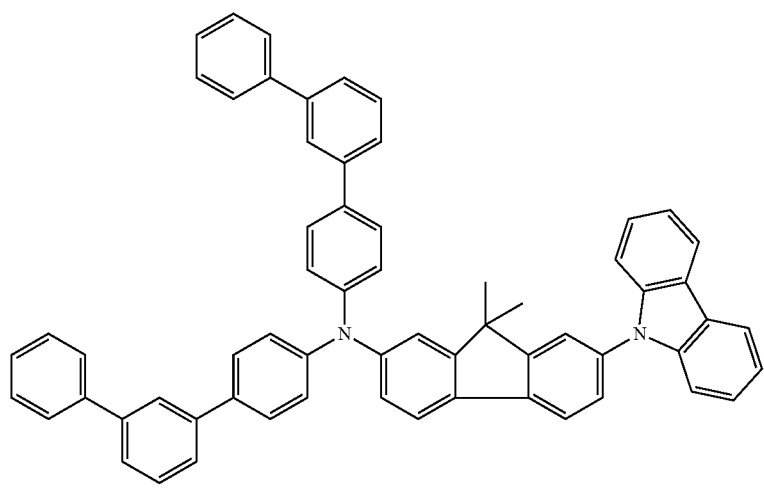
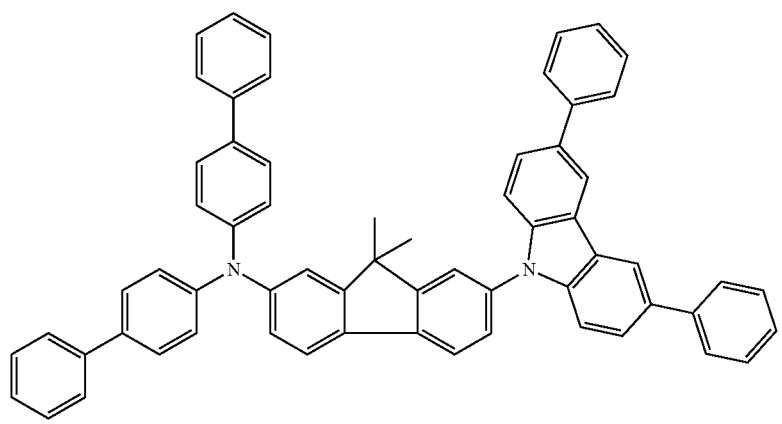
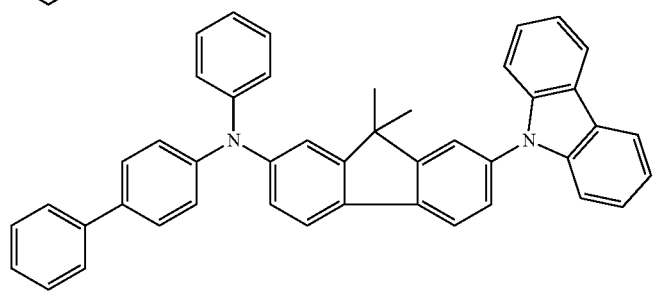

-continued
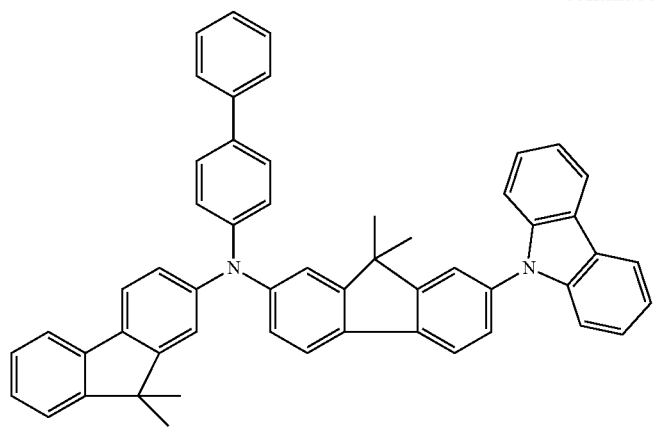
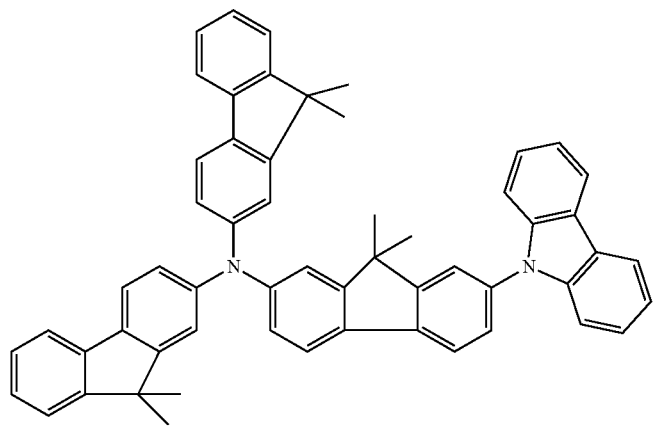
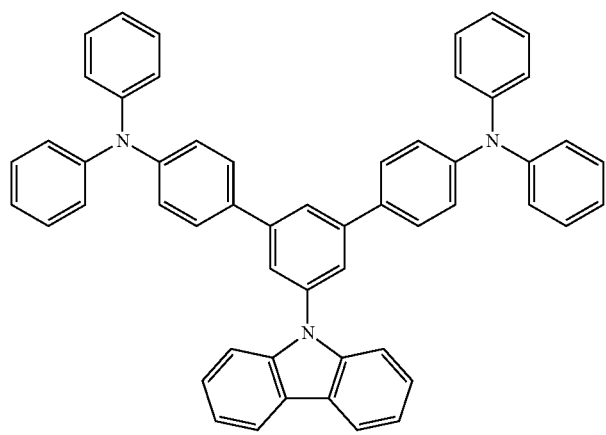
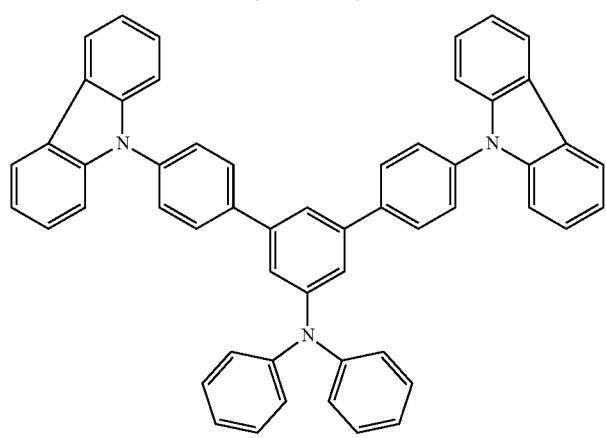

903
-continued
904
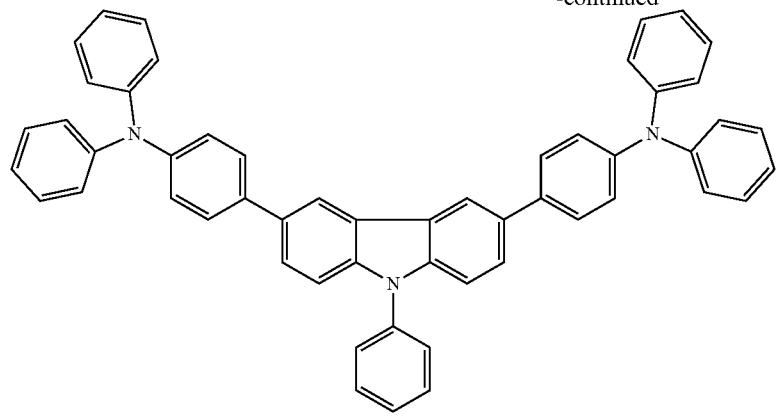
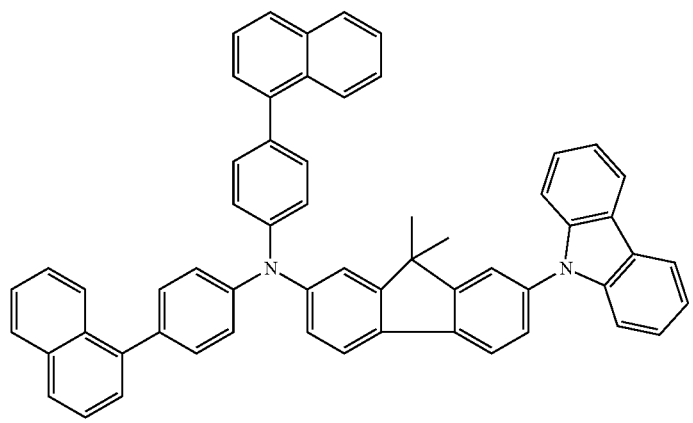
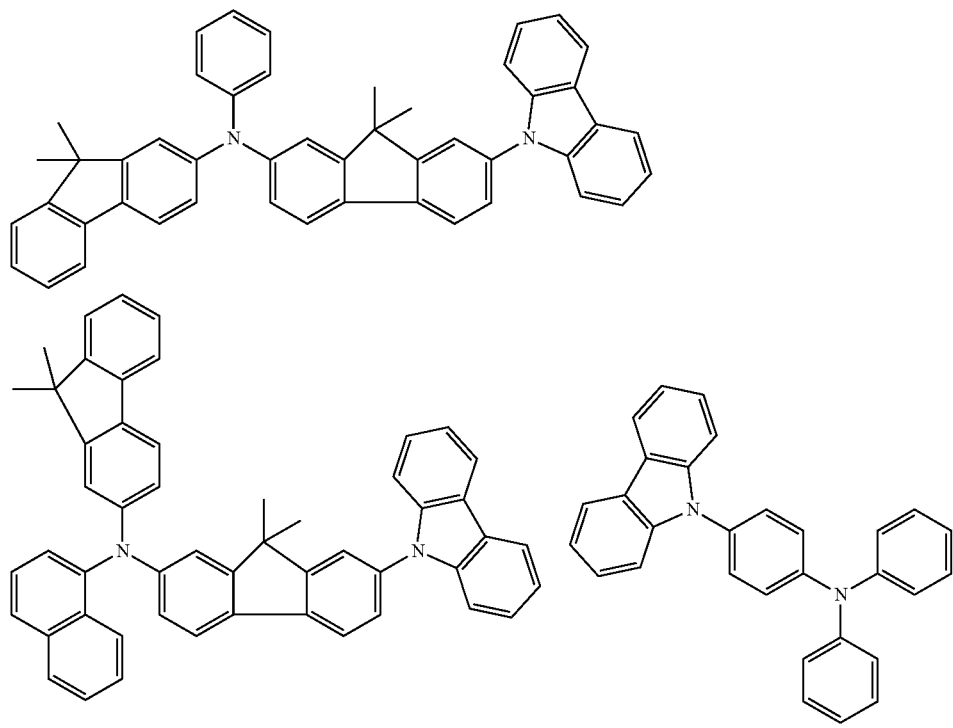

905
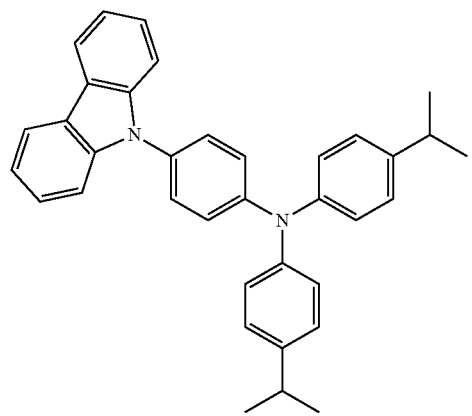
906
-continued
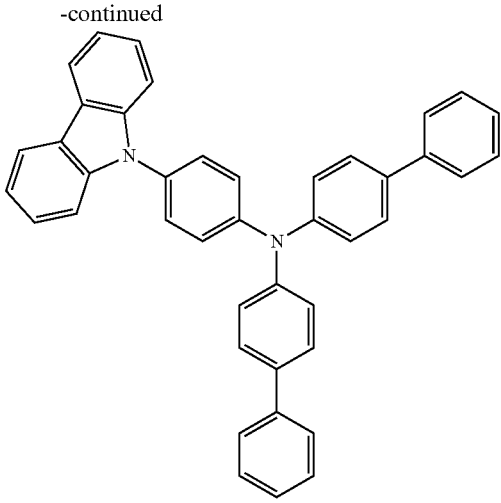
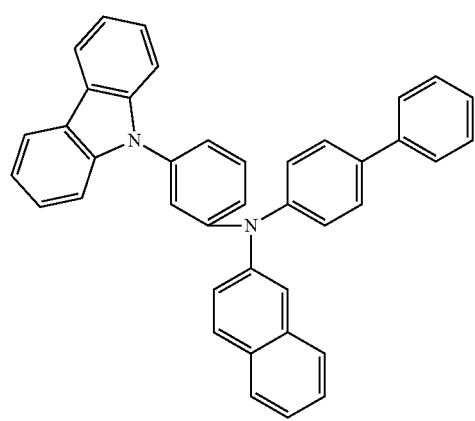
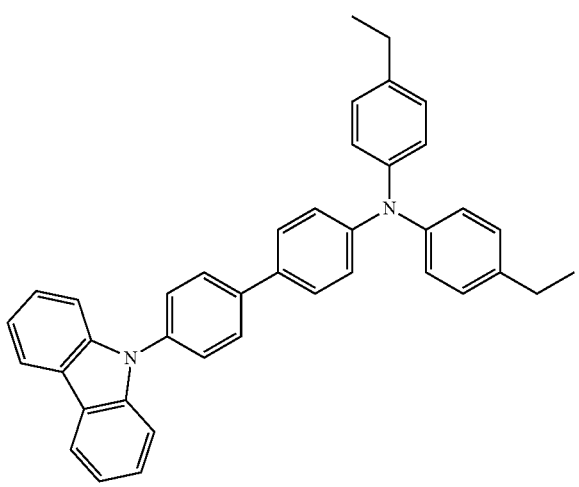
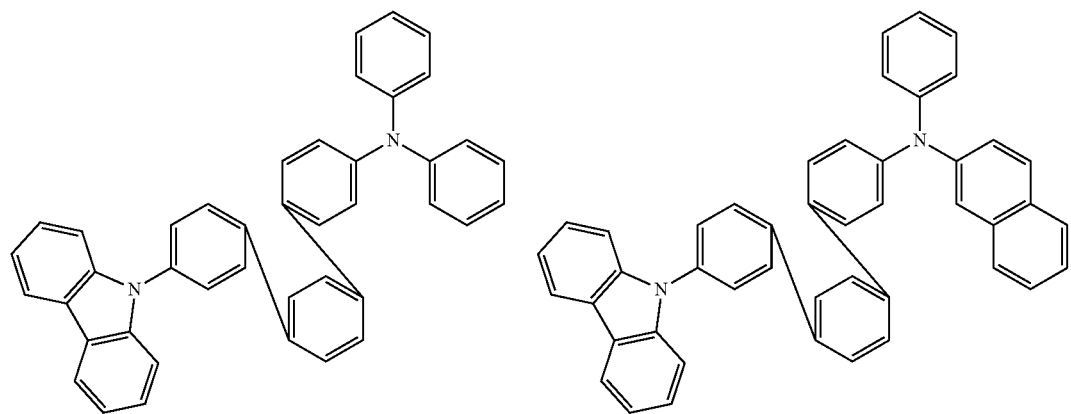

907 908
-continued
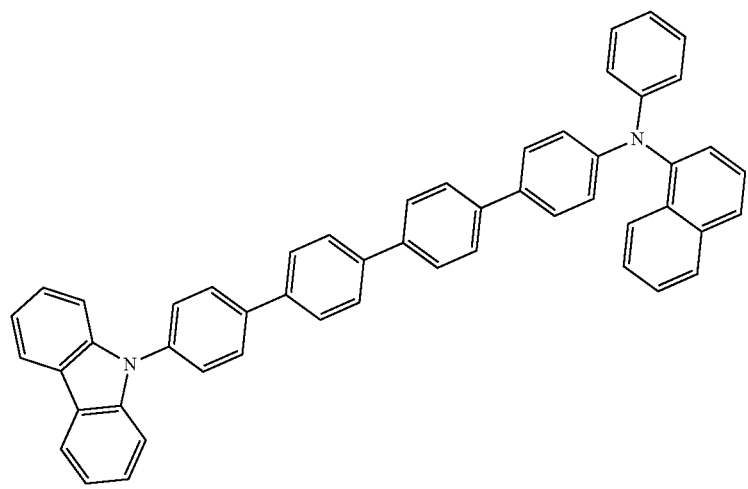
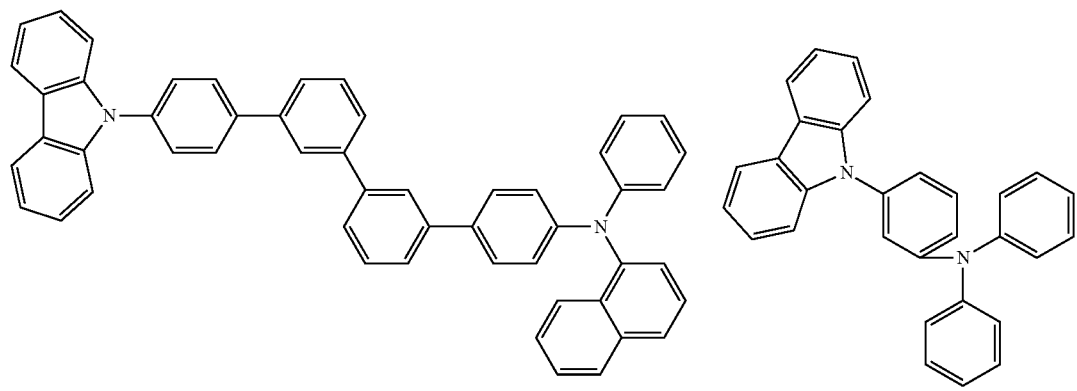
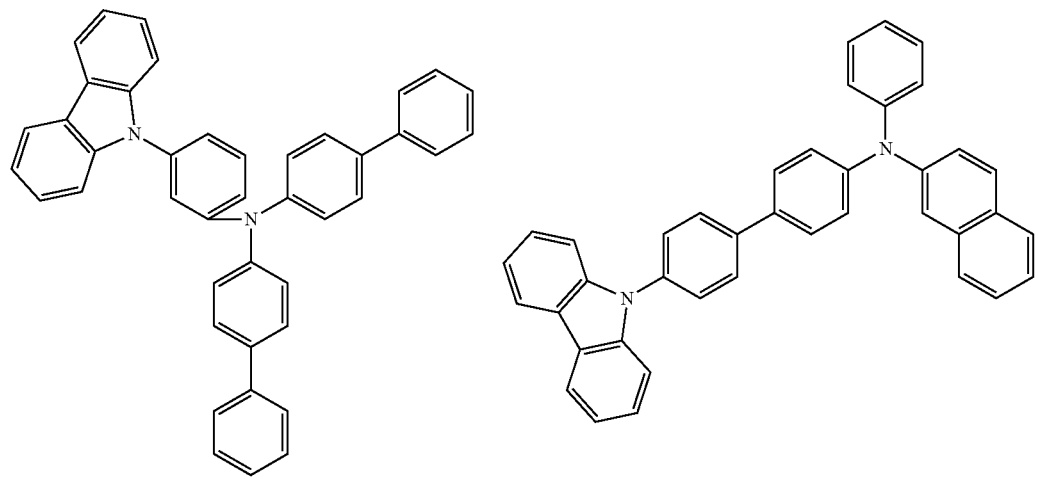

-continued
909
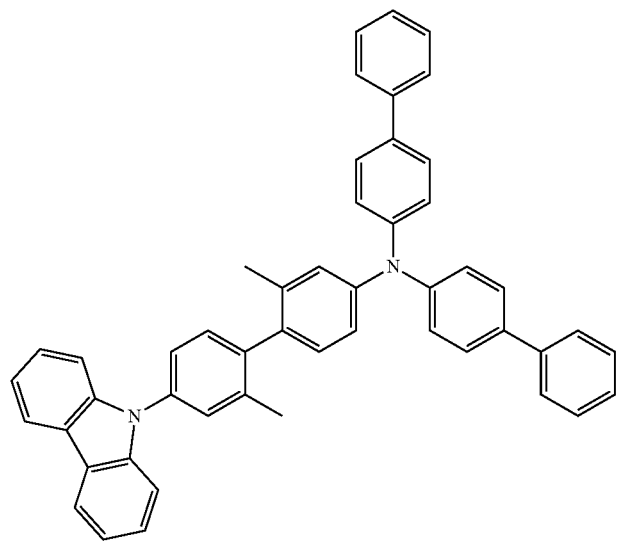
910
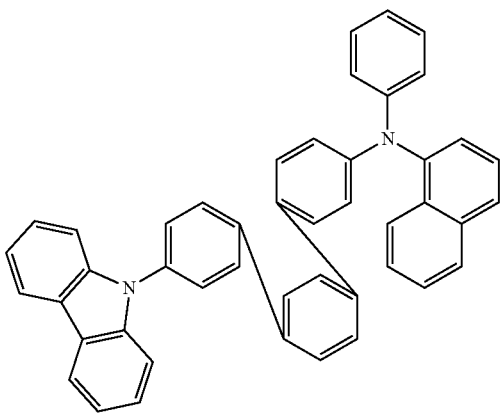
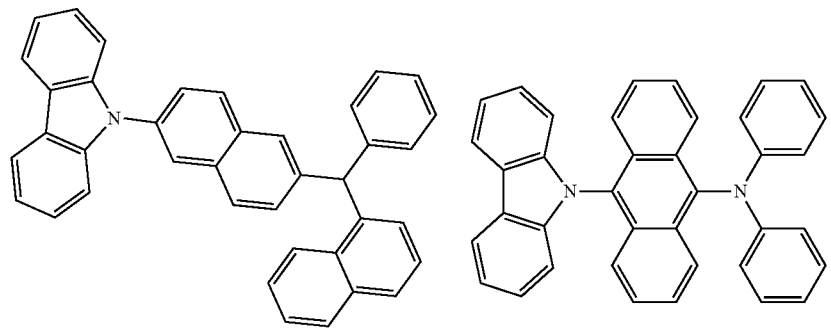
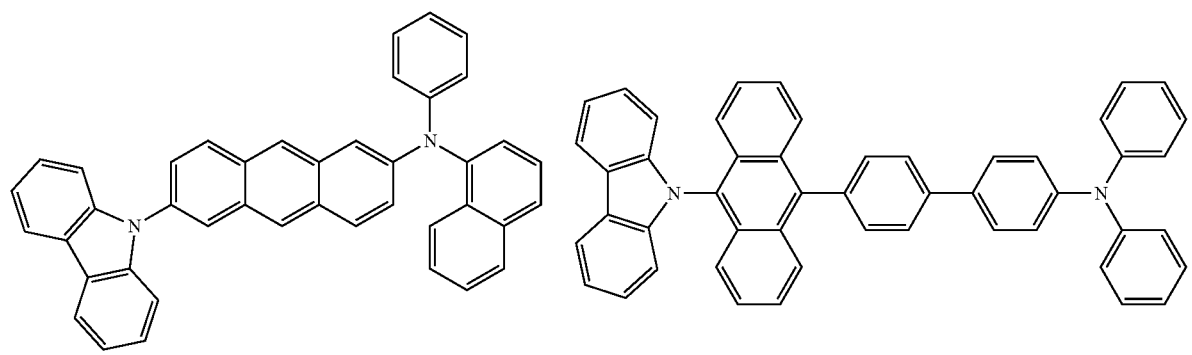
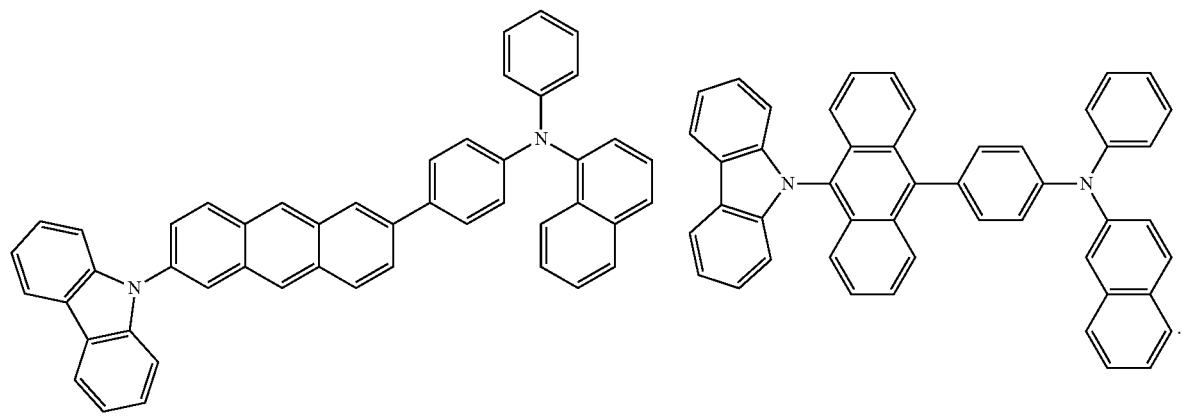

13. The organic light emitting device of claim 11, wherein the compound of Chemical Formula 3 is selected from among the following compounds:
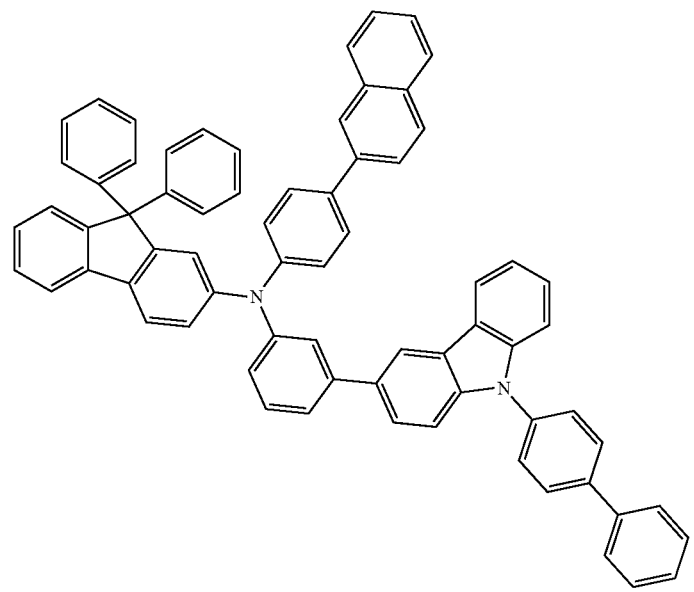
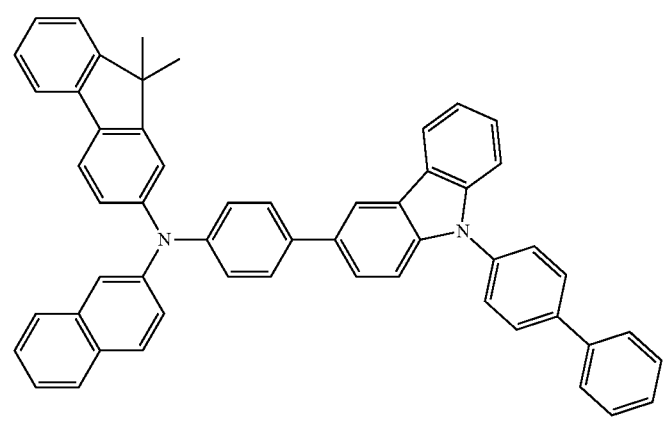
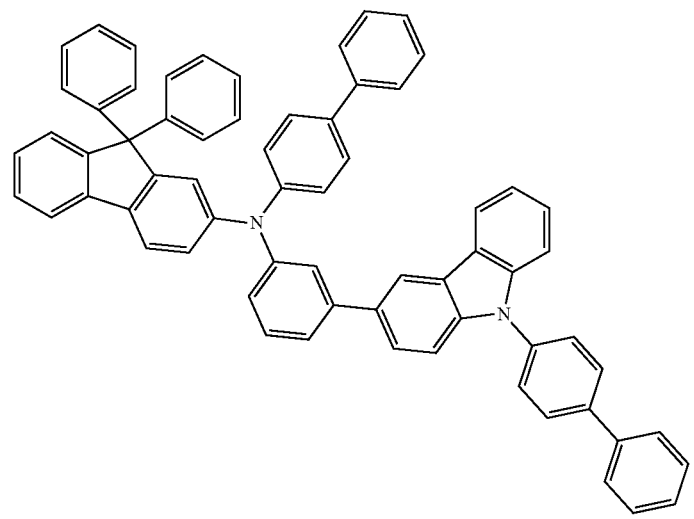

913
914
-continued
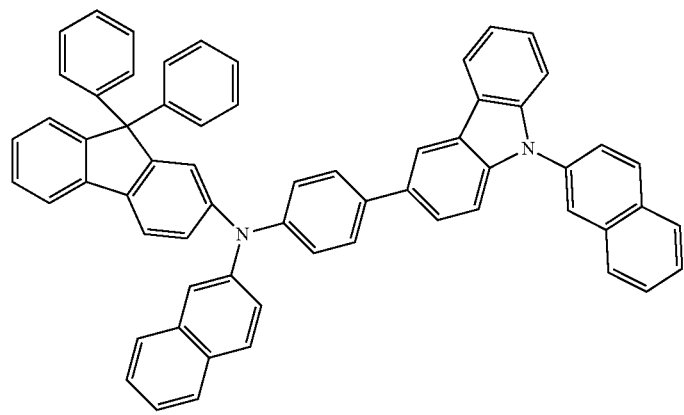
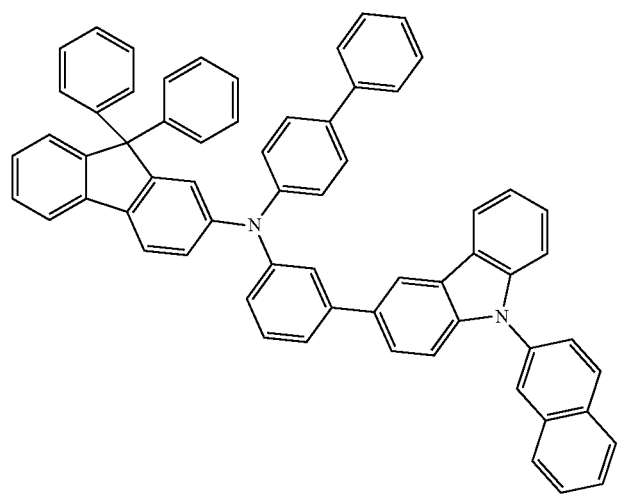
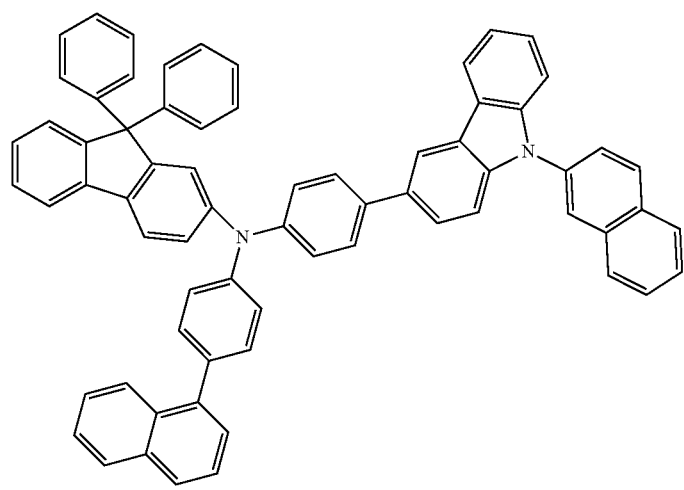

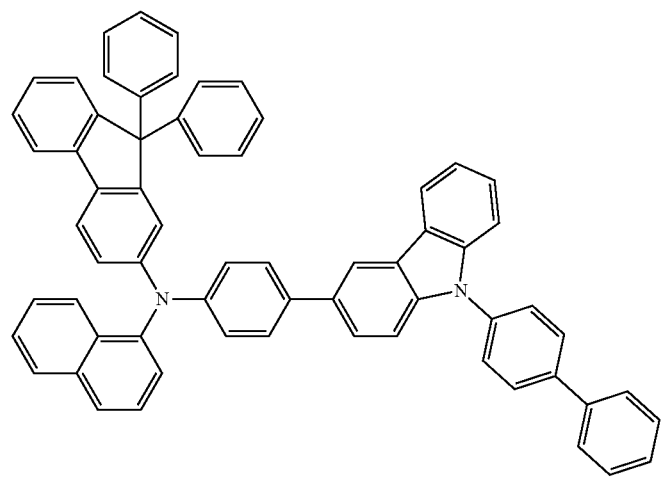
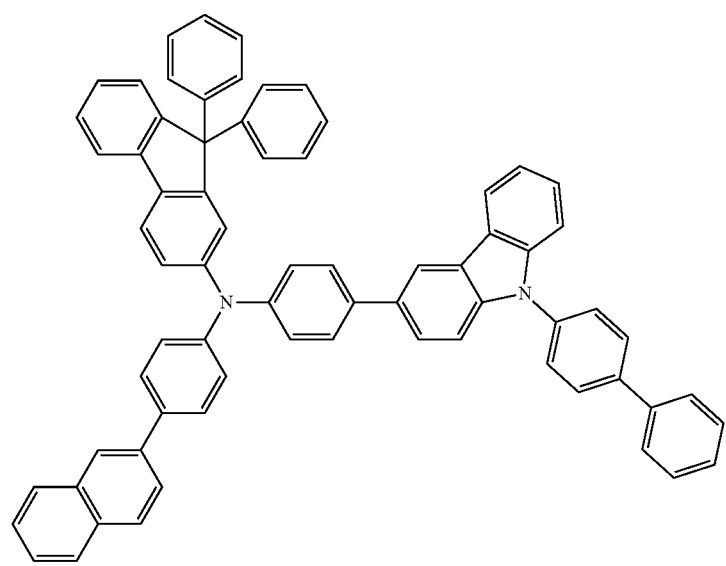
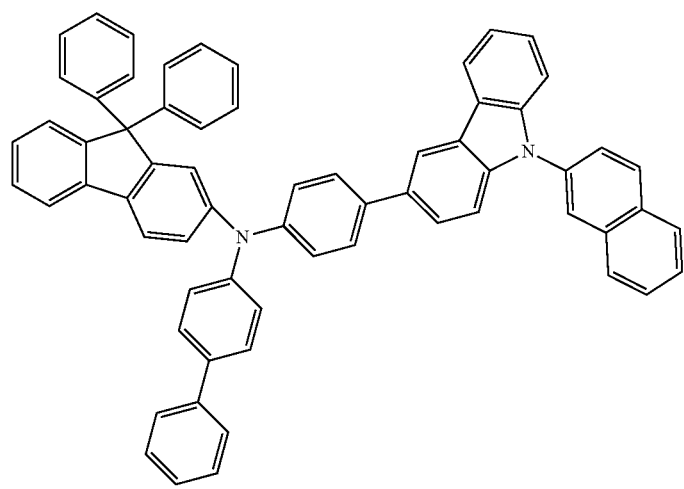

-continued
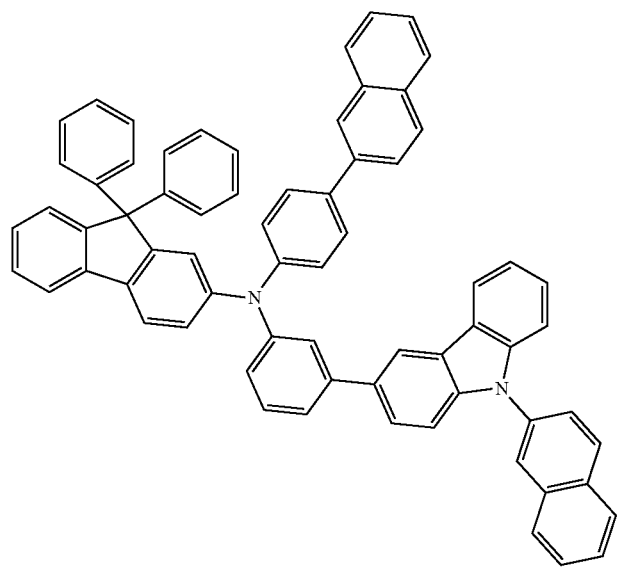
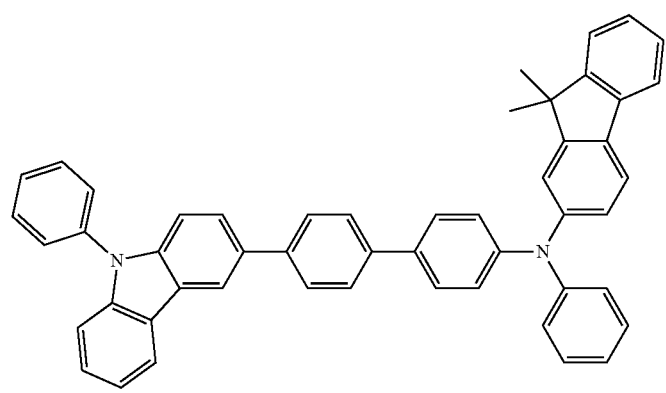
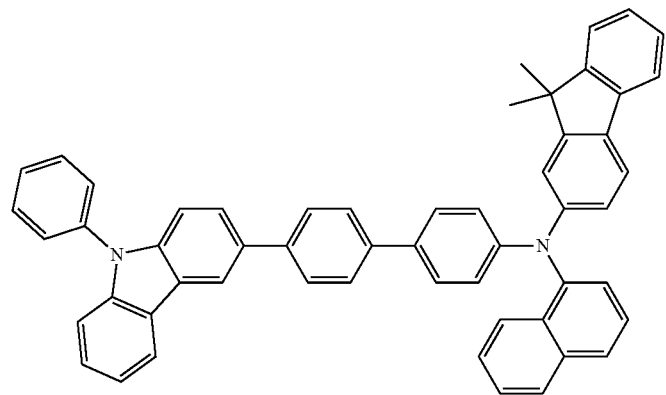

919
920
-continued
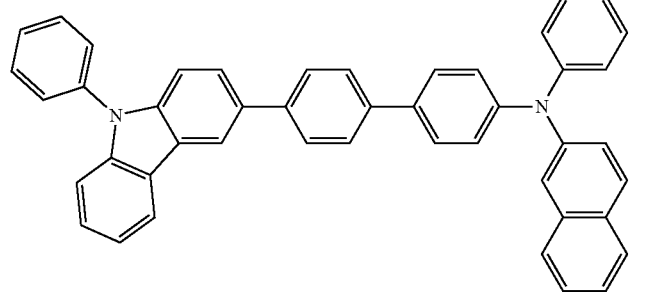
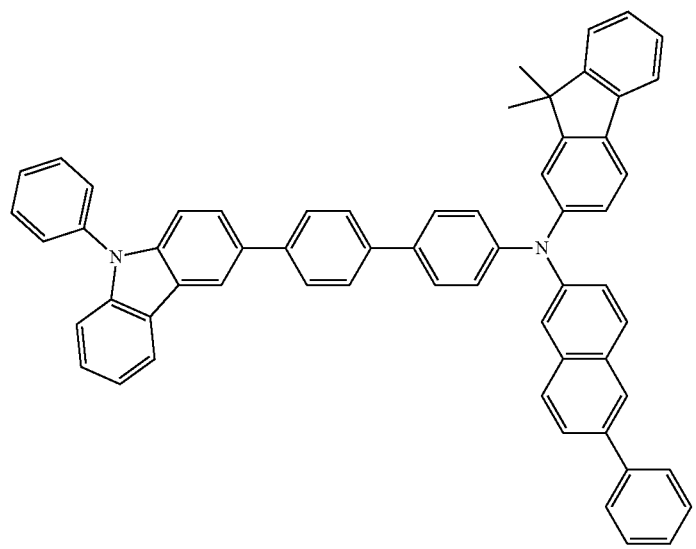
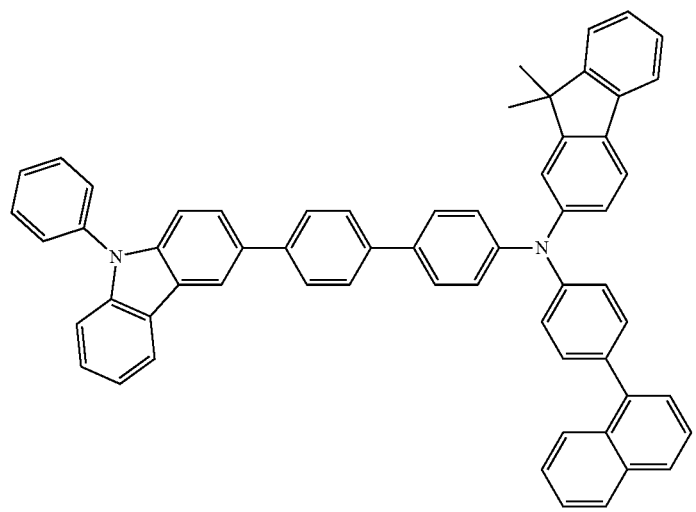

921
-continued
922
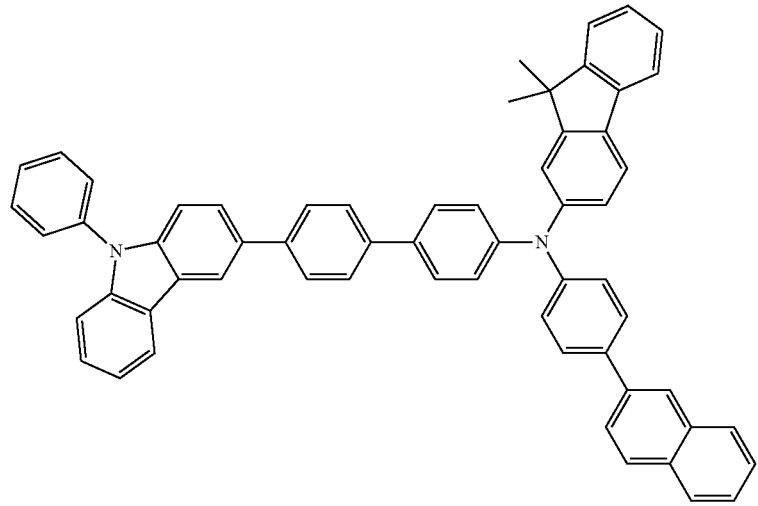
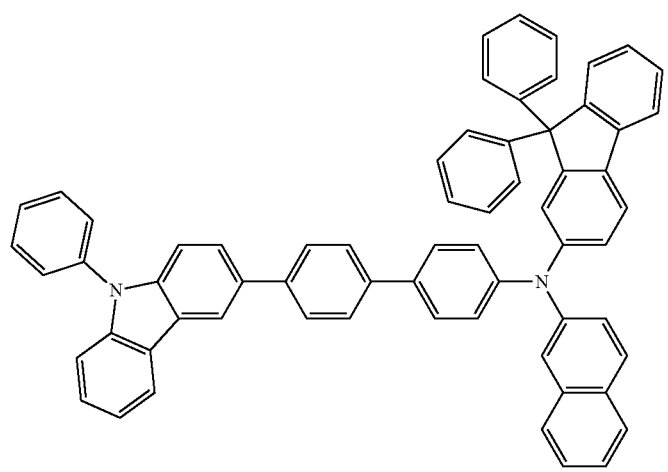
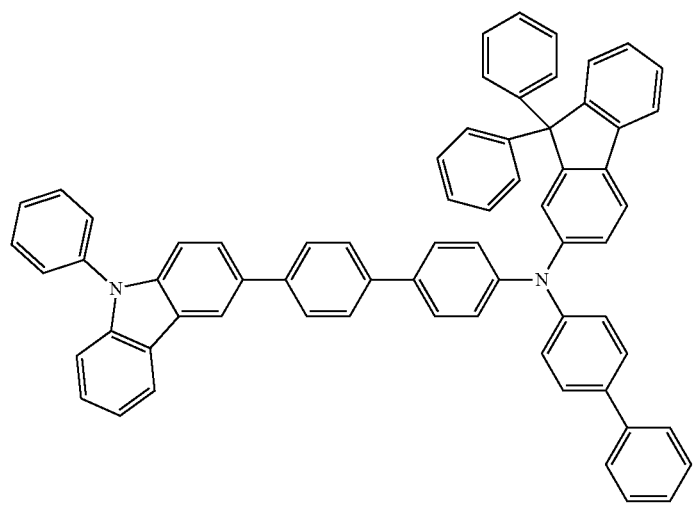

-continued
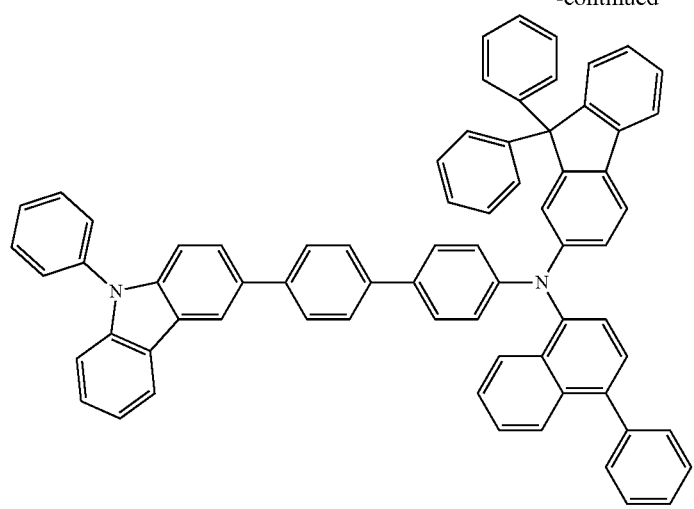
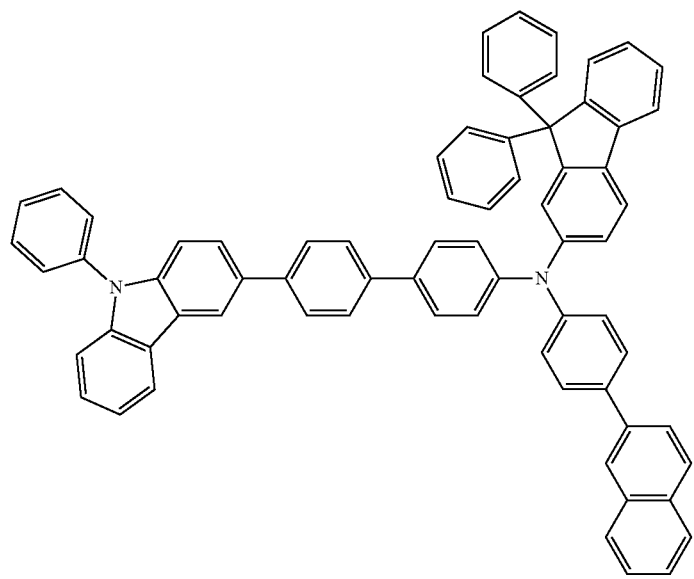
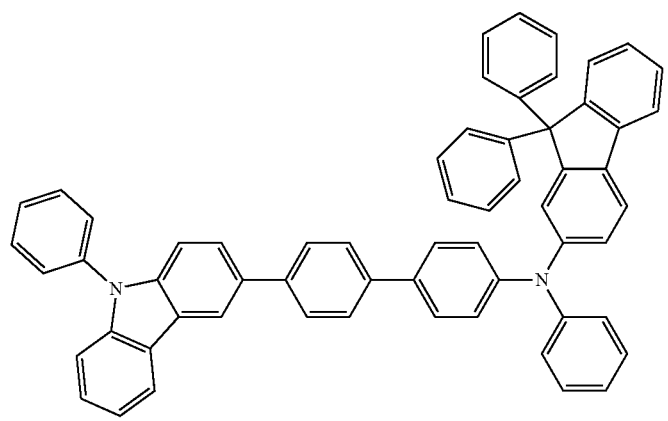

-continued
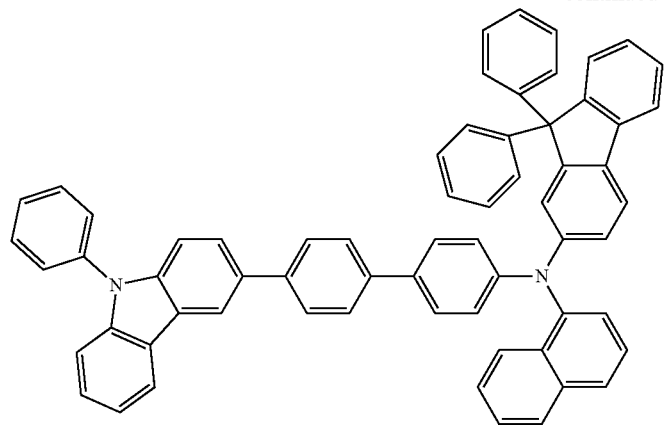
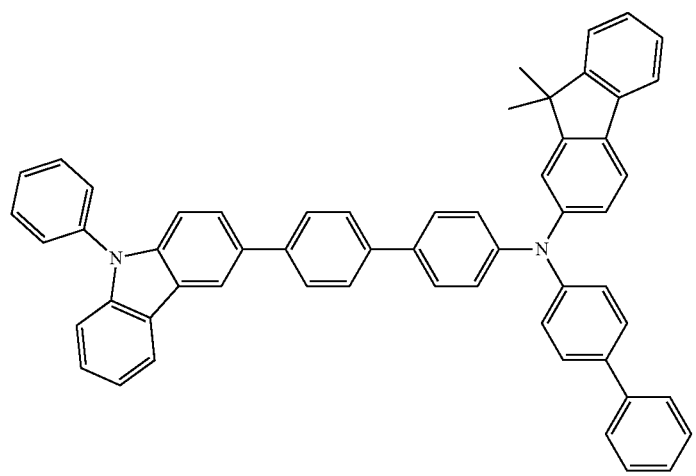
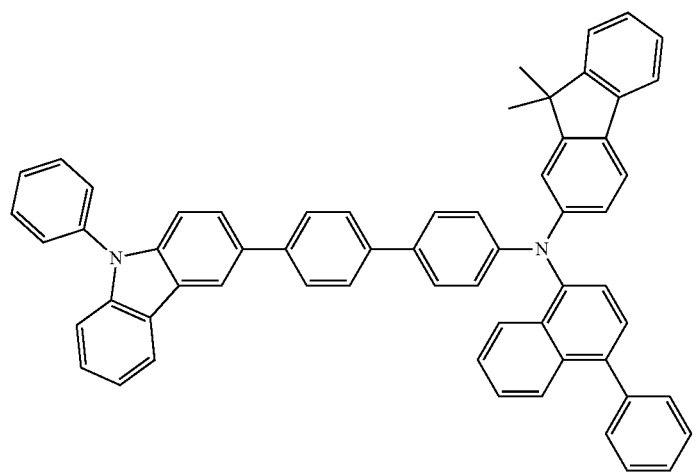

-continued
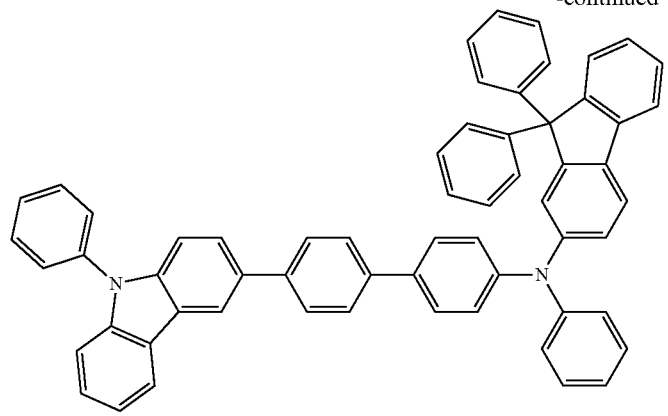
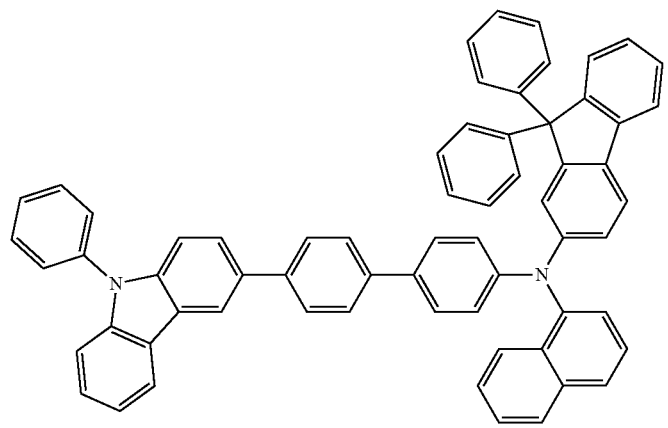
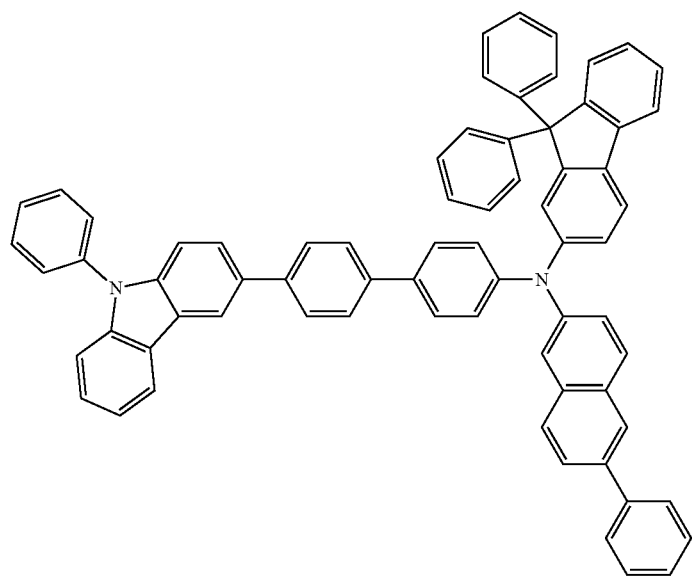

-continued
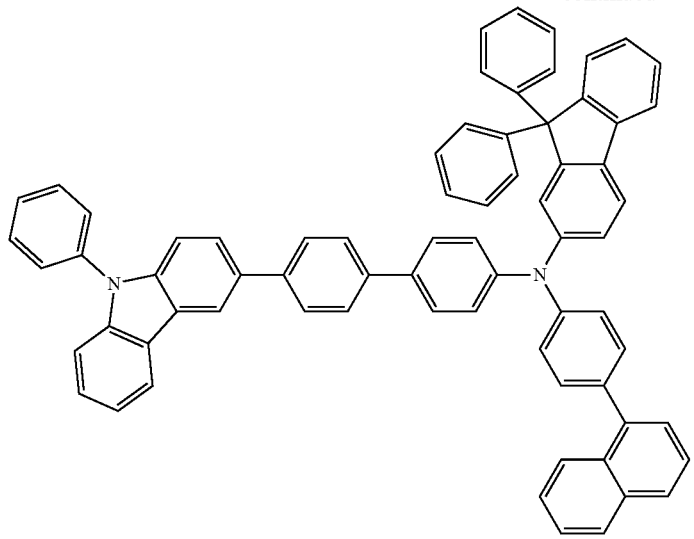
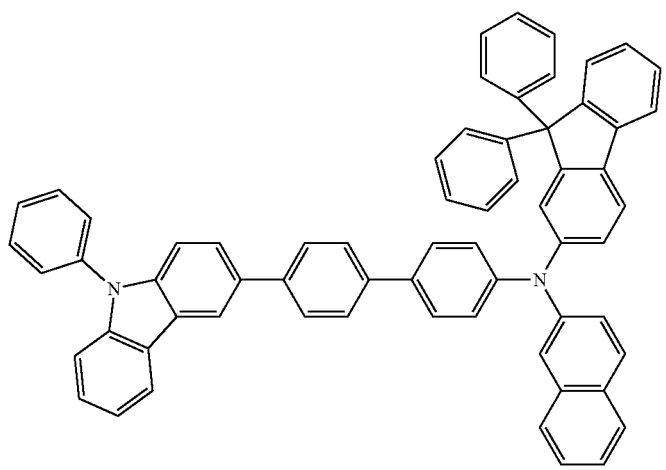
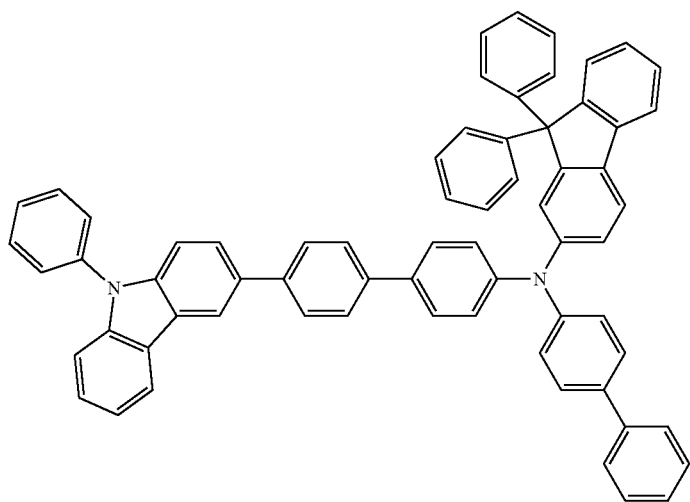

931
932
-continued
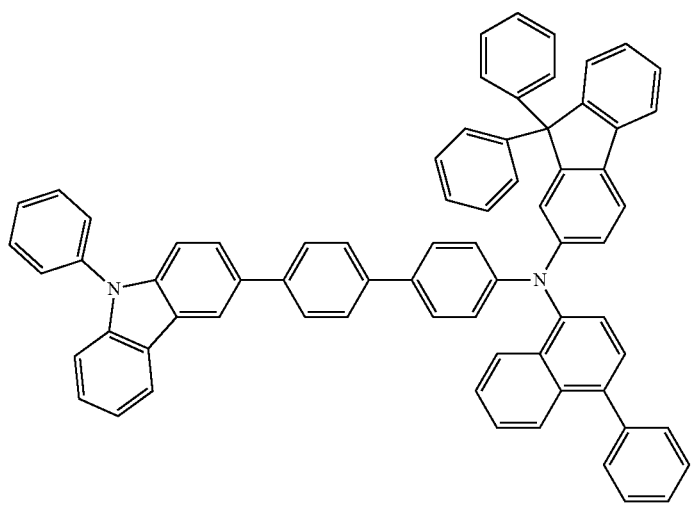
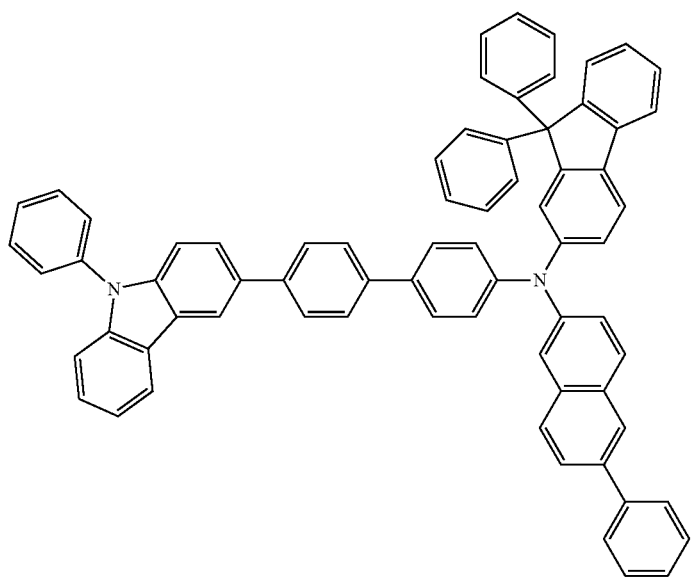
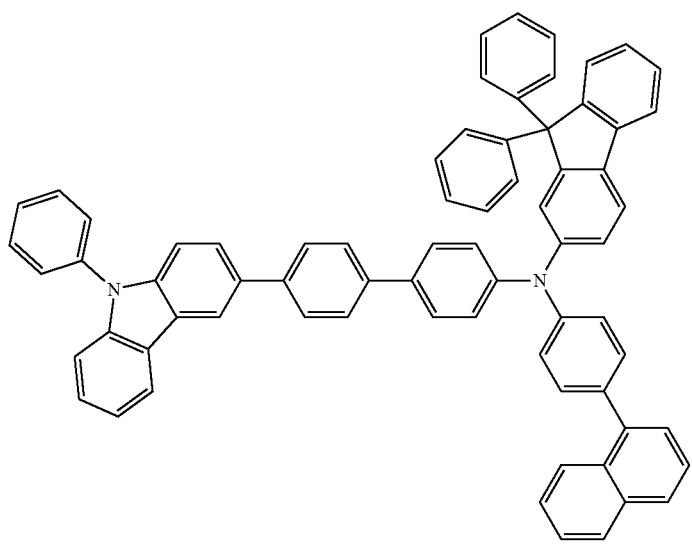

933
934
-continued
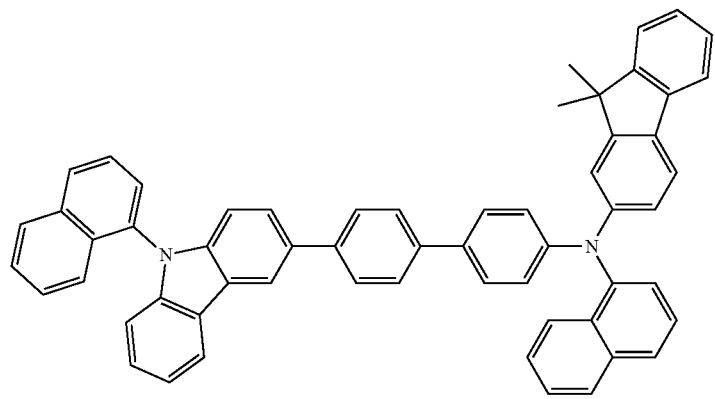
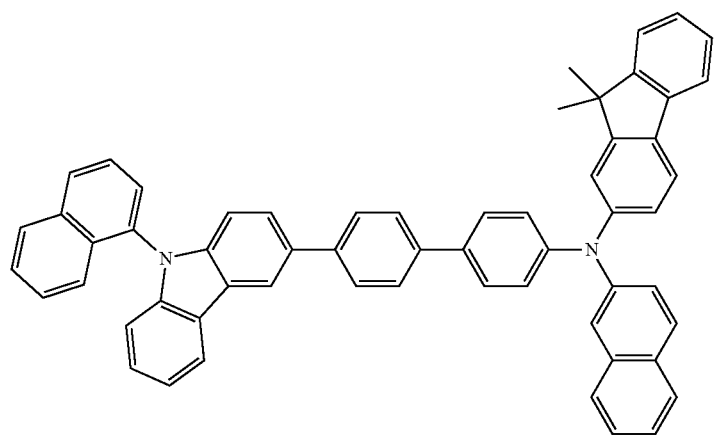
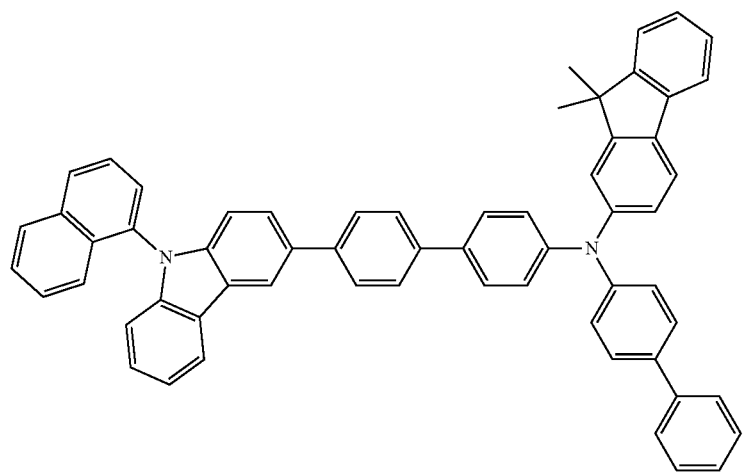

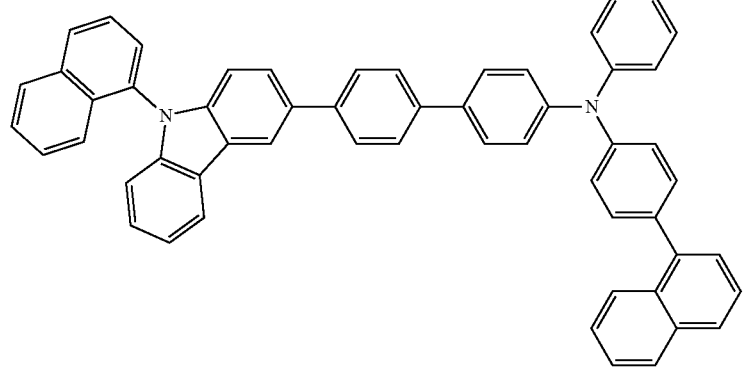
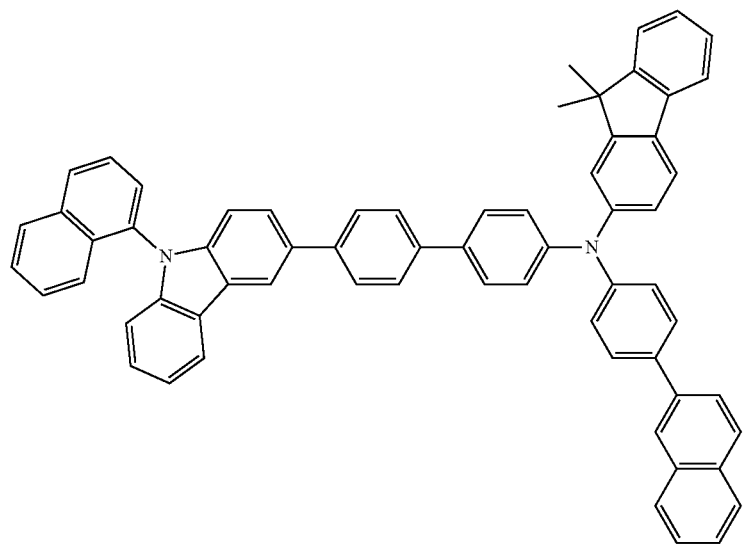
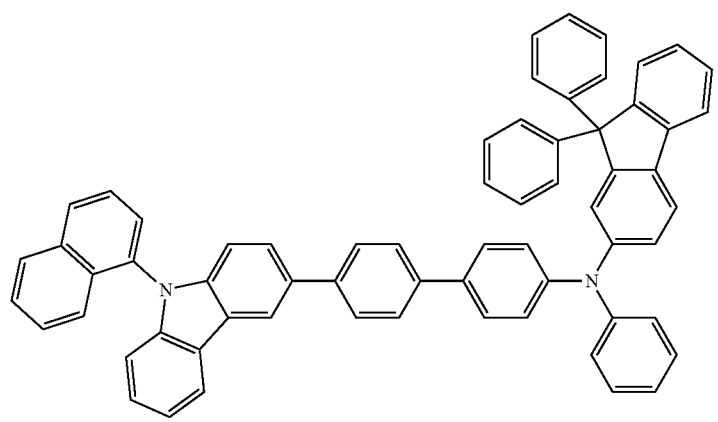

-continued
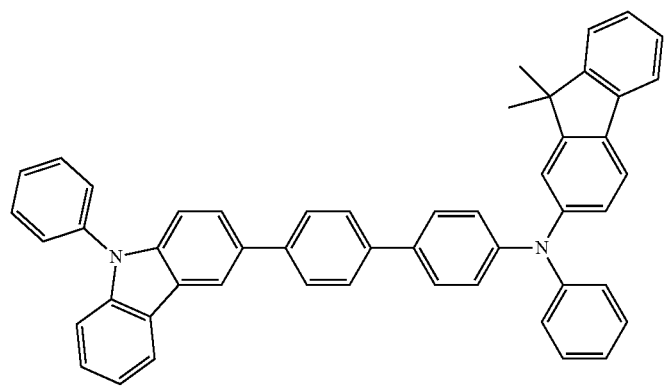
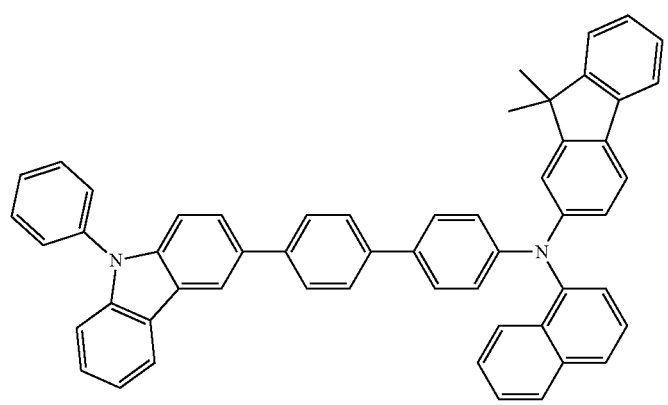
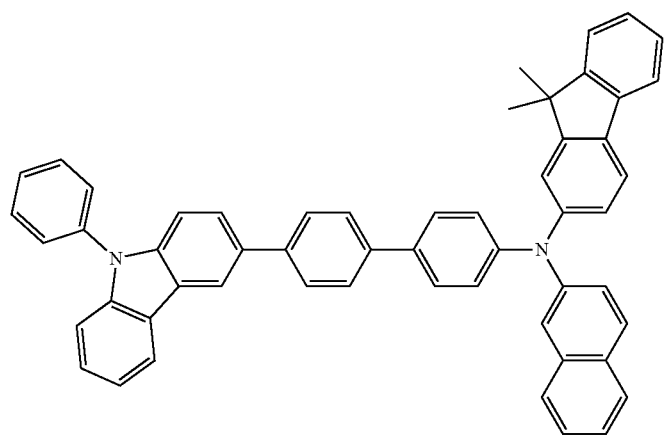

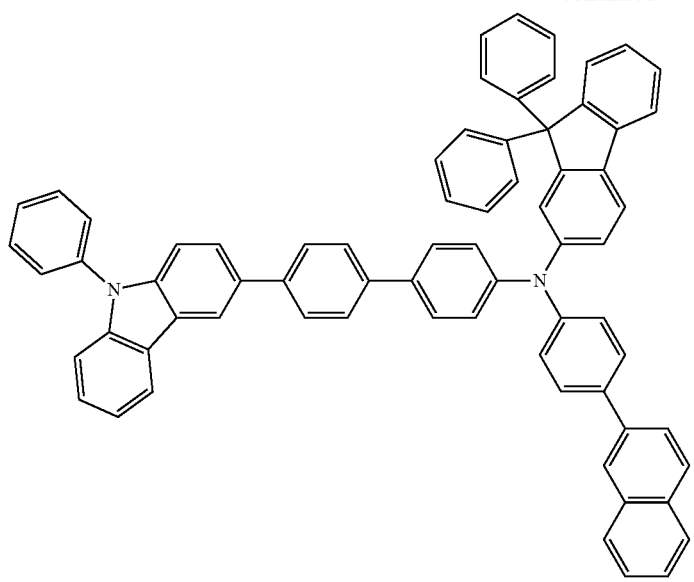
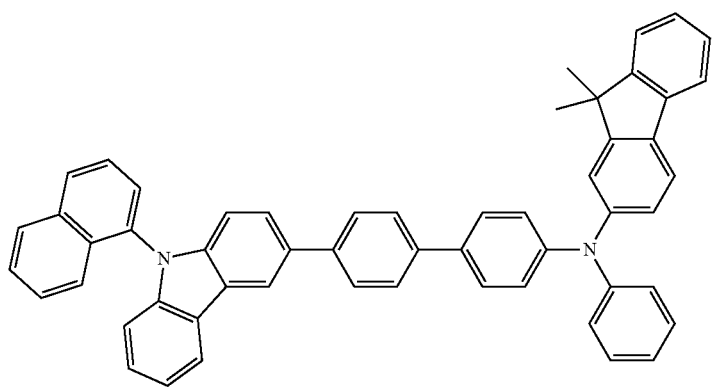
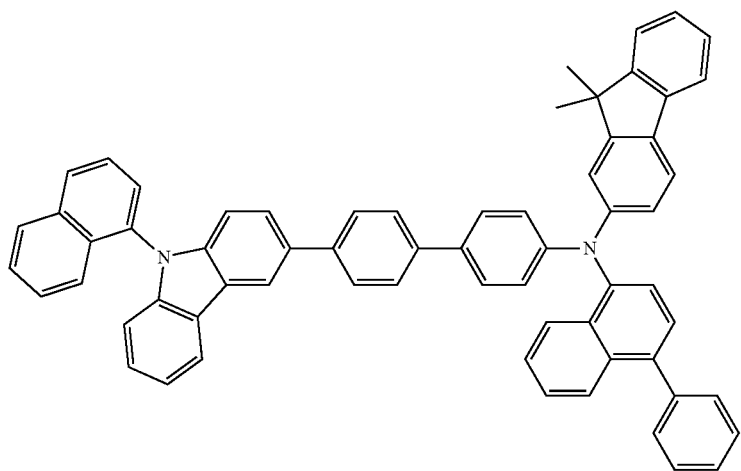

-continued
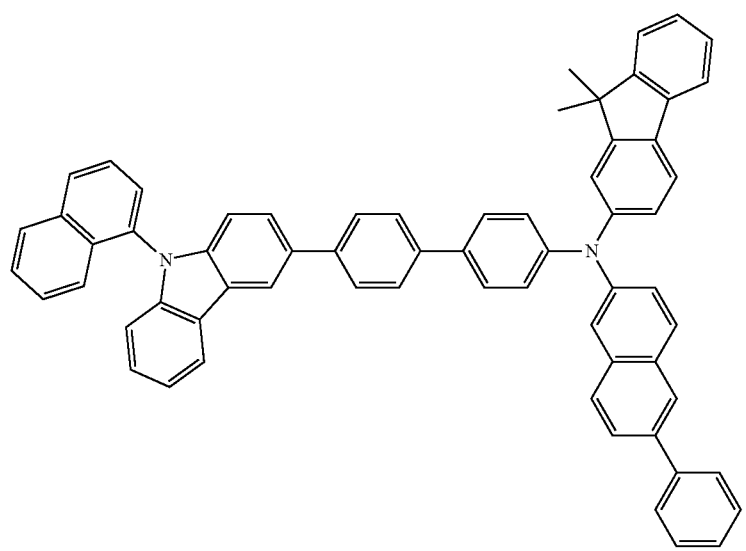
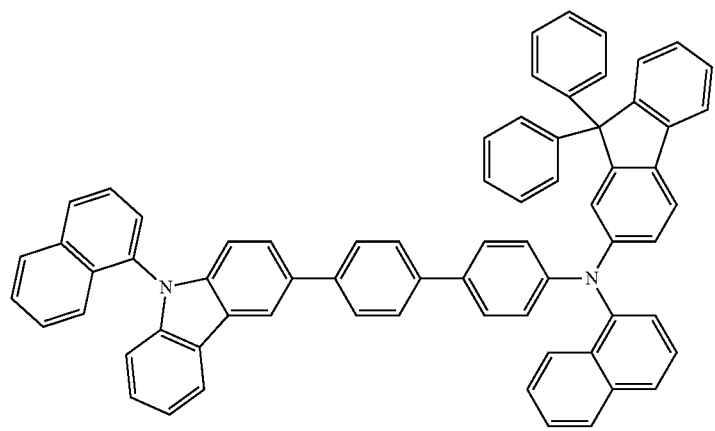
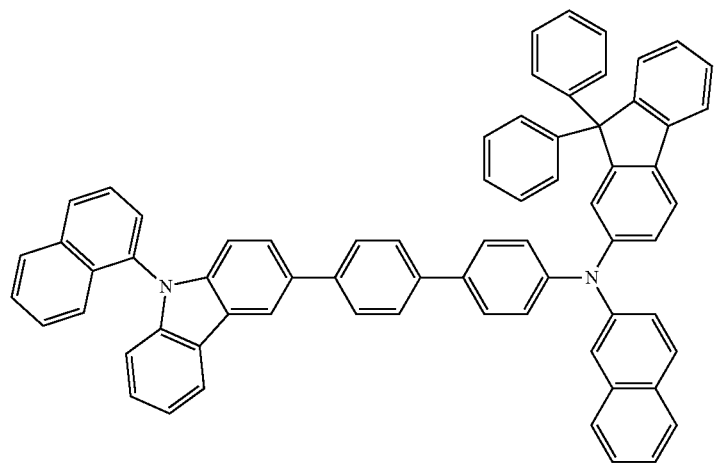

943
-continued
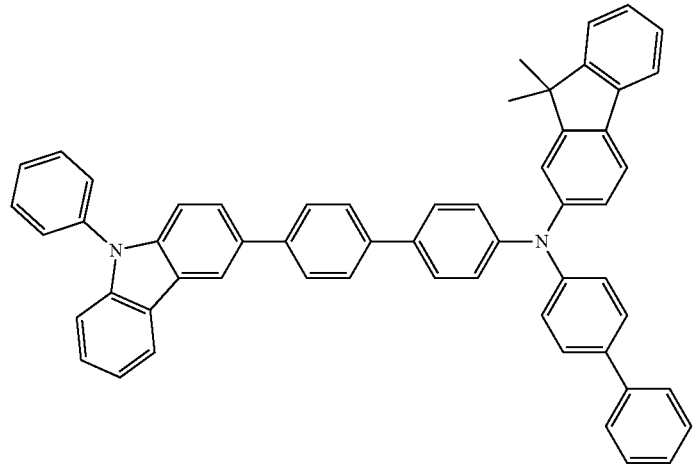
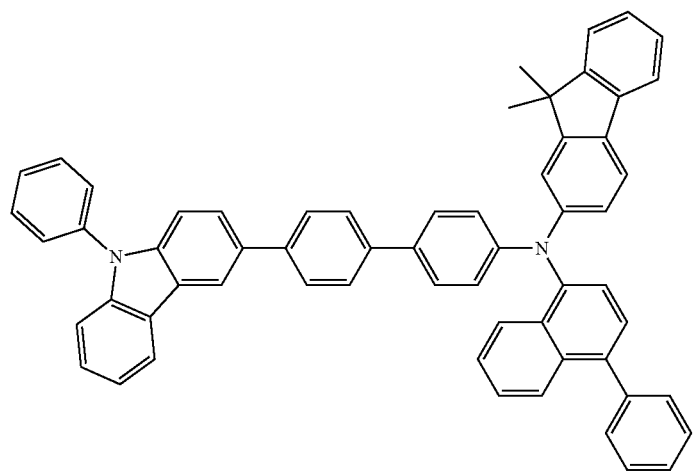
944
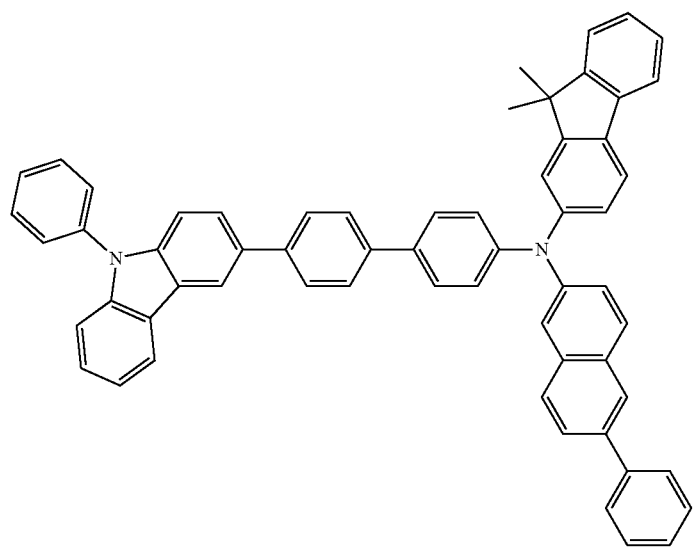

-continued
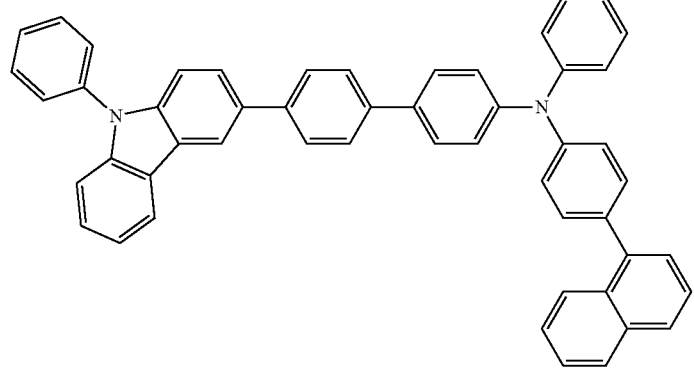
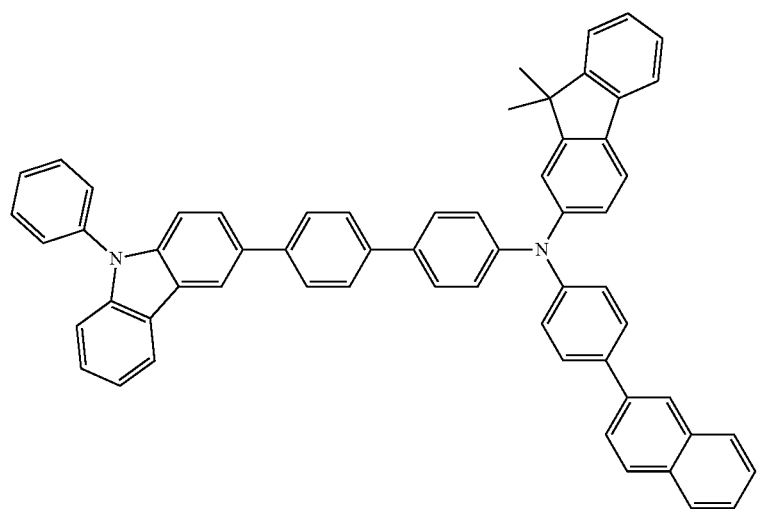
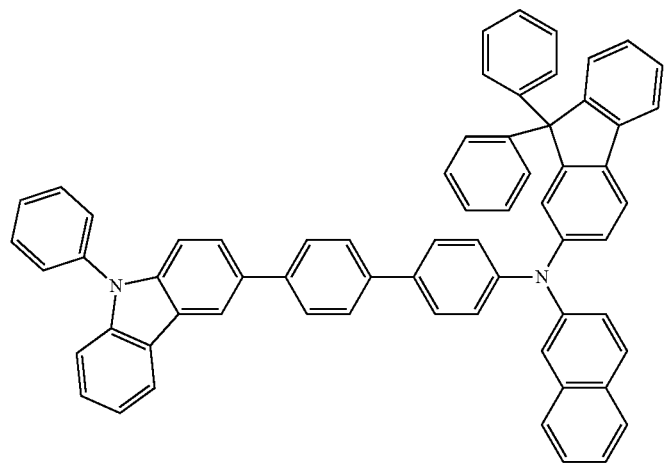

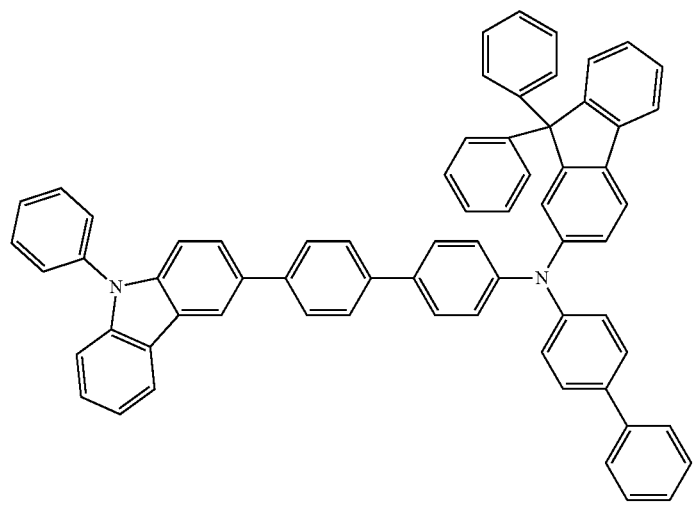
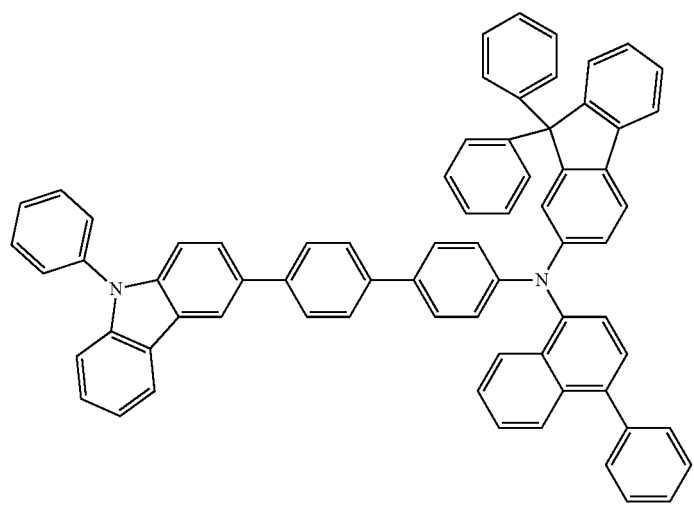
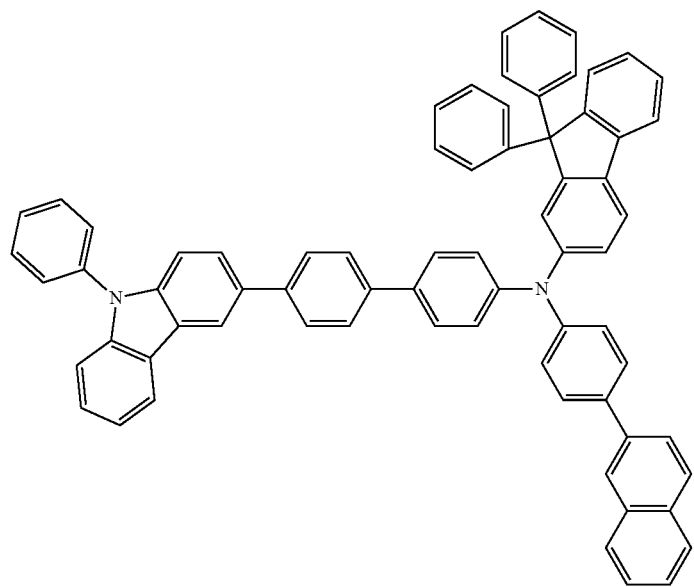

-continued
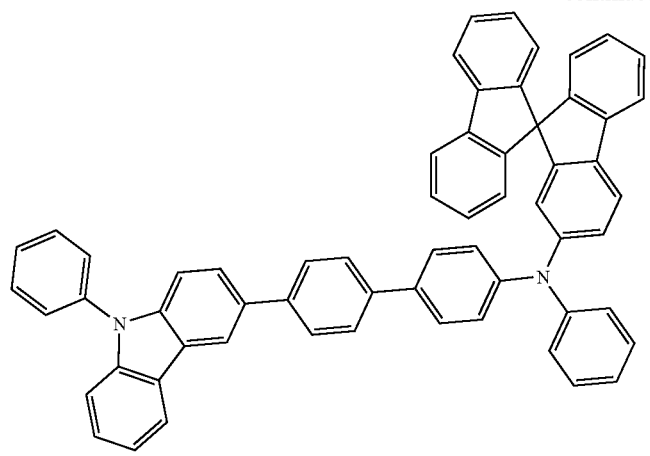
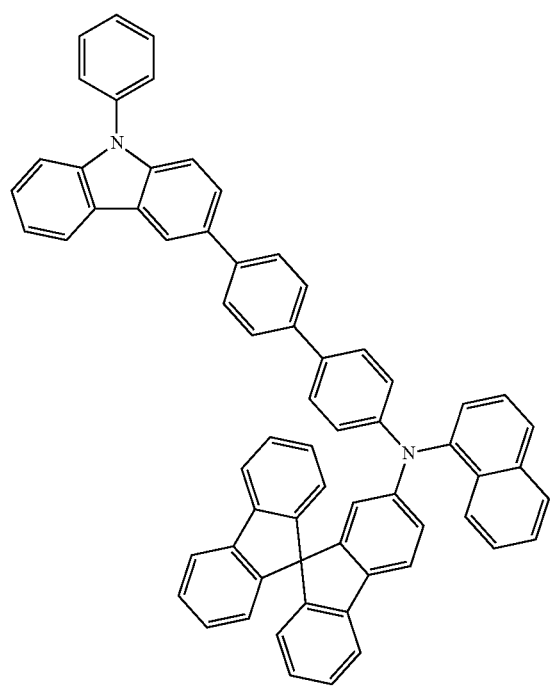
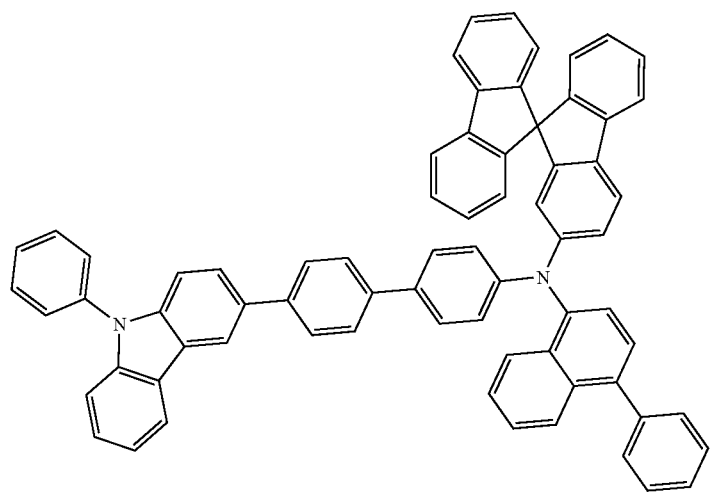

-continued
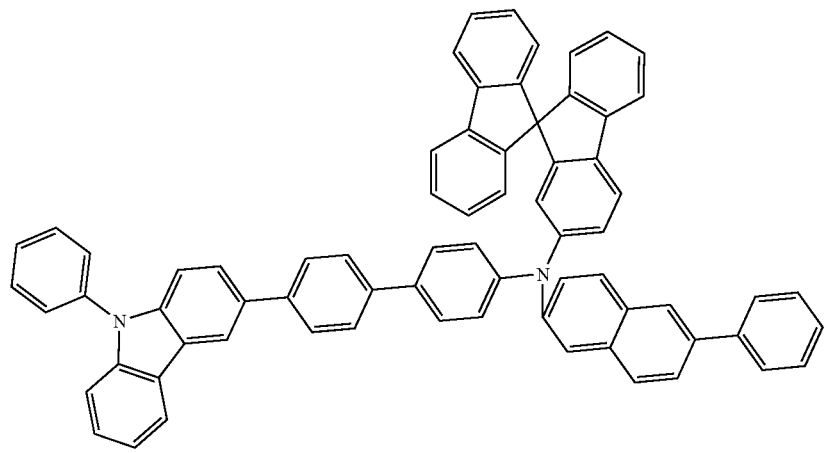
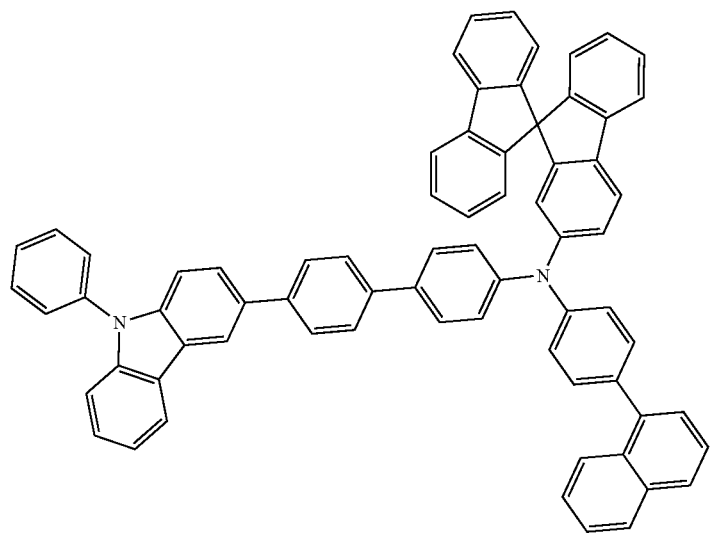
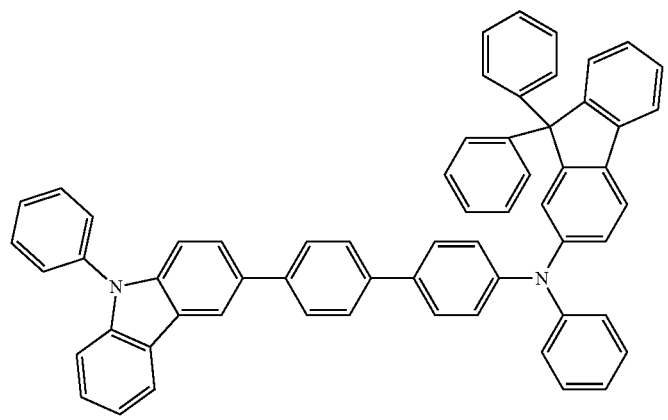

-continued
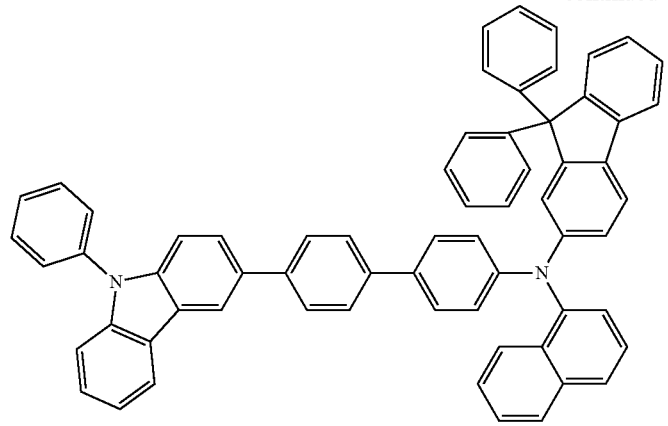
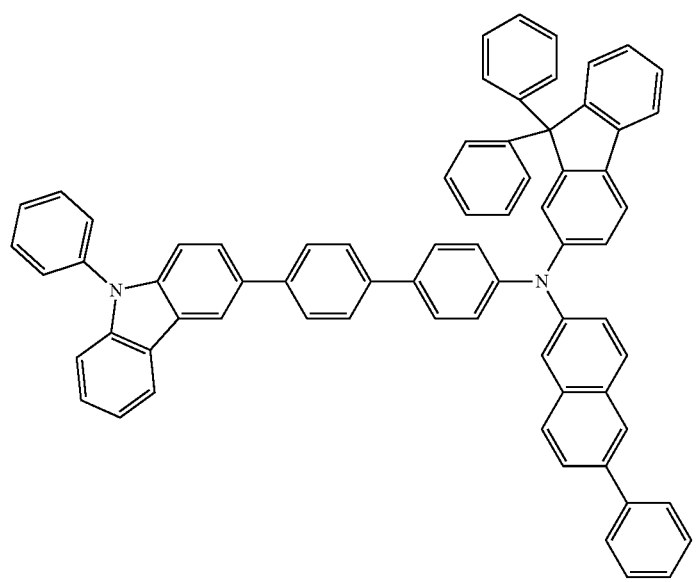
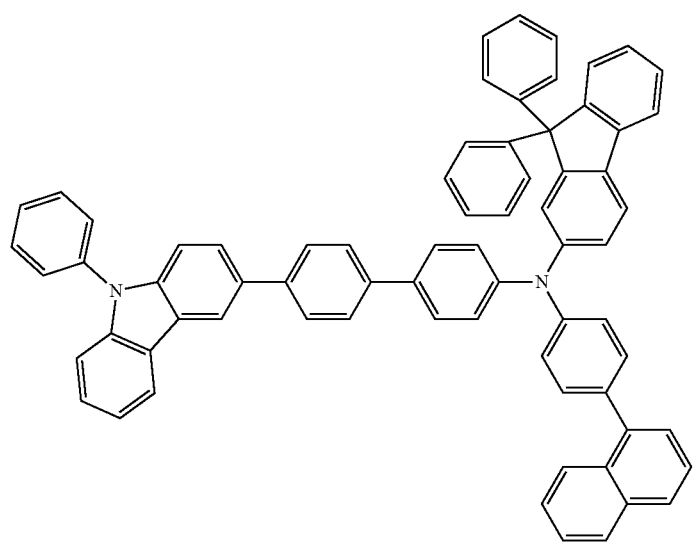

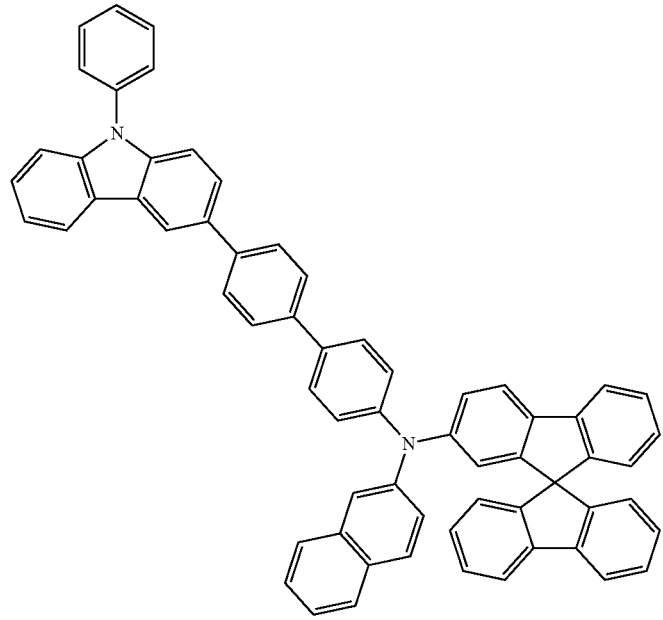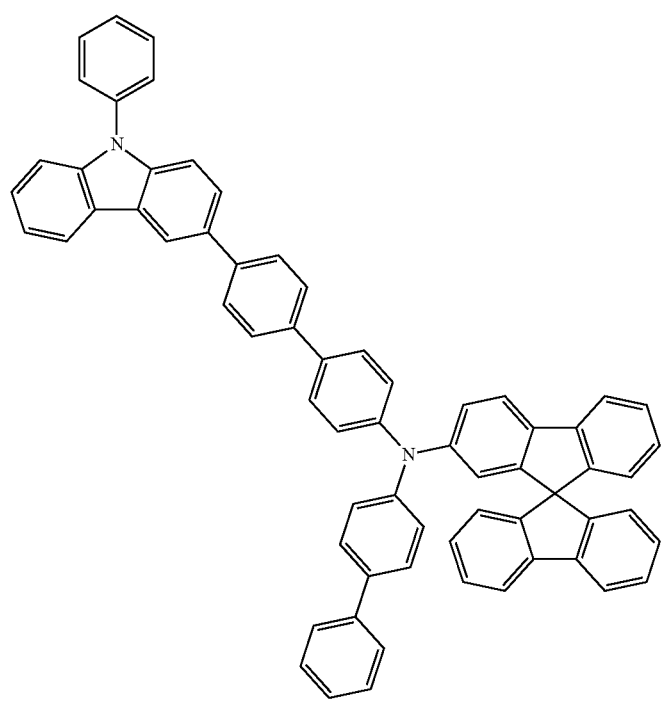

-continued
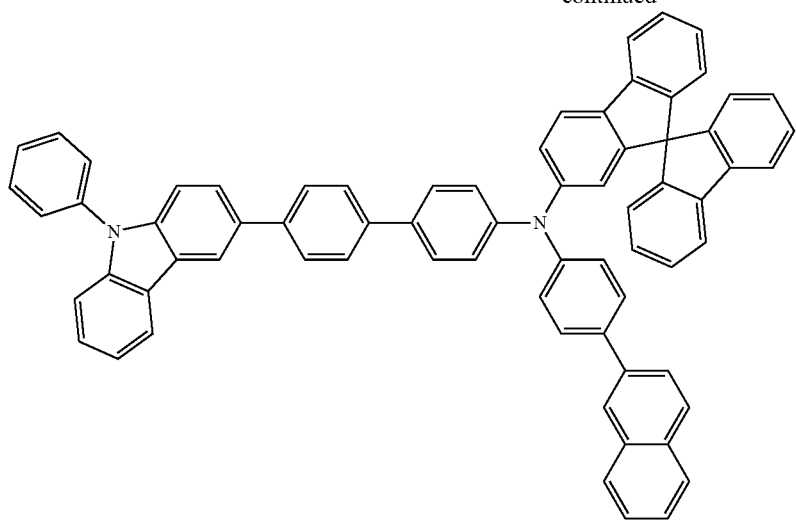
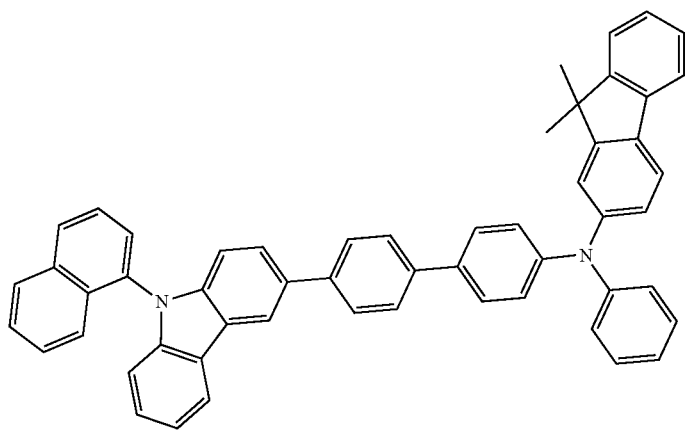
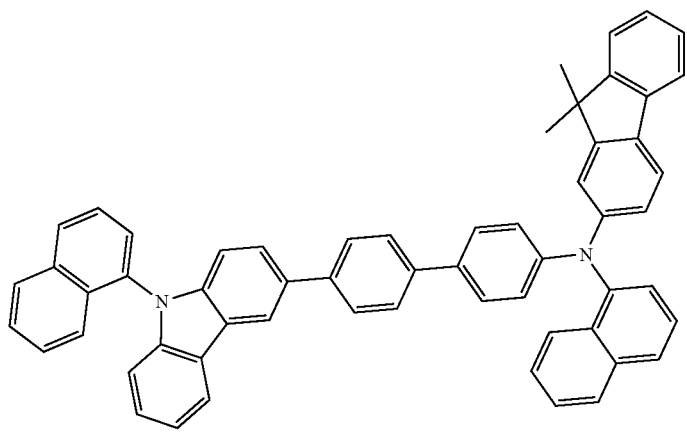

-continued
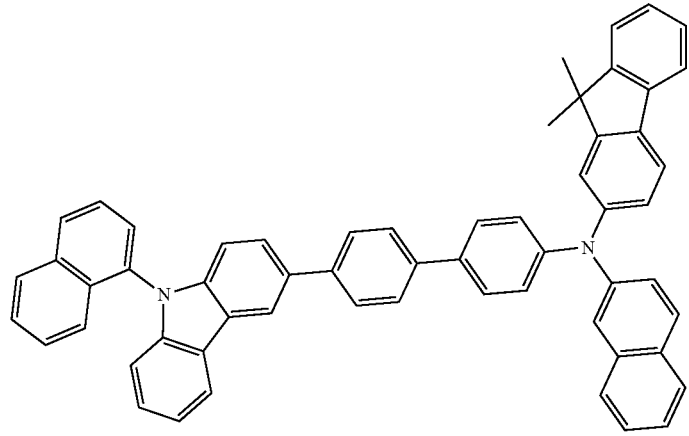
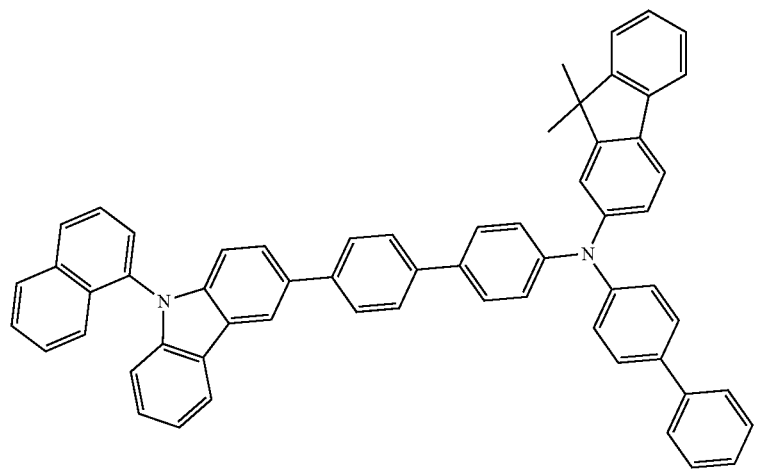
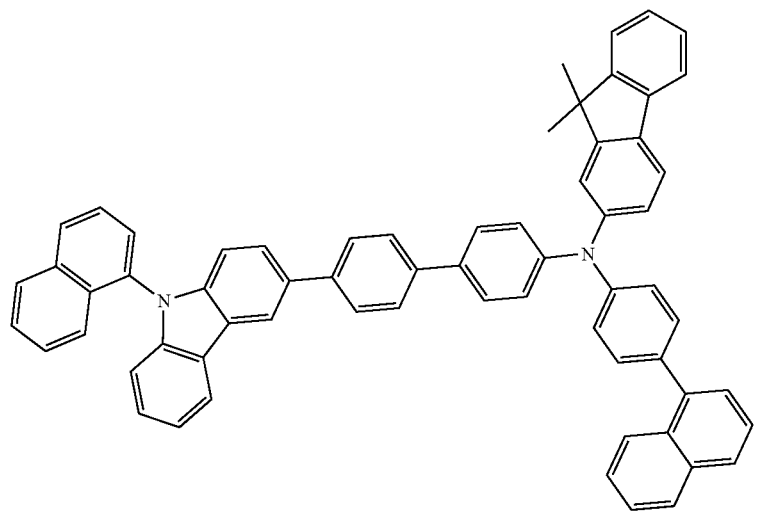

-continued
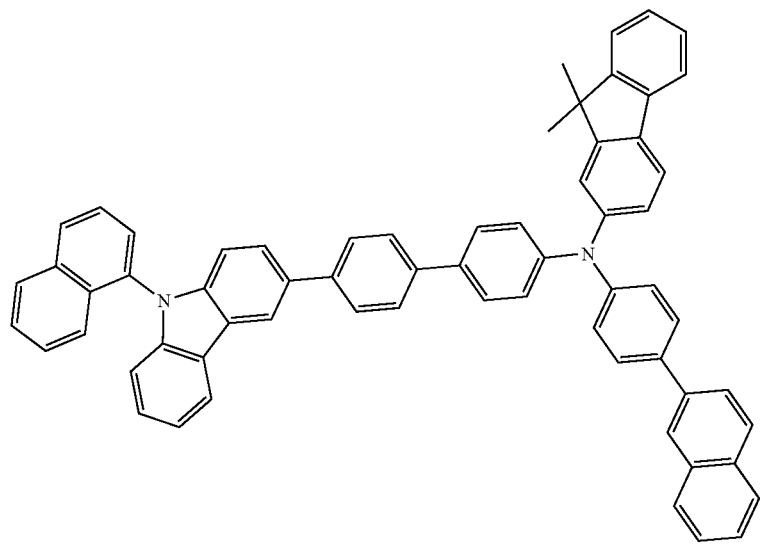
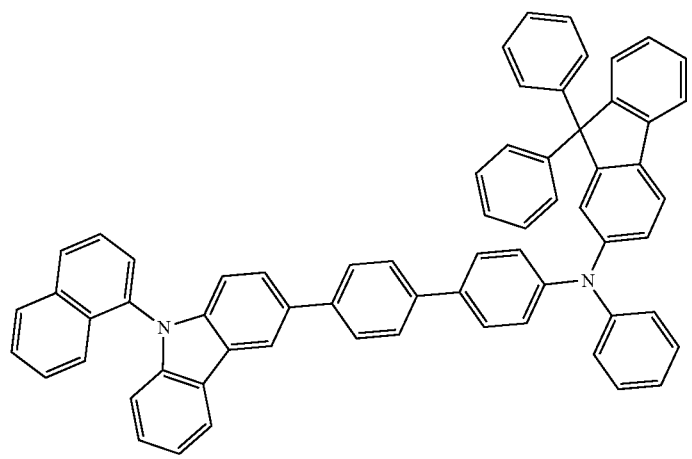
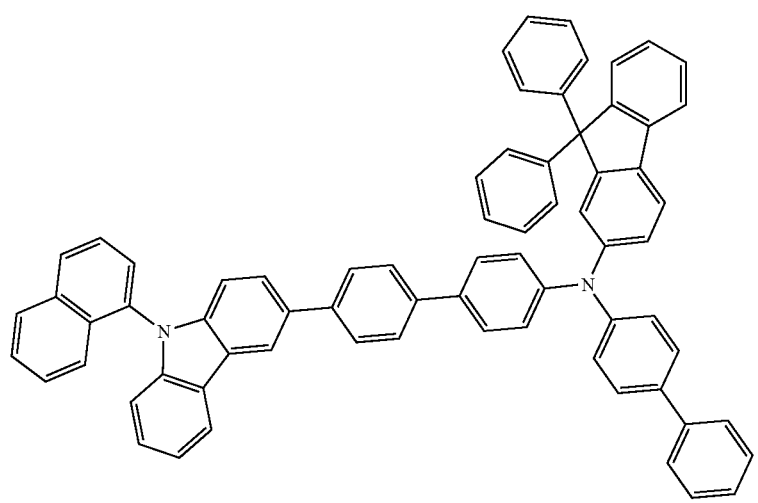

-continued
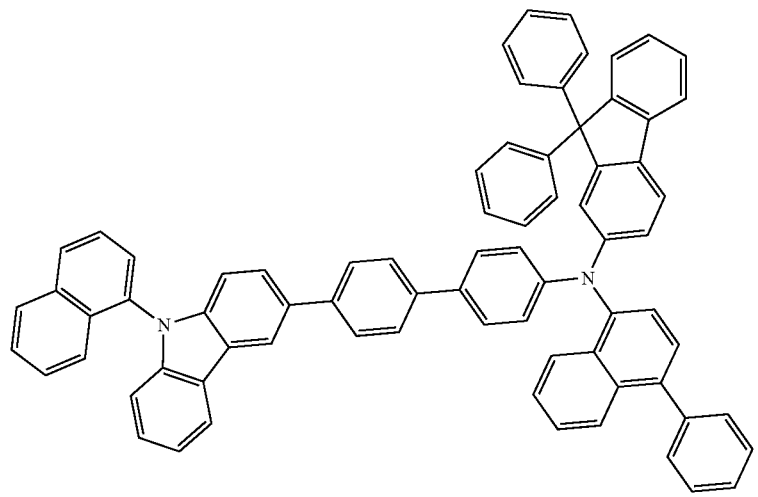
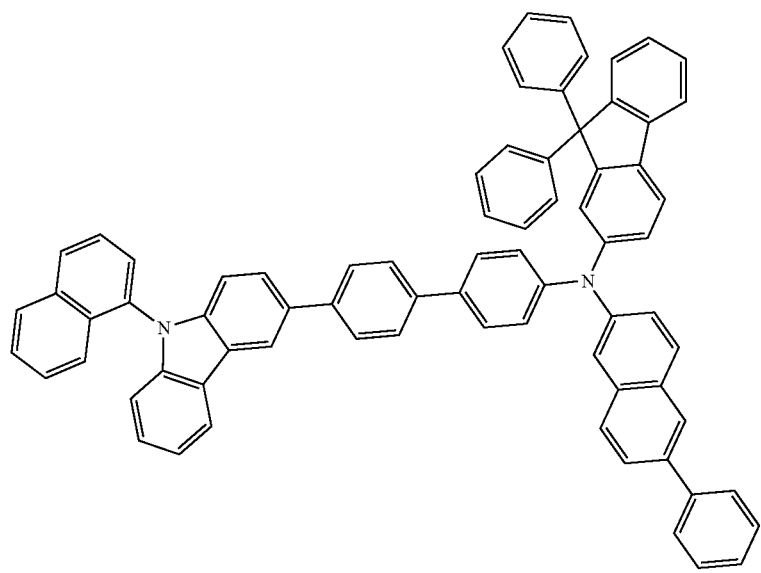
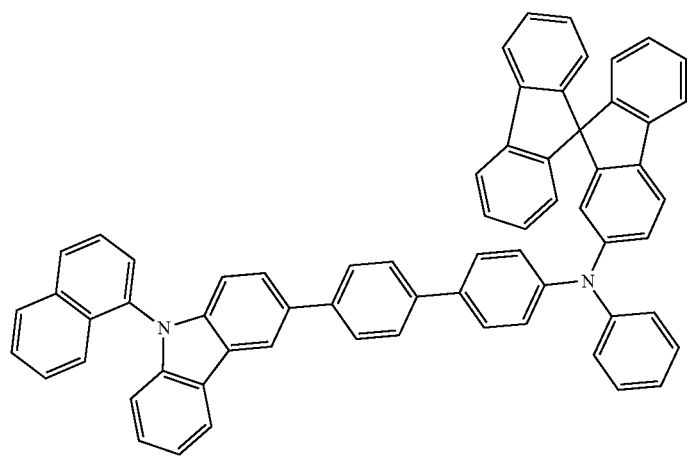

-continued
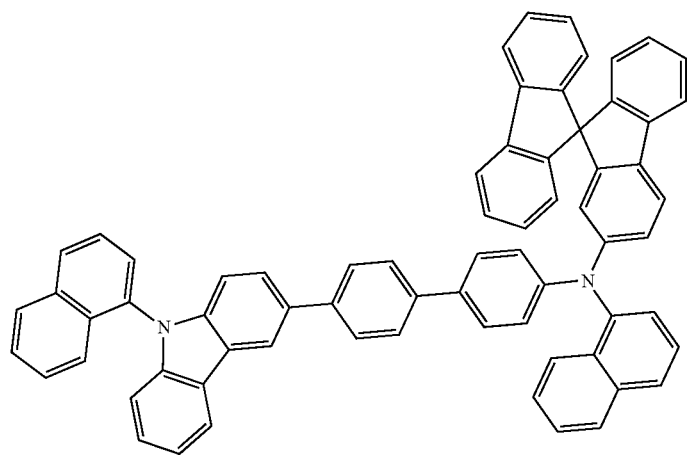
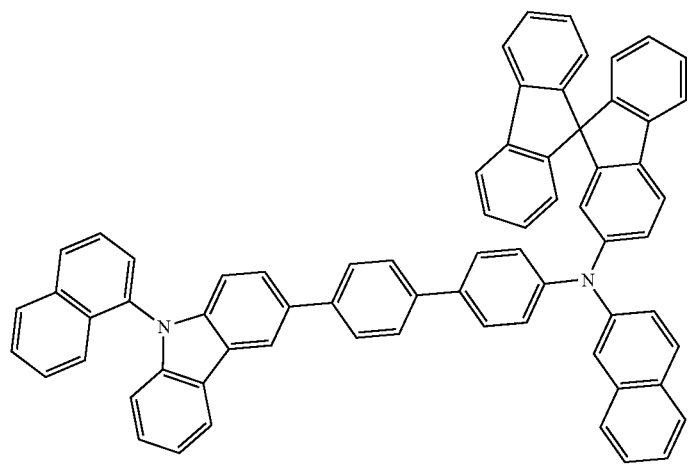
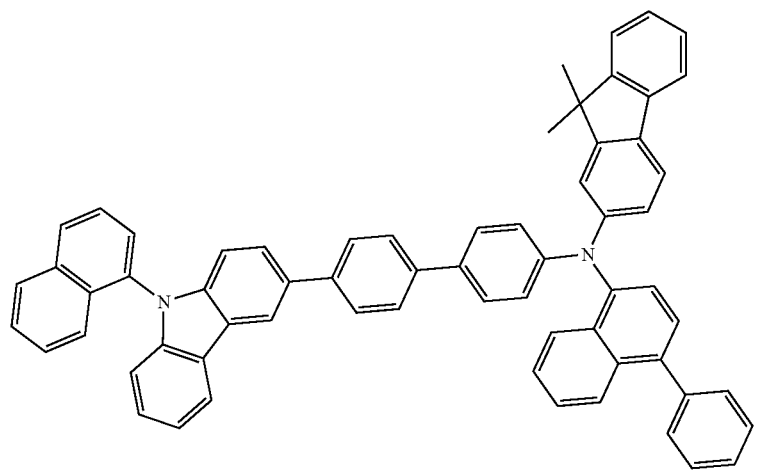

-continued
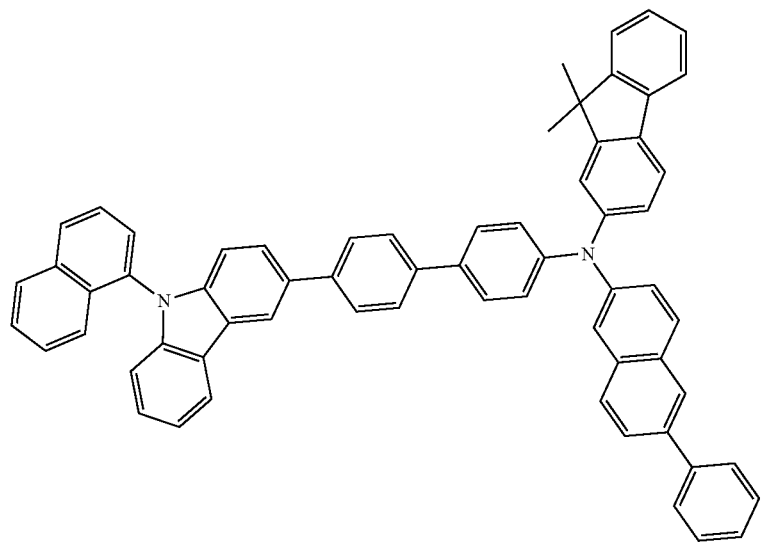
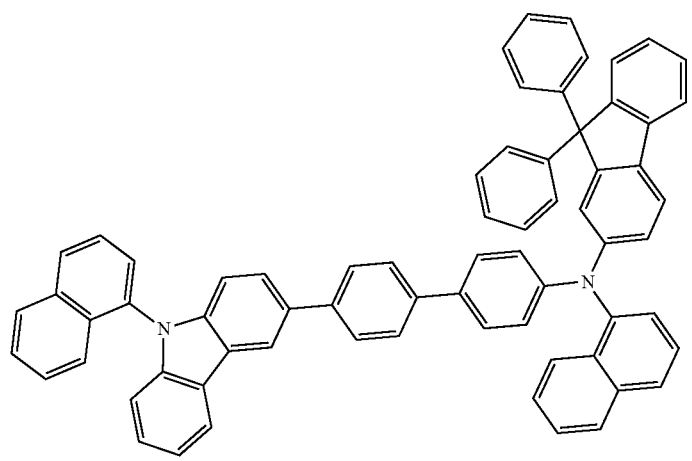
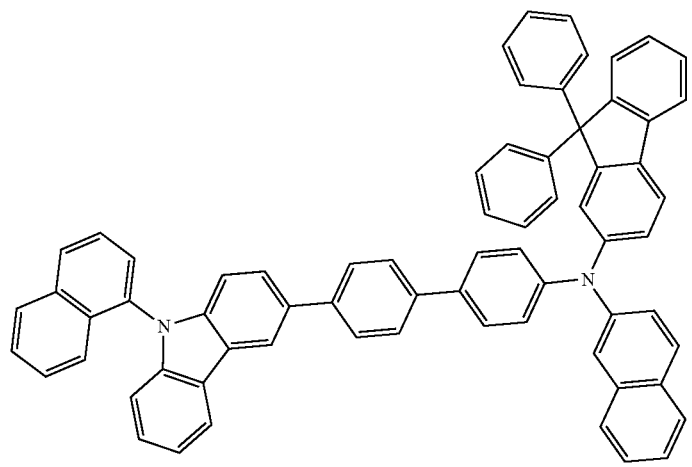

-continued
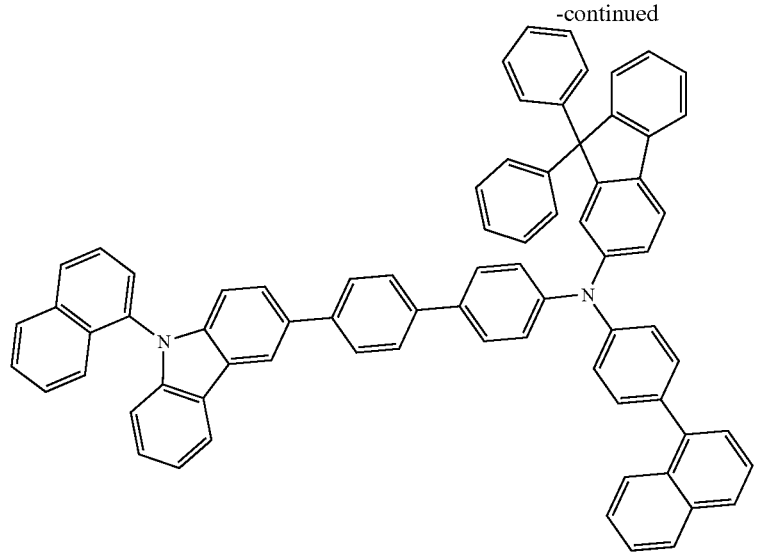
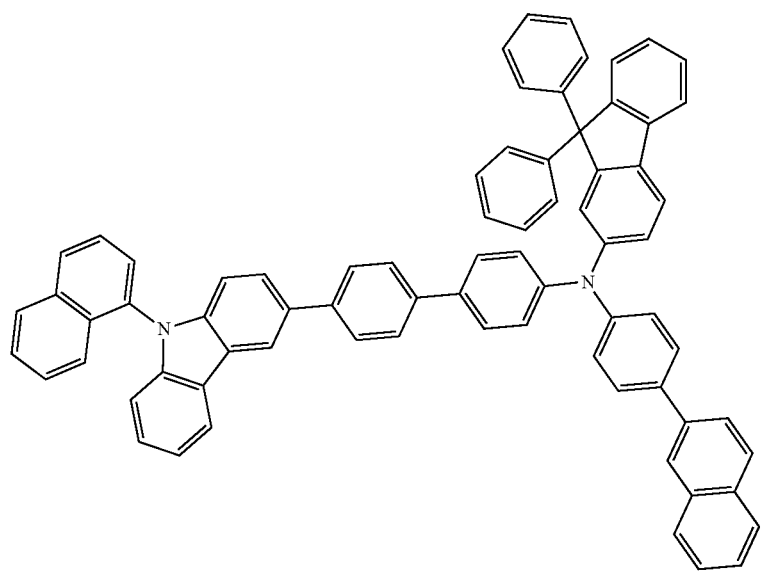
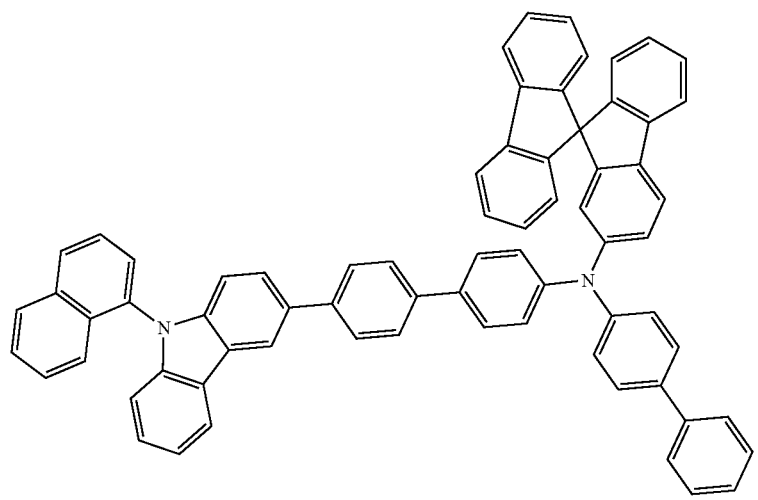

-continued
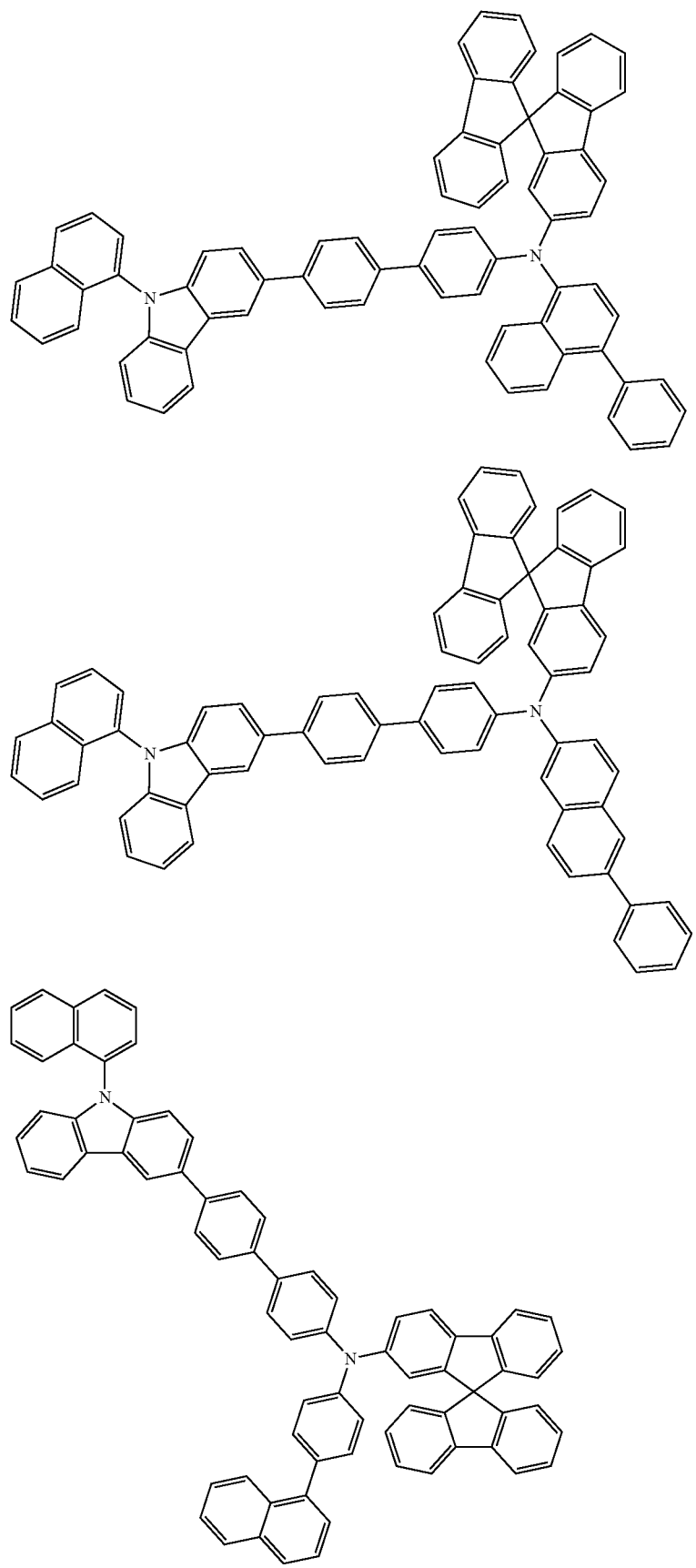

-continued
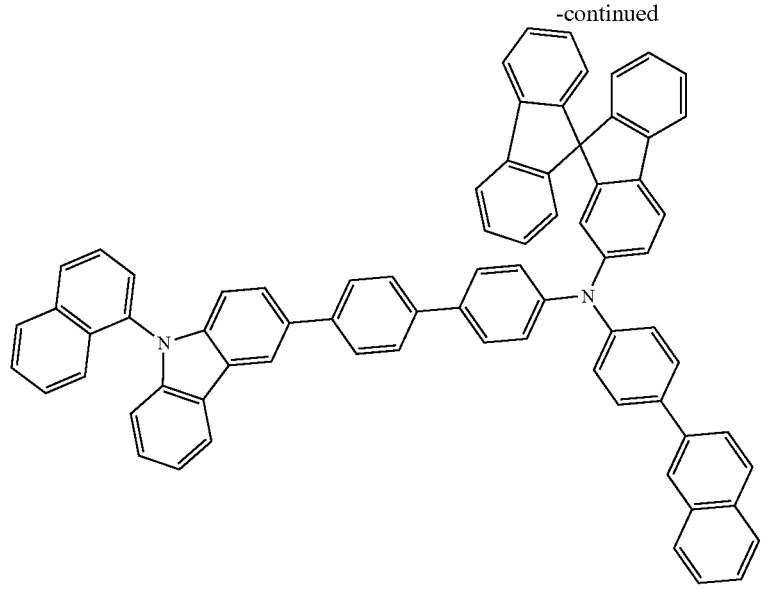
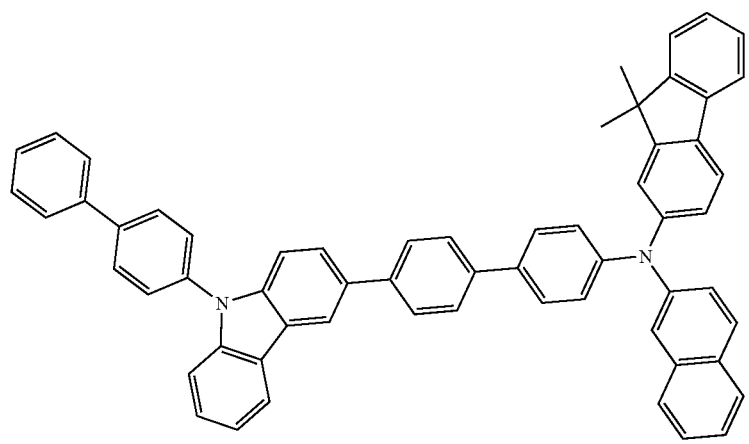
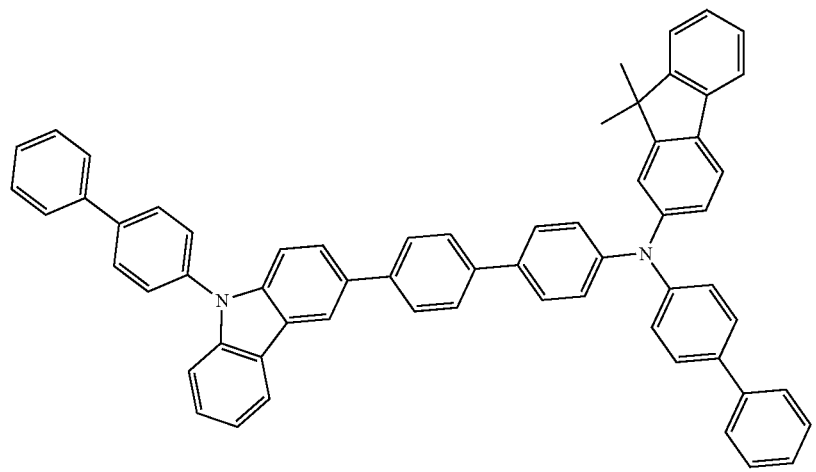

-continued
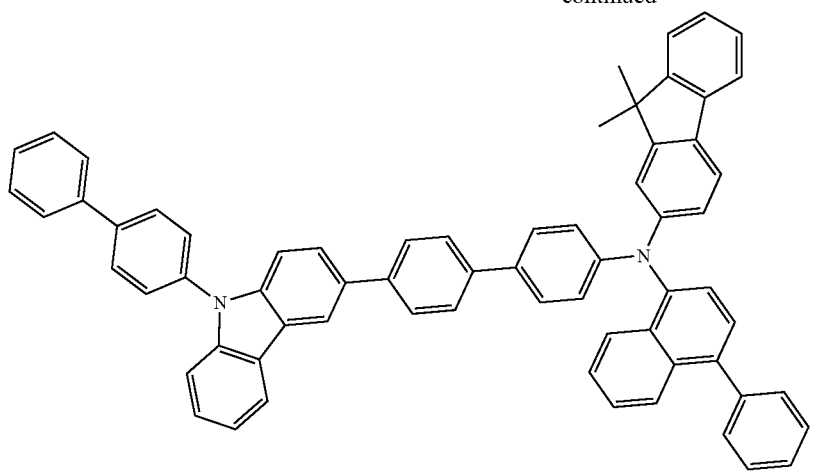
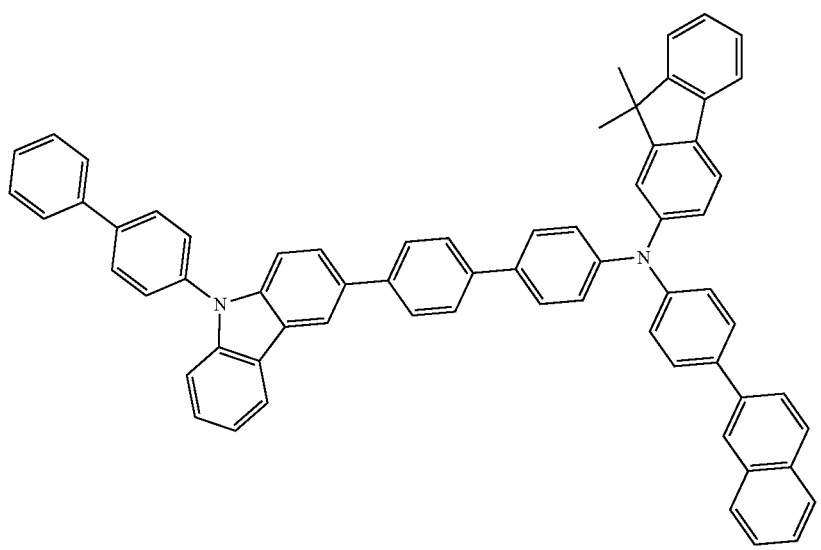
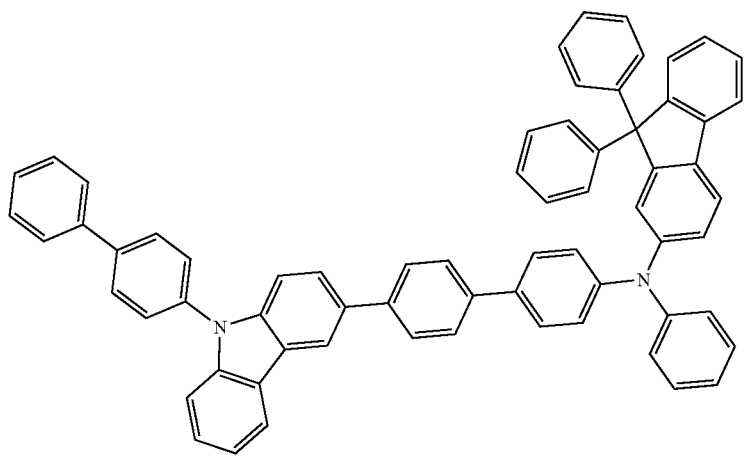

-continued
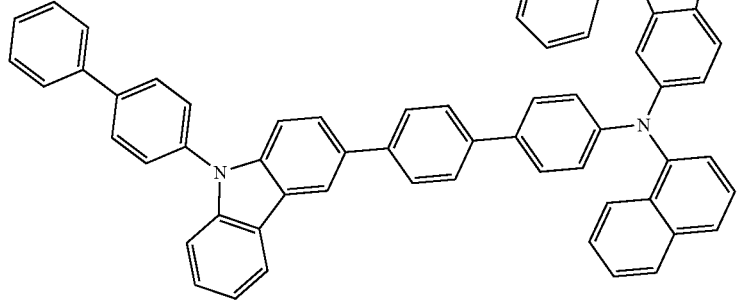
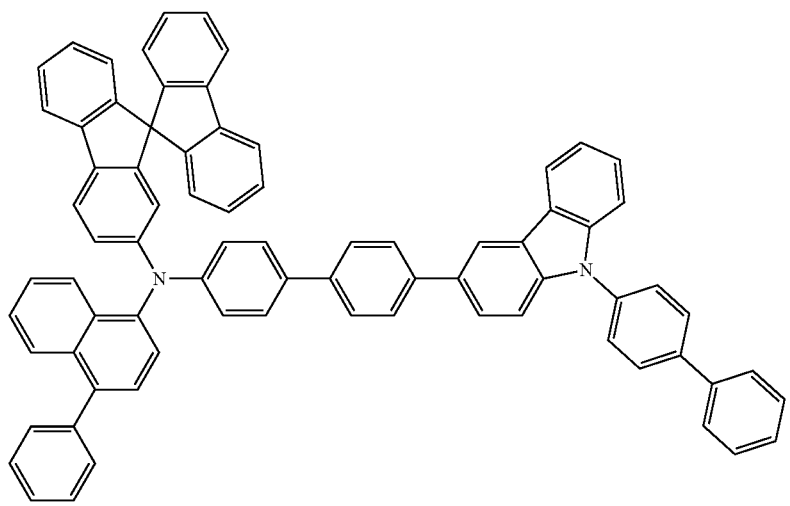
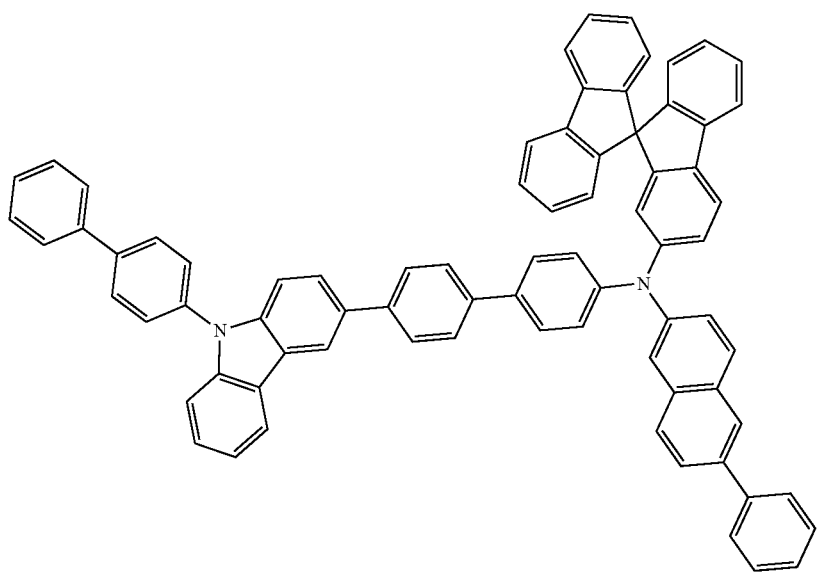

-continued
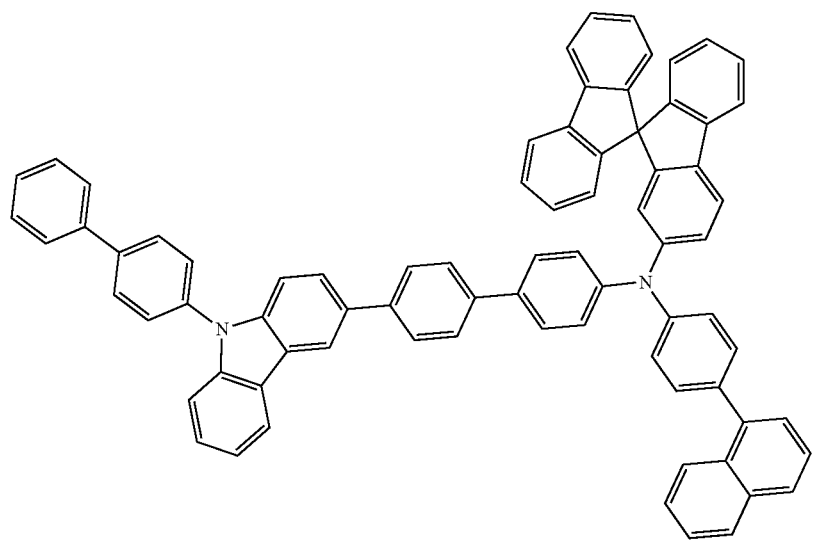
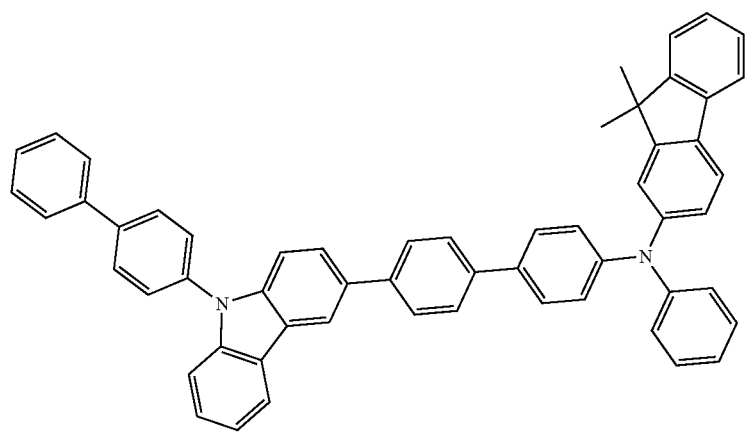
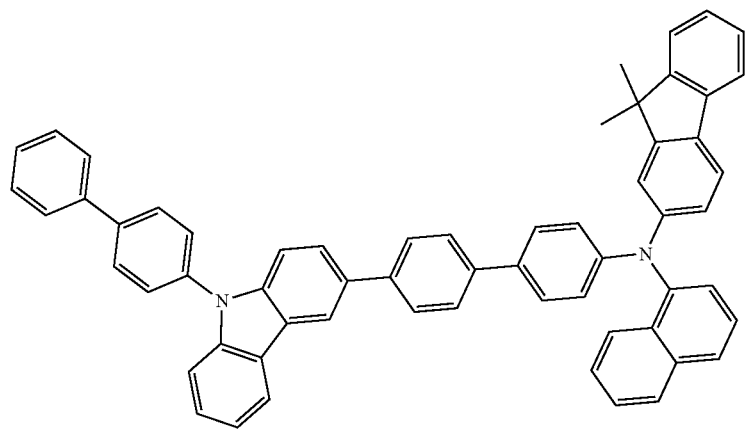

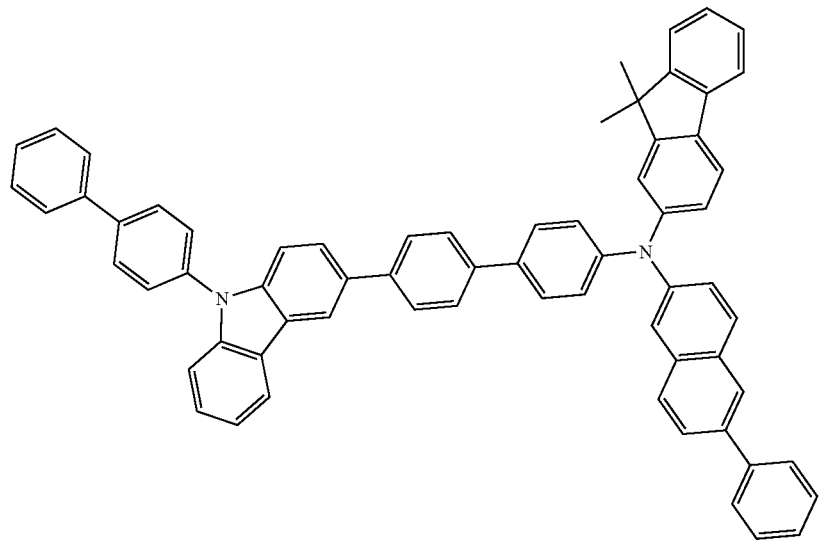
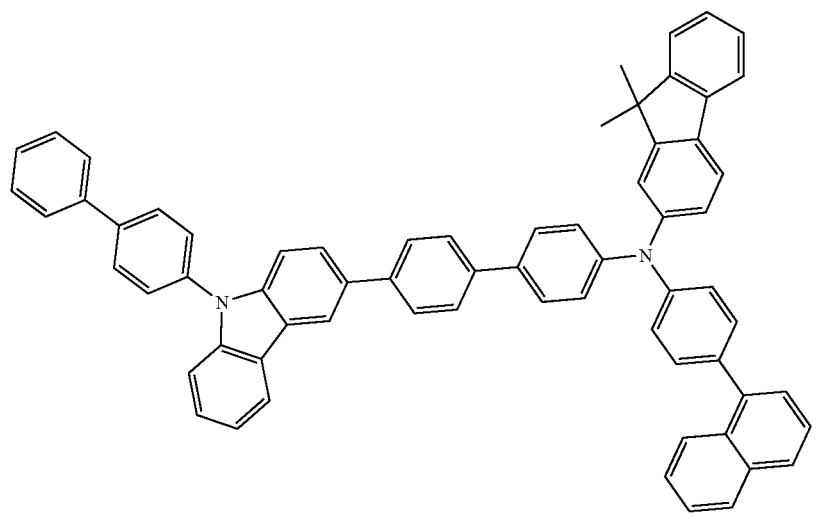
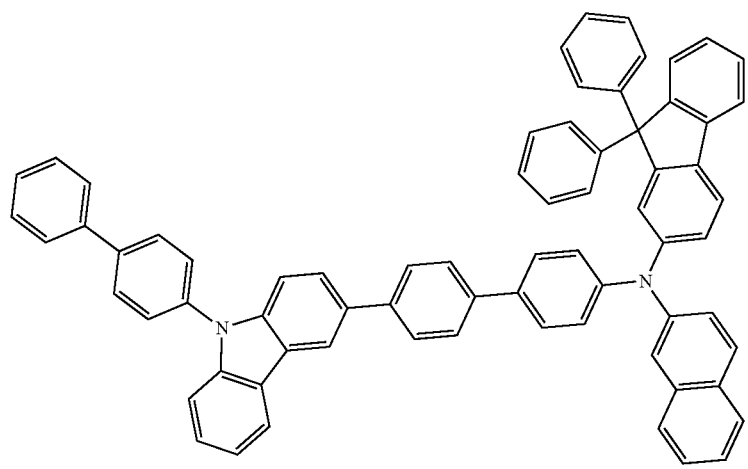

-continued
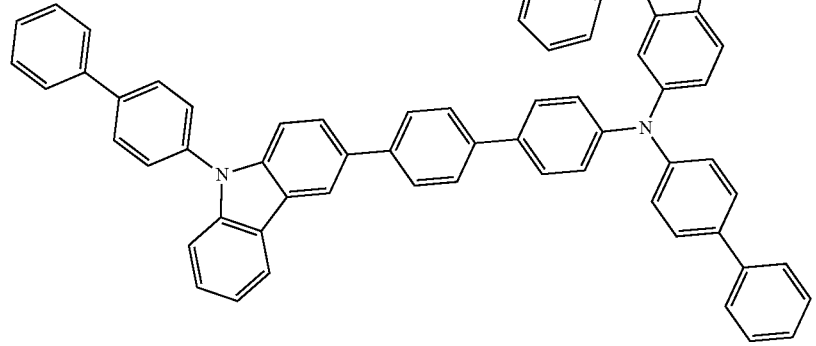
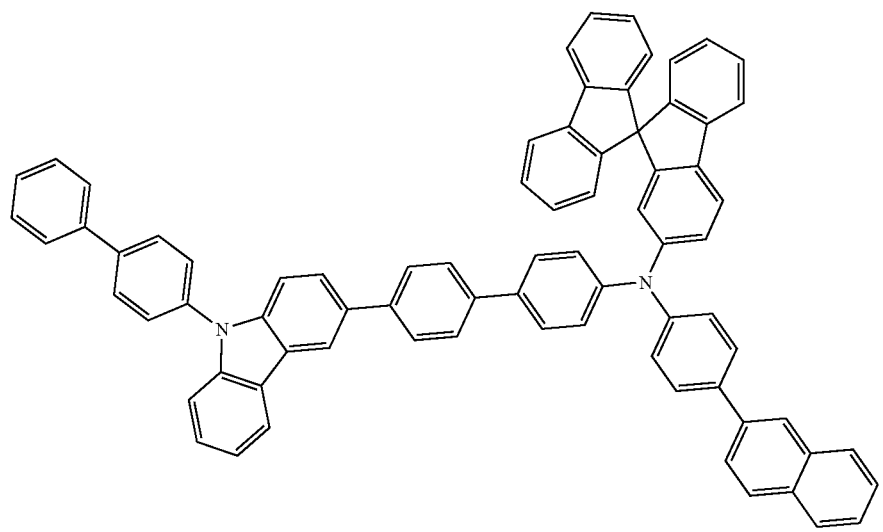
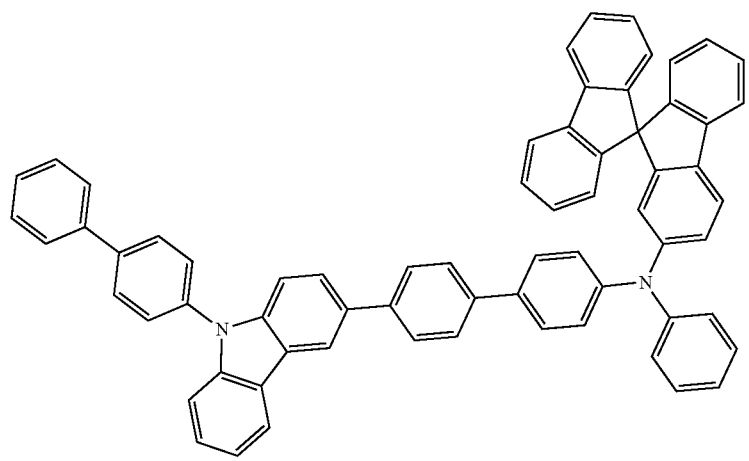

-continued
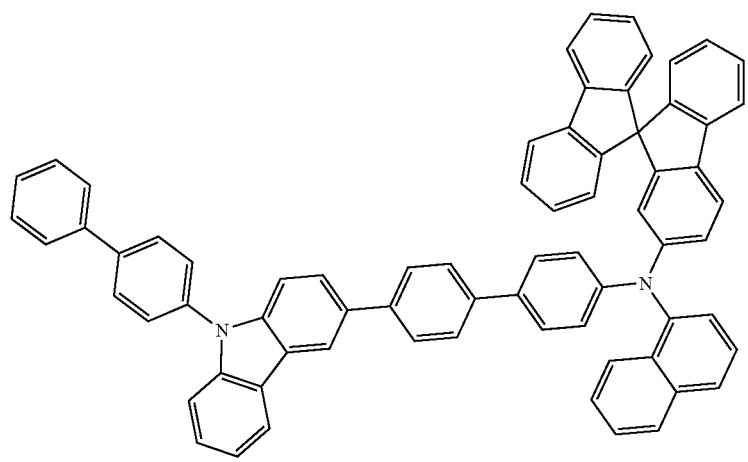
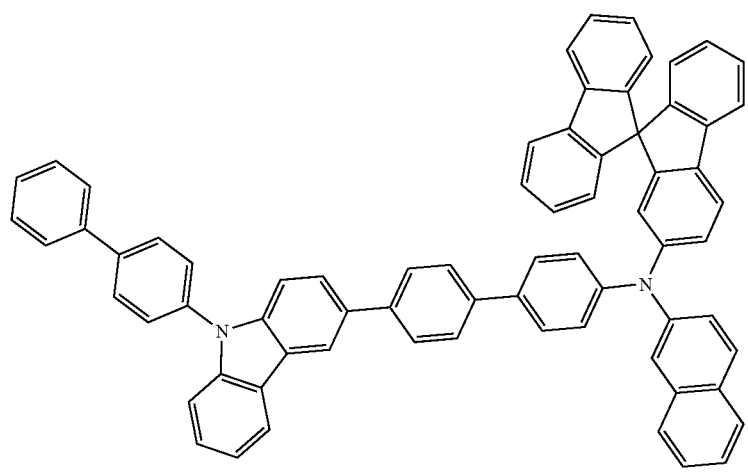
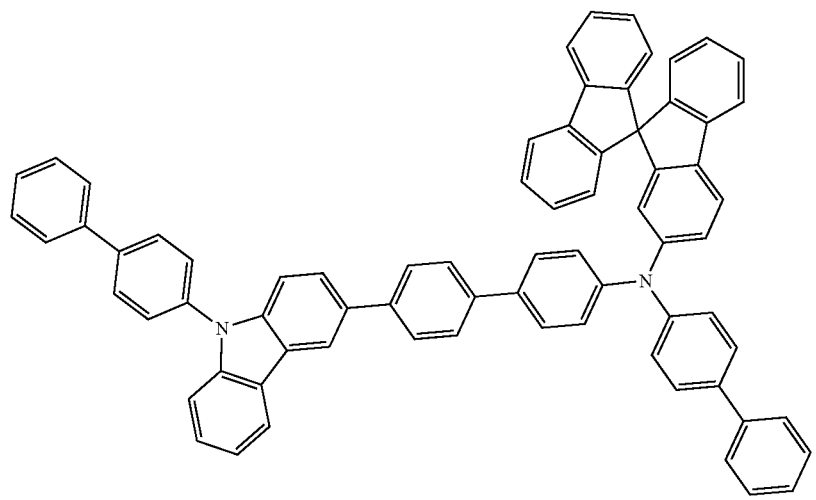

-continued
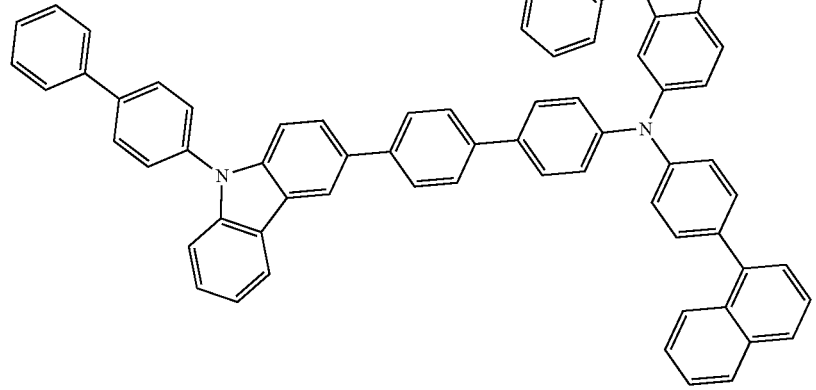
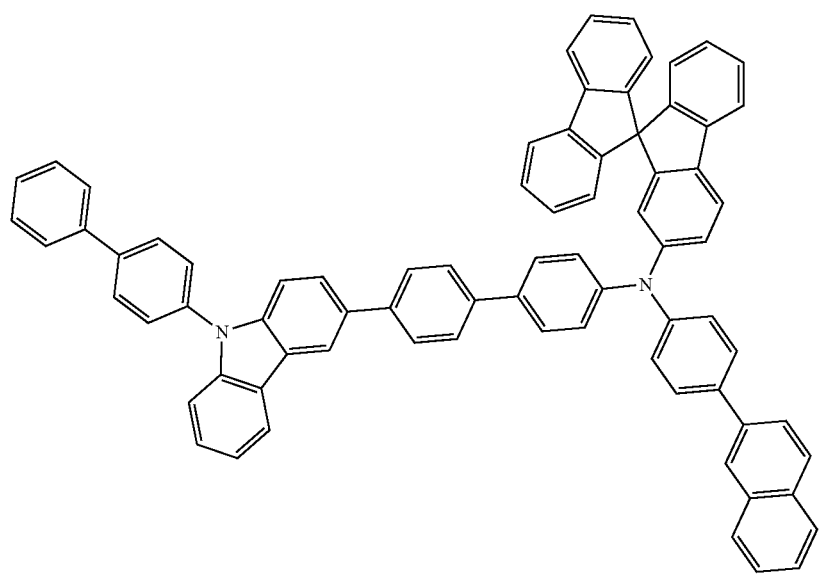
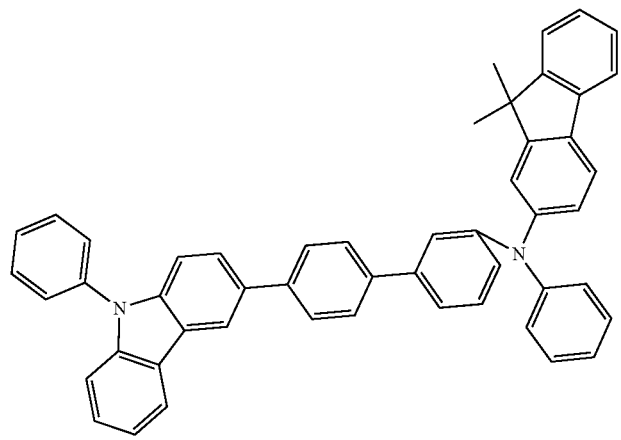

-continued
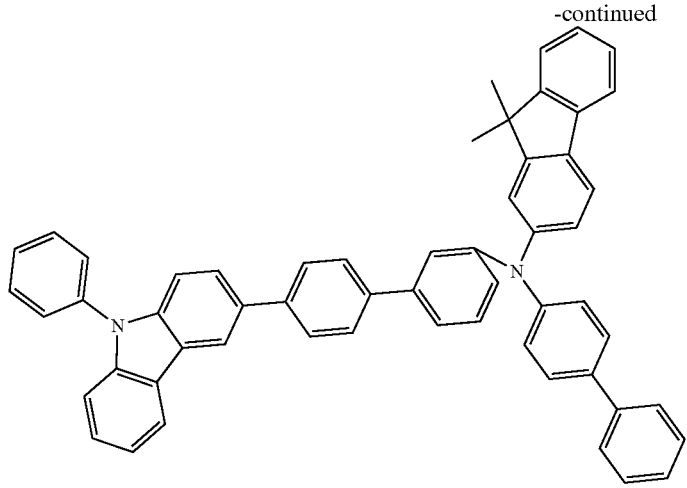
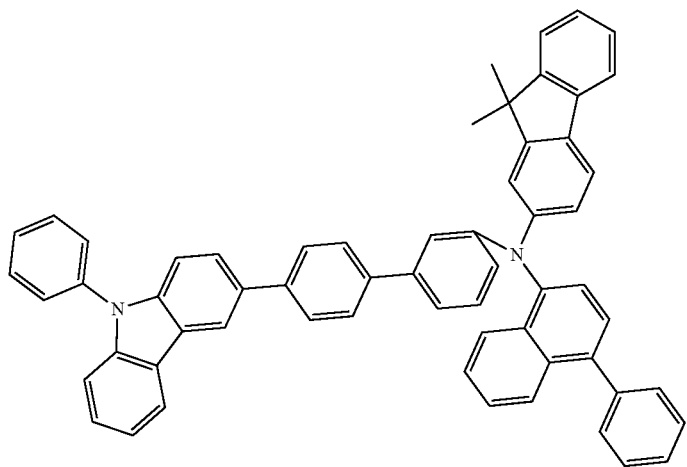
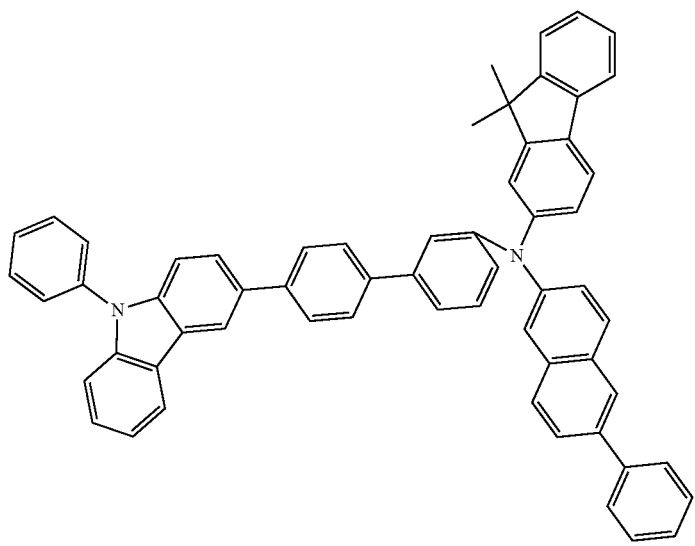

991
-continued
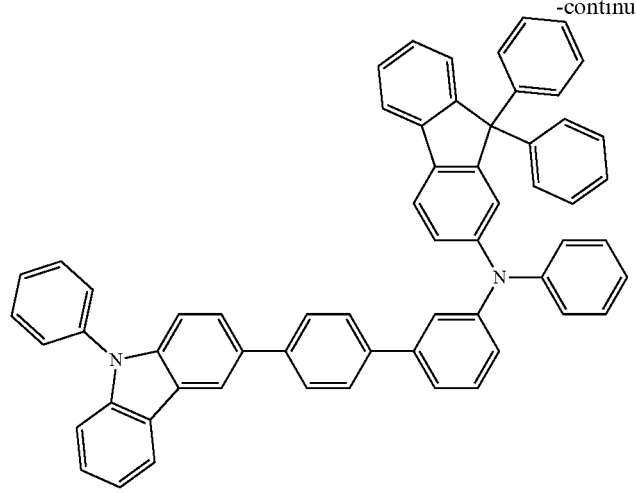
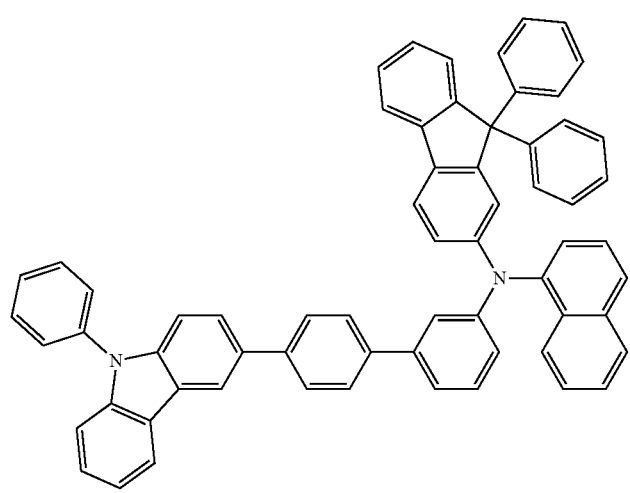
992
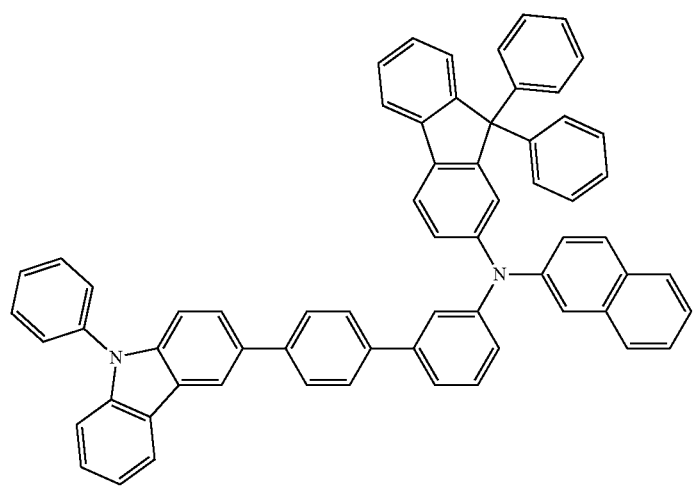

-continued
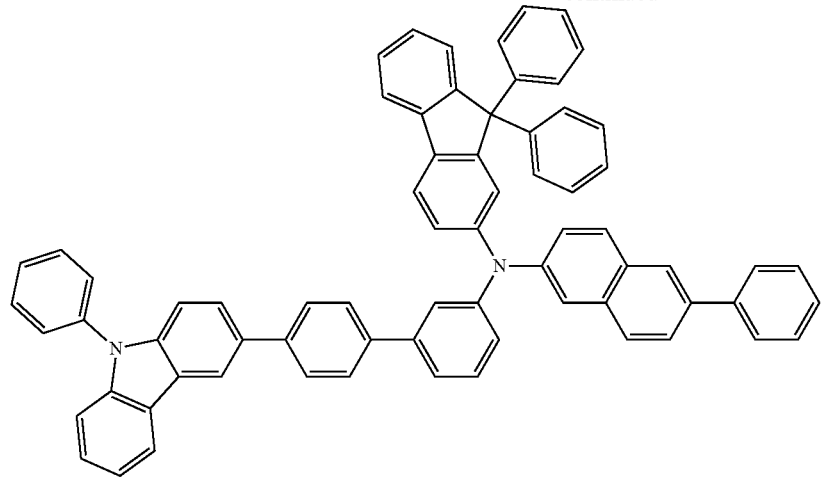
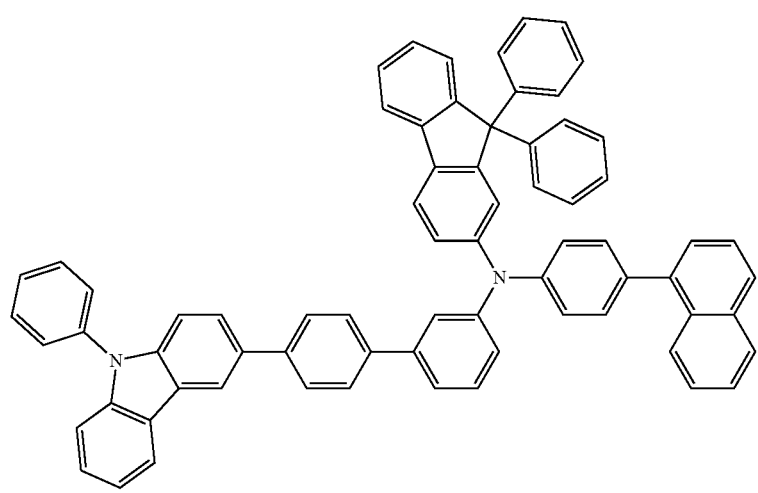
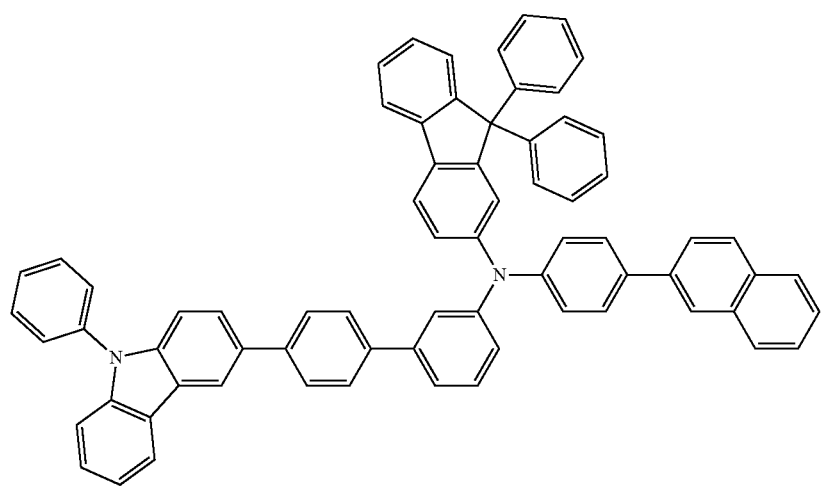

-continued
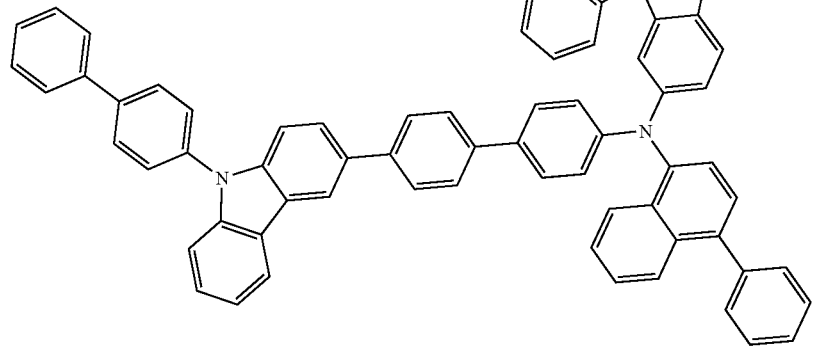
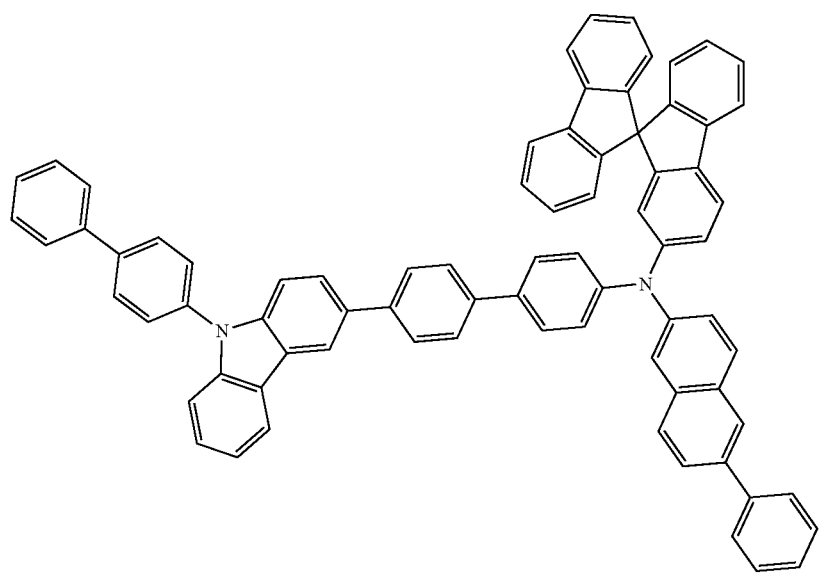
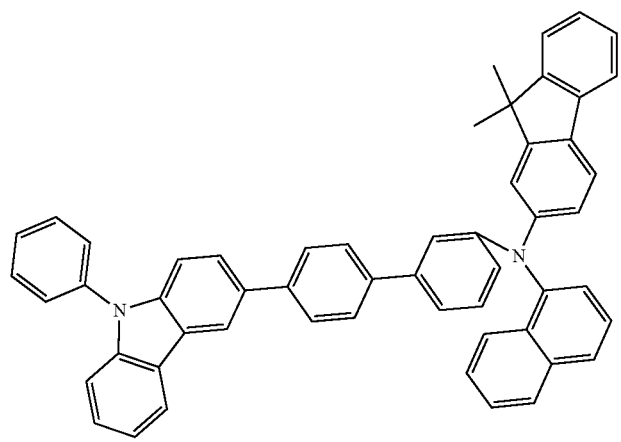

-continued
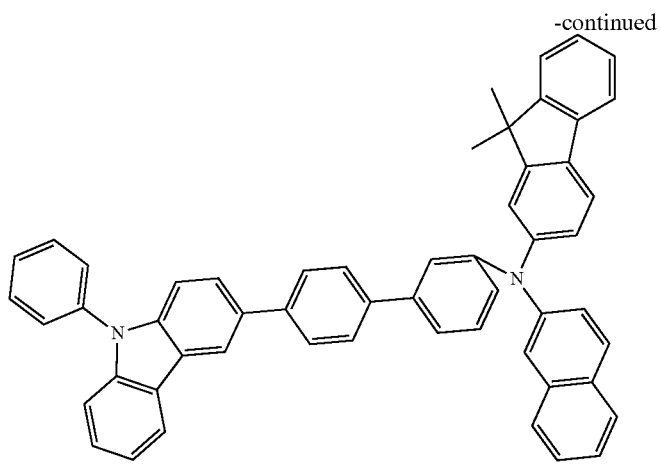
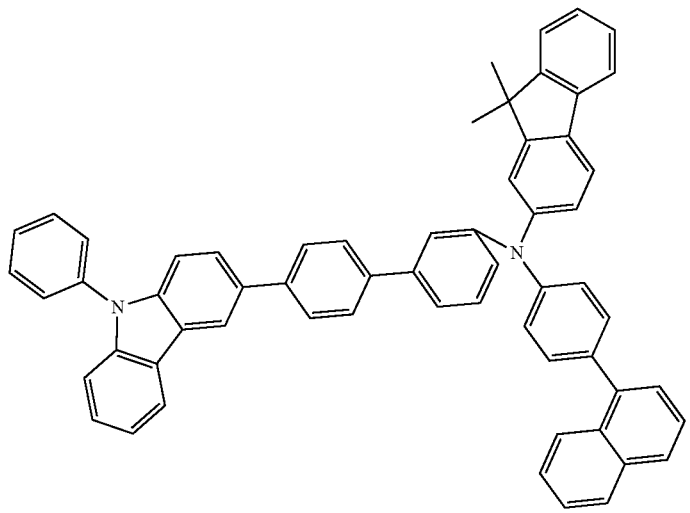 [SMILES: CC1(C)c2ccccc2-c2ccc(N(c3ccc(-c4cccc5ccccc45)cc3)c3cccc(-c4ccc(-c5ccc6c(c5)c5ccccc5n6-c5ccccc5)cc4)c3)cc21]
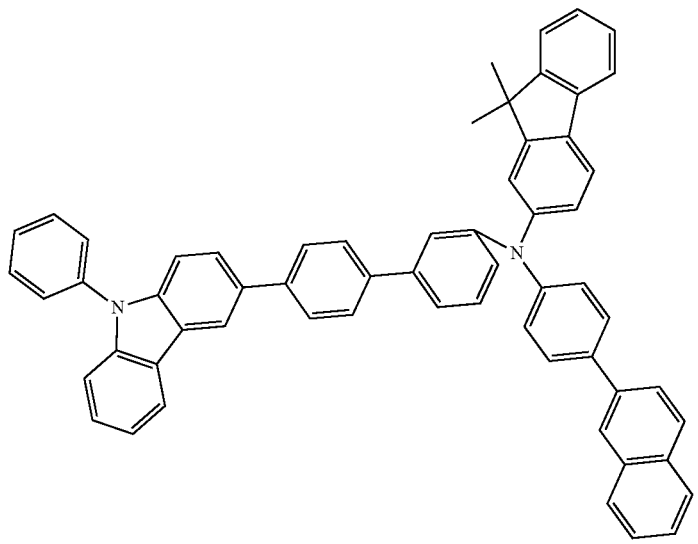

-continued
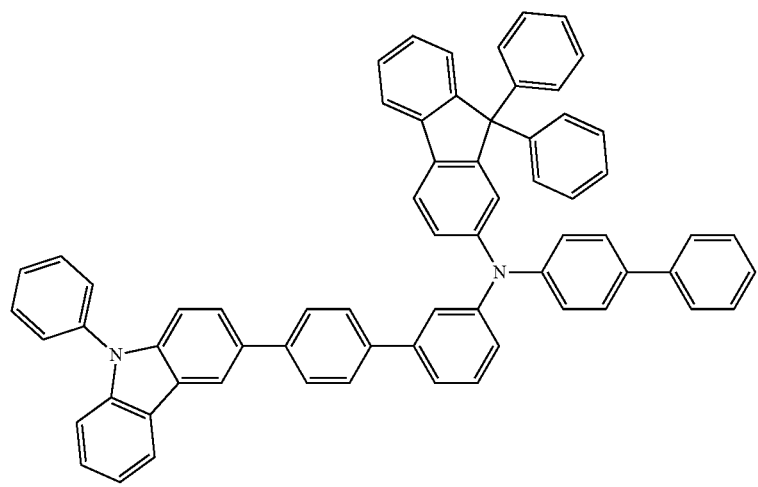
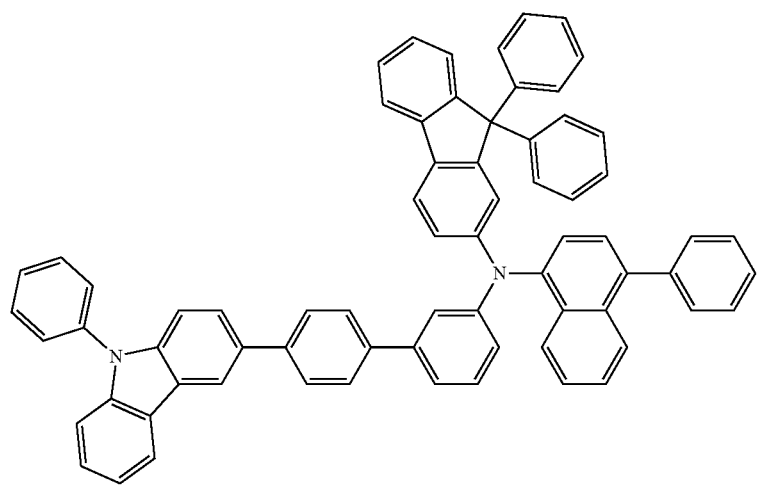
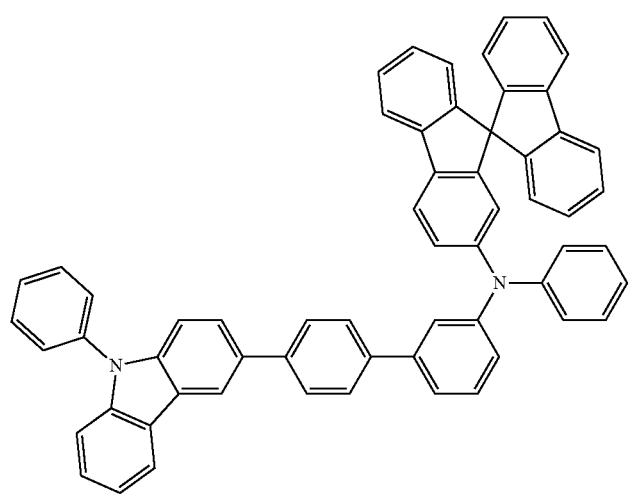

-continued
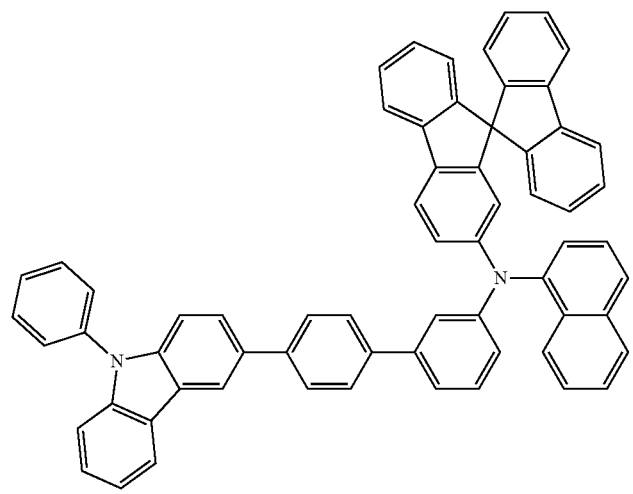
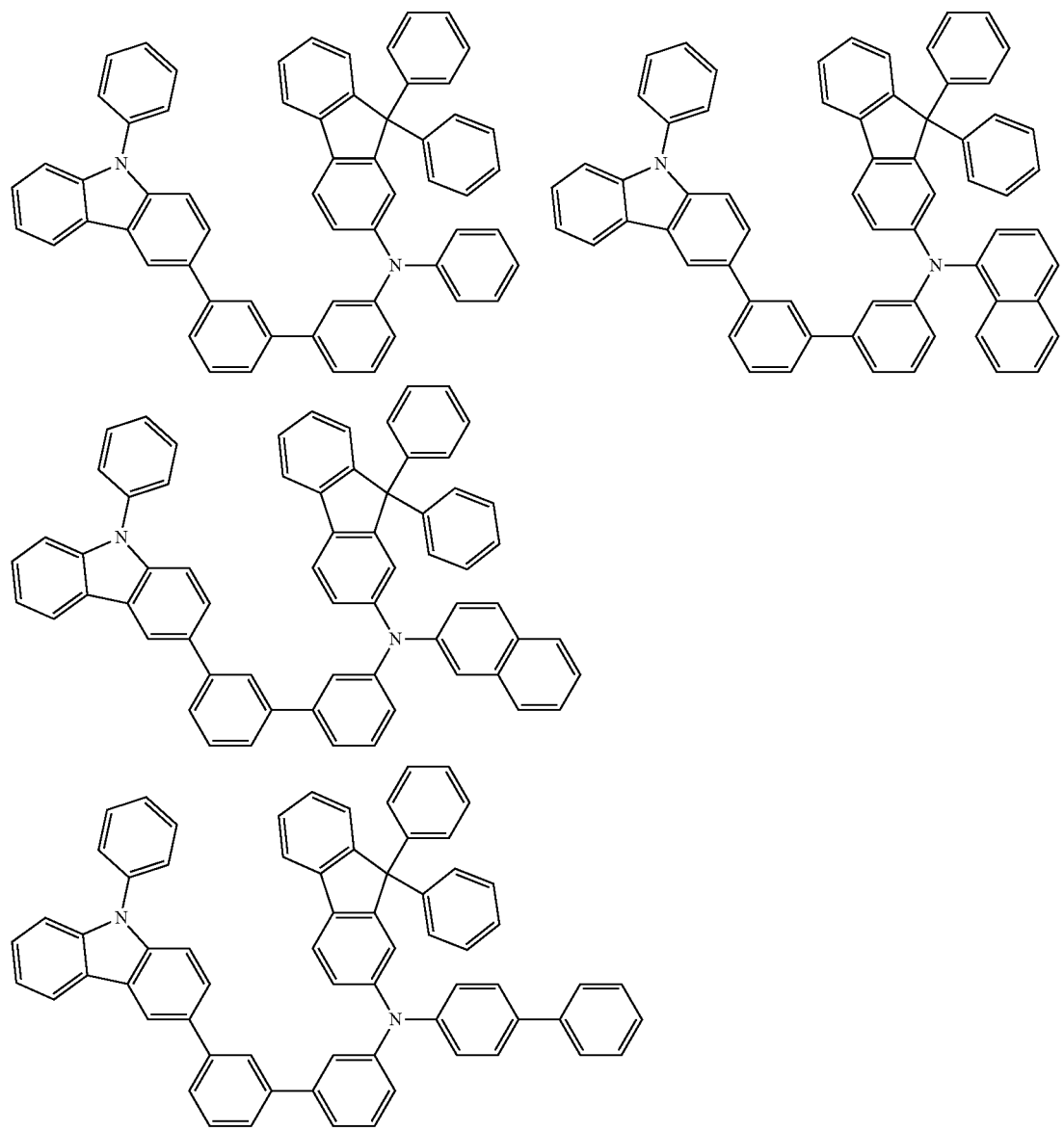

1003 1004
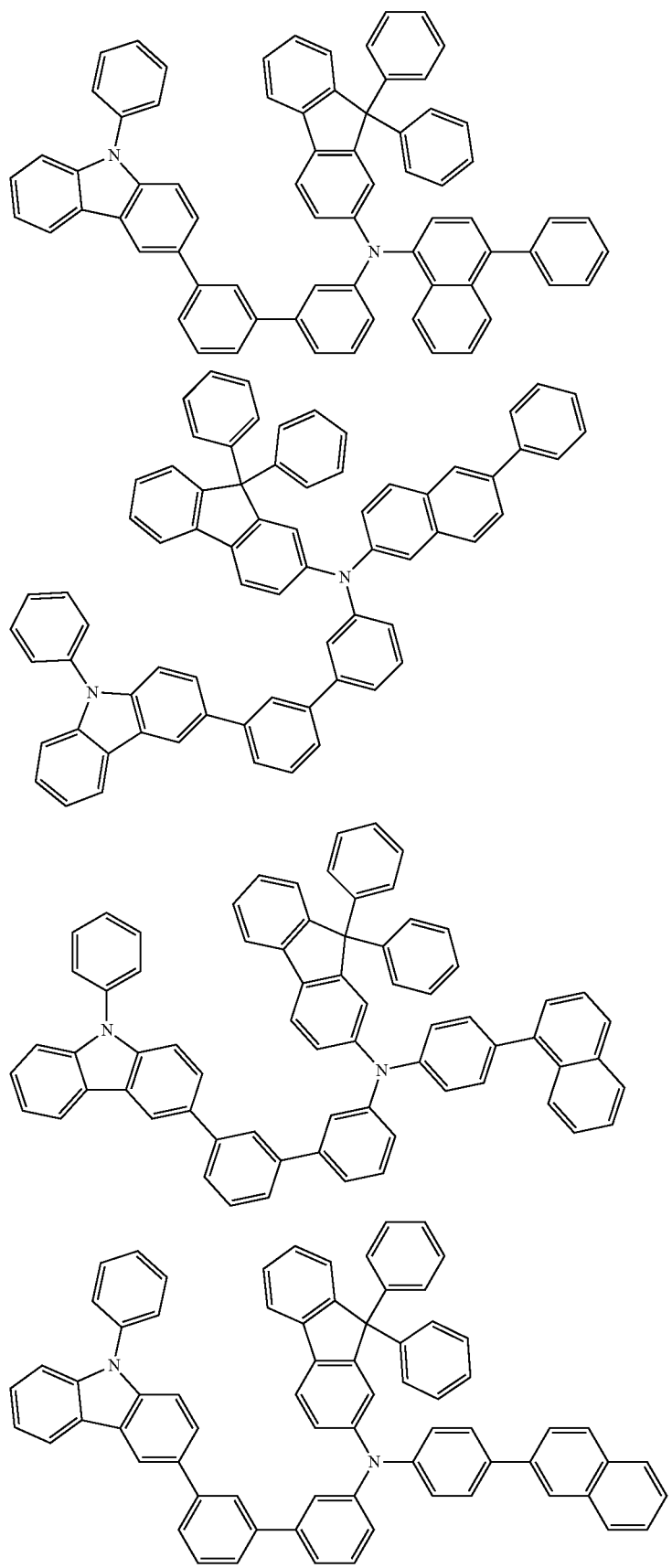

1005
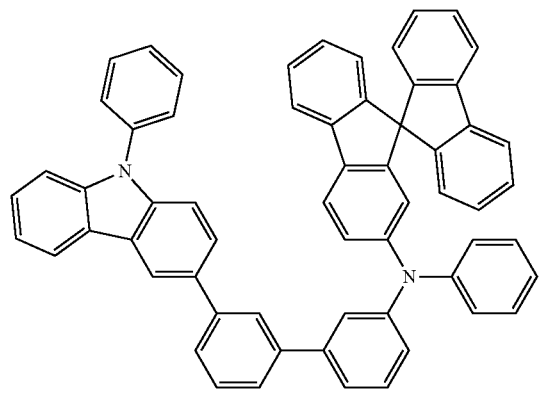
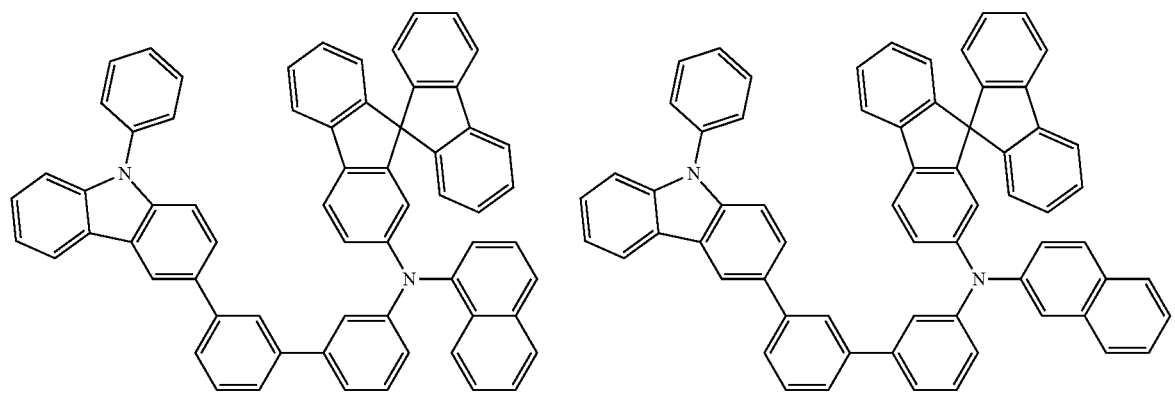
1006
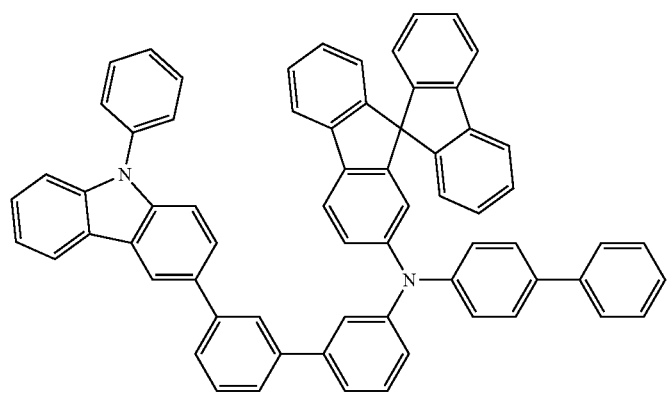
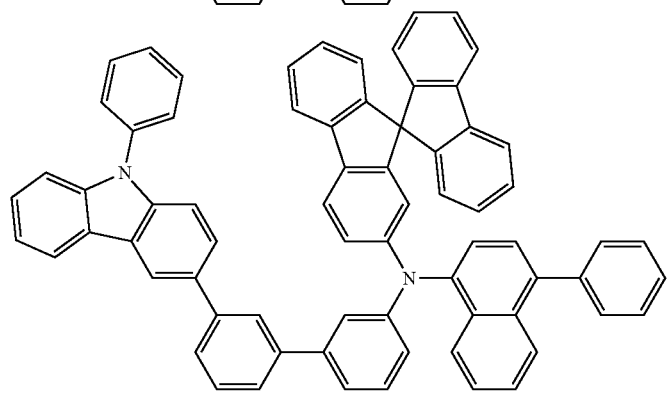

1007
1008
-continued
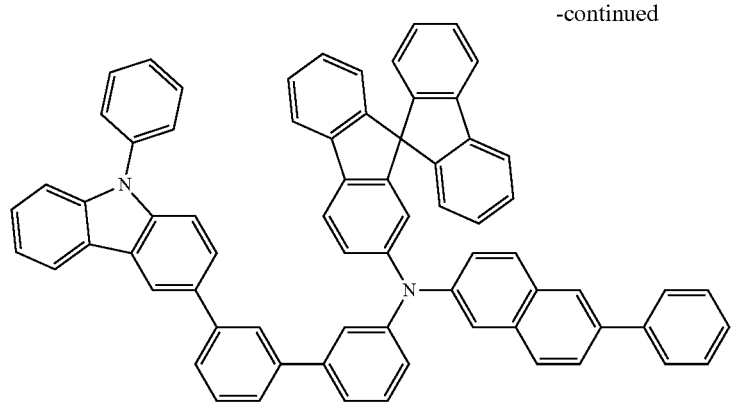
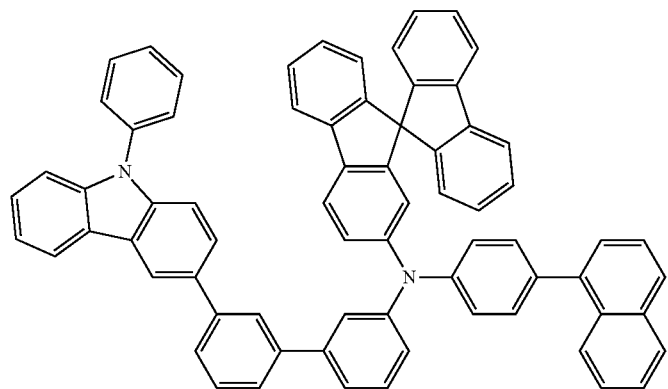
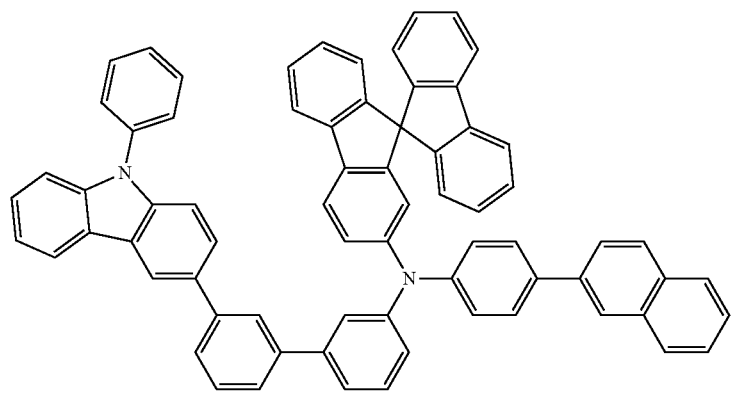
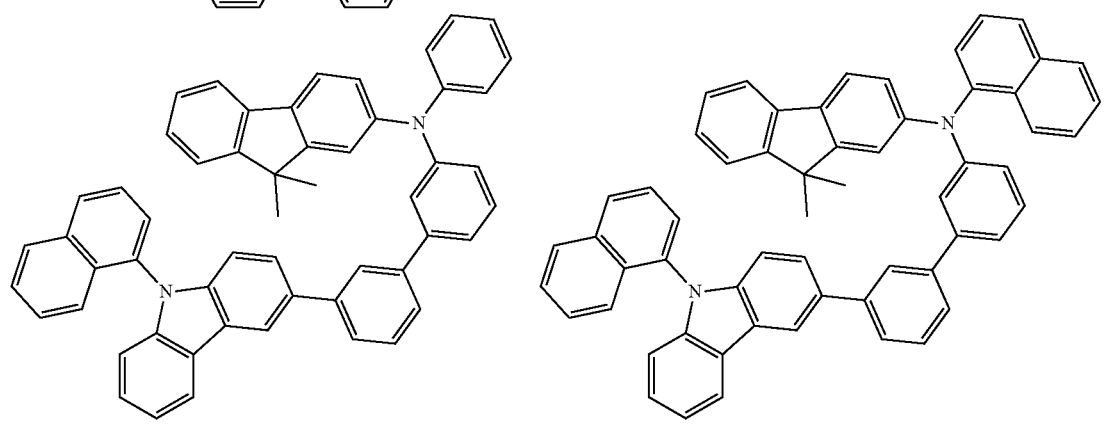

1009 -continued 1010
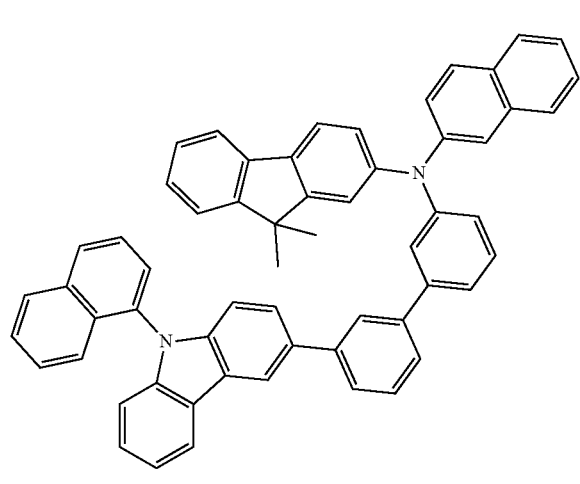
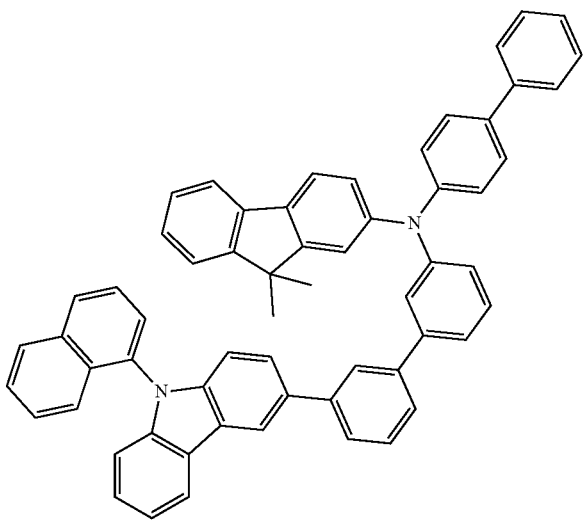
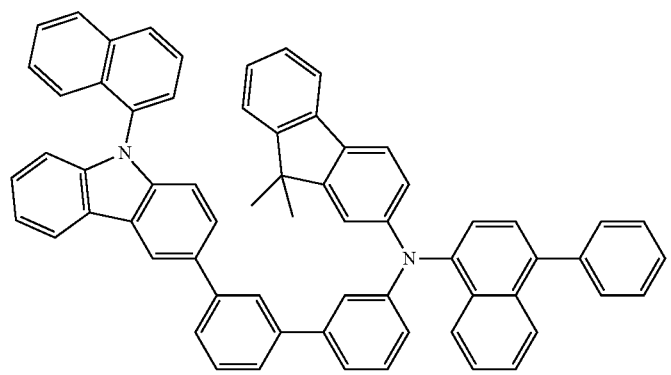
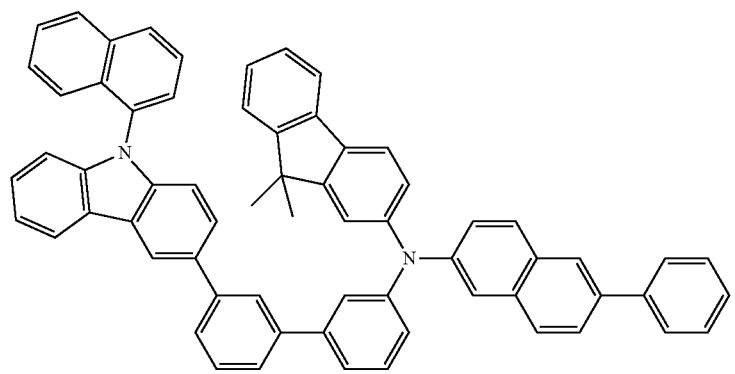
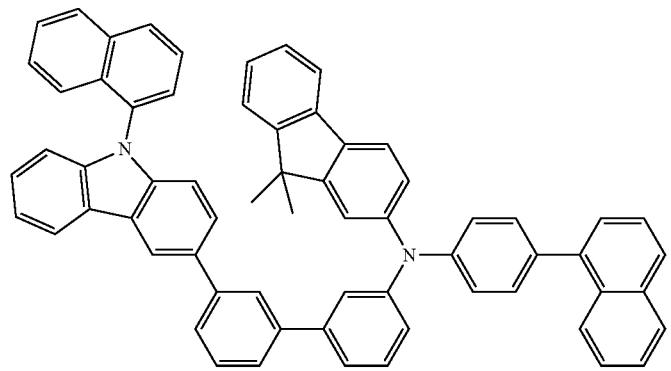

1011 1012
-continued
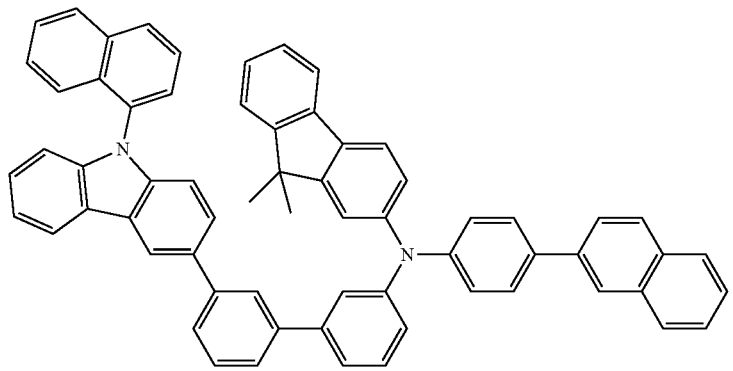
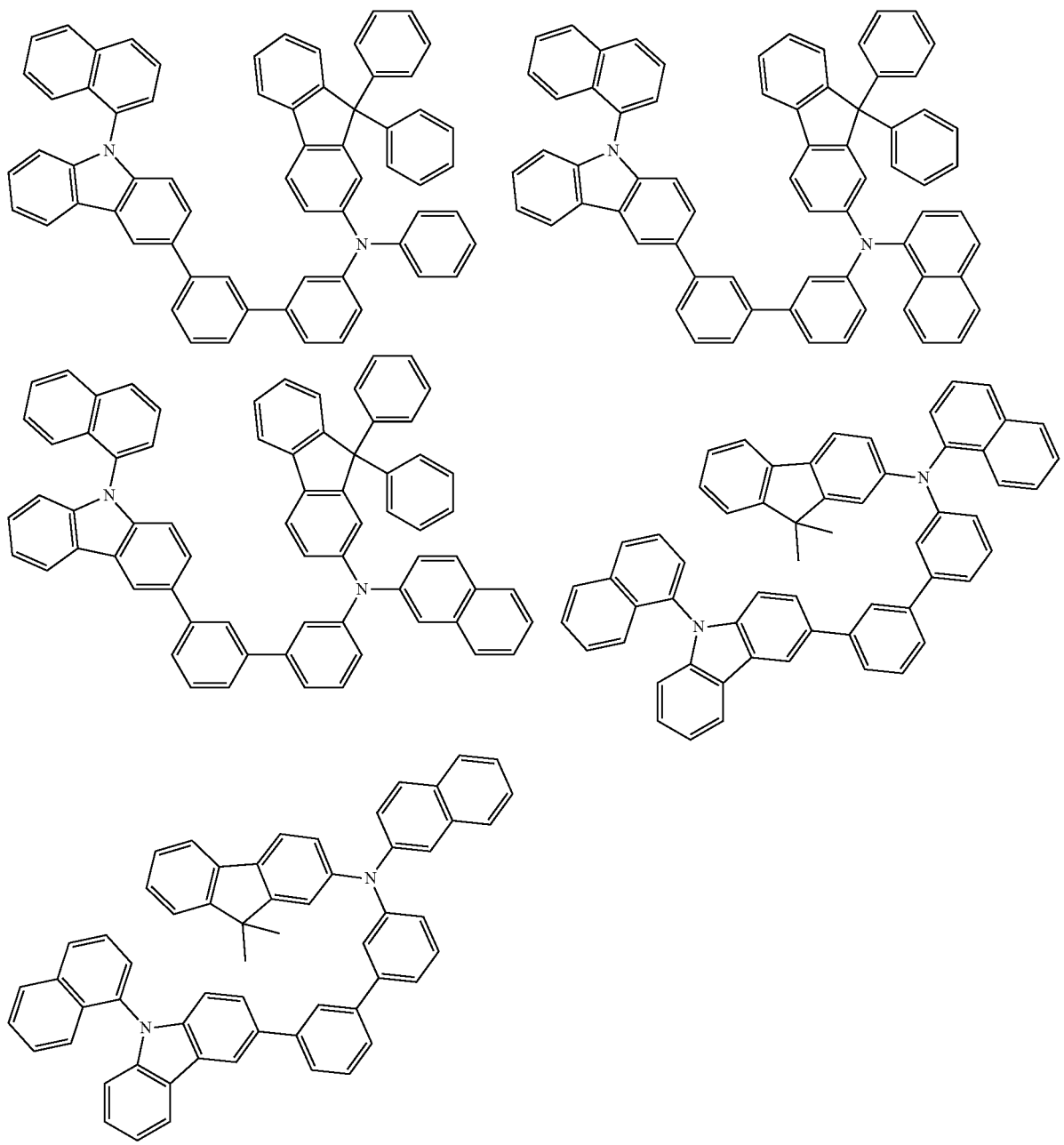

1013 1014
-continued
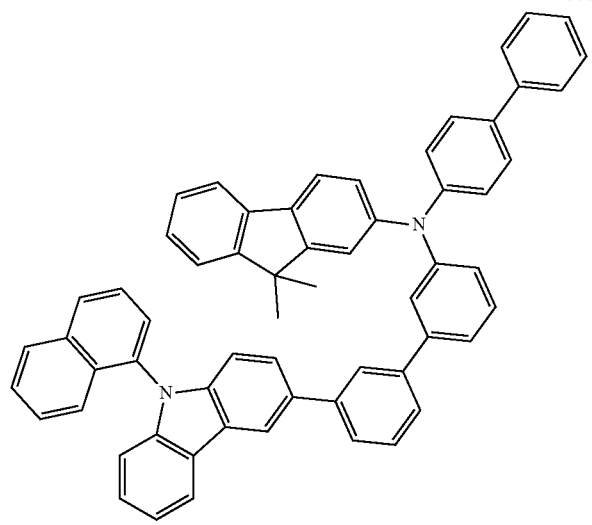
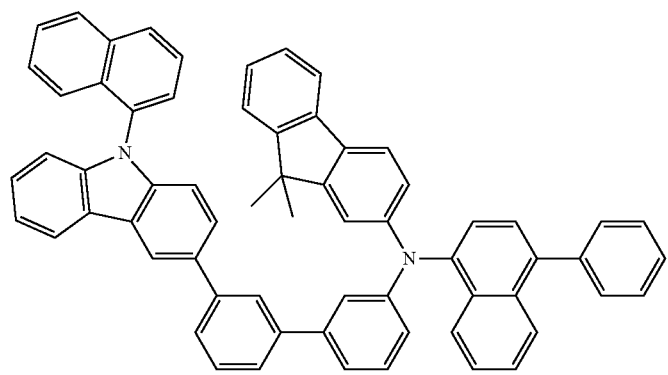
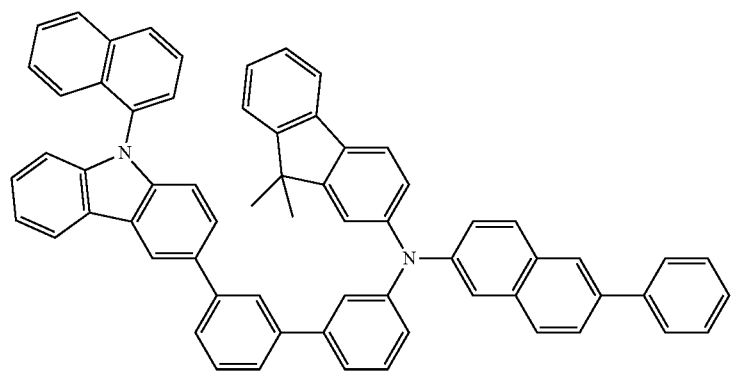
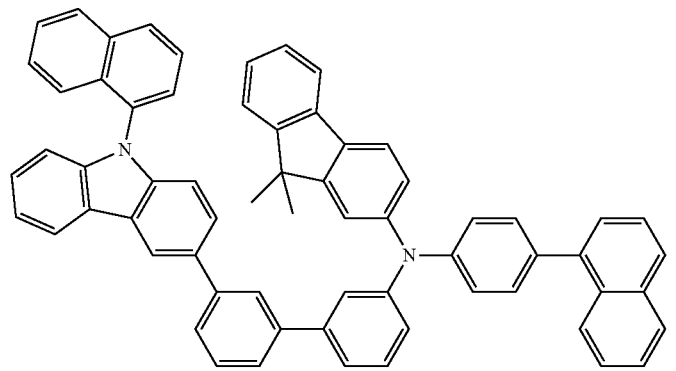

1015
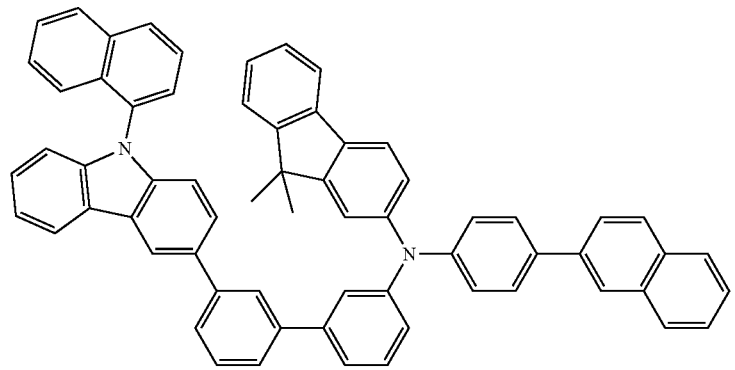
1016
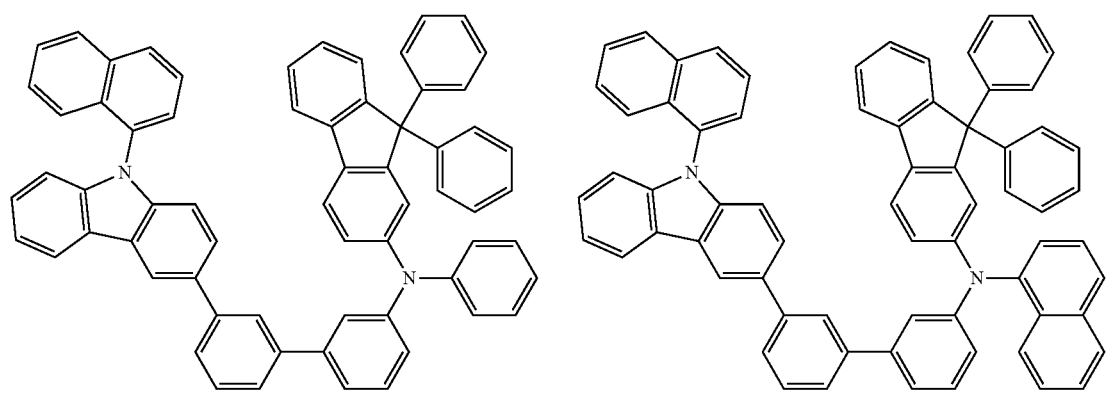
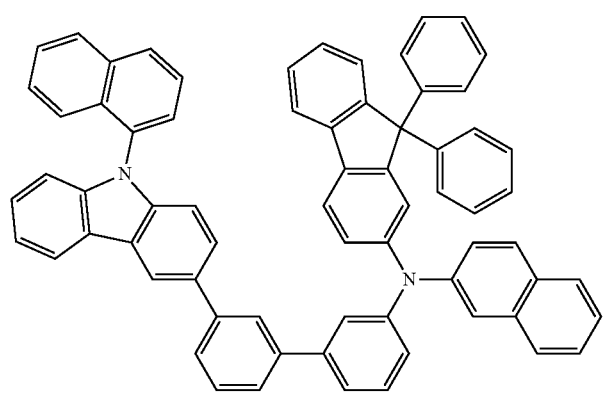
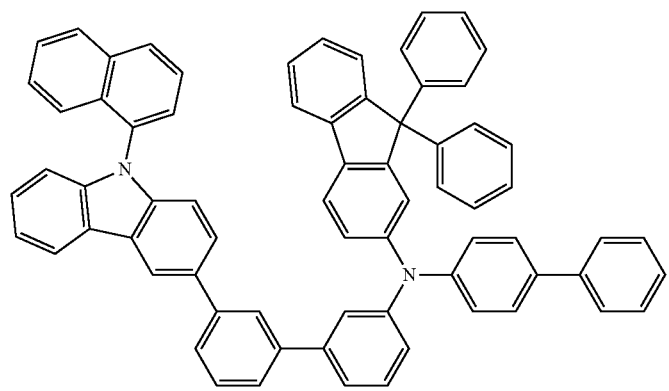

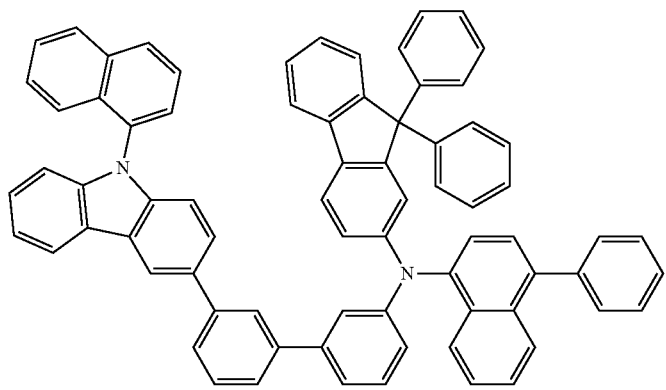
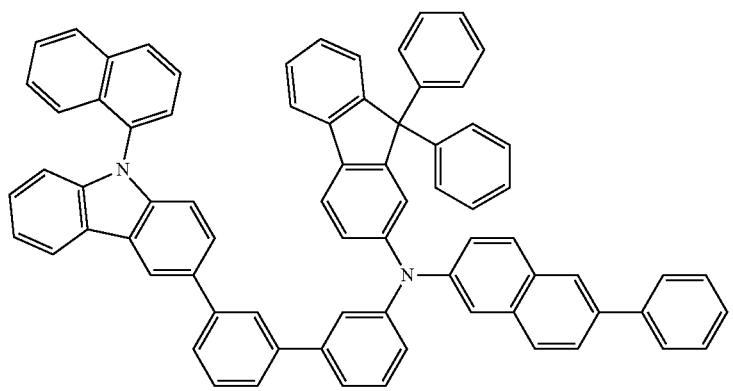
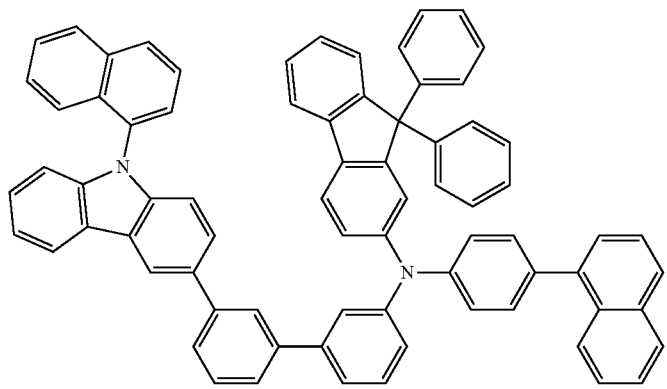
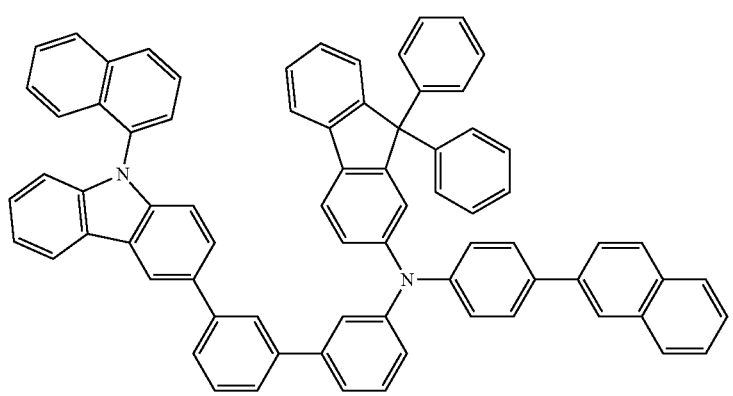

1019 1020
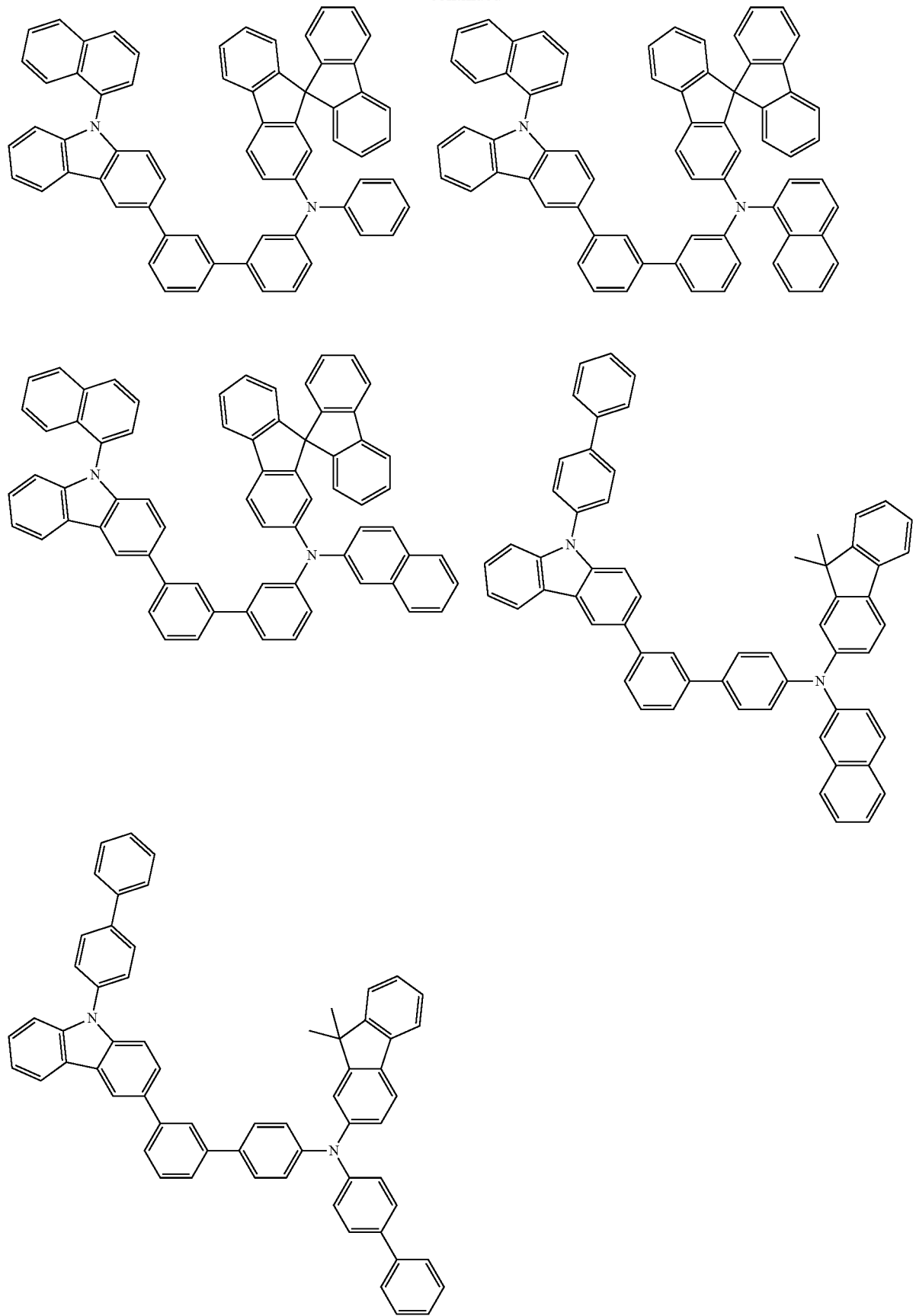

-continued
| 1021 | 1022 |
|---|---|
| 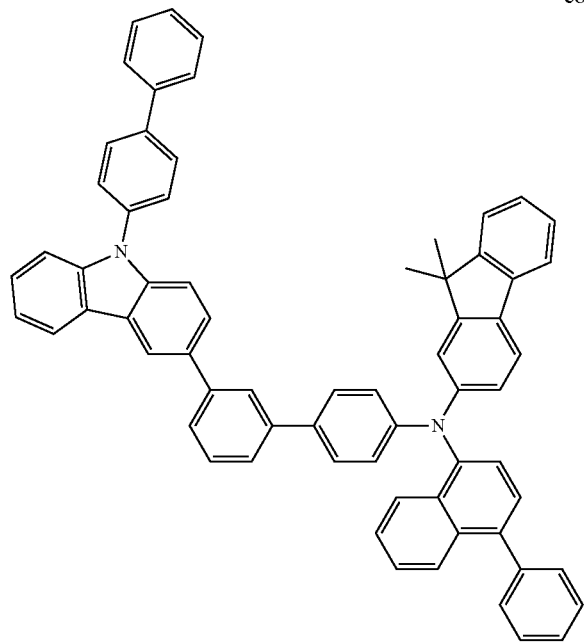 | 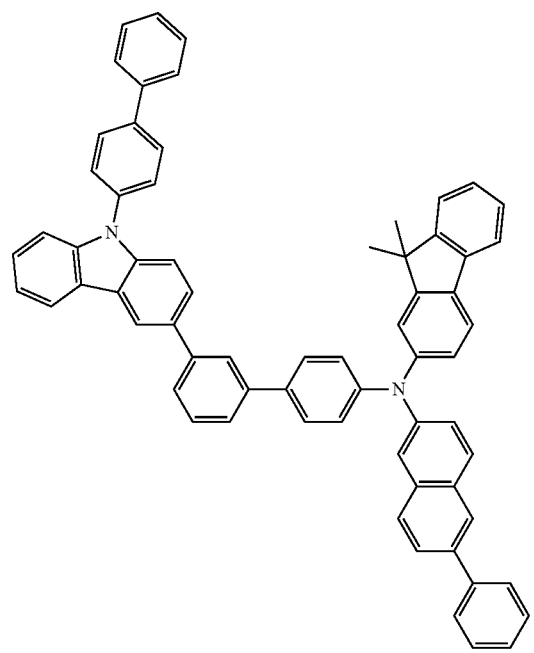 |
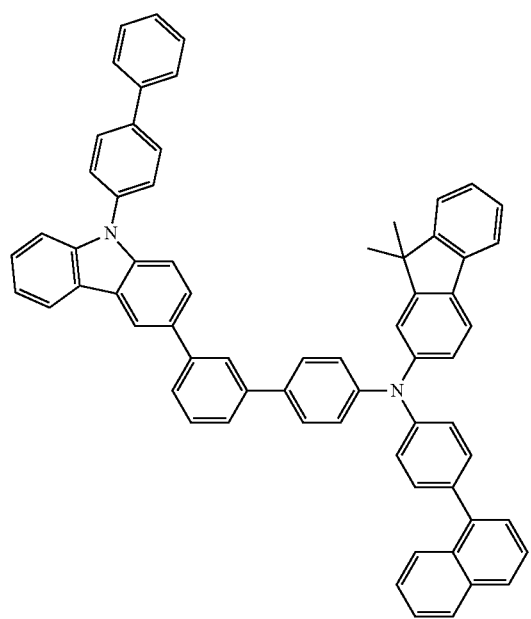

1023 1024
-continued
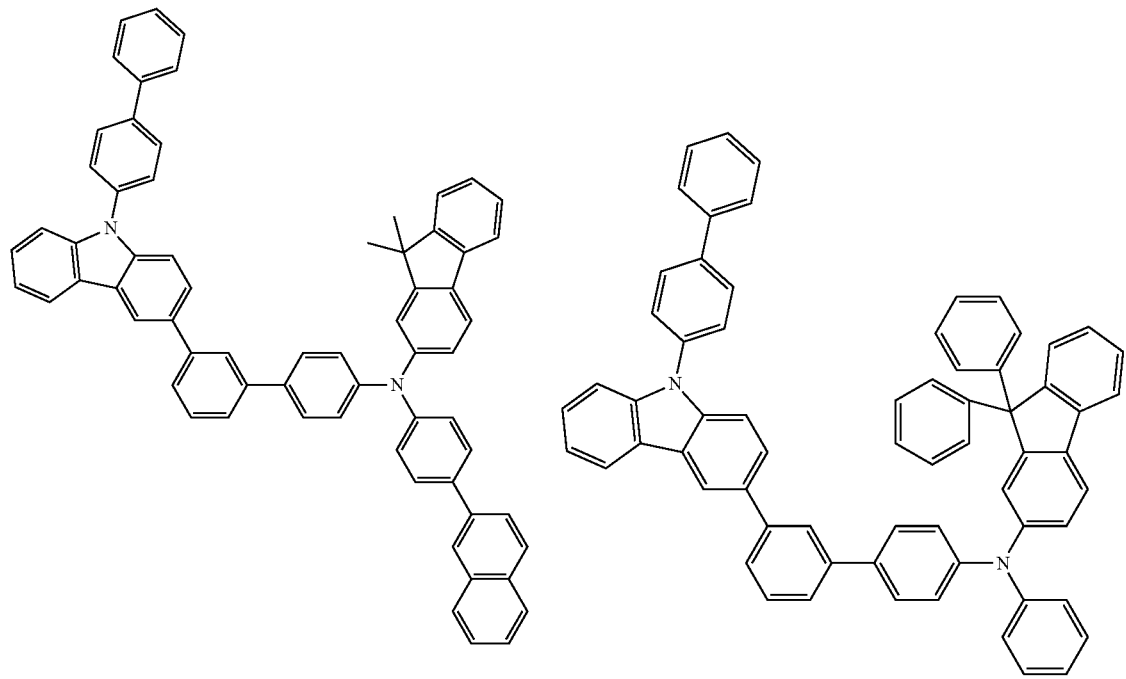
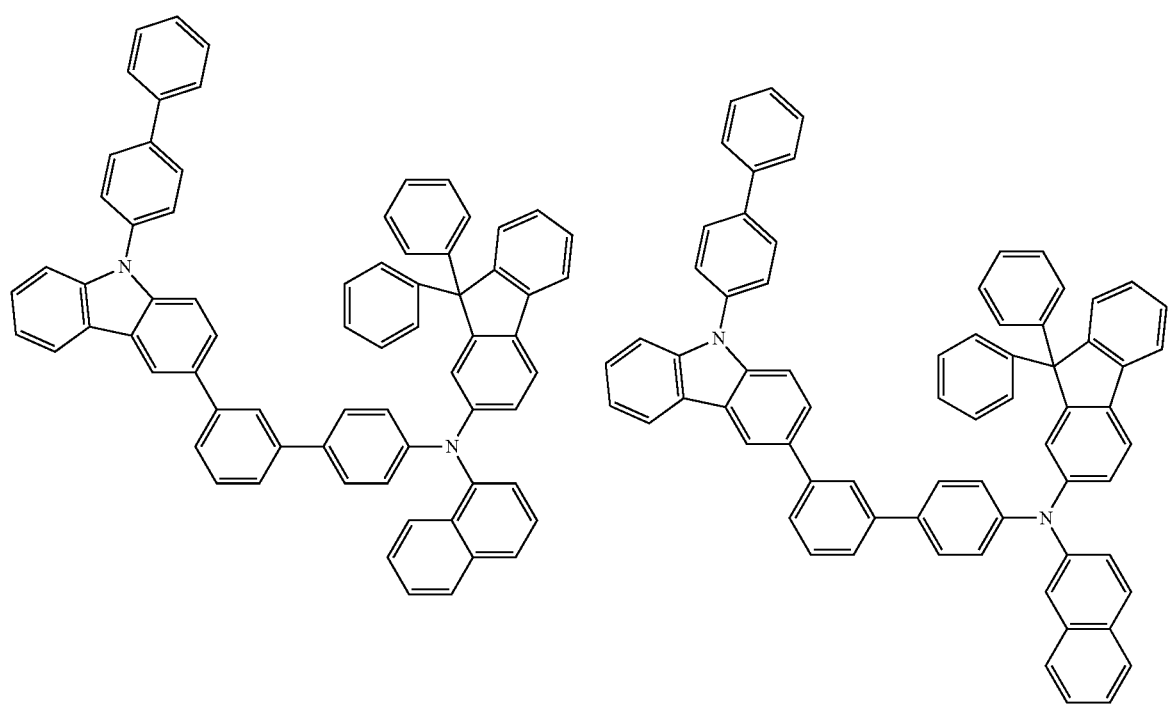

1025
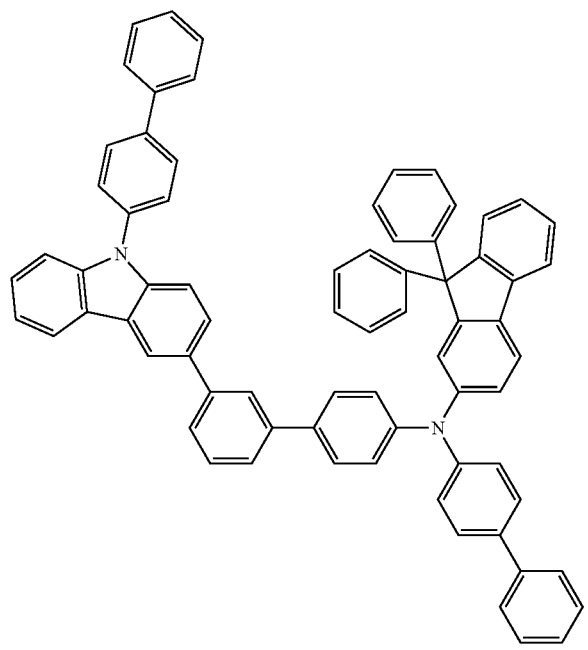
1026
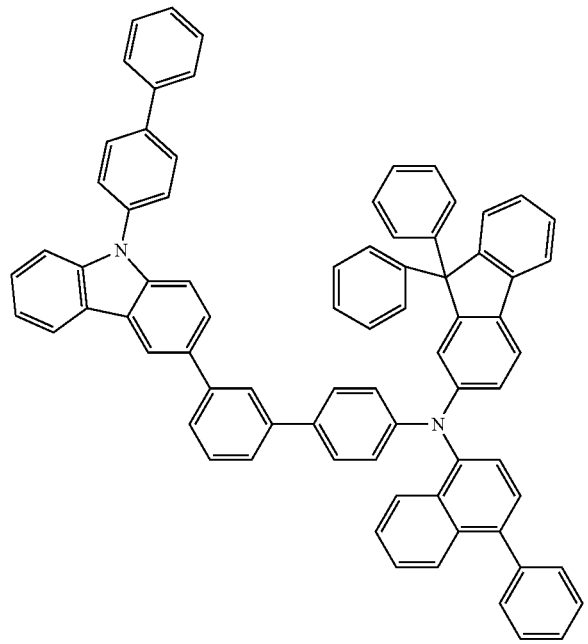
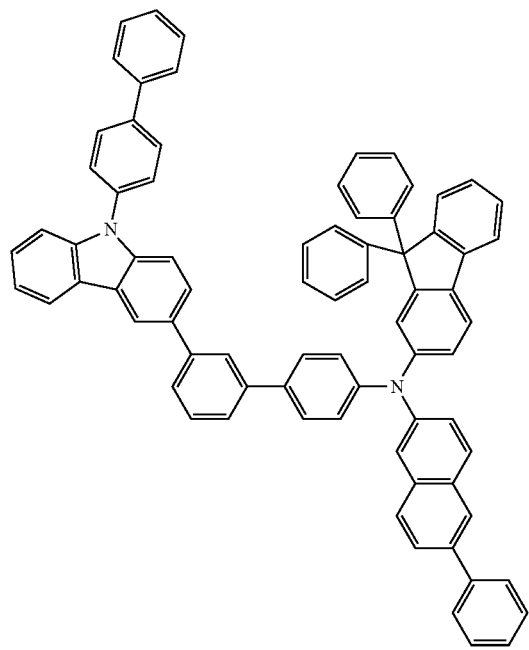
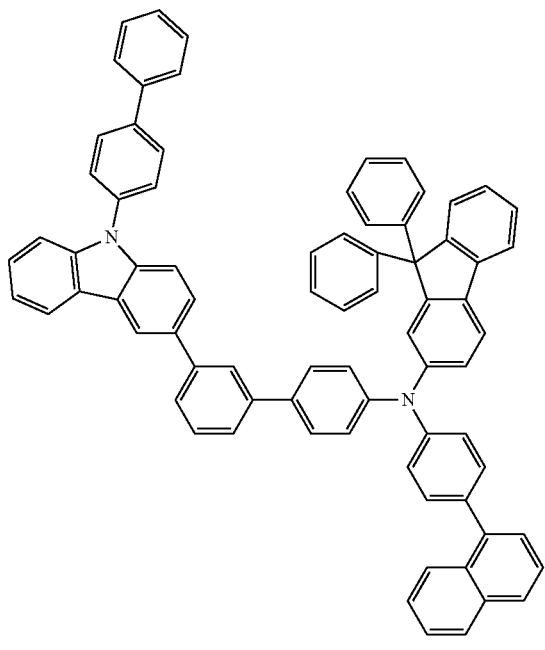

1027
1028
-continued
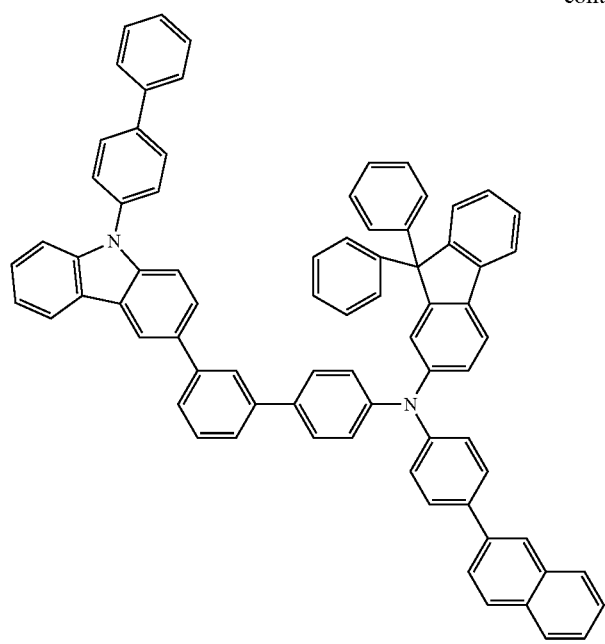
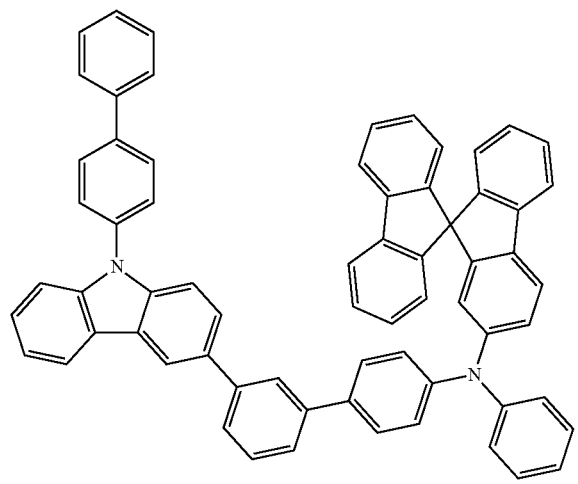
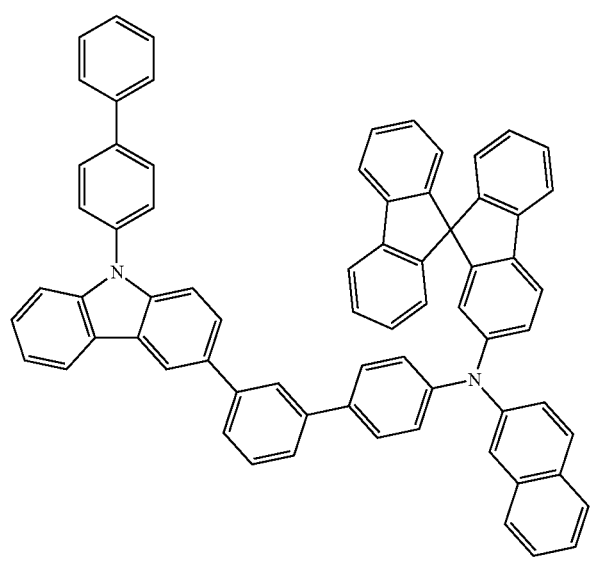

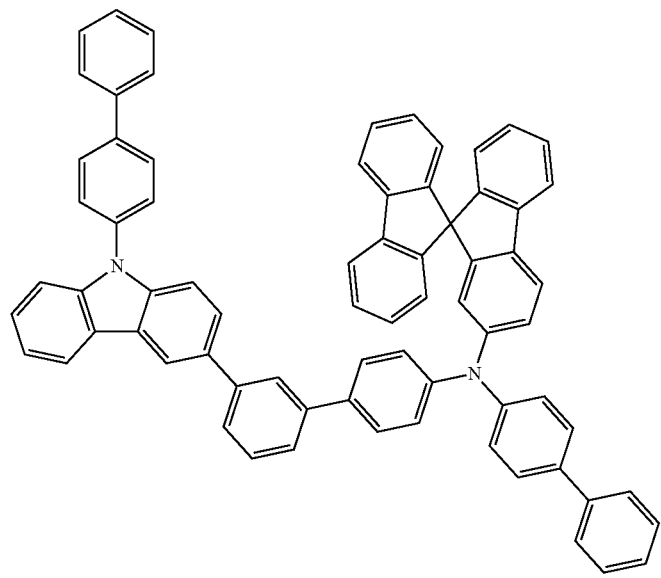
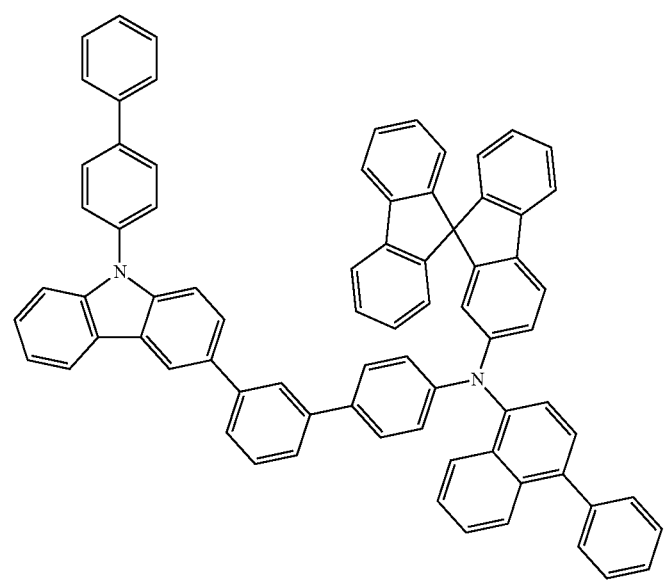

1031
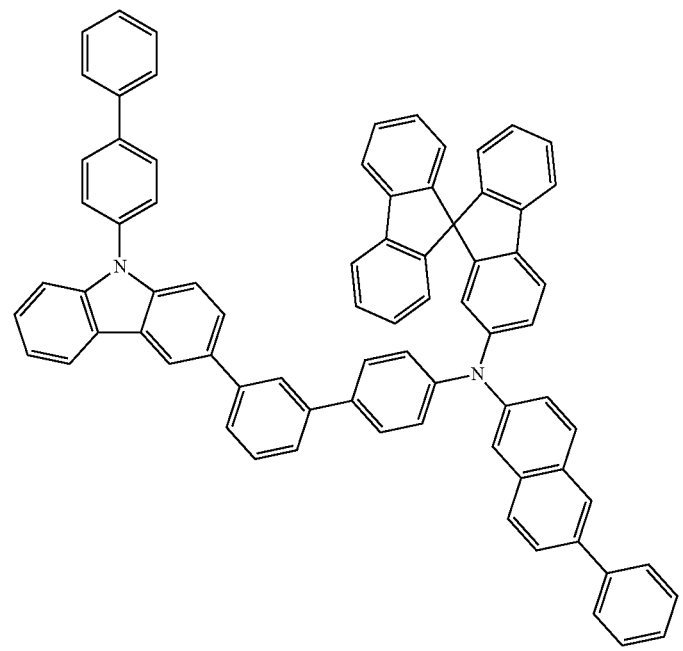
1032
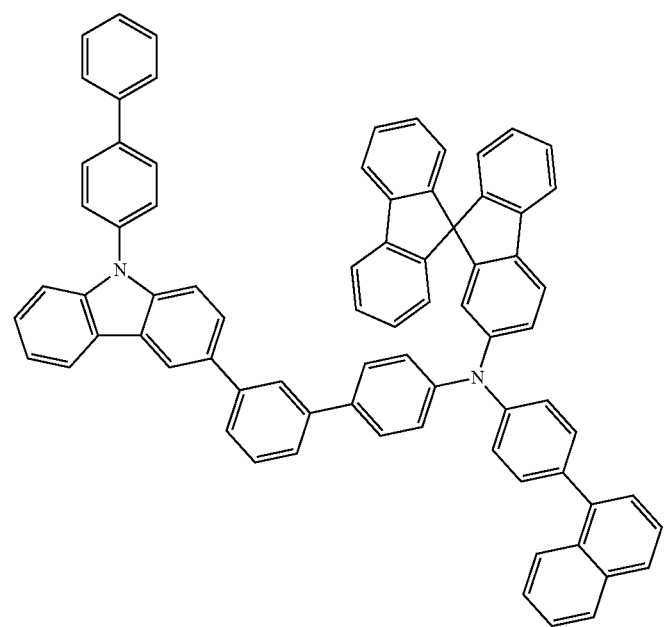

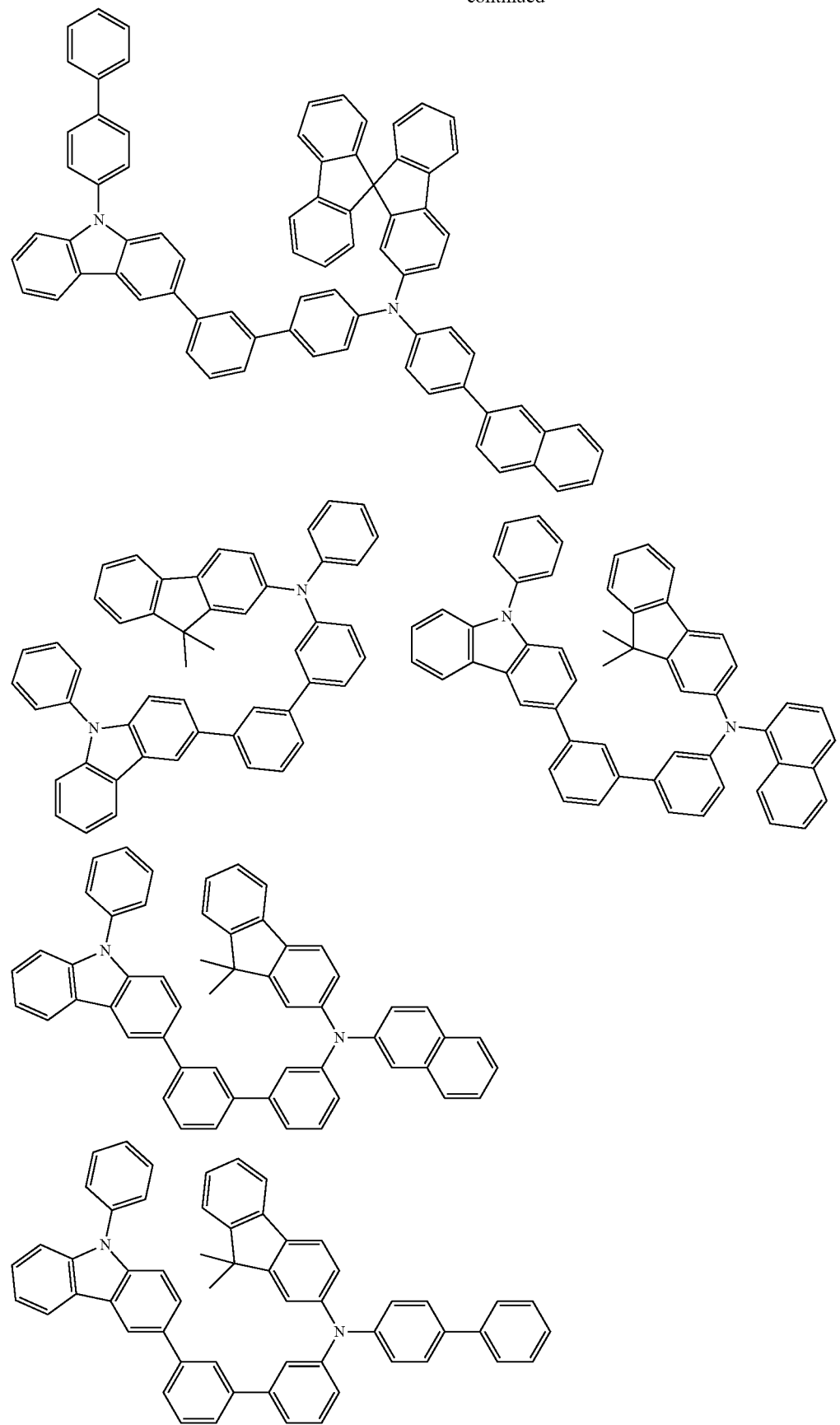

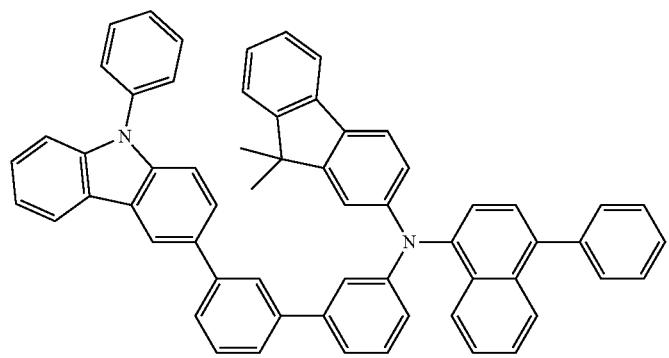
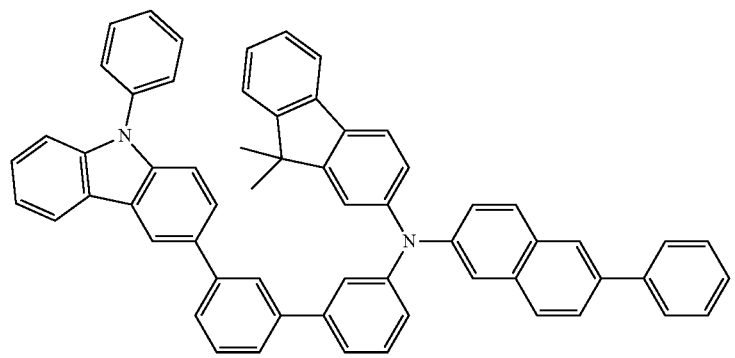
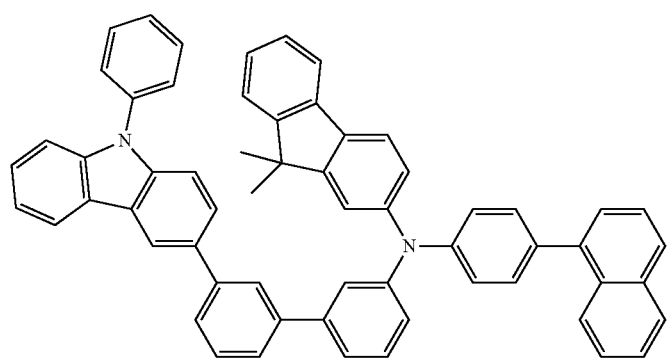
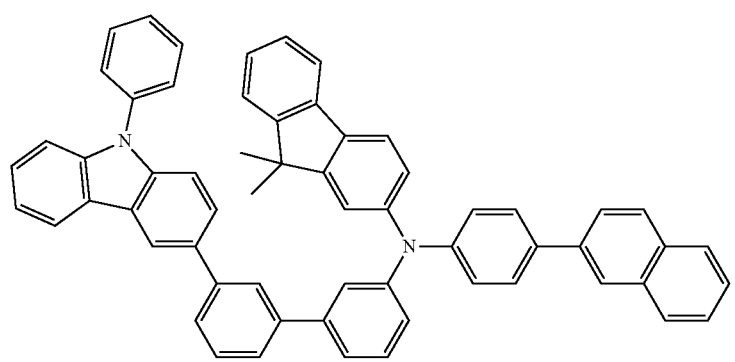

-continued
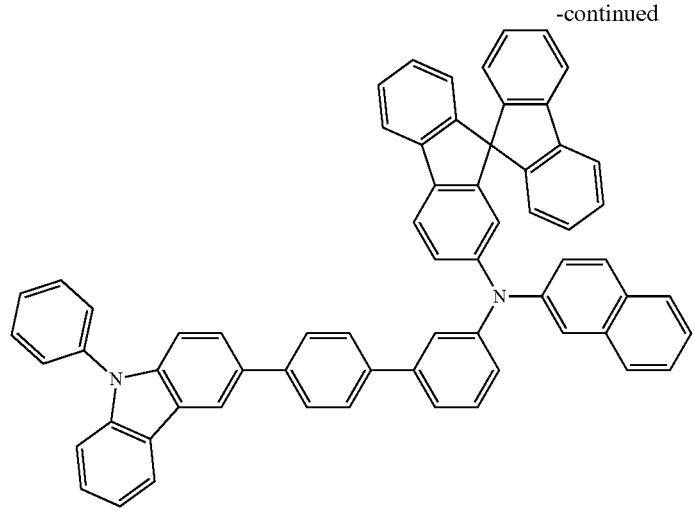
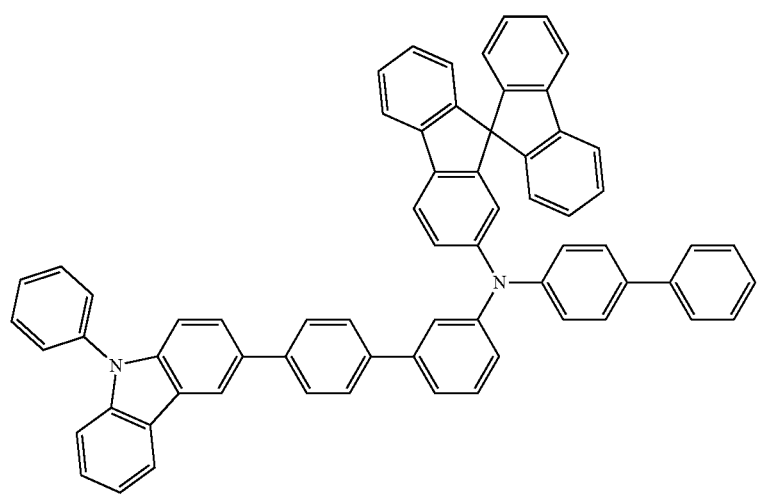
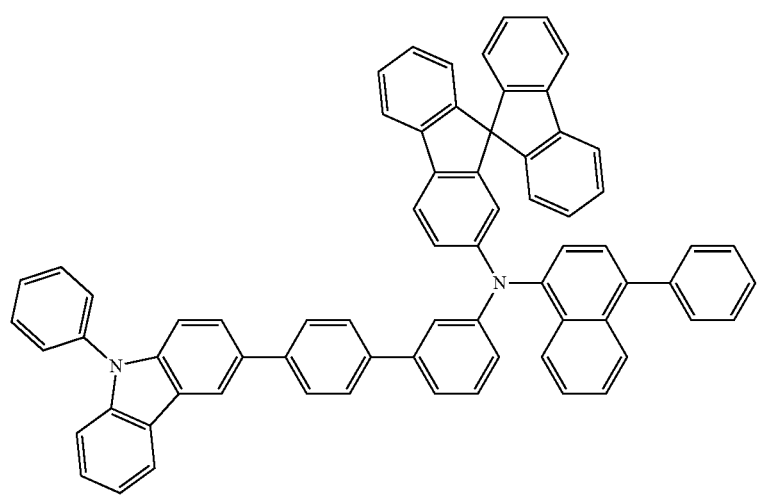

-continued
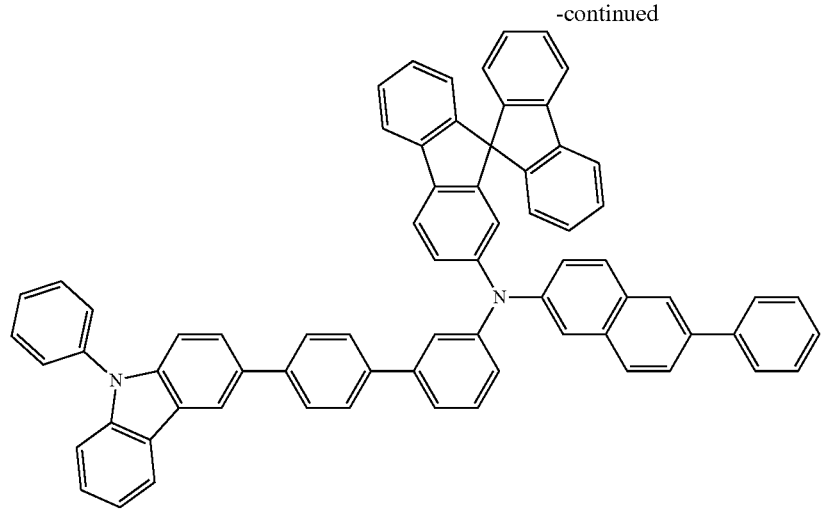
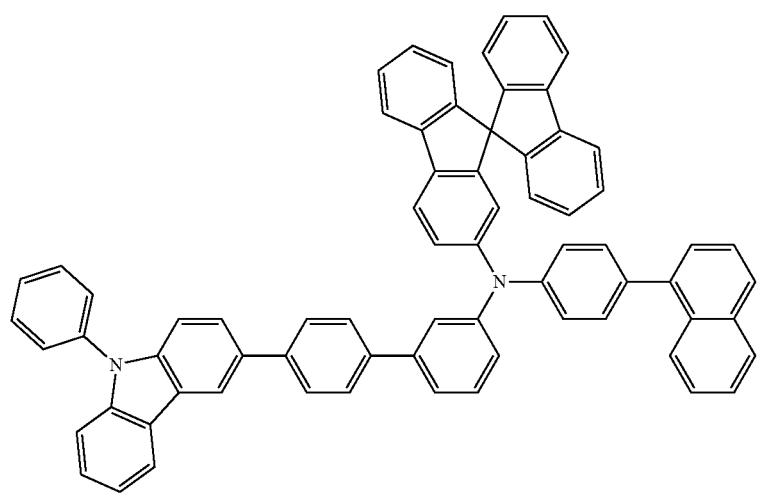
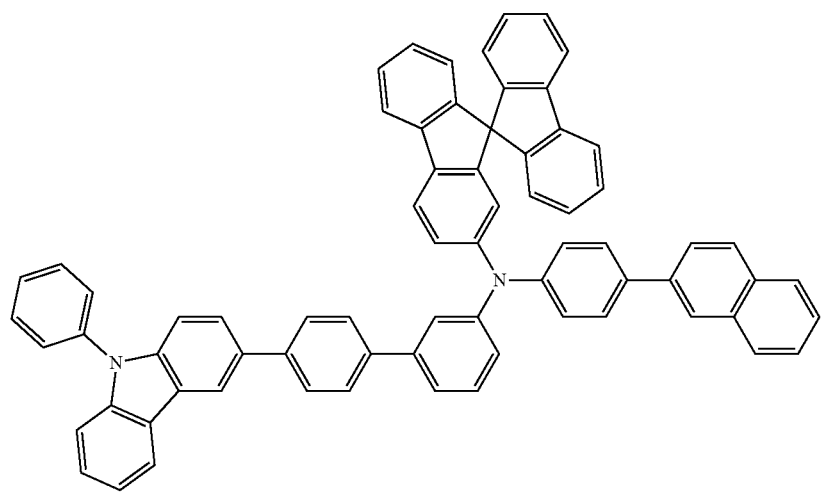

1041　　　　1042
-continued
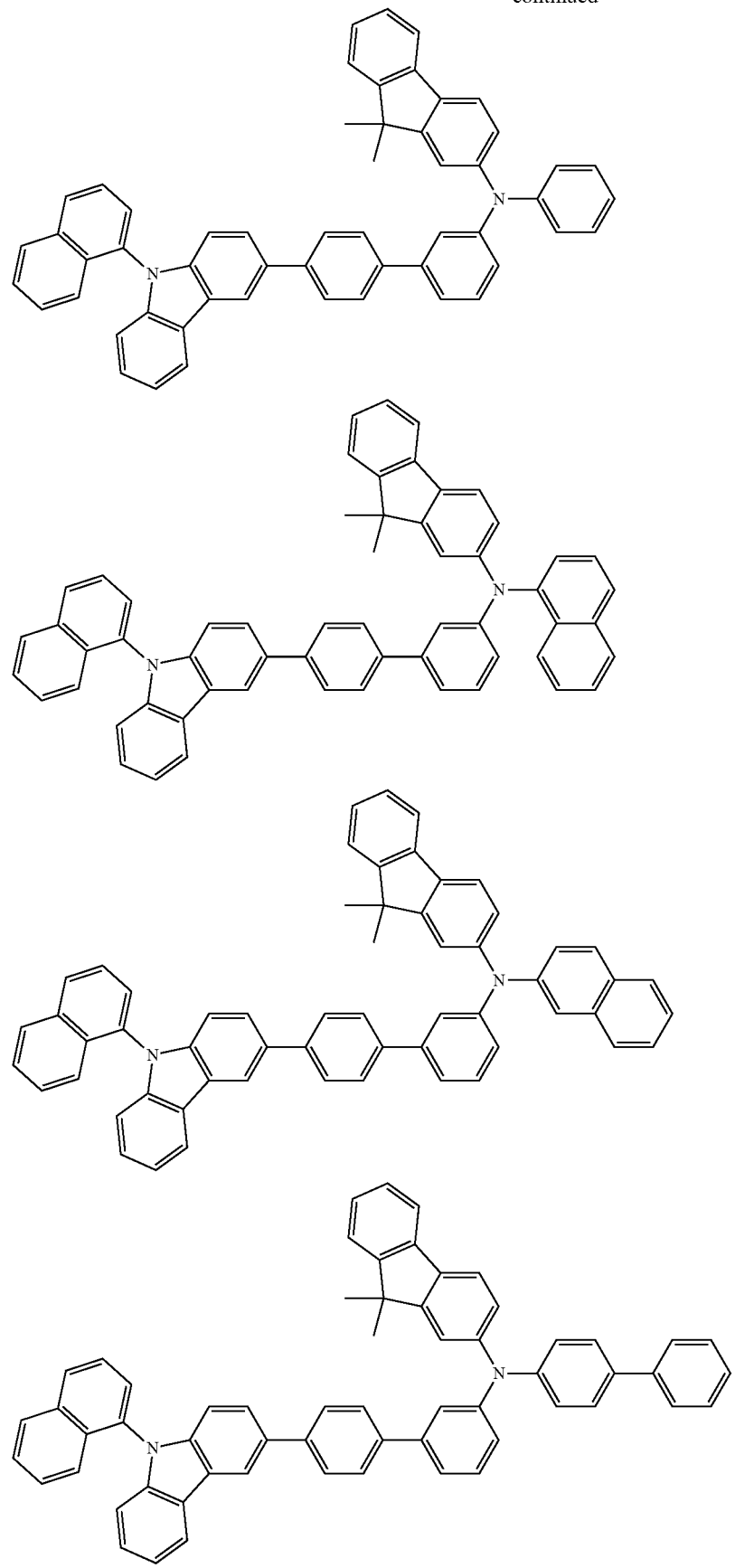

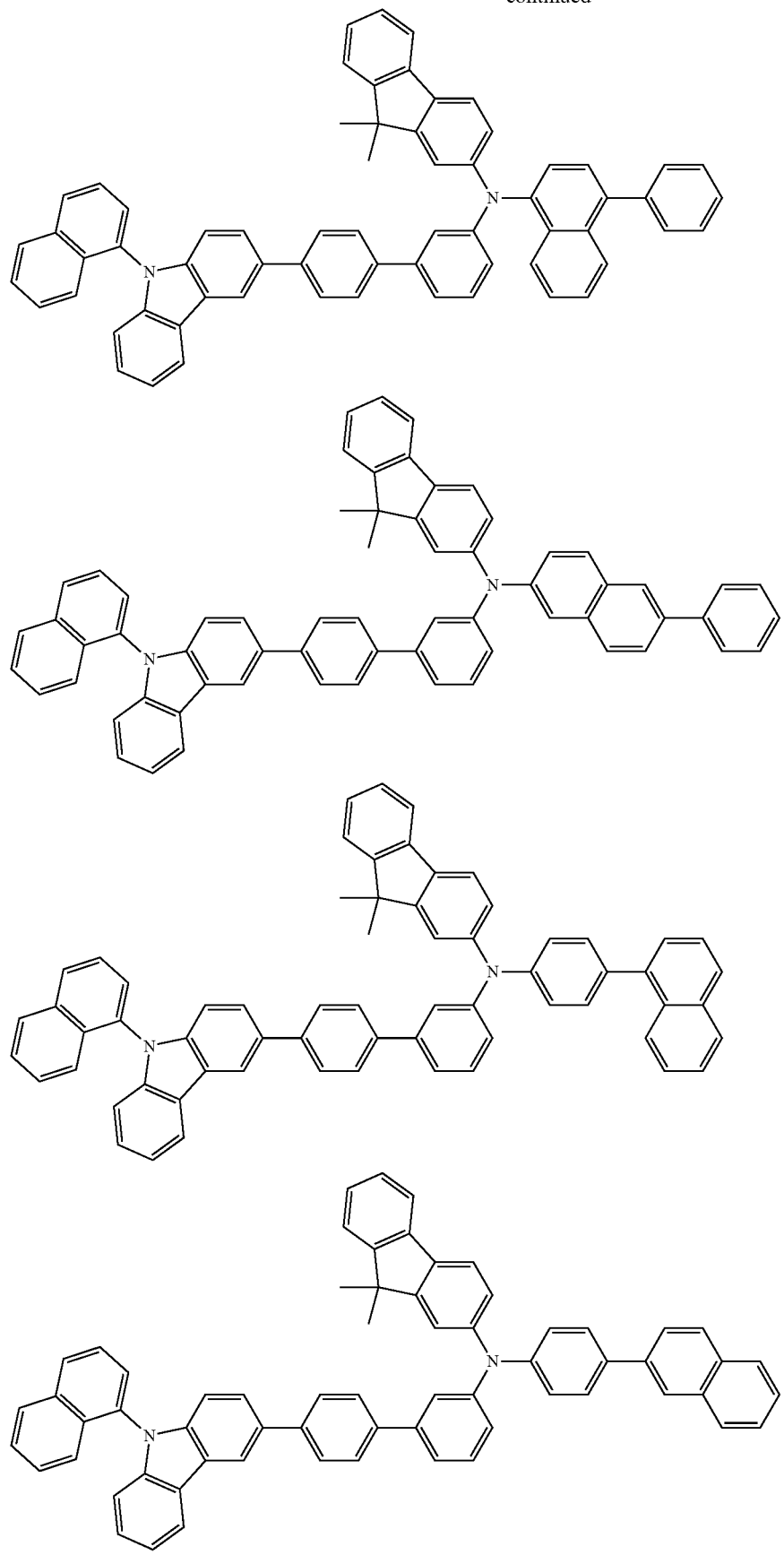

1045
-continued
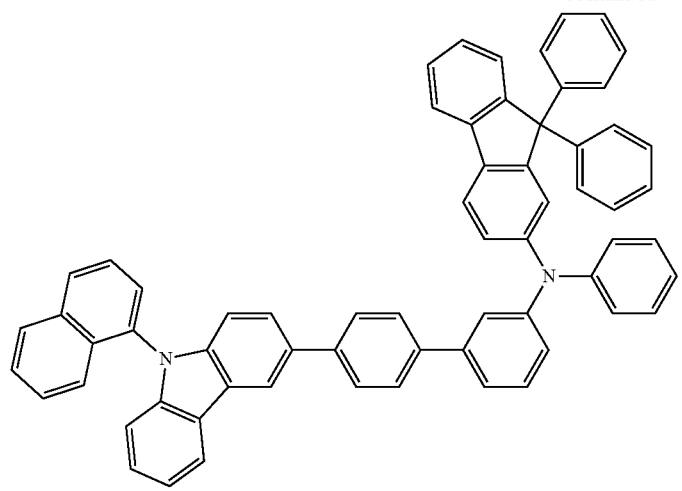
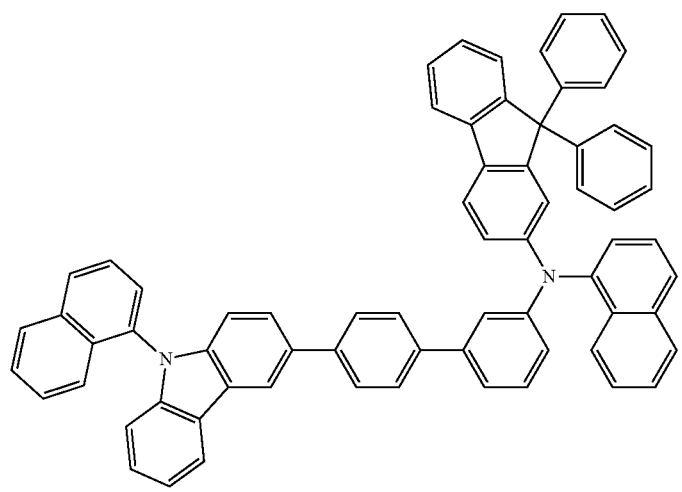
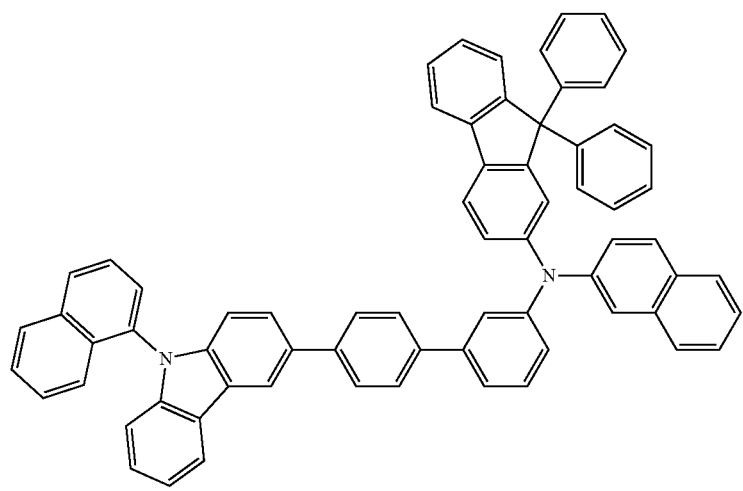
1046

-continued
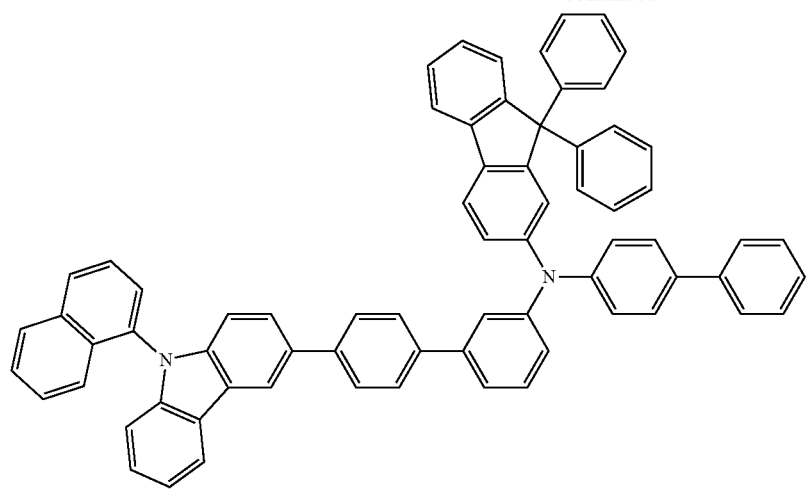
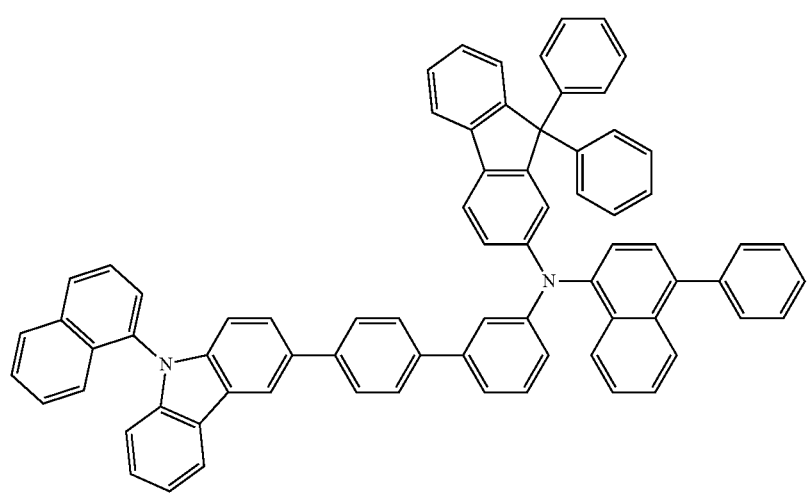
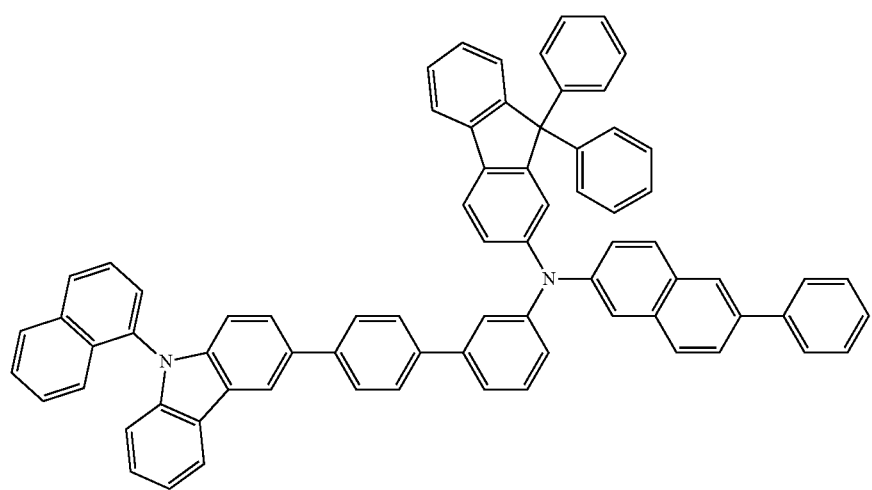

-continued
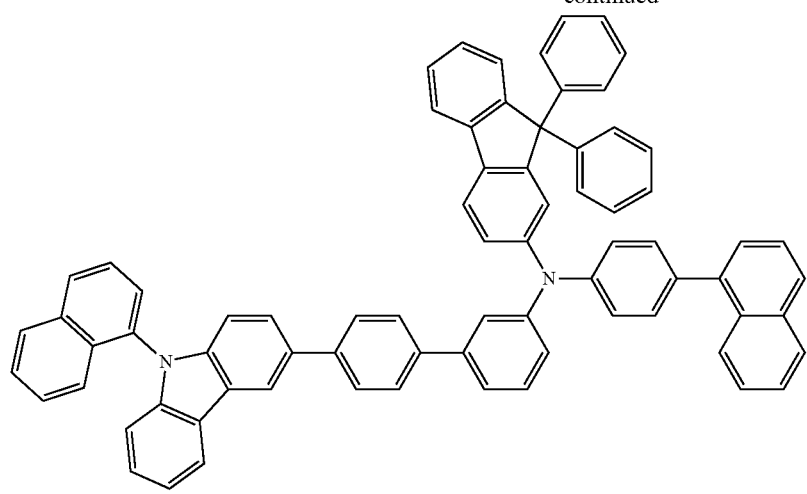
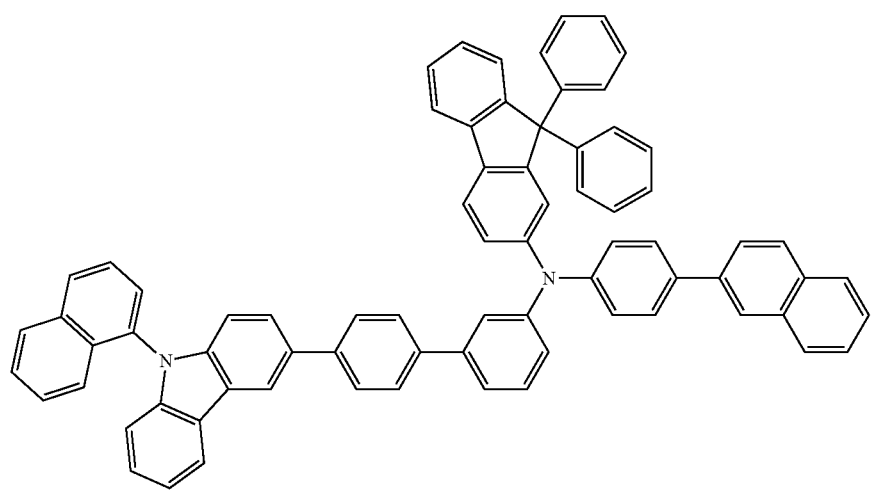
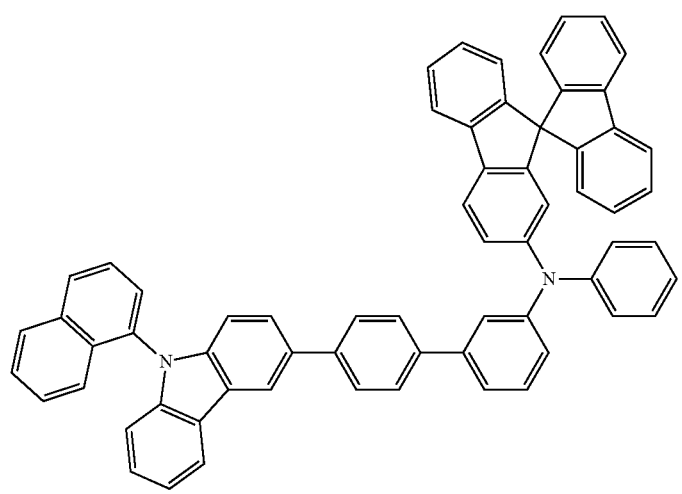

-continued
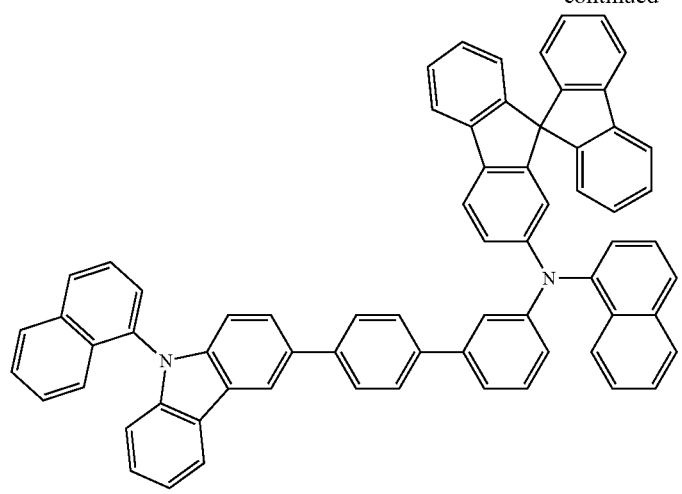
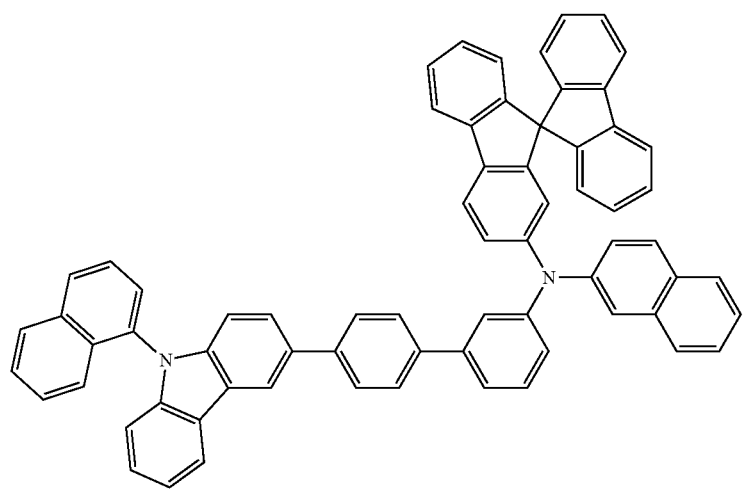
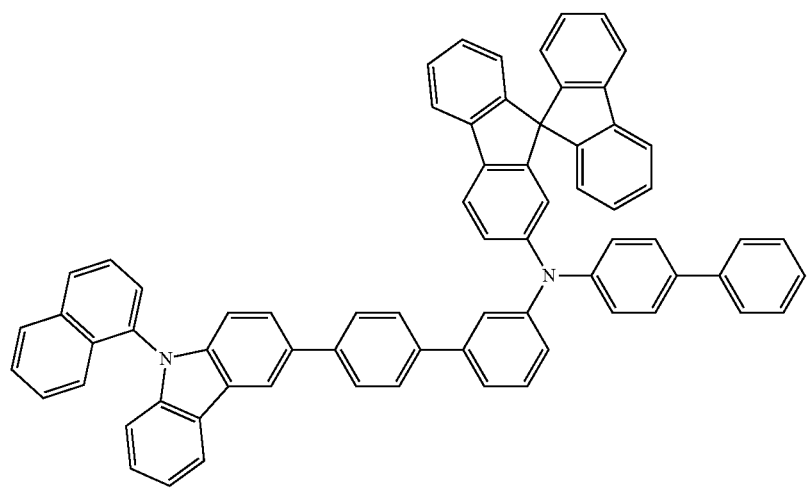

-continued
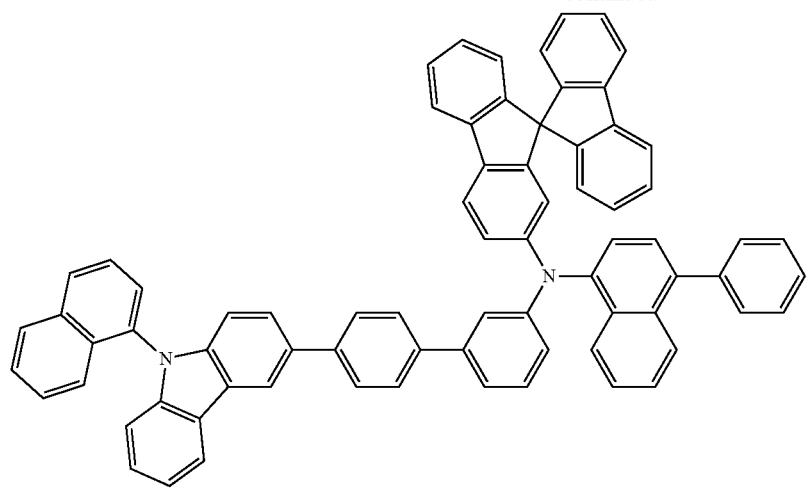
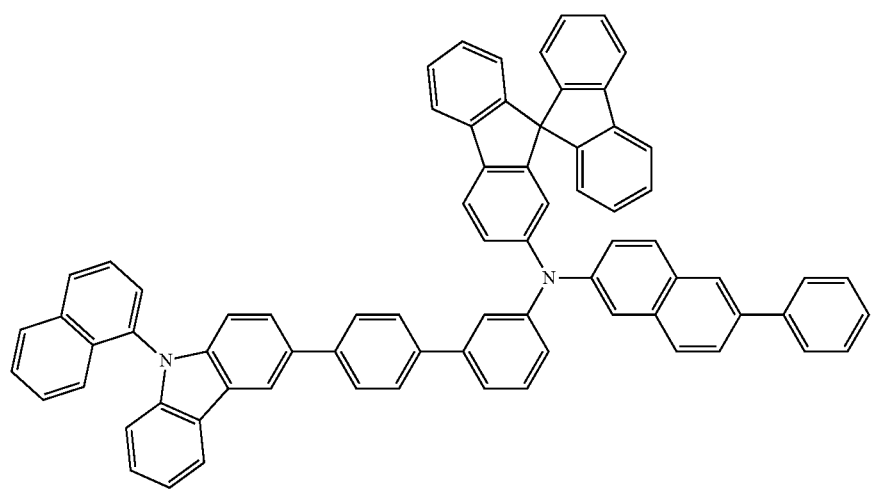
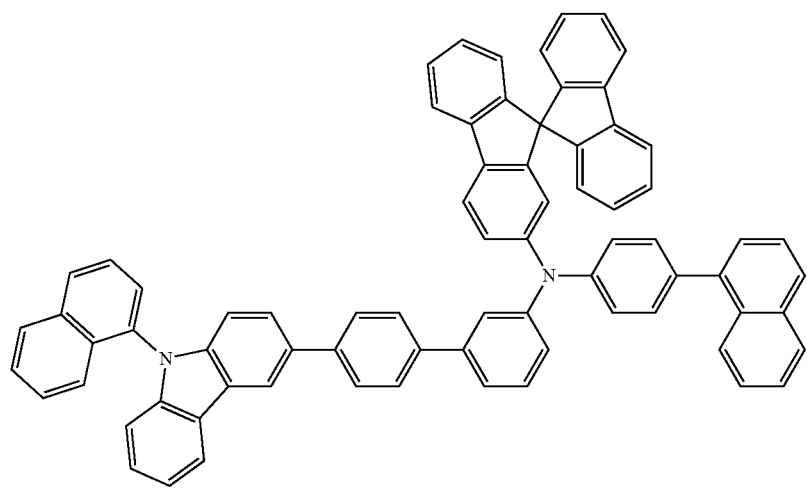

-continued
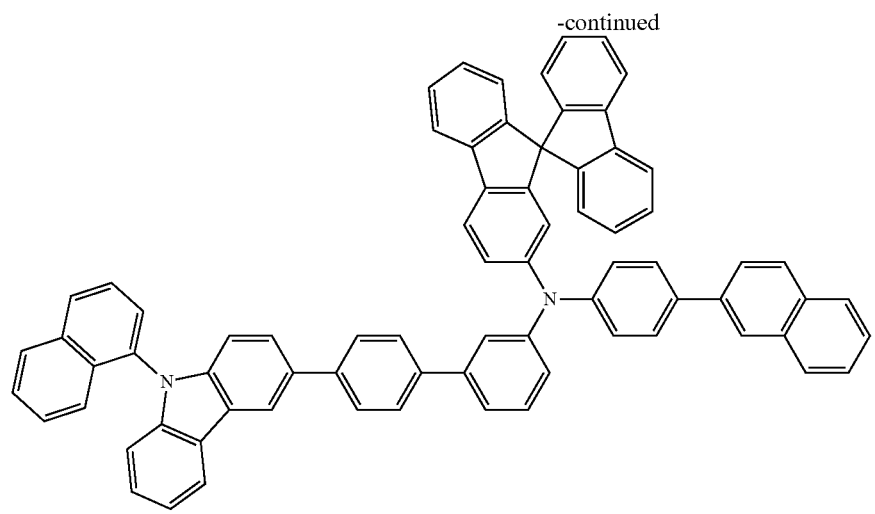
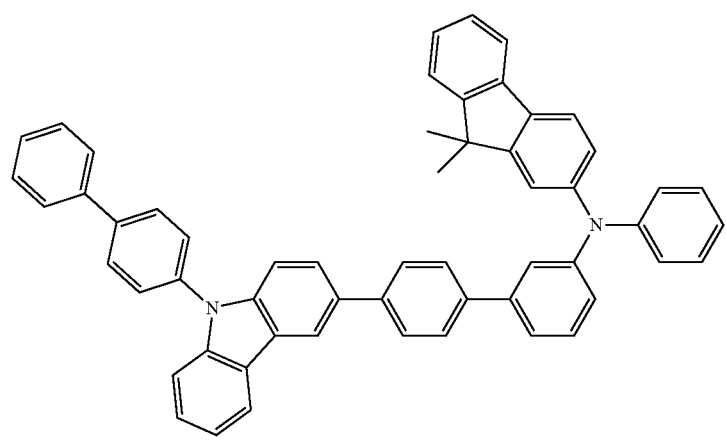
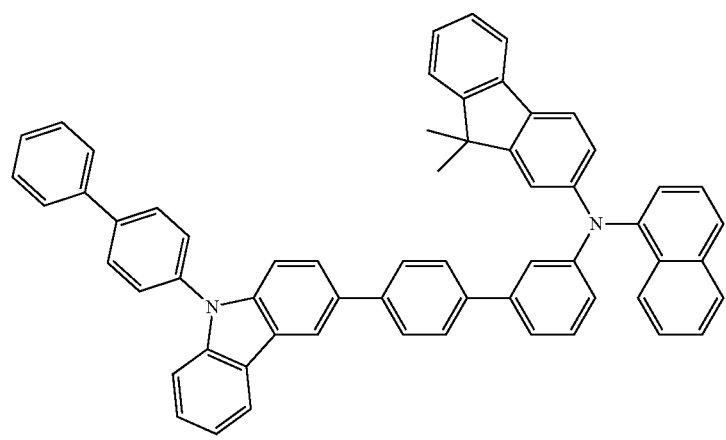

1057
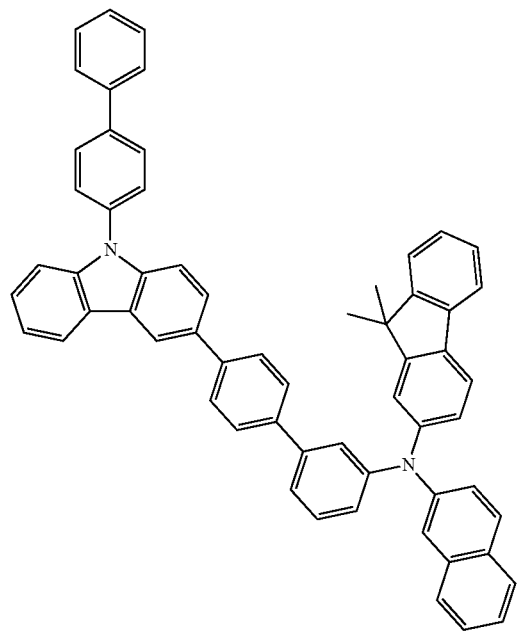
1058
-continued
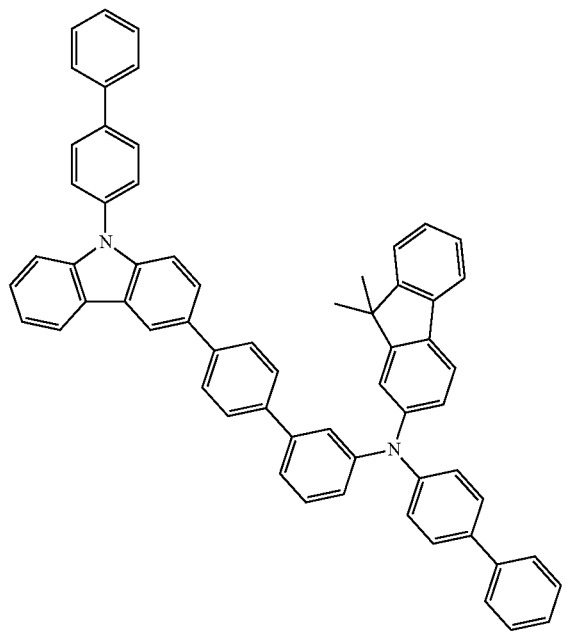
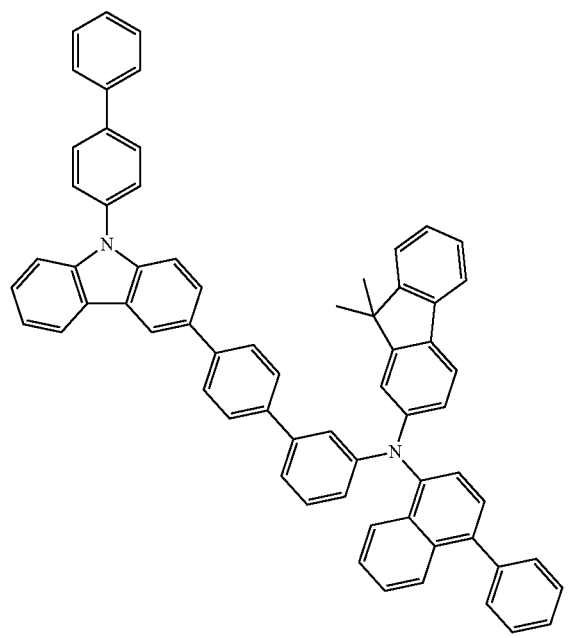

1059
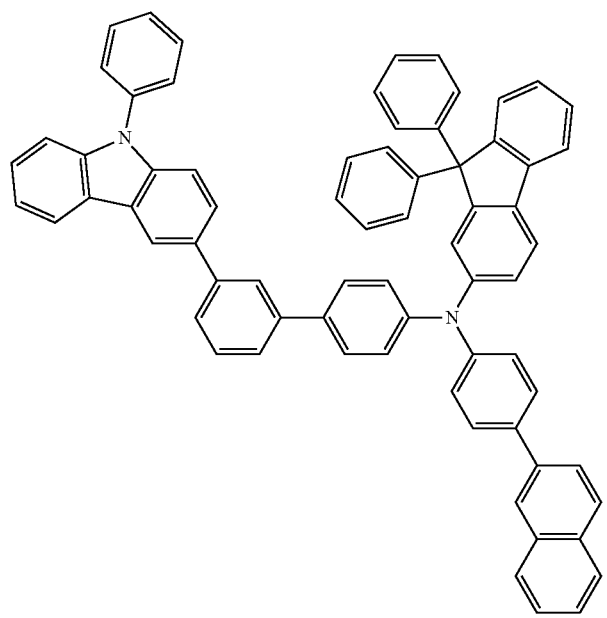
1060
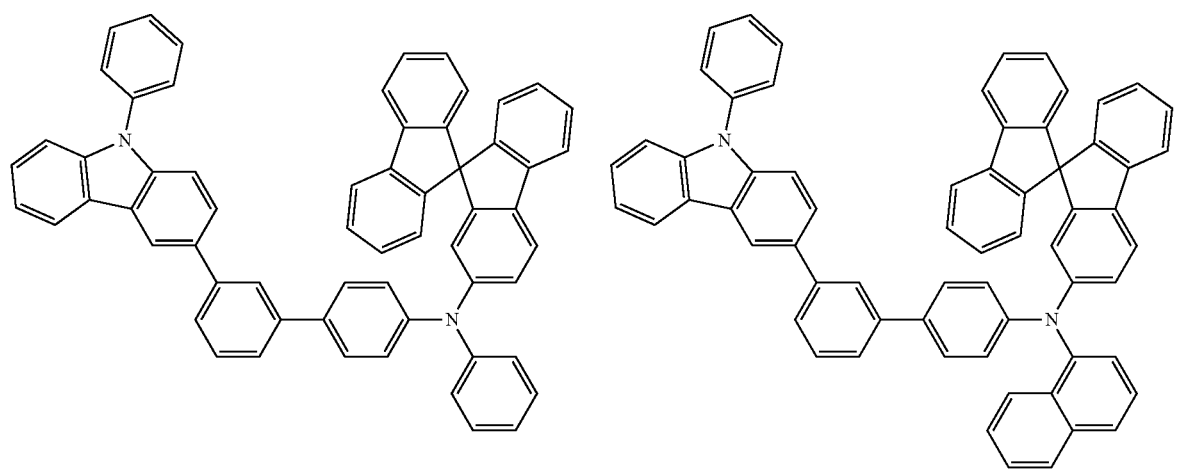
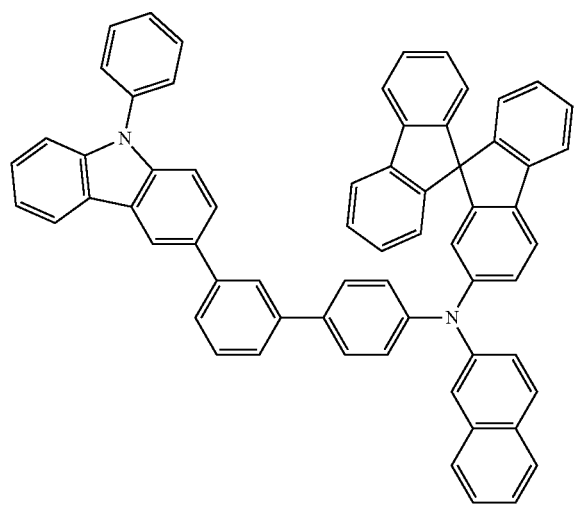

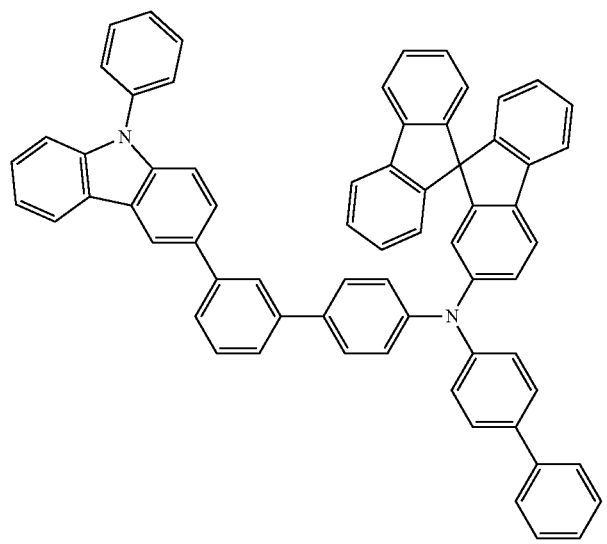
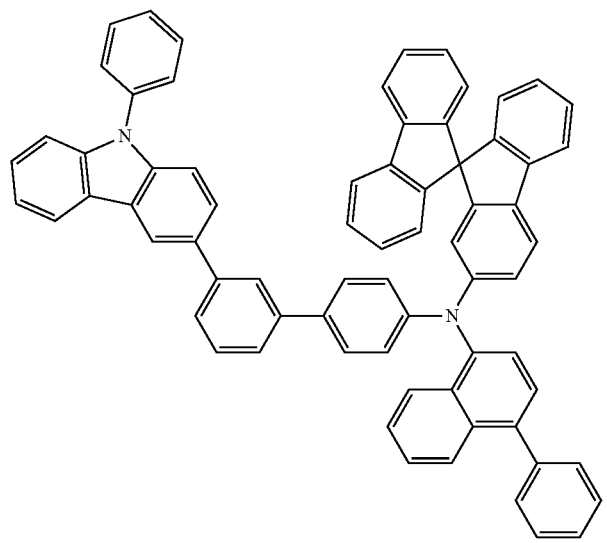
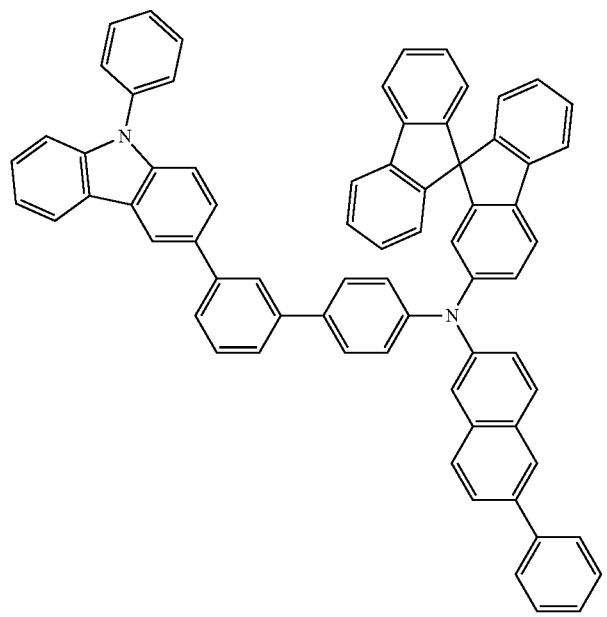

1063
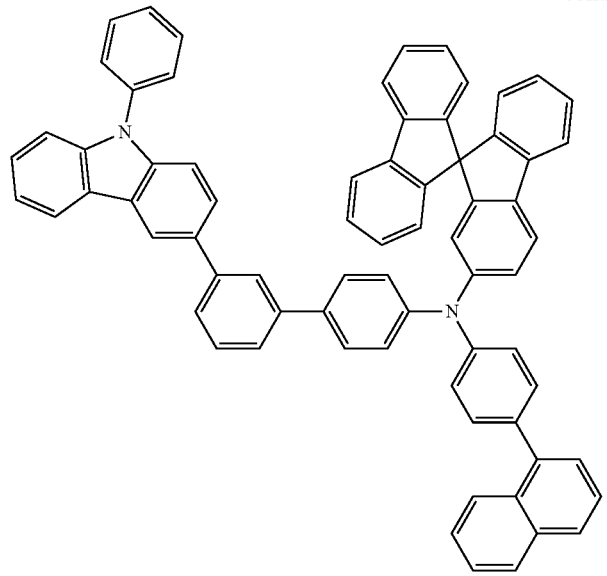
1064
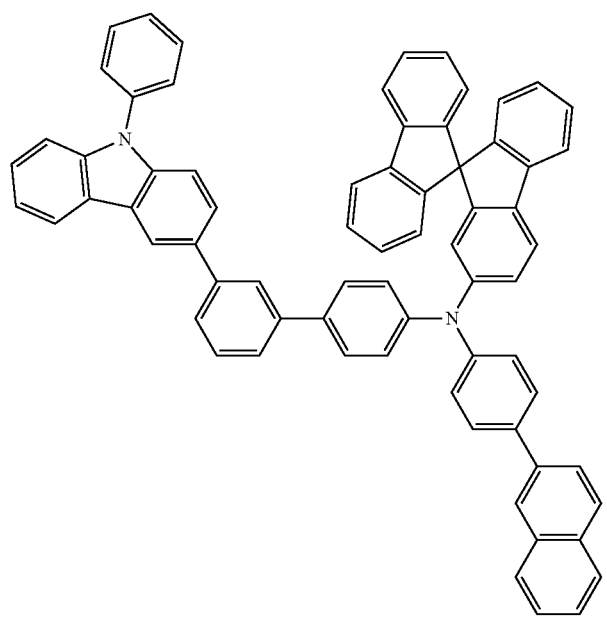
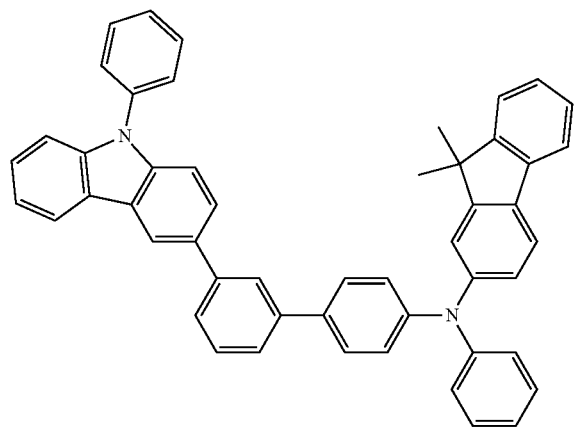
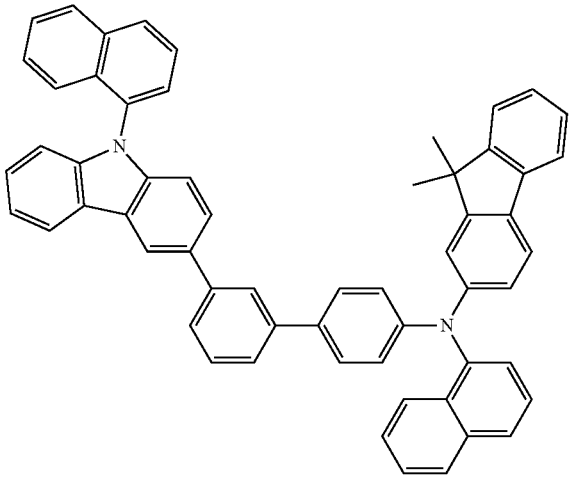

| 1065 | 1066 |
|---|---|
| 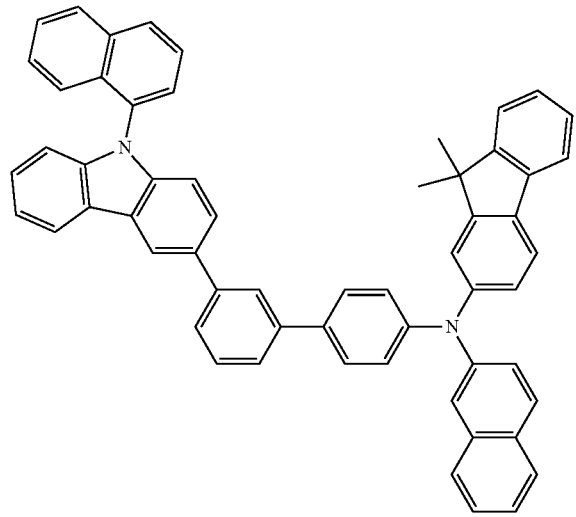 | 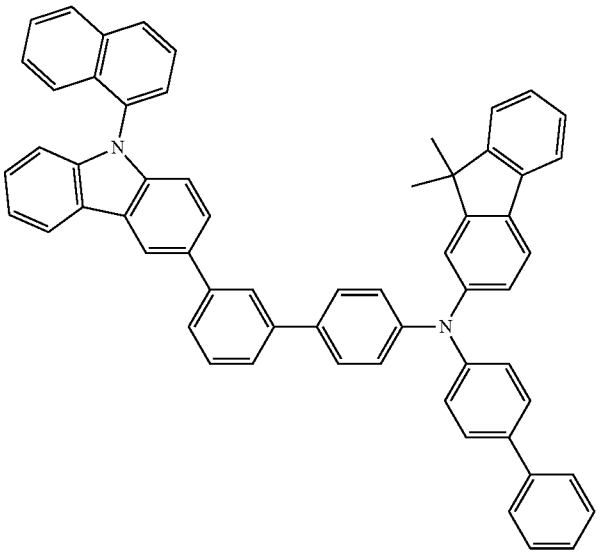 |
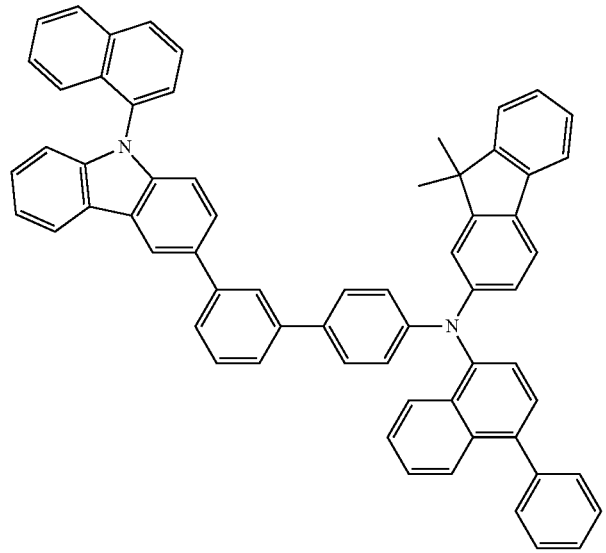
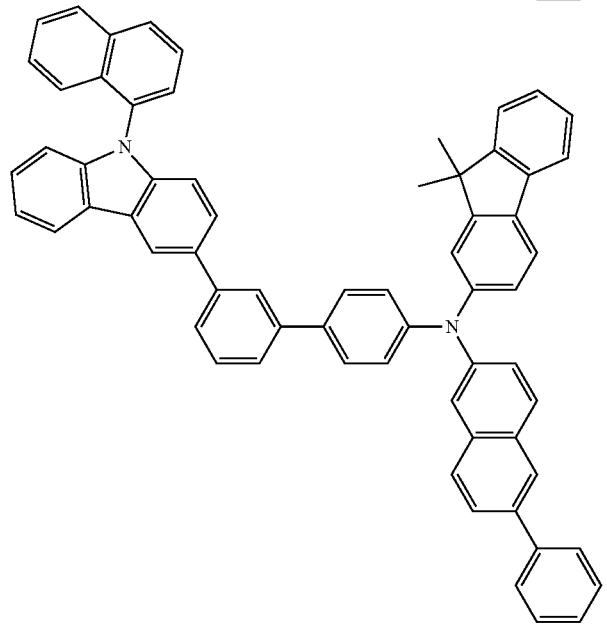

1067 1068
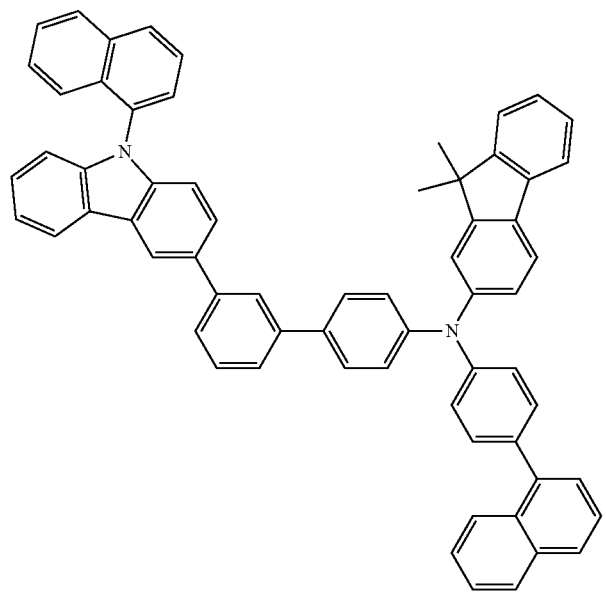
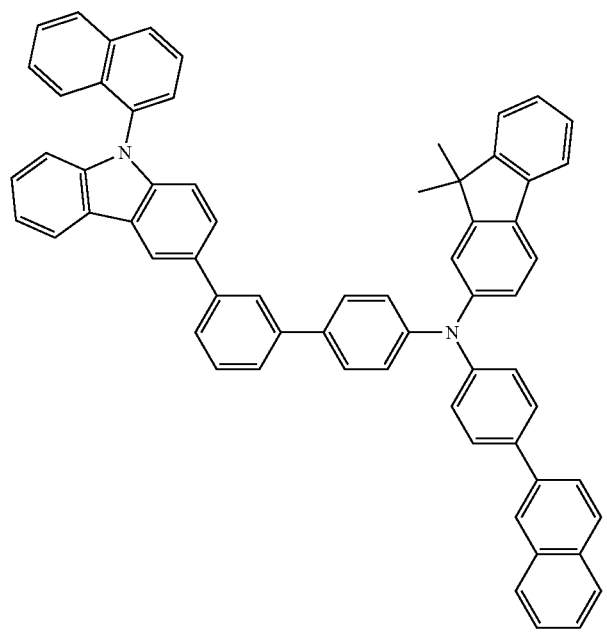
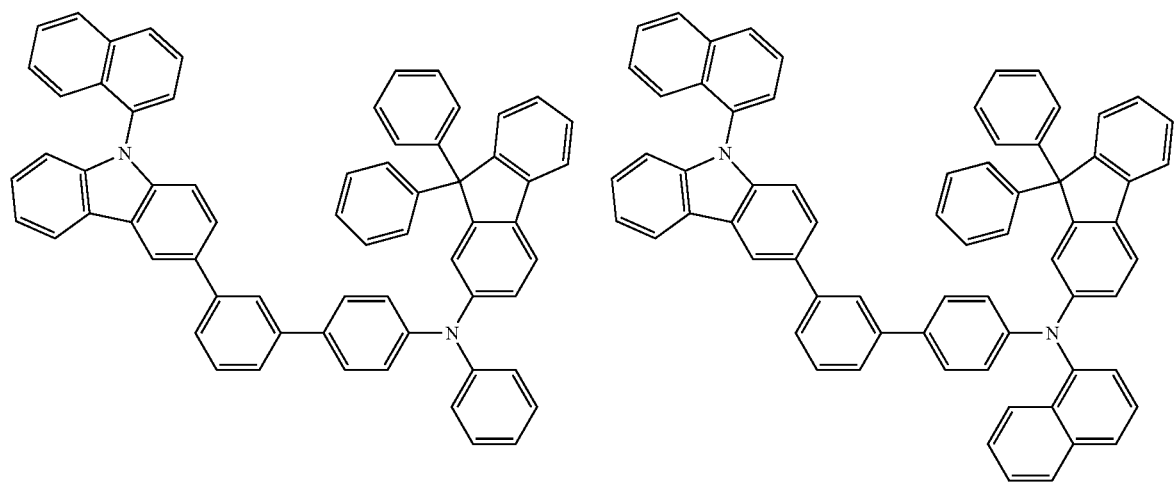

1069 1070
-continued
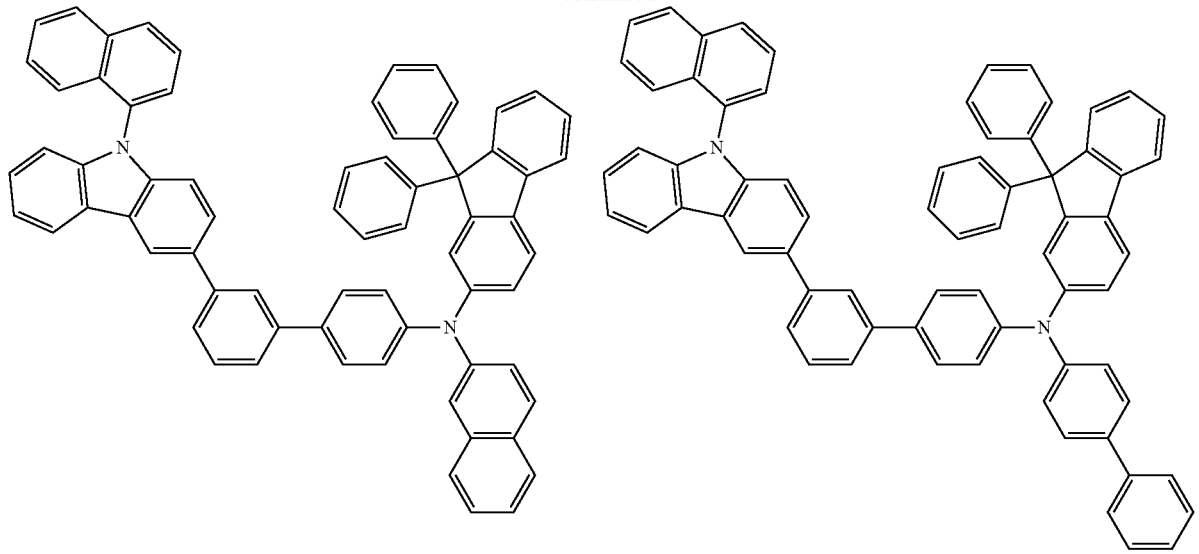
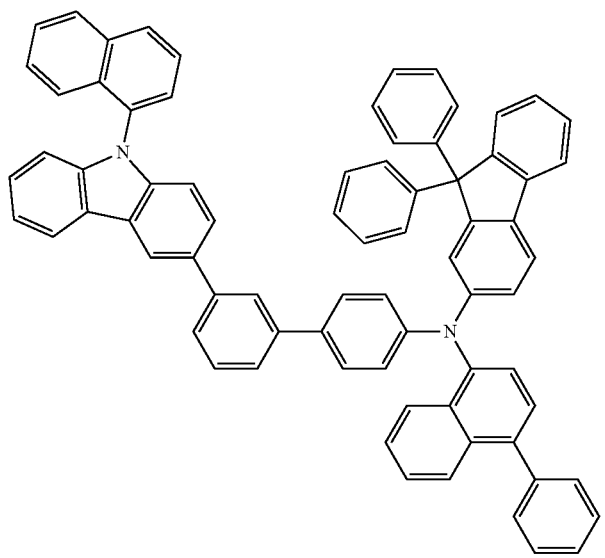
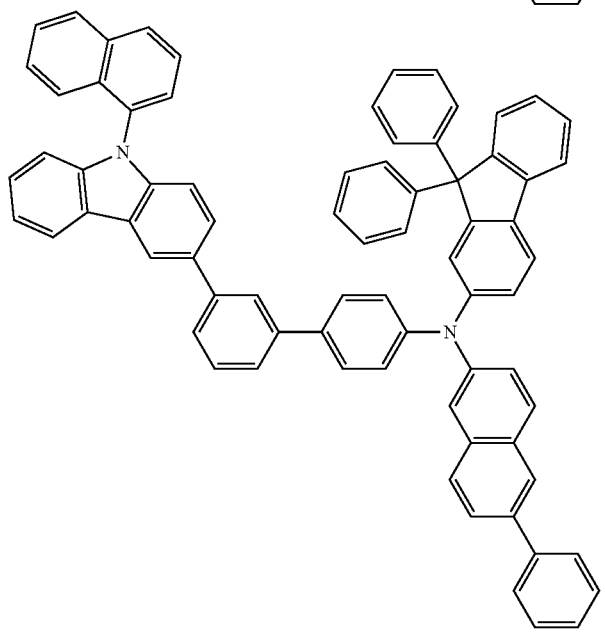

1071
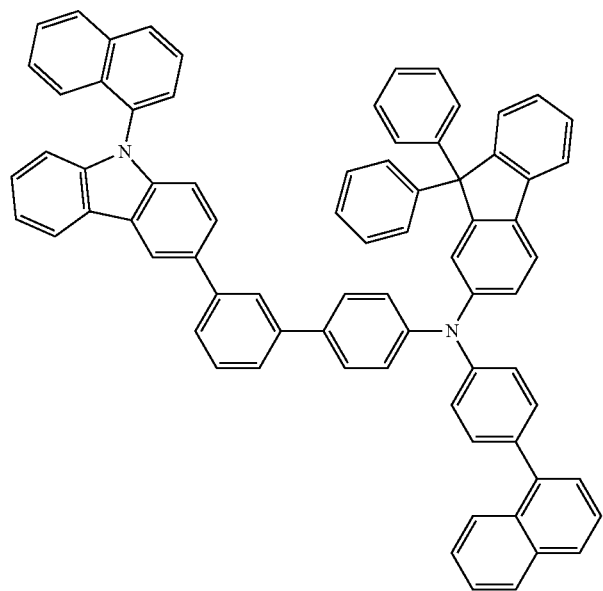
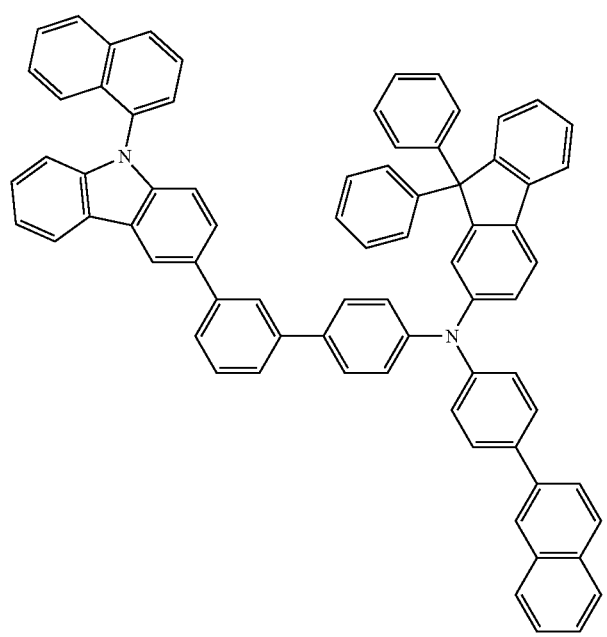
1072
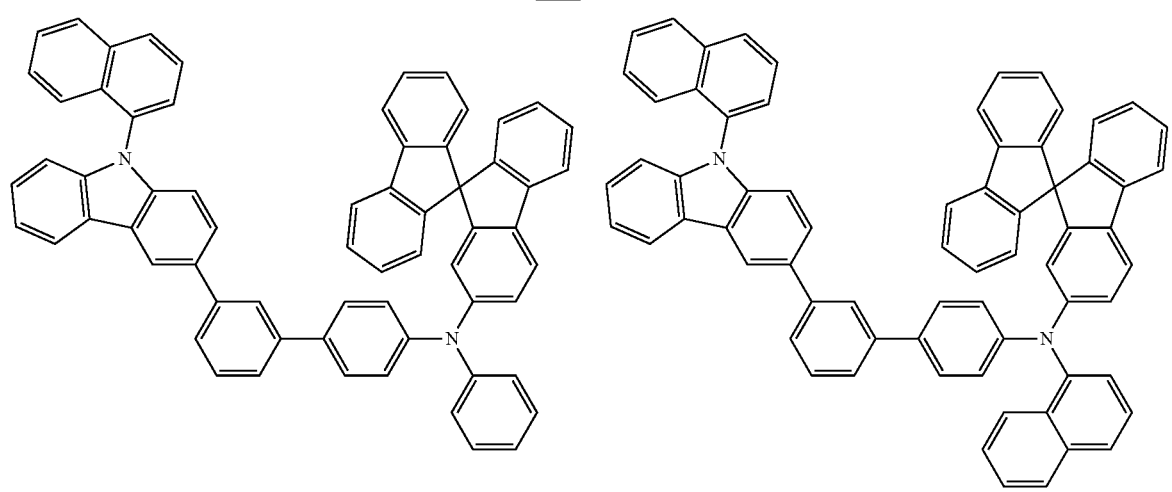

-continued
| 1073 | 1074 |
|---|---|
| 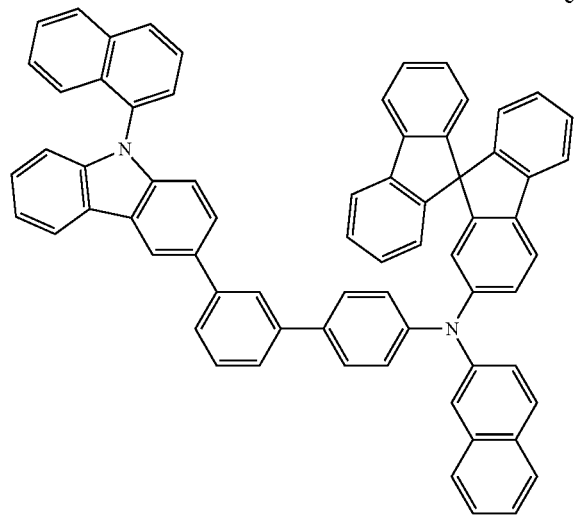 | 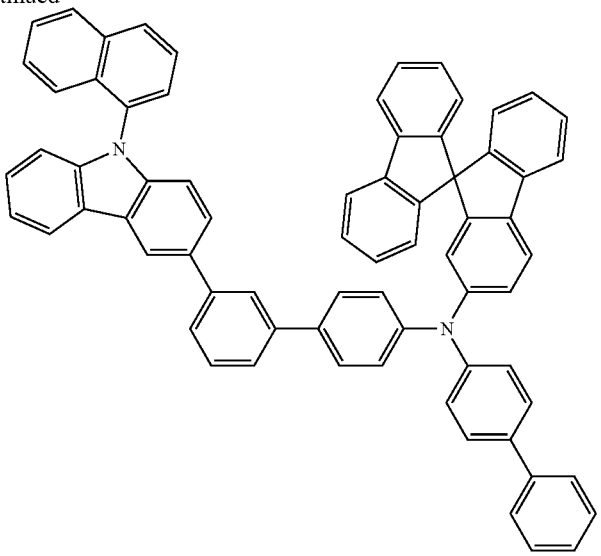 |
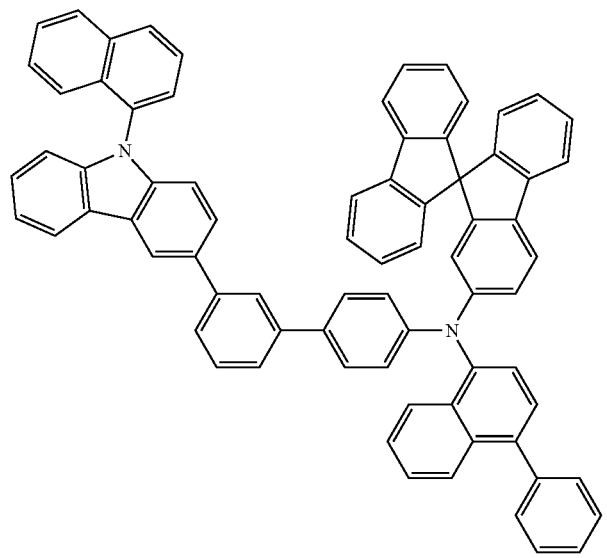
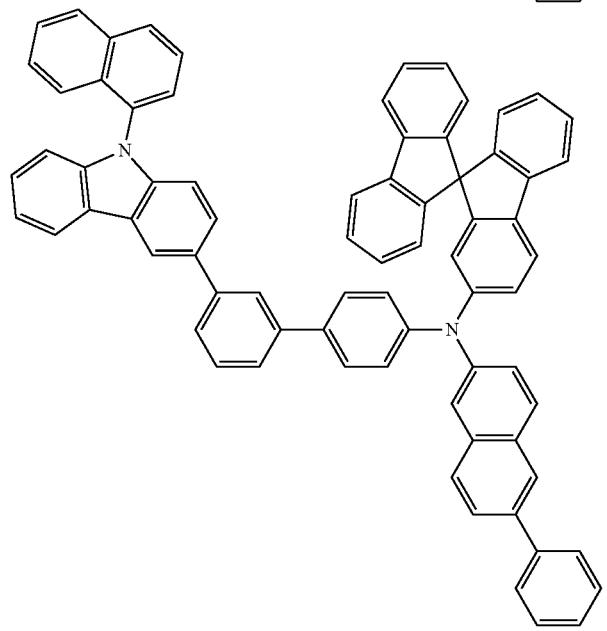

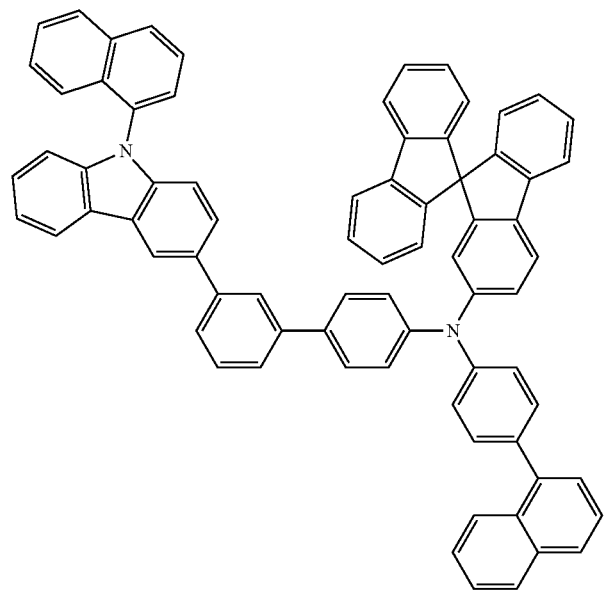
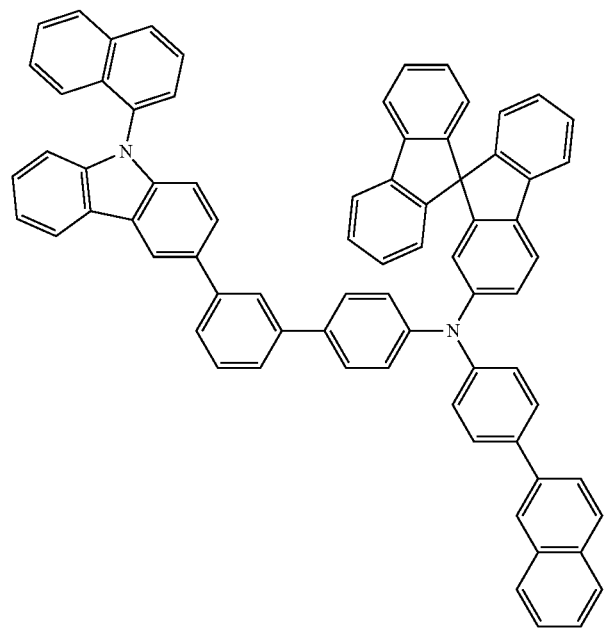

-continued
1077
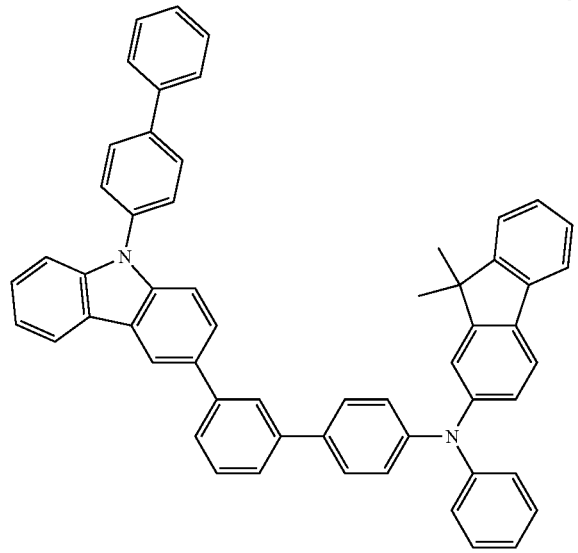
1078
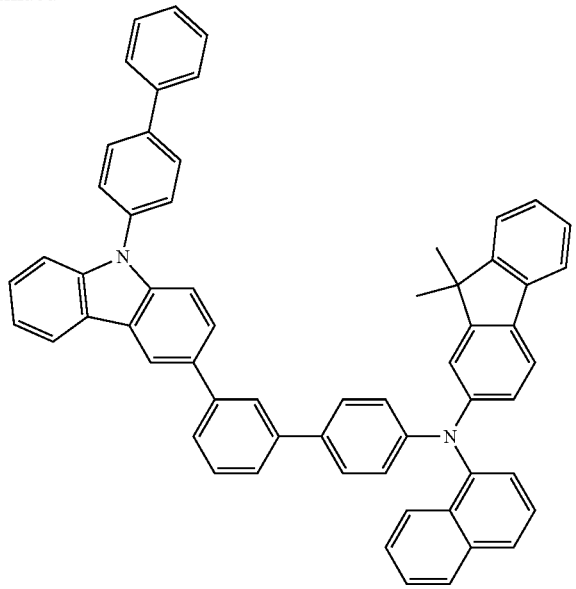
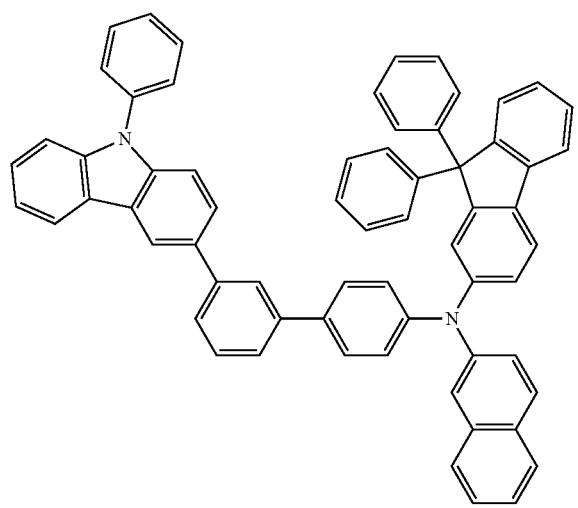
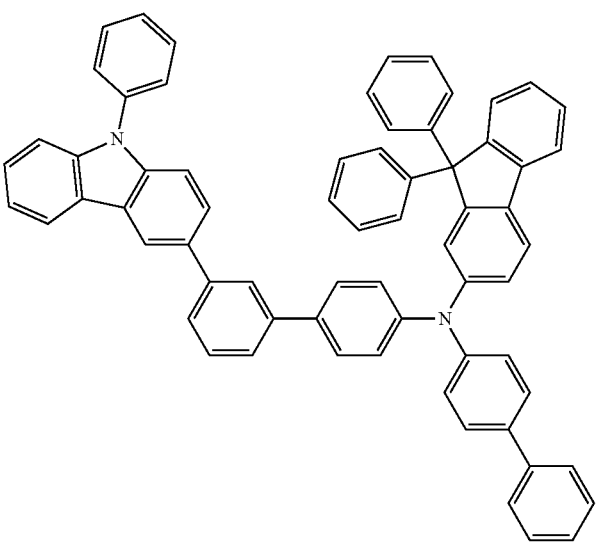
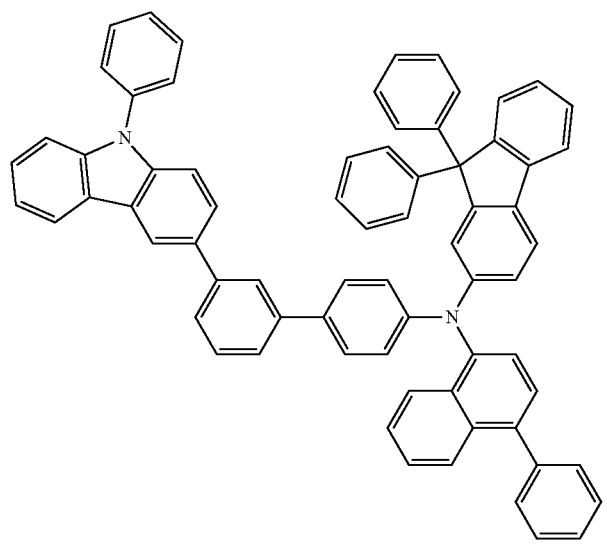

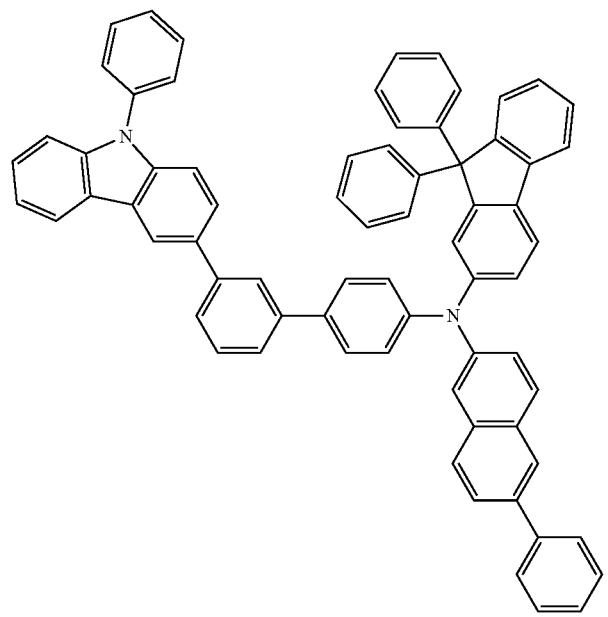
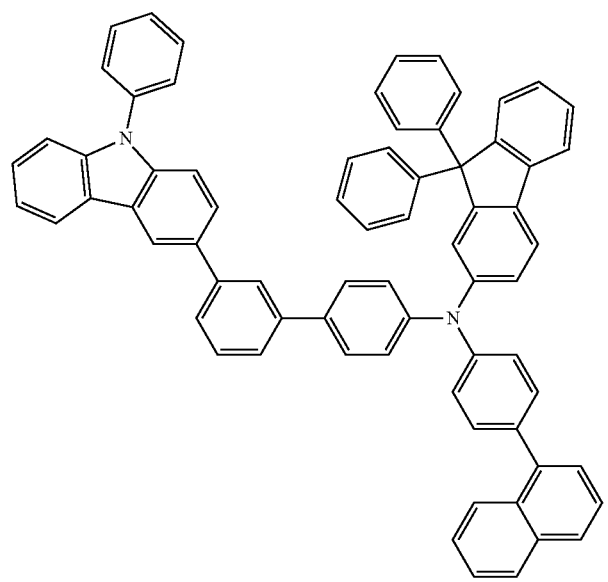

-continued
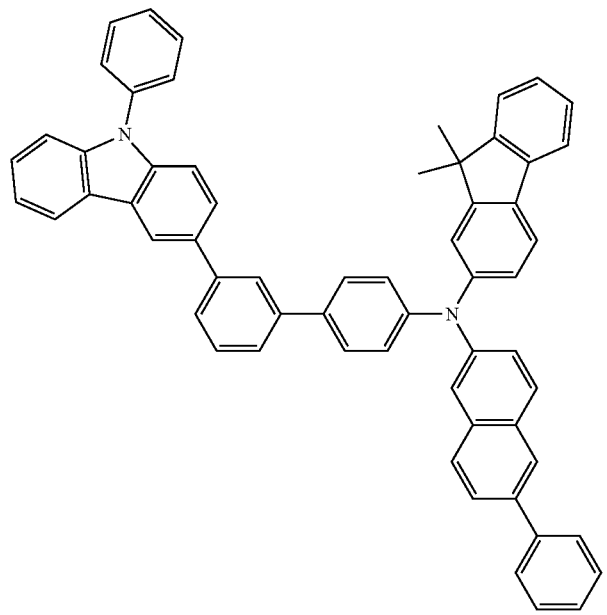
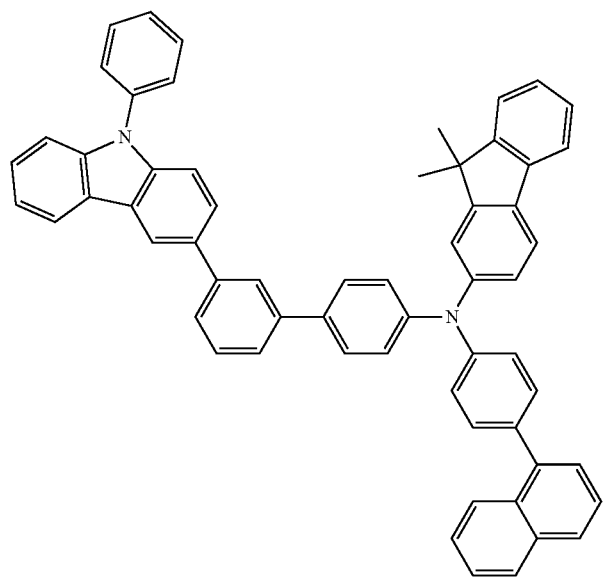

1083
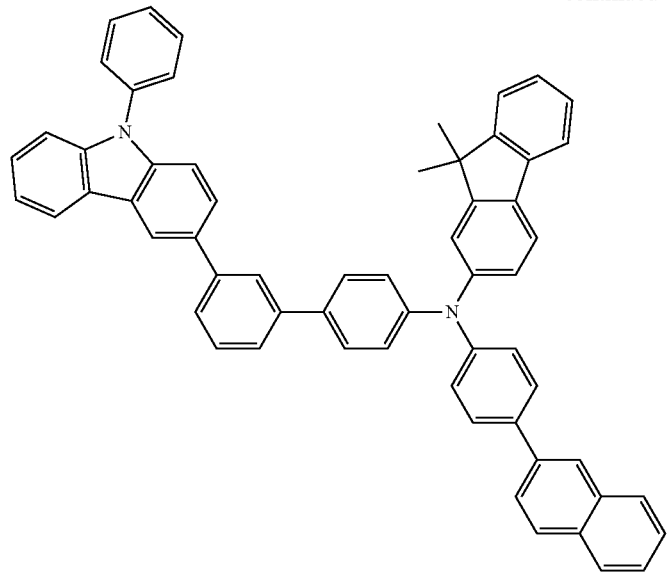
1084
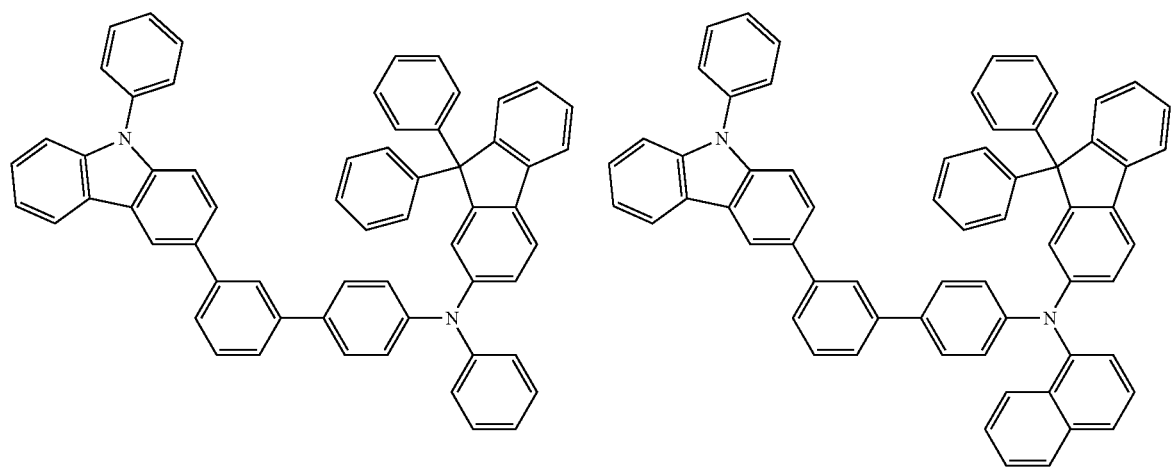
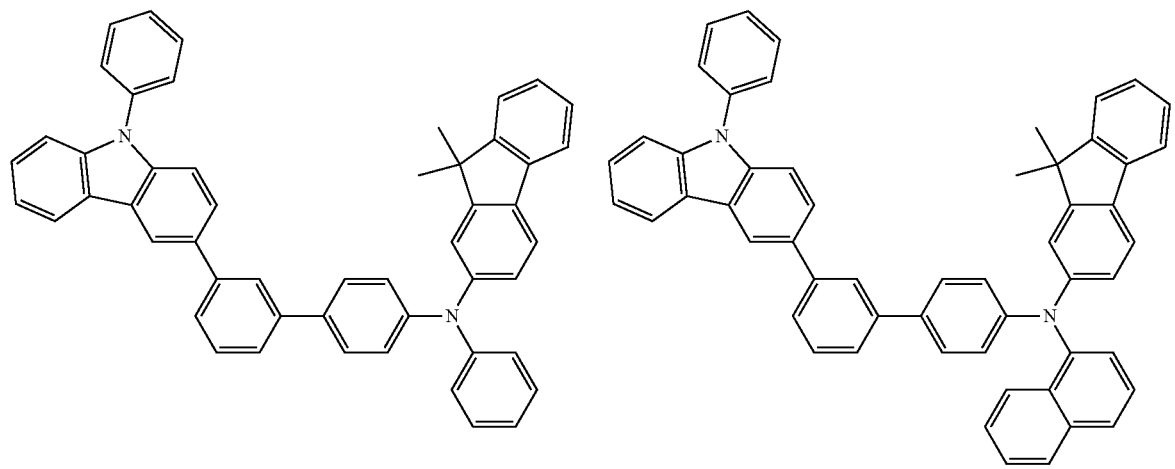

-continued
| 1085 | 1086 |
|---|---|
| 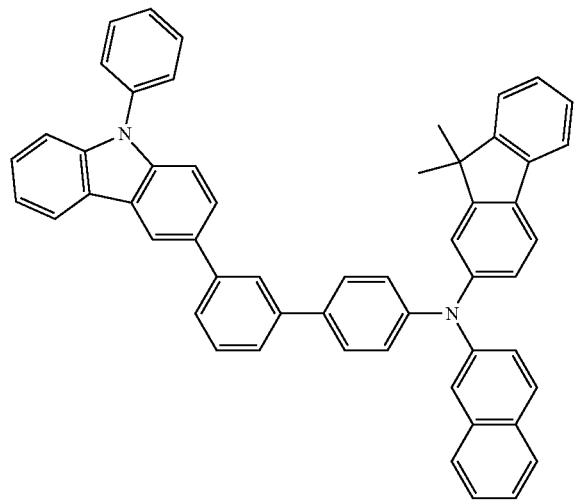 | 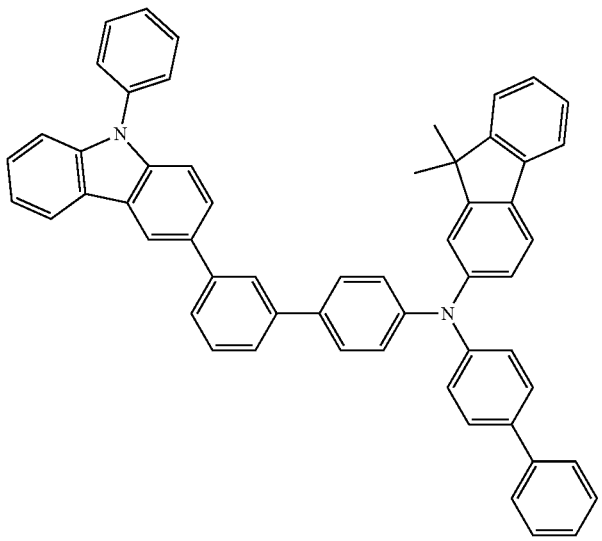 |
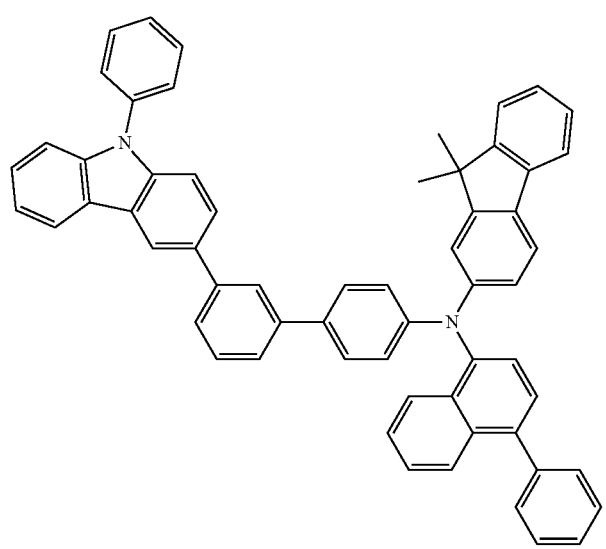
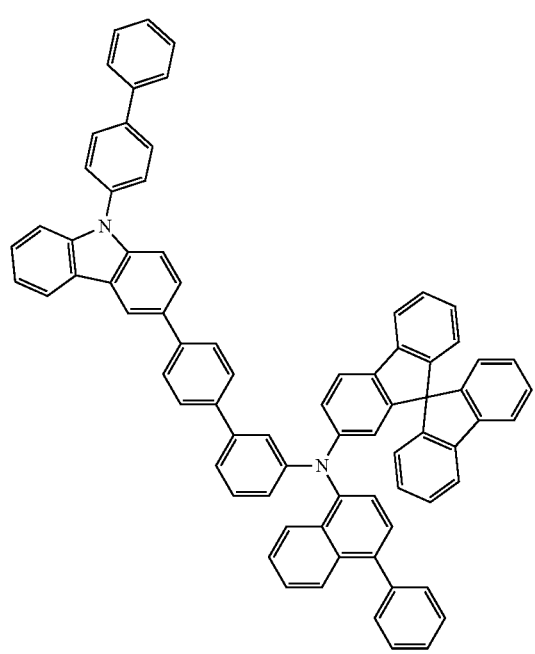

-continued
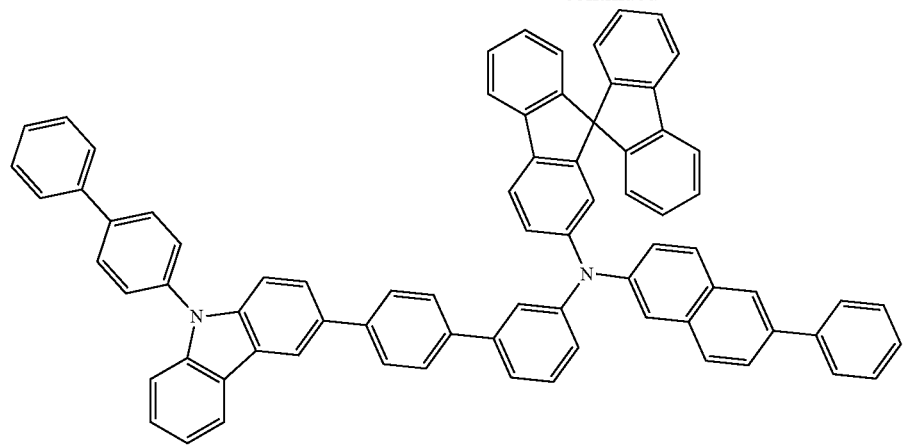
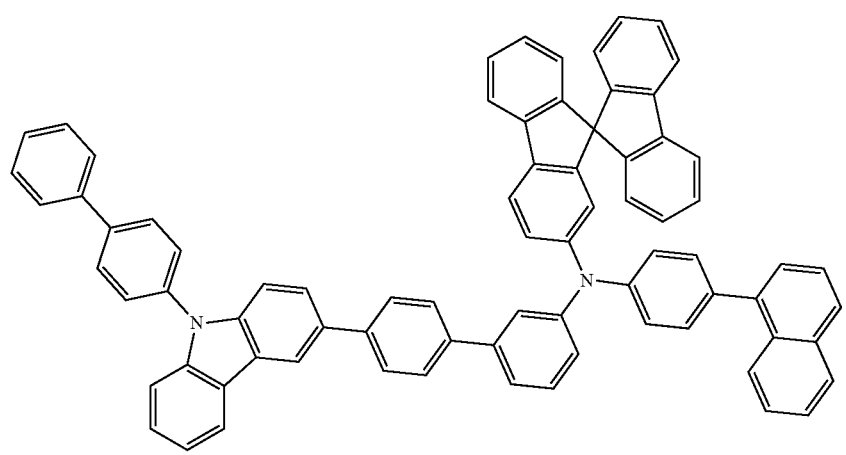
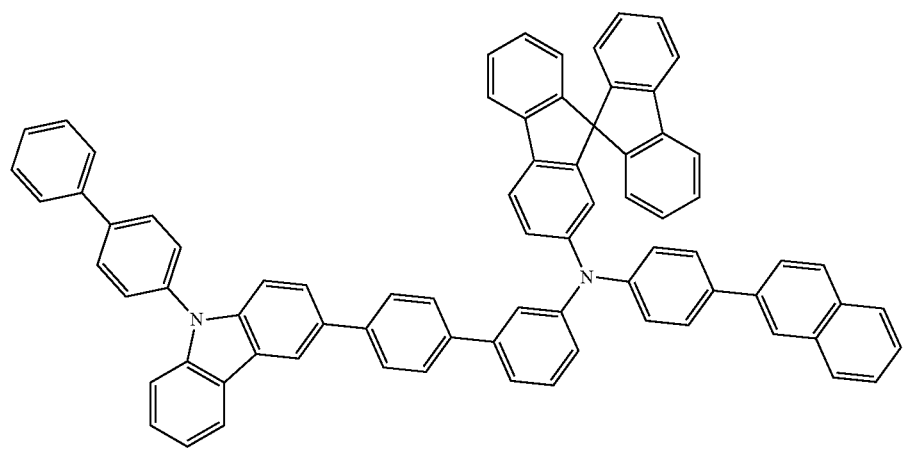

-continued
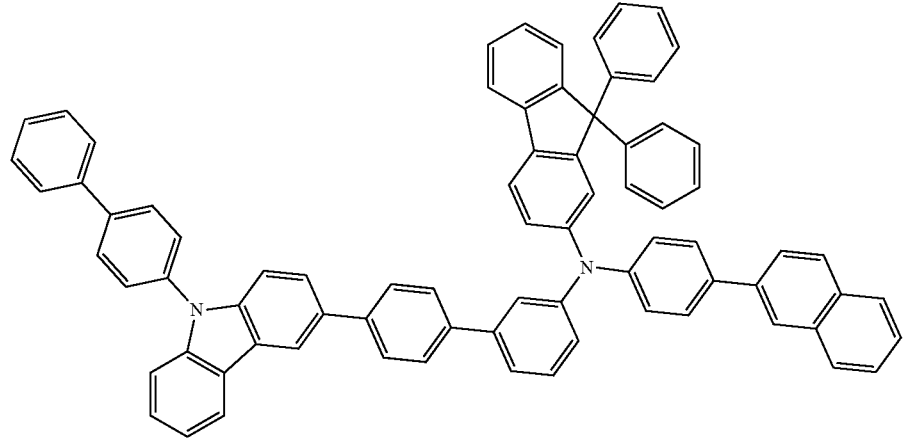
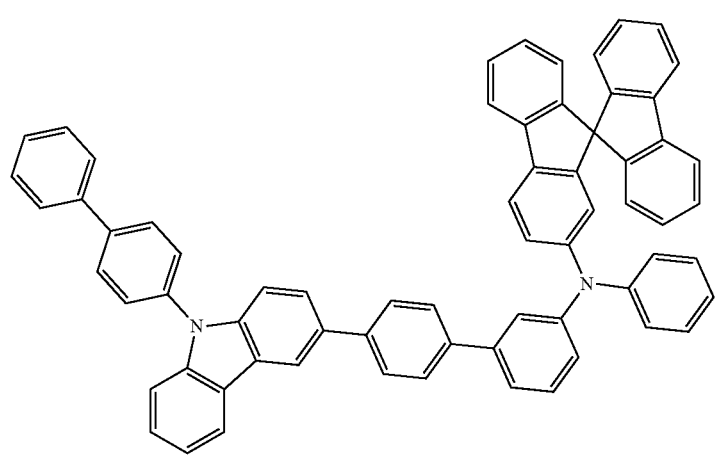
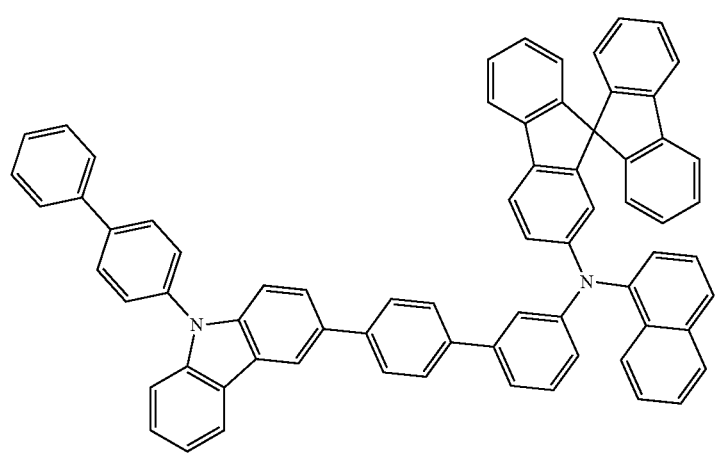

-continued
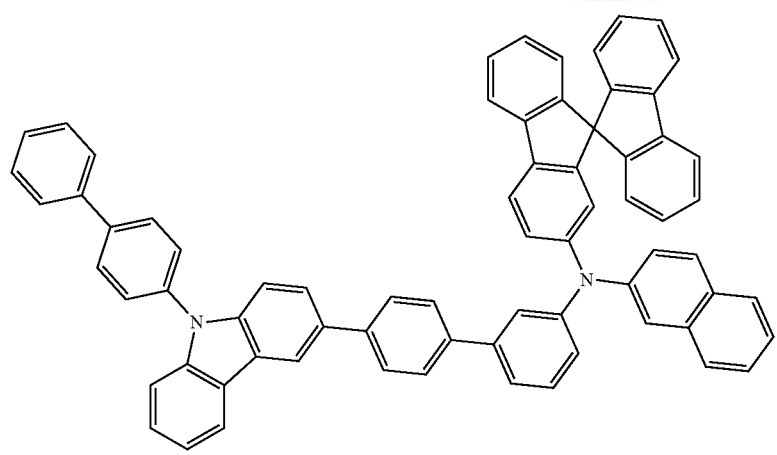
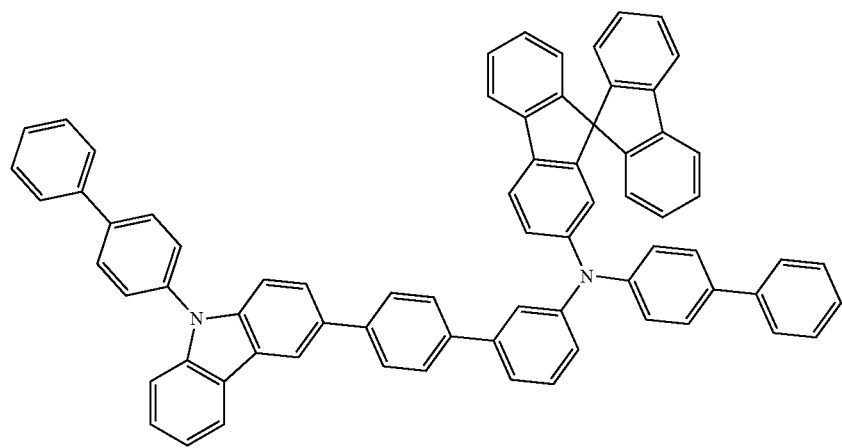
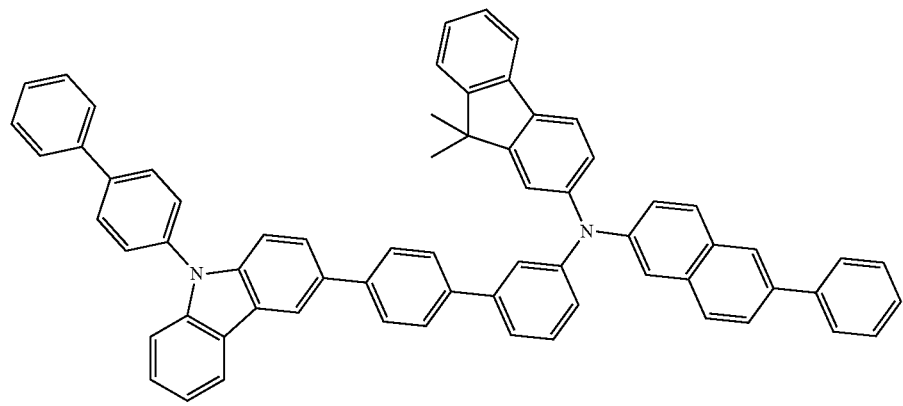
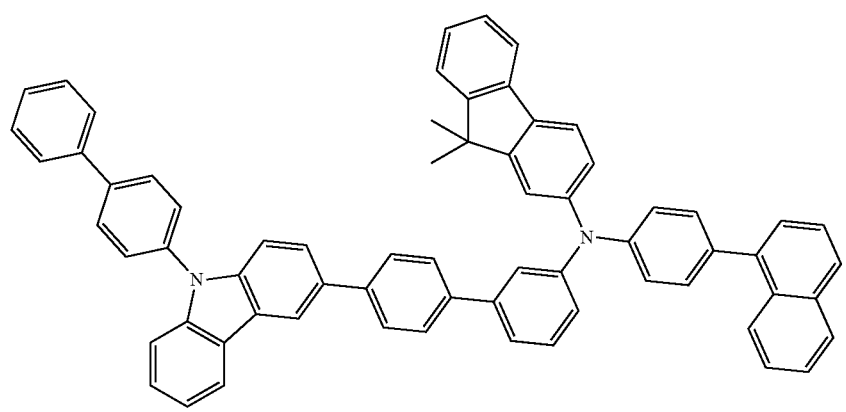

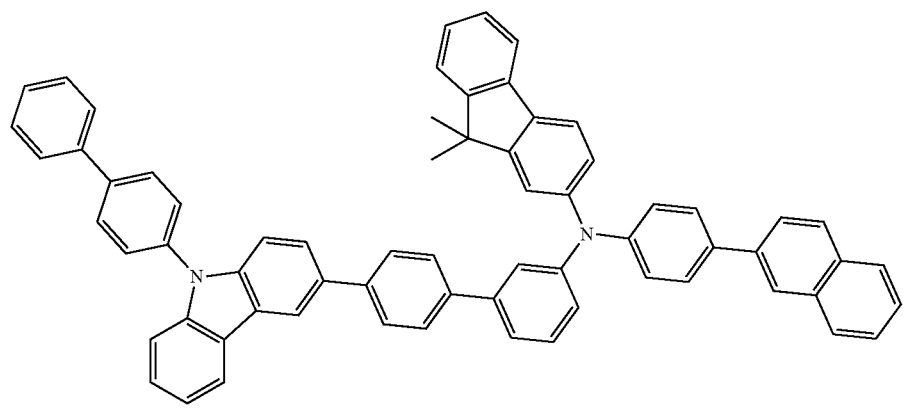
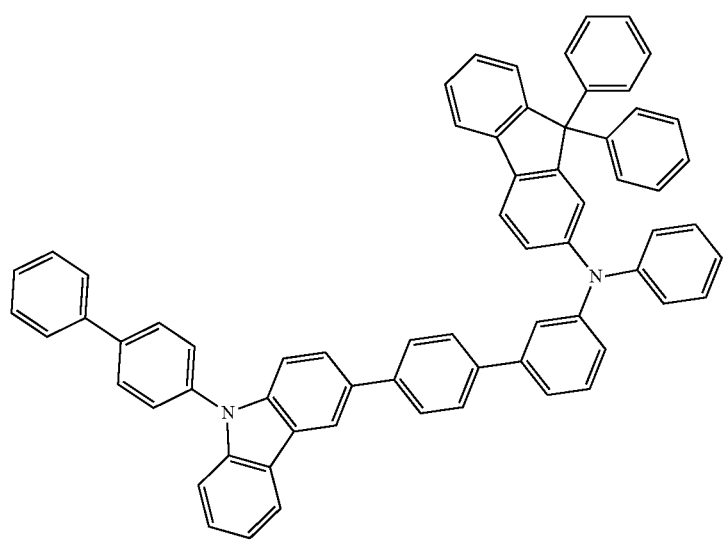
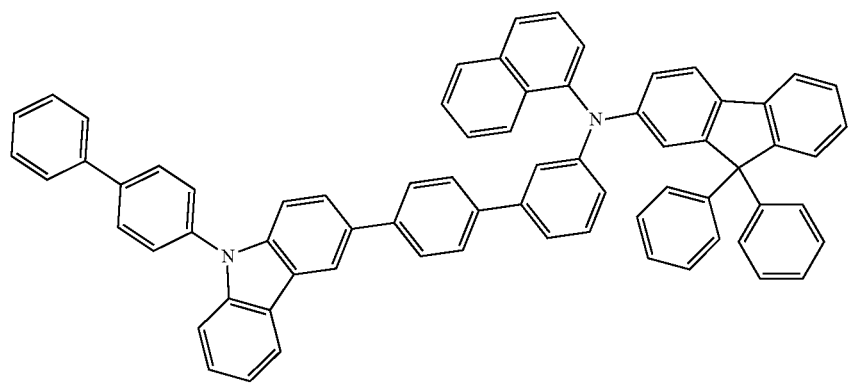

-continued
| 1095 | 1096 |
|---|---|
| 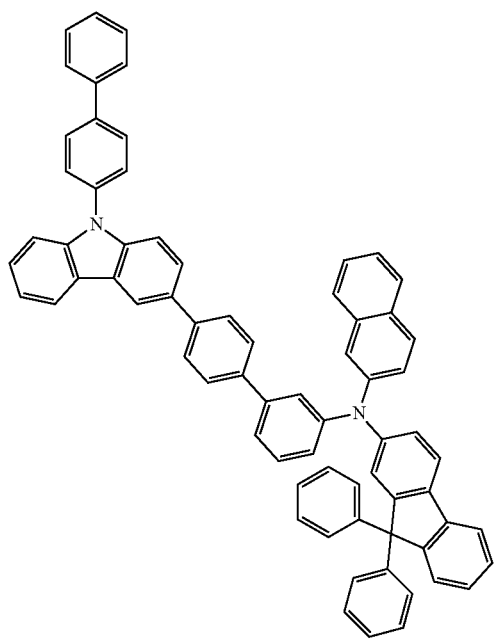 | 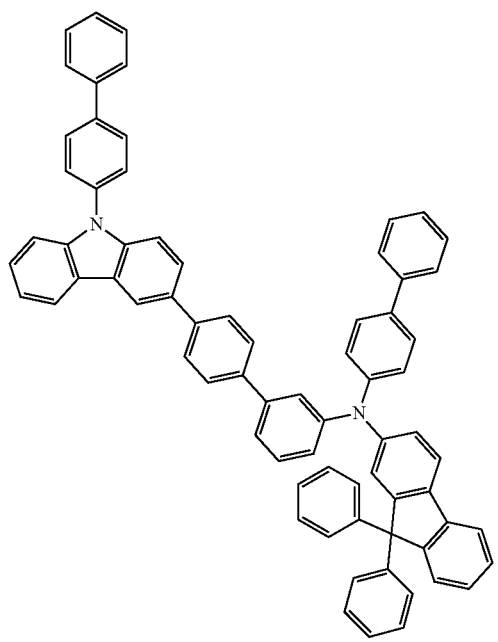 |
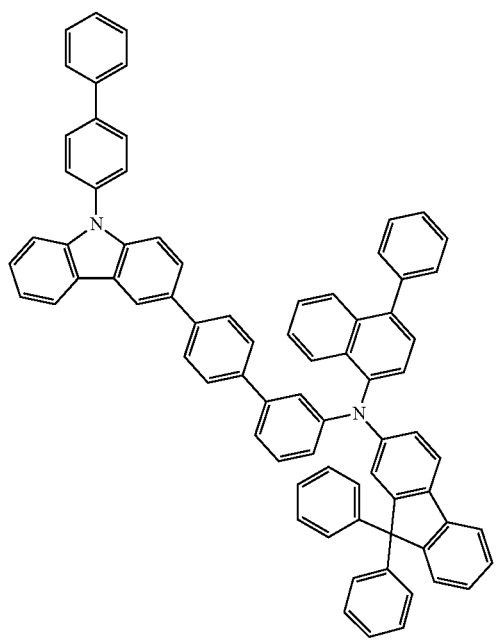

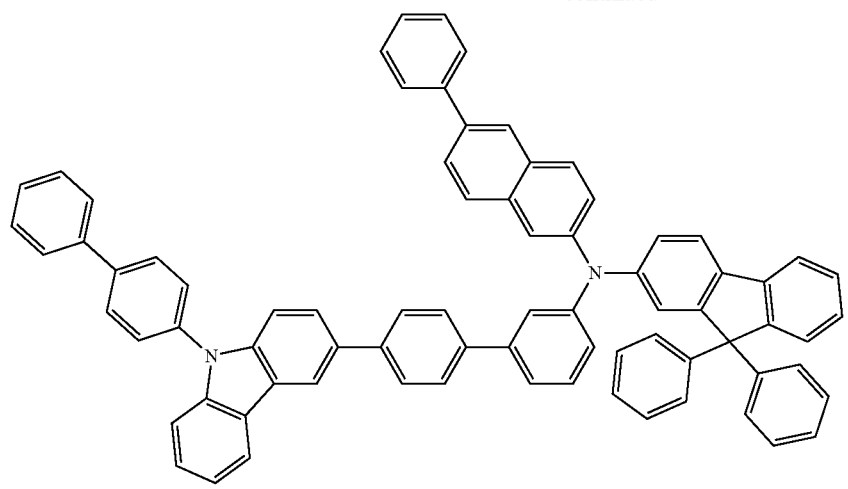
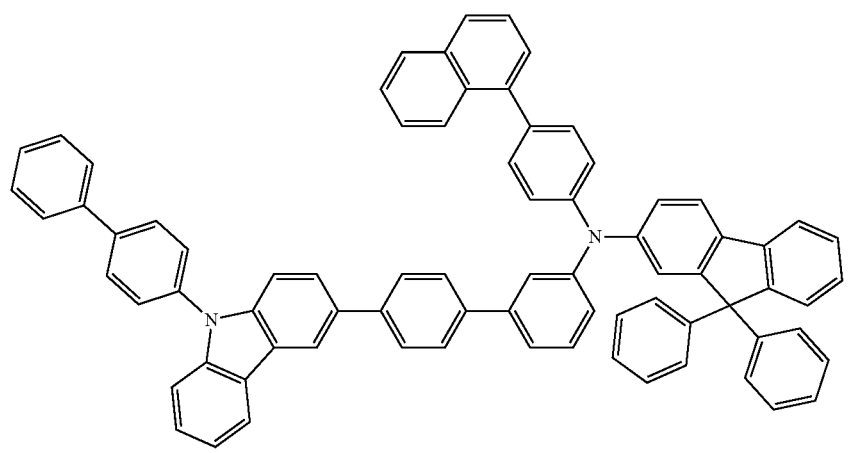
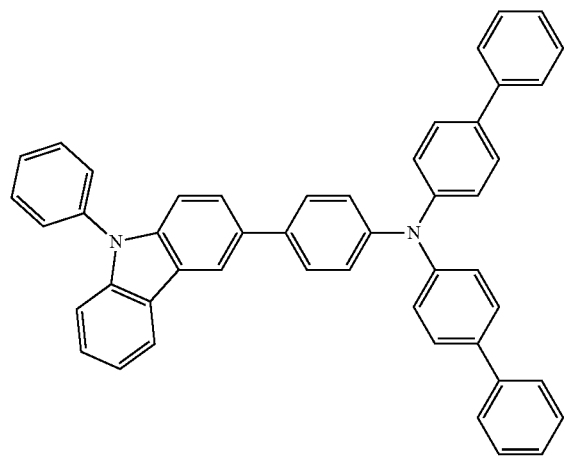

1099                                                    1100
-continued
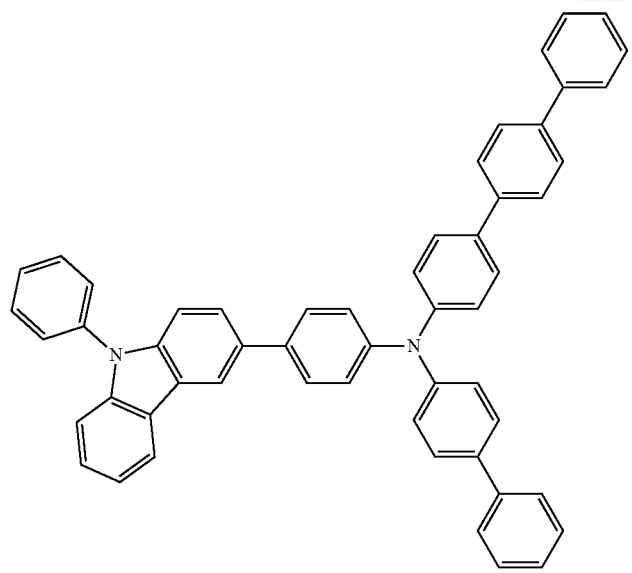
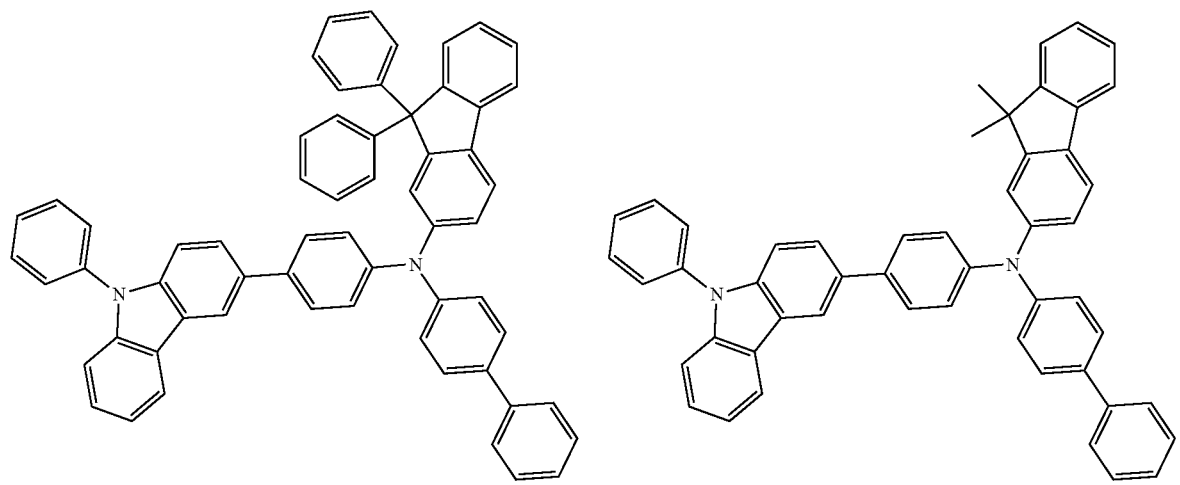
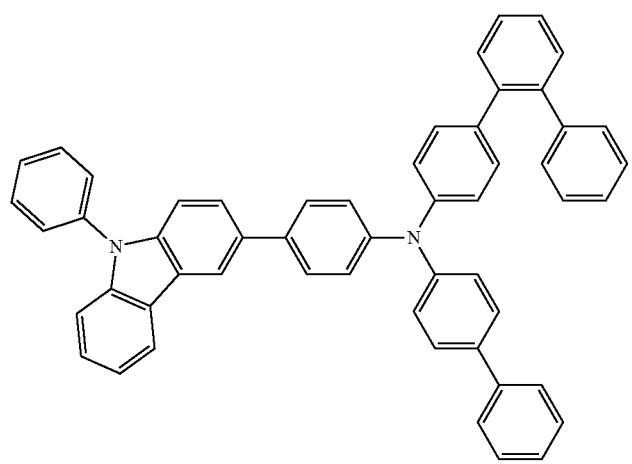

14. The organic light emitting device of claim 11, wherein the compound of Chemical Formula 4 is selected from among the following compounds:
(B114)
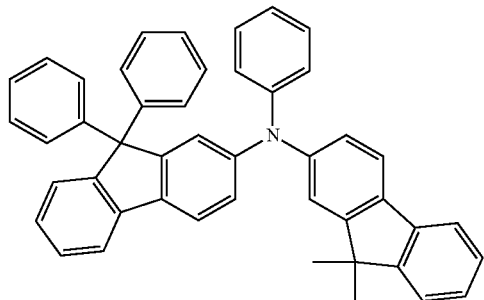
(B115)
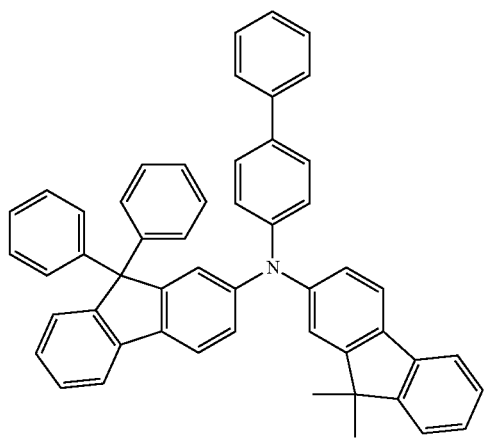
(B116)
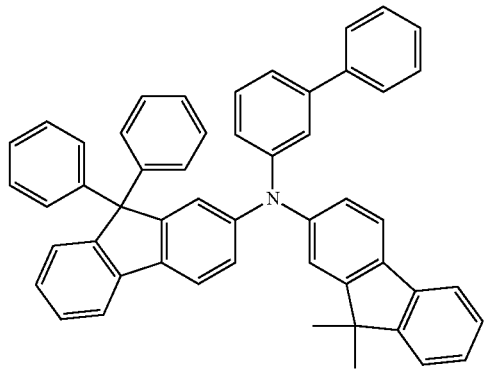
(B117)
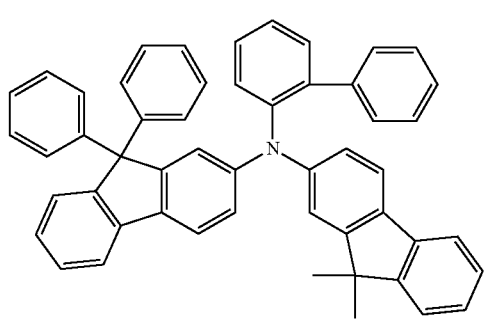
-continued
(B118)
(B120)
(B121)
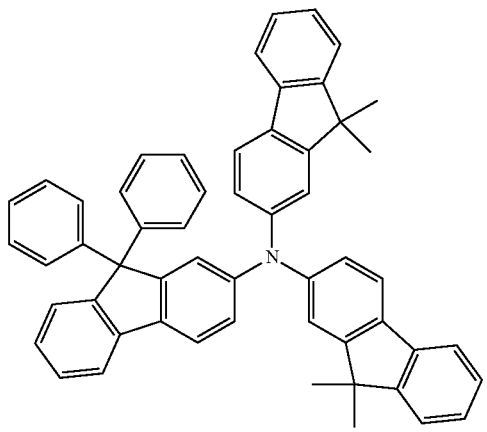
(B122)
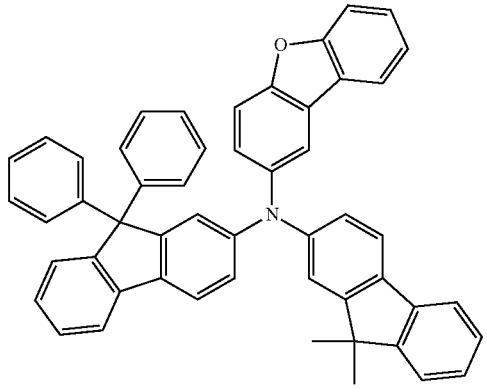

(B123)
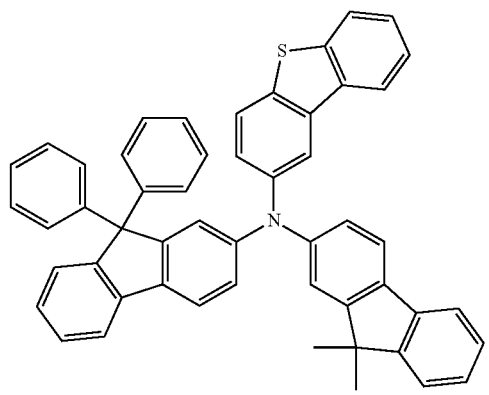
(B124)
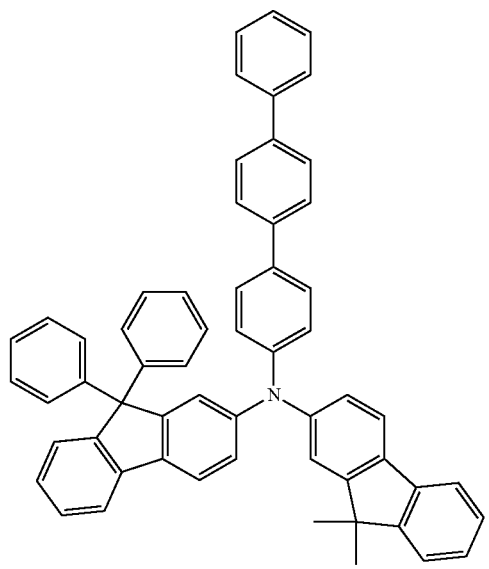
(B125)
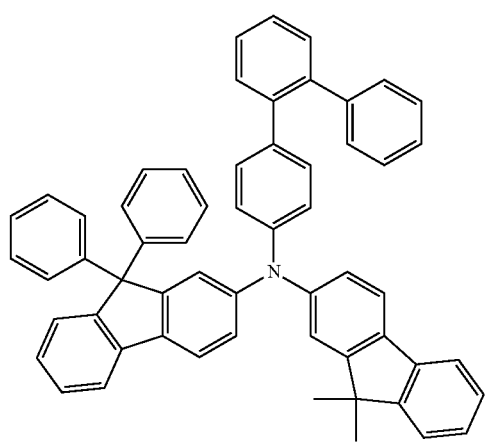
(B126)
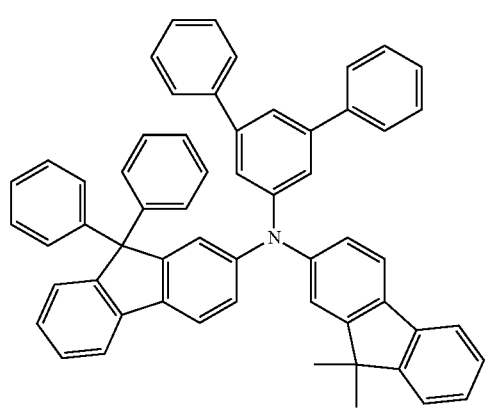
(B127)
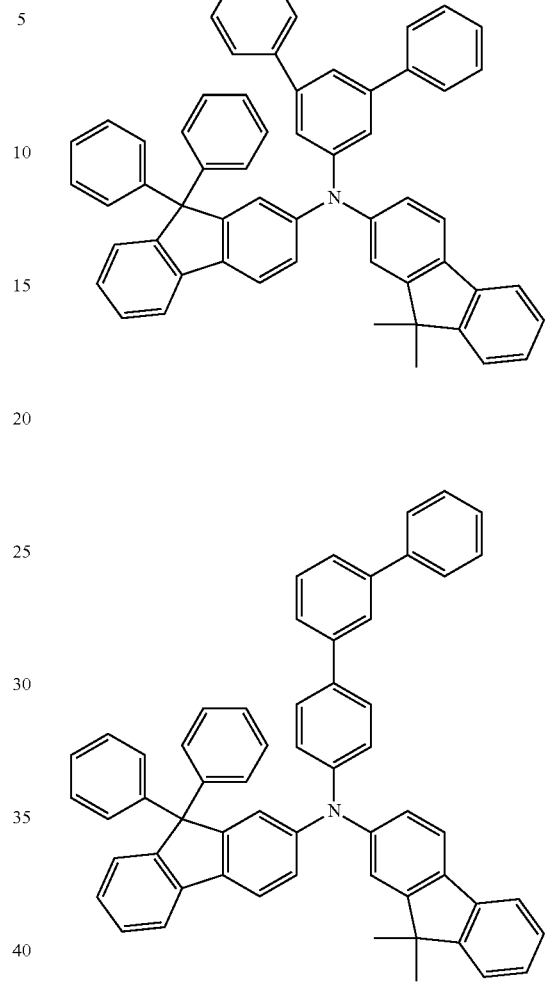
(B128)
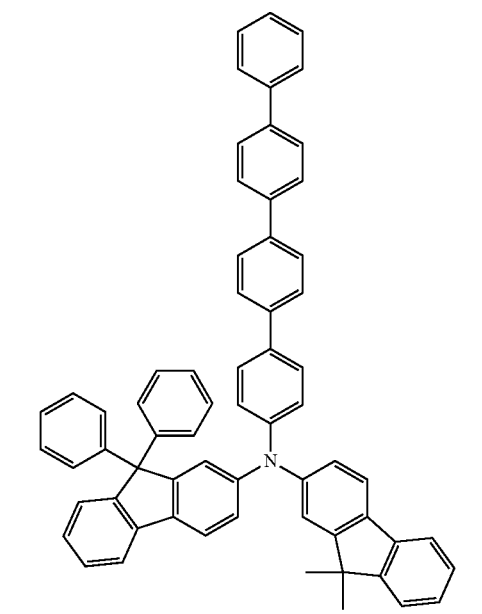

(B129)
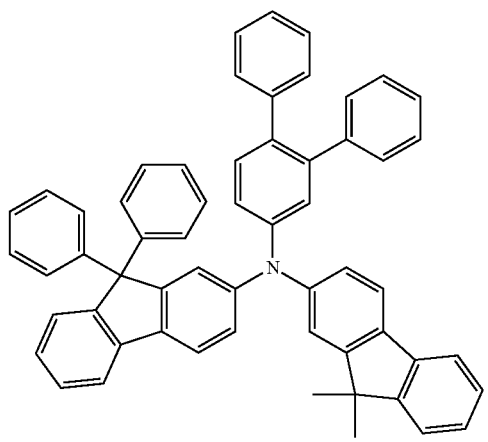
(B130)
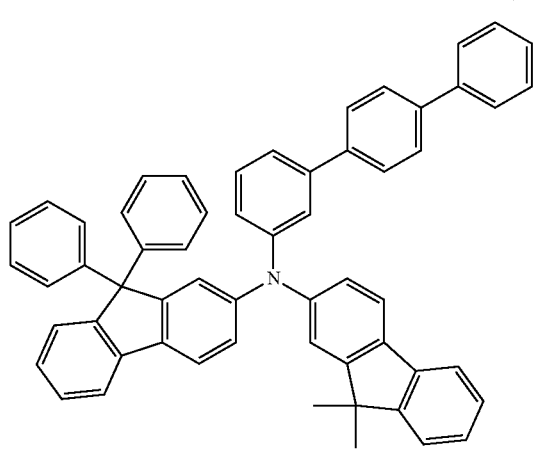
(B131)
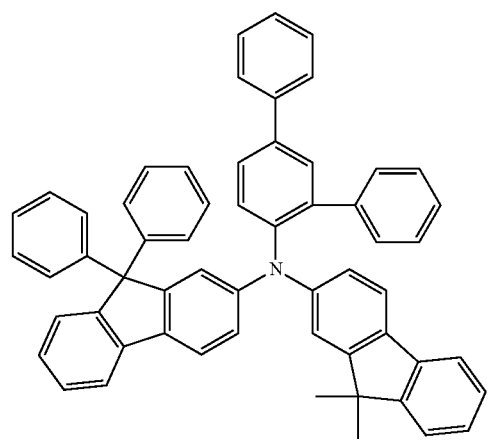
(B132)
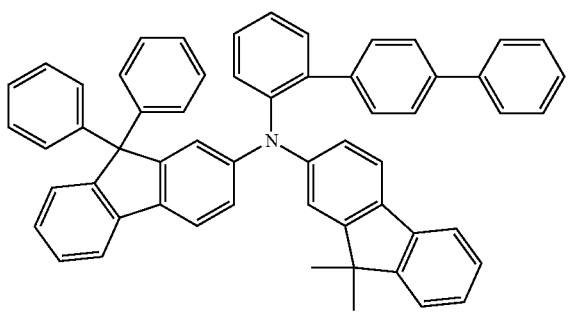
(B133)
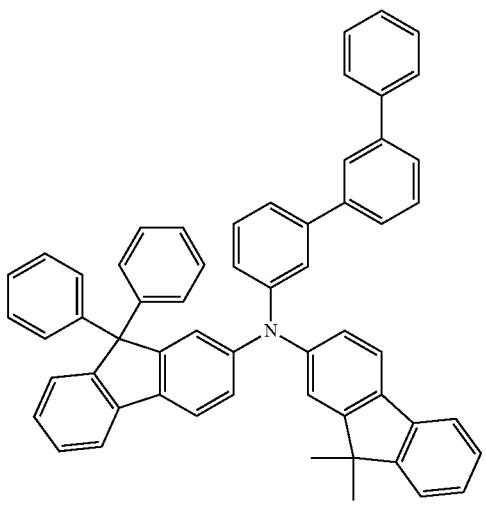
(B134)
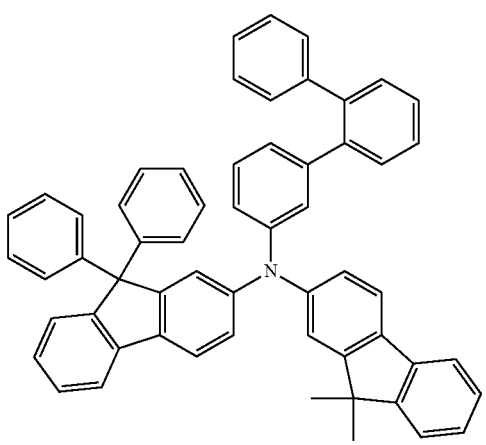

(B135)
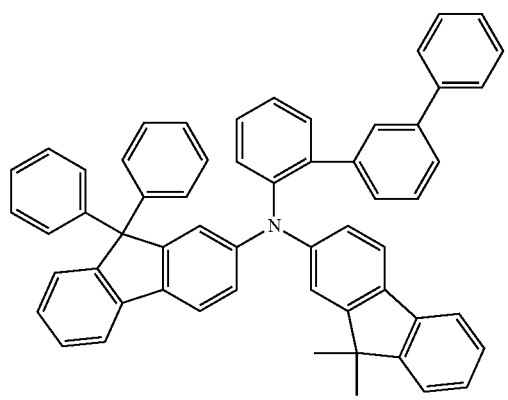
(B136)
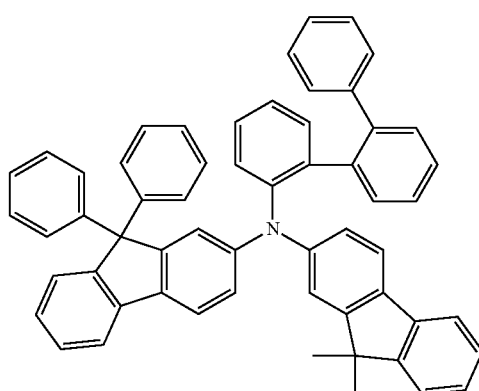
(B137)
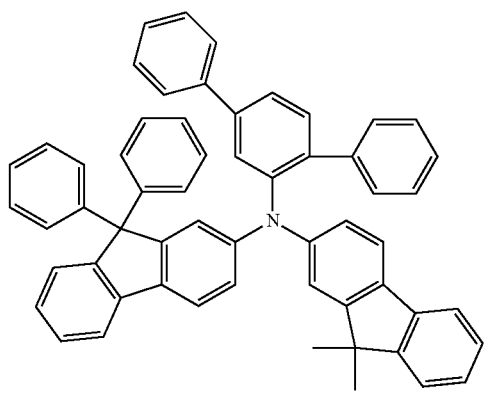
(B138)
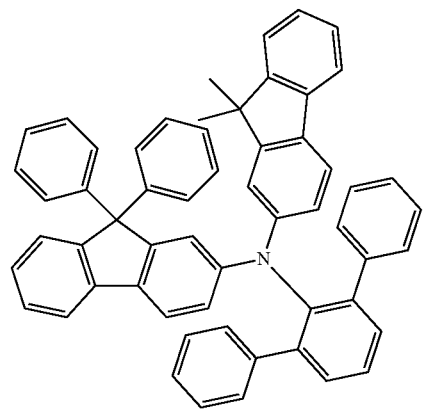
(B139)
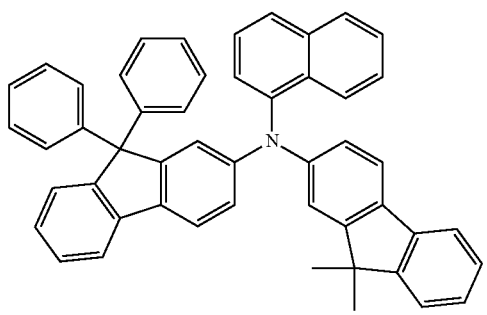
(B140)
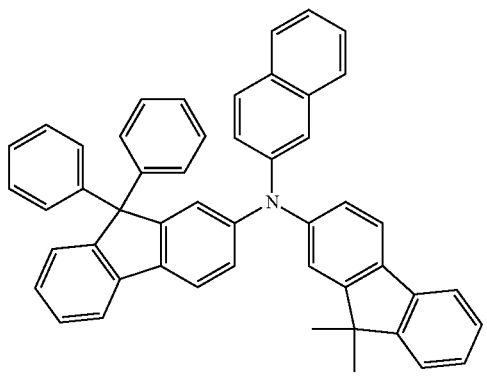
(B141)
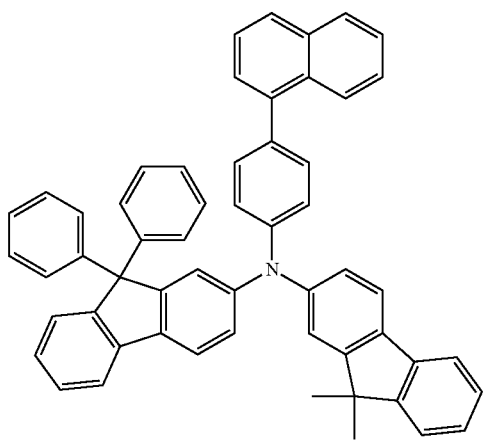

(B142)
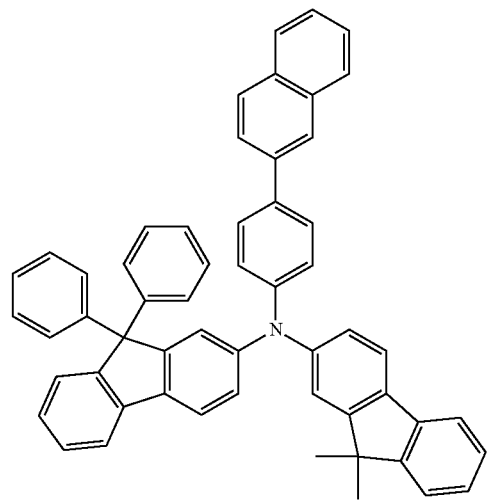
(B143)
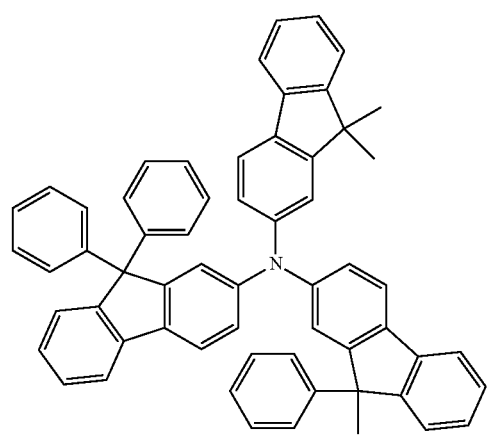
(B144)
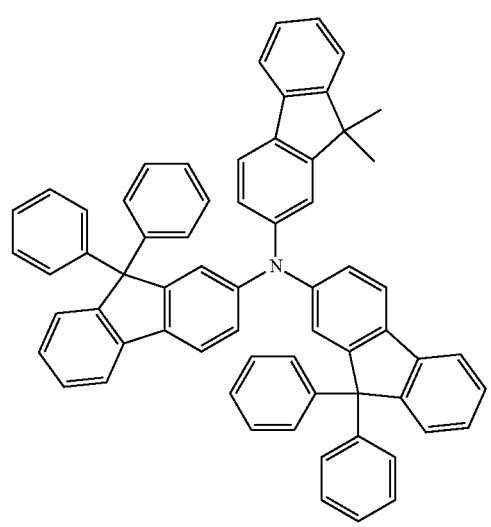
(B145)
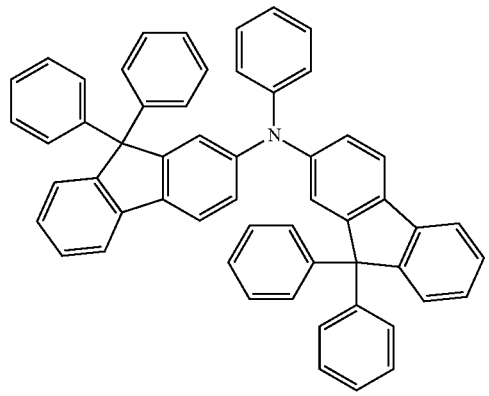
(B146)
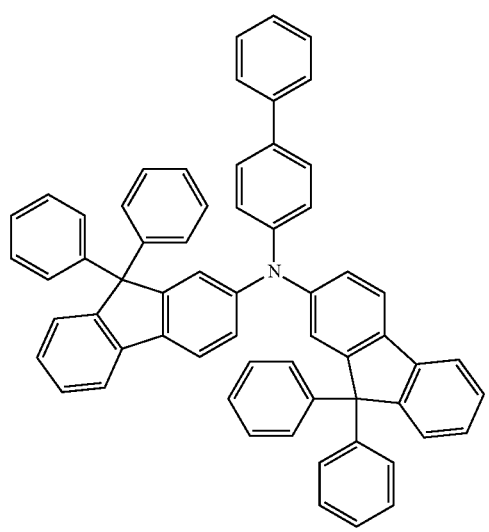
(B147)
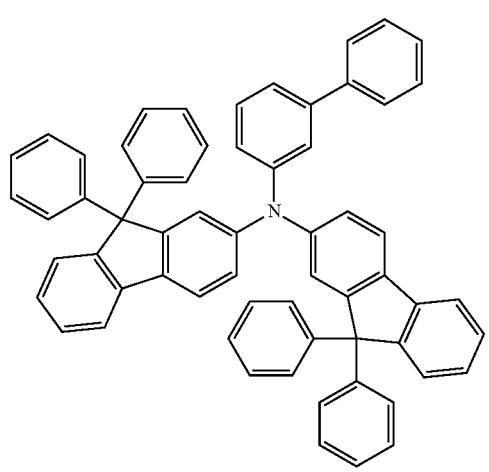

(B148)
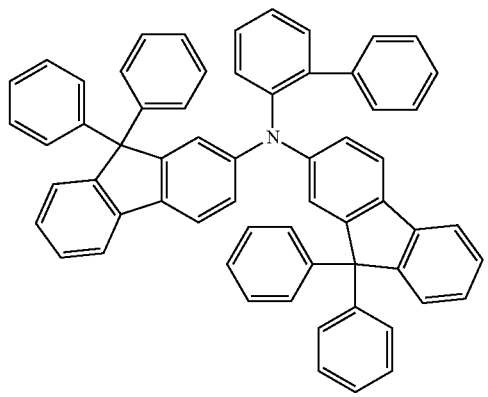
(B149)
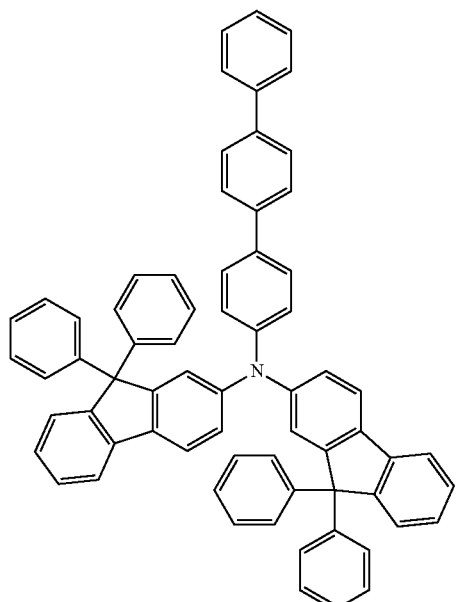
(B150)
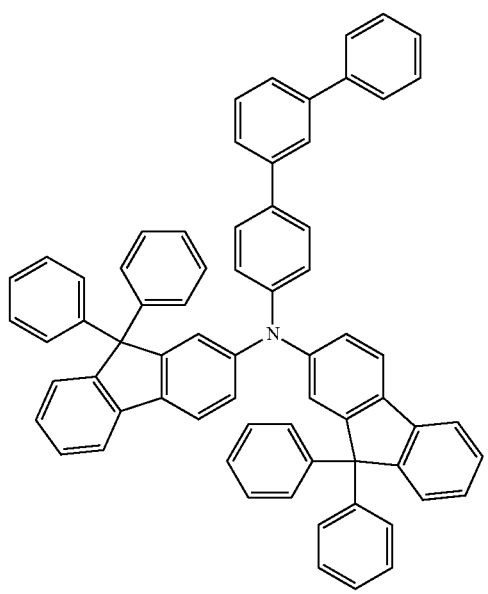
(B151)
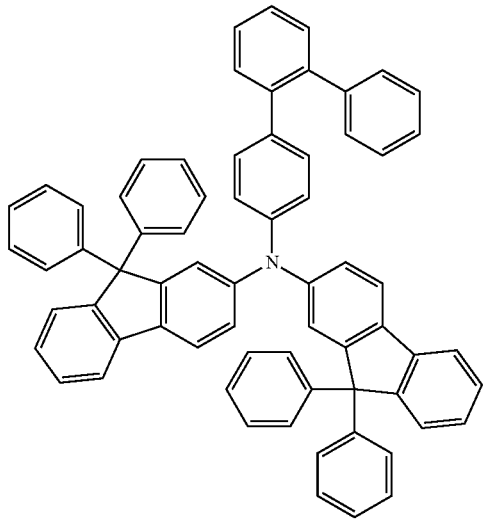
(B152)
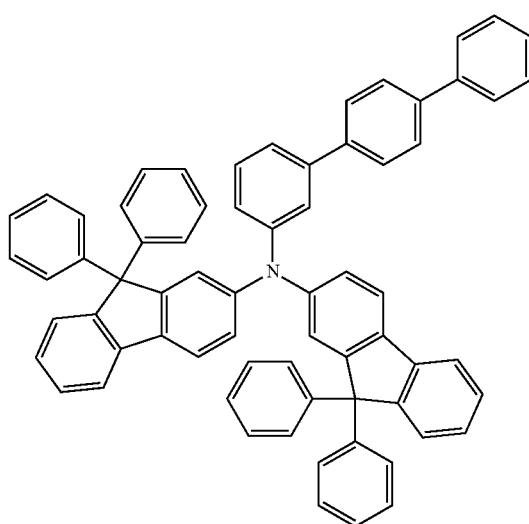
(B153)
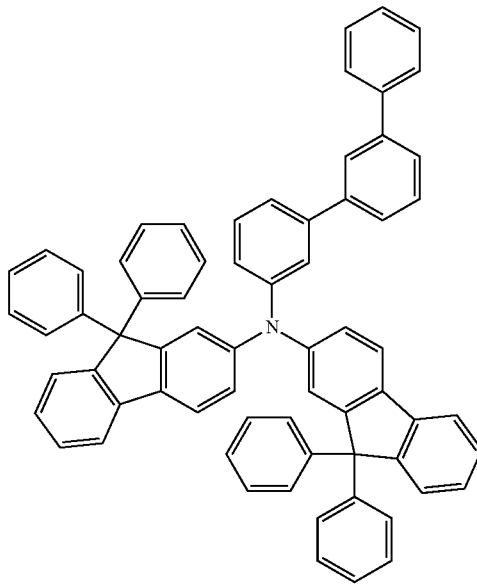

-continued
(B154)
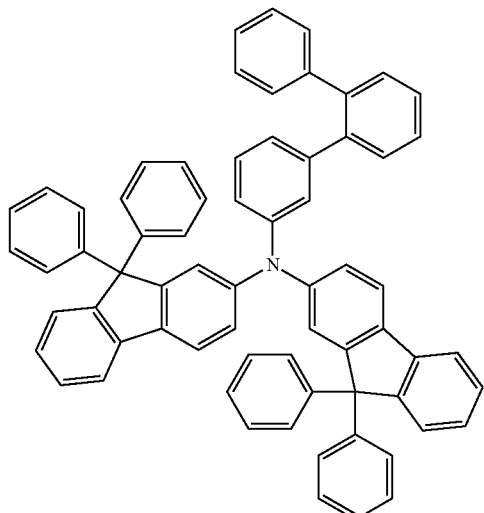
(B155)
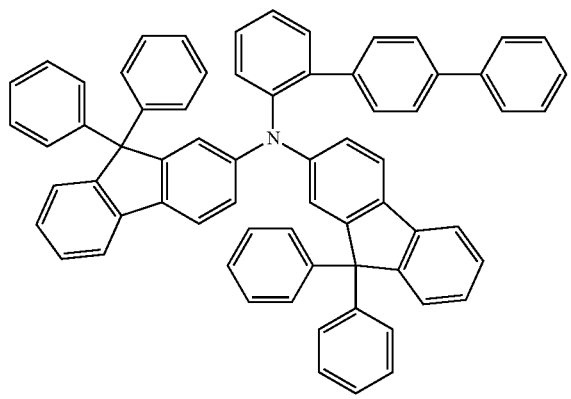
(B156)
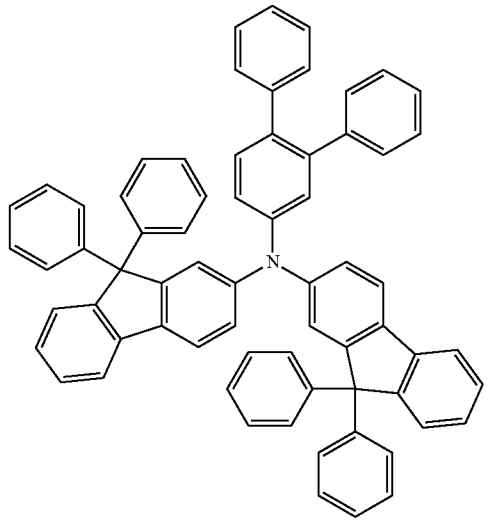
-continued
(B157)
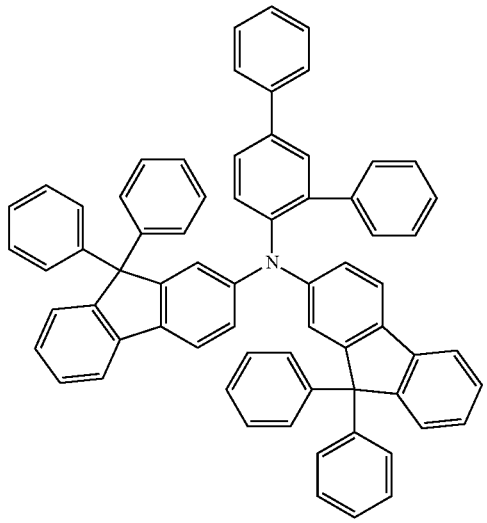
(B158)
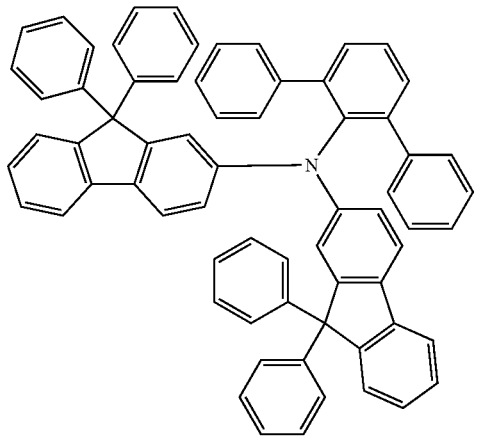
(B159)
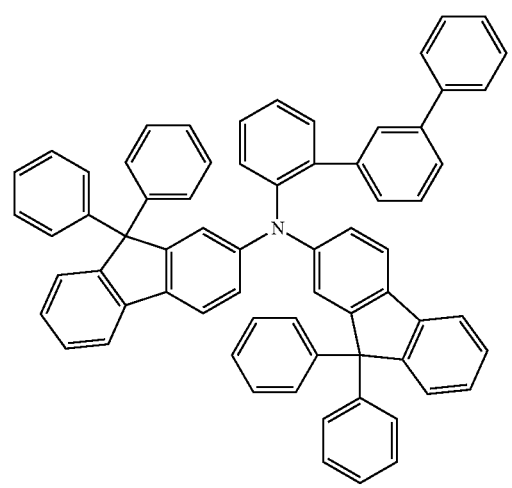

(B160)
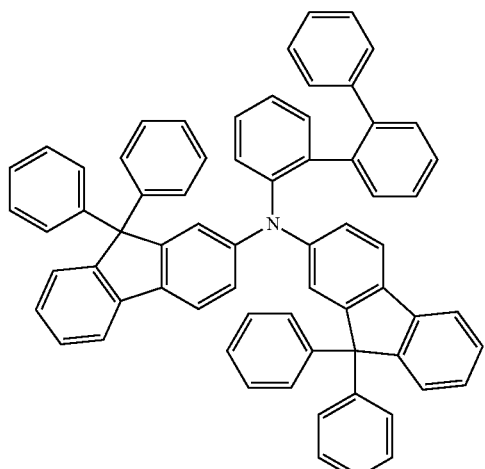
(B161)
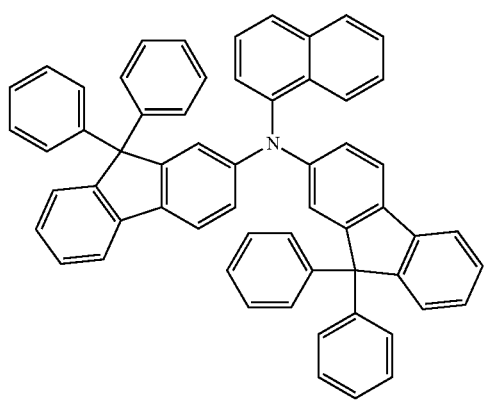
(B162)
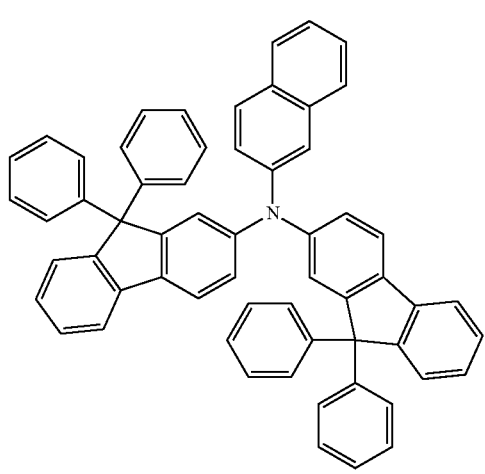
(B163)
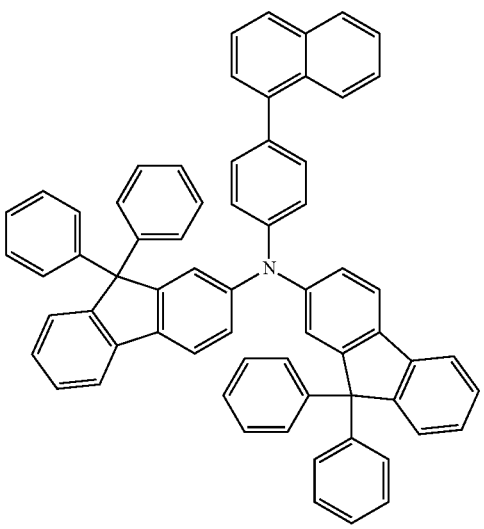
(B164)
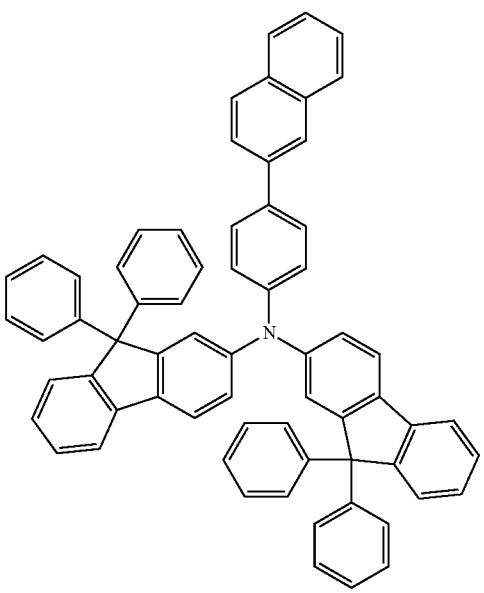
(B165)
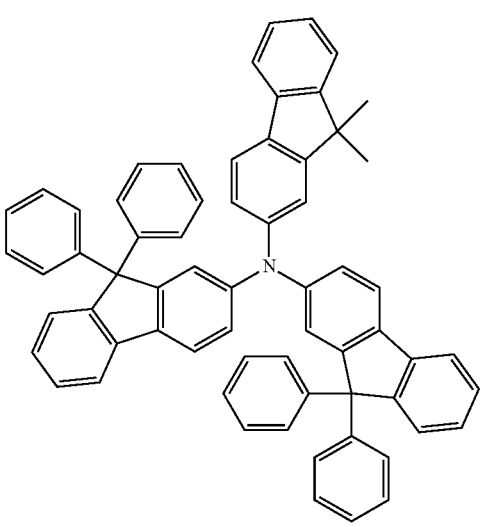

(B166)
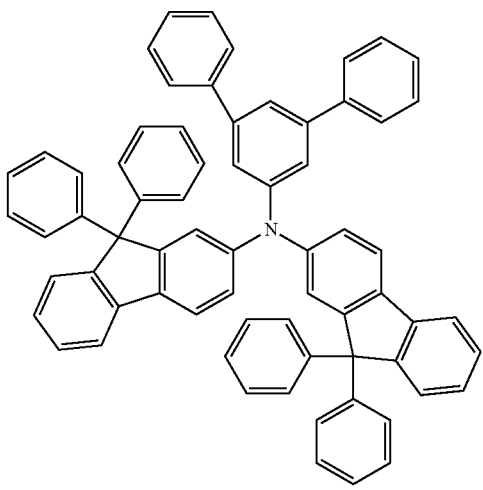
(B167)
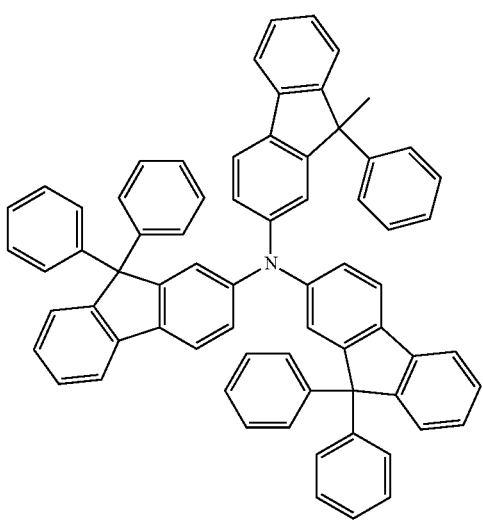
(B168)
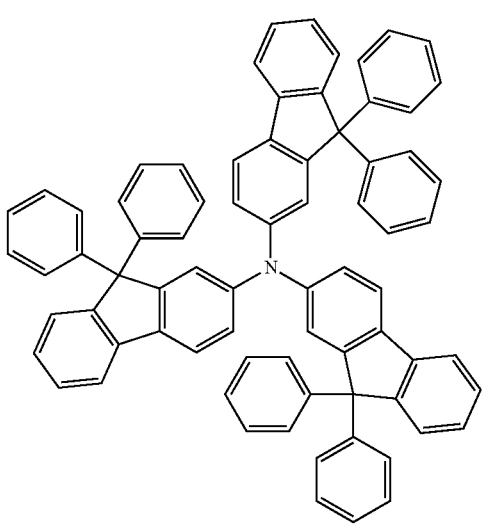
(B169)
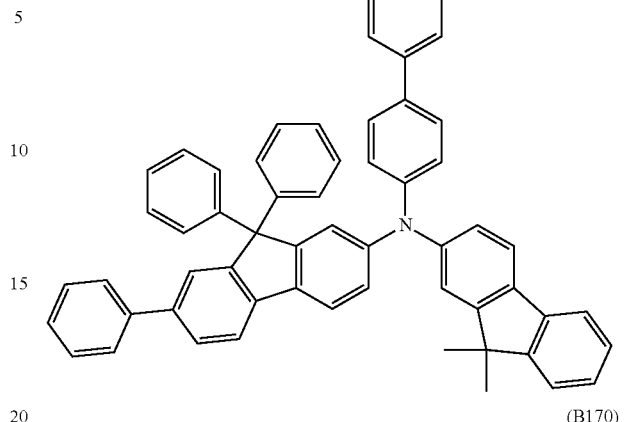
(B170)
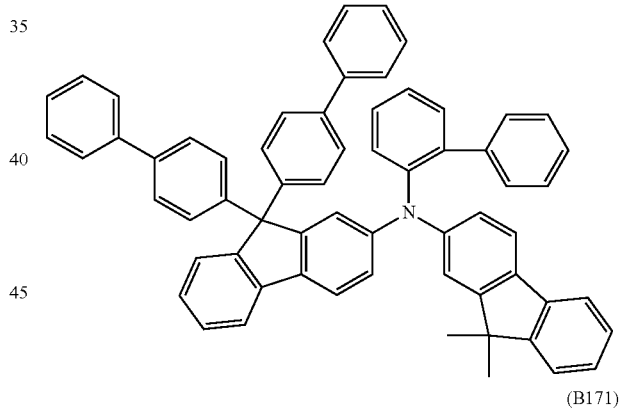
(B1171)
(B171)
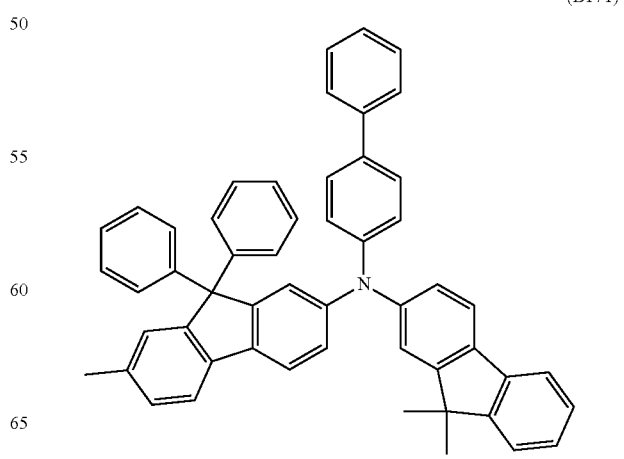

(B172)
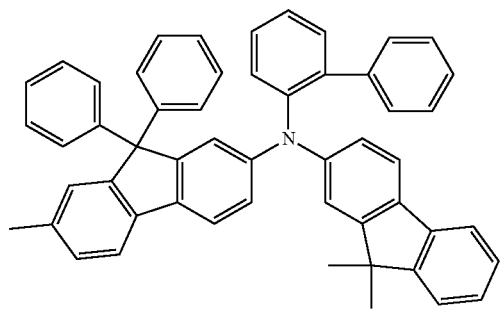
(B173)
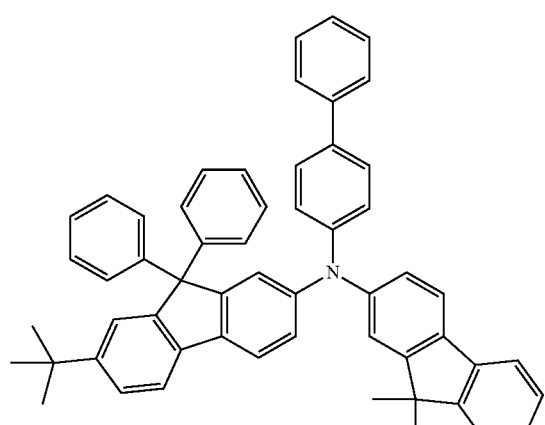
(B174)
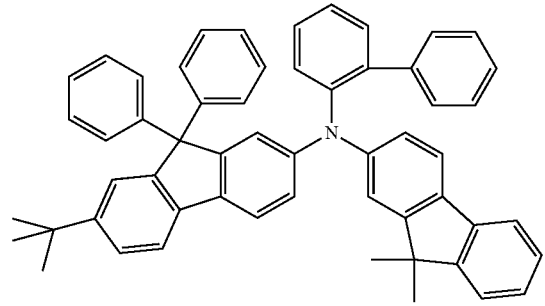
(B175)
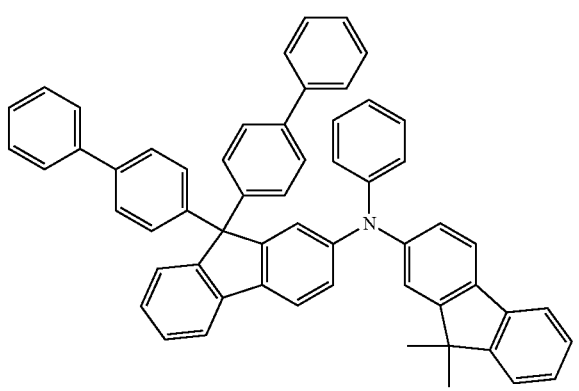
(B176)
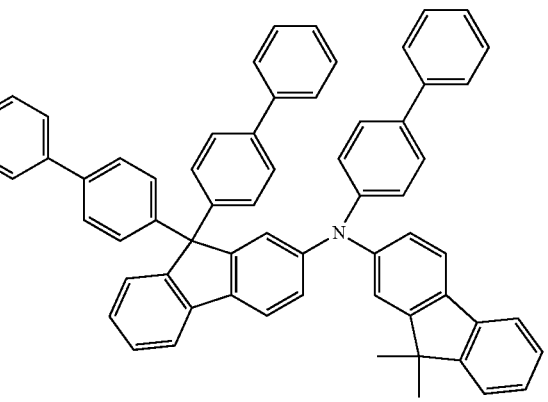
(B177)
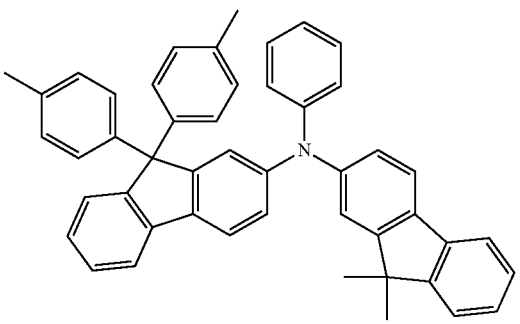
(B178)
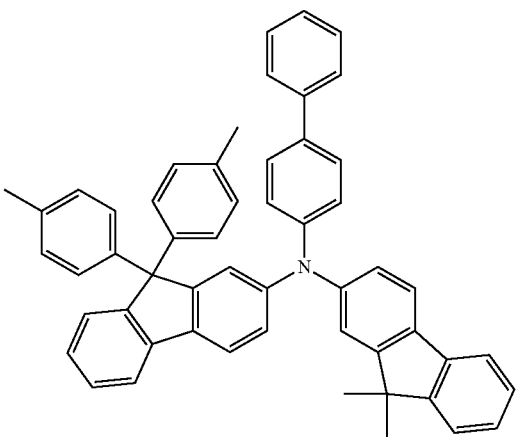

-continued
(B179)
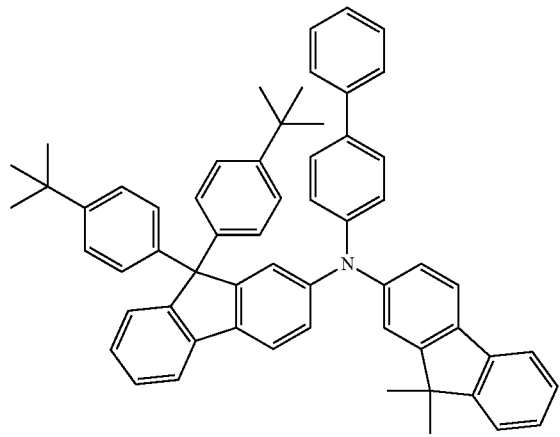
(B180)
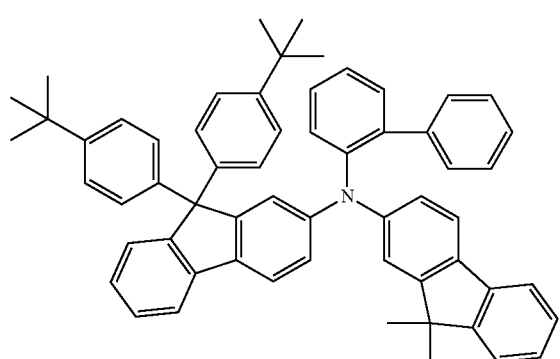
(B181)
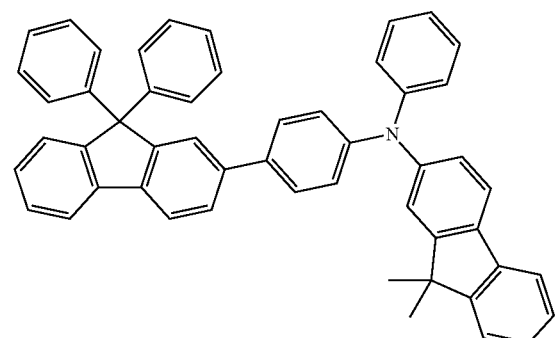
-continued
(B182)
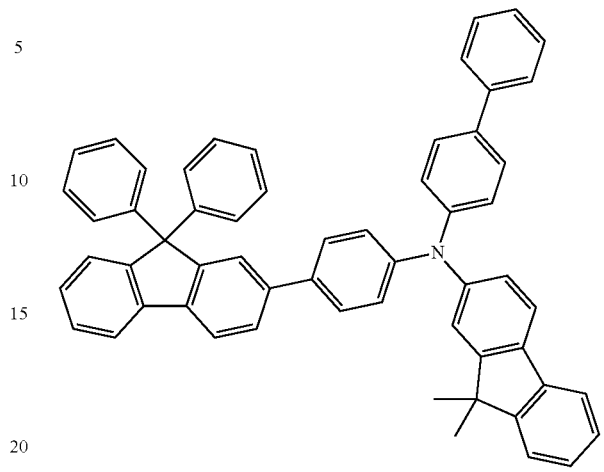
(B183)
(B184)
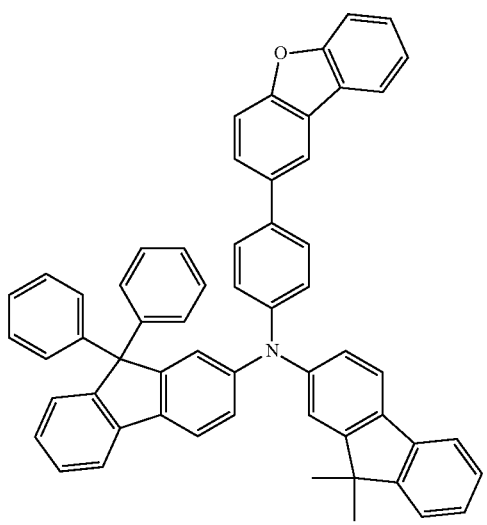

1123
-continued
(B185)
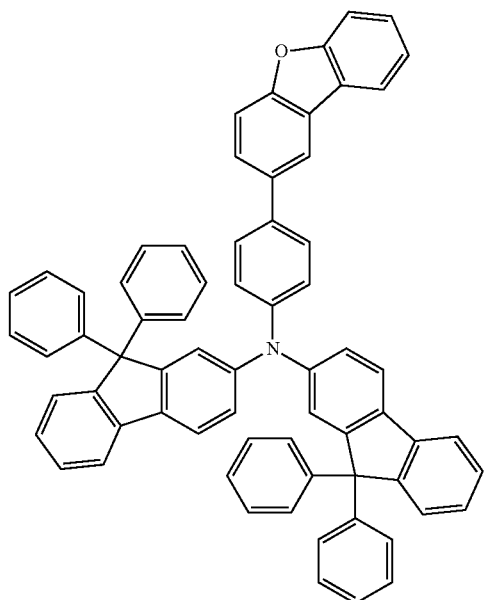
(B186)
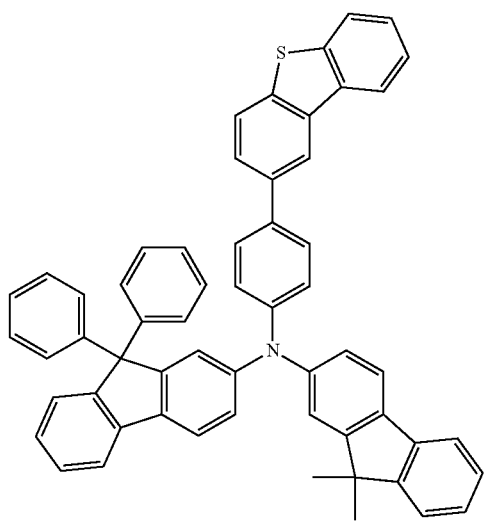
1124
-continued
(B187)
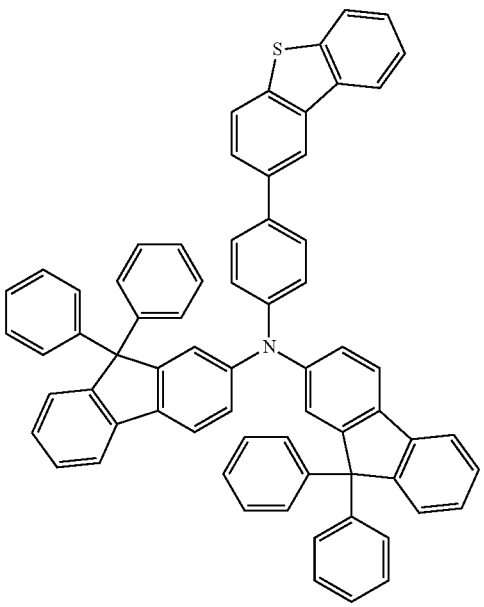
(B188)
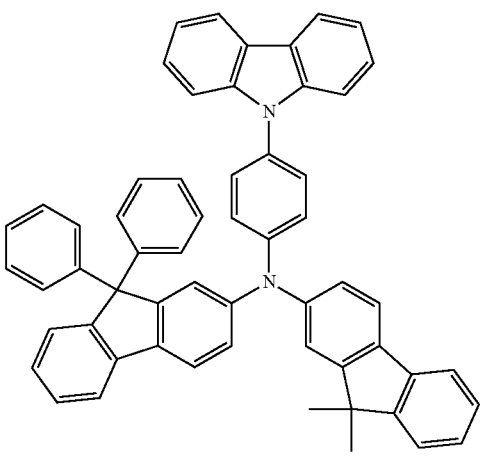
(B189)
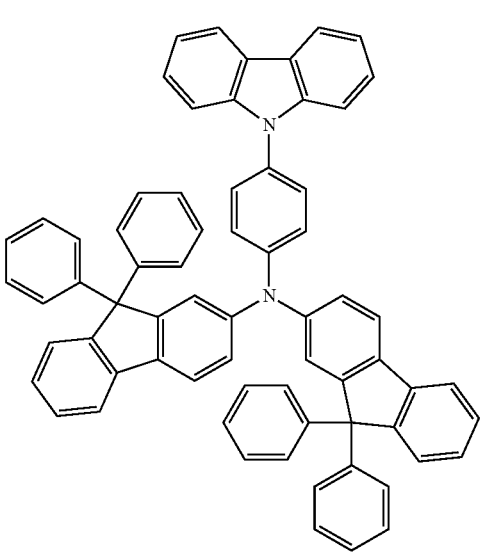

-continued
(B190)
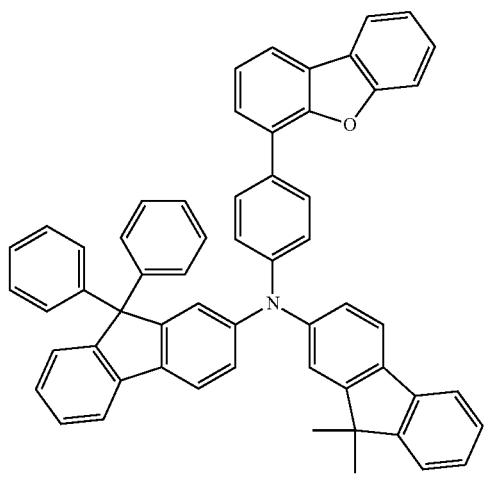
(B191)
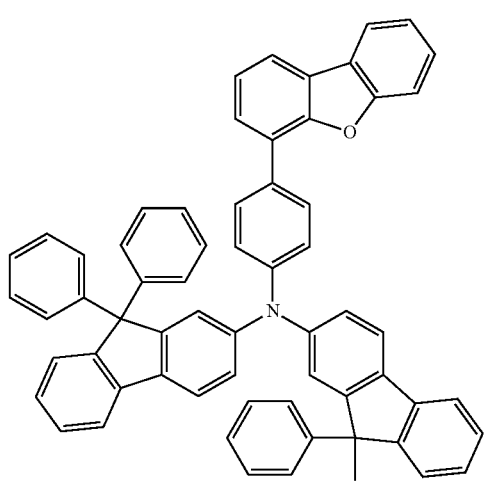
(B192)
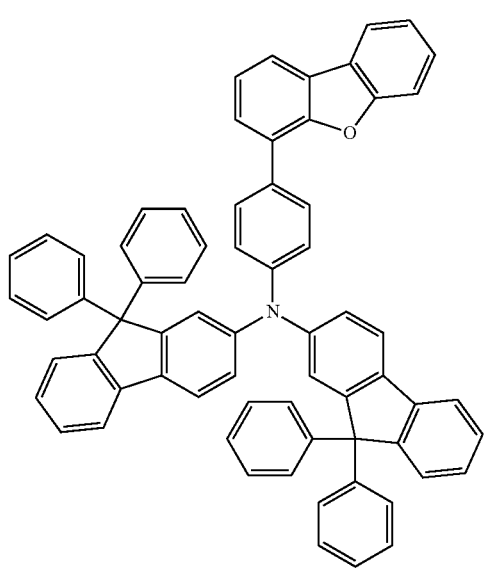
-continued
(B193)
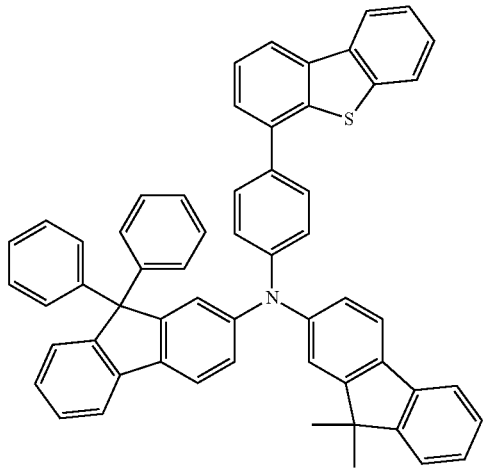
(B194)
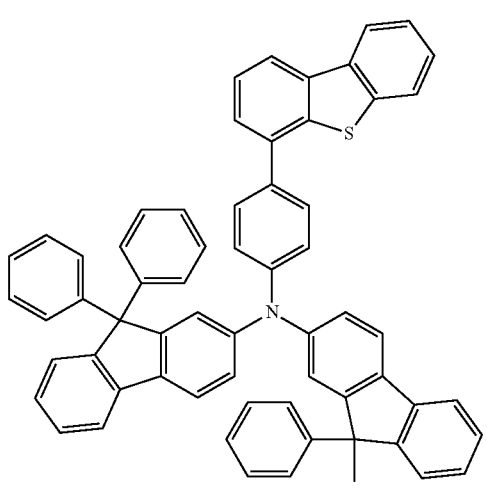
(B195)
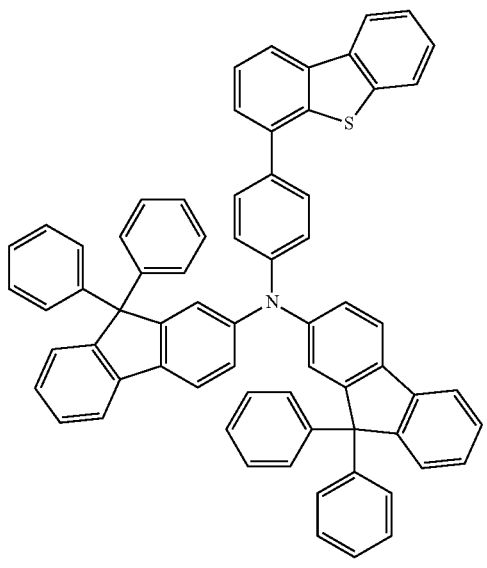

(B196)
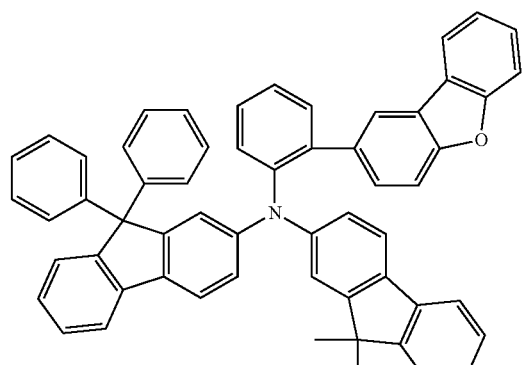
(B197)
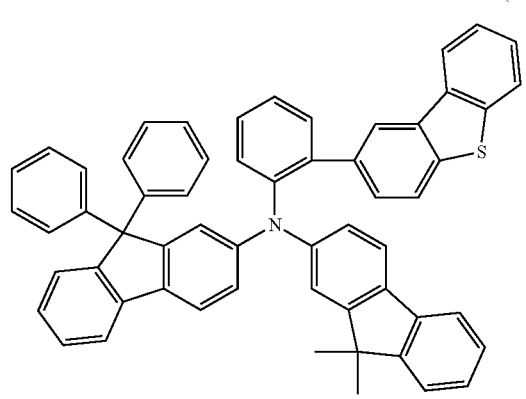
(B198)
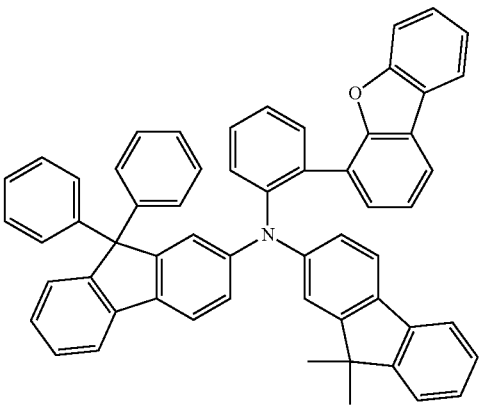
(B199)
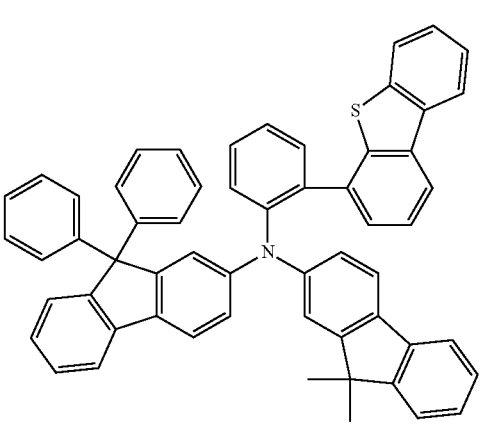
(B200)
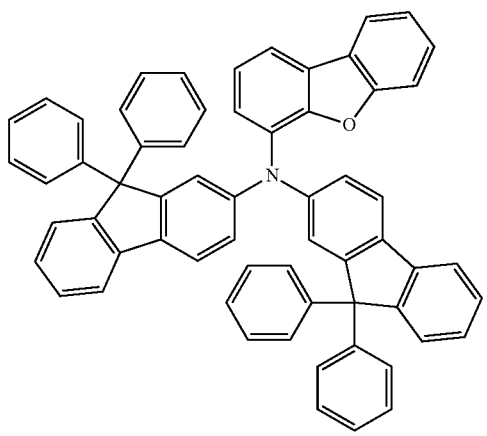
(B201)
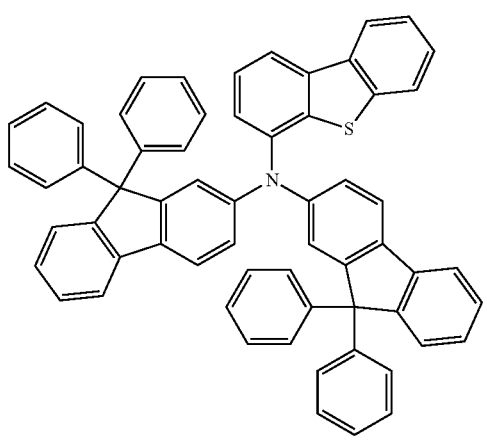
(B202)
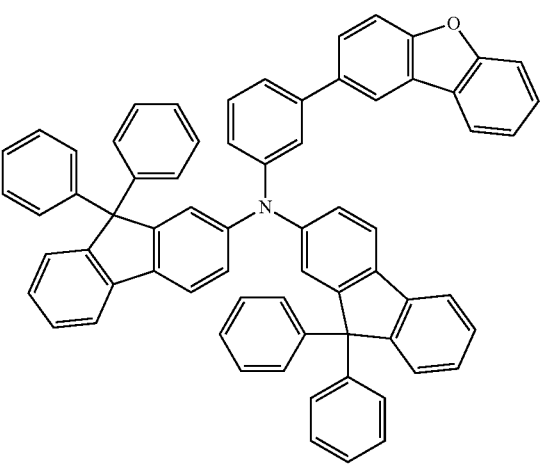

-continued
(B203)
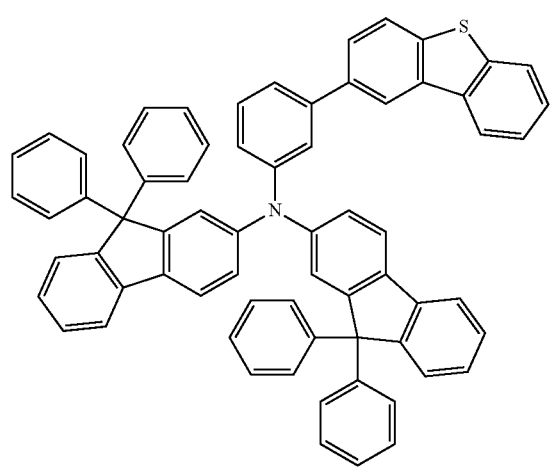
(B204)
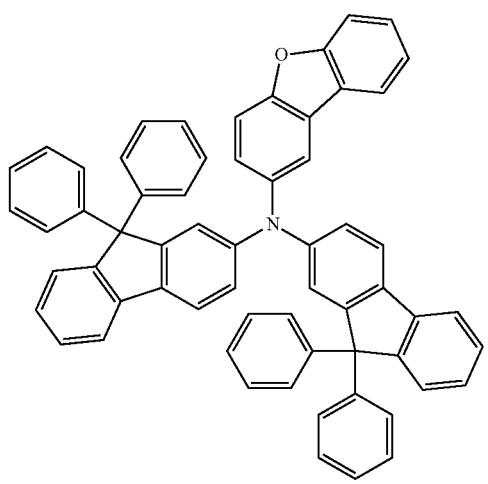
(B205)
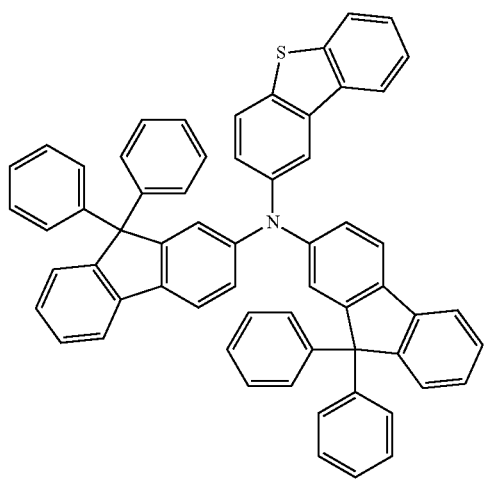
-continued
(B206)
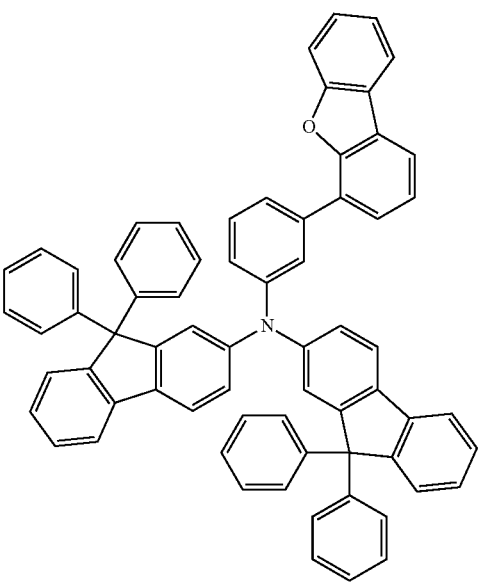
(B207)
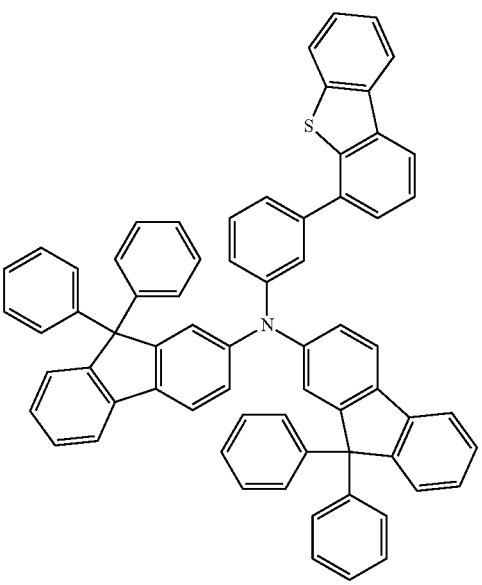

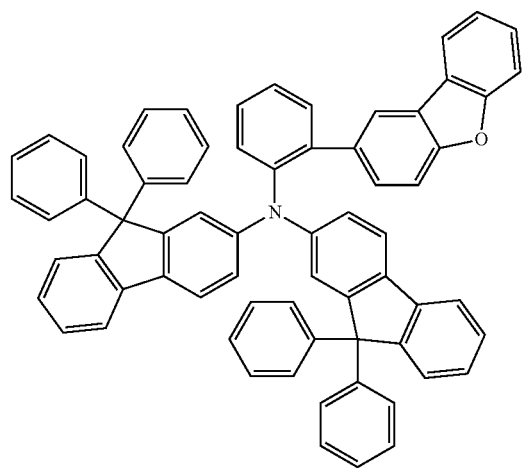
(B208)
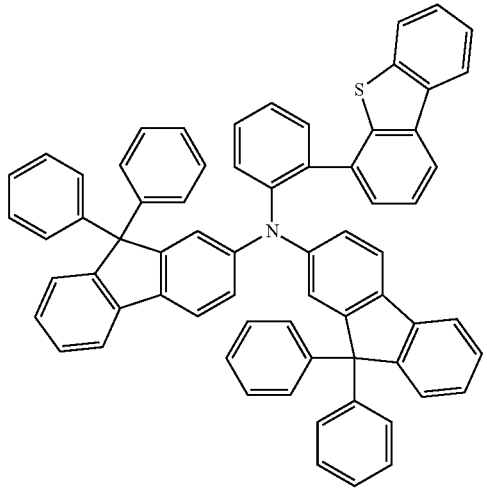
(B211)
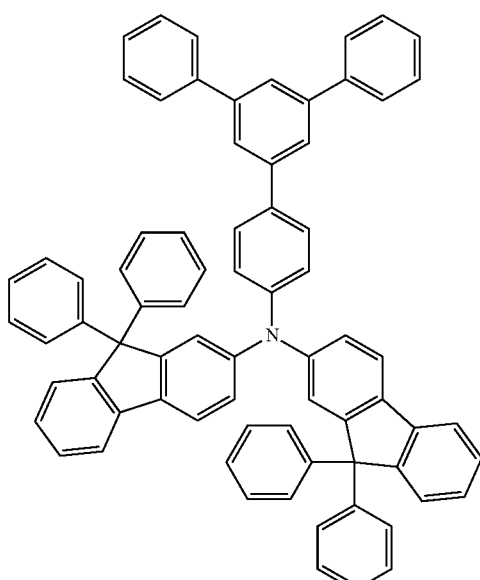
(B209)
(B212)
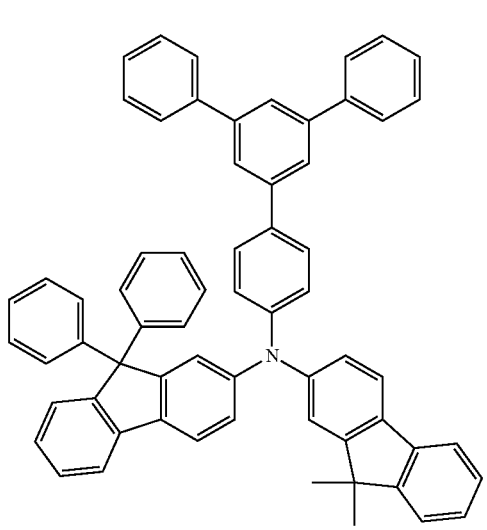
(B210)
(B213)

(B214)
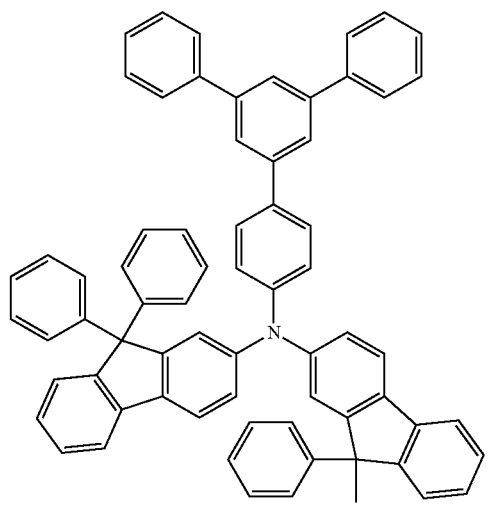
(B215)
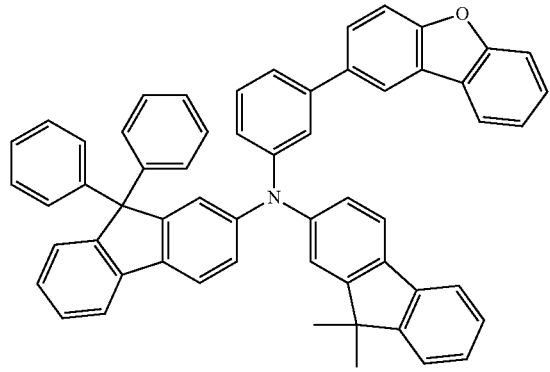
(B216)
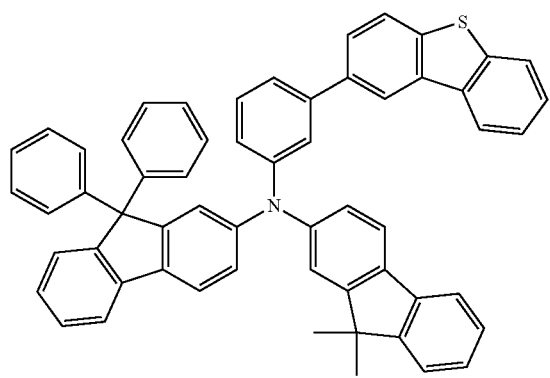
(B217)
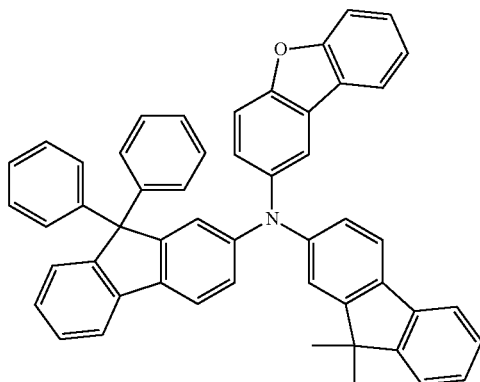
(B218)
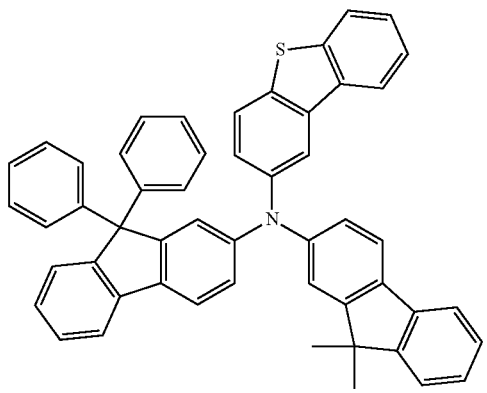
(B219)
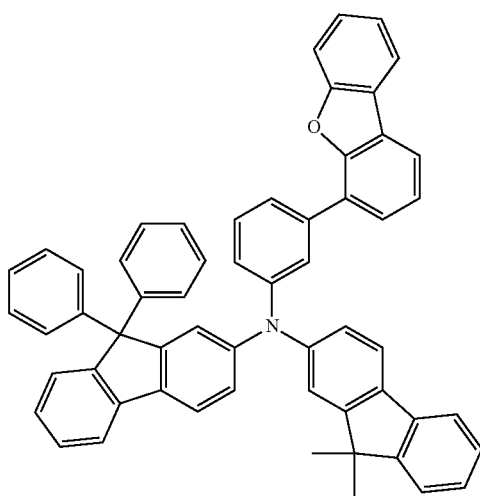

(B220)
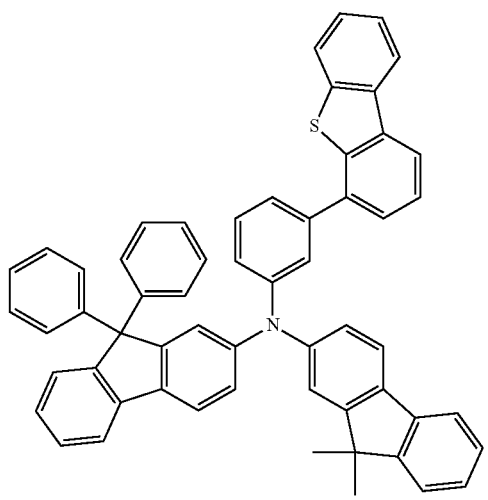
(B223)
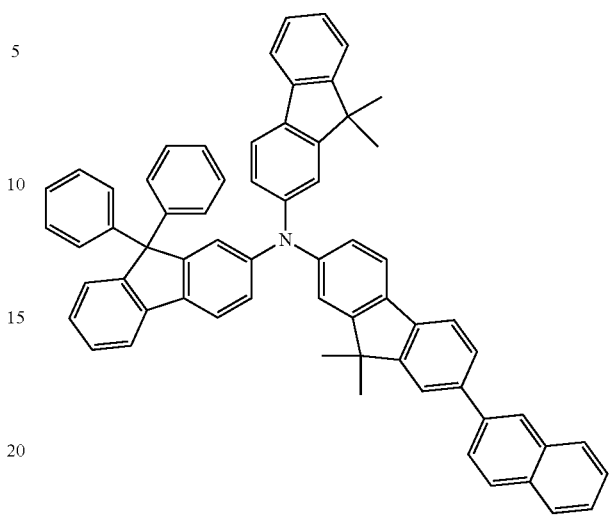
(B221)
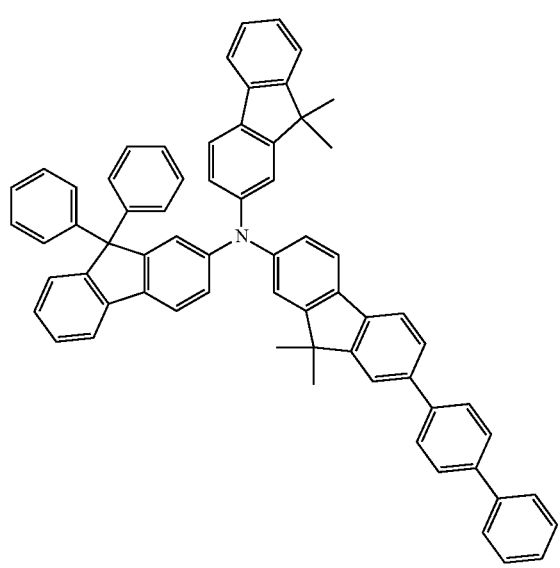
(B1224)
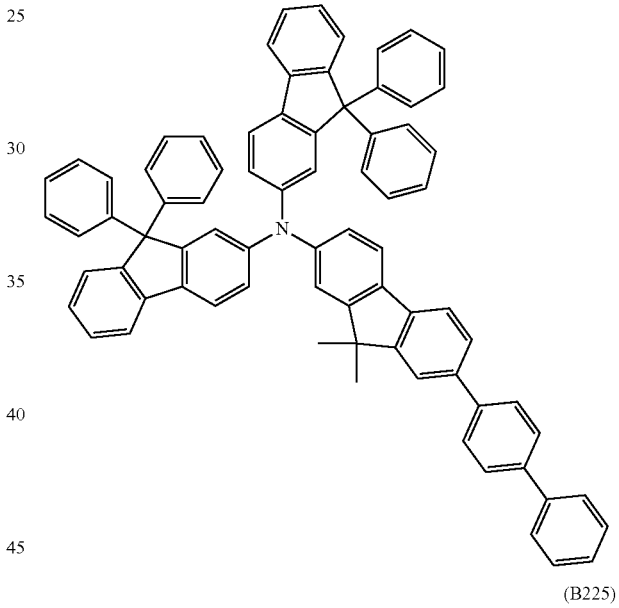
(B222)
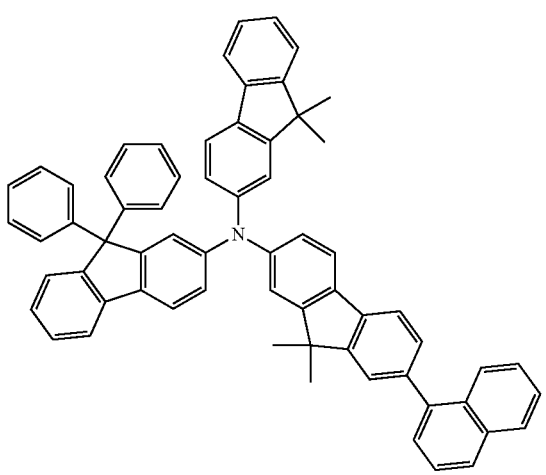
(B225)
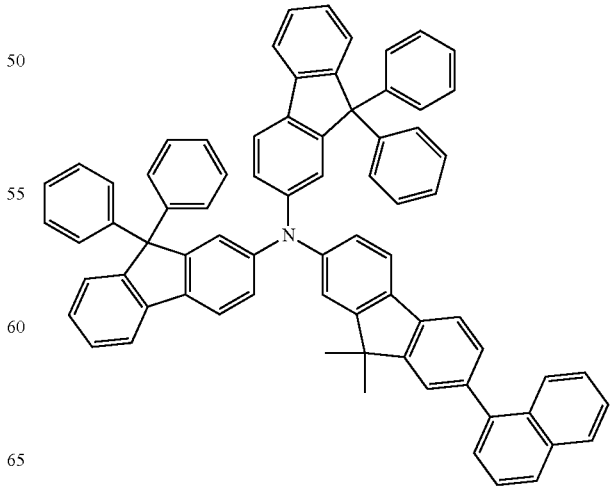

(B226)
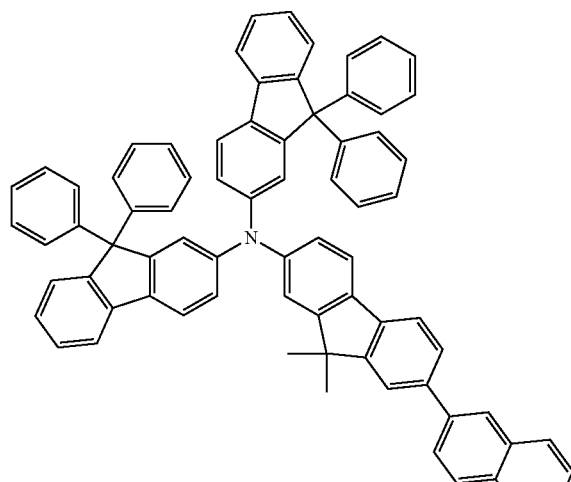
(B227)
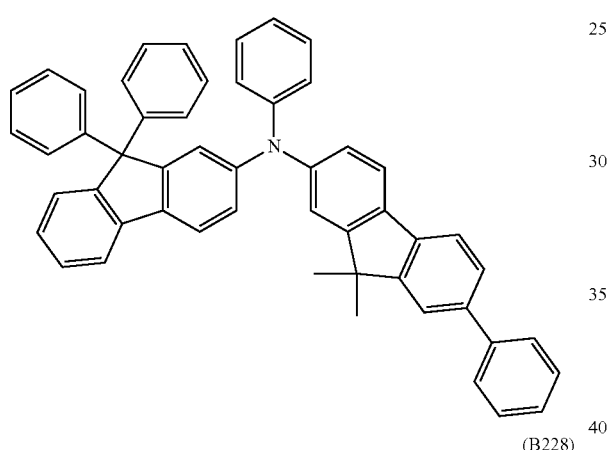
(B228)
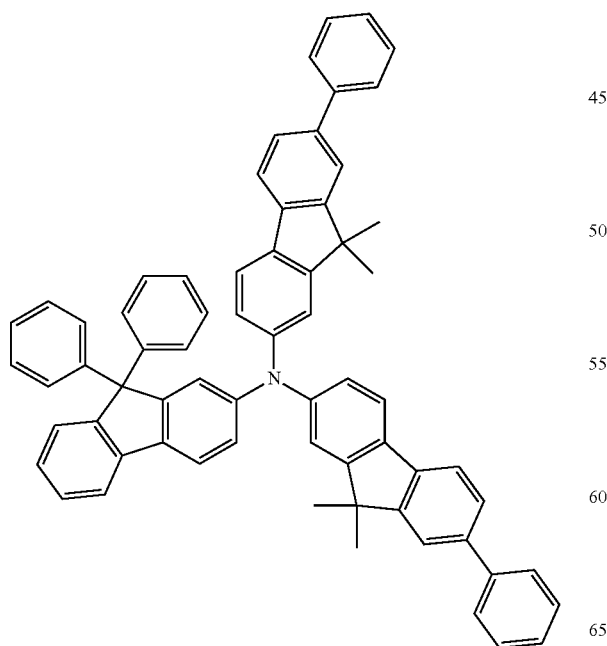
(B229)
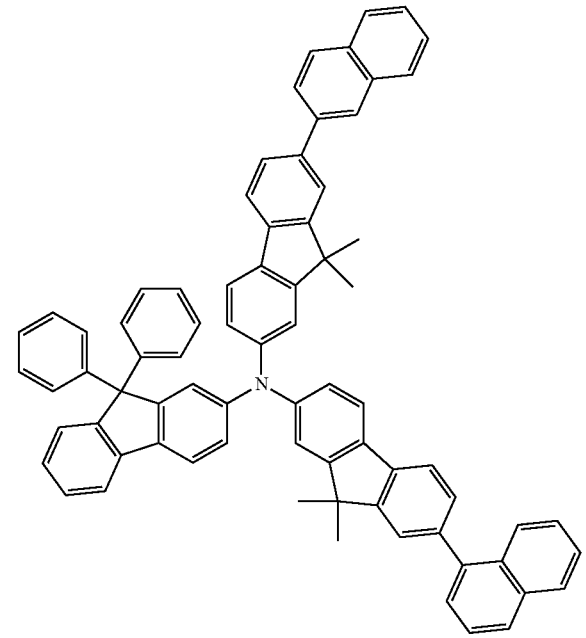
(B230)
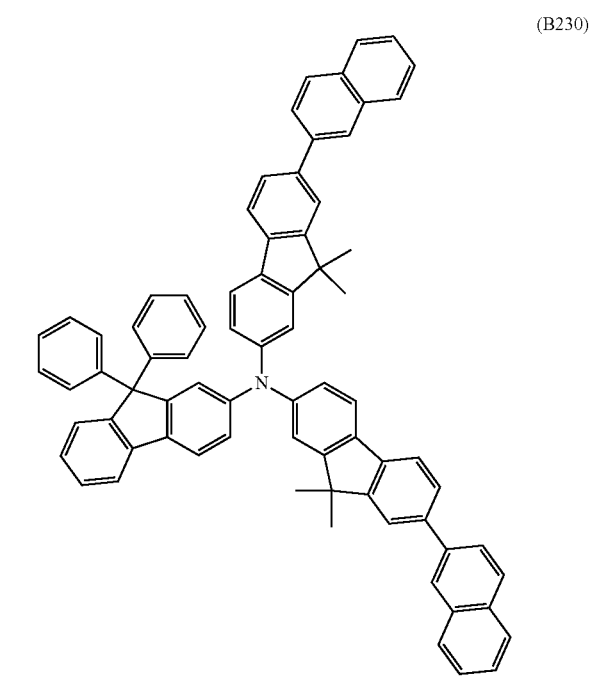

-continued
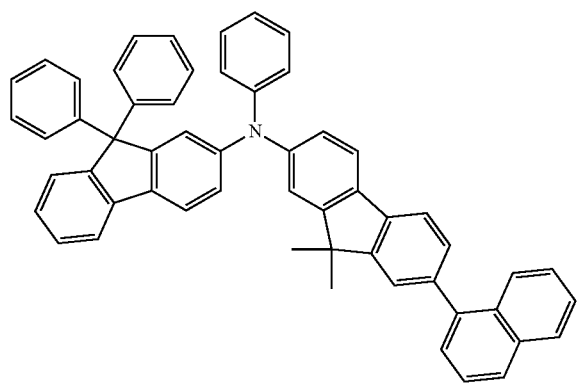
(B231)
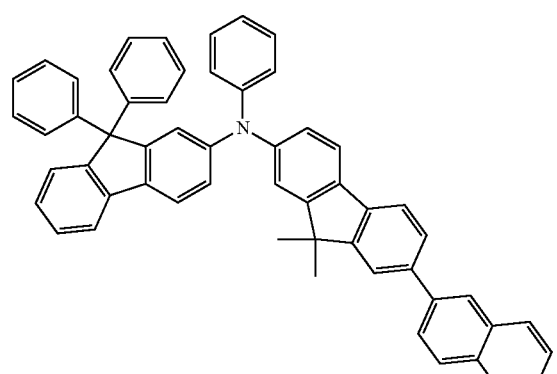
(B232)
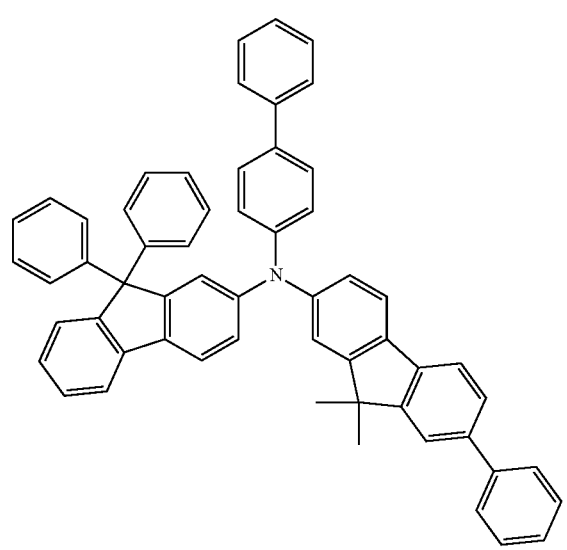
(B233)
-continued
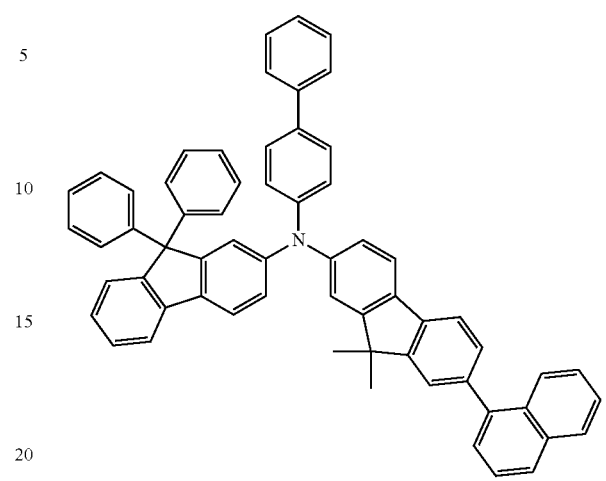
(B234)
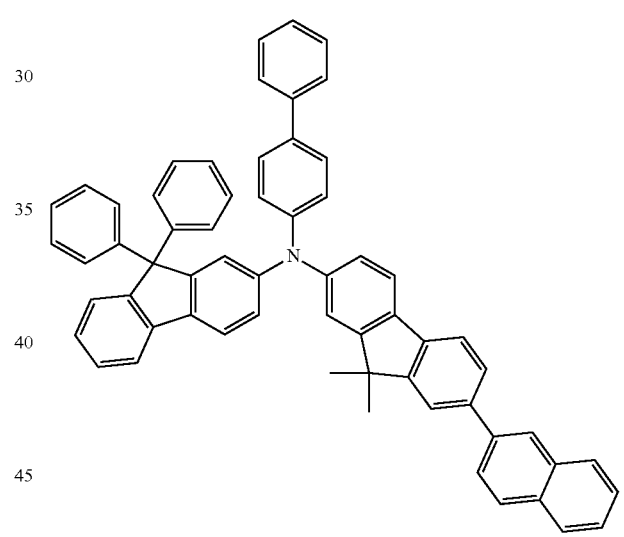
(B235)
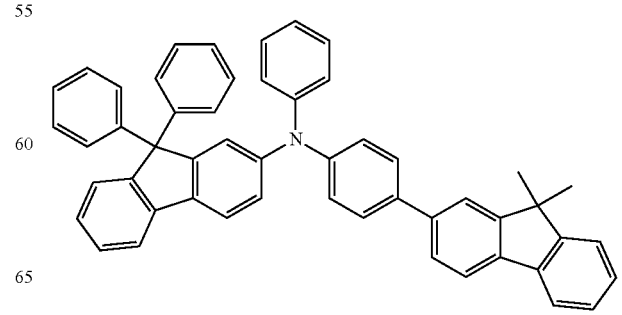
(B236)

(B237)
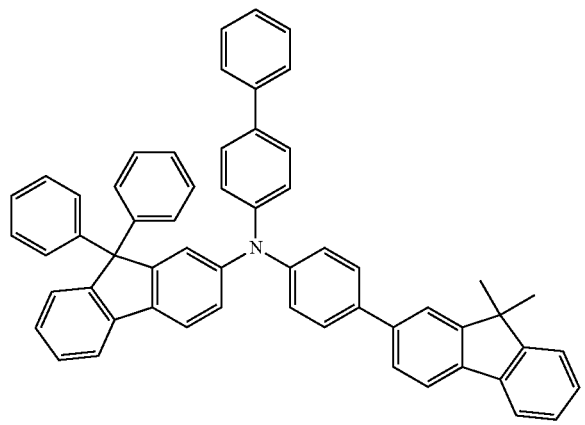
(B238)
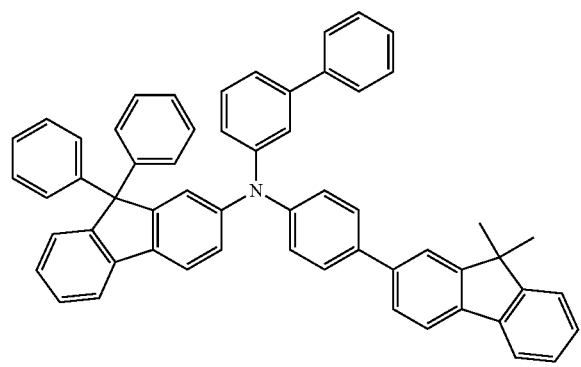
(B239)
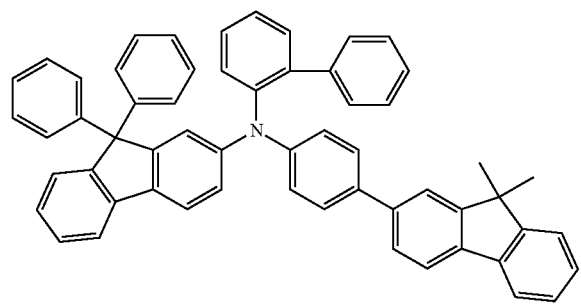
(B240)
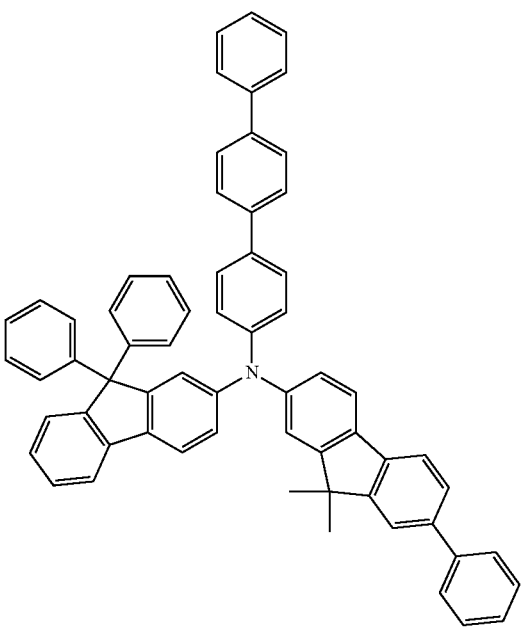
(B241)
(B242)
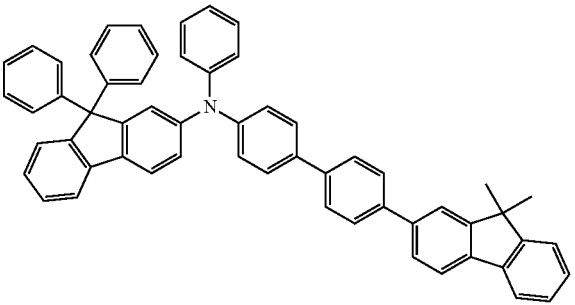

(B243)
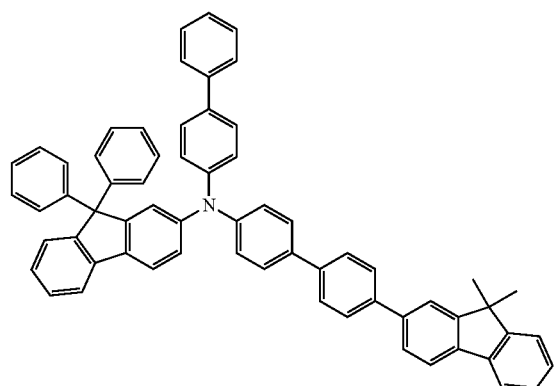
(B266)
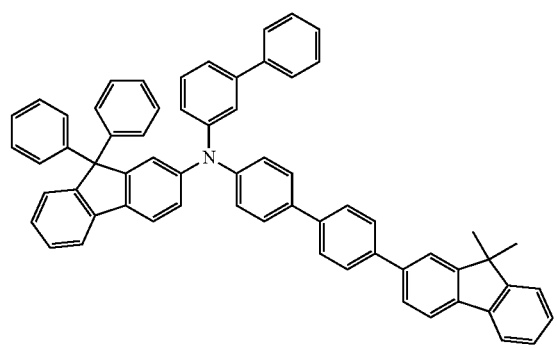
(B244)
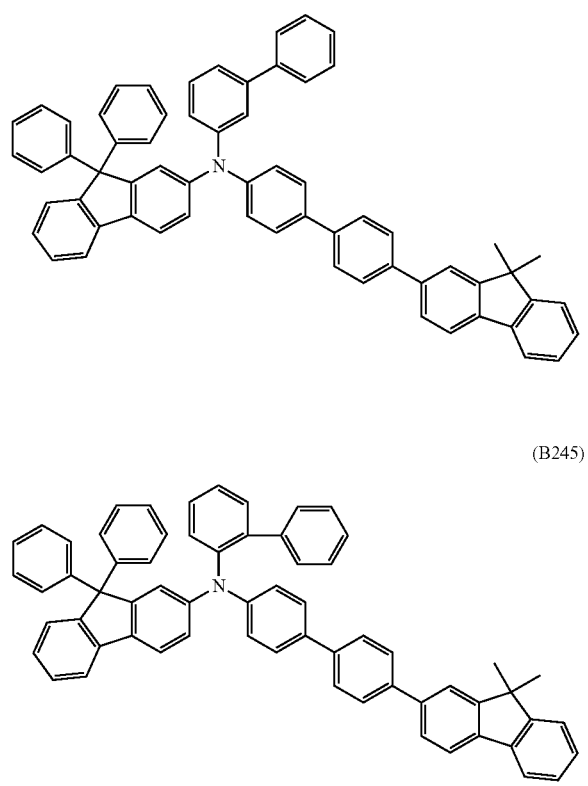
(B245)
(B246)
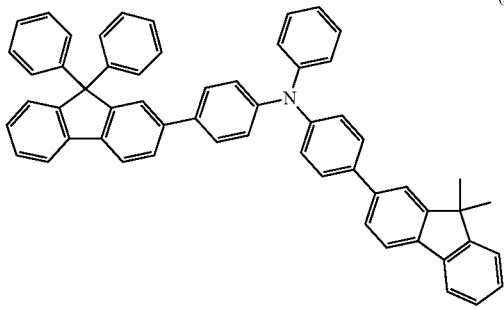
(B247)
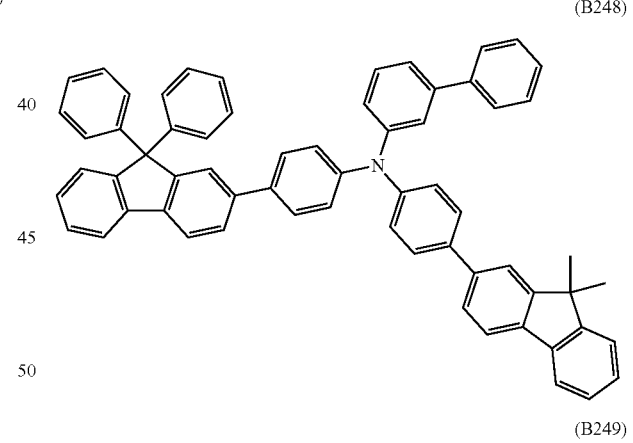
(B248)
(B249)
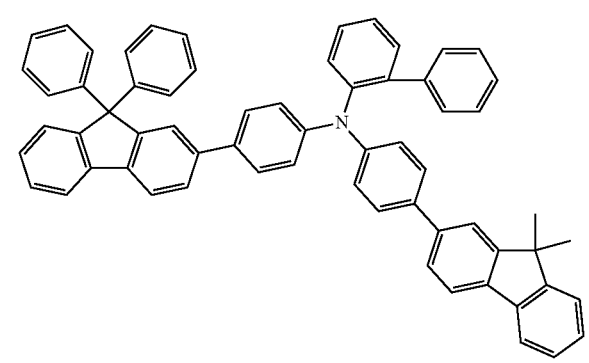

(B250)
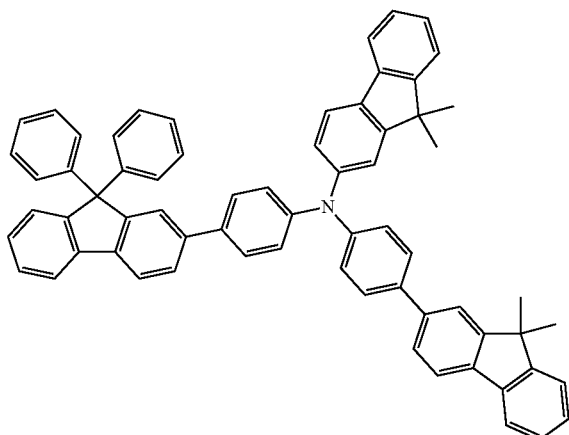
(B252)
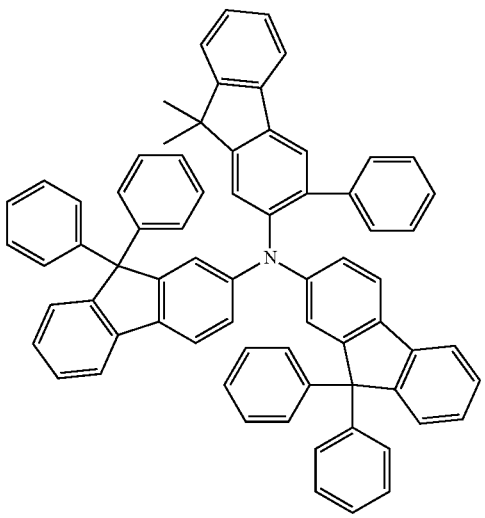
(B250)
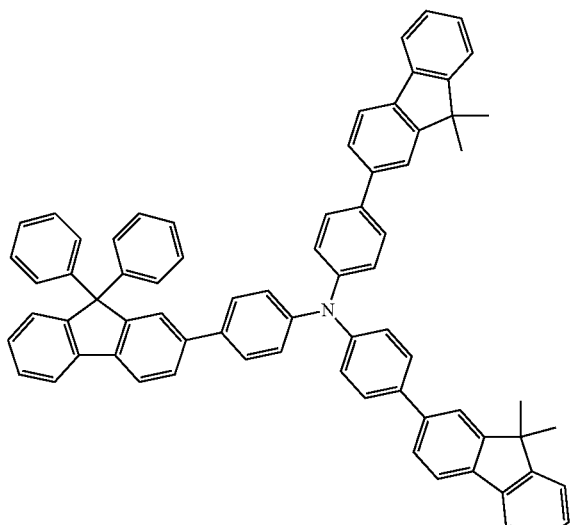
(B253)
(B251)
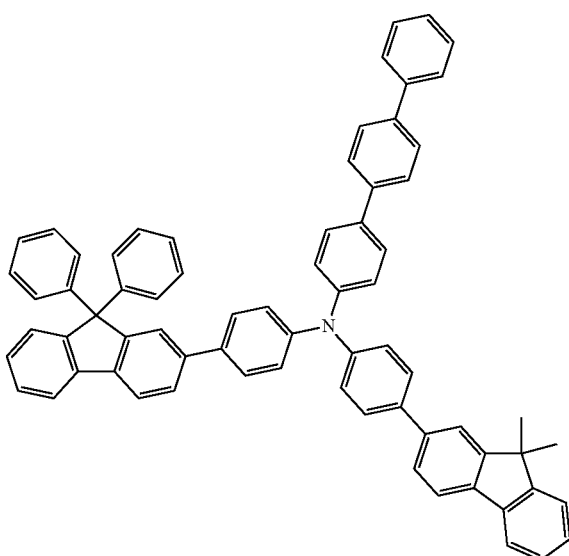
(B254)
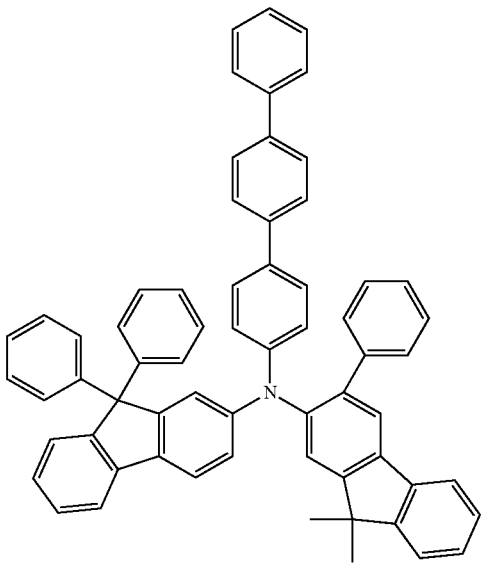

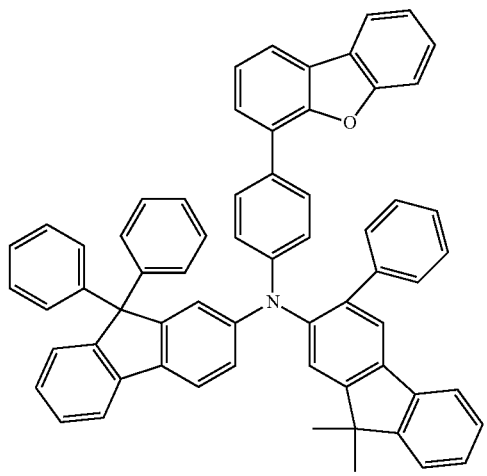
(B255)
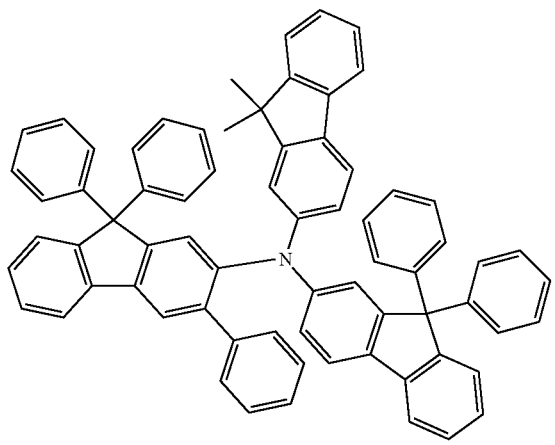
(B256)
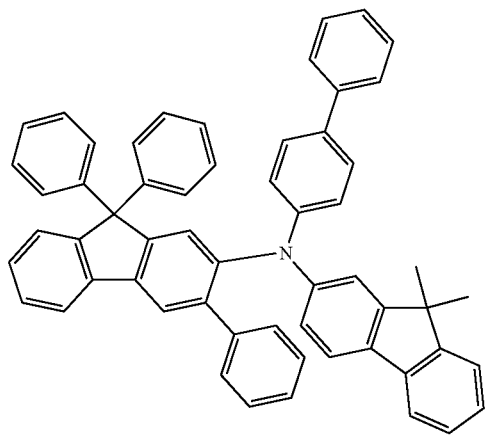
(B257)
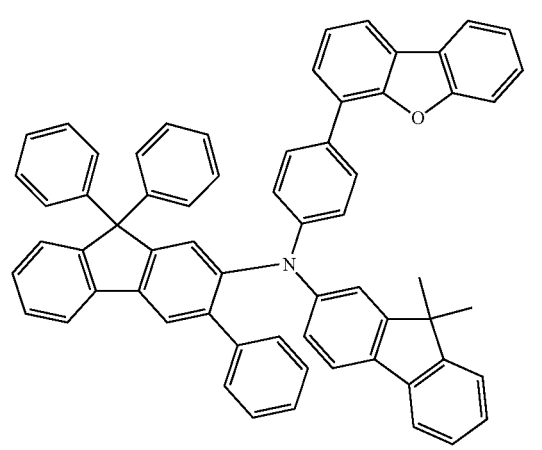
(B258)
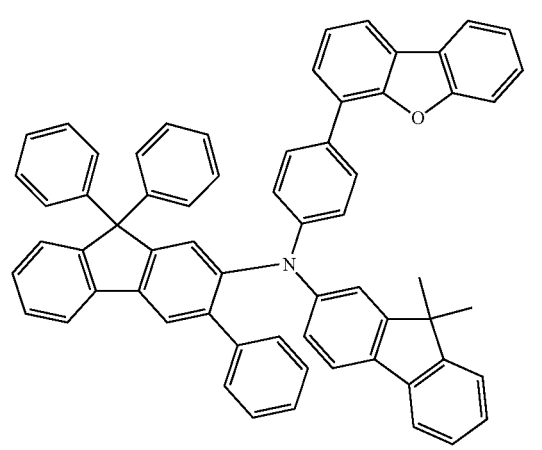
(B259)
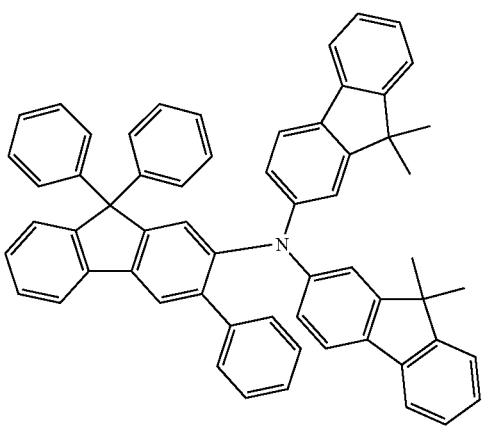
(B260)

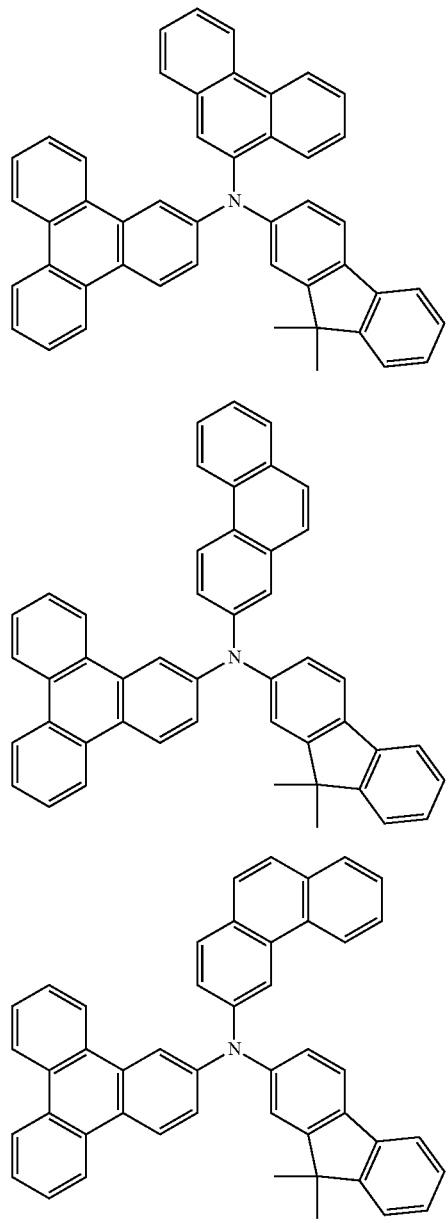
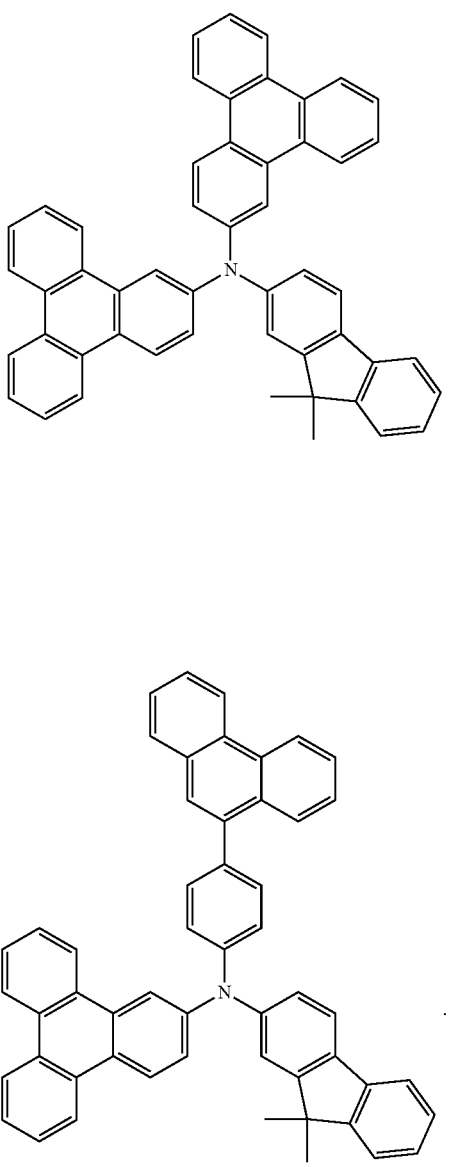
* * * * *

UNITED STATES PATENT AND TRADEMARK OFFICE
CERTIFICATE OF CORRECTION

PATENT NO. : 11,877,464 B2
APPLICATION NO. : 16/497275
DATED : January 16, 2024
INVENTOR(S) : Kim et al.

Page 1 of 13

It is certified that error appears in the above-identified patent and that said Letters Patent is hereby corrected as shown below:

In the Claims

In Claim 4, at Column 279, Lines 51-58, the structure of the compound should be:

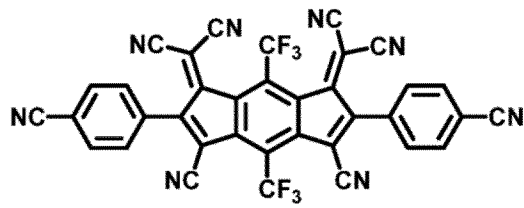

In Claim 4, at Column 280, Lines 50-57, the structure of the compound should be:

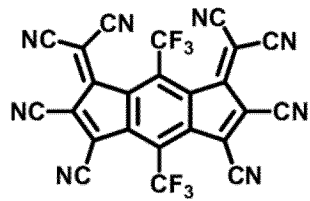

In Claim 4, at Column 285, Lines 50-57, the structure of the compound should be:

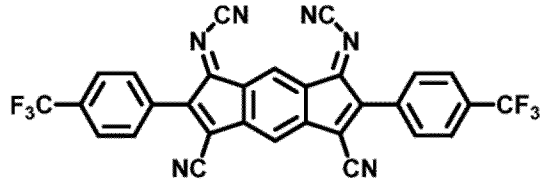

Signed and Sealed this
Thirtieth Day of July, 2024

Katherine Kelly Vidal
*Director of the United States Patent and Trademark Office*

In Claim 4, at Column 286, Lines 2-12, the structure of the compound should be:
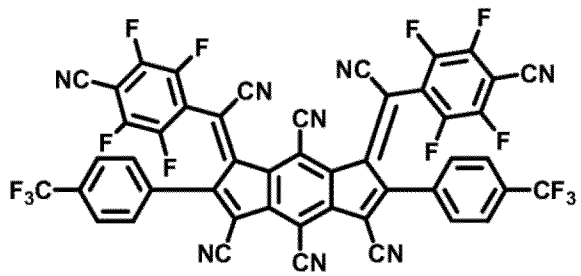
In Claim 4, at Column 286, Lines 18-28, the structure of the compound should be:
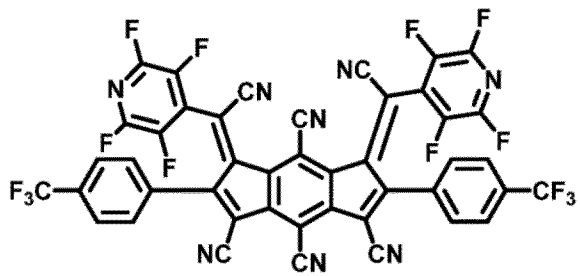
In Claim 4, at Column 286, Lines 30-38, the structure of the compound should be:
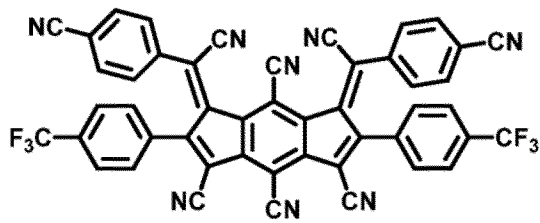
In Claim 4, at Column 286, Lines 43-53, the structure of the compound should be:
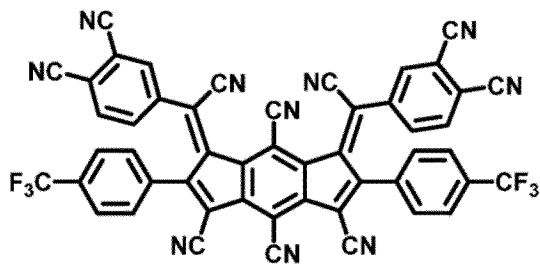
In Claim 4, at Column 286, Lines 56-66, the structure of the compound should be:
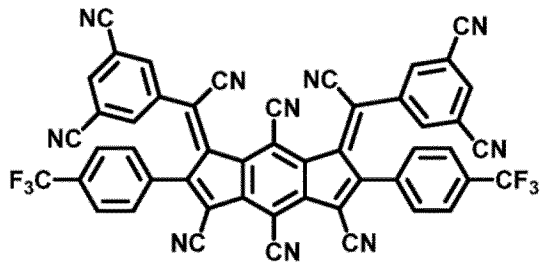

In Claim 4, at Column 287, Lines 2-13, the structure of the compound should be:
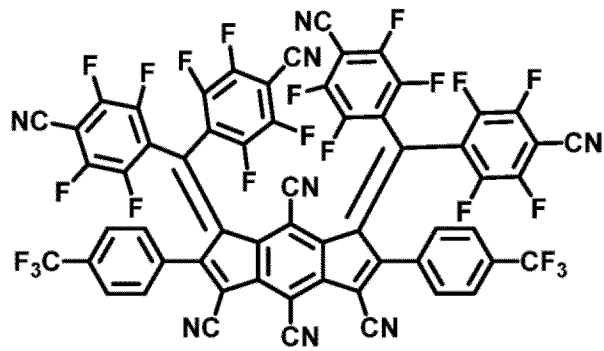
In Claim 4, at Column 287, Lines 14-27, the structure of the compound should be:
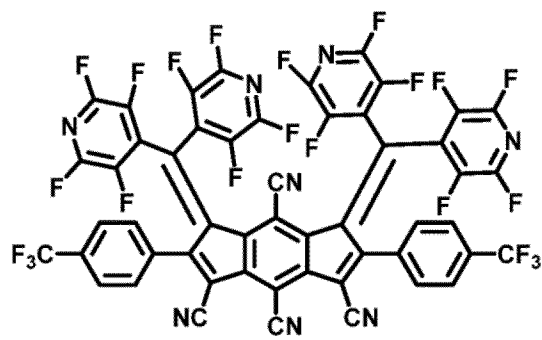
In Claim 4, at Column 287, Lines 37-49, the structure of the compound should be:
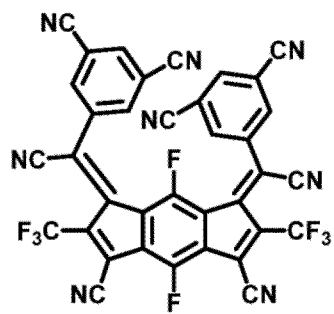
In Claim 4, at Column 288, Lines 22-28, the structure of the compound should be:
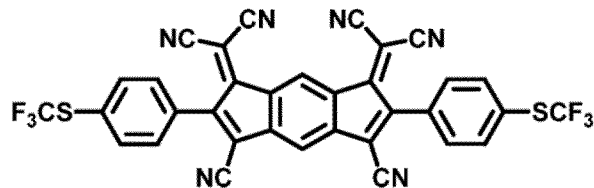

In Claim 4, at Column 288, Lines 29-41, the structure of the compound should be:
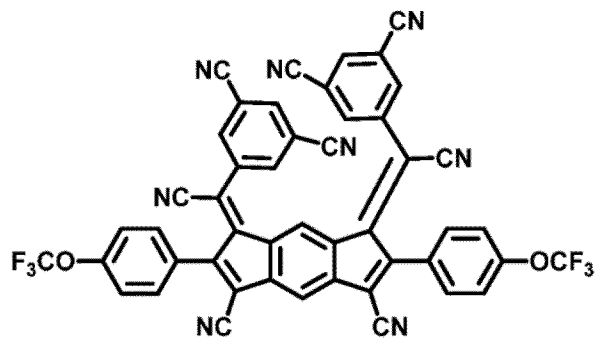
In Claim 4, at Column 289, Lines 2-14, the structure of the compound should be:
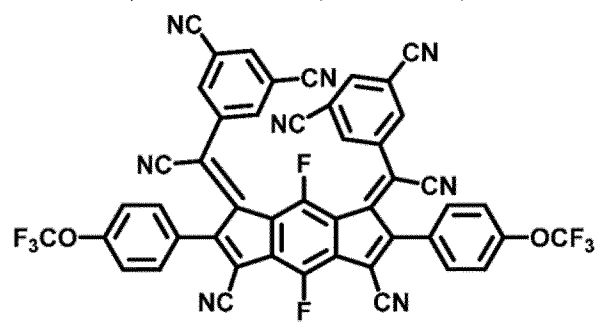
In Claim 4, at Column 289, Lines 17-31, the structure of the compound should be:
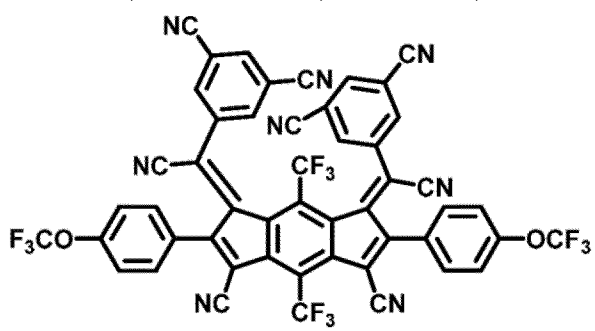
In Claim 4, at Column 289, Lines 35-49, the structure of the compound should be:
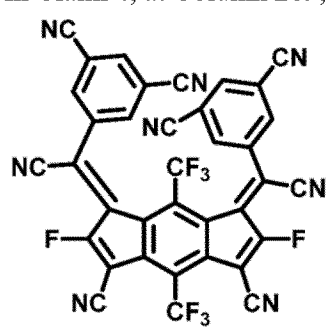

In Claim 4, at Column 290, Lines 2-17, the structure of the compound should be:
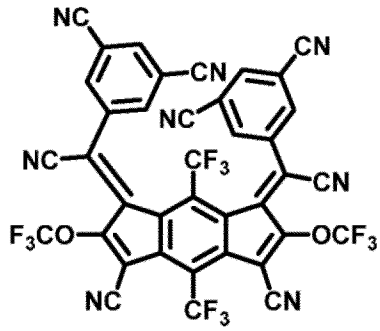
In Claim 4, at Column 290, Lines 21-34, the structure of the compound should be:
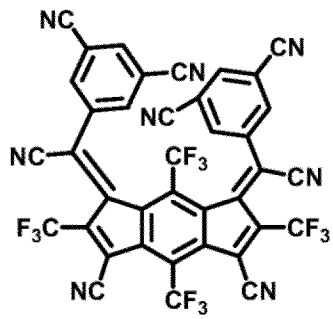
In Claim 4, at Column 294, Lines 31-38, the structure of the compound should be:
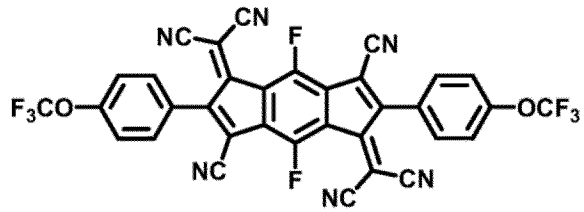
In Claim 4, at Column 294, Lines 58-66, the structure of the compound should be:
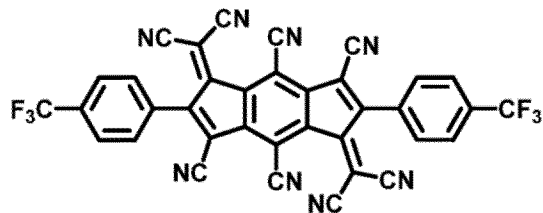
In Claim 4, at Column 295, Lines 2-11, the structure of the compound should be:
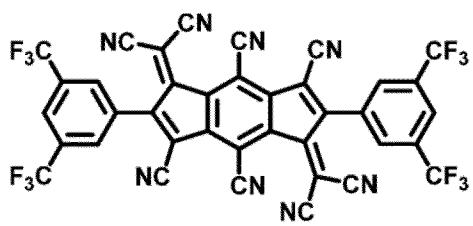

In Claim 4, at Column 295, Lines 22-30, the structure of the compound should be:
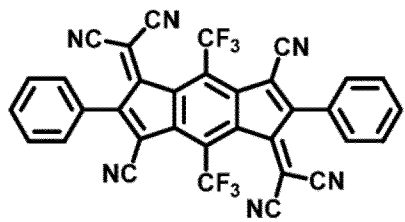
In Claim 4, at Column 295, Lines 31-38, the structure of the compound should be:
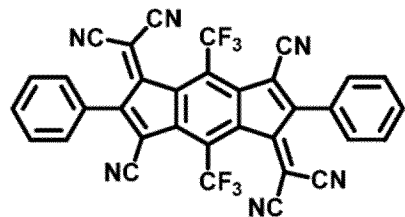
In Claim 4, at Column 295, Lines 40-48, the structure of the compound should be:
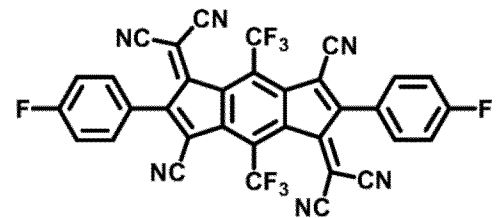
In Claim 4, at Column 295, Lines 49-57, the structure of the compound should be:
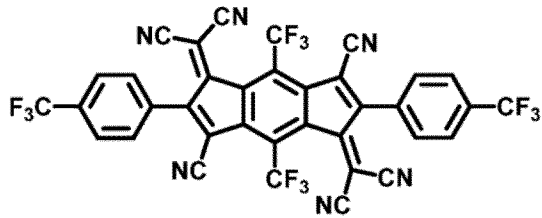
In Claim 4, at Column 296, Lines 2-10, the structure of the compound should be:
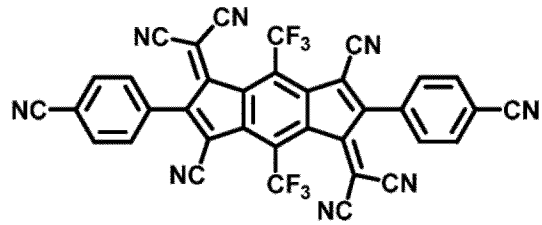

In Claim 4, at Column 298, Lines 20-33, the structure of the compound should be:
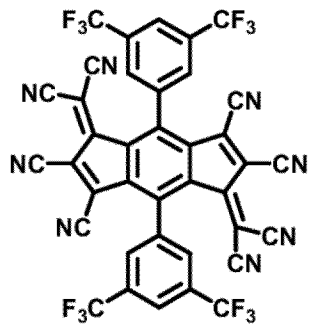
In Claim 4, at Column 304, Lines 38-50, the structure of the compound should be:
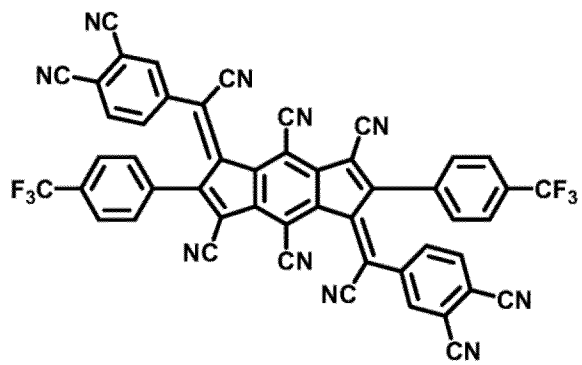
In Claim 4, at Column 304, Lines 53-66, the structure of the compound should be:
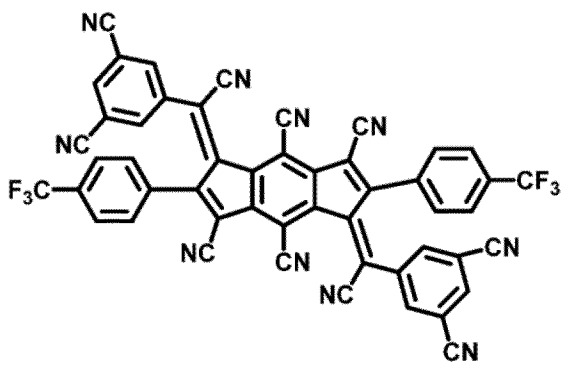

In Claim 4, at Column 305, Lines 49-66, the structure of the compound should be:
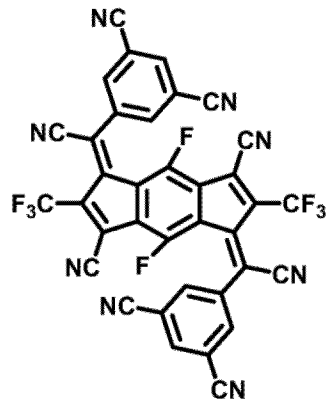
In Claim 4, at Column 306, Lines 43-51, the structure of the compound should be:
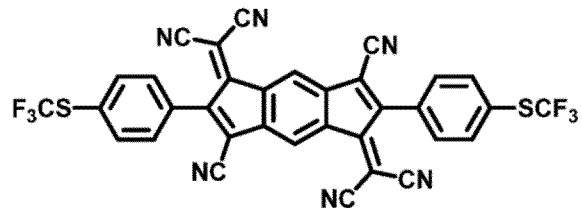
In Claim 4, at Column 306, Lines 51-66, the structure of the compound should be:
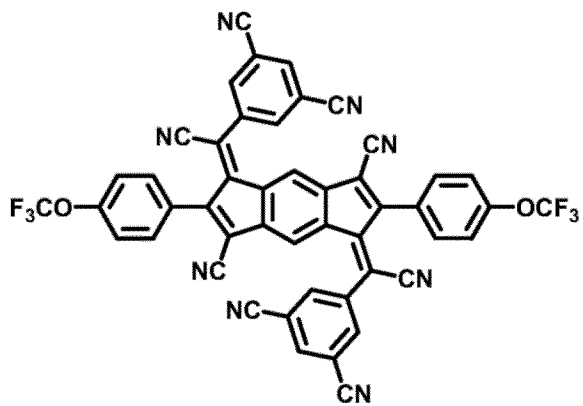
In Claim 4, at Column 307, Lines 35-50, the structure of the compound should be:
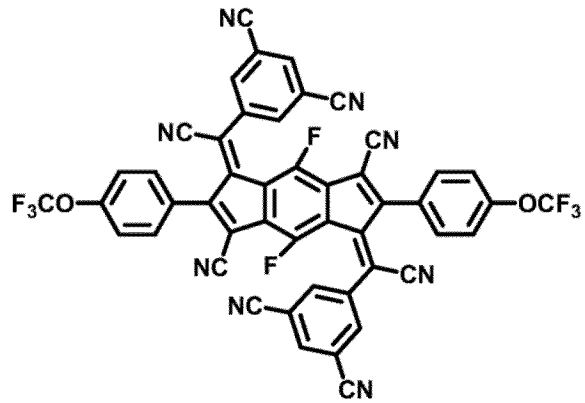

CERTIFICATE OF CORRECTION (continued)

In Claim 4, at Column 307, Lines 51-66, the structure of the compound should be:

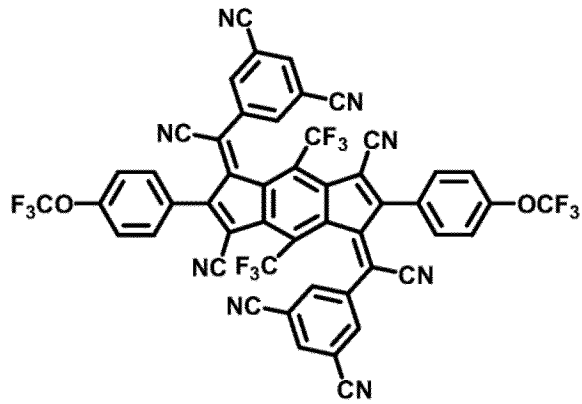

In Claim 4, at Column 309, Lines 2-18, the structure of the compound should be:

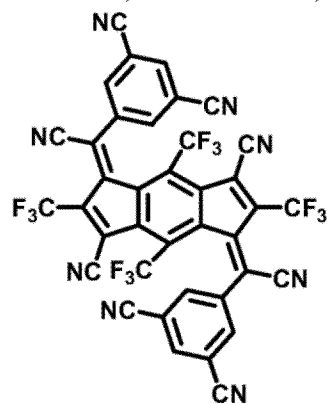

In Claim 5, at Column 322, the structure of the first compound should be:

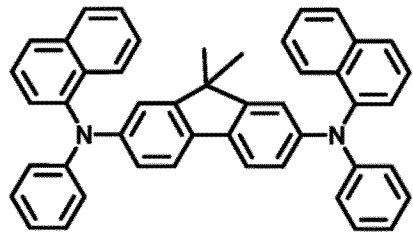

In Claim 6, at Column 381, the structure of the first compound should be:
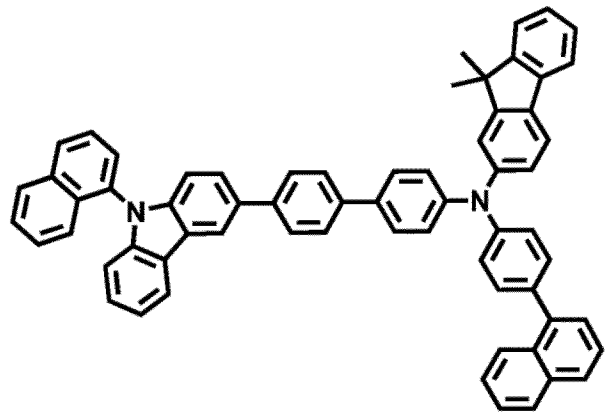
In Claim 6, at Column 381, the structure of the second compound should be:
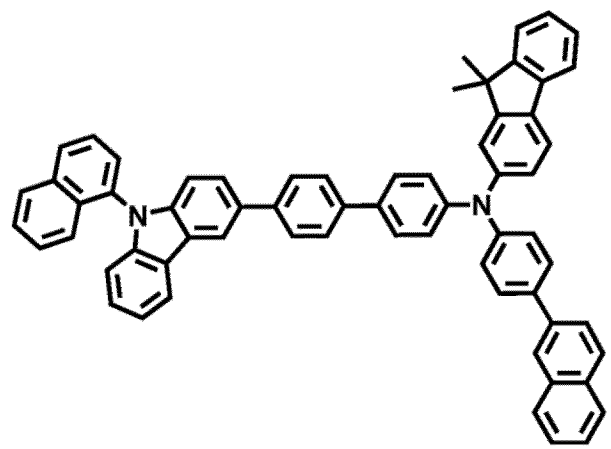
In Claim 6, at Column 381, the structure of the third compound should be:
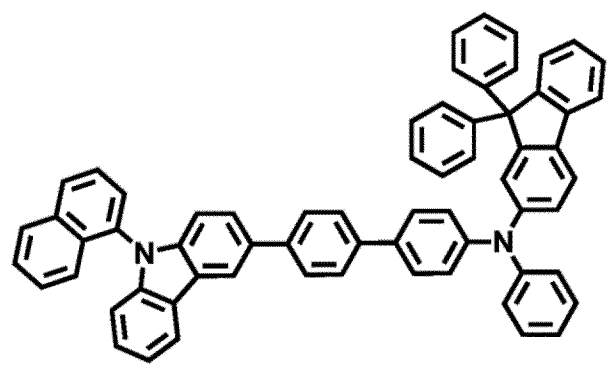
In Claim 6, at Column 383, the structure of the first compound should be:

CERTIFICATE OF CORRECTION (continued)
U.S. Pat. No. 11,877,464 B2

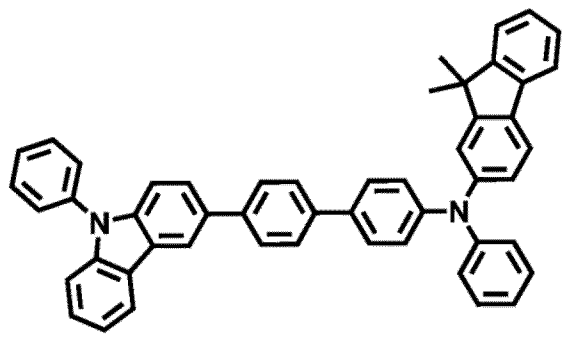

In Claim 6, at Column 383, the structure of the second compound should be:

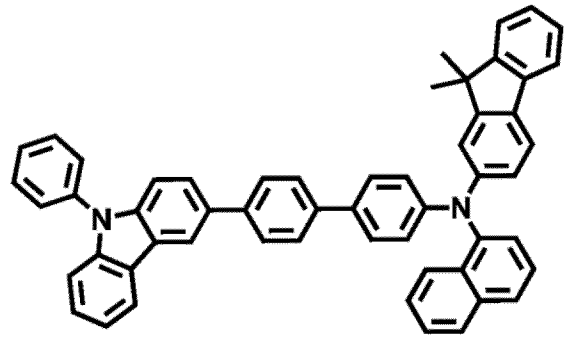

In Claim 6, at Column 383, the structure of the third compound should be:

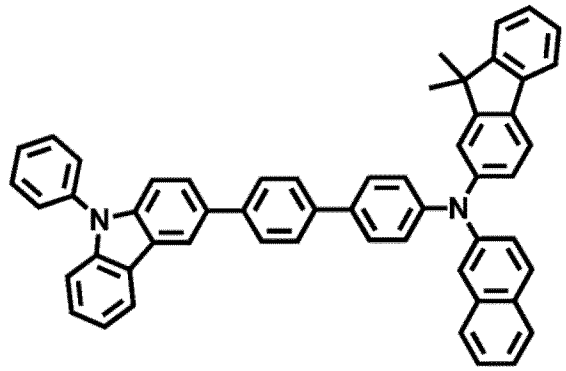

In Claim 6, at Column 539, the following compound should be inserted between the first and second compounds:

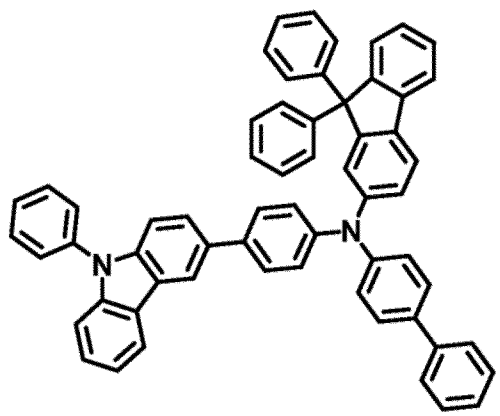

In Claim 7, at Column 582, Lines 54-66, the compound should be deleted.

In Claim 7, at Column 583, Lines 39-53, the compound should be deleted.

In Claim 7, at Column 583, Line 54, "(B245)" should be replaced with –(B244)–.

In Claim 7, at Column 584, Line 2, "(B246)" should be replaced with –(B245)–; and at Line 18, "(B247)" should be replaced with –(B246)–; and at Line 37, "(B248)" should be replaced with –(B247)–; and at Line 53, "(B249)" should be replaced with –(B248)–.

In Claim 7, at Column 585, Line 2, "(B250)" should be replaced with –(B249)–.

In Claim 10, at Column 856, Lines 54-66, the compound should be deleted.

In Claim 10, at Column 857, Lines 38-53, the compound should be deleted.

In Claim 10, at Column 857, Line 54, "(B245)" should be replaced with –(B244)–.

In Claim 10, at Column 858, Line 2, "(B246)" should be replaced with –(B245)–; and at Line 15, "(B247)" should be replaced with –(B246)–; and at Line 37, "(B248)" should be replaced with –(B247)–; and at Line 53, "(B249)" should be replaced with –(B248)–.

In Claim 10, at Column 859, Line 2, "(B250)" should be replaced with –(B249)–.

In Claim 13, at Column 1019, the following compound should be inserted between the second and third compounds:

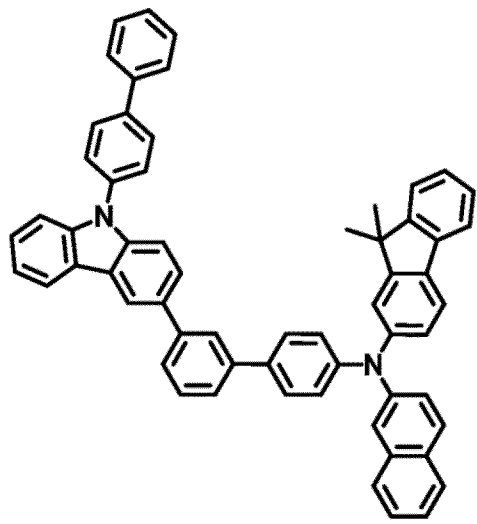

In Claim 14, at Column 1142, Lines 54-66, the compound should be deleted.

In Claim 14, at Column 1143, Lines 36-50, the compound should be deleted.

In Claim 14, at Column 1143, Line 54, "(B245)" should be replaced with –(B244)–.

In Claim 14, at Column 1144, Line 2, "(B246)" should be replaced with –(B245)–; and at Line 17, "(B247)" should be replaced with –(B246)–; and at Line 37, "(B248)" should be replaced with –(B247)–; and at Line 53, "(B249)" should be replaced with –(B248)–.

In Claim 14, at Column 1145, Line 2, "(B250)" should be replaced with –(B249)–.